(12) United States Patent
Wilde et al.

(10) Patent No.: US 10,446,272 B2
(45) Date of Patent: Oct. 15, 2019

(54) METHODS AND COMPOSITIONS FOR CLASSIFICATION OF SAMPLES

(71) Applicant: VERACYTE, INC., South San Francisco, CA (US)

(72) Inventors: Jonathan I. Wilde, Burlingame, CA (US); Darya Chudova, San Jose, CA (US); Giulia C. Kennedy, San Francisco, CA (US)

(73) Assignee: Veracyte, Inc., South San Francsico, CA (US)

( * ) Notice: Subject to any disclaimer, the term of this patent is extended or adjusted under 35 U.S.C. 154(b) by 0 days.

(21) Appl. No.: 15/702,217

(22) Filed: Sep. 12, 2017

(65) Prior Publication Data

US 2018/0122508 A1 May 3, 2018

Related U.S. Application Data

(63) Continuation-in-part of application No. 15/274,492, filed on Sep. 23, 2016, now Pat. No. 9,856,537, which is a continuation of application No. 12/964,666, filed on Dec. 9, 2010, now Pat. No. 9,495,515, which is a continuation-in-part of application No. 13/708,439, filed on Dec. 7, 2012, now abandoned.

(60) Provisional application No. 61/285,165, filed on Dec. 9, 2009, provisional application No. 61/568,870, filed on Dec. 9, 2011.

(51) Int. Cl.
| | |
|---|---|
| *G16H 50/20* | (2018.01) |
| *C12Q 1/6886* | (2018.01) |
| *G01N 33/574* | (2006.01) |
| *G16H 10/40* | (2018.01) |
| *G16B 40/00* | (2019.01) |
| *G16B 40/30* | (2019.01) |
| *G16B 25/00* | (2019.01) |
| *G16B 25/10* | (2019.01) |

(52) U.S. Cl.
CPC .......... *G16H 50/20* (2018.01); *C12Q 1/6886* (2013.01); *G01N 33/57407* (2013.01); *G01N 33/57488* (2013.01); *G16B 40/00* (2019.02); *G16B 40/30* (2019.02); *G16H 10/40* (2018.01); *C12Q 2600/112* (2013.01); *C12Q 2600/158* (2013.01); *G16B 25/00* (2019.02); *G16B 25/10* (2019.02)

(58) Field of Classification Search
None
See application file for complete search history.

(56) References Cited

U.S. PATENT DOCUMENTS

| | | |
|---|---|---|
| 3,645,691 A | 2/1972 | Guenter et al. |
| 3,687,808 A | 8/1972 | Thomas, Jr. et al. |
| 5,130,238 A | 7/1992 | Malek et al. |
| 5,143,854 A | 9/1992 | Pirrung et al. |
| 5,288,514 A | 2/1994 | Ellman et al. |
| 5,384,261 A | 1/1995 | Winkler et al. |
| 5,399,491 A | 3/1995 | Kacian et al. |
| 5,455,166 A | 10/1995 | Walker |
| 5,494,810 A | 2/1996 | Barany et al. |
| 5,538,848 A | 7/1996 | Livak et al. |
| 5,677,195 A | 10/1997 | Winkler et al. |
| 5,705,365 A | 1/1998 | Ryder et al. |
| 5,710,029 A | 1/1998 | Ryder et al. |
| 5,830,711 A | 11/1998 | Barany et al. |
| 5,846,717 A | 12/1998 | Brow et al. |
| 5,854,033 A | 12/1998 | Lizardi et al. |
| 5,888,779 A | 3/1999 | Kacian et al. |
| 5,965,360 A | 10/1999 | Zain et al. |
| 5,985,557 A | 11/1999 | Prudent et al. |
| 5,989,815 A | 11/1999 | Skolnick et al. |
| 5,994,069 A | 11/1999 | Hall et al. |
| 6,001,567 A | 12/1999 | Brow et al. |
| 6,022,692 A | 2/2000 | Coulie et al. |
| 6,027,887 A | 2/2000 | Zavada et al. |
| 6,090,543 A | 7/2000 | Prudent et al. |
| 6,136,182 A | 10/2000 | Dolan et al. |
| 6,225,051 B1 | 5/2001 | Sugiyama et al. |
| 6,251,639 B1 | 6/2001 | Kurn |
| 6,268,142 B1 | 7/2001 | Duff et al. |
| 6,410,278 B1 | 6/2002 | Notomi et al. |
| 6,436,642 B1 | 8/2002 | Gould-Rothberg et al. |
| 6,723,506 B2 | 4/2004 | Fletcher et al. |
| 7,186,514 B2 | 3/2007 | Zavada et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordano et al. |
| 7,662,553 B2 | 2/2010 | Lenz |
| 7,767,391 B2 | 8/2010 | Scott et al. |

(Continued)

FOREIGN PATENT DOCUMENTS

| | | |
|---|---|---|
| CA | 2712773 A1 | 7/2009 |
| CN | 101501214 A | 8/2009 |

(Continued)

OTHER PUBLICATIONS

US 5,962,233 A, 10/1999, Livak et al. (withdrawn)

(Continued)

*Primary Examiner* — Channing S Mahatan
(74) *Attorney, Agent, or Firm* — Wilson Sonsini Goodrich & Rosati

(57) ABSTRACT

Disclosed herein are kits, compositions, and methods relating to the classification of samples. Methods disclosed herein can be used to identify sample mix-ups. Methods disclosed herein can also be used to diagnose conditions or to support treatment-related decisions.

22 Claims, 50 Drawing Sheets

(56) References Cited

U.S. PATENT DOCUMENTS

| | | |
|---|---|---|
| 7,901,881 B2 | 3/2011 | Libutti et al. |
| 7,901,888 B2 | 3/2011 | Kebebew |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,293,880 B2 | 10/2012 | Cote et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon, I et al. |
| 9,074,258 B2 | 7/2015 | Davicioni et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,206,482 B2 | 12/2015 | Davicioni et al. |
| 9,234,244 B2 | 1/2016 | Zeiger et al. |
| 9,495,515 B1 | 11/2016 | Giulia et al. |
| 9,587,279 B2 | 3/2017 | Fahey, III et al. |
| 9,617,604 B2 | 4/2017 | Davicioni et al. |
| 9,708,667 B2 | 7/2017 | Yanai et al. |
| 9,714,452 B2 | 7/2017 | Davicioni et al. |
| 9,994,907 B2 | 6/2018 | Davicioni et al. |
| 1,011,492 A1 | 10/2018 | Kennedy et al. |
| 2001/0051344 A1 | 12/2001 | Shalon et al. |
| 2002/0076735 A1 | 6/2002 | Williams et al. |
| 2002/0169137 A1 | 11/2002 | Reiner et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2004/0019466 A1 | 1/2004 | Minor et al. |
| 2004/0058378 A1 | 3/2004 | Kong et al. |
| 2005/0042222 A1 | 2/2005 | Yamamoto et al. |
| 2005/0048533 A1 | 3/2005 | Sidransky et al. |
| 2005/0137805 A1 | 6/2005 | Lewin et al. |
| 2005/0240357 A1 | 10/2005 | Minor |
| 2005/0250125 A1 | 11/2005 | Novakoff |
| 2005/0266443 A1 | 12/2005 | Croce et al. |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2007/0020657 A1 | 1/2007 | Grebe et al. |
| 2007/0031873 A1 | 2/2007 | Wang et al. |
| 2007/0037186 A1 | 2/2007 | Jiang et al. |
| 2007/0048738 A1 | 3/2007 | Donkena et al. |
| 2007/0065833 A1 | 3/2007 | Gupta |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172844 A1 | 7/2007 | Lancaster et al. |
| 2007/0220621 A1 | 9/2007 | Clarke et al. |
| 2007/0238119 A1 | 10/2007 | Yu et al. |
| 2008/0028302 A1 | 1/2008 | Meschkat |
| 2008/0044824 A1 | 2/2008 | Giordano et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlin |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0191535 A1 | 7/2009 | Connelly et al. |
| 2009/0204333 A1 | 8/2009 | Friend et al. |
| 2009/0280490 A1 | 11/2009 | Baker et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0131286 A1 | 5/2010 | Houlgatte et al. |
| 2010/0131432 A1 | 5/2010 | Kennedy et al. |
| 2010/0178653 A1 | 7/2010 | Aharonov et al. |
| 2010/0285979 A1 | 11/2010 | Zeiger et al. |
| 2011/0092375 A1 | 4/2011 | Zamore et al. |
| 2011/0152110 A1 | 6/2011 | Vierlinger et al. |
| 2011/0212855 A1 | 9/2011 | Rafnar et al. |
| 2011/0229894 A1 | 9/2011 | Levy et al. |
| 2011/0230372 A1 | 9/2011 | Willman et al. |
| 2011/0287946 A1 | 11/2011 | Gudmundsson et al. |
| 2011/0312520 A1 | 12/2011 | Kennedy et al. |
| 2012/0015839 A1 | 1/2012 | Chinnaiyan |
| 2012/0015843 A1 | 1/2012 | Von Hoff et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0214165 A1 | 8/2012 | Walfish et al. |
| 2012/0220474 A1 | 8/2012 | Kennedy et al. |
| 2013/0023434 A1 | 1/2013 | Van Laar |
| 2013/0142728 A1 | 6/2013 | Beaudenon-Huibregtse et al. |
| 2013/0150257 A1 | 6/2013 | Abdueva et al. |
| 2013/0172203 A1 | 7/2013 | Yeatman et al. |
| 2013/0184999 A1 | 7/2013 | Ding |
| 2013/0225662 A1 | 8/2013 | Kennedy et al. |
| 2013/0231258 A1 | 9/2013 | Wilde et al. |
| 2013/0273543 A1 | 10/2013 | Gudmundsson et al. |
| 2013/0302810 A1 | 11/2013 | Latham et al. |
| 2013/0303826 A1 | 11/2013 | Jurisica et al. |
| 2014/0030714 A1 | 1/2014 | Paschke et al. |
| 2014/0087961 A1 | 3/2014 | Sulem et al. |
| 2014/0099261 A1 | 4/2014 | Keutgen et al. |
| 2014/0121126 A1 | 5/2014 | Bivona et al. |
| 2014/0143188 A1 | 5/2014 | Mackey et al. |
| 2014/0228237 A1 | 8/2014 | Kennedy et al. |
| 2014/0243240 A1 | 8/2014 | Soldin et al. |
| 2014/0302042 A1 | 10/2014 | Chin et al. |
| 2014/0315199 A1 | 10/2014 | Rhodes et al. |
| 2014/0315739 A1 | 10/2014 | Aharonov et al. |
| 2014/0349856 A1 | 11/2014 | Schnabel et al. |
| 2014/0349864 A1 | 11/2014 | Kennedy et al. |
| 2014/0371096 A1 | 12/2014 | Umbricht et al. |
| 2015/0038376 A1 | 2/2015 | Tian et al. |
| 2015/0099665 A1 | 4/2015 | Rosenfeld et al. |
| 2015/0141470 A1 | 5/2015 | Garraway et al. |
| 2015/0275306 A1 | 10/2015 | Bernards et al. |
| 2015/0299808 A1 | 10/2015 | Gonzalez et al. |
| 2015/0307947 A1 | 10/2015 | Basu et al. |
| 2015/0329915 A1 | 11/2015 | Davicioni et al. |
| 2015/0368724 A1 | 12/2015 | Aharonov et al. |
| 2016/0024586 A1 | 1/2016 | Delfour et al. |
| 2016/0032400 A1 | 2/2016 | Gomis et al. |
| 2016/0068915 A1 | 3/2016 | Kennedy et al. |
| 2016/0115546 A1 | 4/2016 | Rosenfeld et al. |
| 2016/0120832 A1 | 5/2016 | Rabinowitz et al. |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2017/0016076 A1 | 1/2017 | Barnett-Itzhaki et al. |
| 2017/0145513 A1 | 5/2017 | Kennedy et al. |
| 2017/0145514 A1 | 5/2017 | Kennedy et al. |
| 2017/0166980 A1 | 6/2017 | Fahey, III et al. |
| 2018/0016642 A1 | 1/2018 | Kennedy et al. |
| 2018/0030540 A1 | 2/2018 | Davicioni et al. |
| 2018/0112275 A1 | 4/2018 | Davicioni et al. |
| 2018/0122508 A1 | 5/2018 | Wilde et al. |
| 2018/0349548 A1 | 12/2018 | Walsh et al. |

FOREIGN PATENT DOCUMENTS

| | | |
|---|---|---|
| EP | 0684315 A1 | 11/1995 |
| EP | 1975245 A1 | 10/2008 |

(56) References Cited

FOREIGN PATENT DOCUMENTS

| | | |
|---|---|---|
| EP | 1975252 A1 | 10/2008 |
| EP | 2231874 A2 | 9/2010 |
| EP | 2366800 A1 | 9/2011 |
| EP | 3360978 A2 | 8/2018 |
| JP | 2004526154 A | 8/2004 |
| JP | 2005168432 A | 6/2005 |
| JP | 2005304497 A | 11/2005 |
| JP | 2007513635 A | 5/2007 |
| JP | 2008545400 A | 12/2008 |
| JP | 2008545431 A | 12/2008 |
| WO | WO-9015070 A1 | 12/1990 |
| WO | WO-9210092 A1 | 6/1992 |
| WO | WO-9309668 A1 | 5/1993 |
| WO | WO-9322684 A1 | 11/1993 |
| WO | WO-9515331 A1 | 6/1995 |
| WO | WO-0120035 A2 | 3/2001 |
| WO | WO-2005005601 A2 | 1/2005 |
| WO | WO-2005085471 A2 | 9/2005 |
| WO | WO-2005100608 A2 | 10/2005 |
| WO | WO-2005005601 A3 | 4/2006 |
| WO | WO-2006047484 A2 | 5/2006 |
| WO | WO-2006062118 A1 | 6/2006 |
| WO | WO-2006127537 A2 | 11/2006 |
| WO | WO-2007038792 A2 | 4/2007 |
| WO | WO-2007038792 A3 | 11/2007 |
| WO | WO-2007126882 A2 | 11/2007 |
| WO | WO-2008104380 A2 | 9/2008 |
| WO | WO-2008119776 A1 | 10/2008 |
| WO | WO-2008104380 A3 | 11/2008 |
| WO | WO-2009020905 A2 | 2/2009 |
| WO | WO-2009026605 A2 | 3/2009 |
| WO | WO-2009029266 A2 | 3/2009 |
| WO | WO-2009037337 A1 | 3/2009 |
| WO | WO-2006127537 A3 | 4/2009 |
| WO | WO-2009042728 A1 | 4/2009 |
| WO | WO-2009068591 A2 | 6/2009 |
| WO | WO-2009079450 A2 | 6/2009 |
| WO | WO-2009126271 A1 | 10/2009 |
| WO | WO-2009143603 A1 | 12/2009 |
| WO | WO-2010018601 A2 | 2/2010 |
| WO | WO-2010056374 A2 | 5/2010 |
| WO | WO-2010073248 A2 | 7/2010 |
| WO | WO-2010056374 A3 | 9/2010 |
| WO | WO-2010073248 A3 | 9/2010 |
| WO | WO-2010099598 A1 | 9/2010 |
| WO | WO-2010123626 A1 | 10/2010 |
| WO | WO-2010124372 A1 | 11/2010 |
| WO | WO-2010127322 A1 | 11/2010 |
| WO | WO-2010129934 A2 | 11/2010 |
| WO | WO-2011079846 A2 | 7/2011 |
| WO | WO-2011143361 A2 | 11/2011 |
| WO | WO-2013063544 A1 | 5/2013 |
| WO | WO-2013086429 A2 | 6/2013 |
| WO | WO-2013086522 A1 | 6/2013 |
| WO | WO-2013088457 A1 | 6/2013 |
| WO | WO-2014043803 A1 | 3/2014 |
| WO | WO-2014151764 A2 | 9/2014 |
| WO | WO-2015071876 A2 | 5/2015 |
| WO | WO-2016141127 A1 | 9/2016 |
| WO | WO-2019023517 A2 | 1/2019 |

OTHER PUBLICATIONS

Wessels, et al., A protocol for building and evaluating predictors of disease state based on microarray data, Bioinformatics, 2005, 21:3755-3762.
Abratani, Hiroyuki. Characteristic Diagnosis of Cancer by Gene Expression Profiling. Personalized Diagnosis of Cancer by Gene Expression Profiling. English Translation. Journal of Clinical and Experimental Medicine (IGAKU NO AYUMI), Jun. 1, 2002, vol. 201, No. 9, p. 687-692.
Baloch, et al. Our approach to follicular-patterned lesions of the thyroid. J Clin Pathol. Mar. 2007;60(3):244-50. Epub Jun. 23, 2006.
Co-pending U.S. Appl. No. 15/618,656, filed Jun. 9, 2017.
Co-pending U.S. Appl. No. 15/661,496, filed Jul. 27, 2017.
Co-pending U.S. Appl. No. 15/702,126, filed Sep. 12, 2017.
GeneAnnot website. Probesets for KRAS. Printed Feb. 7, 2017. 2 pages.
GeneAnnot website. Probesets for PROS1. Printed Nov. 8, 2016. 1 page.
GeneAnnot website. Probesets for RXRG. Printed Nov. 8, 2016. 1 page.
Gombos, et al. Characterization of microarray gene expression profiles of early stage thyroid tumours. Cancer Genomics Proteomics. Nov.-Dec. 2007;4(6):403-9.
Irizarry, et al. Exploration, normalization, and summaries of high density oligonucleotide array probe level data. Biostatistics. Apr. 2003;4(2):249-64.
Ito, et al. Distant and lymph node metastases of thyroid nodules with no pathological evidence of malignancy: a limitation of pathological examination. Endocr J. Oct. 2008;55(5):889-94. Epub Jun. 14, 2008.
Kawai, et al. Recent Advances of DNA chip application. Latest Situation in DNA Chip Applications. English Translation. Protein Nucleic Acid and Enzyme, Aug. 1, 2000, vol. 45, No. 11, p. 47-53.
Marsh, et al. Genome-wide copy number imbalances identified in familial and sporadic medullary thyroid carcinoma. J Clin Endocrinol Metab. Apr. 2003;88(4):1866-72.
McCarroll, et al. Integrated detection and population-genetic analysis of SNPs and copy number variation. Nature Genetics 40, 1166-1174 (2008).
Mizukami, et al. Late bone metastasis from an encapsulated follicular carcinoma of the thyroid without capsular and vascular invasion. Pathol Int. Jun. 1996;46(6):457-61.
Notice of Allowance dated Aug. 21, 2017 for U.S. Appl. No. 15/274,492.
Office action dated Jan. 22, 2016 for U.S. Appl. No. 13/708,439.
Office action dated Feb. 4, 2014 for U.S. Appl. No. 13/708,439.
Office Action dated Feb. 13, 2017 for U.S. Appl. No. 15/164,241.
Office Action dated Mar. 9, 2017 for U.S. Appl. No. 13/710,134.
Office Action dated Mar. 21, 2017 for U.S. Appl. No. 15/164,217.
Office Action dated Mar. 21, 2017 for U.S. Appl. No. 15/164,230.
Office Action dated Mar. 23, 2017 for U.S. Appl. No. 15/164,220.
Office Action dated Mar. 23, 2017 for U.S. Appl. No. 15/274,492.
Office action dated Jun. 10, 2014 for U.S. Appl. No. 13/708,439.
Office Action dated Jun. 12, 2017 for U.S. Appl. No. 13/105,756.
Office Action dated Jun. 23, 2017 for U.S. Appl. No. 14/153,219.
Office Action dated Jul. 5, 2017 for U.S. Appl. No. 14/086,716.
Office Action dated Aug. 29, 2017 for U.S. Appl. No. 15/185,960.
Office action dated Sep. 8, 2016 for U.S. Appl. No. 15/164,241.
Office Action dated Oct. 12, 2017 for U.S. Appl. No. 13/589,022.
Office action dated Nov. 7, 2016 for U.S. Appl. No. 13/105,756.
Office action dated Nov. 17, 2016 for U.S. Appl. No. 13/589,022.
Office action dated Nov. 18, 2016 for U.S. Appl. No. 14/153,219.
Office action dated Nov. 30, 2016 for U.S. Appl. No. 13/708,439.
Penland, et al. RNA expression analysis of formalin-fixed paraffin-embedded tumors. Lab Invest. Apr. 2007;87(4):383-91.
Sapio, et al., Detection of RET/PTC, TRK and BRAF mutations in preoperative diagnosis of thyroid nodules with indeterminate cytological findings, C]Jnical Endocrjnology, 2007, 66: 678-683.
Terada. Brain metastasis from thyroid adenomatous nodules or an encapsulated thyroid follicular tumor without capsular and vascular invasion: a case report. Cases J. Jul. 17, 2009;2:7180. doi: 10.4076/1757-1626-2-7180.
Tzen, et al. Is atypical follicular adenoma of the thyroid a preinvasive malignancy? Hum Pathol. Jul. 2003;34(7):666-9.
Abrosimov et al. The cytoplasmic expression of MUC1 in papillary thyroid carcinoma of different histological variants and its correlation with cyclin D1 overexpression. Endocr Pathol. 2007;18(2):68-75.
Abubaker et al. Clinicopathological analysis of papillary thyroid cancer with PIK3CA alterations in a Middle Eastern population. J Clin Endocrinol Metab. 2008;93(2):611-8.
Adapt, The Peterson Institute for Cancer Research, probesets for ARSG, printed Jan. 10, 2013.

(56) References Cited

OTHER PUBLICATIONS

Adapt, The Peterson Institute for Cancer Research, probesets for FREM2, printed Jan. 10, 2013.
Adapt, The Peterson Institute for Cancer Research, probesets for GIMAP2, printed Jan. 10, 2013.
Adapt, The Peterson Institute for Cancer Research, probesets for HRASLS3, printed Jan. 10, 2013.
Adapt, The Peterson Institute for Cancer Research, probesets for PIGN, printed Jan. 10, 2013.
Adapt website. Paterson Institute for Cancer Research. Probesets for AUTS2. Printed Jul. 1, 2014. 2 pages.
Adapt website. Paterson Institute for Cancer Research. Probesets for FXYD6. Printed Jul. 1, 2014. 1 page.
Affymetrix: "Data Sheet Affymetrix(R) Genome-Wide Human SNP Array 6.0", 2007, pp. 1-4, XP002525407. Retrieved from the Internet: URL:http://www.affymetrix.com/support/technical/datasheets/genomewide_snp6_datasheet.pdf.
Affymetrix Technical Note: GeneChip® Gene 1.0 ST Array Design (created Sep. 5, 2007; downloaded from http://media.affymetrix.com/support/technical/technotes/gene_1_0_st_technote.pdf).
Affymetrix website for HG-U133A probe set list version 2004, Archived NetAffx Annotation Files (http://www.affymetrix.com/estore/catalog/131537/AFFY/Human+Genome+U133A+2.0+Array#1_3) printed Mar. 2015.
Afink, et al. Molecular characterization of iodotyrosine dehalogenase deficiency in patients with hypothyroidism. J Clin Endocrinol Metab. Dec. 2008;93(12):4894-901.
Aldred et al. Caveolin-1 and caveolin-2, together with three bone morphogenetic protein-related genes, may encode novel tumor suppressors down-regulated in sporadic follicular thyroid carcinogenesis. Cancer Res. 2003;63(11):2864-71.
Aldred et al. Papillary and follicular thyroid carcinomas show distinctly different microarray expression profiles and can be distinguished by a minimum of five genes. J Clin Oncol. 2004;22(17):3531-9.
Alexander, et al. Preoperative diagnosis of benign thyroid nodules with indeterminate cytology. N Engl J Med. Aug. 23, 2012;367(8):705-15. doi: 10.1056/NEJMoa1203208. Epub Jun. 25, 2012. with supplementary appendix.
Arnesen et al. Expression of N-acetyl transferase human and human Arrest defective 1 proteins in thyroid neoplasms. Thyroid. 2005;15(10):1131-6.
Bai et al. Mutational analysis of thyroid transcription factor-1 gene (TTF-1) in lung carcinomas. In Vitro Cell Dev Biol Anim. 2008;44(1-2):17-25.
Baldi; et al., "DNA microarrays and gene expression: from experiments to data analysis and modeling. Cambridge university press, 2002.".
Banito et al. Aneuploidy and RAS mutations are mutually exclusive events in the development of well-differentiated thyroid follicular tumours. Clin Endocrinol (Oxf). 2007;67(5):706-11.
Barden et al. Classification of follicular thyroid tumors by molecular signature: results of gene profiling. Clin Cancer Res. 2003;9(5):1792-800.
Baris et al. Transcriptional profiling reveals coordinated up-regulation of oxidative metabolism genes in thyroid oncocytic tumors. J Clin Endocrinol Metab. 2004;89(2):994-1005.
Bessarabova, et al. Bimodal gene expression patterns in breast cancer. BMC Genomics. Feb. 10, 2010;11 Suppl 1:S8. doi: 10.1186/1471-2164-11-S1-S8.
Bonora et al. Novel germline variants identified in the inner mitochondrial membrane transporter TIMM44 and their role in predisposition to oncocytic thyroid carcinomas. Br J Cancer. 2006;95(11):1529-36.
Boulesteix, et al. Evaluating microarray-based classifiers: an overview. Cancer Inform. 2008;6:77-97. Epub Feb. 29, 2008.
Brasseur et al. Papillary thyroid carcinoma in a 9-year-old girl with ataxia-telangiectasia. Pediatr Blood Cancer. 2008;50(5):1058-60.
Brozek et al. Thyroid cancer in two siblings with FAP syndrome and APC mutation. Int J Colorectal Dis. 2008;23(3):331-2.
Bugalho et al. Mutation analysis of the RET proto-oncogene and early thyroidectomy: results of a Portuguese cancer centre. Surgery. 2007;141(1):90-5.
Cameselle-Teijeiro et al. Follicular thyroid carcinoma with an unusual glomeruloid pattern of growth. Hum Pathol. 2008;39(10):1540-7.
Carda et al. Anaplastic carcinoma of the thyroid with rhabdomyosarcomatous differentiation: a report of two cases. Virchows Arch. 2005;446(1):46-51.
Castro et al. Adenomas and follicular carcinomas of the thyroid display two major patterns of chromosomal changes. J Pathol. 2005;206(3):305-11.
Castro et al.PAX8-PPARgamma rearrangement is frequently detected in the follicular variant of papillary thyroid carcinoma. J Clin Endocrinol Metab. 2006;91(1):213-20.
Cerutti et al. A preoperative diagnostic test that distinguishes benign from malignant thyroid carcinoma based on gene expression. J Clin Invest. 2004;113(8):1234-42.
Cerutti et al. Diagnosis of suspicious thyroid nodules using four protein biomarkers. Clin Cancer Res. 2006;12(11 Pt 1):3311-8.
Chan, et al. Integrating Transcriptomics and Proteomics. Drug Discovery and Development. Apr. 1, 2006. 4 pages. Published in G&P magazine 2006 vol. 6 No. 3 pp. 20-26.
Chen et al. Restricted kappa/lambda light chain ratio by flow cytometry in germinal center B cells in Hashimoto thyroiditis. Am J Clin Pathol. 2006;125(1):42-8.
Cheung, et al. Immunohistochemical diagnosis of papillary thyroid carcinoma. Mod Pathol. Apr. 2001;14(4):338-42.
Chevillard et al. Gene expression profiling of differentiated thyroid neoplasms: diagnostic and clinical implications. Clin Cancer Res. 2004;10(19):6586-97.
Chiappetta et al. The antiapoptotic protein BAG3 is expressed in thyroid carcinomas and modulates apoptosis mediated by tumor necrosis factor-related apoptosis-inducing ligand. J Clin Endocrinol Metab. 2007;92(3):1159-63.
Chudova, et al. Molecular classification of thyroid nodules using high-dimensionality genomic data. J Clin Endocrinol Metab. Dec. 2010;95(12):5296-304. doi: 10.1210/jc.2010-1087. Epub Sep. 8, 2010.
Chung et al. Detection of BRAFV600E mutation on fine needle aspiration specimens of thyroid nodule refines cyto-pathology diagnosis, especially in BRAF600E mutation-prevalent area. Clin Endocrinol (Oxf). 2006;65(5):660-6.
Ciampi et al. BRAF copy numbers gains in thyroid tumors detected by fluorescence in situ hybridization. Endocr Pathol. 2005;16(2):99-105.
Cibas, et al. The Bethesda System for Reporting Thyroid Cytopathology. Am J Clin Pathol. Nov. 2009;132(5):658-65. doi: 10.1309/AJCPPHLWMI3JV4LA.
Clark et al. Discovery of tissue-specific exons using comprehensive human exon microarrays. Genome Biol. 2007;8(4):R64.
Cohen et al. Mutational analysis of BRAF in fine needle aspiration biopsies of the thyroid: a potential application for the preoperative assessment of thyroid nodules. Clin Cancer Res. 2004;10(8):2761-5.
Combined search report and examination report dated Oct. 1, 2013 for GB Application No. 1315760.7.
Cooper, et al. Management guidelines for patients with thyroid nodules and differentiated thyroid cancer. Thyroid. Feb. 2006;16(2):109-42.
Crescioli et al. Methimazole inhibits CXC chemokine ligand 10 secretion in human thyrocytes. J Endocrinol. 2007;195(1):145-55.
De Lellis et al. The pathobiology of the human calcitonin (C)-cell: a review. Pathol Annu. 1981;16(Pt 2):25-52.
Del Senno et al. c-myc oncogene alterations in human thyroid carcinomas. Cancer Detect Prev. 1987;10(3-4):159-66.
Delellis et al. C-cell hyperplasia. An ultrastructural analysis. Lab Invest. 1977;36(3):237-48.
Derringer, et al. Malignant lymphoma of the thyroid gland: a clinicopathologic study of 108 cases. Am J Surg Pathol. May 2000;24(5):623-39.

(56) References Cited

OTHER PUBLICATIONS

Dettori et al. Aneuploidy in oncocytic lesions of the thyroid gland: diffuse accumulation of mitochondria within the cell is associated with trisomy 7 and progressive numerical chromosomal alterations. Genes Chromosomes Cancer. 2003;38(1):22-31.
Diaz-Uriarte et al. Gene selection and classification of microarray data using random forest. BMC Bioinformatics. 2006;7:3.
Druckenthaner et al. Evidence for Somatostatin receptor 2 in thyroid tissue. Regul Pept. 2007;138(1):32-9.
Durand et al. Evaluation of gene expression profiles in thyroid nodule biopsy material to diagnose thyroid cancer. J Clin Endocrinol Metab. 2008;93(4):1195-202.
Durante, et al. BRAF mutations in papillary thyroid carcinomas inhibit genes involved in iodine metabolism. J Clin Endocrinol Metab. Jul. 2007;92(7):2840-3. Epub May 8, 2007.
Elisei et al. RET genetic screening in patients with medullary thyroid cancer and their relatives: experience with 807 individuals at one center. J Clin Endocrinol Metab. 2007;92(12):4725-9.
Erdogan et al. The prevalence of RET/PTC mutations in papillary thyroid cancers in Turkish population and its relation between tumor histopathology and prognostic factors. Exp Clin Endocrinol Diabetes. 2008;116(4):225-30.
Esperante, et al. Identification and characterization of four PAX8 rare sequence variants (p. T225M, p. L233L, p. G336S and p. A439A) in patients with congenital hypothyroidism and dysgenetic thyroid glands. Clin Endocrinol (Oxf). May 2008;68(5):828-35.
Eszlinger et al. Gene expression analysis reveals evidence for inactivation of the TGF-beta signaling cascade in autonomously functioning thyroid nodules. Oncogene. 2004;23(3):795-804.
Eszlinger et al. Meta- and reanalysis of gene expression profiles of hot and cold thyroid nodules and papillary thyroid carcinoma for gene groups. J Clin Endocrinol Metab. 2006;91(5):1934-42.
Eszlinger et al. Perspectives and limitations of microarray-based gene expression profiling of thyroid tumors. Endocr Rev. 2007;28(3):322-38.
Eszlinger, et al. Perspectives for Improved and More Accurate Classification of Thyroid Epithelial Tumors. J Clin Endocrinol Metab. Sep. 2008;93(9):3286-94. Epub Jul. 1, 2008.
European search report and opinion dated Mar. 5, 2014 for EP Application No. 11781242.0.
European search report and opinion dated Apr. 28, 2016 for EP 16153243.7.
European search report and search opinion dated Jan. 28, 2013 for Application No. 10772919.6.
European search report and search opinion dated Nov. 27, 2012 for Application No. 09826462.5.
Ferrari, et al. An approach to estimate between- and within-group correlation coefficients in multicenter studies: plasma carotenoids as biomarkers of intake of fruits and vegetables. Am J Epidemiol. Sep. 15, 2005;162(6):591-8. Epub Aug. 10, 2005.
Finley et al. Advancing the molecular diagnosis of thyroid nodules: defining benign lesions by molecular profiling. Thyroid. 2005;15(6):562-8.
Finley et al. Discrimination of benign and malignant thyroid nodules by molecular profiling. Ann Surg. 2004;240(3):425-36; discussion 436-7.
Finley et al. Molecular analysis of Hurthle cell neoplasms by gene profiling. Surgery. 2004;136(6):1160-8.
Finley et al. Molecular profiling distinguishes papillary carcinoma from benign thyroid nodules. J Clin Endocrinol Metab. 2004;89(7):3214-23.
Finn, et al. Expression microarray analysis of papillary thyroid carcinoma and benign thyroid tissue: emphasis on the follicular variant and potential markers of malignancy. Virchows Arch. Mar. 2007;450(3):249-60.
Fishel, et al. Meta-analysis of gene expression data: a predictor-based approach. Bioinformatics. Jul. 1, 2007;23(13):1599-606. Epub Apr. 26, 2007.
Fontaine et al. Microarray analysis refines classification of non-medullary thyroid tumours of uncertain malignancy. Oncogene. 2008;27(15):2228-36.
Foppiani et al. Uncommon association of germline mutations of RET proto-oncogene and CDKN2A gene. Eur J Endocrinol. 2008;158(3):417-22.
Frattini, et al. Alternative mutations of BRAF, RET and NTRK1 are associated with similar but distinct gene expression patterns in papillary thyroid cancer. Oncogene. Sep. 23, 2004;23(44):7436-40.
Fryknas et al. Molecular markers for discrimination of benign and malignant follicular thyroid tumors. Tumour Biol. 2006;27(4):211-20.
Fujarewicz, et al. A multi-gene approach to differentiate papillary thyroid carcinoma from benign lesions: gene selection using support vector machines with bootstrapping. Endocr Relat Cancer. Sep. 2007;14(3):809-26.
Garcia-Lopez et al. Thyrocytes from autoimmune thyroid disorders produce the chemokines IP-10 and Mig and attract CXCR3+ lymphocytes. J Clin Endocrinol Metab. 2001;86(10):5008-16.
Gardina et al. Alternative splicing and differential gene expression in colon cancer detected by a whole genome exon array. BMC Genomics. 2006;7:325.
Gasparre et al. Disruptive mitochondrial DNA mutations in complex I subunits are markers of oncocytic phenotype in thyroid tumors. Proc Natl Acad Sci USA. 2007;104(21):9001-6.
"Gene Annot Website. Array Probesets for HOMER2, printed Jan. 2016.".
GeneAnnot website. Probesets for AKT1. Printed Aug. 30, 2016. 1 page.
GeneAnnot website. Probesets for ALK. Printed Aug. 30, 2016. 1 page.
GeneAnnot website. Probesets for BRAF. Printed Aug. 30, 2016. 1 page.
GeneAnnot website. Probesets for CALCA. Printed Aug. 30, 2016. 1 page.
GeneAnnot website. Probesets for CTNNB1. Printed Aug. 30, 2016.1 page.
GeneAnnot website. Probesets for EIF1AY. Printed Aug. 30, 2016. 1 page.
GeneAnnot website. Probesets for IGF2BP2. Printed Aug. 30, 2016. 1 page.
GeneAnnot website. Probesets for KRT7. Printed Aug. 30, 2016. 1 page.
GeneAnnot website. Probesets for MET. Printed Aug. 30, 2016. 1 page.
GeneAnnot website. Probesets for NTRK2. Printed Aug. 30, 2016. 1 page.
GeneAnnot website. Probesets for NTRK3. Printed Aug. 30, 2016. 2 pages.
GeneAnnot website. Probesets for PIK3CA. Printed Aug. 30, 2016. 1 page.
GeneAnnot website. Probesets for PPARGC1A. Printed Aug. 30, 2016. 1 page.
GeneAnnot website. Probesets for PTEN. Printed Aug. 30, 2016. 2 pages.
GeneAnnot website. Probesets for PTH. Printed Aug. 30, 2016. 1 page.
GeneAnnot website. Probesets for RASA1. Printed Aug. 30, 2016. 1 page.
GeneAnnot website. Probesets for RET. Printed Aug. 30, 2016. 1 page.
GeneAnnot website. Probesets for TP53. Printed Aug. 30, 2016. 1 page.
GeneAnnot website. Probesets for TSHR. Printed Aug. 30, 2016. 1 page.
GeneAnnot website. Probesets for TTF1. Printed Aug. 30, 2016. 1 page.
Gereben et al. Pretranslational regulation of type 2 deiodinase. Thyroid. 2005;15(8):855-64.
Giordano et al. Delineation, functional validation, and bioinformatic evaluation of gene expression in thyroid follicular carcinomas with the PAX8-PPARG translocation. Clin Cancer Res. 2006;12(7 Pt 1):1983-93.

(56) References Cited

OTHER PUBLICATIONS

Giordano et al. Distinct transcriptional profiles of adrenocortical tumors uncovered by DNA microarray analysis. Am J Pathol. 2003;162(2):521-31.
Giordano et al. Molecular classification of papillary thyroid carcinoma: distinct BRAF, RAS, and RET/PTC mutation-specific gene expression profiles discovered by DNA microarray analysis. Oncogene. 2005;24(44):6646-56.
Giordano et al. Organ-specific molecular classification of primary lung, colon, and ovarian adenocarcinomas using gene expression profiles. Am J Pathol. 2001;159(4):1231-8.
Giordano. Genome-wide studies in thyroid neoplasia. Endocrinol Metab Clin North Am. 2008;37(2):311-31, vii-viii.
Gonzalez-Campora et al. Blood group antigens in differentiated thyroid neoplasms. Arch Pathol Lab Med. 1998;122(11):957-65.
Gould et al. (1987). Synaptophysin expression in neuroendocrine neoplasms as determined by immunocytochemistry. Am J Pathol. 126(2):243-57.
Greenbaum, et al. Comparing protein abundance and mRNA expression levels on a genomic scale. Genome Biol. 2003;4(9):117. Epub Aug. 29, 2003.
Greenbaum, et al. Interrelating different types of genomic data, from proteome to secretome: 'oming in on function. Genome Res. Sep. 2001;11(9):1463-8.
Griffith et al. Meta-analysis and meta-review of thyroid cancer gene expression profiling studies identifies important diagnostic biomarkers. J Clin Oncol. 2006;24(31):5043-51.
Hadd, et al. Targeted, high-depth, next-generation sequencing of cancer genes in formalin-fixed, paraffin-embedded and fine-needle aspiration tumor specimens. J Mol Diagn. Mar. 2013;15(2):234-47. doi: 10.1016/j.jmoldx.2012.11.006. Epub Jan. 13, 2013.
Harach et al. Histology of familial thyroid tumours linked to a gene mapping to chromosome 19p13.2. J Pathol. 1999;189(3):387-93.
Hartigan, et al. The dip test of unimodality. Annals of Statistics. 1985; 13(1):70-84.
Haugen, et al. Development of a novel molecular classifier to accurately identify benign thyroid nodules in patients with indeterminate FNA cytology. Abstract presented at 14th International Thyroid Congress. Sep. 15, 2010.
Haugen et al. Increased expression of genes encoding mitochondrial proteins in papillary thyroid carcinomas. Thyroid. 2003;13(7):613-20.
Hawthorn, et al. TIMP1 and SERPIN-A overexpression and TFF3 and CRABP1 underexpression as biomarkers for papillary thyroid carcinoma. Head Neck. Dec. 2004;26(12):1069-83.
He, et al. A susceptibility locus for papillary thyroid carcinoma on chromosome 8q24. Cancer Res. Jan. 15, 2009;69(2):625-31.
He et al. The role of microRNA genes in papillary thyroid carcinoma. Proc Natl Acad Sci USA. 2005;102(52):19075-80.
Hellwig, et al. Comparison of scores for bimodality of gene expression distributions and genome-wide evaluation of the prognostic relevance of high-scoring genes. BMC Bioinformatics. May 25, 2010;11:276. doi: 10.1186/1471-2105-11-276.
Hemmer et al. Comparison of benign and malignant follicular thyroid tumours by comparative genomic hybridization. Br J Cancer. 1998;78(8):1012-7.
Hemmer, et al. DNA copy number changes in thyroid carcinoma. Am J Pathol. May 1999;154(5):1539-47.
Heuer et al. Different cytokine mRNA profiles in Graves' disease, Hashimoto's thyroiditis, and nonautoimmune thyroid disorders determined by quantitative reverse transcriptase polymerase chain reaction (RT-PCR). Thyroid. 1996;6(2):97-106.
Holden et al. Tyrosine kinase activating mutations in human malignancies: implications for diagnostic pathology. Exp Mol Pathol. 2008; 85(1):68-75.
Hoshikawa, et al. Hypoxia induces different genes in the lungs of rats compared with mice. Physiol Genomics. Feb. 6, 2003;12(3):209-19.
Hou et al. Genetic alterations and their relationship in the phosphatidylinositol 3-kinase/Akt pathway in thyroid cancer. Clin Cancer Res. 2007;13(4):1161-70.
Hsu et al. Characterization of a novel tripartite nuclear localization sequence in the EGFR family. J Biol Chem. 2007;282(14):10432-40.
Huang et al. A genome-wide approach to identify genetic variants that contribute to etoposide-induced cytotoxicity. Proc Natl Acad Sci USA. 2007;104(23):9758-63.
Huang et al. Gene expression in papillary thyroid carcinoma reveals highly consistent profiles. Proc Natl Acad Sci USA. 2001;98(26):15044-9.
Hunt, et al. A microdissection and molecular genotyping assay to confirm the identity of tissue floaters in paraffin-embedded tissue blocks Arch Pathol Lab Med. 2003; 127(2):213-217.
Inaji et al. Demonstration and diagnostic significance of pro-gastrin-releasing peptide in medullary thyroid carcinoma. Oncology. 2000;59(2):122-5.
International search report and written opinion dated Jan. 19, 2012 for PCT Application No. US2011/36143.
International search report and written opinion dated Feb. 25, 2011 for PCT Application No. US2010/034140.
International search report and written opinion dated Feb. 25, 2013 for PCT Application No. US2012/068804.
International search report and written opinion dated Apr. 17, 2015 for PCT/US2014/026411.
International search report and written opinion dated May 8, 2013 for PCT Application No. US2012/068587.
International search report dated Jul. 29, 2010 for PCT Application No. US2009/06162.
Ito et al. Simultaneous expression of keratan sulphate epitope (a sulphated poly-N-acetyllactosamine) and blood group ABH antigens in papillary carcinomas of the human thyroid gland. Histochem J. 1996;28(9):613-23.
Jacques et al. Two-step differential expression analysis reveals a new set of genes involved in thyroid oncocytic tumors. J Clin Endocrinol Metab. 2005;90(4):2314-20.
Jarzab et al. Gene Expression Profile of Papillary Thyroid Cancer: Sources of Variability and Diagnostic Implications. Cancer Res. 2005;65(4):1587-1597.
Jazdzewski et al. Common SNP in pre-miR-146a decreases mature miR expression and predisposes to papillary thyroid carcinoma. Proc Natl Acad Sci USA. 2008;105(20):7269-74.
Jo, et al. Influence of the BRAF V600E mutation on expression of vascular endothelial growth factor in papillary thyroid cancer. J Clin Endocrinol Metab. Sep. 2006;91(9):3667-70. Epub Jun. 13, 2006.
Johansson, et al. Confirmation of a BRAF mutation-associated gene expression signature in melanoma. Pigment Cell Res. Jun. 2007;20(3):216-21.
Joseph et al. Lack of mutations in the thyroid hormone receptor (TR) alpha and beta genes but frequent hypermethylation of the TRbeta gene in differentiated thyroid tumors. J Clin Endocrinol Metab. 2007;92(12):4766-70.
Jovanovic et al. Most multifocal papillary thyroid carcinomas acquire genetic and morphotype diversity through subclonal evolution following the intra-glandular spread of the initial neoplastic clone. J Pathol. 2008;215(2):145-54.
Kakudo et al. Immunohistochemical study of substance P-like immunoreactivity in human thyroid and medullary carcinoma of the thyroid. J Submicrosc Cytol. 1983;15(2):563-8.
Kang et al. High prevalence of RET, RAS, and ERK expression in Hashimoto's thyroiditis and in papillary thyroid carcinoma in the Korean population. Thyroid. 2007;17(11):1031-8.
Kannengiesser, et al. Gene expression signature associated with BRAF mutations in human primary cutaneous melanomas. Mol Oncol. Apr. 1, 2008 (4):425-30. doi: 10.1016/j.molonc.2008.01.002. Epub Jan. 12, 2008.
Kapadia, et al. Malignant lymphoma of the thyroid gland: a clinicopathologic study. Head Neck Surg. Mar.-Apr. 1982;4(4):270-80.

(56) References Cited

OTHER PUBLICATIONS

Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.
Katoh et al. Thyroid transcription factor-1 in normal, hyperplastic, and neoplastic follicular thyroid cells examined by immunohistochemistry and nonradioactive in situ hybridization. Mod Pathol. 2000;13(5):570-6.
Kebebew et al. Diagnostic and extent of disease multigene assay for malignant thyroid neoplasms. Cancer. 2006;106(12):2592-7.
Kebebew et al. Diagnostic and prognostic value of angiogenesis-modulating genes in malignant thyroid neoplasms. Surgery. Dec. 2005;138(6):1102-9; discussion 1109-10.
Kebebew, et al. The prevalence and prognostic value of BRAF mutation in thyroid cancer. Ann Surg. Sep. 2007;246(3):466-70; discussion 470-1.
Krause, et al. Characterisation of DENAL1 expression in thyroid pathologies. Eur J Endocrinol. Mar. 2007;156(3):295-301.
Krawczak, et al. The mutational spectrum of single base-pair substitutions in mRNA splice junctions of human genes: causes and consequences. Hum Genet. Sep.-Oct. 1992;90(1-2):41-54.
Kreula, et al. Sample size in fine needle aspiration biopsy. Br J Surg. Dec. 1989;76(12):1270-2.
Kristensen, et al. Genetic variation in putative regulatory loci controlling gene expression in breast cancer. Proc Natl Acad Sci U S A. May 16, 2006;103(20):7735-40. Epub May 9, 2006.
Kroese, et al. Genetic tests and their evaluation: can we answer the key questions? Genet Med. Nov.-Dec. 2004;6(6):475-80.
Kwan, et al. Heritability of alternative splicing in the human genome. Genome Res. Aug. 2007;17(8):1210-8.
Lacroix, et al. PAX8 and peroxisome proliferator-activated receptor gamma 1 gene expression status in benign and malignant thyroid tissues. Eur J Endocrinol. Sep. 2004;151(3):367-74.
Lau et al. Thyroid transcription factor-1: a review. Appl Immunohistochem Mol Morphol. 2002;10(2):97-102.
Lauter et al. Mutational analysis of CDKN1B, a candidate tumor-suppressor gene, in refractory secondary/tertiary hyperparathyroidism. Kidney Int. 2008;73(10):1137-40.
Lima et al. Thyroid Peroxidase and Thyroglobulin Expression in Normal Human Thyroid Glands. Endocr Pathol. 1998;9(1):333-338.
Lin et al. Expression of sodium iodide symporter in benign and malignant human thyroid tissues. Endocr Pathol. 2001;12(1):15-21.
Lin, et al. Thyroid ultrasonography with fine-needle aspiration cytology for the diagnosis of thyroid cancer. J Clin Ultrasound. Mar.-Apr. 1997;25(3):111-8.
Liu et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. 2008;93(8):3106-16.
Lubitz et al. 2006;Microarray analysis of thyroid nodule fine-needle aspirates accurately classifies benign and malignant lesions. J Mol Diagn. 8(4):490-8; quiz 528.
Lubitz et al. Molecular analysis of minimally invasive follicular carcinomas by gene profiling. Surgery. 2005;138(6):1042-8; discussion 1048-9.
Lucentini. Gene association studies typically wrong. The Scientist. 2004; 18(24):20.
Lui et al. 2008;CREB3L2-PPARgamma fusion mutation identifies a thyroid signaling pathway regulated by intramembrane proteolysis. Cancer Res. 68(17):7156-64.
Machens et al. Genotype-phenotype based surgical concept of hereditary medullary thyroid carcinoma. World J Surg. 2007;31(5):957-68.
Masini-Repiso et al. Ultrastructural localization of thyroid peroxidase, hydrogen peroxide-generating sites, and monoamine oxidase in benign and malignant thyroid diseases. Hum Pathol. 2004; 35(4):436-46.

Mason, et al. Bimodal distribution of RNA expression levels in human skeletal muscle tissue. BMC Genomics. Feb. 7, 2011;12:98. doi: 10.1186/1471-2164-12-98.
Matsubayashi et al. Gastrin-releasing peptide immunoreactivity in medullary thyroid carcinoma. Cancer. 1984;53(11):2472-7.
Maximo et al. Somatic and germline mutation in GRIM-19, a dual function gene involved in mitochondrial metabolism and cell death, is linked to mitochondrion-rich (Hurthle cell) tumours of the thyroid. Br J Cancer. 2005;92(10):1892-8.
Mazzanti, et al. Using gene expression profiling to differentiate benign versus malignant thyroid tumors. Cancer Res. Apr. 15, 2004;64(8):2898-903.
Mitomo et al. Downregulation of miR-138 is associated with overexpression of human telomerase reverse transcriptase protein in human anaplastic thyroid carcinoma cell lines. Cancer Sci. 2008;99(2):280-6.
Montero-Conde et al. Molecular profiling related to poor prognosis in thyroid carcinoma. Combining gene expression data and biological information. Oncogene. 2008;27(11):1554-61.
Moreno, et al. Mutations in the iodotyrosine deiodinase gene and hypothyroidism. N Engl J Med. Apr. 24, 2008;358(17):1811-8. doi: 10.1056/NEJMoa0706819.
Murphy et al. Identification of immunohistochemical biomarkers for papillary thyroid carcinoma using gene expression profiling. Hum Pathol. 2008;39(3):420-6.
Nakano et al. Apoptosis-induced decrease of intrathyroidal CD4(+)CD25(+) regulatory T cells in autoimmune thyroid diseases. Thyroid. 2007;17(1):25-31.
Nakashima et al. Foci formation of P53-binding protein 1 in thyroid tumors: activation of genomic instability during thyroid carcinogenesis. Int J Cancer. 2008;122(5):1082-8.
Nakashima et al. RET oncogene amplification in thyroid cancer: correlations with radiation-associated and high-grade malignancy. Hum Pathol. 2007;38(4):621-8.
Nakayama et al. High molecular weight caldesmon positive stromal cells in the capsule of thyroid follicular tumours and tumour-like lesions. J Clin Pathol. 2002;55(12):917-20.
Nam, et al. BRAF V600E mutation analysis of thyroid nodules needle aspirates in relation to their ultrasongraphic classification: a potential guide for selection of samples for molecular analysis. Thyroid. Mar. 2010;20(3):273-9. doi: 10.1089/thy.2009.0226.
National Cancer Institute web page: "Common Cancer Types", captured by WayBack machine on Dec. 4, 2011, http://www.cancer.gov/cancertopics/types/commoncancers.
Neonakis et al. Expression of calcitonin and somatostatin peptide and mRNA in medullary thyroid carcinoma. World J Surg. 1994;18(4):588-93.
Nikiforova et al. MicroRNA expression profiling of thyroid tumors: biological significance and diagnostic utility. J Clin Endocrinol Metab. 2008;93(5):1600-8.
Nikolova et al. Genome-wide gene expression profiles of thyroid carcinoma: Identification of molecular targets for treatment of thyroid carcinoma. 2008;Oncol Rep. 20(1):105-21.
Notice of allowance dated Jun. 13, 2013 for U.S. Appl. No. 12/592,065.
Notice of allowance dated Sep. 13, 2016 for U.S. Appl. No. 12/964,666.
Notice of allowance dated Oct. 18, 2013 for U.S. Appl. No. 13/318,751.
Nucera, et al. BRAF(V600E) mutation and the biology of papillary thyroid cancer. Endocr Relat Cancer. Mar. 2008;15(1):191-205. doi: 10.1677/ERC-07-0212.
Oerntoft, et al. Genome-wide study of gene copy numbers, transcripts, and protein levels in pairs of non-invasive and invasive human transitional cell carcinomas. Mol Cell Proteomics. Jan. 2002;1(1):37-45.
Office action dated Jan. 5, 2015 for U.S. Appl. No. 14/086,716.
Office action dated Jan. 16, 2013 for U.S. Appl. No. 12/592,065.
Office action dated Feb. 27, 2015 for U.S. Appl. No. 13/710,134.
Office action dated Mar. 9, 2016 for U.S. Appl. No. 13/589,022.
Office action dated Mar. 23, 2015 for U.S. Appl. No. 13/589,022.
Office action dated Apr. 6, 2012 for U.S. Appl. No. 12/964,666.
Office action dated Apr. 18, 2013 for U.S. Appl. No. 13/318,751.

(56) References Cited

OTHER PUBLICATIONS

Office action dated Apr. 27, 2015 for U.S. Appl. No. 12/964,666.
Office action dated May 8, 2014 for U.S. Appl. No. 13/105,756.
Office action dated May 9, 2016 for U.S. Appl. No. 12/964,666.
Office action dated May 16, 2016 for U.S. Appl. No. 14/153,219.
Office action dated May 27, 2015 for U.S. Appl. No. 13/105,756.
Office action dated Jun. 6, 2012 for U.S. Appl. No. 12/592,065.
Office action dated Jun. 20, 2014 for U.S. Appl. No. 12/964,666.
Office action dated Jul. 6, 2011 for U.S. Appl. No. 12/964,666.
Office action dated Jul. 10, 2014 for U.S. Appl. No. 13/589,022.
Office action dated Jul. 26, 2016 for U.S. Appl. No. 13/710,134.
Office action dated Jul. 30, 2014 for U.S. Appl. No. 13/710,134.
Office action dated Aug. 10, 2016 for U.S. Appl. No. 14/086,716.
"Office action dated Sep. 2, 2015 for U.S. Appl. No. 14/086,716.".
Office action dated Sep. 11, 2012 for U.S. Appl. No. 13/318,751.
Office action dated Sep. 19, 2016 for U.S. Appl. No. 15/164,217.
Office action dated Sep. 19, 2016 for U.S. Appl. No. 15/164,220.
Office action dated Sep. 19, 2016 for U.S. Appl. No. 15/164,230.
Office action dated Oct. 17, 2013 for U.S. Appl. No. 13/105,756.
Office action dated Nov. 19, 2015 for U.S. Appl. No. 13/710,134.
Office action dated Nov. 29, 2013 for U.S. Appl. No. 13/710,134.
"Office action dated Dec. 17, 2015 for U.S. Appl. No. 13/105,756.".
Oler, et al. Gene expression profiling of papillary thyroid carcinoma identifies transcripts correlated with BRAF mutational status and lymph node metastasis. Clin Cancer Res. Aug. 1, 2008;14(15):4735-42. doi: 10.1158/1078-0432.CCR-07-4372.
Owens, et al. Metastatic breast carcinoma involving the thyroid gland diagnosed by fine-needle aspiration: a case report. Diagn Cytopathol. Aug. 2005;33(2):110-5.
Pallante et al. MicroRNA deregulation in human thyroid papillary carcinomas. Endocr Relat Cancer. 2006;13(2):497-508.
Panicker et al. A common variation in deiodinase 1 gene DIO1 is associated with the relative levels of free thyroxine and triiodothyronine. J Clin Endocrinol Metab. 2008;93(8):3075-81.
Pavelic, et al. Molecular genetic alterations of FHIT and p53 genes in benign and malignant thyroid gland lesions. Mutat Res. Jul. 25, 2006;599(1-2):45-57. Epub May 15, 2006.
Pavey, et al. Microarray expression profiling in melanoma reveals a BRAF mutation signature. Oncogene. May 20, 2004;23(23):4060-7.
Phenekos et al. Th1 and Th2 serum cytokine profiles characterize patients with Hashimoto's thyroiditis (Th1) and Graves' disease (Th2). Neuroimmunomodulation. 2004;11(4):209-13.
Pinto et al. mRNA expression of tachykinins and tachykinin receptors in different human tissues. Eur J Pharmacol. 2004;494(2-3):233-9.
Pita et al. Gene expression profiling associated with the progression to poorly differentiated thyroid carcinomas. Br J Cancer. 2009;101(10):1782-1791.
Prasad et al. Identification of genes differentially expressed in benign versus malignant thyroid tumors. Clin Cancer Res. 2008;14(11):3327-37.
Puskas, et al. Gene profiling identifies genes specific for well-differentiated epithelial thyroid tumors. Cell Mol Biol (Noisy-le-grand). Sep. 5, 2005 Sep 5;51(2):177-86.
Qian, et al. Renal cell carcinoma metastatic to Hurthle cell adenoma of thyroid. Ann Diagn Pathol. Oct. 2004;8(5):305-8.
Ramzy; Ibrahim., "Clinical cytopathology and aspiration biopsy: Fundamental principles and practice. McGraw Hill Professional, 2001.".
Reyes, et al. Identification of kallikrein 7, kallikrein 10 and secreted frizzled-related protein 2 as candidate molecular markers for papillary thyroid carcinoma using microarray analysis. Proc Amer Assoc Cancer Res. 2005, vol. 46, Abstract #38.
Ringel et al. Expression of the sodium iodide symporter and thyroglobulin genes are reduced in papillary thyroid cancer. Mod Pathol. 2001;14(4):289-96.
Robinson; et al., "A comparison of Affymetrix gene expression arrays. BMC bioinformatics 8.1 (2007): 449.".

Rodrigues-Serpa, et al. Loss of heterozygosity in follicular and papillary thyroid carcinomas. Cancer Genet Cytogenet. Feb. 2003;141(1):26-31.
Roque, et al. Chromosome imbalances in thyroid follicular neoplasms: a comparison between follicular adenomas and carcinomas. Genes Chromosomes Cancer. Mar. 2003;36(3):292-302.
Rosai et al. Pitfalls in the diagnosis of thyroid neoplasms. Pathol Res Pract. 1987;182(2):169-79.
Rosen et al. A six-gene model for differentiating benign from malignant thyroid tumors on the basis of gene expression. Surgery. 2005;138(6):1050-6; discussion 1056-7.
Roura-Mir et al. Single-cell analysis of intrathyroidal lymphocytes shows differential cytokine expression in Hashimoto's and Graves' disease. Eur J Immunol. 1997;27(12):3290-302.
Saeys, et al. A review of feature selection techniques in bioinformatics. Bioinformatics. Oct. 1, 2007;23(19):2507-17. Epub Aug. 24, 2007.
Saiz et al. Immunohistochemical expression of cyclin D1, E2F-1, and Ki-67 in benign and malignant thyroid lesions. J Pathol. 2002;198(2):157-62.
Salvatore et al. A cell proliferation and chromosomal instability signature in anaplastic thyroid carcinoma. Cancer Res. 2007;67(21):10148-58.
Sambrook; et al., "Molecular Cloning: A Laboratory Manual. Second edition, Cold Spring Harbor Laboratory Press, 1989.".
Santarpia et al. Phosphatidylinositol 3-kinase/akt and ras/raf-mitogen-activated protein kinase pathway mutations in anaplastic thyroid cancer. J Clin Endocrinol Metab. 2008;93(1):278-84.
Satake et al. Overview of the primary structure, tissue-distribution, and functions of tachykinins and their receptors. Curr Drug Targets. 2006;7(8):963-74.
Savagner et al. Defective mitochondrial ATP synthesis in oxyphilic thyroid tumors. J Clin Endocrinol Metab. 2001;86(10):4920-5.
Savagner et al. PGC-1-related coactivator and targets are upregulated in thyroid oncocytoma. Biochem Biophys Res Commun. 2003;310(3):779-84.
Schiff, et al. Epidermal growth factor receptor (EGFR) is overexpressed in anaplastic thyroid cancer, and the EGFR inhibitor gefitinib inhibits the growth of anaplastic thyroid cancer. Clin Cancer Res. Dec. 15, 2004;10(24):8594-602.
Sheu et al. The C allele of the GNB3 C825T polymorphism of the G protein beta3-subunit is associated with an increased risk for the development of oncocytic thyroid tumours. J Pathol. 2007;211(1):60-6.
Shirasawa, S. Susceptibility genes for the development of autoimmune thyroid disease. Nippon Rinsho. Dec. 2006;64(12):2208-14. (Abstract only).
Shvero et al. Immunohistochemical profile and treatment of uncommon types of thyroid carcinomas. Oncol Rep. 2003;10(6):2075-8.
Singh et al. Screening for genetic aberrations in papillary thyroid cancer by using comparative genomic hybridization. Surgery. 2000;128(6):888-93;discussion 893-4.
Siragusa et al. MUC1 oncoprotein promotes refractoriness to chemotherapy in thyroid cancer cells. Cancer Res. 2007;67(11):5522-30.
Smith et al. Methylation status of genes in papillary thyroid carcinoma. Arch Otolaryngol Head Neck Surg. 2007;133(10):1006-11.
Smyth. Linear models and empirical bayes methods for assessing differential expression in microarray experiments. Stat Appl Genet Mol Biol. 2004;3:Article3. Epub Feb. 12, 2004.
Stanta et al. The biochemical and immunohistochemical profile of thyroid neoplasia. Pathol Annu. 1988;23 Pt 1: 129-57.
Subramaniam et al. Clonal characterization of sporadic cribriform-morular variant of papillary thyroid carcinoma by laser microdissection-based APC mutation analysis. Am J Clin Pathol. 2007;128(6):994-1001.
Symmans, et al. Total RNA Yield and Microarray Gene Expression Profiles from Fine-Needle Aspiration Biopsy and Core-Needle Biopsy Samples of Breast Carcinoma. 2003; Cancer 97(12):2960-2971.
Takakura et al. Oncogenic role of miR-17-92 cluster in anaplastic thyroid cancer cells. Cancer Sci. 2008;99(6):1147-54.

(56) References Cited

OTHER PUBLICATIONS

Takano et al. Expression of oncofetal fibronectin messenger ribonucleic acid in fibroblasts in the thyroid: a possible cause of false positive results in molecular-based diagnosis of thyroid carcinomas. J Clin Endocrinol Metab. 2000;85(2):765-8.
Takano et al. Preoperative diagnosis of thyroid papillary and anaplastic carcinomas by real-time quantitative reverse transcription-polymerase chain reaction of oncofetal fibronectin messenger RNA. Cancer Res. 1999;59(18):4542-5.
Tamir et al. Expression and development of a functional plasmalemmal 5-hydroxytryptamine transporter by thyroid follicular cells. Endocrinology. 1996;137(10):4475-86.
Taniguchi et al. Differentiation of follicular thyroid adenoma from carcinoma by means of gene expression profiling with adapter-tagged competitive polymerase chain reaction. Oncology. 2005;69(5):428-35.
Tetzlaff et al. Differential expression of miRNAs in papillary thyroid carcinoma compared to multinodular goiter using formalin fixed paraffin embedded tissues. Endocr Pathol. 2007;18(3):163-73.
Thompson et al. Primary smooth muscle tumors of the thyroid gland. Cancer. 1997;79(3):579-87.
Tian, et al. A combined oncogenic pathway signature of BRAF, KRAS and PI3KCA mutation improves colorectal cancer classification and cetuximab treatment prediction. Gut. Apr. 2013;62(4):540-9. doi: 10.1136/gutjnl-2012-302423. Epub Jul. 14, 2012.
Tian, et al. Effects of Gender on Gene Expression in the Blood of Ischemic Stroke Patients. Journal of Cerebral Blood Flow & Metabolism. J Cereb Blood Flow Metab. May 2012;32(5):780-91. doi: 10.1038/jcbfm.2011.179. Epub Dec. 14, 2011.
Todaro et al. Autocrine production of interleukin-4 and interleukin-10 is required for survival and growth of thyroid cancer cells. Cancer Res. 2006;66(3):1491-9.
Ueda, et al. Analysis of PAX8 Gene in Congenital Hypothyroidism Mass Screening Positive Subjects. Folia Endocrinologica Japonica. Mar. 30, 2007, vol. 82, No. 4, p. 859. (in Japanese with English translation).
Unger et al. Array CGH demonstrates characteristic aberration signatures in human papillary thyroid carcinomas governed by RET/PTC. Oncogene. 2008;27(33):4592-602.
U.S. Appl. No. 12/964,666, filed Dec. 9, 2010.
U.S. Appl. No. 13/105,756, filed May 11, 2011.
U.S. Appl. No. 13/318,751, filed Nov. 3, 2011.
U.S. Appl. No. 13/589,022, filed Aug. 17, 2012.
U.S. Appl. No. 13/708,439, filed Dec. 7, 2012.
U.S. Appl. No. 13/710,134, filed Dec. 10, 2012.
U.S. Appl. No. 14/086,716, filed Nov. 21, 2013.
U.S. Appl. No. 14/153,219, filed Jan. 13, 2014.
Vasko, et al. Gene expression and functional evidence of epithelial-to-mesenchymal transition in papillary thyroid carcinoma invasion. Proc Natl Acad Sci U S A. Feb. 20, 2007;104(8):2803-8. Epub Feb. 12, 2007.
Viale et al. Coexpression of cytokeratins and vimentin in normal and diseased thyroid glands. Lack of diagnostic utility of vimentin immunostaining. Am J Surg Pathol. 1989;13(12):1034-40.
Viney et al. Regulation of the cell-specific calcitonin/calcitonin gene-related peptide enhancer by USF and the Foxa2 forkhead protein. J Biol Chem. 2004;279(48):49948-55.
Visone et al. MicroRNAs (miR)-221 and miR-222, both overexpressed in human thyroid papillary carcinomas, regulate p27Kip1 protein levels and cell cycle. Endocr Relat Cancer. 2007;14(3):791-8.
Visone et al. Specific microRNAs are downregulated in human thyroid anaplastic carcinomas. Oncogene. 2007;26(54):7590-5.
Wang et al. Association of the T1799A BRAF mutation with tumor extrathyroidal invasion, higher peripheral platelet counts, and overexpression of platelet-derived growth factor-B in papillary thyroid cancer. Endocr Relat Cancer. 2008;15(1):183-90.
Wang et al. The expression analysis of ICOS-L on activated T cells and immature dendritic cells as well as malignant B cells and Grave's-disease-derived thyroid tissues by two novel mAbs against human ICOS-L. Tissue Antigens. 2007;69(1):62-72.
Watanabe et al. Decrease of intrathyroidal CD161+Valpha24+Vbeta11+ NKT cells in Graves' disease. Endocr J. 2008; 55(1):199-203.
Wattel, et al. Gene expression in thyroid autonomous adenomas provides insight into their physiopathology. Oncogene. Oct. 20, 2005;24(46):6902-16.
Weber et al. A limited set of human MicroRNA is deregulated in follicular thyroid carcinoma. J Clin Endocrinol Metab. 2006;91(9):3584-91. Epub Jul. 5, 2006.
Weber et al. Genetic classification of benign and malignant thyroid follicular neoplasia based on a three-gene combination. J Clin Endocrinol Metab. 2005;90(5):2512-21.
Weber et al. Silencing of the maternally imprinted tumor suppressor ARHI contributes to follicular thyroid carcinogenesis. J Clin Endocrinol Metab. 2005;90(2):1149-55.
Wessagowit, et al. Normal and abnormal mechanisms of gene splicing and relevance to inherited skin diseases. J Dermatol Sci. Nov. 2005;40(2):73-84. Epub Jul. 27, 2005.
Whitehead, et al. Variation in tissue-specific gene expression among natural populations. Genome Biol. 2005;6(2):R13. Epub Jan. 26, 2005.
Wiseman et al. Molecular phenotyping of thyroid tumors identifies a Marker panel for differentiated thyroid cancer diagnosis. Ann Surg Oncol. 2008;15(10):2811-26.
Wreesmann et al. Genome-wide profiling of papillary thyroid cancer identifies MUC1 as an independent prognostic marker. Cancer Res. 2004;64(11):3780-9.
Wu, et al. A comparative study of 200 fine needle aspiration biopsies performed by clinicians and cytopathologists. Laryngoscope. Jul. 2006;116(7):1212-5.
Wu et al. Uncommon mutation, but common amplifications, of the PIK3CA gene in thyroid tumors. J Clin Endocrinol Metab. 2005;90(8):4688-93.
Xu et al. Differential expression of galectin-1 and galectin-3 in thyroid tumors. Potential diagnostic implications. Am J Pathol. 1995;147(3):815-22.
Yang et al. C-myc, N-myc, N-ras, and c-erb-B: lack of amplification or rearrangement in human medullary thyroid carcinoma and a derivative cell line. Anticancer Res. 1990;10(1):189-92.
Yano et al. Gene expression profiling identifies platelet-derived growth factor as a diagnostic molecular marker for papillary thyroid carcinoma. Clin Cancer Res. 2004;10(6):2035-43.
Yatabe et al. Epidermal growth factor receptor gene amplification is acquired in association with tumor progression of EGFR-mutated lung cancer. Cancer Res. 2008;68(7):2106-11.
Yeh et al. Differentiated thyroid cancer cell invasion is regulated through epidermal growth factor receptor-dependent activation of matrix metalloproteinase (MMP)-2/gelatinase A. Endocr Relat Cancer. 2006;13(4):1173-83.
Yeh et al. Somatic mitochondrial DNA (mtDNA) mutations in papillary thyroid carcinomas and differential mtDNA sequence variants in cases with thyroid tumours. Oncogene. 2000;19(16):2060-6.
Yoon et al. Identification of a novel noncoding RNA gene, NAMA, that is downregulated in papillary thyroid carcinoma with BRAF mutation and associated with growth arrest. Int J Cancer. 2007;121(4):767-75.
Zabel et al. S-100 protein and neuron-specific enolase in parathyroid glands and C-cells of the thyroid. Histochemistry. 1987;86(4):389-92.
Zanna et al. Trop-1 are conserved growth stimulatory molecules that mark early stages of tumor progression. Cancer. 2007;110(2):452-64.
Zeng et al. The contributions of oestrogen receptor isoforms to the development of papillary and anaplastic thyroid carcinomas. J Pathol. 2008;214(4):425-33.
Zhang, et al. Association between single-nucleotide polymorphisms of BRAF and papillary thyroid carcinoma in a Chinese population. Thyroid. Jan. 2013;23(1):38-44. doi: 10.1089/thy.2012.0228.
Zhang, et al. CDC23 Regulates Cancer Cell Phenotype and is Overexpressed in Papillary Thyroid Cancer. Endocr Relat Cancer. Endocr Relat Cancer. Nov. 28, 2011;18(6):731-42. doi: 10.1530/ERC-11-0181. Print 2011.

(56) References Cited

OTHER PUBLICATIONS

Zhang et al. Regulation of tumor necrosis factor-related apoptosis-inducing ligand-induced apoptosis by DJ-1 in thyroid cancer cells. Endocr Relat Cancer. 2008;15(2):535-44.
Zhou et al. RET proto-oncogene mutations are restricted to codons 634 and 918 in mainland Chinese families with MEN2A and MEN2B. Clin Endocrinol (Oxf). 2007;67(4):570-6.
Zhu et al. U1 snRNP-dependent function of TIAR in the regulation of alternative RNA processing of the human calcitonin/CGRP pre-mRNA. Mol Cell Biol. 2003;23(17):5959-71.
Adams, J.U., The Human Genome project set out to sequence all of the 3 billion nucleotides in the human genome. Exactly how was this daunting task done with such incredible speed and accuracy? DNA sequencing technologies. Nature Education, 2008; 1(1):193, pp. 1-6.
Aggarwal et al. Thyroid carcinoma-associated genetic mutations also occur in thyroid lymphomas. Mod Pathol. vol. 25 No. 9. May 11, 2012. pp. 1203-1211.
Agrawal, et al. Cancer Genome Atlas Research Network. Integrated genomic characterization of papillary thyroid carcinoma. Cell. Oct. 23, 2014;159(3):676-90. doi: 10.1016/j.cell.2014.09.050.
Akester et al. Cancer in the thyroid is not always thyroid cancer. Hormones-Athens-2 (2003): 250-255.
Ali et al. Use of the Afirma® Gene Expression Classifier for Preoperative Identification of Benign Thyroid Nodules with Indeterminate Fine Needle Aspiration Cytopathology. PLoS Currents 5:pp. 1-7 (2013).
Ashley. Towards precision medicine. Nature Reviews Genetics 17.9 (2016): 507. 0.
Asseroshn et al. The feasibility of using fine needle aspiration from primary breast cancers for cDNA microarray analyses. Clinical Cancer Research 8.3 (2002): 794-801. 0.
Auton et al. 1000 Genomes Project Consortium. A global reference for human genetic variation. Nature 526, 7571 (2015): 68.
Beaudenon-Huibregtse, et al. Centralized molecular testing for oncogenic gene mutations complements the local cytopathologic diagnosis of thyroid nodules. Thyroid. Oct. 2014;24(10):1479-87. Epub Jun. 18, 2014.
Bolstad, et al. A comparison of normalization methods for high density oligonucleotide array data based on variance and bias. Bioinformatics. Jan. 22, 2003;19(2):185-93.
Byron et al. Translating RNA sequencing into clinical diagnostics: opportunities and challenges. Nature Reviews Genetics 17.5 (2016): 257.
Carroll et al. Promising Molecular Techniques for Discriminating Among Follicuar Thyroid Neoplasms. Surgical Oncology, Blackwell Scientific Publ., Oxford, GB, vol. 15, No. 2, Aug. 1, 2006, pp. 59-64.
Centeno et al. Classification of human tumors using gene expression profiles obtained after microarray analysis of fine-needle aspiration biopsy samples. Cancer Cytopathology: Interdisciplinary International Journal of the American Cancer Society 105.2 (2005): 101-109.
Cheng et al. A Multi-Cancer Mesenchymal Transition Gene Expression Signature Is Associated with Prolonged Time to Recurrence in Glioblastoma. Plos One 7(4):e34705 (2012).
Choi et al. Case-control association testing in the presence of unknown relationships. Genetic epidemiology 33.8 (2009): 668-678.
Cirulli Uncovering the roles of rare variants in common disease through whole-genome sequencing. Nature Reviews Genetics 11.6 (2010): 415.
Cohen et al. Mutational Analysis of BRAF in Fine Needle Aspiration Biopsies of the Thyroid: A Potential Application for the Preoperative Assessment of Thyroid Nodules. Clinical Cancer Research 10:2761-2765 (Apr. 2004).
Co-pending U.S. Appl. No. 15/096,739, filed Apr. 12, 2016.
Co-pending U.S. Appl. No. 16/017,899, filed Jun. 25, 2018.
Co-pending U.S. Appl. No. 16/174,769, filed Oct. 30, 2018.
Co-pending U.S. Appl. No. 16/174,784, filed Oct. 30, 2018.
Co-pending U.S. Appl. No. 16/248,074, filed Jan. 15, 2019.
Costa et al. New somatic mutations and WNK1-B4GALNT3 gene fusion in papillary thyroid carcinoma. Oncotarget 6:11242-11251 (2015).
Cross et al. The promise of molecular profiling for cancer identification and treatment. Clinical medicine & research 2.3 (2004): 147-150.
Dougherty. The fundamental role of pattern recognition for gene-expression/microarray data in bioinformatics. Pattern recognition. 2005; 38:2226-2228.
Endocrine website. http://www.endocrineweb.com/noduleus.html (Accessed Dec. 9, 2011).
Englisch, et al. Chemically Modified Oligonucleotides as Probes and Inhibitors. Angew. Chem. Int. Ed. Eng. 1991; 30:613-629.
Engstrom et al. Systematic evaluation of spliced alignment programs for RNA-seq data. Nature methods 10.12 (2013): 1185.
EP16759458.9 European Search Report dated Sep. 6, 2018.
Erkkila et al. Probabilistic analysis of gene expression measurements from heterogeneous tissues. Bioinformatics 26(20):2571-2577 (2010).
Eszlinger et al., Perspectives and Limitations of Microarray-Based Gene Expression Profiling of Thyroid Tumors. Endocrine Reviews, 2007; 28:322-338.
European Search Report dated Jan. 10, 2018 for EP3265588.
European Search Report dated May 25, 2018 for EP17210850.5.
Extended European Search Report dated Apr. 22, 2016 for European Patent Application No. 13838743.6.
Filicori, et al. Risk stratification of indeterminate thyroid fine-needle aspiration biopsy specimens based on mutation analysis. Surgery. Dec. 2011;150(6):1085-91.
Final Office action dated Aug. 28, 2018 for U.S. Appl. No. 13/105,756.
Final Office action dated Sep. 7, 2018 for U.S. Appl. No. 15/694,157.
Fodor, et al. Light-directed, spatially addressable parallel chemical synthesis. Science. Feb. 15, 1991;251(4995):767-73.
Fontaine, et al. Increasing the number of thyroid lesions classes in microarray analysis improves the relevance of diagnostic markers. PLoS One. Oct. 29, 2009;4(10):e7632.
Frampton, et al. Development and validation of a clinical cancer genomic profiling test based on massively parallel DNA sequencing. Nat Biotechnol. Nov. 2013;31(11):1023-31. Epub Oct. 20, 2013.
GAIT. Chapter 16: Oligoribonucleotides. Antisense Research and Applications, Crookeand Lebleu Eds., CRC Press (pp. 289-302) (1993).
Gene Annot website. Probesets for ALDH1B1. Printed Feb. 2018.
Gene Annot website. Probesets for AUTS2. Printed Feb. 2018.
Gene Annot website. Probesets for CFHR1. Printed Feb. 2018.
Gene Annot website. Probesets for CPE. Printed Feb. 2018.
Gene Annot website. Probesets for FN1. Printed Feb. 2018.
Gene Annot website. Probesets for GABRB2. Printed Feb. 2018.
Gene Annot website. Probesets for PLCB1. Printed Feb. 2018.
Gene Annot website. Probesets for PYGL. Printed Feb. 2018.
Gene Annot website. Probesets for ROS1. Printed Feb. 2018.
GeneAnnot Search for Affymetrix HG-U 133A microarray pro besets for TIMP1, printed Dec. 2018.
GeneAnnot Search for Affymetrix HG-U 133A microarray probesets for SLCA4, printed Dec. 2018.
Gerstung, et al. Combining gene mutation with gene expression data improves outcome prediction in myelodysplastic syndromes. Nat Commun. Jan. 9, 2015;6:5901.
Gill, et al. Nucleic acid isothermal amplification technologies: a review. Nucleosides Nucleotides Nucleic Acids. Mar. 2008;27(3):224-43.
Griffith, et al. Biomarker panel diagnosis of thyroid cancer: a critical review. Expert Rev Anticancer Ther. Sep. 2008;8(9):1399-413.
Ha et al. Localized non-Hodgkin lymphoma involving the thyroid gland. Cancer91.4 (2001): 629-635.
Hamada, et al. Diagnostic usefulness of PCR profiling of the differentially expressed marker genes in thyroid papillary carcinomas. Cancer Lett. Jun. 28, 2005;224(2):289-301. Epub Nov. 18, 2004.
Huang et al. A tool for RNA sequencing sample identity check. Bioinformatics 29.11 (2013): 1463-1464.

(56) References Cited

OTHER PUBLICATIONS

International Search Report and Written Opinion dated Apr. 4, 2017 for International PCT Patent Application No. PCT/US2016/053578.
International Search Report and Written Opinion dated Jun. 2, 2016 for International PCT Patent Application No. PCT/US2016/020583.
International Search Report and Written Opinion dated Nov. 18, 2013 for International PCT Patent Application No. PCT/CA2013/050686.
International Search Report for PCT/CA2010/000266, dated Jul. 12, 2010.
International Search Report for PCT/CA2010/000621, completed Jul. 14, 2010.
Jun et al. Detecting and estimating contamination of human DNA samples in sequencing and array-based genotype data. The American Journal of Human Genetics 91.5 (2012): 839-848.
Kanehisa. Use of statistical criteria for screening potential homologies in nucleic acid sequences. Nucleic Acids Res. Jan. 11, 1984;12(1 Pt 1):203-13.
Koshkin et al. LNA (locked nucleic acids): An RNA mimic forming exceedingly stable LNA: LNA duplexes. J Am Chem Soc 120:13252-13253 (1998).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kroschwitz. The Concise Encyclopedia of Polymer Science and Engineering. (pp. 858-859) (1990).
Kumar, et al. The first analogues of LNA (locked nucleic acids): phosphorothioate-LNA and 2'-thio-LNA. Bioorg Med Chem Lett. Aug. 18, 1998;8(16):2219-22.
Lee et al. NGSCheckMate: software for validating sample identity in next-generation sequencing studies within and across data types. Nucleic acids research 45.11 (2017).
Love, et al. Moderated estimation of fold change and dispersion for RNA-seq data with DESeq2. Genome Biol. Dec 5, 2014;15(12):550.
Manichaikul, et al. Robust relationship inference in genome-wide association studies. Bioinformatics. Nov. 15, 2010;26(22):2867-73. Epub Oct. 5, 2010.
Martin. A New Access to 2'-O-Alkylated Ribonucleosides and Properties of 2'-O-Alkylated Oligoribonucleotides. Helv. Chim. Acta. 1995; 78:486-504. (in German with English abstract).
Mineva, et al. Differential expression of alphaB-crystallin and Hsp27-1 in anaplastic thyroid carcinomas because of tumor-specific alphaB-crystallin gene (CRYAB) silencing. Cell Stress Chaperones. 2005 Autumn;10(3):171-84.
Miyamoto et al. Potential Marker of Oral Squamous Cell Carcinoma Aggressiveness Detected by Fluorescence in Situ Hybridization in Fine-Needle Aspiration Biopsies. Cancer American Cancer Society 95(10):2152-2159 (Jun. 6, 2002).
NCBI gene report for LOC100131599. Printed Feb. 2018.
Nielsen, et al. Sequence-selective recognition of DNA by strand displacement with a thymine-substituted polyamide. Science. 254: 1497-1500 (1991).
Nikiforova, et al. Highly accurate diagnosis of cancer in thyroid nodules with follicular neoplasm/suspicious for a follicular neoplasm cytology by ThyroSeq v2 next-generation sequencing assay. Cancer. Dec. 1, 2014;120(23):3627-34. Epub Sep. 10, 2014.
Nikiforova, et al. Molecular diagnostics and predictors in thyroid cancer. Thyroid. Dec. 2009;19(12):1351-61.
Nikiforova, et al. Targeted Next-Generation Sequencing Panel (ThyroSeq) for Detection of Mutations in Thyroid Cancer. J Clin Endocrinol Metab. Nov. 2013; 98(11): E1852-E1860.
Notice of allowance dated Mar. 27, 2015 for U.S. Appl. No. 13/254,571.
Notice of Allowance dated Mar. 30, 2017 for U.S. Appl. No. 14/727,801.
Notice of Allowance dated Apr. 3, 2018 for U.S. Appl. No. 14/020,183.
Notice of allowance dated Jul. 30, 2015 for U.S. Appl. No. 13/258,429.
Notice of allowance dated Oct. 24, 2018 for U.S. Appl. No. 15/661,496.
Notice of allowance dated Nov. 28, 2016 for U.S. Appl. No. 14/926,349.
Notice of allowance dated Sep. 13, 2018 for U.S. Appl. No. 15/851,377.
Office Action dated Jan. 12, 2018 for U.S. Appl. No. 13/589,022.
Office action dated Jan. 16, 2015 for U.S. Appl. No. 13/258,429.
Office action dated Jan. 16, 2018 for U.S. Appl. No. 13/105,756.
Office Action dated Jan. 25, 2018 for U.S. Appl. No. 15/626,401.
Office action dated Feb. 26, 2016 for U.S. Appl. No. 14/926,349.
Office action dated Mar. 2, 2018 for U.S. Appl. No. 13/589,022.
Office action dated Mar. 11, 2014 for U.S. Appl. No. 13/254,571.
Office action dated Mar. 27, 2018 for U.S. Appl. No. 114/153,219.
Office action dated Mar. 29, 2018 for U.S. Appl. No. 14/086,716.
Office action dated Apr. 8, 2014 for U.S. Appl. No. 13/258,429.
Office Action dated May 5, 2017 for U.S. Appl. No. 14/020,183.
Office action dated Jun. 15, 2018 for U.S. Appl. No. 15/661,496.
Office action dated Jun. 15, 2018 for U.S. Appl. No. 15/851,377.
Office action dated Jun. 29, 2018 for U.S. Appl. No. 15/702,126.
Office action dated Sep. 7, 2016 for U.S. Appl. No. 14/727,801.
Office action dated Sep. 11, 2013 for U.S. Appl. No. 13/258,429.
Office action dated Sep. 19, 2018 for U.S. Appl. No. 15/096,739.
Office Action dated Nov. 9, 2018 for U.S. Appl. No. 14/851,864.
Office Action dated Nov. 20, 2018 for U.S. Appl. No. 13/589,022.
Office action dated Nov. 29, 2018 for U.S. Appl. No. 15/626,401.
Office action dated Dec. 4, 2014 for U.S. Appl. No. 13/254,571.
Office Action dated Dec. 26, 2017 for U.S. Appl. No. 15/185,960.
Pankratz et al. Usual interstitial pneumonia can be detected in transbronchial biopsies using machine learning. Annals of the American Thoracic Society 14.11 (2017): 1646-1654.
PCT/US2018/043984 International Search Report and Written Opinion dated Jan. 21, 2019.
Robinson, et al. A comparison of Affymetrix gene expression arrays. BMC Bioinformatics. Nov. 15, 2007;8:449.
Robinson et al. A dynamic programming approach for the alignment of signal peaks in multiple gas chromatography-mass spectrometry experiments. BMC bioinformatics 8.1 (2007): 419.
Ros et al. Thyroid-specific Gene Expression in the Multi-Step Process of Thyroid Carcinogenesis, Biochimie, Masson, Paris, FR, vol. 81, No. 4, Apr. 1, 1999, pp. 389-396.
Rowe et al. Utility of BRAF V600E Mutation Detection in Cytologically Indeterminate Thyroid Nodules. CytoJoural 3(10):1-10 (Apr. 2006).
Sanghvi. Heterocyclic base modifications in nucleic acids and their applications in antisense oligonucleotides. in Antisense Research and Applications. Crooke, S. T. and Lebleu, B., ed., CRC Press. 1993; Ch 15 274-285.
Schroeder, et al. The RIN: an RNA integrity number for assigning integrity values to RNA measurements. BMC Mol Biol. Jan. 31, 2006;7:3.
Shi, et al. Combined analysis of gene expression, DNA copy number, and mutation profiling data to display biological process anomalies in individual breast cancers. Breast Cancer Res Treat. Apr. 2014;144(3):561-8. Epub Mar. 12, 2014.
Shibru, et al. Does the 3-gene diagnostic assay accurately distinguish benign from malignant thyroid neoplasms? Cancer. Sep. 1, 2008;113(5):930-5.
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Smyth, Gordon K. Linear models and empirical bayes methods for assessing differential expression in microarray experiments. Stat Appl Genet Mol Biol. 2004;3:Article3. Epub Feb. 12, 2004.
Smyth. Limma: Linear Models for Microarray Data. In: Bioinformatics and Computational Biology Solutions using R and Bioconductor, R. Gentleman, V. Carey, S. Dudoit, R. Irizarry, W. Huber (eds.), Springer, New York. 2005; pp. 397-420.
Office Action dated Dec. 12, 2018 for U.S. Appl. No. 14/086,716.
Office action dated Dec. 13, 2018 for U.S. Appl. No. 14/153,219.
Spargo, et al. Detection of M. tuberculosis DNA using thermophilic strand displacement amplification. Mol Cell Probes. Aug. 1996;10(4):247-56.

(56) References Cited

OTHER PUBLICATIONS

Thornton et al. Estimating kinship in admixed populations. The American Journal of Human Genetics 91.1 (2012): 122-138.

Trovisco et al. Molecular Genetics of Papillary Thyroid Carcinoma—Great Expectations . . . Arq Bras Endocrinol Metab, Jul. 1 2007, pp. 643-653.

Tukey. Exploratory Data Analysis: Past, Present, and Future. Technical Report No. 302. Department of Statistics, Princeton University. 1971-1977. 1993.

Ullmannová, et al. The use of housekeeping genes (HKG) as an internal control for the detection of gene expression by quantitative real-time RT-PCR. Folia Biol (Praha). 2003;49(6):211-6.

U.S. Appl. No. 15/185,960 Office Action dated Dec. 21, 2018.

U.S. Appl. No. 15/661,496 Notice of Allowance dated Feb. 11, 2019.

Van Allen et al. Whole-exome sequencing and clinical interpretation of formalin-fixed, paraffin-embedded tumor samples to guide precision cancer medicine. Nature medicine 20.6 (2014): 682.

Van Der Laan, et al. A new algorithm for hybrid hierarchical clustering with visualization and the bootstrap. Journal of Statistical Planning and Inference. Dec. 2003. 117(2):275-303.

Wang et al. RNA-seq: a revolutionary tool for transcriptomics. Nature Reviews Genetics 10:57-63 (2009).

Wharam, et al. Specific detection of DNA and RNA targets using a novel isothermal nucleic acid amplification assay based on the formation of a three-way junction structure. Nucleic Acids Res. Jun. 1, 2001;29(11):E54-4.

Written Opinion of the International Searching Authority for PCT/CA2010/000621, dated Aug. 11, 2010.

Yan, et al. Isothermal amplified detection of DNA and RNA. Mol Biosyst. May 2014;10(5):970-1003.

Yousefi et al. A SNP panel for identification of DNA and RNA specimens. BMC genomics 19.1 (2018): 90.

Yukinawa, et al. A multi-class predictor based on a probabilistic model: application to gene expression profiling-based diagnosis of thyroid tumors. BMC Genomics. Jul. 27, 2006;7:190.

Frohman on Beyond Classic RACE (Rapid Amplification of eDNA Ends) PCR Methods and Applications vol. 4, pp. S40-S58 (Year: 1994).

Nikiforov et al. Impact of Mutational Testing on the Diagnosis and Management of Patients with Cytologically Indeterminate Thyroid Nodules: A Prospective Analysis of 1056 FNA Samples Journal of Clinical Endocrinology and Metabolism vol. 96, pp. 3390-3397 (Year: 2011).

FIG. 2

Gene Biomarker Panels for Diagnosing a Thyroid Condition

| | |
|---|---|
| 1 | Normal Thyroid (NML) |
| 2 | Lymphocytic, Autoimmune Thyroiditis (LCT) |
| 3 | Nodular Hyperplasia (NHP) |
| 4 | Follicular Thyroid Adenoma (FA) |
| 5 | Hurthle Cell Thyroid Adenoma (HA) |
| 6 | Parathyroid (non thyroid tissue) (PTA) |
| 7 | Anaplastic Thyroid Carcinoma (ATC) |
| 8 | Follicular Thyroid Carcinoma (FC) |
| 9 | Hurthle Cell Thyroid Carcinoma (HC) |
| 10 | Papillary Thyroid Carcinoma (PTC) |
| 11 | Follicular Variant of Papillary Carcinoma (FVPTC) |
| 12 | Medullary Thyroid Carcinoma (MTC) |
| 13 | Renal Carcinoma metastasis to the Thyroid (RCC) |
| 14 | Melanoma metastasis to the Thyroid (MMN) |
| 15 | B cell Lymphoma metastasis to the Thyroid (BCL) |
| 16 | Breast Carcinoma metastasis to the Thyroid (BCA) |

FIG. 3

Optimized Gene Classification Panels of Diagnostic Utility in Thyroid FNA

| Classification Panel | Subtype-specific Classifier Components | Number of Markers Per Panel |
|---|---|---|
| 1 | MTC | 5 |
| 2 | RCC | 5 |
| 3 | PTA | 5 |
| 4 | BCA | 5 |
| 5 | MMN | 5 |
| 6 | HA & HC[1] | 33 |
| 7 | Benign/Suspicious[2] | 142 |

[1] denotes the combination of two panels -HA and HC- into a single panel.
[2] denotes the combination of eight panels -FA, FC, NHP, PTC, FVPTC, LCT, HA, HC- into a single panel.

FIG. 4

| TCID | GENE | Gene Description | Classification Panel |
|---|---|---|---|
| 3364127 | CALCA | calcitonin-related polypeptide alpha | MTC |
| 3834341 | CEACAM5 | carcinoembryonic antigen-related cell adhesion molecule 5 | MTC |
| 3594003 | SCG3 | secretogranin III | MTC |
| 2585400 | SCN2A | sodium channel, voltage-gated, type II, alpha subunit | MTC |
| 2585400 | SCN9A | sodium channel, voltage-gated, type IX, alpha subunit | MTC |
| 3805614 | SYT4 | synaptotagmin IV | MTC |
| 2923928 | FABP7 | fatty acid binding protein 7, brain | RCC |
| 3393446 | FXYD2 | FXYD domain containing ion transport regulator 2 | RCC |
| 2883317 | HAVCR1 | hepatitis A virus cellular receptor 1 | RCC |
| 2883317 | LOC100101266 | hepatitis A virus cellular receptor 1 pseudogene | RCC |
| 3428225 | NR1H4 | nuclear receptor subfamily 1, group H, member 4 | RCC |
| 2479698 | PREPL | prolyl endopeptidase-like | RCC |
| 2479698 | SLC3A1 | solute carrier family 3 (cystine, dibasic and neutral amino acid transporters, activator of cystine, dibasic and neutral amino acid transport), member 1 | RCC |
| 3159754 | DMRT2 | doublesex and mab-3 related transcription factor 2 | PTA |
| 2941690 | GCM2 | glial cells missing homolog 2 (Drosophila) | PTA |
| 3363686 | KIDINS220 | kinase D-interacting substrate, 220kDa | PTA |
| 3484895 | KL | klotho | PTA |
| 3363686 | PTH | parathyroid hormone | PTA |
| 2894790 | SYCP2L | synaptonemal complex protein 2-like | PTA |
| 3039830 | AGR3 | anterior gradient homolog 3 (Xenopus laevis) | BCA |
| 3264997 | C10orf81 | chromosome 10 open reading frame 81 | BCA |
| 2926802 | MYB | v-myb myeloblastosis viral oncogene homolog (avian) | BCA |
| 3912079 | SYCP2 | synaptonemal complex protein 2 | BCA |
| 2430163 | VTCN1 | V-set domain containing T cell activation inhibitor 1 | BCA |
| 3811949 | CDH19 | cadherin 19, type 2 | MMN |

FIG. 4 (continued)

| TCID | GENE | Gene Description | Classification Panel |
|---|---|---|---|
| 3161261 | MLANA | melan-A | MMN |
| 3935486 | S100B | S100 calcium binding protein B | MMN |
| 3457336 | SILV | silver homolog (mouse) | MMN |
| 3343832 | TYR | tyrosinase (oculocutaneous albinism IA) | MMN |
| 3343832 | TYRL | tyrosinase-like (pseudogene) | MMN |
| 2566848 | AFF3 | AF4/FMR2 family, member 3 | HA & HC, Benign/Suspicious |
| 2988882 | AIMP2 | aminoacyl tRNA synthetase complex-interacting multifunctional protein 2 | HA & HC, Benign/Suspicious |
| 3169331 | ALDH1B1 | aldehyde dehydrogenase 1 family, member B1 | HA & HC, Benign/Suspicious |
| 2984616 | BRP44L | brain protein 44-like | HA & HC, Benign/Suspicious |
| 2822492 | C5orf30 | chromosome 5 open reading frame 30 | HA & HC, Benign/Suspicious |
| 3326635 | CD44 | CD44 molecule (Indian blood group) | HA & HC, Benign/Suspicious |
| 2750627 | CPE | carboxypeptidase E | HA & HC, Benign/Suspicious |
| 3042001 | CYCS | cytochrome c, somatic | HA & HC, Benign/Suspicious |
| 3122678 | DEFB1 | defensin, beta 1 | HA & HC, Benign/Suspicious |
| 2739308 | EGF | epidermal growth factor (beta-urogastrone) | HA & HC, Benign/Suspicious |
| 2988882 | EIF2AK1 | eukaryotic translation initiation factor 2-alpha kinase 1 | HA & HC, Benign/Suspicious |
| 3603932 | FAH | fumarylacetoacetate hydrolase (fumarylacetoacetase) | HA & HC, Benign/Suspicious |
| 2970897 | FRK | fyn-related kinase | HA & HC, Benign/Suspicious |
| 3212008 | FRMD3 | FERM domain containing 3 | HA & HC, Benign/Suspicious |
| 3302990 | GOT1 | glutamic-oxaloacetic transaminase 1, soluble (aspartate aminotransferase 1) | HA & HC, Benign/Suspicious |
| 3417703 | HSD17B6 | hydroxysteroid (17-beta) dehydrogenase 6 homolog (mouse) | HA & HC, Benign/Suspicious |
| 2877508 | HSPA9 | heat shock 70kDa protein 9 (mortalin) | HA & HC, Benign/Suspicious |

FIG. 4 (continued)

| TCID | GENE | Gene Description | Classification Panel |
|---|---|---|---|
| 2708922 | IGF2BP2 | insulin-like growth factor 2 mRNA binding protein 2 | HA & HC, Benign/Suspicious |
| 2604998 | IQCA1 | IQ motif containing with AAA domain 1 | HA & HC, Benign/Suspicious |
| 3724545 | ITGB3 | integrin, beta 3 (platelet glycoprotein IIIa, antigen CD61) | HA & HC, Benign/Suspicious |
| 3397774 | KCNJ1 | potassium inwardly-rectifying channel, subfamily J, member 1 | HA & HC, Benign/Suspicious |
| 2604998 | LOC100129258 | hypothetical protein LOC100129258 | HA & HC, Benign/Suspicious |
| 3009299 | MDH2 | malate dehydrogenase 2, NAD (mitochondrial) | HA & HC, Benign/Suspicious |
| 3654699 | NUPR1 | nuclear protein, transcriptional regulator, 1 | HA & HC, Benign/Suspicious |
| 4020655 | ODZ1 | odz, odd Oz/ten-m homolog 1(Drosophila) | HA & HC, Benign/Suspicious |
| 3970833 | PDHA1 | pyruvate dehydrogenase (lipoamide) alpha 1 | HA & HC, Benign/Suspicious |
| 2377094 | PFKFB2 | 6-phosphofructo-2-kinase/fructose-2,6-biphosphatase 2 | HA & HC, Benign/Suspicious |
| 3278198 | PHYH | phytanoyl-CoA 2-hydroxylase | HA & HC, Benign/Suspicious |
| 2880051 | PPP2R2B | protein phosphatase 2 (formerly 2A), regulatory subunit B, beta isoform | HA & HC, Benign/Suspicious |
| 3959862 | PVALB | parvalbumin | HA & HC, Benign/Suspicious |
| 2688499 | PVRL2 | poliovirus receptor-related 2 (herpesvirus entry mediator B) | HA & HC, Benign/Suspicious |
| 2604998 | RPL3 | ribosomal protein L3 | HA & HC, Benign/Suspicious |
| 2964231 | RRAGD | Ras-related GTP binding D | HA & HC, Benign/Suspicious |
| 2798538 | SDHA | succinate dehydrogenase complex, subunit A, flavoprotein (Fp) | HA & HC, Benign/Suspicious |
| 2798538 | SDHALP1 | succinate dehydrogenase complex, subunit A, flavoprotein pseudogene 1 | HA & HC, Benign/Suspicious |
| 2798538 | SDHALP2 | succinate dehydrogenase complex, subunit A, flavoprotein pseudogene 2 | HA & HC, Benign/Suspicious |

FIG. 4 (continued)

| TCID | GENE | Gene Description | Classification Panel |
|---|---|---|---|
| 2798538 | SDHAP3 | succinate dehydrogenase complex, subunit A, flavoprotein pseudogene 3 | HA & HC, Benign/Suspicious |
| 2428501 | SLC16A1 | solute carrier family 16, member 1 (monocarboxylic acid transporter 1) | HA & HC, Benign/Suspicious |
| 2877508 | SNORD63 | small nucleolar RNA, C/D box 63 | HA & HC, Benign/Suspicious |
| 2562529 | ST3GAL5 | ST3 beta-galactoside alpha-2,3-sialyltransferase 5 | HA & HC, Benign/Suspicious |
| 2688499 | ZBED2 | zinc finger, BED-type containing 2 | HA & HC, Benign/Suspicious |
| 3450861 | ABCD2 | ATP-binding cassette, sub-family D (ALD), member 2 | Benign/Suspicious |
| 3341061 | ACER3 | alkaline ceramidase 3 | Benign/Suspicious |
| 2796553 | ACSL1 | acyl-CoA synthetase long-chain family member 1 | Benign/Suspicious |
| 3375735 | AHNAK | AHNAK nucleoprotein | Benign/Suspicious |
| 2439554 | AIM2 | absent in melanoma 2 | Benign/Suspicious |
| 3768474 | ARSG | arylsulfatase G | Benign/Suspicious |
| 3214845 | ASPN | asporin | Benign/Suspicious |
| 3006572 | AUTS2 | autism susceptibility candidate 2 | Benign/Suspicious |
| 3902489 | BCL2L1 | BCL2-like 1 | Benign/Suspicious |
| 2688717 | BTLA | B and T lymphocyte associated | Benign/Suspicious |
| 2708855 | C11orf72 | chromosome 11 open reading frame 72 | Benign/Suspicious |
| 2730303 | C4orf7 | chromosome 4 open reading frame 7 | Benign/Suspicious |
| 3259367 | CC2D2B | coiled-coil and C2 domain containing 2B | Benign/Suspicious |
| 3204285 | CCL19 | chemokine (C-C motif) ligand 19 | Benign/Suspicious |
| 3338192 | CCND1 | cyclin D1 | Benign/Suspicious |
| 3010503 | CD36 | CD36 molecule (thrombospondin receptor) | Benign/Suspicious |
| 2326463 | CD52 | CD52 molecule | Benign/Suspicious |
| 2635741 | CD96 | CD96 molecule | Benign/Suspicious |
| 2373336 | CFH | complement factor H | Benign/Suspicious |
| 2373336 | CFHR1 | complement factor H-related 1 | Benign/Suspicious |
| 2710599 | CLDN1 | claudin 1 | Benign/Suspicious |
| 2657808 | CLDN16 | claudin 16 | Benign/Suspicious |

FIG. 4 (continued)

| TCID | GENE | Gene Description | Classification Panel |
|---|---|---|---|
| 2377283 | CR2 | complement component (3d/Epstein Barr virus) receptor 2 | Benign/Suspicious |
| 3242353 | CREM | cAMP responsive element modulator | Benign/Suspicious |
| 2490351 | CTNNA2 | catenin (cadherin-associated protein), alpha 2 | Benign/Suspicious |
| 2732508 | CXCL13 | chemokine (C-X-C motif) ligand 13 | Benign/Suspicious |
| 2854445 | DAB2 | disabled homolog 2, mitogen-responsive phosphoprotein (Drosophila) | Benign/Suspicious |
| 2321911 | DDI2 | DDI1, DNA-damage inducible 1, homolog 2 (S. cerevisiae) | Benign/Suspicious |
| 2642791 | DNAJC13 | DnaJ (Hsp40) homolog, subfamily C, member 13 | Benign/Suspicious |
| 2584018 | DPP4 | dipeptidyl-peptidase 4 | Benign/Suspicious |
| 3032647 | DPP6 | dipeptidyl-peptidase 6 | Benign/Suspicious |
| 2981874 | DYNLT1 | dynein, light chain, Tctex-type 1 | Benign/Suspicious |
| 2638676 | EAF2 | ELL associated factor 2 | Benign/Suspicious |
| 3852832 | EMR3 | egf-like module containing, mucin-like, hormone receptor-like 3 | Benign/Suspicious |
| 3142381 | FABP4 | fatty acid binding protein 4, adipocyte | Benign/Suspicious |
| 2396750 | FBXO2 | F-box protein 2 | Benign/Suspicious |
| 3338192 | FLJ42258 | FLJ42258 protein | Benign/Suspicious |
| 2526806 | FN1 | fibronectin 1 | Benign/Suspicious |
| 2598261 | FN1 | fibronectin 1 | Benign/Suspicious |
| 3839910 | FPR2 | formyl peptide receptor 2 | Benign/Suspicious |
| 3486096 | FREM2 | FRAS1 related extracellular matrix protein 2 | Benign/Suspicious |
| 3393479 | FXYD6 | FXYD domain containing ion transport regulator 6 | Benign/Suspicious |
| 2378068 | G0S2 | G0/G1switch 2 | Benign/Suspicious |
| 2884845 | GABRB2 | gamma-aminobutyric acid (GABA) A receptor, beta 2 | Benign/Suspicious |
| 3063795 | GAL3ST4 | galactose-3-O-sulfotransferase 4 | Benign/Suspicious |
| 3031556 | GIMAP2 | GTPase, IMAP family member 2 | Benign/Suspicious |
| 3861948 | GMFG | glia maturation factor, gamma | Benign/Suspicious |
| 3540862 | GPHN | gephyrin | Benign/Suspicious |
| 3982612 | GPR174 | G protein-coupled receptor 174 | Benign/Suspicious |
| 2809793 | GZMK | granzyme K (granzyme 3; tryptase II) | Benign/Suspicious |
| 2638676 | HCG11 | HLA complex group 11 | Benign/Suspicious |
| 2352609 | HNRNPA3 | heterogeneous nuclear ribonucleoprotein A3 | Benign/Suspicious |
| 3375735 | IGHG1 | immunoglobulin heavy constant gamma 1 (G1m marker) | Benign/Suspicious |
| 2806468 | IL7R | interleukin 7 receptor | Benign/Suspicious |

FIG. 4 (continued)

| TCID | GENE | Gene Description | Classification Panel |
|---|---|---|---|
| 3852832 | ITGB1 | integrin, beta 1 (fibronectin receptor, beta polypeptide, antigen CD29 includes MDF2, MSK12) | Benign/Suspicious |
| 2427619 | KCNA3 | potassium voltage-gated channel, shaker-related subfamily, member 3 | Benign/Suspicious |
| 3404030 | KLRG1 | killer cell lectin-like receptor subfamily G, member 1 | Benign/Suspicious |
| 3512874 | LCP1 | lymphocyte cytosolic protein 1 (L-plastin) | Benign/Suspicious |
| 2708855 | LIPH | lipase, member H | Benign/Suspicious |
| 3875642 | LOC100131599 | hypothetical protein LOC100131599 | Benign/Suspicious |
| 2638676 | LOC647979 | hypothetical LOC647979 | Benign/Suspicious |
| 3147985 | LRP12 | low density lipoprotein-related protein 12 | Benign/Suspicious |
| 2578790 | LRP1B | low density lipoprotein-related protein 1B (deleted in tumors) | Benign/Suspicious |
| 2352609 | MAGI3 | membrane associated guanylate kinase, WW and PDZ domain containing 3 | Benign/Suspicious |
| 3111561 | MAPK6 | mitogen-activated protein kinase 6 | Benign/Suspicious |
| 3108526 | MATN2 | matrilin 2 | Benign/Suspicious |
| 3329343 | MDK | midkine (neurite growth-promoting factor 2) | Benign/Suspicious |
| 3367673 | MPPED2 | metallophosphoesterase domain containing 2 | Benign/Suspicious |
| 3662201 | MT1F | metallothionein 1F | Benign/Suspicious |
| 3692999 | MT1G | metallothionein 1G | Benign/Suspicious |
| 3662201 | MT1H | metallothionein 1H | Benign/Suspicious |
| 3662201 | MT1P2 | metallothionein 1 pseudogene 2 | Benign/Suspicious |
| 3622934 | MYEF2 | myelin expression factor 2 | Benign/Suspicious |
| 3341497 | NDUFC2 | NADH dehydrogenase (ubiquinone) 1, subcomplex unknown, 2, 14.5kDa | Benign/Suspicious |
| 3067478 | NRCAM | neuronal cell adhesion molecule | Benign/Suspicious |
| 3353914 | OR10D1P | olfactory receptor, family 10, subfamily D, member 1 pseudogene | Benign/Suspicious |
| 3982560 | P2RY10 | purinergic receptor P2Y, G-protein coupled, 10 | Benign/Suspicious |
| 2701071 | P2RY13 | purinergic receptor P2Y, G-protein coupled, 13 | Benign/Suspicious |
| 3948047 | PARVG | parvin, gamma | Benign/Suspicious |
| 3606034 | PDE8A | phosphodiesterase 8A | Benign/Suspicious |
| 3811086 | PIGN | phosphatidylinositol glycan anchor biosynthesis, class N | Benign/Suspicious |
| 3744680 | PIK3R5 | phosphoinositide-3-kinase, regulatory subunit 5 | Benign/Suspicious |
| 3111561 | PKHD1L1 | polycystic kidney and hepatic disease 1 (autosomal recessive)-like 1 | Benign/Suspicious |
| 3376529 | PLA2G16 | phospholipase A2, group XVI | Benign/Suspicious |

FIG. 4 (continued)

| TCID | GENE | Gene Description | Classification Panel |
|---|---|---|---|
| 3875642 | PLCB1 | phospholipase C, beta 1 (phosphoinositide-specific) | Benign/Suspicious |
| 2486811 | PLEK | pleckstrin | Benign/Suspicious |
| 3246888 | PRKG1 | protein kinase, cGMP-dependent, type I | Benign/Suspicious |
| 3874751 | PRNP | prion protein | Benign/Suspicious |
| 2685304 | PROS1 | protein S (alpha) | Benign/Suspicious |
| 2373842 | PTPRC | protein tyrosine phosphatase, receptor type, C | Benign/Suspicious |
| 3270270 | PTPRE | protein tyrosine phosphatase, receptor type, E | Benign/Suspicious |
| 3564210 | PYGL | phosphorylase, glycogen, liver | Benign/Suspicious |
| 2362351 | PYHIN1 | pyrin and HIN domain family, member 1 | Benign/Suspicious |
| 3443464 | PZP | pregnancy-zone protein | Benign/Suspicious |
| 2372812 | RGS13 | regulator of G-protein signaling 13 | Benign/Suspicious |
| 3110395 | RIMS2 | regulating synaptic membrane exocytosis 2 | Benign/Suspicious |
| 3895795 | RNF24 | ring finger protein 24 | Benign/Suspicious |
| 2721959 | ROS1 | c-ros oncogene 1 , receptor tyrosine kinase | Benign/Suspicious |
| 2442008 | RXRG | retinoid X receptor, gamma | Benign/Suspicious |
| 3494629 | SCEL | sciellin | Benign/Suspicious |
| 2904485 | SCUBE3 | signal peptide, CUB domain, EGF-like 3 | Benign/Suspicious |
| 3059667 | SEMA3D | sema domain, immunoglobulin domain (Ig), short basic domain, secreted, (semaphorin) 3D | Benign/Suspicious |
| 3365136 | SERGEF | secretion regulating guanine nucleotide exchange factor | Benign/Suspicious |
| 3577612 | SERPINA1 | serpin peptidase inhibitor, clade A (alpha-1 antiproteinase, antitrypsin), member 1 | Benign/Suspicious |
| 3577612 | SERPINA2 | serpin peptidase inhibitor, clade A (alpha-1 antiproteinase, antitrypsin), member 2 | Benign/Suspicious |
| 3759006 | SHC1 | SHC (Src homology 2 domain containing) transforming protein 1 | Benign/Suspicious |
| 2440258 | SLAMF6 | SLAM family member 6 | Benign/Suspicious |
| 3622934 | SLC24A5 | solute carrier family 24, member 5 | Benign/Suspicious |
| 3185522 | SLC31A1 | solute carrier family 31 (copper transporters), member 1 | Benign/Suspicious |
| 2721959 | SLC34A2 | solute carrier family 34 (sodium phosphate), member 2 | Benign/Suspicious |
| 3761959 | SLC35B1 | solute carrier family 35, member B1 | Benign/Suspicious |
| 3373845 | SLC43A3 | solute carrier family 43, member 3 | Benign/Suspicious |
| 3759006 | SLC4A1 | solute carrier family 4, anion exchanger, member 1 (erythrocyte membrane protein band 3, Diego blood group) | Benign/Suspicious |
| 2730746 | SLC4A4 | solute carrier family 4, sodium bicarbonate cotransporter, member 4 | Benign/Suspicious |

FIG. 4 (continued)

| TCID | GENE | Gene Description | Classification Panel |
|---|---|---|---|
| 2777714 | SNCA | synuclein, alpha (non A4 component of amyloid precursor) | Benign/Suspicious |
| 2834282 | STK32A | serine/threonine kinase 32A | Benign/Suspicious |
| 3341497 | THRSP | thyroid hormone responsive (SPOT14 homolog, rat) | Benign/Suspicious |
| 3976341 | TIMP1 | TIMP metallopeptidase inhibitor 1 | Benign/Suspicious |
| 3772661 | TIMP2 | TIMP metallopeptidase inhibitor 2 | Benign/Suspicious |
| 2491271 | TMSB10 | thymosin beta 10 | Benign/Suspicious |
| 3648391 | TNFRSF17 | tumor necrosis factor receptor superfamily, member 17 | Benign/Suspicious |
| 3441849 | TNFRSF1A | tumor necrosis factor receptor superfamily, member 1A | Benign/Suspicious |
| 2412668 | TXNDC12 | thioredoxin domain containing 12 (endoplasmic reticulum) | Benign/Suspicious |
| 3353914 | VWA5A | von Willebrand factor A domain containing 5A | Benign/Suspicious |
| 3976766 | WAS | Wiskott-Aldrich syndrome (eczema-thrombocytopenia) | Benign/Suspicious |
| 3768474 | WIPI1 | WD repeat domain, phosphoinositide interacting 1 | Benign/Suspicious |
| 2817731 | ZFYVE16 | zinc finger, FYVE domain containing 16 | Benign/Suspicious |
| 4027585 | unknown | | Benign/Suspicious |

FIG. 5

|  | Malignant State | | | Benign State | | |
| --- | --- | --- | --- | --- | --- | --- |
| Marker | Subtype 1 | Subtype 2 | Subtype 3 | Subtype 4 | Subtype 5 | Subtype 6 |
| Gene 1 | up-regulated | *down-regulated* | not differentially expressed | *down-regulated* | not differentially expressed | *down-regulated* |
| Gene 2 | up-regulated | *down-regulated* | not differentially expressed | *down-regulated* | not differentially expressed | *down-regulated* |
| Gene 3 | up-regulated | *down-regulated* | not differentially expressed | *down-regulated* | not differentially expressed | *down-regulated* |
| Gene 4 | up-regulated | *down-regulated* | up-regulated | *down-regulated* | not differentially expressed | *down-regulated* |
| Gene 5 | up-regulated | *down-regulated* | up-regulated | *down-regulated* | not differentially expressed | not differentially expressed |
| Gene 6 | up-regulated | *down-regulated* | up-regulated | *down-regulated* | not differentially expressed | not differentially expressed |
| Gene 7 | up-regulated | *down-regulated* | *down-regulated* | not differentially expressed | not differentially expressed | not differentially expressed |
| Gene 8 | up-regulated | not differentially expressed | *down-regulated* | not differentially expressed | up-regulated | not differentially expressed |
| Gene 9 | up-regulated | not differentially expressed | *down-regulated* | not differentially expressed | up-regulated | not differentially expressed |
| Gene 10 | up-regulated | not differentially expressed | not differentially expressed | not differentially expressed | *down-regulated* | up-regulated |
| Gene 11 | up-regulated | not differentially expressed | not differentially expressed | not differentially expressed | *down-regulated* | up-regulated |

FIG. 5 (continued)

| Marker | Malignant State | | | Benign State | | |
|---|---|---|---|---|---|---|
| | Subtype 1 | Subtype 2 | Subtype 3 | Subtype 4 | Subtype 5 | Subtype 6 |
| Gene 12 | up-regulated | up-regulated | not differentially expressed | not differentially expressed | *down-regulated* | up-regulated |
| Gene 13 | not differentially expressed | up-regulated | up-regulated | not differentially expressed | *down-regulated* | not differentially expressed |
| Gene 14 | not differentially expressed | up-regulated | up-regulated | not differentially expressed | *down-regulated* | not differentially expressed |
| Gene 15 | not differentially expressed | up-regulated | up-regulated | not differentially expressed | *down-regulated* | not differentially expressed |
| Gene 16 | not differentially expressed | up-regulated | up-regulated | not differentially expressed | not differentially expressed | not differentially expressed |
| Gene 17 | *down-regulated* | up-regulated | up-regulated | not differentially expressed | not differentially expressed | not differentially expressed |
| Gene 18 | *down-regulated* | up-regulated | up-regulated | not differentially expressed | not differentially expressed | not differentially expressed |
| Gene 19 | *down-regulated* | up-regulated | up-regulated | up-regulated | not differentially expressed | not differentially expressed |
| Gene 20 | *down-regulated* | up-regulated | up-regulated | up-regulated | not differentially expressed | not differentially expressed |

FIG. 6

|         | Malignant State |  |  | Benign State |  |  |
| --- | --- | --- | --- | --- | --- | --- |
| Marker | Subtype 1 | Subtype 2 | Subtype 3 | Subtype 4 | Subtype 5 | Subtype 6 |
| Gene 21 | up-regulated | *down-regulated* | not differentially expressed | *down-regulated* | not differentially expressed | *down-regulated* |
| Gene 22 | up-regulated | *down-regulated* | not differentially expressed | *down-regulated* | not differentially expressed | *down-regulated* |
| Gene 23 | up-regulated | *down-regulated* | not differentially expressed | *down-regulated* | not differentially expressed | *down-regulated* |
| Gene 24 | up-regulated | *down-regulated* | up-regulated | *down-regulated* | not differentially expressed | *down-regulated* |
| Gene 25 | up-regulated | *down-regulated* | up-regulated | *down-regulated* | not differentially expressed | not differentially expressed |
| Gene 26 | up-regulated | *down-regulated* | up-regulated | *down-regulated* | not differentially expressed | not differentially expressed |
| Gene 27 | up-regulated | *down-regulated* | *down-regulated* | not differentially expressed | not differentially expressed | not differentially expressed |
| Gene 28 | up-regulated | not differentially expressed | *down-regulated* | not differentially expressed | up-regulated | not differentially expressed |
| Gene 29 | up-regulated | not differentially expressed | *down-regulated* | not differentially expressed | up-regulated | not differentially expressed |
| Gene 30 | up-regulated | not differentially expressed | not differentially expressed | not differentially expressed | *down-regulated* | up-regulated |
| Gene 31 | up-regulated | not differentially expressed | not differentially expressed | not differentially expressed | *down-regulated* | up-regulated |

FIG. 6 (continued)

| Marker | Malignant State | | | Benign State | | |
|---|---|---|---|---|---|---|
| | Subtype 1 | Subtype 2 | Subtype 3 | Subtype 4 | Subtype 5 | Subtype 6 |
| Gene 32 | up-regulated | up-regulated | not differentially expressed | not differentially expressed | *down-regulated* | up-regulated |
| Gene 33 | not differentially expressed | up-regulated | up-regulated | not differentially expressed | *down-regulated* | not differentially expressed |
| Gene 34 | not differentially expressed | up-regulated | up-regulated | not differentially expressed | *down-regulated* | not differentially expressed |
| Gene 35 | not differentially expressed | up-regulated | up-regulated | not differentially expressed | *down-regulated* | not differentially expressed |
| Gene 36 | not differentially expressed | up-regulated | up-regulated | not differentially expressed | not differentially expressed | not differentially expressed |
| Gene 37 | *down-regulated* | up-regulated | up-regulated | not differentially expressed | not differentially expressed | not differentially expressed |
| Gene 38 | *down-regulated* | up-regulated | up-regulated | not differentially expressed | not differentially expressed | not differentially expressed |
| Gene 39 | *down-regulated* | up-regulated | up-regulated | up-regulated | not differentially expressed | not differentially expressed |
| Gene 40 | *down-regulated* | up-regulated | up-regulated | up-regulated | not differentially expressed | not differentially expressed |

FIG. 7

| Marker | Malignant State | | | Benign State | | |
|---|---|---|---|---|---|---|
| | Subtype 1 | Subtype 2 | Subtype 3 | Subtype 4 | Subtype 5 | Subtype 6 |
| Gene 41 | not differentially expressed | up-regulated | *down-regulated* | up-regulated | not differentially expressed | not differentially expressed |
| Gene 42 | not differentially expressed | up-regulated | *down-regulated* | up-regulated | not differentially expressed | not differentially expressed |
| Gene 43 | not differentially expressed | up-regulated | *down-regulated* | up-regulated | not differentially expressed | not differentially expressed |
| Gene 44 | up-regulated | up-regulated | *down-regulated* | *down-regulated* | not differentially expressed | up-regulated |
| Gene 45 | *down-regulated* | up-regulated | *down-regulated* | up-regulated | not differentially expressed | up-regulated |
| Gene 46 | *down-regulated* | up-regulated | *down-regulated* | up-regulated | not differentially expressed | up-regulated |
| Gene 47 | *down-regulated* | not differentially expressed | *down-regulated* | up-regulated | up-regulated | up-regulated |
| Gene 48 | *down-regulated* | not differentially expressed | *down-regulated* | up-regulated | up-regulated | up-regulated |
| Gene 49 | *down-regulated* | not differentially expressed | up-regulated | up-regulated | up-regulated | *down-regulated* |
| Gene 50 | not differentially expressed | not differentially expressed | up-regulated | up-regulated | up-regulated | *down-regulated* |
| Gene 51 | not differentially expressed | down-regulated | up-regulated | up-regulated | up-regulated | *down-regulated* |

FIG. 7 (continued)

| Marker | Malignant State | | | Benign State | | |
|---|---|---|---|---|---|---|
| | Subtype 1 | Subtype 2 | Subtype 3 | Subtype 4 | Subtype 5 | Subtype 6 |
| Gene 52 | not differentially expressed | *down-regulated* | up-regulated | up-regulated | up-regulated | not differentially expressed |
| Gene 53 | not differentially expressed | *down-regulated* | not differentially expressed | *down-regulated* | up-regulated | *down-regulated* |
| Gene 54 | not differentially expressed | *down-regulated* | not differentially expressed | *down-regulated* | not differentially expressed | *down-regulated* |
| Gene 55 | not differentially expressed | *down-regulated* | not differentially expressed | *down-regulated* | not differentially expressed | *down-regulated* |
| Gene 56 | up-regulated | *down-regulated* | not differentially expressed | not differentially expressed | up-regulated | *down-regulated* |
| Gene 57 | up-regulated | *down-regulated* | not differentially expressed | not differentially expressed | up-regulated | *down-regulated* |
| Gene 58 | up-regulated | *down-regulated* | up-regulated | not differentially expressed | up-regulated | *down-regulated* |
| Gene 59 | up-regulated | not differentially expressed | up-regulated | not differentially expressed | up-regulated | *down-regulated* |
| Gene 60 | up-regulated | not differentially expressed | up-regulated | not differentially expressed | up-regulated | *down-regulated* |

FIG. 8

| Gene Symbol na30 hg19 | TCID | Probeset ID | Repeatability Score | BH adjusted LIMMA p-value | Gene Expression Effect Size | Final Rank |
|---|---|---|---|---|---|---|
| DEFB1 | 3122678 | 3122688 | 1 | 2.68E-09 | 2.14 | 2 |
| PVALB | 3959862 | 3959869 | 1 | 1.09E-08 | 2.30 | 3 |
| ALDH1B1 | 3169331 | 3169333 | 1 | 4.39E-10 | 1.40 | 4 |
| EGF | 2739308 | 2739364 | 1 | 4.72E-11 | 1.15 | 5 |
| KCNJ1 | 3397774 | 3397776 | 1 | 4.72E-11 | 1.08 | 6 |
| ITGB3 | 3724545 | 3724571 | 1 | 2.68E-09 | -1.57 | 7 |
| PFKFB2 | 2377094 | 2377112 | 1 | 1.53E-09 | 1.41 | 8 |
| NUPR1 | 3654699 | 3654707 | 1 | 6.46E-09 | 1.63 | 11 |
| HSD17B6 | 3417703 | 3417718 | 1 | 5.63E-06 | -2.33 | 12 |
| IGF2BP2 | 2708922 | 2708962 | 1 | 8.96E-08 | -1.70 | 16 |
| CD44 | 3326635 | 3326705 | 1 | 1.58E-09 | -1.17 | 17 |
| FRK | 2970897 | 2970926 | 1 | 1.07E-08 | 1.30 | 21 |
| SDHA | 2798538 | 2798548 | 1 | 3.87E-09 | 0.96 | 22 |
| SDHALP1 | 2798538 | 2798548 | 1 | 3.87E-09 | 0.96 | 22 |
| SDHALP2 | 2798538 | 2798548 | 1 | 3.87E-09 | 0.96 | 22 |
| SDHAP3 | 2798538 | 2798548 | 1 | 3.87E-09 | 0.96 | 22 |
| ODZ1 | 4020655 | 4020661 | 1 | 3.44E-05 | -1.91 | 23 |
| ST3GAL5 | 2562529 | 2562540 | 1 | 3.21E-08 | -1.24 | 25 |
| GOT1 | 3302990 | 3303003 | 1 | 8.96E-08 | 1.29 | 26 |
| RRAGD | 2964231 | 2964240 | 1 | 1.73E-07 | 1.27 | 27 |
| CPE | 2750627 | 2750676 | 1 | 9.64E-07 | -1.35 | 28 |
| PPP2R2B | 2880051 | 2880105 | 1 | 3.04E-09 | 0.78 | 29 |
| IQCA1 | 2604998 | 2605065 | 1 | 3.13E-08 | -1.05 | 31 |
| LOC100129258 | 2604998 | 2605065 | 1 | 3.13E-08 | -1.05 | 31 |
| RPL3 | 2604998 | 2605065 | 1 | 3.13E-08 | -1.05 | 31 |
| HSPA9 | 2877508 | 2877521 | 1 | 5.90E-09 | 0.85 | 32 |
| SNORD63 | 2877508 | 2877521 | 1 | 5.90E-09 | 0.85 | 32 |
| PHYH | 3278198 | 3278220 | 1 | 4.44E-08 | 1.13 | 33 |
| C5orf30 | 2822492 | 2822501 | 1 | 3.13E-08 | 0.98 | 35 |
| AIMP2 | 2988882 | 2988893 | 1 | 1.39E-08 | 0.92 | 39 |
| EIF2AK1 | 2988882 | 2988893 | 1 | 1.39E-08 | 0.92 | 39 |
| PVRL2 | 2688499 | 2688512 | 1 | 1.89E-06 | -1.35 | 40 |
| ZBED2 | 2688499 | 2688512 | 1 | 1.89E-06 | -1.35 | 40 |
| PDHA1 | 3970833 | 3970874 | 1 | 4.39E-09 | 0.74 | 41 |
| SLC16A1 | 2428501 | 2428504 | 1 | 3.12E-07 | 1.14 | 42 |
| FAH | 3603932 | 3603960 | 1 | 3.87E-09 | 0.65 | 43 |
| MDH2 | 3009299 | 3009305 | 1 | 2.28E-08 | 0.87 | 44 |
| AFF3 | 2566848 | 2566923 | 1 | 2.30E-09 | 0.40 | 46 |
| BRP44L | 2984616 | 2984647 | 1 | 3.21E-08 | 0.90 | 48 |
| CYCS | 3042001 | 3042003 | 1 | 6.55E-08 | 0.93 | 49 |
| FRMD3 | 3212008 | 3212070 | 1 | 1.44E-05 | -1.42 | 50 |

FIG. 10A
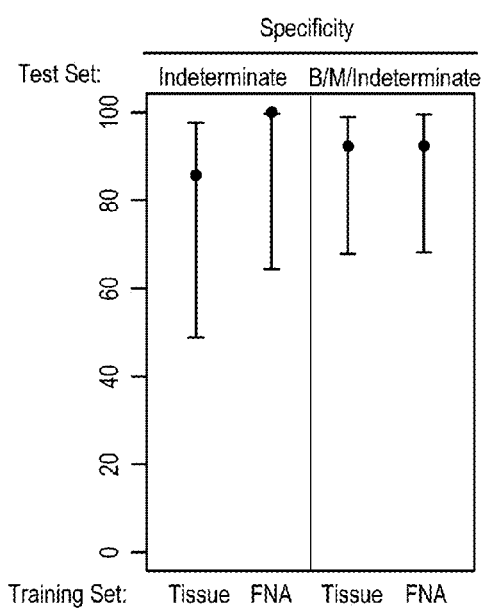
FIG. 10B
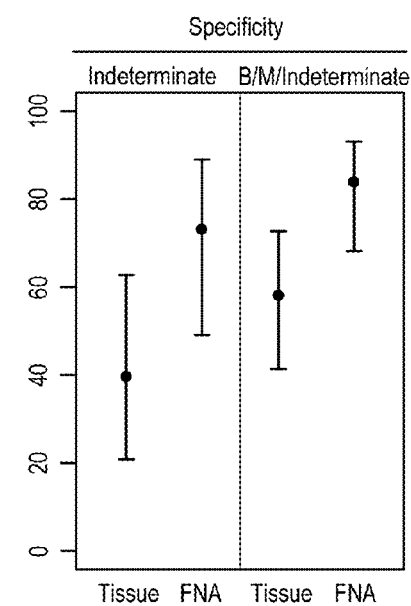
FIG. 10C
| Classifier Prediction | Post-surgical Histopathology | | | | | | | |
|---|---|---|---|---|---|---|---|---|
| | NHP | LCT | FA | BLN | PTC | FVPTC | HC | MLN |
| Benign | 12 | 3 | 13 | 1 | 0 | 1 | 0 | 0 |
| Suspicious | 3 | 1 | 1 | 0 | 6 | 4 | 2 | 1 |
| Total | 15 | 4 | 14 | 1 | 6 | 5 | 2 | 1 |
FIG. 10D
| Classifier Prediction | Post-surgical Histopathology | | | | | |
|---|---|---|---|---|---|---|
| | NHP | LCT | FA | PTC | FVPTC | HC |
| Benign | 5 | 2 | 6 | 0 | 0 | 0 |
| Suspicious | 2 | 1 | 1 | 2 | 3 | 2 |
| Total | 7 | 3 | 7 | 2 | 3 | 2 |

FIG. 11

| Subtype | Tissue Training Set (n=178) | FNA Training Set (n=137) | Independent FNA Test Set Benign, Malignant, & Indeterminate (n=48) | Independent FNA Test Set Indeterminate only (n=24) |
|---|---|---|---|---|
| NHP | 23 | 67 | 15 | 7 |
| LCT | 40 | 18 | 4 | 3 |
| FA | 26 | 9 | 14 | 7 |
| HA | 0 | 2 | 0 | 0 |
| BLN | 0 | 0 | 1 | 0 |
| Total Benign | 89 | 96[a] | 34[b] | 17 |
| HC | 23 | 0 | 2 | 2 |
| FC | 19 | 3 | 0 | 0 |
| FVPTC | 21 | 4 | 5 | 3 |
| PTC | 26 | 34 | 6 | 2 |
| MLN | 0 | 0 | 1 | 0 |
| Total Malignant | 89 | 41[c] | 14 | 7 |

A subset of samples did not have post-surgical histopathology labels; (a) 68/96, (b) 6/34, and (c) 4/41. Abbreviations: FA, follicular adenoma; FC, follicular carcinoma; FVPTC, follicular variant of papillary carcinoma; HA, follicular adenoma; LCT, lymphocytic thyroiditis; NHP, nodular hyperplasia; PTC, papillary thyroid carcinoma; BLN, benign lymph node; MLN, malignant lymph node.

FIG. 14

| KEGG Pathways ORA | | | |
|---|---|---|---|
| Subcategory | Number of Genes Expected | Number of Genes Observed | p-value (FDR) |
| Cell adhesion molecules (CAMs) | 8 | 28 | 4.17e-07 |
| Olfactory transduction | 24 | 3 | 1.80e-06 |
| Focal adhesion | 12 | 29 | 0.0003 |
| Adherens junction | 5 | 15 | 0.0006 |
| Arrhythmic right ventricular cardiomyopathy (ARVC) | 5 | 15 | 0.0006 |
| ECM-receptor interaction | 5 | 16 | 0.0006 |
| Metabolic pathways | 66 | 39 | 0.0006 |
| Tight junction | 8 | 21 | 0.0006 |
| Leukocyte transendothelial migration | 7 | 19 | 0.0009 |
| Complement coagulation cascades | 4 | 13 | 0.0021 |
| GO Pathways ORA | | | |
| Subcategory | Number of Genes Expected | Number of Genes Observed | p-value (FDR) |
| Plasma membrane | 113 | 220 | 2.82e-22 |
| Cell adhesion | 26 | 77 | 8.04e-16 |
| Defense response | 22 | 59 | 1.09e-09 |
| Nuclear part | 75 | 28 | 3.63e-09 |
| Organelle part | 150 | 87 | 1.40e-08 |
| Response to wounding | 17 | 47 | 1.97e-08 |
| Nucleus | 144 | 87 | 2.41e-07 |
| Extracellular region part | 26 | 59 | 2.41e-07 |
| Intracellular | 339 | 266 | 3.24e-07 |
| Locomotion | 17 | 44 | 6.47e-07 |

Numbers in regular font refer to pathways that are over-represented by top differentially expressed genes; those in bold refer to pathways that are under-represented train on tissue test on FNAs

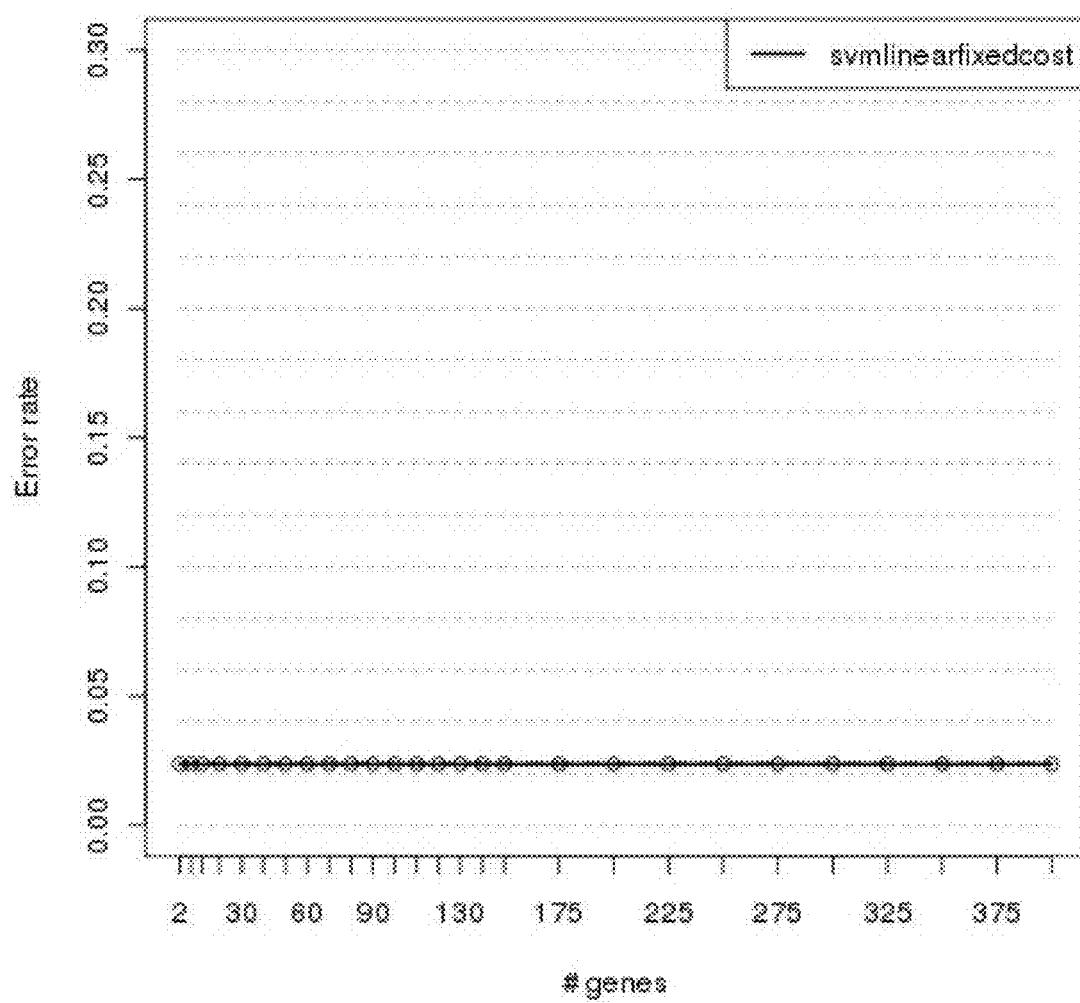

FIG. 24A
| Condition | Total | RIN | | | Concentration, ng/ul | | |
|---|---|---|---|---|---|---|---|
| | | Median | Range | IQR | Median | Range | IQR |
| -80C | 30 | 6.3 | 1 - 8.5 | 6 - 6.6 | 3.4 | 0.1 - 30.1 | 1 - 7.8 |
| 1 day | 30 | 6.4 | 1 - 8.4 | 5.8 - 7 | 7.7 | 0.1 - 188.5 | 1.8 - 18.1 |
| 2 days | 30 | 6.2 | 2.6 - 7.4 | 5.4 - 6.6 | 8.9 | 0.2 - 25.8 | 2.5 - 12.5 |
| 3 days | 30 | 6.4 | 1 - 7.8 | 5.9 - 7.2 | 3.2 | 0.1 - 29.2 | 1.7 - 10.5 |
| 4 days | 30 | 6.5 | 2.5 - 8.3 | 5.9 - 7 | 3.5 | 0.1 - 43.8 | 1 - 8 |
| 5 days | 30 | 6.3 | 1 - 7.6 | 5.9 - 6.8 | 3.2 | 0.1 - 19.8 | 1.5 - 11.7 |
| 6 days | 30 | 6.3 | 3.1 - 8 | 5.4 - 6.8 | 3.3 | 0.2 - 29.7 | 1.2 - 9.1 |
FIG. 24B
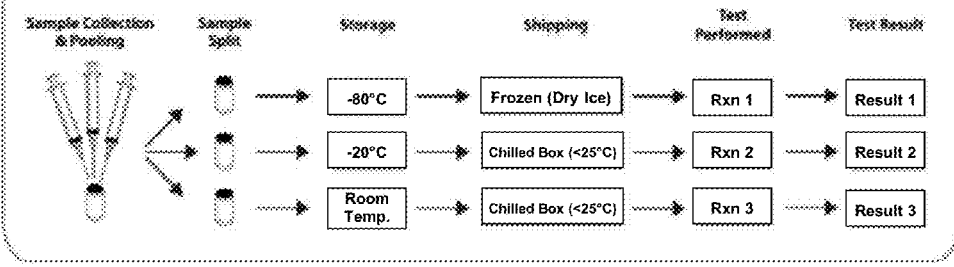
FIG. 24C
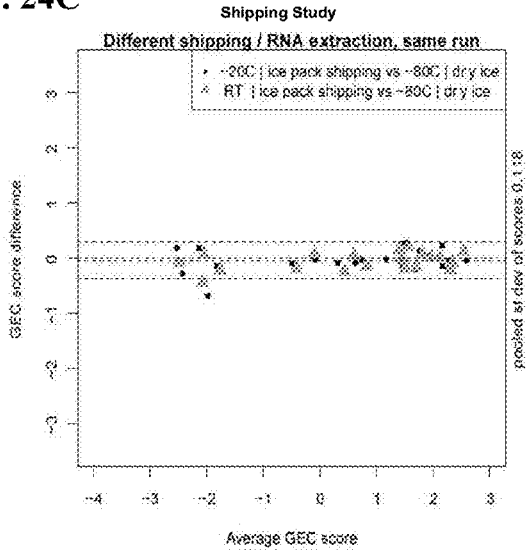

METHODS AND COMPOSITIONS FOR CLASSIFICATION OF SAMPLES

CROSS-REFERENCE

This application is a continuation in part of U.S. patent application Ser. No. 15/274,492, filed Sep. 23, 2016, which is a continuation of U.S. patent application Ser. No. 12/964, 666, filed Dec. 9, 2010, now U.S. Pat. No. 9,495,515, which claims priority to U.S. Provisional Patent Application No. 61/285,165, filed Dec. 9, 2009; this application is also a continuation in part of U.S. patent application Ser. No. 13/708,439, filed on Dec. 7, 2012, which claims priority to U.S. Provisional Patent Appl. No. 61/568,870, filed on Dec. 9, 2011, each of which is entirely incorporated herein by reference.

BACKGROUND OF THE INVENTION

Cancer is one of the leading causes of mortality worldwide; yet for many patients, the process of simply clearing the first step of obtaining an accurate diagnosis is often a frustrating and time-consuming experience. This is true of many cancers, including thyroid cancer. This is also particularly true of relatively rare diseases, such as Hurthle cell adenomas and carcinomas, which account for approximately 5% of thyroid neoplasms.

An inaccurate diagnosis of cancer can lead to unnecessary follow-up procedures, including costly surgical procedures, not to mention unnecessary emotional distress to the patient. In the case of thyroid cancer, it is estimated that out of the approximately 130,000 thyroid removal surgeries performed each year due to suspected malignancy in the United States, only about 54,000 are necessary; therefore, tens of thousands of unnecessary thyroid removal surgeries are performed annually. Continued treatment costs and complications due to the need for lifelong drug therapy to replace the lost thyroid function can cause further economic and physical harm.

SUMMARY OF THE INVENTION

In some embodiments, the invention provides a method to predict the gender of a subject, the method comprising: a. obtaining a biological sample from the subject; b. assaying an expression level of one or more gene expression products in the biological sample; and c. classifying the biological sample as from a male or a female by applying an algorithm to the expression level, thereby predicting the gender of the subject.

In some embodiments, the invention provides a method to identify lymphoma in a biological sample, the method comprising: a. obtaining a biological sample from a subject; b. assaying an expression level of one or more gene expression products; and c. classifying the biological sample as containing or not containing lymphoma by applying an algorithm to the expression levels.

In some embodiments, the invention provides a method to predict genetic mutations, the method comprising: a. obtaining a biological sample from a subject; b. assaying an expression level of one or more gene expression products in the biological sample; and c. applying an algorithm to the expression levels, wherein the algorithm predicts whether the sample comprises a BRAF mutation, thereby predicting genetic mutations.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 2 is a table that lists 16 biomarker panels that can be used to diagnose a thyroid condition.

FIG. 3 is a table that lists 7 classification panels that can be used to diagnose a thyroid condition. Classifier 7 is at times herein referred to as "main classifier."

FIG. 4 is a table that lists biomarkers that can be assigned to the indicated classification panel.

FIG. 5 is a table providing a model of a gene expression matrix that differentiates between malignant and benign thyroid fine needle aspirates (FNA) using a hypothetical panel of 20 biomarkers.

FIG. 6 is a table providing a model of a gene expression matrix that differentiates between malignant and benign thyroid FNA samples using a panel of 20 biomarkers. This figure has the identical biomarker signature to that displayed in FIG. 5, except that the individual biomarkers are different.

FIG. 7 is a table providing a model of a gene expression matrix that differentiates between malignant and benign thyroid FNA samples using a panel of 20 biomarkers. This table uses genetic markers that differ from those in FIG. 5 and FIG. 6 and that also provide a different biomarker signature from that in FIG. 5 and FIG. 6.

FIG. 8 is a table providing an exemplary list of biomarkers that can be used, e.g., to identify the presence of Hurthle cell adenoma and/or Hurthle cell carcinoma in a thyroid tissue sample.

FIG. 10A-FIG. 10D illustrates comparisons of trained molecular classifiers, including measures of sensitivity and specificity with regard to performance on two independent test sets (FIG. 10A and FIG. 10B) and illustrates subtype distribution of the two independent data sets and classifier prediction for each sample (FIG. 10C and FIG. 10D).

FIG. 11 is a table showing the composition of samples used in algorithm training and testing, by subtype, as defined by expert post-surgical histopathology review.

FIG. 14 is a table showing the results of over-representation analysis of top differentially expressed genes.

FIG. 17A, training used a cohort of thyroid tissue samples (n=254), and a classification score cut-off was set at >300. FIG. 17B, independent validation used a cohort of thyroid FNAs (n=483) and incurred only 5 gender prediction errors of samples from females that matched the gene signature observed in samples from males.

FIG. 19A-FIG. 19B illustrates an evaluation of the linear SVM classifier in classifying samples from male and female patients. FIG. 19A, cross-validated performance using Tissue cohort (n=254). FIG. 19B, cross-validated performance using FNA cohort (n=483).

FIG. 24A-FIG. 24C illustrates the RNA quality (RIN value) and quantity for control FNA samples kept at −80 C and FNA samples kept at 25 C for 1 to 6 days (FIG. 24A). Study design for testing FNA storage and shipping conditions (FIG. 24B). GEC intra-assay reproducibility across shipping conditions starting from pooled/split FNA sample (FIG. 24C).

FIG. 27A and FIG. 27B demonstrate markers of thyroid malignancy (cytokeratin-19, CITED1). FIG. 27C-FIG. 27F demonstrate intensity of follicular cell markers (cytokeratin-7, thyrotropin receptor, thyroglobulin, and thyroid transcription factor 1 [TTF-1], respectively). Dashed horizontal lines for follicular markers show 10%, 20%, 30% percentiles of that marker's intensity in the entire cohort of cytologically indeterminate samples.

DETAILED DESCRIPTION OF THE INVENTION

I. Introduction

Figure 1A:
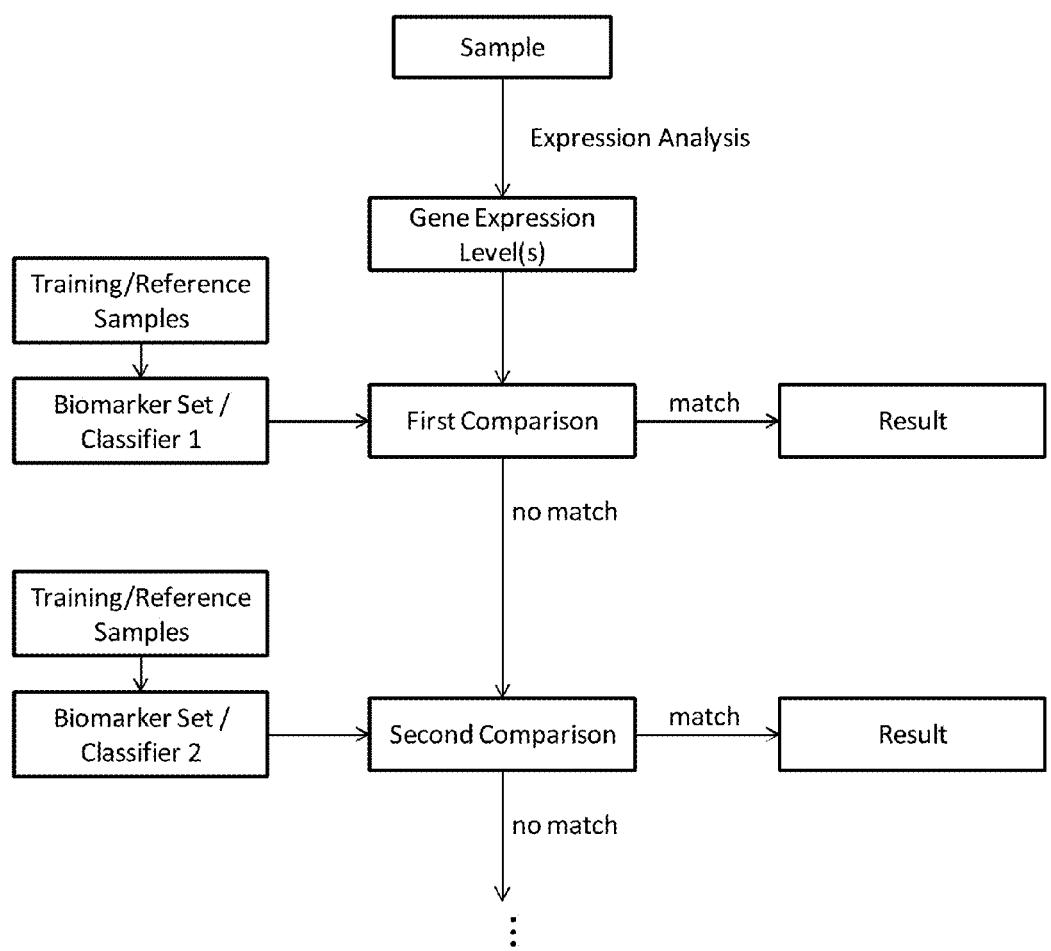
FIG. 1A-FIG. 1C are flow charts illustrating exemplary embodiments (FIG. 1A and FIG. 1B) and an exemplary system architecture (FIG. 1C).

The present disclosure provides methods of identifying, classifying, or characterizing biological samples and related kits and compositions. The methods, and related kits and compositions, disclosed herein can be used for identifying abnormal cellular proliferation in a biological test sample. Methods of differentiating benign from suspicious (or malignant) tissue are provided, as well as methods of identifying definitive benign tissue, and related kits, compositions and business methods. Sets of biomarkers useful for identifying benign or suspicious tissue are provided, as well as methods of obtaining such sets of biomarkers. For example, this disclosure provides novel classification panels that can be obtained from gene expression analysis of sample cohorts exhibiting different pathologies. This disclosure also provides methods of reclassifying an indeterminate biological sample (e.g., surgical tissue, thyroid tissue, thyroid FNA sample, etc.) into a benign versus suspicious (or malignant) category, and related compositions, business methods and kits. In some cases, this disclosure provides a "main classifier" obtained from expression analysis using panels of biomarkers, and that can be used to designate a sample as benign or suspicious (or malignant). This disclosure also provides a series of steps that can precede applying a main classifier to expression level data from a biological sample, such as a clinical sample. Such series of steps can include an initial cytology or histopathology study of the biological sample, followed by analysis of gene (or other biomarker) expression levels in the sample. In some embodiments, the cytology or histopathology study occurs before, concurrently with, or after the step of applying any of the classifiers described herein. The methods, kits, and compositions provided herein can also be used in predicting gender, predicting genetic mutations, and/or pre-screening the samples for the presence of a confounding condition prior to the application of the main classifier.

Expression levels for a sample can be compared to gene expression data for two or more different sets of biomarkers, the gene expression data for each set of biomarkers comprising one or more reference gene expression levels correlated with the presence of one or more tissue types, wherein the expression level is compared to gene expression data for the two or more sets of biomarkers in sequential fashion. Comparison of expression levels to gene expression data for sets of biomarkers can comprise the application of a classifier. For example, analysis of the gene expression levels can involve sequential application of different classifiers described herein to the gene expression data. Such sequential analysis can involve applying a classifier obtained from gene expression analysis of cohorts of diseased tissue, followed by applying a classifier obtained from analysis of a mixture of different biological samples, some of such samples containing diseased tissues and others containing benign tissue. The diseased tissue can be malignant or cancerous tissue (including tissue that has metastasized from another organ). The diseased tissue can be thyroid cancer or a non-thyroid cancer that has metastasized to the thyroid.

The classifier can be obtained from gene expression analysis of samples hosting or containing foreign tissue (e.g., a thyroid tissue sample containing parathyroid tissue).

Classifiers used early in the sequential analysis can be used to either rule-in or rule-out a sample as benign or suspicious. Classifiers used in the sequential analysis can also be used to identify sample mix-ups; screen out samples that are inappropriate for the application of a main classifier; and/or to provide further diagnostic, theranostic, or prognostic information. In some embodiments, such sequential analysis ends with the application of a "main" classifier to data from samples that have not been ruled out by the preceding classifiers, wherein the main classifier is obtained from data analysis of gene expression levels in multiple types of tissue and wherein the main classifier is capable of designating the sample as benign or suspicious (or malignant).

Classifiers can also be used to pre-screen expression data derived from samples in order to determine whether it is appropriate to apply a main classifier to the samples. For example, a classifier can be applied to determine whether an individual sample fits a profile for the samples used to train the main classifier. A classifier can also be used to pre-screen samples to determine whether the sample contains a confounding condition. For example, a classifier can be used to pre-screen thyroid samples for the presence of non-thyroid cell types (e.g., cancers that have metastasized from another tissue, e.g., lymphomas). The use of pre-screening classifiers can reduce the percentage of false positives returned by the main classifier. Classifiers can also be used to screen expression data from samples in order to determine whether there has been a sample mix-up. For example, a classifier can be used in order to predict a gender based upon a sample, which can be compared to identifying information accompanying the samples, in order to determine whether the samples have been mislabeled or otherwise mixed-up.

One example of a condition that can be identified or characterized using the subject methods is thyroid cancer. The thyroid has at least two kinds of cells that make hormones. Follicular cells make thyroid hormone, which affects heart rate, body temperature, and energy level. C cells make calcitonin, a hormone that helps control the level of calcium in the blood. Abnormal growth in the thyroid can result in the formation of nodules, which can be either benign or suspicious (or malignant). Thyroid cancer includes at least four different kinds of malignant tumors of the thyroid gland: papillary, follicular, medullary and anaplastic.

Expression profiling using panels of biomarkers can be used to characterize thyroid tissue as benign, suspicious, and/or malignant. Panels can be derived from analysis of gene expression levels of cohorts containing benign (non-cancerous) thyroid subtypes including follicular adenoma (FA), nodular hyperplasia (NHP), lymphocytic thyroiditis (LCT), and Hurthle cell adenoma (HA); malignant subtypes including follicular carcinoma (FC), papillary thyroid carcinoma (PTC), follicular variant of papillary carcinoma (FVPTC), medullary thyroid carcinoma (MTC), Hürthle cell carcinoma (HC), and anaplastic thyroid carcinoma (ATC). Such panels can also be derived from non-thyroid subtypes including renal carcinoma (RCC), breast carcinoma (BCA), melanoma (MMN), B cell lymphoma (BCL), and parathyroid (PTA). Biomarker panels associated with normal thyroid tissue (NML) can also be used in the methods and compositions provided herein. Exemplary panels of biomarkers are provided in FIG. 2, and will be described further herein. Of note, each panel listed in FIG. 2, relates to a signature, or pattern of biomarker expression (e.g., gene expression), that correlates with samples of that particular pathology or description.

The present disclosure also provides novel methods and compositions for identification of types of aberrant cellular proliferation through an iterative process (e.g., differential diagnosis) such as carcinomas including follicular carcinomas (FC), follicular variant of papillary thyroid carcinomas (FVPTC), Hurthle cell carcinomas (HC), Hurthle cell adenomas (HA); papillary thyroid carcinomas (PTC), medullary thyroid carcinomas (MTC), and anaplastic carcinomas (ATC); adenomas including follicular adenomas (FA); nodule hyperplasias (NHP); colloid nodules (CN); benign nodules (BN); follicular neoplasms (FN); lymphocytic thyroiditis (LCT), including lymphocytic autoimmune thyroiditis; parathyroid tissue; renal carcinoma metastasis to the thyroid; melanoma metastasis to the thyroid; B-cell lymphoma metastasis to the thyroid; breast carcinoma to the thyroid; benign (B) tumors, malignant (M) tumors, and normal (N) tissues. The present disclosure further provides novel gene expression markers and novel groups of genes and markers useful for the characterization, diagnosis, and/or treatment of cellular proliferation. Additionally, the present disclosure provides methods for providing enhanced diagnosis, differential diagnosis, monitoring, and treatment of cellular proliferation.

The present disclosure provides lists of specific biomarkers useful for classifying tissue (e.g., thyroid tissue). However, the present disclosure is not meant to be limited solely to the specific biomarkers disclosed herein. Rather, it is understood that any biomarker, gene, group of genes or group of biomarkers identified through methods described herein is encompassed by the present disclosure.

All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained.

In some cases, the method provides a number, or a range of numbers, of biomarkers (including gene expression products) that can be used to diagnose or otherwise characterize a biological sample. The number of biomarkers used can be between about 1 and about 500; for example about 1-500, 1-400, 1-300, 1-200, 1-100, 1-50, 1-25, 1-10, 10-500, 10-400, 10-300, 10-200, 10-100, 10-50, 10-25, 25-500, 25-400, 25-300, 25-200, 25-100, 25-50, 50-500, 50-400, 50-300, 50-200, 50-100, 100-500, 100-400, 100-300, 100-200, 200-500, 200-400, 200-300, 300-500, 300-400, 400-500, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or any included range or integer. For example, at least about 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, 500 or more total biomarkers can be used. The number of biomarkers used can be less than or equal to about 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, 500, or more.

The present methods and compositions also relate to the use of "biomarker panels" for purposes of identification, classification, diagnosis, or to otherwise characterize a biological sample. The methods and compositions can also use groups of biomarker panels, herein described as "classification panels," examples of which can be found in FIG. 3, FIG. 4, Table 1, Table 2, Table 3, Table 5, Table 9, Table 10, Table 11, Table 12, and Table 13. Often the pattern of levels of gene expression of biomarkers in a panel (also known as a signature) is determined and then used to evaluate the signature of the same panel of biomarkers in a biological sample, such as by a measure of similarity between the sample signature and the reference signature. In some embodiments, the method involves measuring (or obtaining) the levels of two or more gene expression products that are within a biomarker panel and/or within a classification panel. The number of biomarkers in the panel can be between about 1 and about 500; for example about 1-500, 1-400, 1-300, 1-200, 1-100, 1-50, 1-25, 1-10, 10-500, 10-400, 10-300, 10-200, 10-100, 10-50, 10-25, 25-500, 25-400, 25-300, 25-200, 25-100, 25-50, 50-500, 50-400, 50-300, 50-200, 50-100, 100-500, 100-400, 100-300, 100-200, 200-500, 200-400, 200-300, 300-500, 300-400, 400-500, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or any included range or integer. For example, the biomarker panel or a classification panel can contain at least about 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, 500, or more biomarkers. The biomarker panel or a classification panel can contain no more than about 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, or 500 biomarkers. The classification panel can contain between about 1 and about 25 different biomarker panels; for example, about 1-25, 1-20, 1-15, 1-10, 1-5, 5-25, 5-20, 5-15, 5-10, 10-25, 10-20, 10-15, 15-25, 15-20, 20-25, 1, 2, 3, 4, 5, 6, 7, 8, 9, 10, 11, 12, 13, 14, 15, 16, 17, 18, 19, 20, 21, 22, 23, 24, or 25 different biomarker panels. The classification panel can contain at least about 1, 2, 3, 4, 5, 6, 7, 8, 9, 10, 11, 12, 13, 14, 15, 16, 17, 18, 19, 20, 21, 22, 23, 24, or 25 different biomarker panels. The classification panel can contain no more than about 1, 2, 3, 4, 5, 6, 7, 8, 9, 10, 11, 12, 13, 14, 15, 16, 17, 18, 19, 20, 21, 22, 23, 24, or 25 different biomarker panels. The methods can comprise predicting the gender of a subject from which the sample was obtained. The methods can comprise pre-screening samples for the presence of confounding conditions; for example, pre-screening thyroid tissue samples for the presence of lymphomas. The methods can comprise diagnosing a subject with a cancer (e.g., a thyroid cancer). The methods can comprise predicting whether a subject has a genetic mutation (e.g., BRAF V600E) based upon a cohort of gene expression products in a sample from the subject.

The present disclosure provides methods of identifying, classifying, or diagnosing cancer comprising the steps of: obtaining an expression level for one or more gene expression products of a biological sample; and identifying the biological sample as benign wherein the gene expression level indicates a lack of cancer in the biological sample. Also provided are methods of identifying, classifying, or diagnosing cancer comprising the steps of: obtaining an expression level for one or more gene expression products of a biological sample; and identifying the biological sample as malignant or suspicious wherein the gene expression level is indicative of a cancer in the biological sample. For example, this can be done by correlating the patterns of gene expression levels, as defined in classification panels described herein, with the gene expression level in the sample, in order to identify (or rule out) the presence of thyroid cancer in the biological sample. Methods to identify thyroid cancer can also comprise one or more pre- and/or post-screening steps. Screening steps can comprise screening samples for the presence of a confounding condition, such as lymphoma; predicting the gender of the source subject, which can be used to identify sample mix-ups; and/or screening a sample for the presence of a genetic mutation (e.g., BRAF V600E). The methods for identifying, characterizing, diagnosing, and/or screening samples can comprise covariate analysis to account for sample heterogeneity. The gene expression products can be associated with one or more of the biomarkers in FIG. 3, FIG. 4, Table 1, Table 2, Table 3, Table 5, Table 9, Table 10, Table 11, Table 12, Table 13, and/or Table 20.

The present disclosure provides methods of identifying, classifying, and/or characterizing samples (e.g., diagnosing cancer or other condition, predicting gender, predicting genetic mutations, pre-screening for a confounding condition, etc.), wherein both the specificity and sensitivity are between about 50% and about 100%; for example, about 50-100%, 50-99%, 50-95%, 50-90%, 50-80%, 50-70%, 50-60%, 60-100%, 60-99%, 60-95%, 60-90%, 60-80%, 60-70%, 70-100%, 70-99%, 70-95%, 70-90%, 70-80%, 80-100%, 80-99%, 80-95%, 80-90%, 90-100%, 90-99%, 90-95%, 95-100%, 95-99%, 99-100%, 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100%. The methods can comprise comparing gene expression product levels (e.g., profile) from a biological sample with a biomarker panel and/or a classification panel; and characterizing the biological sample (e.g., as cancerous, suspicious, or benign; as male or female; as mutant or wild-type; etc.) based on the comparison. The specificity of the methods disclosed herein can be at least about 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100%. The sensitivity of the methods disclosed herein can be at least about 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100%. In some cases, the specificity can be at least about 50% and the sensitivity of the can be at least about 50%. In some cases, the specificity can be at least about 70% and the sensitivity can be at least about 70%. In some cases, the specificity can be at least about 50%, and the sensitivity can be at least about 70%.

The present disclosure provides methods of identifying, classifying, or characterizing samples (e.g., diagnosing cancer or other condition, predicting gender, predicting genetic mutations, prescreening for a confounding condition, etc.), wherein the negative predictive value (NPV) can be greater than or equal to about 90%; for example, the NPV can be at least about 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100%. The methods can further be characterized by having a specificity (or positive predictive value (PPV)) that can be at least about 30%; for example, the PPV can be at least about 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100%. In some cases, the NPV can be at least 95%, and the specificity can be at least 50%. In some cases, the NPV can be at least 95% and the specificity can be at least 70%.

Marker panels (e.g., classifiers, biomarker panels, classifier panels) can be chosen to accommodate adequate separation of conditions (e.g., benign from non-benign or suspicious expression profiles; male from female expression profiles; mutant from wild-type profiles; mixed tissue from tissue specific profiles; etc.). Training of such multi-dimensional classifiers (e.g., algorithms) can be performed on a plurality of biological samples. The plurality of biological samples can comprise between about 2 samples and about 4000 samples, or more; for example, about 2-4000, 2-2500, 2-1000, 2-500, 2-250, 2-100, 2-50, 2-10, 10-4000, 10-2500, 10-1000, 10-500, 10-250, 10-100, 10-50, 50-4000, 50-2500, 50-1000, 50-500, 50-250, 50-100, 100-4000, 100-2500, 100-1000, 100-500, 100-250, 250-4000, 250-2500, 250-1000, 250-500, 500-4000, 500-2500, 500-1000, 1000-4000, 1000-2500, 2500-4000, 2, 3, 4, 5, 6, 7, 8, 9, 10, 15, 20, 25, 30, 35, 40, 45, 50, 60, 70, 80, 90, 100, 125, 150, 175, 200, 225, 250, 300, 350, 400, 450, 500, 600, 700, 800, 900, 1000, 1250, 1500, 1750, 2000, 2250, 2500, 3000, 3500, 4000 such as at least 50, 100, 200, 300, 400, 500, 600, 700, 800, 900, 1000, 1500, 2000, 2500, 3000, 3500, or 4000, or more, biological samples. The biological samples can be any samples from which genetic material can be obtained. Exemplary sources of biological samples include fine needle aspiration, core needle biopsy, vacuum assisted biopsy, incisional biopsy, excisional biopsy, punch biopsy, shave biopsy or skin biopsy. In some cases, the biological samples comprise fine needle aspiration samples. In some cases, the biological samples comprise tissue samples (e.g., from excisional biopsy, incisional biopsy, or other biopsy). The biological samples can comprise a mixture of two or more sources; for example, fine needle aspirates and tissue samples. The percent of the total sample population that is obtained by FNA's can be greater than 10, 20, 30, 40, 50, 60, 70, 80, 90, or 95%. The biological samples can be samples derived from any tissue type. In some aspects, the biological samples comprise thyroid tissue or cells.

One or more training/test sets can be used in developing an algorithm or classifier. The overall algorithm error rate can be shown as a function of gene number for classification sub-type (e.g., benign vs. non-benign, male vs. female, mutant vs. wildtype, target vs. confounding cell types, etc.) Other performance metrics can be used, such as a performance metric that is a function of gene number for either subtypes or benign vs. malignant (B vs. M). Such performance metric can be obtained using CV, or other method known in the art. All results can be obtained using a support vector machine model which is trained and tested in a cross-validated mode on the samples.

There can be a specific (or range of) difference in gene expression between subtypes or sets of samples being compared to one another. In some examples, the gene expression of some similar subtypes can be merged to form a super-class that is then compared to another subtype, or another super-class, or the set of all other subtypes. The difference in gene expression level can be at least about 5%, 10%, 15%, 20%, 25%, 30%, 35%, 40%, 45%, 50%, 55%, 60%, 65%, 70%, 75%, 80%, 85%, 90%, 95%, 100% or more. The difference in gene expression level can be at least about 2, 3, 4, 5, 6, 7, 8, 9, 10 fold or more.

The present disclosure provides methods of identifying, classifying, or characterizing samples (e.g., diagnosing cancer or other condition, predicting gender, predicting genetic mutations, pre-screening for confounding conditions, etc.), with an accuracy that can be between about 50% and about 100%; for example, about 50-100%, 50-99%, 50-95%, 50-90%, 50-80%, 50-70%, 50-60%, 60-100%, 60-99%, 60-95%, 60-90%, 60-80%, 60-70%, 70-100%, 70-99%, 70-95%, 70-90%, 70-80%, 80-100%, 80-99%, 80-95%, 80-90%, 90-100%, 90-99%, 90-95%, 95-100%, 95-99%, 99-100%, 50%, 55%, 60%, 65%, 70%, 75%, 80%, 82%, 84%, 86%, 88%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100%. In some aspects, the methods can identify a biological sample as suspicious or malignant with an accuracy of at least about 50%, 60%, 70%, 75%, 80%, 85%, 90%, 95%, 99% or more. In some aspects, the biological sample can be identified as benign with an accuracy of greater than about 50%, 60%, 70%, 75%, 80%, 85%, 90%, 95%, 99% or more.

The present disclosure provides gene expression products corresponding to biomarkers selected from FIG. 4. The methods and compositions provided herein can include gene expression products corresponding to any or all of the biomarkers selected from FIG. 4, as well as any subset thereof, in any combination. For example, the methods can use gene expression products corresponding to at least 1, 2, 3, 4, 5, 6, 7, 8, 9, 10, 15, 20, 25, 30, 35, 40, 45 or 50, 100, 120, 140, 160 of the genetic markers provided in FIG. 4. In some cases, certain biomarkers can be excluded or substituted with other biomarkers, for example with biomarkers that exhibit a similar expression level profile with respect to a particular tissue type or sub-type.

The present disclosure provides methods and compositions (e.g., gene expression products, biomarker panels, and/or classifier panels) for use in predicting the gender of a subject from a biological sample obtained from the subject, wherein the compositions correspond to one or more biomarkers selected from Table 1, Table 2, and/or Table 3. The methods and compositions can include gene expression products, biomarker panels, and/or classifier panels corresponding to any or all of the biomarkers from Table 1, Table 2, and or Table 3. The methods and compositions can include gene expression products corresponding to between about 1 and about 110 biomarkers from Table 1, Table 2, and/or Table 3; for example, about 1-110, 1-75, 1-50, 1-25, 1-10, 10-110, 10-75, 10-50, 10-25, 25-110, 25-75, 25-50, 50-110, 50-75, 75-110, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 biomarkers from Table 1, Table 2, and/or Table 3. The methods and compositions can include gene expression products, biomarker panels, and/or classifier panels corresponding to RPS4Y1, EIF1AY, UTY, USP9Y, CYorf15B, and/or DDX3Y. The methods and compositions for use in predicting the gender of the subject can be used to pre-screen samples prior to applying a clinical or main classifier. The methods and compositions for use in predicting the gender of the subject can be used to identify sample mix-ups that can have occurred during sample collection, shipping, or processing.

The present disclosure provides methods and compositions (e.g., gene expression products, biomarker panels, and classifier panels) for use in identifying lymphomas in samples of non-lymphoid origin (e.g., thyroid samples). Lymphomas are cancers that can originate in the lymph nodes, but can metastasize to other tissues (e.g., thyroid tissue). Lymphocytic thyroiditis is group of non-malignant disorders characterized by thyroidal inflammation due to infiltration of the thyroid by lymphocytes. The methods and compositions disclosed herein can be used to separate or classify lymphoma from lymphocytic thyroiditis (LCT) samples. The methods and compositions disclosed herein can be used to separate lymphoma-containing thyroid samples from other thyroid samples. The methods and compositions disclosed herein can be used to pre-screen thyroid samples for the presence of lymphomas prior to the application of a main thyroid classifier (e.g., prior to characterizing or diagnosing a thyroid sample as suspicious/ malignant or benign). The methods and compositions disclosed herein can be used to reduce the rate of false positives when using the main thyroid classifier. The methods and compositions for use in identifying lymphomas in the sample can include gene expression products, biomarker panels, and/or classifier panels corresponding to any or all of the biomarkers from Table 5. The methods and compositions for use in identifying lymphomas in the sample can include gene expression products, biomarker panels, and/or classifier panels corresponding to between about 1 and about 200 biomarkers from Table 5; for example, about 1-200, 1-150, 1-100, 1-75, 1-50, 1-25, 25-200, 25-150, 25-100, 25-75, 25-50, 50-200, 50-150, 50-100, 50-75, 75-200, 75-150, 75-100, 100-200, 100-150, 150-200, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, or 200 biomarkers from Table 5.

The present disclosure provides methods and compositions (e.g., gene expression products, biomarker panels, classifier panels, etc.) to predict a mutation status of a subject from a biological sample obtained from the subject. The mutation status can be a BRAF mutation; for example, the mutation status can be positive or negative for BRAF V600E. The biological sample can be a thyroid sample; for example, the biological sample can be a fine needle aspiration of thyroid tissue. The methods and compositions disclosed herein can be used to categorize biological samples as originating from a subject that is wild-type for the BRAF gene or from a subject that is heterozygous for the BRAF V600E point mutation. The methods and compositions disclosed herein can be used to determine, diagnose, or predict whether a papillary thyroid carcinoma sample comprises the BRAF V600E point mutation. The BRAF V600E point mutation status can be used, for example, to decide upon a course of treatment for papillary thyroid carcinoma. The methods and compositions to predict the mutation status of a subject can include gene expression products, biomarker panels and/or classifier panels corresponding to any or all of the biomarkers in Table 9. The gene expression products, biomarker panels, and/or classifier panels can correspond to between about 1 and about 477 biomarkers from Table 9; for example, about 1-477, 1-300, 1-150, 1-100, 1-50, 1-10, 10-477, 10-300, 10-150, 10-100, 10-50, 50-477, 50-300, 50-150, 50-100, 100-477, 100-300, 100-150, 150-477, 150-300, 300-477, 1, 2, 3, 4, 5, 6, 7, 8, 9, 10, 15, 20, 25, 30, 35, 40, 45, 50, 60, 70, 80, 90, 100, 110, 120, 130, 140, 150, 175, 200, 225, 250, 275, 300, 325, 350, 375, 400, 425, 450, or 477 biomarkers from Table 9.

Methods and compositions (e.g., gene expression products, biomarker panels, classifier panels, etc.) to predict a mutation status of a subject (e.g., BRAF V600E mutation status) can adjust for cellular content variation; for example, by using covariate analysis incorporating cell-type signal strength. For example, methods and compositions to predict mutation status in a thyroid sample can adjust for follicular cell signal strength, lymphocytic cell signal strength, and/or Hurthle cell signal strength. Any or all of the biomarkers in Table 11 (e.g., about 1, 2, 3, 4, 5, 6, 7, 8, 9, or 10 biomarkers from Table 11) can be used to adjust for, or estimate, Follicular cell signal strength. Any or all of the biomarkers in Table 12 (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 biomarkers from Table 12), can be used to adjust for, or estimate, Hurthle cell signal strength. Any or all of the biomarkers in Table 13 (e.g., about 1, 2, 3, 4, 5, 6, 7, 8, 9, 10, 11, 12, 13, 14, 15, 16, 17, 18, 19, 20, 21, 22, or 23 biomarkers from Table 13), can be used to adjust for, or estimate, Lymphocytic cell signal strength. Methods and compositions to predict mutation status (e.g., BRAF V600E mutation status) that comprise covariate analysis can include gene expression products, biomarker panels, and/or classifier panels corresponding to any or all of the biomarkers in Table 10. Methods and compositions to predict mutation status, such as BRAF V600E mutation status, can comprise gene expression products, biomarker panels, and/or classifier panels that correspond to between about 1 and about 36 biomarkers from Table 10; for example, about 1-36, 1-24, 1-12, 1-6, 6-36, 6-24, 6-12, 12-36, 12-24, 24-36, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 biomarkers from Table 10.

The methods of the present disclosure can improve upon the accuracy of current methods of cancer diagnosis. The methods can provide improved accuracy of identifying benign, or definitively benign, samples (e.g., thyroid samples). Improved accuracy can be obtained by using algorithms trained with specific sample cohorts, high numbers of samples, and/or samples from individuals located in diverse geographical regions. The sample cohort can be from at least 1, 2, 3, 4, 5, 6, 67, 8, 9, 10, 15, 20, 25, 30, 35, 40, 45, 50, 55, 60, 65, 70, 75, or 80 different geographical locations (e.g., sites spread out across a nation, such as the United States, across a continent, or across the world). Geographical locations can include, but are not limited to, test centers, medical facilities, medical offices, post office addresses, cities, counties, states, nations, and continents. A classifier that is trained using sample cohorts from a first geographical region (e.g., the United States) can be re-trained for use on sample cohorts from other geographical regions (e.g., India, Asia, Europe, Africa, etc.).

The present disclosure provides methods of classifying cancer, wherein the methods comprise the steps of: obtaining a biological sample comprising gene expression products; determining the expression level for one or more gene expression products of the biological sample that are differentially expressed in different subtypes of a cancer; and identifying the biological sample as cancerous wherein the gene expression level is indicative of a subtype of cancer. In some cases, the subject methods distinguish follicular carcinoma from medullary carcinoma. In some cases, the subject methods are used to classify a thyroid tissue sample as comprising one or more benign or malignant tissue types (e.g. a cancer subtype), including but not limited to follicular adenoma (FA), nodular hyperplasia (NHP), lymphocytic thyroiditis (LCT), and Hurthle cell adenoma (HA), follicular carcinoma (FC), papillary thyroid carcinoma (PTC), follicular variant of papillary carcinoma (FVPTC), medullary thyroid carcinoma (MTC), Hürthle cell carcinoma (HC), and anaplastic thyroid carcinoma (ATC), renal carcinoma (RCC), breast carcinoma (BCA), melanoma (MMN), B cell lymphoma (BCL), and parathyroid (PTA). In some cases, the subject methods are used to classify a sample of thyroid tissue as comprising HC and/or HA tissue types. In some cases, the subject methods distinguish a benign thyroid disease from a malignant thyroid tumor/carcinoma.

In some cases, the biological sample is classified as cancerous or positive for a subtype of cancer with an accuracy of greater than about 75%, 80%, 85%, 86%, 87%, 88%, 89%, 90%, 91%, 92%, 93%, 94%, 95%, 96%, 97%, 98%, 99%, or 99.5%. The classification accuracy as used herein includes specificity, sensitivity, positive predictive value, negative predictive value, and/or false discovery rate.

Gene expression product markers of the present disclosure can provide increased accuracy of identifying, classifying, or characterizing samples (e.g., diagnosing cancer or other condition, predicting gender, predicting genetic mutations, prescreening for a confounding condition, etc.) through the use of multiple gene expression product markers in low quantity and quality, and statistical analysis using the algorithms of the present disclosure. The present disclosure provides, but is not limited to, methods of characterizing, classifying, or diagnosing gene expression profiles associated with thyroid cancer signatures, gender signatures, lymphoma signatures, and BRAF mutation signatures. The present disclosure also provides algorithms for characterizing and classifying biological samples (e.g., thyroid tissue samples) and kits and compositions useful for the application of said methods. The disclosure further includes methods for running a molecular profiling business.

Markers and genes can be identified to have differential expression between conditions (e.g., in thyroid cancer samples compared to thyroid benign samples; in samples from males compared to samples from females; in samples comprising lymphomas compared to samples with benign lymphatic signatures; in samples with genetic mutations such as BRAF V600E compared to wild type BRAF; etc.). Illustrative examples having a benign pathology include follicular adenoma, Hurthle cell adenoma, lymphocytic thyroiditis, and nodular hyperplasia. Illustrative examples having a malignant pathology include follicular carcinoma, follicular variant of papillary thyroid carcinoma, medullary carcinoma, and papillary thyroid carcinoma.

Biological samples can be treated to extract nucleic acids such as DNA or RNA. The nucleic acid can be contacted with an array of probes under conditions to allow hybridization, or the nucleic acids can be sequenced by any method known in the art. The degree of hybridization can be assayed in a quantitative matter using a number of methods known in the art. In some cases, the degree of hybridization at a probe position can be related to the intensity of signal provided by the assay, which therefore is related to the amount of complementary nucleic acid sequence present in the sample. Software can be used to extract, normalize, summarize, and/or analyze array intensity data from probes across the human genome or transcriptome including expressed genes, exons, introns, and miRNAs. The intensity of a given probe in samples (e.g., benign samples, malignant samples, etc.) can be compared against a reference set to determine whether differential expression is occurring in a sample. An increase or decrease in relative intensity at a marker position on an array corresponding to an expressed sequence can be indicative of an increase or decrease respectively of expression of the corresponding expressed sequence. An increase or decrease in relative intensity can also be indicative of a mutation in the expressed sequence.

The resulting intensity values for each sample can be analyzed using feature selection techniques including filter techniques, which can assess the relevance of features by looking at the intrinsic properties of the data; wrapper methods, which embed the model hypothesis within a feature subset search; and/or embedded techniques in which the search for an optimal set of features is built into a classifier algorithm.

Filter techniques useful in the methods of the present disclosure can include (1) parametric methods such as the use of two sample t-tests, ANOVA analyses, Bayesian frameworks, and Gamma distribution models; (2) model free methods such as the use of Wilcoxon rank sum tests, between-within class sum of squares tests, rank products methods, random permutation methods, and/or TNoM (Threshold Number of Misclasifications) which involves setting a threshold point for fold-change differences in expression between two datasets and then detecting the threshold point in each gene that minimizes the number of misclassifications; (3) and multivariate methods such as bivariate methods, correlation based feature selection methods (CFS), minimum redundancy maximum relevance methods (MRMR), Markov blanket filter methods, and/or uncorrelated shrunken centroid methods. Wrapper methods useful in the methods of the present disclosure can include sequential search methods, genetic algorithms, and/or estimation of distribution algorithms. Embedded methods useful in the methods of the present disclosure can include random forest algorithms, weight vector of support vector machine algorithms, and/or weights of logistic regression algorithms. Bioinformatics. 2007 Oct. 1; 23(19):2507-17, which is hereby incorporated by reference in its entirety, provides an overview of the relative merits of the filter techniques provided above for the analysis of intensity data.

Selected features can be classified using a classifier algorithm. Illustrative algorithms can include, but are not limited to, methods that reduce the number of variables such as principal component analysis algorithms, partial least squares methods, and/or independent component analysis algorithms. Illustrative algorithms can further include, but are not limited to, methods that handle large numbers of variables directly such as statistical methods and methods based on machine learning techniques. Statistical methods can include penalized logistic regression, prediction analysis of microarrays (PAM), methods based on shrunken centroids, support vector machine analysis, and regularized linear discriminant analysis. Machine learning techniques can include bagging procedures, boosting procedures, random forest algorithms, and/or combinations thereof. Cancer Inform. 2008; 6: 77-97, which is hereby incorporated by reference in its entirety, provides an overview of the classification techniques provided above for the analysis of microarray intensity data.

The markers and genes of the present disclosure can be utilized to identify, classify, and/or characterize cells or tissues (e.g., as cancerous or benign, as from a male or female, as comprising a genetic mutation or wild-type, etc.). The present disclosure includes methods for identifying, classifying, and/or characterizing tissues or cells comprising determining the differential expression of one or more markers or genes in a biological sample (e.g., a thyroid sample) of a subject wherein at least one of the markers or genes are listed in FIG. 4, Table 1, Table 2, Table 3, Table 5, Table 9, Table 10, Table 11, Table 12, Table 13, and/or Table 20. The present disclosure also includes methods for identifying thyroid pathology subtypes comprising determining the differential expression of one or more markers or genes in a thyroid sample of a subject wherein said markers or genes are listed in FIG. 4 and/or Table 20 along with the corresponding sub-type, as indicated in FIG. 4 and/or Table 20.

In accordance with the foregoing, the differential expression of a gene, genes, markers, mRNA, miRNAs, or a combination thereof as disclosed herein can be determined using northern blotting and employing the sequences as identified herein to develop probes for this purpose. Such probes can be composed of DNA or RNA or synthetic nucleotides or a combination of these and can advantageously be comprised of a contiguous stretch of nucleotide residues matching, or complementary to, a sequence corresponding to a genetic marker identified in FIG. 4, Table 1, Table 2, Table 3, Table 5, Table 9, Table 10, Table 11, Table 12, Table 13, and/or Table 20. Such probes can comprise a contiguous stretch of at least about 10-500 residues, or more; for example, about 10-500, 10-200, 10-150, 10-100, 10-75, 10-50, 10-25, 25-500, 25-200, 25-150, 25-100, 25-75, 25-50, 50-500, 50-200, 50-150, 50-100, 50-75, 75-500, 75-200, 75-150, 75-100, 100-500, 100-200, 100-150, 150-500, 150-200, 200-500, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 110, 120, 130, 140, 150, 160, 170, 180, 190, 200, 225, 250, 275, 300, 325, 350, 375, 400, 425, 450, 475, or 500 nucleotides, or more, derived from one or more of the sequences corresponding to a genetic marker identified in FIG. 4, Table 1, Table 2, Table 3, Table 5, Table 9, Table 10, Table 11, Table 12, Table 13, and/or Table 20. Thus, where a single probe binds multiple times to the transcriptome of a sample of cells that are in a first category (e.g., cancerous, suspected of being cancerous, predisposed to become cancerous, male, mutant, etc.), whereas binding of the same probe to a similar amount of transcriptome derived from the genome of cells of the same organ or tissue in a second category (e.g., benign, non-cancerous, female, wildtype, etc.) results in observably more or less binding, this is indicative of differential expression of a gene, multiple genes, markers, or miRNAs comprising, or corresponding to, the sequences corresponding to a genetic marker identified in FIG. 4, Table 1, Table 2, Table 3, Table 5, Table 9, Table 10, Table 11, Table 12, Table 13, and/or Table 20 from which the probe sequenced was derived.

Altered or differential gene expression between cell types or categories can be determined by measuring the relative amounts of gene expression products. Gene expression products can be RNA. The amount of RNA transcription can be determined, for example, by producing corresponding cDNAs and then analyzing the resulting DNA using probes developed from the gene sequences as corresponding to one or more genetic markers identified in FIG. 4, Table 1, Table 2, Table 3, Table 5, Table 9, Table 10, Table 11, Table 12, Table 13, and/or Table 20. The cDNA produced by use of reverse transcriptase can be amplified using polymerase chain reaction, or some other means, such as linear amplification, isothermal amplification, NASB, or rolling circle amplification, to determine the relative levels of resulting cDNA and, thereby, the relative levels of gene expression.

Altered or differential gene expression can also be determined by measuring gene expression products, such as proteins, by using agents that selectively bind to, and thereby detect, the presence of proteins encoded by the genes disclosed herein. Suitable agents can include antibodies. Antibodies can be bound to a fluorescent label or radiolabel. Antibodies can be generated against one of the polypeptides that is encoded by all or a fragment of one of the gene sequences corresponding to a genetic marker identified in FIG. 4, Table 1, Table 2, Table 3, Table 5, Table 9, Table 10, Table 11, Table 12, Table 13, and/or Table 20. The relative levels of antibody binding to biological samples (e.g., protein extracts of cells or tissues) can be used as a measure of the extent of expression, or differential expression, of the genes. Exemplary antibody related means of detecting protein levels include western blotting, Enzyme-Linked Immunosorbent Assays, protein chip arrays, or any other means known in the art. The genes and biomarkers disclosed herein can be differentially expressed due to increased copy number, decreased copy number, and/or altered transcription levels (e.g., over- or under-transcription, such as where the over-expression is due to over- or under-production of a transcription factor that activates or represses the gene and leads to repeated binding of RNA polymerase), which can thereby generating altered levels of RNA transcripts. Following translation, altered levels of RNA transcripts can produce altered levels of polypeptides or proteins, such as polypeptides encoded by all or a part of a polynucleotide sequence corresponding to a genetic marker identified in FIG. 4, Table 1, Table 2, Table 3, Table 5, Table 9, Table 10, Table 11, Table 12, Table 13, and/or Table 20. Protein level analysis can provide an additional means of ascertaining the expression of the genes identified according to the disclosure and can thereby be used in determining, or categorizing, biological samples (e.g., to diagnose the presence of a cancerous state in a sample derived from a patient to be tested, or the predisposition to develop cancer at a subsequent time in said patient; to predict the gender of the patient; to predict the mutation state of the patient; etc.).

In employing the methods of the disclosure, gene or marker expression indicative of a sample category or classification (e.g., cancerous state vs. benign, male vs. female, mutant vs. wildtype, lymphoma vs. non-lymphoma, etc.) need not be characteristic of every cell in the sample. Thus, the methods disclosed herein are useful for detecting the presence of a condition or state (e.g., a cancerous condition) within a tissue where less than all cells exhibit the complete pattern of differential expression. For example, a set of selected genes or markers, comprising sequences homologous under stringent conditions, or at least 90%, preferably 95%, identical to at least one of the sequences corresponding to a genetic marker identified in FIG. 4, Table 1, Table 2, Table 3, Table 5, Table 9, Table 10, Table 11, Table 12, Table 13, and/or Table 20; or probe sequences complementary to all or a portion thereof, can be found, using appropriate probes (e.g., DNA or RNA probes) to be present in about, less than about, or more than about 20%, 30%, 40%, 50%, 60%, 70%, 80%, 90%, or more of cells derived from a biological sample (e.g., of tumorous or malignant tissue). In some cases, a set of selected genes or markers correlated with a cancerous condition, and forming an expression pattern, can be absent from about, less than about, or more than about 20%, 30%, 40%, 50%, 60%, 70%, 80%, 90%, or more cells derived from corresponding non-cancerous, or otherwise normal, tissue. In one case, an expression pattern of a cancerous condition is detected in at least 70% of cells drawn from a cancerous tissue and absent from at least 70% of a corresponding normal, non-cancerous, tissue sample. In some cases, such expression pattern is found to be present in at least 80% of cells drawn from a cancerous tissue and absent from at least 80% of a corresponding normal, non-cancerous, tissue sample. In some cases, such expression pattern is found to be present in at least 90% of cells drawn from a cancerous tissue and absent from at least 90% of a corresponding normal, non-cancerous, tissue sample. In some cases, such expression pattern is found to be present in at least 100% of cells drawn from a cancerous tissue and absent from at least 100% of a corresponding normal, non-cancerous, tissue sample, although the latter case can represent a rare occurrence. It should also be noted that the expression pattern can be either completely present, partially present, or absent within affected cells, as well as unaffected cells. Therefore, in some cases, the expression pattern is present in variable amounts within affected cells; in some cases, the expression pattern is present in variable amounts within unaffected cells.

Molecular profiling can include detection, analysis, or quantification of one or more gene expression products (e.g., one or more nucleic acids (e.g., DNA or RNA), one or more proteins, or a combination thereof). The diseases or conditions to be diagnosed or characterized by the methods of the present disclosure can include, for example, conditions of abnormal growth, gender, mutation state, and/or heterogeneity of cellular content in one or more tissues of a subject. The tissues analyzed can include, but are not limited to, skin, heart, lung, kidney, breast, pancreas, liver, muscle, smooth muscle, bladder, gall bladder, colon, intestine, brain, esophagus, or prostate. The tissues analyzed by the methods of the present disclosure can include thyroid tissues.

II. Obtaining a Biological Sample

The methods of the present disclosure provide for obtaining a biological sample from a subject. As used herein, the term subject refers to any animal (e.g., a mammal), including but not limited to humans, non-human primates, rodents, dogs, cats, pigs, fish, and the like. The present methods and compositions can apply to biological samples from humans. The human can be a new-born, a baby, a child, an adolescent, a teenager, an adult, or a senior citizen. The human can be between about 1 month and 12 months old; for example, about 1, 2, 3, 4, 5, 6, 7, 8, 9, 10, 11, or 12 months old. The human can be between about 1 years old and about 110 years old; for example, about 1-110, 1-65, 1-35, 1-18, 1-11, 1-6, 1-2, 2-110, 2-65, 2-35, 2-18, 2-11, 2-6, 6-110, 6-65, 6-35, 6-18, 6-11, 11-110, 11-65, 11-35, 11-18, 18-110, 18-65, 18-35, 35-110, 35-65, 65-110, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 90, 100, 110 years of age.

The methods of obtaining provided herein include methods of biopsy including fine needle aspiration, core needle biopsy, vacuum assisted biopsy, incisional biopsy, excisional biopsy, punch biopsy, shave biopsy or skin biopsy. In some cases, the classifiers provided herein are applied to data only from biological samples obtained by FNA. In some cases, the classifiers provided herein are applied to data only from biological samples obtained by FNA or surgical biopsy. In some cases, the classifiers provided herein are applied to data only from biological samples obtained by surgical biopsy. In some cases, the classifiers themselves are obtained from analysis of data from samples obtained by a specific procedure. For example, a cohort of samples, wherein some were obtained by FNA, and others were obtained by surgical biopsy, can be the source of the samples that are analyzed for the classifiers used herein. In other cases, only data from samples obtained by FNA are used to obtain the classifiers herein. In other cases, only data from samples obtained by surgical procedures are used to obtain the classifiers herein.

Biological samples can be obtained from any of the tissues provided herein; including, but not limited to, skin, heart, lung, kidney, breast, pancreas, liver, muscle, smooth muscle, bladder, gall bladder, colon, intestine, brain, prostate, esophagus, or thyroid. Alternatively, the sample can be obtained from any other source; including, but not limited to, blood, sweat, hair follicle, buccal tissue, tears, menses, feces, or saliva. The biological sample can be obtained by a medical professional. The medical professional can refer the subject to a testing center or laboratory for submission of the biological sample. The subject can directly provide the biological sample. In some cases, a molecular profiling business can obtain the sample. In some cases, the molecular profiling business obtains data regarding the biological sample, such as biomarker expression level data, or analysis of such data.

A biological sample can be obtained by methods known in the art such as the biopsy methods provided herein, swabbing, scraping, phlebotomy, or any other suitable method. The biological sample can be obtained, stored, or transported using components of a kit of the present disclosure. In some cases, multiple biological samples, such as multiple thyroid samples, can be obtained for analysis, characterization, or diagnosis according to the methods of the present disclosure. In some cases, multiple biological samples, such as one or more samples from one tissue type (e.g., thyroid) and one or more samples from another tissue type (e.g., buccal) can be obtained for diagnosis or characterization by the methods of the present disclosure. In some cases, multiple samples, such as one or more samples from one tissue type (e.g., thyroid) and one or more samples from another tissue (e.g., buccal) can be obtained at the same or different times. In some cases, the samples obtained at different times are stored and/or analyzed by different methods. For example, a sample can be obtained and analyzed by cytological analysis (e.g., using routine staining). In some cases, a further sample can be obtained from a subject based on the results of a cytological analysis. The diagnosis of cancer or other condition can include an examination of a subject by a physician, nurse or other medical professional. The examination can be part of a routine examination, or the examination can be due to a specific complaint including, but not limited to, one of the following: pain, illness, anticipation of illness, presence of a suspicious lump or mass, a disease, or a condition. The subject may or may not be aware of the disease or condition. The medical professional can obtain a biological sample for testing. In some cases the medical professional can refer the subject to a testing center or laboratory for submission of the biological sample.

In some cases, the subject can be referred to a specialist such as an oncologist, surgeon, or endocrinologist for further diagnosis. The specialist can likewise obtain a biological sample for testing or refer the individual to a testing center or laboratory for submission of the biological sample. In any case, the biological sample can be obtained by a physician, nurse, or other medical professional such as a medical technician, endocrinologist, cytologist, phlebotomist, radiologist, or a pulmonologist. The medical professional can indicate the appropriate test or assay to perform on the sample, or the molecular profiling business of the present disclosure can consult on which assays or tests are most appropriately indicated. The molecular profiling business can bill the individual or medical or insurance provider thereof for consulting work, for sample acquisition and or storage, for materials, or for all products and services rendered.

A medical professional need not be involved in the initial diagnosis or sample acquisition. An individual can alternatively obtain a sample through the use of an over the counter kit. The kit can contain a means for obtaining said sample as described herein, a means for storing the sample for inspection, and instructions for proper use of the kit. In some cases, molecular profiling services are included in the price for purchase of the kit. In other cases, the molecular profiling services are billed separately.

A biological sample suitable for use by the molecular profiling business can be any material containing tissues, cells, nucleic acids, genes, gene fragments, expression products, gene expression products, and/or gene expression product fragments of an individual to be tested. Methods for determining sample suitability and/or adequacy are provided. The biological sample can include, but is not limited to, tissue, cells, and/or biological material from cells or derived from cells of an individual. The sample can be a heterogeneous or homogeneous population of cells or tissues. The biological sample can be obtained using any method known to the art that can provide a sample suitable for the analytical methods described herein.

A biological sample can be obtained by non-invasive methods, such methods including, but not limited to: scraping of the skin or cervix, swabbing of the cheek, saliva collection, urine collection, feces collection, collection of menses, tears, or semen. The biological sample can be obtained by an invasive procedure, such procedures including, but not limited to: biopsy, alveolar or pulmonary lavage, needle aspiration, or phlebotomy. The method of biopsy can further include incisional biopsy, excisional biopsy, punch biopsy, shave biopsy, or skin biopsy. The method of needle aspiration can further include fine needle aspiration, core needle biopsy, vacuum assisted biopsy, or large core biopsy. Multiple biological samples can be obtained by the methods herein to ensure a sufficient amount of biological material. Methods of obtaining suitable samples of thyroid are known in the art and are further described in the ATA Guidelines for thyroid nodule management (Cooper et al. *Thyroid* Vol. 16 No. 2 2006), herein incorporated by reference in its entirety. Generic methods for obtaining biological samples are also known in the art and further described in for example Ramzy, Ibrahim *Clinical Cytopathology and Aspiration Biopsy* 2001 which is herein incorporated by reference in its entirety. The biological sample can be a fine needle aspirate of a thyroid nodule or a suspected thyroid tumor. The fine needle aspirate sampling procedure can be guided by the use of an ultrasound, X-ray, or other imaging device.

A molecular profiling business can obtain a biological sample from a subject directly, from a medical professional, from a third party, and/or from a kit provided by the molecular profiling business or a third party. The biological sample can be obtained by the molecular profiling business after the subject, the medical professional, or the third party acquires and sends the biological sample to the molecular profiling business. The molecular profiling business can provide suitable containers and/or excipients for storage and transport of the biological sample to the molecular profiling business.

III. Storing the Sample

The methods of the present disclosure provide for storing a biological sample for a period of time, wherein the period of time can be seconds, minutes, hours, days, weeks, months, years or longer after the biological sample is obtained and before the biological sample is analyzed by one or more methods of the disclosure. The biological sample obtained from a subject can be subdivided prior to the step of storage or further analysis such that different portions of the biological sample are subject to different downstream methods or processes. The downstream methods or processes can include, but are not limited to, storage, cytological analysis, adequacy tests, nucleic acid extraction, molecular profiling and/or a combination thereof.

A portion of a biological sample can be stored while another portion of the biological sample is further manipulated. Such manipulations can include, but are not limited to, molecular profiling; cytological staining; nucleic acid (RNA or DNA) extraction, detection, or quantification; gene expression product (e.g., RNA or protein) extraction, detection, or quantification; fixation (e.g., formalin fixed paraffin embedded samples); and/or examination. The biological sample can be fixed prior to or during storage by any method known to the art, such methods including, but not limited to, the use of glutaraldehyde, formaldehyde, and/or methanol. In other cases, the sample is obtained and stored and subdivided after the step of storage for further analysis such that different portions of the sample are subject to different downstream methods or processes including but not limited to storage, cytological analysis, adequacy tests, nucleic acid extraction, molecular profiling or a combination thereof. In some cases, one or more biological samples are obtained and analyzed by cytological analysis, and the resulting sample material is further analyzed by one or more molecular profiling methods of the present disclosure. In such cases, the biological samples can be stored between the steps of cytological analysis and the steps of molecular profiling. The biological samples can be stored upon acquisition; for example, to facilitate transport or to wait for the results of other analyses. Biological samples can be stored while awaiting instructions from a physician or other medical professional.

A biological sample can be placed in a suitable medium, excipient, solution, and/or container for short term or long term storage. The storage can involve keeping the biological sample in a refrigerated or frozen environment. The biological sample can be quickly frozen prior to storage in a frozen environment. The biological sample can be contacted with a suitable cryopreservation medium or compound prior to, during, and/or after cooling or freezing the biological sample. The cryopreservation medium or compound can include, but is not limited to: glycerol, ethylene glycol, sucrose, and/or glucose. The suitable medium, excipient, or solution can include, but is not limited to: hanks salt solution; saline; cellular growth medium; an ammonium salt solution, such as ammonium sulphate or ammonium phosphate; and/or water. Suitable concentrations of ammonium salts can include solutions of between about 0.1 g/mL to 2.5 g/L, or higher; for example, about 0.1 g/ml, 0.2 g/ml, 0.3 g/ml, 0.4 g/ml, 0.5 g/ml, 0.6 g/ml, 0.7 g/ml, 0.8 g/ml, 0.9 g/ml, 1.0 g/ml, 1.1 g/ml, 1.2 g/ml, 1.3 g/ml, 1.4 g/ml, 1.5 g/ml, 1.6 g/ml, 1.7 g/ml, 1.8 g/ml, 1.9 g/ml, 2.0 g/ml, 2.2 g/ml, 2.3 g/ml, 2.5 g/ml or higher. The medium, excipient, or solution can optionally be sterile.

A biological sample can be stored at room temperature; at reduced temperatures, such as cold temperatures (e.g., between about 20° C. and about 0° C.); and/or freezing temperatures, including for example about 0° C., −1° C., −2° C., −3° C., −4° C., −5° C., −6° C., −7° C., −8° C., −9° C., −10° C., −12° C., −14° C., −15° C., −16° C., −20° C., −22° C., −25° C., −28° C., −30° C., −35° C., −40° C., −45° C., −50° C., −60° C., −70° C., −80° C., −100° C., −120° C., −140° C., −180° C., −190° C., or −200° C. The biological samples can be stored in a refrigerator, on ice or a frozen gel pack, in a freezer, in a cryogenic freezer, on dry ice, in liquid nitrogen, and/or in a vapor phase equilibrated with liquid nitrogen.

A medium, excipient, or solution for storing a biological sample can contain preservative agents to maintain the sample in an adequate state for subsequent diagnostics or manipulation, or to prevent coagulation. Said preservatives can include, but are not limited to, citrate, ethylene diamine tetraacetic acid, sodium azide, and/or thimersol. The medium, excipient or solution can contain suitable buffers or salts such as Tris buffers, phosphate buffers, sodium salts (e.g., NaCl), calcium salts, magnesium salts, and the like. In some cases, the sample can be stored in a commercial preparation suitable for storage of cells for subsequent cytological analysis, such preparations including, but not limited to Cytyc ThinPrep, SurePath, and/or Monoprep.

A sample container can be any container suitable for storage and or transport of a biological sample; such containers including, but not limited to: a cup, a cup with a lid, a tube, a sterile tube, a vacuum tube, a syringe, a bottle, a microscope slide, or any other suitable container. The container can optionally be sterile.

IV. Transportation of the Sample

The methods of the present disclosure provide for transport of a biological sample. In some cases, the biological sample is transported from a clinic, hospital, doctor's office, or other location to a second location whereupon the sample can be stored and/or analyzed by, for example, cytological analysis or molecular profiling. In some cases, the biological sample can be transported to a molecular profiling company in order to perform the analyses described herein. In other cases, the biological sample can be transported to a laboratory, such as a laboratory authorized or otherwise capable of performing the methods of the present disclosure, such as a Clinical Laboratory Improvement Amendments (CLIA) laboratory. The biological sample can be transported by the individual from whom the biological sample derives. Said transportation by the individual can include the individual appearing at a molecular profiling business or a designated sample receiving point and providing the biological sample. The providing of the biological sample can involve any of the techniques of sample acquisition described herein, or the biological sample can have already have been acquired and stored in a suitable container as described herein. In other cases, the biological sample can be transported to a molecular profiling business using a courier service, the postal service, a shipping service, or any method capable of transporting the biological sample in a suitable manner. In some cases, the biological sample can be provided to the molecular profiling business by a third party testing laboratory (e.g., a cytology lab). In other cases, the biological sample can be provided to the molecular profiling business by the individual's primary care physician, endocrinologist or other medical professional. The cost of transport can be billed to the individual, medical provider, or insurance provider. The molecular profiling business can begin analysis of the sample immediately upon receipt, or can store the sample in any manner described herein. The method of storage can optionally be the same as chosen prior to receipt of the sample by the molecular profiling business.

A biological sample can be transported in any medium or excipient, including any medium or excipient provided herein suitable for storing the biological sample such as a cryopreservation medium or a liquid based cytology preparation. In some cases, the biological sample can be transported frozen or refrigerated, such as at any of the suitable sample storage temperatures provided herein.

Upon receipt of a biological sample by a molecular profiling business, a representative or licensee thereof, a medical professional, researcher, or a third party laboratory or testing center (e.g., a cytology laboratory), the biological sample can be assayed using a variety of analyses known to the art, such as cytological assays and genomic analysis. Such assays or tests can be indicative of cancer, a type of cancer, any other disease or condition, the presence of disease markers, the presence of genetic mutations, or the absence of cancer, diseases, conditions, or disease markers. The tests can take the form of cytological examination including microscopic examination as described below. The tests can involve the use of one or more cytological stains. The biological sample can be manipulated or prepared for the test prior to administration of the test by any suitable method known to the art for biological sample preparation. The specific assay performed can be determined by the molecular profiling business, the physician who ordered the test, or a third party such as a consulting medical professional, cytology laboratory, the subject from whom the sample derives, and/or an insurance provider. The specific assay can be chosen based on the likelihood of obtaining a definite diagnosis, the cost of the assay, the speed of the assay, or the suitability of the assay to the type of material provided.

V. Test for Adequacy

Subsequent to or during biological sample acquisition, including before or after a step of storing the sample, the biological material can be assessed for adequacy, for example, to assess the suitability of the sample for use in the methods and compositions of the present disclosure. The assessment can be performed by an individual who obtains the sample; a molecular profiling business; an individual using a kit; or a third party, such as a cytological lab, pathologist, endocrinologist, or a researcher. The sample can be determined to be adequate or inadequate for further analysis due to many factors, such factors including, but not limited to: insufficient cells; insufficient genetic material; insufficient protein, DNA, or RNA; inappropriate cells for the indicated test; inappropriate material for the indicated test; age of the sample; manner in which the sample was obtained; and/or manner in which the sample was stored or transported. Adequacy can be determined using a variety of methods known in the art such as a cell staining procedure, measurement of the number of cells or amount of tissue, measurement of total protein, measurement of nucleic acid, visual examination, microscopic examination, or temperature or pH determination. Sample adequacy can be determined from a result of performing a gene expression product level analysis experiment. Sample adequacy can be determined by measuring the content of a marker of sample adequacy. Such markers can include elements such as iodine, calcium, magnesium, phosphorous, carbon, nitrogen, sulfur, iron etc.; proteins such as, but not limited to, thyroglobulin; cellular mass; and cellular components such as protein, nucleic acid, lipid, or carbohydrate. The biological sample can be analyzed to determine whether a sample mix-up has occurred; for example, the gender of the subject from which the biological sample was obtained can be predicted according to the methods disclosed herein and compared to information provided with the sample.

Iodine can be measured by a chemical method such as described in U.S. Pat. No. 3,645,691 which is incorporated herein by reference in its entirety or other chemical methods known in the art for measuring iodine content. Chemical methods for iodine measurement include but are not limited to methods based on the Sandell and Kolthoff reaction. Said reaction proceeds according to the following equation:

$$2Ce^{4+}+As^{3+}\rightarrow 2Ce^{3+}+As^{5+}+I.$$

Iodine can have a catalytic effect upon the course of the reaction, e.g., the more iodine present in the preparation to be analyzed, the more rapidly the reaction proceeds. The speed of reaction is proportional to the iodine concentration. In some cases, this analytical method can carried out in the following manner: A predetermined amount of a solution of arsenous oxide As2O3 in concentrated sulfuric or nitric acid is added to the biological sample and the temperature of the mixture is adjusted to reaction temperature, i.e., usually to a temperature between 20° C. and 60° C. A predetermined amount of a cerium (IV) sulfate solution in sulfuric or nitric acid is added thereto. Thereupon, the mixture is allowed to react at the predetermined temperature for a definite period of time. Said reaction time is selected in accordance with the order of magnitude of the amount of iodine to be determined and with the respective selected reaction temperature. The reaction time is usually between about 1 minute and about 40 minutes. Thereafter, the content of the test solution of cerium (IV) ions is determined photometrically. The lower the photometrically determined cerium (IV) ion concentration is, the higher is the speed of reaction and, consequently, the amount of catalytic agent, i.e., of iodine. In this manner the iodine of the sample can directly and quantitatively be determined.

Iodine content of a sample of thyroid tissue can also be measured by detecting a specific isotope of iodine such as for example $^{123}I$, $^{124}I$, $^{125}I$, and $^{123}I$. In still other cases, the marker can be another radioisotope such as an isotope of carbon, nitrogen, sulfur, oxygen, iron, phosphorous, or hydrogen. The radioisotope in some instances can be administered prior to sample collection. Methods of radioisotope administration suitable for adequacy testing are well known in the art and include injection into a vein or artery, or by ingestion. A suitable period of time between administration of the isotope and acquisition of thyroid nodule sample so as to effect absorption of a portion of the isotope into the thyroid tissue can include any period of time between about a minute and a few days or about one week including about 1 minute, 2 minutes, 5 minutes, 10 minutes, 15 minutes, ½ an hour, an hour, 8 hours, 12 hours, 24 hours, 48 hours, 72 hours, or about one, one and a half, or two weeks, and can readily be determined by one skilled in the art. Alternatively, samples can be measured for natural levels of isotopes such as radioisotopes of iodine, calcium, magnesium, carbon, nitrogen, sulfur, oxygen, iron, phosphorous, or hydrogen.

(i) Cell and/or Tissue Content Adequacy Test

Methods for determining the amount of a tissue in a biological sample can include, but are not limited to, weighing the sample or measuring the volume of sample. Methods for determining the amount of cells in the biological sample can include, but are not limited to, counting cells, which can in some cases be performed after dis-aggregation of the biological sample (e.g., with an enzyme such as trypsin or collagenase or by physical means such as using a tissue homogenizer). Alternative methods for determining the amount of cells in the biological sample can include, but are not limited to, quantification of dyes that bind to cellular material or measurement of the volume of cell pellet obtained following centrifugation. Methods for determining that an adequate number of a specific type of cell is present in the biological sample can also include PCR, Q-PCR, RT-PCR, immuno-histochemical analysis, cytological analysis, microscopic, and or visual analysis. The relative levels of difference cell types (e.g., Follicular cells, Hurthle cells, lymphocytic cells, etc.) in a sample of thyroid tissue can be determined by expression profiling of one or more marker disclosed in Table 11, Table 12, and/or Table 13.

(ii) Nucleic Acid Content Adequacy Test

Biological samples can be analyzed by determining nucleic acid content after extraction from the biological sample using a variety of methods known to the art. Nucleic acids, such as RNA or mRNA, can be extracted from other nucleic acids prior to nucleic acid content analysis. Nucleic acid content can be extracted, purified, and measured by ultraviolet absorbance, including but not limited to absorbance at 260 nanometers using a spectrophotometer. Nucleic acid content or adequacy can be measured by fluorometer after contacting the sample with a stain. Nucleic acid content or adequacy can be measured after electrophoresis, or using an instrument such as an Agilent bioanalyzer. It is understood that the methods of the present disclosure are not limited to a specific method for measuring nucleic acid content and or integrity.

In some cases, the RNA quantity or yield from a biological sample is measured shortly after purification using a NanoDrop spectrophotometer in a range of nano- to micrograms. RNA quality can be measured using an Agilent 2100 Bioanalyzer instrument, wherein quality is characterized by a calculated RNA Integrity Number (RIN, 1-10). The NanoDrop is a cuvette-free spectrophotometer. It can use 1 microliter to measure from about 5 ng/μl to about 3,000 ng/μl of sample. Features of the NanoDrop include low volume of sample and no cuvette; large dynamic range 5 ng/μl to 3,000 ng/μl; and it allows quantitation of DNA, RNA and proteins. NanoDrop™ 2000c allows for the analysis of 0.5 μl-2.0 μl samples, without the need for cuvettes or capillaries.

RNA quality in a biological sample can be measured by a calculated RNA Integrity Number (RIN). The RNA integrity number (RIN) is an algorithm for assigning integrity values to RNA measurements. The integrity of RNA can be a major concern for gene expression studies and traditionally has been evaluated using the 28S to 18S rRNA ratio, a method that can be inconsistent. The RIN algorithm is applied to electrophoretic RNA measurements and based on a combination of different features that contribute information about the RNA integrity to provide a more robust universal measure. RNA quality can be measured using an Agilent 2100 Bioanalyzer instrument. Protocols for measuring RNA quality are known and available commercially, for example, at Agilent website. Briefly, in the first step, researchers deposit total RNA sample into an RNA Nano LabChip. In the second step, the LabChip is inserted into the Agilent bioanalyzer and the analysis is run, generating a digital electropherogram. In the third step, the RIN algorithm then analyzes the entire electrophoretic trace of the RNA sample, including the presence or absence of degradation products, to determine sample integrity. Then, the algorithm assigns a 1 to 10 RIN score, where level 10 RNA is completely intact. Because interpretation of the electropherogram is automatic and not subject to individual interpretation, universal and unbiased comparison of samples can be enabled and repeatability of experiments can be improved. The RIN algorithm was developed using neural networks and adaptive learning in conjunction with a large database of eukaryote total RNA samples, which were obtained mainly from human, rat, and mouse tissues. Advantages of RIN can include obtaining a numerical assessment of the integrity of RNA; directly comparing RNA samples (e.g., before and after archival, between different labs); and ensuring repeatability of experiments [e.g., if RIN shows a given value and is suitable for microarray experiments, then the RIN of the same value can always be used for similar experiments given that the same organism/tissue/extraction method is used (Schroeder A, et al. BMC Molecular Biology 2006, 7:3 (2006)), which is hereby incorporated by reference in its entirety].

RNA quality can be measured on a scale of RIN 1 to 10, 10 being highest quality. In one aspect, the present disclosure provides a method of analyzing gene expression from a sample with an RNA RIN value equal or less than 6.0; for example, a sample containing RNA with an RIN number of about 1.0, 2.0, 3.0, 4.0, 5.0 or 6.0 can be analyzed for microarray gene expression using the subject methods and algorithms of the present disclosure. The sample can be a fine needle aspirate of thyroid tissue. The sample can comprise, or yield upon extraction, RNA with an RIN as low as 2.0.

Determination of gene expression in a given sample can be a complex, dynamic, and expensive process. RNA samples with RIN ≤5.0 are typically not used for multi-gene microarray analysis, and can be limited to single-gene RT-PCR and/or TaqMan assays. This dichotomy in the usefulness of RNA according to quality can limit the usefulness of samples and hamper research and/or diagnostic efforts. The present disclosure provides methods via which low quality RNA can be used to obtain meaningful multi-gene expression results from samples containing low concentrations of RNA.

In addition, samples having a low and/or un-measurable RNA concentration by NanoDrop normally deemed inadequate for multi-gene expression profiling, can be measured and analyzed using the subject methods and algorithms of the present disclosure. A sensitive apparatus that can be used to measure nucleic acid yield is the NanoDrop spectrophotometer. Like many quantitative instruments of its kind, the accuracy of a NanoDrop measurement can decrease significantly with very low RNA concentration. The minimum amount of RNA necessary for input into a microarray experiment also limits the usefulness of a given sample. In the present disclosure, a sample containing a very low amount of nucleic acid can be estimated using a combination of the measurements from both the NanoDrop and the Bioanalyzer instruments, thereby optimizing the sample for multi-gene expression assays and analysis.

(iii) Protein Content Adequacy Test

Protein content in a biological sample can be measured using a variety of methods known to the art, including, but not limited to: ultraviolet absorbance at 280 nanometers, cell staining as described herein, or protein staining with for example coomassie blue, or bichichonic acid. In some cases, protein is extracted from the biological sample prior to measurement of the sample. In some cases, multiple tests for adequacy of the sample can be performed in parallel, or one at a time. In some cases, the sample can be divided into aliquots for the purpose of performing multiple diagnostic tests prior to, during, or after assessing adequacy. In some cases, the adequacy test is performed on a small amount of the sample which may or may not be suitable for further diagnostic testing. In other cases, the entire sample is assessed for adequacy. In any case, the test for adequacy can be billed to the subject, medical provider, insurance provider, or government entity.

A biological sample can be tested for adequacy soon or immediately after collection. In some cases, when the sample adequacy test does not indicate a sufficient amount sample or sample of sufficient quality, additional samples can be taken.

In another embodiment, the invention is an algorithm for diagnosing a genetic disorder or cancer comprising: (a) determining the level of gene expression products in a biological sample; (b) deriving the composition of cells in the biological sample based on the expression levels of cell-type specific markers in the sample; (c) removing technical variables prior to and during classification of the biological sample; (d) correcting or normalizing the gene product levels determined in step (a) based on the composition of cells determined in step (b); and (e) classifying the biological sample as positive for a genetic disorder or cancer.

In some embodiments, the present invention utilizes one or more exploratory methods to generate a broad preliminary analysis of the data. These methods are used in order to assess whether technical factors exist in the datasets that may bias downstream analyses. The output from exploratory analyses can be used to flag any suspicious samples, or batch effects. Flagged samples or subsets of samples can then be processed for technical factor removal prior to, and/or during feature selection and classification. Technical factor removal is described in detail in section 3. The methods used for exploratory analyses include but are not limited to:

Principal component analysis (PCA) can be used to assess the effects of various technical factors, such as laboratory processing batches or FNA sample collection media, on the intensity values. To assess the effects of technical factors, the projection of the normalized intensity values to the first few principal components can be visualized in a pair-wise manner, color coded by the values of the technical variable. If a significant number of samples are affected by any given technical factor and the first few principal components show separation according to the factor, this factor can be considered a candidate for computational removal during subsequent phases of analysis.

VI. Analysis of Sample

In one aspect, the present disclosure provides methods for performing microarray gene expression analysis with low quantity and quality of polynucleotide, such as DNA or RNA. The present disclosure describes methods of diagnosing, characterizing and/or monitoring a cancer by analyzing gene expression with low quantity and/or quality of RNA. The cancer can be a thyroid cancer. The present disclosure also describes methods of identifying, classifying, or characterizing samples by predicting subject gender, predicting genetic mutations (e.g., BRAF V600E), and/or prescreening for the presence of a confounding condition (e.g., lymphoma) by analyzing gene expression with low quantity and/or quality of RNA. Samples can be thyroid samples. Thyroid RNA can be obtained from fine needle aspirates (FNA). A gene expression profile can be obtained from samples with an RNA RIN value of less than or equal to about 10.0, 9.0, 8.0, 7.0, 6.0, 5.0, 4.0, 3.0, 2.0, 1.0 or less. The gene expression profile can be obtained from a sample with an RIN of equal or less than about 6 (e.g., about 6.0, 5.0, 4.0, 3.0, 2.0, 1.0 or less). Provided by the present disclosure are methods by which low quality RNA can be used to obtain meaningful gene expression results from samples containing low concentrations of nucleic acid, such as thyroid FNA samples.

Another estimate of sample usefulness is RNA yield, typically measured in nanogram to microgram amounts for gene expression assays. An apparatus that can be used to measure nucleic acid yield in the laboratory is the NanoDrop spectrophotometer. Like many quantitative instruments of its kind, the accuracy of a NanoDrop measurement can decrease significantly with very low RNA concentration. The minimum amount of RNA necessary for input into a microarray experiment can also limits the usefulness of a given sample. In some aspects, the present disclosure solves the low RNA concentration problem by estimating sample input using a combination of the measurements from both the NanoDrop and the Bioanalyzer instruments. Since the quality of data obtained from a gene expression study can be dependent on RNA quantity, meaningful gene expression data can be generated from samples having a low or un-measurable RNA concentration as measured by NanoDrop.

The subject methods and algorithms enable: 1) gene expression analysis of samples containing low amount and/or low quality of nucleic acid; 2) a significant reduction of false positives and false negatives, 3) a determination of the underlying genetic, metabolic, or signaling pathways responsible for the resulting pathology, 4) the ability to assign a statistical probability to the accuracy of the diagnosis of genetic disorders, 5) the ability to resolve ambiguous results, 6) the ability to distinguish between sub-types of cancer, 7) the ability to predict subject gender from a sample, 8) the ability to pre-screen samples for the presence of a confounding condition (e.g., lymphoma), which can be used to assess the suitability of the sample for the main classifier, and 9) the ability to predict whether a sample comprises a genetic mutation (e.g., BRAF V600E). The subject methods and algorithms can comprise covariate analysis to account for varying cell-type signal strength in a sample.

Cytological Analysis

Samples can be analyzed by cell staining combined with microscopic examination of the cells in the biological sample. Cell staining, or cytological examination, can be performed by a number of methods and suitable reagents known to the art including but not limited to: EA stains, hematoxylin stains, cytostain, papanicolaou stain, eosin, nissl stain, toluidine blue, silver stain, azocarmine stain, neutral red, or janus green. In some cases the cells are fixed and/or permeablized with for example methanol, ethanol, glutaraldehyde or formaldehyde prior to or during the staining procedure. In some cases, the cells are not fixed. In some cases, more than one stain is used in combination. In other cases no stain is used at all. In some cases measurement of nucleic acid content is performed using a staining procedure, for example with ethidium bromide, hematoxylin, nissl stain or any nucleic acid stain known to the art.

In some cases of the present disclosure, cells can be smeared onto a slide by standard methods well known in the art for cytological examination. In other cases, liquid based cytology (LBC) methods can be utilized. In some cases, LBC methods provide for an improved means of cytology slide preparation, more homogenous samples, increased sensitivity and specificity, and improved efficiency of handling of samples. In liquid based cytology methods, biological samples are transferred from the subject to a container or vial containing a liquid cytology preparation solution such as for example Cytyc ThinPrep, SurePath, or Monoprep or any other liquid based cytology preparation solution known in the art. Additionally, the sample can be rinsed from the collection device with liquid cytology preparation solution into the container or vial to ensure substantially quantitative transfer of the sample. The solution containing the biological sample in liquid based cytology preparation solution can then be stored and/or processed by a machine or by one skilled in the art to produce a layer of cells on a glass slide. The sample can further be stained and examined under the microscope in the same way as a conventional cytological preparation.

In some cases of the present disclosure, samples can be analyzed by immuno-histochemical staining. Immuno-histochemical staining provides for the analysis of the presence, location, and distribution of specific molecules or antigens by use of antibodies in a biological sample (e.g. cells or tissues). Antigens can be small molecules, proteins, peptides, nucleic acids or any other molecule capable of being specifically recognized by an antibody. Samples can be analyzed by immuno-histochemical methods with or without a prior fixing and/or permeabilization step. In some cases, the antigen of interest can be detected by contacting the sample with an antibody specific for the antigen and then non-specific binding can be removed by one or more washes. The specifically bound antibodies can then be detected by an antibody detection reagent such as for example a labeled secondary antibody, or a labeled avidin/streptavidin. In some cases, the antigen specific antibody can be labeled directly instead. Suitable labels for immuno-histochemistry include but are not limited to fluorophores such as fluoroscein and rhodamine, enzymes such as alkaline phosphatase and horse radish peroxidase, and radionuclides such as $^{32}P$ and $^{125}I$. Gene product markers that can be detected by immuno-histochemical staining include but are not limited to Her2/Neu, Ras, Rho, EGFR, VEGFR, UbcH10, RET/PTC1, cytokeratin 20, calcitonin, GAL-3, thyroid peroxidase, and thyroglobulin.

VII. Assay Results

The results of routine cytological or other assays can indicate a sample as negative (cancer, disease or condition free), ambiguous or suspicious (suggestive of the presence of a cancer, disease or condition), diagnostic (positive diagnosis for a cancer, disease or condition), or non diagnostic (providing inadequate information concerning the presence or absence of cancer, disease, or condition). The diagnostic results can be further classified as malignant or benign. The diagnostic results can also provide a score indicating for example, the severity or grade of a cancer, or the likelihood of an accurate diagnosis, such as via a p-value, a corrected p-value, or a statistical confidence indicator. In some cases, the diagnostic results can be indicative of a particular type of a cancer, disease, or condition, such as for example follicular adenoma (FA), nodular hyperplasia (NHP), lymphocytic thyroiditis (LCT), Hurthle cell adenoma (HA), follicular carcinoma (FC), papillary thyroid carcinoma (PTC), follicular variant of papillary carcinoma (FVPTC), medullary thyroid carcinoma (MTC), Hürthle cell carcinoma (HC), anaplastic thyroid carcinoma (ATC), renal carcinoma (RCC), breast carcinoma (BCA), melanoma (MMN), B cell lymphoma (BCL), parathyroid (PTA), hyperplasia, papillary carcinoma, or any of the diseases or conditions provided herein. In some cases, the diagnostic results can be indicative of a particular stage of a cancer, disease, or condition. The diagnostic results can include information related to the prediction of genetic mutations, such as heterogeneity for the BRAF V600E mutation. The diagnostic results can inform a particular treatment or therapeutic intervention for the condition (e.g., type or stage of the specific cancer disease or condition) diagnosed. In some cases, the results of the assays performed can be entered into a database. The molecular profiling company can bill the individual, insurance provider, medical provider, or government entity for one or more of the following: assays performed, consulting services, reporting of results, database access, or data analysis. In some cases, all or some steps other than molecular profiling are performed by a cytological laboratory or a medical professional.

VIII. Molecular Profiling

Cytological assays mark the current diagnostic standard for many types of suspected tumors, including for example thyroid tumors or nodules. Samples that assay as negative, indeterminate, diagnostic, or non diagnostic can be subjected to subsequent assays to obtain more information. In the present disclosure, these subsequent assays can comprise the steps of molecular profiling of genomic DNA, RNA, mRNA expression product levels, miRNA levels, gene expression product levels and/or gene expression product alternative splicing. Molecular profiling can comprise the determination of the number (e.g., copy number) and/or type of genomic DNA in a biological sample. In some cases, the number and/or type can further be compared to a control sample or a sample considered normal. In some case, genomic DNA can be analyzed for copy number variation, such as an increase (amplification) or decrease in copy number, or variants, such as insertions, deletions, truncations and the like. Molecular profiling can be performed on the same sample, a portion of the same sample, or a new sample can be acquired using any of the methods described herein. A molecular profiling company can request an additional sample by directly contacting the individual or through an intermediary such as a physician, third party testing center or laboratory, or a medical professional. In some cases, samples are assayed using methods and compositions of the disclosure in combination with some or all cytological staining or other diagnostic methods. In other cases, samples are directly assayed using the methods and compositions of the disclosure without the previous use of routine cytological staining or other diagnostic methods. In some cases the results of molecular profiling alone or in combination with cytology or other assays can enable those skilled in the art to characterize a tissue sample, diagnose a subject, or suggest treatment for a subject. In some cases, molecular profiling can be used alone or in combination with cytology to monitor tumors or suspected tumors over time for malignant changes. In some cases, molecular profiling can be used to evaluate whether a sample mix-up has occurred; for example, by comparing a predicted and reported gender source of the samples. In some cases, molecular profiling can be used to predict whether a sample comprises a genetic mutation; for example, whether a sample is heterologous or wild-type with respect to the BRAF V600E mutation. In some cases, molecular profiling can be used to determine whether the samples are suitable for analysis with a main classifier; for example, whether a sample comprises cells indicative of a confounding condition such as lymphoma.

The molecular profiling methods of the present disclosure provide for extracting and analyzing protein or nucleic acid (RNA or DNA) from one or more biological samples from a subject. In some cases, nucleic acid is extracted from the entire sample obtained. In other cases, nucleic acid is extracted from a portion of the sample obtained. In some cases, the portion of the sample not subjected to nucleic acid extraction can be analyzed by cytological examination or immuno-histochemistry. Methods for RNA or DNA extraction from biological samples are well known in the art and include for example the use of a commercial kit, such as the Qiagen DNeasy Blood and Tissue Kit, or the Qiagen EZ1 RNA Universal Tissue Kit.

(i) Tissue-Type Fingerprinting

In many cases, biological samples such as those provided by the methods of the present disclosure can contain several cell types or tissues, including but not limited to thyroid follicular cells, thyroid medullary cells, blood cells (RBCs, WBCs, platelets), smooth muscle cells, ducts, duct cells, basement membrane, lumen, lobules, fatty tissue, skin cells, epithelial cells, and infiltrating macrophages and lymphocytes. In the case of thyroid samples, diagnostic classification of the biological samples can involve for example primarily follicular cells (for cancers derived from the follicular cell such as papillary carcinoma, follicular carcinoma, and anaplastic thyroid carcinoma) and medullary cells (for medullary cancer). The diagnosis of indeterminate biological samples from thyroid biopsies in some cases concerns the distinction of follicular adenoma vs. follicular carcinoma. The molecular profiling signal of a follicular cell for example can thus be diluted out and possibly confounded by other cell types present in the sample. Similarly diagnosis of biological samples from other tissues or organs often involves diagnosing one or more cell types among the many that can be present in the sample.

The methods of the present disclosure provide for an upfront method of determining the cellular make-up of a particular biological sample so that the resulting molecular profiling signatures can be calibrated against the dilution effect due to the presence of other cell and/or tissue types. In one aspect, this upfront method is an algorithm that uses a combination of known cell and/or tissue specific gene expression patterns as an upfront mini-classifier for each component of the sample. This algorithm can utilize this molecular fingerprint to pre-classify the samples according to their composition and then apply a correction/normalization factor (e.g., covariate analysis). This data can in some cases then feed in to a final classification algorithm which would incorporate that information to aid in the final diagnosis.

(ii) Genomic Analysis

Genomic sequence analysis, or genotyping, can be performed on a biological sample. Genotyping can take the form of mutational analysis such as single nucleotide polymorphism (SNP) analysis, insertion deletion polymorphism (InDel) analysis, variable number of tandem repeat (VNTR) analysis, copy number variation (CNV) analysis or partial or whole genome sequencing. Methods for performing genomic analyses are known to the art and can include high throughput sequencing such as but not limited to those methods described in U.S. Pat. Nos. 7,335,762; 7,323,305; 7,264,929; 7,244,559; 7,211,390; 7,361,488; 7,300,788; and 7,280,922. Methods for performing genomic analyses can also include microarray methods as described hereinafter. In some cases, genomic analysis can be performed in combination with any of the other methods herein. For example, a sample can be obtained, tested for adequacy, and divided into aliquots. One or more aliquots can then be used for cytological analysis of the present disclosure, one or more can be used for RNA expression profiling methods of the present disclosure, and one or more can be used for genomic analysis. It is further understood that the present disclosure anticipates that one skilled in the art can perform other analyses on the biological sample that are not explicitly provided herein.

(iii) Expression Product Profiling

Gene expression profiling can comprise the measurement of the activity (or the expression) of one or more genes. Gene expression profiling can comprise the measurement of the activity or expression of a plurality of genes at once, to create a global picture of cellular function. Gene expression profiling can comprise measuring the activity or expression of between about 1 and about 20,000 or more genes; for example, about 1-20000, 1-10000, 1-5000, 1-1000, 1-500, 1-250, 1-100, 1-50, 1-10, 10-20000, 10-10000, 10-5000, 10-1000, 10-500, 10-250, 10-100, 10-50, 50-20000, 50-10000, 50-5000, 50-1000, 50-500, 50-250, 50-100, 100-20000, 100-10000, 100-5000, 100-1000, 100-500, 100-250, 250-20000, 250-10000, 250-5000, 250-1000, 250-500, 500-20000, 500-10000, 500-5000, 500-1000, 1000-20000, 1000-10000, 1000-5000, 5000-20000, 5000-10000, 10000-20000, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 9000, 9500, 10000, 11000, 12000, 13000, 14000, 15000, 16000, 17000, 18000, 19000, 20000 or more genes. Gene expression profiles can be used, for example, to distinguish between cells that are actively dividing, or to show how the cells would be predicted react to a particular treatment. Many experiments of this sort measure an entire genome simultaneously, that is, every gene present in a particular cell. Microarray technology can be used to measure the relative activity of previously identified target genes and other expressed sequences. Sequence based techniques, like serial analysis of gene expression (SAGE, SuperSAGE) are also used for gene expression profiling. SuperSAGE is especially accurate and can measure any active gene, not just a predefined set. In an RNA, mRNA or gene expression profiling microarray, the expression levels of thousands of genes can be simultaneously monitored to study the effects of certain treatments, diseases, and developmental stages on gene expression. For example, microarray-based gene expression profiling can be used to characterize gene signatures of a genetic disorder disclosed herein, or different cancer types, subtypes of a cancer, and/or cancer stages.

RNA (including mRNA, miRNA, siRNA, and cRNA) can be measured by one or more of the following: microarray, SAGE, blotting, RT-PCR, quantitative PCR, sequencing, RNA sequencing, DNA sequencing (e.g., sequencing of cDNA obtained from RNA); Next-Gen sequencing, nanopore sequencing, pyrosequencing, or Nanostring sequencing.

Expression profiling experiments can involve measuring the relative amount of gene expression products, such as mRNA, expressed in two or more experimental conditions. This is because altered levels of a specific sequence of a gene expression product can suggest a changed need for the protein coded for by the gene expression product, perhaps indicating a homeostatic response or a pathological condition. For example, if breast cancer cells express higher levels of mRNA associated with a particular transmembrane receptor than normal cells do, it might be that this receptor plays a role in breast cancer. One aspect of the present disclosure encompasses gene expression profiling as part of a process of identification or characterization of a biological sample, such as a diagnostic test for genetic disorders and cancers (e.g., thyroid cancer or lymphoma), a test to predict the mutation state of one or more genes (e.g., BRAF V600E point mutation state), and/or a test to predict the gender of the subject providing the biological sample. The tests disclosed herein can be used alone or in combination.

In some cases, RNA samples with RIN ≤5.0 are typically not used for multi-gene microarray analysis, and may instead be used only for single-gene RT-PCR and/or TaqMan assays. Microarray, RT-PCR and TaqMan assays are standard molecular techniques well known in the relevant art. TaqMan probe-based assays are widely used in real-time PCR including gene expression assays, DNA quantification and SNP genotyping.

In one case, gene expression products related to cancer that are known to the art are profiled. Such gene expression products have been described and include but are not limited to the gene expression products detailed in U.S. Pat. Nos. 7,358,061; 7,319,011; 5,965,360; 6,436,642; and US patent applications 2003/0186248, 2005/0042222, 2003/0190602, 2005/0048533, 2005/0266443, 2006/0035244, 2006/083744, 2006/0088851, 2006/0105360, 2006/0127907, 2007/0020657, 2007/0037186, 2007/0065833, 2007/0161004, 2007/0238119, and 2008/0044824, each of which is hereby incorporated by reference in its entirety.

It is further anticipated that other gene expression products related to cancer may become known, and that the methods and compositions described herein can include such newly discovered gene expression products.

In some cases of the present disclosure gene expression products are analyzed alternatively or additionally for characteristics other than expression level. For example, gene products can be analyzed for alternative splicing. Alternative splicing, also referred to as alternative exon usage, is the RNA splicing variation mechanism wherein the exons of a primary gene transcript, the pre-mRNA, are separated and reconnected (e.g., spliced) so as to produce alternative mRNA molecules from the same gene. In some cases, these linear combinations then undergo the process of translation where a specific and unique sequence of amino acids is specified by each of the alternative mRNA molecules from the same gene resulting in protein isoforms. Alternative splicing can include incorporating different exons or different sets of exons, retaining certain introns, or utilizing alternate splice donor and acceptor sites.

In some cases, markers or sets of markers can be identified that exhibit alternative splicing that is diagnostic for benign, malignant or normal samples. Additionally, alternative splicing markers can further provide an identifier for a specific type of thyroid cancer (e.g. papillary, follicular, medullary, or anaplastic). Alternative splicing markers diagnostic for malignancy known to the art include those listed in U.S. Pat. No. 6,436,642, which is hereby incorporated by reference in its entirety.

In some cases, expression of gene expression products that do not encode for proteins such as miRNAs, and siRNAs can be assayed by the methods of the present disclosure. Differential expression of these gene expression products can be indicative of benign, malignant or normal samples. Differential expression of these gene expression products can further be indicative of the subtype of the benign sample (e.g. FA, NHP, LCT, BN, CN, HA) or malignant sample (e.g. FC, PTC, FVPTC, ATC, MTC). In some cases, differential expression of miRNAs, siRNAs, alternative splice RNA isoforms, mRNAs or any combination thereof can be assayed by the methods of the present disclosure.

(1) In Vitro Methods of Determining Expression Product Levels

The general methods for determining gene expression product levels are known to the art and can include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, SAGE, enzyme linked immuno-absorbance assays, mass-spectrometry, immuno-histochemistry, blotting, sequencing, RNA sequencing, DNA sequencing (e.g., sequencing of cDNA obtained from RNA); Next-Gen sequencing, nanopore sequencing, pyro-sequencing, or Nanostring sequencing. Gene expression product levels can be normalized to an internal standard such as total mRNA or the expression level of a particular gene including but not limited to glyceraldehyde 3 phosphate dehydrogenase, or tublin.

The gene expression product of the subject methods can be a protein, and the amount of protein in a particular biological sample can be analyzed using a classifier derived from protein data obtained from cohorts of samples. The amount of protein can be determined by one or more of the following: ELISA, mass spectrometry, blotting, immunohistochemistry, protein chip arrays, or any other protein quantitation technique.

Gene expression product markers and alternative splicing markers can be analyzed by microarray analysis using, for example, Affymetrix arrays, cDNA microarrays, oligonucleotide microarrays, spotted microarrays, or other microarray products from Biorad, Agilent, or Eppendorf. Microarrays can provide particular advantages because they can contain a large number of genes or alternative splice variants that can be assayed in a single experiment. In some cases, the microarray device can contain the entire human genome or transcriptome or a substantial fraction thereof allowing a comprehensive evaluation of gene expression patterns, genomic sequence, or alternative splicing. Markers can be found using standard molecular biology and microarray analysis techniques as described in Sambrook *Molecular Cloning a Laboratory Manual* 2001 and Baldi, P., and Hatfield, W. G., *DNA Microarrays and Gene Expression* 2002, which is hereby incorporated by reference in its entirety.

Microarray analysis generally begins with extracting and purifying nucleic acid from a biological sample (e.g., a biopsy or fine needle aspirate) using methods known to the art. For expression and alternative splicing analysis it can be advantageous to extract and/or purify RNA from DNA. It can further be advantageous to extract and/or purify mRNA from other forms of RNA such as tRNA and rRNA.

Purified nucleic acid can further be labeled with a fluorescent label, radionuclide, or chemical label such as biotin, digoxigenin, or digoxin for example by reverse transcription, PCR, ligation, chemical reaction or other techniques. The labeling can be direct or indirect which can further require a coupling stage. The coupling stage can occur before hybridization, for example, using aminoallyl-UTP and NHS amino-reactive dyes (like cyanine dyes) or after, for example, using biotin and labelled streptavidin. In one example, modified nucleotides (e.g. at a 1 aaUTP: 4 TTP ratio) are added enzymatically at a lower rate compared to normal nucleotides, typically resulting in 1 every 60 bases (measured with a spectrophotometer). The aaDNA can then be purified with, for example, a column or a diafiltration device. The aminoallyl group is an amine group on a long linker attached to the nucleobase, which reacts with a reactive label (e.g. a fluorescent dye).

The labeled samples can then be mixed with a hybridization solution which can contain SDS, SSC, dextran sulfate, a blocking agent (such as COT1 DNA, salmon sperm DNA, calf thymum DNA, PolyA or PolyT), Denhardt's solution, formamine, or a combination thereof.

A hybridization probe can be a fragment of DNA or RNA of variable length, which is used to detect in DNA or RNA samples the presence of nucleotide sequences that are complementary to the sequence in the probe. The probe thereby hybridizes to single-stranded nucleic acid (DNA or RNA) whose base sequence allows probe-target base pairing due to complementarity between the probe and target. The labeled probe can be first denatured (by heating or under alkaline conditions) into single DNA strands and then hybridized to the target DNA.

To detect hybridization of the probe to its target sequence, the probe can be tagged (or labeled) with a molecular marker; commonly used markers including 32P or Digoxigenin, which is non-radioactive antibody-based marker. DNA sequences or RNA transcripts that have moderate to high sequence complementarity (e.g., at least about 70%, 80%, 90%, 95%, 96%, 97%, 98%, 99%, or more complementarity) to the probe can then be detected by visualizing the hybridized probe via autoradiography or other imaging techniques. Detection of sequences with moderate or high complementarity can depend on how stringent the hybridization conditions were applied—high stringency, such as high hybridization temperature and low salt in hybridization buffers, can permit only hybridization between nucleic acid sequences that are highly similar, whereas low stringency, such as lower temperature and high salt, allows hybridization when the sequences are less similar. Hybridization probes used in DNA microarrays can comprise DNA covalently attached to an inert surface, such as coated glass slides or gene chips, and to which a mobile cDNA target is hybridized.

A mix comprising target nucleic acid to be hybridized to probes on an array can be denatured by heat or chemical means and added to a port in a microarray. The holes or ports can then be sealed and the microarray hybridized, for example, in a hybridization oven, where the microarray can be mixed by rotation, or in a mixer. After an overnight hybridization, non specific binding can be washed off (e.g., with SDS and SSC). The microarray can then be dried and scanned in a machine comprising an illumination source (e.g., laser) that excites the dye and a detector that measures emission by the dye. The image can be overlaid with a template grid and the intensities of the features (e.g., a feature comprising several pixels) can be quantified.

Various kits can be used for the amplification of nucleic acid and probe generation of the subject methods. Examples of kit that can be used in the present disclosure include but are not limited to Nugen WT-Ovation FFPE kit, cDNA amplification kit with Nugen Exon Module and Frag/Label module. The NuGEN WT-Ovation™ FFPE System V2 is a whole transcriptome amplification system that enables conducting global gene expression analysis on the vast archives of small and degraded RNA derived from FFPE samples. The system is comprised of reagents and a protocol required for amplification of as little as 50 ng of total FFPE RNA. The protocol can be used for qPCR, sample archiving, fragmentation, and labeling. The amplified cDNA can be fragmented and labeled in less than two hours for GeneChip® 3' expression array analysis using NuGEN's FL-Ovation™ cDNA Biotin Module V2. For analysis using Affymetrix GeneChip® Exon and Gene ST arrays, the amplified cDNA can be used with the WT-Ovation Exon Module, then fragmented and labeled using the FL-Ovation™ cDNA Biotin Module V2. For analysis on Agilent arrays, the amplified cDNA can be fragmented and labeled using NuGEN's FL-Ovation™ cDNA Fluorescent Module.

The Ambion WT-expression kit can be used in the subject methods. Ambion WT-expression kit allows amplification of total RNA directly without a separate ribosomal RNA (rRNA) depletion step. With the Ambion® WT Expression Kit, samples as small as 50 ng of total RNA can be analyzed on Affymetrix® GeneChip® Human, Mouse, and Rat Exon and Gene 1.0 ST Arrays. In addition to the lower input RNA requirement and high concordance between the Affymetrix® method and TaqMan® real-time PCR data, the Ambion® WT Expression Kit provides a significant increase in sensitivity. For example, a greater number of probe sets detected above background can be obtained at the exon level with the Ambion® WT Expression Kit as a result of an increased signal-to-noise ratio. Ambion WT-expression kit can be used in combination with additional Affymetrix labeling kit.

The AmpTec Trinucleotide Nano mRNA Amplification kit (6299-A15) can be used in the subject methods. The ExpressArt® TRinucleotide mRNA amplification Nano kit is suitable for a wide range, from 1 ng to 700 ng of input total RNA. According to the amount of input total RNA and the required yields of aRNA, it can be used for 1-round (input >300 ng total RNA) or 2-rounds (minimal input amount 1 ng total RNA), with aRNA yields in the range of >10 µg. AmpTec's proprietary TRinucleotide priming technology results in preferential amplification of mRNAs (independent of the universal eukaryotic 3'-poly(A)-sequence), combined with selection against rRNAs. This kit can be used in combination with cDNA conversion kit and Affymetrix labeling kit.

Raw data from a microarray can then be normalized, for example, by subtracting the background intensity and then dividing the intensities making either the total intensity of the features on each channel equal or the intensities of a reference gene and then the t-value for all the intensities can be calculated. More sophisticated methods, include z-ratio, loess and lowess regression and RMA (robust multichip analysis), such as for Affymetrix chips. Examples of normalized microarray data can be found in Tables 22-52.

(2) In Vivo Methods of Determining Gene Expression Product Levels

It is further anticipated that the methods and compositions of the present disclosure can be used to determine gene expression product levels in an individual without first obtaining a sample. For example, gene expression product levels can be determined in vivo, that is in the individual. Methods for determining gene expression product levels in vivo are known to the art and include imaging techniques such as CAT, MRI; NMR; PET; and optical, fluorescence, or biophotonic imaging of protein or RNA levels using antibodies or molecular beacons. Such methods are described in US 2008/0044824, US 2008/0131892, herein incorporated by reference. Additional methods for in vivo molecular profiling are contemplated to be within the scope of the present disclosure.

Molecular profiling can include the step of binding the sample or a portion of the sample to one or more probes of the present disclosure. Suitable probes bind to components of the sample (e.g., gene expression products, e.g., polynucleotides, DNA, RNA, polypeptides, and/or proteins) that are to be measured, such probes including, but not limited to antibodies or antibody fragments, aptamers, nucleic acids, and oligonucleotides. The binding of the sample, or sample components to the probes of the present disclosure represents a transformation of matter from sample to sample bound to one or more probes. In one case, the method of identifying, characterizing, or diagnosing biological samples (e.g., as cancerous or benign, as male or female, as mutant or wild-type) based on molecular profiling further comprises the steps of detecting gene expression products (e.g., mRNA or protein) levels in the sample; and classifying the test sample by inputting one or more differential gene expression product levels to a trained algorithm of the present disclosure; validating the sample classification using the selection and classification algorithms of the present disclosure; and identifying the sample as belonging to a tested category (e.g., as positive for a genetic disorder, a type of cancer, or any other test disclosed herein).

(i) Comparison of Sample to Normal

Results of molecular profiling performed on a sample from a subject (e.g., a test sample or a biological sample) can be compared to a biological sample that is known or suspected to be normal. A normal sample can be a sample that does not comprise or is expected to not comprise one or more cancers, diseases, or conditions under evaluation, or would test negative in the molecular profiling assay for the one or more cancers, diseases, or conditions under evaluation. A normal sample can be that which is, or is expected to be, free of any cancer, disease, or condition, or a sample that would test negative for any cancer disease or condition in the molecular profiling assay. The normal sample can be from a different subject from the subject being tested, or from the same subject. In some cases, the normal sample is a sample obtained from a buccal swab of a subject such as the subject being tested for example. The normal sample can be assayed at the same time, or at a different time from the test sample.

The results of an assay on the test sample can be compared to the results of the same assay on a normal sample. In some cases the results of the assay on the normal sample are from a database, or a reference. In some cases, the results of the assay on the normal sample are a known or generally accepted value or range of values by those skilled in the art. In some cases the comparison is qualitative. In other cases the comparison is quantitative. In some cases, qualitative or quantitative comparisons can involve but are not limited to one or more of the following: comparing fluorescence values, spot intensities, absorbance values, chemiluminescent signals, histograms, critical threshold values, statistical significance values, gene product expression levels, gene product expression level changes, alternative exon usage, changes in alternative exon usage, protein levels, DNA polymorphisms, copy number variations, indications of the presence or absence of one or more DNA markers or regions, or nucleic acid sequences.

(ii) Evaluation of Results

The molecular profiling results can be evaluated using methods known to the art for correlating gene expression product levels or alternative exon usage with specific phenotypes such as malignancy, the type of malignancy (e.g., follicular carcinoma), benignancy, normalcy (e.g., disease or condition free), male, female, heterozygous, homozygous, mutant, or wild-type. A specified statistical confidence level can be determined in order to provide a diagnostic confidence level. For example, it can be determined that a confidence level of greater than 90% can be a useful predictor of malignancy, type of malignancy, benignancy, normalcy, male, female, heterozygous, homozygous, mutant, or wild-type. In other cases, more or less stringent confidence levels can be chosen. For example, a confidence level of about or at least about 50%, 60%, 70%, 75%, 80%, 85%, 90%, 95%, 97.5%, 99%, 99.5%, or 99.9% can be chosen as a useful phenotypic predictor. The confidence level provided can in some cases be related to the quality of the sample, the quality of the data, the quality of the analysis, the specific methods used, and/or the number of gene expression products analyzed. The specified confidence level for providing a diagnosis can be chosen on the basis of the expected number of false positives or false negatives and/or cost. Methods for choosing parameters for achieving a specified confidence level or for identifying markers with diagnostic power include but are not limited to Receiver Operating Characteristic (ROC) curve analysis, binormal ROC, principal component analysis, partial least squares analysis, singular value decomposition, least absolute shrinkage and selection operator analysis, least angle regression, and the threshold gradient directed regularization method.

(iii) Data Analysis

Raw gene expression level and alternative splicing data can, in some cases, be improved through the application of algorithms designed to normalize and or improve the reliability of the data. The data analysis can require a computer or other device, machine or apparatus for application of the various algorithms described herein due to the large number of individual data points that are processed. A "machine learning algorithm" can refer to a computational-based prediction methodology, also known to persons skilled in the art as a "classifier", employed for characterizing a gene expression profile. The signals corresponding to certain expression levels, which can be obtained by, e.g., microarray-based hybridization assays, can be subjected to the algorithm in order to classify the expression profile. Supervised learning can involve "training" a classifier to recognize the distinctions among classes and then "testing" the accuracy of the classifier on an independent test set. For new, unknown samples, the classifier can be used to predict the class in which the samples belong.

In some cases, the robust multi-array Average (RMA) method can be used to normalize raw data. The RMA method begins by computing background-corrected intensities for each matched cell on a number of microarrays. The background corrected values can be restricted to positive values as described by Irizarry et al. *Biostatistics* 2003 Apr. 4 (2): 249-64, which is hereby incorporated by reference in its entirety. After background correction, the base-2 logarithm of each background corrected matched-cell intensity can then obtained. The background corrected, log-transformed, matched intensity on each microarray can then normalized using the quantile normalization method in which, for each input array and each probe expression value, the array percentile probe value is replaced with the average of all array percentile points. This normalization method is more completely described by Bolstad et al. *Bioinformatics* 2003, which is hereby incorporated by reference in its entirety. Following quantile normalization, the normalized data can then be fit to a linear model to obtain an expression measure for each probe on each microarray. Tukey's median polish algorithm (Tukey, J. W., *Exploratory Data Analysis*. 1977, which is hereby incorporated by reference in its entirety) can then be used to determine the log-scale expression level for the normalized probe set data.

Data can further be filtered to remove data that can be considered suspect. In some cases, data deriving from microarray probes that have fewer than about 4, 5, 6, 7 or 8 guanosine+cytosine nucleotides can be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides can be considered unreliable due to their aberrant hybridization propensity or secondary structure issues.

In some cases, unreliable probe sets can be selected for exclusion from data analysis by ranking probe-set reliability against a series of reference datasets. For example, RefSeq or Ensembl (EMBL) can be considered very high quality reference datasets. Data from probe sets matching RefSeq or Ensembl sequences can, in some cases, be specifically included in microarray analysis experiments due to their expected high reliability. Similarly data from probe-sets matching less reliable reference datasets can be excluded from further analysis, or considered on a case by case basis for inclusion. In some cases, the Ensembl high throughput cDNA (HTC) and/or mRNA reference datasets can be used to determine the probe-set reliability separately or together. In other cases, probe-set reliability can be ranked. For example, probes and/or probe-sets that match perfectly to all reference datasets such as for example RefSeq, HTC, and mRNA, can be ranked as most reliable (1). Furthermore, probes and/or probe-sets that match two out of three reference datasets can be ranked as next most reliable (2), probes and/or probe-sets that match one out of three reference datasets can be ranked next (3) and probes and/or probe sets that match no reference datasets can be ranked last (4). Probes and or probe-sets can then be included or excluded from analysis based on their ranking. For example, one can choose to include data from category 1, 2, 3, and 4 probe-sets; category 1, 2, and 3 probe-sets; category 1 and 2 probe-sets; or category 1 probe-sets for further analysis. In another example, probe-sets can be ranked by the number of base pair mismatches to reference dataset entries. It is understood that there are many methods understood in the art for assessing the reliability of a given probe and/or probe-set for molecular profiling and the methods of the present disclosure encompass any of these methods and combinations thereof.

Data from probe-sets can be excluded from analysis if they are not expressed or expressed at an undetectable level (e.g., not above background). A probe-set can be judged to be expressed above background if for any group:

Integral from T0 to Infinity of the standard normal distribution<Significance (0.01)

Where:

$$T0 = \text{Sqr}(\text{GroupSize}) \, (T-P)/\text{Sqr}(P\text{var}),$$

GroupSize=Number of CEL files in the group,
T=Average of probe scores in probe-set,
P=Average of Background probes averages of GC content, and
Pvar=Sum of Background probe variances/(Number of probes in probe-set)^2, This can allow including probe-sets in which the average of probe-sets in a group is greater than the average expression of background probes of similar GC content as the probe-set probes as the center of background for the probe-set and enables one to derive the probe-set dispersion from the background probe-set variance.

Probe-sets that exhibit no, or low, variance can be excluded from further analysis. Low-variance probe-sets can be excluded from the analysis via a Chi-Square test. A probe-set can be considered to be low-variance if its transformed variance is to the left of the 99 percent confidence interval of the Chi-Squared distribution with (N−1) degrees of freedom.

$$(N-1)*\text{Probe-set Variance}/(\text{Gene Probe-set Variance}) \sim \text{Chi-Sq}(N-1)$$

where N is the number of input CEL files, (N−1) is the degrees of freedom for the Chi-Squared distribution, and the 'probe-set variance for the gene' is the average of probe-set variances across the gene.

Probe-sets for a given gene or transcript cluster can be excluded from further analysis if they contain less than a minimum number of probes that pass through the previously described filter steps for GC content, reliability, variance and the like. For example, probe-sets for a given gene or transcript cluster can be excluded from further analysis if they contain less than about 1, 2, 3, 4, 5, 6, 7, 8, 9, 10, 11, 12, 13, 14, 15, or less than about 20 probes.

Methods of data analysis of gene expression levels or of alternative splicing can further include the use of a feature selection algorithm as provided herein. In some cases, feature selection is provided by use of the LIMMA software package (Smyth, G. K. (2005). Limma: linear models for microarray data. In: *Bioinformatics and Computational Biology Solutions using R and Bioconductor*, R. Gentleman, V. Carey, S. Dudoit, R. Irizarry, W. Huber (eds.), Springer, N.Y., pages 397-420, which is hereby incorporated by reference in its entirety).

Methods of data analysis of gene expression levels and or of alternative splicing can further include the use of a pre-classifier algorithm. For example, an algorithm can use a cell-specific molecular fingerprint to pre-classify the samples according to their composition and then apply a correction/normalization factor. This data/information can then be fed in to a final classification algorithm which would incorporate that information to aid in the final diagnosis. In another example, an algorithm can use a gender-specific expression profile to examine whether a sample mix-up has occurred. In another example, an algorithm can use a confounding condition expression profile, such as a lymphoma signature, prior to application of a main classifier for another condition (e.g., thyroid cancer).

Methods of data analysis of gene expression levels and/or of alternative splicing can further include the use of a classifier algorithm as provided herein. A diagonal linear discriminant analysis, k-nearest neighbor algorithm, support vector machine (SVM) algorithm, linear support vector machine, random forest algorithm, or a probabilistic model-based method or a combination thereof is provided for classification of differential gene expression data (e.g., microarray data). Identified markers that distinguish samples (e.g., benign vs. malignant, normal vs. malignant, male vs. female, mutant vs. wildtype) or distinguish subtypes (e.g. PTC vs. FVPTC) can be selected based on statistical significance of the difference in expression levels between classes of interest. In some cases, the statistical significance is adjusted by applying a Benjamini Hochberg or another correction for false discovery rate (FDR).

In some cases, the classifier algorithm can be supplemented with a meta-analysis approach such as that described by Fishel and Kaufman et al. 2007 *Bioinformatics* 23(13): 1599-606, which is hereby incorporated by reference in its entirety. In some cases, the classifier algorithm can be supplemented with a meta-analysis approach such as a repeatability analysis. In some cases, the repeatability analysis selects markers that appear in at least one predictive expression product marker set.

Methods for deriving and applying posterior probabilities to the analysis of microarray data have been described for example in Smyth, G. K. 2004 *Stat. Appl. Genet. Mol. Biol.* 3: Article 3, which is hereby incorporated by reference in its entirety. In some cases, the posterior probabilities can be used to rank the markers provided by the classifier algorithm. In some cases, markers can be ranked according to their posterior probabilities and those that pass a chosen threshold can be chosen as markers whose differential expression is indicative of, or diagnostic for, samples that are in a category under investigation (e.g., benign, malignant, normal, ATC, PTC, MTC, FC, FN, FA, FVPTC, RCC, BCA, MMN, BCL, PTA, CN, HA, HC, LCT, NHP, male, female, BRAF wildtype, BRAF V600E, etc.). Illustrative threshold values include prior probabilities of about 0.7, 0.75, 0.8, 0.85, 0.9, 0.925, 0.95, 0.975, 0.98, 0.985, 0.99, 0.995 or higher.

A statistical evaluation of the results of the molecular profiling can provide a quantitative value or values indicative of one or more of the following: the likelihood of diagnostic accuracy; the likelihood of cancer, disease or condition; the likelihood of a particular cancer, disease or condition (e.g., tissue type or cancer subtype); the likelihood of a particular gender; the likelihood of a particular mutation state; and the likelihood of the success of a particular therapeutic intervention. Thus a physician, who is not likely to be trained in genetics or molecular biology, need not understand the raw data. Rather, the data can be presented directly to the physician in its most useful form to guide patient care. The results of the molecular profiling can be statistically evaluated using a number of methods known to the art including, but not limited to: the students T test, the two sided T test, pearson rank sum analysis, hidden markov model analysis, analysis of q-q plots, principal component analysis, one way ANOVA, two way ANOVA, LIMMA and the like.

The use of molecular profiling, alone or in combination with cytological analysis, can provide a classification, identification, or diagnosis that is between about 85% accurate and about 99% or about 100% accurate. In some cases, the molecular profiling process and/or cytology provide a classification, identification, diagnosis of malignant, benign, or normal that is about, or at least about 85%, 86%, 87%, 88%, 90%, 91%, 92%, 93%, 94%, 95%, 96%, 97%, 97.5%, 98%, 98.5%, 99%, 99.5%, 99.75%, 99.8%, 99.85%, or 99.9% accurate. In some cases, the molecular profiling process and/or cytology provide a classification, identification, or diagnosis of the presence of a particular tissue type (e.g. NML, FA, NHP, LCT, HA, FC, PTC, FVPTC, MTC, HC, ATC, RCC, BCA, MMN, BCL, and/or PTA) that is about, or at least about 85%, 86%, 87%, 88%, 90%, 91%, 92%, 93%, 94%, 95%, 96%, 97%, 97.5%, 0.98%, 98.5%, 99%, 99.5%, 99.75%, 99.8%, 99.85%, or 99.9% accurate.

In some cases, accuracy can be determined by tracking the subject over time to determine the accuracy of the original diagnosis. In other cases, accuracy can be established in a deterministic manner or using statistical methods. For example, receiver operator characteristic (ROC) analysis can be used to determine the optimal assay parameters to achieve a specific level of accuracy, specificity, positive predictive value, negative predictive value, and/or false discovery rate. Methods for using ROC analysis in cancer diagnosis are known in the art and have been described for example in US Patent Application No. 2006/019615, herein incorporated by reference in its entirety.

Gene expression products and compositions of nucleotides encoding for such products that are determined to exhibit the greatest difference in expression level or the greatest difference in alternative splicing between categories (e.g., benign and normal, benign and malignant, malignant and normal, male and female, lymphoma and LCT, mutant and wildtype, etc.) can be chosen for use as molecular profiling reagents of the present disclosure. Such gene expression products can be particularly useful by providing a wider dynamic range, greater signal to noise, improved diagnostic power, lower likelihood of false positives or false negative, or a greater statistical confidence level than other methods known or used in the art.

The use of molecular profiling alone, or in combination with cytological analysis, can reduce the number of samples scored as non-diagnostic by about, or at least about 100%, 99%, 95%, 90%, 80%, 75%, 70%, 65%, or about 60% when compared to the use of standard cytological techniques known to the art. In some cases, the methods of the present disclosure can reduce the number of samples scored as intermediate or suspicious by about, or at least about100%, 99%, 98%, 97%, 95%, 90%, 85%, 80%, 75%, 70%, 65%, or about 60%, when compared to the standard cytological methods used in the art.

The results of the molecular profiling assays can be entered into a database for access by representatives or agents of a molecular profiling business, a test subject or individual, a medical provider, or an insurance provider. In some cases, assay results include sample classification, identification, or diagnosis by a representative, agent or consultant of the business, such as a medical professional. In other cases, a computer or algorithmic analysis of the data is provided automatically. In some cases, the molecular profiling business can bill the individual, insurance provider, medical provider, researcher, or government entity for one or more of the following: molecular profiling assays performed, consulting services, data analysis, reporting of results, or database access.

Molecular profile results can be presented as a report on a computer screen or as a paper record. In some cases, the report can include, but is not limited to, such information as one or more of the following: the number of genes differentially expressed, the suitability of the original sample, the number of genes showing differential alternative splicing, a diagnosis, a statistical confidence for the diagnosis, the likelihood of cancer or malignancy, and indicated therapies.

(iv) Categorization of Samples Based on Molecular Profiling Results

The results of the molecular profiling can be classified into one of the following: benign (free of a malignant cancer, disease, or condition), malignant (positive diagnosis for a cancer, disease, or condition), or non diagnostic (providing inadequate information concerning the presence or absence of a cancer, disease, or condition; or as unsuitable for the selected test due to a confounding condition). The results of molecular profiling can also be to categorize a sample according to gender and/or mutation state (e.g., BRAF V600E state). In some cases, the results of the molecular profiling can be classified into benign versus suspicious (suspected to be positive for a cancer, disease, or condition) categories. In some cases, a diagnostic result can further classify the type of cancer, disease or condition, such as by identifying the presence or absence of one or more types of tissues, including but not limited to NML, FA, NHP, LCT, HA, FC, PTC, FVPTC, MTC, HC, ATC, RCC, BCA, MMN, BCL, and PTA. In other cases, a diagnostic result can indicate a certain molecular pathway is involved in the cancer disease or condition, or a certain grade or stage of a particular cancer disease or condition. In still other cases a diagnostic result can inform an appropriate therapeutic intervention, such as a specific drug regimen like a kinase inhibitor such as Gleevec or any drug known to the art, or a surgical intervention like a thyroidectomy or a hemithyroidectomy.

Biological samples can be classified using a trained algorithm. Trained algorithms of the present disclosure include algorithms that have been developed using two or more reference sets of known categorization (e.g., malignant, benign, and normal samples including but not limited to samples with one or more histopathologies listed in FIG. 2; male and female samples; mutant and wild-type samples, etc.). The algorithms can be further trained using one or more of the classification panels in FIG. 3, FIG. 11, Table 4, Table 6, Table 7, and/or Table 18, in any combination. Training can comprise comparison of gene expression product levels in a first set of one or more tissue types to gene expression product levels in a second set of one or more tissue types, where the first set of tissue types includes at least one tissue type that is not in the second set. In some cases, either the entire algorithm or portions of the algorithm can be trained using comparisons of expression levels of biomarker panels within a classification panel against all other biomarker panels (or all other biomarker signatures) used in the algorithm. The first set of tissue types and/or the second set of tissue types can include 1, 2, 3, 4, 5, 6, 7, 8, 9, 10, 11, 12, 13, 14, or 15 of the types selected from NML, FA, NHP, LCT, HA, FC, PTC, FVPTC, MTC, HC, ATC, RCC, BCA, MMN, BCL, and PTA, in any combination, and from any source, including surgical and/or FNA samples.

Algorithms suitable for categorization of samples include but are not limited to k-nearest neighbor algorithms, support vector algorithms, naive Bayesian algorithms, neural network algorithms, hidden Markov model algorithms, genetic algorithms, or any combination thereof.

In some cases, trained algorithms of the present disclosure can incorporate data other than gene expression or alternative splicing data such as, but not limited to, DNA polymorphism data, sequencing data, scoring or diagnosis by cytologists or pathologists of the present disclosure, information provided by the pre-classifier algorithm of the present disclosure, or information about the medical history of the subject.

When classifying a biological sample (e.g., for diagnosis of cancer, as male or female, as mutant or wild-type, etc.), there are typically two possible outcomes from a binary classifier. When a binary classifier is compared with actual true values (e.g., known values from the biological sample), there are typically four possible outcomes. If the outcome from a prediction is p (where "p" is a positive classifier output, such as a malignancy, or presence of a particular disease tissue as described herein) and the actual value is also p, then it is called a true positive (TP); however if the actual value is n then it is said to be afalse positive (FP). Conversely, a true negative (e.g., definitive benign) has occurred when both the prediction outcome and the actual value are n (where "n" is a negative classifier output, such as benign, or absence of a particular disease tissue as described herein), and false negative is when the prediction outcome is n while the actual value is p. For example, consider a diagnostic test that seeks to determine whether a person has a certain disease. A false positive in this case occurs when the person tests positive, but actually does not have the disease. A false negative, on the other hand, occurs when the person tests negative, suggesting they are healthy, when they actually do have the disease. In some cases, a Receiver Operator Characteristic (ROC) curve assuming real-world prevalence of subtypes can be generated by re-sampling errors achieved on available samples in relevant proportions.

The positive predictive value (PPV), or precision rate, or post-test probability of a classification or diagnosis (e.g., a disease diagnosis) can be the proportion of patients with positive test results who are correctly diagnosed. The PPV value can be a measure of a diagnostic method as it reflects the probability that a positive test reflects the underlying condition being tested for; however, its value can depend on the prevalence of the condition tested (e.g., disease), which can vary. In one example, FP (false positive); TN (true negative); TP (true positive); FN (false negative).

False positive rate ($\alpha$)=FP/(FP+TN)−specificity

False negative rate ($\beta$)=FN/(TP+FN)−sensitivity

Power=sensitivity=1−$\beta$

Likelihood-ratio positive=sensitivity/(1−specificity)

Likelihood-ratio negative=(1−sensitivity)/specificity

The negative predictive value can be defined as the proportion of patients with negative test results who are correctly diagnosed. PPV and NPV measurements can be derived using appropriate disease subtype prevalence estimates. An estimate of the pooled malignant disease prevalence can be calculated from the pool of indeterminates, which roughly classify into B vs M by surgery. For subtype specific estimates, in some cases, disease prevalence can sometimes be incalculable because there are not any available samples. In these cases, the subtype disease prevalence can be substituted by the pooled disease prevalence estimate.

The level of expression products or alternative exon usage can indicate of one or the following: NML, FA, NHP, LCT, HA, FC, PTC, FVPTC, MTC, HC, ATC, RCC, BCA, MMN, BCL, and PTA. The level of expression products or alternative exon usage can be indicative of one of the following: follicular cell carcinoma, anaplastic carcinoma, medullary carcinoma, or papillary carcinoma. In some cases, the level of gene expression products or alternative exon usage in indicative of Hurthle cell carcinoma or Hurthle cell adenoma. In some cases, the one or more genes selected using the methods of the present disclosure for diagnosing cancer contain representative sequences corresponding to a set of metabolic or signaling pathways indicative of cancer.

The results of the expression analysis of the subject methods can provide a statistical confidence level that a given diagnosis or categorization is correct. The statistical confidence level can be at least about, or more than about 85%, 90%, 91%, 92%, 93%, 94%, 95%, 96%, 97%, 98%, 99% 99.5%, or more.

In another aspect, the present disclosure provides a composition for diagnosing cancer comprising oligonucleotides comprising a portion of one or more of the genes listed in FIG. 4, Table 20, or their complement, and a substrate upon which the oligonucleotides are covalently attached. The composition of the present disclosure is suitable for use in diagnosing cancer at a specified confidence level using a trained algorithm. In one example, the composition of the present disclosure is used to diagnose thyroid cancer.

For example, in the specific case of thyroid cancer, molecular profiling of the present disclosure can further provide a diagnosis for the specific type of thyroid cancer (e.g., papillary, follicular, medullary, or anaplastic), or other tissue type selected from NML, FA, NHP, LCT, HA, FC, PTC, FVPTC, MTC, HC, ATC, RCC, BCA, MMN, BCL, and PTA. The methods of the disclosure can also provide a diagnosis of the presence or absence of Hurthle cell carcinoma or Hurthle cell adenoma. The results of the molecular profiling can further allow one skilled in the art, such as a scientist or medical professional, to suggest or prescribe a specific therapeutic intervention. Molecular profiling of biological samples can also be used to monitor the efficacy of a particular treatment after the initial diagnosis. It is further understood that in some cases, molecular profiling can be used in place of, rather than in addition to, established methods of cancer diagnosis.

In another aspect, the present disclosure provides compositions for predicting subject gender comprising polynucleotides that correspond to all or a fragment of one or more biomarkers found in Table 1, Table 2, and/or Table 3, or their complement. The polynucleotides can be attached to a substrate; for example, the polynucleotides can be attached to a glass slide or a microarray chip. The compositions for predicting subject gender can be used to identify sample mix-ups; for example, in cases where the predicted gender and a reported gender for the subject do not match, it can be that there was a sample mix-up at some point during the collection, transport, processing, or analysis of the biological sample. As such, the compositions, and associated methods, for predicting subject gender can be used alone or in combination with one or more other compositions and methods disclosed herein.

In another aspect, the present disclosure provides compositions for identifying lymphomas in a biological sample comprising polynucleotides that correspond to all or a fragment of one or more biomarkers found in Table 5. The polynucleotides can be attached to a substrate; for example, the polynucleotides can be attached to a glass slide or a microarray chip. The compositions for identifying lymphomas in the biological sample can be used to pre-screen samples prior to the application of a main classifier. In one example, the biological sample can be pre-screened for the presence of lymphoma prior to the application of a diagnostic classifier to identify thyroid cancers. In this example, the presence of a lymphoma signature in the biological sample can indicate that the thyroid cancer classifier should not be used on the sample.

In another aspect, the present disclosure provides compositions for predicting whether a subject is heterozygous, homozygous, or wild-type for a genetic mutation (e.g., a BRAF V600E mutation) comprising polynucleotides corresponding to all or a fragment of one or more genes found in Table 9 and/or Table 10. Compositions are also provided that can be used to adjust for cell content variation in biological samples comprising polynucleotides corresponding to all or a fragment of one or more genes found in Table 11, Table 12, and/or Table 13. The polynucleotides can be attached to a substrate, such as a glass slide or microarray chip. The compositions, and associated methods, for predicting genetic mutations can be used alone or in combination with one or more of the compositions and methods disclosed herein. For example, the compositions and methods for predicting whether a biological sample comprises the BRAF V600E genetic mutation can be used in addition to a main thyroid cancer classifier.

(v) Monitoring of Subjects or Therapeutic Interventions via Molecular Profiling

Subjects can be monitored using methods and compositions of the present disclosure. For example, a subject can be diagnosed with cancer or a genetic disorder. This initial diagnosis can optionally involve the use of molecular profiling. The subject can be prescribed a therapeutic intervention such as a thyroidectomy for a subject suspected of having thyroid cancer. The results of the therapeutic intervention can be monitored on an ongoing basis by molecular profiling to detect the efficacy of the therapeutic intervention. In another example, a subject can be diagnosed with a benign tumor or a precancerous lesion or nodule, and the tumor, nodule, or lesion can be monitored on an ongoing basis by molecular profiling to detect any changes in the state of the tumor or lesion.

Molecular profiling can also be used to ascertain the potential efficacy of a specific therapeutic intervention prior to administering to a subject. For example, a subject can be diagnosed with cancer. Molecular profiling can indicate the upregulation of a gene expression product known to be involved in cancer malignancy, such as for example the RAS oncogene. A tumor sample can be obtained and cultured in vitro using methods known to the art. The application of various inhibitors of the aberrantly activated or dysregulated pathway, or drugs known to inhibit the activity of the pathway can then be tested against the tumor cell line for growth inhibition. Molecular profiling can also be used to monitor the effect of these inhibitors on for example downstream targets of the implicated pathway.

(vi) Molecular Profiling as a Research Tool

Molecular profiling can be used as a research tool to identify new markers for diagnosis of suspected tumors; to monitor the effect of drugs or candidate drugs on biological samples such as tumor cells, cell lines, tissues, or organisms; or to uncover new pathways for oncogenesis and/or tumor suppression.

(vii) Biomarker Groupings Based on Molecular Profiling

The current disclosure provides groupings or panels of biomarkers that can be used to characterize, rule in, rule out, identify, and/or diagnose pathology within the thyroid. Such biomarker panels are obtained from correlations between patterns of gene (or biomarker) expression levels and specific types of samples (e.g., malignant subtypes, benign subtypes, normal tissue, or samples with foreign tissue). The panels of biomarkers can also be used to characterize, rule in, rule out, identify, and/or diagnose benign conditions of the thyroid. In some cases, the number of panels of biomarkers is greater than 1, 2, 3, 4, 5, 6, 7, 8, 9, 10, 11, 12, 13, 14, 15, 16, 17, 18, 19, 20, 25, 30, 40, 50, 60, 70, 80, 90, or 100 panels of biomarkers. The number of panels of biomarkers can be greater than 12 panels, (e.g., 16 panels of biomarkers). Examples of sixteen panels of biomarkers include, but are not limited to the following (they are also provided in FIG. 2):

1 Normal Thyroid (NML)
2 Lymphocytic, Autoimmune Thyroiditis (LCT)
3 Nodular Hyperplasia (NHP)
4 Follicular Thyroid Adenoma (FA)
5 Hurthle Cell Thyroid Adenoma (HC)
6 Parathyroid (non thyroid tissue)
7 Anaplastic Thyroid Carcinoma (ATC)
8 Follicular Thyroid Carcinoma (FC)
9 Hurthle Cell Thyroid Carcinoma (HC)
10 Papillary Thyroid Carcinoma (PTC)
11 Follicular Variant of Papillary Carcinoma (FVPTC)
12 Medullary Thyroid Carcinoma (MTC)
13 Renal Carcinoma metastasis to the Thyroid (RCC)
14 Melanoma metastasis to the Thyroid (MMN)
15 B cell Lymphoma metastasis to the Thyroid (BCL)
16 Breast Carcinoma metastasis to the Thyroid (BCA)

Each panel includes a set of biomarkers (e.g., gene expression products or alternatively spliced exons associated with the particular cell type) that can be used to characterize, rule in, rule out, and/or diagnose a given pathology (or lack thereof) within the thyroid. Biomarkers can be associated with more than one cell type. Panels 1-6 describe benign pathology, while panels 7-16 describe malignant pathology. These multiple panels can be combined (each in different proportion) to create optimized panels that are useful in a two-class classification system (e.g., benign versus malignant). Alternatively, biomarker panels can be used alone or in any combination as a reference or classifier in the classification, identification, or diagnosis of a thyroid tissue sample as comprising one or more tissues selected from NML, FA, NHP, LCT, HA, FC, PTC, FVPTC, MTC, HC, ATC, RCC, BCA, MMN, BCL, and PTA. Combinations of biomarker panels can contain at least about 1, 2, 3, 4, 5, 6, 7, 8, 9, 10, 11, 12, 13, 14, 15, 16, or more biomarker panels. In some cases, where two are more panels are used in the classification, identification, or diagnosis, the comparison is sequential. Sequential comparison can comprise 1, 2, 3, 4, 5, 6, 7, 8, 9, 10, or more sets comprising 2, 3, 4, 5, 6, 7, 8, 9, 10, or more biomarker panels that are compared simultaneously as a step in the sequential comparison, each set comprising at least one different biomarker panel than compared at other steps in the sequence (and can optionally be completely non-overlapping).

The biological nature of the thyroid and each pathology found within it suggest there can be some redundancy between the plurality of biomarkers in one panel versus the plurality of biomarkers in another panel. For each pathology subtype, each diagnostic panel can be heterogeneous and semi-redundant, or not redundant, with the biomarkers in another panel. In general, heterogeneity and redundancy can reflect the biology of the tissues samples in a given thyroid sample (e.g., surgical or FNA sample) and the differences in gene expression that differentiates each pathology subtype from one another.

In one aspect, the diagnostic value of the present disclosure lies in the comparison of i) one or more markers in one panel, versus ii) one or more markers in each additional panel.

The pattern of gene expression demonstrated by a particular biomarker panel reflects the "signature" of each panel. For example, the panel of Lymphocytic Autoimmune Thyroiditis (LCT) can have certain sets of biomarkers that display a particular pattern or signature. Within such signature, specific biomarkers can be upregulated, others can be not differentially expressed, and still others can be down regulated. The signatures of particular panels of biomarkers can themselves be grouped in order to diagnose or otherwise characterize a thyroid condition; such groupings can be referred to as "classification panels". Each classification panel can comprise at least 1, 2, 3, 4, 5, 6, 7, 8, 9, 10, 15, or more than 20 biomarker panels.

Classification panels can contain specified biomarkers (TCIDs) and use information saved during algorithm training to rule in, or rule out a given sample as "benign," "suspicious," or as comprising or not comprising one or more tissue types (e.g. NML, FA, NHP, LCT, HA, FC, PTC, FVPTC, MTC, HC, ATC, RCC, BCA, MMN, BCL, and PTA). Each classification panel can use simple decision rules to filter incoming samples, effectively removing any flagged samples from subsequent evaluation if the decision rules are met (e.g., a sample can be characterized regarding the identity or status of one or more tissue types contained therein). The biomarker panels and classification panels provided herein can be useful for classifying, characterizing, identifying, and/or diagnosing thyroid cancer or other thyroid condition (including diagnosing the thyroid as normal). The biomarker panels and classification panels provided herein can also be useful for classifying, characterizing, identifying, and/or diagnosing samples according to gender, mutation state, cell-type composition, and/or the presence of confounding conditions. However, biomarker panels and classification panels similar to the present panels can be obtained using similar methods and can be used for other diseases or disorders, such as other diseases or disorder described herein.

FIG. 3 provides an example of a set of classification panels that can be used to diagnose a thyroid condition. For example, as shown in FIG. 3, one classification panel can contain a single biomarker panel such as the MTC biomarker panel (e.g., classification panel #1); another classification panel can contain a single biomarker panel such as the RCC biomarker panel (e.g., classification panel #2); yet another classification panel can contain a single biomarker panel such as the PTA biomarker panel (e.g., classification panel #3); yet another classification panel can contain a single biomarker panel such as the BCA biomarker panel (e.g., classification panel #4); yet another classification panel can contain a single biomarker panel such as the MMN biomarker panel (e.g., classification panel #5); yet another classification panel can contain a two biomarker panels such as the HA and HC biomarker panels (e.g., classification panel 6); and yet another classification panel can contain a combination of the FA, FC, NHP, PTC, FVPTC, HA, HC, and LCT panels (e.g., classification panel #7, which is also an example of a "main" classifier). One or more such classifiers can be used simultaneously or in sequence, and in any combination, to classify, characterize, identify, or diagnose a thyroid sample. In some cases, a sample is identified as containing or not containing tissue having an HA or HC tissue type.

Other potential classification panels that can be useful for characterizing, identifying, and/or diagnosing thyroid cancers can include: 1) biomarkers of metastasis to the thyroid from non-thyroid organs (e.g., one of or any combination of two or more of the following: RCC, MTC, MMN, BCL, and BCA panels); 2) biomarkers correlated with thyroid tissue that originated from non-thyroid organs (e.g., any one of or any combination of two or more of the following: RCC, MTC, MMN, BCL, BCA, and PTA panels); 3) biomarkers with significant changes in alternative gene splicing, 4) KEGG Pathways, 5) gene ontology; 6) biomarker panels associated with thyroid cancer (e.g., one of or groups of two or more of the following panels: FC, PTC, FVPTC, MTC, HC, and ATC); 7) biomarker panels associated with benign thyroid conditions (e.g., one of or groups of two or more of the following: FA, NHP, LCT, or HA); 8) biomarker panels associated with benign thyroid conditions or normal thyroid tissue (e.g., one of or groups of two or more of the following: FA, NHP, LCT, HA or NML); 9) biomarkers related to signaling pathways such as adherens pathway, focal adhesion pathway, and tight junction pathway, or other pathway described in International Application No. PCT/US2009/006162, filed Nov. 17, 2009, hereby incorporated by reference in its entirety. In addition, biomarkers that indicate metastasis to the thyroid from a non-thyroid organ can be used in the subject methods and compositions. Metastatic cancers that metastasize to thyroid that can be used for a classifier to diagnose a thyroid condition include but are not limited to: metastatic parathyroid cancer, metastatic melanoma, metastatic renal carcinoma, metastatic breast carcinoma, and metastatic B cell lymphoma.

Classification panels that can be used for characterizing, identifying, and/or diagnosing thyroid cancers can also include panels to identify sample mix-ups, panels to provide further information about the genetic underpinnings of a cancer, and/or panels to pre-screen samples prior to the application of the thyroid cancer classifier panels. For example, a classifier panel to predict gender can be used to identify whether a sample mix-up has occurred during the collection, transport, storage, processing, or analysis of biological samples by comparing the predicted gender to a reported gender. In another example, a classifier panel to predict whether a biological sample is heterozygous or wild type for the BRAF V600E point mutation can be used to further classify a malignant diagnosis. In another example, a classifier panel that can detect or diagnose the presence of lymphoma can be used prior to a thyroid cancer classifier; the used of the lymphoma classifier can reduce the rate of false positives for a thyroid cancer classifier.

In some cases, the method provides a number, or a range of numbers, of biomarkers (including gene expression products) that are used to diagnose or otherwise characterize a biological sample. As described herein, such biomarkers can be identified using the methods provided herein, particularly the methods of correlating gene expression signatures with specific types of tissue, such as the types listed in FIG. 2. The sets of biomarkers indicated in FIG. 4, Table 1, Table 2, Table 3, Table 5, Table 9, Table 10, Table 11, Table 12, Table 13, and/or Table 20, can be obtained using the methods described herein. Said biomarkers can also be used, in turn, to classify tissue. In some cases, all of the biomarkers in FIG. 4, Table 1, Table 2, Table 3, Table 5, Table 9, Table 10, Table 11, Table 12, Table 13, and/or Table 20 are used to diagnose or otherwise characterize thyroid tissue. In some cases, a subset of the biomarkers in FIG. 4, Table 1, Table 2, Table 3, Table 5, Table 9, Table 10, Table 11, Table 12, Table 13, and/or Table 20 are used to diagnose or otherwise characterize thyroid tissue. In some cases, all, or a subset, of the biomarkers in FIG. 4, Table 1, Table 2, Table 3, Table 5, Table 9, Table 10, Table 11, Table 12, Table 13, and/or Table 20, along with additional biomarkers, are used to diagnose or otherwise characterize thyroid tissue. In some cases, at least 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, or 300 total biomarkers are used to diagnose or otherwise characterize thyroid tissue. In other cases, at most 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, or 300 total biomarkers are used to diagnose or otherwise characterize thyroid tissue. In still other cases, at least 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, or more of the biomarkers identified in FIG. 4, Table 1, Table 2, Table 3, Table 5, Table 9, Table 10, Table 11, Table 12, Table 13, and/or Table 20 are used to diagnose or otherwise characterize thyroid tissue.

Exemplary biomarkers and an example of their associated classification panel (and/or biomarker panel) are listed in FIG. 4, Table 1, Table 2, Table 3, Table 5, Table 9, Table 10, Table 11, Table 12, Table 13, and Table 20. The methods and compositions provided herein can use any or all of the biomarkers listed in FIG. 4, Table 1, Table 2, Table 3, Table 5, Table 9, Table 10, Table 11, Table 12, Table 13, and/or Table 20. In some cases, the biomarkers listed in FIG. 4, Table 1, Table 2, Table 3, Table 5, Table 9, Table 10, Table 11, Table 12, Table 13, and/or Table 20 are used as part of the corresponding classification panel indicated in FIG. 4, Table 1, Table 2, Table 3, Table 5, Table 9, Table 10, Table 11, Table 12, Table 13, and/or Table 20. In other cases, the biomarkers in FIG. 4, Table 1, Table 2, Table 3, Table 5, Table 9, Table 10, Table 11, Table 12, Table 13, and/or Table 20 can be used for a different classification panel than the ones indicated in FIG. 4, Table 1, Table 2, Table 3, Table 5, Table 9, Table 10, Table 11, Table 12, Table 13, and/or Table 20.

Optimized classification panels can be assigned specific numbers of biomarkers per classification panel. For example, an optimized classification panel can be assigned between about 1 and about 500; for example about 1-500, 1-400, 1-300, 1-200, 1-100, 1-50, 1-25, 1-10, 10-500, 10-400, 10-300, 10-200, 10-100, 10-50, 10-25, 25-500, 25-400, 25-300, 25-200, 25-100, 25-50, 50-500, 50-400, 50-300, 50-200, 50-100, 100-500, 100-400, 100-300, 100-200, 200-500, 200-400, 200-300, 300-500, 300-400, 400-500, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or any included range or integer. biomarkers. For example, as shown in FIG. 3, a classification panel can contain 5, 33, or 142 biomarkers. Methods and compositions of the disclosure can use biomarkers selected from 1, 2, 3, 4, 5, 6, 7, 8, 9, 10, 11, 12, 13, 14, 15 or 16 or more biomarker panels and each of these biomarker panels can have more than 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, 500, or more biomarkers, in any combination. In some cases, the set of markers combined give a specificity or sensitivity of greater than 60%, 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 90%, 95%, 95.5%, 96%, 96.5%, 97%, 97.5%, 98%, 98.5%, 99%, 99.5% or more.

Analysis of the gene expression levels can involve sequential application of different classifiers described herein to the gene expression data. Such sequential analysis can involve applying a classifier obtained from gene expression analysis of cohorts of diseased thyroid tissue, followed by applying a classifier obtained from analysis of a mixture of different samples of thyroid tissue, with some of the samples containing diseased thyroid tissues and others containing benign thyroid tissue. The diseased tissue can malignant or cancerous tissue (including tissue that has metastasized from a non-thyroid organ). The diseased tissue can be thyroid cancer or a non-thyroid cancer that has metastasized to the thyroid. The classifier can be obtained from analysis of gene expression patterns in benign tissue, normal tissue, and/or non-thyroid tissue (e.g., parathyroid tissue). The diseased tissue can be HA and/or HC tissue.

The classification process can begin when each classification panel receives, as input, biomarker expression levels (e.g., summarized microarray intensity values, qPCR, or sequencing data) derived from a biological sample. The biomarkers and expression levels specified in a classification panel can then be evaluated. If the data from a given sample matches the rules specified within the classification panel (or otherwise correlate with the signature of the classification panel), its data output can flag the sample and prevent it from further evaluation and scoring by the main (downstream) classifier. When a classification panel flags a sample, the system can be configured to automatically return a "suspicious" call for that sample. When a classification panel does not flag a sample, the evaluation can continue downstream to the next classification panel and it can be flagged or not flagged. In some situations, the classification panels are applied in a specific order; in other cases, the order of the applications can be any order. In some cases, classification panels 1-5 from FIG. 3 in the optimized list of thyroid gene signature panels are executed in any particular order, but then are followed by classification panel 6, which then precedes application of the main classifier (e.g., classification panel 7). In some cases, a classification panel to identify a confounding condition can be used to pre-screen samples prior to application of the main classifier. For example, a classification panel comprising any or all of the markers in Table 5 can be used to identify the presence of a lymphoma in the biological sample (e.g., a thyroid sample). Pre-screening samples using the lymphoma classifier panel can reduce the number of false positives returned by the main classifier.

One or more classification panels can be used to further characterize the biological sample. For example, if the sample is positive for a cancer (e.g., a thyroid cancer), a classification panel comprising any or all of the biomarkers in Table 9 can be used to predict whether the biological sample is heterozygous, homozygous, or wild-type for a BRAF V600E point mutation. The classification panel to predict the BRAF V600E point mutation can additionally or alternatively comprise any or all of the markers from Table 10 and can optionally involve covariate analysis to account for cellular heterogeneity. For biological samples of the thyroid (e.g., fine needle aspirations or tissue samples of the thyroid), covariate analysis can comprise evaluation of Follicular cell signal strength (e.g., using any or all of the markers in Table 11), Hurthle cell signal strength (e.g., using any or all of the markers in Table 12), and/or lymphocytic cell signal strength (e.g., using any or all of the markers in Table 13) in any combination.

One or more classification panels can be used to identify sample mix-ups that can occur during collection, transport, processing, storage, and/or analysis of biological samples. For example, a classification panel comprising any or all of the biomarkers in Table 1, Table 2, and/or Table 3 can be used, in any combination, in order to predict a gender (e.g., male or female) for a subject from whom a biological sample has been obtained. The gender classification panel can consist, consist essentially of, or comprise biomarkers corresponding to RPS4Y1 and/or EIF1AY and/or UTY and/or USP9Y and/or CYorf15B and/or DDX3Y in any combination. Comparison of the predicted gender to a reported gender can identify whether a sample mix-up may have occurred; for example, if the predicted gender is male and the reported gender is female, a sample mix-up may have occurred.

An example illustration of a classification process in accordance with the methods of the disclosure is provided in FIG. 1A. The process begins with determining, such as by gene expression analysis, expression level(s) for one or more gene expression products from a sample (e.g., a thyroid tissue sample) from a subject. Separately, one or more sets of reference or training samples can be analyzed to determine gene expression data for at least two different sets of biomarkers, the gene expression data for each biomarker set comprising one or more gene expression levels correlated with the presence of one or more tissue types. The gene expression data for a first set of biomarkers can be used to train a first classifier; gene expression data for a second set can be used to train a second classifier; and so on for 2, 3, 4, 5, 6, 7, 8, 9, 10, 11, 12, 13, 14, 15, 16, or more sets of biomarkers and optionally corresponding classifiers. The sets of reference or training samples used in the analysis of each of the sets of biomarkers can be overlapping or non-overlapping. In some cases, the reference or training samples comprise HA and/or HC tissue. In the next step of the example classification process, a first comparison is made between the gene expression level(s) of the sample and the first set of biomarkers or first classifier. If the result of this first comparison is a match, the classification process ends with a result, such as designating the sample as suspicious, cancerous, or containing a particular tissue type (e.g. HA or HC). If the result of the comparison is not a match, the gene expression level(s) of the sample are compared in a second round of comparison to a second set of biomarkers or second classifier. If the result of this second comparison is a match, the classification process ends with a result, such as designating the sample as suspicious, cancerous, or containing a particular tissue type (e.g. HA or HC). If the result of the comparison is not a match, the process continues in a similar stepwise process of comparisons until a match is found, or until all sets of biomarkers or classifiers included in the classification process are used as a basis of comparison. If no match is found between the gene expression level(s) of the sample and any set of biomarkers or classifiers utilized in the classification process, the sample can be designated as "benign." In some examples, the final comparison in the classification process is between the gene expression level(s) of the sample and a main classifier, as described herein.

Figure 1B:
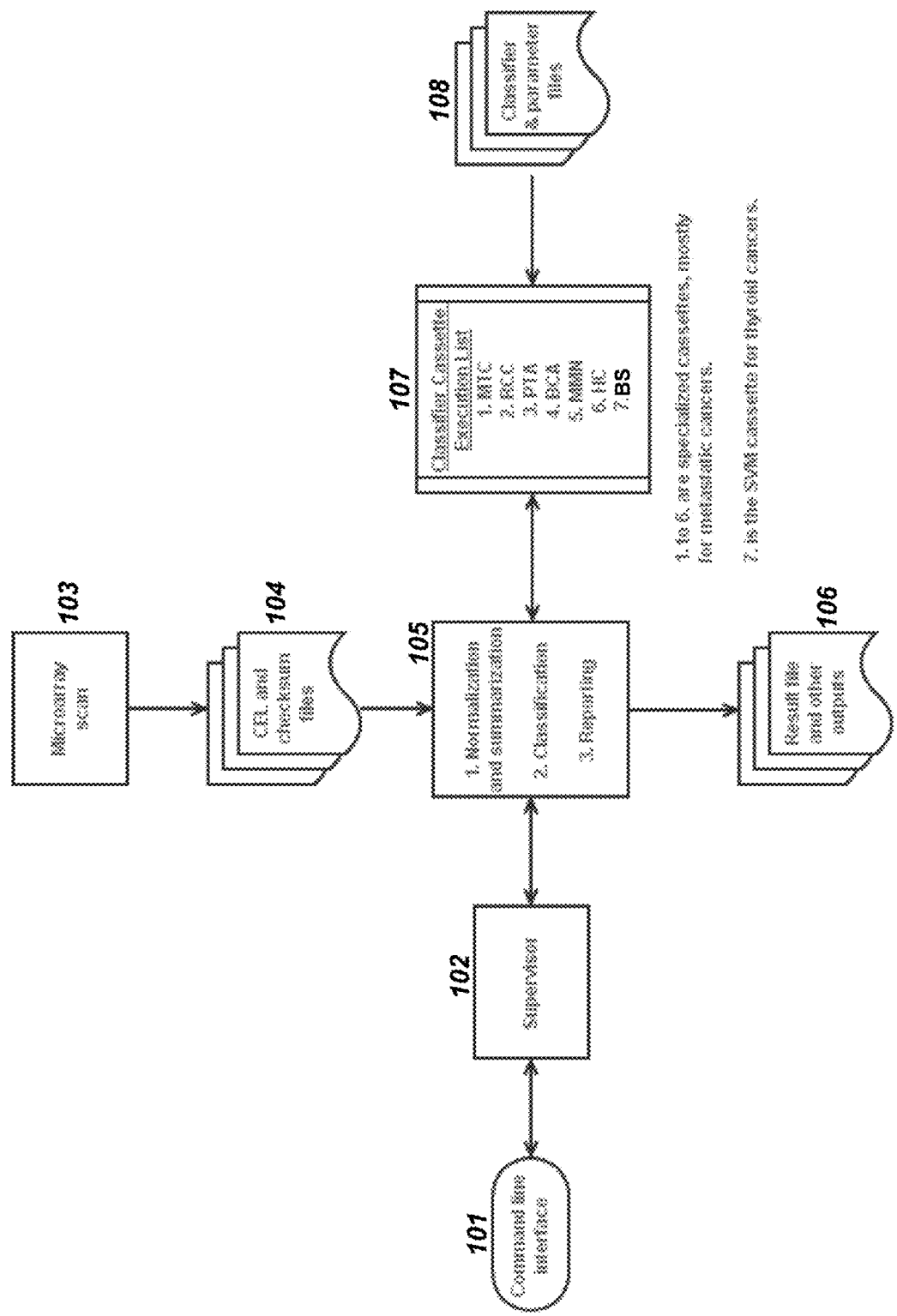

A further example of a classification process in accordance with the methods of the disclosure is illustrated in FIG. 1B. Gene expression analysis is performed by microarray hybridization. Scanning of the microarray 103 produces gene expression data 104 in the form of CEL files (the data) and checksum files (for verification of data integrity). Separately, gene expression data for training samples are analyzed to produce classifier and parameter files 108 comprising gene expression data correlated with the presence of one or more tissue types. Classifier cassettes are compiled into an ordered execution list 107. Analysis of sample data using the classifier cassettes is initiated with input of commands using a command line interface 101, the execution of which commands are coordinated by a supervisor 102. The classification analysis in this example process is further detailed at 105 and 107. Gene expression data 104 is normalized and summarized, and subsequently analyzed with each classifier cassette in sequence for the cassettes in the execution list 105. In this example, gene expression data is classified using classification cassettes comprising biomarker expression data correlated with medullary thyroid carcinoma (MTC), followed in sequence by comparison using classifier cassettes for renal carcinoma metastasis to the thyroid (RCC), parathyroid (PTA), breast carcinoma metastasis to the thyroid (BCA), melanoma metastasis to the thyroid (MMN), Hurthle cell carcinoma and/or Hurthle cell adenoma (HC), and concluding with a main classifier to distinguish benign from suspicious tissue samples (BS). The result of sequentially analyzing the gene expression data with each classifier cassette is then reported in a result file and any other report information or output 106.

The classification process can use a main classifier (e.g., classification panel 7) to designate a sample as "benign" or "suspicious," or as containing or not containing one or more tissues of a particular type (e.g., HA or HC). Gene expression data obtained from the sample can undergo a series of "filtering" steps, where the data is sequentially run through different classification panels or biomarker panels. For example, the sample can be analyzed with the MMN biomarker panel followed by the MTC biomarker panel. In some cases, the sequence of classification panels is classification panels 1 through 5 in any order, followed by classification panel 6, followed by the main classifier (as shown in FIG. 3). In some cases, one classification panel is used followed by the main classifier. In some cases, 1, 2, 3, 4, 5, 6, 7, 8, 9, or 10 classifier panels are used followed by the main classifier. In some cases, classifier 6 (HA and HC combined) is used directly before the main classifier. In some cases, one or more of the classifiers 1 through 5 are applied, in any combination, followed by classifier 7. In some cases, one or more of the classifiers 1 through 5 are applied, in any combination or sequence, followed by application of classifier 6, followed by application of classifier 7. In some cases, one or more of the classifiers 1 through 6 are applied, in any combination or sequence, followed by application of classifier 7 (or other main classifier).

The biomarkers within each panel can be interchangeable (modular). The plurality of biomarkers in all panels can be substituted, increased, reduced, or improved to accommodate the definition of new pathologic subtypes (e.g., new case reports of metastasis to the thyroid from other organs). The current disclosure describes a plurality of biomarkers that define each of sixteen heterogeneous, semi-redundant, and distinct pathologies found in the thyroid. Such biomarkers can allow separation between malignant and benign representatives of the sixteen heterogeneous thyroid pathologies. In some cases, all sixteen panels are required to arrive at an accurate diagnosis, and any given panel alone does not have sufficient power to make a true characterization, classification, identification, or diagnostic determination. In other cases, only a subset of the panels is required to arrive at an accurate characterization, classification, identification, or diagnostic determination, such as less than 2, 3, 4, 5, 6, 7, 8, 9, 10, 11, 12, 13, 14, 15, or 16 of the biomarker panels. In some cases, the biomarkers in each panel are interchanged with a suitable combination of biomarkers, such that the plurality of biomarkers in each panel still defines a given pathology subtype within the context of examining the plurality of biomarkers that define all other pathology subtypes.

Classifiers used early in a sequential analysis can be used to either rule-in or rule-out a sample as benign or suspicious, or as containing or not containing one or more tissues of a particular type (e.g. HA or HC). Classifiers used in the sequential analysis can also be used to identify sample mix-ups, and/or to pre-screen samples for confounding conditions (e.g., conditions that were not represented in training cohorts used to develop the classification panels), and/or to further characterize a classified sample (e.g., by predicting genetic mutations). Sequential analysis can end with the application of a "main" classifier to data from samples that have not been ruled out by the preceding classifiers, wherein the main classifier is obtained from data analysis of gene expression levels in multiple types of tissue and wherein the main classifier is capable of designating the sample as benign or suspicious (or malignant), or as containing or not containing one or more tissues of a particular type (e.g. HA or HC). Sequential analysis can continue after the application of the main classifier; for example, to further characterize a suspicious (or malignant) biological sample.

Provided herein are thyroid biomarker panels. Two or more biomarker panels associated with tissue types selected from NML, FA, NHP, LCT, HA, FC, PTC, FVPTC, MTC, HC, ATC, RCC, BCA, MMN, BCL, and PTA tissue types can be used to distinguish i) benign FNA thyroid samples from malignant (or suspicious) FNA thyroid samples, ii) the presence of from the absence of one or more of NML, FA, NHP, LCT, HA, FC, PTC, FVPTC, MTC, HC, ATC, RCC, BCA, MMN, BCL, and PTA tissue types in a sample, and/or iii) the presence of HA and/or HC tissue from the absence of HA and/or HC tissue in a sample. The benign versus malignant characterization can be more accurate after examination and analysis of the differential gene expression that defines each pathology subtype in the context of all other subtypes. The current disclosure describes a plurality of markers that can be useful in accurate classification of thyroid FNA.

Classification optimization and simultaneous and/or sequential examination of the initial sixteen biomarker panels described in FIG. 2 can be used to select a set of 2, 3, 4, 5, 6, 7, 8, 9, 10 or more (e.g., seven classification panels in FIG. 3), which optimization can include a specified order of sequential comparison using such classification panels. Each modular series of subtype panels can be mutually exclusive and sufficient to arrive at accurate thyroid FNA classification.

Examples of biomarkers that can be used to classify, identify, diagnose, or otherwise characterize biological samples (e.g., thyroid samples, e.g., thyroid tissue and/or fine needle aspirations) are shown in FIG. 4, Table 1, Table 2, Table 3, Table 5, Table 9, Table 10, Table 11, Table 12, Table 13, and Table 20. It can be not necessary for biomarkers to reach statistical significance the benign versus malignant comparison in order to be useful in a panel for accurate classification. In some cases, the benign versus malignant (or benign versus suspicious) comparison is not statistically significant. In some cases, the benign versus malignant (or benign versus suspicious) comparison is statistically significant. In some cases, a comparison or correlation of a specific subtype is not statistically significant. In some cases, a comparison or correlation of a specific subtype is statistically significant.

The sixteen panels described in FIG. 2 represent distinct pathologies found in the thyroid (whether of thyroid origin or not). However, subtype prevalence in a given population can vary. For example, NHP and PTC can be far more common than rare subtypes such as FC or ATC. The relative frequency of biomarkers in each subtype panel can be subsequently adjusted to give the molecular test sufficient sensitivity and specificity.

The biomarker groupings provided herein are examples of biomarker groupings that can be used to characterize biological samples (e.g., for thyroid conditions, gender, genetic mutations, lymphomas, etc.). However, biomarker groupings can be used for other diseases or disorders as well, e.g., any disease or disorder described herein.

(viii) Classification Error Rates

Top biomarkers (e.g., thyroid biomarkers) can be subdivided into bins (e.g., 50 TCIDs per bin) to demonstrate the minimum number of genes required to achieve an overall classification error rate of less than 4%. The original TCIDs used for classification correspond to the Affymetrix Human Exon 1.0ST microarray chip and each can map to more than one gene or no genes at all (Affymetrix annotation file: HuEx-1_0-st-v2.na29.hg18.transcript.csv). When no genes map to a TCID the biomarker is denoted as TCID-######.

IX. Compositions (i) Gene Expression Products and Splice Variants of the Present Disclosure Molecular profiling can also include, but is not limited to, assays of the present disclosure including assays for one or more of the following: proteins, protein expression products, DNA, DNA polymorphisms, RNA, RNA expression products, RNA expression product levels, or RNA expression product splice variants of the genes or markers provided in FIG. 4, Table 1, Table 2, Table 3, Table 5, Table 9, Table 10, Table 11, Table 12, Table 13, and/or Table 20. In some cases, the methods of the present disclosure provide for improved cancer diagnostics by molecular profiling of at least about 1, 2, 3, 4, 5, 6, 7, 8, 9, 10, 15, 20, 25, 30, 35, 40, 45, 50, 60, 70, 80, 90, 100, 120, 140, 160, 180, 200, 240, 280, 300, 350, 400, 450, 500, 600, 700, 800, 1000, 1500, 2000, 2500, 3000, 3500, 4000, 5000 or more DNA polymorphisms, expression product markers, and/or alternative splice variant markers.

Molecular profiling can involve microarray hybridization that is performed to determine gene expression product levels for one or more genes selected from FIG. 4, Table 1, Table 2, Table 3, Table 5, Table 9, Table 10, Table 11, Table 12, Table 13, and/or Table 20. In some cases, gene expression product levels of one or more genes from one group are compared to gene expression product levels of one or more genes in another group or groups. As an example only and without limitation, the expression level of gene TPO can be compared to the expression level of gene GAPDH. In another case, gene expression levels are determined for one or more genes involved in one or more of the following metabolic or signaling pathways: thyroid hormone production and/or release, protein kinase signaling pathways, lipid kinase signaling pathways, and cyclins. In some cases, the methods of the present disclosure provide for analysis of gene expression product levels and or alternative exon usage of at least one gene of 1, 2, 3, 4, 5, 6, 7, 9, 10, 11, 12, 13, 14, or 15 or more different metabolic or signaling pathways.

(ii) Compositions of the Present Disclosure

Compositions of the present disclosure are also provided which composition comprises one or more of the following: polynucleotides (e.g., DNA or RNA) corresponding to the genes or a portion of the genes provided in FIG. 4, Table 1, Table 2, Table 3, Table 5, Table 9, Table 10, Table 11, Table 12, Table 13, and/or Table 20, and nucleotides (e.g., DNA or RNA) corresponding to the complement of the genes or a portion of the complement of the genes provided in FIG. 4, Table 1, Table 2, Table 3, Table 5, Table 9, Table 10, Table 11, Table 12, Table 13, and/or Table 20. This disclosure provides for collections of probes, such as sets of probes that can bind to between about 1 and about 500 of the biomarkers identified in FIG. 4, Table 1, Table 2, Table 3, Table 5, Table 9, Table 10, Table 11, Table 12, Table 13, and/or Table 20; for example about 1-500, 1-400, 1-300, 1-200, 1-100, 1-50, 1-25, 1-10, 10-500, 10-400, 10-300, 10-200, 10-100, 10-50, 10-25, 25-500, 25-400, 25-300, 25-200, 25-100, 25-50, 50-500, 50-400, 50-300, 50-200, 50-100, 100-500, 100-400, 100-300, 100-200, 200-500, 200-400, 200-300, 300-500, 300-400, 400-500, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 of the biomarkers identified in FIG. 4, Table 1, Table 2, Table 3, Table 5, Table 9, Table 10, Table 11, Table 12, Table 13, and/or Table 20.

The nucleotides (including probes) of the present disclosure can be at least about 10, 15, 20, 25, 30, 35, 40, 45, 50, 55, 60, 65, 70, 75, 100, 150, 200, 250, 300, 350, or about 400 or 500 nucleotides in length. The nucleotides (including probes) of the present disclosure can be between about 10-500 residues, or more; for example, about 10-500, 10-200, 10-150, 10-100, 10-75, 10-50, 10-25, 25-500, 25-200, 25-150, 25-100, 25-75, 25-50, 50-500, 50-200, 50-150, 50-100, 50-75, 75-500, 75-200, 75-150, 75-100, 100-500, 100-200, 100-150, 150-500, 150-200, 200-500, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 110, 120, 130, 140, 150, 160, 170, 180, 190, 200, 225, 250, 275, 300, 325, 350, 375, 400, 425, 450, 475, or 500 nucleotides, or more. The nucleotides can be natural or man-made derivatives of ribonucleic acid or deoxyribonucleic acid including, but not limited to, peptide nucleic acids, pyranosyl RNA, nucleosides, methylated nucleic acid, pegylated nucleic acid, cyclic nucleotides, and chemically modified nucleotides. The nucleotides of the present disclosure can be chemically modified to include a detectable label. The biological sample, or gene expression products derived from the biological sample (e.g., DNA, RNA, protein, etc.) can be chemically modified to include a label.

A further composition of the present disclosure comprises oligonucleotides for detecting and/or measuring gene expression products corresponding to the markers or genes provided in FIG. 4, Table 1, Table 2, Table 3, Table 5, Table 9, Table 10, Table 11, Table 12, Table 13, and/or Table 20 and/or their complement. A further composition of the present disclosure comprises oligonucleotides for detecting and/or measuring the gene expression products of polymorphic alleles of the genes provided in FIG. 5 through FIG. 8 and their complement. Such polymorphic alleles include but are not limited to splice site variants, single nucleotide polymorphisms, variable number repeat polymorphisms, insertions, deletions, and homologues. In some cases, the variant alleles are between about 99.9% and about 70% identical to the genes listed in FIG. 4, including about, less than about, or more than about 99.75%, 99.5%, 99.25%, 99%, 97.5%, 95%, 92.5%, 90%, 85%, 80%, 75%, and about 70% identical. In some cases, the variant alleles differ by between about 1 nucleotide and about 500 nucleotides from the genes provided in FIG. 4, including about, less than about, or more than about 1, 2, 3, 5, 7, 10, 15, 20, 25, 30, 35, 50, 75, 100, 150, 200, 250, 300, and about 400 nucleotides.

In some cases, the composition of the present disclosure can be selected from the top differentially expressed gene products between categories (e.g., benign and malignant samples; normal and benign or malignant samples; presence and absence of one or more particular tissue types, such as HA and/or HC; male and female; mutant and wild-type), or the top differentially spliced gene products between (e.g., benign and malignant samples; normal and benign or malignant samples; presence and absence of one or more particular tissue types, such as HA and/or HC; male and female; mutant and wild-type). In some cases the top differentially expressed gene products can be selected from FIG. 4, Table 1, Table 2, Table 3, Table 5, Table 9, Table 10, Table 11, Table 12, Table 13, and/or Table 20.

Diseases and Disorders

In some cases, the subject methods and algorithm are used to diagnose, characterize, detect, exclude and/or monitor thyroid cancer. Thyroid cancer includes any type of thyroid cancer, including but not limited to, any malignancy of the thyroid gland, e.g., papillary thyroid cancer, follicular thyroid cancer, medullary thyroid cancer and/or anaplastic thyroid cancer. In some cases, the thyroid cancer is differentiated. In some cases, the thyroid cancer is undifferentiated. In some cases, the instant methods are used to diagnose, characterize, detect, exclude and/or monitor one or more of the following types of thyroid cancer: papillary thyroid carcinoma (PTC), follicular variant of papillary thyroid carcinoma (FVPTC), follicular carcinoma (FC), Hurthle cell carcinoma (HC) or medullary thyroid carcinoma (MTC).

Other types of cancer that can be diagnosed, characterized and/or monitored using the algorithms and methods of the present disclosure include but are not limited to adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g. uterine sarcoma), vaginal cancer, vulvar cancer, and Waldenstrom's macroglobulinemia.

Expression profiling using panels of biomarkers can be used to characterize thyroid tissue as benign, suspicious, and/or malignant. Panels can be derived from analysis of gene expression levels of cohorts containing benign (non-cancerous) thyroid subtypes including follicular adenoma (FA), nodular hyperplasia (NHP), lymphocytic thyroiditis (LCT), and Hurthle cell adenoma (HA); malignant subtypes including follicular carcinoma (FC), papillary thyroid carcinoma (PTC), follicular variant of papillary carcinoma (FVPTC), medullary thyroid carcinoma (MTC), Hürthle cell carcinoma (HC), and anaplastic thyroid carcinoma (ATC). Such panels can also be derived from non-thyroid subtypes including renal carcinoma (RCC), breast carcinoma (BCA), melanoma (MMN), B cell lymphoma (BCL), and parathyroid (PTA). Biomarker panels associated with normal thyroid tissue (NML) can also be used in the methods and compositions provided herein. Exemplary panels of biomarkers are provided in FIG. 2, and will be described further herein. Of note, each panel listed in FIG. 2, relates to a signature, or pattern of biomarker expression (e.g., gene expression), that correlates with samples of that particular pathology or description.

The present disclosure also provides novel methods and compositions for identification of types of aberrant cellular proliferation through an iterative process (e.g., differential diagnosis) such as carcinomas including follicular carcinomas (FC), follicular variant of papillary thyroid carcinomas (FVPTC), Hurthle cell carcinomas (HC), Hurthle cell adenomas (HA); papillary thyroid carcinomas (PTC), medullary thyroid carcinomas (MTC), and anaplastic carcinomas (ATC); adenomas including follicular adenomas (FA); nodule hyperplasias (NHP); colloid nodules (CN); benign nodules (BN); follicular neoplasms (FN); lymphocytic thyroiditis (LCT), including lymphocytic autoimmune thyroiditis; parathyroid tissue; renal carcinoma metastasis to the thyroid; melanoma metastasis to the thyroid; B-cell lymphoma metastasis to the thyroid; breast carcinoma to the thyroid; benign (B) tumors, malignant (M) tumors, and normal (N) tissues. The present disclosure further provides novel gene expression markers and novel groups of genes and markers useful for the characterization, diagnosis, and/or treatment of cellular proliferation. Additionally the present disclosure provides business methods for providing enhanced diagnosis, differential diagnosis, monitoring, and treatment of cellular proliferation.

In some cases, the diseases or conditions classified, characterized, or diagnosed by the methods of the present disclosure include benign and malignant hyperproliferative disorders including but not limited to cancers, hyperplasias, or neoplasias. In some cases, the hyperproliferative disorders classified, characterized, or diagnosed by the methods of the present disclosure include but are not limited to breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer. In some cases, the diseases or conditions classified, characterized, or diagnosed by the methods of the present disclosure include but are not limited to thyroid disorders such as for example benign thyroid disorders including but not limited to follicular adenomas, Hurthle cell adenomas, lymphocytic throiditis, and thyroid hyperplasia. In some cases, the diseases or conditions classified, characterized, or diagnosed by the methods of the present disclosure include but are not limited to malignant thyroid disorders such as for example follicular carcinomas, follicular variant of papillary thyroid carcinomas, medullary carcinomas, and papillary carcinomas. In some cases, the methods of the present disclosure provide for a classification, characterization, or diagnosis of a tissue as diseased or normal. In other cases, the methods of the present disclosure provide for a classification, characterization, or diagnosis of normal, benign, or malignant. In some cases, the methods of the present disclosure provide for a classification, characterization, or diagnosis of benign/normal, or malignant. In some cases, the methods of the present disclosure provide for a classification, characterization, or diagnosis of one or more of the specific diseases or conditions provided herein.

In one aspect, the present disclosure provides algorithms and methods that can be used for classification, characterization, or diagnosis and monitoring of a genetic disorder. A genetic disorder is an illness caused by abnormalities in genes or chromosomes. While some diseases, such as cancer, are due in part to genetic disorders, they can also be caused by environmental factors. In some cases, the algorithms and the methods disclosed herein are used for classification, characterization, or diagnosis and monitoring of a cancer such as thyroid cancer.

Genetic disorders can be typically grouped into two categories: single gene disorders and multifactorial and polygenic (complex) disorders. A single gene disorder is the result of a single mutated gene. There are estimated to be over 4000 human diseases caused by single gene defects. Single gene disorders can be passed on to subsequent generations in several ways. There are several types of inheriting a single gene disorder including but not limited to autosomal dominant, autosomal recessive, X-linked dominant, X-linked recessive, Y-linked and mitochondrial inheritance. Only one mutated copy of the gene can be necessary for a person to be affected by an autosomal dominant disorder. Examples of autosomal dominant type of disorder include, but are not limited to, Huntington's disease, Neurofibromatosis 1, Marfan Syndrome, Hereditary nonpolyposis colorectal cancer, and Hereditary multiple exostoses. In autosomal recessive disorder, two copies of the gene can be mutated for a person to be affected by an autosomal recessive disorder. Examples of this type of disorder include, but are not limited to, cystic fibrosis, sickle-cell disease (also partial sickle-cell disease), Tay-Sachs disease, Niemann-Pick disease, spinal muscular atrophy, and dry earwax. X-linked dominant disorders are caused by mutations in genes on the X chromosome. Only a few disorders have this inheritance pattern, with a prime example being X-linked hypophosphatemic rickets. Males and females are both affected in these disorders, with males typically being more severely affected than females. Some X-linked dominant conditions such as Rett syndrome, Incontinentia Pigmenti type 2 and Aicardi Syndrome can be fatal in males either in utero or shortly after birth, and are therefore predominantly seen in females. X-linked recessive disorders can also be caused by mutations in genes on the X chromosome. Examples of this type of disorder include, but are not limited to, Hemophilia A, Duchenne muscular dystrophy, red-green color blindness, muscular dystrophy and Androgenetic alopecia. Y-linked disorders can be caused by mutations on the Y chromosome. Examples include but are not limited to Male Infertility and hypertrichosis pinnae. Mitochondrial inheritance, also known as maternal inheritance, applies to genes in mitochondrial DNA. An example of this type of disorder is Leber's Hereditary Optic Neuropathy.

Genetic disorders can also be complex, multifactorial or polygenic. Polygenic genetic disorders can be associated with the effects of multiple genes in combination with lifestyle and environmental factors. Although complex disorders often cluster in families, they can lack a clear-cut pattern of inheritance. This can make it difficult to determine a person's risk of inheriting or passing on these disorders. Complex disorders can also be difficult to study and treat; in some cases, because the specific factors that cause most of these disorders have not yet been identified. Multifactoral, or polygenic, disorders that can be diagnosed, characterized and/or monitored using the algorithms and methods of the present disclosure include but are not limited to heart disease, diabetes, asthma, autism, autoimmune diseases such as multiple sclerosis, cancers, ciliopathies, cleft palate, hypertension, inflammatory bowel disease, mental retardation and obesity.

Other genetic disorders that can be diagnosed, characterized and/or monitored using the algorithms and methods of the present disclosure include but are not limited to 1p36 deletion syndrome, 21-hydroxylase deficiency, 22q11.2 deletion syndrome, 47, XYY syndrome, 48, XXXX, 49, XXXXX, aceruloplasminemia, achondrogenesis, type II, achondroplasia, acute intermittent porphyria, adenylosuccinate lyase deficiency, Adrenoleukodystrophy, ALA deficiency porphyria, ALA dehydratase deficiency, Alexander disease, alkaptonuria, alpha-1 antitrypsin deficiency, Alstrom syndrome, Alzheimer's disease (type 1, 2, 3, and 4), Amelogenesis Imperfecta, amyotrophic lateral sclerosis, Amyotrophic lateral sclerosis type 2, Amyotrophic lateral sclerosis type 4, amyotrophic lateral sclerosis type 4, androgen insensitivity syndrome, Anemia, Angelman syndrome, Apert syndrome, ataxia-telangiectasia, Beare-Stevenson cutis gyrata syndrome, Benjamin syndrome, beta thalassemia, biotinidase deficiency, Birt-Hogg-Dube syndrome, bladder cancer, Bloom syndrome, Bone diseases, breast cancer, CADASIL, Camptomelic dysplasia, Canavan disease, Cancer, Celiac Disease, CGD Chronic Granulomatous Disorder, Charcot-Marie-Tooth disease, Charcot-Marie-Tooth disease Type 1, Charcot-Marie-Tooth disease Type 4, Charcot-Marie-Tooth disease, type 2, Charcot-Marie-Tooth disease, type 4, Cockayne syndrome, Coffin-Lowry syndrome, collagenopathy, types II and XI, Colorectal Cancer, Congenital absence of the vas deferens, congenital bilateral absence of vas deferens, congenital diabetes, congenital erythropoietic porphyria, Congenital heart disease, congenital hypothyroidism, Connective tissue disease, Cowden syndrome, Cri du chat, Crohn's disease, fibrostenosing, Crouzon syndrome, Crouzonodermoskeletal syndrome, cystic fibrosis, De Grouchy Syndrome, Degenerative nerve diseases, Dent's disease, developmental disabilities, DiGeorge syndrome, Distal spinal muscular atrophy type V, Down syndrome, Dwarfism, Ehlers-Danlos syndrome, Ehlers-Danlos syndrome arthrochalasia type, Ehlers-Danlos syndrome classical type, Ehlers-Danlos syndrome dermatosparaxis type, Ehlers-Danlos syndrome kyphoscoliosis type, vascular type, erythropoietic protoporphyria, Fabry's disease, Facial injuries and disorders, factor V Leiden thrombophilia, familial adenomatous polyposis, familial dysautonomia, fanconi anemia, FG syndrome, fragile X syndrome, Friedreich ataxia, Friedreich's ataxia, G6PD deficiency, galactosemia, Gaucher's disease (type 1, 2, and 3), Genetic brain disorders, Glycine encephalopathy, Haemochromatosis type 2, Haemochromatosis type 4, Harlequin Ichthyosis, Head and brain malformations, Hearing disorders and deafness, Hearing problems in children, hemochromatosis (neonatal, type 2 and type 3), hemophilia, hepatoerythropoietic porphyria, hereditary coproporphyria, Hereditary Multiple Exostoses, hereditary neuropathy with liability to pressure palsies, hereditary nonpolyposis colorectal cancer, homocystinuria, Huntington's disease, Hutchinson Gilford Progeria Syndrome, hyperoxaluria, primary, hyperphenylalaninemia, hypochondrogenesis, hypochondroplasia, idic15, incontinentia pigmenti, Infantile Gaucher disease, infantile-onset ascending hereditary spastic paralysis, Infertility, Jackson-Weiss syndrome, Joubert syndrome, Juvenile Primary Lateral Sclerosis, Kennedy disease, Klinefelter syndrome, Kniest dysplasia, Krabbe disease, Learning disability, Lesch-Nyhan syndrome, Leukodystrophies, Li-Fraumeni syndrome, lipoprotein lipase deficiency, familial, Male genital disorders, Marfan syndrome, McCune-Albright syndrome, McLeod syndrome, Mediterranean fever, familial, MEDNIK, Menkes disease, Menkes syndrome, Metabolic disorders, methemoglobinemia beta-globin type, Methemoglobinemia congenital methaemoglobinaemia, methylmalonic acidemia, Micro syndrome, Microcephaly, Movement disorders, Mowat-Wilson syndrome, Mucopolysaccharidosis (MPS I), Muenke syndrome, Muscular dystrophy, Muscular dystrophy, Duchenne and Becker type, muscular dystrophy, Duchenne and Becker types, myotonic dystrophy, Myotonic dystrophy type 1 and type 2, Neonatal hemochromatosis, neurofibromatosis, neurofibromatosis 1, neurofibromatosis 2, Neurofibromatosis type I, neurofibromatosis type II, Neurologic diseases, Neuromuscular disorders, Niemann-Pick disease, Nonketotic hyperglycinemia, nonsyndromic deafness, Nonsyndromic deafness autosomal recessive, Noonan syndrome, osteogenesis imperfecta (type I and type III), otospondylomegaepiphyseal dysplasia, pantothenate kinase-associated neurodegeneration, Patau Syndrome (Trisomy 13), Pendred syndrome, Peutz-Jeghers syndrome, Pfeiffer syndrome, phenylketonuria, porphyria, porphyria cutanea tarda, Prader-Willi syndrome, primary pulmonary hypertension, prion disease, Progeria, propionic acidemia, protein C deficiency, protein S deficiency, pseudo-Gaucher disease, pseudoxanthoma elasticum, Retinal disorders, retinoblastoma, retinoblastoma FA-Friedreich ataxia, Rett syndrome, Rubinstein-Taybi syndrome, SADDAN, Sandhoff disease, sensory and autonomic neuropathy type III, sickle cell anemia, skeletal muscle regeneration, Skin pigmentation disorders, Smith Lemli Opitz Syndrome, Speech and communication disorders, spinal muscular atrophy, spinal-bulbar muscular atrophy, spinocerebellar ataxia, spondyloepimetaphyseal dysplasia, Strudwick type, spondyloepiphyseal dysplasia congenita, Stickler syndrome, Stickler syndrome COL2A1, Tay-Sachs disease, tetrahydrobiopterin deficiency, thanatophoric dysplasia, thiamine-responsive megaloblastic anemia with diabetes mellitus and sensorineural deafness, Thyroid disease, Tourette's Syndrome, Treacher Collins syndrome, triple X syndrome, tuberous sclerosis, Turner syndrome, Usher syndrome, variegate porphyria, von Hippel-Lindau disease, Waardenburg syndrome, Weissenbacher-Zweymüller syndrome, Wilson disease, Wolf-Hirschhorn syndrome, Xeroderma Pigmentosum, X-linked severe combined immunodeficiency, X-linked sideroblastic anemia, and X-linked spinal-bulbar muscle atrophy.

IX. Business Methods

As described herein, the term customer or potential customer refers to individuals or entities that can utilize methods or services of a molecular profiling business (e.g., a business carrying out the methods of the present disclosure). Potential customers for the molecular profiling methods and services described herein include for example, patients, subjects, physicians, cytological labs, health care providers, researchers, insurance companies, government entities such as Medicaid, employers, or any other entity interested in achieving more economical or effective system for diagnosing, monitoring and treating cancer.

Such parties can utilize the molecular profiling results, for example, to selectively indicate drugs or therapeutic interventions to patients likely to benefit the most from said drugs or interventions, or to identify individuals who would not benefit or can be harmed by the unnecessary use of drugs or other therapeutic interventions.

(i) Methods of Marketing

The services of the molecular profiling business of the present disclosure can be marketed to individuals concerned about their health, physicians or other medical professionals, for example as a method of enhancing diagnosis and care; cytological labs, for example as a service for providing enhanced diagnosis to a client; health care providers, insurance companies, and government entities, for example as a method for reducing costs by eliminating unwarranted therapeutic interventions. Methods of marketing to potential clients, further includes marketing of database access for researchers and physicians seeking to find new correlations between gene expression products and diseases or conditions.

The methods of marketing can include the use of print, radio, television, or internet based advertisement to potential customers. Potential customers can be marketed to through specific media, for example, endocrinologists can be marketed to by placing advertisements in trade magazines and medical journals including but not limited to *The Journal of the American Medical Association, Physicians Practice, American Medical News, Consultant, Medical Economics, Physician's Money Digest, American Family Physician, Monthly Prescribing Reference, Physicians' Travel and Meeting Guide, Patient Care, Cortlandt Forum, Internal Medicine News, Hospital Physician, Family Practice Management, Internal Medicine World Report, Women's Health in Primary Care, Family Practice News, Physician's Weekly, Health Monitor, The Endocrinologist, Journal of Endocrinology, The Open Endocrinology Journal*, and *The Journal of Molecular Endocrinology*. Marketing can also take the form of collaborating with a medical professional to perform experiments using the methods and services of the present disclosure and in some cases publish the results or seek funding for further research. In some cases, methods of marketing can include the use of physician or medical professional databases such as, for example, the American Medical Association (AMA) database, to determine contact information.

In one case methods of marketing comprises collaborating with cytological testing laboratories to offer a molecular profiling service to customers whose samples cannot be unambiguously diagnosed using routine methods.

(ii) Methods Utilizing a Computer

Figure 16:
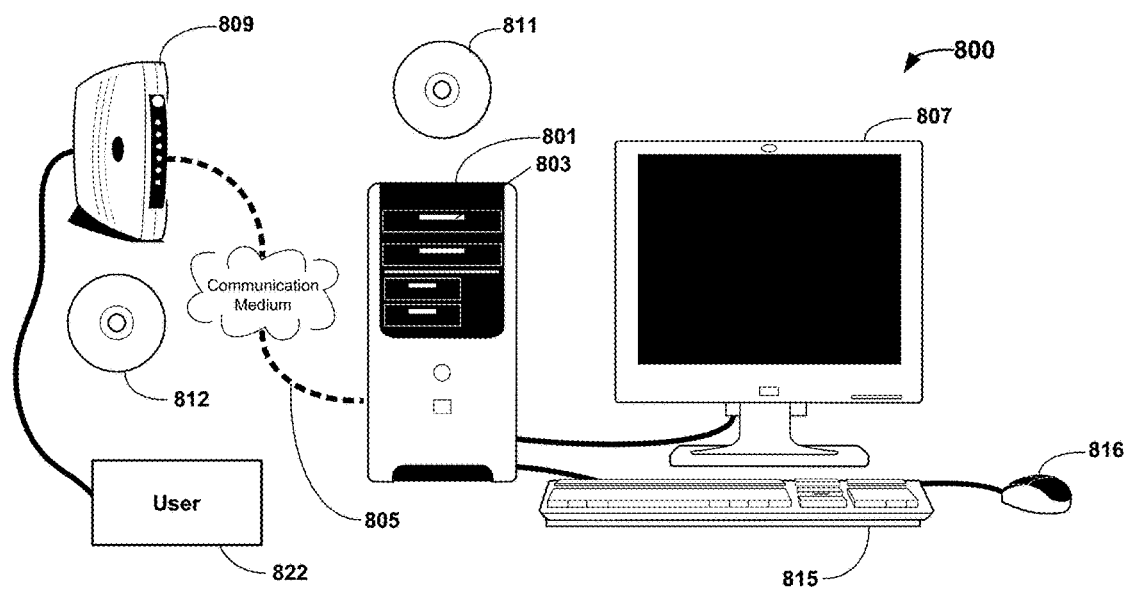
FIG. 16 depicts a computer useful for displaying, storing, retrieving, or calculating diagnostic results from the methods disclosed herein; displaying, storing, retrieving, or calculating raw data from genomic or nucleic acid expression analysis; or displaying, storing, retrieving, or calculating any sample or customer information.

A molecular profiling business can utilize one or more computers in the methods of the present disclosure such as a computer 800 as illustrated in FIG. 16. The computer 800 can be used for managing customer and sample information such as sample or customer tracking, database management, analyzing molecular profiling data, analyzing cytological data, storing data, billing, marketing, reporting results, or storing results. The computer can include a monitor 807 or other graphical interface for displaying data, results, billing information, marketing information (e.g. demographics), customer information, or sample information. The computer can also include means for data or information input 815, 816. The computer can include a processing unit 801 and fixed 803 or removable 811 media or a combination thereof. The computer can be accessed by a user in physical proximity to the computer, for example via a keyboard and/or mouse, or by a user 822 that does not necessarily have access to the physical computer through a communication medium 805 such as a modem, an internet connection, a telephone connection, or a wired or wireless communication signal carrier wave. In some cases, the computer can be connected to a server 809 or other communication device for relaying information from a user to the computer or from the computer to a user. In some cases, the user can store data or information obtained from the computer through a communication medium 805 on media, such as removable media 812. It is envisioned that data relating to the present disclosure can be transmitted over such networks or connections for reception and/or review by a party. The receiving party can be but is not limited to an individual, a health care provider or a health care manager. In one case, a computer-readable medium includes a medium suitable for transmission of a result of an analysis of a biological sample, such as a gene expression profile or other bio-signature. The medium can include a result regarding a gene expression profile or other bio-signature of a subject, wherein such a result is derived using the methods described herein.

Figure 1C:
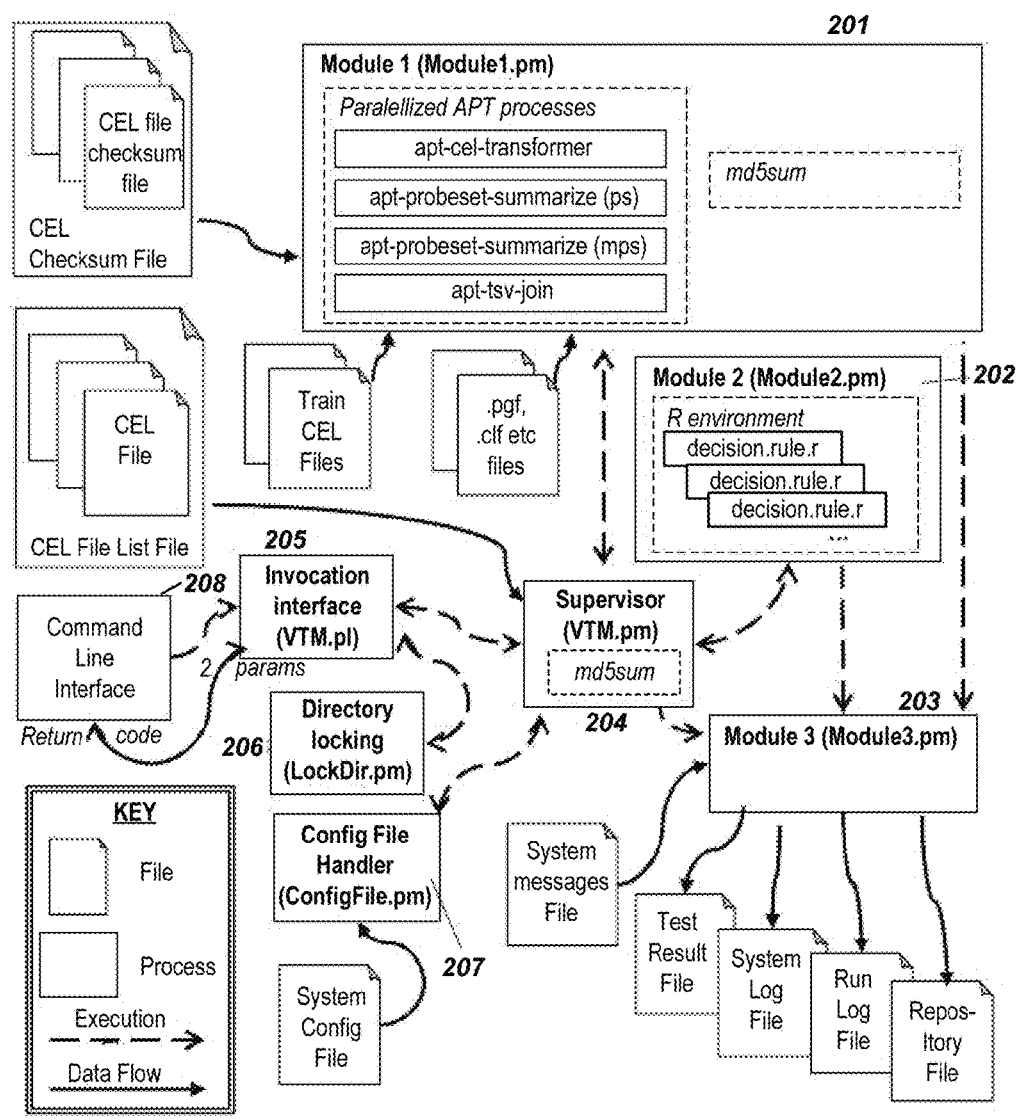

An example architecture of a system for conducting analysis according to the methods of the disclosure is provided in FIG. 1C. This system comprises a number of components for processing, generating, storing, and outputting various files and information. In this example, the process is initiated using a command line interface 208, commands from which are transmitted via an invocation interface 205 to a supervisor 204. The supervisor 204 coordinates the functions of the system to carry out the analysis and comparison steps of the process. The first step in the analysis, illustrated at Module 1 201, includes a quality control check for the data to be analyzed by comparing the gene expression data file ("CEL" file) for a thyroid tissue sample to a corresponding checksum file. If data integrity is confirmed, Module 1 201 progresses to normalization and summarization of the gene expression data, such as by utilizing the Affymetrix Power Tools (APT) suite of programs according to methods known in the art. The system can further comprise files needed for APT processes (e.g., .pgf files, .clf files, and others). Module 1 201 is also applied to gene expression data for training sample sets ("Train CEL Files"), which are grouped to produce classifiers comprising sets of biomarkers, with gene expression data for each set of biomarkers comprising one or more reference gene expression levels correlated with the presence of one or more tissue types. Gene expression data from Module 1 201 is next processed by Module 2 202, which uses the statistical software environment "R" to compare classifiers to gene expression data for the thyroid tissue sample. Each classifier is used to establish a rule for scoring the sample gene expression data as a match or non-match. Each classifier in a set of classifiers for comparison is applied to the gene expression data one after the other. The result of the comparisons performed by Module 2 202 are processed by Module 3 203 to report the result by generating a "test result file," which can contain for each CEL file analyzed the name of the CEL file, a test result (e.g. benign, suspicious, or a specific tissue type), and/or a comment (e.g. classifiers used, matches found, errors encountered, or other details about the comparison process). In some cases, a result of "suspicious" is reported if a sample is scored as a match to any of the classifiers at any point in a sequence of comparisons. In some cases, a result of "benign" is reported if no match between the sample gene expression data and any of the classifiers is found. Module 3 203 also generates system log, run log, and repository files that catalogue what happened at each step of the data handling and analysis, the output from all stages of the analysis (e.g., data integrity check and any error messages), and a table of results from each step, respectively. The log and repository files can be used for diagnosing errors in the comparison process, such as if a data analysis process fails to run through to completion and generation of a result. Module 3 203 can reference a system messages file that contains a list of error messages. The system of this example architecture can also comprise a directory locking component 205 to prevent multiple analyses of the same CEL file at the same time, and a config file handler 207 to contain information regarding file location (e.g., executable files and CEL files) to help manage execution of the work flow of the system processes.

The molecular profiling business can enter sample information into a database for the purpose of one or more of the following: inventory tracking, assay result tracking, order tracking, customer management, customer service, billing, and sales. Sample information can include, but is not limited to: customer name, customer gender, unique customer identification, customer associated medical professional, indicated assay or assays, assay results, adequacy status, indicated adequacy tests, medical history of the individual, preliminary diagnosis, suspected diagnosis, sample history, insurance provider, medical provider, third party testing center or any information suitable for storage in a database. Sample history can include but is not limited to: age of the sample, type of sample, method of acquisition, method of storage, or method of transport.

The database can be accessible by a customer, medical professional, insurance provider, third party, or any individual or entity which the molecular profiling business grants access. Database access can take the form of electronic communication such as a computer or telephone. The database can be accessed through an intermediary such as a customer service representative, business representative, consultant, independent testing center, or medical professional. The availability or degree of database access or sample information, such as assay results, can change upon payment of a fee for products and services rendered or to be rendered. The degree of database access or sample information can be restricted to comply with generally accepted or legal requirements for patient or customer confidentiality. The molecular profiling company can bill the individual, insurance provider, medical provider, or government entity for one or more of the following: sample receipt, sample storage, sample preparation, cytological testing, molecular profiling, input and update of sample information into the database, or database access.

(iii) Business Flow

Biological samples (e.g., thyroid cells), for example, can be obtained by an endocrinologist perhaps via fine needle aspiration. Samples can be subjected to routine cytological staining procedures. Said routine cytological staining can provides, for example, four different possible preliminary diagnoses: non-diagnostic, benign, ambiguous or suspicious, or malignant. The molecular profiling business can then analyze gene expression product levels as described herein. Said analysis of gene expression product levels, molecular profiling, can lead to a definitive diagnosis of malignant or benign. In some cases, only a subset of samples are analyzed by molecular profiling such as those that provide ambiguous and non-diagnostic results during routine cytological examination.

In some cases, the molecular profiling results confirm the routine cytological test results. In other cases, the molecular profiling results differ. In such cases where the results differ, samples can be further tested, data can be reexamined, or the molecular profiling results or cytological assay results can be taken as the correct classification, characterization, or diagnosis. Classification, characterization, or diagnosis as benign can also include diseases or conditions that, while not malignant cancer, can indicate further monitoring or treatment (e.g., HA). Similarly, classification, characterization, or diagnosis as malignant can further include classification, characterization, or diagnosis of the specific type of cancer (e.g., HC) or a specific metabolic or signaling pathway involved in the disease or condition. A classification, characterization, or diagnosis can indicate a treatment or therapeutic intervention such as radioactive iodine ablation, surgery, thyroidectomy, administering one or more therapeutic agents; or further monitoring.

Administering one or more therapeutic agent can comprise administering one or more chemotherapeutic agents. In general, a "chemotherapeutic agent" refers to any agent useful in the treatment of a neoplastic condition. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository. In some cases, the chemotherapeutic is selected from the group consisting of mitotic inhibitors, alkylating agents, antimetabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylomithine (DMFO). Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, and Velcade®.

XI. Kits

Figure 15:
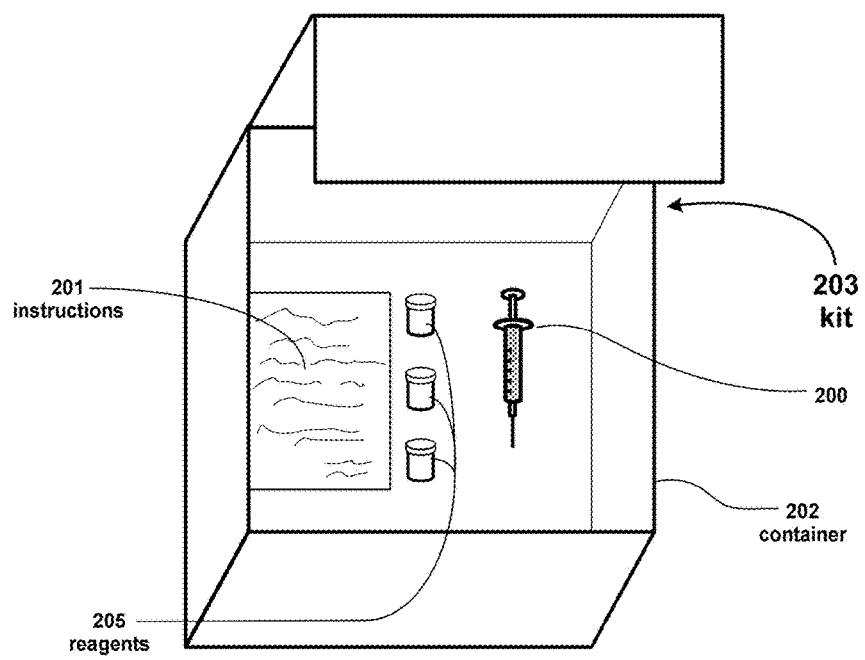
FIG. 15 illustrates an exemplary kit.

The molecular profiling business can provide a kit for obtaining a suitable sample. The kit can comprise a container, a means for obtaining a sample, reagents for storing the sample, and/or instructions for use of the kit. FIG. 15 depicts an exemplary kit 203, comprising a container 202, a means 200 for obtaining a sample, reagents 205 for storing the sample, and instructions 201 for use of the kit. The kit can further comprise reagents and materials for performing the molecular profiling analysis. In some cases, the reagents and materials include a computer program for analyzing the data generated by the molecular profiling methods. In still other cases, the kit contains a means by which the biological sample is stored and transported to a testing facility such as a molecular profiling business or a third party testing center.

The molecular profiling business can also provide a kit for performing molecular profiling. Said kit can comprise a means for extracting protein or nucleic acids, including any or all necessary buffers and reagents; and, a means for analyzing levels of protein or nucleic acids including controls, and reagents. The kit can further comprise software or a license to obtain and use software for analysis of the data provided using the methods and compositions of the present disclosure.

EXAMPLES

Example 1: Classification Panels from Analysis of Clinical Thyroid Samples

Prospective clinical thyroid FNA samples (n=248) and post-surgical thyroid tissues (n=220) were examined with the Affymetrix Human Exon 1.0 ST microarray in order to identify genes that differ significantly in mRNA expression between benign and malignant samples.

Affymetrix software was used to extract, normalize, and summarize intensity data from roughly 6.5 million probes. Approximately 280,000 core probe sets were subsequently used in feature selection and classification. Models used included LIMMA (for feature selection), and SVM (used for classification) (Smyth 2004;). Top genes used in each classification panel were identified in several separate analyses using a combination of LIMMA and algorithms.

While the annotation and mapping of genes to transcript cluster identifiers (TCID) is constantly evolving, the nucleotide sequences in the probes and probe sets that make up a TCID do not change. Furthermore, a number of significant TCIDs do not map any known genes, yet these are equally important biomarkers in the classification of thyroid malignancy. Results are described using both the TCID and the genes currently mapped to each (Affymetrix annotation file: HuEx-1_0-st-v2.na30.hg19.transcript.csv).

Sample Cohorts Used to Train Classifier:

| Subtype | Simplified Classification | Post-Surgical Thyroid Tissue | Thyroid FNA |
|---|---|---|---|
| FA | Benign | 26 | 28 |
| HA | Benign | 0 | 5 |
| LCT | Benign | 40 | 27 |
| NHP | Benign | 23 | 111 |
| PTA | Benign | 5 | 0 |
| OM1 | Malignant | 0 | 3 |
| FC | Malignant | 19 | 5 |
| HC | Malignant | 23 | 0 |
| FVPTC | Malignant | 21 | 11 |
| PTC | Malignant | 26 | 58 |
| MTC | Malignant | 23 | 0 |
| BCA | Malignant | 5 | 0 |
| MMN | Malignant | 4 | 0 |
| RCC | Malignant | 5 | 0 |
| Total | | 220 | 248 |

[1]OM-denotes "other malignant", and consists of extremely rare subtypes of thyroid origin (e.g., metastasized tissue to the lymph node) that were grouped together.

Classification panels for MTC, BCA, MMN, PTA, and RCC were derived using only samples from the post-surgical thyroid tissue cohort. Each subtype was compared against all other subtypes combined, for example the 23 MTC samples were compared to the remaining 197 samples in the cohort.

The HA/HC classification panel was derived by combining samples of these two subtypes from both the tissue and FNA cohorts. The combined HA/HC samples were then compared against all other subtypes combined. The "Benign/Suspicious" classification panel was derived by combining several sub-analyses in which subsets of "benign" and "malignant" samples were compared. The genes in each classification panel (FIG. 3, FIG. 4) can be used to accurately classify clinical thyroid FNAs, such as by methods known in the art.

Example 2: Molecular Profiling of Thyroid Nodule

An individual notices a lump on his thyroid. The individual consults his family physician. The family physician decides to obtain a sample from the lump and subject it to molecular profiling analysis. Said physician uses a kit to obtain the sample via fine needle aspiration, perform an adequacy test, store the sample in a liquid based cytology solution, and sends it to a molecular profiling business. Optionally, the physician can have the cytology examination performed by another party or laboratory. If the cytology examination results in an indeterminate diagnosis, the remaining portion of the sample is sent to the molecular profiling business, or to a third party. The molecular profiling business divides the sample for cytological analysis of one part and for the remainder of the sample extracts mRNA from the sample, analyzes the quality and suitability of the mRNA sample extracted, and analyzes the expression levels and alternative exon usage of a subset of the genes listed in FIG. 4. Optionally, a third party not associated with the molecular profiling business can extract the mRNA and/or identify the expression levels of particular biomarkers. The particular gene expression products profile is determined by the sample type, by the preliminary diagnosis of the physician, and by the molecular profiling company.

The molecular profiling business analyzes the data using the classification system obtained by the methods described in Example 1 and provides a resulting diagnosis to the individual's physician. The results provide 1) a list of gene expression products profiled, 2) the results of the profiling (e.g. the expression level normalized to an internal standard such as total mRNA or the expression of a well characterized gene product such as tubulin, 3) the gene product expression level expected for normal tissue of matching type, and 4) a diagnosis and recommended treatment for individual based on the gene product expression levels. The molecular profiling business bills the individual's insurance provider for products and services rendered.

Example 3: Identification of Hurthle Cell Adenoma and Carcinoma in Thyroid Tissue Post-surgical thyroid tissue samples and clinical thyroid FNA biopsies were examined with the Affymetrix Human Exon 1.0 ST microarray in order to identify biomarkers that differ significantly in mRNA expression between benign and malignant samples. These biomarkers were then used to train a molecular classifier using the same post-surgical tissue sample cohort. The information learned during algorithm training using tissue samples, including but not limited to biomarker selection for each thyroid subtype, was combined with a further step of algorithm training using clinical FNA samples, such that the high-dimensionality nature of biomarker expression in FNA can be preserved and used to train an optimized or next-generation molecular classifier. By combining the information learned from tissue and clinical FNAs, the molecular classifier proved to be an accurate molecular diagnostic of Hurthle cell adenoma and Hurthle cell carcinoma. The cohort of samples used to train the tissue-classifier did not contain any Hurthle cell adenoma samples, and the cohort of samples used to train the FNA classifier did not contain any Hurthle cell carcinoma samples. Thus, each molecular classifier training set was deficient in (and unable to learn) how to classify one subtype or the other, but the classifier trained using both sets was able to properly classify both, overcoming the individual limitations of the tissue and FNA training sample sets. Independent validation of the optimized FNA classifier, using a small cohort of HA (n=2) and HC (n=2), resulted in 100% classification accuracy. This demonstrated that a classifier can be trained to accurately classify a sample of thyroid tissue when a member of the class is not represented in a sample set used to train the classifier.

Affymetrix software was used to extract, normalize, and summarize intensity data from roughly 6.5 million probes on the Affymetrix Human Exon 1.0 ST microarray. Approximately 280,000 core probe sets were subsequently used in feature selection and classification. Feature/biomarker selection was carried out using LIMMA models, while random forest and SVM were used for classification (see e.g. Smyth 2004, Statistical applications in genetics and molecular biology 3: Article 3; and Diaz-Uriarte and Alvarez de Andres 2006, BMC Bioinformatics, 7(3)). Iterative rounds of training, classification, and cross-validation were performed using random subsets of data. Top features were identified in at least three separate analyses using the classification scheme described in this example. Features/biomarkers in this example are referred to by a transcript cluster identifier (TCID), as well as by gene name, where available. Some TCIDs may not correspond to a known gene, which depends in part on the progress of gene mapping and identification. Biomarkers identified in this example are listed in a table in FIG. 8.

Example 4: Molecular Classification Using High-Dimensionality Genomic Data

This examples describes mRNA expression analysis of more than 247,186 transcripts in 363 thyroid nodules comprising multiple subtypes. Starting with surgical tissue from resected thyroid nodules, differentially-expressed transcripts that distinguish benign and malignant nodules are identified. A classifier trained on 178 tissue samples was used to test an independent set of fine needle aspirates (FNAs). Retraining of the algorithm on a set of 137 prospectively collected thyroid FNAs resulted in increased performance, estimated using both 30-fold cross-validation as well as testing on an independent set of FNAs, which included 50% with indeterminate cytopathology. The FNA-trained algorithm was able to classify RNAs in which substantial RNA degradation had occurred and in the presence of blood. Preliminary performance characteristics of the test showed a negative predictive value (NPV) of 96% (95% C.I. 82-99%) and specificity of 84% (95% C.I. 82-99%). The majority of malignant FNAs tolerated a dilution down to 20%.

Specimens and RNA Isolation, Amplification, and Microarray Hybridization

Prospective FNA samples used in this example were either 1) aspirated in vivo at outpatient clinical sites, 2)

aspirated pre-operatively, after administering general anesthesia, but prior to surgical incision, or 3) aspirated ex vivo immediately after surgical excision, then directly placed into RNAprotect preservative solution (Qiagen) and stored frozen at −80 C. Prospectively collected FNAs were scored for bloodiness by visual inspection on a 4 point scale. This scale was developed based on an assessment of red/brown coloration and transparency within the preservative solution as compared to assigned reference samples. A score of zero indicates no coloration and complete transparency; a score of 3 indicates dark red/brown coloration and no transparency. Post surgical thyroid tissue was snap-frozen immediately after excision, and stored at −80° C. Cytology and post-surgical histopathology data (when available) was obtained from the collecting site. In order to validate post-surgical pathology findings, slides were re-examined by an expert pathologist who then adjudicated a gold-standard subtype label used for classification training The specimens in the tissue training set included a 1:1 proportion of benign and malignant samples consisting of 23 nodular hyperplasia (NHP), 40 lymphocytic thyroiditis (Hashimoto's thyroiditis) (LCT), 26 follicular adenoma (FA), 23 Hurthle cell carcinoma (HC), 19 follicular carcinoma (FC), 21 follicular variant of papillary thyroid carcinoma (FVPTC), and 26 papillary thyroid carcinoma (PTC). The specimens in the FNA training set included 96 (70%) benign and 41 (30%) malignant nodules, consisting of 67 NHP, 18 LCT, 9 FA, 2 HA, 3 FC, 4 FVPTC, and 34 PTC. The independent FNA test set (n=48) was prospectively collected subsequent to the training set and included a 50% proportion of indeterminate samples, as determined by FNA cytopathology.

RNA from clinical FNAs was extracted using the AllPrep micro kit (Qiagen). RNA from surgical thyroid tissue was purified using a standard phenol-chloroform extraction and ethanol precipitation method. The quantity and integrity of RNA was determined using a Nanodrop ND-8000 spectrophotometer (Thermo Scientific), Bioanalyzer Picochip system (Agilent Technologies) and Quant-IT RNA kit (Invitrogen). Fifty or twenty-five nanograms of total RNA were then amplified using the NuGEN WT Ovation amplification system, and hybridized to Affymetrix Human Exon 1.0 ST arrays, followed by washing, staining and scanning following manufacturer's protocols (Affymetrix).

The 1.10.2 version of APT (Affymetrix Power Tools) was used to process, normalize, and summarize the .CEL files. Post-hybridization quality control included percent detection above background (DABG), and exon-intron signal separation for control probesets (AUC). Each .CEL file from the independent test set was normalized individually with APT using a quantile normalization sketch and RMA feature effects derived from the training set.

Training Models, Classification, and Biomarker Selection

Classification of samples into benign and malignant categories was done using transcript cluster intensity summaries from the Exon array as features in the model. Selection of markers differentiating benign and malignant categories was done using a LIMMA linear model approach (see e.g. Smyth 2004), as an inner loop of the 30-fold cross-validation process (see e.g. Smyth 2004; and Varma and Simon 2006, BMC Bioinformatics 7(91)). Given a set of informative markers, a linear support vector machine (SVM) model was trained to perform binary classification using R package e1071 (see e.g. Dimitriadou et al. 2009, Misc Functions of the Department of Statistics (e1071); and Cortes and Vapnik 2005, Machine Learning 20:273-297). To estimate performance of the model, both marker selection and model estimation were cross-validated to avoid biases in error estimates. To select optimal number of features in the model, classification performance was estimated as a function of the number of markers in the model. Performance was defined as false positive rate given a fixed false-negative error rate of 5%. Biomarkers of medullary thyroid carcinoma (MTC) were developed separately. A simple linear algorithm applied at the beginning of the analysis, triggered classification of MTC samples, bypassing the molecular classifier described above. The FNA training model was created strictly on FNA samples as described above, except it used the overlap of biomarkers selected from three previous independent analyses using both tissue and FNA samples. When training the classifiers, mapping of SVM scores to a probability space was estimated using a sigmoidal transformation.

In order to determine a classification prediction cut-off value, the cross-validated prediction scores were re-sampled to represent the distribution of subtypes seen in the prospective FNA collection. The target distribution contains approximately 30% malignant samples, in agreement with the reported frequency of indeterminate FNA observed by cytopathology (3-8, 23). The composition of the re-sampled dataset contains the following subtypes: 27.6% NHP, 29.0% FA, 9.5% LCT, 5.4% HA, 1.8% FC, 9% FVPTC, 3.2% HC, 0.5% MTC, and 14% PTC. Since no HC's were accrued in the FNA training set, errors made on the HC subtype were sampled from the FC pool. This represents a conservative estimate of our ability to distinguish HCs since prior analysis based on thyroid tissue has shown comparable error rates between the FC and HC subtypes. Following the re-sampling step, placement of a cut-off value was examined from 0.1 to 0.2 at 0.01 increments. Sensitivity, Specificity, PPV and NPV were produced at each threshold. The threshold that achieved sensitivity above 93%, NPV above 95%, and specificity of at least 70% was chosen; currently the FNA prediction cut-off value is 0.15. Thus, samples with a score less than 0.15 were designated "benign" and those with a score greater than or equal to 0.15 were designated "suspicious."

Cellular Heterogeneity and Mixture Modeling

Markers of follicular content (FOL) were derived from the literature and are as follows: DIO1, DIO2, EGFR, KRT19, KRT7, MUC1, TG, and TPO (24). Lymphocyte markers were used to estimate lymphocytic content (LCT), these were CD4, FOXP3, IFNG, IGK@, IGL@, IL10, IL2, IL2RA, IL4, and KLRB1 (see e.g. Paul 2008, Fundamental Immunology, xviii:1603). The intensity of each marker in each sample was measured, then averaged across each marker set and mean follicular signal (FOL) was plotted as a function of mean lymphocyte signal (LCT) to generate a curve showing the trade-off between these two components within all tissue samples and all FNA samples used in training.

In vitro mixtures of pre-operatively collected PTC and NHP FNAs (each from a single patient) were created by combining total RNA using the following PTC:NHP proportions: 100:0, 40:60, 20:80, 0:100. All dilution ratios were processed in triplicate and carried out to completion including microarray hybridization as described above. In silico modeling from two sources was based on linear additive mixing of signals from individual samples in the original intensity space. Briefly, for any two samples A and B, represented by normalized and log-transformed intensity vectors YA and YB, the expected signal in the mixture sample Yc was modeled as:

$$\textit{,,Y-c.}=\log\text{-2.,}\alpha^{*},2\text{-,}Y\text{-}A\ldots-,1\text{-}\alpha.^{*},2\text{-,}Y\text{-}B\ldots,$$

$$Y_c = \log 2(\alpha * 2^{Y_A} + (1-\alpha) * 2^{Y_B})$$

where α and (1-α) represent the proportion of samples A and B in the mixture respectively. To validate the simulation, observed signals from pure NHP and PTC samples from the in vitro mixing experiment were used to generate predicted profiles at proportions of PTC varying from 0 to 1 at 0.01 increments.

In silico simulations were applied to estimate the tolerance of the classifier to the effects of LCT and NHP backgrounds. Using the equation above, simulated intensity profiles were simulated for mixtures containing one of 39 PTC samples and one of 59 benign samples (7 LCT and 52 NHP samples). The LCT samples were selected among samples with high average intensity for lymphocyte markers as described above. In contrast, the NHP samples were selected among samples with low average intensity for these markers. This filtering step was performed to ensure good representation of LCT and NHP signals in each of the two pools. For each pair of benign and malignant samples, the in silico mixing was done at proportions of PTC varying from 0 to 1 at 0.01 increments, resulting in 100 simulated mixture profiles per pair. The in silico mixtures were then scored with a classifier, so that a prediction call of "suspicious" or "benign" could be recorded for all levels of mixing. For this purpose, the classifier was built excluding the pair of pure samples being mixed in order to estimate true "out-of-sample" tolerance to dilution. Given classifier predictions for 100 estimated mixtures per mixed pair, the mixing proportion of PTC signal at which the classifier call switched from "Suspicious" to "Benign" was estimated, effectively characterizing the tolerance of the classifier to the dilution.

Gene Enrichment Analysis

A subset of top differentially-expressed genes (n=980), resulting from a LIMMA comparison of benign versus malignant FNAs, was filtered by FDR p-value (≤0.05) and absolute effect size (≥0.5), then subjected to over/under-representation analysis (ORA) using GeneTrail software (see e.g. Backes et al. 2007, Nucleic Acids Research 35:W186-192). Pathway analysis included test (n=306) and reference sets (n=5,048) with available annotation in the KEGG database (see e.g. Kanehisa et al. 2010, Nucleic Acids Research 38:D355-360). Gene ontology analysis used larger test (n=671), and reference sets (n=11,218), and was limited to manually curated annotations in the GO database (see e.g. Ashburner et al. 2000, Nature Genetics 25:25-29). Significance was examined using a Fisher's exact test with a threshold of p<0.05 after Benjamini and Hochberg (FDR) correction.

Performance Evaluation of Tissue Models on FNA Samples

Microarray data was first generated from a set of 178 surgical thyroid tissue sample using the Affymetrix Human Exon 1.0 ST array, which measures all known and predicted human transcripts at both the gene and exon level, providing a comprehensive transcriptional profile of the samples. The sample set included the most common benign thyroid nodule subtypes: nodular hyperplasia (NHP), lymphocytic thyroiditis (LCT), follicular adenoma (FA), as well as malignant subtypes such as papillary thyroid carcinoma (PTC), follicular variant of papillary thyroid carcinoma (FVPTC), follicular carcinoma (FC) and Hurthle cell carcinoma (HC). Markers to accurately identify medullary thyroid carcinoma (MTC) were also developed, the identification consisting of applying a simple linear algorithm using a smaller set of markers at the beginning of the analysis, separate from the algorithm used to distinguish the more common thyroid FNA subtypes.

Figure 9A:
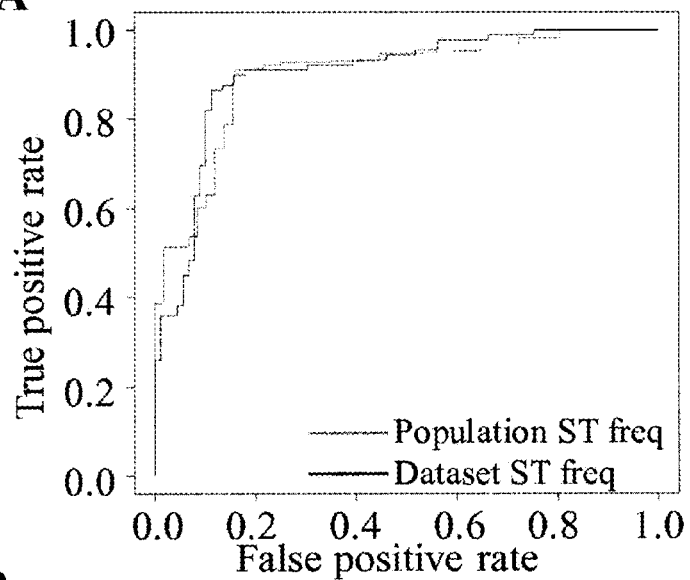
FIG. 9A-FIG. 9B illustrates Receiver Operator Characteristic (ROC) curves for classifiers trained according to the methods disclosed herein.

Machine-learning methods were implemented to train a molecular classifier on tissue samples, and following the evaluation of several analytical methods, the support-vector-machine (SVM) method for classification was chosen (see e.g. Cortes and Vapnik 2005). Using 30-fold cross-validation, false positive and false negative error rates were estimated. True positive rate (1-false negative rate) as a function of false positive rate generated a receiver-operator-characteristic (ROC) curve with an area-under-the-curve (AUC) of 0.90 (FIG. 9A black line). To represent the true prevalence of malignant samples within the indeterminate group, re-sampling was performed to attain a target subtype distribution containing approximately 30% malignant samples The AUC of the re-sampled ROC curve is 0.89 (FIG. 9A gray line). These parameters and models were then used to test an independent set of FNAs to determine whether this performance is generalizable to an unseen data set. A test set of 24 FNAs with indeterminate cytopathology and known surgical pathology diagnoses was combined with an additional 24 FNAs diagnosed as benign or malignant by cytopathology and known surgical pathology diagnoses, for an independent test set of 48 samples. The composition of the sample sets are described in the table in FIG. 11. The performance of the tissue-trained classifier decreased when tested on the independent FNAs, with sensitivity of 92% (95% C.I. 68-99%) and specificity of 58% (95% C.I. 41-73%) on the larger set of 48 FNAs (FIG. 10A-FIG. 10D). Performance on the indeterminate-only subset of 24 FNAs is similar to the cross-validated performance (FIG. 10A-FIG. 10D). Without wishing to be bound by theory, the lower performance of the tissue-trained classifier on FNAs could be due to several reasons; algorithm overfitting, the small sample sizes used for independent testing, or a fundamental difference in the biological or technical properties of tissue samples and FNAs. The third possibility was addressed by first insuring that there were no RNA quality differences between the two sample types used in our analyses, and secondly, by examining cellular heterogeneity as a variable. The first two possibilities are addressed later in this example.

Figure 9B:
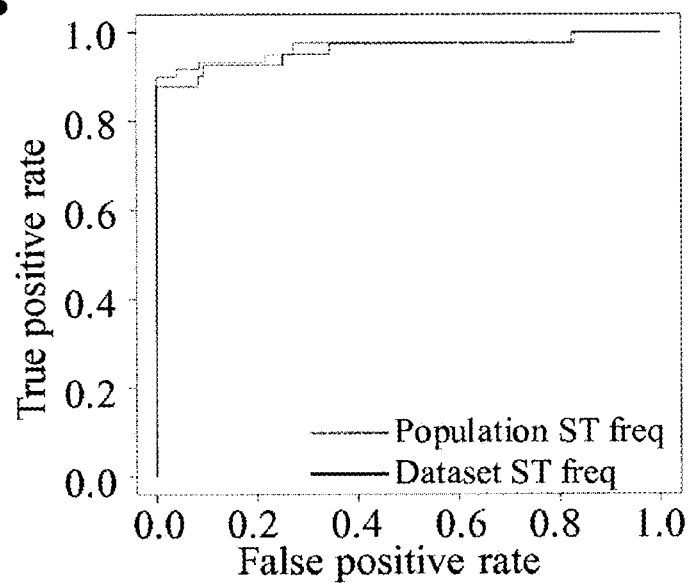

FIG. 9A-FIG. 9B illustrates the performance of a classifier trained on post-surgical thyroid tissues or FNAs. In FIG. 9A, ROC curves measure sensitivity (true positive rate) of the tissue classifier as a function of specificity (1-false positive rate) using 30-fold cross-validation. Two curves were generated, one showing performance on the training set without adjusting for subtype prevalence (black), and the second (gray) adjusting subtype error rates to reflect published subtype prevalence frequencies. The area under the curve (AUC) is 0.9 (black curve) or 0.89 (gray curve). In FIG. 9B, performance of a classifier trained on FNAs is illustrated. Both training sets are described above and in the table in FIG. 11. The AUC is 0.96 for both curves.

FIG. 10A-FIG. 10D illustrates a comparison of tissue-trained and FNA-trained molecular classifiers and their performance on two independent test sets. Sensitivity (FIG. 10A) and specificity (FIG. 10B) of a tissue-trained classifier and an FNA-trained classifier, on two independent data sets are provided. Indeterminate denotes a set of 24 FNA samples with indeterminate cytopathology, and B/M/Indeterminate includes a set of 48 FNA samples with benign, malignant, or indeterminate cytopathology. Point estimates are shown, with 95% Wilson confidence intervals. FIG. 10C and FIG. 10D provide subtype distribution of the two independent data sets and classifier prediction (either benign or suspicious) for each sample. Surgical pathology labels are abbreviated as follows: NHP, nodular hyperplasia; LCT, lymphocytic thyroiditis; FA, follicular adenoma; BLN, benign lymph node; PTC, papillary thyroid carcinoma; FVPTC, follicular variant of papillary thyroid carcinoma; HC, Hurthle cell carcinoma; and MLN, malignant lymph node.

FIG. 11 provides a table illustrating the composition of samples used in algorithm training and testing, by subtype, as defined by expert post-surgical histopathology review. A subset of samples did not have post-surgical histopathology labels, as indicated by superscripts for values in the tables, which are as follows: (a) 68/96, (b) 6/34, and (c) 4/41. Surgical pathology labels are abbreviated in the table as follows: FA, follicular adenoma; FC, follicular carcinoma; FVPTC, follicular variant of papillary carcinoma; HA, Hurthle cell adenoma; LCT, lymphocytic thyroiditis; NHP, nodular hyperplasia; PTC, papillary thyroid carcinoma; BLN, benign lymph node; MLN, malignant lymph node.

Figure 12A:
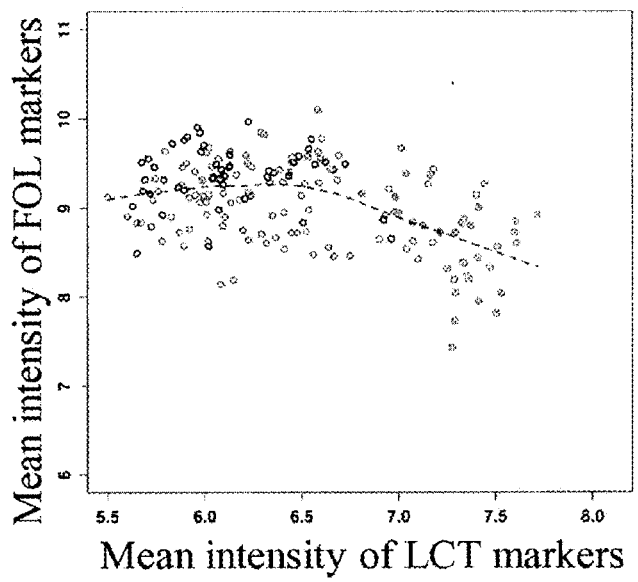
FIG. 12A-FIG. 12B illustrates a comparison of composite follicular (FOL) and lymphocytic (LCT) scores across surgical tissue (FIG. 12A) and fine needle aspirates (FIG. 12B).
Figure 12B:
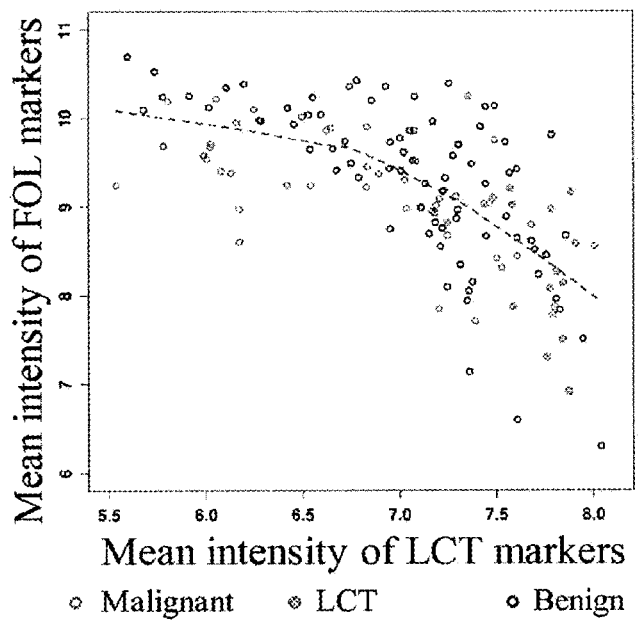

To evaluate cellular heterogeneity between tissues and FNAs, genes known to be present in thyroid follicular cells and lymphocytes were measured, and the measurements were used to create a composite measure of each sample based on the average signal of all follicular content markers as a function of average lymphocyte content markers. Markers were selected that were not differentially expressed in benign versus malignant nodules. This composite measure had significantly higher variability in FNA samples (FIG. 12B) than in surgical tissue samples (FIG. 12A). The data highlight the value of accounting for cellular heterogeneity in biomarker discovery. Specifically, FIG. 12A-FIG. 12B provides a comparison of composite follicular (FOL) and lymphocytic (LCT) scores across surgical tissue (FIG. 12A; n=178) and FNAs (FIG. 12B; n=137). The mean signal intensity of follicular cell biomarkers decreases as the mean signal intensity of lymphocytic markers increases. This trade-off between follicular cell content and lymphocytic background is substantially greater in FNAs than in tissue.

Performance of FNA Models on FNA Samples

A cohort (n=960) of prospectively collected clinical thyroid FNAs from more than 20 clinics across the United States, 137 of which corresponding surgical pathology was available on FNAs encompassing both prevalent and rare thyroid subtypes. The composition of this training set is shown in FIG. 11. Histopathology slides from all patients who underwent surgical resection were subjected to primary review by a surgical pathologist, and when available, subjected to secondary review by a panel of two experts in order to adjudicate gold-standard classification and subtype training labels. Genome-wide expression data from this cohort was used to develop a second-generation classifier, trained on FNAs, to achieve desired clinical performance. First, the classifier performance was estimated using 30-fold cross-validation (similar to the process used with the tissue classifier, see FIG. 9A). The cross-validated ROC curve (sensitivity of the classifier as a function of false positive rate) had an AUC of 0.96 for the training data "as is" and 0.97 when re-sampled to account for the prevalence of subtypes in the indeterminate population. When sensitivity is fixed at 95%, specificity remains very high, at 75% (FIG. 9B) and is unaffected by varying quantities of blood in the FNA. This classifier was then tested on the same independent test sets of prospectively collected clinical FNAs used to test the tissue-trained classifier (FIG. 10A and FIG. 10B). Data shown in FIG. 10A-FIG. 10D indicates that sensitivity and specificity have increased significantly for both the n=24 and n=48 independent FNA test sets using FNA-trained classifiers. While these test sets are small in size, their performance is similar to that of the cross-validated training set, suggesting that the algorithm is not overfitted, and that the FNA-trained classifier is generalizable to unseen data sets. The composition of the test set is approximately 30% malignant subtypes, similar to that described for clinical FNA samples. A multi-center prospective clinical trial across over 40 U.S. academic and community-based sites can be used to validate the performance of this molecular test on a large set of indeterminate FNAs.

In Vitro and In Silico Modeling of Sample Mixtures

In order to determine how sensitive the classifier is to decreasing proportions of malignant cells, a model for in silico simulation of the mixture signals was proposed, the model was validated with in vitro mixing experiments, and computational simulations were used to analyze the tolerance of the classifier to the dilution effects. In general, an in silico model can serve as a reasonable approximation to the mixing process if the deviation of simulated mixture profiles from the actual observed signals is within the noise typically observed for technical replicates. In this example, the distribution of the inter-quartile range of the difference in intensities between in silico predictions and in vitro observed signals for the marker set was similar to that observed for pairs of technical replicates.

Figure 13A:
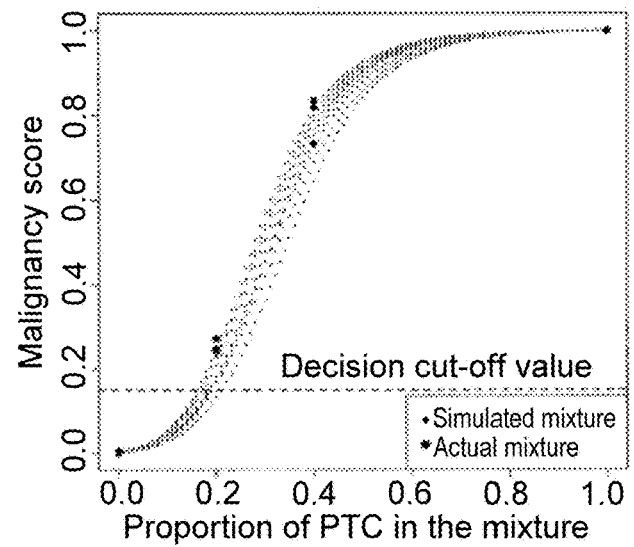
FIG. 13A-FIG. 13C illustrates the effect of in silico simulated mixtures and in vitro mixtures on classifier performance.

FIG. 13A shows the effects of varying proportion of PTC signal in the mixture (x axis) on the classification scores (y axis), and that the classifier performance is highly tolerant to sample dilution and heterogeneity. The in vitro data is nearly superimposable on the in silico predictions made for mixtures with similar PTC content. In the case of this particular PTC sample, the classifier tolerates dilution of the PTC signal to less than 20% of the original level and reports a "suspicious" call for the "mixed" sample. However, a different clinical sample can contain a smaller proportion of malignant cells and can be characterized by smaller tolerance to dilution. Given the agreement established between in silico and in vitro simulations, computational simulations were next used to investigate dilution effects on a broader set of FNAs.

Each of 39 PTC FNA samples were mixed in silico with one of either LCT or NHP samples. Individual FNA samples did not represent pure expression of any single component of the possible cellular types. However, the variety of signal present in many LCT and NHP samples represents the spectrum of the possible composite background signals that could obscure malignant cell signals in clinical biopsies. To separately investigate the effects of LCT and NHP backgrounds, the pool of LCT samples was restricted to seven FNA samples with the highest average intensity of LCT markers derived from this data set. Similarly, the NHP samples were restricted to the 52 samples with the lowest estimated LCT content. This filtering step was performed to ensure good representation of LCT and NHP signals in each of the two sets. For each pair of benign and malignant samples, the mixing was done at proportions of PTC varying from 0 to 1 at 0.01 increments, resulting in 100 simulated mixture profiles per pair. The in silico mixture samples were then scored with a classifier, so that a "suspicious" or "benign" call could be recorded for all levels of mixing. For this purpose, the classifier was built excluding the pair of pure samples being mixed in order to estimate true "out-of-sample" tolerance to dilution. Given classifier predictions, the mixing proportion of PTC signal at which the classifier call switched from "suspicious" to "benign" was estimated, effectively characterizing the tolerance of the classifier to the dilution.

Figure 13B:
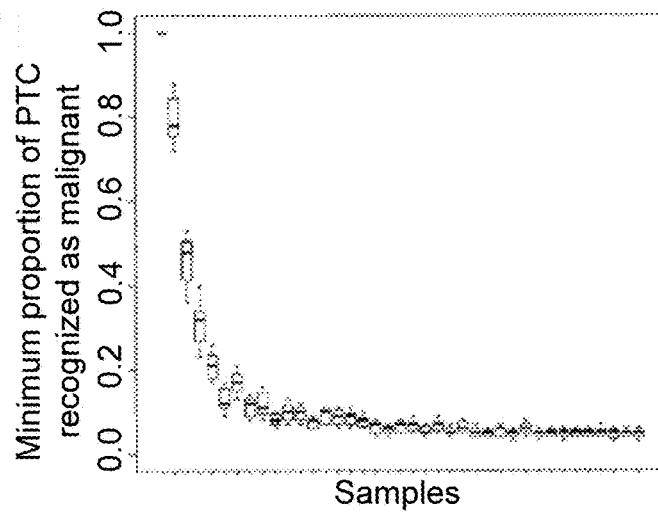
Figure 13C:
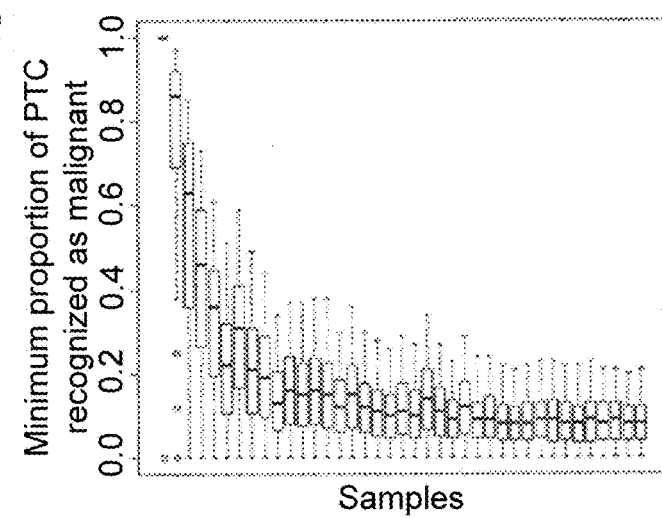

The results of this simulation are summarized in FIG. 13A-FIG. 13C, showing the minimum proportion of the PTC signal that results in a "suspicious" call by the classifier. Prediction score tolerance results for mixing with LCT background are shown in FIG. 13B and prediction score tolerance results for mixing with NHP background are shown in FIG. 13C. Each of the PTC samples is represented by a boxplot, corresponding to mixes with all possible representatives of the benign subtype. The PTC samples are arranged on the x axis in the order of increasing classification scores for the original PTC sample. The values on the y axis are the minimum proportion of PTC that is still reported as "suspicious" by the classifier. Smaller values correspond to higher tolerance to dilution. Tolerance is higher for dilution with LCT signal. Over 80% of all PTC samples in this data set can be diluted to levels below 10% of the original signal with LCT background and still be correctly called by the classifier. Up to 50% of the samples can be diluted to less than 6% of the original sample. PTC samples appear more sensitive to dilutions with N}IP signal, with highest scoring samples tolerating, on average, dilution down to 12% of the original signal, and approximately 80% of PTC samples tolerate dilutions down to 20% of the original signal. The variances of tolerance for any given PTC sample are larger than those observed for LCT background.

Gene Enrichment Analysis

The classifier training process identified many genes well known for their involvement in thyroid malignancy, as well as those previously not associated with this disease. In order to characterize the biological signatures associated with these genes, over representation analysis (ORA) was performed using differentially expressed genes with high statistical support. The analysis tests the likelihood that an observed group of genes (i.e., genes in a pathway), share a non-random connection pointing to the underlying biology. The first analysis focused on the KEGG pathways database and revealed enrichment of cell membrane-mediated pathways (FIG. 14). The extracellular membrane (ECM) receptor interaction, cell adhesion, tight junction, and focal adhesion pathways highlight the role of integrins among other membrane bound mediators in thyroid malignancy. Other top pathways point to TNF-, Rho-, and chemokine gene families long known for their involvement in carcinogenesis. These results are complemented by ORA using the gene ontology (GO) database. Again, endothelial, ECM, and cell membrane signatures represent five out of the top 10 results. Another, top ranked biological signature detected in the GO ORA points to wound healing. This gene expression signature has been associated with diminished survival in breast cancer patients.

FIG. 14 summarizes the ORA of top differentially expressed genes (n=980), with 657 genes being upregulated and 323 genes being down-regulated. Numbers in regular font refer to pathways that are over-represented by top differentially expressed genes, while numbers in bold refer to pathways that are under-represented.

Sample Biomarkers

The fibronectin gene FN1 was among the known genes identified in the gene selection process. Other known genes of interest include thyroid peroxidase (TPO), galectin-3 (LGALS3), calcitonin (CALCA), tissue inhibitor of metalloproteinase (TIMP), angiopoietin-2 (ANGPT2), and telomerase reverse transcriptase(TERT), all genes that have been shown to be implicated in thyroid cancer. In this example, the classifier uses signals from approximately 100-200 genes to achieve high accuracy. The molecular test described in this example can, thus, use high-density genomic information to extract meaningful signal from challenging samples and complement, or optionally replace, routine cytopathological and clinical assessment of thyroid nodules, enabling a more accurate classification of the nodule as benign.

Example 5: Gender Signature

Summary

Derivation of a gender signature was undertaken using mRNA expression data and two analytical approaches. In the first approach, probeset level data was used in an analysis that was limited to markers within the X & Y chromosomes, with the assumption that gender-specific genes are more likely to reside on these chromosomes. Training of this probeset-level classifier used data from a thyroid tissue sample cohort, while classifier performance was independently tested on a cohort of thyroid FNAs (Fine Needle Aspirations). The second approach evaluated each sample cohort (tissue or FNA) separately, and examined all chromosomes at the gene-level using a linear SVM algorithm. Performance of these gene-level classification algorithms was estimated during training using cross-validation. In sum, three lists of mRNA expression biomarkers were generated that are useful in the accurate classification of samples by gender. These methods can be used to make predictions when the actual gender of the original patient sample is unknown and/or to resolve mix up's that can occur during sample processing.

Materials and Methods

Samples

Two cohorts of human thyroid samples were evaluated, either originating from post-surgically collected snap-frozen thyroid tissue or prospectively collected thyroid fine needle aspirates (FNA). Total RNAs prepared from thyroid tissue (n=254) were obtained from a commercial tissue bank. These were annotated as arising from male (n=59) or female (n=195) patients. FNA samples (n=483) were collected from multiple clinical sites across the United States and were annotated as arising from male (n=66) or female (n=417) patients. Total RNA was prepared from FNAs using the Qiagen Allprep kit.

Expression Data

Total RNAs from both tissue and FNA samples were amplified using NuGEN protocols and hybridized to Affymetrix Exon 1.0 ST arrays. The tissue and FNA microarray datasets were then processed independently using Affymetrix's APT software to produce probeset-level and gene-level signal intensity values.

Gender Signature Derived using Probeset Level Data.

Analysis of gender markers using probeset level data was limited to the thyroid tissue sample cohort and to markers within the X & Y chromosomes. Feature (gene) selection was done using Linear Models for Microarray Data (LIMMA), a software package for the analysis of mRNA expression data. The top 50 markers ranked by lowest FDR-adjusted p-value were selected for further evaluation. To classify samples, a simple classifier was trained using the sum of feature intensities given the relative expression sign (upregulated or down-regulated) and effect size of each feature, according to equation 1:

$$\Sigma_{i-1}{}^n F_s S_i \qquad \text{Equation 1:}$$

Where $F_i$ is the intensity of feature i and is $S_i$ is 1 if the absolute value of the mean intensity difference between Male and Female samples of feature is greater than 1.

Figure 17A:
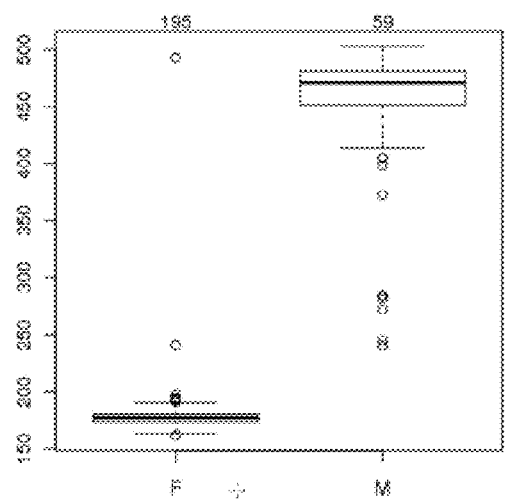
FIG. 17A-FIG. 17B illustrates the performance of top 50 gender markers in thyroid mRNA at the probeset level.

A classification score cutoff value of 300 was empirically identified, as this best separates Male and Female samples in the tissue training set (FIG. 17A). This simple algorithm was chosen since it works as well as more sophisticated algorithms such as linear SVM. Classification performance was independently tested on an FNA dataset using the features and classifier obtained during training with the tissue data set.

Gender Signature Derived Using Gene Level Data.

The probeset analytical process was generalized to data from all chromosomes and further explored mRNA expression at the gene-level. The tissue and FNA sample cohorts were examined in parallel, and independently of each other. Feature selection used LIMMA and classification used a linear SVM algorithm. Top markers from each data set were selected after filtering the LIMMA results by FDR-adjusted p-value (<0.05). The performance of each gene-level classifier was evaluated within each data set (tissue or FNA) using 30-fold cross-validation, as part of the algorithm training process.

Results

Probeset Level Signature

The top 50 probesets from a LIMMA comparison (ranked by FDR-adjusted p-value) were selected and used in algorithm training with the classification score cutoff set at 300. These probesets map to 6 genes (RPS4Y1, EIF1AY, UTY, USP9Y, CYorf15B, and DDX3Y). All six genes are over-expressed in samples from males and are located on the Y chromosome. The complete set of markers is shown in Table 1.

Figure 17B:
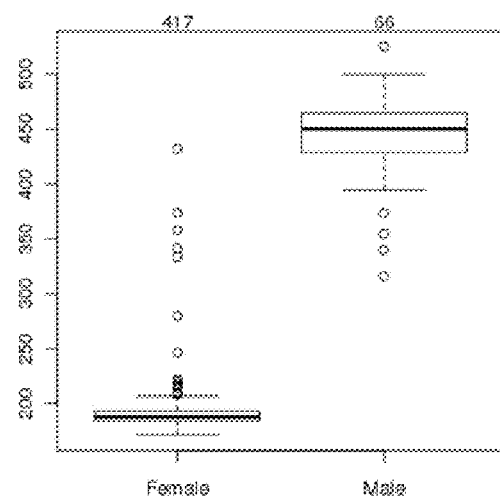
Figure 18:
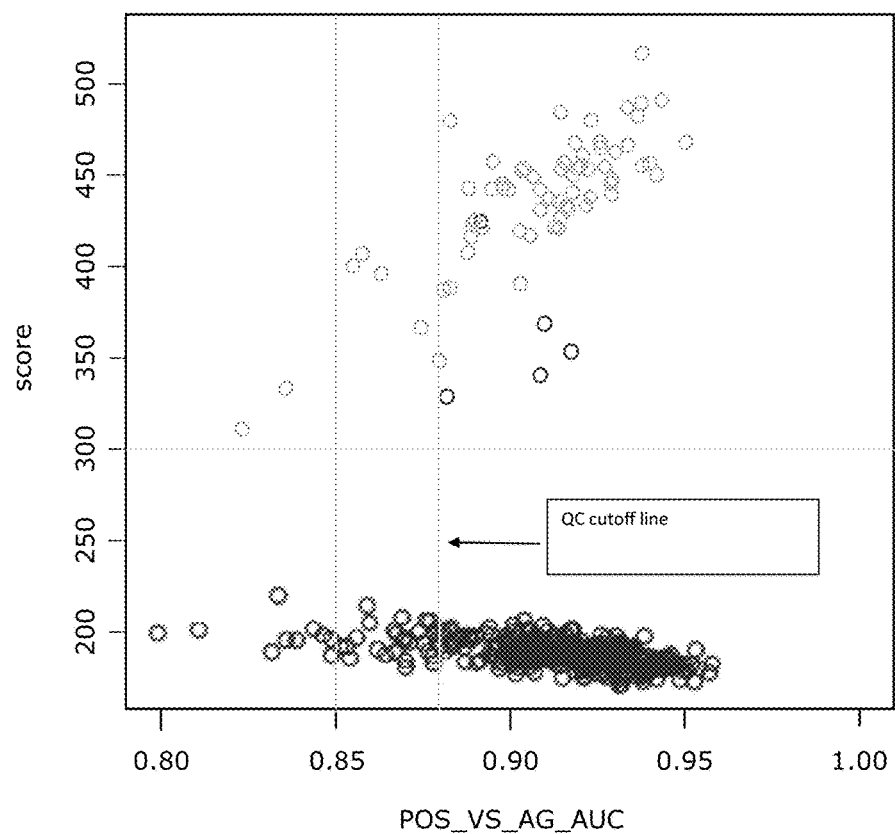
FIG. 18 illustrates the misclassification of five samples is not correlated with Quality Control scores. Black circles represent samples from Females and gray circles represent samples from Males. The "male gender" prediction cut-off is set at a score >300 on the Y-axis, while array hybridization Quality Control cut-off is set at >0.88 on the X-axis.

Independent validation of the tissue-trained classifier on 483 thyroid FNA samples resulted in 5 errors, or a 1% error rate (FIG. 17B). All errors occurred on samples labeled as Female, which were misclassified as Male. All samples labeled as Male were classified correctly. Sample quality was excluded as a reason for misclassification (FIG. 18), and at least one of the misclassified samples has been confirmed as mislabeled from its clinical collection site; this sample was actually collected from a male patient, and subsequently mislabeled. Hence, this simple gender classifier shows robustness as demonstrated by its high sensitivity (100%) and specificity (99%) when validated on an independent test set.

Gene Level Gender Signature

Figure 19B:
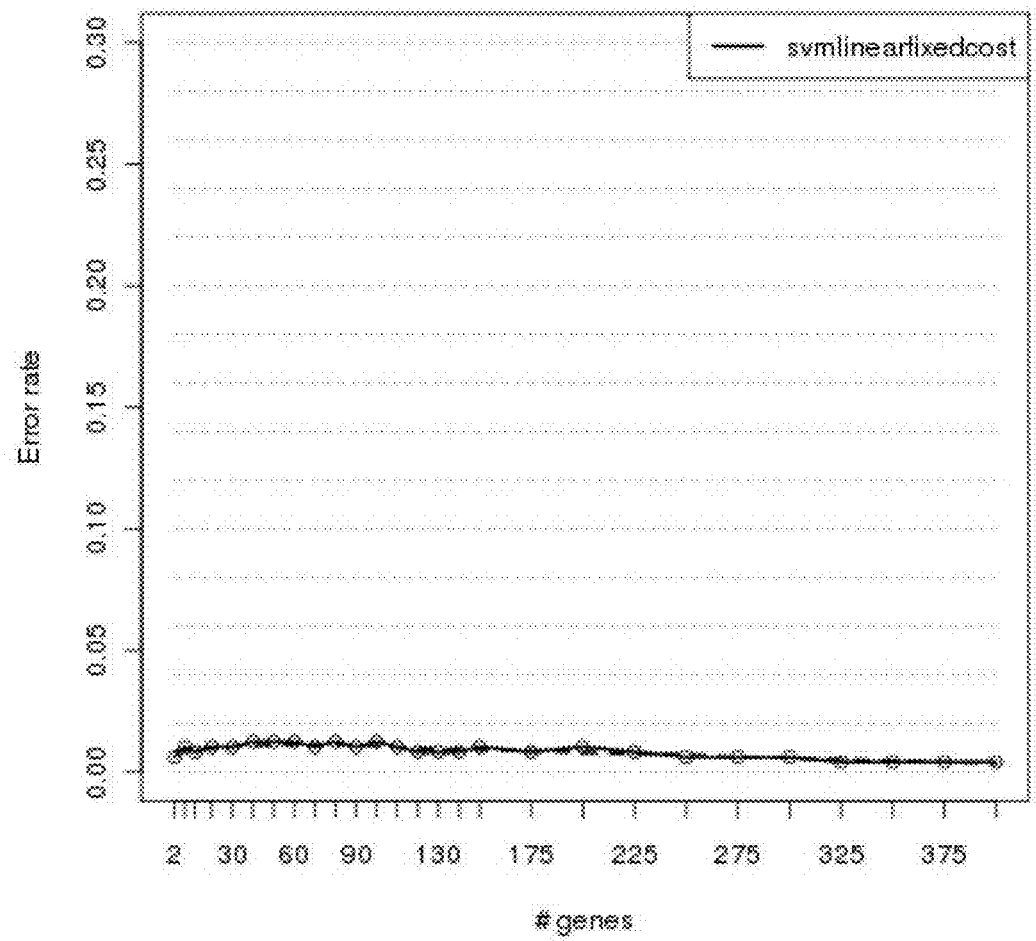

Top transcript clusters from each of two LIMMA comparisons of thyroid tissue and FNA datasets were selected and used to train two linear SVM prediction classifiers. Gene-level analysis of tissue data identified 80 genes useful in gender prediction, while a similar analysis using the FNA dataset identified 53 genes. Classification performance error rates were estimated during cross-validation, and are 3% for the tissue cohort (FIG. 19A), and 1% for the FNA cohort (FIG. 19B).

Conclusion

Figure 20:
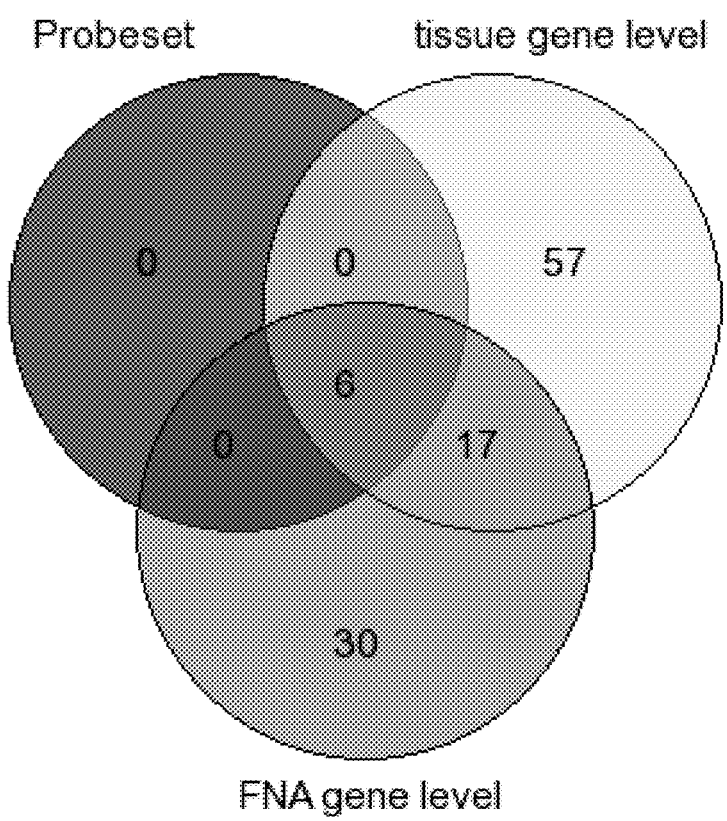
FIG. 20 illustrates a Venn diagram of gender signature markers obtained from three separate analyses.

The six markers identified at the probeset level were also the top markers identified at the gene level when Tissue and FNA datasets were examined separately (FIG. 20). These markers represent useful mRNA expression signatures that can be exploited to predict the gender of a given sample.

TABLE 1

Top 50 gender markers in human thyroid mRNA at the probeset-level.
Table 1: Probeset Level Gender Markers

| Probeset ID | TCID | Gene Symbol | Description | FDR adjusted p-value | Effect Size (log scale, Male minus Female) |
|---|---|---|---|---|---|
| 4028562 | 4028512 | RPS4Y1 | ribosomal protein S4, Y-linked 1 | 5.95E−145 | 8.56 |
| 4028561 | 4028512 | RPS4Y1 | ribosomal protein S4, Y-linked 1 | 3.44E−140 | 6.30 |
| 4028554 | 4028512 | RPS4Y1 | ribosomal protein S4, Y-linked 1 | 1.45E−137 | 7.39 |
| 4028556 | 4028512 | RPS4Y1 | ribosomal protein S4, Y-linked 1 | 8.22E−136 | 6.61 |
| 4031141 | 4031136 | EIF1AY | eukaryotic translation initiation factor 1A, Y-linked | 8.39E−134 | 7.92 |
| 4031142 | 4031136 | EIF1AY | eukaryotic translation initiation factor 1A, Y-linked | 8.83E−132 | 8.03 |
| 4035063 | 4035017 | UTY | ubiquitously transcribed tetratricopeptide repeat gene, Y-linked | 2.91E−130 | 6.95 |
| 4028557 | 4028512 | RPS4Y1 | ribosomal protein S4, Y-linked 1 | 6.44E−125 | 6.11 |
| 4031149 | 4031136 | EIF1AY | eukaryotic translation initiation factor 1A, Y-linked | 7.18E−125 | 7.69 |
| 4030112 | 4030063 | USP9Y | ubiquitin specific peptidase 9, Y-linked | 5.26E−124 | 6.05 |
| 4028558 | 4028512 | RPS4Y1 | ribosomal protein S4, Y-linked 1 | 1.67E−123 | 6.07 |
| 4031144 | 4031136 | EIF1AY | eukaryotic translation initiation factor 1A, Y-linked | 3.74E−121 | 6.62 |
| 4031095 | 4031068 | CYorf15B | chromosome Y open reading frame 15B | 1.72E−117 | 6.64 |
| 4035087 | 4035017 | UTY | ubiquitously transcribed tetratricopeptide repeat gene, Y-linked | 7.01E−117 | 6.60 |
| 4030193 | 4030162 | DDX3Y | DEAD (Asp-Glu-Ala-Asp) box polypeptide 3, Y-linked | 8.12E−117 | 5.17 |
| 4030185 | 4030162 | DDX3Y | DEAD (Asp-Glu-Ala-Asp) box polypeptide 3, Y-linked | 1.33E−116 | 5.80 |
| 4031108 | 4031068 | CYorf15B | chromosome Y open reading frame 15B | 3.22E−116 | 6.40 |
| 4030186 | 4030162 | DDX3Y | DEAD (Asp-Glu-Ala-Asp) box polypeptide 3, Y-linked | 6.51E−116 | 5.90 |
| 4030178 | 4030162 | DDX3Y | DEAD (Asp-Glu-Ala-Asp) box polypeptide 3, Y-linked | 7.97E−116 | 5.23 |
| 4028553 | 4028512 | RPS4Y1 | ribosomal protein S4, Y-linked 1 | 1.10E−112 | 4.34 |
| 4035064 | 4035017 | UTY | ubiquitously transcribed tetratricopeptide repeat gene, Y-linked | 4.20E−112 | 6.08 |
| 4030176 | 4030162 | DDX3Y | DEAD (Asp-Glu-Ala-Asp) box polypeptide 3, Y-linked | 9.76E−111 | 5.26 |

TABLE 1-continued

Top 50 gender markers in human thyroid mRNA at the probeset-level.
Table 1: Probeset Level Gender Markers

| Probeset ID | TCID | Gene Symbol | Description | FDR adjusted p-value | Effect Size (log scale, Male minus Female) |
|---|---|---|---|---|---|
| 4035070 | 4035017 | UTY | ubiquitously transcribed tetratricopeptide repeat gene, Y-linked | 1.47E−109 | 6.07 |
| 4030111 | 4030063 | USP9Y | ubiquitin specific peptidase 9, Y-linked | 1.95E−109 | 5.13 |
| 4035084 | 4035017 | UTY | ubiquitously transcribed tetratricopeptide repeat gene, Y-linked | 1.17E−108 | 5.40 |
| 4030086 | 4030063 | USP9Y | ubiquitin specific peptidase 9, Y-linked | 1.34E−108 | 4.45 |
| 4030179 | 4030162 | DDX3Y | DEAD (Asp-Glu-Ala-Asp) box polypeptide 3, Y-linked | 1.80E−108 | 5.15 |
| 4030187 | 4030162 | DDX3Y | DEAD (Asp-Glu-Ala-Asp) box polypeptide 3, Y-linked | 5.46E−108 | 4.80 |
| 4031091 | 4031068 | CYorf15B | chromosome Y open reading frame 15B | 3.76E−105 | 5.48 |
| 4035092 | 4035017 | UTY | ubiquitously transcribed tetratricopeptide repeat gene, Y-linked | 3.88E−105 | 5.22 |
| 4030194 | 4030162 | DDX3Y | DEAD (Asp-Glu-Ala-Asp) box polypeptide 3, Y-linked | 1.57E−102 | 3.86 |
| 4035069 | 4035017 | UTY | ubiquitously transcribed tetratricopeptide repeat gene, Y-linked | 2.26E−101 | 5.17 |
| 4030144 | 4030063 | USP9Y | ubiquitin specific peptidase 9, Y-linked | 3.41E−101 | 5.32 |
| 4030107 | 4030063 | USP9Y | ubiquitin specific peptidase 9, Y-linked | 1.49E−100 | 4.46 |
| 4031152 | 4031136 | EIF1AY | eukaryotic translation initiation factor 1A, Y-linked | 3.04E−100 | 5.79 |
| 4030136 | 4030063 | USP9Y | ubiquitin specific peptidase 9, Y-linked | 1.47E−99 | 5.26 |
| 4030138 | 4030063 | USP9Y | ubiquitin specific peptidase 9, Y-linked | 4.94E−99 | 3.78 |
| 4035059 | 4035017 | UTY | ubiquitously transcribed tetratricopeptide repeat gene, Y-linked | 4.70E−97 | 4.54 |
| 4030100 | 4030063 | USP9Y | ubiquitin specific peptidase 9, Y-linked | 1.20E−96 | 4.19 |
| 4030116 | 4030063 | USP9Y | ubiquitin specific peptidase 9, Y-linked | 1.25E−95 | 3.58 |
| 4035050 | 4035017 | UTY | ubiquitously transcribed tetratricopeptide repeat gene, Y-linked | 1.50E−95 | 4.70 |
| 4031098 | 4031068 | CYorf15B | chromosome Y open reading frame 15B | 1.64E−95 | 4.10 |
| 4035065 | 4035017 | UTY | ubiquitously transcribed tetratricopeptide repeat gene, Y-linked | 3.89E−95 | 3.63 |
| 4035045 | 4035017 | UTY | ubiquitously transcribed tetratricopeptide repeat gene, Y-linked | 6.56E−95 | 4.13 |
| 4030087 | 4030063 | USP9Y | ubiquitin specific peptidase 9, Y-linked | 1.07E−94 | 4.08 |
| 4031097 | 4031068 | CYorf15B | chromosome Y open reading frame 15B | 1.37E−94 | 4.62 |
| 4035073 | 4035017 | UTY | ubiquitously transcribed tetratricopeptide repeat gene, Y-linked | 2.64E−94 | 4.19 |
| 4035095 | 4035017 | UTY | ubiquitously transcribed tetratricopeptide repeat gene, Y-linked | 5.57E−94 | 4.10 |
| 4031106 | 4031068 | CYorf15B | chromosome Y open reading frame 15B | 5.77E−93 | 3.64 |
| 4030146 | 4030063 | USP9Y | ubiquitin specific peptidase 9, Y-linked | 2.84E−92 | 4.70 |

TABLE 2

Top gender markers in human thyroid mRNA at the gene-level obtained by examining a post-surgical tissue sample cohort.
Table 2: Gene Level Gender Markers Obtained from Tissue

| TCID | Gene Symbol | Description | FDR-adjusted p-value | Effect Size (log scale, Male minus Female) | Chromosomal Location |
|---|---|---|---|---|---|
| 4031136 | EIF1AY | eukaryotic translation initiation factor 1A, Y-linked | 7.11E−124 | 6.37 | Yq11.223 |
| 4030162 | DDX3X | DEAD (Asp-Glu-Ala-Asp) box polypeptide 3, X-linked | 6.06E−121 | 4.13 | Xp11.3-p11.23 |
| 4030162 | DDX3Y | DEAD (Asp-Glu-Ala-Asp) box polypeptide 3, Y-linked | 6.06E−121 | 4.13 | Yq11 |
| 4031068 | CYorf15A | chromosome Y open reading frame 15A | 5.77E−106 | 3.64 | Yq11.222 |
| 4031068 | CYorf15B | chromosome Y open reading frame 15B | 5.77E−106 | 3.64 | Yq11.222 |

TABLE 2-continued

Top gender markers in human thyroid mRNA at the gene-level obtained by examining a post-surgical tissue sample cohort.
Table 2: Gene Level Gender Markers Obtained from Tissue

| TCID | Gene Symbol | Description | FDR-adjusted p-value | Effect Size (log scale, Male minus Female) | Chromosomal Location |
|---|---|---|---|---|---|
| 4030063 | TTTY15 | testis-specific transcript, Y-linked 15 (non-protein coding) | 1.22E−104 | 3.53 | Yq11.1 |
| 4030063 | USP9Y | ubiquitin specific peptidase 9, Y-linked | 1.22E−104 | 3.53 | Yq11.2 |
| 4035017 | KDM6A | lysine (K)-specific demethylase 6A | 6.69E−100 | 2.63 | Xp11.2 |
| 4035017 | UTY | ubiquitously transcribed tetratricopeptide repeat gene, Y-linked | 6.69E−100 | 2.63 | Yq11 |
| 4028512 | RPS4Y1 | ribosomal protein S4, Y-linked 1 | 1.09E−95 | 4.24 | Yp11.3 |
| 4028512 | XG | Xg blood group | 1.09E−95 | 4.24 | Xp22.33 |
| 4028512 | XGPY2 | Xg pseudogene, Y-linked 2 | 1.09E−95 | 4.24 | Yp11.31 |
| 4028568 | ZFX | zinc finger protein, X-linked | 2.52E−62 | 1.61 | Xp21.3 |
| 4028568 | ZFY | zinc finger protein, Y-linked | 2.52E−62 | 1.61 | Yp11.3 |
| 4030371 | NLGN4X | neuroligin 4, X-linked | 8.27E−61 | 1.88 | Xp22.32-p22.31 |
| 4030371 | NLGN4Y | neuroligin 4, Y-linked | 8.27E−61 | 1.88 | Yq11.221 |
| 4029152 | PRKX | protein kinase, X-linked | 1.34E−30 | 0.51 | Xp22.3 |
| 4029152 | PRKY | protein kinase, Y-linked | 1.34E−30 | 0.51 | Yp11.2 |
| 4030259 | TMSB4Y | thymosin beta 4, Y-linked | 5.69E−22 | 0.50 | Yq11.221 |
| 3971923 | ZFX | zinc finger protein, X-linked | 5.79E−11 | −0.64 | Xp21.3 |
| 3971923 | ZFY | zinc finger protein, Y-linked | 5.79E−11 | −0.64 | Yp11.3 |
| 3975467 | KDM6A | lysine (K)-specific demethylase 6A | 5.79E−11 | −0.49 | Xp11.2 |
| 3974838 | DDX3X | DEAD (Asp-Glu-Ala-Asp) box polypeptide 3, X-linked | 1.10E−10 | −0.42 | Xp11.3-p11.23 |
| 3974838 | DDX3Y | DEAD (Asp-Glu-Ala-Asp) box polypeptide 3, Y-linked | 1.10E−10 | −0.42 | Yq11 |
| 4009062 | KDM5C | lysine (K)-specific demethylase 5C | 1.09E−09 | −0.21 | Xp11.22-p11.21 |
| 4031156 | RPS4Y2 | ribosomal protein S4, Y-linked 2 | 1.13E−06 | 0.47 | Yq11.223 |
| 2505386 | FAM128A | family with sequence similarity 128, member A | 3.13E−06 | −0.37 | 2q21.1 |
| 2505386 | FAM128B | family with sequence similarity 128, member B | 3.13E−06 | −0.37 | 2q21.1 |
| 2505386 | SMPD4 | sphingomyelin phosphodiesterase 4, neutral membrane (neutral sphingomyelinase-3) | 3.13E−06 | −0.37 | 2q21.1 |
| 3998632 | PNPLA4 | patatin-like phospholipase domain containing 4 | 3.13E−06 | −0.49 | Xp22.3 |
| 2925953 | ENPP1 | ectonucleotide pyrophosphatase/phosphodiesterase 1 | 1.89E−04 | −1.09 | 6q22-q23 |
| 3981735 | LOC554203 | alanyl-tRNA synthetase domain containing 1 pseudogene | 2.23E−04 | −0.62 | Xq13.2 |
| 3286776 | C10orf10 | chromosome 10 open reading frame 10 | 3.92E−04 | 0.19 | 10q11.21 |
| 3286776 | RASSF4 | Ras association (RalGDS/AF-6) domain family member 4 | 3.92E−04 | 0.19 | 10q11.21 |
| 3108226 | PGCP | plasma glutamate carboxypeptidase | 6.52E−04 | −0.68 | 8q22.2 |
| 3177111 | NTRK2 | neurotrophic tyrosine kinase, receptor, type 2 | 1.21E−03 | −0.79 | 9q22.1 |
| 3150455 | TNFRSF11B | tumor necrosis factor receptor superfamily, member 11b | 6.57E−03 | −0.79 | 8q24 |
| 3998444 | HDHD1A | haloacid dehalogenase-like hydrolase domain containing 1A | 6.57E−03 | −0.32 | Xp22.32 |
| 2515240 | CYBRD1 | cytochrome b reductase 1 | 8.04E−03 | −0.73 | 2q31.1 |
| 3662201 | MT1F | metallothionein 1F | 1.11E−02 | −1.43 | 16q13 |
| 3662201 | MT1H | metallothionein 1H | 1.11E−02 | −1.43 | 16q13 |
| 3662201 | MT1P2 | metallothionein 1 pseudogene 2 | 1.11E−02 | −1.43 | 1q43 |
| 3969855 | CA5B | carbonic anhydrase VB, mitochondrial | 1.39E−02 | −0.34 | Xp21.1 |
| 3969855 | CA5BP | carbonic anhydrase VB pseudogene | 1.39E−02 | −0.34 | Xp22.2 |
| 2676927 | SELK | selenoprotein K | 1.47E−02 | −0.25 | 3p21.31 |
| 3622934 | MYEF2 | myelin expression factor 2 | 1.47E−02 | 0.60 | 15q21.1 |
| 3622934 | SLC24A5 | solute carrier family 24, member 5 | 1.47E−02 | 0.60 | 15q21.1 |
| 3969455 | OFD1 | oral-facial-digital syndrome 1 | 1.81E−02 | −0.26 | Xp22 |
| 3138204 | CYP7B1 | cytochrome P450, family 7, subfamily B, polypeptide 1 | 1.87E−02 | −0.36 | 8q21.3 |
| 3593014 | MYEF2 | myelin expression factor 2 | 1.87E−02 | 0.35 | 15q21.1 |
| 3593014 | SLC24A5 | solute carrier family 24, member 5 | 1.87E−02 | 0.35 | 15q21.1 |
| 2745547 | GAB1 | GRB2-associated binding protein 1 | 2.11E−02 | −0.42 | 4q31.21 |
| 3108146 | SDC2 | syndecan 2 | 2.11E−02 | −0.68 | 8q22-q23 |
| 3728037 | SCPEP1 | serine carboxypeptidase 1 | 2.18E−02 | −0.42 | 17q22 |

TABLE 2-continued

Top gender markers in human thyroid mRNA at the gene-level obtained by examining a post-surgical tissue sample cohort.
Table 2: Gene Level Gender Markers Obtained from Tissue

| TCID | Gene Symbol | Description | FDR-adjusted p-value | Effect Size (log scale, Male minus Female) | Chromosomal Location |
|---|---|---|---|---|---|
| 3768627 | ABCA8 | ATP-binding cassette, sub-family A (ABC1), member 8 | 2.18E−02 | −0.52 | 17q24 |
| 3142381 | FABP4 | fatty acid binding protein 4, adipocyte | 2.28E−02 | −1.37 | 8q21 |
| 2342738 | ST6GALNAC3 | ST6 (alpha-N-acetyl-neuraminyl-2,3-beta-galactosyl-1,3)-N-acetylgalactosaminide alpha-2,6-sialyltransferase 3 | 2.48E−02 | −0.40 | 1p31.1 |
| 2672190 | LRRC2 | leucine rich repeat containing 2 | 2.48E−02 | −0.74 | 3p21.31 |
| 3692999 | MT1G | metallothionein 1G | 2.48E−02 | −1.52 | 16q13 |
| 4002148 | EIF1AP1 | eukaryotic translation initiation factor 1A pseudogene 1 | 2.48E−02 | −0.33 | 1p36.13 |
| 4002148 | EIF1AX | eukaryotic translation initiation factor 1A, X-linked | 2.48E−02 | −0.33 | Xp22.12 |
| 4002148 | SCARNA9L | small Cajal body-specific RNA 9-like (retrotransposed) | 2.48E−02 | −0.33 | Xp22.12 |
| 3921599 | PCP4 | Purkinje cell protein 4 | 2.57E−02 | −1.15 | 21q22.2 |
| 3446137 | LMO3 | LIM domain only 3 (rhombotin-like 2) | 2.62E−02 | −1.00 | 12p12.3 |
| 2711205 | ATP13A4 | ATPase type 13A4 | 2.81E−02 | −0.83 | 3q29 |
| 2711225 | ATP13A4 | ATPase type 13A4 | 2.86E−02 | −0.88 | 3q29 |
| 3327166 | C11orf74 | chromosome 11 open reading frame 74 | 2.88E−02 | −0.72 | 11p12 |
| 3290875 | ANK3 | ankyrin 3, node of Ranvier (ankyrin G) | 3.00E−02 | −0.51 | 10q21 |
| 4013549 | ITM2A | integral membrane protein 2A | 3.00E−02 | −0.57 | Xq13.3-Xq21.2 |
| 2788926 | NR3C2 | nuclear receptor subfamily 3, group C, member 2 | 3.53E−02 | −0.39 | 4q31.1 |
| 3094286 | PROSC | proline synthetase co-transcribed homolog (bacterial) | 3.64E−02 | −0.18 | 8p11.2 |
| 2678298 | DNASE1L3 | deoxyribonuclease I-like 3 | 3.65E−02 | −0.48 | 3p21.1-p14.3 |
| 2990404 | SCIN | scinderin | 3.69E−02 | 0.58 | 7p21.3 |
| 3018605 | LOC286002 | hypothetical LOC286002 | 3.81E−02 | −1.21 | 7q22.3 |
| 3018605 | SLC26A4 | solute carrier family 26, member 4 | 3.81E−02 | −1.21 | 7q31 |
| 2969289 | WASF1 | WAS protein family, member 1 | 3.92E−02 | 0.39 | 6q21-q22 |
| 3096271 | C8orf40 | chromosome 8 open reading frame 40 | 3.92E−02 | −0.35 | 8p11.21 |
| 3147926 | DPYS | dihydropyrimidinase | 3.92E−02 | 0.21 | 8q22 |
| 3360277 | OR52R1 | olfactory receptor, family 52, subfamily R, member 1 | 3.92E−02 | 0.20 | 11p15.4 |
| 3518086 | TBC1D4 | TBC1 domain family, member 4 | 3.92E−02 | −0.39 | 13q22.2 |
| 3662130 | MT1L | metallothionein 1L (gene/pseudogene) | 3.92E−02 | −0.91 | 16q13 |
| 3147971 | LOC100130232 | LP2209 | 3.99E−02 | 0.52 | 8q22.3 |
| 3200982 | MLLT3 | myeloid/lymphoid or mixed-lineage leukemia (trithorax homolog, *Drosophila*); translocated to, 3 | 4.27E−02 | −0.45 | 9p22 |
| 3106559 | CP | ceruloplasmin (ferroxidase) | 4.36E−02 | −1.25 | 3q23-q25 |
| 3106559 | LRRC69 | leucine rich repeat containing 69 | 4.36E−02 | −1.25 | 8q21.3 |
| 3106559 | SLC26A7 | solute carrier family 26, member 7 | 4.36E−02 | −1.25 | 8q23 |
| 3573870 | DIO2 | deiodinase, iodothyronine, type II | 4.42E−02 | −0.94 | 14q24.2-q24.3 |
| 3722535 | ARL4D | ADP-ribosylation factor-like 4D | 4.42E−02 | −0.34 | 17q12-q21 |

TABLE 3

Top gender markers in human thyroid mRNA at the gene-level obtained by examining an FNA sample cohort.
Table 3: Gene Level Gender Markers Obtained from FNA

| TCID | Gene Symbol | Description | FDR-adjusted p-value | Effect Size (log scale, Male minus Female) | Chromosomal Location |
|---|---|---|---|---|---|
| 4030162 | DDX3X | DEAD (Asp-Glu-Ala-Asp) box polypeptide 3, X-linked | 1.03E−288 | 4.51 | Xp11.3-p11.23 |

TABLE 3-continued

Top gender markers in human thyroid mRNA at the gene-level obtained by examining an FNA sample cohort.
Table 3: Gene Level Gender Markers Obtained from FNA

| TCID | Gene Symbol | Description | FDR-adjusted p-value | Effect Size (log scale, Male minus Female) | Chromosomal Location |
|---|---|---|---|---|---|
| 4030162 | DDX3Y | DEAD (Asp-Glu-Ala-Asp) box polypeptide 3, Y-linked | 1.03E−288 | 4.51 | Yq11 |
| 4031136 | EIF1AY | eukaryotic translation initiation factor 1A, Y-linked | 7.34E−288 | 6.47 | Yq11.223 |
| 4028512 | RPS4Y1 | ribosomal protein S4, Y-linked 1 | 1.78E−248 | 5.13 | Yp11.3 |
| 4028512 | XG | Xg blood group | 1.78E−248 | 5.13 | Xp22.33 |
| 4028512 | XGPY2 | Xg pseudogene, Y-linked 2 | 1.78E−248 | 5.13 | Yp11.31 |
| 4035017 | KDM6A | lysine (K)-specific demethylase 6A | 2.70E−235 | 2.90 | Xp11.2 |
| 4035017 | UTY | ubiquitously transcribed tetratricopeptide repeat gene, Y-linked | 2.70E−235 | 2.90 | Yq11 |
| 4030063 | TTTY15 | testis-specific transcript, Y-linked 15 (non-protein coding) | 4.42E−217 | 2.95 | Yq11.1 |
| 4030063 | USP9Y | ubiquitin specific peptidase 9, Y-linked | 4.42E−217 | 2.95 | Yq11.2 |
| 4031068 | CYorf15A | chromosome Y open reading frame 15A | 2.27E−173 | 2.69 | Yq11.222 |
| 4031068 | CYorf15B | chromosome Y open reading frame 15B | 2.27E−173 | 2.69 | Yq11.222 |
| 4028568 | ZFX | zinc finger protein, X-linked | 4.01E−123 | 1.81 | Xp21.3 |
| 4028568 | ZFY | zinc finger protein, Y-linked | 4.01E−123 | 1.81 | Yp11.3 |
| 4030371 | NLGN4X | neuroligin 4, X-linked | 2.06E−92 | 2.05 | Xp22.32-p22.31 |
| 4030371 | NLGN4Y | neuroligin 4, Y-linked | 2.06E−92 | 2.05 | Yq11.221 |
| 4029079 | TBL1X | transducin (beta)-like 1X-linked | 2.65E−52 | 0.70 | Xp22.3 |
| 4029079 | TBL1Y | transducin (beta)-like 1Y-linked | 2.65E−52 | 0.70 | Yp11.2 |
| 4036155 | TTTY10 | testis-specific transcript, Y-linked 10 (non-protein coding) | 2.63E−48 | 0.69 | Yq11.221 |
| 4030259 | TMSB4Y | thymosin beta 4, Y-linked | 8.71E−43 | 0.72 | Yq11.221 |
| 4029152 | PRKX | protein kinase, X-linked | 4.54E−38 | 0.49 | Xp22.3 |
| 4029152 | PRKY | protein kinase, Y-linked | 4.54E−38 | 0.49 | Yp11.2 |
| 4031156 | RPS4Y2 | ribosomal protein S4, Y-linked 2 | 3.08E−26 | 0.80 | Yq11.223 |
| 4009062 | KDM5C | lysine (K)-specific demethylase 5C | 1.54E−14 | −0.42 | Xp11.22-p11.21 |
| 3975467 | KDM6A | lysine (K)-specific demethylase 6A | 2.40E−09 | −0.56 | Xp11.2 |
| 3998444 | HDHD1A | haloacid dehalogenase-like hydrolase domain containing 1A | 1.16E−06 | −0.77 | Xp22.32 |
| 3997946 | PRKX | protein kinase, X-linked | 1.07E−04 | −0.50 | Xp22.3 |
| 3997946 | PRKY | protein kinase, Y-linked | 1.07E−04 | −0.50 | Yp11.2 |
| 4009238 | SMC1A | structural maintenance of chromosomes 1A | 2.21E−04 | −0.48 | Xp11.22-p11.21 |
| 3971923 | ZFX | zinc finger protein, X-linked | 8.63E−04 | −0.55 | Xp21.3 |
| 3971923 | ZFY | zinc finger protein, Y-linked | 8.63E−04 | −0.55 | Yp11.3 |
| 2884727 | ATP10B | ATPase, class V, type 10B | 2.48E−03 | 0.23 | 5q34 |
| 3998632 | PNPLA4 | patatin-like phospholipase domain containing 4 | 2.54E−03 | −0.62 | Xp22.3 |
| 2735129 | IBSP | integrin-binding sialoprotein | 4.04E−03 | 0.32 | 4q21-q25 |
| 3299661 | SLC16A12 | solute carrier family 16, member 12 (monocarboxylic acid transporter 12) | 5.46E−03 | 0.31 | 10q23.31 |
| 3967689 | STS | steroid sulfatase (microsomal), isozyme S | 1.25E−02 | −0.31 | Xp22.32 |
| 3455478 | KRT6A | keratin 6A | 1.58E−02 | 0.56 | 12q12-q13 |
| 3455478 | KRT6B | keratin 6B | 1.58E−02 | 0.56 | 12q12-q13 |
| 3455478 | KRT6C | keratin 6C | 1.58E−02 | 0.56 | 12q13.13 |
| 3875642 | LOC100131599 | hypothetical protein LOC100131599 | 2.06E−02 | 0.28 | 20p12.3 |
| 3875642 | PLCB1 | phospholipase C, beta 1 (phosphoinositide-specific) | 2.06E−02 | 0.28 | 20p12 |
| 3428333 | ANO4 | anoctamin 4 | 2.57E−02 | 0.17 | 12q23.1 |
| 3757177 | KRT14 | keratin 14 | 2.68E−02 | 0.27 | 17q12-q21 |
| 3757177 | KRT16 | keratin 16 | 2.68E−02 | 0.27 | 17q12-q21 |
| 3757177 | LOC400578 | keratin type 16-like | 2.68E−02 | 0.27 | 17p11.2 |
| 3757177 | MGC102966 | similar to Keratin, type I cytoskeletal 16 (Cytokeratin-16) (CK-16) (Keratin-16) (K16) | 2.68E−02 | 0.27 | 17p11.2 |
| 2601230 | SCG2 | secretogranin II (chromogranin C) | 2.82E−02 | 0.32 | 2q35-q36 |
| 3422804 | GLIPR1L1 | GLI pathogenesis-related 1 like 1 | 3.49E−02 | 0.27 | 12q21.2 |
| 3292413 | DNAJC12 | DnaJ (Hsp40) homolog, subfamily C, member 12 | 3.92E−02 | 0.23 | 10q22.1 |
| 2344984 | CLCA2 | chloride channel accessory 2 | 4.25E−02 | 0.25 | 1p31-p22 |
| 2864118 | DMGDH | dimethylglycine dehydrogenase | 4.25E−02 | 0.28 | 5q14.1 |

TABLE 3-continued

Top gender markers in human thyroid mRNA at the gene-level obtained by examining an FNA sample cohort.
Table 3: Gene Level Gender Markers Obtained from FNA

| TCID | Gene Symbol | Description | FDR-adjusted p-value | Effect Size (log scale, Male minus Female) | Chromosomal Location |
|---|---|---|---|---|---|
| 3259087 | C10orf129 | chromosome 10 open reading frame 129 | 4.25E−02 | 0.19 | 10q23.33 |
| 3262129 | INA | internexin neuronal intermediate filament protein, alpha | 4.25E−02 | 0.23 | 10q24.33 |
| 3970166 | CXorf15 | chromosome X open reading frame 15 | 4.29E−02 | −0.29 | Xp22.2 |
| 3817651 | C19orf30 | chromosome 19 open reading frame 30 | 4.37E−02 | 0.25 | 19p13.3 |
| 2933175 | LOC100128551 | hypothetical protein LOC100128551 | 4.46E−02 | −0.20 | 6q25.3 |
| 2933175 | ZDHHC14 | zinc finger, DHHC-type containing 14 | 4.46E−02 | −0.20 | 6q25.3 |
| 3705967 | SERPINF1 | serpin peptidase inhibitor, clade F (alpha-2 antiplasmin, pigment epithelium derived factor), member 1 | 4.84E−02 | −0.53 | 17p13.1 |

Example 6: Lymphoma Signature

Introduction

Derivation and use of a lymphoma gene signature can fall within the general framework of using "cassettes" or "filters" to pre-screen expression profiles generated from incoming patient samples. This pre-screening step can be designed to reduce the number of "unusual" profiles passing on to the "main" thyroid clinical classifier. This can be done in order to prevent the "main" classifier from returning a definitive call on the types of profiles that were not encountered during training.

In general, when applied to new samples, the cassettes can identify profiles matching the signals from a number of rare conditions potentially found in and around the biopsy area. Such conditions could include, for example, metastases from other organs and cancers of adjacent cell populations. In this setting, the filters can be not required to be "comprehensive" and deliver high negative predictive value on respective classes (as can be required of the main classifier). They can merely serve to further minimize the chances of returning a definitive answer on the previously unseen rare disease categories. In this setting, the objective function of training the "cassettes" can be to minimize false positive rate while maintaining some level of sensitivity. This can be the opposite of the main clinical classifier, which can require high sensitivity or negative predictive value, while tolerating low specificity (a modest amount of false positives).

This difference in "usage pattern" between the filters and the main classifier can also propagate itself to the feature (gene) selection and classifier building process. Identification of genes making up the "cassette" signature can be geared not towards characterizing biology or gene expression characteristics of that specific disease process and its variants, but towards identifying markers of the non-thyroid nature of the biopsy.

Finally, distinct types of RNA sources can be present in the collection of samples available at the time of training. The nature of the samples used during classifier training or testing can have an impact on the gene expression profiles generated. Shifts in relative mRNA expression can also occur across samples collected by any distinct method (e.g., all post-surgical Tissue samples) when different sample preservation and/or nucleic acid preparation methods are used downstream. Yet another confounding effect can arise from sample cellular heterogeneity composition, as this can vary across sample types. As an example, post-surgical thyroid tissue samples can have been micro-dissected and their cellular heterogeneity (and mRNA expression pattern) can be lower than clinical FNA samples. Hence, it can be important that markers identifying the non-thyroid nature of any given sample, work well in the sample types likely to be encountered in the commercial use of the diagnostic system. Therefore chosen markers can be maximally invariant to the amount of heterogeneity expected. This presents challenges when the collection of rare non-thyroid conditions can only be collected from banked tissue sources, with few or no clinical FNAs available during training The lymphoma gene signature is an example of a "cassette" or "filter" derived from multiple and heterogeneous data sources with these objectives in mind.

Materials and Methods

Sample Cohorts used in Training Set.

Total RNAs from surgically resected fresh-frozen tissues (n=211) were obtained from tissue banks. This thyroid "Tissue" sample cohort included the histological subtypes atypical thyroid carcinoma (ATC, n=5), follicular adenoma (FA, n=26), follicular carcinoma (FC, n=19), follicular variant of papillary carcinoma (FVPTC, n=21), papillary carcinoma (PTC, n=26), Hurthle cell carcinoma (HC, n=23), lymphocytic thyroiditis (LCT, n=19), medullary thyroid carcinoma (MTC, n=21), and nodular hyperplasia (NHP, n=23). Non-thyroid histopathology tissues also included breast carcinoma (BCA, n=5), melanoma (MMN, n=4), parathyroid adenoma (PTA, n=5), and renal carcinoma (RCC, n=5). The lymphoma subset included B cell lymphoma (BLL) tissues sampled from lymph nodes (n=3) and BLL metastases sampled from the thyroid (n=2). In addition, follicular lymphomas (FLL) sampled from lymph nodes (n=3), and an FLL metastasis sampled from the thyroid (n=1) were also included.

Thyroid FNA samples (n=237) were collected prospectively in clinics, pre-surgically in operating rooms, and/or post-surgically in pathology labs across the US according to IRB approved protocols. This thyroid "FNA" sample cohort included the subtypes benign nodule (BN, n=29), colloid nodule (CN, n=9), cystic nodule (CYN, n=5), follicular adenoma (FA, n=19), follicular carcinoma (FC, n=4), follicular nodule of unknown malignant potential (FT-UMP, n=3), follicular variant of papillary carcinoma (FVPTC, n=9), micro follicular variant of papillary carcinoma (mFVPTC, n=2) papillary carcinoma (PTC, n=52), micro papillary thyroid carcinoma (mPTC, n=2), papillary thyroid carcinoma-tall cell variant (PTC-TCV, n=1), Hurthle cell adenoma (HA, n=6), lymphocytic thyroiditis (LCT, n=16), medullary thyroid carcinoma (MTC, n=1), nodular hyperplasia (NHP, n=68), and well differentiated thyroid of unknown malignant potential (WDT-UMP, n=1). Non-thyroid FNAs also included malignant lymph node (MLN, n=1), other malignant (OM, n=1), and benign FNA by cytology pending conferral (n=8). RNA was extracted from all FNAs using the AllPrep kit from Qiagen and stored at −80 C.

The training set was created by combining the tissue and FNA sample cohorts. Binary training labels were assigned based on the available pathology diagnosis, mapping all lymphoma samples to a binary class labeled "LL", and all other samples into a class labeled "REST".

TABLE 4

Sample cohort used to derive lymphoma signature genes.

| Sample Type | Post-Surgical Diagnosis | | | |
|---|---|---|---|---|
| | Lymphomas (BLL or FLL) | Benign Thyroid | Malignant Thyroid | Pending Conferral |
| Tissue | 9 | 73 | 129 | 0 |
| FNA | 0 | 156 | 73 | 8 |

Sample Cohorts used in the Independent Test Set.

Thyroid FNAs in the independent test set included LCT (n=19) and BLL (n=1).

Expression Profiling

Total RNAs from both tissue and FNA samples were amplified using NuGEN protocols and hybridized to Affymetrix Exon 1.0 ST arrays. Nucleic acid amplification was done using slightly different amplification protocols for tissue (NuGEN PICO) and FNA samples (NuGEN FFPE). Probeset-level intensity values were normalized and summarized into transcript cluster levels summaries using APT software and a common sketch across multiple sample sources and amplification protocols.

Feature Selection

Feature (gene) selection was done using a LIMMA comparison of transcript cluster level summaries between all samples of the "LL" class and the "Rest" of the training samples. Top markers were selected after ranking the LIMMA results by FDR-adjusted p-value.

Algorithm Training and Evaluation

A linear SVM classifier was trained to separate "LL" samples from the "REST", using top features (transcript clusters or genes) identified as described above. A cross-validation procedure including both feature selection and classifier training steps was used to characterize performance of the algorithm on the training data, given a varying number of features. Secondly, an internal loop of the cross-validation step, was used to estimate the cost parameter of the SVM for each of the cross-validation folds. Based on the performance estimates and number of samples available for training within the "LL" class, an optimal number of features were chosen for the final classifier. The execution of the final classifier on an independent set of test samples uses the same algorithmic process as on the full training data set.

Results

Significant differences exist between the two sample sources in the training data set. One could visualize these differences by generating PCA plots of the positive control genes present on the array. This can represent technical variability due to nucleic acid amplification protocol differences being confounded with the sample source. In addition, Tissues and FNAs have been previously characterized as having non-uniform patterns of cellular heterogeneity. This has direct impact on identifying a lymphoma-specific signature within thyroid samples and training the corresponding filter.

Figure 21A:
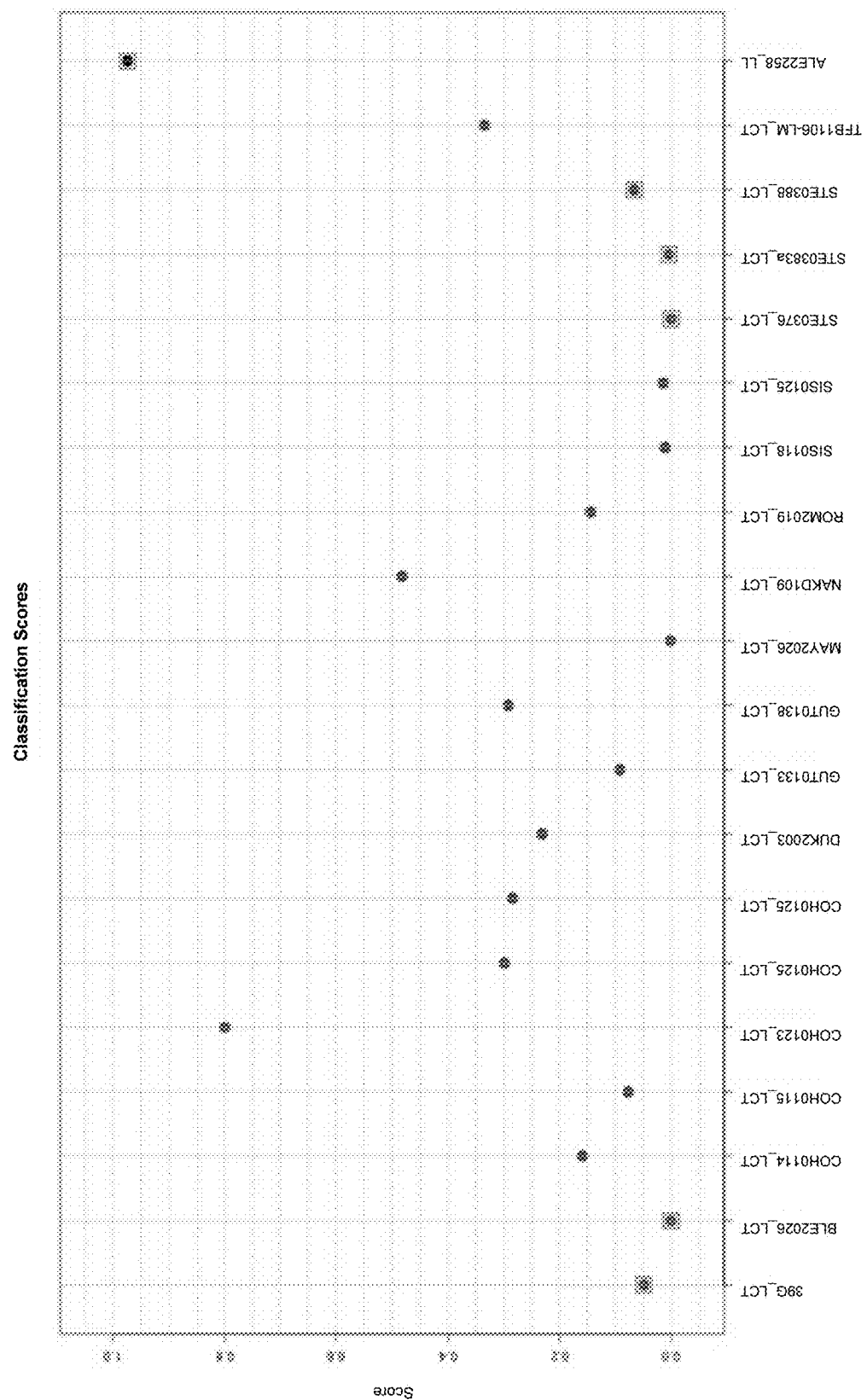
FIG. 21A-FIG. 21B illustrates that thyroid FNA classification using lymphoma signature genes can be improved by joint training using Tissue and FNA gene expression data. Classification scores in thyroid LCT FNA (n=19) and lymphoma FNA (n=1), using a linear SVM model trained solely on Tissue (FIG. 21A) or, jointly trained on Tissue and FNA (FIG. 21B). Low classification scores can indicate the sample is predicted to be benign and high classification scores can indicate the sample is predicted to be malignant by the model.

Specifically, direct training of the model (as described above) on the data set composed purely of tissue samples results in near-perfect cross validation performance characteristics. However, when the classifier is applied to FNA data in validation mode, the filter yielded numerous false positive calls on nearly half of all LCT samples (a histologically benign thyroid subtype), identifying them as lymphomas (FIG. 21A). Lymphomas and LCT are two very distinct diseases, however these share many gene transcripts in common owing to their common lymphoid origin. Lymphoma is a malignant cancer usually forming in the lymph nodes, and often migrating to distant organs, to form solid tumor metastasis composed primarily of lymphoid cells. In contrast, LCT is a group of non-malignant disorders that causes thyroidal inflammation, due to infiltration of lymphocytes into the thyroid.

Because of this observation the training set was constructed by combining available tissue samples with approximately one half (randomly selected) of available FNA samples, leaving the other half of samples available for independent for validation.

In this combined training data set, numerous transcription clusters are differentially expressed between lymphomas and all other samples. The complete set of markers (n=200) passing a filter of absolute effect size ≥1.0 (log scale) and FDR p-value ≤1×10$^{-10}$ is shown in Table 5. Given those results, separation between the classes using a small number of markers can be expected.

Figure 21B:
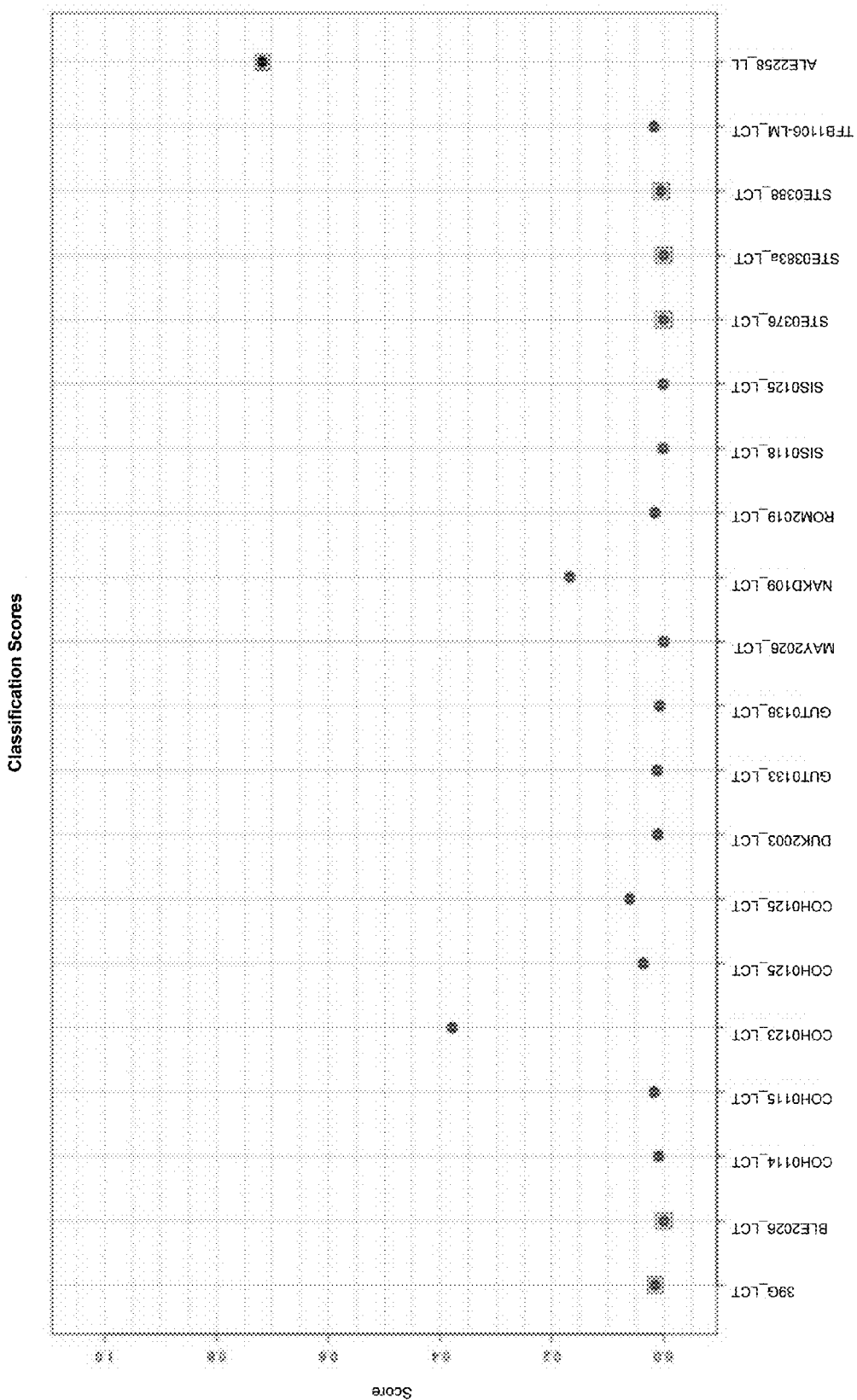

After the final classifier model was fully specified based on the training set, it was evaluated using an independent test set (n=20) composed solely of FNA, including LCT (n=19) and BLL (n=1) samples. As shown in FIG. 21B, this solution produced a model that was able to achieve separation of LCT from lymphoma samples without incurring any false positives.

Discussion

Pathway over-representation analysis on both gene lists is enriched for cell-membrane, cell cycle phase, mitosis, and spindle pathways. Cancer signaling pathways, including tyrosine, beta-catenin, Wnt pathway, and many others are also over-represented in these gene sets. Importantly, lymphoid cell signaling pathways are also over-represented including hematopoietic cell lineage, leukocyte transendothelial migration, and Aurora-B cell cycle regulation pathways.

TABLE 5

Lymphoma signature markers.
Table 5: Lymphoma Markers

| TCID | Gene Symbol | Description | FDR p-value | Effect Size (log scale) |
|---|---|---|---|---|
| 2734784 | AFF1 | AF4/FMR2 family, member 1 | 7.93E−11 | −1.17 |
| 3994231 | AFF2 | AF4/FMR2 family, member 2 | 4.38E−13 | 1.48 |
| 2566848 | AFF3 | AF4/FMR2 family, member 3 | 1.94E−13 | 1.94 |
| 3443206 | AICDA | activation-induced cytidine deaminase | 7.79E−18 | 2.09 |
| 2439554 | AIM2 | absent in melanoma 2 | 1.93E−13 | 3.76 |
| 3714068 | ALDH3A2 | aldehyde dehydrogenase 3 family, member A2 | 9.91E−12 | −1.47 |
| 3391149 | ALG9 | asparagine-linked glycosylation 9, alpha-1,2-mannosyltransferase homolog (*S. cerevisiae*) | 5.18E−15 | −3.65 |
| 3356115 | APLP2 | amyloid beta (A4) precursor-like protein 2 | 8.35E−20 | −2.38 |
| 3927226 | APP | amyloid beta (A4) precursor protein | 1.70E−43 | −2.77 |
| 3587457 | ARHGAP11A | Rho GTPase activating protein 11A | 6.88E−16 | 2.48 |
| 3587457 | ARHGAP11B | Rho GTPase activating protein 11B | 6.88E−16 | 2.48 |
| 2449559 | ASPM | asp (abnormal spindle) homolog, microcephaly associated (*Drosophila*) | 7.22E−18 | 2.60 |
| 2366422 | ATP1B1 | ATPase, Na+/K+ transporting, beta 1 polypeptide | 4.07E−16 | −2.53 |
| 2737596 | BANK1 | B-cell scaffold protein with ankyrin repeats 1 | 2.00E−12 | 2.67 |
| 3736290 | BIRC5 | baculoviral IAP repeat-containing 5 | 3.86E−15 | 1.66 |
| 3608298 | BLM | Bloom syndrome, RecQ helicase-like | 7.50E−21 | 2.27 |
| 2798915 | BRD9 | bromodomain containing 9 | 1.53E−16 | 1.76 |
| 3765580 | BRIP1 | BRCA1 interacting protein C-terminal helicase 1 | 3.42E−16 | 2.17 |
| 3915479 | BTG3 | BTG family, member 3 | 9.84E−12 | −3.70 |
| 2570616 | BUB1 | budding uninhibited by benzimidazoles 1 homolog (yeast) | 1.55E−16 | 2.12 |
| 3589697 | BUB1B | budding uninhibited by benzimidazoles 1 homolog beta (yeast) | 1.54E−15 | 2.39 |
| 3543979 | C14orf45 | chromosome 14 open reading frame 45 | 9.09E−12 | −1.89 |
| 2949971 | C6orf10 | chromosome 6 open reading frame 10 | 1.23E−13 | 1.60 |
| 2382117 | CAPN2 | calpain 2, (m/II) large subunit | 7.01E−17 | −1.43 |
| 3590014 | CASC5 | cancer susceptibility candidate 5 | 5.75E−19 | 2.36 |
| 2784113 | CCNA2 | cyclin A2 | 1.97E−15 | 2.75 |
| 3595979 | CCNB2 | cyclin B2 | 6.37E−13 | 2.92 |
| 3655109 | CD19 | CD19 molecule | 1.10E−16 | 1.30 |
| 3830353 | CD22 | CD22 molecule | 1.57E−16 | 1.36 |
| 3248289 | CDC2 | cell division cycle 2, G1 to S and G2 to M | 4.38E−13 | 1.92 |
| 3936913 | CDC45L | CDC45 cell division cycle 45-like (*S. cerevisiae*) | 8.74E−13 | 1.52 |
| 3720896 | CDC6 | cell division cycle 6 homolog (*S. cerevisiae*) | 2.92E−11 | 2.18 |
| 3090697 | CDCA2 | cell division cycle associated 2 | 5.18E−15 | 1.63 |
| 2516023 | CDCA7 | cell division cycle associated 7 | 1.08E−16 | 2.16 |
| 3666409 | CDH1 | cadherin 1, type 1, E-cadherin (epithelial) | 1.97E−15 | −2.97 |
| 2780172 | CENPE | centromere protein E, 312 kDa | 1.03E−22 | 2.75 |
| 2379863 | CENPF | centromere protein F, 350/400ka (mitosin) | 2.10E−14 | 2.64 |
| 2813442 | CENPH | centromere protein H | 1.29E−12 | 1.63 |
| 3258444 | CEP55 | centrosomal protein 55 kDa | 1.86E−13 | 2.39 |
| 3354799 | CHEK1 | CHK1 checkpoint homolog (*S. pombe*) | 2.02E−13 | 2.51 |
| 2571457 | CKAP2L | cytoskeleton associated protein 2-like | 1.18E−14 | 1.88 |
| 3404436 | CLEC2D | C-type lectin domain family 2, member D | 2.36E−11 | 2.94 |
| 2406420 | CLSPN | claspin homolog (*Xenopus laevis*) | 1.76E−16 | 2.26 |
| 3391149 | CRYAB | crystallin, alpha B | 5.18E−15 | −3.65 |
| 2830946 | CTNNA1 | catenin (cadherin-associated protein), alpha 1, 102 kDa | 2.73E−12 | −1.35 |
| 3331487 | CTNND1 | catenin (cadherin-associated protein), delta 1 | 5.75E−19 | −1.81 |
| 3915479 | CXADR | coxsackie virus and adenovirus receptor | 9.84E−12 | −3.70 |
| 3915479 | CXADRP2 | coxsackie virus and adenovirus receptor pseudogene 2 | 9.84E−12 | −3.70 |
| 2417528 | DEPDC1 | DEP domain containing 1 | 4.08E−12 | 2.31 |
| 3565663 | DLGAP5 | discs, large (*Drosophila*) homolog-associated protein 5 | 6.95E−16 | 3.06 |
| 3269939 | DOCK1 | dedicator of cytokinesis 1 | 2.15E−13 | −1.98 |
| 3150715 | DSCC1 | defective in sister chromatid cohesion 1 homolog (*S. cerevisiae*) | 6.65E−14 | 2.02 |
| 2893794 | DSP | desmoplakin | 5.05E−11 | −2.56 |
| 3365776 | E2F8 | E2F transcription factor 8 | 5.87E−22 | 1.94 |
| 2883878 | EBF1 | early B-cell factor 1 | 3.53E−12 | 1.99 |
| 3343202 | EED | embryonic ectoderm development | 1.67E−15 | 1.17 |
| 3621623 | ELL3 | elongation factor RNA polymerase II-like 3 | 4.09E−11 | 1.52 |
| 2480961 | EPCAM | epithelial cell adhesion molecule | 1.67E−15 | −3.74 |
| 2388219 | EXO1 | exonuclease 1 | 1.88E−17 | 2.05 |
| 3078348 | EZH2 | enhancer of zeste homolog 2 (*Drosophila*) | 8.91E−20 | 2.74 |
| 3331903 | FAM111B | family with sequence similarity 111, member B | 2.08E−11 | 2.51 |
| 4052881 | FAM72A | family with sequence similarity 72, member A | 2.78E−21 | 3.26 |

TABLE 5-continued

Lymphoma signature markers.
Table 5: Lymphoma Markers

| TCID | Gene Symbol | Description | FDR p-value | Effect Size (log scale) |
|---|---|---|---|---|
| 4052881 | FAM72B | family with sequence similarity 72, member B | 2.78E-21 | 3.26 |
| 4052881 | FAM72C | family with sequence similarity 72, member C | 2.78E-21 | 3.26 |
| 4052881 | FAM72D | family with sequence similarity 72, member D | 2.78E-21 | 3.26 |
| 3704980 | FANCA | Fanconi anemia, complementation group A | 4.48E-20 | 1.17 |
| 2610241 | FANCD2 | Fanconi anemia, complementation group D2 | 5.90E-21 | 1.46 |
| 3607537 | FANCI | Fanconi anemia, complementation group I | 1.47E-17 | 2.24 |
| 3257031 | FAS | Fas (TNF receptor superfamily, member 6) | 1.52E-16 | 2.42 |
| 2980241 | FBXO5 | F-box protein 5 | 9.91E-12 | 1.48 |
| 2439101 | FCRL1 | Fc receptor-like 1 | 4.50E-13 | 1.82 |
| 2439052 | FCRL2 | Fc receptor-like 2 | 3.19E-41 | 2.22 |
| 2439001 | FCRL3 | Fc receptor-like 3 | 8.17E-37 | 2.89 |
| 2438892 | FCRL5 | Fc receptor-like 5 | 3.91E-36 | 2.39 |
| 2363852 | FCRLA | Fc receptor-like A | 5.82E-12 | 1.90 |
| 3391149 | FDXACB1 | ferredoxin-fold anticodon binding domain containing 1 | 5.18E-15 | -3.65 |
| 2923661 | GJA1 | gap junction protein, alpha 1, 43 kDa | 4.25E-12 | -2.71 |
| 3210808 | GNAQ | guanine nucleotide binding protein (G protein), q polypeptide | 7.23E-16 | -1.36 |
| 2417272 | GNG12 | guanine nucleotide binding protein (G protein), gamma 12 | 1.54E-15 | -2.63 |
| 3456805 | GTSF1 | gametocyte specific factor 1 | 1.09E-13 | 3.28 |
| 3445123 | HEBP1 | heme binding protein 1 | 1.45E-11 | -1.97 |
| 3258910 | HELLS | helicase, lymphoid-specific | 3.87E-17 | 2.56 |
| 2604254 | HJURP | Holliday junction recognition protein | 2.35E-15 | 1.81 |
| 2838656 | HMMR | hyaluronan-mediated motility receptor (RHAMM) | 2.10E-16 | 2.73 |
| 2897453 | ID4 | inhibitor of DNA binding 4, dominant negative helix-loop-helix protein | 2.33E-13 | -2.57 |
| 3610958 | IGF1R | insulin-like growth factor 1 receptor | 6.65E-14 | -2.01 |
| 3755862 | IKZF3 | IKAROS family zinc finger 3 (Aiolos) | 3.73E-11 | 2.92 |
| 2452948 | IL10 | interleukin 10 | 2.37E-12 | 1.18 |
| 3988538 | IL13RA1 | interleukin 13 receptor, alpha 1 | 6.18E-13 | -1.64 |
| 3689880 | ISY1 | ISY1 splicing factor homolog (S. cerevisiae) | 1.24E-13 | 2.09 |
| 2748198 | KIAA0922 | KIAA0922 | 1.70E-11 | 2.02 |
| 3258168 | KIF11 | kinesin family member 11 | 4.30E-16 | 3.03 |
| 3599811 | KIF23 | kinesin family member 23 | 9.99E-18 | 2.57 |
| 2334098 | KIF2C | kinesin family member 2C | 2.19E-17 | 1.18 |
| 3980560 | KIF4A | kinesin family member 4A | 4.89E-16 | 2.08 |
| 3980560 | KIF4B | kinesin family member 4B | 4.89E-16 | 2.08 |
| 3435362 | KNTC1 | kinetochore associated 1 | 5.74E-14 | 1.84 |
| 2720251 | LCORL | ligand dependent nuclear receptor corepressor-like | 1.08E-16 | 2.66 |
| 3777470 | LOC100128219 | hypothetical protein LOC100128219 | 4.81E-11 | -2.11 |
| 3756193 | LOC100131821 | hypothetical protein LOC100131821 | 4.64E-13 | 3.07 |
| 2364677 | LOC100131938 | hypothetical LOC100131938 | 5.37E-14 | -2.41 |
| 3599811 | LOC145694 | hypothetical protein LOC145694 | 9.99E-18 | 2.57 |
| 2709486 | LOC730139 | hypothetical protein LOC730139 | 2.02E-12 | 1.66 |
| 3661718 | LPCAT2 | lysophosphatidylcholine acyltransferase 2 | 2.52E-12 | -2.69 |
| 3408505 | LRMP | lymphoid-restricted membrane protein | 1.95E-12 | 3.30 |
| 3113180 | MAL2 | mal, T-cell differentiation protein 2 | 8.22E-14 | -3.47 |
| 3861413 | MAP4K1 | mitogen-activated protein kinase kinase kinase kinase 1 | 2.77E-11 | 1.53 |
| 3235789 | MCM10 | minichromosome maintenance complex component 10 | 7.44E-18 | 1.52 |
| 2577896 | MCM6 | minichromosome maintenance complex component 6 | 7.16E-11 | 1.66 |
| 2420642 | MCOLN2 | mucolipin 2 | 1.44E-28 | 3.26 |
| 3168508 | MELK | maternal embryonic leucine zipper kinase | 1.76E-16 | 2.52 |
| 3312490 | MKI67 | antigen identified by monoclonal antibody Ki-67 | 6.32E-18 | 2.98 |
| 2734784 | MLL | myeloid/lymphoid or mixed-lineage leukemia (trithorax homolog, Drosophila) | 7.93E-11 | -1.17 |
| 2748163 | MND1 | meiotic nuclear divisions 1 homolog (S. cerevisiae) | 1.69E-12 | 3.02 |
| 3541073 | MPP5 | membrane protein, palmitoylated 5 (MAGUK p55 subfamily member 5) | 5.43E-11 | -1.29 |
| 3332403 | MS4A1 | membrane-spanning 4-domains, subfamily A, member 1 | 1.22E-11 | 2.84 |
| 2926802 | MYB | v-myb myeloblastosis viral oncogene homolog (avian) | 9.80E-11 | 1.79 |
| 2720251 | NCAPG | non-SMC condensin I complex, subunit G | 1.08E-16 | 2.66 |
| 2494484 | NCAPH | non-SMC condensin I complex, subunit H | 2.84E-17 | 1.82 |
| 2590736 | NCKAP1 | NCK-associated protein 1 | 1.60E-11 | -2.43 |

TABLE 5-continued

Lymphoma signature markers.
Table 5: Lymphoma Markers

| TCID | Gene Symbol | Description | FDR p-value | Effect Size (log scale) |
|---|---|---|---|---|
| 3776139 | NDC80 | NDC80 homolog, kinetochore complex component (*S. cerevisiae*) | 7.27E−14 | 2.52 |
| 2454444 | NEK2 | NIMA (never in mitosis gene a)-related kinase 2 | 5.74E−14 | 2.39 |
| 4019465 | NKRF | NFKB repressing factor | 2.30E−14 | 1.20 |
| 3842456 | NLRP4 | NLR family, pyrin domain containing 4 | 4.48E−12 | 1.26 |
| 3404436 | NPM1 | nucleophosmin (nucleolar phosphoprotein B23, numatrin) | 2.36E−11 | 2.94 |
| 2571457 | NT5DC4 | 5′-nucleotidase domain containing 4 | 1.18E−14 | 1.88 |
| 2364438 | NUF2 | NUF2, NDC80 kinetochore complex component, homolog (*S. cerevisiae*) | 6.32E−18 | 2.91 |
| 3741547 | P2RX5 | purinergic receptor P2X, ligand-gated ion channel, 5 | 5.24E−13 | 1.66 |
| 3589697 | PAK6 | p21 protein (Cdc42/Rac)-activated kinase 6 | 1.54E−15 | 2.39 |
| 3284596 | PARD3 | par-3 partitioning defective 3 homolog (*C. elegans*) | 3.42E−11 | −1.88 |
| 2638988 | PARP15 | poly (ADP-ribose) polymerase family, member 15 | 1.86E−18 | 2.83 |
| 3129149 | PBK | PDZ binding kinase | 3.72E−13 | 2.42 |
| 2364677 | PBX1 | pre-B-cell leukemia homeobox 1 | 5.37E−14 | −2.41 |
| 3921599 | PCP4 | Purkinje cell protein 4 | 3.03E−13 | −4.08 |
| 3452970 | PFKM | phosphofructokinase, muscle | 2.94E−14 | 1.07 |
| 3108226 | PGCP | plasma glutamate carboxypeptidase | 1.94E−12 | −2.14 |
| 2742985 | PLK4 | polo-like kinase 4 (*Drosophila*) | 1.74E−18 | 1.99 |
| 2699564 | PLOD2 | procollagen-lysine, 2-oxoglutarate 5-dioxygenase 2 | 4.66E−16 | −3.39 |
| 3987996 | PLS3 | plastin 3 (T isoform) | 1.70E−13 | −3.23 |
| 3607537 | POLG | polymerase (DNA directed), gamma | 1.47E−17 | 2.24 |
| 3130211 | PPP2CB | protein phosphatase 2 (formerly 2A), catalytic subunit, beta isoform | 6.81E−11 | −1.46 |
| 3639031 | PRC1 | protein regulator of cytokinesis 1 | 3.02E−11 | 1.90 |
| 2548500 | PRKD3 | protein kinase D3 | 1.74E−14 | 1.69 |
| 3777470 | PTPRM | protein tyrosine phosphatase, receptor type, M | 4.81E−11 | −2.11 |
| 3689880 | RAB43 | RAB43, member RAS oncogene family | 1.24E−13 | 2.09 |
| 3590086 | RAD51 | RAD51 homolog (RecA homolog, *E. coli*) (*S. cerevisiae*) | 1.67E−15 | 1.67 |
| 3401804 | RAD51AP1 | RAD51 associated protein 1 | 5.50E−11 | 2.00 |
| 2369339 | RALGPS2 | Ral GEF with PH domain and SH3 binding motif 2 | 1.25E−13 | 2.08 |
| 2476671 | RASGRP3 | RAS guanyl releasing protein 3 (calcium and DAG-regulated) | 2.31E−13 | 2.26 |
| 3485074 | RFC3 | replication factor C (activator 1) 3, 38 kDa | 1.01E−14 | 1.78 |
| 2709486 | RFC4 | replication factor C (activator 1) 4, 37 kDa | 2.02E−12 | 1.66 |
| 2372812 | RGS13 | regulator of G-protein signaling 13 | 9.59E−19 | 5.19 |
| 3391149 | RPL37AP8 | ribosomal protein L37a pseudogene 8 | 5.18E−15 | −3.65 |
| 2469252 | RRM2 | ribonucleotide reductase M2 | 2.73E−12 | 3.58 |
| 4045676 | S100A1 | S100 calcium binding protein A1 | 1.22E−11 | −1.92 |
| 4045676 | S100A13 | S100 calcium binding protein A13 | 1.22E−11 | −1.92 |
| 3108146 | SDC2 | syndecan 2 | 1.11E−14 | −3.08 |
| 3452970 | SENP1 | SUMO1/sentrin specific peptidase 1 | 2.94E−14 | 1.07 |
| 3621623 | SERINC4 | serine incorporator 4 | 4.09E−11 | 1.52 |
| 3577683 | SERPINA9 | serpin peptidase inhibitor, clade A (alpha-1 antiproteinase, antitrypsin), member 9 | 1.17E−12 | 1.60 |
| 2665572 | SGOL1 | shugoshin-like 1 (*S. pombe*) | 7.41E−20 | 2.85 |
| 2914693 | SH3BGRL2 | SH3 domain binding glutamic acid-rich protein like 2 | 1.37E−23 | −3.77 |
| 3689880 | SHCBP1 | SHC SH2-domain binding protein 1 | 1.24E−13 | 2.09 |
| 3182781 | SMC2 | structural maintenance of chromosomes 2 | 8.44E−11 | 1.47 |
| 2427007 | SORT1 | sortilin 1 | 3.10E−17 | −2.06 |
| 2531233 | SP140 | SP140 nuclear body protein | 1.76E−12 | 3.27 |
| 2531233 | SP140L | SP140 nuclear body protein-like | 1.76E−12 | 3.27 |
| 2585933 | SPC25 | SPC25, NDC80 kinetochore complex component, homolog (*S. cerevisiae*) | 2.24E−13 | 3.29 |
| 3257031 | STAMBPL1 | STAM binding protein-like 1 | 1.52E−16 | 2.42 |
| 2411228 | STIL | SCL/TAL1 interrupting locus | 4.36E−12 | 1.22 |
| 2902178 | TCF19 | transcription factor 19 | 1.96E−11 | 1.07 |
| 3264621 | TCF7L2 | transcription factor 7-like 2 (T-cell specific, HMG-box) | 1.17E−12 | −1.44 |
| 3615579 | TJP1 | tight junction protein 1 (zona occludens 1) | 3.75E−13 | −2.43 |
| 2766192 | TLR10 | toll-like receptor 10 | 1.64E−16 | 3.65 |
| 3331487 | TMX2 | thioredoxin-related transmembrane protein 2 | 5.75E−19 | −1.81 |
| 3756193 | TOP2A | topoisomerase (DNA) II alpha 170 kDa | 4.64E−13 | 3.07 |
| 3881443 | TPX2 | TPX2, microtubule-associated, homolog (*Xenopus laevis*) | 1.52E−12 | 2.36 |

TABLE 5-continued

Lymphoma signature markers.
Table 5: Lymphoma Markers

| TCID | Gene Symbol | Description | FDR p-value | Effect Size (log scale) |
|---|---|---|---|---|
| 2378662 | TRAF5 | TNF receptor-associated factor 5 | 3.17E−11 | 2.04 |
| 2798915 | TRIP13 | thyroid hormone receptor interactor 13 | 1.53E−16 | 1.76 |
| 2914777 | TTK | TTK protein kinase | 1.52E−12 | 1.90 |
| 2451200 | UBE2T | ubiquitin-conjugating enzyme E2T (putative) | 3.78E−11 | 1.80 |
| 3340697 | UVRAG | UV radiation resistance associated gene | 1.97E−15 | 1.48 |
| 3985523 | WBP5 | WW domain binding protein 5 | 6.27E−11 | −2.21 |
| 3591704 | WDR76 | WD repeat domain 76 | 1.59E−15 | 2.19 |
| 3704980 | ZNF276 | zinc finger protein 276 | 4.48E−20 | 1.17 |

Example 7: BRAF mRNA Signature

V600E is the most common somatic point mutation in papillary thyroid carcinomas (PTC), detectable in approximately 70% of all PTCs. The BRAF mutational status was characterized in a cohort of prospectively collected thyroid FNAs (n=59), for which definitive post-surgical histopathology diagnosis as PTC was available. In order to identify a BRAF-specific mRNA signature, the samples were also examined at the gene level using the Affymetrix Exon 1.0 ST microarray. Two LIMMA analyses were performed comparing gene expression profiles between PTC BRAF heterozygous mutant and PTC BRAF wild type thyroid samples. A linear SVM classifier was trained using these data in order to predict BRAF DNA mutation status.

Each LIMMA Comparison was Performed Using:

1. A differential gene expression model that did not adjust for covariates of follicular cell signal strength, lymphocytic cell signal strength, or Hurthle cell signal strength (no covs) according to the equation below. This model was used to train a linear SVM classifier in order to predict BRAF DNA mutation status of unknown samples.

$$Y_g = \alpha.BRAF + \varepsilon$$

2. A differential gene expression model that included covariates adjusting for follicular cell signal strength, lymphocytic cell signal strength, and Hurthle cell signal strength (with covs) according to the equation below. This model was not used in classifier training, but was used to identify markers whose differential gene expression is affected by these covariates.

$$Y_g = \alpha.BRAF + \beta.LCT + \gamma.FOL + \delta.Hurthle + \varepsilon$$

a. These covariates consisted of three panels of biomarkers used bioinformatically as surrogates for the amount of various cell types present in the cellular mixture of thyroid FNAs. (Chudova, D., J. I. Wilde, E. T. Wang, H. Wang, N. Rabbee, C. M. Egidio, J. Reynolds, E. Tom, M. Pagan, C. Ted Rigl, L. Friedman, C. C. Wang, R. B. Lanman, M. Zeiger, E. Kebebew, J. Rosai, G. Fellegara, V. A. Livolsi, and G. C. Kennedy. 2010. Molecular Classification of Thyroid Nodules Using High-Dimensionality Genomic Data. The Journal of clinical endocrinology and metabolism 95(12):5301-5309; which is hereby incorporated by reference in its entirety).

The Output of Each Analysis was Filtered by:

1. LIMMA FDR p-value ≤0.00001 (no covariates analysis) or ≤0.01 (covariates analysis). See each biomarker table for individual filtering criteria.

FNA biopsies can contain highly variable (heterogeneous) cellular content and a diverse number of distinct cellular types mixed together in unknowable proportions. The very nature of the thyroid FNA sample can pose difficulties in interpreting gene expression profiles across many samples. In order to distill a highly accurate BRAF mRNA signature, the gene expression data were analyzed using two classification models. A primary analysis used a standard LIMMA comparison of PTC BRAF het mut vs. PTC BRAF wild type (results shown in Table 9). A secondary analysis examined the same gene expression data while adjusting for the confounding effects of cellular content variation. The effects of three cellular types (Follicular, Lymphoid, and Hurthle cells, listed in Tables 11-13) known to co-exist in the thyroid were examined simultaneously using biomarkers known to change very little between malignant and benign thyroid samples. The results of this analysis (Table 10) demonstrate mRNA biomarkers that are significantly correlated with the BRAF V600E point mutation, and are otherwise difficult to observe due to an obscuring background of cellular content variation between samples.

Pathway over-representation analysis on both gene lists is enriched for cell-membrane, extracellular space, adhesion, and junction pathways. Cancer signaling pathways, including tyrosine, beta-catenin, Wnt pathway, and many others are also over-represented in these gene sets.

TABLE 6

Sample cohort used in training by FNA cytology result (n = 59).

| DNA Mutation Status | Benign | Indeterminate | Malignant | NA |
|---|---|---|---|---|
| BRAF het mut | 0 | 1 | 23 | 0 |
| BRAF wild type | 2 | 12 | 19 | 2 |
| Totals (n = 59) | 2 | 13 | 42 | 2 |

TABLE 7

Sample cohort used in training by post-surgical pathology result (n = 59).

| DNA Mutation Status | PTC Subtype |
|---|---|
| BRAF heterozygous mutant | 24/59 |
| BRAF wild type | 35/59 |

TABLE 8

Summary of significant BRAF biomarkers

| Comparison | Total Genes After Filtering | |
|---|---|---|
| | No covariates | With covariates |
| PTC het mut vs. PTC wild type | 477 | 36 |

Classification using Mutant BRAF mRNA Expression Signature Markers.

Figure 22:
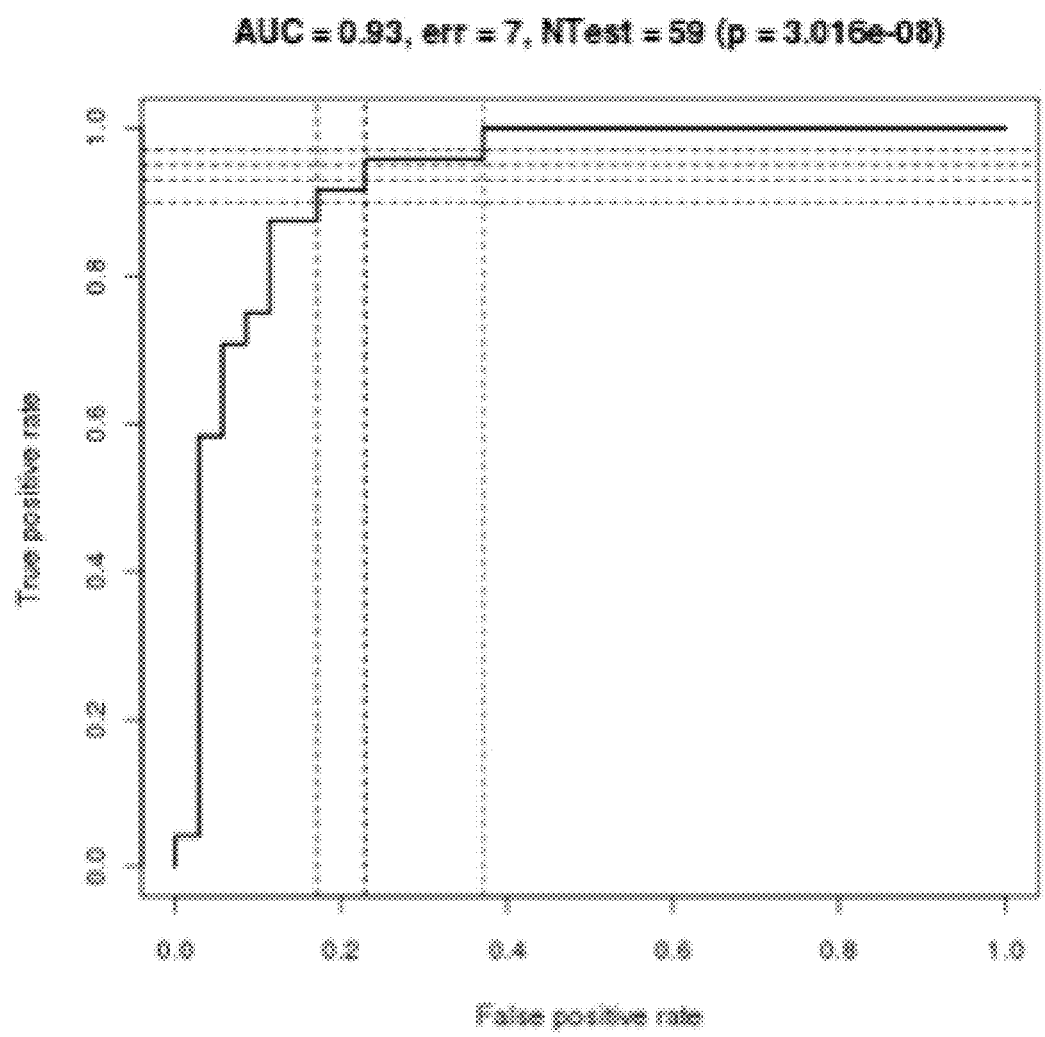
FIG. 22 illustrates classification performance using BRAF mRNA signature. ROC curve using top genes (n=16, ranked by FDR p-value) in PTC het mut vs. PTC wild type comparison (no covariates).

Classification performance was estimated for the PTC (HET MUT) vs. PTC(WT), comparison using the "no covariates" model. The feature selection method used was LIMMA and top differentially expressed markers were ranked based on lowest p-value. The classifier used was linear SVM. Error rates were estimated during training using 30-fold cross validation (FIG. 22).

TABLE 9

BRAF signature biomarkers. PTC hetmut vs. PTC wild type, no covariates.
The results from a LIMMA analysis (without adjusting for additional confounding covariates) were filtered based on FDR p-value ($\leq 0.0001$). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 3417249 | ERBB3 | v-erb-b2 erythroblastic leukemia viral oncogene homolog 3 (avian) | 1.56 | 4.25E−08 |
| 2560625 | FAM176A | family with sequence similarity 176, member A | 0.59 | 9.66E−08 |
| 2828441 | PDLIM4 | PDZ and LIM domain 4 | 1.14 | 9.66E−08 |
| 3678462 | PPL | periplakin | 0.98 | 1.32E−07 |
| 2414958 | TACSTD2 | tumor-associated calcium signal transducer 2 | 1.48 | 1.32E−07 |
| 2358949 | CGN | cingulin | 0.58 | 2.55E−07 |
| 2378256 | SYT14 | synaptotagmin XIV | 2.34 | 2.55E−07 |
| 2622970 | DOCK3 | dedicator of cytokinesis 3 | 0.94 | 3.28E−07 |
| 3040518 | MACC1 | metastasis associated in colon cancer 1 | 1.89 | 3.28E−07 |
| 2973376 | PTPRK | protein tyrosine phosphatase, receptor type, K | 1.28 | 3.28E−07 |
| 2560076 | RTKN | rhotekin | 0.51 | 3.28E−07 |
| 2648535 | SGEF | Src homology 3 domain-containing guanine nucleotide exchange factor | 1.00 | 3.28E−07 |
| 2991860 | ITGB8 | integrin, beta 8 | 1.60 | 3.37E−07 |
| 3110608 | TM7SF4 | transmembrane 7 superfamily member 4 | 2.72 | 3.44E−07 |
| 2333318 | PTPRF | protein tyrosine phosphatase, receptor type, F | 0.99 | 3.56E−07 |
| 3352438 | POU2F3 | POU class 2 homeobox 3 | 0.60 | 3.91E−07 |
| 2738664 | SGMS2 | sphingomyelin synthase 2 | 1.57 | 4.15E−07 |
| 2622121 | DAG1 | dystroglycan 1 (dystrophin-associated glycoprotein 1) | 0.75 | 5.98E−07 |
| 2903782 | ITPR3 | inositol 1,4,5-triphosphate receptor, type 3 | 1.03 | 5.98E−07 |
| 3890333 | TFAP2C | transcription factor AP-2 gamma (activating enhancer binding protein 2 gamma) | 0.66 | 6.08E−07 |
| 2809245 | ITGA2 | integrin, alpha 2 (CD49B, alpha 2 subunit of VLA-2 receptor) | 2.17 | 6.13E−07 |
| 2371139 | LAMC2 | laminin, gamma 2 | 1.44 | 7.90E−07 |
| 3109687 | GRHL2 | grainyhead-like 2 (*Drosophila*) | 1.15 | 1.03E−06 |
| 3868783 | KLK7 | kallikrein-related peptidase 7 | 1.66 | 1.03E−06 |
| 2452478 | LEMD1 | LEM domain containing 1 | 1.61 | 1.03E−06 |
| 3154002 | KCNQ3 | potassium voltage-gated channel, KQT-like subfamily, member 3 | 0.84 | 1.06E−06 |
| 2611779 | TMEM43 | transmembrane protein 43 | 0.70 | 1.06E−06 |
| 3636391 | HOMER2 | homer homolog 2 (*Drosophila*) | 0.96 | 1.10E−06 |
| 3636391 | LOC100131860 | hypothetical protein LOC100131860 | 0.96 | 1.10E−06 |
| 2423829 | ARHGAP29 | Rho GTPase activating protein 29 | 1.80 | 1.14E−06 |
| 3529908 | NFATC4 | nuclear factor of activated T-cells, cytoplasmic, calcineurin-dependent 4 | 0.46 | 1.14E−06 |
| 2360677 | EFNA1 | ephrin-A1 | 0.77 | 1.14E−06 |
| 2344888 | CYR61 | cysteine-rich, angiogenic inducer, 61 | 0.86 | 1.20E−06 |
| 2910680 | LRRC1 | leucine rich repeat containing 1 | 0.87 | 1.20E−06 |
| 3390195 | EXPH5 | exophilin 5 | 1.22 | 1.21E−06 |
| 3269694 | FANK1 | fibronectin type III and ankyrin repeat domains 1 | 1.20 | 1.21E−06 |
| 2323899 | UBXN10 | UBX domain protein 10 | 1.06 | 1.21E−06 |
| 2451309 | COX7C | cytochrome c oxidase subunit VIIc | 0.70 | 1.42E−06 |
| 2451309 | KDM5B | lysine (K)-specific demethylase 5B | 0.70 | 1.42E−06 |
| 2783596 | PDE5A | phosphodiesterase 5A, cGMP-specific | 2.06 | 1.44E−06 |
| 3198974 | MPDZ | multiple PDZ domain protein | 1.36 | 1.54E−06 |
| 2759582 | AFAP1 | actin filament associated protein 1 | 0.64 | 2.00E−06 |
| 2468811 | ASAP2 | ArfGAP with SH3 domain, ankyrin repeat and PH domain 2 | 1.21 | 2.00E−06 |
| 2484970 | EHBP1 | EH domain binding protein 1 | 1.00 | 2.00E−06 |
| 3696226 | ESRP2 | epithelial splicing regulatory protein 2 | 0.51 | 2.00E−06 |

TABLE 9-continued

BRAF signature biomarkers. PTC hetmut vs. PTC wild type, no covariates.
The results from a LIMMA analysis (without adjusting for additional confounding covariates) were filtered
based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 2759582 | LOC389199 | hypothetical LOC389199 | 0.64 | 2.00E−06 |
| 3183111 | SLC44A1 | solute carrier family 44, member 1 | 1.09 | 2.00E−06 |
| 3104698 | ZBTB10 | zinc finger and BTB domain containing 10 | 0.60 | 2.00E−06 |
| 2356818 | BCL9 | B-cell CLL/lymphoma 9 | 0.89 | 2.15E−06 |
| 3040967 | RAPGEF5 | Rap guanine nucleotide exchange factor (GEF) 5 | 1.05 | 2.15E−06 |
| 3456081 | RARG | retinoic acid receptor, gamma | 0.49 | 2.15E−06 |
| 4045643 | S100A16 | S100 calcium binding protein A16 | 1.58 | 2.15E−06 |
| 2437118 | MUC1 | mucin 1, cell surface associated | 1.38 | 2.21E−06 |
| 3868828 | KLK10 | kallikrein-related peptidase 10 | 1.56 | 2.42E−06 |
| 2830861 | EGR1 | early growth response 1 | 1.44 | 2.59E−06 |
| 2582562 | ACVR1 | activin A receptor, type I | 1.04 | 2.66E−06 |
| 2385873 | KCNK1 | potassium channel, subfamily K, member 1 | 0.90 | 2.74E−06 |
| 3807595 | LOC441420 | similar to KIAA1119 protein | 1.12 | 2.79E−06 |
| 3807595 | MYO5B | myosin VB | 1.12 | 2.79E−06 |
| 3523318 | NALCN | sodium leak channel, non-selective | 0.71 | 2.79E−06 |
| 2453881 | IRF6 | interferon regulatory factor 6 | 1.03 | 2.88E−06 |
| 3556990 | JUB | jub, ajuba homolog (*Xenopus laevis*) | 1.14 | 2.88E−06 |
| 3628832 | DAPK2 | death-associated protein kinase 2 | 1.39 | 2.89E−06 |
| 3020273 | CAV2 | caveolin 2 | 1.71 | 2.92E−06 |
| 2685304 | PROS1 | protein S (alpha) | 1.92 | 2.92E−06 |
| 2525533 | LOC648149 | hypothetical protein LOC648149 | 1.35 | 2.96E−06 |
| 2525533 | MAP2 | microtubule-associated protein 2 | 1.35 | 2.96E−06 |
| 3173880 | LOC100289287 | similar to tight junction protein 2 (zona occludens 2) | 1.02 | 2.98E−06 |
| 3173880 | TJP2 | tight junction protein 2 (zona occludens 2) | 1.02 | 2.98E−06 |
| 3183757 | RAD23B | RAD23 homolog B (*S. cerevisiae*) | 0.61 | 3.08E−06 |
| 3705491 | FAM57A | family with sequence similarity 57, member A | 0.70 | 3.13E−06 |
| 3795942 | YES1 | v-yes-1 Yamaguchi sarcoma viral oncogene homolog 1 | 0.76 | 3.28E−06 |
| 2742109 | FGF2 | fibroblast growth factor 2 (basic) | 0.97 | 3.44E−06 |
| 3108489 | LAPTM4B | lysosomal protein transmembrane 4 beta | 1.08 | 3.44E−06 |
| 2742109 | NUDT6 | nudix (nucleoside diphosphate linked moiety X)-type motif 6 | 0.97 | 3.44E−06 |
| 3863640 | CXCL17 | chemokine (C—X—C motif) ligand 17 | 1.93 | 3.56E−06 |
| 2976360 | PERP | PERP, TP53 apoptosis effector | 1.59 | 3.64E−06 |
| 2405284 | TMEM54 | transmembrane protein 54 | 0.94 | 3.66E−06 |
| 3056264 | ABHD11 | abhydrolase domain containing 11 | 0.57 | 3.83E−06 |
| 2593407 | PGAP1 | post-GPI attachment to proteins 1 | 1.16 | 3.84E−06 |
| 3726154 | ITGA3 | integrin, alpha 3 (antigen CD49C, alpha 3 subunit of VLA-3 receptor) | 1.45 | 3.92E−06 |
| 3783529 | DSG2 | desmoglein 2 | 1.77 | 4.41E−06 |
| 2700365 | TM4SF1 | transmembrane 4 L six family member 1 | 2.20 | 4.41E−06 |
| 3973692 | PRRG1 | proline rich Gla (G-carboxyglutamic acid) 1 | 1.68 | 4.44E−06 |
| 3401217 | TULP3 | tubby like protein 3 | 0.81 | 4.44E−06 |
| 2875454 | SEPT8 | septin 8 | 0.85 | 4.65E−06 |
| 3110272 | FZD6 | frizzled homolog 6 (*Drosophila*) | 1.61 | 4.65E−06 |
| 3110272 | LOC100131102 | hypothetical protein LOC100131102 | 1.61 | 4.65E−06 |
| 3928415 | CLDN8 | claudin 8 | 1.49 | 4.77E−06 |
| 3653123 | PRKCB | protein kinase C, beta | −1.44 | 4.96E−06 |
| 3368940 | ABTB2 | ankyrin repeat and BTB (POZ) domain containing 2 | 0.43 | 5.09E−06 |
| 2351787 | C1orf88 | chromosome 1 open reading frame 88 | 1.34 | 5.09E−06 |
| 2327310 | SMPDL3B | sphingomyelin phosphodiesterase, acid-like 3B | 0.89 | 5.79E−06 |
| 3408831 | SSPN | sarcospan (Kras oncogene-associated gene) | 1.26 | 6.08E−06 |
| 3385951 | NOX4 | NADPH oxidase 4 | 0.71 | 6.12E−06 |
| 2434178 | MTMR11 | myotubularin related protein 11 | 0.44 | 6.20E−06 |
| 3473750 | FLJ20674 | hypothetical protein FLJ20674 | 0.66 | 6.24E−06 |
| 3580791 | BAG5 | BCL2-associated athanogene 5 | 0.57 | 6.34E−06 |
| 2632453 | ARL13B | ADP-ribosylation factor-like 13B | 0.98 | 6.38E−06 |
| 3235516 | CAMK1D | calcium/calmodulin-dependent protein kinase ID | −0.75 | 6.38E−06 |
| 2708817 | TMEM41A | transmembrane protein 41A | 0.63 | 6.54E−06 |
| 3050609 | COBL | cordon-bleu homolog (mouse) | 0.60 | 6.66E−06 |
| 2567167 | LONRF2 | LON peptidase N-terminal domain and ring finger 2 | 1.61 | 8.04E−06 |
| 2590582 | PDE1A | phosphodiesterase 1A, calmodulin-dependent | 1.76 | 8.82E−06 |

TABLE 9-continued

BRAF signature biomarkers. PTC hetmut vs. PTC wild type, no covariates.
The results from a LIMMA analysis (without adjusting for additional confounding covariates) were filtered
based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 2734270 | CDS1 | CDP-diacylglycerol synthase (phosphatidate cytidylyltransferase) 1 | 1.13 | 8.89E−06 |
| 3590164 | SPINT1 | serine peptidase inhibitor, Kunitz type 1 | 0.78 | 8.89E−06 |
| 2341083 | GADD45A | growth arrest and DNA-damage-inducible, alpha | 0.84 | 9.03E−06 |
| 3757108 | KRT19 | keratin 19 | 1.26 | 9.13E−06 |
| 3994710 | MAMLD1 | mastermind-like domain containing 1 | 0.68 | 9.13E−06 |
| 2412312 | TTC39A | tetratricopeptide repeat domain 39A | 1.04 | 9.13E−06 |
| 3975893 | PHF16 | PHD finger protein 16 | 0.72 | 9.57E−06 |
| 3056292 | CLDN3 | claudin 3 | 1.04 | 9.58E−06 |
| 2346625 | EPHX4 | epoxide hydrolase 4 | 1.00 | 1.02E−05 |
| 3389976 | SLC35F2 | solute carrier family 35, member F2 | 1.02 | 1.02E−05 |
| 2548776 | ATL2 | atlastin GTPase 2 | 1.12 | 1.05E−05 |
| 2635906 | PHLDB2 | pleckstrin homology-like domain, family B, member 2 | 1.28 | 1.05E−05 |
| 2511820 | PKP4 | plakophilin 4 | 1.23 | 1.05E−05 |
| 3351200 | TMPRSS4 | transmembrane protease, serine 4 | 1.40 | 1.05E−05 |
| 2457842 | TP53BP2 | tumor protein p53 binding protein, 2 | 0.70 | 1.07E−05 |
| 3012019 | CLDN12 | claudin 12 | 1.35 | 1.07E−05 |
| 3012019 | PFTK1 | PFTAIRE protein kinase 1 | 1.35 | 1.07E−05 |
| 3522398 | AIDA | axin interactor, dorsalization associated | 1.51 | 1.07E−05 |
| 3522398 | DOCK9 | dedicator of cytokinesis 9 | 1.51 | 1.07E−05 |
| 2649609 | MLF1 | myeloid leukemia factor 1 | 1.24 | 1.07E−05 |
| 3757329 | JUP | junction plakoglobin | 0.90 | 1.09E−05 |
| 3679959 | EMP2 | epithelial membrane protein 2 | 1.43 | 1.10E−05 |
| 3219885 | PTPN3 | protein tyrosine phosphatase, non-receptor type 3 | 1.01 | 1.10E−05 |
| 2732844 | ANXA3 | annexin A3 | 1.44 | 1.10E−05 |
| 2408499 | SCMH1 | sex comb on midleg homolog 1 (Drosophila) | 0.62 | 1.11E−05 |
| 2931090 | PPP1R14C | protein phosphatase 1, regulatory (inhibitor) subunit 14C | 1.11 | 1.13E−05 |
| 3453252 | ADCY6 | adenylate cyclase 6 | 0.31 | 1.13E−05 |
| 3020302 | CAV1 | caveolin 1, caveolae protein, 22 kDa | 1.97 | 1.13E−05 |
| 3007960 | CLDN4 | claudin 4 | 1.60 | 1.13E−05 |
| 2686023 | DCBLD2 | discoidin, CUB and LCCL domain containing 2 | 1.30 | 1.13E−05 |
| 2625907 | FLNB | filamin B, beta | 0.81 | 1.13E−05 |
| 3079005 | RARRES2 | retinoic acid receptor responder (tazarotene induced) 2 | 0.76 | 1.13E−05 |
| 3034027 | DNAJB6 | DnaJ (Hsp40) homolog, subfamily B, member 6 | −0.57 | 1.14E−05 |
| 3034027 | TMEM135 | transmembrane protein 135 | −0.57 | 1.14E−05 |
| 2708855 | C11orf72 | chromosome 11 open reading frame 72 | 2.07 | 1.14E−05 |
| 2708855 | LIPH | lipase, member H | 2.07 | 1.14E−05 |
| 3600283 | THSD4 | thrombospondin, type I, domain containing 4 | 0.63 | 1.19E−05 |
| 2827525 | KDELC1 | KDEL (Lys-Asp-Glu-Leu) containing 1 | 1.10 | 1.19E−05 |
| 2539607 | MBOAT2 | membrane bound O-acyltransferase domain containing 2 | 1.29 | 1.19E−05 |
| 2827525 | SLC12A2 | solute carrier family 12 (sodium/potassium/chloride transporters), member 2 | 1.10 | 1.19E−05 |
| 2936857 | MLLT4 | myeloid/lymphoid or mixed-lineage leukemia (trithorax homolog, Drosophila); translocated to, 4 | 1.29 | 1.26E−05 |
| 4024373 | CDR1 | cerebellar degeneration-related protein 1, 34 kDa | 1.97 | 1.29E−05 |
| 3351498 | TMEM25 | transmembrane protein 25 | 0.48 | 1.29E−05 |
| 3351498 | TTC36 | tetratricopeptide repeat domain 36 | 0.48 | 1.29E−05 |
| 4024373 | YTHDC2 | YTH domain containing 2 | 1.97 | 1.29E−05 |
| 2450798 | LAD1 | ladinin 1 | 0.43 | 1.29E−05 |
| 3044129 | GGCT | gamma-glutamyl cyclotransferase | 1.09 | 1.30E−05 |
| 2594951 | ALS2CR4 | amyotrophic lateral sclerosis 2 (juvenile) chromosome region, candidate 4 | 0.83 | 1.31E−05 |
| 2881860 | CCDC69 | coiled-coil domain containing 69 | −0.94 | 1.31E−05 |
| 2643901 | PPP2R3A | protein phosphatase 2 (formerly 2A), regulatory subunit B", alpha | 0.68 | 1.31E−05 |
| 4018454 | AMOT | angiomotin | 1.09 | 1.32E−05 |
| 3581221 | AHNAK2 | AHNAK nucleoprotein 2 | 1.45 | 1.34E−05 |

TABLE 9-continued

BRAF signature biomarkers. PTC hetmut vs. PTC wild type, no covariates.
The results from a LIMMA analysis (without adjusting for additional confounding covariates) were filtered
based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 3683377 | GPRC5B | G protein-coupled receptor, family C, group 5, member B | 1.37 | 1.34E−05 |
| 2790823 | MAP9 | microtubule-associated protein 9 | 0.71 | 1.34E−05 |
| 2402431 | PAQR7 | progestin and adipoQ receptor family member VII | 0.56 | 1.34E−05 |
| 3284596 | PARD3 | par-3 partitioning defective 3 homolog (*C. elegans*) | 1.11 | 1.34E−05 |
| 3911217 | PMEPA1 | prostate transmembrane protein, androgen induced 1 | 0.47 | 1.34E−05 |
| 2662087 | SRGAP3 | SLIT-ROBO Rho GTPase activating protein 3 | 0.45 | 1.34E−05 |
| 2653114 | NAALADL2 | N-acetylated alpha-linked acidic dipeptidase-like 2 | 0.77 | 1.36E−05 |
| 2590736 | NCKAP1 | NCK-associated protein 1 | 1.49 | 1.36E−05 |
| 3217361 | ANKS6 | ankyrin repeat and sterile alpha motif domain containing 6 | 0.72 | 1.39E−05 |
| 3832280 | C19orf33 | chromosome 19 open reading frame 33 | 1.13 | 1.39E−05 |
| 4045665 | S100A14 | S100 calcium binding protein A14 | 1.41 | 1.39E−05 |
| 3832280 | YIF1B | Yip1 interacting factor homolog B (*S. cerevisiae*) | 1.13 | 1.39E−05 |
| 2370123 | XPR1 | xenotropic and polytropic retrovirus receptor | 1.07 | 1.41E−05 |
| 2750594 | SC4MOL | sterol-C4-methyl oxidase-like | 0.90 | 1.42E−05 |
| 3154263 | SLA | Src-like-adaptor | −1.17 | 1.42E−05 |
| 2608469 | ITPR1 | inositol 1,4,5-triphosphate receptor, type 1 | −1.06 | 1.44E−05 |
| 3320944 | TEAD1 | TEA domain family member 1 (SV40 transcriptional enhancer factor) | 1.34 | 1.44E−05 |
| 3087167 | TUSC3 | tumor suppressor candidate 3 | 1.84 | 1.44E−05 |
| 3335894 | CST6 | cystatin E/M | 2.04 | 1.45E−05 |
| 2610707 | HRH1 | histamine receptor H1 | 0.77 | 1.45E−05 |
| 2617188 | ITGA9 | integrin, alpha 9 | 1.32 | 1.45E−05 |
| 2807359 | OSMR | oncostatin M receptor | 1.49 | 1.45E−05 |
| 2400177 | CAMK2N1 | calcium/calmodulin-dependent protein kinase II inhibitor 1 | 1.76 | 1.48E−05 |
| 3044072 | NOD1 | nucleotide-binding oligomerization domain containing 1 | 0.97 | 1.51E−05 |
| 2822215 | PAM | peptidylglycine alpha-amidating monooxygenase | 1.38 | 1.51E−05 |
| 2645906 | PLS1 | plastin 1 (I isoform) | 1.03 | 1.51E−05 |
| 2853642 | C5orf42 | chromosome 5 open reading frame 42 | 0.86 | 1.52E−05 |
| 2783099 | TRAM1L1 | translocation associated membrane protein 1-like 1 | 1.12 | 1.52E−05 |
| 2945440 | DCDC2 | doublecortin domain containing 2 | 1.23 | 1.55E−05 |
| 2945440 | KAAG1 | kidney associated antigen 1 | 1.23 | 1.55E−05 |
| 2520138 | MFSD6 | major facilitator superfamily domain containing 6 | 0.65 | 1.57E−05 |
| 3703665 | ZCCHC14 | zinc finger, CCHC domain containing 14 | 0.68 | 1.57E−05 |
| 3048886 | PURB | purine-rich element binding protein B | 0.43 | 1.60E−05 |
| 2734421 | ARHGAP24 | Rho GTPase activating protein 24 | −0.98 | 1.61E−05 |
| 2893794 | DSP | desmoplakin | 1.50 | 1.62E−05 |
| 2820925 | RHOBTB3 | Rho-related BTB domain containing 3 | 1.26 | 1.63E−05 |
| 3159483 | KANK1 | KN motif and ankyrin repeat domains 1 | 0.53 | 1.64E−05 |
| 3159483 | LOC100133062 | similar to Uncharacterized protein C6orf146 | 0.53 | 1.64E−05 |
| 2816298 | IQGAP2 | IQ motif containing GTPase activating protein 2 | −1.35 | 1.66E−05 |
| 3020343 | MET | met proto-oncogene (hepatocyte growth factor receptor) | 2.11 | 1.66E−05 |
| 2373336 | CFH | complement factor H | 1.96 | 1.67E−05 |
| 2373336 | CFHR1 | complement factor H-related 1 | 1.96 | 1.67E−05 |
| 2773545 | BTC | betacellulin | 0.94 | 1.70E−05 |
| 2858592 | DEPDC1B | DEP domain containing 1B | 1.20 | 1.89E−05 |
| 3751002 | RAB34 | RAB34, member RAS oncogene family | 0.90 | 1.94E−05 |
| 3717870 | TMEM98 | transmembrane protein 98 | 1.73 | 2.02E−05 |
| 2326327 | CNKSR1 | connector enhancer of kinase suppressor of Ras 1 | 0.47 | 2.03E−05 |
| 3585905 | APBA2 | amyloid beta (A4) precursor protein-binding, family A, member 2 | −0.50 | 2.04E−05 |
| 2819044 | RASA1 | RAS p21 protein activator (GTPase activating protein) 1 | 0.73 | 2.11E−05 |
| 3110395 | RIMS2 | regulating synaptic membrane exocytosis 2 | 1.10 | 2.15E−05 |
| 2451931 | GOLT1A | golgi transport 1 homolog A (*S. cerevisiae*) | 1.03 | 2.17E−05 |
| 2768654 | OCIAD2 | OCIA domain containing 2 | 0.98 | 2.17E−05 |

TABLE 9-continued

BRAF signature biomarkers. PTC hetmut vs. PTC wild type, no covariates.
The results from a LIMMA analysis (without adjusting for additional confounding covariates) were filtered
based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 2872848 | LOX | lysyl oxidase | 1.53 | 2.19E−05 |
| 3321150 | ARNTL | aryl hydrocarbon receptor nuclear translocator-like | 1.17 | 2.22E−05 |
| 3839206 | MYH14 | myosin, heavy chain 14 | 0.39 | 2.26E−05 |
| 2954355 | CUL7 | cullin 7 | 0.39 | 2.29E−05 |
| 2954355 | CUL9 | cullin 9 | 0.39 | 2.29E−05 |
| 2954355 | KLC4 | kinesin light chain 4 | 0.39 | 2.29E−05 |
| 3046197 | ELMO1 | engulfment and cell motility 1 | −1.07 | 2.29E−05 |
| 2350596 | CELSR2 | cadherin, EGF LAG seven-pass G-type receptor 2 (flamingo homolog, Drosophila) | 0.38 | 2.30E−05 |
| 3755323 | CISD3 | CDGSH iron sulfur domain 3 | 0.81 | 2.31E−05 |
| 3099566 | FAM110B | family with sequence similarity 110, member B | 0.80 | 2.31E−05 |
| 3755323 | PCGF2 | polycomb group ring finger 2 | 0.81 | 2.31E−05 |
| 2827057 | GRAMD3 | GRAM domain containing 3 | 1.35 | 2.33E−05 |
| 4001223 | RAI2 | retinoic acid induced 2 | 0.64 | 2.33E−05 |
| 3412345 | TMEM117 | transmembrane protein 117 | 1.04 | 2.33E−05 |
| 2327817 | PTPRU | protein tyrosine phosphatase, receptor type, U | 0.56 | 2.48E−05 |
| 3336486 | C11orf80 | chromosome 11 open reading frame 80 | 0.63 | 2.49E−05 |
| 3336486 | RCE1 | RCE1 homolog, prenyl protein peptidase (S. cerevisiae) | 0.63 | 2.49E−05 |
| 3087501 | ZDHHC2 | zinc finger, DHHC-type containing 2 | 0.77 | 2.49E−05 |
| 2601287 | AP1S3 | adaptor-related protein complex 1, sigma 3 subunit | 0.72 | 2.51E−05 |
| 3238962 | KIAA1217 | KIAA1217 | 1.48 | 2.51E−05 |
| 3238962 | PRINS | psoriasis associated RNA induced by stress (non-protein coding) | 1.48 | 2.51E−05 |
| 2583465 | ITGB6 | integrin, beta 6 | 1.40 | 2.55E−05 |
| 3815116 | PALM | paralemmin | 0.36 | 2.56E−05 |
| 3942350 | MTP18 | mitochondrial protein 18 kDa | 0.69 | 2.63E−05 |
| 3942350 | SEC14L2 | SEC14-like 2 (S. cerevisiae) | 0.69 | 2.63E−05 |
| 3338552 | CTTN | cortactin | 0.91 | 2.81E−05 |
| 3494137 | LMO7 | LIM domain 7 | 1.21 | 2.81E−05 |
| 3188883 | OLFML2A | olfactomedin-like 2A | 0.48 | 2.81E−05 |
| 3463522 | PAWR | PRKC, apoptosis, WT1, regulator | 1.07 | 2.81E−05 |
| 3850457 | AP1M2 | adaptor-related protein complex 1, mu 2 subunit | 1.06 | 2.85E−05 |
| 3062868 | BAIAP2L1 | BAI1-associated protein 2-like 1 | 0.73 | 2.94E−05 |
| 2675171 | HYAL2 | hyaluronoglucosaminidase 2 | 0.72 | 2.94E−05 |
| 2339139 | INADL | InaD-like (Drosophila) | 0.93 | 2.94E−05 |
| 2958670 | RAB23 | RAB23, member RAS oncogene family | 1.22 | 2.94E−05 |
| 3654956 | LAT | linker for activation of T cells | −0.82 | 2.96E−05 |
| 3654956 | LOC100288332 | similar to acyl-CoA synthetase medium-chain family member 2 | −0.82 | 2.96E−05 |
| 3654956 | LOC100288442 | hypothetical LOC100288442 | −0.82 | 2.96E−05 |
| 3654956 | LOC100289169 | hypothetical protein LOC100289169 | −0.82 | 2.96E−05 |
| 3654956 | LOC728734 | similar to NPIP-like protein ENSP00000283050 | −0.82 | 2.96E−05 |
| 3654956 | LOC728741 | hypothetical LOC728741 | −0.82 | 2.96E−05 |
| 3654956 | LOC728888 | similar to acyl-CoA synthetase medium-chain family member 2 | −0.82 | 2.96E−05 |
| 3654956 | LOC729602 | NPIP-like protein ENSP00000283050 | −0.82 | 2.96E−05 |
| 3654956 | LOC730153 | NPIP-like protein ENSP00000346774 | −0.82 | 2.96E−05 |
| 2363248 | LY9 | lymphocyte antigen 9 | −0.83 | 2.96E−05 |
| 3654956 | NPIPL2 | nuclear pore complex interacting protein-like 2 | −0.82 | 2.96E−05 |
| 3654956 | NPIPL3 | nuclear pore complex interacting protein-like 3 | −0.82 | 2.96E−05 |
| 3654956 | SPIN1 | spindlin 1 | −0.82 | 2.96E−05 |
| 3654956 | SPNS1 | spinster homolog 1 (Drosophila) | −0.82 | 2.96E−05 |
| 2781736 | CFI | complement factor I | 1.87 | 2.98E−05 |
| 3922793 | LOC100132338 | hypothetical protein LOC100132338 | 0.69 | 2.99E−05 |
| 3922793 | PDE9A | phosphodiesterase 9A | 0.69 | 2.99E−05 |
| 3459120 | LRIG3 | leucine-rich repeats and immunoglobulin-like domains 3 | 1.46 | 3.06E−05 |
| 2673181 | PLXNB1 | plexin B1 | 0.38 | 3.07E−05 |
| 3088213 | SH2D4A | SH2 domain containing 4A | 1.32 | 3.10E−05 |
| 2555830 | TMEM17 | transmembrane protein 17 | 1.08 | 3.10E−05 |
| 2329041 | KIAA1522 | KIAA1522 | 0.50 | 3.12E−05 |

TABLE 9-continued

BRAF signature biomarkers. PTC hetmut vs. PTC wild type, no covariates.
The results from a LIMMA analysis (without adjusting for additional confounding covariates) were filtered
based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 2455418 | AP3S1 | adaptor-related protein complex 3, sigma 1 subunit | 1.02 | 3.14E−05 |
| 2455418 | LOC643454 | adaptor-related protein complex 3, sigma 1 subunit pseudogene | 1.02 | 3.14E−05 |
| 2455418 | PTPN14 | protein tyrosine phosphatase, non-receptor type 14 | 1.02 | 3.14E−05 |
| 2659039 | MUC20 | mucin 20, cell surface associated | 0.70 | 3.19E−05 |
| 2659039 | SDHA | succinate dehydrogenase complex, subunit A, flavoprotein (Fp) | 0.70 | 3.19E−05 |
| 2659039 | SDHALP1 | succinate dehydrogenase complex, subunit A, flavoprotein pseudogene 1 | 0.70 | 3.19E−05 |
| 2659039 | SDHALP2 | succinate dehydrogenase complex, subunit A, flavoprotein pseudogene 2 | 0.70 | 3.19E−05 |
| 2452977 | FAIM3 | Fas apoptotic inhibitory molecule 3 | −1.55 | 3.23E−05 |
| 2751936 | GALNT7 | UDP-N-acetyl-alpha-D-galactosamine:polypeptide N-acetylgalactosaminyltransferase 7 (GalNAc-T7) | 0.92 | 3.23E−05 |
| 3031573 | GIMAP5 | GTPase, IMAP family member 5 | −1.36 | 3.28E−05 |
| 2342904 | ST6GALNAC5 | ST6 (alpha-N-acetyl-neuraminyl-2,3-beta-galactosyl-1,3)-N-acetylgalactosaminide alpha-2,6-sialyltransferase 5 | 0.45 | 3.28E−05 |
| 2348437 | SNX7 | sorting nexin 7 | 1.00 | 3.29E−05 |
| 2407786 | LOC100130627 | hypothetical LOC100130627 | 0.74 | 3.33E−05 |
| 2407786 | RHBDL2 | rhomboid, veinlet-like 2 (Drosophila) | 0.74 | 3.33E−05 |
| 3630668 | CALML4 | calmodulin-like 4 | −0.79 | 3.52E−05 |
| 2603987 | NGEF | neuronal guanine nucleotide exchange factor | 0.43 | 3.60E−05 |
| 2451870 | ETNK2 | ethanolamine kinase 2 | 1.26 | 3.64E−05 |
| 3535628 | GNG2 | guanine nucleotide binding protein (G protein), gamma 2 | −1.34 | 3.64E−05 |
| 3329343 | MDK | midkine (neurite growth-promoting factor 2) | 1.09 | 3.64E−05 |
| 3464417 | MGAT4C | mannosyl (alpha-1,3-)-glycoprotein beta-1,4-N-acetylglucosaminyltransferase, isozyme C (putative) | 1.60 | 3.64E−05 |
| 3997825 | MXRA5 | matrix-remodelling associated 5 | 1.18 | 3.64E−05 |
| 2378121 | TRAF3IP3 | TRAF3 interacting protein 3 | −1.18 | 3.64E−05 |
| 2325002 | KDM1 | lysine (K)-specific demethylase 1 | 0.59 | 3.65E−05 |
| 2424102 | CNN3 | calponin 3, acidic | 1.48 | 3.69E−05 |
| 3346453 | YAP1 | Yes-associated protein 1, 65 kDa | 0.94 | 3.69E−05 |
| 2951500 | TEAD3 | TEA domain family member 3 | 0.56 | 3.88E−05 |
| 3067478 | NRCAM | neuronal cell adhesion molecule | 1.55 | 4.09E−05 |
| 2649113 | LOC100287227 | hypothetical LOC100287227 | 0.92 | 4.16E−05 |
| 2649113 | TIPARP | TCDD-inducible poly(ADP-ribose) polymerase | 0.92 | 4.16E−05 |
| 3753860 | CCL5 | chemokine (C-C motif) ligand 5 | −1.22 | 4.23E−05 |
| 2986825 | C7orf20 | chromosome 7 open reading frame 20 | 0.61 | 4.45E−05 |
| 2397025 | DHRS3 | dehydrogenase/reductase (SDR family) member 3 | 1.18 | 4.45E−05 |
| 3759587 | LOC100129115 | hypothetical protein LOC100129115 | 0.55 | 4.45E−05 |
| 3842264 | NAT14 | N-acetyltransferase 14 (GCN5-related, putative) | 0.30 | 4.45E−05 |
| 3759587 | PLCD3 | phospholipase C, delta 3 | 0.55 | 4.45E−05 |
| 2986825 | UNC84A | unc-84 homolog A (C. elegans) | 0.61 | 4.45E−05 |
| 3092415 | LOC100129846 | hypothetical protein LOC100129846 | 1.07 | 4.52E−05 |
| 3092415 | RBPMS | RNA binding protein with multiple splicing | 1.07 | 4.52E−05 |
| 3092415 | SDHALP2 | succinate dehydrogenase complex, subunit A, flavoprotein pseudogene 2 | 1.07 | 4.52E−05 |
| 2523689 | ABI2 | abl-interactor 2 | 0.90 | 4.52E−05 |
| 3518086 | TBC1D4 | TBC1 domain family, member 4 | −0.54 | 4.58E−05 |
| 2708610 | MAGEF1 | melanoma antigen family F, 1 | 0.55 | 4.61E−05 |
| 2656146 | MAP3K13 | mitogen-activated protein kinase kinase kinase 13 | 0.93 | 4.70E−05 |
| 3107342 | PDP1 | pyruvate dehydrogenase phosphatase catalytic subunit 1 | 0.70 | 4.70E−05 |
| 3720402 | ERBB2 | v-erb-b2 erythroblastic leukemia viral oncogene homolog 2, neuro/glioblastoma derived oncogene homolog (avian) | 0.75 | 4.72E−05 |

TABLE 9-continued

BRAF signature biomarkers. PTC hetmut vs. PTC wild type, no covariates.
The results from a LIMMA analysis (without adjusting for additional confounding covariates) were filtered
based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 3415320 | KRT7 | keratin 7 | 1.12 | 4.72E−05 |
| 3389273 | CASP4 | caspase 4, apoptosis-related cysteine peptidase | −1.32 | 4.73E−05 |
| 2458338 | ENAH | enabled homolog (*Drosophila*) | 1.21 | 4.73E−05 |
| 3104323 | FAM164A | family with sequence similarity 164, member A | 1.17 | 4.73E−05 |
| 3389273 | LOC643733 | hypothetical LOC643733 | −1.32 | 4.73E−05 |
| 3219621 | CTNNAL1 | catenin (cadherin-associated protein), alpha-like 1 | 1.29 | 4.77E−05 |
| 3361381 | CYB5R2 | cytochrome b5 reductase 2 | 0.62 | 4.77E−05 |
| 3610804 | IGF1R | insulin-like growth factor 1 receptor | 0.78 | 4.77E−05 |
| 3113180 | MAL2 | mal, T-cell differentiation protein 2 | 1.41 | 4.77E−05 |
| 2721959 | ROS1 | c-ros oncogene 1, receptor tyrosine kinase | 2.41 | 4.77E−05 |
| 2721959 | SLC34A2 | solute carrier family 34 (sodium phosphate), member 2 | 2.41 | 4.77E−05 |
| 2611122 | TSEN2 | tRNA splicing endonuclease 2 homolog (*S. cerevisiae*) | 0.44 | 4.77E−05 |
| 3876245 | SNAP25 | synaptosomal-associated protein, 25 kDa | 0.54 | 4.79E−05 |
| 2420832 | DDAH1 | dimethylarginine dimethylaminohydrolase 1 | 1.50 | 4.80E−05 |
| 3784344 | MAPRE2 | microtubule-associated protein, RP/EB family, member 2 | −0.75 | 4.80E−05 |
| 3495076 | NDFIP2 | Nedd4 family interacting protein 2 | 1.01 | 4.80E−05 |
| 2871896 | CDO1 | cysteine dioxygenase, type I | 1.14 | 4.82E−05 |
| 3818547 | VAV1 | vav 1 guanine nucleotide exchange factor | −1.08 | 4.85E−05 |
| 2417272 | GNG12 | guanine nucleotide binding protein (G protein), gamma 12 | 1.45 | 4.85E−05 |
| 3417809 | NAB2 | NGFI-A binding protein 2 (EGR1 binding protein 2) | 0.56 | 4.85E−05 |
| 2673873 | IMPDH2 | IMP (inosine monophosphate) dehydrogenase 2 | 0.61 | 4.92E−05 |
| 2948790 | CDSN | corneodesmosin | 0.78 | 4.97E−05 |
| 2615892 | CMTM8 | CKLF-like MARVEL transmembrane domain containing 8 | 0.70 | 4.97E−05 |
| 3780981 | KIAA1772 | KIAA1772 | 0.72 | 4.97E−05 |
| 2371065 | LAMC1 | laminin, gamma 1 (formerly LAMB2) | 1.14 | 4.97E−05 |
| 3765689 | LOC100129112 | hypothetical protein LOC100129112 | 0.64 | 4.97E−05 |
| 3765689 | MED13 | mediator complex subunit 13 | 0.64 | 4.97E−05 |
| 3355733 | EWSR1 | Ewing sarcoma breakpoint region 1 | −1.26 | 5.09E−05 |
| 3355733 | FLI1 | Friend leukemia virus integration 1 | −1.26 | 5.09E−05 |
| 2402517 | SLC30A2 | solute carrier family 30 (zinc transporter), member 2 | 0.62 | 5.16E−05 |
| 2924330 | TPD52L1 | tumor protein D52-like 1 | 1.42 | 5.16E−05 |
| 2870964 | EPB41L4A | erythrocyte membrane protein band 4.1 like 4A | 1.05 | 5.18E−05 |
| 3564919 | FERMT2 | fermitin family homolog 2 (*Drosophila*) | 1.19 | 5.18E−05 |
| 2519229 | ITGAV | integrin, alpha V (vitronectin receptor, alpha polypeptide, antigen CD51) | 1.19 | 5.18E−05 |
| 2435218 | TDRKH | tudor and KH domain containing | 0.92 | 5.19E−05 |
| 2361257 | RAB25 | RAB25, member RAS oncogene family | 1.44 | 5.22E−05 |
| 2347132 | FNBP1L | formin binding protein 1-like | 1.28 | 5.27E−05 |
| 3175494 | GCNT1 | glucosaminyl (N-acetyl) transferase 1, core 2 (beta-1,6-N-acetylglucosaminyltransferase) | 0.75 | 5.31E−05 |
| 3326461 | EHF | ets homologous factor | 1.32 | 5.38E−05 |
| 3638204 | MFGE8 | milk fat globule-EGF factor 8 protein | 1.49 | 5.38E−05 |
| 3638204 | QTRT1 | queuine tRNA-ribosyltransferase 1 | 1.49 | 5.38E−05 |
| 3267382 | INPP5F | inositol polyphosphate-5-phosphatase F | 0.84 | 5.41E−05 |
| 3471327 | HVCN1 | hydrogen voltage-gated channel 1 | −0.91 | 5.41E−05 |
| 2580802 | RND3 | Rho family GTPase 3 | 1.53 | 5.41E−05 |
| 4024685 | SLITRK4 | SLIT and NTRK-like family, member 4 | 0.98 | 5.41E−05 |
| 3471327 | TCTN1 | tectonic family member 1 | −0.91 | 5.41E−05 |
| 3456805 | GTSF1 | gametocyte specific factor 1 | −1.37 | 5.52E−05 |
| 2881607 | LOC134466 | zinc finger protein 300 pseudogene | 0.88 | 5.52E−05 |
| 3424442 | TMTC2 | transmembrane and tetratricopeptide repeat containing 2 | 0.49 | 5.52E−05 |
| 2881607 | ZNF300 | zinc finger protein 300 | 0.88 | 5.52E−05 |
| 3842675 | LOC283788 | FSHD region gene 1 pseudogene | 0.67 | 5.54E−05 |
| 3211938 | RASEF | RAS and EF-hand domain containing | 1.38 | 5.54E−05 |
| 3842675 | ZNF542 | zinc finger protein 542 | 0.67 | 5.54E−05 |

TABLE 9-continued

BRAF signature biomarkers. PTC hetmut vs. PTC wild type, no covariates.
The results from a LIMMA analysis (without adjusting for additional confounding covariates) were filtered
based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 2364189 | UAP1 | UDP-N-acteylglucosamine pyrophosphorylase 1 | 0.83 | 5.56E−05 |
| 3656223 | ITGAL | integrin, alpha L (antigen CD11A (p180), lymphocyte function-associated antigen 1; alpha polypeptide) | −1.04 | 5.59E−05 |
| 4024420 | CXorf18 | chromosome X open reading frame 18 | 1.13 | 5.64E−05 |
| 4024420 | LDOC1 | leucine zipper, down-regulated in cancer 1 | 1.13 | 5.64E−05 |
| 3397877 | RICS | Rho GTPase-activating protein | 0.56 | 5.73E−05 |
| 3577612 | SERPINA1 | serpin peptidase inhibitor, clade A (alpha-1 antiproteinase, antitrypsin), member 1 | 0.70 | 5.73E−05 |
| 3577612 | SERPINA2 | serpin peptidase inhibitor, clade A (alpha-1 antiproteinase, antitrypsin), member 2 | 0.70 | 5.73E−05 |
| 4013018 | ZDHHC15 | zinc finger, DHHC-type containing 15 | 0.65 | 5.88E−05 |
| 2622912 | MAPKAPK3 | mitogen-activated protein kinase-activated protein kinase 3 | 0.59 | 5.90E−05 |
| 2337716 | PRKAA2 | protein kinase, AMP-activated, alpha 2 catalytic subunit | 1.29 | 5.91E−05 |
| 3070712 | WASL | Wiskott-Aldrich syndrome-like | 0.72 | 5.91E−05 |
| 2524016 | PARD3B | par-3 partitioning defective 3 homolog B (*C. elegans*) | 0.52 | 6.14E−05 |
| 3547696 | TTC8 | tetratricopeptide repeat domain 8 | 0.71 | 6.14E−05 |
| 2358993 | TUFT1 | tuftelin 1 | 0.46 | 6.14E−05 |
| 3710870 | RICH2 | Rho-type GTPase-activating protein RICH2 | 0.64 | 6.21E−05 |
| 3959350 | APOL3 | apolipoprotein L, 3 | −0.62 | 6.37E−05 |
| 3407096 | PLEKHA5 | pleckstrin homology domain containing, family A member 5 | 1.09 | 6.37E−05 |
| 3497195 | CLDN10 | claudin 10 | 1.15 | 6.39E−05 |
| 3497195 | DZIP1 | DAZ interacting protein 1 | 1.15 | 6.39E−05 |
| 3696142 | DPEP2 | dipeptidase 2 | −1.07 | 6.50E−05 |
| 2792127 | NPY1R | neuropeptide Y receptor Y1 | 1.31 | 6.50E−05 |
| 3615579 | TJP1 | tight junction protein 1 (zona occludens 1) | 1.28 | 6.50E−05 |
| 3409211 | PPFIBP1 | PTPRF interacting protein, binding protein 1 (liprin beta 1) | 1.04 | 6.53E−05 |
| 2949038 | ATP6V1G2 | ATPase, H+ transporting, lysosomal 13 kDa, V1 subunit G2 | 0.30 | 6.57E−05 |
| 2949038 | BAT1 | HLA-B associated transcript 1 | 0.30 | 6.57E−05 |
| 3838385 | CD37 | CD37 molecule | −1.41 | 6.57E−05 |
| 2949038 | SNORD117 | small nucleolar RNA, C/D box 117 | 0.30 | 6.57E−05 |
| 2949038 | SNORD84 | small nucleolar RNA, C/D box 84 | 0.30 | 6.57E−05 |
| 3752709 | MYO1D | myosin ID | 1.02 | 6.67E−05 |
| 3031466 | GIMAP8 | GTPase, IMAP family member 8 | −0.91 | 6.77E−05 |
| 3031466 | LOC285972 | hypothetical protein LOC285972 | −0.91 | 6.77E−05 |
| 2962026 | LCA5 | Leber congenital amaurosis 5 | 1.42 | 6.90E−05 |
| 3357397 | GLB1L2 | galactosidase, beta 1-like 2 | 0.81 | 6.93E−05 |
| 3795184 | LOC100127994 | hypothetical protein LOC100127994 | −0.35 | 6.93E−05 |
| 3795184 | NFATC1 | nuclear factor of activated T-cells, cytoplasmic, calcineurin-dependent 1 | −0.35 | 6.93E−05 |
| 3670918 | PLCG2 | phospholipase C, gamma 2 (phosphatidylinositol-specific) | −0.98 | 6.93E−05 |
| 3648306 | SNN | stannin | −0.40 | 6.93E−05 |
| 3648306 | TXNDC11 | thioredoxin domain containing 11 | −0.40 | 6.93E−05 |
| 2769346 | FIP1L1 | FIP1 like 1 (*S. cerevisiae*) | 0.75 | 6.94E−05 |
| 2769346 | LNX1 | ligand of numb-protein X 1 | 0.75 | 6.94E−05 |
| 3445786 | ARHGDIB | Rho GDP dissociation inhibitor (GDI) beta | −0.60 | 7.00E−05 |
| 2673830 | DALRD3 | DALR anticodon binding domain containing 3 | 0.28 | 7.24E−05 |
| 3870533 | TMC4 | transmembrane channel-like 4 | 0.72 | 7.24E−05 |
| 2673830 | WDR6 | WD repeat domain 6 | 0.28 | 7.24E−05 |
| 3871935 | ZNF667 | zinc finger protein 667 | 0.72 | 7.24E−05 |
| 3457891 | GLS2 | glutaminase 2 (liver, mitochondrial) | 0.35 | 7.26E−05 |
| 2991233 | AHR | aryl hydrocarbon receptor | 0.88 | 7.27E−05 |
| 3624513 | LOC100129973 | hypothetical protein LOC100129973 | 1.10 | 7.29E−05 |
| 3624513 | MYO5C | myosin VC | 1.10 | 7.29E−05 |
| 3294576 | USP54 | ubiquitin specific peptidase 54 | 0.81 | 7.35E−05 |

TABLE 9-continued

BRAF signature biomarkers. PTC hetmut vs. PTC wild type, no covariates.
The results from a LIMMA analysis (without adjusting for additional confounding covariates) were filtered
based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 3345427 | ENDOD1 | endonuclease domain containing 1 | 0.61 | 7.47E−05 |
| 2438458 | CRABP2 | cellular retinoic acid binding protein 2 | 1.43 | 7.51E−05 |
| 2827645 | SLC27A6 | solute carrier family 27 (fatty acid transporter), member 6 | 2.18 | 7.66E−05 |
| 3307939 | ABLIM1 | actin binding LIM protein 1 | 0.68 | 7.68E−05 |
| 3151607 | FBXO32 | F-box protein 32 | 0.80 | 7.68E−05 |
| 3450234 | PKP2 | plakophilin 2 | 0.71 | 7.74E−05 |
| 2469157 | GRHL1 | grainyhead-like 1 (*Drosophila*) | 0.55 | 7.74E−05 |
| 3781124 | MIB1 | mindbomb homolog 1 (*Drosophila*) | 0.59 | 7.74E−05 |
| 3279982 | PTPLA | protein tyrosine phosphatase-like (proline instead of catalytic arginine), member A | 0.85 | 7.74E−05 |
| 3097152 | MCM4 | minichromosome maintenance complex component 4 | 0.74 | 7.83E−05 |
| 3289235 | SGMS1 | sphingomyelin synthase 1 | 0.70 | 7.87E−05 |
| 3107548 | ESRP1 | epithelial splicing regulatory protein 1 | 1.52 | 7.92E−05 |
| 2839543 | WWC1 | WW and C2 domain containing 1 | 0.63 | 7.92E−05 |
| 3493543 | KLF5 | Kruppel-like factor 5 (intestinal) | 0.54 | 7.99E−05 |
| 3868998 | NKG7 | natural killer cell group 7 sequence | −1.29 | 7.99E−05 |
| 2706297 | TBL1XR1 | transducin (beta)-like 1 X-linked receptor 1 | 0.58 | 8.17E−05 |
| 2966193 | C6orf168 | chromosome 6 open reading frame 168 | 0.92 | 8.19E−05 |
| 2914070 | MYO6 | myosin VI | 1.35 | 8.19E−05 |
| 3394660 | TRIM29 | tripartite motif-containing 29 | 0.51 | 8.26E−05 |
| 2598261 | FN1 | fibronectin 1 | 1.52 | 8.35E−05 |
| 3420713 | CAND1 | cullin-associated and neddylation-dissociated 1 | 0.62 | 8.36E−05 |
| 3227574 | FAM78A | family with sequence similarity 78, member A | −0.89 | 8.37E−05 |
| 2720584 | SLIT2 | slit homolog 2 (*Drosophila*) | 1.52 | 8.41E−05 |
| 2700585 | PFN2 | profilin 2 | 1.39 | 8.48E−05 |
| 3143643 | MMP16 | matrix metallopeptidase 16 (membrane-inserted) | 1.58 | 8.56E−05 |
| 3610958 | IGF1R | insulin-like growth factor 1 receptor | 1.03 | 8.64E−05 |
| 2462160 | NID1 | nidogen 1 | 0.50 | 8.64E−05 |
| 3622934 | MYEF2 | myelin expression factor 2 | 0.91 | 8.65E−05 |
| 3622934 | SLC24A5 | solute carrier family 24, member 5 | 0.91 | 8.65E−05 |
| 2600689 | EPHA4 | EPH receptor A4 | 1.47 | 8.67E−05 |
| 2380055 | KCTD3 | potassium channel tetramerisation domain containing 3 | 0.93 | 8.67E−05 |
| 2927255 | PEX7 | peroxisomal biogenesis factor 7 | 0.62 | 8.67E−05 |
| 3645555 | TNFRSF12A | tumor necrosis factor receptor superfamily, member 12A | 1.24 | 8.67E−05 |
| 2960955 | SLC17A5 | solute carrier family 17 (anion/sugar transporter), member 5 | 0.97 | 8.76E−05 |
| 3753568 | SLFN11 | schlafen family member 11 | 0.85 | 8.81E−05 |
| 3753568 | SLFN13 | schlafen family member 13 | 0.85 | 8.81E−05 |
| 2377229 | CD55 | CD55 molecule, decay accelerating factor for complement (Cromer blood group) | 0.68 | 8.89E−05 |
| | | | 0.44 | 8.94E−05 |
| 2829542 | C5orf24 | chromosome 5 open reading frame 24 | 0.64 | 9.06E−05 |
| 3319937 | WEE1 | WEE1 homolog (*S. pombe*) | 0.70 | 9.06E−05 |
| 2582701 | CCDC148 | coiled-coil domain containing 148 | 1.43 | 9.16E−05 |
| 3079103 | GIMAP6 | GTPase, IMAP family member 6 | −0.84 | 9.16E−05 |
| 2820394 | NR2F1 | nuclear receptor subfamily 2, group F, member 1 | 0.32 | 9.16E−05 |
| 2420521 | SSX2IP | synovial sarcoma, X breakpoint 2 interacting protein | 0.56 | 9.16E−05 |
| 3025545 | CALD1 | caldesmon 1 | 1.03 | 9.20E−05 |
| 3604287 | IL16 | interleukin 16 (lymphocyte chemoattractant factor) | −0.54 | 9.40E−05 |
| 3402506 | CD27 | CD27 molecule | −0.93 | 9.41E−05 |
| 3621728 | FRMD5 | FERM domain containing 5 | 0.79 | 9.41E−05 |
| 3621728 | hCG_1789710 | protein (peptidylprolyl cis/trans isomerase) NIMA-interacting, 4 (parvulin) pseudogene | 0.79 | 9.41E−05 |
| 3402506 | LOC678655 | hypothetical locus LOC678655 | −0.93 | 9.41E−05 |
| 3621728 | PIN4 | protein (peptidylprolyl cis/trans isomerase) NIMA-interacting, 4 (parvulin) | 0.79 | 9.41E−05 |
| 2338625 | HOOK1 | hook homolog 1 (*Drosophila*) | 1.15 | 9.42E−05 |

TABLE 9-continued

BRAF signature biomarkers. PTC hetmut vs. PTC wild type, no covariates.
The results from a LIMMA analysis (without adjusting for additional confounding covariates) were filtered based on FDR p-value (≤0.0001). Listed below are the 477 genes that passed the filter.
Table 9: BRAF markers, no covariates

| TCID na30hg19 | GENE | Description | Effect Size (log scale) no covariates | FDR adjusted p-value no covariates |
|---|---|---|---|---|
| 2523419 | ALS2CR8 | amyotrophic lateral sclerosis 2 (juvenile) chromosome region, candidate 8 | 0.61 | 9.43E−05 |
| 2900195 | ZNF165 | zinc finger protein 165 | 0.48 | 9.55E−05 |
| 3569754 | ZFP36L1 | zinc finger protein 36, C3H type-like 1 | 0.38 | 9.61E−05 |
| 2975385 | AHI1 | Abelson helper integration site 1 | 0.75 | 9.62E−05 |
| 3925639 | NRIP1 | nuclear receptor interacting protein 1 | 0.82 | 9.63E−05 |
| 3301914 | PIK3AP1 | phosphoinositide-3-kinase adaptor protein 1 | −1.01 | 9.63E−05 |
| 3959953 | TMPRSS6 | transmembrane protease, serine 6 | 0.34 | 9.67E−05 |
| 4015397 | TSPAN6 | tetraspanin 6 | 1.43 | 9.67E−05 |

TABLE 10

BRAF signature biomarkers. PTC hetmut vs. PTC wild type, with covariates.
The results from a LIMMA analysis (after adjusting for additional confounding covariates) were filtered based on FDR p-value (≤0.05). Listed below are the 36 genes that passed the filter.
Table 10: BRAF Markers, with covariates

| TCID | Gene Symbol | Description | Effect size (log scale) with covariates | FDR adjusted p-value with covariates |
|---|---|---|---|---|
| 3628498 | CA12 | carbonic anhydrase XII | −1.14 | 1.29E−02 |
| 3396770 | CDON | Cdon homolog (mouse) | −1.13 | 1.31E−02 |
| 3595315 | CGNL1 | cingulin-like 1 | −1.07 | 1.55E−02 |
| 3863640 | CXCL17 | chemokine (C—X—C motif) ligand 17 | 1.36 | 2.69E−02 |
| 2858592 | DEPDC1B | DEP domain containing 1B | 1.31 | 1.85E−03 |
| 3113280 | DEPDC6 | DEP domain containing 6 | −1.07 | 1.63E−02 |
| 2358360 | ECM1 | extracellular matrix protein 1 | −1.76 | 2.28E−02 |
| 3331903 | FAM111B | family with sequence similarity 111, member B | 1.23 | 2.60E−02 |
| 4019784 | FAM70A | family with sequence similarity 70, member A | −1.06 | 3.27E−02 |
| 3507282 | FLT1 | fms-related tyrosine kinase 1 (vascular endothelial growth factor/vascular permeability factor receptor) | −1.06 | 1.31E−02 |
| 3151086 | HAS2 | hyaluronan synthase 2 | −2.02 | 2.09E−02 |
| 3727583 | HLF | hepatic leukemia factor | −1.58 | 9.85E−04 |
| 3049292 | IGFBP3 | insulin-like growth factor binding protein 3 | −1.40 | 8.62E−03 |
| 2809245 | ITGA2 | integrin, alpha 2 (CD49B, alpha 2 subunit of VLA-2 receptor) | 1.27 | 2.79E−02 |
| 2608469 | ITPR1 | inositol 1,4,5-triphosphate receptor, type 1 | −1.08 | 7.28E−03 |
| 2648991 | KCNAB1 | potassium voltage-gated channel, shaker-related subfamily, beta member 1 | −1.01 | 2.10E−02 |
| 3868783 | KLK7 | kallikrein-related peptidase 7 | 1.41 | 8.84E−03 |
| 2872848 | LOX | lysyl oxidase | 1.32 | 2.57E−02 |
| 2586038 | LRP2 | low density lipoprotein-related protein 2 | −1.15 | 4.03E−02 |
| 3040518 | MACC1 | metastasis associated in colon cancer 1 | 1.21 | 7.28E−03 |
| 2539607 | MBOAT2 | membrane bound O-acyltransferase domain containing 2 | 1.03 | 2.87E−02 |
| 3692999 | MT1G | metallothionein 1G | −1.95 | 3.55E−02 |
| 2437118 | MUC1 | mucin 1, cell surface associated | 1.09 | 7.28E−03 |
| 3527514 | NP | nucleoside phosphorylase | 1.09 | 1.00E−02 |
| 2792127 | NPY1R | neuropeptide Y receptor Y1 | 1.11 | 4.93E−02 |
| 2816681 | PDE8B | phosphodiesterase 8B | −1.24 | 7.28E−03 |
| 4000560 | PIR | pirin (iron-binding nuclear protein) | −1.11 | 4.30E−02 |
| 2967276 | POPDC3 | popeye domain containing 3 | −1.28 | 3.47E−02 |
| 3246888 | PRKG1 | protein kinase, cGMP-dependent, type I | −1.07 | 2.25E−02 |
| 2580802 | RND3 | Rho family GTPase 3 | 1.17 | 1.00E−02 |
| 3467949 | SLC5A8 | solute carrier family 5 (iodide transporter), member 8 | −1.04 | 3.45E−02 |
| 2378256 | SYT14 | synaptotagmin XIV | 1.08 | 7.28E−03 |
| 2414958 | TACSTD2 | tumor-associated calcium signal transducer 2 | 1.05 | 7.28E−03 |
| 3110608 | TM7SF4 | transmembrane 7 superfamily member 4 | 2.51 | 1.85E−03 |
| 3351200 | TMPRSS4 | transmembrane protease, serine 4 | 1.14 | 2.69E−02 |
| 2466554 | TPO | thyroid peroxidase | −1.75 | 2.69E−02 |

TABLE 11

Markers of Follicular cell signal strength.
Follicular Cell Markers

| TCID | Gene Symbol |
|---|---|
| 3415320 | KRT7 |
| 3666409 | CDH1 |
| 3113180 | MAL2 |
| 3107548 | RBM35A |
| 4045676 | S100A13 |
| 2480961 | TACSTD1 |
| 3615579 | TJP1 |
| 3987996 | PLS3 |
| 2699564 | PLOD2 |
| 2700585 | PFN2 |

TABLE 12

Markers of Hurthle cell signal strength.
Hurthle Cell Markers

| TCID | Gene Symbol |
|---|---|
| 2566848 | AFF3 |
| 2988882 | AIMP2 |
| 3169331 | ALDH1B1 |
| 2984616 | BRP44L |
| 2822492 | C5orf30 |
| 3326635 | CD44 |
| 2750627 | CPE |
| 3042001 | CYCS |
| 3122678 | DEFB1 |
| 2739308 | EGF |
| 2988882 | EIF2AK1 |
| 3603932 | FAH |
| 2970897 | FRK |
| 3212008 | FRMD3 |
| 3302990 | GOT1 |
| 3417703 | HSD17B6 |
| 2877508 | HSPA9 |
| 2708922 | IGF2BP2 |
| 2604998 | IQCA1 |
| 3724545 | ITGB3 |
| 3397774 | KCNJ1 |
| 2604998 | LOC100129258 |
| 3009299 | MDH2 |
| 3654699 | NUPR1 |
| 4020655 | ODZ1 |
| 3970833 | PDHA1 |
| 2377094 | PFKFB2 |
| 3278198 | PHYH |
| 2880051 | PPP2R2B |
| 3959862 | PVALB |
| 2688499 | PVRL2 |
| 2604998 | RPL3 |
| 2964231 | RRAGD |
| 2798538 | SDHA |
| 2798538 | SDHALP1 |
| 2798538 | SDHALP2 |
| 2798538 | SDHAP3 |
| 2428501 | SLC16A1 |
| 2877508 | SNORD63 |
| 2562529 | ST3GAL5 |
| 2688499 | ZBED2 |

TABLE 13

Markers of Lymphocytic cell signal strength.
LCT markers

| TCID | Gene Symbol |
|---|---|
| 3648391 | TNFRSF17 |
| 3982612 | GPR174 |
| 3404030 | KLRG1 |
| 2732508 | CXCL13 |
| 2809810 | GZMA |
| 3046520 | TARP |
| 3046520 | TRGC2 |
| 2377283 | CR2 |
| 3450861 | ABCD2 |
| 3444086 | KLRC4 |
| 3444086 | KLRK1 |
| 2440258 | SLAMF6 |
| 2427619 | KCNA3 |
| 3982560 | P2RY10 |
| 2635349 | TRAT1 |
| 2809793 | GZMK |
| 2373842 | PTPRC |
| 2363202 | SLAMF7 |
| 3204285 | CCL19 |
| 3031556 | GIMAP2 |
| 2806468 | IL7R |
| 3443464 | PZP |
| 2362351 | PYHIN1 |

Example 8: Analytical Performance Verification of a Molecular Diagnostic for Cytology-Indeterminate Thyroid Nodules Introduction Studies included evaluation of FNA stability during collection and shipment, analytical sensitivity as applied to input RNA mass and FNA malignant content, analytical specificity as applied to blood and genomic DNA, and several reproducibility studies; intra-nodule reproducibility, intra- and inter-assay reproducibility, and inter-laboratory reproducibility, demonstrating robustness to changes across a range of analytical variables. Quality control recommendations were extensively implemented and verified via the use of control materials and in-process quality checkpoints at key steps in the GEC procedure.

Materials and Methods

Specimens

Prospective FNA samples were obtained from human subjects. Either one or two needle passes were: 1) aspirated in vivo at outpatient clinical sites; 2) aspirated in vivo preoperatively; or 3) aspirated ex vivo immediately after surgical excision, and placed into FNAprotect preservative solution. Samples were shipped under controlled temperature conditions (chilled or frozen) and stored at −0° C. upon receipt.

Control Materials

Control material for the RNA extraction step of the assay was prepared by homogenization of thyroid tissue using the Homogenizer TH-01 and lysis buffer, dilution of the lysate to a standard volume and concentration, and storage at −80° C. until use. Total RNA controls for the amplification, hybridization, and classification steps of the assay were prepared using benign and malignant thyroid tissue. Total RNA was extracted using an AllPrep Micro Kit followed by dilution to a standard concentration, and storage of aliquots at −80° C. until use.

RNA Extraction, Amplification, and Microarray Hybridization

RNA from clinical FNA specimens was extracted using the AllPrep Micro Kit. Yield was determined using Quant-IT and quality was determined with a Bioanalyzer Picochip System, generating an RNA Integrity Number (RIN). Positive (tissue lysate) and negative (water) controls were included in each extraction batch and pre-defined yield and quality specifications were used as acceptance criteria to ensure the reliability of every run. For each sample, 15 ng of total RNA was amplified using the WT-Ovation FFPE RNA Amplification System, followed by conversion to sense strand cDNA using the WT-Ovation Exon Module. Samples were fragmented and labeled using the Encore Biotin Module (NuGEN), followed by overnight hybridization of 3.5 ug biotin-labeled cDNA to a microarray. The arrays were then washed, stained, and scanned on a Gene Chip System GCS3 000 or DXv2 following manufacturer's protocols. Positive (total RNA) and negative (water) controls were included in each GEC batch starting from the amplification step. Pre-defined specifications for yield, quality, and classification of control samples (1 malignant and 1 benign per batch) were used as acceptance criteria.

Data Analysis and Specimen Classification

Figure 23:
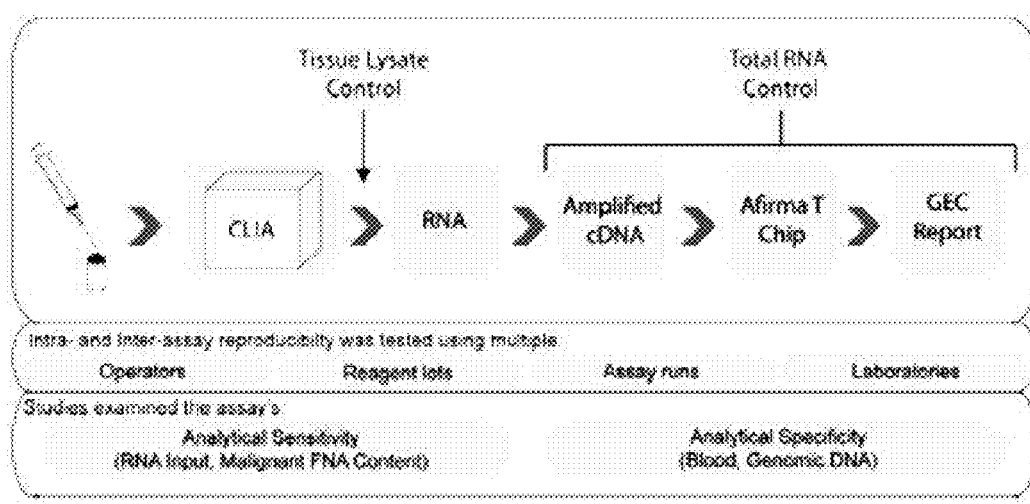
FIG. 23 illustrates the Gene Expression Classifier (GEC); total RNA is extracted and amplified to generate cDNA, which is subsequently labeled and hybridized to a custom Afirma-T microarray. Array signals are analyzed via a classification algorithm, producing a GEC report with either a Benign or Suspicious GEC call.

The microarray was designed using selected content from the Human Exon 1.0 ST array, including probesets for normalization and quality control. Signal separation between housekeeping and anti-genomic control probes was used as a per-chip QC metric. Array data were normalized, summarized, and 167 transcript cluster intensity summaries were used as features in the classification model. Array data was first analyzed by a series of 6 linear filters designed to flag medullary, parathyroid, Hürthle, and certain non-thyroid metastatic samples as "Suspicious", followed by analysis with the linear support vector machine (SVM) classifier. All samples with an SVM result (i.e. GEC score) above a predetermined cutoff value were assigned a "Benign" call, while those below the cutoff were assigned a "Suspicious" call (FIG. 23).

Statistical Analysis

Comparisons of RNA concentration were done using t-test (for two-group comparisons) or F-test (for multi-group comparison), after log 2 transformation. Comparisons of RIN values were done using Wilcoxon test (for two-group comparisons) or Kruskal-Wallis test (for multiple group comparisons). Correlations and $R^2$ values for microarray intensity values were computed using normalized and summarized signals for genes employed by the linear SVM classifier. Confidence intervals for pooled standard deviation of GEC scores were estimated using Chi-square distribution. Using corresponding ANOVA models, the studies were designed to have sufficient power/sample size to detect clinically significant differences in GEC scores due to conditions tested.

Results

Control Materials

Multiple lots of tissue lysate were manufactured and used as process controls during RNA extraction. Three different lots were tested over several weeks of independent runs by three different operators. Tissue lysate controls consistently produced the expected quantity and quality of total RNA, resulting in within-lot coefficients of variation (CV) ranging from 5-15% for yield and 4-5% for RIN. Similarly, multiple lots of benign and malignant total RNA were manufactured and used as process controls for amplification and hybridization steps. These controls were tested extensively in reproducibility studies outlined below. The reproducible GEC results obtained from these controls enabled concurrent monitoring of assay performance for each run. All GEC tests and studies outlined below included one benign and one malignant total RNA control.

FNA Stability

Standard FNA collection procedure for the GEC involved aspiration into a preservative, subsequent handling at room temperature prior to shipment (typically, same day), and shipment in chilled boxes (typically, overnight). To demonstrate the stability of FNA samples under room temperature conditions, FNA samples preserved in FNAprotect were stored for up to six days at room temperature in the molecular laboratory. This length of time is required to account for sample collection, shipping, transport and processing in the laboratory. Samples frozen immediately at −80° C. served as controls. Total RNA was then extracted and evaluated for quantity and quality (FIG. 24A). There was no statistically significant difference between any of the test groups and the control group in RIN (0.2 RIN units largest median difference, p=0.56) or yield (<6 ng/ul largest median difference, p=0.58).

The standard FNA collection procedure was also evaluated along with an alternative (−20° C.) storage condition and compared to the −80° C. control condition. FNA samples from 28 different patient nodules were collected; for each patient nodule a total of three FNA passes were combined into a single tube of FNAprotect (3× volume), and then divided equally into three different tubes of FNAprotect. Each of the three tubes was then subjected to different storage and shipping temperatures (FIG. 24B). RNA QC results indicated no significant difference in total RNA concentration (<0.25 log 2 (ng/ul) difference between the groups, p-value 0.076), but suggested small differences in RIN (<0.4 RIN units difference between the groups, p-value <0.005). Such small differences in RIN value are within the claimed measurement error for the Bioanalyzer and were found to not be practically significant for this test, as seen from the analysis of GEC results described below. Sixty-nine samples from 24 nodules were processed and evaluated through to final GEC results. All samples from the same nodule produced concordant GEC calls irrespective of the shipping method. Analysis of the GEC results indicated no systematic difference in test conditions versus the control condition (<0.04 score unit differences between groups for scores spanning a range of over 5 units, p-value 0.55, FIG. 24C). Pooled standard deviation of GEC scores (SD=0.118 [95% CI 0.098-0.148]) was comparable to standard intra-run reproducibility starting from total RNA. Signal intensities for transcripts used by the GEC were highly reproducible for each nodule across the three conditions tested (median $R^2$ 0.984, rang 0.970-0.993), indicating that the sample splitting procedure successfully produced three equivalent FNA samples. Thus, this study demonstrates a high level of technical reproducibility over the entire assay, from FNA collection, shipment, and RNA extraction to GEC results. Based on these data, room temperature storage at the clinical site and chilled box shipping was successfully verified for routine practice.

Analytical Sensitivity—Total RNA input quantity

While the standard total RNA input quantity to the GEC assay is fixed (15 ng), some measurement variability around this nominal input amount can be expected in routine practice. Thus, a study was performed to characterize the tolerance of transcript array signal intensities and GEC results to variability in total RNA input, down to 5 ng. Total RNA was extracted from each of three different FNA samples, and processed through the GEC in triplicate at varying total RNA input (5, 10, 15, 25 ng). Samples were chosen to represent low, medium, and high ranges of the GEC score. GEC scores for each FNA did not differ significantly regardless of RNA input (<0.11 absolute mean GEC score difference to the standard amount of 15 ng, p-value=0.32). Overall, pooled SD of GEC scores across input amounts was 0.129 [95% CI 0.104-0.170], consistent with intra-run expectations (Table 14). The transcript signal intensities were highly correlated within any set of sample triplicates, and within each single group of RNA input [median $R^2$ coefficients of 0.973 (5 ng input), 0.985 (10 ng input), 0.986 (15 ng input), 0.988 (25 ng input)]. A decrease in signal reproducibility at the 5 ng range was small but significant (p-value <0.001). Transcript signal intensities from all three FNA samples were also highly correlated between triplicates processed at test input amounts and standard 15 ng condition [median $R^2$ coefficients of 0.980 (5 ng vs 15 ng), 0.986 (10 ng vs 15 ng), and 0.986 (25 ng vs 15 ng)]. Overall, this study demonstrated high tolerance to RNA input variation within the tested range, showing that the 10 ng results were indistinguishable from the standard 15 ng input.

Analytical Sensitivity—Dilution of Malignant FNA Content

The malignant content of an FNA obtained from a malignant nodule can vary from sample to sample. Tolerance of the GEC to dilution of malignant content was evaluated using in vitro total RNA mixtures derived from three cytopathology malignant papillary thyroid carcinoma (PTC) nodules from different patients and adjacent normal ex vivo FNAs from one of the patients with a malignant nodule. The pure adjacent normal tissue was called "Benign" by the GEC, while all pure PTC samples and mixtures (with up to 80% adjacent normal content) resulted in "Suspicious" GEC calls (Table 15). Tolerance of GEC results to dilution of benign content was evaluated in a similar manner for two benign nodules. All pure benign samples and mixtures tested resulted in "Benign" GEC calls. GEC scores for the in vitro mixtures were in close agreement with an in silico mixture model, further demonstrating that the signature present in malignant FNAs is sufficiently strong to withstand a wide range of dilution.

TABLE 14

Summary of analytical verification studies performed on the GEC, including pre-analytical factors, analytical sensitivity, specificity, and reproducibility.

| Study | Sample source | Design Summary | Number of calls | GEC calls Concordance | GEC scores Pooled SD | Intensity R^2 Median | Intensity R^2 Range |
|---|---|---|---|---|---|---|---|
| Pre-analytical | | | | | | | |
| Variability in shipping conditions | Clinical and pre-operative FNA | 24 samples tested in up to 3 different shipping conditions | 69 | 100% | 0.118 [0.098-0.148] | 0.984 | 0.970-0.993 |
| Analytical sensitivity and specificity | | | | | | | |
| Variability in RNA input quantity | Clinical FNA | 3 samples tested at four RNA input [5 ng, 10 ng, 15 ng, 25 ng] in triplicate | 36 | — | 0.129 [0.104-0.170] | 0.984 | 0.923-0.993 |
| Dilution with adjacent normal tissue | Ex-vivo FNA, in-vitro RNA mixtures | 2 benign & 3 malignant FNA mixed with ANT from malignant nodule, down to 20% FNA content | 15 | 100% | — | — | — |
| Dilution with whole blood | Clinical FNA and whole blood samples, in-vitro RNA mixtures | 1 benign & 2 malignant FNA mixed with one of 9 whole blood samples, down to 17% FNA content | 27 | 100% | — | — | — |
| Genomic DNA contamination | Tissue controls | 2 samples with and without 30% contamination and 6 replicates | 24 | 100% | 0.115 [0.089-0.162] | 0.981 | 0.971-0.988 |
| Reproducibility | | | | | | | |
| Intra-assay | Clinical FNA and total RNA controls | 33 samples from 81 experimental plates with up to 3 replicates per plate | 243 | — | 0.121 [0.109-0.136] | 0.988 | 0.945-0.994 |
| Intra-assay | Clinical FNA | 37 samples in 4 runs of reagents & operators; enriched near decision boundary | 148 | 97.3%* | 0.158 [0.140-0.182] | 0.979 | 0.946-0.994 |
| Inter-laboratory | Clinical FNA | 20 samples run in 2 laboratories | 39 | 100% | 0.138 [0.105-0.201] | 0.981 | 0.953-0.989 |
| Intra-nodule | Ex-vivo FNA | 9 nodules with up to 5 FNA sampled | 43 | — | 0.411 0.241-0.702]* | 0.952 | 0.548-0.985 |

*Concordance evaluated relative to the majority call for the sample.
** Robust estimate of pooled standard deviation.
ANT; adjacent normal tissue.

TABLE 15

Classification results for the malignant FNA/adjacent normal tissue in vitro mixtures. Gray rows correspond to paired mixtures of malignant and adjacent normal samples obtained from the same patient.

Adjacent normal mixtures

|  | Specimen | Mixing proportion | Classifier Call |
|---|---|---|---|
| Pure Samples | ANT | | Benign |
| | BFN | | Benign |
| | FA | | Benign |
| | PTC | | Suspicious |
| | PTC | | Suspicious |
| | PTC | | Suspicious |
| Benign mixtures | BFN + ANT | 50/50 | Benign |
| | FA + ANT | 20/80 | Benign |
| | | 60/40 | Benign |
| Malignant mixtures | PTC + ANT | 20/80 | Suspicious |
| | | 40/60 | Suspicious |
| | | 50/50 | Suspicious |
| | | 60/40 | Suspicious |
| | PTC + ANT | 20/80 | Suspicious |
| | | 50/50 | Suspicious |
| | PTC + ANT | 20/80 | Suspicious |

Analytical Specificity—Blood

FNA samples may contain varying amounts of blood due to variation in the needle collection procedure. To test the impact of blood on the GEC results, in vitro mixtures were created whereby total RNA from malignant or benign FNAs were mixed into a background of total RNA derived from fresh whole blood. The percentage of blood tested was 0, 50, 66, 83 and 100%. Whole blood samples (starting from 100 uL fresh blood in FNAprotect) resulted in a median RNA yield of 335 ng (range 243 ng-491 ng), with a median RIN of 7.5 (range 6.9-7.9). GEC calls for pure whole blood were "Suspicious" in 7/9 samples; malignant FNA/blood mixtures were correctly classified as "Suspicious" for all tested samples, even those with up to 83% blood content (Table 16). This included a mixture of PTC-2 with WB-04, where pure blood classified as "Benign", demonstrating that 17% malignant FNA content is sufficient to correctly classify the mixture. Further in silico mixing experiments with signals from pure blood samples indicated that 80% of all malignant samples, including PTC and non-PTC indeterminate FNAs, maintained a correct "Suspicious" GEC call up to at least 80% blood content (data not shown).

Analytical Specificity—Genomic DNA

Genomic DNA was tested as a potentially interfering substance, as presence of DNA can occur from inadvertent deviations from the RNA extraction process. Routine in-process QC methods using the Bioanalyzer are capable of detecting >30% genomic DNA content in total RNA isolates, preventing such samples from further processing. Thus, assay testing was only necessary for up to 30% genomic DNA contamination (i.e. 15 ng total RNA+6.4 ng genomic DNA from the same sample). Benign and malignant total RNA control samples were tested in a standard and test condition with 6 replicates per condition. GEC scores for samples contaminated with "worst case" 30% genomic DNA had a small systematic bias of −0.11 (p-value <0.02) towards "Suspicious" GEC calls, resulting in a slight potential false positive rate increase in the highly unlikely case of inadvertent contamination with genomic DNA (Table 14). Importantly, the data show that this type of potential interference does not affect the false negative characteristics of the GEC, the most important factor in clinical validity.

Intra-Nodule Reproducibility

Figure 25A:
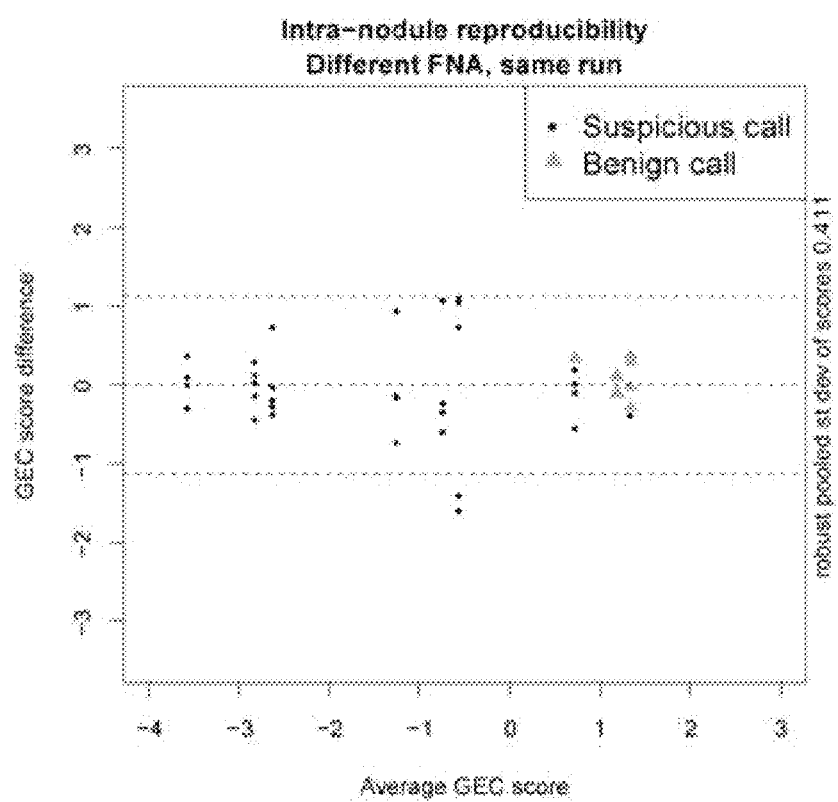
FIG. 25A-FIG. 25E illustrates the intra-nodule reproducibility with each vertical column of data representing samplings from a single nodule (FIG. 25A); comparison of GEC score standard deviations for all sets of replicates across multiple studies (FIG. 25B). GEC intra-assay reproducibility (FIG. 25C), inter-assay reproducibility across 4 runs (FIG. 25D), and inter-laboratory reproducibility (FIG. 25E).
Figure 25B:
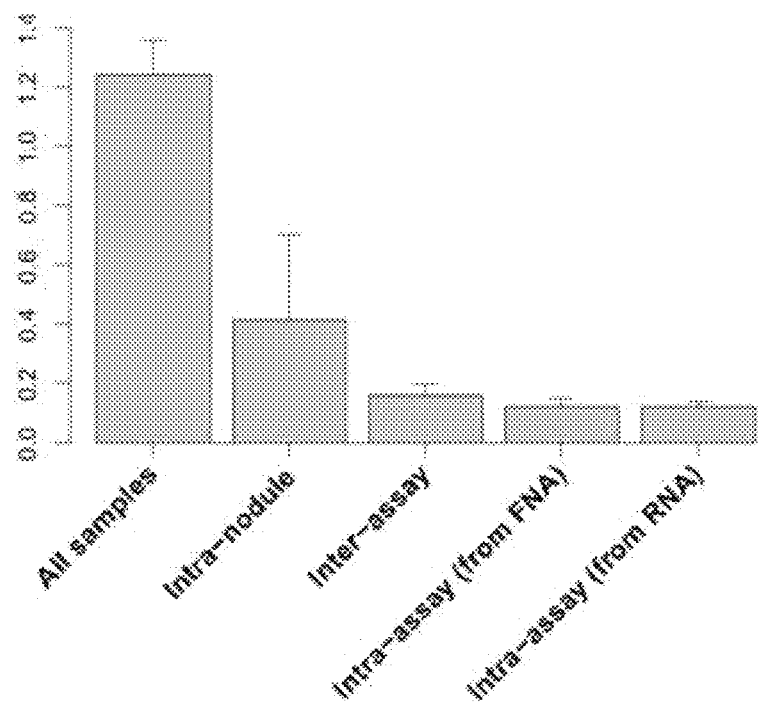

Thyroid FNA sampling variability presents a potential challenge in accurate FNA interpretation. To evaluate the reproducibility of GEC results for different double-pass FNA samplings from the same nodule, 43 samples collected ex vivo from nine independent nodules were processed, with up to five FNA samplings per nodule. Six of nine nodules tested had cytopathology and surgical histopathology classifications of malignant, and all replicates from each of these samples classified correctly in the GEC as "Suspicious" (FIG. 25A). A robust estimate of within-nodule pooled standard deviation in GEC scores for all nine nodules was 0.411, [95% CI 0.241-0.702]. One nodule had significantly higher within-nodule standard deviation in GEC scores compared to the other eight nodules (1.36 SD, p-value <0.001), yet each of its FNA samplings was correctly classified. The transcript signal intensities from different samplings of the same nodule had median $R^2$ coefficients of 0.952 (range 0.548-0.985). These data suggest that biological variability accounts for a larger component of variation in GEC scores compared to technical/assay variability (FIG. 25B).

TABLE 16

GEC results from in vitro mixtures of total RNA from FNA and blood.

| | Thyroid FNA Mixture (%) | Blood in Mixture (%) | Undiluted FNA | WB-01 | WB-02 | WB-03 | WB-04 | WB-05 | WB-06 | WB-07 | WB-08 | WB-09 |
|---|---|---|---|---|---|---|---|---|---|---|---|---|
| PTC-1 | 100 | 0 | S/S | | | | | | | | | |
| | 50 | 50 | | | | | S/S | | S | | | |
| | 33 | 66 | | | | | S/S | | S | | | |
| | 17 | 83 | | S | S | | | S/S | | S | | |
| PTC-2 | 100 | 0 | S/S | | | | | | | | | |
| | 50 | 50 | | | | | | | S | | | |
| | 33 | 66 | | | | | | | S | | | |
| | 17 | 83 | | | S | S | | | | S | | |
| LCT | 100 | 0 | B/B | | | | | | | | | |
| | 50 | 50 | | | | | S/S | | B | | | |
| | 33 | 66 | | | | | S/S | | B | | | |
| | 17 | 83 | | | | S | S/S | S | S | | | |
| Pure Blood | 0 | 100 | | S | S | S | B | S | S/S | S | S/S | B/B |

Assay Reproducibility

Figure 25C:
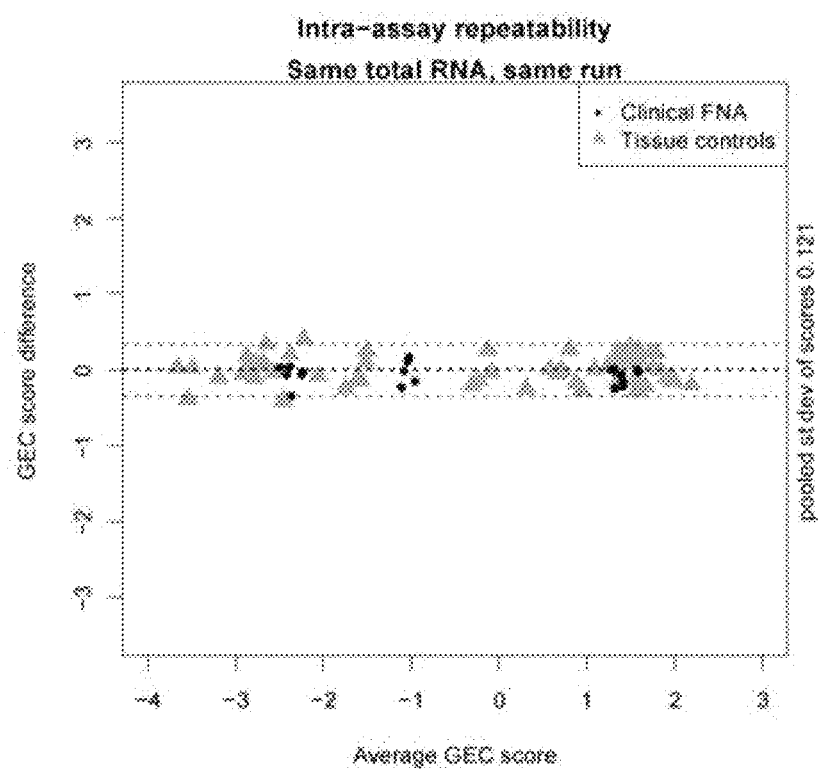

The within-run repeatability of the GEC was evaluated using total RNA from 33 FNA samples and controls, processed in triplicate in a series of 81 experimental runs (243 GEC results), varying reagent lots and operators, and spanning more than 15 months. The pooled within-run standard deviation of GEC scores was estimated to be 0.121, [95% CI 0.109-0.1364] (FIG. 25C). Variation of GEC scores was similar across the range of GEC scores, as measured by the dependence of absolute residuals of the scores on the mean scores (p-value 0.86). The within-run standard deviation of GEC score for total RNA controls (0.130 [95% CI 0.115-0.149], estimated from 59 triplicates of 28 unique tissue control lots) was not smaller than the variation in triplicate FNA samples (0.092 [95% CI 0.077-0.117], estimated from 22 triplicates of 5 unique FNA samples). The transcript signal intensities from within-run replicates had median $R^2$ coefficients of 0.988 (range 0.945-0.994).

Figure 25D:
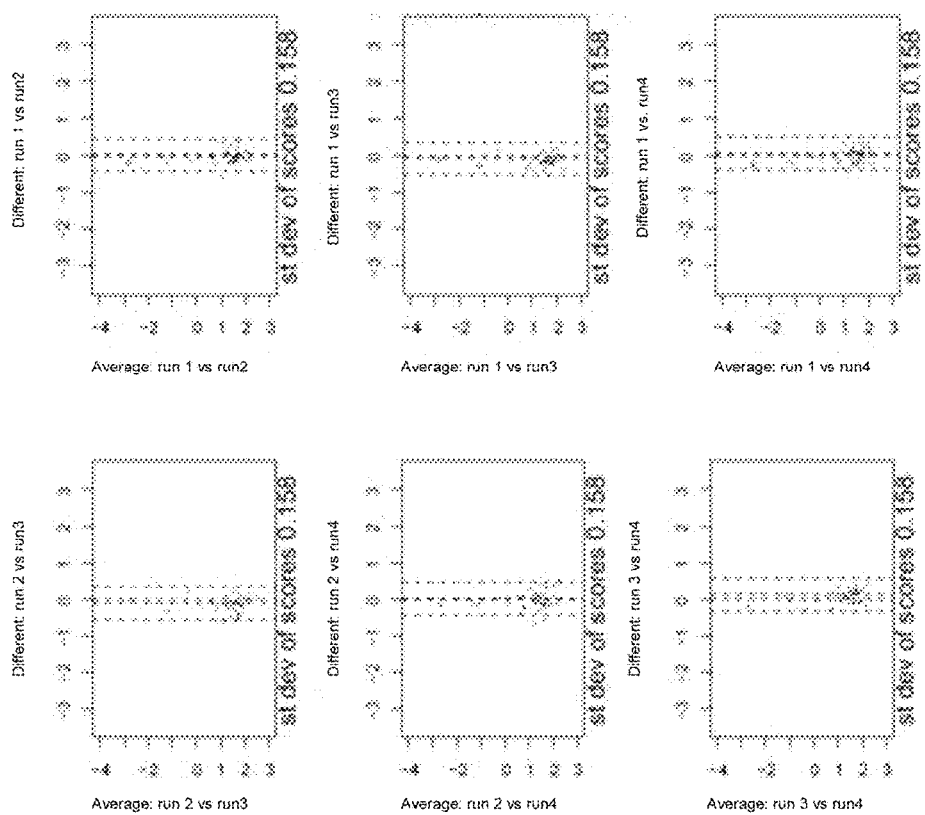

In a study of inter-run reproducibility, total RNA from 37 different FNAs were tested in four different runs corresponding to four different pre-qualified lots of critical reagents, with each run performed by one of three different operators. FNA samples with GEC scores concentrated around the clinical decision boundary were chosen for this study in order to increase the statistical power to detect changes in this range. Of 37 samples tested, 36 resulted in concordant GEC calls across all four runs (97% concordance). The GEC scores were estimated to have an inter-run pooled standard deviation of 0.158 [95% CI 0.140-0.182] across all FNAs in this study (FIG. 25D). The transcript signal intensities from across-run replicates had median $R^2$ coefficients of 0.979 (range 0.946-0.994). Thus, GEC call concordance demonstrated high reproducibility across reagent lots, operators, and processing runs.

Inter-Laboratory Reproducibility

Figure 25E:
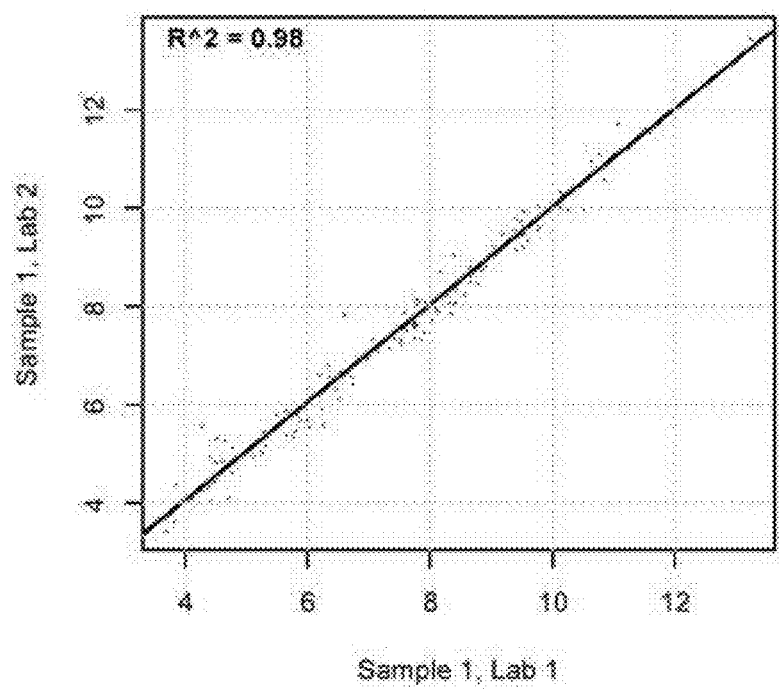

Total RNA from twenty different patient FNA samples was processed through the GEC in the laboratory where the test was developed. A second aliquot of RNA from the same samples was later tested in a different, CLIA-certified reference laboratory using different operators, reagent lots, and equipment. The GEC calls for all samples were 100% concordant between the two laboratories, and also 100% concordant with available surgical pathology diagnosis, thus demonstrating inter-laboratory reproducibility and accuracy of GEC results. Inter-laboratory pooled standard deviation of GEC scores was estimated to be 0.138 [95% CI 0.105-0.201], which is in agreement with the 0.158 calculated for within-lab inter-assay reproducibility. Similarly, transcript signal intensities were highly correlated between laboratories across all samples (median $R^2$ 0.981, range 0.953-0.989), consistent with expectations for inter-assay results (FIG. 25E).

Discussion

The entire process from collection, storage, shipping, sample processing and classification was evaluated. Nucleic acids extracted from clinical FNAs were stable and yielded reproducible results across a variety of conditions. In this study, samples were collected prospectively and consecutively, and high GEC call concordance rates represent those in a hypothetical clinically-relevant population.

Tissue lysate and total RNA controls yielded reproducible results. These controls allowed the laboratory to assess quality control concurrently with samples at key steps of the assay, supporting multiple in-process quality monitoring steps. The standard 15 ng input RNA was verified to be within the operating range of the assay.

Analytical specificity was thoroughly evaluated with two distinct studies. The GEC test was robust in the presence of blood, maintaining correct classification of malignant samples mixed with up to 83% blood RNA. Thus, the GEC overcomes limitations in cytological assessment, where blood may significantly interfere. One potential contaminant to any RNA-based test is the presence of DNA during amplification. The scenario of 30% DNA contamination was evaluated and noted a minor bias toward a false positive result. These studies demonstrated that the GEC was extremely sensitive to malignant signals arising from heterogeneous or dilute samples, and false negatives are unlikely to result.

Analytical reproducibility was evaluated by following the technical assessment criteria outlined by EGAPP, ACCE and AHRQ, using clinical samples with GEC scores covering the GEC score range and concentrated around the clinically critical cut-point.

The results in the laboratory used in the study were identical to these generated in the laboratory where the test was developed. In total, the GEC achieved EGAPP level I analytic validity criteria. Technical validation involved the extensive use of well-characterized samples with multiple reference standard comparison methods including cytology, histopathology, and reference laboratory. The role of intra-nodule heterogeneity was also evaluated. The data reveal that biological variability within a nodule accounts for a larger component of GEC score variation than do technical factors.

The robustness of the GEC to induced variables, including those that may be encountered in clinical samples, indicated that routine testing of FNA specimens is feasible at high confidence from the standpoint of analytical performance and reproducibility.

Supplemental Materials & Methods

FNA Stability

The stability of samples preserved in FNAprotect and stored at room temperature in the molecular laboratory was tested at one-day increments ranging from day 1 to day 6. These were compared against a group of control samples that had been kept at −80° C. until RNA extraction. Since splitting individual FNA samples seven-ways was not possible, each test group consisted of 30 unique, prospectively collected FNAs, for a grand total of 210 samples, ensuring sufficient power to detect changes in RNA quality (as defined by a drop of 1 RIN unit or more between the test and control conditions). Data was analyzed using Kruskal-Wallis test for RIN values, and one-way ANOVA for log 2 (concentration).

FNA Storage & Shipping

FNA samples were collected from twenty-eight different patient nodules either pre-operatively or in the clinic. For each patient nodule a total of three FNA passes were combined into a single tube of FNAprotect (3× volume), and then split equally into three different tubes of FNAprotect (1× volume). Each of the three tubes was then subjected to different storage and shipping temperatures, where the control condition (A) was −80° C. storage/dry ice shipping, test condition (B) was −20° C. storage/ice pack shipping, and test condition (C) was room temperature storage/ice pack shipping. The ice pack shipping container was separately verified to hold <25° C. for up to 48 hours, including induced temperature spikes. This study has 80% power (at p=0.05 level) to detect changes in RNA quality (1 RIN unit) or GEC score (0.1 score unit). Data was analyzed using ANOVA with nodule identity and shipping method as two categorical factors.

Analytical Sensitivity—Total RNA Input Quantity

To evaluate tolerance to input variability—including input levels below the nominal 15 ng-total RNA from three different FNAs previously tested and known to represent high (benign), medium, and low (suspicious) GEC scores were again examined in triplicate using 5, 10, 15 and 25 ng of total RNA. The sample size was chosen to ensure 70% power to detect clinically-significant differences in GEC scores at the p=0.05 level. Reproducibility of signal intensities was characterized for the 142 transcript clusters used by the SVM classifier using RA^2 coefficient between each of the replicates of the same total RNA. Resulting GEC scores were compared using ANOVA with sample identity and input amount as two categorical factors.

Analytical Sensitivity—Dilution of Malignant FNA Content

To characterize the analytical sensitivity for diluted levels of malignant RNA, paired malignant and adjacent normal FNA samples were collected ex vivo from the same patient. Normal adjacent tissue sample with "Benign" GEC call and sufficient RNA material for multiple mixing experiments was selected for in vitro mixing Total RNA was extracted from the FNA samples, and total RNA from the malignant FNA nodule was diluted at various levels (0, 20, 40, 60, 100% malignant FNA RNA by mass) into a background of total RNA from normal adjacent tissue (either from the same or different patient). These mixed samples were tested in the GEC under standard conditions (at 15 ng total RNA input). Signal intensities and GEC scores obtained with in vitro mixtures were compared to in silico predictions. In silico methodology was used to evaluate mixtures of cytopathology indeterminate samples with malignant histopathology (and highly negative GEC scores representing as much as possible pure malignant content) as the starting point for the mixtures with normal adjacent tissue.

Analytical Specificity—Blood

To test for any potential interference from blood, fresh whole blood was collected from 10 individuals (in preservative-free collection tubes) and 100 uL was immediately placed into FNAprotect (1.25 mL). Blood samples were processed through to total RNA as with any standard FNA sample. Total RNA from blood was then mixed with total RNA from benign or malignant FNAs and processed through the GEC, keeping the input RNA of the assay constant at 15 ng for all conditions. The percentage of blood RNA tested was 0, 50, 66, 83 and 100%, with the complement of RNA being from malignant or benign FNA.

Analytical Specificity—Genomic DNA

Genomic DNA was also tested as a potentially interfering substance: 15 ng of total RNA from either benign or malignant thyroid tissue (6 replicates) was spiked with 6.4 ng of genomic DNA from the same tissue (i.e. 30% of total nucleic acid by mass), and processed through the GEC. The sample size was chosen to ensure 80% power to detect changes in GEC scores (0.1 unit) at the p=0.05 level. Data was analyzed using ANOVA with sample identity and genomic DNA spike-in as two categorical factors.

Intra-Nodule Reproducibility

To test the reproducibility of classification results for different FNA passes from the same nodule (n=9), up to 5 FNA samplings (double-pass for each sample) were done from the same nodule ex vivo or post-operatively. Samplings from the same nodule were placed independently into tubes of FNAprotect and processed through the GEC within the same run. Significance of the increase in the standard deviation within individual nodules was evaluated using Chi-squared test. Confidence interval for within-nodule standard deviation of the GEC score was estimated as a normal 95% two-sided confidence interval for log-transformed standard deviations within individual nodules.

Intra-Assay Reproducibility

Total RNA from three FNA samples representing a range of GEC scores were tested by a single operator (three runs) or three operators (one run each), where every run tested intra-assay reproducibility of each FNA and control samples in triplicate. Other studies have also contributed triplicate runs of FNA and control material. Here cumulative results for intra-assay reproducibility obtained from triplicates processed in the same run across 82 different experimental runs are reported. Confidence interval for pooled intra-assay standard deviation is evaluated using Chi-squared distribution.

Inter-Assay Reproducibility

The between-run reproducibility was evaluated using total RNA from 35 different FNA samples, whereby each FNA sample was tested in four different runs/reagent lots. One of three different operators performed each run on separate days, utilizing one of four different pre-qualified lots of critical reagents. This reagent lot pre-qualification incorporated QC functional testing including measurement and assignment of GEC score 'calibration offset values', enabling adjustment for any systematic lot bias in all subsequent runs utilizing those critical reagent lot combinations.

Inter-Laboratory Reproducibility

Total RNA from twenty different clinical FNA samples were processed through the GEC in the laboratory where the test was developed and later tested again in a different reference laboratory using different operators, reagent lots, and equipment.

Example 9: Validation of a Novel Gene Expression Classifier to Preoperatively Identify Benign Thyroid Nodules with Indeterminate FNA Cytology Abstract Background: Following fine needle aspiration, 15-30% of thyroid nodules are not clearly benign or malignant. These cytologically indeterminate nodules are often referred for diagnostic surgery, though most prove benign. A novel diagnostic test measuring the expression of 167 genes showed promise in improving pre-operative risk assessment. This test was evaluated in a prospective, multicenter study.

Methods: Over 2 years, a prospective study was performed at 49 clinical sites enrolling 3,789 patients and collecting 4,812 samples from thyroid nodules >1 cm requiring evaluation. 577 cytologically indeterminate aspirates, with corresponding histopathology of excised lesions on 413 were obtained. Central blinded histopathologic review served as the reference ("gold") standard. After applying inclusion criteria, gene expression classifier results were obtained for 265 nodules used in the analysis and performance was calculated.

Results: 85 of 265 indeterminate nodules were malignant. The gene expression classifier correctly identified 78 of 85 as 'suspicious' (91.8% sensitivity, [83.8%-96.6%] 95% two-sided exact binomial confidence interval (CI)). Specificity was 51.7%, [44.1%-59.2%] CI. The negative predictive value was 95%, 94%, and 85%, respectively, for aspirates with AUS/FLUS, FN/SFN, or 'suspicious' cytology. Analysis of false negative errors revealed a paucity of thyroid follicular cells, suggesting that insufficient sampling of the nodule had occurred.

Conclusions: A novel gene expression classifier can modify the pre-operative cancer risk in patients with indeterminate thyroid nodules where diagnostic surgery is otherwise recommended. Though individualized clinical care is recommended, these data support consideration of a conservative approach for most patients with indeterminate FNA cytology and benign gene expression classifier results.

Background

Thyroid nodules are common, with 48,100 new cases identified each year in the U.S. Though most are asymptomatic and incidental, identification of a 1-1.5 cm nodule often prompts diagnostic evaluation, as 5-15% of these nodules are malignant. The ultimate goal of diagnostic evaluation is to reliably and accurately determine whether nodules have a high or low risk of malignancy, ideally through a method that also optimizes patient safety, reduces morbidity and limits health care costs.

The cornerstone of thyroid nodule evaluation is fine needle aspiration (FNA), with over 450,000 performed yearly in the U.S. First introduced over 50 years ago, thyroid nodule FNA is a minimally invasive, low-risk ambulatory procedure performed without need for sedation or general anesthesia. Cytologic evaluation of aspirated cells provides assessment of cellular morphology (and therefore risk of malignancy) otherwise unobtainable through clinical assessment or radiologic imaging. Preoperative ultrasound-guided FNA has been shown to accurately identify 62-85% of thyroid nodules as benign, enabling diagnostic surgery to be avoided in most patients.

Despite its benefits, morphologic assessment of thyroid nodule cells remains imprecise, as 15-30% of all FNAs yield indeterminate cytology. Indeterminate cytology can include three subtypes: atypia or follicular lesion of undetermined significance (AUS/FLUS), follicular neoplasm/suspicious for follicular neoplasm (FN/SFN), and suspicious for malignancy (SUSP). Though sufficient in sample quantity, indeterminate aspirates demonstrate cytologic features that increase concern for thyroid cancer. With few other diagnostic modalities able to more accurately quantify cancer risk, most patients with indeterminate FNA cytology are referred for surgical removal of all or part of their thyroid gland. However, the majority of patients with indeterminate thyroid nodule cytology ultimately prove to have benign disease. For these individuals, therapeutic thyroid surgery was unnecessary, yet exposed them to a 4-10% rate of serious surgical complications, and most to a lifelong requirement for levothyroxine replacement. Together, these data confirm the critical need for improved preoperative diagnostic evaluation in patients with indeterminate FNA cytology.

Molecular analysis of thyroid tissue can be an adjunct to visual microscopic evaluation. Sixty to seventy percent of well-differentiated thyroid cancers harbor at least one known genetic mutation not commonly found in benign follicular cells. Four recent investigations demonstrate the potential benefits of combined microscopic and molecular analysis of thyroid nodules. When cytologically indeterminate aspirates are analyzed for the presence of BRAF and RAS mutations, and RET/PTC and PAX8-PPARy gene rearrangements, the diagnostic findings alter surgical management in 20-30% of cases. These genetic markers typically seek to identify which indeterminate thyroid nodules are malignant, and therefore have high specificity and positive predictive value (PPV). Marker positivity can lead to a recommendation for total thyroidectomy rather than hemi-thyroidectomy or watchful waiting. In doing so, patients avoid a second 'completion' thyroidectomy when their initial hemi-thyroidectomy reveals a malignancy. This clinical scenario is also similar to reports investigating epigenetic and peripheral blood markers. Though useful as positive predictors of malignancy, it is important to note that these markers have limited sensitivity. In a recent study of over 1,000 cytologically indeterminate thyroid nodules, molecular testing of these four markers failed to detect over one third of thyroid cancers, rendering their false negative rate (39%) too high to assist physicians with regard to the difficult decision of watchful waiting in lieu of diagnostic thyroid surgery. In addition, although several mutational markers of malignancy occur with high frequency in cytologically malignant FNAs, they occur with lower frequency in cytologically indeterminate samples. For these reasons, the currently available molecular markers have been unable to exclude cancer with sufficient certainty to avoid surgery in patients with indeterminate nodules.

Recent studies have attempted to develop gene expression classifiers capable of distinguishing benign and malignant thyroid nodules. In order to aid in the decision to avoid surgery, such a test would need to exhibit high sensitivity and high negative predictive value (NPV). However, most previously published genomic classifiers are limited in sensitivity and have not been validated on independent test sets in sufficient numbers of patients. If validated on a large cohort, such a diagnostic test could be translated into the care of patients with cytologically indeterminate aspirates and, when negative, reduce unnecessary surgery on nodules highly likely to be benign. Recently, a promising gene expression classifier was developed to optimize the identification of benign rather than malignant nodules. This classifier was independently tested on a modest set of prospectively collected FNAs and shown to have an NPV of 95%. In this report, the results of a large, prospective, double-blind, multi-center study validating the utility of the gene expression classifier in patients whose FNA is cytologically indeterminate are described.

Methods

Study Design and Oversight

This study was designed and supervised by the sponsor and the co-principal investigators with oversight by a Steering Committee. Samples were tested in a CLIA-certified laboratory and statistical analysis performed by statisticians. This protocol was approved by a central, as well as by institution-specific, investigational review boards (IRB). All patients provided written informed consent for participation prior to study entry. The two co-principal investigators had full access to all study data and analyses.

Study Population & Protocol

A double-blind, prospective, multicenter validation trial (VERA001) was performed, in which patients were enrolled with a sonographically confirmed thyroid nodule >1 cm that underwent routine FNA evaluation. Patients and physicians were blind to gene expression classifier results throughout the study. The study cohort was comprised of FNA samples obtained from 49 U.S. sites and samples from 43 were included in the primary data set (see Supplement (infra) for site characteristics). Study sites were representative of both academic (29%) and community centers (71%) in 26 different states, reflecting patient population diversity expected in the clinical use of the test. Ultrasound-guided FNA (UG-FNA) was performed in 99% of cases. Most often, UG-FNA consisted of 2-5 needle sticks within each nodule as part of diagnostic aspiration. One additional needle stick was thereafter obtained and processed for the purposes of this investigation and shipped frozen on dry ice (Amendment 1, A1). Midway through the study, laboratory analyses confirmed many aspirates lacked sufficient RNA for analysis. The protocol was subsequently modified (Amendment 2, A2) to dedicate two needle sticks for study analysis. Amendment 2 also included a change in shipping protocol to use of cold packs. For each enrolled subject, patient age, self-identified race, and gender were recorded. Clinical histories of hypothyroidism, hyperthyroidism, the presence of thyroid cancer risk factors, and information on thyroid-specific therapy were documented. Ultrasound data were used to precisely confirm nodule location and size.

Following FNA, local cytology reports were collected for all subjects and reviewed by three expert cytopathologists, who reclassified each report within The Bethesda System for Reporting Thyroid Cytopathology (AUS/FLUS, FN/SFN, or SUSP). Majority vote between the three was used to establish cytology classification for each study sample. In three cases where a majority vote was not possible, the sample diagnosis was provided by a fourth experienced cytopathologist. The local cytology report was considered "indeterminate" if it was classified as AUS/FLUS, FN/SFN, or SUSP by the reviewing cytopathologists. Thyroid surgery was performed based on the clinical judgment of the treating physician at each study site without any knowledge of gene expression classifier results. Study was open for enrollment between Jun. 23, 2009 and Dec. 3, 2010, and patients with confirmed surgery before Jan. 31, 2011 were assessed for eligibility. Following surgery, the local histopathology report and histopathologic slides were collected. All histology slides were de-identified, scanned to construct a permanent digital file of microscopic images (Aperio, Vista, Calif.) and independently evaluated by two expert endocrine pathologists. When both expert pathologists' diagnoses were concordant, it was considered the reference (or "gold") standard. In cases where categorical (defined as benign or malignant) pathology diagnoses were discordant (51 of 352, or 14% of cases), the two experts conferred and provided a consensus categorical diagnosis which resolved most cases. However, in 2% of cases consensus could not be reached even after conferral. In these rare circumstances a third blinded pathologist provided an independent diagnosis and final histologic diagnosis was defined by majority vote among these three experts. Throughout the study, all expert pathologists were unaware of local histopathology diagnosis and molecular test results until re-review of false negative cases.

The histopathology gold standard results and the gene expression classifier results were maintained in two separate, password-protected databases. Upon study completion, unblinding and merging of these two datasets was performed by an independent third party not affiliated with the sponsor or study sites. Following unblinding, it was determined that 36 samples in the study fell outside the 14-day shipping requirements specified a priori in the protocol, 5 samples were outside of clinical eligibility requirements {nodule size below 1 cm (n=1); patient age under 21 years (n=1); cytology benign (n=1); not independent from training set patients (n=2)} and 5 separate FNA samples represented duplicate aspirations from the same nodules performed at different clinical visits. One additional sample was determined to have insufficient referential integrity for inclusion, as the pathology experts could not independently confirm that the sonographically aspirated nodule corresponded to the tissue submitted for histologic analysis. Therefore, these 47 samples were removed from the study and not included in the primary analysis. Data on the sample set prior to these exclusions is described in the Supplement (infra).

Laboratory Methods

Detailed descriptions of the gene expression classifier are provided in the Supplement (infra) and prior publications. Briefly, total RNA was extracted from thyroid nodule samples, amplified, labeled and hybridized to microarrays (Affymetrix, Inc.). The gene expression classifier was trained on a diverse set of benign and malignant thyroid samples. Characteristics of the 468 samples used in training the classifier are shown in the Supplement. All training samples were independent from the validation set used in this study. The classifier was trained on labeled data representing two classes: histologically benign or malignant. The algorithm utilizes expression of 167 genes to classify aspirated material from thyroid nodules as either benign or suspicious. There are 142 genes in the main benign/suspicious classifier and 25 genes that act to filter out samples in a series of "cassettes" (see Supplement). The list of these genes and their annotations is shown in Table 23. The genes participate in a wide variety of biological and cellular processes, the most common of which are related to energy metabolism, cell differentiation, and cellular development. Many genes are concentrated in energy-generating pathways such as glycolysis, gluconeogenesis and the tricarboxylic acid cycle. Shifts in energy-producing pathways, exemplified by the Warburg effect, are commonly observed in cancer cells. A linear modeling approach was used for feature selection and a support-vector machine (SVM) for classification. Receiver operating characteristic (ROC) curves were used to identify a decision boundary on training data that allowed for high sensitivity while maintaining acceptable specificity.

Statistical Analysis

Statistical analysis was performed using R software, version 2.13. Continuous variables were analyzed via the Student's t-test and Wilcoxon rank sum test (for nodule size). Sensitivity, specificity, NPV, and PPV were calculated via the usual manner. P values <0.05 were considered significant. Confidence intervals for proportions are reported as 95% two-sided exact binomial confidence intervals.

Results

Figure 26:
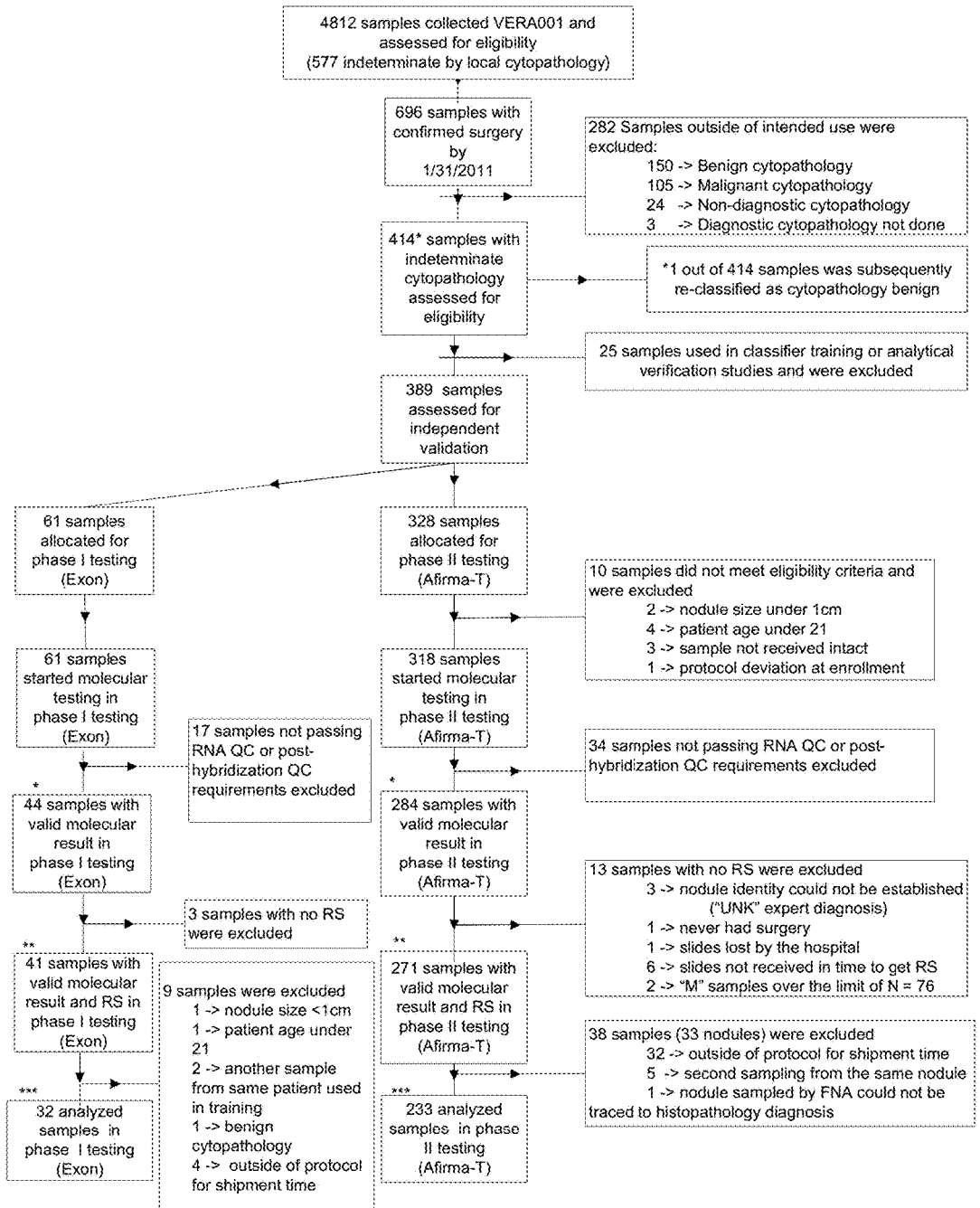
FIG. 26 illustrates the study population accrued from 49 different clinical sites over a 2 year period. Key: *, samples with gene expression classifier results; , samples with gene expression classifier results and available "gold" reference standard (RS); *, samples included and analyzed in the study. M, malignant.

To independently validate the gene expression classifier, 4,812 nodule aspirations were prospectively collected from 3,789 patients, at 49 clinical sites in the United States over a 2-year period. Among the 4,812 samples, 577 were interpreted as indeterminate by the local cytopathologist (12%) and all were confirmed indeterminate by three expert cytopathologists. Surgery was carried out on 413 out of 577 samples (71%, median follow-up time 301 days), allowing for blinded histopathologic review by experts to serve as the reference ("gold") standard. Of these, a small fraction of samples (n=25) were used for training and analytical verification studies, and therefore excluded. Of the remaining, 61 samples were separately tested in phase I of the validation trial using Affymetrix Human Exon 1.0 ST arrays, while 318 were evaluated in phase II of the validation trial using custom Afirma-T arrays. Ten samples were determined to be ineligible prior to the beginning of the validation, and therefore excluded (FIG. 26).

Using pre-defined laboratory quality control metrics, 328 samples were successfully processed through the assay and resulted in valid classifier results. Gold standard histopathology diagnosis was available for 312 of these samples (95%). As described previously, 47 samples were then excluded (FIG. 26). Therefore, a total of 265 independent nodules remained and served as our primary analysis set. These samples were inclusive of all subclasses of indeterminate cytology (AUS/FLUS, 49% of samples; FN/SFN, 31%; and SUSP, 21%). Patient demographics and baseline data of this study cohort are shown in Table 17. Age, gender, clinical risk factors, nodule size, as well as proportion of samples collected at community centers did not differ significantly between the primary study population and the entire cohort of samples with indeterminate cytopathology (N=577). There was a statistically significant difference in the proportion of Amendment 1 (A1) and Amendment 2 (A2) samples in the total accruals versus final validation set (p=0.003) and for indeterminates with confirmed surgery (N=413) versus final validation set (N=265, p=0.004). This can be due to the fact that the exclusion by site storage time affected mostly A1 samples. In addition to cytology indeterminate samples, a subset of cytology benign and cytology malignant samples were included to further assess the gene expression classifier. 47 cytology benign and 55 cytology malignant samples were selected from independent patients for analysis, all of whom had also undergone surgical removal of the nodule such that histologic slides were available.

TABLE 17

Descriptive characteristics of the entire validation cohort and 265 cytologically indeterminate samples.

| | | Total: | Indeterminate Cytology | Indeterminate Cytology and confirmed surgery | Final Validation Set |
|---|---|---|---|---|---|
| Accruals | Samples | 4812 | 577 | 413 | 265 |
| | Nodules | 4775 | 567 | 403 | 265 |
| | Patients | 3789 | 532 | 378 | 249 |
| | Site type (academic/community) | 21.4%/78.6% | 34.1%/65.9% | 37.3%/62.7% | 35.1%/64.9% |
| | Protocol amendment (A1/A2) | 52.9%/46.5% | 51.1%/48.9% | 55%/45% | 43.4%/56.6% |
| Patients | Age (yr) | | | | |
| | Mean | 53.2 | 52.8 | 51.8 | 51.5 |
| | Range | 18-91 | 19-85 | 19-85 | 22-85 |
| | Gender | | | | |
| | Male | 696 (18.4%) | 116 (21.8%) | 84 (22.2%) | 55 (22.1%) |
| | Female | 3093 (81.6%) | 416 (78.2%) | 294 (77.8%) | 194 (77.9%) |
| | Radiation exposure to H/N | 91 (2.4%) | 14 (2.6%) | 8 (2.1%) | 8 (3.2%) |
| | Family History of Thyroid Carcinoma | 174 (4.6%) | 32 (6%) | 28 (7.4%) | 18 (7.2%) |
| Nodules | Nodule Size (Ultrasound) | | | | |
| | Median | 1.9 | 2.2 | 2.3 | 2.3 |
| | Range | 0.6-11 | 0.75-10.3 | 0.75-10.3 | 1-9.1 |
| | <1 cm | 37 (0.8%) | 4 (0.7%) | 3 (0.7%) | 0 (0%) |
| | 1-1.99 cm | 2503 (52%) | 230 (39.9%) | 153 (37%) | 102 (38.5%) |
| | 2-2.99 cm | 1204 (25%) | 153 (26.5%) | 111 (26.9%) | 76 (28.7%) |
| | 3-3.99 cm | 621 (12.9%) | 105 (18.2%) | 76 (18.4%) | 45 (17%) |
| | >4 cm | 391 (8.1%) | 74 (12.8%) | 60 (14.5%) | 42 (15.8%) |

Of the 265 indeterminate FNAs (from 265 independent nodules), 85 were diagnosed as malignant (32%) on blinded histopathologic review. When applied to the indeterminate cohort, the gene expression classifier correctly identified 78 of 85 malignant samples as "suspicious," yielding a sensitivity of 92% [83.8%-96.6%, 95% CI]; 93 of 180 non-malignant samples were correctly identified as benign by the gene expression classifier yielding a specificity of 52% [44.1%-59.2%, 95% CI] (Table 18). For nodules with AUS/FLUS cytology, the sensitivity was 90% [74.2%-98%, 95% CI]. For nodules with FN/SFN cytology, sensitivity was 90% [68.3%-98.8%, 95% CI], and for nodules with SUSP cytology, sensitivity was 94% [80.3%-99.3%, 95% CI]. The study prevalence of malignancy among these three categories was 24%, 25% and 62%, respectively, yielding NPV's of 95%, 94% and 85% as shown in Table 18. Out of 47 samples in the cytology benign category, 3 resulted in malignant diagnoses by histopathology. The gene expression classifier correctly identified all 3 as 'suspicious' (100% sensitivity). Out of 55 samples in the cytology malignant category, all resulted in malignant diagnoses by histopathology and all were called 'suspicious' by the gene expression classifier (100% sensitivity).

TABLE 18

Performance of the Gene Expression Classifier (GEC) in Cytology Subgroups.

Performance across the entire data set of N = 265 indeterminate nodules

| GEC result | Malignant reference standard (N = 85) | Benign reference standard (n = 180) |
|---|---|---|
| Suspicious | 78 | 87 |
| Benign | 7 | 93 |
| Sensitivity | | 91.8% |
| Specificity | | 51.7% |
| PPV | | 47.3% |
| NPV | | 93.0% |
| Malig prev | | 32.1% |

Atypia of undetermined significance/Follicular lesion of undetermined significance (AUS/FLUS)(n = 129, 48.7%)

| GEC result | Malignant reference standard (N = 31) | Benign reference standard (n = 98) |
|---|---|---|
| Suspicious | 28 | 46 |
| Benign | 3 | 52 |
| Sensitivity | | 90.3% |
| Specificity | | 53.1% |
| PPV | | 37.8% |
| NPV | | 94.5% |
| Malig prev | | 24.0% |

TABLE 18-continued

Performance of the Gene Expression Classifier (GEC) in Cytology Subgroups.

Follicular or Hürthle cell neoplasm/Suspicious for follicular neoplasm (FN/SFN)(n = 81, 30.6%)

| GEC result | Malignant reference standard (N = 20) | Benign reference standard (n = 61) |
|---|---|---|
| Suspicious | 18 | 31 |
| Benign | 2 | 30 |
| Sensitivity | | 90.0% |
| Specificity | | 49.2% |
| PPV | | 36.7% |
| NPV | | 93.8% |
| Malig prev | | 24.7% |

Suspicious for malignancy (n = 55, 20.8%)

| GEC result | Malignant reference standard (N = 34) | Benign reference standard (n = 21) |
|---|---|---|
| Suspicious | 32 | 10 |
| Benign | 2 | 11 |
| Sensitivity | | 94.1% |
| Specificity | | 52.4% |
| PPV | | 76.2% |
| NPV | | 84.6% |
| Malig prev | | 61.8% |

Performance on cytology benign samples (n = 47)

| GEC result | Malignant reference standard (N = 3) | Benign reference standard (n = 44) |
|---|---|---|
| Suspicious | 3 | 13 |
| Benign | 0 | 31 |
| Sensitivity | | 100% |
| Specificity | | 70.5% |
| Malig prev | | 6.4% |

Performance on cytology malignant samples (n = 55)

| GEC result | Malignant reference standard (N = 55) | Benign reference standard (n = 0) |
|---|---|---|
| Suspicious | 55 | 0 |
| Sensitivity | | 100% |
| Malig prev | | 100% |

A wide variety of malignant subtypes were correctly classified as 'suspicious' by the test (Table 19). These included papillary, medullary and follicular thyroid carcinomas (including those with oncocytic or Hürthle cell features), poorly differentiated thyroid carcinomas, and thyroid lymphomas. Classification results for some of the rare thyroid subtypes are discussed in the Supplement (infra).

TABLE 19

Performance of gene expression classifier by histopathology sub type.

| | Number | % of Total | B call/S call |
|---|---|---|---|
| Histopathology: Benign | | | |
| Benign follicular nodule (1 CN) | 71 | 39.4 | 41/30 |
| Follicular adenoma | 64 | 35.6 | 37/27 |
| Follicular tumor, UMP | 11 | 6.1 | 5/6 |
| Well differentiated tumor, UMP | 9 | 5.0 | 4/5 |
| Hurthle cell adenoma | 21 | 11.7 | 4/17 |
| Chronic lymphocytic thyroiditis | 2 | 1.1 | 0/2 |
| Hyalinizing trabecular adenoma | 2 | 1.1 | 2/0 |

TABLE 19-continued

Performance of gene expression classifier by histopathology sub type.

| | Number | % of Total | B call/S call |
|---|---|---|---|
| Histopathology: Malignant | | | |
| Papillary carcinoma (1 PTC-TCV) | 38 | 44.7 | 2/36 |
| Papillary carcinoma, micro | 4 | 4.7 | 2/2 |
| Papillary thyroid, follicular variant (1 micro) | 19 | 22.4 | 2/17 |
| Hurthle cell carcinoma (8 HCC-c, 2 HCC-v) | 10 | 11.8 | 1/9 |
| Follicular carcinoma (4FC-c, 1 FC-v, 4 WDC-NOS, 1 PDC) | 10 | 11.8 | 0/10 |
| Medullary thyroid cancer | 2 | 2.4 | 0/2 |
| Malignant lymphoma | 2 | 2.4 | 0/2 |

Benign subtypes are grouped at the top and malignant subtypes at the bottom. Number of samples in each category, percentage of total in each class, and gene expression classifier results (ie B or S "call") are indicated for each subtype.
Abbreviations are as follows:
CN, colloid nodule;
UMP, uncertain malignant potential,
PTC-TCV, papillary thyroid carcinoma, tall-cell variant;
HCC-c, Hürthle cell carcinoma with capsular invasion;
HCC-v, Hürthle cell carcinoma with vascular invasion;
FC-c, follicular carcinoma with capsular invasion;
FC-v, follicular carcinoma with vascular invasion;
PDC, poorly-differentiated carcinoma;
WDC-NOS, well-differentiated carcinoma, not otherwise specified.

Figure 27A:
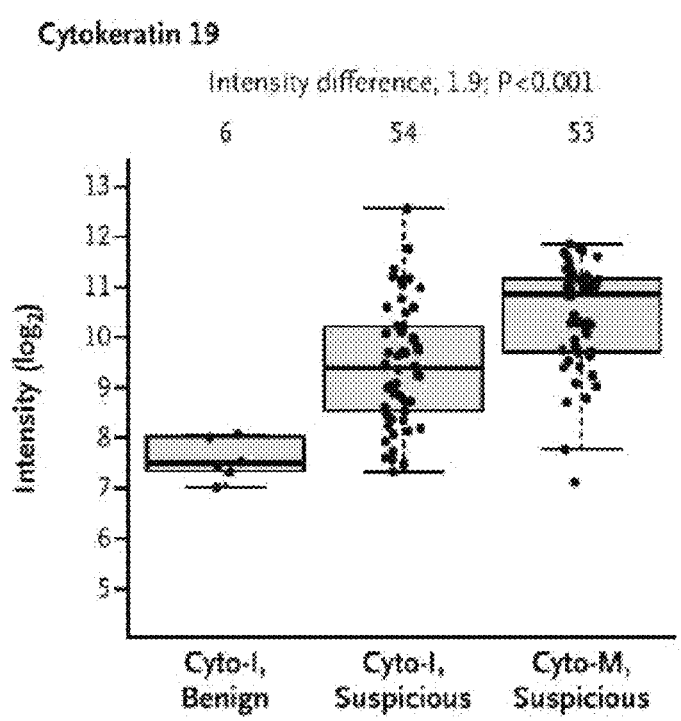
FIG. 27A-FIG. 27F illustrates a comparison of molecular signal intensities in samples of papillary carcinoma (including follicular variant). Signal intensity is stratified by cytology category (I, indeterminate; M, malignant) and gene expression classifier test result e.g. "call" (B, benign; S, suspicious). For each plot, false negatives are shown in the boxplot on the left, true negatives are shown in the center, and true positives are shown in the right boxplot. Numbers above plots show number of samples within the respective category.
Figure 27B:
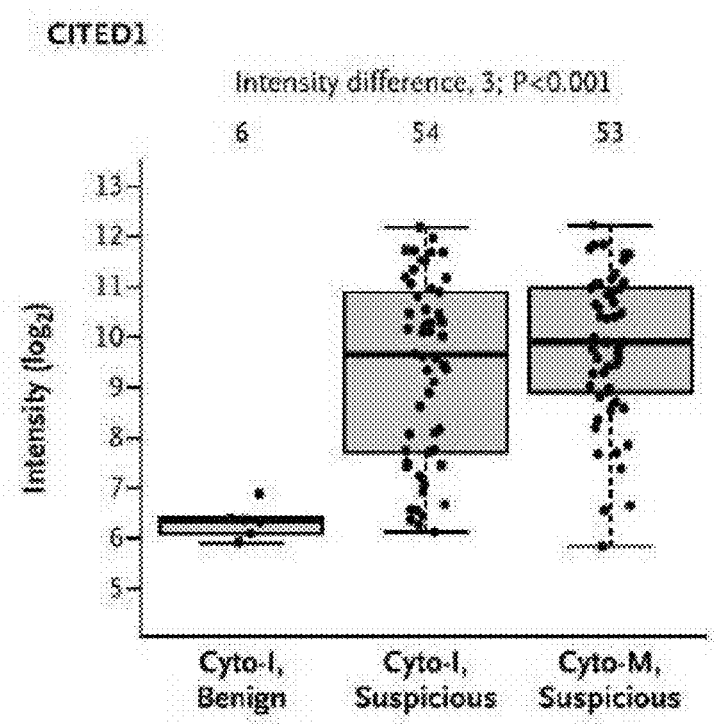
Figure 27C:
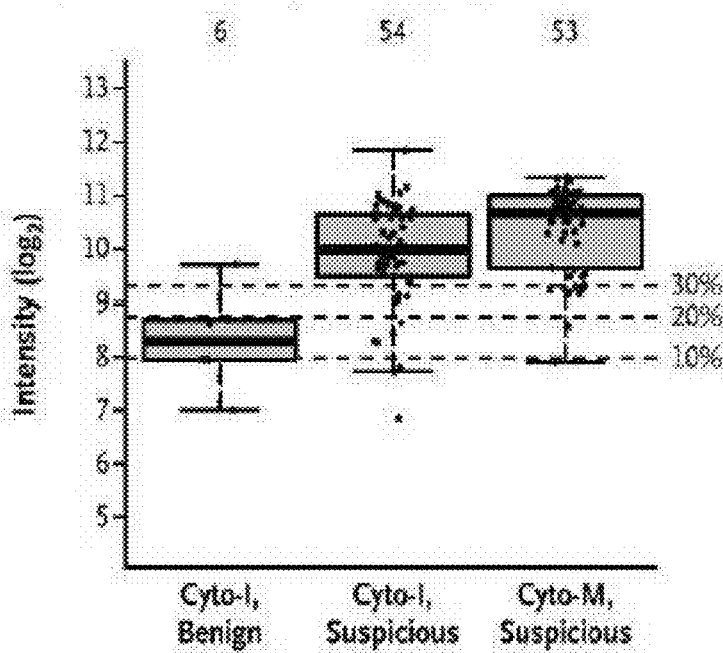
Figure 27D:
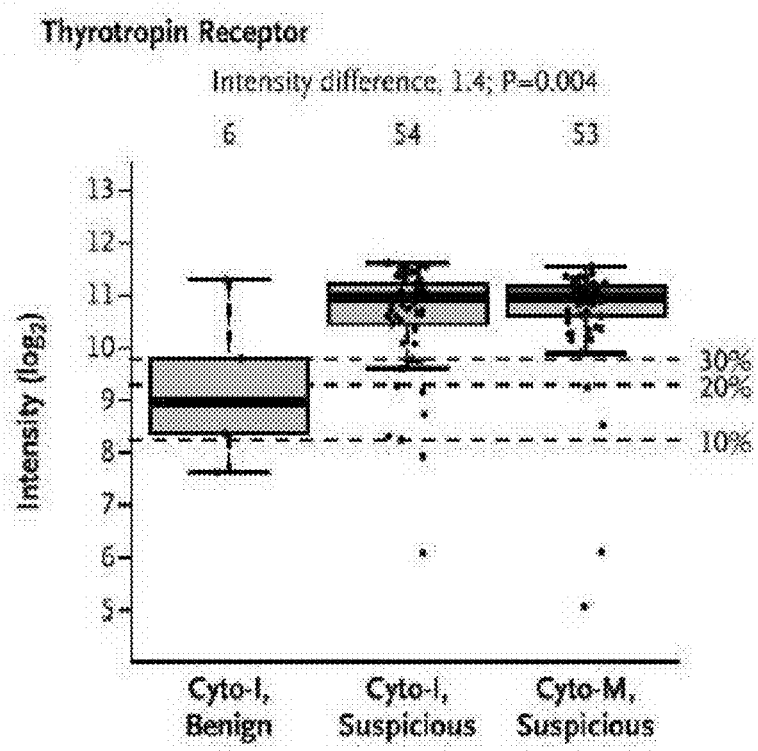
Figure 27E:
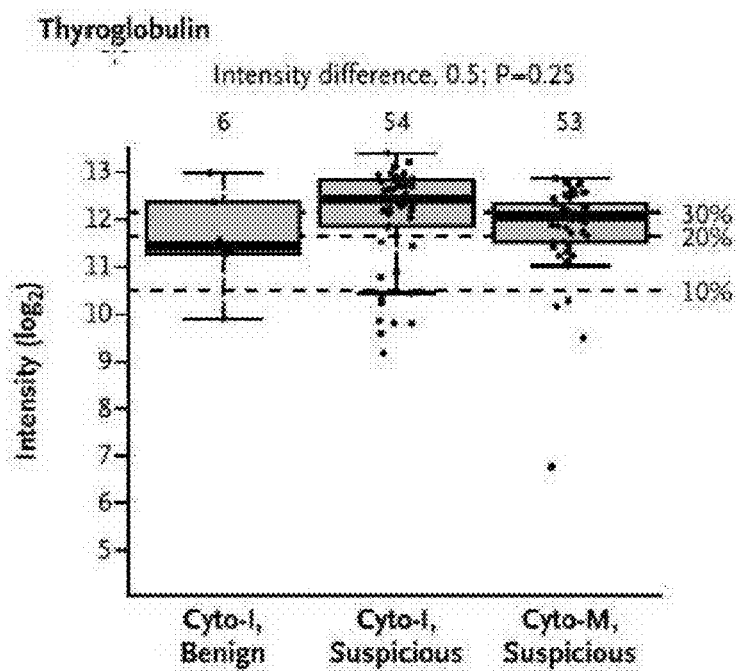
Figure 27F:
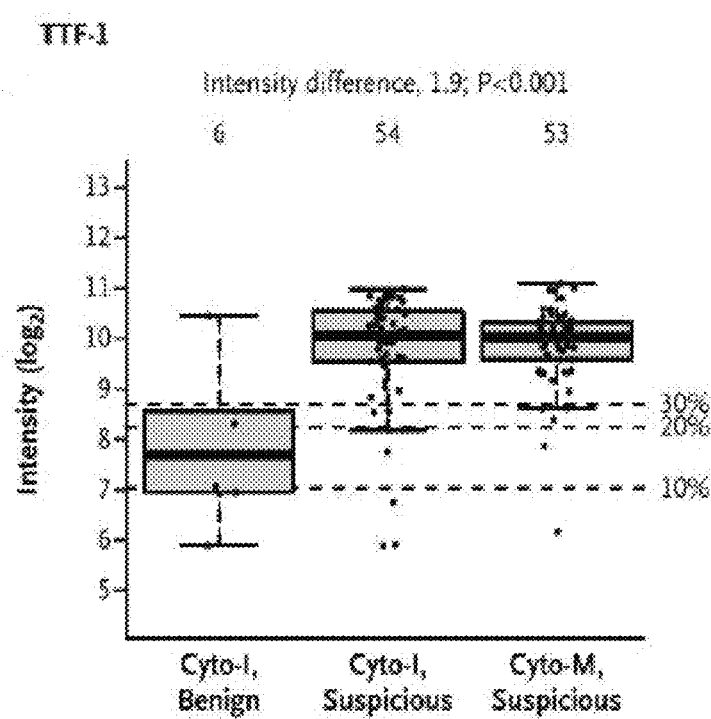

Seven false negative errors occurred, as shown in Table 20. One was a Hürthle cell carcinoma. The other six were papillary thyroid carcinomas (PTCs). Two of these six cancers measured <1 cm in histologic diameter despite ultrasound measurement >1 cm at time of aspiration, and are thus classified as papillary microcarcinomas. To better understand potential causes for false negative error, these samples were further investigated by measuring single molecular markers described in the literature as being elevated in PTC. Two markers of PTC (neither used in the gene expression classifier), Cytokeratin 19 (KRT19) and CITED1, were measured for signal intensity. For both markers, expression was significantly lower in all 6 false negative PTC samples compared to those PTC samples correctly identified by the gene expression classifier (mean log 2(fold change) 1.9, p<0.001 for KRT19; mean log 2(fold change) 3, p<0.001 for CITED1), as shown in FIG. 27A and FIG. 27B demonstrate markers of thyroid malignancy (cytokeratin-19, CITED1); FIG. 27C through FIG. 27F demonstrate intensity of follicular cell markers (cytokeratin-7, thyrotropin receptor, thyroglobulin, and thyroid transcription factor 1 [TTF-1], respectively)). This finding strongly suggests that assay failure is not responsible for the false negativity of these 6 samples. Separately lack of PTC signal in the false negatives, was investigated to see if the false negative could be due to an overall paucity of thyroid follicular cells present in the FNA sample itself. Markers of epithelial and thyroid follicular cell content were measured using keratin 7 (KRT7), thyroglobulin (TG), thyroid stimulating hormone receptor (TSHR) and thyroid transcription factor 1 (TTF-1). None of these markers are used by the gene expression classifier. Expression patterns of these markers showed that 5 of 6 false negative PTC samples exhibited low follicular content (3 samples fell within the lowest 10% of all indeterminate samples, 2 more samples within the lowest 20%). The difference in follicular content between the false negative and true positive PTC samples using any of the four markers is statistically significant with a mean log 2-fold change above 1.4 (p<0.003).

TABLE 20

Description and analysis of 7 false negative errors.

| | Initial Evaluation | | Surgical Pathology Evaluation | | | | | | |
|---|---|---|---|---|---|---|---|---|---|
| Sample | Gender | Ultrasound Nodule Size, cm | Pathology Nodule Size, cm | Reference Standard | Subtype | Expert 1 Diagnosis | Expert 1 background features | Expert 2 Diagnosis | Expert 2 background features |
| 2018-17 | F | 2.9 | 3.5 | M | HCC-v | HCC-v | N/A | FC-c | N/A |
| 4011-52 | F | 2.18 | 1 | M | FVPTC | FVPTC | mPTC | PTC | CLT |
| 4022-13 | F | 3.2 | 3 | M | FVPTC | FVPTC | N/A | FVPTC | N/A |
| 4150-70 | M | 1.1 | 1.2 | M | PTC | PTC | HN, mPTC | PTC | mPTC |
| 4005-56 | M | 1.3 | 1.2 | M | PTC | PTC | N/A | PTC | CLT |
| 4034-57 | F | 1.1 | 0.6 | M | mPTC | mPTC-TCV | N/A | PTC | CLT |
| 2229-83 | F | 1.1 | 0.6 | M | mPTC | mPTC | mFVPTC | PTC | CLT, mPTC |

| | Initial Evaluation | | Cytology Evaluation | | | Laboratory Evaluation | |
|---|---|---|---|---|---|---|---|
| Sample | Gender | Ultrasound Nodule Size, cm | Expert 1 diagnosis | Expert 2 diagnosis | Expert 3 diagnosis | RNA Concentration (ng/ul) | RIN |
| 2018-17 | F | 2.9 | FN/SFN | FN/SFN | FN/SFN | 8.6 | 7.7 |
| 4011-52 | F | 2.18 | SUSP | SUSP | SUSP | 31.1 | 7.6 |
| 4022-13 | F | 3.2 | FN/SFN | FN/SFN | FN/SFN | 7.6 | 7.4 |
| 4150-70 | M | 1.1 | AUS/FLUS | AUS/FLUS | AUS/FLUS | 6.5 | 7.2 |
| 4005-56 | M | 1.3 | AUS/FLUS | AUS/FLUS | AUS/FLUS | 38.2 | 7.4 |
| 4034-57 | F | 1.1 | AUS/FLUS | AUS/FLUS | AUS/FLUS | 18.1 | 6.9 |
| 2229-83 | F | 1.1 | SUSP | SUSP | SUSP | 2 | 6.8 |

Abbreviations:
Gender: M (male), F (female);
Reference Standard M (malignant);
Surgical Pathology evaluation: mPTC (micro papillary thyroid carcinoma), HCC-v (Hurthle-cell carcinoma with vascular invasion), FVPTC (follicular variant of papillary thyroid carcinoma), PTC (papillary thyroid carcinoma), PTC-TCV (papillary thyroid carcinoma, tall cell variant), FC-c (Follicular carcinoma, capsular invasion), CLT (lymphocytic thyroiditis), HN (hyperplastic nodule);
Cytology evaluation: SUSP (suspicious for malignancy), FN/SFN (follicular neoplasm/suspicious for follicular neoplasm), AUS/FLUS (atypia of undetermined significance/follicular lesion of undetermined significance);
RIN (RNA integrity number).

Other potential causes for false negative error were considered. Expert disagreement in defining the "gold standard" was 14% (37 out of 265). However, none of the false negative errors occurred in samples where such disagreement occurred. A variety of clinical factors were also tested for an association with false negative error. Of these, age, gender and ethnicity were not associated. Logistical factors including time from FNA collection to nucleic acid extraction, and time from FNA collection to surgery were also looked at. No associations were found. An examination of RNA QC metrics such as RNA integrity, RNA concentration and microarray QC metrics also failed to detect associations predicting false negative errors. A trend was noted (not statistically significant) for false negative errors to occur in smaller nodules as compared to true positives, both for ultrasound nodule size measurements (median 1.3 cm vs 2.2 cm, p=0.14) and for histopathology nodule size measurements (median 1.2 cm vs 1.8 cm, p=0.06). In total, these results implicate insufficient nodule sampling rather than classifier error as causes for the false negative errors in this study.

Discussion

This study describes the prospective validation of a novel gene expression classifier that seeks to identify benign, rather than malignant, nodules in a population of FNA samples with indeterminate cytology. When applied to patients with indeterminate nodules, this test can significantly impact assessment of preoperative cancer risk. This test demonstrated a negative predictive value of 95% and 94%, respectively, when applied to aspirates labeled AUS/FLUS and FN/SFN, suggesting that patients with a follicular lesion, but a benign gene expression classifier result, have a malignancy rate comparable to that of a cytologically benign FNA result. A benign classifier result decreases the risk of malignancy in indeterminate biopsies from ~30% (pre-test) to a post-test risk of malignancy of 5-6%, providing a compelling rationale for following these patients similarly to those with benign cytology. Although NPV on SUSP aspirates was lower at 85%, ascertainment of a 15% risk of malignancy can nonetheless be useful in the pre-operative decision to perform hemi-thyroidectomy versus total thyroidectomy. The observed test sensitivity of 100% in cytology benign and cytology malignant lesions provides independent evidence of classifier performance. Together, these data suggest that this novel gene expression classifier can significantly improve pre-operative cancer risk assessment in patients with indeterminate cytology, and thereby impact important management decisions.

Benign thyroid disease is usually an indolent process and often requires no therapy. Well-differentiated thyroid carcinoma also affords an excellent prognosis, though it requires appropriate surgical management. Published reports confirm high operative efficacy in surgical removal of thyroid cancer, though unfortunately also demonstrate a 4-10% rate of significant, long-term morbidity from the procedure. These reports indicate that surgery should be ideally performed only for therapeutic purposes (e.g., when the health benefits significantly outweigh risks). Presently, surgery for patients with indeterminate aspirates is performed for both diagnostic as well as therapeutic purposes. Results of this investigation confirm that the gene expression classifier can improve care in this regard. A benign classifier result for AUS/FLUS and FN/SFN nodules suggests that a strategy of watchful waiting can be reasonable, given a cancer risk comparable to nodules with benign cytology. Furthermore, implementation of the classifier into routine practice can also afford cost savings while increasing quality-adjusted-life-years (QALY), primarily by reducing surgical resection rates.

The overall NPV in this investigation is calculated using an unadjusted 32% prevalence of malignancy among our study cohort. This study prevalence is higher than the 20-25% cancer rate expected in the typical population. In order to achieve statistical power for computing sensitivity, as many malignant cases as possible were intentionally recruited, resulting in higher study prevalence than that typically observed in clinical practice. When these sensitivity and specificity measurements are applied to a cytologically indeterminate population with a 20-25% malignancy rate, prevalence-adjusted test NPV exceeds 95% for the overall study.

A strength of this investigation lies in the inclusion of a wide range of community and academic practice settings, geographies and patient demographics. This supports high transferability of these data into everyday patient care. As a result of the >4000 samples collected, the gene expression classifier was validated on >12 sub-types of benign and malignant thyroid neoplasms, an important feature for clinical utility across the spectrum of thyroid tumor sub-types. However, such a protocol also uncovers several immutable realities and suggests there can be a practical limit to test perfection. For example, even with histopathology analysis by leading experts in their field, initial blinded expert classifications were discordant in 14% of cases. As this analysis served as the 'gold-standard' upon which the classifier was judged, an imperfect inter-rater agreement can impact sensitivity or specificity, as pathologic assessment of benign versus malignant disease is not always absolute. More importantly, 5 of the 6 false negative PTC results occurred in samples with low signals of follicular thyroid markers that failed to demonstrate independent molecular signatures of PTC. This suggests these false negative errors are likely not related to assay performance, but rather sampling error secondary to cellular heterogeneity or FNA technical skill. Regardless, such issues have long been a part of the clinical care of patients with thyroid nodular disease, and likely are impossible to completely resolve. They serve as a confirmation of the inherent complexities in caring for patients with this illness.

In summary, this study demonstrates the ability of a novel gene expression classifier to modify the pre-operative cancer risk assessment in a population of patients where diagnostic surgery is otherwise recommended. Though each clinical decision can be individualized, these data support that a more conservative clinical approach be considered for those with indeterminate FNA cytology, and a benign gene expression classifier result. By doing so, operative intervention is targeted toward patients who receive its therapeutic benefit, while preventing unnecessary morbidity.

Supplement

Sample Collection

Prospective FNA samples from VERA001 for molecular analysis were aspirated in vivo, using either one or two passes, at outpatient clinical sites and directly placed into FNAprotect preservative solution (Qiagen, Valencia, Calif.). Samples were shipped either chilled or frozen. Temperature stability studies indicate that RNA quality and quantity are preserved with both shipping methods (Walsh et al. manuscript in preparation). Samples were stored at −80° C. upon receipt.

RNA Isolation, Amplification, and Microarray Hybridization

RNA from clinical FNAs was extracted using the AllPrep micro kit (Qiagen). The quantity of RNA was determined using a Quant-iT RNA kit (Invitrogen, Carlsbad, Calif.) and RNA quality determined using the Bioanalyzer Picochip system (Agilent Technologies, Santa Clara, Calif.) to generate a RNA integrity number (RIN). An initial randomization step was carried out to ensure all extraction batches were balanced for key clinical characteristics (gender, clinical site, local cytology diagnosis and number of passes (phase II only)). Positive (thyroid tissue lysate) and negative (water) controls were included in each RNA extraction batch and can be required to meet pre-specified quantity and quality values. Phase I samples had a median RNA concentration of 18.28 ng/μl (interquartile range [IQR]: 31.32) and a median RIN of 7.00 (IQR: 1.20). Phase II samples had a median RNA concentration of 13.13 ng/μl (IQR: 22.36) and a median RIN of 6.90 (IQR: 1.0). For phase I testing, samples with an RNA concentration ≥2 ng/μl and RIN >2 were eligible for further analysis. For phase II testing, samples with an RNA concentration ≥1.5 ng/μl and RIN >2 were eligible for further analysis. Fifteen nanograms of total RNA were amplified using the NuGEN (San Carlos, Calif.) WT Ovation amplification system (WT-Ovation FFPEv2, WT Ovation Exon module, Encore Biotin module), and 5.0 μg (phase I, Exon 1.0 ST array) or 3.5 μg (phase II, Afirma-T) of biotin-labeled cDNA was hybridized to the microarray. This was followed by washing, staining and scanning on a GeneChip Fluidics 450/Scanner 3000 7 G system for phase I samples and Gene Chip system DX v2 for phase II samples (Affymetrix, Santa Clara, Calif.) following manufacturer's protocols. An initial randomization step was carried out to ensure all amplification batches were balanced for key clinical characteristics (gender, clinical site, local cytology diagnosis and number of passes (phase II only) and RNA extraction batch). Positive (total RNA from benign and malignant thyroid tissue) and negative (water only) controls were included in each amplification batch and were required to meet cDNA yield, post-hybridization QC and classification result criteria. The Afirma-T microarray was designed using selected content from the Human Exon 1.0 ST array (Affymetrix), including probe sets required for normalization and quality control steps and manufactured as a 400-format cartridge array by Affymetrix using standard processes.

Post-Hybridization, Quality Control and Normalization

Phase I samples on the Exon array were analyzed using proprietary software (VTM 0.2.0 to process, normalize, and summarize the .CEL files. Post-hybridization quality control included assessment of the fraction of probesets detected above background at a p-value cut-off of $1 \times 10^{-4}$ of those synthesized on the Afirma-T chip (≥0.366). Phase II samples on the Afirma-T array were analyzed using proprietary software (VTM 2.1.0) to process, normalize, and summarize the .CEL files. Post-hybridization quality control included percent detection above background (pDET or DABG ≥0.21), and a house-keeping to antigenomic signal AUC for control probes (HAAUC≥0.88).

Composition of the Training Set

A previous version of the classifier has been described (Chudova et al. 2010). Additional training and feature selection was performed to generate the classifier and associated software used for this study. A description of all samples used in training is shown in Table 21. The training set for the main classifier was composed of 468 samples, including 220 tissue samples and 248 FNA samples (of those FNA samples, 165 samples were collected prospectively at the clinical sites, 69 were collected pre-operatively, and 14 were collected as post-surgical ex-vivo FNAs). Training labels were defined based on histopathology diagnosis for patients with surgically resected thyroid nodules (220 tissue samples and 160 FNA samples), and based on cytopathology diagnosis for patients with either benign or malignant cytology who did not have surgical records (85 samples benign by cytology and 3 samples malignant by cytology). All indeterminate FNA training samples had an established histopathology diagnosis. The training set was comprised of a rich variety of pathological subtypes.

TABLE 21

List of 468 samples used in the gene expression classifier training and their clinical characteristics.
Source of Samples

| Histologic Diagnosis | Banked Tissue | Ex vivo Operative FNA | Prospective Clinical FNA | Total |
|---|---|---|---|---|
| BN | 0 | 1 | 28 | 29 |
| BCA | 5 | 0 | 0 | 0 |
| CN | 0 | 0 | 8 | 8 |
| CYN | 0 | 0 | 5 | 5 |
| FA | 26 | 1 | 22 | 49 |
| FC | 19 | 1 | 2 | 22 |
| FT-UMP | 0 | 0 | 5 | 5 |
| FVPTC | 21 | 0 | 10 | 31 |
| HA | 0 | 0 | 5 | 5 |
| HC | 23 | 0 | 0 | 23 |
| LCT | 40 | 1 | 26 | 67 |
| mFVPTC | 0 | 0 | 2 | 2 |
| MLN | 0 | 0 | 1 | 1 |
| MMN | 4 | 0 | 0 | 0 |
| mPTC | 0 | 0 | 4 | 4 |
| MTC | 23 | 0 | 1 | 1 |
| NHP | 23 | 7 | 61 | 91 |
| OM | 0 | 0 | 1 | 1 |
| PTA | 5 | 0 | 0 | 0 |
| PTC | 26 | 3 | 51 | 80 |
| PTC-TCV | 0 | 0 | 1 | 1 |
| RCC | 5 | 0 | 0 | 0 |
| WDC-NOS | 0 | 0 | 1 | 1 |
| Total | 220 | 14 | 234 | 468 |

Abbreviations:
Benign nodule (BN),
breast carcinoma (BCA),
colloid nodule (CN),
cystic nodule (CYN),
follicular adenoma (FA),
follicular carcinoma (FC),
follicular tumor of uncertain malignant potential (FT-UMP),
follicular variant of papillary thyroid carcinoma (F PTC),
Hürthle cell adenoma (HA),
Hürthle cell carcinoma (HC),
lymphocytic thyroiditis (LCT),
microfollicular variant of papillary thyroid carcinoma (mFVPTC),
malignant lymph node (MLN),
melanoma (MMN),
micropapillary thyroid carcinoma (mPTC),
medullary thyroid carcinoma (MTC),
nodular hyperplasia (NHP),
other malignant (OM),
papillary thyroid adenoma (PTA),
papillary thyroid carcinoma (PTC),
tall-cell variant of papillary thyroid carcinoma (PTC-TCV),
renal cell carcinoma (RCC),
well differentiated carcinoma-not otherwise specified (WDC-NOS).

Classifier Training and Feature Selection

The main thyroid classifier is a binary classifier attempting to classify follicular cell-derived nodules as either benign or suspicious across a number of subtypes. Linear regression methods were used to merge FNA and tissue data sets for each gene when training the main classifier, using tissue versus FNA attribute as a covariate in the model. A sequential procedure for feature selection was used to identify markers differentiating individual subtypes. Limma analysis of subtype-specific expression was applied to the tissue data set (Smythe, 2005). Top markers from this tissue analysis (using p-value ranking) were included in the initial feature set. This feature set was then expanded using joint analysis of the entire training set of FNA and tissue samples. Additional features were identified as markers that provide statistically significant improvement in explaining subtype-specific differences in observed intensities after controlling for information contained in the tissue-based marker set. Markers from multiple subtypes were ranked jointly based on their relative strength (p-values and number of markers exceeding 0.1 false discovery rate threshold), and evaluated in the context of the classifier performance using nested cross-validation (as detailed below). Multiple classification methods were compared, and a support vector machine using a linear kernel function (SVM) (Vapnik, Cortes 1995) was chosen as the final classifier.

Rare Subtype Classification Via SVM-Based Cassettes

A challenge in building an FNA-based classifier to determine the potential for malignancy in any one thyroid nodule can lie in the potential heterogeneity both of cell origin as well as the path(s) to malignancy within that nodule. To address this challenge, the molecular classifier proceeds in a step-wise fashion, first applying multiple (six) cassettes before applying the final benign vs. malignant classifier. These cassettes, each a linear classifier differentiating a specific, rare subtype from the rest of the training samples, act as filters and can halt further processing of a sample if any cassette returns a 'suspicious' result. This prevents some of the rare, non-follicular cell-derived sub-types from being scored by the main thyroid classifier. These cassettes classify samples representing (1) malignant melanoma, (2) renal cell carcinoma, (3) breast carcinoma, (4) parathyroid tissue, and (5) medullary thyroid carcinoma. A final cassette (6) was also trained using Hürthle cell adenomas and carcinomas from a combination of FNAs and surgical tissue. The classifier software suite evaluates every test sample independently from all others and, as a whole, returns a result of either "Benign" or "Suspicious" for any sample passing post-hybridization QC requirements.

Performance Assessment and Model Selection

To assess performance of the models and identify a single model as the final main classifier, 60-fold cross-validation was used to estimate partial area under the ROC curve and false positive rate at a fixed false negative threshold of 5%. Partial area under the ROC curve was limited to false negative rates below 10% and false positive rates below 40%. To ensure validity of performance estimates, all three components associated with model building (linear regression for merging FNA and tissue data sets, feature selection, and classifier training) were included in the inner loop of the cross-validation procedure. In addition, nested cross-validation was used to select the cost parameter C of the linear SVM. Cross-validation was performed on the entire training set, but only FNA samples from the training set contributed to performance estimation. To ensure fair representation of subtypes within the set of FNA samples for performance evaluation, ROC curves were generated after resampling the cross-validated classifier scores proportionately to the estimated prevalence of various histopathological subtypes within the set of cytologically indeterminate FNA samples (nodular hyperplasia 28%, follicular adenoma 21%, papillary thyroid carcinoma 15%, papillary thyroid carcinoma, follicular variant 0.14%, Wirthle cell adenoma 7%, lymphocytic thyroiditis 4%, follicular carcinoma 4%, Hürthle cell carcinoma 3%, medullary thyroid carcinoma 2% (Banks et al. 2008)). Using this methodology for performance evaluation, a comparison of alternative feature selection methods and classifiers led to the selection of the linear SVM with 142 transcript clusters chosen by the feature selection method as described above for the main Benign/Suspicious classifier (Table 23). The decision cut-off value for the linear SVM was chosen that corresponded to 7% false negative error rate based on cross-validated performance, after adjustment for subtype prevalence.

Calibration of Classifier Scores between Human Exon ST 1.0 and custom Afirma-T Arrays The main classifier and cassettes were fixed after training on Human Exon ST 1.0 data, and subsequently an analytical study was carried out to characterize their performance on the custom Afirma-T arrays. The study was conducted by comparing classifier performance on a set of RNA samples processed using both systems. It was observed that the intensity signals from both systems were highly correlated. The classifier retained its predictive power on custom arrays, but indicated a small systematic shift in the score values. This enabled the same linear classifier to be used in both phases of the validation trial, after updating the decision cut-off value based on the results of the analytical study. It was also noted that small but systematic changes in the scores were associated with variability in reagent batches used to process samples; a method was implemented to calibrate specific reagent combinations. This change was implemented prior to unblinding validation study samples, and thus the entire validation process was conducted using a fully pre-specified system, including decision values.

Description of Performance on the Entire Sample Set Prior to Exclusions

As illustrated in FIG. 26, some samples were processed through the assay yielding valid gene expression classifier results, but were excluded. Samples were found that did not meet pre-specified protocol eligibility requirements for shipping time (36 samples), nodule size (1), patient age (1), cytopathology classification (1), and usage of another sample from the same patient in classifier training or analytical verification studies (2). Secondly, there were 5 nodules from which two different samples were obtained from two separate aspirations separated in time. As inclusion of both samples from a single nodule would inappropriately bias the study cohort, the repeat sampling were excluded, ensuring internal independence of all test results within the primary data set. The earlier sampling was chosen as it represents typical flow for clinical application of the test. Lastly, there was one sample for which pathology experts could not confirm which nodule was sampled for FNA. Thus matching of surgical histopathology diagnosis to the same nodule aspirated by FNA was not possible and the sample was excluded. Table 22 tabulates performance of the gene expression classifier on the full set of samples with valid classifier results to serve as a lower bound on the performance with no post-hoc exclusions.

TABLE 22

Performance of the gene expression classifier on the full set of samples with available gene expression classifier results and reference standard diagnosis (similar to intention-to-treat population). Performance across the entire data set of N = 312 indeterminate samples where both molecular test results and reference standard are available

| Test result | Malignant reference standard (N = 100) | Benign reference standard (n = 212) |
|---|---|---|
| Suspicious call | 87 | 100 |
| Benign call | 13 | 112 |
| Sensitivity | 87% | [78.8-92.9] |
| Specificity | 52.8% | [45.9-59.7] |
| PPV | 46.5% | [39.2-53.9] |
| NPV | 89.6% | [82.9-94.3] |
| Malig prev | 32.1% | |

TABLE 23

List of 167 Transcript cluster identification numbers (TCID) in the gene expression classifier and their gene annotations.

| TCID | GENE | Description |
|---|---|---|
| | | Main Classifier |
| 3450861 | ABCD2 | ATP-binding cassette, sub-family D (ALD), member 2 |
| 3341061 | ACER3 | alkaline ceramidase 3 |
| 2796553 | ACSL1 | acyl-CoA synthetase long-chain family member 1 |
| 2566848 | AFF3 | AF4/FMR2 family, member 3 |
| 3375735 | AHNAK | AHNAK nucleoprotein |
| 2439554 | AIM2 | absent in melanoma 2 |
| 2988882 | AIMP2 | aminoacyl tRNA synthetase complex-interacting multifunctional protein 2 |
| 3169331 | ALDH1B1 | aldehyde dehydrogenase 1 family, member B1 |
| 3768474 | ARSG | arylsulfatase G |
| 3214845 | ASPN | Aspirin |
| 3006572 | AUTS2 | autism susceptibility candidate 2 |
| 3902489 | BCL2L1 | BCL2-like 1 |
| 2984616 | BRP44L | brain protein 44-like |
| 2688717 | BTLA | B and T lymphocyte associated |
| 2730303 | C4orf7 | chromosome 4 open reading frame 7 |
| 2822492 | C5orf30 | chromosome 5 open reading frame 30 |
| 3259367 | CC2D2B | coiled-coil and C2 domain containing 2B |
| 3204285 | CCL19 | chemokine (C-C motif) ligand 19 |
| 3338192 | CCND1 | cyclin D1 |
| 3010503 | CD36 | CD36 molecule (thrombospondin receptor) |
| 3326635 | CD44 | CD44 molecule (Indian blood group) |
| 2326463 | CD52 | CD52 molecule |

TABLE 23-continued

List of 167 Transcript cluster identification numbers (TCID) in the gene expression classifier and their gene annotations.

| TCID | GENE | Description |
|---|---|---|
| 2635741 | CD96 | CD96 molecule |
| 2373336 | CFH | complement factor H |
| 2373336 | CFHR1 | complement factor H-related 1 |
| 2710599 | CLDN1 | claudin 1 |
| 2657808 | CLDN16 | claudin 16 |
| 2750627 | CPE | carboxypeptidase E |
| 2377283 | CR2 | complement component (3d/Epstein Barr virus) receptor 2 |
| 3242353 | CREM | cAMP responsive element modulator |
| 2490351 | CTNNA2 | catenin (cadherin-associated protein), alpha 2 |
| 2732508 | CXCL13 | chemokine (C—X—C motif) ligand 13 |
| 3042001 | CYCS | cytochrome c, somatic |
| 2854445 | DAB2 | disabled homolog 2, mitogen-responsive phosphoprotein (*Drosophila*) |
| 2321911 | DDI2 | DNA-damage inducible 1 homolog 2 (*S. cerevisiae*) |
| 3122678 | DEFB1 | defensin, beta 1 |
| 2642791 | DNAJC13 | DnaJ (Hsp40) homolog, subfamily C, member 13 |
| 2584018 | DPP4 | dipeptidyl-peptidase 4 |
| 3032647 | DPP6 | dipeptidyl-peptidase 6 |
| 2981874 | DYNLT1 | dynein, light chain, Tctex-type 1 |
| 2638676 | EAF2 | ELL associated factor 2 |
| 2739308 | EGF | epidermal growth factor |
| 2988882 | EIF2AK1 | eukaryotic translation initiation factor 2-alpha kinase 1 |
| 3852832 | EMR3 | egf-like module containing, mucin-like, hormone receptor-like 3 |
| 3142381 | FABP4 | fatty acid binding protein 4, adipocyte |
| 3603932 | FAH | fumarylacetoacetate hydrolase (fumarylacetoacetase) |
| 2396750 | FBXO2 | F-box protein 2 |
| 2396750 | FBXO44 | F-box protein 44 |
| 2526806 | FN1 | fibronectin 1 |
| 2598261 | FN1 | fibronectin 1 |
| 3839910 | FPR2 | formyl peptide receptor 2 |
| 3486096 | FREM2 | FRAS1 related extracellular matrix protein 2 |
| 2970897 | FRK | fyn-related kinase |
| 3212008 | FRMD3 | FERM domain containing 3 |
| 3393479 | FXYD6 | FXYD domain containing ion transport regulator 6 |
| 2378068 | G0S2 | G0/G1switch 2 |
| 2884845 | GABRB2 | gamma-aminobutyric acid (GABA) A receptor, beta 2 |
| 3063795 | GAL3ST4 | galactose-3-O-sulfotransferase 4 |
| 3031556 | GIMAP2 | GTPase, IMAP family member 2 |
| 3861948 | GMFG | glia maturation factor, gamma |
| 3302990 | GOT1 | glutamic-oxaloacetic transaminase 1, soluble (aspartate aminotransferase 1) |
| 3540862 | GPHN | Gephyrin |
| 3982612 | GPR174 | G protein-coupled receptor 174 |
| 2809793 | GZMK | granzyme K (granzyme 3; tryptase II) |
| 2638676 | HCG11 | HLA complex group 11 |
| 3417703 | HSD17B6 | hydroxysteroid (17-beta) dehydrogenase 6 homolog (mouse) |
| 2877508 | HSPA9 | heat shock 70 kDa protein 9 (mortalin) |
| 2708922 | IGF2BP2 | insulin-like growth factor 2 mRNA binding protein 2 |
| 3375735 | IGHG1 | immunoglobulin heavy constant gamma 1 (G1m marker) |
| 2806468 | IL7R | interleukin 7 receptor |
| 2604998 | IQCA1 | IQ motif containing with AAA domain 1 |
| 3852832 | ITGB1 | integrin, beta 1 (fibronectin receptor, beta polypeptide, antigen CD29 includes MDF2, MSK12) |
| 3724545 | ITGB3 | integrin, beta 3 (platelet glycoprotein IIIa, antigen CD61) |
| 2427619 | KCNA3 | potassium voltage-gated channel, shaker-related subfamily, member 3 |
| 3397774 | KCNJ1 | potassium inwardly-rectifying channel, subfamily J, member 1 |
| 3404030 | KLRG1 | killer cell lectin-like receptor subfamily G, member 1 |
| 3512874 | LCP1 | lymphocyte cytosolic protein 1 (L-plastin) |
| 2708855 | LIPH | lipase, member H |
| 3875642 | LOC100131599 | hypothetical protein LOC100131599 |
| 2526806 | LOC100507488 | histone demethylase UTY-like |
| 2638676 | LOC647979 | hypothetical LOC647979 |
| 3147985 | LRP12 | low density lipoprotein receptor-related protein 12 |
| 2578790 | LRP1B | low density lipoprotein receptor-related protein 1B |
| 2352609 | MAGI3 | membrane associated guanylate kinase, WW and PDZ domain containing 3 |
| 3111561 | MAPK6 | mitogen-activated protein kinase 6 |
| 3108526 | MATN2 | matrilin 2 |
| 3009299 | MDH2 | malate dehydrogenase 2, NAD (mitochondrial) |
| 3329343 | MDK | midkine (neurite growth-promoting factor 2) |
| 3768474 | MIR635 | microRNA 635 |
| 3367673 | MPPED2 | metallophosphoesterase domain containing 2 |
| 3662201 | MT1F | metallothionein 1F |
| 3692999 | MT1G | metallothionein 1G |
| 3662201 | MT1H | metallothionein 1H |
| 3622934 | MYEF2 | myelin expression factor 2 |

TABLE 23-continued

List of 167 Transcript cluster identification numbers (TCID)
in the gene expression classifier and their gene annotations.

| TCID | GENE | Description |
|---|---|---|
| 3341497 | NDUFC2 | NADH dehydrogenase (ubiquinone) 1, subcomplex unknown, 2, 14.5 kDa |
| 3067478 | NRCAM | neuronal cell adhesion molecule |
| 3654699 | NUPR1 | nuclear protein, transcriptional regulator, 1 |
| 4020655 | ODZ1 | odz, odd Oz/ten-m homolog 1(Drosophila) |
| 3353914 | OR10D1P | olfactory receptor, family 10, subfamily D, member 1 pseudogene |
| 3982560 | P2RY10 | purinergic receptor P2Y, G-protein coupled, 10 |
| 2701071 | P2RY13 | purinergic receptor P2Y, G-protein coupled, 13 |
| 3948047 | PARVG | parvin, gamma |
| 3606034 | PDE8A | phosphodiesterase 8A |
| 3970833 | PDHA1 | pyruvate dehydrogenase (lipoamide) alpha 1 |
| 2377094 | PFKFB2 | 6-phosphofructo-2-kinase/fructose-2,6-biphosphatase 2 |
| 3278198 | PHYH | phytanoyl-CoA 2-hydroxylase |
| 3811086 | PIGN | phosphatidylinositol glycan anchor biosynthesis, class N |
| 3744680 | PIK3R5 | phosphoinositide-3-kinase, regulatory subunit 5 |
| 3111561 | PKHD1L1 | polycystic kidney and hepatic disease 1 (autosomal recessive)-like 1 |
| 3376529 | PLA2G16 | phospholipase A2, group XVI |
| 3875642 | PLCB1 | phospholipase C, beta 1 (phosphoinositide-specific) |
| 2486811 | PLEK | Pleckstrin |
| 2880051 | PPP2R2B | protein phosphatase 2, regulatory subunit B, beta |
| 3246888 | PRKG1 | protein kinase, cGMP-dependent, type I |
| 3874751 | PRNP | prion protein |
| 2685304 | PROS1 | protein S (alpha) |
| 2373842 | PTPRC | protein tyrosine phosphatase, receptor type, C |
| 3270270 | PTPRE | protein tyrosine phosphatase, receptor type, E |
| 3959862 | PVALB | Parvalbumin |
| 2688499 | PVRL2 | poliovirus receptor-related 2 (herpesvirus entry mediator B) |
| 3564210 | PYGL | phosphorylase, glycogen, liver |
| 2362351 | PYHIN1 | pyrin and HIN domain family, member 1 |
| 3443464 | PZP | pregnancy-zone protein |
| 2372812 | RGS13 | regulator of G-protein signaling 13 |
| 3110395 | RIMS2 | regulating synaptic membrane exocytosis 2 |
| 3895795 | RNF24 | ring finger protein 24 |
| 2964231 | RRAGD | Ras-related GTP binding D |
| 2442008 | RXRG | retinoid X receptor, gamma |
| 3494629 | SCEL | Sciellin |
| 2904485 | SCUBE3 | signal peptide, CUB domain, EGF-like 3 |
| 2798538 | SDHA | succinate dehydrogenase complex, subunit A, flavoprotein (Fp) |
| 3059667 | SEMA3D | sema domain, immunoglobulin domain (Ig), short basic domain, secreted, (semaphorin) 3D |
| 3365136 | SERGEF | secretion regulating guanine nucleotide exchange factor |
| 3577612 | SERPINA1 | serpin peptidase inhibitor, Glade A (alpha-1 antiproteinase, antitrypsin), member 1 |
| 3577612 | SERPINA2 | serpin peptidase inhibitor, Glade A (alpha-1 antiproteinase, antitrypsin), member 2 |
| 2440258 | SLAMF6 | SLAM family member 6 |
| 2428501 | SLC16A1 | solute carrier family 16, member 1 (monocarboxylic acid transporter 1) |
| 3622934 | SLC24A5 | solute carrier family 24, member 5 |
| 3185522 | SLC31A1 | solute carrier family 31 (copper transporters), member 1 |
| 2721959 | SLC34A2 | solute carrier family 34 (sodium phosphate), member 2 |
| 3761959 | SLC35B1 | solute carrier family 35, member B1 |
| 3373845 | SLC43A3 | solute carrier family 43, member 3 |
| 3759006 | SLC4A1 | solute carrier family 4, anion exchanger, member 1 (erythrocyte membrane protein band 3, Diego blood group) |
| 2730746 | SLC4A4 | solute carrier family 4, sodium bicarbonate cotransporter, member 4 |
| 2777714 | SNCA | synuclein, alpha (non A4 component of amyloid precursor) |
| 2877508 | SNORD63 | small nucleolar RNA, C/D box 63 |
| 2562529 | ST3GAL5 | ST3 beta-galactoside alpha-2,3-sialyltransferase 5 |
| 2834282 | STK32A | serine/threonine kinase 32A |
| 3341497 | THRSP | thyroid hormone responsive |
| 3976341 | TIMP1 | TIMP metallopeptidase inhibitor 1 |
| 3772661 | TIMP2 | TIMP metallopeptidase inhibitor 2 |
| 2491271 | TMSB10 | thymosin beta 10 |
| 3648391 | TNFRSF17 | tumor necrosis factor receptor superfamily, member 17 |
| 3441849 | TNFRSF1A | tumor necrosis factor receptor superfamily, member IA |
| 2412668 | TXNDC12 | thioredoxin domain containing 12 (endoplasmic reticulum) |
| 4027585 | unknown | |
| 3353914 | VWA5A | von Willebrand factor A domain containing 5A |
| 3976766 | WAS | Wiskott-Aldrich syndrome (eczema-thrombocytopenia) |
| 3768474 | WIPI1 | WD repeat domain, phosphoinositide interacting 1 |
| 2688499 | ZBED2 | zinc finger, BED-type containing 2 |
| 2817731 | ZFYVE16 | zinc finger, FYVE domain containing 16 |

TABLE 23-continued

List of 167 Transcript cluster identification numbers (TCID)
in the gene expression classifier and their gene annotations.

| TCID | GENE | Description |
|---|---|---|
| \multicolumn{3}{c}{Medullary Carcinoma Cassette} | | |
| 3364127 | CALCA | calcitonin-related polypeptide alpha |
| 3834341 | CEACAM5 | carcinoembryonic antigen-related cell adhesion molecule 5 |
| 3594003 | SCG3 | secretogranin III |
| 2585400 | SCN9A | sodium channel, voltage-gated, type DC, alpha subunit |
| 3805614 | SYT4 | synaptotagmin IV |
| \multicolumn{3}{c}{Renal Carcinoma Cassette} | | |
| 2923928 | FABP7 | fatty acid binding protein 7, brain |
| 3393446 | FXYD2 | FXYD domain containing ion transport regulator 2 |
| 2883317 | HAVCR1 | hepatitis A virus cellular receptor 1 |
| 2883317 | LOC100101266 | hepatitis A virus cellular receptor 1 pseudogene |
| 3428225 | NR1H4 | nuclear receptor subfamily 1, group H, member 4 |
| 2479698 | PREPL | prolyl endopeptidase-like |
| 2479698 | SLC3A1 | solute carrier family 3 (cystine, dibasic and neutral amino acid transporters, activator of cystine, dibasic and neutral amino acid transport), member 1 |
| \multicolumn{3}{c}{Parathyroid Cassette} | | |
| 3159754 | DMRT2 | doublesex and mab-3 related transcription factor 2 |
| 2941690 | GCM2 | glial cells missing homolog 2 (Drosophila) |
| 3363686 | ICIDINS220 | kinase D-interacting substrate, 220 kDa |
| 3484895 | KL | klotho |
| 3363686 | PTH | parathyroid hormone |
| 2894790 | SYCP2L | synaptonemal complex protein 2-like |
| 2894790 | TMEM14B | transmembrane protein 14B |
| \multicolumn{3}{c}{Breast Carcinoma Cassette} | | |
| 3039830 | AGR3 | anterior gradient homolog 3 (Xenopus laevis) |
| 3264997 | C10orf81 | chromosome 10 open reading frame 81 |
| 2926802 | MYB | v-myb myeloblastosis viral oncogene homolog (avian) |
| 3912079 | SYCP2 | synaptonemal complex protein 2 |
| 2430163 | VTCN1 | V-set domain containing T cell activation inhibitor 1 |
| \multicolumn{3}{c}{Melanoma Cassette} | | |
| 3811949 | CDH19 | cadherin 19, type 2 |
| 3161261 | MLANA | melan-A |
| 3935486 | S100B | S100 calcium binding protein B |
| 3457336 | SILV | silver homolog (mouse) |
| 3343832 | TYR | tyrosinase (oculocutaneous albinism IA) |
| 3343832 | TYRL | tyrosinase-like (pseudogene) |
| \multicolumn{3}{c}{Hürthle Cassette} | | |
| 2566848 | AFF3 | AF4/FMR2 family, member 3 |
| 2988882 | AIMP2 | aminoacyl tRNA synthetase complex-interacting multifunctional protein 2 |
| 3169331 | ALDH1B1 | aldehyde dehydrogenase 1 family, member B1 |
| 2984616 | BRP44L | brain protein 44-like |
| 2822492 | C5orf30 | chromosome 5 open reading frame 30 |
| 3326635 | CD44 | CD44 molecule (Indian blood group) |
| 2750627 | CPE | carboxypeptidase E |
| 3042001 | CYCS | cytochrome c, somatic |
| 3122678 | DEFB1 | defensin, beta 1 |
| 2739308 | EGF | epidermal growth factor |
| 2988882 | EIF2AK1 | eukaryotic translation initiation factor 2-alpha kinase 1 |
| 3603932 | FAH | fumarylacetoacetate hydrolase (fumarylacetoacetase) |
| 2970897 | FRK | fyn-related kinase |
| 3212008 | FRMD3 | FERM domain containing 3 |
| 3302990 | GOT1 | glutamic-oxaloacetic transaminase 1, soluble (aspartate aminotransferase 1) |
| 3417703 | HSD17B6 | hydroxysteroid (17-beta) dehydrogenase 6 homolog (mouse) |
| 2877508 | HSPA9 | heat shock 70 kDa protein 9 (mortalin) |
| 2708922 | IGF2BP2 | insulin-like growth factor 2 mRNA binding protein 2 |
| 2604998 | IQCA1 | IQ motif containing with AAA domain 1 |
| 3724545 | ITGB3 | integrin, beta 3 (platelet glycoprotein IIIa, antigen CD61) |
| 3397774 | KCNJ1 | potassium inwardly-rectifying channel, subfamily J, member 1 |
| 3009299 | MDH2 | malate dehydrogenase 2, NAD (mitochondrial) |
| 3654699 | NUPR1 | nuclear protein, transcriptional regulator, 1 |
| 4020655 | ODZ1 | odz, odd Oz/ten-m homolog 1 (Drosophila) |
| 3970833 | PDHA1 | pyruvate dehydrogenase (lipoamide) alpha 1 |
| 2377094 | PFKFB2 | 6-phosphofructo-2-kinase/fructose-2,6-biphosphatase 2 |
| 3278198 | PHYH | phytanoyl-CoA 2-hydroxylase |
| 2880051 | PPP2R2B | protein phosphatase 2, regulatory subunit B, beta |
| 3959862 | PVALB | parvalbumin |

TABLE 23-continued

List of 167 Transcript cluster identification numbers (TCID) in the gene expression classifier and their gene annotations.

| TCID | GENE | Description |
|---|---|---|
| 2688499 | PVRL2 | poliovirus receptor-related 2 (herpesvirus entry mediator B) |
| 2964231 | RRAGD | Ras-related GTP binding D |
| 2798538 | SDHA | succinate dehydrogenase complex, subunit A, flavoprotein (Fp) |
| 2428501 | SLC16A1 | solute carrier family 16, member 1 (monocarboxylic acid transporter 1) |
| 2877508 | SNORD63 | small nucleolar RNA, C/D box 63 |
| 2562529 | ST3GAL5 | ST3 beta-galactoside alpha-2,3-sialyltransferase 5 |
| 2688499 | ZBED2 | zinc finger, BED-type containing 2 |
| | | Additional Genes Analyzed |
| 3116614 | TG | |
| 3415320 | KRT7 | |
| 3757108 | KRT19 | |
| 4012178 | CITED1 | |
| 3546213 | TSHR | |
| 3561381 | TFF1 | |

TABLE 24

Distribution of indeterminate study samples by collection site and histopathology diagnosis.

| Site number | Site type (Community vs. Academic) | Total samples | % of Total | Benign (#) | Malignant (#) | Malignancy rate |
|---|---|---|---|---|---|---|
| 1 | Community | 35 | 13.20 | 20 | 15 | 43% |
| 2 | Community | 18 | 6.80% | 12 | 6 | 33% |
| 3 | Community | 16 | 6% | 7 | 9 | 56% |
| 4 | Community | 14 | 5.30% | 7 | 7 | 50% |
| 5 | Community | 11 | 4.10% | 6 | 5 | 46% |
| 6 | Community | 10 | 3.80% | 10 | 0 | 0% |
| 7 | Community | 7 | 2.60% | 4 | 3 | 43% |
| 8 | Community | 7 | 2.60% | 7 | 0 | 0% |
| 9 | Community | 5 | 1.90% | 3 | 2 | 40% |
| 10 | Community | 4 | 1.50% | 3 | 1 | 25% |
| 11 | Community | 4 | 1.50% | 2 | 2 | 50% |
| 12 | Community | 4 | 1.50% | 3 | 1 | 25% |
| 13 | Community | 4 | 1.50% | 2 | 2 | 50% |
| 14 | Community | 4 | 1.50% | 2 | 2 | 50% |
| 15 | Community | 3 | 1.10% | 2 | 1 | 33% |
| 16 | Community | 2 | 0.80% | 1 | 1 | 50% |
| 17 | Community | 2 | 0.80% | 2 | 0 | 0% |
| 18 | Community | 2 | 0.80% | 1 | 1 | 50% |
| 19 | Community | 2 | 0.80% | 2 | 0 | 0% |
| 20 | Community | 2 | 0.80% | 1 | 1 | 50% |
| 21 | Community | 2 | 0.80% | 1 | 1 | 50% |
| 22 | Community | 2 | 0.80% | 2 | 0 | 0% |
| 23 | Community | 2 | 0.80% | 1 | 1 | 50% |
| 24 | Community | 2 | 0.80% | 2 | 0 | 0% |
| 25 | Community | 2 | 0.80% | 2 | 0 | 0% |
| 26 | Community | 2 | 0.80% | 1 | 1 | 50% |
| 27 | Community | 1 | 0.40% | 0 | 1 | 100% |
| 28 | Community | 1 | 0.40% | 0 | 1 | 100% |
| 29 | Community | 1 | 0.40% | 0 | 1 | 100% |
| 30 | Community | 1 | 0.40% | 0 | 1 | 100% |
| 31 | Community | 1 | 0.40% | 1 | 0 | 0% |
| 32 | Academic | 48 | 18% | 39 | 9 | 19% |
| 33 | Academic | 11 | 4.10% | 8 | 3 | 27% |
| 34 | Academic | 8 | 3% | 6 | 2 | 25% |
| 35 | Academic | 7 | 2.60% | 5 | 2 | 29% |
| 36 | Academic | 6 | 2.30% | 5 | 1 | 17% |
| 37 | Academic | 4 | 1.50% | 3 | 1 | 25% |
| 38 | Academic | 3 | 1.10% | 2 | 1 | 33% |
| 39 | Academic | 2 | 0.80% | 1 | 1 | 50% |
| 40 | Academic | 1 | 0.40% | 1 | 0 | 0% |
| 41 | Academic | 1 | 0.40% | 1 | 0 | 0% |
| 42 | Academic | 1 | 0.40% | 1 | 0 | 0% |
| 43 | Academic | 1 | 0.40% | 1 | 0 | 0% |

Tables 25-52 contain the normalized intensity of microarray data for the samples analyzed. The normalized intensity data for an individual sample across all TCIDs examined is organized in a single column. The genes associated with the TCIDs enumerated in the left-most column of Tables 25-52 can be found in Table 23.

TABLE 25

Normalized intensity of microarray data for a set of samples.

| TCID | V01 0001 | V01 0002 | V01 0003 | V01 0004 | V01 0005 | V01 0006 | V01 0007 | V01 0008 | V01 0009 | V01 0010 | V01 0011 | V01 0012 |
|---|---|---|---|---|---|---|---|---|---|---|---|---|
| 2604998 | 7.90 | 9.13 | 9.15 | 7.29 | 7.48 | 4.97 | 7.86 | 8.30 | 5.40 | 8.56 | 7.71 | 8.46 |
| 3603932 | 6.71 | 7.04 | 7.39 | 8.10 | 7.47 | 6.94 | 8.12 | 9.02 | 8.24 | 8.23 | 6.67 | 7.27 |
| 2710599 | 6.95 | 8.47 | 11.45 | 6.30 | 10.13 | 5.51 | 7.94 | 7.13 | 10.32 | 11.95 | 11.40 | 11.61 |
| 2440258 | 8.26 | 6.76 | 5.67 | 8.28 | 6.96 | 9.39 | 7.41 | 5.89 | 7.57 | 6.87 | 8.58 | 7.98 |
| 3169331 | 6.99 | 7.33 | 6.71 | 7.65 | 6.98 | 6.27 | 6.86 | 10.10 | 6.97 | 7.10 | 6.78 | 7.03 |
| 2988882 | 9.81 | 9.74 | 9.78 | 10.07 | 10.16 | 9.59 | 9.71 | 11.12 | 10.45 | 9.45 | 9.80 | 9.68 |
| 2964231 | 8.58 | 8.27 | 9.21 | 9.67 | 8.77 | 8.70 | 9.93 | 10.70 | 9.57 | 10.26 | 8.81 | 8.20 |
| 3111561 | 10.53 | 7.10 | 6.97 | 7.76 | 9.49 | 6.04 | 10.47 | 6.02 | 8.02 | 4.61 | 4.80 | 6.06 |
| 2562529 | 9.13 | 10.11 | 10.88 | 8.25 | 8.64 | 8.66 | 9.72 | 9.25 | 8.88 | 10.47 | 10.07 | 10.95 |
| 3692999 | 12.59 | 9.10 | 9.92 | 11.56 | 11.89 | 6.65 | 11.69 | 11.63 | 6.62 | 9.38 | 7.82 | 7.26 |
| 2439554 | 6.83 | 6.63 | 5.45 | 6.70 | 6.57 | 9.04 | 6.22 | 5.53 | 6.87 | 5.81 | 7.88 | 8.01 |
| 2685304 | 7.45 | 8.37 | 11.47 | 8.17 | 9.30 | 7.45 | 8.48 | 7.83 | 7.53 | 11.26 | 11.30 | 11.11 |
| 2578790 | 7.17 | 6.77 | 4.22 | 4.79 | 6.56 | 6.82 | 4.39 | 4.50 | 6.28 | 4.57 | 5.08 | 4.08 | 4.37 |
| 2373842 | 11.87 | 10.97 | 9.07 | 11.98 | 11.44 | 12.22 | 10.77 | 10.14 | 11.80 | 10.32 | 11.21 | 10.40 |
| 2750627 | 9.56 | 10.46 | 10.47 | 6.13 | 8.69 | 5.81 | 9.94 | 6.59 | 7.17 | 8.53 | 8.92 | 10.88 |
| 3397774 | 4.46 | 4.82 | 4.84 | 7.88 | 4.64 | 5.08 | 4.48 | 10.35 | 5.54 | 8.49 | 4.61 | 4.71 |
| 2635741 | 8.61 | 7.53 | 6.28 | 8.69 | 7.35 | 9.32 | 7.04 | 6.51 | 8.42 | 7.54 | 8.95 | 7.82 |
| 3970833 | 9.69 | 10.12 | 9.80 | 10.13 | 9.46 | 9.21 | 9.73 | 11.33 | 10.20 | 10.12 | 9.53 | 9.73 |
| 3577612 | 11.07 | 10.42 | 11.77 | 10.89 | 11.08 | 11.54 | 9.76 | 9.74 | 10.84 | 11.61 | 11.71 | 11.91 |
| 2708922 | 8.65 | 8.19 | 8.14 | 9.34 | 8.38 | 8.91 | 7.96 | 6.58 | 7.67 | 7.75 | 8.07 | 7.84 |
| 2970897 | 5.07 | 5.55 | 4.68 | 6.68 | 6.03 | 4.93 | 5.54 | 8.51 | 6.90 | 5.16 | 4.82 | 4.42 |
| 3724545 | 9.65 | 9.57 | 9.33 | 9.62 | 9.94 | 9.38 | 9.10 | 6.89 | 9.85 | 9.33 | 9.47 | 9.32 |
| 2798538 | 9.65 | 8.69 | 8.94 | 8.83 | 9.30 | 9.31 | 9.32 | 10.85 | 9.15 | 9.26 | 9.11 | 8.97 |
| 2806468 | 11.64 | 10.03 | 8.73 | 11.47 | 10.63 | 11.84 | 9.97 | 8.81 | 10.88 | 9.65 | 11.23 | 9.80 |
| 2880051 | 6.11 | 6.18 | 5.77 | 6.91 | 6.71 | 6.62 | 5.89 | 7.47 | 7.15 | 6.28 | 5.78 | 6.15 |
| 2732508 | 3.49 | 3.52 | 3.23 | 3.84 | 3.93 | 4.65 | 3.21 | 4.21 | 3.64 | 5.00 | 7.98 | 8.35 |
| 2822492 | 5.29 | 6.20 | 5.38 | 5.84 | 5.93 | 5.83 | 6.27 | 7.76 | 6.12 | 5.81 | 5.15 | 4.84 |
| 3404030 | 8.24 | 7.29 | 5.89 | 8.08 | 6.85 | 8.53 | 7.72 | 6.14 | 8.82 | 6.38 | 7.71 | 6.78 |
| 3059667 | 10.41 | 6.17 | 6.62 | 5.10 | 8.53 | 5.49 | 10.49 | 4.08 | 5.12 | 5.10 | 4.80 | 7.61 |
| 3108526 | 10.79 | 8.59 | 9.77 | 8.84 | 9.34 | 5.88 | 9.62 | 10.90 | 8.12 | 9.66 | 7.10 | 8.47 |
| 2526806 | 8.27 | 9.01 | 12.76 | 10.78 | 12.89 | 7.59 | 11.64 | 9.79 | 6.03 | 12.63 | 13.00 | 12.59 |
| 2428501 | 7.17 | 5.85 | 7.98 | 7.74 | 8.00 | 7.63 | 7.31 | 8.73 | 8.77 | 7.84 | 7.34 | 6.83 |
| 2657808 | 5.31 | 9.41 | 11.81 | 6.15 | 6.89 | 5.66 | 6.93 | 5.42 | 6.45 | 11.56 | 11.09 | 11.41 |
| 2584018 | 7.75 | 7.79 | 10.58 | 7.73 | 9.24 | 8.56 | 10.10 | 6.24 | 7.13 | 10.87 | 10.63 | 7.66 |
| 3976341 | 9.39 | 9.81 | 11.15 | 9.55 | 9.86 | 10.59 | 9.58 | 8.81 | 9.81 | 10.61 | 11.47 | 12.41 |
| 2739308 | 4.98 | 5.66 | 4.61 | 6.00 | 4.75 | 5.89 | 4.53 | 6.60 | 6.92 | 4.94 | 4.23 | 4.37 |
| 3959862 | 4.28 | 5.81 | 3.84 | 8.24 | 4.63 | 5.59 | 5.37 | 11.81 | 5.92 | 7.89 | 4.50 | 4.42 |
| 2362351 | 7.70 | 6.31 | 5.91 | 7.34 | 6.86 | 8.26 | 6.93 | 6.10 | 7.96 | 6.41 | 7.48 | 7.00 |
| 3648391 | 5.42 | 4.65 | 3.88 | 4.74 | 3.85 | 8.83 | 3.75 | 4.54 | 6.48 | 6.47 | 7.71 | 7.16 |
| 3009299 | 10.62 | 11.21 | 10.52 | 11.04 | 10.66 | 10.59 | 10.85 | 12.18 | 11.12 | 11.07 | 10.67 | 10.51 |
| 3443464 | 5.39 | 5.57 | 5.07 | 5.88 | 5.57 | 5.64 | 5.37 | 5.55 | 6.45 | 5.15 | 5.48 | 5.19 |
| 2730746 | 8.39 | 8.64 | 6.35 | 7.43 | 7.14 | 5.63 | 8.24 | 9.75 | 6.14 | 8.06 | 5.08 | 5.63 |
| 2427619 | 8.88 | 7.51 | 5.89 | 9.26 | 7.22 | 10.30 | 7.29 | 6.73 | 8.09 | 7.52 | 8.65 | 7.58 |
| 3042001 | 8.41 | 8.92 | 8.48 | 9.37 | 8.93 | 8.89 | 8.71 | 11.18 | 9.57 | 9.00 | 8.36 | 8.51 |
| 2566848 | 5.32 | 5.24 | 4.81 | 5.98 | 5.35 | 6.45 | 4.99 | 5.74 | 6.27 | 4.78 | 6.05 | 5.17 |
| 2984616 | 8.75 | 9.20 | 8.91 | 9.59 | 8.76 | 8.56 | 9.10 | 11.10 | 10.39 | 9.43 | 9.08 | 9.29 |
| 2378068 | 6.91 | 7.59 | 8.46 | 7.88 | 6.67 | 7.79 | 8.24 | 8.86 | 10.48 | 9.70 | 8.79 | 8.79 |
| 2721959 | 6.95 | 7.21 | 12.80 | 6.09 | 9.46 | 5.82 | 6.84 | 6.20 | 6.02 | 12.28 | 12.76 | 11.20 |
| 2877508 | 10.51 | 10.20 | 10.45 | 10.70 | 10.31 | 9.92 | 10.64 | 11.33 | 11.30 | 10.80 | 10.35 | 10.13 |
| 3450861 | 6.90 | 5.73 | 4.66 | 6.58 | 5.61 | 7.41 | 4.74 | 4.42 | 6.12 | 5.42 | 5.76 | 5.59 |
| 2688717 | 9.48 | 7.89 | 5.78 | 9.36 | 7.30 | 10.60 | 6.39 | 6.13 | 8.06 | 7.63 | 9.95 | 9.02 |
| 3270270 | 9.16 | 8.15 | 8.50 | 9.03 | 8.59 | 10.04 | 8.38 | 7.46 | 8.55 | 8.03 | 8.79 | 8.32 |
| 3417703 | 9.36 | 4.54 | 9.94 | 4.78 | 5.29 | 5.53 | 10.29 | 5.36 | 4.73 | 4.45 | 6.42 | 7.08 |
| 3302990 | 7.26 | 7.98 | 7.87 | 8.92 | 7.54 | 7.00 | 7.81 | 10.82 | 10.34 | 8.48 | 7.36 | 7.68 |
| 2377283 | 4.67 | 4.35 | 3.99 | 5.42 | 5.01 | 6.35 | 4.23 | 4.55 | 4.50 | 4.48 | 8.87 | 7.97 |
| 3122678 | 4.59 | 4.40 | 4.47 | 8.95 | 5.05 | 4.83 | 4.53 | 8.40 | 6.80 | 5.99 | 4.98 | 3.99 |
| 2688499 | 9.20 | 8.71 | 11.02 | 7.74 | 8.11 | 7.28 | 9.43 | 6.23 | 7.79 | 8.32 | 9.16 | 10.21 |
| 2377094 | 9.04 | 8.95 | 8.87 | 9.60 | 8.64 | 7.67 | 9.44 | 11.02 | 9.25 | 9.91 | 8.30 | 8.32 |
| 3278198 | 8.35 | 8.43 | 8.69 | 9.10 | 8.02 | 6.98 | 8.59 | 10.26 | 8.58 | 8.97 | 7.92 | 8.08 |
| 2598261 | 7.84 | 8.37 | 12.76 | 9.95 | 12.37 | 7.00 | 11.08 | 9.21 | 6.27 | 12.46 | 13.05 | 12.28 |
| 3982612 | 9.67 | 7.52 | 7.26 | 8.80 | 8.00 | 10.24 | 7.23 | 6.60 | 7.73 | 8.03 | 9.96 | 9.19 |
| 2884845 | 4.48 | 4.96 | 10.09 | 4.65 | 4.96 | 5.10 | 4.91 | 5.11 | 5.17 | 10.00 | 8.99 | 9.02 |
| 3982560 | 7.40 | 5.96 | 4.84 | 7.61 | 6.18 | 8.46 | 6.03 | 5.45 | 6.38 | 5.63 | 7.69 | 7.15 |
| 3204285 | 5.09 | 5.49 | 5.10 | 5.49 | 6.06 | 5.96 | 5.02 | 5.69 | 6.18 | 5.97 | 10.11 | 8.01 |
| 3654699 | 11.60 | 9.97 | 10.93 | 12.01 | 12.12 | 7.54 | 12.28 | 12.53 | 12.10 | 12.01 | 11.46 | 10.01 |
| 2638676 | 7.42 | 6.25 | 6.22 | 7.38 | 7.90 | 8.63 | 6.85 | 5.36 | 7.11 | 7.16 | 9.10 | 8.36 |
| 3367673 | 8.66 | 8.92 | 6.40 | 7.10 | 8.18 | 4.48 | 8.53 | 9.24 | 5.15 | 7.20 | 4.63 | 5.28 |
| 3212008 | 6.55 | 9.92 | 9.17 | 6.46 | 6.03 | 6.93 | 6.93 | 5.76 | 6.48 | 6.76 | 6.92 | 9.63 |
| 3326635 | 10.21 | 10.45 | 9.80 | 10.25 | 10.17 | 10.41 | 10.33 | 9.44 | 10.07 | 10.12 | 10.24 | 10.34 |
| 3031556 | 9.93 | 8.30 | 7.17 | 10.08 | 9.20 | 10.28 | 8.85 | 7.12 | 9.88 | 8.36 | 9.76 | 8.80 |

TABLE 25-continued

Normalized intensity of microarray data for a set of samples.

| TCID | V01 0001 | V01 0002 | V01 0003 | V01 0004 | V01 0005 | V01 0006 | V01 0007 | V01 0008 | V01 0009 | V01 0010 | V01 0011 | V01 0012 |
|---|---|---|---|---|---|---|---|---|---|---|---|---|
| 3662201 | 12.58 | 9.44 | 9.82 | 10.70 | 11.58 | 7.64 | 11.58 | 11.79 | 7.16 | 7.93 | 8.52 | 7.97 |
| 2809793 | 8.85 | 6.67 | 6.83 | 8.36 | 7.05 | 9.87 | 7.22 | 6.09 | 8.67 | 6.56 | 9.40 | 8.75 |
| 2817731 | 7.93 | 7.83 | 7.89 | 7.44 | 7.77 | 8.71 | 8.73 | 7.47 | 7.66 | 7.38 | 7.63 | 7.35 |
| 4020655 | 4.96 | 8.51 | 7.29 | 5.01 | 4.70 | 5.29 | 5.44 | 4.66 | 5.76 | 7.77 | 6.46 | 7.41 |
| 3494629 | 4.72 | 5.07 | 8.35 | 4.73 | 4.88 | 4.43 | 4.42 | 5.90 | 7.55 | 9.22 | 8.09 | 7.40 |
| 3852832 | 10.13 | 8.95 | 5.75 | 9.85 | 9.08 | 10.62 | 7.39 | 7.54 | 8.45 | 7.14 | 6.99 | 5.34 |
| 3761959 | 9.26 | 9.64 | 9.17 | 8.70 | 9.28 | 8.74 | 9.69 | 9.77 | 8.83 | 9.11 | 9.08 | 9.47 |
| 2834282 | 5.91 | 7.96 | 9.16 | 6.67 | 6.50 | 5.92 | 5.95 | 7.35 | 8.82 | 7.53 | 7.83 | 8.03 |
| 3341497 | 5.45 | 8.15 | 8.48 | 6.24 | 6.80 | 6.04 | 5.00 | 6.06 | 6.49 | 8.62 | 6.00 | 6.52 |
| 2372812 | 4.74 | 4.86 | 4.33 | 4.95 | 4.89 | 5.91 | 4.24 | 4.94 | 5.47 | 4.99 | 9.03 | 7.59 |
| 2486811 | 9.99 | 9.12 | 7.91 | 9.95 | 10.16 | 10.83 | 10.10 | 7.64 | 9.54 | 8.53 | 9.05 | 9.20 |
| 3768474 | 7.88 | 7.93 | 7.70 | 8.50 | 8.46 | 8.82 | 8.40 | 8.55 | 8.17 | 8.13 | 8.06 | 7.89 |
| 3142381 | 5.84 | 7.78 | 4.47 | 6.63 | 3.96 | 3.81 | 8.22 | 6.24 | 3.67 | 3.57 | 4.16 | 3.21 |
| 2396750 | 7.26 | 8.07 | 8.39 | 7.00 | 7.46 | 7.02 | 6.97 | 7.89 | 6.74 | 7.77 | 7.65 | 8.38 |
| 3902489 | 11.74 | 10.31 | 9.66 | 12.04 | 11.04 | 11.65 | 10.80 | 9.79 | 10.41 | 9.87 | 10.36 | 9.79 |
| 3032647 | 7.73 | 6.16 | 5.61 | 6.34 | 7.02 | 6.12 | 6.52 | 5.95 | 7.61 | 5.71 | 5.63 | 5.98 |
| 3875642 | 6.25 | 5.78 | 4.72 | 6.01 | 5.57 | 6.88 | 5.00 | 5.28 | 6.04 | 4.89 | 4.94 | 4.84 |
| 4027585 | 11.00 | 9.84 | 9.01 | 11.50 | 11.14 | 11.60 | 11.12 | 9.66 | 10.16 | 9.10 | 9.20 | 9.25 |
| 2352609 | 7.00 | 8.08 | 7.30 | 5.87 | 6.91 | 5.59 | 6.66 | 6.70 | 6.57 | 6.99 | 6.25 | 6.64 |
| 3376529 | 8.28 | 8.58 | 10.14 | 8.63 | 8.49 | 7.72 | 7.99 | 9.86 | 8.70 | 9.51 | 9.43 | 9.23 |
| 2491271 | 13.15 | 12.97 | 13.19 | 13.23 | 13.51 | 13.53 | 13.42 | 12.55 | 13.22 | 12.85 | 13.39 | 13.38 |
| 3874751 | 9.25 | 8.88 | 9.70 | 8.79 | 9.34 | 8.69 | 9.91 | 9.25 | 9.05 | 9.70 | 9.52 | 9.64 |
| 2326463 | 11.74 | 11.10 | 10.51 | 12.29 | 11.79 | 12.54 | 12.43 | 10.15 | 12.04 | 10.08 | 12.37 | 11.22 |
| 3341061 | 7.45 | 6.68 | 7.47 | 7.87 | 8.55 | 8.42 | 8.81 | 7.03 | 6.89 | 7.15 | 6.94 | 7.69 |
| 3839910 | 9.86 | 8.83 | 4.67 | 9.81 | 8.82 | 10.61 | 7.20 | 7.21 | 9.18 | 6.71 | 7.04 | 6.12 |
| 2708855 | 3.83 | 5.88 | 8.55 | 4.38 | 4.39 | 4.78 | 4.00 | 4.03 | 4.15 | 8.65 | 8.46 | 7.43 |
| 3512874 | 12.44 | 11.55 | 9.98 | 12.29 | 11.98 | 12.56 | 11.67 | 10.30 | 11.99 | 11.23 | 11.62 | 11.23 |
| 2701071 | 11.12 | 10.02 | 7.58 | 10.87 | 10.34 | 11.45 | 8.77 | 8.39 | 10.26 | 8.50 | 8.30 | 8.13 |
| 3486096 | 7.38 | 8.06 | 7.49 | 6.61 | 6.46 | 5.55 | 8.08 | 7.82 | 5.42 | 8.83 | 6.59 | 6.62 |
| 2412668 | 8.81 | 8.11 | 8.65 | 8.15 | 8.39 | 8.59 | 8.86 | 7.93 | 8.26 | 8.16 | 7.96 | 8.83 |
| 3329343 | 6.65 | 8.75 | 8.65 | 7.27 | 8.14 | 7.31 | 6.92 | 8.04 | 7.30 | 7.92 | 9.09 | 9.84 |
| 3259367 | 4.31 | 5.72 | 6.70 | 4.17 | 4.22 | 4.29 | 4.81 | 4.03 | 6.66 | 4.57 | 4.07 | 4.54 |
| 3373845 | 10.33 | 8.09 | 8.97 | 8.87 | 9.35 | 9.28 | 10.96 | 7.69 | 8.62 | 8.89 | 10.03 | 9.78 |
| 2321911 | 8.51 | 8.34 | 7.90 | 8.94 | 8.58 | 9.08 | 8.55 | 7.97 | 8.45 | 7.52 | 8.09 | 7.99 |
| 3353914 | 6.14 | 6.67 | 8.09 | 6.48 | 7.23 | 6.85 | 9.48 | 7.01 | 6.36 | 7.02 | 7.23 | 7.25 |
| 3744680 | 8.12 | 7.36 | 6.67 | 8.10 | 7.94 | 8.70 | 7.81 | 7.26 | 7.99 | 6.83 | 7.07 | 6.66 |
| 2373336 | 7.66 | 5.48 | 9.88 | 5.81 | 9.22 | 6.10 | 6.67 | 5.24 | 4.91 | 8.72 | 9.96 | 8.78 |
| 3067478 | 4.90 | 6.74 | 8.75 | 5.62 | 6.81 | 4.81 | 6.12 | 5.86 | 7.06 | 8.57 | 7.63 | 8.68 |
| 3976766 | 8.97 | 7.91 | 6.10 | 8.83 | 8.46 | 9.78 | 8.04 | 7.34 | 8.83 | 6.97 | 7.71 | 7.43 |
| 3246888 | 6.09 | 7.39 | 4.49 | 6.21 | 6.50 | 5.70 | 7.25 | 5.87 | 5.41 | 7.34 | 4.41 | 4.96 |
| 3147985 | 6.33 | 6.41 | 7.40 | 6.23 | 6.82 | 6.96 | 8.49 | 6.06 | 6.21 | 7.06 | 6.88 | 7.41 |
| 3185522 | 9.38 | 9.50 | 9.49 | 9.28 | 9.94 | 9.39 | 10.69 | 9.28 | 8.88 | 9.74 | 9.19 | 9.80 |
| 3861948 | 12.72 | 12.47 | 10.59 | 12.98 | 12.79 | 13.23 | 11.78 | 11.10 | 12.69 | 11.31 | 12.46 | 11.69 |
| 3393479 | 9.33 | 8.57 | 8.87 | 8.52 | 9.21 | 8.17 | 10.07 | 7.95 | 7.54 | 7.91 | 9.02 | 7.76 |
| 3540862 | 6.59 | 6.74 | 7.33 | 8.66 | 6.57 | 6.44 | 6.82 | 9.45 | 7.68 | 8.45 | 6.72 | 6.69 |
| 2777714 | 11.64 | 10.73 | 8.41 | 12.15 | 11.24 | 11.90 | 10.74 | 9.91 | 11.23 | 9.13 | 9.67 | 9.55 |
| 3110395 | 4.88 | 4.92 | 4.54 | 4.98 | 5.60 | 4.55 | 5.20 | 4.34 | 7.27 | 5.65 | 6.13 | 5.78 |
| 3895795 | 9.29 | 8.82 | 7.70 | 9.06 | 8.42 | 10.00 | 7.54 | 7.68 | 8.47 | 7.73 | 7.86 | 7.29 |
| 2854445 | 9.05 | 7.44 | 9.36 | 9.26 | 11.21 | 9.00 | 11.14 | 8.06 | 7.63 | 9.29 | 8.80 | 9.06 |
| 3606034 | 7.07 | 7.59 | 7.60 | 7.11 | 7.65 | 7.32 | 8.04 | 7.60 | 7.61 | 7.13 | 7.02 | 7.18 |
| 3375735 | 8.14 | 7.44 | 7.70 | 8.31 | 8.06 | 8.54 | 8.13 | 6.96 | 7.97 | 7.92 | 8.04 | 7.47 |
| 3948047 | 8.55 | 7.52 | 7.22 | 8.65 | 8.83 | 9.55 | 8.71 | 7.41 | 8.46 | 7.48 | 8.18 | 7.85 |
| 3010503 | 10.11 | 8.28 | 7.09 | 9.77 | 10.31 | 10.61 | 10.87 | 7.40 | 8.76 | 7.59 | 7.14 | 5.92 |
| 3622934 | 7.21 | 7.99 | 8.22 | 7.15 | 7.42 | 6.02 | 6.56 | 7.91 | 8.21 | 7.81 | 8.11 | 7.77 |
| 3441849 | 10.48 | 9.79 | 9.60 | 10.19 | 10.06 | 10.88 | 9.78 | 9.34 | 9.97 | 9.80 | 9.70 | 10.04 |
| 3006572 | 6.32 | 6.83 | 6.11 | 6.69 | 6.60 | 6.44 | 6.17 | 6.03 | 6.75 | 6.80 | 6.63 | 6.71 |
| 3365136 | 8.27 | 11.27 | 9.48 | 8.51 | 7.95 | 8.36 | 9.00 | 8.58 | 8.47 | 9.11 | 8.54 | 9.70 |
| 2642791 | 8.77 | 8.18 | 8.36 | 8.33 | 8.65 | 8.34 | 8.86 | 8.58 | 8.24 | 8.77 | 8.41 | 8.31 |
| 2904485 | 8.94 | 8.04 | 7.85 | 6.98 | 7.91 | 6.83 | 8.96 | 6.94 | 7.43 | 6.66 | 7.38 | 8.33 |
| 3772661 | 9.96 | 9.11 | 9.86 | 10.22 | 10.68 | 10.57 | 11.55 | 8.86 | 9.15 | 9.59 | 9.75 | 9.99 |
| 2796553 | 10.70 | 10.71 | 8.57 | 10.62 | 10.03 | 11.65 | 9.83 | 9.44 | 10.68 | 8.98 | 8.83 | 8.31 |
| 3063795 | 7.31 | 7.43 | 7.22 | 8.00 | 9.09 | 7.66 | 8.22 | 7.57 | 7.28 | 8.20 | 7.20 | 8.46 |
| 3338192 | 8.34 | 9.92 | 10.84 | 7.99 | 8.98 | 7.43 | 9.27 | 8.45 | 9.10 | 10.16 | 10.63 | 9.88 |
| 3214845 | 4.05 | 4.31 | 5.59 | 4.19 | 4.56 | 4.42 | 4.42 | 4.38 | 4.26 | 4.55 | 5.53 | 4.73 |
| 2730303 | 4.16 | 4.13 | 3.97 | 4.33 | 4.30 | 4.94 | 3.97 | 4.42 | 4.22 | 4.24 | 7.78 | 5.91 |
| 3811086 | 7.89 | 7.45 | 8.08 | 7.37 | 8.18 | 7.79 | 7.86 | 8.09 | 7.67 | 6.97 | 7.67 | 7.83 |
| 2981874 | 10.14 | 10.10 | 10.08 | 10.37 | 10.44 | 10.48 | 10.40 | 10.49 | 10.34 | 9.82 | 10.49 | 10.03 |
| 3242353 | 6.06 | 6.10 | 5.95 | 5.66 | 6.15 | 5.95 | 6.18 | 6.11 | 6.00 | 5.94 | 6.13 | 6.25 |
| 2442008 | 5.20 | 7.50 | 8.53 | 5.69 | 5.40 | 5.67 | 5.16 | 5.52 | 5.55 | 7.38 | 7.00 | 9.38 |
| 3564210 | 10.42 | 10.11 | 8.54 | 10.15 | 10.13 | 11.40 | 9.71 | 7.80 | 9.44 | 8.69 | 8.48 | 7.41 |
| 2490351 | 3.99 | 3.99 | 3.87 | 4.27 | 4.01 | 4.38 | 3.87 | 4.18 | 4.20 | 3.93 | 3.96 | 3.72 |
| 3759006 | 10.29 | 8.53 | 6.67 | 10.29 | 9.71 | 10.51 | 8.86 | 7.67 | 8.56 | 7.22 | 7.48 | 8.08 |
| 3264997 | 3.91 | 4.03 | 3.84 | 4.46 | 5.11 | 4.29 | 3.80 | 4.12 | 4.22 | 4.15 | 3.82 | 3.75 |
| 3912079 | 3.61 | 3.91 | 3.30 | 3.93 | 3.59 | 4.55 | 3.73 | 3.54 | 3.62 | 3.50 | 3.53 | 3.49 |
| 2926802 | 5.10 | 5.26 | 4.68 | 5.70 | 6.41 | 6.61 | 4.42 | 5.35 | 5.33 | 5.41 | 5.91 | 4.88 |

TABLE 25-continued

Normalized intensity of microarray data for a set of samples.

| TCID | V01 0001 | V01 0002 | V01 0003 | V01 0004 | V01 0005 | V01 0006 | V01 0007 | V01 0008 | V01 0009 | V01 0010 | V01 0011 | V01 0012 |
|---|---|---|---|---|---|---|---|---|---|---|---|---|
| 2430163 | 3.86 | 3.87 | 4.23 | 3.97 | 6.55 | 4.08 | 3.93 | 3.72 | 3.91 | 3.72 | 6.58 | 3.62 |
| 3039830 | 3.24 | 3.05 | 3.12 | 3.14 | 3.20 | 3.27 | 3.09 | 3.26 | 3.10 | 3.32 | 2.96 | 3.06 |
| 3935486 | 4.76 | 6.24 | 7.58 | 5.45 | 8.33 | 5.97 | 8.02 | 5.01 | 6.27 | 6.43 | 8.47 | 6.21 |
| 3457336 | 5.27 | 5.31 | 5.21 | 5.57 | 5.62 | 5.54 | 5.12 | 5.43 | 5.72 | 5.53 | 5.19 | 4.92 |
| 3811949 | 3.57 | 3.42 | 3.30 | 3.86 | 3.46 | 3.72 | 3.37 | 3.56 | 3.68 | 3.32 | 3.30 | 3.27 |
| 3343832 | 3.79 | 3.84 | 3.57 | 4.02 | 3.80 | 3.90 | 3.69 | 3.88 | 3.83 | 4.55 | 3.60 | 3.75 |
| 3161261 | 6.11 | 6.47 | 5.22 | 6.33 | 5.57 | 6.43 | 5.04 | 5.03 | 6.21 | 6.35 | 5.84 | 4.80 |
| 3594003 | 3.63 | 3.74 | 3.40 | 3.87 | 4.07 | 3.93 | 3.61 | 3.69 | 3.67 | 3.78 | 3.56 | 3.61 |
| 3805614 | 4.49 | 4.42 | 4.24 | 5.33 | 4.81 | 5.54 | 4.76 | 4.88 | 4.78 | 4.26 | 4.45 | 4.30 |
| 3364127 | 6.80 | 7.02 | 6.35 | 7.73 | 6.98 | 7.06 | 6.35 | 7.51 | 7.41 | 7.05 | 6.35 | 6.53 |
| 3834341 | 3.98 | 3.82 | 4.07 | 4.26 | 4.04 | 4.03 | 3.62 | 3.95 | 4.28 | 4.03 | 3.82 | 3.86 |
| 2585400 | 4.55 | 4.19 | 4.19 | 4.44 | 4.65 | 4.77 | 4.25 | 4.24 | 4.42 | 4.05 | 4.21 | 4.23 |
| 2941690 | 4.06 | 4.01 | 4.12 | 4.91 | 4.68 | 4.48 | 4.30 | 4.05 | 4.47 | 4.06 | 3.93 | 3.99 |
| 3484895 | 4.64 | 5.36 | 6.30 | 4.81 | 4.72 | 5.57 | 4.72 | 5.21 | 5.22 | 4.69 | 5.03 | 5.84 |
| 3159754 | 3.65 | 3.75 | 3.74 | 3.85 | 3.51 | 3.76 | 3.59 | 4.22 | 3.89 | 3.70 | 3.57 | 3.58 |
| 2894790 | 3.78 | 3.74 | 3.63 | 4.09 | 3.59 | 4.29 | 3.77 | 3.87 | 4.01 | 3.58 | 3.67 | 3.62 |
| 3363686 | 3.27 | 3.32 | 3.14 | 3.44 | 3.34 | 3.74 | 3.41 | 3.62 | 4.30 | 3.95 | 3.53 | 3.24 |
| 2923928 | 4.30 | 4.50 | 4.00 | 4.56 | 4.16 | 4.47 | 3.97 | 4.60 | 4.68 | 4.22 | 4.03 | 4.04 |
| 2883317 | 5.00 | 4.44 | 4.21 | 5.05 | 5.10 | 4.97 | 4.49 | 4.73 | 5.21 | 4.74 | 4.89 | 4.63 |
| 2479698 | 5.96 | 6.55 | 5.84 | 6.05 | 5.84 | 5.91 | 5.67 | 6.43 | 6.14 | 6.08 | 5.90 | 5.75 |
| 3428225 | 3.81 | 3.58 | 3.57 | 4.03 | 3.47 | 4.00 | 3.66 | 3.50 | 3.79 | 3.45 | 3.50 | 3.39 |
| 3393446 | 7.19 | 6.76 | 6.65 | 7.76 | 7.50 | 7.69 | 8.04 | 7.44 | 7.15 | 6.94 | 7.32 | 6.53 |
| 3116614 | 13.17 | 13.17 | 12.76 | 11.39 | 12.51 | 8.52 | 12.85 | 12.54 | 12.60 | 11.99 | 10.29 | 12.27 |
| 3415320 | 9.69 | 9.64 | 10.51 | 9.68 | 10.59 | 6.34 | 10.01 | 11.24 | 10.95 | 10.51 | 10.67 | 9.47 |
| 3757108 | 7.59 | 9.04 | 10.13 | 7.55 | 10.56 | 7.75 | 7.72 | 7.87 | 7.82 | 9.53 | 11.22 | 9.80 |
| 4012178 | 6.44 | 9.78 | 9.90 | 6.47 | 6.17 | 6.51 | 7.71 | 7.61 | 6.41 | 9.89 | 9.03 | 11.52 |
| 3546213 | 10.81 | 11.41 | 11.24 | 8.80 | 9.96 | 5.83 | 10.97 | 11.09 | 9.43 | 10.85 | 10.37 | 11.31 |
| 3561381 | 9.68 | 10.86 | 10.43 | 7.97 | 8.56 | 4.43 | 10.13 | 10.08 | 8.98 | 9.86 | 9.68 | 10.19 |

TABLE 26

Normalized intensity of microarray data for a set of samples.

| TCID | V01 0013 | V01 0014 | V01 0015 | V01 0016 | V01 0017 | V01 0018 | V01 0019 | V01 0020 | V01 0021 | V01 0022 | V01 0023 | V01 0024 |
|---|---|---|---|---|---|---|---|---|---|---|---|---|
| 2604998 | 7.10 | 8.02 | 8.77 | 5.02 | 8.45 | 7.69 | 8.38 | 7.97 | 8.92 | 4.78 | 8.52 | 7.39 |
| 3603932 | 6.25 | 7.37 | 7.25 | 7.04 | 7.27 | 6.85 | 6.89 | 6.80 | 7.97 | 8.65 | 6.94 | 6.70 |
| 2710599 | 6.41 | 8.74 | 10.60 | 5.28 | 11.58 | 6.80 | 11.57 | 11.67 | 10.81 | 7.08 | 8.98 | 8.55 |
| 2440258 | 8.91 | 8.98 | 4.87 | 9.58 | 5.90 | 8.84 | 7.57 | 6.42 | 5.21 | 7.64 | 7.63 | 6.76 |
| 3169331 | 6.35 | 6.84 | 7.26 | 8.09 | 6.21 | 7.17 | 6.34 | 7.05 | 7.65 | 6.94 | 6.79 | 7.10 |
| 2988882 | 9.75 | 9.27 | 9.37 | 10.43 | 9.59 | 10.17 | 9.72 | 9.27 | 9.84 | 10.21 | 10.21 | 9.53 |
| 2964231 | 8.38 | 8.26 | 8.08 | 7.30 | 9.33 | 8.49 | 8.35 | 8.50 | 10.66 | 10.89 | 8.72 | 8.98 |
| 3111561 | 8.33 | 8.03 | 9.61 | 4.83 | 5.00 | 8.43 | 8.10 | 8.56 | 8.36 | 5.19 | 10.77 | 8.41 |
| 2562529 | 9.13 | 10.16 | 10.66 | 8.64 | 10.79 | 9.01 | 10.40 | 10.72 | 10.31 | 9.45 | 9.82 | 8.29 |
| 3692999 | 11.69 | 12.26 | 10.56 | 7.52 | 6.99 | 11.83 | 7.85 | 8.86 | 12.19 | 11.03 | 11.11 | 9.89 |
| 2439554 | 7.07 | 6.57 | 4.32 | 11.25 | 4.47 | 7.24 | 5.79 | 5.06 | 4.94 | 6.55 | 6.29 | 6.67 |
| 2685304 | 6.35 | 7.84 | 9.44 | 5.21 | 11.93 | 6.96 | 11.20 | 11.39 | 8.69 | 8.92 | 7.72 | 7.65 |
| 2578790 | 5.78 | 6.08 | 6.31 | 4.55 | 4.07 | 6.29 | 4.60 | 6.28 | 7.62 | 4.40 | 6.12 | 6.16 |
| 2373842 | 11.93 | 11.91 | 8.40 | 11.30 | 8.21 | 11.62 | 10.88 | 10.41 | 9.26 | 10.88 | 10.80 | 11.13 |
| 2750627 | 9.32 | 9.25 | 10.26 | 5.38 | 10.24 | 9.21 | 10.42 | 9.62 | 10.15 | 4.04 | 10.44 | 8.26 |
| 3397774 | 4.67 | 5.05 | 4.67 | 5.45 | 4.57 | 5.41 | 4.48 | 4.83 | 6.41 | 5.22 | 4.70 | 4.45 |
| 2635741 | 9.22 | 8.84 | 6.57 | 8.75 | 6.16 | 9.04 | 7.88 | 7.21 | 6.24 | 6.42 | 7.60 | 6.92 |
| 3970833 | 9.20 | 9.25 | 10.04 | 10.01 | 9.93 | 9.59 | 9.39 | 9.57 | 10.87 | 9.96 | 9.26 | 9.51 |
| 3577612 | 10.62 | 10.83 | 9.72 | 7.79 | 11.33 | 10.82 | 11.28 | 11.64 | 9.14 | 10.49 | 10.02 | 10.47 |
| 2708922 | 8.00 | 8.06 | 9.14 | 6.00 | 8.24 | 8.91 | 8.97 | 8.28 | 6.49 | 7.33 | 8.35 | 9.12 |
| 2970897 | 4.81 | 5.87 | 5.32 | 8.76 | 4.88 | 5.17 | 5.77 | 6.17 | 7.41 | 5.77 | 5.61 | 8.14 |
| 3724545 | 10.05 | 8.69 | 8.95 | 6.89 | 9.74 | 9.70 | 9.96 | 9.59 | 9.54 | 8.35 | 9.81 | 8.71 |
| 2798538 | 9.47 | 8.67 | 8.27 | 9.44 | 9.21 | 8.95 | 9.05 | 8.85 | 9.62 | 10.32 | 9.05 | 9.14 |
| 2806468 | 11.90 | 11.71 | 7.54 | 9.26 | 7.68 | 11.67 | 10.44 | 10.39 | 8.77 | 9.66 | 10.55 | 9.94 |
| 2880051 | 7.00 | 6.42 | 5.91 | 6.13 | 6.08 | 7.03 | 6.10 | 6.37 | 6.00 | 5.89 | 6.47 | 5.69 |
| 2732508 | 3.38 | 3.47 | 3.38 | 10.27 | 3.18 | 4.27 | 3.74 | 3.55 | 3.71 | 3.53 | 3.60 | 4.05 |
| 2822492 | 5.95 | 5.61 | 5.46 | 6.20 | 5.22 | 5.52 | 5.02 | 5.34 | 5.94 | 5.58 | 5.80 | 5.60 |
| 3404030 | 9.98 | 9.14 | 6.13 | 6.55 | 4.93 | 9.13 | 7.42 | 6.95 | 6.20 | 6.81 | 7.78 | 6.30 |
| 3059667 | 10.99 | 8.84 | 11.39 | 4.38 | 4.22 | 10.46 | 7.01 | 9.86 | 5.55 | 4.44 | 9.78 | 8.70 |
| 3108526 | 9.39 | 8.25 | 8.86 | 5.49 | 9.09 | 10.20 | 8.36 | 8.96 | 10.68 | 6.41 | 9.96 | 8.95 |
| 2526806 | 7.57 | 8.47 | 8.29 | 9.11 | 13.07 | 9.46 | 12.81 | 12.90 | 10.58 | 10.84 | 9.23 | 11.80 |
| 2428501 | 6.40 | 5.89 | 6.56 | 8.35 | 7.43 | 6.37 | 8.11 | 6.49 | 6.15 | 8.81 | 6.37 | 10.11 |
| 2657808 | 6.02 | 6.95 | 9.62 | 5.24 | 9.89 | 5.40 | 10.94 | 11.12 | 8.69 | 5.89 | 8.86 | 5.92 |
| 2584018 | 7.56 | 8.81 | 7.05 | 7.77 | 10.59 | 7.39 | 10.43 | 10.59 | 8.10 | 10.87 | 9.90 | 6.86 |
| 3976341 | 9.47 | 9.63 | 9.25 | 10.57 | 11.53 | 9.69 | 11.15 | 11.37 | 8.91 | 10.90 | 8.73 | 10.02 |
| 2739308 | 4.96 | 4.94 | 6.05 | 4.62 | 4.42 | 5.55 | 4.57 | 4.78 | 5.41 | 4.44 | 5.71 | 5.29 |

TABLE 26-continued

Normalized intensity of microarray data for a set of samples.

| TCID | V01 0013 | V01 0014 | V01 0015 | V01 0016 | V01 0017 | V01 0018 | V01 0019 | V01 0020 | V01 0021 | V01 0022 | V01 0023 | V01 0024 |
|---|---|---|---|---|---|---|---|---|---|---|---|---|
| 3959862 | 4.33 | 4.74 | 4.73 | 4.80 | 4.11 | 4.59 | 4.11 | 4.35 | 6.77 | 6.01 | 5.00 | 4.72 |
| 2362351 | 8.72 | 8.07 | 5.78 | 8.61 | 5.16 | 8.34 | 7.01 | 6.43 | 5.66 | 6.60 | 7.02 | 6.41 |
| 3648391 | 4.99 | 5.08 | 5.29 | 8.63 | 3.82 | 4.20 | 5.26 | 3.87 | 3.90 | 4.38 | 4.19 | 5.30 |
| 3009299 | 10.74 | 10.56 | 10.88 | 11.58 | 10.78 | 10.43 | 10.56 | 10.49 | 11.24 | 11.07 | 10.68 | 10.99 |
| 3443464 | 7.07 | 6.43 | 5.42 | 5.39 | 4.75 | 6.37 | 5.44 | 5.09 | 5.06 | 5.61 | 5.43 | 5.25 |
| 2730746 | 7.37 | 7.18 | 8.82 | 5.07 | 5.16 | 8.16 | 5.93 | 6.38 | 9.16 | 5.16 | 8.11 | 6.41 |
| 2427619 | 9.67 | 9.52 | 5.96 | 8.31 | 5.21 | 9.25 | 8.11 | 7.00 | 5.54 | 7.22 | 7.82 | 7.23 |
| 3042001 | 8.77 | 8.28 | 8.49 | 8.75 | 8.88 | 8.88 | 8.48 | 7.90 | 9.00 | 8.95 | 8.67 | 9.04 |
| 2566848 | 5.46 | 5.81 | 4.90 | 8.65 | 4.85 | 5.22 | 5.02 | 5.08 | 5.11 | 5.66 | 5.30 | 5.11 |
| 2984616 | 8.82 | 8.88 | 8.60 | 8.76 | 9.17 | 8.44 | 8.71 | 8.77 | 10.17 | 9.69 | 9.21 | 8.49 |
| 2378068 | 7.95 | 6.65 | 8.39 | 10.23 | 9.16 | 7.53 | 8.31 | 9.16 | 7.79 | 9.36 | 8.09 | 8.73 |
| 2721959 | 8.54 | 7.26 | 7.91 | 6.18 | 12.74 | 6.92 | 12.25 | 12.80 | 10.09 | 7.46 | 7.45 | 9.69 |
| 2877508 | 10.35 | 9.77 | 10.09 | 10.80 | 10.48 | 10.32 | 10.16 | 9.96 | 11.04 | 10.88 | 10.29 | 10.23 |
| 3450861 | 6.85 | 6.95 | 4.69 | 4.85 | 4.61 | 7.69 | 6.15 | 5.02 | 4.83 | 4.97 | 5.26 | 5.58 |
| 2688717 | 9.36 | 9.61 | 5.64 | 8.37 | 5.75 | 8.75 | 8.54 | 7.37 | 5.88 | 6.07 | 7.54 | 7.52 |
| 3270270 | 9.31 | 9.07 | 6.89 | 8.38 | 8.77 | 9.02 | 9.70 | 8.62 | 6.48 | 8.92 | 8.08 | 8.49 |
| 3417703 | 10.63 | 7.94 | 5.45 | 5.27 | 7.84 | 8.41 | 8.37 | 7.26 | 4.78 | 4.58 | 11.43 | 7.26 |
| 3302990 | 7.15 | 6.44 | 7.16 | 8.18 | 7.68 | 7.25 | 7.36 | 7.72 | 9.03 | 8.22 | 7.15 | 7.63 |
| 2377283 | 4.81 | 5.25 | 4.19 | 8.74 | 4.19 | 4.53 | 4.41 | 3.99 | 4.32 | 4.29 | 4.36 | 3.84 |
| 3122678 | 4.56 | 4.88 | 6.38 | 5.52 | 7.98 | 4.88 | 4.42 | 5.51 | 4.47 | 5.38 | 4.61 | 4.63 |
| 2688499 | 9.02 | 9.14 | 9.69 | 11.15 | 10.62 | 8.42 | 10.80 | 9.29 | 8.74 | 7.16 | 10.48 | 8.53 |
| 2377094 | 8.63 | 9.10 | 9.59 | 7.57 | 8.62 | 8.83 | 7.65 | 9.23 | 10.59 | 9.09 | 9.27 | 8.91 |
| 3278198 | 7.42 | 7.52 | 7.59 | 8.06 | 8.66 | 7.57 | 7.07 | 7.98 | 9.61 | 8.61 | 8.37 | 7.08 |
| 2598261 | 7.15 | 7.69 | 7.93 | 8.52 | 12.95 | 9.21 | 12.85 | 13.10 | 9.85 | 10.23 | 7.78 | 11.04 |
| 3982612 | 9.86 | 9.58 | 4.41 | 9.40 | 4.43 | 9.93 | 7.52 | 7.49 | 6.51 | 6.35 | 7.97 | 6.83 |
| 2884845 | 4.89 | 4.69 | 4.51 | 4.92 | 10.74 | 4.66 | 9.74 | 9.14 | 5.22 | 4.60 | 4.92 | 4.36 |
| 3982560 | 7.27 | 7.58 | 4.88 | 8.53 | 5.21 | 7.25 | 5.97 | 5.54 | 4.81 | 5.38 | 6.48 | 5.43 |
| 3204285 | 5.17 | 5.45 | 5.11 | 8.51 | 5.10 | 6.14 | 5.43 | 6.52 | 5.09 | 5.56 | 5.16 | 5.67 |
| 3654699 | 9.80 | 10.37 | 10.60 | 9.66 | 10.98 | 11.50 | 10.45 | 11.01 | 12.27 | 12.99 | 9.86 | 12.09 |
| 2638676 | 7.08 | 7.00 | 6.02 | 10.27 | 5.93 | 7.34 | 6.50 | 5.81 | 6.04 | 7.46 | 6.96 | 7.73 |
| 3367673 | 8.07 | 7.61 | 8.38 | 4.35 | 4.49 | 7.27 | 6.00 | 7.40 | 8.81 | 4.97 | 9.38 | 7.59 |
| 3212008 | 7.21 | 9.44 | 10.14 | 6.11 | 8.24 | 6.57 | 7.23 | 8.30 | 7.99 | 6.18 | 6.99 | 6.09 |
| 3326635 | 10.27 | 10.57 | 10.60 | 10.41 | 10.14 | 9.95 | 10.03 | 10.05 | 9.92 | 10.41 | 10.31 | 10.68 |
| 3031556 | 9.91 | 10.24 | 6.16 | 8.25 | 6.39 | 9.82 | 8.85 | 8.25 | 6.59 | 9.78 | 8.93 | 8.79 |
| 3662201 | 11.94 | 12.02 | 10.41 | 9.21 | 8.36 | 12.00 | 8.58 | 9.07 | 11.71 | 10.09 | 11.74 | 10.50 |
| 2809793 | 9.17 | 9.69 | 4.77 | 8.21 | 5.70 | 8.51 | 6.94 | 7.49 | 5.20 | 6.68 | 7.86 | 6.32 |
| 2817731 | 8.61 | 7.41 | 7.56 | 7.39 | 7.49 | 7.87 | 8.14 | 7.34 | 7.15 | 9.76 | 7.61 | 7.52 |
| 4020655 | 6.09 | 9.35 | 9.09 | 5.03 | 6.52 | 5.31 | 5.88 | 7.46 | 7.28 | 4.81 | 5.08 | 4.73 |
| 3494629 | 4.90 | 5.45 | 8.73 | 4.55 | 9.57 | 4.44 | 8.44 | 8.52 | 5.33 | 4.82 | 5.96 | 4.67 |
| 3852832 | 10.31 | 9.45 | 5.84 | 6.98 | 6.10 | 9.54 | 8.77 | 7.56 | 6.20 | 6.41 | 8.36 | 8.98 |
| 3761959 | 9.03 | 8.73 | 9.50 | 9.28 | 9.14 | 8.92 | 8.88 | 8.29 | 9.49 | 9.83 | 9.03 | 9.22 |
| 2834282 | 6.89 | 8.14 | 9.62 | 5.33 | 7.79 | 6.22 | 7.97 | 7.88 | 6.03 | 6.00 | 6.97 | 6.18 |
| 3341497 | 5.97 | 7.92 | 8.63 | 6.36 | 9.40 | 6.35 | 6.66 | 6.72 | 8.45 | 6.03 | 5.18 | 5.54 |
| 2372812 | 4.38 | 5.07 | 4.54 | 12.43 | 4.76 | 4.52 | 4.48 | 4.34 | 4.70 | 4.59 | 4.84 | 4.56 |
| 2486811 | 10.22 | 9.49 | 5.12 | 10.42 | 6.98 | 9.97 | 8.97 | 8.44 | 6.87 | 10.68 | 9.51 | 9.22 |
| 3768474 | 8.50 | 8.00 | 7.99 | 7.96 | 7.60 | 7.92 | 7.93 | 7.37 | 8.16 | 10.01 | 7.98 | 8.80 |
| 3142381 | 3.70 | 6.31 | 6.28 | 4.12 | 4.44 | 6.42 | 5.35 | 8.73 | 5.38 | 6.88 | 6.81 | 4.24 |
| 2396750 | 6.26 | 7.12 | 7.45 | 6.95 | 7.75 | 7.37 | 7.76 | 7.59 | 8.00 | 6.65 | 6.48 | 6.45 |
| 3902489 | 11.11 | 10.89 | 9.77 | 10.23 | 10.18 | 11.60 | 11.49 | 10.58 | 9.71 | 10.27 | 11.55 | 11.21 |
| 3032647 | 6.88 | 6.12 | 6.67 | 6.03 | 5.99 | 7.90 | 6.10 | 6.20 | 6.13 | 5.89 | 5.92 | 7.06 |
| 3875642 | 6.64 | 6.06 | 5.15 | 5.01 | 4.86 | 5.87 | 5.24 | 5.16 | 5.86 | 5.47 | 5.25 | 6.94 |
| 4027585 | 10.49 | 10.48 | 8.64 | 7.94 | 8.90 | 11.65 | 11.05 | 9.49 | 9.63 | 11.59 | 11.27 | 10.51 |
| 2352609 | 7.63 | 7.31 | 8.38 | 6.00 | 6.87 | 6.48 | 6.38 | 6.98 | 8.10 | 5.43 | 7.12 | 6.05 |
| 3376529 | 8.05 | 8.93 | 8.42 | 6.92 | 10.45 | 8.37 | 10.00 | 9.74 | 9.78 | 8.37 | 8.66 | 8.84 |
| 2491271 | 13.36 | 13.35 | 12.12 | 13.56 | 13.31 | 13.23 | 13.54 | 13.16 | 12.14 | 13.68 | 13.01 | 13.24 |
| 3874751 | 9.50 | 8.96 | 8.42 | 7.85 | 10.17 | 9.37 | 9.23 | 9.73 | 9.50 | 10.20 | 9.03 | 9.61 |
| 2326463 | 12.33 | 12.20 | 8.85 | 12.84 | 9.58 | 12.04 | 11.32 | 10.39 | 9.08 | 12.38 | 11.32 | 11.19 |
| 3341061 | 6.64 | 6.73 | 6.36 | 7.72 | 6.54 | 7.03 | 7.40 | 6.81 | 7.25 | 9.44 | 6.92 | 6.83 |
| 3839910 | 10.05 | 8.48 | 5.84 | 6.38 | 5.59 | 9.39 | 8.14 | 7.14 | 5.71 | 6.71 | 8.68 | 8.78 |
| 2708855 | 4.43 | 5.99 | 6.39 | 5.69 | 8.96 | 4.56 | 8.52 | 8.30 | 6.48 | 3.93 | 4.91 | 4.43 |
| 3512874 | 12.25 | 12.12 | 8.99 | 12.43 | 9.47 | 12.06 | 11.26 | 11.11 | 10.13 | 11.96 | 11.49 | 11.76 |
| 2701061 | 10.84 | 10.49 | 6.84 | 6.14 | 7.20 | 10.55 | 9.48 | 8.41 | 8.02 | 9.41 | 10.07 | 10.16 |
| 3486096 | 6.91 | 7.17 | 8.76 | 5.51 | 7.09 | 7.26 | 5.90 | 7.83 | 8.78 | 5.69 | 8.84 | 9.65 |
| 2412668 | 8.78 | 7.59 | 8.16 | 8.33 | 8.26 | 8.31 | 7.89 | 8.06 | 8.25 | 9.43 | 8.46 | 8.12 |
| 3329343 | 6.89 | 7.02 | 7.52 | 7.59 | 8.81 | 7.34 | 9.23 | 8.78 | 8.08 | 6.87 | 8.17 | 8.74 |
| 3259367 | 4.66 | 5.73 | 4.94 | 4.17 | 5.52 | 4.22 | 4.44 | 3.97 | 5.95 | 4.14 | 4.31 | 3.96 |
| 3373845 | 8.23 | 8.42 | 7.21 | 9.79 | 9.80 | 9.46 | 10.43 | 9.93 | 7.97 | 10.75 | 9.12 | 9.07 |
| 2321911 | 8.22 | 8.30 | 8.48 | 8.97 | 7.89 | 8.95 | 8.29 | 7.88 | 8.07 | 8.89 | 8.55 | 8.13 |
| 3353914 | 6.30 | 6.47 | 6.77 | 6.18 | 7.68 | 6.11 | 7.77 | 7.44 | 7.16 | 9.63 | 7.33 | 6.46 |
| 3744680 | 8.10 | 7.80 | 6.63 | 7.33 | 6.45 | 8.11 | 7.33 | 6.91 | 6.45 | 8.90 | 7.27 | 7.61 |
| 2373336 | 6.64 | 5.52 | 7.18 | 6.08 | 10.27 | 6.44 | 10.68 | 9.57 | 5.19 | 5.31 | 9.74 | 8.10 |
| 3067478 | 6.80 | 6.09 | 7.81 | 4.76 | 8.65 | 5.90 | 8.12 | 7.95 | 8.15 | 4.71 | 6.82 | 7.17 |
| 3976766 | 8.78 | 8.62 | 6.30 | 9.02 | 6.39 | 8.79 | 7.73 | 7.08 | 6.56 | 8.42 | 7.85 | 8.16 |
| 3246888 | 6.18 | 6.55 | 7.56 | 4.91 | 4.88 | 6.99 | 5.29 | 5.87 | 8.47 | 4.65 | 7.55 | 6.67 |
| 3147985 | 6.22 | 6.10 | 6.47 | 6.14 | 7.65 | 6.84 | 7.55 | 6.88 | 6.73 | 8.78 | 7.01 | 8.99 |

TABLE 26-continued

Normalized intensity of microarray data for a set of samples.

| TCID | V01 0013 | V01 0014 | V01 0015 | V01 0016 | V01 0017 | V01 0018 | V01 0019 | V01 0020 | V01 0021 | V01 0022 | V01 0023 | V01 0024 |
|---|---|---|---|---|---|---|---|---|---|---|---|---|
| 3185522 | 9.44 | 9.24 | 8.90 | 9.21 | 10.39 | 9.02 | 9.60 | 8.88 | 9.23 | 11.53 | 9.54 | 10.00 |
| 3861948 | 13.03 | 12.76 | 9.85 | 13.00 | 9.52 | 12.94 | 12.13 | 11.38 | 10.42 | 12.46 | 12.16 | 12.41 |
| 3393479 | 8.55 | 8.39 | 9.12 | 8.41 | 8.60 | 8.55 | 9.30 | 8.65 | 7.80 | 10.12 | 10.45 | 9.28 |
| 3540862 | 6.96 | 6.71 | 7.33 | 5.40 | 7.70 | 6.55 | 6.65 | 7.26 | 8.18 | 6.80 | 7.11 | 6.23 |
| 2777714 | 11.51 | 11.44 | 9.47 | 7.29 | 9.22 | 11.90 | 11.27 | 10.21 | 10.11 | 9.51 | 11.39 | 11.18 |
| 3110395 | 5.23 | 5.24 | 6.22 | 4.52 | 6.40 | 5.25 | 4.43 | 5.48 | 4.92 | 4.39 | 4.26 | 4.22 |
| 3895795 | 9.33 | 8.90 | 7.96 | 7.37 | 7.88 | 8.97 | 7.97 | 8.29 | 7.23 | 7.81 | 8.77 | 8.59 |
| 2854445 | 8.25 | 8.62 | 7.58 | 7.21 | 7.58 | 8.69 | 9.47 | 8.35 | 7.03 | 11.77 | 9.36 | 9.28 |
| 3606034 | 7.25 | 7.37 | 7.56 | 6.75 | 7.49 | 7.26 | 7.19 | 6.98 | 7.91 | 9.29 | 7.62 | 7.04 |
| 3375735 | 8.09 | 8.40 | 8.07 | 8.09 | 8.51 | 7.90 | 8.12 | 8.00 | 7.24 | 9.03 | 8.16 | 8.16 |
| 3948047 | 8.90 | 8.67 | 6.76 | 9.48 | 6.80 | 8.32 | 7.77 | 7.32 | 7.26 | 9.30 | 7.82 | 8.16 |
| 3010503 | 9.20 | 9.25 | 6.74 | 6.21 | 8.84 | 9.20 | 8.75 | 7.58 | 6.69 | 10.93 | 9.30 | 8.70 |
| 3622934 | 6.59 | 7.40 | 8.73 | 8.05 | 7.70 | 5.62 | 8.27 | 7.51 | 7.26 | 5.73 | 8.09 | 7.60 |
| 3441849 | 10.41 | 9.90 | 9.07 | 8.17 | 9.75 | 10.13 | 10.00 | 9.85 | 9.11 | 10.29 | 9.77 | 9.97 |
| 3006572 | 6.60 | 6.75 | 6.72 | 6.17 | 6.39 | 6.65 | 6.85 | 7.01 | 6.41 | 6.15 | 6.41 | 6.37 |
| 3365136 | 8.57 | 10.04 | 9.91 | 8.45 | 9.39 | 8.52 | 8.82 | 8.70 | 10.16 | 8.50 | 9.55 | 8.21 |
| 2642791 | 8.79 | 8.22 | 7.85 | 8.86 | 8.07 | 8.29 | 8.03 | 7.90 | 8.67 | 9.52 | 8.56 | 8.86 |
| 2904485 | 8.65 | 8.32 | 8.99 | 6.77 | 6.77 | 8.64 | 7.90 | 7.93 | 7.40 | 6.89 | 9.70 | 8.02 |
| 3772661 | 9.79 | 9.75 | 7.97 | 7.83 | 9.22 | 9.89 | 10.21 | 10.07 | 8.50 | 11.76 | 9.81 | 9.76 |
| 2796553 | 10.92 | 9.77 | 8.60 | 9.40 | 9.81 | 10.04 | 9.32 | 8.78 | 10.29 | 9.77 | 10.43 | |
| 3063795 | 6.90 | 7.24 | 6.89 | 7.15 | 7.20 | 7.84 | 6.91 | 7.02 | 7.06 | 9.16 | 7.43 | 7.79 |
| 3338192 | 8.58 | 9.76 | 10.54 | 7.59 | 10.47 | 8.56 | 11.07 | 10.56 | 10.04 | 7.75 | 9.61 | 8.47 |
| 3214845 | 5.81 | 4.16 | 5.88 | 4.81 | 4.43 | 4.62 | 4.88 | 8.78 | 4.59 | 4.41 | 3.92 | 5.76 |
| 2730303 | 4.06 | 4.25 | 4.17 | 4.88 | 3.96 | 4.35 | 3.77 | 4.01 | 4.45 | 4.34 | 4.20 | 3.90 |
| 3811086 | 7.91 | 7.23 | 8.47 | 8.07 | 7.47 | 7.86 | 7.47 | 7.34 | 7.67 | 8.35 | 8.26 | 7.84 |
| 2981874 | 10.36 | 10.27 | 9.07 | 10.08 | 10.18 | 10.47 | 10.21 | 9.83 | 9.98 | 10.33 | 10.05 | 10.32 |
| 3242353 | 5.69 | 5.84 | 5.44 | 7.41 | 5.99 | 6.26 | 5.94 | 5.73 | 5.95 | 6.75 | 6.28 | 6.04 |
| 2442008 | 5.43 | 7.10 | 6.71 | 5.68 | 8.63 | 5.75 | 5.97 | 7.22 | 5.41 | 5.42 | 5.26 | 5.29 |
| 3564210 | 10.46 | 9.55 | 6.99 | 7.23 | 8.52 | 10.34 | 9.61 | 8.60 | 7.61 | 10.32 | 9.16 | 10.23 |
| 2490351 | 4.09 | 4.24 | 4.07 | 4.50 | 3.91 | 4.11 | 3.89 | 3.94 | 3.90 | 4.13 | 3.95 | 3.86 |
| 3759006 | 9.31 | 8.84 | 7.00 | 6.97 | 7.56 | 10.57 | 9.96 | 7.82 | 8.20 | 7.07 | 9.76 | 9.17 |
| 3264997 | 4.05 | 4.26 | 4.03 | 4.22 | 3.97 | 4.17 | 4.00 | 3.84 | 3.98 | 4.18 | 3.98 | 3.96 |
| 3912079 | 3.88 | 3.69 | 4.09 | 3.66 | 3.61 | 3.76 | 3.43 | 3.79 | 3.73 | 3.68 | 3.77 | 3.99 |
| 2926802 | 5.70 | 5.90 | 4.85 | 6.04 | 5.14 | 6.00 | 5.51 | 5.02 | 5.57 | 5.26 | 5.04 | 5.91 |
| 2430163 | 3.82 | 4.11 | 3.82 | 4.14 | 4.34 | 4.01 | 4.55 | 4.50 | 4.04 | 4.26 | 3.75 | 3.82 |
| 3039830 | 3.17 | 3.35 | 3.27 | 3.28 | 3.29 | 3.24 | 3.04 | 3.06 | 3.11 | 3.12 | 4.10 | 3.23 |
| 3935486 | 6.12 | 5.35 | 5.01 | 5.37 | 6.75 | 8.44 | 6.94 | 8.97 | 6.35 | 7.64 | 5.24 | 8.01 |
| 3457336 | 5.49 | 5.54 | 6.03 | 5.67 | 5.65 | 5.39 | 5.05 | 5.16 | 5.32 | 5.39 | 5.39 | 5.05 |
| 3811949 | 3.41 | 3.52 | 3.44 | 3.57 | 3.34 | 3.60 | 3.33 | 3.37 | 3.51 | 3.56 | 3.40 | 3.27 |
| 3343832 | 3.82 | 3.90 | 3.99 | 4.29 | 4.13 | 3.89 | 3.69 | 3.73 | 3.59 | 3.98 | 3.77 | 3.79 |
| 3161261 | 6.53 | 6.11 | 6.77 | 6.57 | 5.48 | 6.46 | 5.45 | 5.37 | 5.02 | 5.69 | 5.70 | 5.75 |
| 3594003 | 3.72 | 3.70 | 3.57 | 4.19 | 3.48 | 3.91 | 3.37 | 3.80 | 3.85 | 4.34 | 3.78 | 3.35 |
| 3805614 | 4.73 | 4.88 | 4.30 | 5.24 | 4.50 | 5.04 | 4.41 | 4.50 | 4.42 | 5.38 | 4.41 | 4.68 |
| 3364127 | 6.86 | 7.09 | 6.85 | 6.59 | 6.63 | 6.97 | 6.42 | 7.03 | 6.85 | 7.01 | 6.57 | 7.03 |
| 3834341 | 4.12 | 3.99 | 3.91 | 3.93 | 3.85 | 3.95 | 3.83 | 4.01 | 3.99 | 4.13 | 3.80 | 7.22 |
| 2585400 | 5.41 | 4.24 | 4.32 | 4.38 | 4.20 | 4.25 | 5.10 | 4.57 | 4.22 | 4.88 | 4.34 | 7.16 |
| 2941690 | 4.08 | 3.84 | 3.91 | 4.74 | 4.13 | 4.78 | 3.81 | 4.39 | 4.41 | 4.35 | 4.18 | 3.92 |
| 3484895 | 4.61 | 4.94 | 4.82 | 4.93 | 4.94 | 4.76 | 5.93 | 5.12 | 5.31 | 4.82 | 4.58 | 4.54 |
| 3159754 | 3.85 | 3.76 | 3.77 | 4.16 | 3.69 | 3.86 | 3.53 | 3.84 | 3.73 | 3.83 | 3.63 | 4.40 |
| 2894790 | 3.91 | 3.77 | 4.41 | 3.89 | 3.69 | 3.70 | 3.53 | 3.71 | 3.81 | 3.90 | 4.21 | 3.65 |
| 3363686 | 3.73 | 3.33 | 3.60 | 3.62 | 3.23 | 3.35 | 3.37 | 3.43 | 3.39 | 3.50 | 3.54 | 3.29 |
| 2923928 | 4.38 | 4.71 | 4.61 | 6.86 | 4.04 | 4.57 | 6.22 | 4.20 | 4.05 | 4.24 | 4.22 | 4.06 |
| 2883317 | 5.17 | 5.11 | 4.63 | 5.15 | 3.96 | 4.97 | 4.99 | 4.53 | 4.56 | 5.39 | 4.57 | 4.71 |
| 2479698 | 6.25 | 6.07 | 6.44 | 6.03 | 6.08 | 5.95 | 5.91 | 5.87 | 6.37 | 5.90 | 6.00 | 5.88 |
| 3428225 | 3.59 | 3.87 | 3.65 | 3.89 | 3.61 | 3.77 | 3.45 | 3.57 | 3.70 | 3.89 | 3.66 | 3.56 |
| 3393446 | 7.04 | 7.43 | 7.26 | 8.46 | 6.60 | 7.28 | 6.67 | 7.06 | 6.71 | 7.88 | 6.76 | 7.02 |
| 3116614 | 12.76 | 12.81 | 13.20 | 6.70 | 12.16 | 12.66 | 12.11 | 12.12 | 13.14 | 7.57 | 12.84 | 11.19 |
| 3415320 | 10.27 | 8.96 | 9.38 | 6.18 | 11.09 | 10.53 | 10.66 | 11.11 | 10.50 | 6.95 | 9.76 | 8.20 |
| 3757108 | 7.66 | 7.82 | 7.90 | 7.48 | 11.01 | 7.71 | 10.76 | 11.04 | 7.52 | 7.51 | 8.18 | 12.61 |
| 4012178 | 5.96 | 8.61 | 9.11 | 6.67 | 11.17 | 6.60 | 10.85 | 10.73 | 6.16 | 6.36 | 6.04 | |
| 3546213 | 11.07 | 10.76 | 11.48 | 5.04 | 10.83 | 10.33 | 10.65 | 10.97 | 11.59 | 5.96 | 11.48 | 9.31 |
| 3561381 | 9.62 | 10.44 | 10.38 | 4.51 | 9.59 | 9.46 | 9.92 | 10.29 | 10.28 | 5.31 | 10.40 | 7.73 |

TABLE 27

Normalized intensity of microarray data for a set of samples.

| TCID | V01 0025 | V01 0026 | V01 0027 | V01 0028 | V01 0029 | V01 0030 | V01 0031 | V01 0032 | V01 0033 | V01 0034 | V01 0035 | V01 0036 |
|---|---|---|---|---|---|---|---|---|---|---|---|---|
| 2604998 | 7.11 | 7.77 | 8.36 | 9.20 | 8.92 | 7.37 | 7.16 | 6.31 | 8.61 | 5.73 | 7.40 | 7.58 |
| 3603932 | 6.72 | 7.07 | 8.86 | 7.37 | 7.35 | 8.11 | 7.75 | 7.20 | 6.63 | 7.34 | 6.63 | 6.24 |

TABLE 27-continued

Normalized intensity of microarray data for a set of samples.

| TCID | V01 0025 | V01 0026 | V01 0027 | V01 0028 | V01 0029 | V01 0030 | V01 0031 | V01 0032 | V01 0033 | V01 0034 | V01 0035 | V01 0036 |
|---|---|---|---|---|---|---|---|---|---|---|---|---|
| 2710599 | 6.86 | 8.22 | 7.25 | 11.50 | 10.24 | 9.18 | 11.19 | 5.44 | 7.68 | 6.38 | 7.76 | 6.63 |
| 2440258 | 8.91 | 8.41 | 5.66 | 7.25 | 4.69 | 7.61 | 5.59 | 8.72 | 7.41 | 8.50 | 8.53 | 7.94 |
| 3169331 | 6.84 | 6.63 | 8.49 | 6.77 | 7.07 | 6.93 | 7.20 | 6.90 | 7.40 | 6.84 | 6.11 | 5.82 |
| 2988882 | 9.74 | 9.58 | 10.62 | 9.73 | 9.85 | 10.13 | 9.97 | 9.86 | 10.02 | 9.93 | 9.30 | 9.47 |
| 2964231 | 7.94 | 8.46 | 9.30 | 8.17 | 9.56 | 10.66 | 10.59 | 8.99 | 8.46 | 9.00 | 8.95 | 9.36 |
| 3111561 | 7.25 | 7.52 | 8.74 | 4.58 | 9.95 | 9.79 | 4.76 | 7.51 | 11.08 | 5.69 | 8.81 | 9.12 |
| 2562529 | 8.53 | 9.43 | 9.54 | 11.01 | 10.82 | 10.00 | 11.01 | 7.98 | 9.66 | 8.64 | 8.64 | 9.46 |
| 3692999 | 8.73 | 9.50 | 9.25 | 9.42 | 13.04 | 11.18 | 7.92 | 9.75 | 11.37 | 6.38 | 10.71 | 8.19 |
| 2439554 | 7.22 | 7.53 | 6.17 | 7.65 | 4.94 | 5.94 | 5.24 | 7.56 | 6.01 | 7.12 | 7.05 | 7.33 |
| 2685304 | 8.21 | 9.25 | 7.77 | 11.18 | 8.71 | 8.30 | 11.83 | 8.38 | 7.54 | 7.78 | 7.78 | 6.84 |
| 2578790 | 5.59 | 5.23 | 5.60 | 4.35 | 6.54 | 6.40 | 4.86 | 5.01 | 7.93 | 4.93 | 6.27 | 7.08 |
| 2373842 | 12.03 | 11.82 | 10.39 | 10.07 | 7.73 | 10.78 | 8.12 | 11.87 | 10.88 | 11.82 | 11.69 | 11.69 |
| 2750627 | 6.94 | 8.69 | 7.74 | 9.93 | 10.59 | 8.90 | 8.92 | 7.75 | 10.44 | 5.59 | 8.70 | 8.15 |
| 3397774 | 5.30 | 4.95 | 7.88 | 4.67 | 4.89 | 4.83 | 4.79 | 4.88 | 4.71 | 5.29 | 4.88 | 5.07 |
| 2635741 | 9.31 | 8.35 | 7.39 | 7.44 | 6.61 | 6.88 | 5.84 | 8.95 | 8.10 | 9.23 | 9.18 | 8.04 |
| 3970833 | 9.36 | 9.41 | 10.90 | 9.70 | 9.68 | 9.77 | 9.90 | 9.27 | 9.40 | 8.79 | 9.44 | 9.49 |
| 3577612 | 11.01 | 11.17 | 9.49 | 11.47 | 9.10 | 9.09 | 11.11 | 11.19 | 9.94 | 11.01 | 11.23 | 11.16 |
| 2708922 | 8.54 | 8.95 | 6.78 | 8.20 | 8.20 | 7.26 | 9.02 | 9.43 | 7.75 | 8.24 | 8.20 | 8.00 |
| 2970897 | 4.90 | 4.85 | 7.47 | 4.62 | 6.08 | 6.51 | 4.64 | 5.40 | 5.36 | 5.22 | 5.04 | 4.88 |
| 3724545 | 10.31 | 10.36 | 6.76 | 9.58 | 9.94 | 8.78 | 10.00 | 10.54 | 9.34 | 8.65 | 9.74 | 8.11 |
| 2798538 | 9.32 | 9.20 | 9.74 | 8.80 | 8.75 | 9.96 | 9.72 | 9.80 | 9.07 | 8.64 | 10.33 | 9.22 |
| 2806468 | 11.59 | 11.29 | 8.54 | 8.83 | 7.67 | 9.29 | 6.72 | 11.34 | 10.02 | 11.41 | 11.88 | 10.80 |
| 2880051 | 6.89 | 6.63 | 7.22 | 6.03 | 5.61 | 5.98 | 6.16 | 6.55 | 6.29 | 6.86 | 6.45 | 6.50 |
| 2732508 | 3.54 | 3.57 | 4.17 | 7.62 | 3.72 | 3.46 | 3.80 | 3.95 | 3.58 | 5.12 | 3.54 | 3.49 |
| 2822492 | 5.35 | 6.13 | 6.97 | 4.82 | 6.40 | 5.34 | 6.12 | 5.59 | 5.32 | 5.26 | 5.20 | 5.22 |
| 3404030 | 9.92 | 8.80 | 7.55 | 6.18 | 5.59 | 7.80 | 5.48 | 8.15 | 8.10 | 9.87 | 8.78 | 7.61 |
| 3059667 | 7.60 | 10.84 | 4.56 | 4.84 | 11.31 | 9.73 | 7.20 | 7.47 | 11.62 | 6.34 | 8.25 | 8.18 |
| 3108526 | 9.59 | 7.48 | 10.39 | 8.09 | 11.15 | 9.43 | 8.94 | 8.43 | 10.47 | 6.30 | 9.09 | 9.44 |
| 2526806 | 8.81 | 11.09 | 10.91 | 12.10 | 9.11 | 9.51 | 12.34 | 8.08 | 8.01 | 10.02 | 10.81 | 10.00 |
| 2428501 | 6.85 | 7.25 | 8.18 | 6.82 | 4.87 | 7.77 | 6.95 | 7.21 | 5.85 | 7.65 | 7.01 | 6.35 |
| 2657808 | 5.49 | 5.78 | 5.92 | 11.55 | 7.96 | 8.24 | 10.64 | 5.38 | 6.89 | 6.03 | 5.35 | 5.57 |
| 2584018 | 8.19 | 7.43 | 6.48 | 10.81 | 9.10 | 10.60 | 10.32 | 8.06 | 7.46 | 9.27 | 8.73 | 8.31 |
| 3976341 | 10.41 | 10.66 | 7.85 | 11.33 | 10.06 | 9.27 | 11.19 | 9.96 | 8.70 | 10.06 | 9.91 | 9.47 |
| 2739308 | 5.76 | 6.48 | 5.28 | 4.53 | 5.19 | 4.58 | 4.69 | 6.41 | 5.12 | 5.52 | 5.68 | 4.68 |
| 3959862 | 5.91 | 5.93 | 11.26 | 5.50 | 4.23 | 4.13 | 4.44 | 4.70 | 4.51 | 4.91 | 5.31 | 5.30 |
| 2362351 | 8.70 | 8.04 | 7.34 | 6.59 | 5.83 | 6.39 | 5.70 | 8.01 | 7.42 | 8.34 | 7.50 | 7.77 |
| 3648391 | 5.33 | 4.70 | 4.64 | 5.34 | 4.07 | 5.22 | 3.94 | 5.24 | 4.93 | 5.22 | 5.52 | 4.67 |
| 3009299 | 10.49 | 10.66 | 11.37 | 10.51 | 11.03 | 10.90 | 11.04 | 10.56 | 10.50 | 10.35 | 10.49 | 10.51 |
| 3443464 | 7.26 | 5.75 | 6.64 | 5.11 | 5.05 | 5.81 | 5.12 | 5.77 | 5.87 | 7.13 | 5.92 | 5.67 |
| 2730746 | 7.28 | 7.20 | 8.19 | 6.95 | 9.12 | 7.83 | 6.58 | 6.95 | 8.15 | 5.69 | 7.13 | 7.30 |
| 2427619 | 9.52 | 8.94 | 7.25 | 6.90 | 5.20 | 7.19 | 5.17 | 9.84 | 8.17 | 9.70 | 9.58 | 8.45 |
| 3042001 | 8.84 | 8.52 | 9.57 | 8.68 | 8.36 | 9.06 | 8.83 | 8.69 | 8.55 | 9.33 | 8.80 | 8.27 |
| 2566848 | 5.72 | 5.70 | 5.55 | 5.21 | 4.92 | 5.10 | 4.97 | 6.01 | 5.27 | 6.35 | 5.58 | 5.79 |
| 2984616 | 8.68 | 9.39 | 9.34 | 8.70 | 9.35 | 9.48 | 9.23 | 8.46 | 9.06 | 9.03 | 8.42 | 8.37 |
| 2378068 | 7.77 | 7.45 | 6.91 | 10.38 | 5.38 | 9.05 | 10.06 | 7.27 | 7.64 | 8.72 | 7.53 | 8.33 |
| 2721959 | 6.10 | 6.77 | 6.22 | 10.85 | 8.65 | 7.62 | 12.95 | 6.00 | 7.83 | 6.08 | 7.84 | 6.59 |
| 2877508 | 10.05 | 10.14 | 11.38 | 10.35 | 10.30 | 10.97 | 10.69 | 10.05 | 10.34 | 9.79 | 10.07 | 10.17 |
| 3450861 | 6.34 | 6.41 | 5.41 | 5.07 | 4.82 | 4.78 | 5.30 | 7.29 | 5.97 | 7.11 | 6.78 | 6.52 |
| 2688717 | 9.03 | 9.04 | 6.86 | 8.62 | 6.35 | 6.94 | 5.34 | 9.74 | 7.62 | 9.99 | 9.10 | 9.92 |
| 3270270 | 9.44 | 9.44 | 7.24 | 8.03 | 7.16 | 8.75 | 8.26 | 9.73 | 7.79 | 8.99 | 9.62 | 8.86 |
| 3417703 | 6.90 | 5.01 | 4.53 | 7.92 | 10.35 | 8.38 | 6.88 | 7.19 | 10.88 | 4.84 | 6.97 | 4.67 |
| 3302990 | 7.37 | 7.53 | 9.91 | 7.56 | 6.94 | 7.85 | 8.66 | 6.84 | 7.27 | 6.76 | 6.97 | 6.88 |
| 2377283 | 4.81 | 4.81 | 4.46 | 9.62 | 4.20 | 4.17 | 4.13 | 5.07 | 4.24 | 5.90 | 5.24 | 5.32 |
| 3122678 | 4.90 | 4.98 | 6.38 | 4.37 | 4.27 | 4.30 | 4.70 | 4.34 | 4.51 | 5.02 | 4.27 | 4.02 |
| 2688499 | 7.85 | 9.76 | 6.98 | 9.47 | 11.05 | 8.60 | 7.78 | 6.82 | 10.10 | 8.04 | 8.76 | 8.57 |
| 2377094 | 8.44 | 8.37 | 11.22 | 8.40 | 9.73 | 9.36 | 9.76 | 7.92 | 9.79 | 8.05 | 8.21 | 8.70 |
| 3278198 | 7.20 | 6.65 | 9.92 | 7.97 | 8.76 | 8.42 | 9.18 | 6.69 | 8.25 | 6.61 | 7.42 | 7.79 |
| 2598261 | 8.37 | 10.38 | 10.08 | 11.70 | 9.10 | 8.58 | 12.17 | 7.51 | 7.48 | 9.70 | 10.53 | 9.78 |
| 3982612 | 9.32 | 8.49 | 7.07 | 7.98 | 6.49 | 6.80 | 6.47 | 9.07 | 8.47 | 9.44 | 9.45 | 8.97 |
| 2884845 | 4.63 | 4.65 | 4.59 | 8.05 | 5.58 | 4.69 | 7.53 | 4.41 | 4.65 | 4.78 | 4.99 | 4.95 |
| 3982560 | 7.37 | 7.24 | 5.22 | 5.88 | 4.88 | 5.23 | 5.04 | 8.14 | 6.35 | 7.64 | 7.98 | 6.86 |
| 3204285 | 5.47 | 5.57 | 5.78 | 6.82 | 5.62 | 5.16 | 5.43 | 5.86 | 5.50 | 6.86 | 5.44 | 5.50 |
| 3654699 | 10.54 | 9.30 | 12.58 | 10.71 | 10.95 | 12.52 | 12.11 | 10.17 | 11.54 | 12.15 | 10.93 | 11.33 |
| 2638676 | 7.22 | 7.20 | 6.51 | 7.49 | 5.85 | 6.46 | 5.26 | 8.03 | 6.76 | 7.15 | 7.65 | 8.04 |
| 3367673 | 7.03 | 6.55 | 7.90 | 5.29 | 9.09 | 7.74 | 6.71 | 5.19 | 9.25 | 6.12 | 7.45 | 8.43 |
| 3212008 | 6.70 | 7.95 | 6.16 | 9.87 | 8.97 | 7.23 | 8.85 | 6.47 | 7.99 | 6.31 | 6.32 | 6.53 |
| 3326635 | 10.16 | 10.24 | 8.84 | 10.61 | 10.02 | 10.32 | 10.08 | 10.13 | 10.03 | 9.85 | 10.22 | 10.33 |
| 3031556 | 10.07 | 10.16 | 7.19 | 8.08 | 6.13 | 8.46 | 5.82 | 10.15 | 8.50 | 10.26 | 10.03 | 9.54 |
| 3662201 | 8.16 | 9.26 | 8.90 | 8.61 | 12.76 | 10.22 | 7.76 | 9.57 | 11.55 | 7.57 | 10.64 | 9.11 |
| 2809793 | 9.43 | 8.30 | 7.15 | 7.64 | 4.51 | 6.56 | 4.67 | 9.47 | 8.51 | 9.62 | 8.40 | 7.98 |
| 2817731 | 7.76 | 8.01 | 7.56 | 7.50 | 7.03 | 10.01 | 7.68 | 8.07 | 7.21 | 8.11 | 8.03 | 8.46 |
| 4020655 | 5.51 | 6.96 | 5.25 | 7.82 | 8.37 | 4.99 | 8.39 | 5.42 | 5.03 | 5.72 | 5.36 | 5.04 |
| 3494629 | 4.39 | 4.93 | 5.31 | 8.20 | 6.37 | 4.51 | 8.13 | 4.38 | 5.03 | 4.41 | 4.63 | 4.30 |
| 3852832 | 9.44 | 10.04 | 7.33 | 5.61 | 5.62 | 6.90 | 6.05 | 10.34 | 7.86 | 9.60 | 10.42 | 7.86 |
| 3761959 | 9.12 | 8.77 | 8.78 | 9.39 | 10.07 | 9.50 | 9.38 | 8.72 | 8.98 | 8.45 | 8.66 | 7.89 |

TABLE 27-continued

Normalized intensity of microarray data for a set of samples.

| TCID | V01 0025 | V01 0026 | V01 0027 | V01 0028 | V01 0029 | V01 0030 | V01 0031 | V01 0032 | V01 0033 | V01 0034 | V01 0035 | V01 0036 |
|---|---|---|---|---|---|---|---|---|---|---|---|---|
| 2834282 | 5.80 | 6.19 | 6.95 | 8.37 | 8.64 | 5.30 | 8.25 | 6.17 | 6.79 | 6.09 | 6.20 | 6.00 |
| 3341497 | 6.32 | 6.01 | 6.73 | 8.80 | 7.43 | 7.43 | 8.77 | 6.40 | 7.27 | 6.53 | 5.50 | 6.54 |
| 2372812 | 5.38 | 4.99 | 5.78 | 8.44 | 4.90 | 4.53 | 4.68 | 5.34 | 4.72 | 4.82 | 4.65 | 4.78 |
| 2486811 | 10.22 | 10.13 | 7.83 | 8.75 | 7.30 | 10.98 | 6.03 | 10.52 | 8.45 | 10.45 | 10.40 | 10.50 |
| 3768474 | 8.29 | 8.44 | 8.39 | 7.79 | 7.87 | 8.95 | 7.79 | 8.86 | 7.02 | 8.05 | 8.24 | 8.11 |
| 3142381 | 4.36 | 4.17 | 4.51 | 4.17 | 4.86 | 6.52 | 3.87 | 4.14 | 8.71 | 4.78 | 6.94 | 8.05 |
| 2396750 | 7.38 | 7.52 | 6.74 | 8.23 | 7.91 | 6.78 | 8.32 | 7.13 | 6.98 | 7.14 | 6.95 | 6.75 |
| 3902489 | 11.83 | 11.76 | 9.87 | 10.01 | 9.04 | 10.66 | 9.08 | 12.35 | 10.61 | 11.29 | 11.85 | 11.89 |
| 3032647 | 7.42 | 5.97 | 6.89 | 5.39 | 7.09 | 5.86 | 5.94 | 6.49 | 7.06 | 6.13 | 7.07 | 7.35 |
| 3875642 | 6.76 | 6.55 | 5.85 | 4.93 | 5.12 | 4.97 | 6.63 | 6.39 | 6.33 | 6.27 | 6.27 | 6.28 |
| 4027585 | 11.48 | 11.55 | 9.39 | 9.20 | 8.43 | 11.11 | 8.66 | 12.26 | 10.03 | 11.42 | 11.82 | 11.33 |
| 2352609 | 6.55 | 6.78 | 6.36 | 6.69 | 7.95 | 6.53 | 7.99 | 7.03 | 7.38 | 5.90 | 6.50 | 6.53 |
| 3376529 | 7.77 | 8.18 | 9.43 | 9.11 | 9.62 | 8.16 | 10.14 | 8.00 | 8.23 | 8.25 | 8.06 | 8.32 |
| 2491271 | 13.31 | 13.56 | 12.71 | 13.15 | 12.77 | 13.52 | 12.96 | 13.11 | 12.92 | 13.32 | 13.37 | 13.33 |
| 3874751 | 9.25 | 9.13 | 8.89 | 9.56 | 9.44 | 9.69 | 10.15 | 8.46 | 9.29 | 9.63 | 9.10 | 9.17 |
| 2326463 | 12.05 | 12.27 | 10.19 | 10.35 | 9.28 | 12.89 | 8.32 | 11.84 | 11.33 | 12.40 | 12.06 | 11.89 |
| 3341061 | 7.06 | 7.19 | 6.55 | 7.07 | 6.97 | 9.33 | 6.68 | 7.60 | 5.93 | 8.19 | 7.62 | 7.31 |
| 3839910 | 9.72 | 10.09 | 6.54 | 4.99 | 4.80 | 6.80 | 5.55 | 10.16 | 7.37 | 9.09 | 10.09 | 8.80 |
| 2708855 | 4.11 | 4.70 | 4.20 | 8.41 | 6.86 | 4.29 | 8.37 | 4.20 | 4.63 | 4.18 | 5.03 | 3.94 |
| 3512874 | 12.20 | 12.26 | 10.60 | 11.08 | 9.21 | 11.86 | 9.41 | 12.45 | 11.22 | 12.21 | 12.39 | 12.22 |
| 2701071 | 10.71 | 10.98 | 8.31 | 7.45 | 6.57 | 8.61 | 7.28 | 10.82 | 9.14 | 10.49 | 10.89 | 10.54 |
| 3486096 | 6.36 | 6.67 | 7.01 | 6.81 | 9.19 | 8.16 | 8.20 | 7.34 | 8.29 | 5.65 | 6.73 | 7.31 |
| 2412668 | 8.45 | 8.31 | 7.61 | 7.91 | 8.32 | 8.83 | 8.27 | 8.18 | 7.38 | 8.26 | 8.46 | 8.49 |
| 3329343 | 7.82 | 7.70 | 8.17 | 9.63 | 8.20 | 6.58 | 8.00 | 7.09 | 7.43 | 7.40 | 7.27 | 7.38 |
| 3259367 | 4.27 | 4.35 | 4.38 | 6.21 | 5.36 | 5.69 | 5.28 | 4.50 | 4.32 | 4.35 | 4.19 | 4.37 |
| 3373845 | 8.88 | 9.00 | 7.48 | 8.78 | 8.26 | 11.04 | 9.12 | 8.84 | 8.84 | 9.62 | 9.23 | 9.38 |
| 2321911 | 8.56 | 8.73 | 7.39 | 7.76 | 7.40 | 9.00 | 8.29 | 9.34 | 8.12 | 8.63 | 8.87 | 8.53 |
| 3353954 | 6.11 | 6.35 | 6.38 | 6.89 | 7.22 | 9.20 | 7.49 | 6.43 | 6.28 | 6.96 | 6.49 | 7.16 |
| 3744680 | 8.46 | 8.42 | 7.15 | 6.65 | 6.38 | 7.96 | 6.78 | 8.75 | 6.93 | 8.64 | 8.52 | 8.07 |
| 2373336 | 5.78 | 7.90 | 5.57 | 9.42 | 6.07 | 5.68 | 5.81 | 6.22 | 7.94 | 6.81 | 7.15 | 6.26 |
| 3067478 | 6.54 | 6.29 | 7.31 | 8.19 | 7.86 | 5.45 | 7.42 | 5.52 | 5.67 | 4.91 | 5.58 | 4.78 |
| 3976766 | 9.16 | 9.26 | 7.06 | 6.72 | 6.48 | 7.89 | 6.57 | 9.36 | 7.84 | 9.09 | 9.24 | 9.01 |
| 3246888 | 5.69 | 7.09 | 6.40 | 7.25 | 8.28 | 6.81 | 4.87 | 6.47 | 7.27 | 5.26 | 6.20 | 5.97 |
| 3147985 | 6.82 | 6.59 | 5.91 | 7.30 | 7.13 | 8.45 | 7.81 | 6.55 | 6.07 | 6.04 | 6.31 | 6.48 |
| 3185522 | 9.38 | 9.30 | 9.54 | 9.88 | 9.81 | 10.88 | 8.44 | 9.27 | 8.87 | 10.00 | 9.25 | 10.60 |
| 3861948 | 12.83 | 13.01 | 11.52 | 11.21 | 9.29 | 12.01 | 9.29 | 13.05 | 12.11 | 12.82 | 12.92 | 12.49 |
| 3393479 | 9.50 | 9.85 | 7.85 | 7.68 | 9.40 | 10.36 | 7.92 | 9.14 | 10.19 | 9.51 | 9.28 | 9.29 |
| 3540862 | 6.70 | 6.46 | 9.56 | 6.99 | 7.43 | 6.65 | 9.03 | 6.46 | 6.84 | 6.21 | 6.45 | 6.57 |
| 2777714 | 11.90 | 11.65 | 9.62 | 9.20 | 7.76 | 10.76 | 7.77 | 12.44 | 10.91 | 11.73 | 11.91 | 12.13 |
| 3110395 | 5.67 | 4.53 | 6.57 | 4.71 | 5.59 | 4.16 | 6.45 | 5.42 | 4.79 | 4.42 | 4.23 | 4.29 |
| 3895795 | 8.91 | 9.51 | 7.66 | 8.20 | 7.82 | 7.79 | 8.45 | 9.77 | 7.90 | 9.20 | 9.85 | 8.45 |
| 2854445 | 8.75 | 8.71 | 7.49 | 8.95 | 8.01 | 10.97 | 6.43 | 8.78 | 8.68 | 9.73 | 8.98 | 10.35 |
| 3606034 | 7.28 | 7.13 | 7.21 | 7.44 | 7.62 | 8.78 | 7.62 | 7.14 | 7.65 | 7.40 | 7.20 | 7.32 |
| 3375735 | 8.42 | 8.39 | 7.75 | 7.38 | 7.62 | 8.79 | 7.47 | 7.66 | 7.62 | 8.55 | 8.88 | 8.29 |
| 3948047 | 8.94 | 9.03 | 7.60 | 7.52 | 7.39 | 8.87 | 6.75 | 8.78 | 7.64 | 9.13 | 9.16 | 8.84 |
| 3010503 | 9.51 | 9.89 | 7.47 | 7.36 | 6.18 | 11.28 | 5.72 | 10.07 | 8.65 | 9.14 | 10.12 | 9.68 |
| 3622934 | 6.21 | 6.92 | 8.40 | 8.10 | 7.56 | 7.20 | 8.42 | 6.54 | 7.48 | 6.42 | 6.12 | 6.63 |
| 3441849 | 10.43 | 10.57 | 8.96 | 10.22 | 9.63 | 9.34 | 10.06 | 10.65 | 9.06 | 10.33 | 10.85 | 10.52 |
| 3006572 | 6.86 | 6.69 | 6.72 | 7.15 | 6.65 | 6.14 | 6.42 | 6.37 | 6.23 | 6.88 | 6.54 | 6.61 |
| 3365136 | 8.72 | 8.19 | 8.51 | 10.98 | 9.60 | 8.35 | 9.64 | 7.76 | 9.10 | 8.28 | 8.15 | 7.64 |
| 2642791 | 8.43 | 8.50 | 8.27 | 8.18 | 8.68 | 9.20 | 8.44 | 8.34 | 8.33 | 8.55 | 8.67 | 8.61 |
| 2904485 | 8.62 | 8.88 | 7.21 | 7.45 | 9.19 | 7.67 | 7.52 | 8.20 | 8.54 | 7.13 | 8.17 | 7.80 |
| 3772661 | 9.98 | 10.14 | 8.66 | 10.01 | 9.73 | 11.67 | 9.32 | 10.50 | 8.93 | 10.69 | 10.49 | 10.67 |
| 2796553 | 10.25 | 10.91 | 9.58 | 8.68 | 8.42 | 10.40 | 9.11 | 11.31 | 9.16 | 10.68 | 10.96 | 10.95 |
| 3063795 | 7.45 | 6.91 | 7.97 | 8.10 | 7.03 | 6.93 | 6.76 | 7.67 | 6.95 | 9.09 | 7.62 | 7.92 |
| 3338192 | 8.43 | 9.45 | 8.50 | 10.50 | 10.40 | 9.12 | 10.21 | 7.54 | 9.47 | 7.83 | 7.78 | 8.12 |
| 3214845 | 4.49 | 4.25 | 4.64 | 5.50 | 3.93 | 4.17 | 4.35 | 6.28 | 6.22 | 6.41 | 4.45 | 4.13 |
| 2730303 | 4.27 | 4.28 | 4.01 | 8.26 | 4.29 | 4.00 | 4.20 | 4.38 | 4.12 | 4.30 | 4.33 | 4.27 |
| 3811086 | 7.73 | 7.62 | 7.62 | 7.17 | 7.68 | 8.43 | 7.92 | 7.42 | 7.78 | 7.35 | 7.61 | 7.33 |
| 2981874 | 10.25 | 10.54 | 10.59 | 9.74 | 9.92 | 10.51 | 10.30 | 10.36 | 10.42 | 10.31 | 10.07 | 10.11 |
| 3242353 | 6.05 | 6.12 | 5.86 | 6.06 | 5.85 | 6.19 | 6.05 | 6.04 | 5.71 | 6.04 | 5.46 | 5.80 |
| 2442008 | 5.30 | 6.99 | 5.28 | 8.90 | 7.34 | 5.25 | 5.27 | 5.27 | 5.72 | 5.49 | 5.28 | 5.28 |
| 3564210 | 10.21 | 10.84 | 8.29 | 7.87 | 6.94 | 9.73 | 6.99 | 11.06 | 8.56 | 10.26 | 10.88 | 9.37 |
| 2490351 | 4.27 | 4.20 | 4.58 | 3.94 | 3.95 | 4.00 | 4.00 | 4.28 | 4.13 | 4.45 | 4.16 | 4.10 |
| 3759006 | 10.30 | 10.30 | 7.94 | 7.85 | 6.74 | 8.75 | 6.73 | 11.15 | 8.69 | 9.88 | 11.18 | 10.45 |
| 3264997 | 4.48 | 4.42 | 4.13 | 3.81 | 3.92 | 4.00 | 4.14 | 4.35 | 4.06 | 4.48 | 4.15 | 4.02 |
| 3912079 | 3.74 | 4.21 | 3.86 | 3.38 | 3.46 | 3.57 | 3.78 | 3.89 | 3.57 | 4.11 | 3.83 | 4.07 |
| 2926802 | 5.64 | 5.61 | 5.83 | 5.04 | 4.56 | 4.69 | 4.57 | 6.80 | 4.93 | 5.78 | 5.60 | 5.04 |
| 2430163 | 4.12 | 4.27 | 3.72 | 3.58 | 3.75 | 3.82 | 3.58 | 4.10 | 3.76 | 4.14 | 3.87 | 3.93 |
| 3039830 | 3.15 | 3.11 | 3.08 | 2.97 | 5.39 | 3.17 | 3.07 | 3.18 | 3.07 | 3.18 | 3.40 | 3.37 |
| 3935486 | 6.44 | 7.77 | 5.61 | 6.31 | 6.07 | 9.11 | 5.21 | 6.26 | 5.26 | 9.16 | 5.30 | 6.11 |
| 3457336 | 5.81 | 5.41 | 5.56 | 4.81 | 5.44 | 8.39 | 5.31 | 5.41 | 5.62 | 5.79 | 5.67 | 5.44 |
| 3811949 | 3.58 | 3.52 | 3.48 | 3.29 | 3.37 | 3.38 | 3.43 | 3.90 | 3.55 | 3.60 | 3.59 | 3.48 |
| 3343832 | 3.92 | 3.82 | 3.87 | 3.61 | 3.83 | 3.64 | 3.98 | 3.80 | 3.82 | 4.10 | 3.87 | 3.87 |
| 3161261 | 6.48 | 5.90 | 6.53 | 5.19 | 5.31 | 5.84 | 6.10 | 6.45 | 5.86 | 6.63 | 5.94 | 6.13 |

TABLE 27-continued

Normalized intensity of microarray data for a set of samples.

| TCID | V01 0025 | V01 0026 | V01 0027 | V01 0028 | V01 0029 | V01 0030 | V01 0031 | V01 0032 | V01 0033 | V01 0034 | V01 0035 | V01 0036 |
|---|---|---|---|---|---|---|---|---|---|---|---|---|
| 3594003 | 3.75 | 3.71 | 3.66 | 3.50 | 3.69 | 3.58 | 3.59 | 3.80 | 3.62 | 4.05 | 3.92 | 4.03 |
| 3805614 | 5.06 | 4.92 | 4.58 | 4.42 | 4.34 | 4.50 | 4.81 | 5.05 | 4.67 | 5.11 | 4.69 | 4.71 |
| 3364127 | 7.09 | 6.82 | 7.45 | 6.38 | 6.56 | 6.96 | 6.57 | 7.08 | 6.73 | 7.37 | 6.91 | 7.04 |
| 3834341 | 4.28 | 4.16 | 4.08 | 3.81 | 3.91 | 3.93 | 4.24 | 3.76 | 3.94 | 4.40 | 3.93 | 4.01 |
| 2585400 | 4.35 | 4.21 | 4.34 | 3.98 | 4.15 | 4.17 | 4.26 | 4.43 | 4.43 | 4.66 | 4.58 | 4.65 |
| 2941690 | 4.49 | 4.23 | 4.62 | 3.96 | 4.24 | 4.17 | 4.20 | 4.32 | 4.20 | 4.72 | 3.95 | 4.45 |
| 3484895 | 4.82 | 4.95 | 5.36 | 4.86 | 5.28 | 4.60 | 5.38 | 4.53 | 5.20 | 5.48 | 4.91 | 4.79 |
| 3159754 | 3.84 | 3.75 | 3.93 | 3.58 | 3.79 | 3.85 | 3.56 | 3.61 | 3.84 | 4.05 | 3.73 | 3.66 |
| 2894790 | 4.10 | 3.90 | 3.76 | 3.69 | 3.86 | 3.74 | 3.79 | 4.06 | 3.79 | 4.21 | 3.91 | 3.91 |
| 3363686 | 3.52 | 3.41 | 3.41 | 3.26 | 3.54 | 3.40 | 3.47 | 3.33 | 3.61 | 3.69 | 3.26 | 3.44 |
| 2923928 | 4.37 | 4.02 | 4.37 | 4.02 | 4.17 | 4.14 | 4.17 | 4.30 | 4.14 | 4.40 | 4.74 | 4.58 |
| 2883317 | 5.29 | 5.08 | 4.96 | 4.50 | 4.37 | 5.29 | 4.30 | 5.71 | 5.01 | 5.13 | 5.15 | 4.79 |
| 2479698 | 6.22 | 5.99 | 6.25 | 5.66 | 5.92 | 5.86 | 6.42 | 6.16 | 6.22 | 6.08 | 6.10 | 6.01 |
| 3428225 | 4.05 | 3.54 | 3.75 | 3.47 | 3.59 | 3.65 | 3.68 | 3.98 | 3.63 | 4.09 | 3.58 | 3.68 |
| 3393446 | 7.47 | 7.40 | 7.64 | 6.64 | 6.42 | 8.18 | 6.77 | 7.42 | 7.26 | 7.59 | 7.01 | 8.45 |
| 3116614 | 12.84 | 12.14 | 10.92 | 12.59 | 13.11 | 12.73 | 12.66 | 11.93 | 13.00 | 9.41 | 12.72 | 11.96 |
| 3415320 | 10.70 | 9.13 | 11.13 | 10.10 | 10.97 | 8.82 | 11.46 | 9.71 | 9.77 | 7.03 | 9.21 | 8.66 |
| 3757108 | 7.99 | 8.70 | 7.73 | 9.23 | 8.61 | 7.58 | 10.24 | 7.60 | 8.74 | 8.08 | 7.64 | 7.64 |
| 4012178 | 6.37 | 7.09 | 6.68 | 11.09 | 10.13 | 7.32 | 11.92 | 7.36 | 7.69 | 6.64 | 6.42 | 6.12 |
| 3546213 | 9.63 | 9.69 | 11.53 | 11.42 | 11.62 | 10.14 | 11.22 | 8.90 | 11.21 | 7.11 | 9.78 | 9.42 |
| 3561381 | 8.44 | 9.43 | 9.10 | 10.56 | 10.85 | 9.13 | 10.76 | 7.75 | 10.06 | 6.45 | 7.53 | 9.24 |

TABLE 28

Normalized intensity of microarray data for a set of samples.

| TCID | V01 0037 | V01 0038 | V01 0039 | V01 0040 | V01 0041 | V01 0042 | V01 0043 | V01 0044 | V01 0045 | V01 0046 | V01 0047 | V01 0048 |
|---|---|---|---|---|---|---|---|---|---|---|---|---|
| 2604998 | 8.47 | 5.53 | 8.30 | 8.61 | 7.52 | 5.99 | 9.02 | 8.33 | 8.39 | 5.40 | 7.37 | 7.97 |
| 3603932 | 6.59 | 7.32 | 6.49 | 6.78 | 7.47 | 8.60 | 7.94 | 7.29 | 7.01 | 7.09 | 7.33 | 7.01 |
| 2710599 | 6.32 | 6.83 | 5.52 | 8.16 | 10.23 | 8.51 | 10.84 | 9.92 | 10.69 | 6.42 | 5.44 | 7.53 |
| 2440258 | 8.18 | 9.31 | 6.59 | 5.75 | 8.39 | 7.26 | 6.16 | 7.73 | 7.19 | 8.99 | 9.34 | 8.29 |
| 3169331 | 7.31 | 6.55 | 6.96 | 7.12 | 6.69 | 7.03 | 6.83 | 7.00 | 6.84 | 6.77 | 6.03 | 7.93 |
| 2988882 | 9.64 | 9.73 | 9.82 | 10.05 | 9.71 | 10.47 | 9.76 | 9.35 | 10.02 | 9.51 | 9.87 | 10.28 |
| 2964231 | 8.27 | 8.56 | 7.23 | 8.58 | 9.38 | 11.11 | 10.19 | 7.91 | 10.02 | 7.78 | 7.33 | 9.69 |
| 3111561 | 10.34 | 7.40 | 8.83 | 11.06 | 4.47 | 5.75 | 9.83 | 9.86 | 7.80 | 7.32 | 8.94 | 8.86 |
| 2562529 | 8.94 | 7.94 | 9.95 | 9.66 | 10.26 | 9.33 | 10.77 | 10.39 | 9.72 | 8.96 | 9.37 | 9.26 |
| 3692999 | 12.75 | 8.75 | 9.12 | 13.04 | 7.30 | 8.02 | 13.20 | 12.26 | 11.24 | 7.26 | 10.76 | 12.94 |
| 2439554 | 6.12 | 7.87 | 5.33 | 5.05 | 9.00 | 7.51 | 4.39 | 6.35 | 5.33 | 7.61 | 6.83 | 7.12 |
| 2685304 | 6.77 | 7.74 | 5.97 | 7.44 | 10.09 | 8.89 | 9.97 | 8.65 | 9.99 | 8.19 | 7.02 | 6.40 |
| 2578790 | 8.42 | 5.64 | 7.20 | 7.59 | 4.15 | 5.34 | 4.58 | 6.15 | 6.48 | 5.30 | 5.90 | 4.64 |
| 2373842 | 11.58 | 11.67 | 10.08 | 10.04 | 11.06 | 11.10 | 8.44 | 11.03 | 11.02 | 11.93 | 11.67 | 11.59 |
| 2750627 | 9.37 | 7.92 | 10.17 | 11.00 | 10.01 | 6.47 | 10.32 | 9.90 | 9.42 | 8.92 | 9.04 | 6.32 |
| 3397774 | 4.51 | 5.12 | 5.51 | 5.18 | 4.62 | 4.85 | 5.08 | 5.62 | 5.07 | 5.55 | 5.35 | 5.32 |
| 2635741 | 8.77 | 9.47 | 7.03 | 7.37 | 8.11 | 7.72 | 5.69 | 7.68 | 8.31 | 9.25 | 9.06 | 8.63 |
| 3970833 | 9.48 | 9.06 | 9.62 | 9.89 | 9.32 | 9.77 | 10.02 | 9.59 | 9.48 | 9.10 | 9.27 | 9.88 |
| 3577612 | 10.60 | 10.80 | 9.45 | 9.74 | 11.18 | 10.41 | 10.14 | 9.70 | 10.47 | 11.18 | 11.03 | 10.55 |
| 2708922 | 7.74 | 10.16 | 8.25 | 8.28 | 7.96 | 6.82 | 8.45 | 8.15 | 7.93 | 9.11 | 8.98 | 7.23 |
| 2970897 | 5.79 | 4.63 | 5.39 | 6.12 | 4.75 | 6.47 | 5.52 | 5.35 | 5.08 | 4.97 | 5.50 | 6.84 |
| 3724545 | 10.22 | 9.30 | 9.68 | 8.90 | 9.35 | 8.52 | 9.70 | 10.44 | 9.81 | 9.53 | 8.90 | 9.34 |
| 2798538 | 8.77 | 9.38 | 8.55 | 8.94 | 9.45 | 9.57 | 8.48 | 8.36 | 7.90 | 9.12 | 8.45 | 8.81 |
| 2806468 | 11.15 | 11.91 | 9.38 | 9.14 | 10.64 | 10.21 | 7.33 | 10.23 | 11.03 | 11.53 | 11.64 | 11.01 |
| 2880051 | 6.65 | 6.92 | 6.36 | 6.36 | 6.06 | 6.05 | 6.39 | 6.61 | 6.60 | 6.99 | 6.99 | 6.85 |
| 2732508 | 3.48 | 3.79 | 3.54 | 3.61 | 7.09 | 3.52 | 3.53 | 3.68 | 3.60 | 3.84 | 5.13 | 4.36 |
| 2822492 | 5.58 | 5.91 | 5.33 | 5.78 | 5.00 | 5.65 | 6.92 | 5.54 | 5.55 | 5.44 | 5.69 | 5.94 |
| 3404030 | 8.40 | 9.69 | 7.10 | 7.72 | 7.56 | 7.33 | 5.69 | 8.03 | 7.07 | 9.17 | 9.18 | 9.66 |
| 3059667 | 10.57 | 6.10 | 11.72 | 11.95 | 4.86 | 6.12 | 10.04 | 9.57 | 9.41 | 7.04 | 8.84 | 7.34 |
| 3108526 | 10.09 | 7.70 | 10.29 | 10.96 | 6.76 | 7.36 | 9.36 | 9.04 | 10.33 | 7.77 | 8.79 | 10.83 |
| 2526806 | 6.63 | 9.44 | 6.80 | 8.56 | 12.54 | 11.16 | 8.90 | 9.29 | 12.34 | 10.39 | 5.79 | 9.67 |
| 2428501 | 5.81 | 7.11 | 5.29 | 6.14 | 7.77 | 8.41 | 4.90 | 6.11 | 7.37 | 7.53 | 7.50 | 6.88 |
| 2657808 | 5.76 | 5.01 | 6.09 | 8.61 | 9.71 | 5.77 | 9.60 | 7.64 | 9.60 | 5.88 | 5.76 | 5.59 |
| 2584018 | 7.49 | 8.58 | 5.22 | 6.96 | 9.55 | 11.06 | 9.79 | 8.53 | 9.87 | 8.57 | 8.09 | 6.75 |
| 3976341 | 9.10 | 10.06 | 7.59 | 8.33 | 10.99 | 10.41 | 9.90 | 8.64 | 9.79 | 9.45 | 9.63 | 9.45 |
| 2739308 | 4.99 | 6.10 | 5.04 | 4.86 | 4.56 | 5.02 | 5.45 | 5.42 | 5.06 | 5.59 | 5.49 | 5.50 |
| 3959862 | 4.22 | 5.07 | 5.06 | 4.79 | 5.17 | 5.50 | 4.79 | 4.73 | 6.10 | 5.53 | 5.89 | 4.64 |
| 2362351 | 7.71 | 8.13 | 6.20 | 6.40 | 7.59 | 7.44 | 5.39 | 7.17 | 6.72 | 8.62 | 8.40 | 8.27 |
| 3648391 | 4.76 | 6.26 | 4.99 | 3.80 | 6.35 | 4.98 | 4.49 | 4.35 | 5.58 | 4.29 | 5.43 | 7.90 |
| 3009299 | 10.34 | 10.83 | 11.12 | 10.53 | 10.71 | 10.90 | 11.18 | 10.39 | 10.61 | 10.17 | 10.52 | 10.75 |
| 3443464 | 5.55 | 6.08 | 5.62 | 5.41 | 5.71 | 5.68 | 5.05 | 6.34 | 5.48 | 6.77 | 6.25 | 6.45 |
| 2730746 | 8.02 | 5.84 | 8.64 | 8.10 | 5.15 | 5.63 | 9.56 | 8.12 | 7.89 | 6.60 | 6.94 | 8.52 |
| 2427619 | 8.78 | 9.57 | 7.24 | 7.22 | 8.12 | 7.65 | 5.33 | 7.56 | 7.88 | 9.72 | 9.45 | 8.95 |

TABLE 28-continued

Normalized intensity of microarray data for a set of samples.

| TCID | V01 0037 | V01 0038 | V01 0039 | V01 0040 | V01 0041 | V01 0042 | V01 0043 | V01 0044 | V01 0045 | V01 0046 | V01 0047 | V01 0048 |
|---|---|---|---|---|---|---|---|---|---|---|---|---|
| 3042001 | 9.04 | 8.39 | 8.84 | 8.51 | 8.97 | 8.83 | 8.55 | 8.26 | 8.87 | 8.29 | 8.45 | 8.79 |
| 2566848 | 5.27 | 5.94 | 5.22 | 5.04 | 6.00 | 5.55 | 5.18 | 5.50 | 5.33 | 6.41 | 6.09 | 5.37 |
| 2984616 | 9.14 | 9.21 | 8.95 | 8.87 | 9.15 | 9.71 | 9.74 | 7.93 | 8.96 | 8.89 | 8.73 | 9.53 |
| 2378068 | 6.18 | 9.21 | 6.40 | 6.35 | 8.87 | 8.88 | 7.54 | 7.13 | 8.68 | 8.20 | 6.41 | 7.33 |
| 2721959 | 6.59 | 7.53 | 5.96 | 6.79 | 11.48 | 8.41 | 7.20 | 8.12 | 11.16 | 6.10 | 6.27 | 6.82 |
| 2877508 | 10.27 | 9.81 | 10.01 | 9.97 | 10.51 | 10.82 | 10.82 | 9.31 | 10.47 | 10.05 | 9.72 | 10.38 |
| 3450861 | 6.18 | 6.84 | 4.98 | 5.06 | 6.35 | 5.37 | 4.46 | 5.87 | 5.78 | 7.52 | 7.35 | 6.47 |
| 2688717 | 9.06 | 9.99 | 7.44 | 7.05 | 9.33 | 8.39 | 7.59 | 8.38 | 8.48 | 9.77 | 9.81 | 9.67 |
| 3270270 | 8.67 | 8.99 | 7.25 | 7.29 | 8.88 | 9.31 | 6.77 | 7.92 | 8.57 | 9.40 | 8.92 | 8.48 |
| 3417703 | 9.87 | 6.10 | 11.14 | 11.52 | 7.49 | 5.64 | 9.56 | 8.42 | 7.07 | 4.42 | 9.51 | 7.71 |
| 3302990 | 7.62 | 8.08 | 7.70 | 7.84 | 7.50 | 7.72 | 7.49 | 7.33 | 7.56 | 7.25 | 6.56 | 7.87 |
| 2377283 | 4.62 | 5.78 | 4.30 | 4.60 | 8.19 | 4.97 | 4.44 | 4.87 | 4.29 | 5.36 | 4.73 | 4.81 |
| 3122678 | 4.45 | 5.11 | 5.05 | 5.13 | 4.55 | 5.00 | 5.83 | 5.19 | 4.70 | 5.36 | 5.15 | 5.24 |
| 2688499 | 8.97 | 7.14 | 9.78 | 11.09 | 10.01 | 7.07 | 9.39 | 8.59 | 9.26 | 7.93 | 9.50 | 9.28 |
| 2377094 | 9.19 | 7.53 | 9.37 | 9.34 | 8.27 | 8.53 | 9.53 | 8.35 | 8.60 | 6.49 | 8.28 | 10.05 |
| 3278198 | 7.62 | 8.24 | 8.25 | 7.96 | 8.09 | 9.26 | 9.03 | 7.54 | 8.52 | 7.30 | 6.75 | 9.36 |
| 2598261 | 7.25 | 8.98 | 6.58 | 8.12 | 12.47 | 10.55 | 8.00 | 8.84 | 11.90 | 9.99 | 5.85 | 9.31 |
| 3982612 | 8.80 | 9.91 | 6.91 | 7.82 | 8.81 | 7.29 | 4.81 | 7.49 | 8.23 | 9.91 | 10.46 | 8.90 |
| 2884845 | 4.59 | 4.79 | 4.84 | 4.42 | 8.99 | 4.73 | 4.64 | 5.74 | 4.98 | 4.64 | 4.75 | 4.65 |
| 3982560 | 6.72 | 7.82 | 5.51 | 5.18 | 6.42 | 6.04 | 4.98 | 5.94 | 6.47 | 7.94 | 8.23 | 7.34 |
| 3204285 | 5.11 | 5.93 | 6.05 | 5.23 | 7.20 | 5.57 | 5.12 | 5.31 | 5.63 | 5.83 | 5.99 | 5.82 |
| 3654699 | 10.61 | 9.47 | 10.09 | 9.81 | 11.69 | 12.60 | 11.51 | 11.12 | 12.33 | 9.77 | 8.74 | 12.32 |
| 2638676 | 5.78 | 8.31 | 6.35 | 6.04 | 8.53 | 7.39 | 6.04 | 6.37 | 6.31 | 7.19 | 7.60 | 8.07 |
| 3367673 | 8.89 | 6.42 | 8.31 | 9.57 | 4.99 | 6.38 | 8.67 | 7.97 | 8.04 | 6.16 | 8.10 | 8.19 |
| 3212008 | 6.71 | 7.05 | 6.60 | 6.65 | 8.74 | 6.30 | 10.60 | 9.13 | 7.29 | 6.47 | 6.51 | 6.36 |
| 3326635 | 9.94 | 10.31 | 9.78 | 9.93 | 10.22 | 10.36 | 10.83 | 10.40 | 10.18 | 10.18 | 10.14 | 9.86 |
| 3031556 | 9.25 | 10.61 | 7.40 | 8.25 | 9.16 | 9.53 | 6.53 | 8.03 | 8.92 | 10.22 | 10.11 | 9.21 |
| 3662201 | 12.77 | 9.61 | 9.43 | 12.95 | 8.22 | 9.19 | 13.11 | 12.14 | 11.51 | 7.29 | 10.95 | 13.04 |
| 2809793 | 7.09 | 10.13 | 6.32 | 6.43 | 9.27 | 8.13 | 5.08 | 7.12 | 7.59 | 8.26 | 9.22 | 9.20 |
| 2817731 | 7.53 | 7.27 | 7.59 | 7.34 | 8.56 | 9.75 | 7.40 | 7.43 | 8.73 | 8.05 | 7.79 | 7.70 |
| 4020655 | 5.27 | 5.30 | 5.58 | 4.99 | 7.71 | 4.73 | 9.27 | 8.97 | 5.75 | 5.55 | 5.68 | 5.11 |
| 3494629 | 4.55 | 4.45 | 4.55 | 5.52 | 7.16 | 4.79 | 7.61 | 6.83 | 6.03 | 5.02 | 4.61 | 4.50 |
| 3852832 | 8.93 | 9.50 | 7.27 | 7.25 | 6.79 | 7.77 | 5.89 | 7.84 | 8.34 | 9.97 | 9.53 | 8.69 |
| 3761959 | 9.02 | 8.31 | 9.39 | 9.27 | 9.41 | 9.66 | 9.45 | 8.68 | 9.22 | 8.02 | 8.19 | 9.16 |
| 2834282 | 6.80 | 6.58 | 6.34 | 7.17 | 6.74 | 5.90 | 8.95 | 8.30 | 7.40 | 5.54 | 6.35 | 5.67 |
| 3341497 | 6.48 | 6.25 | 6.18 | 6.14 | 6.43 | 5.72 | 10.05 | 7.26 | 6.60 | 6.51 | 5.66 | 5.76 |
| 2372812 | 4.52 | 5.16 | 4.70 | 4.61 | 8.54 | 4.78 | 4.72 | 4.46 | 4.72 | 5.93 | 5.12 |  |
| 2486811 | 9.36 | 10.60 | 8.05 | 7.62 | 10.48 | 10.95 | 5.60 | 8.37 | 9.77 | 10.32 | 10.10 | 10.07 |
| 3768474 | 7.77 | 9.01 | 8.11 | 6.85 | 8.34 | 9.54 | 7.34 | 7.38 | 8.76 | 8.25 | 7.97 | 7.89 |
| 3142381 | 5.79 | 7.12 | 6.52 | 6.71 | 5.27 | 5.90 | 3.44 | 4.17 | 4.04 | 7.31 | 4.91 | 4.03 |
| 2396751 | 6.71 | 6.81 | 6.88 | 7.34 | 6.94 | 6.95 | 7.86 | 7.71 | 7.52 | 7.37 | 6.45 | 7.11 |
| 3902489 | 10.96 | 12.20 | 10.25 | 10.79 | 10.13 | 10.38 | 9.52 | 10.13 | 10.51 | 12.04 | 11.69 | 10.34 |
| 3032647 | 7.40 | 6.18 | 6.41 | 7.88 | 5.50 | 6.10 | 6.18 | 6.38 | 7.88 | 6.45 | 6.14 | 8.37 |
| 3875642 | 5.58 | 6.46 | 5.82 | 5.05 | 5.38 | 5.48 | 6.42 | 5.74 | 5.52 | 7.44 | 5.94 | 5.48 |
| 4027585 | 10.29 | 12.12 | 9.41 | 10.58 | 10.43 | 11.29 | 8.77 | 9.81 | 10.07 | 12.23 | 11.63 | 10.23 |
| 2352609 | 6.84 | 5.55 | 7.62 | 6.46 | 5.73 | 5.59 | 8.99 | 7.30 | 6.43 | 5.76 | 6.27 | 6.66 |
| 3376529 | 7.63 | 8.35 | 8.19 | 9.24 | 8.76 | 8.82 | 9.39 | 7.69 | 8.77 | 7.73 | 8.03 | 9.08 |
| 2491271 | 13.02 | 13.32 | 12.50 | 12.52 | 13.79 | 13.54 | 12.30 | 12.53 | 13.28 | 13.24 | 13.30 | 13.23 |
| 3874751 | 8.91 | 8.99 | 10.46 | 9.47 | 9.84 | 9.67 | 9.60 | 8.91 | 9.33 | 9.15 | 8.78 | 9.21 |
| 2326463 | 11.83 | 12.32 | 10.39 | 10.31 | 11.75 | 13.06 | 9.31 | 10.92 | 12.61 | 11.97 | 12.45 | 11.76 |
| 3341061 | 7.00 | 7.07 | 6.73 | 6.08 | 8.29 | 9.51 | 6.71 | 6.39 | 8.01 | 6.63 | 6.97 | 7.16 |
| 3839910 | 8.95 | 10.17 | 7.60 | 6.29 | 7.09 | 7.95 | 5.47 | 7.84 | 8.53 | 9.08 | 9.84 | 8.80 |
| 2708855 | 3.94 | 4.95 | 4.14 | 4.22 | 7.17 | 4.21 | 8.01 | 6.55 | 6.54 | 4.48 | 4.34 | 4.30 |
| 3512874 | 12.05 | 12.22 | 10.83 | 10.71 | 11.75 | 11.79 | 9.10 | 11.19 | 11.53 | 12.46 | 12.15 | 11.91 |
| 2701071 | 10.21 | 11.03 | 9.02 | 8.27 | 9.56 | 10.18 | 6.97 | 9.54 | 9.91 | 10.79 | 10.23 | 9.93 |
| 3486096 | 7.89 | 5.93 | 9.21 | 8.94 | 6.12 | 5.45 | 9.21 | 7.43 | 7.66 | 5.57 | 7.29 | 8.22 |
| 2412668 | 7.74 | 8.71 | 8.23 | 8.38 | 8.21 | 9.14 | 7.93 | 7.60 | 8.05 | 8.31 | 8.66 | 8.26 |
| 3329343 | 6.90 | 7.81 | 7.41 | 8.24 | 8.84 | 7.17 | 8.05 | 7.99 | 8.18 | 7.20 | 7.27 | 7.15 |
| 3259367 | 4.32 | 4.16 | 4.50 | 4.93 | 5.37 | 4.40 | 5.71 | 6.40 | 4.09 | 4.30 | 4.78 | 4.14 |
| 3373845 | 9.30 | 8.79 | 7.21 | 9.13 | 9.63 | 10.79 | 7.17 | 7.70 | 9.87 | 8.98 | 9.39 | 8.62 |
| 2321911 | 8.47 | 9.54 | 8.56 | 8.27 | 8.26 | 8.76 | 7.69 | 8.35 | 8.50 | 9.53 | 9.15 | 8.50 |
| 3353914 | 6.26 | 6.25 | 5.81 | 7.16 | 7.72 | 9.57 | 6.97 | 6.27 | 7.77 | 6.45 | 6.52 | 6.96 |
| 3744680 | 7.77 | 8.22 | 6.96 | 7.00 | 7.80 | 8.82 | 6.21 | 7.57 | 7.54 | 8.62 | 8.24 | 7.64 |
| 2373336 | 8.13 | 7.14 | 6.16 | 8.13 | 8.24 | 6.50 | 5.26 | 6.01 | 9.00 | 7.00 | 5.91 | 6.48 |
| 3067478 | 5.66 | 4.60 | 7.12 | 8.29 | 7.64 | 5.22 | 8.64 | 7.45 | 6.95 | 5.07 | 5.13 | 6.78 |
| 3976766 | 8.53 | 9.37 | 7.49 | 6.86 | 8.05 | 8.59 | 6.21 | 7.74 | 8.41 | 9.16 | 9.28 | 8.41 |
| 3246888 | 7.27 | 6.99 | 7.15 | 7.70 | 5.13 | 4.92 | 8.72 | 7.53 | 5.95 | 5.63 | 6.14 | 5.49 |
| 3147985 | 6.34 | 6.23 | 6.24 | 6.97 | 7.78 | 8.74 | 7.42 | 6.39 | 7.38 | 5.97 | 5.86 | 6.09 |
| 3185522 | 8.88 | 9.08 | 9.04 | 8.65 | 10.71 | 11.19 | 10.07 | 8.91 | 10.14 | 8.91 | 9.24 | 8.95 |
| 3861948 | 12.47 | 13.02 | 11.80 | 11.41 | 12.38 | 12.57 | 9.92 | 11.94 | 12.49 | 12.94 | 12.94 | 12.72 |
| 3393479 | 9.03 | 8.43 | 9.31 | 9.98 | 8.80 | 10.39 | 7.54 | 8.52 | 9.76 | 8.82 | 9.05 | 9.51 |
| 3540862 | 7.19 | 6.51 | 7.53 | 7.00 | 6.70 | 7.05 | 7.34 | 7.23 | 6.98 | 6.11 | 6.77 | 6.74 |
| 2777714 | 11.14 | 12.16 | 10.36 | 10.74 | 9.45 | 10.25 | 9.33 | 10.68 | 11.14 | 12.33 | 12.00 | 10.79 |
| 3110395 | 5.00 | 4.30 | 4.37 | 4.38 | 5.89 | 4.52 | 5.66 | 6.08 | 5.24 | 4.29 | 4.58 | 4.31 |
| 3895795 | 8.91 | 8.96 | 7.76 | 7.84 | 7.51 | 8.20 | 7.90 | 8.67 | 8.40 | 9.37 | 8.79 | 8.76 |

TABLE 28-continued

Normalized intensity of microarray data for a set of samples.

| TCID | V01 0037 | V01 0038 | V01 0039 | V01 0040 | V01 0041 | V01 0042 | V01 0043 | V01 0044 | V01 0045 | V01 0046 | V01 0047 | V01 0048 |
|---|---|---|---|---|---|---|---|---|---|---|---|---|
| 2854445 | 8.78 | 8.80 | 8.66 | 7.03 | 10.79 | 11.71 | 6.79 | 7.37 | 10.12 | 8.39 | 8.69 | 8.15 |
| 3606034 | 7.49 | 6.50 | 7.66 | 7.60 | 7.60 | 8.96 | 7.63 | 7.28 | 8.18 | 6.89 | 7.14 | 7.14 |
| 3375735 | 7.72 | 8.30 | 7.94 | 8.46 | 7.89 | 9.04 | 7.47 | 7.70 | 7.84 | 8.80 | 8.83 | 7.90 |
| 3948047 | 8.01 | 8.89 | 7.44 | 7.67 | 8.55 | 9.22 | 7.00 | 7.62 | 8.60 | 8.89 | 8.72 | 8.18 |
| 3010503 | 9.07 | 10.02 | 7.95 | 7.02 | 9.41 | 10.42 | 6.34 | 6.72 | 9.26 | 9.74 | 9.34 | 8.45 |
| 3622934 | 7.01 | 6.12 | 7.72 | 7.09 | 7.70 | 5.65 | 8.48 | 7.69 | 6.56 | 6.71 | 6.88 | 6.42 |
| 3441849 | 9.84 | 10.24 | 9.38 | 9.81 | 9.94 | 10.30 | 9.49 | 9.81 | 9.90 | 10.56 | 10.08 | 9.73 |
| 3006572 | 6.62 | 7.02 | 6.59 | 6.26 | 6.40 | 6.32 | 7.09 | 6.91 | 6.50 | 7.14 | 6.87 | 6.74 |
| 3365136 | 7.83 | 8.01 | 9.20 | 9.36 | 9.09 | 8.64 | 11.32 | 10.41 | 9.23 | 8.28 | 8.64 | 8.52 |
| 2642791 | 8.53 | 8.32 | 8.95 | 8.05 | 8.61 | 9.21 | 8.03 | 8.10 | 8.41 | 8.23 | 8.42 | 8.23 |
| 2904485 | 9.22 | 7.08 | 9.76 | 9.41 | 7.38 | 6.77 | 8.32 | 8.50 | 8.53 | 7.24 | 8.56 | 8.66 |
| 3772661 | 9.89 | 9.98 | 9.15 | 8.14 | 10.83 | 11.75 | 9.05 | 8.90 | 10.73 | 10.44 | 9.80 | 9.11 |
| 2796553 | 9.95 | 10.44 | 9.25 | 9.12 | 9.88 | 10.70 | 8.98 | 9.12 | 10.00 | 10.88 | 9.88 | 9.92 |
| 3063795 | 7.25 | 7.30 | 7.41 | 6.74 | 8.58 | 7.89 | 6.80 | 7.66 | 7.25 | 7.55 | 7.73 | 7.46 |
| 3338192 | 8.99 | 7.94 | 9.49 | 9.58 | 9.63 | 8.09 | 10.23 | 9.98 | 8.91 | 7.64 | 8.58 | 8.22 |
| 3214845 | 5.94 | 5.93 | 4.65 | 6.35 | 4.44 | 4.61 | 4.10 | 5.55 | 5.18 | 4.95 | 4.55 | 4.88 |
| 2730303 | 4.16 | 4.38 | 4.56 | 4.29 | 6.70 | 4.21 | 4.02 | 4.66 | 4.13 | 4.42 | 4.64 | 4.45 |
| 3811086 | 7.66 | 8.05 | 8.18 | 7.23 | 7.82 | 8.48 | 7.91 | 7.90 | 7.78 | 7.35 | 7.99 | 7.69 |
| 2981874 | 10.55 | 10.45 | 10.42 | 10.14 | 10.39 | 10.72 | 10.08 | 9.43 | 10.41 | 9.69 | 10.18 | 10.67 |
| 3242353 | 6.12 | 5.90 | 5.83 | 6.49 | 6.21 | 6.61 | 6.11 | 5.92 | 6.11 | 5.72 | 6.22 | 6.23 |
| 2442008 | 5.51 | 5.43 | 5.41 | 5.53 | 7.66 | 5.48 | 8.61 | 7.03 | 6.37 | 5.67 | 5.66 | 5.66 |
| 3564210 | 9.13 | 10.02 | 8.21 | 7.98 | 9.46 | 9.78 | 7.95 | 8.25 | 9.49 | 10.47 | 9.91 | 9.63 |
| 2490351 | 4.09 | 4.29 | 4.43 | 4.14 | 3.98 | 4.09 | 4.04 | 4.36 | 3.99 | 4.35 | 4.37 | 4.18 |
| 3759006 | 9.09 | 10.94 | 7.97 | 8.70 | 7.38 | 7.87 | 7.25 | 7.74 | 8.91 | 11.06 | 10.67 | 8.66 |
| 3264997 | 4.10 | 4.18 | 4.26 | 4.06 | 3.93 | 4.05 | 4.16 | 4.45 | 4.35 | 4.25 | 4.25 | 4.13 |
| 3912079 | 3.84 | 3.90 | 3.63 | 3.56 | 3.57 | 3.55 | 3.76 | 3.63 | 3.58 | 3.90 | 3.79 | 3.77 |
| 2926802 | 4.80 | 6.04 | 5.01 | 5.34 | 5.41 | 4.56 | 4.52 | 4.99 | 5.03 | 6.29 | 5.65 | 5.33 |
| 2430163 | 3.99 | 3.89 | 4.14 | 3.90 | 3.89 | 4.21 | 3.64 | 4.09 | 3.83 | 3.92 | 3.86 | 3.79 |
| 3039830 | 3.23 | 3.02 | 3.27 | 3.44 | 3.05 | 3.01 | 3.04 | 3.21 | 3.16 | 3.14 | 3.15 | 3.15 |
| 3935486 | 6.02 | 5.81 | 5.39 | 6.41 | 8.46 | 9.47 | 4.93 | 6.37 | 9.04 | 6.38 | 5.73 | 8.46 |
| 3457336 | 5.65 | 5.78 | 6.17 | 5.45 | 5.12 | 5.44 | 5.44 | 5.85 | 5.18 | 5.72 | 5.83 | 5.49 |
| 3811949 | 3.50 | 3.94 | 3.72 | 3.42 | 3.31 | 3.42 | 3.52 | 3.50 | 3.56 | 3.57 | 3.64 | 3.63 |
| 3343832 | 3.92 | 3.90 | 3.89 | 3.79 | 3.80 | 4.17 | 3.82 | 4.14 | 3.96 | 4.28 | 4.37 | 3.89 |
| 3161261 | 6.14 | 5.61 | 6.59 | 5.50 | 5.22 | 6.00 | 5.02 | 6.01 | 5.02 | 6.04 | 6.79 | 6.46 |
| 3594003 | 3.87 | 3.62 | 3.59 | 3.73 | 3.79 | 3.82 | 3.53 | 3.72 | 4.13 | 3.78 | 4.06 | 3.73 |
| 3805614 | 4.43 | 4.91 | 4.87 | 4.79 | 4.68 | 5.09 | 4.55 | 4.86 | 4.96 | 5.06 | 5.20 | 4.91 |
| 3364127 | 7.13 | 7.09 | 7.17 | 6.69 | 6.54 | 6.98 | 6.66 | 7.44 | 9.11 | 7.22 | 7.18 | 6.86 |
| 3834341 | 4.19 | 4.12 | 4.17 | 4.13 | 3.61 | 4.15 | 4.03 | 4.46 | 4.04 | 4.46 | 4.32 | 4.34 |
| 2585400 | 4.66 | 4.43 | 6.18 | 4.17 | 4.53 | 4.69 | 4.20 | 4.44 | 4.36 | 4.70 | 4.84 | 4.53 |
| 2941690 | 4.31 | 4.49 | 4.33 | 4.94 | 3.98 | 4.42 | 4.05 | 4.75 | 3.92 | 4.28 | 4.73 | 4.51 |
| 3484895 | 4.80 | 5.27 | 5.07 | 4.59 | 5.55 | 4.54 | 4.86 | 5.02 | 4.68 | 5.03 | 5.33 | 4.81 |
| 3159754 | 3.65 | 3.76 | 3.64 | 4.15 | 3.61 | 4.00 | 3.82 | 4.02 | 3.64 | 3.66 | 3.87 | 3.88 |
| 2894790 | 4.13 | 3.78 | 3.89 | 4.05 | 3.75 | 3.90 | 4.36 | 4.08 | 3.77 | 3.84 | 4.23 | 3.83 |
| 3363686 | 3.42 | 3.83 | 3.48 | 3.24 | 3.24 | 3.58 | 3.39 | 3.70 | 3.20 | 3.55 | 3.65 | 3.74 |
| 2923928 | 4.65 | 5.40 | 4.16 | 4.23 | 3.99 | 4.10 | 4.15 | 4.98 | 4.30 | 4.52 | 4.34 | 4.30 |
| 2883317 | 4.53 | 5.52 | 4.71 | 4.97 | 5.43 | 5.80 | 4.57 | 5.45 | 4.93 | 5.43 | 5.77 | 4.86 |
| 2479698 | 6.16 | 6.04 | 6.43 | 6.32 | 5.93 | 5.99 | 6.31 | 6.70 | 5.86 | 6.20 | 6.14 | 6.30 |
| 3428225 | 3.59 | 3.90 | 3.89 | 3.89 | 3.62 | 3.94 | 3.56 | 4.15 | 3.72 | 4.03 | 3.99 | 3.82 |
| 3393446 | 7.43 | 7.74 | 7.18 | 6.94 | 7.00 | 8.58 | 6.74 | 7.53 | 7.35 | 6.99 | 7.08 | 6.88 |
| 3116614 | 13.22 | 10.61 | 12.91 | 13.00 | 11.88 | 10.44 | 13.17 | 13.19 | 12.90 | 11.05 | 11.98 | 12.81 |
| 3415320 | 10.02 | 7.51 | 10.89 | 10.08 | 9.26 | 7.65 | 9.63 | 9.57 | 10.72 | 7.54 | 8.01 | 9.92 |
| 3757108 | 7.77 | 7.87 | 8.03 | 7.87 | 9.41 | 7.85 | 7.66 | 8.17 | 9.04 | 7.55 | 7.83 | 8.11 |
| 4012178 | 6.55 | 6.71 | 6.33 | 6.82 | 9.58 | 6.64 | 11.53 | 10.19 | 8.41 | 6.76 | 6.74 | 7.22 |
| 3546213 | 10.85 | 7.99 | 11.48 | 11.21 | 10.63 | 7.79 | 11.48 | 11.35 | 10.88 | 7.88 | 9.05 | 10.65 |
| 3561381 | 9.75 | 6.81 | 10.90 | 10.85 | 9.17 | 7.52 | 10.99 | 10.56 | 10.29 | 5.57 | 10.00 | 9.57 |

TABLE 29

Normalized intensity of microarray data for a set of samples.

| TCID | V01 0049 | V01 0050 | V01 0051 | V01 0052 | V01 0053 | V01 0054 | V01 0055 | V01 0056 | V01 0057 | V01 0058 | V01 0059 | V01 0060 |
|---|---|---|---|---|---|---|---|---|---|---|---|---|
| 2604998 | 7.82 | 8.81 | 4.86 | 6.68 | 7.85 | 5.43 | 7.64 | 8.38 | 8.27 | 7.71 | 7.11 | 6.55 |
| 3603932 | 9.08 | 6.67 | 9.21 | 6.56 | 7.09 | 7.20 | 6.86 | 6.85 | 8.04 | 7.44 | 6.84 | 7.05 |
| 2710599 | 7.56 | 11.71 | 7.03 | 10.12 | 6.59 | 9.63 | 7.67 | 9.60 | 9.53 | 7.45 | 6.62 | 5.28 |
| 2440258 | 5.00 | 5.88 | 7.44 | 9.13 | 8.49 | 9.30 | 8.40 | 7.43 | 7.62 | 7.88 | 8.79 | 8.99 |
| 3169331 | 8.74 | 6.71 | 7.39 | 6.49 | 6.71 | 6.88 | 6.61 | 6.78 | 7.26 | 7.14 | 7.09 | 6.98 |
| 2988882 | 10.11 | 9.55 | 10.20 | 9.76 | 9.48 | 9.88 | 9.03 | 9.19 | 10.19 | 10.15 | 9.90 | 10.36 |
| 2964231 | 11.30 | 8.50 | 10.97 | 8.83 | 8.38 | 8.15 | 8.63 | 8.89 | 9.41 | 8.97 | 8.45 | 8.86 |
| 3111561 | 6.14 | 7.50 | 4.67 | 6.54 | 10.04 | 7.05 | 10.23 | 7.20 | 10.91 | 9.16 | 9.50 | 9.04 |
| 2562529 | 9.51 | 10.93 | 9.77 | 9.46 | 8.94 | 9.19 | 9.68 | 10.00 | 10.07 | 8.80 | 9.16 | 8.65 |

TABLE 29-continued

Normalized intensity of microarray data for a set of samples.

| TCID | V01 0049 | V01 0050 | V01 0051 | V01 0052 | V01 0053 | V01 0054 | V01 0055 | V01 0056 | V01 0057 | V01 0058 | V01 0059 | V01 0060 |
|---|---|---|---|---|---|---|---|---|---|---|---|---|
| 3692999 | 8.77 | 6.86 | 8.06 | 6.65 | 13.08 | 9.18 | 8.00 | 8.34 | 10.81 | 11.42 | 10.82 | 9.95 |
| 2439554 | 4.86 | 5.49 | 6.89 | 7.43 | 7.94 | 9.03 | 7.07 | 6.61 | 6.17 | 6.39 | 8.93 | 8.64 |
| 2685304 | 10.82 | 11.70 | 8.91 | 9.55 | 7.60 | 8.92 | 8.54 | 8.12 | 8.19 | 8.98 | 6.91 | 7.65 |
| 2578790 | 5.28 | 4.52 | 4.45 | 4.31 | 7.45 | 4.79 | 6.28 | 6.52 | 7.25 | 6.71 | 6.26 | 6.31 |
| 2373842 | 7.66 | 9.34 | 10.80 | 11.87 | 11.51 | 12.03 | 11.91 | 11.41 | 10.60 | 11.32 | 11.77 | 11.86 |
| 2750627 | 11.32 | 10.80 | 5.30 | 9.26 | 9.98 | 4.64 | 8.37 | 9.76 | 9.68 | 8.53 | 9.22 | 8.84 |
| 3397774 | 8.64 | 4.38 | 5.83 | 4.89 | 4.82 | 5.15 | 5.08 | 4.52 | 4.79 | 5.15 | 5.35 | 5.36 |
| 2635741 | 5.20 | 6.77 | 6.30 | 9.39 | 8.89 | 9.56 | 8.82 | 7.79 | 7.78 | 8.83 | 8.64 | 9.23 |
| 3970833 | 11.37 | 9.59 | 10.30 | 9.03 | 9.60 | 9.36 | 9.27 | 9.75 | 9.67 | 9.26 | 9.32 | 8.99 |
| 3577612 | 7.17 | 11.35 | 10.32 | 11.27 | 10.59 | 11.17 | 11.17 | 10.81 | 10.39 | 10.90 | 11.09 | 11.10 |
| 2708922 | 5.12 | 8.36 | 7.75 | 8.87 | 8.53 | 9.80 | 8.60 | 8.43 | 6.62 | 9.13 | 8.33 | 9.94 |
| 2970897 | 8.14 | 4.99 | 5.22 | 5.12 | 6.53 | 5.32 | 5.41 | 5.59 | 5.63 | 6.18 | 4.96 | 4.96 |
| 3724545 | 5.92 | 9.94 | 9.01 | 10.18 | 10.22 | 9.87 | 10.20 | 10.14 | 9.73 | 10.26 | 8.60 | 10.03 |
| 2798538 | 10.48 | 9.13 | 10.04 | 9.41 | 9.06 | 9.83 | 8.42 | 9.38 | 9.36 | 9.08 | 9.22 | 9.13 |
| 2806468 | 6.20 | 9.43 | 9.59 | 11.81 | 11.80 | 11.45 | 11.29 | 10.79 | 10.80 | 11.77 | 11.26 | 11.86 |
| 2880051 | 7.05 | 5.90 | 6.46 | 6.84 | 6.32 | 7.10 | 6.94 | 6.15 | 5.97 | 6.79 | 6.57 | 6.81 |
| 2732508 | 3.51 | 3.73 | 3.55 | 4.11 | 6.93 | 7.26 | 3.80 | 5.58 | 4.59 | 3.97 | 6.51 | 3.75 |
| 2822492 | 8.27 | 5.42 | 5.82 | 5.72 | 5.59 | 5.81 | 5.41 | 5.89 | 5.23 | 5.68 | 5.68 | 5.46 |
| 3404030 | 5.80 | 6.51 | 6.53 | 9.44 | 7.53 | 10.49 | 8.86 | 7.30 | 7.16 | 9.56 | 8.29 | 9.18 |
| 3059667 | 4.47 | 6.38 | 4.31 | 5.12 | 9.36 | 4.09 | 8.80 | 9.02 | 11.13 | 7.67 | 8.97 | 9.49 |
| 3108526 | 10.61 | 8.47 | 7.22 | 6.93 | 10.03 | 7.29 | 8.61 | 7.76 | 9.92 | 9.12 | 8.80 | 9.52 |
| 2526806 | 10.70 | 12.79 | 11.30 | 12.60 | 9.43 | 11.23 | 8.44 | 10.14 | 11.82 | 12.38 | 8.60 | 6.59 |
| 2428501 | 7.98 | 8.16 | 8.96 | 7.57 | 6.70 | 7.67 | 6.87 | 5.98 | 8.83 | 7.68 | 7.28 | 6.54 |
| 2657808 | 5.71 | 10.76 | 5.52 | 8.66 | 5.51 | 6.32 | 7.08 | 6.47 | 8.30 | 5.13 | 5.76 | 5.55 |
| 2584018 | 4.75 | 10.84 | 11.04 | 9.30 | 8.03 | 8.78 | 8.46 | 8.18 | 9.31 | 8.17 | 7.39 | 8.10 |
| 3976341 | 6.90 | 11.21 | 10.50 | 10.61 | 9.65 | 10.15 | 9.89 | 9.85 | 10.05 | 9.81 | 9.54 | 10.08 |
| 2739308 | 6.01 | 4.47 | 4.83 | 6.37 | 5.76 | 6.38 | 5.92 | 4.86 | 4.61 | 5.91 | 5.17 | 5.24 |
| 3959862 | 10.71 | 4.69 | 7.50 | 4.96 | 4.10 | 4.72 | 4.59 | 4.16 | 4.61 | 5.45 | 5.27 | 5.42 |
| 2362351 | 5.16 | 6.14 | 6.18 | 8.24 | 7.93 | 8.73 | 7.96 | 7.04 | 6.87 | 7.59 | 7.95 | 8.23 |
| 3648391 | 4.22 | 4.20 | 4.45 | 6.75 | 6.75 | 5.07 | 5.32 | 4.16 | 5.02 | 4.72 | 7.06 | 5.08 |
| 3009299 | 11.54 | 10.58 | 11.15 | 10.45 | 10.81 | 10.78 | 10.13 | 10.74 | 10.91 | 10.68 | 10.74 | 10.52 |
| 3443464 | 5.34 | 5.05 | 5.52 | 6.04 | 5.65 | 7.15 | 6.48 | 5.89 | 5.40 | 6.15 | 5.90 | 6.14 |
| 2730746 | 8.85 | 6.26 | 5.87 | 5.63 | 8.93 | 6.30 | 6.46 | 7.87 | 7.80 | 7.48 | 6.90 | 6.72 |
| 2427619 | 5.03 | 6.41 | 6.28 | 10.30 | 9.40 | 9.86 | 9.09 | 8.03 | 7.65 | 8.97 | 9.14 | 9.87 |
| 3042001 | 10.77 | 8.70 | 9.35 | 8.24 | 9.41 | 9.03 | 8.11 | 8.05 | 9.06 | 9.35 | 8.32 | 8.47 |
| 2566848 | 5.16 | 4.71 | 5.14 | 6.01 | 5.63 | 5.30 | 5.78 | 5.49 | 4.92 | 5.49 | 6.39 | 5.60 |
| 2984616 | 10.82 | 8.76 | 9.86 | 8.76 | 9.40 | 8.97 | 8.20 | 8.93 | 9.25 | 8.55 | 9.03 | 9.46 |
| 2378068 | 7.10 | 8.62 | 9.40 | 8.52 | 6.87 | 7.85 | 7.51 | 7.77 | 9.05 | 7.90 | 8.32 | 7.74 |
| 2721959 | 5.97 | 12.64 | 6.65 | 11.00 | 6.07 | 9.51 | 6.00 | 8.60 | 8.19 | 7.70 | 7.52 | 6.23 |
| 2877508 | 11.60 | 10.46 | 11.06 | 10.25 | 10.10 | 10.44 | 9.90 | 10.20 | 10.60 | 10.31 | 10.21 | 10.09 |
| 3450861 | 4.53 | 4.77 | 5.12 | 7.75 | 7.34 | 7.53 | 7.03 | 5.48 | 4.99 | 6.95 | 6.17 | 6.90 |
| 2688717 | 5.56 | 6.28 | 6.47 | 9.96 | 9.67 | 9.00 | 9.13 | 9.04 | 7.67 | 8.81 | 9.46 | 9.63 |
| 3270270 | 6.56 | 9.10 | 9.24 | 9.59 | 8.37 | 9.57 | 9.03 | 8.47 | 8.14 | 8.66 | 8.94 | 9.84 |
| 3417703 | 4.54 | 8.90 | 4.73 | 6.43 | 10.83 | 4.56 | 9.01 | 9.22 | 9.98 | 7.84 | 8.88 | 8.17 |
| 3302990 | 10.87 | 7.40 | 8.77 | 7.06 | 7.56 | 7.44 | 6.73 | 7.06 | 7.85 | 7.42 | 6.77 | 7.12 |
| 2377283 | 4.23 | 3.90 | 4.55 | 5.06 | 6.73 | 4.65 | 5.35 | 4.64 | 4.22 | 5.00 | 8.21 | 4.99 |
| 3122678 | 4.80 | 4.09 | 8.74 | 5.81 | 4.76 | 5.23 | 5.19 | 5.31 | 4.36 | 4.51 | 5.13 | 4.80 |
| 2688499 | 6.76 | 11.18 | 7.04 | 8.67 | 9.45 | 8.14 | 8.72 | 8.23 | 9.80 | 8.94 | 9.18 | 8.66 |
| 2377094 | 10.78 | 7.81 | 9.24 | 7.84 | 9.24 | 8.50 | 8.57 | 9.44 | 8.40 | 8.45 | 8.45 | 8.58 |
| 3278198 | 9.99 | 8.04 | 9.58 | 7.23 | 7.52 | 7.51 | 7.81 | 7.52 | 8.04 | 7.75 | 7.71 | 7.30 |
| 2598261 | 10.01 | 12.94 | 10.76 | 12.13 | 9.03 | 10.36 | 8.13 | 9.47 | 11.49 | 11.88 | 7.98 | 6.89 |
| 3982612 | 4.31 | 6.84 | 5.90 | 9.67 | 10.13 | 10.08 | 8.55 | 8.34 | 7.66 | 9.15 | 9.49 | 9.67 |
| 2884845 | 4.88 | 10.32 | 4.82 | 8.78 | 4.38 | 4.38 | 4.43 | 5.93 | 4.99 | 4.74 | 4.64 | 4.93 |
| 3982560 | 4.77 | 5.02 | 5.36 | 8.19 | 7.92 | 7.47 | 6.91 | 6.43 | 5.98 | 7.04 | 7.84 | 7.79 |
| 3204285 | 5.34 | 5.35 | 5.69 | 5.71 | 7.56 | 6.50 | 5.52 | 5.64 | 5.90 | 6.46 | 6.14 | 5.55 |
| 3654699 | 12.32 | 9.94 | 12.60 | 9.98 | 11.36 | 10.99 | 11.18 | 11.16 | 12.16 | 12.27 | 10.60 | 10.73 |
| 2638676 | 4.45 | 5.10 | 7.39 | 8.26 | 8.07 | 7.69 | 7.28 | 6.13 | 6.76 | 7.14 | 9.03 | 7.53 |
| 3367673 | 9.84 | 5.61 | 5.25 | 4.83 | 7.70 | 5.02 | 9.28 | 8.39 | 7.23 | 7.09 | 7.09 | 7.52 |
| 3212008 | 5.97 | 8.72 | 6.13 | 6.76 | 6.55 | 6.81 | 8.14 | 8.58 | 7.45 | 6.42 | 7.07 | 6.75 |
| 3326635 | 8.50 | 10.03 | 10.21 | 10.50 | 10.35 | 10.38 | 10.26 | 10.43 | 10.51 | 10.22 | 10.11 | 10.16 |
| 3031556 | 6.26 | 7.05 | 9.10 | 10.17 | 10.15 | 10.54 | 9.57 | 8.82 | 8.71 | 9.45 | 9.45 | 10.13 |
| 3662201 | 8.60 | 8.58 | 8.30 | 7.60 | 12.98 | 10.10 | 7.22 | 8.69 | 10.65 | 11.43 | 11.17 | 10.03 |
| 2809793 | 4.73 | 5.25 | 5.38 | 9.21 | 9.03 | 10.24 | 7.31 | 7.38 | 8.54 | 8.90 | 9.73 | 9.06 |
| 2817731 | 7.44 | 7.96 | 9.96 | 8.43 | 7.71 | 7.87 | 8.14 | 7.69 | 8.62 | 7.68 | 7.63 | 7.87 |
| 4020655 | 4.81 | 8.21 | 4.82 | 6.00 | 4.93 | 5.10 | 5.97 | 9.91 | 5.04 | 4.98 | 5.26 | 5.00 |
| 3494629 | 4.84 | 8.53 | 4.54 | 6.00 | 4.61 | 7.47 | 4.45 | 4.69 | 4.76 | 4.47 | 4.49 | 4.56 |
| 3852832 | 5.72 | 6.85 | 7.74 | 10.49 | 9.24 | 9.37 | 9.45 | 8.90 | 6.74 | 9.21 | 10.16 | 10.25 |
| 3761959 | 9.81 | 8.96 | 10.11 | 8.87 | 9.44 | 8.99 | 8.64 | 8.63 | 9.64 | 8.97 | 8.90 | 8.59 |
| 2834282 | 6.21 | 7.82 | 6.24 | 6.35 | 5.93 | 6.42 | 7.69 | 7.68 | 7.45 | 6.26 | 6.21 | 5.90 |
| 3341497 | 7.86 | 7.05 | 5.98 | 5.73 | 6.60 | 6.36 | 6.67 | 7.60 | 6.18 | 6.42 | 6.62 | 5.93 |
| 2372812 | 4.56 | 4.30 | 4.56 | 4.88 | 4.82 | 4.73 | 4.86 | 4.90 | 4.52 | 4.88 | 9.61 | 5.40 |
| 2486811 | 5.65 | 7.90 | 10.84 | 10.57 | 9.83 | 10.79 | 10.36 | 9.56 | 10.35 | 9.91 | 10.24 | 10.39 |
| 3768474 | 7.87 | 7.67 | 9.57 | 8.09 | 7.69 | 8.44 | 8.14 | 8.24 | 8.21 | 8.36 | 7.90 | 8.60 |
| 3142381 | 7.08 | 4.61 | 6.24 | 5.68 | 7.44 | 6.27 | 4.61 | 5.55 | 4.59 | 10.35 | 6.31 | 6.24 |
| 2396750 | 7.63 | 7.34 | 7.19 | 6.89 | 7.16 | 6.69 | 6.90 | 6.81 | 7.36 | 6.63 | 6.98 | 6.96 |

TABLE 29-continued

Normalized intensity of microarray data for a set of samples.

| TCID | V01 0049 | V01 0050 | V01 0051 | V01 0052 | V01 0053 | V01 0054 | V01 0055 | V01 0056 | V01 0057 | V01 0058 | V01 0059 | V01 0060 |
|---|---|---|---|---|---|---|---|---|---|---|---|---|
| 3902489 | 8.73 | 10.27 | 10.53 | 12.06 | 11.09 | 12.42 | 11.30 | 10.96 | 10.30 | 12.29 | 11.58 | 12.21 |
| 3032647 | 5.86 | 5.34 | 5.86 | 6.23 | 8.02 | 5.86 | 6.58 | 6.32 | 7.29 | 7.67 | 6.45 | 7.04 |
| 3875642 | 5.06 | 5.00 | 5.31 | 6.59 | 5.75 | 6.04 | 6.18 | 5.64 | 5.15 | 6.38 | 6.20 | 5.82 |
| 4027585 | 8.80 | 8.13 | 11.38 | 11.79 | 10.75 | 12.24 | 11.26 | 10.51 | 10.46 | 11.88 | 11.25 | 11.93 |
| 2352609 | 8.74 | 7.00 | 5.26 | 5.87 | 6.75 | 5.99 | 6.83 | 7.22 | 7.11 | 6.85 | 6.32 | 6.56 |
| 3376529 | 10.12 | 10.00 | 7.50 | 8.50 | 8.56 | 7.98 | 7.89 | 7.79 | 7.42 | 9.17 | 7.80 | 7.51 |
| 2491271 | 12.40 | 13.43 | 13.59 | 13.49 | 13.24 | 13.50 | 13.15 | 13.15 | 13.42 | 13.23 | 13.17 | 13.38 |
| 3874751 | 9.79 | 9.70 | 10.43 | 9.36 | 9.73 | 9.09 | 8.98 | 8.86 | 9.78 | 9.87 | 9.08 | 8.80 |
| 2326463 | 7.39 | 9.52 | 12.58 | 12.32 | 12.14 | 12.00 | 11.75 | 11.75 | 11.68 | 11.91 | 11.89 | 12.18 |
| 3341061 | 6.90 | 7.13 | 9.85 | 7.67 | 6.92 | 7.79 | 7.51 | 6.94 | 8.74 | 8.19 | 6.90 | 7.14 |
| 3839910 | 4.81 | 6.16 | 7.46 | 10.27 | 8.83 | 9.45 | 9.19 | 8.82 | 5.73 | 7.75 | 9.49 | 10.41 |
| 2708855 | 4.03 | 8.81 | 4.13 | 7.06 | 4.20 | 5.22 | 4.14 | 5.94 | 4.48 | 4.51 | 4.51 | 4.17 |
| 3512874 | 8.81 | 10.13 | 12.07 | 12.42 | 11.89 | 12.46 | 12.38 | 11.89 | 11.57 | 11.97 | 12.35 | 12.35 |
| 2701071 | 6.07 | 7.77 | 9.70 | 10.95 | 9.85 | 10.57 | 10.65 | 10.34 | 8.55 | 9.88 | 10.57 | 10.98 |
| 3486096 | 8.29 | 7.52 | 5.29 | 5.52 | 7.63 | 6.12 | 7.34 | 8.79 | 7.50 | 6.25 | 6.36 | 7.14 |
| 2412668 | 8.29 | 8.04 | 9.29 | 8.79 | 8.38 | 8.27 | 8.31 | 8.25 | 8.38 | 8.36 | 8.23 | 8.68 |
| 3329343 | 8.09 | 9.30 | 7.12 | 8.50 | 6.69 | 7.59 | 7.59 | 7.94 | 7.36 | 7.35 | 7.07 | 7.27 |
| 3259367 | 3.94 | 5.35 | 4.00 | 4.47 | 4.38 | 4.28 | 5.18 | 5.22 | 4.72 | 4.83 | 4.51 | 4.11 |
| 3373845 | 6.55 | 9.29 | 10.97 | 9.60 | 9.75 | 9.29 | 8.52 | 8.42 | 10.32 | 9.62 | 9.84 | 9.21 |
| 2321911 | 7.39 | 7.85 | 8.95 | 9.01 | 8.67 | 8.98 | 8.40 | 8.27 | 8.89 | 8.89 | 8.61 | 9.20 |
| 3353914 | 7.29 | 7.83 | 9.80 | 6.90 | 6.36 | 6.86 | 6.72 | 7.08 | 8.06 | 7.35 | 6.26 | 6.34 |
| 3744680 | 6.26 | 6.39 | 8.78 | 8.42 | 7.81 | 8.25 | 8.25 | 7.31 | 7.67 | 7.92 | 8.11 | 8.40 |
| 2373336 | 5.14 | 10.88 | 5.43 | 8.77 | 6.75 | 6.76 | 6.74 | 5.59 | 8.04 | 6.55 | 5.84 | 7.48 |
| 3067478 | 7.19 | 8.91 | 4.73 | 6.12 | 5.70 | 5.20 | 5.51 | 7.18 | 5.78 | 4.77 | 4.84 | 5.49 |
| 3976766 | 5.95 | 5.93 | 8.45 | 9.31 | 8.55 | 9.20 | 8.95 | 7.75 | 7.74 | 8.59 | 9.07 | 9.51 |
| 3246888 | 7.90 | 5.48 | 4.93 | 5.47 | 6.35 | 5.67 | 6.48 | 7.65 | 7.14 | 6.06 | 5.80 | 6.87 |
| 3147985 | 7.12 | 7.80 | 9.68 | 6.90 | 6.55 | 6.69 | 7.02 | 6.29 | 8.37 | 6.86 | 6.20 | 6.54 |
| 3185522 | 10.03 | 9.21 | 11.34 | 9.27 | 9.43 | 9.60 | 9.53 | 9.46 | 10.73 | 10.13 | 9.33 | 9.22 |
| 3861948 | 9.18 | 10.21 | 12.39 | 13.04 | 12.68 | 12.89 | 12.78 | 12.53 | 11.96 | 12.65 | 12.98 | 12.99 |
| 3393479 | 7.65 | 9.19 | 10.50 | 8.88 | 8.85 | 8.63 | 9.04 | 8.24 | 9.24 | 9.36 | 8.86 | 9.43 |
| 3540862 | 9.55 | 7.42 | 7.20 | 6.21 | 6.33 | 6.89 | 6.71 | 7.44 | 6.65 | 6.70 | 6.73 | 6.89 |
| 2777714 | 8.57 | 8.25 | 10.20 | 12.16 | 11.63 | 12.25 | 11.77 | 10.99 | 10.12 | 12.16 | 11.87 | 12.15 |
| 3110395 | 4.81 | 6.53 | 4.31 | 4.68 | 4.34 | 4.49 | 4.90 | 6.06 | 4.52 | 4.33 | 4.52 | 4.52 |
| 3895795 | 6.46 | 8.10 | 8.00 | 9.40 | 8.48 | 8.68 | 9.19 | 8.26 | 7.97 | 8.36 | 9.03 | 9.20 |
| 2854445 | 6.87 | 8.17 | 11.55 | 9.59 | 8.74 | 9.71 | 9.23 | 9.10 | 10.75 | 9.89 | 8.05 | 9.16 |
| 3606034 | 8.14 | 7.61 | 9.26 | 7.07 | 7.36 | 7.38 | 7.56 | 7.53 | 7.76 | 7.74 | 7.10 | 7.00 |
| 3375735 | 8.26 | 7.71 | 9.06 | 7.96 | 7.81 | 8.79 | 8.59 | 7.96 | 7.82 | 8.08 | 8.31 | 8.41 |
| 3948047 | 6.83 | 6.41 | 9.58 | 9.08 | 8.47 | 9.19 | 8.81 | 8.00 | 8.18 | 8.45 | 8.59 | 9.09 |
| 3010503 | 6.71 | 6.40 | 11.49 | 10.12 | 9.13 | 10.36 | 9.77 | 8.85 | 9.58 | 10.15 | 9.14 | 9.96 |
| 3622934 | 8.33 | 8.49 | 5.83 | 6.36 | 6.90 | 6.22 | 7.01 | 7.77 | 6.72 | 6.40 | 7.48 | 6.89 |
| 3441849 | 8.96 | 9.74 | 10.12 | 10.64 | 9.81 | 10.18 | 10.36 | 10.03 | 9.75 | 9.99 | 10.30 | 10.67 |
| 3006572 | 6.11 | 6.81 | 6.00 | 6.57 | 6.74 | 6.71 | 6.83 | 6.52 | 6.42 | 6.59 | 6.91 | 6.37 |
| 3365136 | 9.13 | 9.50 | 8.15 | 8.85 | 8.32 | 8.16 | 9.08 | 10.14 | 8.84 | 8.47 | 8.95 | 8.08 |
| 2642791 | 8.88 | 8.34 | 9.42 | 8.53 | 8.93 | 8.70 | 8.49 | 8.25 | 8.58 | 8.73 | 8.36 | 8.71 |
| 2904485 | 6.33 | 7.71 | 6.76 | 7.05 | 8.78 | 7.22 | 8.55 | 8.08 | 9.00 | 8.83 | 7.92 | 7.81 |
| 3772661 | 7.81 | 10.02 | 11.88 | 10.45 | 9.16 | 10.02 | 10.28 | 9.83 | 10.93 | 10.29 | 10.05 | 10.20 |
| 2796553 | 9.41 | 8.67 | 10.69 | 10.82 | 9.75 | 10.23 | 10.93 | 10.13 | 9.66 | 10.10 | 10.61 | 11.01 |
| 3063795 | 6.83 | 6.68 | 7.92 | 8.00 | 7.61 | 7.82 | 7.15 | 7.44 | 8.33 | 7.92 | 7.02 | 7.48 |
| 3338192 | 8.40 | 10.96 | 7.87 | 9.21 | 8.66 | 8.44 | 8.83 | 9.14 | 9.12 | 8.55 | 8.45 | 8.23 |
| 3214845 | 4.28 | 4.07 | 4.34 | 5.36 | 4.42 | 4.53 | 4.33 | 5.17 | 4.40 | 4.21 | 4.51 | 4.40 |
| 2730303 | 4.13 | 4.06 | 4.14 | 4.22 | 5.28 | 4.64 | 4.11 | 4.38 | 4.11 | 4.45 | 7.61 | 4.38 |
| 3811086 | 7.76 | 7.76 | 8.64 | 7.61 | 7.88 | 7.78 | 7.63 | 7.79 | 8.34 | 8.03 | 7.69 | 7.78 |
| 2981874 | 10.65 | 9.85 | 10.56 | 10.36 | 10.39 | 10.59 | 9.77 | 10.15 | 9.82 | 10.53 | 9.90 | 10.64 |
| 3242353 | 6.61 | 6.02 | 6.56 | 5.90 | 6.38 | 6.13 | 5.71 | 5.48 | 6.42 | 6.23 | 5.89 | 6.58 |
| 2442008 | 5.30 | 8.09 | 5.63 | 6.14 | 5.81 | 5.75 | 5.46 | 7.02 | 5.15 | 5.47 | 5.38 | 5.47 |
| 3564210 | 8.22 | 8.86 | 10.43 | 10.87 | 9.08 | 9.92 | 10.53 | 9.69 | 9.35 | 10.10 | 9.74 | 10.85 |
| 2490351 | 4.40 | 3.76 | 4.15 | 4.16 | 4.11 | 4.23 | 4.21 | 4.14 | 3.99 | 4.18 | 4.14 | 4.19 |
| 3759006 | 6.66 | 6.44 | 8.23 | 10.67 | 9.67 | 11.50 | 9.53 | 8.71 | 7.66 | 10.75 | 10.02 | 10.77 |
| 3264997 | 3.94 | 4.04 | 4.13 | 4.24 | 3.93 | 4.03 | 4.19 | 4.07 | 3.98 | 4.11 | 4.15 | 4.14 |
| 3911079 | 3.43 | 3.60 | 3.60 | 4.12 | 3.77 | 4.06 | 4.10 | 3.57 | 3.64 | 3.94 | 3.77 | 3.79 |
| 2926802 | 5.96 | 4.62 | 4.93 | 6.22 | 5.90 | 5.89 | 5.39 | 5.22 | 4.72 | 6.77 | 5.77 | 6.60 |
| 2430163 | 3.68 | 6.01 | 4.02 | 4.44 | 4.00 | 3.97 | 3.99 | 3.94 | 3.95 | 4.02 | 4.24 | 3.95 |
| 3039830 | 3.17 | 3.07 | 3.09 | 3.15 | 3.00 | 3.05 | 3.04 | 3.19 | 3.12 | 3.08 | 3.10 | 3.16 |
| 3935486 | 5.26 | 8.70 | 9.03 | 8.07 | 6.53 | 5.80 | 7.79 | 7.62 | 10.16 | 9.74 | 6.67 | 5.16 |
| 3457336 | 5.62 | 5.35 | 9.13 | 5.19 | 5.32 | 5.44 | 5.58 | 5.11 | 5.15 | 5.40 | 5.42 | 5.36 |
| 3811949 | 3.45 | 3.33 | 3.48 | 3.65 | 3.53 | 3.45 | 3.53 | 3.40 | 3.44 | 3.51 | 3.67 | 3.67 |
| 3343832 | 3.84 | 3.73 | 3.94 | 4.10 | 3.87 | 4.01 | 3.93 | 3.74 | 3.75 | 3.81 | 3.99 | 3.93 |
| 3161261 | 5.77 | 5.55 | 6.00 | 6.13 | 6.06 | 6.42 | 6.56 | 5.68 | 5.12 | 5.77 | 5.93 | 6.32 |
| 3594003 | 3.57 | 3.53 | 3.98 | 3.87 | 3.79 | 3.91 | 3.91 | 4.12 | 3.57 | 3.87 | 3.61 | 3.95 |
| 3805614 | 4.76 | 4.35 | 5.43 | 4.67 | 4.80 | 4.71 | 5.03 | 4.52 | 4.29 | 4.87 | 4.70 | 4.75 |
| 3364127 | 6.61 | 6.25 | 8.56 | 6.67 | 6.73 | 7.16 | 7.14 | 6.92 | 7.82 | 6.76 | 7.10 | 6.98 |
| 3834341 | 3.77 | 3.66 | 4.03 | 3.89 | 3.90 | 4.19 | 4.21 | 3.97 | 4.07 | 4.00 | 4.10 | 4.02 |
| 2585400 | 4.20 | 6.13 | 4.62 | 4.66 | 4.34 | 4.39 | 4.56 | 4.25 | 4.51 | 4.45 | 4.48 | 4.80 |
| 2941690 | 4.06 | 3.80 | 4.07 | 3.99 | 4.39 | 4.42 | 4.88 | 4.23 | 4.06 | 4.27 | 4.15 | 4.39 |
| 3484895 | 4.90 | 6.53 | 4.82 | 5.52 | 5.11 | 4.86 | 4.88 | 4.77 | 4.75 | 4.45 | 4.88 | 4.89 |

TABLE 29-continued

Normalized intensity of microarray data for a set of samples.

| TCID | V01 0049 | V01 0050 | V01 0051 | V01 0052 | V01 0053 | V01 0054 | V01 0055 | V01 0056 | V01 0057 | V01 0058 | V01 0059 | V01 0060 |
|---|---|---|---|---|---|---|---|---|---|---|---|---|
| 3159754 | 3.79 | 3.30 | 3.64 | 3.73 | 3.78 | 3.67 | 3.98 | 3.61 | 3.59 | 3.77 | 3.61 | 3.55 |
| 2894790 | 4.51 | 3.59 | 3.89 | 4.09 | 3.71 | 3.91 | 3.89 | 4.22 | 3.63 | 3.72 | 3.72 | 4.21 |
| 3363686 | 3.50 | 3.44 | 3.30 | 3.44 | 3.74 | 3.51 | 4.06 | 3.48 | 3.40 | 4.18 | 3.40 | 3.59 |
| 2923928 | 3.81 | 3.83 | 4.38 | 3.98 | 4.11 | 4.26 | 4.40 | 4.38 | 3.87 | 4.17 | 4.46 | 4.43 |
| 2883317 | 4.84 | 4.39 | 5.59 | 5.13 | 4.76 | 5.19 | 4.84 | 5.40 | 4.47 | 4.93 | 5.18 | 4.61 |
| 2479698 | 6.06 | 6.12 | 5.96 | 6.16 | 6.00 | 6.05 | 6.28 | 6.25 | 5.95 | 5.97 | 5.92 | 5.94 |
| 3428225 | 3.74 | 3.57 | 3.94 | 3.81 | 3.61 | 3.96 | 4.02 | 3.78 | 3.68 | 3.60 | 3.93 | 3.81 |
| 3393446 | 6.78 | 6.69 | 8.63 | 7.18 | 7.15 | 7.25 | 7.20 | 7.10 | 7.30 | 6.99 | 7.11 | 7.29 |
| 3116614 | 12.71 | 12.09 | 8.20 | 11.03 | 13.05 | 10.71 | 12.37 | 13.22 | 12.87 | 12.85 | 12.38 | 12.40 |
| 3415320 | 10.78 | 11.07 | 8.67 | 9.16 | 8.93 | 8.15 | 8.75 | 9.52 | 9.17 | 10.39 | 9.25 | 9.05 |
| 3757108 | 7.03 | 11.24 | 7.76 | 9.10 | 7.74 | 8.05 | 7.56 | 7.91 | 8.28 | 7.98 | 7.83 | 7.66 |
| 4012178 | 6.63 | 9.56 | 6.26 | 7.38 | 7.09 | 6.55 | 6.92 | 9.21 | 5.98 | 6.49 | 7.20 | 6.28 |
| 3546213 | 11.27 | 11.35 | 6.32 | 9.24 | 10.74 | 7.54 | 10.01 | 11.27 | 11.00 | 9.91 | 10.08 | 9.68 |
| 3561381 | 10.08 | 10.08 | 6.40 | 7.87 | 8.91 | 6.55 | 9.45 | 10.15 | 9.58 | 8.04 | 8.91 | 8.24 |

TABLE 30

Normalized intensity of microarray data for a set of samples.

| TCID | V01 0061 | V01 0062 | V01 0063 | V01 0064 | V01 0065 | V01 0066 | V01 0067 | V01 0068 | V01 0069 | V01 0070 | V01 0071 | V01 0072 |
|---|---|---|---|---|---|---|---|---|---|---|---|---|
| 2604998 | 8.58 | 7.41 | 7.14 | 8.62 | 5.92 | 7.87 | 7.88 | 7.26 | 8.99 | 7.77 | 5.51 | 8.11 |
| 3603932 | 6.20 | 6.40 | 7.05 | 6.80 | 7.24 | 8.57 | 7.09 | 7.17 | 7.26 | 9.00 | 7.73 | 7.34 |
| 2710599 | 5.32 | 6.21 | 6.07 | 8.32 | 6.56 | 10.63 | 7.12 | 8.77 | 9.75 | 10.29 | 6.22 | 11.53 |
| 2440258 | 4.74 | 7.48 | 8.62 | 8.01 | 9.04 | 7.64 | 8.05 | 8.61 | 7.30 | 7.39 | 8.45 | 6.95 |
| 3169331 | 7.92 | 6.82 | 7.18 | 7.05 | 6.98 | 6.65 | 6.91 | 8.68 | 6.34 | 6.56 | 6.85 | 6.32 |
| 2988882 | 9.89 | 10.36 | 9.83 | 10.07 | 9.71 | 9.99 | 9.55 | 10.34 | 9.47 | 9.88 | 9.24 | 9.63 |
| 2964231 | 7.75 | 7.23 | 9.28 | 7.76 | 8.94 | 10.56 | 8.61 | 9.07 | 8.35 | 10.39 | 8.91 | 8.84 |
| 3111561 | 10.24 | 9.20 | 8.64 | 9.82 | 6.14 | 4.72 | 5.50 | 7.07 | 8.95 | 5.44 | 7.38 | 5.51 |
| 2562529 | 8.76 | 8.63 | 9.08 | 9.78 | 8.96 | 9.90 | 9.10 | 8.98 | 10.55 | 10.04 | 8.32 | 10.26 |
| 3692999 | 10.62 | 11.41 | 12.61 | 12.77 | 9.17 | 8.75 | 5.38 | 12.15 | 10.19 | 7.97 | 10.80 | 7.61 |
| 2439554 | 5.42 | 6.73 | 7.38 | 5.86 | 7.35 | 7.05 | 8.07 | 9.47 | 5.58 | 6.88 | 8.81 | 7.04 |
| 2685304 | 6.32 | 6.56 | 6.66 | 7.10 | 8.04 | 10.85 | 7.82 | 7.09 | 7.47 | 10.24 | 9.02 | 10.71 |
| 2578790 | 7.18 | 6.41 | 7.12 | 6.57 | 5.24 | 4.20 | 4.48 | 5.78 | 5.58 | 4.25 | 5.16 | 4.28 |
| 2373842 | 9.09 | 11.28 | 11.76 | 11.38 | 11.71 | 10.72 | 11.71 | 11.16 | 10.95 | 10.47 | 11.87 | 10.60 |
| 2750627 | 9.78 | 9.99 | 9.10 | 10.07 | 5.87 | 10.51 | 8.99 | 5.47 | 9.61 | 10.56 | 6.78 | 10.28 |
| 3397774 | 5.10 | 5.13 | 5.02 | 4.72 | 5.27 | 4.52 | 4.85 | 6.26 | 4.88 | 4.64 | 5.26 | 4.58 |
| 2635741 | 5.73 | 8.03 | 9.23 | 8.40 | 9.40 | 7.72 | 8.85 | 8.04 | 8.14 | 7.33 | 8.99 | 8.17 |
| 3970833 | 10.24 | 9.94 | 9.44 | 9.33 | 9.26 | 9.91 | 9.49 | 10.02 | 9.37 | 9.91 | 8.55 | 9.39 |
| 3577612 | 8.49 | 10.89 | 11.20 | 10.53 | 11.08 | 11.26 | 10.70 | 9.45 | 10.38 | 11.18 | 11.48 | 11.29 |
| 2708922 | 6.20 | 9.55 | 8.36 | 9.10 | 8.22 | 8.04 | 8.37 | 6.18 | 8.29 | 7.82 | 9.61 | 8.43 |
| 2970897 | 5.68 | 5.48 | 5.62 | 5.72 | 4.96 | 6.12 | 5.03 | 5.69 | 5.24 | 4.97 | 6.29 | 5.50 |
| 3724545 | 10.99 | 10.66 | 10.42 | 8.50 | 9.41 | 9.15 | 10.34 | 8.18 | 10.48 | 8.97 | 10.73 | 10.17 |
| 2798538 | 8.29 | 9.25 | 9.13 | 8.93 | 9.02 | 9.33 | 9.10 | 9.40 | 8.13 | 9.75 | 9.01 | 8.86 |
| 2806468 | 8.23 | 10.92 | 11.30 | 10.77 | 11.30 | 10.34 | 11.42 | 9.47 | 10.78 | 10.25 | 11.00 | 11.14 |
| 2880051 | 6.60 | 7.12 | 7.11 | 6.40 | 7.09 | 5.69 | 6.57 | 6.32 | 6.76 | 6.00 | 6.74 | 5.81 |
| 2732508 | 3.46 | 3.61 | 3.88 | 3.53 | 5.38 | 3.39 | 3.73 | 7.37 | 3.72 | 3.55 | 3.74 | 4.36 |
| 2822492 | 6.13 | 5.52 | 5.55 | 5.06 | 5.39 | 5.17 | 6.47 | 5.35 | 5.57 | 5.26 | 5.81 | 5.09 |
| 3404030 | 6.60 | 7.49 | 9.74 | 7.88 | 10.00 | 7.36 | 8.23 | 7.27 | 7.64 | 6.17 | 7.84 | 7.49 |
| 3059667 | 11.92 | 10.92 | 9.00 | 11.02 | 5.87 | 4.14 | 8.03 | 5.89 | 10.48 | 5.61 | 7.27 | 6.77 |
| 3108526 | 11.55 | 10.19 | 10.11 | 9.53 | 7.42 | 8.31 | 10.16 | 10.30 | 9.33 | 7.34 | 7.62 | 7.55 |
| 2526806 | 6.61 | 7.61 | 7.88 | 12.32 | 10.49 | 12.56 | 9.54 | 11.43 | 6.07 | 12.38 | 6.68 | 12.66 |
| 2428501 | 5.70 | 6.73 | 7.76 | 7.04 | 7.87 | 8.03 | 5.96 | 7.80 | 6.12 | 8.75 | 7.69 | 7.36 |
| 2657808 | 5.51 | 5.53 | 5.56 | 6.02 | 5.77 | 8.78 | 5.56 | 7.15 | 8.19 | 8.97 | 6.51 | 11.18 |
| 2584018 | 4.68 | 7.14 | 7.95 | 8.14 | 10.08 | 10.58 | 8.01 | 6.97 | 7.68 | 10.42 | 8.03 | 10.35 |
| 3976341 | 7.14 | 8.92 | 9.91 | 9.10 | 9.96 | 11.61 | 9.85 | 8.55 | 9.96 | 11.40 | 10.59 | 11.38 |
| 2739308 | 5.99 | 5.38 | 5.93 | 5.19 | 5.11 | 4.51 | 6.85 | 5.18 | 4.96 | 4.40 | 7.63 | 4.61 |
| 3959862 | 4.28 | 5.79 | 4.46 | 4.81 | 5.77 | 5.38 | 5.49 | 4.94 | 4.65 | 4.62 | 7.07 | 4.96 |
| 2362351 | 5.82 | 7.08 | 8.14 | 8.04 | 8.96 | 6.76 | 7.85 | 7.68 | 6.65 | 6.89 | 8.17 | 6.88 |
| 3648391 | 4.32 | 6.09 | 6.54 | 3.87 | 5.79 | 3.96 | 5.53 | 8.01 | 4.85 | 4.79 | 5.58 | 3.99 |
| 3009299 | 11.07 | 10.56 | 10.72 | 10.29 | 10.67 | 10.80 | 10.87 | 10.99 | 10.62 | 10.86 | 10.39 | 10.46 |
| 3443464 | 5.60 | 5.92 | 6.30 | 5.70 | 7.74 | 5.22 | 6.27 | 5.88 | 6.15 | 5.06 | 5.91 | 6.08 |
| 2730746 | 9.19 | 8.28 | 8.15 | 7.30 | 6.31 | 5.11 | 8.14 | 7.27 | 7.73 | 5.98 | 5.98 | 5.21 |
| 2427619 | 6.14 | 7.97 | 9.23 | 8.23 | 9.67 | 6.59 | 9.50 | 8.75 | 8.25 | 6.82 | 9.74 | 7.55 |
| 3042001 | 8.87 | 9.08 | 8.37 | 8.43 | 8.13 | 8.53 | 8.54 | 9.05 | 8.46 | 8.76 | 8.47 | 8.40 |
| 2566848 | 5.12 | 5.45 | 5.76 | 5.66 | 6.14 | 5.01 | 5.78 | 6.61 | 6.34 | 5.11 | 5.93 | 5.14 |
| 2984616 | 9.19 | 8.90 | 9.04 | 8.66 | 9.13 | 9.36 | 8.95 | 9.27 | 9.35 | 9.23 | 9.27 | 9.12 |
| 2378068 | 7.00 | 7.87 | 7.42 | 9.86 | 7.75 | 9.68 | 6.90 | 9.19 | 7.20 | 10.34 | 7.75 | 8.42 |
| 2721959 | 5.72 | 6.09 | 6.02 | 8.55 | 7.99 | 12.00 | 5.78 | 10.43 | 7.60 | 11.23 | 6.14 | 12.16 |
| 2877508 | 10.81 | 10.42 | 10.36 | 9.82 | 10.13 | 10.82 | 10.17 | 10.67 | 9.75 | 10.80 | 9.64 | 10.15 |
| 3450861 | 4.55 | 5.79 | 7.20 | 6.12 | 7.75 | 4.81 | 7.15 | 6.08 | 5.94 | 4.74 | 6.71 | 5.03 |

TABLE 30-continued

Normalized intensity of microarray data for a set of samples.

| TCID | V01 0061 | V01 0062 | V01 0063 | V01 0064 | V01 0065 | V01 0066 | V01 0067 | V01 0068 | V01 0069 | V01 0070 | V01 0071 | V01 0072 |
|---|---|---|---|---|---|---|---|---|---|---|---|---|
| 2688717 | 6.54 | 8.49 | 9.17 | 8.99 | 9.71 | 6.98 | 9.35 | 9.25 | 8.10 | 6.79 | 9.14 | 8.04 |
| 3270270 | 6.49 | 8.45 | 9.05 | 8.26 | 9.25 | 8.96 | 9.07 | 7.59 | 8.14 | 9.40 | 9.69 | 8.60 |
| 3417703 | 9.69 | 8.62 | 8.94 | 10.40 | 6.10 | 5.81 | 9.68 | 4.67 | 7.93 | 8.09 | 6.99 | 8.77 |
| 3302990 | 7.14 | 7.46 | 7.80 | 6.47 | 7.00 | 7.90 | 7.68 | 8.61 | 6.80 | 7.76 | 7.43 | 7.19 |
| 2377283 | 4.33 | 4.88 | 4.66 | 4.86 | 5.70 | 4.07 | 5.51 | 10.85 | 5.20 | 3.94 | 5.46 | 4.82 |
| 3122678 | 5.13 | 5.76 | 4.89 | 4.93 | 5.27 | 3.97 | 4.89 | 5.00 | 5.57 | 4.51 | 5.34 | 5.31 |
| 2688499 | 8.23 | 8.00 | 9.05 | 10.06 | 8.81 | 9.93 | 8.14 | 9.28 | 8.72 | 10.27 | 7.84 | 10.46 |
| 2377094 | 9.81 | 9.51 | 9.34 | 8.76 | 8.20 | 8.48 | 8.78 | 9.73 | 8.71 | 8.03 | 8.06 | 8.22 |
| 3278198 | 8.41 | 7.36 | 7.41 | 7.45 | 7.21 | 8.66 | 7.47 | 8.20 | 7.27 | 9.02 | 6.90 | 7.66 |
| 2598261 | 5.96 | 6.65 | 6.66 | 11.98 | 9.76 | 12.22 | 9.03 | 10.64 | 6.70 | 12.16 | 6.27 | 12.68 |
| 3982612 | 5.70 | 8.64 | 9.23 | 8.64 | 9.82 | 6.42 | 9.58 | 9.27 | 8.14 | 7.03 | 9.26 | 7.64 |
| 2884845 | 4.57 | 4.94 | 4.76 | 4.91 | 4.48 | 9.59 | 4.75 | 4.67 | 4.51 | 9.97 | 4.78 | 10.02 |
| 3982560 | 5.71 | 6.67 | 7.47 | 6.19 | 7.52 | 4.92 | 7.97 | 7.15 | 5.88 | 5.46 | 8.04 | 5.46 |
| 3204285 | 5.76 | 6.02 | 5.45 | 5.97 | 5.97 | 5.46 | 5.62 | 6.83 | 5.91 | 5.78 | 6.07 | 6.25 |
| 3654699 | 12.68 | 11.81 | 12.29 | 11.26 | 11.75 | 12.53 | 10.99 | 12.54 | 10.73 | 12.08 | 9.69 | 11.23 |
| 2638676 | 5.51 | 7.49 | 7.33 | 7.50 | 7.90 | 7.20 | 8.09 | 10.01 | 6.52 | 7.55 | 8.13 | 6.11 |
| 3367673 | 7.62 | 7.06 | 8.38 | 8.58 | 6.80 | 4.90 | 8.17 | 7.69 | 8.79 | 5.03 | 6.32 | 4.81 |
| 3212008 | 7.03 | 6.39 | 6.67 | 6.65 | 6.69 | 6.96 | 7.76 | 6.19 | 9.44 | 8.76 | 7.12 | 7.76 |
| 3326635 | 9.00 | 9.77 | 10.28 | 10.12 | 10.14 | 10.59 | 10.61 | 9.57 | 10.47 | 10.55 | 10.09 | 10.25 |
| 3031556 | 6.58 | 8.21 | 9.72 | 9.04 | 10.16 | 8.91 | 9.74 | 7.95 | 8.58 | 8.54 | 9.95 | 8.88 |
| 3662201 | 10.79 | 11.56 | 12.50 | 12.89 | 8.92 | 8.69 | 7.07 | 12.41 | 11.37 | 8.69 | 10.74 | 8.04 |
| 2809793 | 5.16 | 8.05 | 8.83 | 9.34 | 10.14 | 7.45 | 8.20 | 8.32 | 8.41 | 6.51 | 8.62 | 7.24 |
| 2817731 | 8.08 | 7.87 | 7.57 | 7.90 | 8.24 | 9.40 | 8.07 | 7.01 | 7.16 | 9.53 | 8.32 | 7.90 |
| 4020655 | 6.81 | 5.55 | 5.18 | 4.87 | 5.35 | 7.08 | 7.73 | 4.89 | 9.41 | 8.12 | 5.43 | 6.40 |
| 3494629 | 4.55 | 4.55 | 4.40 | 4.93 | 4.37 | 5.55 | 4.64 | 4.46 | 5.07 | 6.09 | 4.44 | 8.06 |
| 3852832 | 7.18 | 9.22 | 9.55 | 8.00 | 9.29 | 8.01 | 9.34 | 6.11 | 8.83 | 7.18 | 10.86 | 6.96 |
| 3761959 | 10.10 | 9.39 | 9.22 | 8.43 | 8.99 | 9.94 | 9.04 | 9.00 | 9.01 | 9.78 | 8.40 | 9.40 |
| 2834282 | 6.69 | 6.25 | 6.21 | 7.16 | 5.86 | 7.37 | 7.06 | 6.64 | 8.64 | 7.21 | 6.12 | 7.59 |
| 3341497 | 6.23 | 6.56 | 6.67 | 6.38 | 6.51 | 6.58 | 5.86 | 6.47 | 8.35 | 6.25 | 6.37 | 6.59 |
| 2372812 | 4.55 | 4.85 | 4.79 | 4.76 | 5.76 | 4.56 | 4.83 | 10.84 | 4.83 | 5.02 | 4.72 | 4.46 |
| 2486811 | 6.74 | 9.67 | 10.16 | 9.80 | 10.66 | 10.54 | 10.04 | 10.07 | 9.10 | 10.78 | 10.57 | 9.81 |
| 3768474 | 8.55 | 8.51 | 8.35 | 8.10 | 8.72 | 9.13 | 7.87 | 7.88 | 7.88 | 8.71 | 8.71 | 8.31 |
| 3142381 | 6.15 | 5.40 | 4.91 | 6.51 | 3.96 | 6.29 | 7.87 | 4.16 | 4.00 | 7.06 | 5.26 | 6.28 |
| 2396750 | 6.42 | 6.66 | 7.15 | 6.66 | 7.13 | 8.27 | 6.50 | 7.35 | 7.45 | 7.49 | 7.35 | 7.22 |
| 3902489 | 9.01 | 11.63 | 11.50 | 11.39 | 10.96 | 10.17 | 11.32 | 9.29 | 11.06 | 10.22 | 12.29 | 10.56 |
| 3032647 | 8.64 | 7.97 | 8.50 | 7.11 | 6.49 | 6.69 | 7.34 | 7.55 | 6.70 | 5.88 | 6.63 | 5.77 |
| 3875642 | 6.03 | 5.60 | 5.61 | 6.04 | 6.48 | 5.16 | 6.34 | 5.08 | 5.58 | 5.43 | 6.28 | 5.18 |
| 4027585 | 8.76 | 11.90 | 11.39 | 11.48 | 11.30 | 11.01 | 10.84 | 8.92 | 10.69 | 11.15 | 12.01 | 10.46 |
| 2352609 | 8.44 | 6.52 | 6.85 | 6.70 | 5.88 | 6.61 | 7.56 | 6.46 | 7.51 | 6.05 | 5.77 | 6.29 |
| 3376529 | 8.49 | 8.54 | 8.50 | 8.21 | 8.00 | 9.36 | 8.71 | 8.00 | 8.68 | 8.92 | 7.79 | 9.24 |
| 2491271 | 12.09 | 12.81 | 13.25 | 13.28 | 13.67 | 13.48 | 13.28 | 13.33 | 13.01 | 13.66 | 13.35 | 13.28 |
| 3874751 | 10.31 | 9.83 | 9.14 | 9.08 | 9.77 | 10.08 | 9.36 | 8.70 | 8.76 | 9.94 | 8.83 | 9.73 |
| 2326463 | 9.58 | 11.42 | 12.03 | 11.92 | 12.24 | 12.25 | 11.85 | 11.63 | 11.65 | 12.29 | 12.13 | 11.41 |
| 3341061 | 6.56 | 6.69 | 7.63 | 7.24 | 8.01 | 9.23 | 7.50 | 6.58 | 6.43 | 9.23 | 7.69 | 7.95 |
| 3839910 | 6.55 | 9.26 | 9.88 | 7.42 | 8.52 | 7.44 | 9.43 | 6.34 | 8.43 | 6.67 | 10.82 | 7.07 |
| 2708855 | 4.16 | 4.00 | 4.41 | 4.50 | 5.02 | 7.00 | 4.81 | 4.43 | 6.31 | 6.86 | 5.71 | 8.13 |
| 3512874 | 9.72 | 11.87 | 12.24 | 11.83 | 12.21 | 11.58 | 12.18 | 12.14 | 11.49 | 11.70 | 12.37 | 11.35 |
| 2701071 | 8.20 | 9.89 | 10.87 | 9.39 | 10.47 | 9.15 | 10.74 | 8.04 | 9.74 | 8.89 | 11.45 | 8.79 |
| 3486096 | 8.59 | 7.21 | 6.58 | 7.39 | 5.82 | 6.45 | 6.70 | 7.67 | 7.35 | 6.48 | 5.74 | 6.50 |
| 2412668 | 8.17 | 7.67 | 8.38 | 7.84 | 8.81 | 8.91 | 7.98 | 7.75 | 7.59 | 8.99 | 8.47 | 8.05 |
| 3329343 | 6.80 | 7.15 | 7.31 | 7.81 | 7.59 | 8.92 | 7.37 | 7.56 | 7.99 | 8.89 | 7.18 | 9.02 |
| 3259367 | 4.27 | 3.99 | 4.09 | 4.49 | 4.76 | 4.29 | 4.35 | 4.11 | 6.57 | 4.83 | 4.56 | 4.42 |
| 3373845 | 7.13 | 7.60 | 9.58 | 10.11 | 9.55 | 10.50 | 8.58 | 9.24 | 8.10 | 10.44 | 8.90 | 9.96 |
| 2321911 | 9.18 | 8.53 | 8.77 | 8.16 | 8.73 | 8.67 | 8.62 | 8.20 | 8.09 | 8.38 | 9.17 | 7.91 |
| 3353914 | 6.37 | 6.36 | 6.28 | 6.74 | 7.71 | 9.50 | 6.97 | 6.42 | 6.62 | 9.53 | 6.94 | 7.96 |
| 3744680 | 6.82 | 7.74 | 8.01 | 7.66 | 8.43 | 8.58 | 7.98 | 7.25 | 7.80 | 8.34 | 8.84 | 7.52 |
| 2373336 | 8.23 | 5.66 | 5.50 | 7.48 | 7.56 | 7.58 | 5.19 | 6.33 | 5.84 | 8.03 | 6.19 | 9.91 |
| 3067478 | 6.82 | 6.51 | 5.89 | 5.23 | 5.03 | 8.33 | 7.85 | 6.59 | 6.67 | 7.81 | 4.85 | 7.85 |
| 3976766 | 7.23 | 8.46 | 8.76 | 7.83 | 8.84 | 7.91 | 8.93 | 8.10 | 8.37 | 8.06 | 9.67 | 7.68 |
| 3246888 | 7.34 | 6.52 | 7.09 | 6.80 | 5.13 | 5.62 | 6.06 | 5.32 | 6.74 | 5.67 | 6.39 | 4.93 |
| 3147985 | 6.68 | 6.48 | 6.53 | 6.50 | 6.97 | 8.81 | 6.74 | 5.35 | 6.57 | 9.56 | 6.79 | 7.82 |
| 3185522 | 9.43 | 9.20 | 9.11 | 9.32 | 10.24 | 11.16 | 9.79 | 9.53 | 9.03 | 11.29 | 9.15 | 10.41 |
| 3861948 | 10.93 | 12.74 | 12.95 | 12.44 | 12.98 | 12.41 | 12.90 | 12.26 | 12.52 | 12.61 | 13.30 | 12.01 |
| 3393479 | 8.47 | 8.38 | 8.94 | 8.29 | 9.71 | 10.02 | 8.14 | 8.52 | 7.85 | 9.58 | 8.56 | 9.31 |
| 3540862 | 8.03 | 6.92 | 6.92 | 6.83 | 6.57 | 6.84 | 6.68 | 7.25 | 6.48 | 6.97 | 5.69 | 6.78 |
| 2777714 | 9.69 | 11.88 | 11.79 | 11.86 | 11.20 | 9.92 | 11.61 | 8.58 | 11.49 | 9.27 | 12.14 | 10.85 |
| 3110395 | 8.00 | 5.07 | 5.06 | 4.26 | 4.77 | 5.24 | 5.33 | 4.35 | 6.58 | 5.05 | 4.49 | 4.61 |
| 3895795 | 7.54 | 8.80 | 9.04 | 8.25 | 8.70 | 7.75 | 9.06 | 6.83 | 8.51 | 7.67 | 10.09 | 7.59 |
| 2854445 | 6.65 | 8.86 | 8.42 | 10.48 | 11.15 | 11.37 | 8.54 | 8.42 | 7.30 | 11.28 | 9.33 | 10.52 |
| 3606034 | 7.40 | 7.42 | 7.64 | 7.43 | 7.16 | 8.30 | 7.40 | 6.33 | 7.26 | 8.49 | 6.76 | 7.56 |
| 3375735 | 7.28 | 7.61 | 7.94 | 8.11 | 8.80 | 8.13 | 8.22 | 7.09 | 7.85 | 8.17 | 8.43 | 7.95 |
| 3948047 | 7.09 | 8.27 | 8.93 | 8.30 | 9.11 | 8.67 | 8.65 | 8.23 | 8.20 | 8.72 | 9.27 | 8.16 |
| 3010503 | 7.13 | 9.05 | 9.42 | 9.33 | 10.18 | 10.60 | 9.16 | 6.95 | 7.73 | 10.50 | 10.09 | 9.33 |
| 3622934 | 7.87 | 6.45 | 6.65 | 7.48 | 6.71 | 7.23 | 6.66 | 8.29 | 7.95 | 7.51 | 5.82 | 7.73 |
| 3441849 | 8.64 | 9.66 | 10.27 | 9.69 | 10.39 | 10.11 | 10.02 | 8.56 | 9.65 | 10.29 | 10.95 | 9.79 |

TABLE 30-continued

Normalized intensity of microarray data for a set of samples.

| TCID | V01 0061 | V01 0062 | V01 0063 | V01 0064 | V01 0065 | V01 0066 | V01 0067 | V01 0068 | V01 0069 | V01 0070 | V01 0071 | V01 0072 |
|---|---|---|---|---|---|---|---|---|---|---|---|---|
| 3006572 | 6.53 | 6.76 | 6.84 | 6.73 | 6.90 | 6.54 | 6.34 | 6.40 | 6.76 | 6.33 | 6.77 | 6.91 |
| 3365136 | 8.81 | 8.57 | 8.78 | 8.66 | 8.43 | 9.03 | 7.95 | 8.61 | 10.88 | 9.45 | 8.25 | 9.06 |
| 2642791 | 8.18 | 7.80 | 8.42 | 8.47 | 9.01 | 8.99 | 8.55 | 8.31 | 7.76 | 8.58 | 8.43 | 8.31 |
| 2904485 | 9.27 | 9.24 | 8.30 | 8.69 | 7.72 | 7.05 | 8.84 | 7.36 | 8.27 | 7.09 | 7.54 | 7.59 |
| 3772661 | 8.72 | 9.48 | 10.02 | 10.27 | 10.89 | 11.53 | 9.91 | 9.29 | 9.08 | 11.47 | 10.66 | 10.60 |
| 2796553 | 8.79 | 10.50 | 10.61 | 9.21 | 10.24 | 10.59 | 10.44 | 8.84 | 9.27 | 10.59 | 11.31 | 9.46 |
| 3063795 | 6.97 | 7.63 | 7.37 | 8.20 | 8.69 | 7.71 | 7.07 | 8.38 | 7.09 | 7.48 | 7.68 | 7.42 |
| 3338192 | 8.65 | 8.38 | 8.26 | 8.99 | 7.68 | 9.08 | 8.79 | 8.44 | 10.03 | 9.44 | 8.06 | 10.88 |
| 3214845 | 4.37 | 4.28 | 4.50 | 5.00 | 4.46 | 4.01 | 4.31 | 4.38 | 4.48 | 4.14 | 4.53 | 4.48 |
| 2730303 | 4.47 | 4.32 | 4.25 | 4.21 | 4.72 | 4.03 | 4.22 | 8.87 | 4.35 | 3.94 | 4.54 | 4.00 |
| 3811086 | 8.80 | 7.60 | 7.80 | 7.98 | 8.06 | 8.10 | 7.93 | 7.50 | 7.41 | 8.37 | 7.09 | 7.37 |
| 2981874 | 10.19 | 10.52 | 10.47 | 9.78 | 10.31 | 10.36 | 10.66 | 10.06 | 10.14 | 10.66 | 10.59 | 10.22 |
| 3242353 | 6.27 | 6.49 | 6.03 | 6.51 | 6.09 | 6.76 | 5.81 | 6.70 | 5.79 | 7.14 | 6.20 | 6.08 |
| 2442008 | 5.54 | 5.75 | 5.44 | 5.53 | 5.57 | 8.26 | 5.43 | 5.59 | 7.39 | 8.39 | 5.90 | 7.62 |
| 3564210 | 7.84 | 9.60 | 10.17 | 9.42 | 10.07 | 10.00 | 9.37 | 7.39 | 9.17 | 10.06 | 11.17 | 9.54 |
| 2490351 | 4.23 | 4.33 | 4.19 | 4.14 | 4.22 | 3.85 | 4.04 | 4.11 | 4.29 | 3.91 | 4.26 | 3.98 |
| 3759006 | 7.41 | 10.79 | 10.01 | 10.71 | 10.12 | 7.14 | 9.26 | 7.35 | 9.80 | 6.84 | 11.51 | 8.79 |
| 3264997 | 4.21 | 4.42 | 4.17 | 4.17 | 4.29 | 3.99 | 4.15 | 4.32 | 4.51 | 3.94 | 4.51 | 4.02 |
| 3912079 | 3.64 | 3.64 | 3.78 | 3.70 | 4.21 | 3.53 | 3.60 | 3.57 | 3.90 | 3.55 | 4.00 | 3.70 |
| 2926802 | 4.58 | 5.10 | 5.29 | 5.66 | 5.54 | 4.82 | 5.60 | 5.62 | 5.83 | 4.97 | 6.69 | 5.16 |
| 2430163 | 3.73 | 4.03 | 3.86 | 4.08 | 4.02 | 3.74 | 4.02 | 3.92 | 4.07 | 5.05 | 4.45 | 4.26 |
| 3039830 | 3.11 | 3.27 | 3.09 | 3.08 | 3.17 | 3.06 | 3.09 | 3.06 | 3.13 | 3.11 | 3.27 | 3.07 |
| 3935486 | 5.30 | 6.36 | 7.32 | 7.20 | 8.38 | 9.87 | 4.78 | 5.51 | 6.30 | 9.85 | 5.95 | 7.96 |
| 3457152 | 5.74 | 5.74 | 5.55 | 5.45 | 5.55 | 5.01 | 5.44 | 5.41 | 5.62 | 5.17 | 5.87 | 5.16 |
| 3811949 | 3.71 | 3.68 | 3.48 | 3.53 | 3.69 | 3.25 | 3.52 | 3.46 | 3.53 | 3.37 | 3.77 | 3.53 |
| 3343832 | 3.79 | 4.16 | 4.01 | 4.01 | 3.97 | 3.86 | 3.88 | 3.92 | 3.91 | 3.81 | 4.18 | 3.72 |
| 3161261 | 6.90 | 6.84 | 5.75 | 6.35 | 6.15 | 5.19 | 5.97 | 5.35 | 5.83 | 4.97 | 5.90 | 5.46 |
| 3594003 | 3.92 | 3.84 | 3.58 | 3.54 | 3.98 | 3.63 | 3.79 | 3.59 | 3.61 | 3.84 | 4.04 | 3.75 |
| 3805614 | 5.06 | 5.04 | 5.08 | 4.96 | 5.22 | 4.99 | 4.96 | 4.86 | 4.96 | 4.59 | 5.28 | 4.59 |
| 3364127 | 6.86 | 7.34 | 7.10 | 7.21 | 6.85 | 6.34 | 6.92 | 8.05 | 7.52 | 6.26 | 6.99 | 6.40 |
| 3834341 | 4.37 | 4.16 | 4.25 | 4.15 | 4.24 | 3.74 | 3.89 | 4.23 | 4.67 | 3.64 | 4.55 | 4.02 |
| 2585400 | 6.08 | 5.38 | 4.39 | 5.11 | 5.99 | 4.69 | 4.71 | 4.39 | 4.24 | 4.66 | 4.81 | 4.60 |
| 2941690 | 4.39 | 4.36 | 4.41 | 4.76 | 4.56 | 3.87 | 4.17 | 4.04 | 4.74 | 4.36 | 4.81 | 3.97 |
| 3484895 | 5.28 | 5.19 | 5.03 | 4.68 | 4.90 | 4.87 | 4.79 | 4.87 | 5.00 | 4.94 | 5.13 | 5.09 |
| 3159754 | 3.77 | 4.04 | 3.98 | 3.63 | 3.68 | 3.31 | 3.75 | 3.75 | 3.87 | 3.47 | 3.84 | 3.71 |
| 2894790 | 3.85 | 4.01 | 3.74 | 4.17 | 3.79 | 3.81 | 3.78 | 3.83 | 3.90 | 3.92 | 4.31 | 3.71 |
| 3363686 | 3.47 | 3.58 | 3.44 | 4.03 | 3.54 | 3.49 | 3.60 | 3.45 | 3.43 | 3.70 | 3.63 | 3.63 |
| 2923928 | 4.33 | 4.68 | 4.29 | 4.56 | 5.05 | 3.82 | 4.88 | 4.28 | 4.43 | 4.34 | 5.20 | 4.41 |
| 2883317 | 4.62 | 5.18 | 6.28 | 4.77 | 5.23 | 5.13 | 6.34 | 5.56 | 4.72 | 4.61 | 4.90 | 4.96 |
| 2479698 | 6.56 | 6.06 | 6.16 | 5.87 | 6.23 | 5.90 | 6.02 | 6.24 | 6.41 | 5.79 | 6.07 | 6.04 |
| 3428225 | 4.01 | 4.29 | 3.78 | 3.78 | 3.89 | 3.59 | 3.77 | 3.71 | 3.74 | 3.59 | 4.09 | 3.68 |
| 3393446 | 7.53 | 7.62 | 7.87 | 7.22 | 7.67 | 7.93 | 6.70 | 7.57 | 7.23 | 7.45 | 8.03 | 7.34 |
| 3116614 | 13.31 | 12.98 | 13.03 | 12.32 | 11.12 | 11.94 | 12.87 | 12.13 | 13.23 | 11.87 | 11.16 | 12.19 |
| 3415320 | 11.24 | 10.86 | 10.41 | 8.70 | 7.61 | 9.16 | 9.32 | 9.65 | 9.72 | 9.55 | 7.44 | 10.31 |
| 3757108 | 7.83 | 7.74 | 7.71 | 8.57 | 8.10 | 8.78 | 7.12 | 7.92 | 8.44 | 9.24 | 7.84 | 10.59 |
| 4012178 | 6.00 | 6.35 | 7.06 | 6.17 | 6.18 | 9.78 | 11.28 | 6.46 | 10.48 | 9.34 | 6.52 | 7.75 |
| 3546213 | 11.72 | 10.86 | 10.34 | 10.62 | 7.70 | 10.61 | 10.51 | 9.99 | 11.09 | 10.82 | 8.21 | 10.60 |
| 3561381 | 9.62 | 9.18 | 8.75 | 9.87 | 6.16 | 8.62 | 8.97 | 7.73 | 10.84 | 9.54 | 6.86 | 9.94 |

TABLE 31

Normalized intensity of microarray data for a set of samples.

| TCID | V01 0073 | V01 0074 | V01 0075 | V01 0076 | V01 0077 | V01 0078 | V01 0079 | V01 0080 | V01 0081 | V01 0082 | V01 0083 | V01 0084 |
|---|---|---|---|---|---|---|---|---|---|---|---|---|
| 2604998 | 8.49 | 8.97 | 6.56 | 9.18 | 8.31 | 5.09 | 7.80 | 8.40 | 8.61 | 7.21 | 7.24 | 6.80 |
| 3603932 | 7.17 | 8.22 | 6.88 | 7.29 | 6.74 | 7.22 | 7.07 | 7.46 | 7.70 | 6.68 | 6.67 | 7.59 |
| 2710599 | 9.30 | 11.41 | 6.39 | 11.84 | 10.46 | 5.70 | 7.71 | 11.93 | 11.33 | 11.35 | 5.61 | 7.06 |
| 2440258 | 5.12 | 6.16 | 8.64 | 4.33 | 7.78 | 9.28 | 8.02 | 4.66 | 5.88 | 9.64 | 8.75 | 9.63 |
| 3169331 | 7.74 | 6.53 | 6.98 | 6.53 | 6.62 | 6.54 | 7.36 | 6.13 | 6.61 | 7.19 | 6.72 | 6.64 |
| 2988882 | 10.28 | 9.63 | 10.00 | 9.64 | 8.69 | 10.07 | 9.92 | 10.11 | 9.85 | 9.81 | 9.82 | 10.20 |
| 2964231 | 8.39 | 9.43 | 8.17 | 7.13 | 9.11 | 8.76 | 7.59 | 10.03 | 10.22 | 9.34 | 8.60 | 8.35 |
| 3111561 | 11.18 | 4.54 | 7.42 | 6.33 | 5.23 | 5.69 | 9.10 | 5.58 | 4.74 | 5.56 | 9.10 | 9.68 |
| 2562529 | 9.88 | 10.24 | 8.98 | 11.07 | 10.46 | 8.46 | 9.05 | 10.96 | 11.33 | 9.92 | 8.74 | 9.24 |
| 3692999 | 12.06 | 7.71 | 9.97 | 5.58 | 12.11 | 6.26 | 11.26 | 8.26 | 8.22 | 7.68 | 9.38 | 11.24 |
| 2439554 | 4.38 | 6.17 | 8.02 | 4.59 | 6.52 | 8.84 | 6.84 | 4.64 | 6.03 | 8.78 | 7.83 | 7.35 |
| 2685304 | 8.54 | 10.75 | 6.87 | 11.40 | 8.90 | 6.65 | 7.04 | 11.88 | 11.60 | 10.27 | 7.74 | 8.11 |
| 2578790 | 6.99 | 4.18 | 6.85 | 4.13 | 4.42 | 4.80 | 5.75 | 4.17 | 4.44 | 4.24 | 6.48 | 4.97 |
| 2373842 | 9.22 | 10.29 | 11.95 | 7.16 | 11.39 | 11.92 | 11.60 | 7.76 | 9.09 | 11.22 | 11.87 | 11.95 |
| 2750627 | 9.89 | 10.90 | 7.92 | 10.36 | 9.70 | 5.14 | 8.17 | 10.08 | 10.82 | 9.69 | 8.17 | 9.29 |
| 3397774 | 5.03 | 4.51 | 4.95 | 4.67 | 4.79 | 5.46 | 4.70 | 4.39 | 4.72 | 4.74 | 4.95 | 5.14 |

TABLE 31-continued

Normalized intensity of microarray data for a set of samples.

| TCID | V01 0073 | V01 0074 | V01 0075 | V01 0076 | V01 0077 | V01 0078 | V01 0079 | V01 0080 | V01 0081 | V01 0082 | V01 0083 | V01 0084 |
|---|---|---|---|---|---|---|---|---|---|---|---|---|
| 2635741 | 6.58 | 6.81 | 9.24 | 5.70 | 8.53 | 9.63 | 8.74 | 5.89 | 6.18 | 9.05 | 9.03 | 9.64 |
| 3970833 | 9.95 | 9.56 | 9.40 | 9.64 | 9.55 | 8.68 | 9.56 | 9.73 | 9.80 | 9.74 | 9.28 | 9.07 |
| 3577612 | 8.92 | 11.39 | 11.41 | 11.11 | 10.29 | 11.58 | 10.87 | 11.66 | 11.70 | 11.71 | 11.27 | 10.81 |
| 2708922 | 7.22 | 8.02 | 8.15 | 8.40 | 9.14 | 8.79 | 8.18 | 8.42 | 8.79 | 7.36 | 8.43 | 9.26 |
| 2970897 | 6.96 | 4.99 | 5.05 | 5.28 | 4.98 | 4.92 | 4.66 | 4.42 | 5.52 | 4.96 | 4.86 | 5.79 |
| 3724545 | 8.65 | 10.15 | 9.60 | 10.21 | 9.56 | 8.84 | 10.06 | 9.82 | 9.69 | 8.74 | 10.49 | 9.87 |
| 2798538 | 8.27 | 9.18 | 9.32 | 8.21 | 8.62 | 9.69 | 9.57 | 9.02 | 8.83 | 9.58 | 8.88 | 8.67 |
| 2806468 | 7.83 | 9.73 | 11.67 | 5.74 | 10.80 | 11.76 | 11.63 | 5.83 | 7.63 | 10.87 | 11.64 | 12.05 |
| 2880051 | 6.00 | 5.77 | 6.71 | 5.90 | 6.64 | 7.30 | 6.86 | 5.68 | 6.13 | 6.33 | 6.80 | 6.93 |
| 2732508 | 3.47 | 3.47 | 3.45 | 3.23 | 3.53 | 3.64 | 3.94 | 3.45 | 3.32 | 8.53 | 3.46 | 3.96 |
| 2822492 | 5.86 | 5.22 | 5.74 | 5.18 | 5.71 | 5.91 | 5.80 | 5.99 | 5.44 | 4.87 | 5.27 | 6.02 |
| 3404030 | 6.55 | 5.49 | 8.13 | 5.33 | 8.35 | 9.87 | 8.38 | 5.90 | 5.79 | 7.29 | 9.99 | 10.20 |
| 3059667 | 10.74 | 3.89 | 5.59 | 8.68 | 5.41 | 5.87 | 10.71 | 6.17 | 5.94 | 5.79 | 10.05 | 9.14 |
| 3108526 | 9.91 | 7.99 | 7.56 | 8.20 | 9.10 | 6.17 | 10.61 | 8.70 | 9.90 | 7.11 | 9.47 | 8.38 |
| 2526806 | 9.12 | 12.48 | 7.73 | 12.73 | 10.70 | 7.11 | 10.56 | 13.00 | 12.05 | 12.65 | 8.41 | 8.92 |
| 2428511 | 5.84 | 8.07 | 7.61 | 7.27 | 6.33 | 7.88 | 7.44 | 8.89 | 6.75 | 8.37 | 6.83 | 7.02 |
| 2657808 | 9.37 | 10.21 | 5.51 | 11.66 | 7.24 | 5.83 | 5.98 | 10.92 | 11.21 | 8.55 | 5.75 | 6.71 |
| 2584018 | 7.63 | 10.35 | 8.00 | 11.14 | 7.68 | 8.53 | 7.44 | 10.55 | 10.05 | 9.25 | 7.77 | 8.96 |
| 3976341 | 7.68 | 11.74 | 10.28 | 11.84 | 10.11 | 10.61 | 9.70 | 11.74 | 11.82 | 11.48 | 9.73 | 10.16 |
| 2739308 | 4.68 | 4.55 | 5.39 | 4.60 | 5.18 | 5.96 | 5.27 | 4.47 | 5.10 | 4.33 | 6.12 | 5.70 |
| 3959862 | 5.05 | 4.57 | 5.38 | 4.35 | 6.08 | 5.54 | 4.72 | 3.55 | 4.15 | 6.84 | 4.58 | 5.86 |
| 2362351 | 5.60 | 6.17 | 8.16 | 5.50 | 7.74 | 8.51 | 7.75 | 5.26 | 5.73 | 7.78 | 8.32 | 8.61 |
| 3648391 | 4.87 | 4.21 | 4.51 | 4.48 | 5.45 | 6.24 | 5.08 | 3.72 | 3.92 | 7.07 | 5.25 | 7.55 |
| 3009299 | 10.68 | 10.61 | 10.77 | 10.68 | 10.83 | 10.81 | 10.53 | 10.57 | 10.99 | 11.09 | 10.46 | 10.57 |
| 3443464 | 5.57 | 5.19 | 5.53 | 4.83 | 5.67 | 6.50 | 6.02 | 4.92 | 5.05 | 5.53 | 6.81 | 6.32 |
| 2730746 | 8.85 | 5.81 | 6.77 | 5.46 | 7.10 | 5.74 | 8.14 | 6.23 | 6.78 | 5.01 | 7.59 | 7.22 |
| 2427619 | 5.31 | 6.66 | 9.66 | 5.17 | 8.35 | 9.88 | 8.85 | 4.40 | 5.74 | 8.59 | 9.43 | 9.94 |
| 3042001 | 9.03 | 8.33 | 8.38 | 8.12 | 8.11 | 8.62 | 8.36 | 8.90 | 8.35 | 8.89 | 8.56 | 8.45 |
| 2566848 | 5.26 | 5.16 | 5.86 | 4.87 | 5.56 | 6.17 | 5.58 | 4.88 | 5.09 | 6.35 | 5.73 | 5.92 |
| 2984616 | 9.50 | 9.30 | 9.28 | 8.82 | 9.01 | 9.03 | 8.93 | 9.55 | 9.21 | 9.47 | 8.85 | 8.73 |
| 2378068 | 8.14 | 9.64 | 7.31 | 9.46 | 8.34 | 8.01 | 6.98 | 9.70 | 10.27 | 9.68 | 7.41 | 7.82 |
| 2721959 | 7.41 | 11.26 | 6.34 | 12.43 | 7.76 | 6.26 | 5.73 | 13.06 | 13.09 | 11.18 | 6.05 | 6.84 |
| 2877508 | 10.20 | 10.66 | 9.80 | 10.04 | 9.91 | 9.71 | 10.30 | 11.06 | 10.58 | 10.62 | 10.22 | 10.32 |
| 3450861 | 4.67 | 4.30 | 7.40 | 4.77 | 5.98 | 7.34 | 6.91 | 4.04 | 5.08 | 6.43 | 6.59 | 7.47 |
| 2688717 | 6.80 | 6.83 | 9.64 | 5.17 | 8.57 | 9.86 | 8.76 | 5.22 | 6.74 | 9.86 | 9.36 | 10.06 |
| 3270270 | 6.78 | 9.31 | 9.52 | 8.51 | 8.33 | 9.88 | 8.79 | 9.14 | 8.48 | 8.72 | 9.19 | 9.09 |
| 3417703 | 8.64 | 8.41 | 8.30 | 9.09 | 7.87 | 4.68 | 6.42 | 6.38 | 7.27 | 5.26 | 8.84 | 9.59 |
| 3302990 | 7.75 | 7.37 | 7.04 | 7.59 | 7.39 | 6.86 | 6.95 | 9.17 | 8.31 | 7.60 | 7.43 | 6.89 |
| 2377283 | 4.27 | 3.85 | 4.76 | 4.32 | 4.94 | 5.36 | 4.56 | 3.87 | 4.20 | 9.76 | 5.03 | 5.66 |
| 3122678 | 4.80 | 4.37 | 4.61 | 4.60 | 4.86 | 5.65 | 5.00 | 4.25 | 4.33 | 6.89 | 4.57 | 4.75 |
| 2688499 | 10.74 | 10.58 | 7.69 | 10.46 | 9.47 | 7.69 | 8.03 | 10.74 | 9.50 | 9.44 | 8.89 | 9.14 |
| 2377094 | 9.13 | 7.96 | 7.85 | 7.77 | 8.66 | 8.23 | 8.67 | 9.15 | 9.22 | 8.30 | 8.77 | 8.41 |
| 3278198 | 8.86 | 7.62 | 7.89 | 8.09 | 8.35 | 6.16 | 7.78 | 9.03 | 9.36 | 7.90 | 7.39 | 7.19 |
| 2598261 | 8.59 | 12.21 | 7.58 | 12.66 | 9.75 | 6.69 | 9.60 | 13.05 | 11.52 | 12.31 | 8.03 | 8.23 |
| 3982612 | 6.86 | 6.03 | 9.79 | 4.08 | 8.91 | 10.04 | 8.73 | 5.29 | 6.28 | 10.21 | 9.35 | 10.47 |
| 2884845 | 5.17 | 9.86 | 4.46 | 10.78 | 4.68 | 4.76 | 4.75 | 10.36 | 8.55 | 9.50 | 4.48 | 4.93 |
| 3982560 | 4.80 | 4.61 | 7.42 | 4.70 | 7.00 | 8.03 | 7.38 | 4.51 | 5.10 | 8.09 | 7.23 | 7.97 |
| 3204285 | 5.59 | 5.10 | 5.90 | 5.63 | 5.55 | 6.16 | 5.45 | 5.37 | 5.69 | 9.53 | 5.09 | 5.55 |
| 3654699 | 12.00 | 12.00 | 10.51 | 9.04 | 10.58 | 7.56 | 10.44 | 11.94 | 11.60 | 12.29 | 11.73 | 9.86 |
| 2638676 | 6.64 | 6.89 | 7.71 | 5.30 | 7.31 | 8.70 | 7.34 | 5.10 | 5.71 | 8.98 | 8.02 | 8.78 |
| 3367673 | 9.32 | 4.48 | 8.26 | 5.62 | 8.99 | 5.55 | 6.56 | 5.66 | 4.68 | 4.85 | 8.17 | 7.57 |
| 3212008 | 7.56 | 8.20 | 7.30 | 9.05 | 9.65 | 7.09 | 6.87 | 9.02 | 9.56 | 7.03 | 6.82 | 6.62 |
| 3326635 | 10.35 | 10.22 | 10.42 | 9.96 | 10.76 | 10.40 | 10.18 | 10.14 | 10.27 | 10.45 | 10.20 | 10.43 |
| 3031556 | 6.73 | 8.10 | 10.15 | 5.12 | 9.65 | 10.57 | 9.55 | 6.09 | 7.93 | 9.59 | 10.07 | 9.92 |
| 3662201 | 12.27 | 9.16 | 9.89 | 7.20 | 12.01 | 6.16 | 11.07 | 9.07 | 8.34 | 8.63 | 10.45 | 11.58 |
| 2809793 | 5.28 | 5.98 | 8.26 | 3.99 | 8.04 | 9.62 | 9.49 | 4.32 | 7.59 | 9.60 | 10.26 | 10.44 |
| 2817731 | 7.68 | 8.89 | 7.83 | 7.48 | 7.55 | 8.31 | 7.88 | 7.98 | 7.47 | 7.78 | 7.87 | 7.68 |
| 4020655 | 6.76 | 7.10 | 5.78 | 6.27 | 9.78 | 5.94 | 7.34 | 8.93 | 6.63 | 5.62 | 5.54 | 5.54 |
| 3494629 | 4.65 | 7.29 | 4.81 | 8.72 | 5.03 | 4.44 | 4.29 | 7.97 | 7.99 | 6.36 | 4.33 | 4.72 |
| 3852832 | 6.83 | 8.08 | 9.90 | 5.86 | 8.49 | 10.65 | 9.58 | 6.03 | 6.67 | 5.85 | 10.35 | 9.25 |
| 3761959 | 9.68 | 9.69 | 8.64 | 9.21 | 8.71 | 8.72 | 8.56 | 9.60 | 9.38 | 9.42 | 8.63 | 8.84 |
| 2834282 | 7.20 | 8.75 | 5.96 | 8.40 | 8.02 | 5.55 | 6.00 | 9.39 | 7.89 | 7.25 | 5.70 | 6.62 |
| 3341497 | 7.18 | 7.25 | 6.28 | 8.24 | 7.75 | 6.55 | 5.84 | 7.44 | 8.66 | 5.90 | 6.15 | 6.11 |
| 2372812 | 4.69 | 4.24 | 5.04 | 4.54 | 4.69 | 4.93 | 4.68 | 4.34 | 4.72 | 8.96 | 4.59 | 4.66 |
| 2486811 | 8.58 | 10.03 | 10.25 | 5.94 | 10.03 | 10.95 | 9.97 | 6.55 | 7.43 | 10.64 | 10.18 | 10.60 |
| 3768474 | 7.80 | 8.31 | 8.84 | 7.70 | 7.85 | 8.76 | 7.92 | 7.95 | 7.72 | 8.30 | 8.28 | 8.26 |
| 3142381 | 8.38 | 5.90 | 6.24 | 4.88 | 4.52 | 4.85 | 4.34 | 3.52 | 4.31 | 4.47 | 5.58 | 5.84 |
| 2396750 | 7.63 | 7.40 | 7.19 | 8.25 | 7.68 | 7.59 | 6.76 | 7.14 | 8.07 | 8.10 | 7.03 | 6.94 |
| 3902489 | 9.48 | 10.01 | 11.24 | 10.16 | 11.45 | 12.04 | 11.60 | 9.47 | 10.43 | 10.06 | 11.69 | 12.23 |
| 3032647 | 7.29 | 5.39 | 6.39 | 5.46 | 5.95 | 6.38 | 7.36 | 5.78 | 5.83 | 7.75 | 6.41 |
| 3875642 | 5.26 | 4.71 | 5.89 | 4.91 | 6.17 | 6.68 | 6.58 | 5.42 | 4.86 | 5.20 | 6.59 | 6.26 |
| 4027585 | 8.74 | 10.45 | 11.26 | 7.63 | 10.93 | 11.86 | 11.30 | 8.17 | 10.03 | 9.94 | 11.37 | 12.10 |
| 2352609 | 7.33 | 6.64 | 6.61 | 6.62 | 7.18 | 5.71 | 6.93 | 7.40 | 7.78 | 6.02 | 6.13 | 6.37 |
| 3376529 | 8.72 | 9.99 | 8.34 | 10.02 | 9.22 | 7.78 | 7.93 | 10.39 | 10.18 | 8.74 | 7.88 | 8.02 |
| 2491271 | 12.67 | 13.55 | 13.38 | 13.29 | 13.22 | 13.46 | 13.43 | 13.25 | 13.21 | 13.81 | 13.36 | 13.45 |

TABLE 31-continued

Normalized intensity of microarray data for a set of samples.

| TCID | V01 0073 | V01 0074 | V01 0075 | V01 0076 | V01 0077 | V01 0078 | V01 0079 | V01 0080 | V01 0081 | V01 0082 | V01 0083 | V01 0084 |
|---|---|---|---|---|---|---|---|---|---|---|---|---|
| 3874751 | 9.25 | 9.66 | 9.04 | 9.78 | 9.12 | 9.44 | 9.29 | 10.27 | 9.98 | 9.88 | 9.18 | 9.26 |
| 2326463 | 10.99 | 11.68 | 12.61 | 7.70 | 11.96 | 12.49 | 12.05 | 9.68 | 10.28 | 12.21 | 12.11 | 12.65 |
| 3341061 | 6.68 | 8.33 | 7.28 | 7.17 | 6.82 | 8.10 | 7.54 | 7.38 | 6.26 | 8.20 | 6.80 | 8.13 |
| 3839910 | 5.50 | 8.04 | 10.29 | 4.55 | 8.41 | 11.00 | 9.34 | 5.33 | 6.26 | 5.54 | 10.15 | 9.21 |
| 2708855 | 4.29 | 8.17 | 4.28 | 9.26 | 6.27 | 4.21 | 4.18 | 8.77 | 8.25 | 6.58 | 4.62 | 5.09 |
| 3512874 | 9.96 | 11.41 | 12.46 | 8.32 | 11.85 | 12.59 | 12.26 | 9.55 | 10.12 | 11.97 | 12.53 | 12.20 |
| 2701071 | 7.06 | 9.07 | 11.18 | 6.14 | 9.63 | 11.17 | 10.66 | 6.74 | 8.36 | 9.30 | 11.10 | 10.64 |
| 3486096 | 9.02 | 5.28 | 6.07 | 6.22 | 6.79 | 5.60 | 5.43 | 7.39 | 8.37 | 5.43 | 7.28 | 6.95 |
| 2412668 | 8.23 | 8.72 | 8.91 | 7.94 | 7.68 | 8.72 | 7.80 | 7.69 | 8.50 | 8.65 | 8.44 | 8.41 |
| 3329343 | 8.26 | 9.14 | 6.76 | 9.51 | 8.27 | 7.51 | 7.10 | 7.92 | 8.30 | 8.72 | 7.01 | 7.22 |
| 3259367 | 6.35 | 4.95 | 4.68 | 5.68 | 5.16 | 4.70 | 4.23 | 4.88 | 6.32 | 4.28 | 4.12 | 4.44 |
| 3373845 | 10.86 | 10.22 | 9.33 | 10.34 | 8.46 | 9.65 | 9.31 | 8.90 | 7.86 | 10.20 | 9.30 | 9.58 |
| 2321911 | 7.50 | 8.40 | 8.89 | 7.82 | 8.26 | 8.88 | 9.07 | 7.79 | 7.75 | 8.36 | 8.50 | 9.33 |
| 3353914 | 6.96 | 8.40 | 6.56 | 8.01 | 6.92 | 6.56 | 6.59 | 7.72 | 7.34 | 7.55 | 6.38 | 7.56 |
| 3744680 | 6.57 | 7.66 | 8.35 | 6.23 | 7.42 | 8.75 | 8.00 | 6.25 | 6.72 | 7.66 | 8.46 | 8.08 |
| 2373336 | 5.20 | 9.35 | 6.16 | 10.54 | 5.03 | 6.45 | 6.82 | 10.25 | 7.29 | 8.91 | 6.40 | 6.65 |
| 3067478 | 6.00 | 7.84 | 5.40 | 8.65 | 7.39 | 4.88 | 5.19 | 9.29 | 7.68 | 7.19 | 5.51 | 6.03 |
| 3976766 | 6.66 | 7.60 | 9.28 | 6.01 | 8.23 | 9.82 | 8.80 | 6.43 | 6.99 | 8.32 | 9.05 | 8.90 |
| 3246888 | 8.25 | 5.56 | 6.12 | 5.90 | 7.21 | 5.22 | 6.95 | 4.47 | 6.16 | 4.78 | 6.98 | 5.72 |
| 3147985 | 7.23 | 8.37 | 6.17 | 7.45 | 6.75 | 5.63 | 6.27 | 7.58 | 8.41 | 7.01 | 6.82 | 7.47 |
| 3185522 | 9.51 | 10.26 | 9.18 | 9.33 | 8.96 | 9.35 | 9.36 | 9.46 | 9.29 | 11.29 | 9.38 | 9.94 |
| 3861948 | 11.43 | 12.25 | 13.24 | 9.42 | 12.73 | 13.36 | 12.84 | 9.45 | 11.06 | 12.74 | 13.23 | 13.04 |
| 3393479 | 8.65 | 9.68 | 9.04 | 7.84 | 7.89 | 9.05 | 7.80 | 8.69 | 7.48 | 9.34 | 9.31 | 8.70 |
| 3540862 | 7.05 | 6.96 | 6.83 | 7.02 | 7.16 | 6.25 | 7.20 | 8.42 | 7.41 | 6.53 | 6.59 | 6.55 |
| 2777714 | 9.00 | 9.05 | 11.46 | 7.83 | 11.62 | 11.94 | 11.92 | 7.74 | 11.17 | 8.77 | 11.70 | 12.28 |
| 3110395 | 5.67 | 5.61 | 4.60 | 4.64 | 5.93 | 4.58 | 7.39 | 7.68 | 6.11 | 4.94 | 5.37 | 4.32 |
| 3895795 | 7.42 | 8.19 | 9.09 | 8.03 | 8.52 | 9.91 | 8.88 | 8.26 | 8.09 | 7.38 | 9.58 | 8.58 |
| 2854445 | 8.24 | 10.98 | 8.97 | 7.57 | 8.63 | 8.29 | 9.50 | 8.19 | 7.16 | 10.84 | 8.28 | 9.35 |
| 3606034 | 7.91 | 7.88 | 7.13 | 7.06 | 7.23 | 6.91 | 7.39 | 7.76 | 7.47 | 7.46 | 7.20 | 7.41 |
| 3375735 | 7.53 | 7.97 | 8.17 | 8.03 | 7.57 | 8.68 | 7.81 | 7.89 | 7.42 | 8.10 | 7.95 | 8.44 |
| 3948047 | 7.13 | 8.23 | 9.33 | 6.74 | 8.20 | 9.82 | 8.61 | 6.69 | 7.45 | 8.98 | 9.01 | 9.06 |
| 3010503 | 8.56 | 10.45 | 10.06 | 6.04 | 8.73 | 10.35 | 9.51 | 6.21 | 7.84 | 7.54 | 9.54 | 10.11 |
| 3622934 | 7.95 | 8.30 | 6.59 | 7.98 | 8.04 | 6.08 | 5.85 | 8.44 | 8.66 | 7.52 | 6.78 | 7.40 |
| 3441849 | 9.08 | 10.16 | 10.44 | 9.78 | 9.69 | 10.97 | 10.10 | 9.74 | 9.81 | 9.82 | 10.63 | 10.07 |
| 3006572 | 6.44 | 6.74 | 6.58 | 7.50 | 6.78 | 6.81 | 6.55 | 6.60 | 6.11 | 6.78 | 6.54 | 6.65 |
| 3365136 | 10.00 | 10.35 | 8.31 | 10.32 | 10.25 | 8.39 | 8.48 | 9.39 | 9.56 | 8.99 | 9.21 | 8.76 |
| 2642791 | 8.58 | 8.56 | 8.51 | 7.96 | 8.11 | 8.88 | 8.35 | 8.64 | 8.28 | 8.36 | 8.64 | 8.41 |
| 2904485 | 9.44 | 7.15 | 8.24 | 7.38 | 7.48 | 7.41 | 8.44 | 6.76 | 7.38 | 6.92 | 8.48 | 7.96 |
| 3772661 | 9.23 | 10.74 | 10.26 | 10.16 | 9.48 | 10.60 | 9.77 | 9.41 | 9.27 | 11.07 | 10.01 | 10.14 |
| 2796553 | 8.80 | 9.78 | 10.33 | 7.81 | 9.82 | 11.28 | 9.75 | 8.55 | 8.25 | 9.29 | 10.73 | 10.29 |
| 3063795 | 7.19 | 7.52 | 7.68 | 6.68 | 7.84 | 7.73 | 8.34 | 6.50 | 7.31 | 8.39 | 7.07 | 7.33 |
| 3338192 | 9.92 | 10.49 | 8.29 | 11.46 | 9.43 | 7.48 | 8.20 | 10.80 | 10.20 | 9.52 | 8.08 | 8.48 |
| 3214845 | 4.64 | 4.20 | 4.39 | 4.67 | 4.23 | 4.80 | 4.81 | 4.52 | 4.05 | 4.14 | 4.26 | 4.59 |
| 2730303 | 4.39 | 3.99 | 4.22 | 4.12 | 4.22 | 4.56 | 4.32 | 4.14 | 4.09 | 8.55 | 4.25 | 4.16 |
| 3811086 | 8.13 | 8.06 | 7.40 | 7.40 | 7.34 | 7.75 | 8.22 | 8.24 | 7.71 | 7.56 | 7.62 | 7.74 |
| 2981874 | 10.11 | 10.29 | 10.39 | 10.50 | 10.00 | 10.49 | 10.14 | 10.37 | 10.32 | 10.30 | 10.60 | 10.13 |
| 3242353 | 6.63 | 6.21 | 5.67 | 6.10 | 5.81 | 6.14 | 5.88 | 6.06 | 6.04 | 6.53 | 5.79 | 5.60 |
| 2442008 | 5.57 | 8.21 | 5.60 | 8.44 | 7.69 | 6.05 | 5.58 | 8.11 | 9.41 | 7.46 | 5.44 | 5.28 |
| 3564210 | 7.94 | 9.54 | 10.37 | 8.34 | 9.33 | 10.97 | 9.68 | 7.94 | 7.74 | 9.06 | 10.56 | 9.91 |
| 2490351 | 4.06 | 3.84 | 4.30 | 3.91 | 4.15 | 4.49 | 3.95 | 3.87 | 4.07 | 4.00 | 4.42 | 4.30 |
| 3759006 | 7.33 | 6.65 | 9.17 | 6.63 | 9.49 | 10.84 | 10.26 | 6.55 | 8.74 | 6.78 | 10.34 | 11.52 |
| 3264997 | 4.18 | 3.80 | 4.26 | 4.19 | 4.15 | 4.60 | 4.19 | 3.77 | 4.16 | 4.25 | 4.21 | 4.15 |
| 3912079 | 4.41 | 3.60 | 4.27 | 3.52 | 4.12 | 4.52 | 3.55 | 4.07 | 3.93 | 3.57 | 3.88 | 3.94 |
| 2926802 | 4.57 | 4.65 | 5.79 | 4.73 | 4.95 | 6.20 | 5.80 | 4.47 | 4.60 | 5.78 | 6.56 | 5.93 |
| 2430163 | 3.96 | 3.95 | 3.93 | 6.22 | 3.84 | 4.18 | 3.74 | 3.63 | 3.91 | 3.94 | 3.97 | 3.76 |
| 3039830 | 3.15 | 3.09 | 3.04 | 3.06 | 3.05 | 3.26 | 2.92 | 3.04 | 3.25 | 3.09 | 3.13 | 3.07 |
| 3935486 | 5.95 | 9.16 | 7.92 | 6.33 | 5.67 | 5.30 | 7.42 | 5.51 | 7.75 | 9.18 | 7.00 | 6.66 |
| 3457336 | 5.46 | 5.13 | 5.57 | 5.37 | 5.39 | 5.83 | 5.42 | 5.02 | 5.34 | 4.98 | 5.33 | 5.33 |
| 3811949 | 3.55 | 3.35 | 3.40 | 3.33 | 3.51 | 3.82 | 3.34 | 3.34 | 3.49 | 3.46 | 3.48 | 3.57 |
| 3343832 | 4.00 | 3.59 | 3.82 | 3.84 | 3.88 | 4.28 | 3.97 | 3.63 | 3.82 | 3.85 | 3.95 | 4.02 |
| 3161261 | 5.68 | 5.11 | 5.99 | 5.53 | 5.55 | 6.77 | 7.24 | 5.37 | 5.56 | 5.73 | 6.30 | 5.91 |
| 3594003 | 3.75 | 3.56 | 3.89 | 3.43 | 3.79 | 3.85 | 3.58 | 3.57 | 4.16 | 3.87 | 4.03 | 4.11 |
| 3805614 | 4.82 | 4.36 | 4.92 | 4.52 | 5.01 | 5.48 | 4.74 | 4.53 | 4.93 | 4.24 | 5.07 | 4.73 |
| 3364127 | 7.25 | 6.33 | 9.23 | 6.44 | 6.95 | 7.05 | 6.99 | 6.45 | 6.54 | 6.53 | 6.96 | 6.98 |
| 3834341 | 4.06 | 3.73 | 4.42 | 4.07 | 4.12 | 4.50 | 4.15 | 3.83 | 4.09 | 4.10 | 4.31 | 4.05 |
| 2585400 | 4.20 | 4.37 | 4.77 | 4.08 | 4.24 | 5.28 | 4.69 | 4.26 | 4.14 | 4.44 | 4.41 | 4.44 |
| 2941690 | 4.40 | 4.10 | 4.84 | 4.08 | 4.74 | 4.84 | 3.82 | 4.16 | 4.22 | 4.06 | 4.61 | 4.69 |
| 3484895 | 5.44 | 6.04 | 4.74 | 6.64 | 5.00 | 5.56 | 4.70 | 5.45 | 6.43 | 5.23 | 4.85 | 5.13 |
| 3159754 | 3.96 | 3.60 | 4.04 | 3.56 | 3.81 | 4.36 | 3.69 | 3.61 | 3.82 | 3.76 | 3.74 | 3.56 |
| 2894790 | 3.85 | 3.52 | 3.86 | 3.67 | 3.78 | 3.96 | 3.62 | 3.62 | 3.72 | 3.66 | 4.03 | 3.92 |
| 3363686 | 3.44 | 3.40 | 3.70 | 3.41 | 3.60 | 3.97 | 3.46 | 3.28 | 3.83 | 3.61 | 3.77 | 3.53 |
| 2923928 | 4.37 | 4.00 | 4.73 | 4.16 | 4.69 | 5.03 | 4.28 | 3.83 | 3.80 | 4.07 | 4.79 | 4.67 |
| 2883317 | 5.02 | 4.74 | 5.15 | 4.17 | 4.53 | 4.95 | 5.95 | 4.35 | 4.26 | 5.24 | 4.48 | 5.58 |
| 2479698 | 6.32 | 6.01 | 6.02 | 5.82 | 6.19 | 6.02 | 6.06 | 6.00 | 5.97 | 5.89 | 6.41 | 6.06 |
| 3428225 | 4.29 | 3.61 | 3.84 | 3.73 | 3.74 | 4.04 | 3.72 | 3.72 | 3.75 | 3.62 | 3.96 | 3.87 |

TABLE 31-continued

Normalized intensity of microarray data for a set of samples.

| TCID | V01 0073 | V01 0074 | V01 0075 | V01 0076 | V01 0077 | V01 0078 | V01 0079 | V01 0080 | V01 0081 | V01 0082 | V01 0083 | V01 0084 |
|---|---|---|---|---|---|---|---|---|---|---|---|---|
| 3393446 | 7.55 | 6.86 | 7.58 | 6.85 | 7.39 | 7.61 | 6.65 | 6.77 | 7.31 | 8.29 | 7.39 | 7.27 |
| 3116614 | 13.02 | 12.13 | 12.39 | 12.28 | 12.63 | 7.62 | 12.76 | 12.15 | 12.61 | 10.17 | 12.58 | 11.74 |
| 3415320 | 10.27 | 9.53 | 8.62 | 10.91 | 9.74 | 6.78 | 10.64 | 11.12 | 10.82 | 9.60 | 9.31 | 7.25 |
| 3757108 | 8.39 | 10.27 | 7.55 | 11.34 | 8.24 | 7.99 | 7.70 | 10.91 | 10.10 | 9.74 | 7.61 | 7.75 |
| 4012178 | 7.16 | 9.00 | 6.88 | 9.28 | 11.18 | 6.77 | 6.10 | 10.96 | 11.98 | 8.55 | 6.67 | 6.35 |
| 3546213 | 11.36 | 11.10 | 9.69 | 11.32 | 11.06 | 5.46 | 10.71 | 10.95 | 11.59 | 10.27 | 9.95 | 9.51 |
| 3561381 | 10.74 | 9.81 | 9.04 | 10.18 | 10.65 | 5.82 | 8.96 | 10.08 | 10.61 | 9.31 | 9.02 | 8.71 |

TABLE 32

Normalized intensity of microarray data for a set of samples.

| TCID | V01 0085 | V01 0086 | V01 0087 | V01 0088 | V01 0089 | V01 0090 | V01 0091 | V01 0092 | V01 0093 | V01 0094 | V01 0095 | V01 0096 |
|---|---|---|---|---|---|---|---|---|---|---|---|---|
| 2604998 | 6.60 | 8.22 | 8.33 | 9.13 | 7.67 | 7.68 | 7.66 | 9.25 | 9.42 | 9.20 | 7.36 | 6.57 |
| 3603932 | 8.28 | 6.63 | 6.85 | 6.80 | 7.50 | 6.67 | 6.67 | 7.18 | 6.95 | 7.00 | 7.20 | 8.21 |
| 2710599 | 10.26 | 9.29 | 11.29 | 10.59 | 9.87 | 6.54 | 8.32 | 11.17 | 10.87 | 12.04 | 8.18 | 8.42 |
| 2440258 | 8.13 | 8.05 | 8.51 | 6.37 | 8.27 | 8.57 | 7.49 | 7.03 | 5.09 | 5.99 | 8.43 | 8.23 |
| 3169331 | 7.53 | 6.55 | 7.27 | 6.68 | 9.85 | 7.03 | 7.28 | 6.72 | 6.53 | 5.98 | 6.41 | 7.43 |
| 2988882 | 10.36 | 9.64 | 9.95 | 9.24 | 9.89 | 9.77 | 10.16 | 10.00 | 9.61 | 9.10 | 9.89 | 10.08 |
| 2964231 | 10.26 | 7.97 | 8.89 | 8.26 | 10.35 | 8.16 | 9.02 | 9.65 | 7.33 | 8.81 | 8.67 | 10.00 |
| 3111561 | 5.44 | 9.72 | 6.21 | 5.61 | 9.20 | 8.37 | 8.07 | 10.49 | 4.71 | 5.18 | 6.13 | 7.57 |
| 2562529 | 9.63 | 9.75 | 10.21 | 10.84 | 9.73 | 8.65 | 8.34 | 10.79 | 10.86 | 10.76 | 8.92 | 8.73 |
| 3692999 | 8.88 | 12.61 | 10.15 | 9.48 | 12.50 | 10.86 | 11.09 | 9.32 | 5.69 | 6.39 | 10.04 | 11.51 |
| 2439554 | 7.78 | 6.09 | 7.83 | 5.66 | 8.38 | 7.10 | 7.06 | 5.45 | 5.42 | 5.91 | 7.66 | 6.72 |
| 2685304 | 9.74 | 7.55 | 10.99 | 8.61 | 7.19 | 8.19 | 6.95 | 8.89 | 11.56 | 11.42 | 8.20 | 8.70 |
| 2578790 | 4.65 | 6.14 | 5.08 | 4.47 | 7.39 | 6.08 | 7.12 | 6.08 | 4.18 | 3.99 | 4.89 | 6.43 |
| 2373842 | 10.83 | 11.63 | 10.83 | 11.03 | 10.98 | 11.90 | 11.43 | 10.30 | 9.51 | 9.63 | 11.88 | 11.39 |
| 2750627 | 7.98 | 7.97 | 9.79 | 9.92 | 6.26 | 8.15 | 6.73 | 10.64 | 11.26 | 10.73 | 8.62 | 7.44 |
| 3397774 | 4.86 | 4.58 | 4.94 | 5.15 | 6.50 | 5.01 | 6.62 | 5.33 | 4.60 | 4.47 | 5.05 | 5.28 |
| 2635741 | 7.58 | 8.96 | 8.19 | 7.30 | 8.78 | 8.75 | 7.97 | 7.77 | 6.01 | 6.98 | 8.91 | 8.31 |
| 3970833 | 9.59 | 9.27 | 9.56 | 9.66 | 10.07 | 9.38 | 9.96 | 9.93 | 9.97 | 9.59 | 9.19 | 9.68 |
| 3577612 | 10.95 | 11.45 | 11.79 | 10.60 | 10.34 | 11.04 | 10.81 | 10.20 | 11.27 | 11.57 | 11.35 | 10.71 |
| 2708922 | 7.49 | 8.76 | 8.37 | 8.80 | 6.61 | 8.24 | 8.12 | 7.78 | 9.08 | 7.80 | 9.29 | 7.51 |
| 2970897 | 6.48 | 5.08 | 4.70 | 4.62 | 7.07 | 5.42 | 5.46 | 4.77 | 4.47 | 5.45 | 4.95 | 5.45 |
| 3724545 | 8.77 | 8.20 | 9.61 | 10.39 | 9.07 | 10.49 | 9.37 | 9.83 | 10.36 | 10.66 | 10.15 | 9.44 |
| 2798538 | 9.75 | 9.25 | 8.27 | 8.38 | 9.97 | 9.15 | 8.87 | 8.89 | 8.36 | 8.47 | 9.02 | 9.59 |
| 2806468 | 10.05 | 10.85 | 9.67 | 10.14 | 10.21 | 11.52 | 10.78 | TEIN | 8.29 | 9.00 | 11.35 | 11.03 |
| 2880051 | 6.30 | 6.95 | 6.13 | 5.86 | 6.13 | 6.68 | 6.80 | 6.36 | 5.83 | 5.90 | 6.54 | 6.34 |
| 2732508 | 6.23 | 3.68 | 8.24 | 3.38 | 7.66 | 3.88 | 4.14 | 3.34 | 3.42 | 4.23 | 3.79 | 3.76 |
| 2822492 | 5.46 | 5.52 | 5.30 | 5.15 | 5.98 | 5.22 | 5.32 | 5.31 | 4.95 | 4.93 | 5.42 | 5.48 |
| 3404030 | 7.32 | 9.14 | 7.66 | 7.12 | 8.08 | 8.63 | 7.58 | 7.75 | 5.96 | 5.72 | 8.55 | 8.85 |
| 3059667 | 4.62 | 4.52 | 6.10 | 9.29 | 8.69 | 10.22 | 7.30 | 11.37 | 4.55 | 5.26 | 6.86 | 5.39 |
| 3108526 | 6.40 | 8.03 | 7.79 | 9.19 | 11.07 | 9.96 | 9.51 | 10.18 | 7.86 | 7.79 | 7.20 | 9.04 |
| 2526806 | 12.58 | 10.25 | 12.87 | 10.08 | 11.31 | 10.45 | 9.74 | 9.86 | 12.31 | 13.08 | 7.50 | 11.85 |
| 2428501 | 8.26 | 6.64 | 6.81 | 6.55 | 7.34 | 7.26 | 6.76 | 6.76 | 5.99 | 6.16 | 6.74 | 7.79 |
| 2657808 | 9.83 | 8.50 | 10.76 | 7.61 | 7.96 | 5.60 | 6.38 | 9.39 | 8.46 | 11.58 | 5.57 | 5.60 |
| 2584018 | 10.73 | 7.71 | 9.81 | 7.25 | 8.82 | 7.69 | 6.24 | 8.28 | 10.09 | 10.92 | 8.02 | 10.78 |
| 3976341 | 10.48 | 9.94 | 11.73 | 10.25 | 8.99 | 9.55 | 8.68 | 10.38 | 12.18 | 12.09 | 10.46 | 10.78 |
| 2739308 | 4.49 | 5.17 | 4.47 | 5.04 | 5.31 | 5.87 | 5.44 | 4.81 | 4.49 | 4.20 | 5.93 | 4.94 |
| 3959862 | 5.73 | 5.24 | 5.07 | 4.96 | 4.65 | 5.73 | 4.60 | 4.55 | 4.39 | 5.19 | 6.19 | 6.75 |
| 2362351 | 7.57 | 8.42 | 7.65 | 6.74 | 7.40 | 7.93 | 7.32 | 6.92 | 5.87 | 5.74 | 8.04 | 7.52 |
| 3648391 | 5.72 | 6.18 | 7.90 | 4.49 | 8.15 | 5.24 | 5.32 | 4.46 | 4.30 | 3.79 | 6.15 | 5.37 |
| 3009299 | 10.88 | 10.80 | 10.73 | 10.54 | 10.99 | 10.63 | 10.70 | 10.91 | 10.23 | 10.46 | 10.67 | 10.81 |
| 3443464 | 5.70 | 6.86 | 5.79 | 5.25 | 5.55 | 6.07 | 6.16 | 5.65 | 5.07 | 5.02 | 6.10 | 6.13 |
| 2730746 | 5.03 | 7.71 | 5.92 | 7.60 | 8.51 | 7.74 | 7.59 | 8.88 | 4.64 | 4.85 | 6.10 | 6.55 |
| 2427619 | 7.54 | 8.81 | 8.07 | 7.66 | 9.25 | 9.32 | 8.14 | 7.38 | 5.73 | 6.65 | 9.34 | 8.65 |
| 3042001 | 8.95 | 8.92 | 8.41 | 8.18 | 9.09 | 8.86 | 9.08 | 8.34 | 8.13 | 8.95 | 8.33 | 8.36 |
| 2566848 | 5.30 | 5.62 | 5.22 | 5.37 | 6.16 | 6.02 | 5.79 | 4.94 | 4.96 | 4.94 | 5.83 | 5.48 |
| 2984616 | 9.79 | 9.07 | 8.80 | 8.85 | 9.57 | 8.52 | 8.60 | 9.08 | 8.95 | 8.81 | 8.96 | 9.54 |
| 2378068 | 9.44 | 7.01 | 8.58 | 7.28 | 7.37 | 7.38 | 7.62 | 7.33 | 7.62 | 9.60 | 7.79 | 9.07 |
| 2721959 | 11.12 | 6.41 | 12.33 | 9.02 | 11.44 | 5.61 | 8.56 | 8.78 | 11.77 | 12.68 | 6.57 | 9.07 |
| 2877508 | 10.63 | 10.19 | 10.24 | 10.10 | 11.23 | 10.52 | 10.47 | 10.56 | 10.07 | 10.15 | 9.73 | 10.60 |
| 3450861 | 5.67 | 6.18 | 5.55 | 5.29 | 6.50 | 6.88 | 5.90 | 5.62 | 4.76 | 4.72 | 6.91 | 6.43 |
| 2688717 | 8.46 | 8.67 | 8.11 | 8.21 | 9.20 | 9.88 | 8.94 | 7.26 | 6.20 | 7.19 | 9.59 | 8.63 |
| 3270270 | 8.80 | 9.14 | 8.72 | 8.24 | 7.49 | 9.04 | 8.69 | 7.66 | 8.80 | 8.96 | 9.84 | 9.31 |
| 3417703 | 5.69 | 9.76 | 7.21 | 7.00 | 7.10 | 4.71 | 4.95 | 8.51 | 7.70 | 8.96 | 5.86 | 5.06 |
| 3302990 | 7.77 | 7.40 | 7.78 | 6.98 | 8.96 | 7.35 | 8.18 | 7.54 | 7.69 | 7.51 | 6.58 | 8.03 |
| 2377283 | 4.91 | 4.75 | 6.38 | 4.32 | 5.99 | 5.64 | 5.03 | 4.26 | 4.10 | 3.96 | 5.51 | 4.89 |
| 3122678 | 6.39 | 5.46 | 4.98 | 4.25 | 4.96 | 5.38 | 4.92 | 4.90 | 4.53 | 5.79 | 4.68 | 4.34 |
| 2688499 | 7.86 | 9.55 | 9.98 | 9.94 | 10.04 | 9.45 | 8.79 | 10.12 | 10.34 | 10.01 | 7.90 | 7.91 |

TABLE 32-continued

Normalized intensity of microarray data for a set of samples.

| TCID | V01 0085 | V01 0086 | V01 0087 | V01 0088 | V01 0089 | V01 0090 | V01 0091 | V01 0092 | V01 0093 | V01 0094 | V01 0095 | V01 0096 |
|---|---|---|---|---|---|---|---|---|---|---|---|---|
| 2377094 | 8.31 | 8.56 | 8.90 | 8.67 | 10.34 | 8.90 | 9.84 | 9.62 | 7.74 | 7.65 | 8.10 | 9.38 |
| 3278198 | 8.94 | 7.45 | 8.29 | 7.92 | 9.18 | 7.50 | 8.56 | 8.82 | 8.20 | 7.82 | 6.80 | 8.34 |
| 2598261 | 12.37 | 9.82 | 13.07 | 9.34 | 10.59 | 9.83 | 9.08 | 8.43 | 11.97 | 13.02 | 6.93 | 11.45 |
| 3982612 | 8.56 | 8.91 | 8.79 | 6.85 | 9.33 | 9.70 | 8.96 | 8.12 | 6.03 | 6.36 | 9.58 | 8.60 |
| 2884845 | 6.47 | 6.65 | 9.67 | 5.30 | 4.56 | 4.55 | 4.87 | 4.57 | 10.74 | 11.02 | 4.56 | 5.56 |
| 3982560 | 6.38 | 7.86 | 6.51 | 6.12 | 7.31 | 7.70 | 6.79 | 5.75 | 4.55 | 5.14 | 8.35 | 6.83 |
| 3204285 | 6.36 | 6.28 | 8.34 | 5.86 | 6.30 | 5.69 | 6.64 | 5.22 | 5.55 | 5.78 | 6.01 | 6.35 |
| 3654699 | 12.84 | 8.42 | 11.47 | 9.95 | 13.00 | 10.43 | 12.76 | 11.97 | 9.81 | 9.69 | 9.37 | 12.69 |
| 2638676 | 8.08 | 6.45 | 8.83 | 6.47 | 8.71 | 7.20 | 7.55 | 6.65 | 5.24 | 6.10 | 7.65 | 7.75 |
| 3367673 | 5.27 | 5.13 | 6.63 | 7.56 | 8.47 | 6.81 | 8.19 | 8.80 | 4.46 | 4.05 | 7.14 | 7.72 |
| 3212008 | 6.46 | 6.40 | 7.49 | 9.51 | 6.28 | 6.08 | 6.67 | 9.52 | 9.58 | 8.11 | 7.90 | 6.18 |
| 3326635 | 10.07 | 10.79 | 10.21 | 10.39 | 9.53 | 10.19 | 9.66 | 10.72 | 10.16 | 10.35 | 10.41 | 10.10 |
| 3031556 | 9.48 | 9.67 | 9.25 | 8.48 | 8.81 | 10.03 | 8.55 | 7.98 | 6.76 | 7.72 | 9.95 | 9.49 |
| 3662201 | 9.69 | 12.80 | 10.16 | 10.54 | 12.68 | 10.43 | 10.81 | 9.45 | 6.31 | 7.56 | 10.43 | 11.40 |
| 2809793 | 8.94 | 9.40 | 9.64 | 6.68 | 8.89 | 9.25 | 7.57 | 7.73 | 5.92 | 6.36 | 8.95 | 9.42 |
| 2817731 | 9.30 | 7.70 | 7.59 | 7.80 | 7.73 | 8.07 | 7.80 | 7.70 | 7.46 | 7.71 | 8.16 | 9.10 |
| 4020655 | 5.06 | 5.42 | 6.41 | 9.35 | 4.45 | 5.00 | 5.82 | 6.97 | 8.81 | 7.22 | 6.52 | 4.83 |
| 3494629 | 6.76 | 4.55 | 7.50 | 7.51 | 4.73 | 4.33 | 4.48 | 6.01 | 7.72 | 8.48 | 4.77 | 4.60 |
| 3852832 | 6.70 | 9.48 | 6.81 | 8.63 | 7.23 | 9.64 | 9.50 | 7.25 | 7.50 | 6.05 | 10.56 | 9.36 |
| 3761959 | 9.53 | 8.64 | 9.46 | 9.14 | 9.74 | 8.56 | 8.84 | 9.35 | 9.12 | 9.48 | 8.91 | 9.23 |
| 2834282 | 6.22 | 7.46 | 7.08 | 7.75 | 7.29 | 6.82 | 6.71 | 7.87 | 7.65 | 7.46 | 6.35 | 6.63 |
| 3341497 | 6.16 | 6.50 | 6.17 | 7.47 | 6.23 | 6.08 | 6.53 | 8.85 | 6.99 | 7.51 | 6.64 | 6.17 |
| 2372812 | 4.89 | 5.11 | 5.86 | 4.68 | 4.33 | 4.76 | 4.97 | 4.32 | 4.73 | 4.54 | 4.82 | 4.78 |
| 2486811 | 10.56 | 9.73 | 9.56 | 8.41 | 9.19 | 10.28 | 9.18 | 8.26 | 7.51 | 8.52 | 10.55 | 10.53 |
| 3768474 | 9.10 | 7.75 | 8.09 | 7.96 | 8.18 | 8.35 | 8.23 | 7.70 | 7.55 | 7.47 | 8.80 | 9.05 |
| 3142381 | 7.23 | 5.20 | 4.18 | 5.06 | 4.66 | 6.37 | 4.22 | 6.73 | 3.77 | 4.13 | 4.22 | 4.91 |
| 2396750 | 7.11 | 7.30 | 7.96 | 7.37 | 7.31 | 7.00 | 7.17 | 7.58 | 8.20 | 8.02 | 7.28 | 6.82 |
| 3902489 | 10.71 | 11.17 | 9.93 | 10.65 | 10.05 | 11.12 | 11.27 | 10.02 | 9.71 | 10.42 | 11.77 | 10.45 |
| 3032647 | 5.83 | 6.20 | 6.26 | 5.99 | 6.63 | 8.41 | 6.67 | 8.21 | 5.60 | 5.37 | 6.01 | 6.47 |
| 3875642 | 5.10 | 6.67 | 4.99 | 5.55 | 4.96 | 6.59 | 5.55 | 5.14 | 5.08 | 4.83 | 6.29 | 5.71 |
| 4027585 | 11.21 | 10.54 | 9.25 | 10.43 | 9.37 | 11.14 | 11.16 | 9.59 | 9.34 | 8.95 | 11.83 | 11.28 |
| 2352609 | 5.85 | 6.58 | 6.33 | 7.96 | 6.66 | 6.33 | 7.46 | 8.30 | 6.89 | 6.33 | 6.21 | 6.29 |
| 3376529 | 8.39 | 8.38 | 9.30 | 9.24 | 9.67 | 8.16 | 9.04 | 9.56 | 9.95 | 9.74 | 7.98 | 8.58 |
| 2491271 | 13.58 | 13.54 | 13.42 | 12.92 | 13.08 | 13.33 | 13.06 | 12.87 | 13.12 | 13.47 | 13.27 | 13.36 |
| 3874751 | 10.09 | 8.82 | 9.52 | 9.00 | 9.31 | 8.85 | 8.55 | 9.34 | 10.06 | 9.71 | 8.61 | 9.65 |
| 2326463 | 12.55 | 12.06 | 11.68 | 11.00 | 11.35 | 12.20 | 11.50 | 11.38 | 9.59 | 10.56 | 12.34 | 12.77 |
| 3341061 | 9.02 | 6.82 | 7.10 | 7.12 | 7.08 | 7.41 | 6.53 | 7.68 | 7.21 | 7.66 | 7.61 | 8.64 |
| 3839910 | 7.65 | 8.14 | 6.90 | 8.90 | 7.45 | 9.72 | 9.02 | 6.87 | 7.31 | 6.47 | 10.32 | 8.60 |
| 2708855 | 6.89 | 4.50 | 8.07 | 6.55 | 4.33 | 4.26 | 4.21 | 6.17 | 8.07 | 9.30 | 5.46 | 4.48 |
| 3512874 | 11.70 | 12.10 | 11.34 | 11.45 | 11.46 | 12.29 | 11.90 | 10.78 | 10.17 | 10.52 | 12.42 | 12.06 |
| 2701071 | 9.68 | 10.33 | 8.92 | 10.14 | 8.94 | 10.84 | 10.63 | 8.47 | 8.33 | 8.09 | 11.48 | 10.23 |
| 3486096 | 6.27 | 8.21 | 7.28 | 8.10 | 8.78 | 5.77 | 7.35 | 8.63 | 5.61 | 6.91 | 6.01 | 6.70 |
| 2412668 | 9.22 | 8.23 | 8.36 | 7.51 | 8.11 | 8.29 | 7.86 | 8.10 | 7.95 | 7.89 | 8.59 | 8.85 |
| 3329343 | 8.51 | 8.35 | 9.75 | 7.78 | 8.01 | 6.76 | 7.46 | 8.36 | 9.16 | 9.44 | 7.37 | 7.15 |
| 3259367 | 4.18 | 4.07 | 4.53 | 6.42 | 4.20 | 4.26 | 4.18 | 5.78 | 6.45 | 5.09 | 5.23 | 4.28 |
| 3373845 | 10.61 | 10.18 | 9.97 | 7.33 | 7.98 | 8.52 | 8.75 | 8.24 | 8.81 | 10.59 | 8.86 | 10.48 |
| 2321911 | 8.90 | 8.38 | 8.10 | 8.35 | 8.23 | 9.29 | 9.01 | 8.35 | 8.12 | 7.94 | 9.14 | 8.94 |
| 3353914 | 9.19 | 6.36 | 7.18 | 6.78 | 7.09 | 6.55 | 6.53 | 6.93 | 7.22 | 7.42 | 6.69 | 9.00 |
| 3744680 | 8.65 | 8.09 | 7.17 | 7.23 | 7.00 | 7.72 | 7.64 | 6.98 | 6.72 | 6.66 | 8.39 | 8.20 |
| 2373336 | 9.19 | 6.97 | 9.85 | 6.02 | 7.66 | 6.78 | 5.50 | 7.16 | 7.88 | 10.43 | 5.73 | 7.60 |
| 3067478 | 5.85 | 6.97 | 8.36 | 7.94 | 7.70 | 6.45 | 6.39 | 7.51 | 9.20 | 8.75 | 6.02 | 5.85 |
| 3976766 | 8.11 | 9.01 | 7.70 | 7.76 | 7.44 | 8.49 | 8.50 | 7.05 | 6.77 | 6.64 | 9.53 | 8.82 |
| 3246888 | 5.15 | 5.89 | 5.76 | 6.95 | 5.23 | 6.05 | 6.55 | 7.81 | 4.71 | 5.27 | 6.04 | 5.37 |
| 3147985 | 8.40 | 6.19 | 6.78 | 6.05 | 6.36 | 6.30 | 5.94 | 6.92 | 7.66 | 7.68 | 6.70 | 7.99 |
| 3185522 | 11.34 | 9.08 | 10.18 | 8.84 | 9.27 | 9.32 | 8.81 | 9.75 | 8.90 | 9.29 | 9.09 | 10.55 |
| 3861948 | 12.71 | 12.90 | 12.26 | 12.36 | 11.74 | 12.98 | 12.83 | 11.37 | 11.03 | 11.08 | 13.10 | 12.76 |
| 3393479 | 10.52 | 8.66 | 8.88 | 7.80 | 10.05 | 8.54 | 7.88 | 8.70 | 8.55 | 8.73 | 8.67 | 9.90 |
| 3540862 | 6.70 | 6.37 | 6.86 | 7.26 | 7.40 | 6.94 | 7.36 | 7.55 | 7.34 | 7.48 | 6.33 | 6.86 |
| 2777714 | 10.44 | 11.34 | 9.54 | 10.88 | 10.17 | 11.86 | 11.53 | 10.22 | 9.45 | 9.87 | 12.09 | 10.58 |
| 3110395 | 5.22 | 4.82 | 6.05 | 5.62 | 4.54 | 4.64 | 5.02 | 5.05 | 7.13 | 4.90 | 4.23 | 4.43 |
| 3895795 | 7.15 | 8.81 | 7.75 | 8.41 | 7.39 | 8.74 | 9.11 | 7.92 | 8.12 | 8.30 | 9.63 | 8.48 |
| 2854445 | 11.64 | 8.59 | 9.66 | 8.11 | 7.95 | 8.69 | 8.07 | 9.03 | 7.18 | 8.80 | 8.41 | 11.34 |
| 3606034 | 9.24 | 8.02 | 6.82 | 7.38 | 7.36 | 7.94 | 6.77 | 7.97 | 7.31 | 7.07 | 7.11 | 7.78 |
| 3375735 | 8.73 | 8.37 | 7.58 | 7.50 | 7.54 | 7.89 | 7.45 | 7.56 | 8.21 | 7.93 | 8.40 | 8.21 |
| 3948047 | 9.18 | 9.05 | 8.36 | 8.03 | 7.71 | 8.72 | 8.34 | 7.45 | 7.23 | 7.27 | 9.39 | 9.08 |
| 3010503 | 10.56 | 8.80 | 7.38 | 8.63 | 7.62 | 9.12 | 8.26 | 8.41 | 6.81 | 7.73 | 10.39 | 10.56 |
| 3622934 | 6.73 | 6.94 | 8.19 | 8.42 | 7.15 | 6.18 | 7.12 | 7.65 | 8.07 | 7.93 | 6.49 | 6.46 |
| 3441849 | 10.08 | 10.05 | 9.69 | 9.34 | 8.97 | 9.97 | 10.11 | 9.26 | 9.79 | 9.75 | 10.56 | 10.15 |
| 3006572 | 6.34 | 7.06 | 6.60 | 6.49 | 6.43 | 6.37 | 6.45 | 6.59 | 6.85 | 7.59 | 6.49 | 6.52 |
| 3365136 | 8.56 | 7.73 | 8.98 | 9.48 | 8.45 | 8.17 | 8.60 | 10.65 | 10.19 | 8.95 | 8.84 | 8.71 |
| 2642791 | 9.04 | 8.28 | 8.18 | 8.06 | 9.00 | 8.76 | 8.26 | 8.35 | 8.17 | 8.16 | 8.57 | 9.04 |
| 2904485 | 7.06 | 8.39 | 7.82 | 8.32 | 7.75 | 8.01 | 7.85 | 8.67 | 7.62 | 7.92 | 7.58 | 7.48 |
| 3772661 | 11.79 | 9.29 | 10.15 | 9.15 | 9.16 | 10.19 | 9.77 | 9.85 | 9.70 | 10.23 | 10.33 | 11.18 |
| 2796553 | 10.49 | 9.85 | 9.01 | 10.10 | 9.34 | 10.42 | 10.72 | 9.17 | 8.65 | 8.79 | 10.89 | 10.18 |
| 3063795 | 8.38 | 7.62 | 8.34 | 7.32 | 7.85 | 7.50 | 7.42 | 6.88 | 7.11 | 7.29 | 7.30 | 7.77 |

TABLE 32-continued

Normalized intensity of microarray data for a set of samples.

| TCID | V01 0085 | V01 0086 | V01 0087 | V01 0088 | V01 0089 | V01 0090 | V01 0091 | V01 0092 | V01 0093 | V01 0094 | V01 0095 | V01 0096 |
|---|---|---|---|---|---|---|---|---|---|---|---|---|
| 3338192 | 9.52 | 9.62 | 10.22 | 9.93 | 9.13 | 8.75 | 8.57 | 10.14 | 10.43 | 10.94 | 8.72 | 8.06 |
| 3214845 | 4.14 | 4.70 | 5.34 | 4.68 | 3.84 | 4.13 | 4.52 | 4.15 | 4.49 | 4.80 | 4.13 | 3.97 |
| 2730303 | 4.54 | 4.35 | 5.80 | 4.10 | 4.47 | 4.08 | 4.67 | 4.09 | 4.17 | 3.81 | 4.26 | 4.21 |
| 3811086 | 8.07 | 7.45 | 7.48 | 7.55 | 7.88 | 7.91 | 7.56 | 7.75 | 7.00 | 7.42 | 7.65 | 8.21 |
| 2981874 | 10.92 | 10.41 | 10.53 | 9.90 | 10.44 | 10.25 | 10.50 | 10.15 | 10.14 | 10.28 | 10.65 | 10.51 |
| 3242353 | 6.75 | 6.09 | 6.10 | 5.81 | 6.13 | 5.49 | 6.28 | 5.68 | 6.30 | 5.77 | 5.89 | 6.36 |
| 2442008 | 5.49 | 5.36 | 7.50 | 7.57 | 5.32 | 5.52 | 5.88 | 5.86 | 9.96 | 8.80 | 6.22 | 5.17 |
| 3564210 | 9.99 | 9.76 | 8.45 | 9.49 | 8.59 | 10.38 | 10.18 | 8.43 | 8.27 | 8.55 | 11.01 | 9.90 |
| 2490351 | 4.10 | 4.24 | 3.95 | 4.03 | 3.86 | 4.05 | 4.21 | 3.94 | 3.91 | 3.83 | 4.43 | 4.26 |
| 3759006 | 8.26 | 9.10 | 7.11 | 8.40 | 7.69 | 9.51 | 10.22 | 7.92 | 7.53 | 7.93 | 11.16 | 8.64 |
| 3264997 | 4.29 | 4.22 | 3.97 | 4.10 | 3.93 | 4.09 | 4.35 | 3.83 | 3.92 | 3.91 | 4.13 | 4.32 |
| 3912079 | 3.66 | 3.94 | 3.64 | 4.10 | 3.62 | 3.78 | 3.88 | 3.77 | 3.85 | 3.58 | 4.07 | 3.76 |
| 2926802 | 5.13 | 5.57 | 5.04 | 5.00 | 5.13 | 5.51 | 5.41 | 4.56 | 4.74 | 4.94 | 6.51 | 6.59 |
| 2430163 | 7.15 | 4.16 | 5.20 | 3.86 | 3.85 | 3.62 | 3.78 | 3.71 | 3.73 | 6.18 | 3.72 | 4.09 |
| 3039830 | 3.14 | 3.49 | 3.07 | 3.30 | 3.09 | 3.08 | 3.46 | 3.22 | 3.05 | 3.01 | 3.10 | 3.07 |
| 3935486 | 9.67 | 10.47 | 7.00 | 6.16 | 5.06 | 7.91 | 6.04 | 5.08 | 6.24 | 6.64 | 6.53 | 8.40 |
| 3457336 | 5.25 | 5.64 | 5.40 | 5.19 | 5.06 | 5.30 | 5.81 | 5.13 | 5.20 | 5.01 | 5.42 | 5.25 |
| 3811949 | 3.59 | 3.60 | 3.36 | 3.42 | 3.32 | 3.58 | 3.50 | 3.33 | 3.39 | 3.35 | 3.43 | 3.62 |
| 3343832 | 3.96 | 3.91 | 3.85 | 3.92 | 3.79 | 3.85 | 3.84 | 3.67 | 3.99 | 3.77 | 3.68 | 3.79 |
| 3161261 | 5.47 | 6.05 | 5.18 | 5.79 | 5.85 | 6.28 | 6.23 | 5.58 | 5.65 | 5.08 | 5.90 | 5.73 |
| 3594003 | 4.21 | 3.70 | 3.54 | 3.53 | 3.62 | 3.80 | 3.77 | 3.49 | 3.60 | 3.40 | 3.78 | 3.74 |
| 3805614 | 5.11 | 4.99 | 4.53 | 4.62 | 4.21 | 4.70 | 4.72 | 4.52 | 4.63 | 4.52 | 4.97 | 4.65 |
| 3364127 | 6.96 | 6.74 | 6.60 | 6.95 | 6.66 | 6.80 | 7.28 | 6.50 | 6.58 | 6.29 | 7.06 | 6.93 |
| 3834341 | 4.07 | 4.06 | 3.92 | 4.32 | 3.69 | 4.13 | 4.05 | 3.99 | 3.98 | 3.63 | 4.10 | 4.20 |
| 2585400 | 4.63 | 4.78 | 4.37 | 4.21 | 4.08 | 4.33 | 4.40 | 4.13 | 4.06 | 4.14 | 4.49 | 4.69 |
| 2941690 | 4.45 | 4.22 | 4.45 | 4.14 | 4.25 | 4.29 | 4.27 | 4.08 | 4.19 | 3.77 | 4.27 | 4.32 |
| 3484895 | 4.89 | 5.16 | 5.85 | 5.18 | 4.49 | 4.80 | 5.03 | 4.76 | 6.49 | 5.81 | 5.33 | 4.72 |
| 3159754 | 3.68 | 3.75 | 3.70 | 3.85 | 3.58 | 3.82 | 4.12 | 3.52 | 3.79 | 3.56 | 3.93 | 3.90 |
| 2894790 | 4.53 | 3.99 | 3.61 | 4.09 | 3.71 | 3.96 | 3.79 | 3.79 | 3.97 | 3.60 | 3.71 | 3.73 |
| 3363686 | 3.60 | 3.61 | 3.37 | 3.52 | 3.54 | 3.48 | 3.33 | 3.15 | 3.24 | 3.27 | 3.83 | 3.57 |
| 2923928 | 3.76 | 4.66 | 3.89 | 4.41 | 4.07 | 4.76 | 4.82 | 3.97 | 4.41 | 4.10 | 4.11 | 4.43 |
| 2883317 | 6.52 | 5.82 | 5.57 | 5.18 | 4.96 | 5.56 | 5.57 | 4.35 | 4.62 | 4.04 | 4.63 | 5.27 |
| 2479698 | 5.82 | 6.02 | 6.17 | 6.23 | 5.93 | 6.07 | 6.27 | 6.26 | 6.09 | 5.83 | 6.09 | 5.94 |
| 3428225 | 3.72 | 3.76 | 3.71 | 3.55 | 3.55 | 3.81 | 3.88 | 3.53 | 3.47 | 3.86 | 3.86 | 3.60 |
| 3393446 | 7.85 | 7.55 | 7.68 | 7.12 | 6.66 | 7.33 | 7.38 | 6.70 | 6.72 | 6.65 | 7.83 | 8.41 |
| 3116614 | 9.60 | 8.39 | 11.97 | 13.21 | 12.86 | 12.57 | 12.69 | 13.35 | 12.63 | 12.28 | 12.43 | 12.06 |
| 3415320 | 9.05 | 10.28 | 10.35 | 9.87 | 10.60 | 10.03 | 10.70 | 10.15 | 10.30 | 10.73 | 8.49 | 9.11 |
| 3757108 | 9.63 | 9.49 | 10.38 | 8.54 | 8.58 | 7.32 | 7.89 | 7.76 | 10.29 | 10.98 | 7.74 | 8.44 |
| 4012178 | 6.45 | 6.46 | 8.91 | 10.55 | 7.05 | 6.80 | 6.88 | 10.14 | 12.21 | 9.36 | 8.91 | 6.23 |
| 3546213 | 8.24 | 10.91 | 11.17 | 11.57 | 10.83 | 10.14 | 10.85 | 11.63 | 11.37 | 11.14 | 10.28 | 8.94 |
| 3561381 | 8.20 | 10.58 | 9.87 | 10.25 | 9.49 | 8.62 | 8.69 | 9.95 | 10.95 | 10.07 | 7.92 | 7.91 |

TABLE 33

Normalized intensity of microarray data for a set of samples.

| TCID | V01 0097 | V01 0098 | V01 0099 | V01 0100 | V01 0101 | V01 0102 | V01 0103 | V01 0104 | V01 0105 | V01 0106 | V01 0107 | V01 0108 |
|---|---|---|---|---|---|---|---|---|---|---|---|---|
| 2604998 | 5.99 | 6.08 | 6.41 | 5.94 | 8.64 | 5.69 | 7.05 | 9.17 | 7.28 | 6.89 | 6.18 | 7.18 |
| 3603932 | 9.37 | 6.46 | 7.17 | 6.72 | 6.75 | 7.02 | 9.35 | 7.54 | 6.50 | 8.91 | 6.36 | 8.73 |
| 2710599 | 6.52 | 7.22 | 6.12 | 6.52 | 6.99 | 7.08 | 6.61 | 9.49 | 8.57 | 7.11 | 7.72 | 7.49 |
| 2440258 | 7.45 | 9.13 | 9.01 | 9.83 | 7.49 | 9.17 | 6.22 | 4.85 | 9.11 | 7.78 | 9.68 | 6.60 |
| 3169331 | 6.87 | 6.58 | 6.45 | 6.73 | 6.79 | 7.13 | 9.30 | 7.71 | 7.04 | 7.28 | 7.15 | 8.69 |
| 2988882 | 10.16 | 9.88 | 9.93 | 9.67 | 9.60 | 10.00 | 10.79 | 9.94 | 9.86 | 10.06 | 9.75 | 10.92 |
| 2964231 | 10.47 | 8.39 | 8.62 | 7.23 | 8.75 | 8.48 | 10.85 | 8.87 | 8.90 | 10.24 | 8.72 | 10.82 |
| 3111561 | 7.59 | 6.78 | 6.80 | 6.78 | 9.77 | 8.64 | 8.99 | 7.96 | 7.61 | 8.51 | 6.77 | 8.96 |
| 2562529 | 9.74 | 8.01 | 8.69 | 9.36 | 9.88 | 8.70 | 8.85 | 10.70 | 9.45 | 9.35 | 8.82 | 8.95 |
| 3692999 | 9.94 | 8.53 | 8.57 | 8.31 | 12.95 | 11.22 | 11.01 | 10.07 | 12.55 | 9.71 | 9.18 | 11.16 |
| 2439554 | 7.43 | 7.62 | 7.44 | 8.75 | 5.77 | 6.64 | 5.35 | 6.23 | 9.47 | 6.60 | 10.30 | 5.28 |
| 2685304 | 9.08 | 7.48 | 8.05 | 7.23 | 7.98 | 8.17 | 9.27 | 9.33 | 8.11 | 8.70 | 7.19 | 7.90 |
| 2578790 | 5.46 | 5.15 | 4.60 | 4.82 | 6.35 | 5.85 | 5.55 | 4.42 | 5.65 | 6.40 | 5.20 | 4.31 |
| 2373842 | 10.41 | 11.93 | 11.79 | 11.83 | 11.20 | 12.01 | 9.92 | 9.65 | 11.79 | 10.93 | 11.58 | 10.82 |
| 2750627 | 6.79 | 8.47 | 7.53 | 6.37 | 10.51 | 7.54 | 9.49 | 10.55 | 8.79 | 7.59 | 5.27 | 6.01 |
| 3397774 | 5.28 | 5.51 | 4.97 | 5.01 | 4.80 | 5.08 | 10.05 | 5.03 | 5.28 | 4.88 | 5.27 | 5.93 |
| 2635741 | 6.30 | 9.43 | 8.94 | 9.82 | 7.96 | 9.14 | 6.75 | 5.86 | 8.72 | 7.65 | 8.65 | 7.35 |
| 3970833 | 9.73 | 8.95 | 9.16 | 9.45 | 9.62 | 9.17 | 11.62 | 9.86 | 9.86 | 9.97 | 9.74 | 10.94 |
| 3577612 | 9.32 | 11.15 | 11.33 | 10.56 | 10.21 | 11.57 | 9.27 | 9.95 | 10.37 | 10.21 | 10.17 | 10.23 |
| 2708922 | 7.77 | 8.93 | 8.34 | 8.39 | 8.51 | 9.12 | 6.26 | 8.61 | 7.37 | 7.40 | 5.81 | 5.81 |
| 2970897 | 7.86 | 4.88 | 5.20 | 4.91 | 4.95 | 5.42 | 8.97 | 5.79 | 5.76 | 5.58 | 5.86 | 8.22 |
| 3724545 | 9.57 | 9.22 | 9.76 | 9.79 | 8.36 | 9.31 | 7.34 | 9.92 | 9.31 | 8.79 | 8.36 | 7.52 |
| 2798538 | 10.05 | 8.93 | 9.35 | 9.77 | 8.70 | 9.44 | 11.42 | 8.57 | 9.27 | 9.60 | 9.18 | 9.81 |

TABLE 33-continued

Normalized intensity of microarray data for a set of samples.

| TCID | V01 0097 | V01 0098 | V01 0099 | V01 0100 | V01 0101 | V01 0102 | V01 0103 | V01 0104 | V01 0105 | V01 0106 | V01 0107 | V01 0108 |
|---|---|---|---|---|---|---|---|---|---|---|---|---|
| 2806468 | 8.66 | 11.98 | 11.81 | 11.67 | 11.20 | 11.75 | 9.12 | 8.48 | 10.75 | 10.41 | 10.14 | 10.21 |
| 2880051 | 6.17 | 6.66 | 7.03 | 6.52 | 6.26 | 6.69 | 6.29 | 6.59 | 6.62 | 5.99 | 6.17 | 7.19 |
| 2732508 | 3.66 | 5.02 | 3.71 | 8.50 | 3.35 | 3.46 | 3.41 | 3.57 | 8.02 | 3.63 | 9.41 | 3.73 |
| 2822492 | 5.31 | 5.34 | 6.07 | 5.30 | 6.42 | 5.85 | 7.07 | 5.87 | 5.53 | 5.31 | 5.14 | 5.69 |
| 3404030 | 8.25 | 8.72 | 9.53 | 9.37 | 8.19 | 8.25 | 6.41 | 6.53 | 9.02 | 7.62 | 6.56 | 6.95 |
| 3059667 | 8.13 | 7.76 | 6.10 | 6.32 | 11.84 | 8.27 | 4.58 | 5.71 | 6.71 | 8.31 | 5.85 | 4.19 |
| 3108526 | 7.93 | 8.17 | 7.96 | 7.68 | 9.27 | 8.91 | 9.77 | 9.90 | 9.62 | 7.56 | 8.96 | 10.47 |
| 2526806 | 11.26 | 9.85 | 6.49 | 7.55 | 9.29 | 11.30 | 13.24 | 9.34 | 10.52 | 10.28 | 10.62 | 12.82 |
| 2428501 | 9.27 | 6.63 | 7.76 | 8.03 | 6.43 | 7.64 | 9.82 | 6.10 | 7.27 | 8.34 | 8.87 | 9.21 |
| 2657808 | 5.47 | 5.80 | 5.86 | 6.68 | 6.40 | 6.43 | 5.01 | 7.85 | 7.73 | 5.75 | 8.16 | 5.30 |
| 2584018 | 11.16 | 8.79 | 7.73 | 8.42 | 6.65 | 8.71 | 6.85 | 7.62 | 7.83 | 11.13 | 7.04 | 7.28 |
| 3976341 | 9.71 | 9.81 | 10.44 | 9.65 | 8.82 | 10.90 | 7.58 | 10.02 | 10.66 | 9.07 | 8.79 |
| 2739308 | 4.80 | 5.05 | 5.95 | 5.86 | 4.87 | 5.23 | 7.52 | 6.35 | 4.93 | 4.58 | 4.72 | 6.86 |
| 3959862 | 5.04 | 7.84 | 5.52 | 6.79 | 5.14 | 6.36 | 11.81 | 4.65 | 5.45 | 5.00 | 5.79 | 5.40 |
| 2362351 | 6.51 | 8.41 | 8.41 | 8.72 | 7.16 | 8.21 | 6.38 | 6.01 | 8.13 | 6.96 | 8.18 | 6.57 |
| 3648391 | 4.20 | 5.70 | 4.71 | 7.92 | 4.94 | 4.55 | 4.39 | 4.33 | 7.27 | 4.07 | 8.63 | 4.22 |
| 3009299 | 11.11 | 10.71 | 10.55 | 10.96 | 10.58 | 10.72 | 12.03 | 10.86 | 10.94 | 10.86 | 11.24 | 11.68 |
| 3443464 | 5.59 | 5.96 | 6.44 | 5.83 | 5.60 | 5.62 | 5.37 | 5.15 | 5.65 | 5.93 | 5.32 | 5.62 |
| 2730746 | 6.23 | 6.28 | 7.22 | 5.98 | 9.03 | 6.23 | 9.26 | 8.93 | 7.32 | 6.07 | 6.11 | 8.13 |
| 2427619 | 6.12 | 9.96 | 9.30 | 9.98 | 7.92 | 9.51 | 6.80 | 5.40 | 9.09 | 7.55 | 8.54 | 7.39 |
| 3042001 | 8.42 | 8.39 | 8.43 | 8.50 | 7.94 | 8.21 | 10.88 | 8.94 | 8.93 | 8.85 | 8.84 | 9.74 |
| 2566848 | 5.19 | 6.61 | 5.99 | 7.35 | 5.24 | 5.96 | 5.73 | 5.05 | 6.55 | 5.17 | 7.64 | 6.76 |
| 2984616 | 9.55 | 9.23 | 9.25 | 8.94 | 9.12 | 8.65 | 11.07 | 9.48 | 9.15 | 9.52 | 9.24 | 10.94 |
| 2378068 | 10.15 | 8.76 | 8.07 | 8.45 | 7.97 | 6.69 | 8.11 | 7.41 | 8.84 | 9.63 | 9.18 | 7.98 |
| 2721959 | 7.34 | 7.45 | 6.20 | 6.23 | 7.12 | 9.12 | 5.89 | 7.36 | 10.82 | 8.29 | 9.43 | 5.94 |
| 2877508 | 10.79 | 10.01 | 9.68 | 10.31 | 9.74 | 10.00 | 11.80 | 10.68 | 10.61 | 10.86 | 10.85 | 11.41 |
| 3450861 | 4.91 | 7.24 | 7.23 | 8.23 | 5.87 | 7.11 | 5.61 | 4.47 | 6.00 | 6.10 | 6.52 | 5.47 |
| 2688717 | 7.54 | 10.52 | 9.66 | 10.87 | 8.26 | 9.80 | 6.91 | 6.66 | 9.84 | 6.40 | 10.24 | 7.87 |
| 3270270 | 9.13 | 9.41 | 9.46 | 8.88 | 7.88 | 9.59 | 7.06 | 7.60 | 8.25 | 8.79 | 8.15 | 7.26 |
| 3417703 | 7.50 | 6.11 | 8.10 | 5.30 | 10.44 | 6.20 | 4.65 | 10.22 | 6.25 | 7.40 | 6.66 | 4.50 |
| 3302990 | 8.06 | 7.39 | 7.06 | 7.10 | 6.99 | 6.71 | 11.04 | 7.77 | 7.93 | 7.75 | 8.04 | 10.31 |
| 2377283 | 5.34 | 5.86 | 5.33 | 10.67 | 4.49 | 5.69 | 4.60 | 4.39 | 10.36 | 4.60 | 11.46 | 4.50 |
| 3122678 | 5.31 | 4.89 | 5.00 | 5.64 | 4.55 | 4.49 | 11.62 | 5.05 | 4.98 | 4.84 | 4.58 | 11.00 |
| 2688499 | 7.95 | 8.12 | 7.69 | 8.52 | 9.68 | 8.65 | 7.56 | 10.35 | 9.54 | 7.87 | 8.78 | 8.11 |
| 2377094 | 8.30 | 8.03 | 8.01 | 7.93 | 9.19 | 8.35 | 11.19 | 8.93 | 9.17 | 8.79 | 8.68 | 10.56 |
| 3278198 | 8.51 | 7.33 | 6.80 | 5.88 | 8.23 | 7.08 | 10.42 | 8.68 | 7.65 | 9.09 | 7.02 | 10.30 |
| 2598261 | 11.04 | 9.27 | 6.34 | 7.23 | 8.62 | 10.77 | 12.98 | 8.77 | 9.58 | 9.72 | 9.84 | 12.57 |
| 3982612 | 6.41 | 10.19 | 9.31 | 11.09 | 8.11 | 9.56 | 6.65 | 5.71 | 9.58 | 6.71 | 10.00 | 8.20 |
| 2884845 | 4.62 | 4.44 | 4.77 | 4.56 | 5.05 | 4.80 | 5.37 | 4.37 | 4.68 | 4.96 | 4.22 | 4.98 |
| 3982560 | 5.90 | 8.25 | 7.31 | 9.42 | 6.12 | 7.58 | 5.12 | 4.96 | 7.73 | 5.58 | 8.11 | 6.02 |
| 3204285 | 5.45 | 9.39 | 6.02 | 10.81 | 5.30 | 5.61 | 5.37 | 5.86 | 7.16 | 5.37 | 8.15 | 5.60 |
| 3654699 | 12.35 | 10.39 | 10.46 | 8.98 | 10.74 | 10.49 | 12.67 | 11.64 | 12.17 | 12.04 | 11.37 | 12.44 |
| 2638676 | 7.36 | 8.81 | 7.16 | 9.74 | 6.68 | 6.93 | 5.93 | 6.99 | 9.14 | 7.56 | 10.52 | 6.27 |
| 3367673 | 6.56 | 6.46 | 7.00 | 6.49 | 9.36 | 6.82 | 6.12 | 8.67 | 7.96 | 7.32 | 5.85 | 8.26 |
| 3212008 | 6.36 | 6.88 | 6.90 | 6.47 | 7.67 | 6.58 | 5.76 | 9.50 | 6.48 | 6.60 | 6.02 | 6.40 |
| 3326635 | 10.05 | 10.38 | 10.19 | 10.38 | 10.43 | 10.31 | 8.65 | 10.63 | 9.76 | 10.30 | 9.70 | 9.32 |
| 3031556 | 8.90 | 10.15 | 10.01 | 10.45 | 8.99 | 10.06 | 7.80 | 6.97 | 9.41 | 8.94 | 9.37 | 9.02 |
| 3662201 | 10.48 | 8.08 | 9.26 | 8.65 | 12.93 | 11.50 | 10.88 | 8.42 | 12.47 | 10.37 | 9.65 | 11.19 |
| 2809793 | 6.33 | 9.97 | 9.72 | 10.69 | 8.92 | 9.47 | 6.53 | 4.66 | 9.22 | 7.07 | 9.56 | 7.35 |
| 2817731 | 9.71 | 7.99 | 7.88 | 7.30 | 7.71 | 8.43 | 7.50 | 7.53 | 7.28 | 9.55 | 7.39 | 8.08 |
| 4020655 | 4.70 | 4.94 | 5.33 | 5.00 | 5.46 | 5.40 | 4.74 | 8.44 | 4.97 | 5.08 | 4.73 | 4.75 |
| 3494629 | 4.36 | 4.27 | 4.49 | 4.30 | 4.94 | 4.83 | 4.64 | 5.73 | 4.47 | 4.41 | 4.33 | 5.09 |
| 3852832 | 7.09 | 10.17 | 10.82 | 9.16 | 8.49 | 10.88 | 7.18 | 6.82 | 8.04 | 7.42 | 7.02 | 7.70 |
| 3761959 | 9.84 | 8.61 | 8.43 | 8.77 | 8.67 | 8.61 | 9.10 | 9.71 | 8.90 | 9.77 | 9.08 | 10.39 |
| 2834282 | 5.74 | 6.05 | 5.97 | 5.77 | 6.66 | 5.91 | 6.66 | 7.58 | 6.28 | 6.58 | 5.68 | 6.63 |
| 3341497 | 6.08 | 6.17 | 8.24 | 6.09 | 6.55 | 6.44 | 6.42 | 8.42 | 6.71 | 5.63 | 6.00 | 9.81 |
| 2372812 | 5.14 | 5.12 | 4.86 | 8.31 | 4.43 | 4.55 | 4.58 | 4.96 | 10.07 | 4.71 | 11.37 | 4.96 |
| 2486811 | 11.32 | 10.36 | 10.11 | 10.26 | 8.68 | 10.76 | 7.50 | 8.14 | 10.18 | 11.01 | 10.47 | 8.85 |
| 3768474 | 9.35 | 8.00 | 8.82 | 7.96 | 7.62 | 8.39 | 8.39 | 8.14 | 7.96 | 9.23 | 7.47 | 9.02 |
| 3142381 | 10.10 | 5.19 | 4.99 | 5.46 | 9.57 | 4.55 | 4.73 | 5.60 | 4.25 | 9.22 | 4.59 | 7.04 |
| 2396750 | 6.50 | 7.86 | 6.89 | 6.82 | 6.82 | 6.59 | 7.46 | 6.93 | 7.04 | 6.77 | 7.01 | 7.31 |
| 3902489 | 10.55 | 11.89 | 11.41 | 11.77 | 11.41 | 11.35 | 10.35 | 10.68 | 10.67 | 10.26 | 9.53 | 10.21 |
| 3032647 | 6.32 | 6.55 | 7.02 | 6.28 | 6.05 | 6.64 | 6.10 | 7.64 | 6.62 | 6.58 | 6.26 | 5.94 |
| 3875642 | 5.23 | 6.85 | 6.50 | 5.73 | 6.72 | 6.92 | 5.94 | 5.10 | 5.29 | 5.27 | 5.14 | 5.52 |
| 4027585 | 11.33 | 11.80 | 11.24 | 11.27 | 10.64 | 11.35 | 9.67 | 10.43 | 10.06 | 11.43 | 9.40 | 10.12 |
| 2352609 | 5.85 | 6.05 | 6.23 | 5.61 | 7.37 | 6.01 | 6.57 | 8.32 | 6.75 | 6.13 | 5.64 | 6.58 |
| 3376529 | 8.07 | 7.90 | 7.82 | 8.06 | 8.21 | 7.97 | 9.28 | 8.75 | 8.47 | 7.51 | 7.92 | 9.76 |
| 2491271 | 13.45 | 13.53 | 13.36 | 13.52 | 13.20 | 13.38 | 12.45 | 12.62 | 13.22 | 13.54 | 13.56 | 13.03 |
| 3874751 | 10.61 | 8.91 | 9.27 | 8.86 | 8.93 | 9.34 | 9.08 | 9.21 | 8.92 | 10.21 | 8.96 | 9.95 |
| 2326463 | 12.94 | 12.43 | 12.33 | 12.77 | 11.29 | 12.14 | 9.20 | 9.40 | 12.09 | 11.89 | 12.06 | 10.97 |
| 3341061 | 9.54 | 7.24 | 7.86 | 6.89 | 6.78 | 7.80 | 7.74 | 7.12 | 6.61 | 9.20 | 7.87 | 7.12 |
| 3839910 | 6.35 | 10.16 | 10.78 | 8.74 | 7.83 | 10.53 | 6.65 | 6.56 | 8.10 | 6.62 | 6.23 | 6.94 |
| 2708855 | 4.53 | 4.66 | 4.61 | 4.00 | 4.25 | 4.61 | 4.90 | 7.10 | 4.95 | 4.07 | 3.92 | 4.50 |
| 3512874 | 11.85 | 12.35 | 12.35 | 12.36 | 11.69 | 12.39 | 10.87 | 10.62 | 12.24 | 11.88 | 12.40 | 11.58 |
| 2701071 | 8.52 | 11.12 | 10.97 | 10.07 | 9.51 | 11.16 | 8.40 | 8.41 | 9.40 | 9.81 | 8.47 | 8.98 |

TABLE 33-continued

Normalized intensity of microarray data for a set of samples.

| TCID | V01 0097 | V01 0098 | V01 0099 | V01 0100 | V01 0101 | V01 0102 | V01 0103 | V01 0104 | V01 0105 | V01 0106 | V01 0107 | V01 0108 |
|---|---|---|---|---|---|---|---|---|---|---|---|---|
| 3486096 | 5.92 | 5.72 | 6.57 | 5.69 | 8.54 | 6.00 | 6.30 | 8.43 | 7.20 | 6.26 | 6.60 | 8.59 |
| 2412668 | 9.33 | 8.35 | 8.74 | 8.46 | 8.58 | 8.76 | 8.00 | 8.07 | 7.94 | 9.17 | 8.16 | 8.53 |
| 3329343 | 7.70 | 7.63 | 7.54 | 7.79 | 7.79 | 7.64 | 8.67 | 7.42 | 7.54 | 7.12 | 7.69 | 7.78 |
| 3259367 | 4.15 | 4.10 | 4.58 | 4.31 | 4.31 | 4.52 | 3.96 | 7.43 | 5.51 | 4.86 | 4.19 | 4.34 |
| 3373845 | 11.06 | 8.79 | 9.09 | 8.96 | 10.43 | 9.61 | 7.08 | 7.34 | 8.48 | 10.41 | 9.45 | 9.45 |
| 2321911 | 8.43 | 9.90 | 8.73 | 9.42 | 8.37 | 8.71 | 7.87 | 8.06 | 8.58 | 9.13 | 8.51 | 8.01 |
| 3353914 | 9.56 | 6.41 | 6.28 | 6.90 | 6.06 | 6.85 | 7.57 | 7.37 | 6.55 | 9.31 | 6.71 | 7.03 |
| 3744680 | 8.50 | 8.15 | 8.52 | 7.85 | 7.25 | 8.68 | 6.96 | 7.07 | 7.72 | 8.42 | 7.33 | 7.36 |
| 2373336 | 6.10 | 6.95 | 5.97 | 6.22 | 7.34 | 8.44 | 5.44 | 5.17 | 6.20 | 6.15 | 6.64 | 5.50 |
| 3067478 | 4.78 | 5.52 | 5.13 | 4.83 | 6.44 | 5.27 | 6.22 | 6.77 | 6.04 | 5.67 | 5.37 | 4.42 |
| 3976766 | 8.14 | 8.95 | 9.57 | 9.21 | 7.97 | 9.73 | 6.89 | 7.12 | 8.32 | 8.15 | 8.46 | 7.64 |
| 3246888 | 5.01 | 5.90 | 5.54 | 5.54 | 7.75 | 5.68 | 7.13 | 7.83 | 5.62 | 6.56 | 5.05 | 4.67 |
| 3147985 | 9.91 | 6.29 | 5.94 | 6.12 | 6.08 | 6.14 | 7.17 | 7.54 | 5.84 | 9.12 | 6.25 | 6.18 |
| 3185522 | 11.92 | 9.18 | 9.59 | 8.35 | 8.69 | 9.48 | 10.73 | 9.28 | 9.18 | 11.30 | 9.90 | 10.13 |
| 3861948 | 12.38 | 13.13 | 13.15 | 12.99 | 12.34 | 13.15 | 11.01 | 10.87 | 12.44 | 12.41 | 12.52 | 12.15 |
| 3393479 | 10.46 | 8.84 | 9.44 | 8.63 | 9.47 | 8.84 | 7.88 | 7.97 | 8.16 | 9.99 | 8.49 | 11.00 |
| 3540862 | 6.64 | 6.74 | 6.17 | 6.15 | 6.67 | 6.24 | 9.93 | 6.82 | 6.67 | 6.93 | 6.83 | 8.41 |
| 2777714 | 10.06 | 12.02 | 11.82 | 11.68 | 11.67 | 11.78 | 9.90 | 10.86 | 11.03 | 9.87 | 8.92 | 9.96 |
| 3110395 | 4.29 | 5.32 | 4.57 | 4.42 | 4.08 | 4.45 | 4.53 | 5.88 | 4.25 | 5.01 | 4.40 | 4.32 |
| 3895795 | 7.73 | 9.33 | 9.48 | 8.64 | 8.11 | 9.55 | 6.69 | 8.08 | 7.82 | 7.72 | 6.88 | 8.05 |
| 2854445 | 11.49 | 8.68 | 8.95 | 8.53 | 9.17 | 9.75 | 7.52 | 9.26 | 8.40 | 12.08 | 9.05 | 9.09 |
| 3606034 | 8.71 | 7.14 | 7.11 | 6.95 | 7.50 | 7.61 | 7.61 | 7.89 | 7.07 | 8.45 | 6.76 | 6.91 |
| 3375735 | 8.50 | 7.87 | 8.36 | 8.23 | 7.71 | 8.64 | 7.20 | 7.39 | 7.67 | 8.31 | 7.58 | 7.59 |
| 3948047 | 9.20 | 8.97 | 9.24 | 9.35 | 7.70 | 9.49 | 7.32 | 7.29 | 8.50 | 8.80 | 8.78 | 7.94 |
| 3010503 | 11.47 | 9.75 | 10.07 | 8.96 | 9.65 | 10.21 | 6.99 | 8.47 | 8.05 | 11.23 | 6.59 | 8.30 |
| 3622934 | 5.74 | 6.64 | 5.17 | 7.61 | 6.80 | 6.79 | 8.85 | 8.70 | 8.08 | 6.38 | 8.23 | 7.52 |
| 3441849 | 10.07 | 10.01 | 10.80 | 9.65 | 9.56 | 10.73 | 9.20 | 9.41 | 9.49 | 10.42 | 8.82 | 9.82 |
| 3006572 | 6.07 | 6.50 | 6.94 | 6.88 | 6.53 | 6.60 | 6.62 | 6.75 | 6.45 | 6.30 | 6.41 | 7.20 |
| 3365136 | 8.17 | 8.77 | 8.29 | 8.78 | 8.69 | 8.50 | 8.34 | 9.84 | 8.66 | 8.53 | 8.07 | 9.11 |
| 2642791 | 9.16 | 8.54 | 8.56 | 8.45 | 8.71 | 9.05 | 8.56 | 8.41 | 8.62 | 9.25 | 8.66 | 7.66 |
| 2904485 | 7.46 | 7.31 | 8.10 | 7.30 | 8.44 | 7.82 | 6.73 | 9.42 | 7.71 | 7.57 | 7.03 | 7.10 |
| 3772661 | 11.79 | 10.00 | 10.39 | 9.28 | 9.46 | 10.55 | 9.33 | 9.05 | 9.21 | 11.87 | 9.67 | 10.04 |
| 2796553 | 10.43 | 10.89 | 10.85 | 9.57 | 9.62 | 11.25 | 9.87 | 9.09 | 9.66 | 10.47 | 9.15 | 9.32 |
| 3063795 | 8.93 | 7.71 | 7.83 | 7.66 | 7.38 | 7.64 | 7.28 | 6.96 | 7.08 | 9.22 | 7.97 | 8.17 |
| 3338192 | 8.89 | 7.96 | 8.31 | 7.69 | 10.06 | 8.33 | 8.66 | 10.25 | 8.50 | 8.01 | 8.07 | 8.04 |
| 3214845 | 4.47 | 4.66 | 5.30 | 4.74 | 6.39 | 5.51 | 3.87 | 4.23 | 4.41 | 4.78 | 4.37 | 4.48 |
| 2730303 | 4.78 | 4.82 | 4.31 | 8.33 | 4.08 | 4.16 | 4.37 | 4.22 | 8.46 | 4.25 | 9.76 | 4.36 |
| 3811086 | 8.29 | 7.91 | 7.73 | 7.81 | 7.91 | 7.60 | 7.61 | 7.50 | 7.78 | 8.80 | 7.95 | 8.34 |
| 2981874 | 10.49 | 10.49 | 10.53 | 10.11 | 9.83 | 10.17 | 10.65 | 9.88 | 10.25 | 10.34 | 9.93 | 11.02 |
| 3242353 | 6.96 | 5.60 | 6.25 | 5.96 | 6.24 | 5.75 | 6.13 | 6.24 | 6.31 | 6.95 | 6.66 | 6.70 |
| 2442008 | 5.64 | 5.43 | 5.86 | 5.40 | 5.23 | 5.39 | 5.36 | 7.37 | 5.18 | 5.41 | 5.17 | 5.45 |
| 3564210 | 9.86 | 10.43 | 10.67 | 9.12 | 9.09 | 10.87 | 8.44 | 8.06 | 8.62 | 10.39 | 8.37 | 8.31 |
| 2490351 | 4.23 | 3.97 | 4.38 | 4.10 | 3.94 | 4.29 | 4.11 | 4.10 | 4.03 | 4.02 | 3.93 | 4.08 |
| 3759006 | 7.95 | 10.60 | 10.18 | 10.20 | 9.38 | 10.02 | 7.59 | 8.68 | 8.61 | 7.45 | 7.18 | 8.14 |
| 3264997 | 4.24 | 4.19 | 4.26 | 4.00 | 3.90 | 4.19 | 4.13 | 3.90 | 4.07 | 4.12 | 4.16 | 4.27 |
| 3912079 | 3.56 | 3.70 | 4.24 | 3.71 | 3.58 | 4.01 | 3.64 | 3.46 | 3.67 | 3.58 | 3.49 | 3.73 |
| 2926802 | 5.43 | 6.44 | 5.88 | 7.04 | 4.65 | 6.37 | 5.22 | 4.93 | 5.75 | 4.89 | 6.78 | 4.76 |
| 2430163 | 4.29 | 3.93 | 4.00 | 3.86 | 3.82 | 3.96 | 5.20 | 3.77 | 3.95 | 3.88 | 3.68 | 4.37 |
| 3039830 | 3.17 | 3.06 | 3.10 | 3.26 | 3.07 | 3.10 | 3.24 | 3.14 | 3.06 | 3.05 | 3.10 | 3.15 |
| 3935486 | 8.47 | 6.92 | 6.92 | 7.75 | 6.24 | 5.70 | 5.32 | 7.39 | 7.00 | 9.80 | 7.18 | 5.94 |
| 3457336 | 5.57 | 5.34 | 5.89 | 5.28 | 5.24 | 5.39 | 5.46 | 5.32 | 5.30 | 5.35 | 6.51 | 5.52 |
| 3811949 | 3.65 | 3.41 | 3.73 | 3.46 | 3.48 | 3.70 | 3.46 | 3.49 | 3.35 | 3.41 | 3.33 | 3.54 |
| 3343832 | 4.11 | 3.94 | 4.23 | 3.82 | 3.72 | 3.94 | 4.10 | 3.95 | 3.88 | 3.92 | 3.86 | 3.87 |
| 3161261 | 5.57 | 6.39 | 6.41 | 6.13 | 5.57 | 6.23 | 5.69 | 5.73 | 5.49 | 6.91 | 5.89 | 5.63 |
| 3594003 | 4.56 | 4.34 | 4.10 | 3.98 | 3.54 | 3.80 | 3.72 | 3.54 | 3.67 | 4.22 | 3.85 | 3.75 |
| 3805614 | 5.18 | 5.73 | 5.18 | 4.87 | 4.61 | 5.00 | 4.37 | 4.69 | 4.84 | 4.86 | 5.05 | 5.00 |
| 3364127 | 6.97 | 6.78 | 7.29 | 6.98 | 6.62 | 7.17 | 7.56 | 6.60 | 6.78 | 6.79 | 6.79 | 8.19 |
| 3834341 | 4.37 | 4.06 | 4.37 | 4.06 | 3.99 | 4.41 | 4.12 | 4.19 | 4.15 | 3.86 | 4.09 | 4.08 |
| 2585400 | 4.33 | 4.66 | 4.55 | 4.52 | 4.25 | 5.26 | 4.20 | 4.22 | 4.20 | 5.82 | 4.27 | 4.19 |
| 2941690 | 4.77 | 7.52 | 4.71 | 4.46 | 4.19 | 4.49 | 4.39 | 3.98 | 4.29 | 4.09 | 4.06 | 4.52 |
| 3484895 | 4.89 | 8.47 | 5.26 | 4.90 | 5.20 | 4.91 | 4.61 | 4.71 | 4.83 | 4.75 | 4.48 | 4.76 |
| 3159754 | 4.03 | 4.96 | 3.71 | 3.86 | 3.57 | 3.61 | 3.81 | 3.89 | 3.61 | 3.59 | 3.63 | 3.86 |
| 2894790 | 3.86 | 6.67 | 3.94 | 3.91 | 3.81 | 4.03 | 3.81 | 3.94 | 3.65 | 3.91 | 3.63 | 4.12 |
| 3363686 | 3.42 | 12.48 | 3.78 | 3.63 | 3.56 | 3.53 | 3.40 | 3.40 | 3.22 | 3.21 | 3.23 | 3.70 |
| 2923928 | 4.18 | 4.11 | 8.93 | 4.25 | 4.24 | 4.50 | 4.44 | 3.97 | 3.97 | 4.71 | 4.58 | 4.32 |
| 2883317 | 5.26 | 5.79 | 5.12 | 5.67 | 4.72 | 4.81 | 5.13 | 5.19 | 5.63 | 6.15 | 4.83 | 4.65 |
| 2479698 | 5.85 | 6.11 | 5.99 | 6.01 | 6.02 | 6.18 | 6.08 | 6.08 | 6.08 | 6.12 | 5.91 | 6.18 |
| 3428225 | 4.06 | 3.83 | 4.16 | 3.72 | 3.55 | 3.80 | 3.82 | 3.70 | 3.62 | 3.61 | 3.64 | 3.93 |
| 3393446 | 8.73 | 7.79 | 7.42 | 7.64 | 6.81 | 7.88 | 7.03 | 7.10 | 7.17 | 7.76 | 7.39 | 7.45 |
| 3116614 | 10.78 | 11.42 | 12.15 | 10.88 | 12.86 | 11.54 | 11.38 | 13.30 | 12.47 | 11.62 | 11.53 | 9.80 |
| 3415320 | 7.75 | 7.68 | 8.33 | 7.85 | 9.95 | 8.76 | 11.75 | 10.24 | 9.57 | 7.58 | 8.21 | 10.40 |
| 3757108 | 8.01 | 7.74 | 7.63 | 7.59 | 8.14 | 8.38 | 8.54 | 7.36 | 7.48 | 7.20 | 7.55 | 9.59 |
| 4012178 | 6.56 | 6.83 | 6.89 | 6.19 | 6.70 | 6.75 | 6.73 | 8.29 | 7.71 | 6.03 | 6.45 | 6.15 |

TABLE 33-continued

Normalized intensity of microarray data for a set of samples.

| TCID | V01 0097 | V01 0098 | V01 0099 | V01 0100 | V01 0101 | V01 0102 | V01 0103 | V01 0104 | V01 0105 | V01 0106 | V01 0107 | V01 0108 |
|---|---|---|---|---|---|---|---|---|---|---|---|---|
| 3546213 | 8.61 | 8.86 | 8.93 | 8.10 | 11.31 | 9.42 | 10.67 | 11.48 | 10.34 | 9.19 | 8.65 | 8.09 |
| 3561381 | 7.27 | 6.16 | 7.58 | 7.01 | 10.21 | 7.63 | 9.17 | 10.78 | 8.66 | 7.00 | 7.88 | 9.07 |

TABLE 34

Normalized intensity of microarray data for a set of samples.

| TCID | V01 0109 | V01 0110 | V01 0111 | V01 0112 | V01 0113 | V01 0114 | V01 0115 | V01 0116 | V01 0117 | V01 0118 | V01 0119 | V01 0120 |
|---|---|---|---|---|---|---|---|---|---|---|---|---|
| 2604998 | 7.28 | 8.17 | 7.96 | 8.45 | 8.72 | 7.44 | 8.86 | 9.89 | 7.35 | 7.36 | 8.61 | 7.70 |
| 3603932 | 7.64 | 6.49 | 7.82 | 7.53 | 7.17 | 7.03 | 7.45 | 7.17 | 6.58 | 6.96 | 6.75 | 8.34 |
| 2710599 | 6.32 | 7.10 | 9.86 | 11.85 | 11.60 | 11.69 | 11.20 | 11.53 | 6.86 | 5.46 | 5.12 | 7.78 |
| 2440258 | 7.92 | 8.23 | 8.15 | 5.69 | 5.24 | 7.54 | 7.70 | 5.35 | 9.29 | 7.87 | 6.31 | 7.81 |
| 3169331 | 6.76 | 6.72 | 7.08 | 6.48 | 6.56 | 6.69 | 6.59 | 6.42 | 6.84 | 7.49 | 7.29 | 7.43 |
| 2988882 | 10.21 | 9.67 | 9.81 | 9.93 | 9.65 | 9.66 | 9.69 | 9.45 | 9.76 | 9.52 | 10.59 | 10.34 |
| 2964231 | 9.37 | 8.31 | 9.84 | 9.70 | 9.47 | 9.59 | 8.98 | 7.54 | 8.43 | 7.33 | 7.65 | 10.25 |
| 3111561 | 7.80 | 10.93 | 9.18 | 4.71 | 4.39 | 4.77 | 8.36 | 4.68 | 7.87 | 8.87 | 5.45 | 8.81 |
| 2562529 | 9.34 | 9.90 | 9.81 | 10.65 | 10.96 | 11.01 | 10.69 | 10.97 | 9.30 | 8.83 | 8.81 | 9.44 |
| 3692999 | 12.59 | 12.97 | 12.25 | 9.22 | 6.97 | 7.02 | 11.61 | 6.72 | 9.17 | 10.75 | 9.49 | 10.99 |
| 2439554 | 7.26 | 6.99 | 6.82 | 5.82 | 5.28 | 8.09 | 6.85 | 4.83 | 9.01 | 6.85 | 5.67 | 7.49 |
| 2685304 | 7.65 | 7.24 | 9.07 | 11.53 | 11.67 | 11.73 | 10.71 | 11.19 | 6.73 | 6.83 | 6.65 | 7.71 |
| 2578790 | 5.94 | 6.51 | 4.84 | 4.12 | 4.13 | 4.02 | 4.82 | 4.29 | 5.82 | 6.88 | 5.43 | 6.07 |
| 2373842 | 11.63 | 11.44 | 11.56 | 10.04 | 8.80 | 10.01 | 10.35 | 8.36 | 12.12 | 11.66 | 10.06 | 10.87 |
| 2750627 | 9.64 | 10.76 | 9.21 | 8.04 | 10.37 | 9.57 | 10.00 | 10.86 | 8.93 | 9.21 | 10.17 | 9.48 |
| 3397774 | 4.71 | 4.98 | 4.51 | 4.50 | 4.66 | 4.38 | 4.55 | 4.61 | 5.26 | 5.32 | 4.82 | 4.91 |
| 2635741 | 8.51 | 8.38 | 8.72 | 6.72 | 6.21 | 7.04 | 7.62 | 5.74 | 8.99 | 8.40 | 7.09 | 7.69 |
| 3970833 | 9.49 | 9.42 | 9.44 | 9.93 | 9.69 | 9.65 | 9.62 | 9.88 | 8.86 | 8.88 | 9.87 | 9.74 |
| 3577612 | 11.08 | 10.91 | 10.75 | 11.64 | 11.75 | 11.91 | 10.86 | 11.72 | 11.67 | 10.75 | 9.44 | 9.80 |
| 2708922 | 9.42 | 8.70 | 8.84 | 7.96 | 8.35 | 8.14 | 7.89 | 8.80 | 8.48 | 9.01 | 10.19 | 7.34 |
| 2970897 | 4.65 | 5.24 | 6.30 | 5.42 | 5.31 | 5.22 | 4.71 | 4.47 | 4.80 | 4.87 | 5.72 | 5.48 |
| 3724545 | 9.96 | 9.71 | 9.58 | 10.22 | 9.81 | 9.33 | 9.43 | 10.24 | 8.72 | 10.13 | 7.68 | 9.27 |
| 2798538 | 9.34 | 8.90 | 9.36 | 8.83 | 8.68 | 8.77 | 9.20 | 8.49 | 8.80 | 8.35 | 9.21 | 9.64 |
| 2806468 | 11.28 | 11.12 | 11.37 | 9.47 | 7.58 | 8.84 | 9.44 | 6.95 | 11.46 | 11.31 | 9.26 | 9.95 |
| 2880051 | 5.95 | 6.03 | 6.15 | 5.72 | 6.07 | 5.78 | 6.11 | 5.94 | 6.86 | 6.81 | 6.63 | 6.39 |
| 2732508 | 3.36 | 3.47 | 3.69 | 3.26 | 3.84 | 7.90 | 6.69 | 3.41 | 3.55 | 3.78 | 3.65 | 3.58 |
| 2822492 | 6.44 | 5.23 | 5.35 | 5.05 | 5.43 | 5.47 | 4.63 | 5.50 | 5.19 | 5.71 | 7.38 | 5.70 |
| 3404030 | 8.20 | 7.70 | 8.20 | 5.54 | 5.87 | 5.55 | 6.94 | 6.16 | 9.43 | 8.00 | 6.98 | 7.10 |
| 3059667 | 11.85 | 11.37 | 9.71 | 5.45 | 3.49 | 5.02 | 9.56 | 5.62 | 10.44 | 11.16 | 12.34 | 10.09 |
| 3108526 | 8.10 | 10.03 | 8.93 | 8.93 | 8.23 | 8.82 | 9.10 | 8.55 | 7.86 | 9.93 | 8.70 | 9.61 |
| 2526806 | 9.60 | 6.06 | 11.42 | 12.82 | 12.86 | 12.90 | 12.22 | 12.56 | 7.43 | 7.19 | 7.10 | 10.24 |
| 2428501 | 7.41 | 7.46 | 7.53 | 7.27 | 6.79 | 7.76 | 6.35 | 5.62 | 6.92 | 6.88 | 6.21 | 8.13 |
| 2657808 | 5.80 | 6.86 | 7.23 | 11.90 | 10.91 | 11.44 | 10.47 | 11.24 | 6.09 | 6.24 | 6.41 | 5.78 |
| 2584018 | 7.89 | 7.72 | 10.00 | 10.70 | 10.02 | 10.67 | 10.28 | 9.41 | 7.41 | 7.20 | 6.29 | 9.34 |
| 3976341 | 9.58 | 9.41 | 9.91 | 11.21 | 11.79 | 11.58 | 11.32 | 12.64 | 10.35 | 9.45 | 7.77 | 10.45 |
| 2739308 | 5.84 | 5.51 | 5.04 | 4.54 | 4.37 | 4.03 | 4.44 | 4.66 | 5.49 | 5.21 | 4.84 | 5.02 |
| 3959862 | 5.49 | 5.18 | 5.15 | 3.98 | 4.64 | 4.24 | 5.03 | 4.41 | 5.14 | 5.03 | 4.72 | 5.12 |
| 2362351 | 7.48 | 7.22 | 7.69 | 5.92 | 5.93 | 6.47 | 6.82 | 5.80 | 8.32 | 7.59 | 6.21 | 6.97 |
| 3648391 | 4.47 | 5.36 | 4.23 | 3.62 | 4.19 | 6.26 | 5.53 | 4.69 | 5.84 | 4.92 | 4.84 | 4.21 |
| 3009299 | 10.65 | 10.41 | 10.79 | 10.62 | 10.63 | 10.48 | 10.84 | 10.58 | 10.51 | 10.35 | 11.16 | 11.05 |
| 3443464 | 5.71 | 5.34 | 5.67 | 5.03 | 4.97 | 4.79 | 5.57 | 5.10 | 6.23 | 5.80 | 5.36 | 5.73 |
| 2730746 | 9.04 | 8.02 | 7.43 | 5.47 | 5.20 | 5.12 | 7.15 | 5.01 | 7.56 | 7.70 | 9.35 | 7.61 |
| 2427619 | 9.06 | 8.59 | 9.14 | 6.16 | 5.46 | 7.16 | 7.73 | 5.26 | 9.56 | 8.74 | 5.93 | 7.13 |
| 3042001 | 8.32 | 8.31 | 8.65 | 8.07 | 8.28 | 8.35 | 8.46 | 8.65 | 8.70 | 8.17 | 8.93 | 9.12 |
| 2566848 | 5.88 | 5.20 | 5.50 | 4.98 | 5.06 | 5.58 | 5.24 | 5.20 | 5.58 | 5.86 | 4.95 | 5.63 |
| 2984616 | 8.93 | 8.91 | 9.35 | 9.16 | 8.73 | 8.88 | 8.63 | 9.07 | 8.86 | 8.34 | 8.79 | 9.57 |
| 2378068 | 7.83 | 7.04 | 8.31 | 8.86 | 8.85 | 9.85 | 9.58 | 10.95 | 8.05 | 7.35 | 6.98 | 10.25 |
| 2721959 | 5.83 | 6.20 | 9.26 | 12.99 | 12.88 | 13.04 | 10.61 | 11.97 | 6.44 | 6.58 | 6.44 | 7.87 |
| 2877508 | 10.49 | 10.11 | 10.63 | 10.58 | 10.32 | 10.66 | 10.45 | 10.30 | 9.70 | 10.14 | 10.37 | 10.85 |
| 3450861 | 6.11 | 6.52 | 6.97 | 4.62 | 4.61 | 5.44 | 5.76 | 4.39 | 6.98 | 6.92 | 4.81 | 5.05 |
| 2688717 | 9.03 | 8.84 | 9.14 | 6.49 | 6.00 | 8.42 | 8.66 | 6.65 | 9.45 | 9.90 | 7.20 | 7.46 |
| 3270270 | 9.22 | 8.56 | 8.70 | 8.57 | 8.85 | 8.93 | 8.08 | 8.53 | 9.68 | 8.99 | 6.97 | 8.70 |
| 3417703 | 6.19 | 11.36 | 7.28 | 7.31 | 7.38 | 7.31 | 8.64 | 6.95 | 7.37 | 7.04 | 7.02 | 7.02 |
| 3302990 | 6.97 | 6.92 | 7.75 | 8.23 | 7.95 | 7.81 | 7.31 | 7.64 | 6.39 | 7.54 | 7.44 | 7.96 |
| 2377283 | 4.97 | 4.23 | 4.98 | 4.02 | 4.25 | 10.03 | 9.22 | 4.08 | 4.87 | 5.15 | 4.45 | 4.23 |
| 3122678 | 4.69 | 4.39 | 4.74 | 4.68 | 5.14 | 4.33 | 3.94 | 4.57 | 4.65 | 4.93 | 5.31 | 5.26 |
| 2688499 | 8.60 | 10.34 | 9.48 | 10.15 | 10.00 | 10.07 | 9.72 | 10.35 | 8.49 | 9.45 | 9.29 | 8.26 |
| 2377094 | 8.94 | 9.39 | 8.75 | 8.75 | 8.81 | 8.66 | 8.77 | 8.08 | 8.60 | 8.53 | 8.73 | 8.95 |
| 3278198 | 8.41 | 7.60 | 8.27 | 9.00 | 8.62 | 8.84 | 8.05 | 7.74 | 6.92 | 7.17 | 7.25 | 8.68 |
| 2598261 | 9.19 | 5.99 | 10.67 | 12.93 | 12.86 | 13.08 | 11.77 | 12.32 | 6.04 | 7.24 | 6.68 | 9.35 |
| 3982612 | 8.61 | 8.58 | 8.84 | 5.90 | 5.47 | 8.27 | 8.49 | 5.77 | 9.71 | 9.41 | 7.38 | 7.17 |
| 2884845 | 4.41 | 4.54 | 4.71 | 9.97 | 10.48 | 9.90 | 9.19 | 10.62 | 4.52 | 4.88 | 5.05 | 4.86 |

TABLE 34-continued

Normalized intensity of microarray data for a set of samples.

| TCID | V01 0109 | V01 0110 | V01 0111 | V01 0112 | V01 0113 | V01 0114 | V01 0115 | V01 0116 | V01 0117 | V01 0118 | V01 0119 | V01 0120 |
| --- | --- | --- | --- | --- | --- | --- | --- | --- | --- | --- | --- | --- |
| 3982560 | 7.48 | 6.57 | 7.52 | 4.68 | 4.78 | 6.44 | 6.51 | 4.70 | 7.46 | 7.44 | 5.99 | 6.32 |
| 3204285 | 5.34 | 5.23 | 5.48 | 5.74 | 6.33 | 7.59 | 6.94 | 4.98 | 5.30 | 5.86 | 5.30 | 5.34 |
| 3654699 | 11.20 | 8.68 | 12.18 | 11.56 | 10.59 | 10.56 | 11.12 | 9.42 | 9.26 | 11.11 | 8.08 | 11.61 |
| 2638676 | 7.17 | 6.94 | 7.60 | 5.83 | 5.94 | 8.32 | 7.87 | 5.45 | 8.51 | 7.67 | 5.15 | 7.19 |
| 3367673 | 7.08 | 9.13 | 7.48 | 4.59 | 4.87 | 4.51 | 6.82 | 4.74 | 7.59 | 7.99 | 7.82 | 7.60 |
| 3212008 | 7.20 | 6.70 | 8.05 | 7.69 | 9.20 | 8.75 | 9.29 | 9.45 | 6.82 | 7.17 | 8.45 | 6.05 |
| 3326635 | 10.66 | 10.09 | 10.34 | 10.00 | 9.87 | 10.09 | 10.38 | 10.64 | 10.68 | 10.07 | 10.35 | 10.04 |
| 3031556 | 9.61 | 9.37 | 9.82 | 7.64 | 6.63 | 7.50 | 8.38 | 6.33 | 10.47 | 9.69 | 7.68 | 9.50 |
| 3662201 | 12.64 | 13.01 | 12.07 | 9.81 | 7.67 | 7.23 | 10.98 | 7.39 | 9.52 | 10.36 | 10.09 | 11.71 |
| 2809793 | 8.39 | 6.97 | 8.24 | 5.48 | 5.56 | 7.20 | 8.17 | 5.26 | 9.76 | 8.18 | 6.21 | 7.11 |
| 2817731 | 8.46 | 7.75 | 8.54 | 8.23 | 7.55 | 7.47 | 7.92 | 7.58 | 8.20 | 7.74 | 7.57 | 9.32 |
| 4020655 | 5.79 | 4.82 | 7.05 | 6.26 | 7.88 | 6.65 | 8.37 | 7.58 | 5.48 | 5.37 | 6.56 | 4.83 |
| 3494629 | 5.08 | 5.75 | 5.05 | 8.54 | 8.12 | 8.35 | 6.26 | 7.93 | 5.18 | 4.61 | 5.99 | 4.50 |
| 3852832 | 9.99 | 9.19 | 8.41 | 7.33 | 6.19 | 5.71 | 6.37 | 5.95 | 10.33 | 9.82 | 7.32 | 7.16 |
| 3761959 | 9.33 | 8.58 | 9.28 | 9.29 | 9.38 | 8.67 | 9.17 | 9.23 | 8.67 | 9.10 | 9.37 | 9.85 |
| 2834282 | 6.13 | 5.79 | 7.49 | 8.37 | 8.58 | 7.85 | 8.11 | 8.55 | 5.45 | 6.77 | 6.09 | 5.76 |
| 3341497 | 5.71 | 5.95 | 6.37 | 7.52 | 7.67 | 7.06 | 7.19 | 7.45 | 6.05 | 6.40 | 6.56 | 6.06 |
| 2372812 | 4.72 | 4.38 | 4.53 | 4.64 | 4.66 | 8.93 | 8.09 | 4.60 | 4.87 | 5.38 | 4.89 | 6.15 |
| 2486811 | 10.45 | 9.43 | 10.26 | 9.17 | 6.92 | 7.97 | 9.26 | 5.86 | 10.79 | 9.99 | 7.96 | 10.96 |
| 3768474 | 8.52 | 8.05 | 8.59 | 8.35 | 7.70 | 7.56 | 7.62 | 7.12 | 8.11 | 8.58 | 7.59 | 8.53 |
| 3142381 | 8.58 | 6.06 | 6.41 | 5.85 | 3.90 | 5.33 | 5.58 | 3.86 | 5.30 | 5.00 | 6.36 | 9.44 |
| 2396750 | 6.54 | 7.14 | 6.92 | 8.02 | 7.73 | 8.06 | 8.01 | 8.78 | 6.89 | 6.90 | 6.65 | 6.47 |
| 3902489 | 12.05 | 11.77 | 11.23 | 10.20 | 9.45 | 9.97 | 9.51 | 9.31 | 11.51 | 11.92 | 10.31 | 9.99 |
| 3032647 | 8.61 | 7.36 | 7.65 | 5.57 | 5.59 | 5.75 | 6.10 | 6.20 | 6.48 | 8.12 | 9.96 | 7.08 |
| 3875642 | 5.90 | 5.57 | 5.43 | 4.75 | 5.74 | 4.58 | 4.97 | 5.35 | 5.76 | 6.02 | 5.37 | 5.46 |
| 4027585 | 11.74 | 11.29 | 11.49 | 9.82 | 8.06 | 7.72 | 9.34 | 8.95 | 11.54 | 11.71 | 9.73 | 11.21 |
| 2352609 | 7.17 | 6.93 | 6.90 | 7.09 | 6.99 | 6.97 | 6.81 | 6.82 | 6.25 | 6.65 | 8.33 | 6.50 |
| 3376529 | 8.30 | 9.09 | 8.47 | 10.05 | 9.94 | 9.42 | 8.88 | 10.03 | 8.28 | 7.18 | 6.75 | 7.80 |
| 2491271 | 13.44 | 13.17 | 13.49 | 13.25 | 13.22 | 13.24 | 13.42 | 13.25 | 13.64 | 12.96 | 12.76 | 13.46 |
| 3874751 | 9.23 | 9.22 | 9.82 | 9.75 | 9.83 | 10.03 | 9.68 | 10.10 | 9.14 | 9.96 | 8.35 | 10.00 |
| 2326463 | 12.19 | 11.21 | 12.44 | 10.92 | 9.37 | 10.76 | 11.81 | 9.22 | 12.67 | 11.53 | 10.33 | 12.57 |
| 3341061 | 7.86 | 6.98 | 9.00 | 7.44 | 7.09 | 7.06 | 7.70 | 6.37 | 8.04 | 6.07 | 6.59 | 9.14 |
| 3839910 | 9.67 | 9.26 | 9.00 | 7.22 | 5.22 | 4.68 | 5.52 | 5.36 | 10.83 | 9.59 | 7.30 | 7.04 |
| 2708855 | 4.24 | 4.43 | 5.34 | 8.22 | 8.51 | 8.85 | 8.16 | 8.63 | 4.13 | 4.40 | 3.97 | 3.89 |
| 3512874 | 12.12 | 12.09 | 11.88 | 11.00 | 9.52 | 11.10 | 11.16 | 9.50 | 12.43 | 12.13 | 10.58 | 11.86 |
| 2701071 | 10.59 | 10.65 | 10.28 | 8.66 | 6.77 | 6.85 | 8.43 | 7.51 | 11.77 | 10.67 | 8.52 | 9.60 |
| 3486096 | 9.20 | 8.52 | 7.38 | 7.73 | 7.49 | 7.11 | 7.81 | 5.78 | 7.35 | 6.12 | 9.21 | 6.87 |
| 2412668 | 8.63 | 8.66 | 8.83 | 8.38 | 8.21 | 8.04 | 7.85 | 8.43 | 9.44 | 8.36 | 8.72 | 8.41 |
| 3329343 | 6.81 | 7.35 | 7.05 | 8.24 | 9.22 | 8.51 | 8.15 | 8.97 | 7.02 | 7.30 | 7.80 | 7.12 |
| 3259367 | 4.02 | 4.86 | 4.71 | 5.01 | 4.88 | 4.38 | 5.51 | 5.31 | 4.43 | 4.42 | 4.12 | 3.95 |
| 3373845 | 9.24 | 9.92 | 9.54 | 10.08 | 9.08 | 9.44 | 9.02 | 8.83 | 9.00 | 8.18 | 7.74 | 10.18 |
| 2321911 | 8.90 | 8.66 | 8.98 | 8.09 | 7.53 | 7.55 | 8.36 | 7.80 | 9.03 | 9.29 | 8.51 | 8.53 |
| 3353914 | 7.69 | 6.80 | 8.72 | 8.42 | 7.97 | 8.08 | 8.06 | 7.41 | 6.17 | 6.46 | 6.05 | 9.50 |
| 3744680 | 8.07 | 7.77 | 7.99 | 6.98 | 6.31 | 6.42 | 7.08 | 6.63 | 8.39 | 8.15 | 7.14 | 8.32 |
| 2373336 | 5.30 | 6.95 | 7.76 | 10.71 | 9.36 | 10.19 | 8.74 | 9.97 | 6.28 | 5.54 | 5.09 | 6.07 |
| 3067478 | 7.61 | 4.76 | 6.61 | 8.37 | 8.56 | 8.61 | 8.20 | 9.08 | 5.99 | 6.46 | 8.95 | 6.59 |
| 3976766 | 8.71 | 8.36 | 8.31 | 7.09 | 6.34 | 7.03 | 6.81 | 6.47 | 9.37 | 9.09 | 7.56 | 8.26 |
| 3246888 | 7.08 | 7.57 | 6.65 | 5.81 | 5.08 | 4.52 | 7.58 | 5.29 | 6.06 | 6.67 | 7.46 | 6.89 |
| 3147985 | 7.51 | 7.49 | 7.91 | 7.72 | 7.50 | 7.54 | 7.73 | 7.73 | 6.54 | 6.17 | 6.61 | 8.76 |
| 3185522 | 9.93 | 9.04 | 10.34 | 10.02 | 9.06 | 9.31 | 9.72 | 8.40 | 9.87 | 9.32 | 8.96 | 10.90 |
| 3861948 | 12.77 | 12.71 | 12.58 | 11.60 | 10.36 | 11.10 | 11.76 | 9.93 | 13.38 | 12.76 | 11.67 | 12.43 |
| 3393479 | 8.73 | 9.03 | 9.74 | 9.60 | 9.35 | 8.62 | 8.65 | 8.55 | 9.32 | 8.70 | 10.68 | 9.44 |
| 3540862 | 6.91 | 6.92 | 6.74 | 7.48 | 7.10 | 7.14 | 7.17 | 7.30 | 6.46 | 6.44 | 7.85 | 6.88 |
| 2777714 | 11.87 | 11.70 | 11.72 | 9.84 | 7.55 | 6.92 | 8.77 | 8.92 | 11.69 | 12.10 | 10.86 | 9.73 |
| 3110395 | 4.35 | 4.19 | 5.24 | 4.72 | 6.51 | 6.52 | 4.44 | 6.82 | 4.25 | 5.75 | 5.26 | 4.81 |
| 3895795 | 9.25 | 9.15 | 8.17 | 8.03 | 7.80 | 7.26 | 7.71 | 8.00 | 9.98 | 8.80 | 7.30 | 7.85 |
| 2854445 | 9.65 | 8.44 | 11.39 | 10.32 | 8.34 | 8.36 | 9.76 | 7.14 | 8.49 | 8.93 | 6.79 | 11.58 |
| 3606034 | 7.70 | 7.54 | 8.18 | 7.56 | 7.33 | 7.44 | 7.44 | 7.58 | 7.11 | 6.96 | 6.42 | 7.72 |
| 3375735 | 7.99 | 8.28 | 7.98 | 7.75 | 7.93 | 7.73 | 7.53 | 7.75 | 8.29 | 8.06 | 7.67 | 7.87 |
| 3948047 | 8.75 | 8.40 | 8.86 | 7.61 | 7.26 | 7.32 | 7.78 | 6.75 | 9.08 | 8.62 | 7.42 | 9.04 |
| 3010503 | 10.68 | 9.41 | 10.28 | 8.48 | 5.68 | 4.34 | 9.47 | 5.34 | 10.45 | 9.18 | 6.86 | 10.81 |
| 3622934 | 5.75 | 7.28 | 6.62 | 8.14 | 8.08 | 8.34 | 8.35 | 8.11 | 6.79 | 5.24 | 7.81 | 5.33 |
| 3441849 | 10.30 | 10.21 | 9.99 | 9.64 | 9.78 | 9.72 | 9.59 | 9.92 | 10.80 | 10.02 | 9.32 | 10.01 |
| 3006572 | 5.97 | 6.49 | 6.39 | 6.70 | 6.28 | 6.16 | 7.21 | 7.04 | 6.71 | 6.88 | 6.72 | 6.08 |
| 3365136 | 8.58 | 8.98 | 9.02 | 9.11 | 9.17 | 9.09 | 9.90 | 10.34 | 8.37 | 8.24 | 7.91 | 7.18 |
| 2642791 | 8.45 | 8.82 | 8.79 | 8.62 | 8.27 | 8.52 | 8.25 | 8.25 | 8.49 | 7.84 | 7.70 | 8.73 |
| 2904485 | 8.94 | 9.24 | 8.02 | 7.21 | 7.85 | 7.14 | 7.59 | 8.20 | 8.09 | 8.71 | 9.68 | 8.12 |
| 3772661 | 10.62 | 9.50 | 11.11 | 10.21 | 9.66 | 9.15 | 10.10 | 9.71 | 10.38 | 9.52 | 8.10 | 11.40 |
| 2796553 | 10.66 | 10.17 | 10.01 | 9.40 | 8.26 | 8.25 | 8.94 | 7.51 | 11.43 | 10.07 | 8.42 | 10.13 |
| 3063795 | 7.30 | 7.19 | 7.77 | 7.66 | 7.21 | 7.02 | 6.89 | 6.76 | 7.06 | 7.89 | 7.19 | 8.23 |
| 3338192 | 8.96 | 9.66 | 8.79 | 10.57 | 10.37 | 10.72 | 10.17 | 10.37 | 8.41 | 8.42 | 10.05 | 8.60 |
| 3214845 | 4.16 | 4.58 | 5.93 | 4.19 | 8.14 | 6.65 | 4.55 | 4.90 | 4.47 | 4.60 | 4.40 | 4.27 |
| 2730303 | 3.99 | 4.15 | 4.15 | 3.92 | 4.83 | 8.59 | 7.88 | 4.10 | 4.24 | 4.44 | 4.20 | 4.24 |
| 3811086 | 7.79 | 7.85 | 8.06 | 7.65 | 7.89 | 7.83 | 7.49 | 7.55 | 7.79 | 7.60 | 8.62 | 8.17 |
| 2981874 | 10.38 | 10.23 | 10.46 | 10.19 | 10.29 | 9.98 | 10.01 | 9.80 | 11.13 | 10.12 | 10.39 | 10.80 |

TABLE 34-continued

Normalized intensity of microarray data for a set of samples.

| TCID | V01 0109 | V01 0110 | V01 0111 | V01 0112 | V01 0113 | V01 0114 | V01 0115 | V01 0116 | V01 0117 | V01 0118 | V01 0119 | V01 0120 |
|---|---|---|---|---|---|---|---|---|---|---|---|---|
| 3242353 | 5.91 | 6.11 | 6.14 | 6.14 | 6.17 | 5.99 | 5.86 | 5.91 | 6.25 | 5.73 | 5.66 | 6.77 |
| 2442008 | 5.18 | 5.21 | 5.59 | 7.47 | 8.89 | 8.22 | 8.96 | 9.84 | 5.49 | 5.73 | 5.75 | 5.40 |
| 3564210 | 10.48 | 9.88 | 10.15 | 8.91 | 7.48 | 7.33 | 8.28 | 7.06 | 10.91 | 9.60 | 8.01 | 9.91 |
| 2490351 | 3.94 | 3.93 | 3.96 | 3.77 | 4.02 | 3.73 | 3.79 | 3.91 | 4.29 | 4.34 | 4.06 | 4.02 |
| 3759006 | 11.28 | 10.04 | 10.06 | 7.92 | 6.46 | 6.46 | 6.96 | 7.56 | 9.40 | 10.53 | 8.55 | 7.09 |
| 3264997 | 3.97 | 4.13 | 3.89 | 3.80 | 4.15 | 3.80 | 3.94 | 3.94 | 4.48 | 4.53 | 4.18 | 4.14 |
| 3912079 | 3.71 | 3.77 | 3.76 | 3.39 | 3.61 | 3.26 | 3.60 | 3.56 | 3.95 | 3.61 | 3.54 | 3.56 |
| 2926802 | 6.00 | 4.94 | 5.67 | 4.83 | 4.78 | 4.91 | 5.40 | 4.47 | 5.63 | 5.90 | 4.91 | 4.60 |
| 2430163 | 3.93 | 3.70 | 3.71 | 5.08 | 4.29 | 3.92 | 3.49 | 3.70 | 4.01 | 4.06 | 3.95 | 4.45 |
| 3039830 | 3.06 | 3.23 | 3.09 | 3.07 | 3.06 | 3.04 | 3.08 | 3.10 | 3.26 | 3.15 | 3.06 | 3.25 |
| 3935486 | 5.64 | 5.93 | 9.08 | 8.09 | 6.90 | 8.03 | 6.09 | 8.63 | 6.97 | 6.84 | 5.72 | 8.19 |
| 3457336 | 5.11 | 5.37 | 8.63 | 5.11 | 5.30 | 4.96 | 5.13 | 5.08 | 5.62 | 5.64 | 5.49 | 5.46 |
| 3811949 | 3.44 | 3.35 | 3.35 | 3.41 | 3.36 | 3.34 | 3.33 | 3.41 | 3.54 | 3.77 | 3.62 | 3.37 |
| 3343832 | 3.72 | 3.80 | 3.79 | 3.58 | 3.79 | 3.76 | 3.65 | 3.79 | 3.93 | 4.22 | 3.93 | 3.89 |
| 3161261 | 5.52 | 5.86 | 5.64 | 5.51 | 5.36 | 5.01 | 5.00 | 5.59 | 6.14 | 7.26 | 6.29 | 5.36 |
| 3594003 | 3.74 | 3.60 | 3.81 | 3.59 | 3.65 | 3.55 | 3.65 | 3.61 | 3.89 | 4.03 | 3.66 | 4.20 |
| 3805614 | 4.77 | 4.85 | 4.76 | 4.24 | 4.58 | 4.69 | 4.66 | 4.66 | 4.98 | 5.07 | 4.72 | 4.74 |
| 3364127 | 6.46 | 6.76 | 6.41 | 6.50 | 6.98 | 6.40 | 6.33 | 6.61 | 7.20 | 7.51 | 7.05 | 6.70 |
| 3834341 | 3.93 | 4.14 | 3.71 | 4.13 | 3.95 | 3.89 | 3.93 | 3.95 | 4.29 | 4.94 | 4.24 | 4.08 |
| 2585400 | 4.55 | 4.21 | 4.77 | 4.01 | 4.43 | 4.39 | 4.37 | 4.84 | 4.84 | 4.81 | 4.57 | 5.18 |
| 2941690 | 4.18 | 4.58 | 3.95 | 4.14 | 4.36 | 3.81 | 3.86 | 4.01 | 4.18 | 4.63 | 4.47 | 4.02 |
| 3484895 | 4.61 | 4.70 | 4.95 | 5.44 | 5.96 | 5.13 | 4.80 | 5.90 | 5.31 | 5.43 | 4.92 | 4.92 |
| 3159754 | 3.65 | 3.68 | 3.45 | 3.62 | 3.55 | 3.56 | 3.61 | 3.56 | 3.62 | 4.38 | 3.90 | 3.63 |
| 2894790 | 4.09 | 3.92 | 3.70 | 3.61 | 3.75 | 3.54 | 3.64 | 3.78 | 4.03 | 3.89 | 5.87 | 4.06 |
| 3363686 | 3.47 | 3.59 | 3.37 | 3.54 | 3.75 | 3.84 | 3.36 | 3.45 | 3.36 | 3.97 | 3.71 | 3.47 |
| 2923928 | 4.29 | 4.17 | 4.19 | 3.82 | 4.05 | 3.83 | 3.92 | 4.14 | 4.65 | 4.26 | 4.09 | 4.05 |
| 2883317 | 4.91 | 4.49 | 5.13 | 4.61 | 4.31 | 4.12 | 5.69 | 4.39 | 4.48 | 5.26 | 5.05 | 5.00 |
| 2479698 | 5.87 | 5.91 | 5.83 | 5.94 | 6.03 | 5.88 | 5.83 | 6.31 | 6.14 | 6.53 | 5.94 | 6.00 |
| 3428225 | 3.64 | 3.58 | 3.67 | 3.48 | 3.60 | 3.58 | 3.54 | 3.55 | 3.72 | 3.87 | 3.89 | 3.85 |
| 3393446 | 7.52 | 6.83 | 7.56 | 6.63 | 6.77 | 6.32 | 6.81 | 6.86 | 7.54 | 7.90 | 7.37 | 8.22 |
| 3116614 | 12.32 | 12.68 | 12.52 | 12.12 | 12.45 | 11.53 | 12.93 | 12.54 | 11.91 | 12.82 | 12.14 | 12.43 |
| 3415320 | 8.91 | 9.27 | 8.95 | 11.06 | 10.81 | 10.77 | 9.37 | 10.60 | 8.34 | 10.73 | 10.10 | 9.19 |
| 3757108 | 9.12 | 7.53 | 7.81 | 10.49 | 10.92 | 10.97 | 8.34 | 10.22 | 8.05 | 7.91 | 10.04 | 7.98 |
| 4012178 | 6.22 | 6.14 | 7.79 | 9.45 | 11.66 | 10.60 | 10.47 | 11.53 | 6.48 | 6.69 | 6.82 | 6.20 |
| 3546213 | 9.94 | 10.75 | 10.58 | 11.23 | 11.11 | 11.02 | 11.08 | 11.01 | 9.99 | 10.30 | 11.37 | 10.17 |
| 3561381 | 9.52 | 9.92 | 8.89 | 10.01 | 10.97 | 9.87 | 10.76 | 10.47 | 8.18 | 8.95 | 11.87 | 8.67 |

TABLE 35

Normalized intensity of microarray data for a set of samples.

| TCID | V01 0121 | V01 0122 | V01 0123 | V01 0124 | V01 0125 | V01 0126 | V01 0127 | V01 0128 | V01 0129 | V01 0130 | V01 0131 | V01 0132 |
|---|---|---|---|---|---|---|---|---|---|---|---|---|
| 2604998 | 5.90 | 7.84 | 5.25 | 7.05 | 7.37 | 8.02 | 8.45 | 8.54 | 7.00 | 8.64 | 7.50 | 8.66 |
| 3603932 | 8.24 | 7.31 | 6.85 | 8.82 | 8.77 | 7.20 | 7.32 | 6.76 | 7.12 | 7.16 | 8.03 | 7.60 |
| 2710599 | 7.71 | 9.95 | 5.36 | 9.31 | 6.19 | 6.32 | 9.18 | 6.16 | 7.29 | 9.92 | 9.84 | 10.55 |
| 2440258 | 8.18 | 8.35 | 9.71 | 7.51 | 7.63 | 8.23 | 7.45 | 6.61 | 9.40 | 8.00 | 7.69 | 7.03 |
| 3169331 | 7.29 | 6.65 | 6.90 | 7.00 | 6.74 | 6.73 | 7.10 | 7.27 | 7.78 | 6.42 | 6.50 | 6.64 |
| 2988882 | 10.21 | 10.11 | 9.90 | 10.19 | 9.85 | 10.23 | 9.56 | 9.80 | 10.08 | 9.74 | 9.78 | 9.70 |
| 2964231 | 10.25 | 8.26 | 7.79 | 10.56 | 10.77 | 8.70 | 8.64 | 7.92 | 8.97 | 9.13 | 9.78 | 7.96 |
| 3111561 | 6.37 | 8.43 | 6.15 | 6.28 | 9.05 | 9.20 | 7.94 | 9.80 | 7.36 | 5.98 | 8.64 | 6.21 |
| 2562529 | 8.77 | 10.07 | 8.55 | 9.79 | 9.74 | 8.33 | 9.59 | 9.28 | 8.59 | 11.18 | 9.37 | 11.15 |
| 3692999 | 10.44 | 10.16 | 7.04 | 10.06 | 9.84 | 10.88 | 11.59 | 12.46 | 11.77 | 12.06 | 11.61 | 10.16 |
| 2439542 | 7.01 | 7.11 | 8.04 | 6.46 | 6.84 | 6.12 | 6.25 | 5.40 | 9.32 | 6.51 | 7.35 | 6.00 |
| 2685304 | 10.59 | 7.59 | 7.90 | 9.09 | 8.60 | 7.72 | 7.63 | 6.03 | 6.98 | 10.00 | 7.84 | 10.02 |
| 2578790 | 4.43 | 4.37 | 4.60 | 4.64 | 5.56 | 6.20 | 6.16 | 7.14 | 5.85 | 4.20 | 5.76 | 4.42 |
| 2373842 | 11.54 | 11.74 | 12.04 | 10.79 | 10.79 | 11.91 | 11.03 | 11.15 | 11.88 | 11.30 | 11.78 | 10.92 |
| 2750627 | 6.10 | 9.64 | 7.37 | 6.19 | 8.25 | 8.14 | 9.56 | 9.03 | 6.11 | 9.21 | 7.85 | 9.29 |
| 3397774 | 7.00 | 4.75 | 5.08 | 5.21 | 4.87 | 4.91 | 5.27 | 5.18 | 6.11 | 4.61 | 5.83 | 5.67 |
| 2635741 | 8.63 | 8.36 | 9.82 | 7.02 | 6.72 | 8.76 | 7.33 | 7.74 | 9.10 | 8.41 | 8.55 | 7.88 |
| 3970833 | 10.42 | 9.63 | 9.20 | 9.78 | 9.78 | 9.33 | 9.59 | 9.40 | 9.84 | 9.83 | 9.61 | 9.64 |
| 3577612 | 10.36 | 10.86 | 11.29 | 10.64 | 9.29 | 10.76 | 10.14 | 10.13 | 10.66 | 10.93 | 11.05 | 11.14 |
| 2708922 | 7.86 | 8.52 | 8.29 | 7.51 | 7.59 | 9.39 | 8.67 | 7.17 | 7.89 | 8.73 | 9.18 | 8.85 |
| 2970897 | 6.76 | 4.93 | 4.95 | 5.27 | 5.97 | 6.37 | 4.80 | 5.37 | 6.24 | 4.81 | 5.66 | 4.93 |
| 3724545 | 10.00 | 10.56 | 9.98 | 8.90 | 8.85 | 9.20 | 11.12 | 10.46 | 9.16 | 8.48 | 9.62 | 8.98 |
| 2798538 | 10.41 | 9.05 | 9.39 | 9.45 | 9.74 | 8.78 | 8.94 | 8.87 | 9.07 | 9.04 | 9.11 | 8.82 |
| 2806468 | 11.22 | 10.61 | 11.77 | 9.63 | 8.40 | 11.67 | 10.68 | 10.82 | 11.08 | 10.84 | 11.05 | 10.29 |
| 2880051 | 7.48 | 6.54 | 6.87 | 5.76 | 5.80 | 6.69 | 6.49 | 6.49 | 6.32 | 6.24 | 6.40 | 6.05 |
| 2732508 | 3.32 | 3.59 | 5.89 | 3.64 | 3.58 | 4.01 | 3.90 | 4.08 | 7.34 | 3.57 | 3.69 | 3.80 |
| 2822492 | 6.41 | 5.73 | 5.62 | 5.62 | 5.46 | 5.87 | 5.51 | 5.85 | 6.01 | 6.19 | 5.22 | 6.10 |
| 3404030 | 8.95 | 8.20 | 9.98 | 7.47 | 7.46 | 9.12 | 7.39 | 6.82 | 8.07 | 8.51 | 7.69 | 8.02 |

TABLE 35-continued

Normalized intensity of microarray data for a set of samples.

| TCID | V01 0121 | V01 0122 | V01 0123 | V01 0124 | V01 0125 | V01 0126 | V01 0127 | V01 0128 | V01 0129 | V01 0130 | V01 0131 | V01 0132 |
|---|---|---|---|---|---|---|---|---|---|---|---|---|
| 3059667 | 5.67 | 7.18 | 6.21 | 4.69 | 9.03 | 7.72 | 8.84 | 9.83 | 5.75 | 6.51 | 4.51 | 6.86 |
| 3108526 | 9.11 | 8.63 | 6.81 | 6.77 | 8.20 | 8.63 | 8.79 | 9.85 | 9.09 | 7.67 | 9.06 | 8.60 |
| 2526806 | 12.30 | 8.73 | 8.21 | 11.45 | 7.99 | 9.23 | 6.12 | 9.01 | 10.79 | 10.19 | 10.13 | 8.84 |
| 2428501 | 8.65 | 6.74 | 7.44 | 8.11 | 8.12 | 7.11 | 6.38 | 5.56 | 7.60 | 6.66 | 7.70 | 6.57 |
| 2657808 | 5.50 | 6.76 | 5.56 | 5.79 | 6.19 | 5.50 | 7.05 | 6.20 | 5.73 | 6.42 | 8.44 | 8.89 |
| 2584018 | 8.09 | 6.88 | 8.36 | 10.53 | 11.49 | 7.32 | 7.95 | 6.49 | 7.40 | 10.26 | 8.60 | 10.76 |
| 3976341 | 9.92 | 10.33 | 10.38 | 11.36 | 9.32 | 9.73 | 9.69 | 8.06 | 9.34 | 10.13 | 9.81 | 10.85 |
| 2739308 | 6.28 | 5.84 | 5.82 | 4.89 | 4.68 | 5.75 | 5.78 | 5.11 | 4.83 | 4.86 | 5.75 | 4.81 |
| 3959862 | 10.47 | 5.82 | 7.09 | 5.96 | 7.65 | 4.85 | 5.40 | 4.80 | 5.73 | 4.85 | 5.47 | 4.58 |
| 2362351 | 7.52 | 8.29 | 8.79 | 6.71 | 6.69 | 8.02 | 6.73 | 6.83 | 8.18 | 7.63 | 7.56 | 6.88 |
| 3648391 | 5.41 | 5.39 | 7.71 | 4.15 | 3.89 | 4.36 | 4.86 | 5.00 | 8.30 | 5.82 | 5.56 | 4.77 |
| 3009299 | 11.48 | 10.66 | 10.78 | 10.90 | 10.91 | 10.65 | 10.88 | 10.33 | 10.93 | 10.75 | 10.65 | 10.88 |
| 3443464 | 6.34 | 5.88 | 5.96 | 6.22 | 5.83 | 6.05 | 5.59 | 5.80 | 5.62 | 5.66 | 6.19 | 5.30 |
| 2730746 | 8.11 | 7.78 | 6.08 | 5.69 | 6.01 | 6.83 | 7.91 | 8.11 | 7.18 | 7.68 | 6.94 | 7.46 |
| 2427619 | 9.16 | 8.85 | 10.11 | 7.21 | 6.39 | 9.14 | 7.70 | 7.95 | 9.36 | 8.44 | 8.87 | 7.87 |
| 3042001 | 9.64 | 8.55 | 8.71 | 9.06 | 8.67 | 9.44 | 9.05 | 9.01 | 8.88 | 8.69 | 8.95 | 8.37 |
| 2566848 | 5.56 | 5.40 | 6.84 | 5.26 | 5.29 | 5.74 | 5.32 | 5.57 | 6.24 | 5.32 | 5.64 | 5.65 |
| 2984616 | 10.33 | 9.30 | 9.19 | 9.68 | 9.65 | 9.01 | 9.19 | 8.67 | 9.27 | 9.20 | 9.65 | 9.00 |
| 2378068 | 9.93 | 7.06 | 8.71 | 9.56 | 8.66 | 7.91 | 7.55 | 6.56 | 8.58 | 8.27 | 7.42 | 9.09 |
| 2721959 | 6.00 | 7.75 | 5.82 | 9.02 | 6.15 | 6.10 | 7.21 | 6.04 | 9.53 | 7.85 | 9.28 | 7.96 |
| 2877508 | 11.12 | 10.56 | 10.26 | 10.93 | 10.73 | 10.11 | 10.21 | 9.58 | 10.66 | 10.17 | 10.52 | 10.11 |
| 3450861 | 6.50 | 5.84 | 7.47 | 5.84 | 5.52 | 6.88 | 4.85 | 5.86 | 6.47 | 6.61 | 6.42 | 5.40 |
| 2688717 | 9.04 | 8.51 | 10.60 | 7.23 | 6.24 | 9.45 | 8.81 | 8.44 | 9.73 | 8.44 | 8.70 | 7.82 |
| 3270270 | 9.01 | 8.91 | 9.56 | 9.01 | 8.77 | 9.09 | 7.94 | 7.65 | 8.67 | 8.61 | 9.27 | 8.41 |
| 3417703 | 4.38 | 9.34 | 4.97 | 5.54 | 7.94 | 4.94 | 9.85 | 9.01 | 4.72 | 10.05 | 4.76 | 8.45 |
| 3302990 | 9.87 | 7.75 | 7.17 | 7.65 | 7.83 | 8.00 | 7.68 | 7.77 | 7.24 | 7.45 | 7.90 | 7.05 |
| 2377283 | 4.90 | 5.10 | 7.83 | 4.32 | 4.27 | 4.81 | 4.87 | 4.68 | 9.22 | 4.54 | 4.98 | 4.79 |
| 3122678 | 10.29 | 4.63 | 4.68 | 6.58 | 4.79 | 6.56 | 5.24 | 5.14 | 4.97 | 4.93 | 5.85 | 4.57 |
| 2688499 | 7.04 | 9.60 | 7.65 | 7.51 | 8.16 | 8.08 | 9.05 | 8.70 | 8.68 | 10.38 | 9.12 | 9.25 |
| 2377094 | 10.44 | 8.29 | 7.88 | 8.20 | 8.52 | 10.32 | 8.66 | 9.05 | 9.48 | 8.19 | 9.33 | 8.59 |
| 3278198 | 9.53 | 6.89 | 6.70 | 8.99 | 8.77 | 8.16 | 7.64 | 7.12 | 8.44 | 7.66 | 8.40 | 8.15 |
| 2598261 | 11.64 | 7.61 | 7.65 | 10.89 | 7.43 | 8.63 | 5.94 | 8.19 | 9.86 | 9.63 | 8.92 | 7.86 |
| 3982612 | 8.81 | 8.90 | 10.81 | 6.15 | 6.19 | 9.15 | 8.35 | 7.59 | 9.84 | 8.70 | 9.09 | 7.98 |
| 2884845 | 4.61 | 5.23 | 4.54 | 6.86 | 4.51 | 4.45 | 4.61 | 5.08 | 4.47 | 5.86 | 4.62 | 8.00 |
| 3982560 | 6.79 | 7.34 | 9.19 | 5.69 | 4.90 | 7.71 | 6.37 | 6.93 | 7.99 | 6.59 | 7.58 | 6.15 |
| 3204285 | 5.77 | 5.46 | 7.14 | 5.50 | 5.44 | 5.87 | 5.76 | 5.77 | 7.89 | 5.37 | 5.50 | 5.23 |
| 3654699 | 12.07 | 11.02 | 8.49 | 12.55 | 13.07 | 11.87 | 11.26 | 11.56 | 12.11 | 11.47 | 12.32 | 11.43 |
| 2638676 | 6.66 | 7.54 | 8.70 | 7.01 | 6.73 | 5.69 | 6.36 | 6.98 | 10.08 | 7.14 | 7.24 | 6.49 |
| 3367673 | 6.34 | 8.66 | 5.32 | 4.65 | 6.63 | 7.97 | 8.11 | 9.30 | 7.51 | 7.31 | 7.57 | 6.64 |
| 3212008 | 6.34 | 8.44 | 6.68 | 7.35 | 6.92 | 7.07 | 9.08 | 6.61 | 6.43 | 9.49 | 7.11 | 9.05 |
| 3326635 | 10.32 | 10.45 | 10.27 | 10.26 | 10.11 | 10.23 | 10.55 | 10.13 | 10.06 | 10.84 | 9.96 | 10.73 |
| 3031556 | 9.46 | 9.80 | 10.64 | 9.24 | 8.96 | 10.12 | 8.62 | 8.72 | 9.97 | 9.42 | 9.79 | 8.64 |
| 3662201 | 10.40 | 10.50 | 7.59 | 10.59 | 10.00 | 11.07 | 11.59 | 12.09 | 11.71 | 11.73 | 11.14 | 9.52 |
| 2809793 | 9.59 | 7.91 | 10.54 | 6.50 | 5.98 | 8.91 | 8.02 | 6.99 | 9.58 | 7.71 | 7.73 | 7.95 |
| 2817731 | 8.63 | 8.09 | 7.69 | 9.58 | 10.40 | 7.89 | 7.39 | 7.86 | 7.77 | 7.94 | 8.08 | 7.52 |
| 4020655 | 4.81 | 8.06 | 5.54 | 6.05 | 4.82 | 5.29 | 8.53 | 5.33 | 4.95 | 8.09 | 5.67 | 7.83 |
| 3494629 | 7.10 | 4.47 | 4.44 | 4.61 | 4.39 | 4.80 | 4.85 | 4.48 | 4.73 | 5.49 | 7.05 | 5.29 |
| 3852832 | 8.97 | 9.18 | 9.98 | 7.08 | 6.76 | 9.89 | 8.50 | 8.51 | 9.29 | 9.11 | 10.30 | 8.83 |
| 3761959 | 9.03 | 9.55 | 8.82 | 10.00 | 9.58 | 8.94 | 10.39 | 8.81 | 8.96 | 9.23 | 8.65 | 9.09 |
| 2834282 | 6.61 | 6.69 | 6.19 | 7.04 | 6.26 | 5.98 | 7.81 | 6.19 | 5.59 | 7.76 | 7.57 | 7.99 |
| 3341497 | 6.52 | 6.07 | 6.07 | 6.37 | 6.18 | 6.17 | 7.46 | 6.53 | 5.81 | 7.04 | 7.65 | 7.76 |
| 2372812 | 5.12 | 4.64 | 5.24 | 4.71 | 4.63 | 4.52 | 4.94 | 4.76 | 10.47 | 4.92 | 4.82 | 4.75 |
| 2486815 | 10.87 | 9.82 | 10.65 | 10.94 | 10.82 | 10.17 | 8.21 | 8.51 | 10.20 | 9.77 | 10.14 | 8.71 |
| 3768474 | 8.65 | 8.40 | 8.37 | 9.38 | 9.39 | 8.82 | 8.53 | 7.82 | 7.79 | 7.84 | 8.85 | 7.96 |
| 3142381 | 5.90 | 3.67 | 7.34 | 8.49 | 5.14 | 5.82 | 5.19 | 5.56 | 4.72 | 4.56 | 4.87 | 5.53 |
| 2396750 | 8.04 | 7.25 | 7.14 | 7.51 | 7.10 | 7.18 | 7.41 | 6.89 | 6.94 | 6.99 | 6.72 | 8.05 |
| 3902489 | 10.62 | 11.77 | 10.94 | 10.68 | 10.25 | 12.25 | 11.64 | 10.93 | 11.43 | 11.04 | 12.03 | 11.08 |
| 3032647 | 6.00 | 6.79 | 6.00 | 6.02 | 6.32 | 7.10 | 6.06 | 7.97 | 6.49 | 5.64 | 6.09 | 5.80 |
| 3875642 | 5.78 | 5.76 | 6.68 | 5.42 | 4.89 | 6.32 | 5.56 | 6.11 | 5.19 | 5.39 | 5.89 | 6.44 |
| 4027585 | 10.99 | 11.39 | 11.23 | 11.42 | 11.14 | 12.10 | 11.15 | 10.34 | 11.22 | 10.32 | 11.67 | 10.76 |
| 2352609 | 6.49 | 7.12 | 5.59 | 6.07 | 6.14 | 6.57 | 8.02 | 7.47 | 5.95 | 6.84 | 6.81 | 7.06 |
| 3376529 | 9.01 | 8.40 | 8.40 | 9.00 | 6.98 | 7.80 | 9.05 | 7.63 | 8.79 | 9.31 | 9.29 | 9.60 |
| 2491271 | 13.43 | 13.30 | 13.50 | 13.59 | 13.69 | 13.08 | 12.78 | 12.83 | 13.54 | 13.44 | 13.14 | 13.26 |
| 3874751 | 9.69 | 9.11 | 9.42 | 10.29 | 10.60 | 8.30 | 9.31 | 9.35 | 8.98 | 9.29 | 9.29 | 9.36 |
| 2326463 | 12.28 | 12.17 | 12.81 | 12.02 | 13.01 | 12.01 | 11.35 | 11.14 | 12.42 | 12.17 | 12.00 | 11.45 |
| 3341061 | 7.88 | 7.47 | 7.60 | 9.10 | 9.73 | 6.98 | 6.65 | 6.31 | 7.18 | 7.28 | 6.85 | 7.22 |
| 3839910 | 9.30 | 8.91 | 9.62 | 7.58 | 6.19 | 9.69 | 8.18 | 8.84 | 9.15 | 8.18 | 10.12 | 8.69 |
| 2708855 | 4.39 | 5.62 | 4.86 | 5.39 | 3.97 | 4.48 | 6.78 | 4.15 | 4.57 | 7.47 | 4.93 | 8.32 |
| 3512874 | 12.03 | 12.01 | 12.39 | 11.91 | 11.65 | 12.29 | 11.48 | 11.49 | 12.30 | 11.77 | 12.13 | 11.37 |
| 2701071 | 10.02 | 10.31 | 11.00 | 8.86 | 9.86 | 10.93 | 9.65 | 9.92 | 10.56 | 10.18 | 10.99 | 9.61 |
| 3486096 | 5.30 | 7.43 | 5.60 | 5.51 | 6.09 | 6.68 | 7.67 | 7.39 | 7.44 | 8.88 | 7.87 | 8.81 |
| 2412668 | 8.50 | 8.09 | 8.83 | 8.94 | 9.13 | 7.93 | 7.93 | 7.29 | 8.05 | 8.12 | 8.62 | 8.16 |
| 3329343 | 8.30 | 8.42 | 7.23 | 7.82 | 6.95 | 6.99 | 7.76 | 7.56 | 7.12 | 7.71 | 7.21 | 8.29 |
| 3259367 | 4.24 | 6.24 | 4.38 | 5.08 | 4.37 | 4.43 | 7.57 | 4.43 | 4.34 | 5.63 | 4.84 | 5.16 |
| 3373845 | 9.43 | 9.06 | 9.19 | 10.30 | 10.83 | 8.64 | 8.26 | 7.68 | 8.94 | 8.88 | 8.60 | 8.01 |

TABLE 35-continued

Normalized intensity of microarray data for a set of samples.

| TCID | V01 0121 | V01 0122 | V01 0123 | V01 0124 | V01 0125 | V01 0126 | V01 0127 | V01 0128 | V01 0129 | V01 0130 | V01 0131 | V01 0132 |
|---|---|---|---|---|---|---|---|---|---|---|---|---|
| 2321911 | 8.17 | 8.94 | 8.84 | 9.19 | 9.25 | 9.23 | 8.56 | 8.75 | 8.72 | 8.06 | 9.41 | 8.34 |
| 3353914 | 7.58 | 6.43 | 6.81 | 9.70 | 10.07 | 6.29 | 6.60 | 6.40 | 6.32 | 7.43 | 6.83 | 7.00 |
| 3744680 | 7.92 | 7.82 | 8.49 | 8.42 | 8.61 | 8.20 | 7.34 | 7.34 | 7.81 | 7.62 | 7.94 | 7.54 |
| 2373336 | 5.67 | 5.43 | 7.19 | 5.80 | 5.21 | 6.88 | 5.39 | 5.41 | 6.40 | 5.24 | 5.69 | 5.75 |
| 3067478 | 4.90 | 7.03 | 5.24 | 5.98 | 4.45 | 5.14 | 6.59 | 5.72 | 5.97 | 7.98 | 5.61 | 8.15 |
| 3976766 | 8.48 | 8.35 | 9.55 | 7.87 | 8.06 | 8.95 | 7.61 | 7.88 | 8.75 | 8.09 | 8.81 | 8.09 |
| 3246888 | 5.59 | 8.21 | 5.40 | 5.10 | 5.36 | 6.24 | 7.62 | 6.03 | 5.46 | 7.13 | 6.28 | 7.04 |
| 3147985 | 8.30 | 7.05 | 6.87 | 9.39 | 8.81 | 6.53 | 6.37 | 6.42 | 5.96 | 7.08 | 6.59 | 6.67 |
| 3185522 | 10.33 | 9.00 | 8.87 | 11.02 | 11.63 | 8.78 | 8.92 | 8.34 | 9.40 | 9.73 | 9.21 | 9.58 |
| 3861948 | 12.60 | 12.71 | 13.14 | 12.41 | 12.31 | 12.92 | 12.08 | 12.23 | 12.89 | 12.54 | 12.97 | 12.40 |
| 3393479 | 8.67 | 8.83 | 9.10 | 9.95 | 10.76 | 8.10 | 7.94 | 8.41 | 8.57 | 9.36 | 8.85 | 8.56 |
| 3540862 | 8.05 | 6.62 | 6.54 | 6.95 | 6.82 | 7.14 | 7.20 | 7.28 | 6.58 | 7.11 | 7.33 | 7.04 |
| 2777714 | 11.05 | 11.95 | 11.59 | 10.82 | 10.41 | 12.36 | 11.77 | 11.24 | 11.66 | 10.89 | 11.88 | 11.34 |
| 3110395 | 4.85 | 6.06 | 4.52 | 4.33 | 4.55 | 4.53 | 5.00 | 4.47 | 4.20 | 4.72 | 4.42 | 5.24 |
| 3895795 | 8.30 | 8.62 | 9.06 | 8.91 | 7.57 | 9.37 | 8.39 | 8.46 | 8.31 | 8.87 | 9.45 | 8.66 |
| 2854445 | 10.73 | 8.39 | 9.69 | 11.54 | 11.50 | 8.53 | 7.30 | 7.33 | 8.83 | 9.74 | 9.11 | 8.22 |
| 3606034 | 7.58 | 7.58 | 7.20 | 8.68 | 9.20 | 7.36 | 7.53 | 8.39 | 6.92 | 7.34 | 6.85 | 6.91 |
| 3375735 | 8.30 | 8.10 | 8.77 | 8.83 | 8.80 | 7.56 | 7.38 | 7.96 | 7.77 | 8.00 | 7.39 | 7.75 |
| 3948047 | 8.42 | 8.54 | 9.65 | 8.94 | 9.52 | 8.60 | 7.65 | 7.94 | 8.89 | 8.09 | 8.70 | 8.16 |
| 3010503 | 10.23 | 9.60 | 9.85 | 11.49 | 11.26 | 9.68 | 8.47 | 7.92 | 9.41 | 9.65 | 10.03 | 8.93 |
| 3622934 | 7.13 | 6.96 | 6.92 | 6.85 | 5.65 | 6.81 | 7.44 | 6.64 | 7.55 | 8.23 | 7.12 | 7.91 |
| 3441849 | 9.95 | 9.92 | 10.40 | 10.16 | 9.73 | 10.10 | 9.62 | 9.34 | 9.84 | 10.09 | 10.09 | 9.89 |
| 3006572 | 6.50 | 7.25 | 7.07 | 6.55 | 6.20 | 6.56 | 6.83 | 6.47 | 6.51 | 6.25 | 6.59 | 6.62 |
| 3365136 | 8.32 | 9.26 | 8.70 | 8.64 | 8.58 | 7.96 | 10.37 | 8.40 | 8.29 | 10.21 | 8.97 | 11.47 |
| 2642791 | 8.56 | 8.46 | 8.66 | 8.89 | 9.22 | 7.86 | 7.73 | 7.63 | 8.76 | 8.14 | 8.26 | 7.82 |
| 2904485 | 6.62 | 8.83 | 7.20 | 7.52 | 7.90 | 7.79 | 9.10 | 9.79 | 7.25 | 7.91 | 6.94 | 8.21 |
| 3772661 | 10.98 | 9.65 | 10.28 | 11.46 | 11.84 | 9.89 | 8.99 | 8.61 | 9.69 | 10.43 | 9.86 | 9.88 |
| 2796553 | 10.44 | 9.95 | 9.93 | 10.47 | 10.14 | 10.89 | 9.47 | 9.04 | 9.81 | 10.25 | 10.99 | 9.35 |
| 3063795 | 8.46 | 7.18 | 7.68 | 8.02 | 8.32 | 7.78 | 6.99 | 7.46 | 6.98 | 7.30 | 7.56 | 7.83 |
| 3338192 | 8.89 | 9.70 | 7.83 | 8.57 | 7.90 | 7.66 | 9.46 | 8.48 | 8.20 | 10.42 | 8.93 | 10.49 |
| 3214845 | 4.36 | 4.31 | 4.84 | 4.89 | 4.19 | 5.09 | 4.41 | 4.58 | 4.73 | 4.16 | 4.59 | 4.60 |
| 2730303 | 4.44 | 4.23 | 6.13 | 4.13 | 3.97 | 4.74 | 4.26 | 4.14 | 7.91 | 3.96 | 4.53 | 4.26 |
| 3811086 | 7.39 | 7.67 | 7.82 | 7.92 | 8.35 | 7.42 | 7.26 | 8.20 | 7.85 | 7.54 | 7.95 | 7.02 |
| 2981874 | 10.47 | 10.48 | 10.27 | 10.55 | 10.57 | 10.34 | 10.68 | 10.72 | 10.76 | 10.32 | 10.59 | 10.27 |
| 3242353 | 6.23 | 5.98 | 6.16 | 6.83 | 6.15 | 5.74 | 6.07 | 5.91 | 6.16 | 5.60 | 5.91 | 5.48 |
| 2442008 | 5.55 | 6.80 | 5.64 | 6.04 | 5.53 | 5.72 | 6.55 | 5.73 | 5.72 | 8.51 | 6.34 | 8.78 |
| 3564210 | 9.72 | 9.72 | 10.08 | 9.75 | 9.82 | 10.14 | 9.24 | 8.34 | 9.63 | 9.40 | 9.77 | 8.99 |
| 2490351 | 4.17 | 4.10 | 4.13 | 4.28 | 4.15 | 4.16 | 4.27 | 4.32 | 4.18 | 4.00 | 4.34 | 4.26 |
| 3759006 | 9.28 | 10.09 | 9.45 | 8.72 | 7.32 | 11.22 | 10.25 | 8.68 | 9.75 | 9.21 | 10.65 | 9.67 |
| 3264997 | 4.55 | 3.98 | 4.11 | 4.30 | 4.17 | 4.32 | 4.20 | 4.60 | 3.99 | 4.09 | 4.18 | 4.13 |
| 3912079 | 3.69 | 3.61 | 3.92 | 3.69 | 3.73 | 4.01 | 3.58 | 3.73 | 3.84 | 3.56 | 3.79 | 3.66 |
| 2926802 | 5.10 | 5.35 | 6.11 | 4.74 | 4.76 | 5.52 | 5.08 | 5.25 | 6.06 | 4.98 | 6.51 | 5.63 |
| 2430163 | 4.03 | 3.78 | 4.03 | 4.37 | 3.83 | 4.32 | 3.83 | 4.15 | 3.98 | 3.91 | 3.84 | 3.88 |
| 3039830 | 3.12 | 3.09 | 3.14 | 3.33 | 3.08 | 3.46 | 3.11 | 3.34 | 3.08 | 3.09 | 3.13 | 3.16 |
| 3935486 | 7.20 | 5.86 | 7.53 | 8.35 | 7.86 | 6.59 | 5.42 | 6.20 | 6.08 | 6.56 | 6.23 | 5.53 |
| 3457336 | 5.80 | 5.45 | 5.50 | 5.60 | 5.43 | 5.85 | 5.74 | 5.81 | 5.36 | 5.27 | 5.51 | 5.66 |
| 3811949 | 3.38 | 3.48 | 3.68 | 3.56 | 3.42 | 3.60 | 3.45 | 3.68 | 3.48 | 3.39 | 3.64 | 3.35 |
| 3343832 | 4.15 | 3.63 | 4.05 | 3.84 | 3.92 | 4.12 | 4.13 | 3.92 | 4.11 | 3.80 | 4.08 | 4.07 |
| 3161261 | 5.75 | 6.13 | 6.52 | 5.47 | 5.91 | 6.35 | 6.17 | 6.90 | 6.07 | 6.23 | 5.90 | 5.71 |
| 3594003 | 4.05 | 3.69 | 3.94 | 3.92 | 4.36 | 3.57 | 3.62 | 3.80 | 3.66 | 3.59 | 3.77 | 3.59 |
| 3805614 | 5.00 | 4.75 | 4.95 | 5.15 | 5.05 | 4.60 | 4.80 | 5.07 | 4.73 | 4.81 | 4.80 | 4.86 |
| 3364127 | 8.36 | 6.96 | 6.88 | 8.35 | 7.16 | 10.55 | 7.21 | 7.50 | 6.98 | 6.42 | 7.46 | 6.93 |
| 3834341 | 3.99 | 4.08 | 4.10 | 4.17 | 4.06 | 4.05 | 4.13 | 4.03 | 3.96 | 3.95 | 4.28 | 4.04 |
| 2585400 | 4.53 | 4.80 | 4.58 | 4.54 | 4.20 | 4.52 | 4.41 | 4.36 | 4.25 | 4.41 | 4.30 | 4.23 |
| 2941690 | 4.07 | 4.42 | 4.33 | 4.22 | 4.22 | 4.44 | 4.43 | 4.96 | 4.48 | 4.17 | 4.67 | 4.26 |
| 3484895 | 5.43 | 4.60 | 5.11 | 4.96 | 4.76 | 5.04 | 4.99 | 5.26 | 4.93 | 4.68 | 5.07 | 5.34 |
| 3159754 | 4.18 | 3.60 | 3.65 | 3.73 | 3.72 | 3.65 | 3.99 | 4.00 | 3.67 | 3.62 | 3.78 | 3.58 |
| 2894790 | 3.87 | 3.91 | 4.00 | 3.92 | 3.84 | 4.05 | 3.89 | 4.06 | 3.71 | 3.85 | 3.90 | 4.35 |
| 3363686 | 3.38 | 3.55 | 3.42 | 3.47 | 3.29 | 4.01 | 3.38 | 3.68 | 3.49 | 3.49 | 3.65 | 3.57 |
| 2923928 | 4.16 | 4.18 | 4.22 | 5.29 | 4.52 | 4.35 | 4.47 | 5.10 | 4.31 | 4.34 | 4.61 | 4.25 |
| 2883317 | 5.50 | 4.97 | 5.95 | 5.30 | 5.65 | 5.58 | 4.69 | 4.70 | 6.01 | 4.24 | 4.86 | 5.39 |
| 2479698 | 5.97 | 6.22 | 5.95 | 6.03 | 6.00 | 6.32 | 6.25 | 6.47 | 5.85 | 6.00 | 6.09 | 5.90 |
| 3428225 | 3.91 | 3.56 | 3.85 | 3.82 | 3.72 | 3.84 | 3.92 | 4.03 | 3.62 | 3.58 | 4.03 | 3.73 |
| 3393446 | 7.65 | 7.04 | 7.69 | 8.14 | 8.72 | 7.64 | 7.29 | 7.67 | 7.46 | 6.77 | 7.62 | 7.37 |
| 3116614 | 9.99 | 12.81 | 9.17 | 10.25 | 11.62 | 12.15 | 13.25 | 13.25 | 12.37 | 12.30 | 12.47 | 12.05 |
| 3415320 | 10.48 | 9.71 | 6.84 | 8.29 | 7.89 | 9.35 | 10.00 | 10.44 | 8.97 | 9.12 | 9.85 | 9.27 |
| 3757108 | 8.12 | 8.13 | 7.33 | 9.36 | 7.57 | 7.83 | 7.64 | 8.08 | 7.50 | 9.42 | 7.77 | 9.03 |
| 4012178 | 6.74 | 7.51 | 6.55 | 6.56 | 6.07 | 6.96 | 8.95 | 6.47 | 6.88 | 7.77 | 8.64 | 9.47 |
| 3546213 | 9.46 | 10.94 | 6.09 | 9.79 | 9.13 | 9.32 | 11.66 | 10.79 | 9.80 | 10.75 | 9.67 | 11.08 |
| 3561381 | 8.69 | 9.61 | 5.89 | 7.76 | 7.84 | 9.03 | 10.56 | 10.30 | 8.33 | 10.74 | 9.12 | 10.48 |

TABLE 36

Normalized intensity of microarray data for a set of samples.

| TCID | V01 0133 | V01 0134 | V01 0135 | V01 0136 | V01 0137 | V01 0138 | V01 0139 | V01 0140 | V01 0141 | V01 0142 | V01 0143 | V01 0144 |
|---|---|---|---|---|---|---|---|---|---|---|---|---|
| 2604998 | 5.25 | 8.29 | 6.62 | 7.52 | 7.60 | 7.73 | 8.29 | 9.43 | 5.27 | 6.55 | 7.40 | 8.78 |
| 3603932 | 8.60 | 8.14 | 6.32 | 6.94 | 7.16 | 6.68 | 7.59 | 7.31 | 7.38 | 6.87 | 8.94 | 6.85 |
| 2710599 | 6.60 | 9.16 | 9.65 | 11.97 | 6.96 | 6.35 | 11.84 | 10.70 | 6.69 | 7.46 | 8.01 | 9.70 |
| 2440258 | 7.45 | 6.59 | 9.61 | 8.06 | 9.35 | 8.33 | 6.69 | 4.94 | 9.26 | 9.91 | 7.71 | 7.20 |
| 3169331 | 7.13 | 7.36 | 6.80 | 7.93 | 6.73 | 6.95 | 7.33 | 6.31 | 7.29 | 6.87 | 7.50 | 7.35 |
| 2988882 | 9.76 | 10.56 | 10.17 | 10.13 | 9.58 | 9.64 | 9.70 | 9.66 | 9.79 | 9.92 | 9.91 | 10.11 |
| 2964231 | 9.39 | 9.39 | 7.37 | 8.63 | 9.21 | 7.71 | 10.08 | 7.14 | 8.28 | 7.58 | 10.43 | 8.31 |
| 3111561 | 5.51 | 10.39 | 4.78 | 4.80 | 9.01 | 9.21 | 4.94 | 7.04 | 6.61 | 6.44 | 8.38 | 10.76 |
| 2562529 | 8.76 | 9.68 | 9.44 | 10.01 | 8.70 | 8.67 | 10.79 | 11.73 | 8.16 | 8.27 | 9.67 | 10.35 |
| 3692999 | 8.48 | 10.55 | 8.63 | 6.40 | 9.84 | 10.38 | 9.74 | 9.51 | 7.57 | 12.17 | 9.71 | 11.96 |
| 2439554 | 6.54 | 5.11 | 9.08 | 6.75 | 7.77 | 7.39 | 6.21 | 5.05 | 7.39 | 7.35 | 6.73 | 6.56 |
| 2685304 | 7.39 | 8.42 | 8.68 | 11.09 | 7.74 | 7.06 | 11.89 | 10.87 | 7.93 | 6.82 | 9.13 | 6.67 |
| 2578790 | 5.05 | 6.37 | 4.79 | 4.15 | 5.75 | 5.75 | 4.08 | 4.71 | 4.64 | 5.27 | 5.87 | 5.85 |
| 2373842 | 11.24 | 9.81 | 11.34 | 10.72 | 11.82 | 11.61 | 10.25 | 8.55 | 11.84 | 12.19 | 10.82 | 10.86 |
| 2750627 | 5.15 | 10.03 | 7.54 | 7.44 | 8.63 | 8.09 | 10.50 | 10.08 | 5.45 | 5.83 | 8.23 | 10.33 |
| 3397774 | 5.90 | 4.69 | 5.22 | 4.67 | 5.09 | 4.93 | 4.35 | 4.86 | 5.25 | 5.11 | 5.35 | 5.30 |
| 2635741 | 8.19 | 6.66 | 8.94 | 8.42 | 9.48 | 8.79 | 7.12 | 6.11 | 9.43 | 9.88 | 7.29 | 7.66 |
| 3970833 | 9.40 | 9.83 | 9.34 | 9.26 | 9.18 | 9.84 | 9.78 | 9.75 | 8.90 | 9.17 | 9.87 | 9.93 |
| 3577612 | 10.83 | 9.44 | 10.84 | 11.13 | 11.10 | 10.69 | 11.23 | 10.55 | 11.08 | 11.27 | 10.57 | 10.01 |
| 2708922 | 7.36 | 6.23 | 7.31 | 8.18 | 8.36 | 6.87 | 8.44 | 8.71 | 10.13 | 8.46 | 6.73 | 7.08 |
| 2970897 | 5.20 | 6.71 | 5.29 | 5.02 | 5.25 | 5.08 | 5.81 | 4.89 | 4.92 | 5.16 | 5.73 | 6.49 |
| 3724545 | 6.93 | 10.25 | 7.91 | 9.99 | 9.14 | 10.71 | 9.97 | 9.32 | 10.18 | 9.14 | 9.28 | 10.13 |
| 2798538 | 9.59 | 9.49 | 9.42 | 9.51 | 9.47 | 8.69 | 9.25 | 8.73 | 9.26 | 9.04 | 9.96 | 8.71 |
| 2806468 | 10.77 | 9.39 | 11.40 | 10.95 | 11.59 | 11.05 | 10.14 | 7.90 | 12.25 | 12.47 | 9.75 | 9.83 |
| 2880051 | 6.73 | 6.33 | 6.67 | 5.97 | 6.85 | 7.23 | 5.73 | 6.04 | 6.75 | 7.29 | 5.96 | 6.40 |
| 2732508 | 4.19 | 3.68 | 7.05 | 3.84 | 4.65 | 5.67 | 3.46 | 3.94 | 3.92 | 3.57 | 3.62 | 3.58 |
| 2822492 | 5.71 | 6.52 | 4.99 | 6.13 | 5.81 | 5.76 | 5.30 | 5.69 | 5.80 | 5.47 | 5.75 | 6.11 |
| 3404030 | 7.55 | 6.64 | 8.17 | 7.73 | 9.54 | 9.19 | 6.53 | 5.85 | 9.56 | 9.71 | 7.11 | 6.90 |
| 3059667 | 5.33 | 7.97 | 6.50 | 5.56 | 8.23 | 10.03 | 4.25 | 8.14 | 5.00 | 7.85 | 10.23 | 11.17 |
| 3108526 | 6.08 | 10.47 | 7.32 | 6.75 | 9.34 | 9.38 | 8.49 | 8.71 | 6.43 | 8.44 | 8.83 | 10.10 |
| 2526806 | 7.20 | 12.05 | 12.57 | 12.71 | 11.70 | 7.77 | 13.08 | 8.63 | 6.11 | 10.17 | 12.04 | 5.36 |
| 2428501 | 7.59 | 7.64 | 7.65 | 8.26 | 7.66 | 7.11 | 7.72 | 6.18 | 7.51 | 7.71 | 8.74 | 6.02 |
| 2657808 | 6.22 | 6.67 | 8.47 | 11.83 | 5.82 | 6.20 | 11.64 | 8.88 | 5.81 | 5.53 | 5.31 | 8.46 |
| 2584018 | 9.59 | 8.16 | 8.37 | 10.47 | 8.13 | 6.99 | 10.74 | 11.16 | 8.76 | 8.81 | 10.89 | 7.31 |
| 3976341 | 10.71 | 10.00 | 10.66 | 11.16 | 10.15 | 8.94 | 11.42 | 11.35 | 10.45 | 10.85 | 10.57 | 8.38 |
| 2739308 | 5.54 | 6.39 | 4.73 | 4.76 | 5.33 | 5.35 | 4.37 | 4.79 | 6.79 | 5.42 | 4.64 | 5.24 |
| 3959862 | 4.90 | 4.84 | 5.81 | 4.36 | 5.75 | 4.57 | 4.30 | 4.74 | 7.56 | 4.29 | 6.84 | 4.24 |
| 2362351 | 8.19 | 5.79 | 7.81 | 7.26 | 8.49 | 8.11 | 6.41 | 5.69 | 8.56 | 8.82 | 7.10 | 6.90 |
| 3648391 | 4.20 | 3.91 | 9.41 | 4.89 | 7.00 | 5.12 | 3.99 | 4.40 | 6.55 | 6.55 | 4.13 | 4.82 |
| 3009299 | 11.05 | 11.20 | 11.00 | 11.01 | 10.72 | 10.61 | 10.74 | 10.71 | 10.61 | 10.55 | 10.85 | 11.61 |
| 3443464 | 7.41 | 5.06 | 5.65 | 5.39 | 6.73 | 6.23 | 5.05 | 5.21 | 6.04 | 5.55 | 5.51 | 5.25 |
| 2730746 | 5.30 | 9.08 | 5.44 | 5.92 | 7.70 | 7.63 | 5.89 | 7.32 | 5.96 | 6.33 | 7.36 | 8.56 |
| 2427619 | 8.10 | 5.74 | 9.53 | 8.30 | 9.69 | 8.28 | 6.91 | 5.40 | 10.02 | 10.30 | 6.79 | 7.42 |
| 3042001 | 9.36 | 8.88 | 8.59 | 8.30 | 8.70 | 8.74 | 8.96 | 8.73 | 8.21 | 8.66 | 8.90 | 9.39 |
| 2566848 | 6.25 | 4.84 | 7.55 | 5.89 | 5.71 | 5.54 | 4.92 | 6.02 | 6.41 | 6.78 | 5.26 | 5.04 |
| 2984616 | 8.92 | 9.51 | 8.67 | 8.66 | 9.24 | 8.90 | 9.27 | 8.71 | 9.74 | 8.95 | 9.46 | 9.27 |
| 2378068 | 9.01 | 8.87 | 8.38 | 8.45 | 7.70 | 7.48 | 9.06 | 8.68 | 9.13 | 7.49 | 9.41 | 6.88 |
| 2721959 | 6.77 | 8.32 | 11.14 | 12.65 | 8.10 | 5.90 | 12.99 | 7.20 | 6.05 | 5.90 | 9.26 | 6.87 |
| 2877508 | 10.50 | 10.89 | 10.30 | 10.66 | 10.16 | 9.90 | 10.96 | 10.02 | 9.72 | 9.96 | 10.80 | 10.49 |
| 3450861 | 6.17 | 5.11 | 7.09 | 6.61 | 7.56 | 6.34 | 5.01 | 4.80 | 7.97 | 8.00 | 5.14 | 5.13 |
| 2688717 | 8.40 | 6.37 | 10.64 | 9.38 | 9.34 | 8.84 | 7.02 | 6.25 | 10.62 | 10.78 | 7.75 | 7.68 |
| 3270270 | 9.25 | 7.62 | 8.07 | 8.53 | 9.12 | 8.49 | 9.21 | 7.92 | 9.34 | 9.15 | 9.09 | 7.90 |
| 3417703 | 5.45 | 8.63 | 5.55 | 6.25 | 8.90 | 7.48 | 6.54 | 9.71 | 4.69 | 7.11 | 6.34 | 10.17 |
| 3302990 | 7.59 | 8.07 | 7.34 | 8.30 | 7.59 | 7.08 | 8.76 | 7.07 | 6.84 | 7.57 | 8.42 | 7.45 |
| 2377283 | 5.10 | 4.13 | 9.02 | 5.19 | 5.37 | 4.40 | 4.09 | 4.59 | 6.34 | 6.02 | 4.25 | 4.53 |
| 3122678 | 5.89 | 4.74 | 4.74 | 5.60 | 5.84 | 5.47 | 6.36 | 4.79 | 5.18 | 4.71 | 4.98 | 5.07 |
| 2688499 | 8.28 | 10.84 | 8.64 | 10.37 | 8.58 | 8.07 | 10.32 | 9.72 | 6.97 | 8.13 | 8.00 | 10.00 |
| 2377094 | 8.19 | 8.91 | 8.14 | 8.08 | 8.23 | 8.82 | 9.03 | 8.13 | 7.18 | 8.22 | 8.81 | 9.54 |
| 3278198 | 7.89 | 8.77 | 6.93 | 8.46 | 7.85 | 7.46 | 9.16 | 7.08 | 7.76 | 7.52 | 8.70 | 8.58 |
| 2598261 | 7.63 | 11.31 | 12.32 | 12.90 | 10.64 | 7.47 | 13.01 | 7.86 | 6.57 | 9.00 | 11.36 | 6.05 |
| 3982612 | 8.13 | 6.42 | 10.86 | 9.31 | 10.32 | 9.09 | 7.52 | 5.23 | 10.36 | 10.74 | 7.64 | 7.45 |
| 2884845 | 4.96 | 4.86 | 6.40 | 8.81 | 4.93 | 4.46 | 8.23 | 6.23 | 4.87 | 4.71 | 4.73 | 4.33 |
| 3982560 | 6.40 | 5.57 | 8.66 | 7.57 | 8.00 | 6.61 | 5.26 | 4.74 | 8.58 | 8.60 | 6.05 | 5.53 |
| 3204285 | 6.80 | 4.78 | 8.26 | 7.05 | 6.03 | 6.17 | 5.69 | 5.49 | 5.95 | 5.15 | 5.87 | 5.80 |
| 3654699 | 11.94 | 12.27 | 10.25 | 11.23 | 12.17 | 12.17 | 11.85 | 10.28 | 8.39 | 10.05 | 12.49 | 10.82 |
| 2638676 | 7.63 | 6.35 | 10.30 | 7.04 | 8.16 | 6.44 | 6.28 | 6.04 | 9.18 | 8.46 | 7.36 | 6.30 |
| 3367673 | 5.46 | 8.10 | 6.07 | 4.28 | 7.75 | 7.43 | 4.86 | 5.89 | 4.84 | 6.39 | 7.46 | 8.49 |
| 3212008 | 6.85 | 6.90 | 6.80 | 6.89 | 6.74 | 6.79 | 8.27 | 9.73 | 6.61 | 6.28 | 6.46 | 8.81 |
| 3326635 | 10.28 | 10.59 | 10.03 | 10.35 | 10.24 | 9.72 | 10.08 | 10.02 | 10.38 | 10.41 | 10.18 | 10.46 |
| 3031556 | 9.71 | 7.65 | 9.58 | 9.09 | 10.22 | 9.73 | 7.98 | 5.77 | 10.99 | 10.53 | 9.26 | 8.41 |
| 3662201 | 9.32 | 11.15 | 8.38 | 7.90 | 10.16 | 10.69 | 9.61 | 9.59 | 8.53 | 12.17 | 8.82 | 10.13 |
| 2809793 | 8.05 | 5.77 | 10.50 | 8.63 | 9.89 | 7.82 | 6.90 | 5.31 | 9.45 | 9.42 | 7.25 | 7.80 |
| 2817731 | 9.26 | 8.11 | 6.37 | 7.45 | 8.13 | 7.73 | 8.11 | 7.55 | 7.83 | 7.78 | 9.92 | 7.36 |
| 4020655 | 5.79 | 4.44 | 5.57 | 5.46 | 5.04 | 5.07 | 6.60 | 8.96 | 5.59 | 5.48 | 4.71 | 7.18 |
| 3494629 | 4.57 | 5.79 | 5.69 | 8.54 | 4.31 | 4.54 | 8.57 | 4.71 | 5.11 | 4.38 | 4.80 | 5.46 |

TABLE 36-continued

Normalized intensity of microarray data for a set of samples.

| TCID | V01 0133 | V01 0134 | V01 0135 | V01 0136 | V01 0137 | V01 0138 | V01 0139 | V01 0140 | V01 0141 | V01 0142 | V01 0143 | V01 0144 |
|---|---|---|---|---|---|---|---|---|---|---|---|---|
| 3852832 | 8.64 | 6.29 | 6.73 | 8.69 | 10.15 | 8.61 | 7.56 | 6.53 | 10.10 | 9.86 | 8.22 | 8.50 |
| 3761959 | 8.99 | 10.23 | 9.06 | 9.04 | 9.01 | 8.85 | 9.49 | 9.51 | 8.54 | 8.82 | 9.94 | 10.49 |
| 2834282 | 6.68 | 8.46 | 6.90 | 8.59 | 5.98 | 6.20 | 7.99 | 8.55 | 6.49 | 6.25 | 6.34 | 7.09 |
| 3341497 | 7.05 | 7.56 | 6.30 | 6.09 | 5.96 | 6.48 | 8.27 | 6.77 | 6.92 | 6.30 | 5.93 | 7.52 |
| 2372812 | 5.21 | 4.40 | 9.79 | 4.34 | 5.19 | 4.91 | 4.35 | 4.74 | 5.51 | 4.74 | 4.79 | 5.11 |
| 2486811 | 10.90 | 9.89 | 9.52 | 9.10 | 10.27 | 10.14 | 8.83 | 7.22 | 10.35 | 10.65 | 11.02 | 8.34 |
| 3768474 | 9.04 | 8.32 | 8.62 | 7.70 | 8.51 | 7.54 | 8.07 | 7.42 | 8.85 | 8.48 | 9.05 | 8.21 |
| 3142381 | 4.10 | 5.02 | 4.96 | 5.88 | 5.75 | 4.28 | 6.18 | 4.28 | 9.59 | 5.06 | 8.38 | 3.69 |
| 2396750 | 7.47 | 7.25 | 7.88 | 7.42 | 7.37 | 6.52 | 7.62 | 7.82 | 7.33 | 6.69 | 6.82 | 6.90 |
| 3902489 | 9.60 | 9.92 | 9.78 | 10.99 | 11.41 | 10.65 | 10.35 | 9.26 | 12.63 | 11.79 | 10.66 | 9.93 |
| 3032647 | 6.50 | 9.51 | 6.91 | 5.98 | 7.27 | 6.79 | 5.48 | 6.37 | 6.27 | 7.51 | 6.08 | 6.66 |
| 3875642 | 5.94 | 4.90 | 5.42 | 5.27 | 5.70 | 6.25 | 4.86 | 4.90 | 6.35 | 6.78 | 5.30 | 5.35 |
| 4027585 | 11.51 | 9.39 | 8.71 | 10.13 | 11.21 | 10.74 | 9.57 | 7.56 | 12.38 | 11.77 | 11.29 | 9.50 |
| 2352609 | 6.11 | 8.10 | 5.97 | 6.35 | 6.66 | 6.97 | 7.00 | 7.34 | 5.76 | 6.31 | 6.28 | 8.92 |
| 3376529 | 7.47 | 9.55 | 8.14 | 9.75 | 8.66 | 7.98 | 10.21 | 9.18 | 8.57 | 8.31 | 7.97 | 8.24 |
| 2491271 | 13.26 | 13.06 | 13.57 | 13.56 | 13.63 | 13.41 | 13.34 | 13.02 | 13.54 | 13.53 | 13.65 | 12.88 |
| 3874751 | 8.78 | 9.03 | 8.69 | 9.52 | 9.50 | 8.41 | 9.85 | 9.26 | 9.18 | 9.43 | 10.65 | 8.90 |
| 2326463 | 12.34 | 11.22 | 12.66 | 11.68 | 12.42 | 12.36 | 10.52 | 10.06 | 12.79 | 12.89 | 12.51 | 10.71 |
| 3341061 | 7.87 | 7.43 | 6.22 | 7.06 | 7.61 | 6.87 | 7.72 | 7.14 | 6.52 | 7.44 | 9.07 | 6.68 |
| 3839910 | 8.53 | 6.69 | 6.51 | 8.36 | 9.94 | 8.43 | 7.90 | 6.01 | 9.81 | 9.83 | 6.72 | 7.90 |
| 2708855 | 4.26 | 4.08 | 5.38 | 7.94 | 4.33 | 3.93 | 8.68 | 7.26 | 5.43 | 4.40 | 4.52 | 6.06 |
| 3512874 | 12.13 | 10.99 | 12.11 | 11.50 | 12.10 | 12.12 | 11.00 | 9.66 | 12.55 | 12.38 | 12.01 | 11.10 |
| 2701071 | 9.16 | 8.21 | 8.27 | 9.61 | 10.81 | 10.28 | 8.80 | 7.54 | 11.14 | 10.95 | 9.41 | 9.68 |
| 3486096 | 5.96 | 8.19 | 6.10 | 5.21 | 6.80 | 6.92 | 8.17 | 8.18 | 5.49 | 5.42 | 6.88 | 8.51 |
| 2412668 | 8.15 | 8.24 | 8.54 | 8.31 | 8.91 | 7.91 | 8.35 | 7.88 | 9.22 | 9.03 | 9.18 | 7.81 |
| 3329343 | 7.83 | 7.51 | 9.04 | 9.06 | 7.39 | 7.58 | 8.91 | 8.69 | 7.29 | 7.31 | 7.36 | 7.50 |
| 3259367 | 4.62 | 3.75 | 3.84 | 4.15 | 4.32 | 4.62 | 5.25 | 6.10 | 4.47 | 3.95 | 3.99 | 4.06 |
| 3373845 | 9.45 | 9.96 | 9.57 | 9.12 | 9.31 | 8.51 | 9.20 | 7.54 | 8.59 | 9.06 | 10.93 | 7.78 |
| 2321911 | 8.85 | 8.15 | 8.30 | 8.15 | 8.37 | 8.20 | 8.07 | 8.08 | 10.20 | 8.88 | 8.67 | 8.11 |
| 3353914 | 8.49 | 7.49 | 6.44 | 7.72 | 6.63 | 6.07 | 7.89 | 6.94 | 6.82 | 6.46 | 9.24 | 6.70 |
| 3744680 | 8.53 | 6.75 | 7.44 | 7.36 | 8.33 | 7.62 | 6.91 | 6.75 | 8.48 | 8.38 | 8.33 | 7.13 |
| 2373336 | 5.57 | 6.18 | 8.08 | 9.41 | 6.39 | 5.84 | 9.83 | 5.37 | 6.63 | 6.93 | 6.56 | 5.14 |
| 3067478 | 5.23 | 7.23 | 6.10 | 7.77 | 5.05 | 6.42 | 8.09 | 8.58 | 4.77 | 5.07 | 4.96 | 6.89 |
| 3976766 | 9.04 | 7.14 | 8.83 | 7.92 | 8.89 | 8.23 | 7.29 | 6.65 | 9.45 | 9.26 | 8.17 | 7.68 |
| 3246888 | 5.23 | 6.44 | 5.26 | 5.00 | 5.91 | 6.13 | 4.87 | 7.10 | 5.86 | 5.55 | 5.94 | 7.49 |
| 3147985 | 8.02 | 7.95 | 5.37 | 7.45 | 6.50 | 5.95 | 7.48 | 7.57 | 6.55 | 6.21 | 8.98 | 5.95 |
| 3185522 | 10.20 | 10.24 | 8.38 | 9.21 | 9.89 | 9.09 | 9.96 | 9.64 | 8.71 | 9.07 | 11.13 | 9.83 |
| 3861948 | 12.79 | 11.32 | 12.74 | 12.25 | 13.05 | 12.73 | 11.61 | 10.37 | 13.25 | 13.12 | 12.55 | 11.52 |
| 3393479 | 9.11 | 8.96 | 8.21 | 8.73 | 9.70 | 8.14 | 9.23 | 9.66 | 9.07 | 8.80 | 10.38 | 8.85 |
| 3540862 | 6.57 | 6.37 | 6.87 | 6.73 | 6.60 | 6.95 | 7.81 | 7.03 | 6.64 | 6.39 | 6.52 | 7.52 |
| 2777714 | 9.85 | 9.71 | 8.94 | 10.75 | 11.66 | 11.00 | 9.75 | 8.51 | 12.50 | 12.18 | 9.82 | 10.18 |
| 3110395 | 4.66 | 4.11 | 4.59 | 5.50 | 4.51 | 6.11 | 6.16 | 4.85 | 4.61 | 4.40 | 4.72 | 5.27 |
| 3895795 | 8.63 | 8.08 | 7.32 | 8.36 | 9.00 | 8.29 | 8.48 | 8.41 | 9.24 | 8.76 | 7.68 | 8.69 |
| 2854445 | 11.82 | 9.72 | 8.14 | 8.84 | 9.76 | 7.71 | 9.45 | 7.79 | 9.18 | 8.08 | 11.55 | 7.49 |
| 3606034 | 7.88 | 7.81 | 6.58 | 7.10 | 7.42 | 7.44 | 7.45 | 7.21 | 7.41 | 8.31 | 7.45 | 7.45 |
| 3375735 | 9.11 | 7.89 | 7.81 | 8.20 | 8.34 | 7.71 | 7.73 | 7.47 | 8.30 | 8.12 | 8.59 | 7.75 |
| 3948047 | 9.20 | 7.82 | 8.92 | 7.97 | 9.09 | 8.60 | 7.26 | 6.94 | 9.29 | 9.13 | 8.81 | 7.52 |
| 3010503 | 10.53 | 8.53 | 6.14 | 8.52 | 9.67 | 8.66 | 8.79 | 6.04 | 10.56 | 9.12 | 11.31 | 8.13 |
| 3622934 | 6.32 | 6.93 | 7.10 | 7.88 | 6.26 | 7.07 | 8.16 | 8.86 | 6.71 | 6.35 | 6.16 | 7.70 |
| 3441849 | 10.54 | 9.20 | 8.90 | 10.04 | 10.35 | 9.65 | 9.66 | 10.18 | 10.90 | 10.28 | 10.15 | 9.57 |
| 3006572 | 7.11 | 6.15 | 7.03 | 6.73 | 6.55 | 6.50 | 6.16 | 6.29 | 6.61 | 6.94 | 6.06 | 6.56 |
| 3365136 | 8.55 | 9.51 | 8.84 | 8.42 | 8.54 | 8.23 | 8.89 | 10.58 | 8.81 | 8.58 | 8.33 | 9.98 |
| 2642791 | 8.76 | 8.58 | 7.98 | 8.36 | 8.54 | 8.35 | 8.57 | 7.43 | 8.13 | 8.50 | 8.95 | 7.78 |
| 2904485 | 7.68 | 9.34 | 7.81 | 6.86 | 8.35 | 8.81 | 6.89 | 8.46 | 6.98 | 7.92 | 7.72 | 9.47 |
| 3772661 | 10.88 | 10.18 | 8.98 | 10.56 | 10.42 | 9.43 | 10.10 | 9.73 | 9.86 | 9.54 | 11.64 | 9.18 |
| 2796553 | 10.21 | 9.52 | 7.70 | 9.24 | 10.43 | 9.54 | 9.64 | 7.77 | 10.61 | 10.15 | 10.42 | 9.54 |
| 3063795 | 8.22 | 7.58 | 7.70 | 7.92 | 8.20 | 7.34 | 7.11 | 7.68 | 7.47 | 7.27 | 8.29 | 6.88 |
| 3338192 | 7.78 | 9.06 | 9.31 | 11.57 | 7.88 | 8.49 | 10.78 | 11.21 | 7.57 | 8.08 | 8.67 | 9.99 |
| 3214845 | 6.10 | 4.00 | 7.87 | 4.93 | 4.44 | 4.96 | 3.92 | 4.43 | 5.55 | 4.97 | 5.06 | 4.03 |
| 2730303 | 4.71 | 4.16 | 6.97 | 4.21 | 4.27 | 4.39 | 4.11 | 4.07 | 4.35 | 4.23 | 4.29 | 4.28 |
| 3811086 | 7.43 | 7.58 | 7.57 | 7.53 | 7.46 | 7.89 | 7.86 | 7.90 | 7.81 | 7.64 | 8.68 | 7.80 |
| 2981874 | 9.91 | 10.42 | 9.85 | 10.51 | 10.73 | 10.26 | 9.93 | 10.61 | 9.88 | 10.34 | 8.67 | 9.96 |
| 3242353 | 6.41 | 6.69 | 6.05 | 6.14 | 6.34 | 5.94 | 6.45 | 5.62 | 6.48 | 6.01 | 6.65 | 6.05 |
| 2442008 | 6.01 | 5.24 | 6.09 | 5.27 | 5.42 | 5.48 | 7.90 | 8.98 | 5.86 | 5.64 | 5.35 | 5.71 |
| 3564210 | 10.33 | 8.45 | 7.24 | 9.18 | 10.27 | 9.05 | 9.09 | 7.31 | 10.51 | 9.76 | 10.09 | 9.21 |
| 2490351 | 4.90 | 4.10 | 4.16 | 3.94 | 4.07 | 4.29 | 3.87 | 4.13 | 4.34 | 4.25 | 4.04 | 4.09 |
| 3759006 | 8.16 | 7.34 | 7.55 | 9.11 | 9.56 | 8.88 | 6.92 | 7.03 | 11.17 | 10.81 | 7.83 | 7.86 |
| 3264997 | 4.90 | 4.06 | 4.14 | 3.97 | 4.43 | 4.34 | 3.72 | 4.11 | 4.47 | 4.30 | 4.16 | 4.12 |
| 3912079 | 3.85 | 3.45 | 3.58 | 3.59 | 4.06 | 3.59 | 3.86 | 3.56 | 3.96 | 4.39 | 3.49 | 3.46 |
| 2926802 | 6.24 | 4.55 | 5.90 | 5.19 | 5.99 | 5.10 | 4.73 | 6.80 | 5.73 | 4.35 | 4.05 | 5.16 |
| 2430163 | 4.93 | 3.64 | 4.07 | 4.42 | 3.78 | 4.05 | 6.66 | 3.94 | 4.29 | 3.91 | 4.03 | 4.05 |
| 3039830 | 3.17 | 3.21 | 3.13 | 3.04 | 3.24 | 3.16 | 3.19 | 3.35 | 3.13 | 3.10 | 3.25 | 3.62 |
| 3935486 | 8.36 | 6.53 | 8.60 | 7.49 | 7.48 | 6.51 | 5.79 | 5.63 | 5.51 | 7.41 | 8.79 | 6.10 |
| 3457336 | 6.11 | 6.14 | 5.48 | 5.31 | 5.44 | 5.81 | 5.37 | 5.59 | 5.77 | 5.51 | 5.33 | 5.58 |
| 3811949 | 4.17 | 3.41 | 3.42 | 3.40 | 3.56 | 3.57 | 3.33 | 3.56 | 3.63 | 3.74 | 3.46 | 3.30 |

TABLE 36-continued

Normalized intensity of microarray data for a set of samples.

| TCID | V01 0133 | V01 0134 | V01 0135 | V01 0136 | V01 0137 | V01 0138 | V01 0139 | V01 0140 | V01 0141 | V01 0142 | V01 0143 | V01 0144 |
|---|---|---|---|---|---|---|---|---|---|---|---|---|
| 3343832 | 4.45 | 3.79 | 3.90 | 3.73 | 3.89 | 4.07 | 3.66 | 3.99 | 4.04 | 4.01 | 3.84 | 3.92 |
| 3161261 | 7.38 | 5.17 | 6.66 | 5.29 | 6.12 | 6.71 | 5.23 | 5.92 | 5.83 | 6.23 | 5.30 | 5.80 |
| 3594003 | 3.71 | 3.65 | 3.75 | 3.61 | 3.77 | 3.61 | 3.59 | 4.02 | 3.92 | 3.78 | 3.73 | 3.72 |
| 3805614 | 5.96 | 4.32 | 4.93 | 4.48 | 5.03 | 5.32 | 4.46 | 4.96 | 4.97 | 5.17 | 4.64 | 4.72 |
| 3364127 | 8.05 | 6.38 | 8.31 | 6.39 | 6.58 | 7.15 | 6.44 | 7.09 | 6.87 | 7.03 | 6.84 | 7.08 |
| 3834341 | 4.76 | 3.82 | 4.24 | 3.95 | 4.26 | 4.62 | 4.21 | 4.31 | 4.29 | 4.18 | 3.93 | 4.12 |
| 2585400 | 4.91 | 4.21 | 4.60 | 4.43 | 4.14 | 4.40 | 4.13 | 4.20 | 4.59 | 4.32 | 4.40 | 4.15 |
| 2941690 | 4.77 | 4.13 | 4.68 | 4.21 | 4.06 | 5.01 | 3.93 | 4.35 | 4.84 | 4.58 | 4.13 | 4.16 |
| 3484895 | 5.66 | 4.38 | 5.19 | 4.59 | 4.92 | 5.06 | 6.21 | 6.55 | 5.33 | 4.84 | 4.52 | 4.70 |
| 3159754 | 4.21 | 3.60 | 3.84 | 3.56 | 3.74 | 3.84 | 3.43 | 3.66 | 4.12 | 3.90 | 3.72 | 3.70 |
| 2894790 | 4.00 | 4.07 | 3.76 | 3.71 | 3.96 | 4.18 | 3.69 | 3.92 | 4.14 | 4.10 | 3.69 | 3.71 |
| 3363686 | 4.17 | 3.52 | 3.82 | 3.46 | 3.60 | 3.62 | 3.33 | 3.77 | 3.59 | 3.56 | 3.34 | 3.63 |
| 2923928 | 5.25 | 3.90 | 4.19 | 3.93 | 4.54 | 4.06 | 3.89 | 4.68 | 4.82 | 4.31 | 4.21 | 4.41 |
| 2883317 | 6.04 | 4.33 | 5.13 | 4.81 | 5.56 | 5.09 | 4.48 | 4.64 | 5.86 | 5.15 | 5.48 | 4.77 |
| 2479698 | 5.94 | 6.01 | 6.04 | 5.98 | 6.23 | 6.13 | 6.11 | 6.16 | 6.04 | 6.19 | 5.90 | 6.22 |
| 3428225 | 4.46 | 3.57 | 3.76 | 3.41 | 3.74 | 3.81 | 3.49 | 3.70 | 3.89 | 3.88 | 3.73 | 3.85 |
| 3393446 | 8.32 | 7.52 | 7.58 | 6.94 | 8.26 | 7.26 | 7.13 | 7.06 | 7.60 | 7.53 | 8.36 | 7.20 |
| 3116614 | 8.52 | 13.27 | 10.33 | 10.79 | 12.53 | 12.96 | 12.24 | 11.74 | 9.28 | 11.68 | 11.85 | 13.15 |
| 3415320 | 7.06 | 10.78 | 9.67 | 11.86 | 9.03 | 10.55 | 11.16 | 9.24 | 7.00 | 8.39 | 9.30 | 10.55 |
| 3757108 | 8.21 | 9.07 | 9.46 | 12.58 | 7.73 | 7.55 | 11.35 | 10.28 | 7.84 | 7.93 | 7.97 | 7.66 |
| 4012178 | 7.09 | 9.34 | 8.18 | 8.07 | 6.51 | 6.64 | 10.96 | 7.86 | 6.55 | 6.46 | 6.03 | 8.36 |
| 3546213 | 6.49 | 11.37 | 9.28 | 9.16 | 9.99 | 10.80 | 11.01 | 11.36 | 5.90 | 8.47 | 9.76 | 11.71 |
| 3561381 | 5.96 | 9.29 | 9.16 | 8.84 | 8.92 | 9.51 | 9.94 | 11.02 | 5.22 | 7.78 | 8.22 | 10.52 |

TABLE 37

Normalized intensity of microarray data for a set of samples.

| TCID | V01 0145 | V01 0146 | V01 0147 | V01 0148 | V01 0149 | V01 0150 | V01 0151 | V01 0152 | V01 0153 | V01 0154 | V01 0155 | V01 0156 |
|---|---|---|---|---|---|---|---|---|---|---|---|---|
| 2604998 | 6.82 | 6.80 | 8.48 | 8.98 | 8.47 | 7.69 | 8.88 | 8.79 | 9.07 | 9.16 | 8.29 | 9.44 |
| 3603932 | 8.25 | 7.16 | 6.94 | 7.27 | 7.59 | 7.29 | 6.96 | 7.02 | 6.90 | 6.84 | 7.61 | 6.77 |
| 2710599 | 9.81 | 10.10 | 6.31 | 11.79 | 10.93 | 6.19 | 11.68 | 10.94 | 8.13 | 7.65 | 7.15 | 8.31 |
| 2440258 | 7.34 | 9.41 | 6.82 | 4.63 | 7.34 | 8.87 | 5.13 | 5.81 | 5.87 | 5.48 | 6.90 | 5.57 |
| 3169331 | 7.16 | 7.47 | 6.98 | 7.04 | 7.14 | 7.06 | 6.47 | 6.51 | 8.04 | 8.60 | 6.69 | 7.62 |
| 2988882 | 10.01 | 9.99 | 9.99 | 9.81 | 9.79 | 10.30 | 9.63 | 9.94 | 9.98 | 10.11 | 9.69 | 9.81 |
| 2964231 | 10.64 | 8.05 | 8.84 | 9.40 | 8.80 | 7.86 | 8.84 | 7.64 | 8.96 | 8.16 | 9.86 | 8.62 |
| 3111561 | 8.93 | 5.93 | 8.23 | 4.32 | 9.86 | 8.90 | 4.30 | 5.03 | 10.94 | 11.02 | 9.62 | 11.26 |
| 2562529 | 9.61 | 8.67 | 9.07 | 10.61 | 9.98 | 9.42 | 10.97 | 11.39 | 9.72 | 9.55 | 9.78 | 10.68 |
| 3692999 | 11.95 | 9.63 | 10.27 | 7.19 | 11.47 | 10.59 | 6.88 | 8.06 | 12.55 | 12.64 | 11.10 | 11.10 |
| 2439554 | 7.54 | 8.57 | 7.90 | 4.92 | 7.78 | 8.04 | 4.73 | 4.52 | 5.18 | 4.78 | 6.41 | 5.21 |
| 2685304 | 9.43 | 8.46 | 6.81 | 11.94 | 9.13 | 6.33 | 12.00 | 11.17 | 7.64 | 7.91 | 8.45 | 7.12 |
| 2578790 | 5.47 | 4.99 | 4.27 | 4.32 | 7.10 | 5.96 | 4.20 | 4.52 | 8.04 | 7.71 | 6.98 | 7.35 |
| 2373842 | 10.82 | 11.54 | 11.16 | 8.05 | 10.87 | 11.76 | 9.17 | 9.32 | 10.38 | 9.25 | 11.21 | 9.30 |
| 2750627 | 8.15 | 7.87 | 10.59 | 9.90 | 10.11 | 7.99 | 10.56 | 10.94 | 10.30 | 10.98 | 9.66 | 11.34 |
| 3397774 | 4.71 | 4.93 | 4.69 | 4.47 | 4.44 | 5.00 | 4.76 | 4.81 | 4.94 | 4.54 | 4.71 | 5.08 |
| 2635741 | 7.40 | 9.28 | 7.40 | 5.80 | 8.09 | 9.18 | 5.90 | 6.76 | 7.21 | 6.65 | 7.53 | 6.53 |
| 3970833 | 9.62 | 9.32 | 9.63 | 9.91 | 9.41 | 8.93 | 9.61 | 9.92 | 9.68 | 9.80 | 9.48 | 10.20 |
| 3577612 | 10.98 | 10.76 | 10.24 | 11.69 | 10.86 | 11.50 | 11.89 | 11.35 | 9.97 | 8.94 | 10.47 | 8.61 |
| 2708922 | 6.42 | 7.90 | 9.69 | 8.30 | 7.14 | 9.50 | 8.89 | 8.81 | 7.88 | 6.91 | 7.90 | 8.23 |
| 2970897 | 6.83 | 6.02 | 4.56 | 5.71 | 5.13 | 4.87 | 4.98 | 4.98 | 5.31 | 6.47 | 5.85 | 5.62 |
| 3724545 | 8.50 | 10.10 | 8.34 | 9.95 | 9.66 | 9.74 | 9.99 | 9.98 | 9.88 | 9.67 | 9.89 | 8.94 |
| 2798538 | 9.21 | 9.24 | 9.32 | 9.13 | 9.04 | 9.08 | 9.16 | 8.45 | 8.61 | 8.68 | 9.00 | 9.05 |
| 2806468 | 9.77 | 11.60 | 9.76 | 6.74 | 11.03 | 11.72 | 8.73 | 8.99 | 10.20 | 8.68 | 9.75 | 8.91 |
| 2880051 | 6.17 | 6.32 | 6.01 | 5.82 | 6.24 | 6.43 | 6.02 | 6.05 | 6.18 | 5.99 | 6.20 | 5.93 |
| 2732508 | 4.04 | 7.74 | 5.88 | 3.62 | 5.13 | 4.14 | 3.63 | 3.75 | 3.66 | 3.64 | 4.15 | 4.07 |
| 2822492 | 5.97 | 5.19 | 6.76 | 5.71 | 5.08 | 5.25 | 5.34 | 5.48 | 5.58 | 5.77 | 5.79 | 7.29 |
| 3404030 | 7.39 | 9.10 | 7.25 | 5.62 | 7.33 | 8.87 | 5.85 | 6.40 | 6.46 | 6.02 | 7.03 | 6.16 |
| 3059667 | 8.64 | 7.55 | 12.65 | 5.07 | 9.94 | 10.28 | 4.37 | 5.91 | 11.34 | 12.12 | 11.54 | 12.79 |
| 3108526 | 8.84 | 7.91 | 8.10 | 9.36 | 9.88 | 9.15 | 7.89 | 8.62 | 10.32 | 11.33 | 9.49 | 10.17 |
| 2526806 | 11.71 | 13.05 | 10.20 | 12.91 | 12.66 | 7.34 | 13.18 | 12.30 | 7.55 | 8.98 | 9.60 | 7.21 |
| 2428501 | 8.30 | 7.49 | 6.20 | 7.30 | 6.98 | 7.03 | 7.31 | 6.08 | 6.31 | 6.39 | 7.00 | 5.95 |
| 2657808 | 6.28 | 5.86 | 6.24 | 11.19 | 9.53 | 5.76 | 11.16 | 10.54 | 7.97 | 6.88 | 6.87 | 7.70 |
| 2584018 | 11.00 | 8.93 | 5.94 | 10.95 | 9.63 | 7.83 | 10.68 | 9.07 | 7.80 | 5.61 | 10.06 | 4.82 |
| 3976341 | 10.23 | 9.95 | 8.72 | 11.94 | 10.57 | 10.69 | 11.92 | 11.40 | 8.32 | 8.33 | 9.90 | 7.37 |
| 2739308 | 4.42 | 5.22 | 4.85 | 4.45 | 4.51 | 5.78 | 4.36 | 4.73 | 5.34 | 5.46 | 5.55 | 4.45 |
| 3959862 | 5.90 | 5.39 | 4.33 | 3.95 | 4.50 | 5.42 | 4.73 | 4.50 | 4.75 | 3.60 | 4.78 | 4.17 |
| 2362351 | 7.16 | 8.01 | 7.20 | 5.67 | 7.36 | 7.85 | 5.60 | 5.79 | 6.14 | 5.63 | 7.01 | 6.14 |
| 3648391 | 4.11 | 7.20 | 5.36 | 4.02 | 6.35 | 6.23 | 3.86 | 4.04 | 4.09 | 4.30 | 4.48 | 4.62 |
| 3009299 | 10.93 | 10.82 | 10.74 | 10.73 | 10.47 | 10.90 | 10.38 | 10.40 | 10.55 | 10.67 | 10.57 | 10.69 |
| 3443464 | 5.35 | 5.79 | 5.24 | 4.96 | 5.35 | 5.55 | 5.21 | 5.10 | 5.37 | 5.06 | 5.79 | 5.27 |

TABLE 37-continued

Normalized intensity of microarray data for a set of samples.

| TCID | V01 0145 | V01 0146 | V01 0147 | V01 0148 | V01 0149 | V01 0150 | V01 0151 | V01 0152 | V01 0153 | V01 0154 | V01 0155 | V01 0156 |
|---|---|---|---|---|---|---|---|---|---|---|---|---|
| 2730746 | 6.79 | 5.92 | 10.02 | 5.90 | 8.32 | 7.09 | 4.79 | 7.60 | 8.74 | 9.40 | 8.33 | 9.97 |
| 2427619 | 6.80 | 9.40 | 7.37 | 4.96 | 7.66 | 9.78 | 5.22 | 6.00 | 7.50 | 6.59 | 8.13 | 6.21 |
| 3042001 | 8.44 | 8.73 | 9.01 | 8.38 | 8.44 | 8.49 | 8.41 | 8.04 | 8.71 | 8.88 | 8.34 | 8.86 |
| 2566848 | 5.15 | 6.38 | 5.26 | 4.85 | 6.03 | 6.19 | 5.01 | 5.16 | 5.13 | 4.83 | 5.18 | 4.82 |
| 2984616 | 9.78 | 9.10 | 9.07 | 9.00 | 9.25 | 9.01 | 9.17 | 9.20 | 8.96 | 8.80 | 9.39 | 9.41 |
| 2378068 | 7.81 | 9.89 | 7.76 | 9.36 | 9.30 | 7.72 | 9.31 | 9.27 | 6.62 | 6.65 | 8.24 | 6.61 |
| 2721959 | 8.84 | 10.78 | 5.59 | 12.93 | 10.36 | 5.69 | 12.93 | 11.87 | 6.58 | 7.21 | 7.06 | 8.12 |
| 2877508 | 10.59 | 10.24 | 10.28 | 10.51 | 9.97 | 10.13 | 10.49 | 10.02 | 10.30 | 10.49 | 10.46 | 10.33 |
| 3450861 | 5.37 | 6.77 | 5.63 | 4.34 | 5.06 | 6.55 | 4.46 | 4.98 | 5.19 | 4.55 | 5.28 | 5.18 |
| 2688717 | 7.02 | 10.30 | 7.20 | 4.76 | 8.46 | 10.03 | 5.60 | 7.37 | 7.70 | 6.82 | 8.29 | 6.19 |
| 3270270 | 8.26 | 8.59 | 8.05 | 8.68 | 7.77 | 9.37 | 9.10 | 8.28 | 7.30 | 6.85 | 8.28 | 6.14 |
| 3417703 | 6.62 | 5.54 | 7.80 | 7.87 | 7.69 | 9.66 | 5.60 | 7.48 | 10.82 | 7.83 | 7.00 | 10.16 |
| 3302990 | 8.10 | 7.28 | 7.51 | 7.92 | 7.28 | 6.93 | 7.51 | 7.56 | 7.24 | 7.93 | 7.48 | 7.89 |
| 2377283 | 4.15 | 10.51 | 4.43 | 4.20 | 7.22 | 5.58 | 3.99 | 4.23 | 4.62 | 4.11 | 4.77 | 4.24 |
| 3122678 | 5.01 | 4.85 | 4.68 | 5.87 | 4.91 | 5.16 | 4.84 | 4.56 | 4.88 | 4.44 | 4.34 | 4.37 |
| 2688499 | 9.81 | 8.55 | 10.03 | 11.00 | 9.71 | 8.93 | 9.98 | 10.54 | 10.76 | 10.99 | 9.77 | 10.70 |
| 2377094 | 8.39 | 7.73 | 8.82 | 8.65 | 8.92 | 8.43 | 8.61 | 8.46 | 9.60 | 9.49 | 8.84 | 9.82 |
| 3278198 | 8.96 | 6.88 | 7.71 | 8.85 | 8.41 | 7.48 | 8.06 | 7.81 | 7.92 | 8.75 | 8.15 | 8.79 |
| 2598261 | 11.31 | 12.57 | 9.36 | 12.95 | 12.68 | 7.09 | 13.24 | 12.04 | 7.51 | 8.51 | 8.94 | 7.29 |
| 3982612 | 8.29 | 10.47 | 7.65 | 5.09 | 7.74 | 9.14 | 4.14 | 6.53 | 7.50 | 5.91 | 7.60 | 6.99 |
| 2884845 | 4.61 | 4.45 | 4.30 | 10.30 | 5.61 | 4.73 | 10.14 | 7.29 | 4.57 | 4.43 | 4.33 | 4.45 |
| 3982560 | 5.85 | 8.15 | 5.87 | 4.39 | 6.44 | 7.70 | 4.75 | 5.47 | 5.37 | 5.21 | 5.75 | 4.93 |
| 3204285 | 6.30 | 7.25 | 5.30 | 5.47 | 7.04 | 5.29 | 5.88 | 6.27 | 5.06 | 5.39 | 5.37 | 5.44 |
| 3654699 | 12.59 | 11.42 | 8.95 | 10.89 | 11.73 | 11.30 | 10.84 | 9.38 | 11.58 | 12.41 | 12.10 | 11.10 |
| 2638676 | 7.94 | 9.70 | 7.15 | 5.62 | 7.73 | 8.38 | 5.57 | 6.00 | 5.77 | 4.98 | 7.26 | 6.46 |
| 3367673 | 6.34 | 6.02 | 7.73 | 4.99 | 8.32 | 7.34 | 4.41 | 5.62 | 9.14 | 9.59 | 8.71 | 10.27 |
| 3212008 | 6.20 | 5.97 | 8.62 | 7.90 | 6.95 | 7.39 | 8.17 | 9.53 | 8.82 | 6.24 | 6.86 | 7.62 |
| 3326635 | 9.94 | 10.38 | 10.76 | 9.97 | 10.19 | 10.66 | 10.23 | 10.35 | 10.21 | 9.83 | 10.05 | 10.43 |
| 3031556 | 9.60 | 9.88 | 9.33 | 5.46 | 8.53 | 10.36 | 6.50 | 7.55 | 7.69 | 7.03 | 9.39 | 7.52 |
| 3662201 | 11.85 | 10.19 | 10.36 | 8.12 | 10.91 | 10.74 | 8.41 | 7.50 | 12.69 | 12.83 | 9.92 | 10.33 |
| 2809793 | 8.90 | 9.69 | 7.40 | 5.01 | 8.37 | 9.33 | 4.89 | 6.39 | 6.42 | 5.59 | 7.36 | 5.71 |
| 2817731 | 9.19 | 7.72 | 8.28 | 7.48 | 7.95 | 7.85 | 7.84 | 7.47 | 7.38 | 7.61 | 8.58 | 7.96 |
| 4020655 | 4.65 | 5.24 | 6.84 | 4.74 | 5.12 | 5.30 | 7.50 | 8.73 | 5.05 | 4.61 | 4.67 | 5.12 |
| 3494629 | 4.72 | 4.52 | 5.27 | 9.11 | 5.46 | 4.65 | 7.96 | 8.63 | 4.98 | 4.74 | 4.36 | 4.57 |
| 3852832 | 6.46 | 9.08 | 7.97 | 5.96 | 7.52 | 9.12 | 6.52 | 6.64 | 7.43 | 7.60 | 8.39 | 6.42 |
| 3761959 | 9.61 | 8.90 | 9.38 | 9.41 | 9.19 | 9.08 | 9.01 | 9.29 | 9.16 | 9.59 | 9.62 | 9.67 |
| 2834282 | 5.91 | 5.68 | 5.50 | 8.20 | 7.12 | 5.70 | 8.44 | 7.34 | 7.34 | 5.37 | 7.11 | 6.80 |
| 3341497 | 6.11 | 5.81 | 6.30 | 7.80 | 5.89 | 5.84 | 7.05 | 8.06 | 7.91 | 6.30 | 6.53 | 5.72 |
| 2372812 | 4.53 | 9.29 | 4.44 | 4.59 | 7.73 | 5.29 | 4.44 | 4.89 | 4.96 | 4.38 | 4.72 | 4.39 |
| 2486811 | 10.83 | 9.96 | 9.38 | 7.03 | 9.64 | 10.17 | 8.38 | 7.16 | 7.74 | 7.03 | 10.42 | 7.12 |
| 3768474 | 9.40 | 8.08 | 7.88 | 7.69 | 8.51 | 8.81 | 7.91 | 6.89 | 7.66 | 7.96 | 8.63 | 7.48 |
| 3142381 | 7.98 | 3.84 | 4.76 | 3.87 | 6.17 | 4.53 | 5.16 | 4.27 | 6.32 | 8.97 | 7.77 | 4.01 |
| 2396750 | 7.50 | 7.16 | 6.35 | 7.49 | 7.12 | 7.01 | 7.34 | 8.09 | 6.84 | 6.75 | 6.81 | 6.71 |
| 3902489 | 10.09 | 11.55 | 10.49 | 9.78 | 10.05 | 12.23 | 10.20 | 9.72 | 11.00 | 9.72 | 10.49 | 9.07 |
| 3032647 | 6.36 | 6.47 | 9.75 | 5.95 | 7.91 | 7.11 | 5.62 | 5.88 | 7.29 | 9.80 | 6.33 | 8.39 |
| 3875642 | 4.84 | 6.33 | 5.16 | 4.88 | 5.14 | 5.93 | 4.97 | 5.30 | 5.48 | 4.92 | 5.49 | 6.09 |
| 4027585 | 11.08 | 11.09 | 9.81 | 7.95 | 10.42 | 11.70 | 8.47 | 8.91 | 10.80 | 9.03 | 11.11 | 8.67 |
| 2352609 | 5.96 | 5.66 | 7.59 | 7.10 | 6.75 | 6.95 | 6.72 | 6.73 | 8.17 | 7.43 | 6.94 | 7.57 |
| 3376529 | 8.89 | 8.83 | 8.32 | 10.34 | 8.32 | 8.15 | 9.81 | 10.17 | 8.62 | 8.98 | 8.38 | 7.54 |
| 2491271 | 13.56 | 13.70 | 13.39 | 13.38 | 13.35 | 13.74 | 13.33 | 13.10 | 12.59 | 12.72 | 13.28 | 12.58 |
| 3874751 | 10.23 | 8.71 | 8.67 | 9.89 | 9.34 | 9.60 | 9.52 | 9.52 | 9.17 | 9.07 | 10.10 | 9.16 |
| 2326463 | 12.88 | 12.68 | 11.06 | 8.60 | 11.79 | 12.72 | 10.79 | 10.01 | 10.76 | 9.63 | 12.05 | 9.08 |
| 3341061 | 9.63 | 8.13 | 7.02 | 7.04 | 8.08 | 7.44 | 7.89 | 6.42 | 6.48 | 6.45 | 8.59 | 6.82 |
| 3839910 | 6.69 | 8.32 | 8.63 | 5.28 | 6.81 | 9.63 | 5.41 | 6.47 | 7.85 | 7.47 | 8.44 | 6.86 |
| 2708855 | 4.78 | 4.76 | 4.20 | 8.95 | 5.89 | 4.41 | 9.27 | 8.26 | 4.01 | 3.87 | 5.30 | 4.09 |
| 3512874 | 11.79 | 12.12 | 11.50 | 9.33 | 11.56 | 12.24 | 10.53 | 9.89 | 10.97 | 9.54 | 11.68 | 9.48 |
| 2701071 | 9.63 | 10.02 | 9.97 | 6.46 | 9.49 | 10.99 | 7.44 | 8.58 | 8.85 | 8.42 | 9.96 | 7.66 |
| 3486096 | 5.49 | 5.81 | 10.71 | 7.50 | 7.50 | 6.12 | 6.94 | 6.43 | 8.91 | 8.82 | 7.89 | 9.95 |
| 2412668 | 9.43 | 8.43 | 8.83 | 8.34 | 7.67 | 8.54 | 7.42 | 8.29 | 7.73 | 8.14 | 8.61 | 8.48 |
| 3329343 | 7.31 | 8.24 | 7.50 | 8.70 | 8.63 | 7.39 | 9.41 | 9.24 | 7.34 | 7.73 | 7.42 | 7.72 |
| 3259367 | 4.13 | 4.18 | 3.91 | 4.46 | 4.06 | 4.47 | 4.49 | 5.25 | 4.87 | 4.04 | 4.07 | 4.24 |
| 3373845 | 11.01 | 9.93 | 8.32 | 9.75 | 9.98 | 10.75 | 9.75 | 7.89 | 9.75 | 7.89 | 9.29 | 7.01 |
| 2321911 | 8.64 | 8.95 | 7.92 | 7.58 | 8.01 | 9.35 | 7.81 | 8.19 | 8.04 | 8.09 | 8.49 | 7.80 |
| 3353914 | 8.93 | 7.41 | 6.32 | 8.53 | 6.75 | 6.55 | 8.02 | 7.56 | 6.46 | 6.53 | 7.64 | 6.48 |
| 3744680 | 8.21 | 7.77 | 7.04 | 6.31 | 7.31 | 8.19 | 6.72 | 6.56 | 6.63 | 6.47 | 7.86 | 6.48 |
| 2373336 | 9.68 | 6.52 | 5.00 | 10.76 | 9.08 | 5.80 | 10.24 | 8.79 | 6.69 | 10.07 | 5.39 | 6.73 |
| 3067478 | 5.31 | 5.80 | 8.87 | 8.60 | 6.55 | 4.81 | 9.16 | 8.71 | 6.18 | 5.88 | 5.43 | 7.36 |
| 3976766 | 8.23 | 8.81 | 8.00 | 6.32 | 7.52 | 9.30 | 6.58 | 6.41 | 7.50 | 6.29 | 8.26 | 6.44 |
| 3246888 | 5.92 | 5.42 | 7.68 | 5.25 | 6.39 | 6.38 | 4.82 | 6.71 | 7.43 | 8.05 | 6.61 | 8.29 |
| 3147985 | 8.18 | 7.13 | 7.05 | 7.69 | 7.28 | 6.81 | 7.74 | 7.79 | 6.66 | 7.35 | 7.18 | 6.99 |
| 3185522 | 11.35 | 9.40 | 9.62 | 9.27 | 9.94 | 9.30 | 9.58 | 8.69 | 8.68 | 9.11 | 10.53 | 9.17 |
| 3861948 | 12.71 | 12.95 | 12.32 | 9.94 | 12.18 | 12.96 | 10.79 | 11.16 | 11.95 | 11.31 | 12.55 | 10.47 |
| 3393479 | 10.50 | 8.59 | 10.90 | 9.61 | 9.24 | 8.79 | 9.60 | 7.75 | 9.66 | 10.43 | 10.30 | 10.31 |
| 3540862 | 6.44 | 6.50 | 6.63 | 7.16 | 6.75 | 6.78 | 7.07 | 7.37 | 7.28 | 7.32 | 6.64 | 7.43 |
| 2777714 | 9.68 | 11.62 | 10.97 | 7.23 | 10.40 | 11.97 | 7.86 | 9.78 | 11.58 | 9.55 | 10.91 | 8.56 |

TABLE 37-continued

Normalized intensity of microarray data for a set of samples.

| TCID | V01 0145 | V01 0146 | V01 0147 | V01 0148 | V01 0149 | V01 0150 | V01 0151 | V01 0152 | V01 0153 | V01 0154 | V01 0155 | V01 0156 |
|---|---|---|---|---|---|---|---|---|---|---|---|---|
| 3110395 | 4.24 | 4.79 | 5.76 | 6.12 | 4.34 | 4.60 | 6.80 | 6.62 | 4.60 | 4.26 | 4.69 | 4.09 |
| 3895795 | 7.49 | 8.29 | 8.23 | 7.95 | 7.95 | 9.86 | 8.37 | 7.97 | 8.15 | 7.54 | 8.11 | 7.33 |
| 2854445 | 11.43 | 9.51 | 8.72 | 7.93 | 10.10 | 8.98 | 9.45 | 7.54 | 7.33 | 8.16 | 11.02 | 7.88 |
| 3606034 | 8.61 | 6.85 | 7.04 | 7.57 | 7.21 | 7.14 | 7.61 | 7.37 | 8.05 | 7.66 | 7.54 | 7.56 |
| 3375735 | 8.94 | 7.99 | 7.78 | 8.12 | 7.31 | 8.01 | 8.12 | 8.11 | 7.47 | 7.69 | 8.39 | 7.58 |
| 3948047 | 9.16 | 9.00 | 7.71 | 6.87 | 8.38 | 9.16 | 7.37 | 7.24 | 7.52 | 7.06 | 8.30 | 6.68 |
| 3010503 | 10.88 | 9.38 | 8.79 | 5.88 | 8.75 | 10.32 | 7.58 | 6.13 | 8.21 | 8.26 | 10.65 | 5.85 |
| 3622934 | 5.72 | 7.39 | 7.89 | 8.16 | 6.98 | 6.31 | 8.63 | 8.32 | 7.38 | 7.42 | 6.77 | 7.04 |
| 3441849 | 10.13 | 9.54 | 9.51 | 9.77 | 9.67 | 10.48 | 9.79 | 9.77 | 9.33 | 9.08 | 9.92 | 8.88 |
| 3006572 | 6.20 | 6.42 | 6.33 | 6.48 | 6.58 | 6.47 | 6.77 | 6.62 | 6.65 | 6.11 | 6.24 | 6.83 |
| 3365136 | 8.60 | 8.37 | 8.17 | 9.54 | 8.26 | 8.64 | 9.08 | 9.93 | 9.42 | 8.45 | 8.38 | 8.77 |
| 2642791 | 9.20 | 8.40 | 8.11 | 8.55 | 8.22 | 8.34 | 8.53 | 7.96 | 8.35 | 8.74 | 8.61 | 8.80 |
| 2904485 | 7.59 | 7.41 | 8.31 | 7.13 | 8.64 | 8.88 | 7.19 | 7.59 | 8.95 | 8.77 | 8.36 | 9.93 |
| 3772661 | 11.71 | 9.86 | 9.53 | 9.75 | 10.26 | 10.16 | 10.41 | 9.21 | 8.50 | 8.68 | 10.87 | 8.09 |
| 2796553 | 10.03 | 8.91 | 10.14 | 8.33 | 9.00 | 9.73 | 8.70 | 8.16 | 8.93 | 9.39 | 10.08 | 8.36 |
| 3063795 | 8.59 | 7.88 | 7.33 | 6.97 | 7.68 | 7.30 | 7.57 | 7.22 | 6.58 | 6.76 | 7.74 | 6.72 |
| 3338192 | 8.62 | 8.65 | 9.12 | 11.00 | 8.84 | 8.45 | 10.32 | 10.26 | 9.52 | 9.46 | 9.01 | 10.10 |
| 3214845 | 4.16 | 4.87 | 4.22 | 4.14 | 4.38 | 4.03 | 7.08 | 5.68 | 4.59 | 5.12 | 4.59 | 4.69 |
| 2730303 | 4.10 | 8.52 | 4.13 | 4.24 | 6.76 | 4.12 | 4.23 | 4.21 | 4.20 | 4.24 | 4.08 | 4.03 |
| 3811086 | 8.58 | 7.81 | 7.86 | 7.68 | 7.91 | 7.79 | 7.50 | 7.73 | 8.23 | 8.07 | 8.44 | 8.52 |
| 2981874 | 10.55 | 10.27 | 10.95 | 10.51 | 10.50 | 10.38 | 10.32 | 10.21 | 9.98 | 10.80 | 10.17 | 10.48 |
| 3242353 | 6.56 | 5.99 | 6.17 | 6.31 | 5.98 | 5.96 | 5.92 | 5.99 | 6.15 | 6.44 | 6.33 | 6.24 |
| 2442008 | 5.55 | 5.52 | 5.30 | 8.26 | 5.52 | 5.62 | 7.75 | 9.63 | 5.51 | 5.51 | 5.24 | 5.13 |
| 3564210 | 9.91 | 9.33 | 8.84 | 8.17 | 8.55 | 9.67 | 8.06 | 7.69 | 8.00 | 8.21 | 9.92 | 7.22 |
| 2490351 | 4.01 | 4.03 | 3.98 | 3.88 | 3.94 | 4.18 | 3.95 | 4.04 | 4.28 | 4.00 | 4.00 | 3.96 |
| 3759006 | 7.16 | 9.47 | 8.71 | 6.50 | 7.68 | 11.29 | 6.78 | 7.57 | 10.22 | 7.48 | 8.88 | 6.90 |
| 3264997 | 4.08 | 4.08 | 3.91 | 4.23 | 4.24 | 4.14 | 3.92 | 4.17 | 4.35 | 4.01 | 3.99 | 4.02 |
| 3912079 | 3.60 | 3.61 | 3.56 | 3.60 | 3.55 | 3.61 | 3.49 | 3.64 | 3.83 | 3.70 | 3.47 | 3.74 |
| 2926802 | 6.88 | 6.35 | 4.98 | 4.84 | 4.73 | 6.15 | 4.88 | 4.49 | 4.91 | 4.30 | 5.11 | 4.78 |
| 2430163 | 4.55 | 4.36 | 3.87 | 6.38 | 4.20 | 3.75 | 5.50 | 3.90 | 3.75 | 3.75 | 3.74 | 3.94 |
| 3039830 | 3.26 | 3.12 | 3.13 | 3.05 | 3.11 | 3.17 | 3.08 | 3.22 | 3.29 | 4.00 | 3.10 | 3.30 |
| 3935486 | 10.02 | 6.89 | 5.66 | 5.59 | 10.30 | 6.90 | 8.20 | 7.44 | 5.90 | 5.73 | 6.01 | 5.36 |
| 3457336 | 5.18 | 5.41 | 5.17 | 5.44 | 5.25 | 5.37 | 5.07 | 5.20 | 5.70 | 5.19 | 5.35 | 5.38 |
| 3811949 | 3.36 | 3.48 | 3.44 | 3.39 | 3.27 | 3.56 | 3.42 | 3.49 | 3.64 | 3.52 | 3.39 | 3.38 |
| 3343832 | 3.85 | 3.81 | 3.85 | 3.87 | 3.81 | 3.99 | 3.91 | 3.77 | 3.87 | 3.93 | 3.89 | 3.68 |
| 3161261 | 5.55 | 6.16 | 5.37 | 5.17 | 5.60 | 5.87 | 5.40 | 5.39 | 5.72 | 5.36 | 6.15 | 5.77 |
| 3594003 | 4.11 | 3.75 | 3.64 | 3.57 | 3.77 | 3.92 | 3.60 | 3.81 | 3.69 | 3.57 | 3.90 | 3.47 |
| 3805614 | 4.98 | 4.94 | 4.55 | 4.65 | 4.45 | 4.57 | 4.48 | 4.54 | 4.61 | 4.28 | 4.80 | 4.64 |
| 3364127 | 6.77 | 6.81 | 6.58 | 6.61 | 9.37 | 6.68 | 6.52 | 6.71 | 6.96 | 7.52 | 7.20 | 6.72 |
| 3834341 | 4.15 | 4.09 | 3.98 | 4.07 | 4.04 | 3.74 | 4.00 | 3.95 | 4.08 | 3.81 | 3.96 | 3.93 |
| 2585400 | 5.54 | 4.37 | 4.20 | 4.12 | 4.57 | 4.87 | 4.68 | 4.11 | 4.28 | 4.30 | 4.22 | 4.10 |
| 2941690 | 4.23 | 4.64 | 4.09 | 4.12 | 4.16 | 4.82 | 4.06 | 4.40 | 4.16 | 4.26 | 4.04 | 4.36 |
| 3484895 | 4.75 | 4.91 | 4.41 | 5.84 | 4.54 | 4.88 | 5.53 | 6.60 | 5.00 | 4.74 | 4.56 | 4.58 |
| 3159754 | 3.63 | 3.74 | 3.64 | 3.60 | 3.58 | 3.88 | 3.60 | 3.73 | 3.81 | 3.58 | 3.73 | 3.67 |
| 2894790 | 3.71 | 3.72 | 5.69 | 3.74 | 3.69 | 3.89 | 3.61 | 4.03 | 4.03 | 3.69 | 3.65 | 3.96 |
| 3363686 | 3.32 | 3.49 | 3.48 | 3.33 | 3.28 | 3.40 | 3.36 | 3.34 | 3.61 | 3.26 | 3.48 | 3.34 |
| 2923928 | 4.15 | 3.99 | 4.00 | 4.37 | 4.24 | 4.24 | 4.54 | 4.40 | 4.43 | 4.03 | 4.60 | 4.10 |
| 2883317 | 5.12 | 5.62 | 4.59 | 4.46 | 4.82 | 5.71 | 4.61 | 4.58 | 4.56 | 4.65 | 4.93 | 5.03 |
| 2479698 | 5.96 | 6.00 | 5.90 | 6.07 | 6.07 | 6.22 | 5.79 | 6.50 | 6.08 | 5.97 | 6.16 | 6.14 |
| 3428225 | 3.82 | 3.81 | 3.62 | 3.70 | 3.69 | 3.93 | 3.72 | 3.72 | 3.73 | 3.60 | 3.65 | 3.58 |
| 3393446 | 8.20 | 7.41 | 6.95 | 6.83 | 6.84 | 7.50 | 7.28 | 6.74 | 6.80 | 6.77 | 7.52 | 6.76 |
| 3116614 | 11.48 | 11.25 | 12.35 | 12.08 | 12.78 | 12.77 | 11.24 | 12.75 | 13.05 | 13.27 | 12.41 | 13.14 |
| 3415320 | 9.28 | 9.79 | 9.53 | 11.34 | 10.83 | 9.26 | 11.08 | 10.48 | 9.84 | 10.57 | 9.64 | 10.34 |
| 3757108 | 9.22 | 10.78 | 9.74 | 11.58 | 9.62 | 7.40 | 11.17 | 9.69 | 7.71 | 8.57 | 7.69 | 7.52 |
| 4012178 | 6.12 | 6.18 | 6.01 | 10.65 | 6.64 | 6.62 | 10.50 | 10.92 | 8.07 | 6.64 | 6.37 | 6.79 |
| 3546213 | 9.39 | 7.88 | 9.87 | 10.99 | 11.24 | 10.28 | 10.93 | 10.70 | 11.34 | 11.50 | 10.95 | 11.71 |
| 3561381 | 7.86 | 6.79 | 10.83 | 10.27 | 10.59 | 9.12 | 9.90 | 10.49 | 11.04 | 10.96 | 9.38 | 10.51 |

TABLE 38

Normalized intensity of microarray data for a set of samples.

| TCID | V01 0157 | V01 0158 | V01 0159 | V01 0160 | V01 0161 | V01 0162 | V01 0163 | V01 0164 | V01 0165 | V01 0166 | V01 0167 | V01 0168 |
|---|---|---|---|---|---|---|---|---|---|---|---|---|
| 2604998 | 6.66 | 8.99 | 8.22 | 8.54 | 6.23 | 7.55 | 6.94 | 8.30 | 7.95 | 7.73 | 9.13 | 7.26 |
| 3603932 | 7.12 | 6.86 | 7.02 | 7.28 | 8.10 | 7.48 | 8.54 | 7.19 | 6.73 | 7.35 | 7.26 | 6.96 |
| 2710599 | 6.94 | 5.75 | 6.97 | 9.85 | 9.35 | 9.97 | 6.25 | 5.51 | 8.84 | 9.02 | 10.26 | 9.43 |
| 2440258 | 8.46 | 6.48 | 8.28 | 8.45 | 8.14 | 7.49 | 8.64 | 7.54 | 8.65 | 8.53 | 7.67 | 8.53 |
| 3169331 | 6.87 | 7.02 | 7.18 | 7.37 | 7.01 | 7.05 | 7.20 | 7.89 | 7.28 | 6.44 | 6.52 | 6.60 |
| 2988882 | 10.05 | 9.75 | 10.29 | 9.76 | 10.01 | 9.92 | 9.96 | 9.59 | 9.76 | 9.76 | 9.81 | 9.79 |
| 2964231 | 8.70 | 8.36 | 8.19 | 9.54 | 10.48 | 9.74 | 10.27 | 8.97 | 8.62 | 7.65 | 8.74 | 7.93 |

TABLE 38-continued

Normalized intensity of microarray data for a set of samples.

| TCID | V01 0157 | V01 0158 | V01 0159 | V01 0160 | V01 0161 | V01 0162 | V01 0163 | V01 0164 | V01 0165 | V01 0166 | V01 0167 | V01 0168 |
|---|---|---|---|---|---|---|---|---|---|---|---|---|
| 3111561 | 8.58 | 10.28 | 7.62 | 10.48 | 4.93 | 8.89 | 8.79 | 9.90 | 9.27 | 6.78 | 10.31 | 6.36 |
| 2562529 | 8.64 | 9.10 | 9.21 | 9.93 | 9.66 | 9.91 | 9.35 | 8.43 | 9.30 | 9.62 | 10.21 | 9.77 |
| 3692999 | 11.67 | 10.68 | 11.27 | 12.09 | 11.17 | 9.50 | 11.14 | 12.08 | 13.09 | 10.95 | 10.69 | 10.46 |
| 2439554 | 8.54 | 5.90 | 6.96 | 6.55 | 9.30 | 8.14 | 6.66 | 7.30 | 7.05 | 7.15 | 6.26 | 8.07 |
| 2685304 | 9.38 | 7.86 | 8.60 | 8.89 | 9.36 | 9.55 | 8.48 | 6.79 | 7.67 | 8.13 | 8.28 | 8.92 |
| 2578790 | 5.56 | 7.79 | 6.98 | 6.91 | 4.51 | 6.17 | 5.85 | 5.03 | 7.13 | 5.55 | 6.26 | 4.59 |
| 2373842 | 11.97 | 10.30 | 11.54 | 11.49 | 11.38 | 10.85 | 11.50 | 11.28 | 11.69 | 11.85 | 10.69 | 11.80 |
| 2750627 | 9.06 | 10.11 | 9.23 | 9.68 | 4.55 | 9.07 | 8.65 | 9.70 | 9.40 | 9.09 | 10.46 | 9.08 |
| 3397774 | 5.44 | 4.58 | 4.76 | 7.98 | 4.68 | 4.58 | 4.97 | 5.09 | 4.97 | 5.00 | 5.29 | 5.46 |
| 2635741 | 8.80 | 7.07 | 8.40 | 8.69 | 8.24 | 7.67 | 8.48 | 8.40 | 8.93 | 8.93 | 7.80 | 9.32 |
| 3970833 | 9.37 | 9.84 | 9.02 | 9.67 | 9.62 | 9.31 | 9.63 | 9.90 | 9.51 | 9.40 | 9.66 | 9.30 |
| 3577612 | 11.26 | 9.74 | 10.86 | 10.18 | 10.78 | 10.62 | 10.33 | 10.54 | 11.16 | 10.97 | 10.02 | 11.23 |
| 2708922 | 10.00 | 7.10 | 10.50 | 7.87 | 6.40 | 6.90 | 7.59 | 7.25 | 8.37 | 9.14 | 7.92 | 8.83 |
| 2970897 | 5.19 | 6.76 | 5.07 | 5.57 | 6.62 | 5.01 | 5.21 | 6.02 | 5.72 | 4.96 | 5.29 | 5.06 |
| 3724545 | 10.75 | 9.25 | 8.95 | 9.70 | 8.16 | 8.87 | 8.28 | 9.47 | 10.28 | 10.24 | 9.80 | 10.03 |
| 2798538 | 9.43 | 8.94 | 8.28 | 9.31 | 8.97 | 9.00 | 9.35 | 8.92 | 9.78 | 8.51 | 8.95 | 8.66 |
| 2806468 | 11.06 | 9.69 | 11.18 | 11.34 | 10.03 | 10.55 | 10.32 | 11.19 | 11.62 | 11.20 | 10.70 | 11.79 |
| 2880051 | 6.10 | 6.06 | 6.17 | 6.43 | 6.14 | 6.14 | 6.57 | 6.83 | 6.88 | 6.68 | 6.02 | 6.34 |
| 2732508 | 3.41 | 3.77 | 3.28 | 3.38 | 8.06 | 6.62 | 3.81 | 4.54 | 3.61 | 3.50 | 3.59 | 3.59 |
| 2822492 | 6.14 | 5.28 | 5.40 | 5.61 | 5.29 | 5.09 | 5.51 | 6.01 | 6.36 | 5.69 | 5.24 | 5.49 |
| 3404030 | 8.63 | 7.11 | 8.19 | 7.94 | 7.75 | 7.39 | 9.16 | 7.98 | 9.45 | 9.74 | 7.65 | 9.05 |
| 3059667 | 8.78 | 11.15 | 10.58 | 10.39 | 4.29 | 9.66 | 8.89 | 7.46 | 8.00 | 7.48 | 11.27 | 6.71 |
| 3108526 | 8.59 | 10.92 | 10.12 | 10.22 | 7.69 | 9.18 | 8.12 | 10.19 | 9.77 | 8.33 | 10.07 | 7.37 |
| 2526806 | 8.41 | 8.03 | 11.34 | 8.06 | 12.23 | 12.36 | 9.23 | 8.83 | 10.37 | 8.14 | 9.26 | 8.16 |
| 2428501 | 7.17 | 5.96 | 7.96 | 7.47 | 8.47 | 7.52 | 7.36 | 6.84 | 6.20 | 7.19 | 6.11 | 7.58 |
| 2657808 | 5.43 | 5.16 | 7.59 | 8.64 | 7.73 | 7.46 | 5.90 | 5.37 | 6.24 | 7.19 | 8.80 | 8.34 |
| 2584018 | 8.31 | 5.59 | 7.55 | 9.34 | 9.92 | 10.06 | 10.61 | 8.07 | 7.79 | 8.26 | 6.46 | 8.88 |
| 3976341 | 10.28 | 8.27 | 9.96 | 9.58 | 10.62 | 11.46 | 10.47 | 9.48 | 10.20 | 10.52 | 9.66 | 10.43 |
| 2739308 | 6.41 | 4.59 | 5.16 | 5.47 | 4.26 | 4.37 | 4.80 | 5.49 | 5.57 | 6.15 | 5.16 | 5.90 |
| 3959862 | 5.51 | 4.53 | 4.37 | 4.59 | 4.97 | 4.18 | 5.05 | 4.85 | 4.47 | 5.16 | 4.83 | 7.57 |
| 2362351 | 8.19 | 6.85 | 7.46 | 7.79 | 7.90 | 7.26 | 8.05 | 7.59 | 8.00 | 8.01 | 6.85 | 8.15 |
| 3648391 | 6.02 | 4.61 | 4.81 | 6.04 | 7.49 | 6.87 | 4.50 | 5.52 | 4.54 | 5.12 | 5.00 | 5.29 |
| 3009299 | 10.60 | 10.45 | 10.22 | 10.85 | 10.85 | 10.57 | 10.75 | 10.73 | 10.62 | 10.62 | 10.89 | 10.35 |
| 3443464 | 5.53 | 5.56 | 5.67 | 5.19 | 5.77 | 5.55 | 6.93 | 5.60 | 5.98 | 7.26 | 5.67 | 5.93 |
| 2730746 | 6.81 | 9.04 | 8.02 | 7.89 | 5.69 | 6.74 | 6.61 | 8.67 | 8.32 | 7.47 | 8.52 | 6.28 |
| 2427619 | 9.11 | 7.69 | 8.56 | 9.58 | 7.35 | 8.39 | 8.43 | 8.29 | 9.49 | 9.26 | 7.87 | 9.50 |
| 3042001 | 8.57 | 8.75 | 8.42 | 8.78 | 8.14 | 8.68 | 9.04 | 8.95 | 8.87 | 8.56 | 8.56 | 8.41 |
| 2566848 | 5.68 | 5.07 | 5.52 | 5.63 | 5.77 | 5.43 | 5.67 | 5.26 | 5.42 | 5.70 | 5.13 | 5.78 |
| 2984616 | 9.39 | 9.47 | 9.17 | 9.37 | 9.35 | 9.28 | 9.72 | 9.14 | 8.76 | 8.94 | 9.12 | 8.79 |
| 2378068 | 7.18 | 6.70 | 7.44 | 7.67 | 9.31 | 9.37 | 8.24 | 7.76 | 6.83 | 7.88 | 7.27 | 9.18 |
| 2721959 | 7.08 | 6.33 | 10.80 | 9.36 | 10.48 | 10.60 | 6.83 | 6.35 | 8.51 | 6.71 | 8.42 | 7.80 |
| 2877508 | 10.05 | 10.24 | 9.57 | 10.51 | 10.83 | 10.36 | 10.70 | 10.17 | 10.08 | 9.77 | 10.33 | 10.05 |
| 3450861 | 6.17 | 4.84 | 6.22 | 7.13 | 6.26 | 5.72 | 6.02 | 6.20 | 6.58 | 7.13 | 6.11 | 7.29 |
| 2688717 | 9.11 | 7.68 | 9.57 | 10.04 | 8.65 | 8.14 | 8.44 | 8.39 | 9.43 | 9.37 | 7.40 | 9.87 |
| 3270270 | 9.60 | 7.54 | 8.56 | 8.38 | 9.35 | 8.30 | 8.71 | 8.64 | 8.81 | 9.09 | 7.56 | 9.27 |
| 3417703 | 9.16 | 9.60 | 9.20 | 8.26 | 4.37 | 7.16 | 8.43 | 10.17 | 8.93 | 6.03 | 7.45 | 6.62 |
| 3302990 | 7.31 | 8.08 | 6.94 | 8.24 | 7.71 | 7.45 | 7.44 | 8.67 | 7.61 | 6.80 | 6.94 | 6.90 |
| 2377283 | 5.05 | 4.15 | 5.09 | 5.17 | 9.96 | 6.51 | 4.56 | 4.98 | 4.62 | 4.63 | 4.52 | 5.19 |
| 3122678 | 4.99 | 4.38 | 4.74 | 5.04 | 5.26 | 5.33 | 5.44 | 4.65 | 5.27 | 4.94 | 4.82 | 4.64 |
| 2688499 | 9.61 | 9.80 | 9.74 | 9.64 | 7.93 | 9.07 | 8.45 | 9.27 | 8.76 | 8.91 | 9.97 | 8.60 |
| 2377094 | 8.28 | 9.65 | 8.50 | 9.57 | 9.10 | 8.61 | 8.42 | 8.84 | 8.68 | 8.38 | 9.74 | 7.98 |
| 3278198 | 7.25 | 8.47 | 8.06 | 8.78 | 8.67 | 8.32 | 8.62 | 7.93 | 8.18 | 7.77 | 8.63 | 7.37 |
| 2598261 | 8.29 | 7.03 | 10.76 | 7.46 | 11.68 | 12.16 | 8.60 | 8.34 | 9.71 | 7.64 | 8.54 | 7.66 |
| 3982612 | 9.17 | 7.39 | 8.73 | 9.81 | 9.28 | 8.21 | 8.91 | 8.41 | 9.46 | 9.28 | 7.96 | 9.69 |
| 2884845 | 4.70 | 4.61 | 6.11 | 4.50 | 5.17 | 7.37 | 4.83 | 4.71 | 4.45 | 4.58 | 4.55 | 4.83 |
| 3982560 | 7.96 | 5.46 | 6.75 | 7.70 | 6.75 | 6.35 | 6.60 | 6.90 | 7.35 | 6.88 | 6.40 | 7.72 |
| 3204285 | 5.92 | 5.21 | 6.63 | 5.30 | 5.98 | 7.40 | 4.93 | 5.56 | 5.23 | 5.54 | 5.48 | 5.47 |
| 3654699 | 8.39 | 12.23 | 11.12 | 11.97 | 12.70 | 11.86 | 12.39 | 11.79 | 11.69 | 9.79 | 11.55 | 9.45 |
| 2638676 | 7.90 | 6.87 | 7.40 | 7.34 | 9.23 | 8.36 | 7.30 | 6.03 | 6.99 | 7.84 | 6.72 | 8.12 |
| 3367673 | 7.97 | 9.80 | 8.88 | 8.13 | 5.45 | 7.50 | 7.33 | 8.06 | 8.42 | 7.65 | 9.12 | 6.76 |
| 3212008 | 6.25 | 6.95 | 6.90 | 7.95 | 6.50 | 6.86 | 6.82 | 6.19 | 6.36 | 8.84 | 9.50 | 8.16 |
| 3326635 | 10.18 | 9.58 | 9.74 | 10.38 | 10.18 | 10.34 | 10.30 | 10.06 | 10.25 | 10.22 | 10.66 | 10.55 |
| 3031556 | 9.99 | 8.37 | 9.19 | 9.61 | 9.59 | 9.40 | 9.83 | 9.60 | 9.45 | 9.92 | 8.37 | 10.35 |
| 3662201 | 12.16 | 9.26 | 11.43 | 11.92 | 10.87 | 9.58 | 11.66 | 12.14 | 13.15 | 10.66 | 9.47 | 10.77 |
| 2809793 | 7.18 | 6.17 | 8.56 | 9.45 | 8.86 | 8.56 | 8.17 | 7.84 | 9.58 | 9.34 | 7.89 | 9.59 |
| 2817731 | 8.10 | 7.94 | 7.56 | 7.69 | 9.44 | 8.82 | 9.12 | 7.71 | 7.55 | 8.08 | 7.72 | 7.91 |
| 4020655 | 5.39 | 4.45 | 5.47 | 6.80 | 4.63 | 5.84 | 5.22 | 4.86 | 5.05 | 7.69 | 7.41 | 6.70 |
| 3494629 | 4.48 | 4.81 | 4.81 | 8.12 | 5.79 | 6.94 | 4.61 | 4.60 | 4.90 | 5.09 | 5.77 | 6.27 |
| 3852832 | 10.45 | 7.88 | 8.36 | 9.00 | 6.20 | 6.27 | 8.70 | 9.12 | 9.78 | 10.00 | 7.70 | 9.99 |
| 3761959 | 8.49 | 8.96 | 8.87 | 9.54 | 9.57 | 9.32 | 8.92 | 8.85 | 8.87 | 9.35 | 8.87 | 8.41 |
| 2834282 | 6.10 | 6.12 | 5.67 | 7.86 | 5.15 | 6.98 | 6.75 | 5.82 | 7.52 | 7.44 | 7.44 | 6.86 |
| 3341497 | 6.00 | 7.48 | 6.19 | 7.98 | 5.86 | 6.10 | 6.30 | 6.26 | 6.10 | 7.85 | 8.12 | 6.94 |
| 2372812 | 4.88 | 4.82 | 4.61 | 4.59 | 9.49 | 5.32 | 4.80 | 5.33 | 4.59 | 4.94 | 4.62 | 4.92 |
| 2486811 | 10.52 | 7.74 | 9.07 | 9.91 | 10.84 | 10.79 | 11.12 | 9.65 | 9.73 | 10.00 | 8.16 | 10.41 |
| 3768474 | 8.57 | 7.45 | 7.72 | 7.93 | 8.80 | 8.66 | 8.70 | 7.75 | 7.41 | 8.26 | 7.90 | 8.14 |

TABLE 38-continued

Normalized intensity of microarray data for a set of samples.

| TCID | V01 0157 | V01 0158 | V01 0159 | V01 0160 | V01 0161 | V01 0162 | V01 0163 | V01 0164 | V01 0165 | V01 0166 | V01 0167 | V01 0168 |
|---|---|---|---|---|---|---|---|---|---|---|---|---|
| 3142381 | 5.97 | 10.51 | 8.56 | 6.52 | 3.85 | 5.89 | 6.25 | 7.43 | 4.11 | 5.42 | 4.97 | 5.02 |
| 2396750 | 7.32 | 6.59 | 7.16 | 7.52 | 6.37 | 7.39 | 6.65 | 7.34 | 6.63 | 6.83 | 7.37 | 7.17 |
| 3902489 | 12.55 | 10.53 | 12.19 | 11.33 | 9.92 | 9.91 | 10.50 | 10.89 | 11.77 | 12.14 | 10.22 | 11.66 |
| 3032647 | 6.43 | 8.90 | 7.88 | 7.73 | 5.74 | 7.15 | 6.00 | 8.50 | 7.89 | 5.94 | 7.55 | 5.85 |
| 3875642 | 6.13 | 5.18 | 5.25 | 5.38 | 4.88 | 5.36 | 5.94 | 6.15 | 5.57 | 5.91 | 5.17 | 6.28 |
| 4027585 | 12.24 | 9.82 | 11.96 | 10.65 | 11.04 | 10.65 | 11.31 | 10.93 | 10.99 | 11.94 | 9.86 | 11.45 |
| 2352609 | 5.82 | 7.97 | 6.56 | 7.32 | 5.36 | 6.23 | 6.35 | 7.17 | 6.99 | 6.98 | 8.31 | 6.35 |
| 3376529 | 7.90 | 8.99 | 7.79 | 9.41 | 8.65 | 8.35 | 7.59 | 8.96 | 8.41 | 8.39 | 9.36 | 8.19 |
| 2491271 | 13.34 | 12.81 | 12.93 | 13.16 | 13.41 | 13.49 | 13.54 | 13.04 | 13.21 | 12.96 | 12.82 | 13.37 |
| 3874751 | 8.68 | 9.31 | 8.79 | 9.16 | 10.29 | 9.75 | 10.19 | 9.81 | 9.31 | 8.99 | 9.01 | 9.02 |
| 2326463 | 11.90 | 10.24 | 11.77 | 11.90 | 11.73 | 12.24 | 12.25 | 11.52 | 12.10 | 12.03 | 11.20 | 12.08 |
| 3341061 | 7.52 | 6.73 | 6.71 | 6.77 | 8.90 | 8.91 | 8.77 | 7.28 | 7.58 | 7.53 | 7.28 | 6.72 |
| 3839910 | 10.49 | 6.89 | 9.46 | 8.86 | 6.47 | 7.03 | 8.20 | 8.34 | 9.59 | 9.56 | 6.84 | 10.11 |
| 2708855 | 4.93 | 3.77 | 4.44 | 6.30 | 5.74 | 5.09 | 4.09 | 4.28 | 5.10 | 6.15 | 6.60 | 6.33 |
| 3512874 | 12.38 | 10.76 | 11.72 | 11.86 | 11.95 | 11.56 | 11.99 | 12.05 | 12.23 | 12.13 | 11.12 | 12.28 |
| 2701071 | 11.11 | 9.03 | 9.90 | 10.09 | 9.97 | 8.91 | 10.27 | 9.72 | 10.63 | 10.75 | 9.03 | 11.07 |
| 3486096 | 7.02 | 8.62 | 7.78 | 8.64 | 5.97 | 6.19 | 6.05 | 7.57 | 6.24 | 6.66 | 8.67 | 6.09 |
| 2412668 | 8.45 | 7.99 | 8.12 | 8.18 | 9.08 | 8.54 | 8.88 | 8.92 | 8.11 | 8.17 | 7.82 | 8.49 |
| 3329343 | 7.27 | 6.99 | 7.92 | 7.34 | 7.98 | 8.18 | 7.25 | 6.95 | 7.03 | 7.60 | 7.66 | 7.90 |
| 3259367 | 4.42 | 4.40 | 4.28 | 5.43 | 4.15 | 4.21 | 5.07 | 4.08 | 4.12 | 5.64 | 5.65 | 5.30 |
| 3373845 | 8.82 | 7.75 | 9.11 | 8.91 | 10.51 | 10.09 | 10.06 | 9.18 | 8.40 | 8.45 | 7.83 | 8.69 |
| 2321911 | 8.94 | 8.21 | 9.16 | 8.33 | 8.42 | 8.10 | 9.07 | 8.15 | 8.74 | 8.83 | 8.45 | 9.14 |
| 3353914 | 6.76 | 6.53 | 6.14 | 6.76 | 8.53 | 8.50 | 8.36 | 6.57 | 6.80 | 6.29 | 6.96 | 6.82 |
| 3744680 | 8.49 | 6.93 | 7.44 | 7.36 | 8.09 | 7.91 | 8.63 | 7.87 | 7.90 | 8.12 | 7.09 | 7.86 |
| 2373336 | 6.94 | 5.07 | 7.07 | 7.49 | 8.65 | 9.36 | 6.63 | 6.50 | 8.93 | 7.18 | 5.90 | 6.88 |
| 3067478 | 6.18 | 5.72 | 5.58 | 7.00 | 6.18 | 6.49 | 4.67 | 4.89 | 7.11 | 7.00 | 6.84 | 6.13 |
| 3976766 | 9.55 | 6.84 | 8.73 | 8.20 | 8.43 | 7.91 | 8.60 | 8.41 | 8.59 | 8.64 | 7.75 | 8.66 |
| 3246888 | 6.74 | 7.81 | 6.23 | 7.69 | 4.82 | 5.89 | 5.65 | 5.26 | 6.96 | 7.24 | 7.46 | 7.14 |
| 3147985 | 6.59 | 6.12 | 6.31 | 6.46 | 8.10 | 8.86 | 8.01 | 6.49 | 6.17 | 6.21 | 6.69 | 6.49 |
| 3185522 | 9.07 | 8.72 | 9.23 | 8.87 | 11.62 | 10.84 | 10.69 | 9.70 | 8.89 | 8.80 | 9.32 | 9.31 |
| 3861948 | 13.03 | 11.71 | 12.56 | 12.49 | 12.61 | 12.27 | 12.65 | 12.41 | 12.89 | 12.75 | 12.02 | 13.14 |
| 3393479 | 9.40 | 10.83 | 9.10 | 8.19 | 9.98 | 9.83 | 10.81 | 9.57 | 9.23 | 8.26 | 8.58 | 8.54 |
| 3540862 | 6.57 | 7.29 | 6.92 | 7.12 | 6.80 | 7.03 | 6.96 | 6.66 | 6.88 | 7.01 | 6.96 | 6.58 |
| 2777714 | 12.22 | 10.61 | 12.51 | 11.73 | 9.26 | 9.16 | 10.87 | 11.21 | 11.74 | 12.20 | 10.56 | 11.97 |
| 3110395 | 4.36 | 4.17 | 4.62 | 4.69 | 4.27 | 4.22 | 4.83 | 4.26 | 4.12 | 5.29 | 4.60 | 4.58 |
| 3895795 | 9.40 | 7.50 | 7.89 | 8.21 | 7.27 | 7.45 | 8.14 | 7.87 | 9.22 | 9.14 | 8.22 | 9.06 |
| 2854445 | 9.38 | 8.21 | 7.76 | 8.18 | 11.16 | 11.32 | 11.54 | 9.44 | 8.86 | 8.24 | 8.49 | 8.96 |
| 3606034 | 6.87 | 7.84 | 7.09 | 7.32 | 8.26 | 7.69 | 7.69 | 7.60 | 7.56 | 7.10 | 7.84 | 7.11 |
| 3375735 | 8.56 | 7.23 | 8.13 | 7.88 | 8.38 | 7.70 | 8.76 | 7.83 | 7.94 | 8.18 | 7.42 | 7.89 |
| 3948047 | 9.05 | 7.28 | 7.83 | 7.97 | 8.90 | 8.43 | 8.98 | 8.27 | 8.39 | 8.91 | 7.59 | 8.52 |
| 3010503 | 10.22 | 9.01 | 8.93 | 9.10 | 10.39 | 10.01 | 11.18 | 8.74 | 8.35 | 9.89 | 7.90 | 10.09 |
| 3622934 | 6.33 | 7.09 | 6.14 | 6.92 | 6.97 | 6.63 | 6.04 | 7.07 | 7.04 | 7.43 | 7.48 | 7.20 |
| 3441849 | 10.66 | 8.77 | 9.65 | 9.64 | 10.15 | 10.15 | 10.17 | 10.17 | 10.20 | 10.23 | 9.26 | 10.19 |
| 3006572 | 6.62 | 6.48 | 6.62 | 6.31 | 6.58 | 6.24 | 6.39 | 6.45 | 6.23 | 6.47 | 6.69 | 6.51 |
| 3365136 | 8.56 | 8.34 | 8.22 | 9.84 | 8.03 | 8.90 | 8.59 | 8.69 | 7.47 | 9.52 | 10.80 | 9.46 |
| 2642791 | 8.64 | 8.42 | 7.84 | 8.57 | 9.23 | 8.63 | 8.94 | 9.01 | 8.86 | 8.60 | 7.80 | 8.61 |
| 2904485 | 8.27 | 9.25 | 8.65 | 8.16 | 6.40 | 7.55 | 7.99 | 9.50 | 8.72 | 7.87 | 8.41 | 7.64 |
| 3772661 | 10.57 | 8.93 | 9.28 | 9.42 | 11.59 | 11.20 | 11.23 | 10.27 | 9.74 | 9.78 | 9.26 | 10.00 |
| 2796553 | 11.26 | 9.51 | 10.29 | 9.72 | 10.36 | 9.94 | 10.49 | 9.61 | 10.53 | 10.60 | 9.54 | 10.47 |
| 3063795 | 7.69 | 6.96 | 7.44 | 6.92 | 7.79 | 8.53 | 7.57 | 7.47 | 7.46 | 7.36 | 7.30 | 7.60 |
| 3338192 | 8.32 | 8.73 | 9.04 | 9.18 | 8.45 | 8.71 | 8.23 | 8.69 | 8.60 | 9.14 | 9.94 | 8.93 |
| 3214845 | 4.51 | 5.50 | 4.73 | 4.26 | 4.32 | 6.23 | 4.61 | 4.62 | 4.38 | 4.61 | 4.23 | 4.57 |
| 2730303 | 4.23 | 4.21 | 4.24 | 4.03 | 8.27 | 6.02 | 4.15 | 4.45 | 4.13 | 4.17 | 4.08 | 4.20 |
| 3811086 | 7.66 | 8.09 | 7.51 | 7.89 | 8.79 | 8.07 | 8.38 | 7.87 | 8.15 | 7.42 | 7.75 | 8.12 |
| 2981874 | 10.50 | 10.56 | 10.06 | 10.47 | 10.64 | 10.47 | 10.63 | 10.65 | 10.30 | 10.08 | 9.60 | 10.20 |
| 3242353 | 5.81 | 6.36 | 5.68 | 5.87 | 7.03 | 6.85 | 6.42 | 6.42 | 6.02 | 5.44 | 5.52 | 6.33 |
| 2442008 | 5.91 | 6.06 | 5.62 | 5.76 | 5.46 | 5.97 | 5.43 | 5.32 | 5.35 | 6.20 | 6.47 | 6.68 |
| 3564210 | 11.02 | 8.29 | 9.11 | 9.11 | 9.98 | 9.69 | 10.13 | 9.67 | 9.22 | 9.41 | 8.15 | 10.17 |
| 2490351 | 4.18 | 4.09 | 4.02 | 3.84 | 3.94 | 3.93 | 4.21 | 4.18 | 4.10 | 4.23 | 4.01 | 4.28 |
| 3759006 | 11.87 | 8.80 | 11.62 | 9.86 | 7.08 | 7.01 | 8.65 | 9.50 | 9.77 | 11.03 | 8.25 | 9.96 |
| 3264997 | 4.16 | 3.99 | 3.96 | 3.78 | 4.12 | 4.20 | 4.09 | 4.14 | 4.06 | 4.30 | 4.08 | 4.28 |
| 3912079 | 3.91 | 3.57 | 4.15 | 3.56 | 3.54 | 3.56 | 3.58 | 3.76 | 4.10 | 3.53 | 4.19 | |
| 2926802 | 6.55 | 4.53 | 4.97 | 5.68 | 4.94 | 4.87 | 5.01 | 5.38 | 5.40 | 6.01 | 5.05 | 6.24 |
| 2430163 | 3.93 | 3.73 | 4.04 | 3.73 | 4.15 | 3.90 | 3.94 | 3.94 | 4.46 | 4.11 | 3.66 | 3.90 |
| 3039830 | 3.20 | 3.05 | 3.13 | 3.08 | 3.06 | 3.25 | 3.14 | 3.30 | 3.70 | 3.10 | 3.44 | 3.17 |
| 3935486 | 7.55 | 5.57 | 6.34 | 5.99 | 7.91 | 8.23 | 6.22 | 6.14 | 5.57 | 5.35 | 5.30 | 6.85 |
| 3457336 | 5.46 | 5.59 | 5.42 | 5.22 | 8.90 | 8.13 | 6.80 | 5.45 | 5.65 | 5.61 | 5.63 | 5.71 |
| 3811949 | 3.49 | 3.34 | 3.49 | 3.34 | 3.34 | 3.36 | 3.56 | 3.52 | 3.60 | 3.61 | 3.43 | 3.58 |
| 3343832 | 3.89 | 4.04 | 3.88 | 3.65 | 3.72 | 3.90 | 3.80 | 4.04 | 3.79 | 3.98 | 3.82 | 3.89 |
| 3161261 | 6.11 | 5.88 | 5.93 | 5.59 | 5.09 | 5.60 | 6.03 | 5.99 | 6.45 | 6.12 | 5.77 | 5.80 |
| 3594003 | 3.62 | 3.71 | 3.96 | 3.79 | 4.15 | 3.64 | 4.08 | 3.66 | 3.77 | 3.83 | 3.53 | 3.97 |
| 3805614 | 4.73 | 4.38 | 4.88 | 4.16 | 4.94 | 4.77 | 5.22 | 4.39 | 4.35 | 5.30 | 4.57 | 4.99 |
| 3364127 | 6.81 | 6.80 | 7.21 | 6.39 | 6.76 | 6.85 | 8.34 | 7.59 | 6.99 | 6.81 | 6.69 | 6.99 |
| 3834341 | 3.99 | 3.95 | 4.25 | 3.72 | 3.84 | 4.08 | 4.27 | 4.21 | 4.03 | 4.31 | 4.03 | 4.16 |
| 2585400 | 4.63 | 4.31 | 4.71 | 4.18 | 4.16 | 4.38 | 4.32 | 4.54 | 4.46 | 4.23 | 4.14 | 4.24 |

TABLE 38-continued

Normalized intensity of microarray data for a set of samples.

| TCID | V01 0157 | V01 0158 | V01 0159 | V01 0160 | V01 0161 | V01 0162 | V01 0163 | V01 0164 | V01 0165 | V01 0166 | V01 0167 | V01 0168 |
|---|---|---|---|---|---|---|---|---|---|---|---|---|
| 2941690 | 4.38 | 4.20 | 4.63 | 3.83 | 4.02 | 4.23 | 4.33 | 4.31 | 4.07 | 4.37 | 4.41 | 4.79 |
| 3484895 | 4.87 | 5.31 | 5.01 | 4.72 | 4.72 | 4.65 | 4.94 | 5.03 | 4.76 | 5.08 | 4.74 | 4.86 |
| 3159754 | 3.61 | 3.76 | 3.80 | 3.61 | 3.67 | 3.62 | 3.95 | 4.06 | 3.61 | 3.89 | 3.63 | 3.75 |
| 2894790 | 4.42 | 4.03 | 3.99 | 3.57 | 3.66 | 3.89 | 3.82 | 3.91 | 3.88 | 3.74 | 3.76 | 3.92 |
| 3363686 | 3.52 | 3.45 | 3.49 | 3.51 | 3.40 | 3.16 | 3.42 | 3.40 | 3.91 | 3.59 | 3.43 | 3.55 |
| 2923928 | 4.26 | 4.25 | 4.60 | 4.03 | 4.12 | 4.21 | 4.65 | 4.11 | 4.61 | 4.35 | 4.19 | 4.61 |
| 2883317 | 5.08 | 4.93 | 5.01 | 4.27 | 4.85 | 5.24 | 5.02 | 4.83 | 4.71 | 4.49 | 4.78 | 5.50 |
| 2479698 | 6.05 | 6.25 | 6.12 | 6.14 | 5.85 | 5.98 | 6.02 | 5.92 | 6.23 | 5.91 | 6.34 | 6.06 |
| 3428225 | 3.75 | 3.51 | 3.82 | 3.45 | 3.64 | 3.59 | 4.03 | 3.73 | 3.73 | 3.77 | 3.65 | 3.91 |
| 3393446 | 7.52 | 6.75 | 7.20 | 7.07 | 8.17 | 7.42 | 8.32 | 7.14 | 7.11 | 7.58 | 7.41 | 7.22 |
| 3116614 | 11.80 | 12.98 | 12.82 | 12.95 | 9.86 | 12.18 | 12.25 | 13.06 | 13.08 | 12.82 | 13.26 | 12.20 |
| 3415320 | 8.12 | 10.53 | 9.44 | 10.24 | 9.46 | 9.70 | 8.97 | 10.74 | 10.59 | 9.14 | 10.06 | 8.26 |
| 3757108 | 7.84 | 7.72 | 8.16 | 7.60 | 9.01 | 9.22 | 7.92 | 7.76 | 8.86 | 7.56 | 8.44 | 7.93 |
| 4012178 | 6.50 | 6.84 | 8.58 | 10.15 | 6.12 | 7.24 | 6.27 | 6.56 | 5.94 | 9.58 | 10.24 | 8.63 |
| 3546213 | 9.07 | 11.01 | 10.73 | 10.93 | 7.92 | 10.73 | 9.66 | 10.81 | 10.89 | 10.54 | 11.55 | 9.76 |
| 3561381 | 7.08 | 10.29 | 9.83 | 9.71 | 5.92 | 9.03 | 7.76 | 9.16 | 8.98 | 9.47 | 10.07 | 8.55 |

TABLE 39

Normalized intensity of microarray data for a set of samples.

| TCID | V01 0169 | V01 0170 | V01 0171 | V01 0172 | V01 0173 | V01 0174 | V01 0175 | V01 0176 | V01 0177 | V01 0178 | V01 0179 | V01 0180 |
|---|---|---|---|---|---|---|---|---|---|---|---|---|
| 2604998 | 7.96 | 8.36 | 9.41 | 8.97 | 9.32 | 8.91 | 7.08 | 8.26 | 9.27 | 8.65 | 8.58 | 7.40 |
| 3603932 | 7.15 | 7.41 | 7.15 | 7.24 | 6.85 | 7.49 | 7.62 | 7.44 | 7.33 | 6.91 | 6.71 | 8.19 |
| 2710599 | 9.14 | 8.27 | 10.56 | 10.39 | 11.34 | 10.52 | 6.91 | 9.43 | 8.09 | 8.03 | 6.46 | 8.62 |
| 2440258 | 7.69 | 8.11 | 5.49 | 5.68 | 4.60 | 6.28 | 8.55 | 7.79 | 6.34 | 5.50 | 8.49 | 8.48 |
| 3169331 | 6.53 | 7.18 | 6.67 | 7.20 | 6.63 | 7.26 | 6.95 | 7.48 | 7.56 | 7.58 | 7.27 | 7.01 |
| 2988882 | 9.53 | 10.27 | 9.60 | 9.50 | 9.79 | 9.17 | 9.78 | 9.85 | 9.75 | 9.86 | 9.93 | |
| 2964231 | 8.59 | 8.70 | 7.61 | 9.42 | 7.44 | 8.61 | 10.32 | 9.61 | 7.77 | 8.49 | 7.64 | 10.22 |
| 3111561 | 9.28 | 10.51 | 5.39 | 7.34 | 5.81 | 5.87 | 9.23 | 8.33 | 11.39 | 11.39 | 10.75 | 4.90 |
| 2562529 | 9.26 | 9.34 | 11.22 | 10.92 | 10.67 | 10.60 | 9.14 | 9.46 | 10.23 | 10.09 | 9.08 | 9.54 |
| 3692999 | 10.41 | 11.32 | 6.15 | 9.48 | 7.63 | 10.15 | 10.50 | 12.63 | 12.77 | 11.08 | 12.49 | 9.92 |
| 2439554 | 7.29 | 6.08 | 4.59 | 4.96 | 4.83 | 6.35 | 7.51 | 6.78 | 5.01 | 4.82 | 6.85 | 7.61 |
| 2685304 | 7.56 | 7.31 | 11.14 | 9.76 | 11.56 | 10.55 | 8.20 | 7.75 | 5.77 | 7.42 | 6.47 | 9.21 |
| 2578790 | 8.29 | 7.54 | 4.47 | 4.53 | 4.08 | 5.72 | 6.24 | 7.37 | 7.78 | 8.09 | 6.25 | 4.42 |
| 2373842 | 11.48 | 10.96 | 8.86 | 9.74 | 8.15 | 10.13 | 11.41 | 10.75 | 9.79 | 8.87 | 11.68 | 11.57 |
| 2750627 | 9.06 | 9.94 | 11.28 | 10.54 | 10.92 | 10.60 | 8.17 | 9.46 | 11.28 | 10.44 | 10.56 | 7.44 |
| 3397774 | 4.63 | 4.77 | 4.64 | 5.37 | 4.75 | 4.59 | 4.90 | 4.63 | 5.29 | 5.22 | 5.16 | 4.89 |
| 2635741 | 8.25 | 8.40 | 5.87 | 6.34 | 6.29 | 6.94 | 8.39 | 8.48 | 6.91 | 6.90 | 8.87 | 8.84 |
| 3970833 | 9.47 | 9.63 | 9.62 | 9.82 | 9.43 | 9.78 | 9.67 | 9.67 | 9.47 | 9.41 | 8.94 | 9.64 |
| 3577612 | 10.48 | 9.89 | 11.58 | 9.84 | 11.57 | 9.59 | 10.29 | 10.21 | 8.74 | 8.83 | 10.54 | 10.53 |
| 2708922 | 7.35 | 8.73 | 8.78 | 8.61 | 8.47 | 8.54 | 7.57 | 7.05 | 8.34 | 7.71 | 8.77 | 8.69 |
| 2970897 | 5.82 | 6.72 | 4.81 | 4.56 | 5.03 | 4.99 | 5.10 | 5.14 | 5.24 | 5.11 | 6.14 | 5.36 |
| 3724545 | 9.75 | 9.33 | 10.48 | 9.58 | 10.30 | 10.11 | 8.56 | 9.59 | 9.12 | 9.33 | 9.00 | 9.36 |
| 2798538 | 8.93 | 9.02 | 8.16 | 9.05 | 8.23 | 8.55 | 9.79 | 9.37 | 8.39 | 9.01 | 9.15 | 9.84 |
| 2806468 | 10.80 | 11.07 | 8.53 | 9.23 | 7.22 | 8.83 | 10.86 | 10.30 | 8.89 | 8.34 | 11.50 | 11.16 |
| 2880051 | 6.37 | 6.44 | 5.76 | 5.82 | 5.85 | 6.75 | 6.11 | 6.16 | 6.37 | 6.38 | 6.21 | 6.30 |
| 2732508 | 3.81 | 3.89 | 3.45 | 3.41 | 3.43 | 4.95 | 5.14 | 7.52 | 3.35 | 3.53 | 3.30 | 3.42 |
| 2822492 | 6.06 | 5.15 | 5.41 | 6.19 | 5.52 | 5.08 | 5.28 | 5.96 | 6.06 | 5.81 | 5.80 | 5.80 |
| 3404030 | 8.13 | 8.78 | 6.18 | 6.47 | 5.17 | 6.46 | 8.37 | 7.52 | 7.74 | 6.65 | 7.69 | 8.53 |
| 3059667 | 8.97 | 11.42 | 5.33 | 8.18 | 6.09 | 8.95 | 9.19 | 8.70 | 11.72 | 11.91 | 11.06 | 5.27 |
| 3108526 | 9.34 | 10.00 | 8.31 | 9.69 | 8.67 | 9.42 | 7.81 | 10.44 | 10.49 | 11.02 | 10.41 | 7.90 |
| 2526806 | 12.62 | 7.77 | 12.89 | 11.95 | 12.40 | 8.83 | 10.56 | 11.82 | 7.78 | 9.58 | 6.50 | 10.42 |
| 2428501 | 7.12 | 5.93 | 6.07 | 6.43 | 6.51 | 7.42 | 7.97 | 7.35 | 5.95 | 5.79 | 7.22 | 8.14 |
| 2657808 | 6.42 | 7.06 | 11.12 | 7.49 | 11.56 | 8.02 | 6.73 | 5.64 | 7.38 | 6.90 | 5.96 | 5.80 |
| 2584018 | 9.23 | 7.56 | 9.88 | 9.30 | 10.14 | 11.06 | 10.16 | 8.93 | 6.07 | 6.93 | 8.07 | 10.82 |
| 3976341 | 9.27 | 9.45 | 11.99 | 10.38 | 11.93 | 10.49 | 9.58 | 9.68 | 7.85 | 8.66 | 9.08 | 10.49 |
| 2739308 | 5.11 | 5.08 | 4.35 | 4.51 | 4.56 | 4.57 | 5.42 | 4.72 | 5.21 | 5.11 | 5.61 | 5.17 |
| 3959862 | 4.71 | 5.08 | 4.59 | 4.36 | 3.84 | 4.94 | 4.99 | 5.65 | 4.33 | 4.99 | 5.25 | 6.19 |
| 2362351 | 7.13 | 7.57 | 5.55 | 5.54 | 5.73 | 6.10 | 7.58 | 6.92 | 6.80 | 6.01 | 7.74 | 7.75 |
| 3648391 | 6.12 | 5.20 | 4.64 | 4.45 | 3.89 | 4.49 | 4.26 | 5.97 | 5.44 | 4.24 | 4.46 | 5.09 |
| 3009299 | 10.41 | 10.61 | 10.43 | 10.88 | 10.38 | 10.47 | 10.76 | 10.77 | 10.46 | 10.39 | 10.52 | 10.91 |
| 3443464 | 6.18 | 5.94 | 5.28 | 5.29 | 4.91 | 5.13 | 6.04 | 5.48 | 5.65 | 5.68 | 5.67 | 5.91 |
| 2730746 | 7.94 | 7.98 | 5.70 | 8.49 | 5.57 | 7.59 | 7.05 | 8.76 | 8.75 | 8.69 | 8.19 | 6.26 |
| 2427819 | 7.88 | 8.40 | 5.38 | 6.20 | 5.59 | 6.69 | 8.56 | 8.40 | 6.89 | 6.26 | 9.49 | 9.10 |
| 3042001 | 8.62 | 8.89 | 8.37 | 8.23 | 8.32 | 8.58 | 8.44 | 8.84 | 7.93 | 8.64 | 8.47 | 8.65 |
| 2566848 | 5.49 | 5.36 | 5.12 | 4.99 | 5.07 | 4.93 | 5.37 | 5.12 | 5.36 | 5.27 | 5.63 | 5.52 |
| 2984616 | 9.18 | 9.37 | 8.64 | 9.11 | 9.00 | 8.85 | 9.38 | 9.25 | 9.78 | 9.24 | 8.87 | 9.36 |
| 2378068 | 7.43 | 6.80 | 9.96 | 8.82 | 9.68 | 8.56 | 9.13 | 9.39 | 6.25 | 7.58 | 7.41 | 8.92 |
| 2721959 | 9.47 | 6.96 | 11.80 | 8.71 | 12.53 | 7.76 | 7.09 | 10.06 | 5.81 | 7.11 | 5.69 | 7.77 |

TABLE 39-continued

Normalized intensity of microarray data for a set of samples.

| TCID | V01 0169 | V01 0170 | V01 0171 | V01 0172 | V01 0173 | V01 0174 | V01 0175 | V01 0176 | V01 0177 | V01 0178 | V01 0179 | V01 0180 |
|---|---|---|---|---|---|---|---|---|---|---|---|---|
| 2877508 | 10.14 | 10.13 | 10.20 | 10.32 | 10.14 | 10.08 | 10.48 | 10.63 | 10.13 | 9.89 | 9.94 | 10.66 |
| 3450861 | 5.81 | 5.92 | 4.31 | 4.63 | 4.75 | 4.40 | 6.38 | 5.91 | 5.08 | 5.16 | 6.68 | 6.43 |
| 2688717 | 8.74 | 8.69 | 6.84 | 6.79 | 5.03 | 6.58 | 9.23 | 8.61 | 7.27 | 7.01 | 9.33 | 9.82 |
| 3270270 | 8.58 | 8.18 | 8.89 | 8.02 | 8.86 | 8.43 | 8.48 | 7.69 | 6.52 | 6.88 | 8.52 | 8.90 |
| 3417703 | 8.84 | 9.51 | 8.21 | 9.32 | 8.76 | 9.50 | 8.46 | 9.44 | 11.69 | 10.31 | 10.82 | 4.75 |
| 3302990 | 7.56 | 7.34 | 7.18 | 7.37 | 7.73 | 7.68 | 7.41 | 8.22 | 7.59 | 7.27 | 7.17 | 7.29 |
| 2377283 | 4.47 | 4.42 | 4.21 | 4.24 | 4.09 | 5.42 | 5.92 | 4.65 | 4.40 | 4.46 | 5.25 | 4.82 |
| 3122678 | 4.48 | 5.04 | 4.38 | 4.35 | 4.84 | 4.45 | 4.74 | 4.72 | 5.00 | 5.01 | 4.73 | 5.56 |
| 2688499 | 8.08 | 9.79 | 10.30 | 9.48 | 11.26 | 9.66 | 8.66 | 9.23 | 11.14 | 9.89 | 11.03 | 7.57 |
| 2377094 | 8.95 | 9.49 | 8.17 | 9.35 | 7.98 | 8.18 | 8.70 | 9.42 | 9.41 | 9.18 | 8.76 | 8.24 |
| 3278198 | 7.62 | 8.37 | 8.18 | 8.69 | 7.90 | 7.32 | 8.43 | 8.73 | 8.51 | 8.42 | 7.52 | 8.68 |
| 2598261 | 12.03 | 6.72 | 12.60 | 11.23 | 12.21 | 8.17 | 9.68 | 11.09 | 6.97 | 8.74 | 5.99 | 9.64 |
| 3982612 | 8.18 | 8.46 | 6.45 | 5.71 | 4.85 | 7.14 | 8.86 | 8.75 | 7.34 | 5.53 | 9.33 | 9.39 |
| 2884845 | 4.68 | 4.30 | 10.29 | 8.06 | 10.26 | 6.72 | 4.83 | 4.66 | 4.41 | 5.09 | 4.63 | 4.46 |
| 3982560 | 6.47 | 6.68 | 4.53 | 4.58 | 4.36 | 5.55 | 6.23 | 6.64 | 4.70 | 5.73 | 7.89 | 7.25 |
| 3204285 | 5.30 | 5.59 | 5.32 | 5.57 | 5.46 | 5.36 | 5.71 | 6.18 | 5.79 | 5.53 | 5.47 | 5.36 |
| 3654699 | 11.83 | 12.06 | 9.27 | 10.82 | 10.00 | 10.41 | 12.42 | 12.55 | 9.32 | 11.67 | 9.07 | 12.67 |
| 2638676 | 7.13 | 6.40 | 5.91 | 5.19 | 5.76 | 5.79 | 7.26 | 7.68 | 6.13 | 5.80 | 6.78 | 7.25 |
| 3367673 | 8.46 | 8.62 | 5.16 | 8.40 | 5.49 | 7.11 | 7.55 | 8.93 | 9.75 | 9.02 | 9.31 | 6.19 |
| 3212008 | 7.21 | 6.78 | 9.64 | 9.73 | 8.89 | 9.78 | 6.96 | 6.45 | 6.63 | 8.37 | 6.57 | 7.78 |
| 3326635 | 10.12 | 10.16 | 10.44 | 10.61 | 9.97 | 9.74 | 10.39 | 10.16 | 10.32 | 10.09 | 10.26 | 10.29 |
| 3031556 | 9.24 | 9.05 | 6.76 | 7.54 | 6.55 | 8.11 | 10.00 | 8.77 | 7.52 | 6.25 | 10.01 | 10.01 |
| 3662201 | 10.31 | 10.66 | 6.73 | 10.22 | 8.41 | 10.76 | 10.67 | 12.73 | 12.75 | 11.39 | 12.74 | 8.97 |
| 2809793 | 7.50 | 8.41 | 4.51 | 5.57 | 4.78 | 6.07 | 7.94 | 9.09 | 6.38 | 5.69 | 7.30 | 8.24 |
| 2817731 | 8.54 | 7.29 | 7.37 | 7.73 | 7.66 | 7.55 | 8.68 | 8.35 | 7.69 | 7.66 | 7.63 | 8.94 |
| 4020655 | 5.65 | 4.97 | 8.90 | 9.54 | 7.56 | 8.45 | 4.96 | 4.69 | 4.83 | 5.47 | 4.77 | 7.31 |
| 3494629 | 4.44 | 4.74 | 7.77 | 5.88 | 6.57 | 4.56 | 4.49 | 6.85 | 5.22 | 4.70 | 4.86 | 5.00 |
| 3852832 | 8.96 | 8.41 | 6.34 | 7.35 | 5.48 | 7.92 | 8.31 | 6.92 | 6.76 | 6.67 | 8.93 | 8.40 |
| 3761959 | 9.10 | 8.74 | 9.44 | 9.68 | 9.29 | 9.62 | 8.97 | 9.14 | 9.10 | 9.13 | 8.45 | 9.40 |
| 2834282 | 6.16 | 6.24 | 7.75 | 7.99 | 8.34 | 7.44 | 6.14 | 6.05 | 6.31 | 7.64 | 5.94 | 6.54 |
| 3341497 | 6.16 | 6.85 | 7.19 | 7.93 | 6.95 | 7.57 | 6.55 | 5.93 | 6.41 | 6.87 | 5.75 | 7.28 |
| 2372812 | 4.66 | 4.58 | 4.51 | 4.72 | 4.56 | 5.17 | 4.68 | 4.56 | 4.73 | 4.81 | 4.71 | 4.68 |
| 2486811 | 9.91 | 9.11 | 6.41 | 8.12 | 7.07 | 8.54 | 10.64 | 9.90 | 7.64 | 9.11 | 9.53 | 10.65 |
| 3768474 | 8.35 | 7.86 | 6.92 | 7.88 | 7.17 | 7.40 | 8.93 | 8.01 | 7.13 | 7.57 | 7.99 | 9.08 |
| 3142381 | 5.67 | 8.10 | 3.72 | 4.30 | 7.49 | 8.68 | 5.76 | 5.55 | 8.02 | 6.50 | 3.91 | 7.67 |
| 2396750 | 6.51 | 6.79 | 8.07 | 7.56 | 7.50 | 7.19 | 6.68 | 6.40 | 6.61 | 7.63 | 7.10 | 7.24 |
| 3902489 | 10.43 | 11.52 | 9.21 | 9.27 | 9.37 | 10.23 | 11.15 | 9.78 | 9.09 | 10.12 | 11.72 | 11.71 |
| 3032647 | 7.29 | 6.81 | 5.90 | 6.49 | 6.46 | 5.71 | 6.33 | 8.62 | 7.41 | 8.47 | 7.66 | 5.63 |
| 3875642 | 5.61 | 5.66 | 5.68 | 5.28 | 5.12 | 5.25 | 5.30 | 5.26 | 5.10 | 5.49 | 5.43 | 5.66 |
| 4027585 | 10.77 | 11.59 | 8.60 | 8.93 | 8.65 | 9.62 | 11.25 | 9.95 | 8.88 | 9.10 | 11.22 | 11.58 |
| 2352609 | 7.17 | 6.54 | 6.31 | 8.22 | 6.74 | 5.92 | 6.28 | 6.75 | 6.84 | 7.58 | 6.64 | 6.20 |
| 3376529 | 7.93 | 8.38 | 10.04 | 9.37 | 10.14 | 9.85 | 8.06 | 9.16 | 8.68 | 8.26 | 8.88 | 7.90 |
| 2491271 | 13.31 | 13.13 | 13.16 | 12.92 | 13.34 | 13.02 | 13.60 | 13.29 | 12.74 | 12.57 | 13.38 | 13.77 |
| 3874751 | 9.12 | 9.17 | 9.69 | 9.37 | 10.14 | 9.29 | 9.81 | 9.37 | 8.85 | 8.90 | 8.81 | 10.02 |
| 2326463 | 11.93 | 11.78 | 9.53 | 9.71 | 9.27 | 9.76 | 12.69 | 11.72 | 10.24 | 10.37 | 12.08 | 12.55 |
| 3341061 | 7.86 | 6.35 | 7.04 | 7.04 | 7.35 | 7.17 | 9.40 | 7.20 | 6.89 | 6.38 | 6.67 | 9.13 |
| 3839910 | 9.35 | 7.98 | 5.97 | 7.40 | 4.78 | 8.15 | 8.11 | 6.90 | 5.93 | 6.52 | 8.76 | 8.64 |
| 2708855 | 4.48 | 4.40 | 8.76 | 7.25 | 7.62 | 6.21 | 4.13 | 4.28 | 4.11 | 4.13 | 4.10 | 6.43 |
| 3512874 | 11.84 | 11.45 | 9.56 | 10.65 | 8.95 | 10.93 | 11.85 | 11.58 | 10.05 | 9.77 | 11.83 | 11.99 |
| 2701071 | 10.61 | 9.32 | 7.38 | 8.66 | 6.98 | 9.47 | 10.35 | 9.00 | 7.81 | 7.39 | 10.50 | 9.96 |
| 3486096 | 7.23 | 8.36 | 6.60 | 9.34 | 5.80 | 8.72 | 6.72 | 8.02 | 9.55 | 8.27 | 8.43 | 6.19 |
| 2412668 | 7.69 | 8.24 | 7.59 | 7.93 | 8.13 | 7.80 | 8.81 | 8.24 | 7.81 | 7.66 | 8.12 | 8.82 |
| 3329343 | 7.16 | 7.71 | 9.49 | 7.92 | 10.12 | 9.30 | 7.37 | 7.66 | 7.88 | 7.79 | 7.01 | 7.12 |
| 3259367 | 5.00 | 5.03 | 5.05 | 6.21 | 5.40 | 7.82 | 4.26 | 4.06 | 4.95 | 5.04 | 4.44 | 4.44 |
| 3373845 | 9.42 | 11.19 | 8.65 | 8.07 | 8.87 | 7.95 | 10.00 | 9.85 | 7.17 | 11.03 | 8.10 | 10.28 |
| 2321911 | 8.49 | 8.84 | 7.86 | 8.56 | 7.73 | 8.14 | 8.83 | 8.54 | 8.25 | 8.18 | 8.62 | 8.87 |
| 3353914 | 6.95 | 6.20 | 7.17 | 6.87 | 7.61 | 7.11 | 7.59 | 7.20 | 6.52 | 6.99 | 6.85 | 9.59 |
| 3744680 | 7.65 | 7.24 | 6.48 | 6.62 | 6.58 | 6.74 | 8.15 | 7.11 | 6.58 | 6.92 | 7.63 | 8.41 |
| 2373336 | 7.70 | 6.76 | 9.15 | 5.82 | 9.58 | 5.52 | 6.06 | 8.11 | 5.34 | 8.32 | 5.99 | 5.80 |
| 3067478 | 5.95 | 4.83 | 9.51 | 8.75 | 9.14 | 8.17 | 4.74 | 7.00 | 7.11 | 5.40 | 6.79 | 6.27 |
| 3976766 | 7.88 | 7.94 | 6.35 | 6.70 | 6.36 | 7.08 | 8.47 | 7.75 | 6.52 | 6.21 | 8.22 | 8.41 |
| 3246888 | 6.37 | 6.37 | 7.37 | 5.22 | 8.24 | 4.63 | 7.74 | 6.48 | 6.59 | 8.50 | 7.59 | 6.07 |
| 3147985 | 6.81 | 6.64 | 8.11 | 7.04 | 8.01 | 7.12 | 7.58 | 7.35 | 7.34 | 6.76 | 6.77 | 8.48 |
| 3185522 | 9.71 | 8.89 | 8.61 | 9.39 | 9.50 | 9.40 | 11.03 | 10.14 | 8.93 | 9.02 | 9.06 | 10.70 |
| 3861948 | 12.53 | 12.42 | 10.40 | 11.34 | 10.07 | 11.80 | 12.64 | 12.15 | 10.75 | 10.71 | 12.62 | 12.78 |
| 3393479 | 9.27 | 9.99 | 7.96 | 7.99 | 9.02 | 8.92 | 10.13 | 9.59 | 8.87 | 9.87 | 9.24 | 9.81 |
| 3540862 | 6.48 | 6.76 | 7.21 | 7.92 | 6.99 | 6.99 | 6.70 | 6.70 | 7.13 | 7.32 | 6.97 | 6.74 |
| 2777714 | 10.97 | 11.93 | 8.98 | 9.31 | 7.71 | 10.43 | 11.40 | 10.01 | 8.91 | 10.22 | 11.88 | 11.89 |
| 3110395 | 4.40 | 4.52 | 6.53 | 6.59 | 5.65 | 4.94 | 4.30 | 4.25 | 4.23 | 4.69 | 4.27 | 4.52 |
| 3895795 | 8.72 | 8.46 | 8.00 | 7.84 | 8.39 | 8.30 | 7.98 | 7.70 | 8.07 | 8.51 | 8.17 | 8.17 |
| 2854445 | 10.08 | 8.20 | 7.19 | 8.41 | 8.87 | 8.56 | 11.50 | 9.72 | 6.60 | 8.41 | 7.23 | 11.20 |
| 3606034 | 7.79 | 7.71 | 7.66 | 7.65 | 7.41 | 7.40 | 7.92 | 7.63 | 8.36 | 7.92 | 7.53 | 8.13 |
| 3375735 | 7.90 | 8.05 | 8.05 | 7.62 | 7.58 | 7.59 | 8.37 | 7.88 | 7.76 | 7.58 | 7.77 | 8.37 |
| 3948047 | 8.45 | 7.87 | 7.30 | 7.29 | 7.15 | 7.33 | 8.90 | 7.83 | 7.34 | 7.01 | 8.21 | 9.24 |
| 3010503 | 9.82 | 9.04 | 6.18 | 8.04 | 5.23 | 8.60 | 10.73 | 9.30 | 7.52 | 7.08 | 8.76 | 11.35 |

TABLE 39-continued

Normalized intensity of microarray data for a set of samples.

| TCID | V01 0169 | V01 0170 | V01 0171 | V01 0172 | V01 0173 | V01 0174 | V01 0175 | V01 0176 | V01 0177 | V01 0178 | V01 0179 | V01 0180 |
|---|---|---|---|---|---|---|---|---|---|---|---|---|
| 3622934 | 6.60 | 7.54 | 8.36 | 8.39 | 8.49 | 8.47 | 6.33 | 6.30 | 7.34 | 7.58 | 6.44 | 6.16 |
| 3441849 | 9.77 | 9.41 | 9.27 | 9.37 | 9.91 | 9.98 | 9.75 | 9.37 | 8.89 | 9.00 | 9.63 | 10.21 |
| 3006572 | 6.16 | 6.31 | 6.57 | 6.45 | 6.83 | 6.63 | 6.41 | 6.08 | 6.70 | 6.57 | 6.26 | 6.44 |
| 3365136 | 8.80 | 8.83 | 10.54 | 9.79 | 10.21 | 10.51 | 8.25 | 8.43 | 9.46 | 9.42 | 8.73 | 8.75 |
| 2642791 | 8.72 | 8.49 | 8.11 | 8.06 | 7.96 | 7.96 | 8.83 | 8.56 | 8.60 | 8.24 | 8.47 | 8.91 |
| 2904485 | 8.75 | 8.50 | 8.19 | 8.32 | 7.42 | 8.15 | 7.81 | 8.88 | 10.00 | 9.92 | 9.01 | 6.67 |
| 3772661 | 10.37 | 9.11 | 9.59 | 9.66 | 9.69 | 9.54 | 11.49 | 10.24 | 8.64 | 9.34 | 9.29 | 11.46 |
| 2796553 | 10.46 | 9.43 | 7.39 | 9.36 | 7.57 | 9.44 | 9.73 | 9.64 | 9.17 | 8.31 | 9.96 | 10.41 |
| 3063795 | 7.76 | 6.92 | 7.06 | 7.39 | 7.97 | 7.93 | 8.11 | 7.80 | 7.13 | 7.36 | 7.17 | 7.65 |
| 3338192 | 8.62 | 9.69 | 10.55 | 10.19 | 10.63 | 10.69 | 8.11 | 8.96 | 9.86 | 9.08 | 9.35 | 8.41 |
| 3214845 | 4.58 | 4.95 | 5.95 | 4.34 | 4.69 | 4.44 | 4.36 | 5.94 | 4.42 | 6.31 | 4.40 | 4.41 |
| 2730303 | 4.15 | 4.19 | 4.26 | 4.23 | 4.01 | 4.41 | 5.90 | 4.24 | 4.10 | 4.09 | 4.17 | 4.36 |
| 3811086 | 8.14 | 8.00 | 7.34 | 7.87 | 7.66 | 7.69 | 7.92 | 8.12 | 8.43 | 8.11 | 7.98 | 8.22 |
| 2981874 | 10.59 | 10.37 | 9.85 | 10.03 | 10.19 | 10.42 | 10.57 | 10.46 | 9.86 | 10.23 | 10.64 | 10.40 |
| 3242353 | 6.27 | 5.88 | 6.07 | 5.79 | 6.07 | 6.22 | 6.25 | 6.11 | 6.44 | 6.07 | 6.38 | 6.30 |
| 2442008 | 5.28 | 5.26 | 9.64 | 7.55 | 8.78 | 10.27 | 5.53 | 5.12 | 5.44 | 5.29 | 5.21 | 6.84 |
| 3564210 | 9.52 | 8.72 | 7.58 | 8.22 | 7.61 | 9.03 | 9.70 | 8.63 | 7.41 | 7.90 | 9.13 | 10.17 |
| 2490351 | 4.11 | 4.18 | 4.00 | 3.97 | 4.02 | 3.95 | 4.24 | 3.98 | 4.05 | 4.24 | 4.18 | 3.99 |
| 3759006 | 8.78 | 10.58 | 6.69 | 7.17 | 6.82 | 7.81 | 9.74 | 7.60 | 7.14 | 8.12 | 10.38 | 9.80 |
| 3264997 | 4.14 | 4.11 | 3.97 | 4.17 | 4.01 | 4.15 | 4.14 | 4.08 | 4.10 | 4.56 | 4.09 | 3.91 |
| 3912079 | 3.76 | 3.57 | 3.47 | 3.75 | 3.58 | 3.72 | 3.80 | 3.57 | 3.47 | 4.01 | 3.65 | 3.75 |
| 2926802 | 5.34 | 5.48 | 4.36 | 4.48 | 5.59 | 4.99 | 5.23 | 5.27 | 4.47 | 4.53 | 5.59 | 5.25 |
| 2430163 | 3.93 | 3.99 | 4.07 | 3.70 | 3.97 | 3.64 | 4.18 | 3.70 | 4.20 | 4.32 | 3.78 | 4.04 |
| 3039830 | 3.11 | 3.11 | 3.14 | 3.26 | 3.09 | 3.09 | 3.29 | 3.12 | 3.20 | 3.30 | 3.80 | 3.14 |
| 3935486 | 8.82 | 5.57 | 6.94 | 5.71 | 6.16 | 5.15 | 7.48 | 6.17 | 5.00 | 5.46 | 5.61 | 8.18 |
| 3457336 | 5.53 | 5.58 | 5.12 | 5.42 | 5.13 | 5.12 | 5.36 | 5.93 | 5.38 | 5.68 | 5.30 | 8.09 |
| 3811949 | 3.41 | 3.55 | 3.34 | 3.34 | 3.42 | 3.38 | 3.54 | 3.38 | 3.41 | 3.59 | 3.53 | 3.42 |
| 3343832 | 3.90 | 3.90 | 3.83 | 3.88 | 3.68 | 3.84 | 3.91 | 3.96 | 3.83 | 3.96 | 3.85 | 3.81 |
| 3161261 | 6.05 | 6.24 | 5.26 | 5.73 | 5.48 | 5.18 | 5.82 | 5.53 | 6.16 | 5.96 | 6.43 | 5.73 |
| 3594003 | 3.97 | 3.62 | 3.56 | 3.74 | 3.52 | 3.62 | 3.74 | 3.62 | 3.55 | 3.75 | 3.61 | 3.92 |
| 3805614 | 4.71 | 4.84 | 4.71 | 4.82 | 4.46 | 4.52 | 5.29 | 4.42 | 4.69 | 5.05 | 4.68 | 5.00 |
| 3364127 | 7.30 | 6.74 | 6.84 | 6.81 | 6.72 | 6.44 | 7.07 | 6.89 | 6.88 | 7.03 | 6.59 | 6.47 |
| 3834341 | 3.94 | 4.02 | 3.78 | 3.86 | 3.86 | 3.83 | 4.14 | 3.78 | 4.24 | 4.29 | 4.30 | 3.99 |
| 2585400 | 4.25 | 4.50 | 4.18 | 4.22 | 4.38 | 4.22 | 4.67 | 4.39 | 4.04 | 4.40 | 4.43 | 4.49 |
| 2941690 | 4.17 | 4.53 | 4.17 | 4.34 | 4.41 | 3.73 | 4.23 | 3.95 | 4.78 | 4.44 | 4.57 | 4.23 |
| 3484895 | 4.83 | 5.24 | 6.87 | 4.87 | 7.04 | 4.73 | 4.83 | 4.78 | 4.71 | 4.78 | 4.69 | 4.99 |
| 3159754 | 3.63 | 3.78 | 3.58 | 3.64 | 3.63 | 3.39 | 3.72 | 3.63 | 3.83 | 3.75 | 3.70 | 3.87 |
| 2894790 | 3.90 | 3.91 | 3.68 | 3.89 | 3.86 | 3.82 | 3.88 | 3.63 | 4.41 | 3.97 | 4.21 | 3.83 |
| 3363686 | 3.50 | 3.33 | 3.58 | 3.29 | 3.25 | 3.28 | 3.64 | 3.32 | 3.36 | 3.58 | 3.31 | 3.67 |
| 2923928 | 4.51 | 4.22 | 4.16 | 4.57 | 4.12 | 4.06 | 4.25 | 4.07 | 4.47 | 4.67 | 4.35 | 4.04 |
| 2883317 | 5.08 | 4.65 | 4.82 | 4.56 | 4.55 | 4.37 | 4.73 | 5.04 | 4.29 | 4.76 | 4.95 | 4.87 |
| 2479698 | 6.10 | 6.23 | 6.55 | 6.27 | 5.78 | 6.30 | 5.99 | 5.93 | 6.16 | 6.38 | 6.09 | 5.93 |
| 3428225 | 3.73 | 3.85 | 3.65 | 3.66 | 3.73 | 3.58 | 3.86 | 3.57 | 3.79 | 3.84 | 3.85 | 3.97 |
| 3393446 | 7.18 | 6.93 | 6.84 | 7.15 | 6.70 | 6.93 | 8.02 | 7.29 | 6.85 | 7.37 | 6.85 | 7.78 |
| 3116614 | 13.05 | 12.95 | 12.90 | 13.10 | 11.44 | 12.85 | 11.91 | 13.14 | 12.92 | 13.09 | 12.89 | 11.68 |
| 3415320 | 9.65 | 10.31 | 10.41 | 10.21 | 10.17 | 7.73 | 8.46 | 10.36 | 9.67 | 10.19 | 8.94 | 8.50 |
| 3757108 | 8.41 | 7.90 | 9.81 | 8.73 | 10.28 | 8.36 | 8.03 | 8.54 | 7.37 | 8.18 | 7.43 | 8.05 |
| 4012178 | 6.83 | 6.62 | 11.69 | 10.82 | 9.75 | 7.71 | 5.95 | 6.42 | 6.65 | 6.65 | 6.02 | 10.18 |
| 3546213 | 10.66 | 11.08 | 11.55 | 11.33 | 11.19 | 11.45 | 9.78 | 11.08 | 11.12 | 11.74 | 10.80 | 9.49 |
| 3561381 | 9.38 | 10.75 | 10.41 | 10.80 | 11.09 | 10.57 | 8.20 | 9.52 | 11.14 | 10.58 | 9.81 | 8.27 |

TABLE 40

Normalized intensity of microarray data for a set of samples.

| TCID | V01 0181 | V01 0182 | V01 0183 | V01 0184 | V01 0185 | V01 0186 | V01 0187 | V01 0188 | V01 0189 | V01 0190 | V01 0191 | V01 0192 |
|---|---|---|---|---|---|---|---|---|---|---|---|---|
| 2604998 | 8.34 | 6.14 | 5.09 | 7.65 | 8.92 | 7.03 | 4.99 | 7.19 | 8.30 | 8.89 | 8.25 | 9.16 |
| 3603932 | 7.13 | 6.77 | 7.34 | 6.83 | 7.20 | 8.63 | 6.72 | 9.32 | 7.75 | 7.11 | 7.18 | 7.02 |
| 2710599 | 11.32 | 6.50 | 5.75 | 11.12 | 11.72 | 8.37 | 7.14 | 9.00 | 11.23 | 10.90 | 8.88 | 11.75 |
| 2440258 | 8.22 | 9.04 | 8.99 | 8.76 | 5.20 | 7.43 | 9.90 | 5.07 | 6.57 | 7.46 | 7.89 | 5.02 |
| 3169331 | 6.84 | 6.74 | 6.44 | 5.96 | 6.73 | 6.95 | 6.99 | 9.05 | 6.59 | 6.25 | 6.59 | 7.17 |
| 2988882 | 9.07 | 9.75 | 9.88 | 9.53 | 9.81 | 9.61 | 9.87 | 11.38 | 9.80 | 9.45 | 9.35 | 9.75 |
| 2964231 | 7.92 | 8.99 | 8.84 | 8.31 | 9.46 | 10.44 | 7.52 | 11.27 | 9.49 | 9.12 | 8.27 | 9.39 |
| 3111561 | 8.02 | 8.28 | 6.03 | 5.20 | 6.86 | 8.97 | 5.03 | 9.26 | 5.66 | 5.93 | 8.44 | 6.83 |
| 2562529 | 10.39 | 9.18 | 8.25 | 10.75 | 10.44 | 9.89 | 8.97 | 9.54 | 10.48 | 10.33 | 9.81 | 10.33 |
| 3692999 | 10.61 | 10.29 | 7.13 | 11.10 | 10.54 | 11.09 | 5.90 | 11.47 | 5.84 | 7.65 | 9.45 | 10.67 |
| 2439554 | 6.29 | 7.53 | 9.05 | 7.32 | 4.77 | 6.23 | 10.00 | 5.04 | 5.83 | 6.06 | 6.27 | 5.05 |
| 2685304 | 10.45 | 7.98 | 8.23 | 8.81 | 11.76 | 8.61 | 6.81 | 9.76 | 10.63 | 11.35 | 8.12 | 11.65 |
| 2578790 | 4.26 | 5.18 | 4.48 | 4.33 | 5.36 | 4.33 | 4.40 | 4.39 | 4.04 | 4.39 | 7.30 | 4.40 |
| 2373842 | 11.40 | 12.08 | 12.05 | 11.91 | 8.83 | 10.43 | 11.96 | 9.26 | 10.57 | 11.00 | 11.45 | 8.69 |

TABLE 40-continued

Normalized intensity of microarray data for a set of samples.

| TCID | V01 0181 | V01 0182 | V01 0183 | V01 0184 | V01 0185 | V01 0186 | V01 0187 | V01 0188 | V01 0189 | V01 0190 | V01 0191 | V01 0192 |
|---|---|---|---|---|---|---|---|---|---|---|---|---|
| 2750627 | 9.40 | 6.98 | 4.98 | 7.80 | 10.42 | 8.90 | 6.21 | 6.71 | 10.28 | 10.87 | 9.32 | 8.96 |
| 3397774 | 5.02 | 5.14 | 5.04 | 4.66 | 4.38 | 5.64 | 4.90 | 6.40 | 4.54 | 4.63 | 5.19 | 4.73 |
| 2635741 | 7.66 | 9.63 | 8.81 | 8.93 | 5.47 | 6.55 | 10.11 | 6.10 | 6.85 | 7.75 | 7.97 | 5.78 |
| 3970833 | 9.12 | 9.09 | 8.98 | 9.57 | 9.67 | 9.58 | 9.62 | 11.63 | 9.51 | 9.70 | 9.72 | 9.69 |
| 3577612 | 10.88 | 11.19 | 11.34 | 11.27 | 11.88 | 8.94 | 9.65 | 8.06 | 11.29 | 11.52 | 10.80 | 11.48 |
| 2708922 | 9.21 | 8.33 | 9.89 | 8.82 | 8.35 | 8.18 | 6.90 | 6.90 | 8.27 | 8.63 | 8.13 | 8.13 |
| 2970897 | 5.22 | 5.17 | 5.26 | 5.13 | 4.74 | 5.17 | 5.12 | 9.13 | 4.68 | 4.52 | 5.25 | 5.93 |
| 3724545 | 9.76 | 9.48 | 9.61 | 9.45 | 10.35 | 9.58 | 7.20 | 7.11 | 10.09 | 9.74 | 11.01 | 10.39 |
| 2798538 | 8.36 | 9.79 | 9.00 | 9.04 | 8.95 | 9.62 | 9.73 | 11.26 | 9.09 | 9.40 | 8.31 | 8.82 |
| 2806468 | 11.17 | 12.01 | 11.00 | 11.46 | 8.32 | 9.76 | 11.80 | 8.19 | 10.56 | 10.03 | 10.77 | 7.68 |
| 2880051 | 6.24 | 6.93 | 6.46 | 6.23 | 5.77 | 6.02 | 6.33 | 6.93 | 6.21 | 6.02 | 6.47 | 6.02 |
| 2732508 | 3.38 | 3.56 | 7.20 | 3.81 | 3.31 | 3.38 | 9.45 | 3.75 | 3.16 | 3.46 | 3.46 | 3.44 |
| 2822492 | 4.86 | 5.82 | 5.40 | 5.68 | 5.73 | 5.82 | 4.93 | 8.02 | 4.99 | 5.20 | 5.34 | 5.08 |
| 3404030 | 8.42 | 9.75 | 8.71 | 9.19 | 5.35 | 6.44 | 9.05 | 6.51 | 6.42 | 8.04 | 7.77 | 5.53 |
| 3059667 | 8.42 | 6.12 | 4.31 | 5.79 | 7.01 | 10.18 | 5.84 | 4.33 | 5.12 | 6.06 | 8.45 | 6.15 |
| 3108526 | 8.18 | 7.92 | 6.58 | 7.48 | 9.15 | 9.04 | 8.33 | 10.58 | 7.60 | 9.52 | 8.32 | 8.98 |
| 2526806 | 11.24 | 11.21 | 7.89 | 10.88 | 12.81 | 11.39 | 8.91 | 8.60 | 12.63 | 12.52 | 6.90 | 12.72 |
| 2428501 | 6.22 | 7.67 | 8.00 | 6.27 | 6.63 | 8.46 | 8.65 | 9.47 | 8.14 | 6.17 | 5.90 | 7.33 |
| 2657808 | 10.57 | 5.51 | 6.13 | 10.68 | 10.71 | 7.39 | 7.62 | 6.77 | 10.86 | 9.93 | 6.83 | 11.59 |
| 2584018 | 9.84 | 9.01 | 7.61 | 9.23 | 10.39 | 11.29 | 8.35 | 7.14 | 11.17 | 10.50 | 7.41 | 10.88 |
| 3976341 | 11.06 | 10.18 | 10.13 | 10.38 | 11.53 | 9.38 | 9.22 | 8.26 | 11.46 | 11.29 | 9.81 | 11.25 |
| 2739308 | 5.17 | 5.48 | 5.99 | 5.95 | 4.56 | 4.75 | 4.68 | 6.38 | 4.21 | 4.71 | 5.41 | 4.54 |
| 3959862 | 4.67 | 4.74 | 6.71 | 5.99 | 4.79 | 4.43 | 5.13 | 10.31 | 5.44 | 5.88 | 5.96 | 4.33 |
| 2362351 | 7.69 | 8.55 | 8.36 | 8.07 | 5.11 | 6.09 | 8.81 | 5.50 | 6.48 | 6.82 | 7.31 | 5.82 |
| 3648391 | 4.52 | 5.74 | 7.52 | 4.74 | 3.66 | 3.86 | 8.70 | 4.00 | 3.76 | 6.86 | 5.03 | 4.85 |
| 3009299 | 10.38 | 10.61 | 10.53 | 10.64 | 10.69 | 10.91 | 11.09 | 12.52 | 10.74 | 10.60 | 10.18 | 10.64 |
| 3443464 | 5.65 | 6.73 | 6.01 | 6.46 | 5.08 | 5.58 | 6.28 | 5.26 | 5.20 | 5.49 | 6.31 | 5.06 |
| 2730746 | 6.08 | 6.92 | 5.13 | 7.47 | 6.56 | 6.64 | 5.37 | 9.17 | 4.79 | 7.04 | 7.17 | 7.09 |
| 2427619 | 8.47 | 10.13 | 9.29 | 9.37 | 4.93 | 6.68 | 10.07 | 5.82 | 6.41 | 7.97 | 7.92 | 6.17 |
| 3042001 | 8.04 | 8.54 | 8.16 | 8.41 | 7.96 | 8.77 | 9.40 | 11.18 | 8.38 | 8.28 | 8.96 | 8.57 |
| 2566848 | 5.17 | 6.27 | 6.79 | 5.69 | 4.83 | 5.04 | 7.99 | 5.81 | 5.21 | 5.09 | 5.58 | 4.87 |
| 2984616 | 8.95 | 9.14 | 8.81 | 8.81 | 9.01 | 9.23 | 8.81 | 11.29 | 9.17 | 9.22 | 8.88 | 9.13 |
| 2378068 | 10.11 | 8.47 | 8.20 | 7.39 | 8.91 | 11.08 | 9.13 | 8.08 | 9.07 | 9.89 | 6.80 | 7.26 |
| 2721959 | 10.05 | 6.65 | 5.95 | 9.65 | 12.81 | 6.91 | 5.82 | 7.08 | 12.39 | 12.94 | 7.04 | 12.99 |
| 2877508 | 9.64 | 10.33 | 10.07 | 10.15 | 10.37 | 10.77 | 10.85 | 12.02 | 10.37 | 10.30 | 9.33 | 10.42 |
| 3450861 | 5.85 | 8.29 | 6.89 | 6.67 | 4.64 | 5.23 | 7.97 | 4.60 | 5.00 | 5.70 | 5.39 | 4.72 |
| 2688717 | 8.49 | 9.57 | 9.90 | 9.30 | 6.21 | 7.25 | 10.77 | 5.97 | 7.98 | 7.59 | 7.99 | 6.50 |
| 3270270 | 8.73 | 9.61 | 10.04 | 9.35 | 8.82 | 8.54 | 8.56 | 6.85 | 8.85 | 8.84 | 8.77 | 8.35 |
| 3417703 | 8.36 | 5.89 | 4.73 | 7.29 | 8.54 | 10.55 | 5.17 | 4.27 | 7.78 | 7.77 | 8.34 | 9.77 |
| 3302990 | 6.76 | 6.56 | 6.76 | 7.24 | 7.51 | 7.28 | 7.74 | 11.53 | 7.26 | 7.36 | 7.80 | 7.97 |
| 2377283 | 4.41 | 5.40 | 9.64 | 4.61 | 4.15 | 4.24 | 11.35 | 4.09 | 4.01 | 4.38 | 4.59 | 4.04 |
| 3122678 | 4.31 | 5.15 | 4.49 | 4.53 | 4.94 | 4.40 | 4.62 | 9.37 | 4.86 | 4.22 | 5.26 | 5.05 |
| 2688499 | 9.02 | 8.20 | 7.24 | 8.17 | 9.80 | 9.62 | 7.69 | 6.87 | 10.05 | 10.35 | 8.21 | 10.30 |
| 2377094 | 8.10 | 7.97 | 7.76 | 8.28 | 8.91 | 9.37 | 7.89 | 11.22 | 7.96 | 9.11 | 8.62 | 9.24 |
| 3278198 | 7.20 | 7.23 | 6.29 | 7.14 | 8.41 | 8.58 | 6.92 | 10.49 | 8.01 | 8.44 | 7.65 | 8.88 |
| 2598261 | 10.68 | 10.39 | 7.64 | 10.03 | 12.98 | 11.08 | 8.21 | 7.96 | 12.59 | 12.27 | 6.68 | 13.05 |
| 3982612 | 8.88 | 10.06 | 10.18 | 9.60 | 4.72 | 6.43 | 11.25 | 6.91 | 7.06 | 7.91 | 7.90 | 4.29 |
| 2884845 | 7.05 | 4.66 | 4.73 | 5.50 | 10.08 | 4.21 | 4.17 | 4.94 | 9.48 | 10.13 | 6.48 | 9.44 |
| 3982560 | 6.70 | 8.52 | 8.11 | 7.64 | 4.68 | 5.27 | 9.07 | 5.03 | 5.83 | 6.40 | 6.52 | 4.30 |
| 3204285 | 6.05 | 5.13 | 7.58 | 5.30 | 5.49 | 5.61 | 9.37 | 5.94 | 5.91 | 5.25 | 5.82 | 5.86 |
| 3654699 | 9.74 | 10.67 | 8.75 | 8.01 | 11.17 | 12.49 | 9.21 | 12.59 | 11.27 | 10.97 | 10.11 | 11.48 |
| 2638676 | 6.17 | 8.09 | 9.27 | 6.97 | 5.35 | 7.18 | 10.30 | 6.26 | 7.24 | 6.32 | 6.75 | 6.57 |
| 3367673 | 6.06 | 6.65 | 4.51 | 6.39 | 6.47 | 8.18 | 5.17 | 9.35 | 4.68 | 5.14 | 8.09 | 6.08 |
| 3212008 | 8.74 | 6.48 | 6.61 | 9.07 | 8.69 | 8.84 | 6.07 | 6.02 | 7.87 | 9.36 | 8.87 | 8.78 |
| 3326635 | 10.55 | 10.29 | 10.22 | 10.66 | 10.06 | 10.62 | 10.25 | 8.38 | 10.35 | 10.12 | 10.06 | 9.61 |
| 3031556 | 9.17 | 10.40 | 10.30 | 9.97 | 6.35 | 8.43 | 10.49 | 6.30 | 8.60 | 8.67 | 9.06 | 6.85 |
| 3662201 | 9.83 | 9.56 | 7.54 | 10.80 | 10.54 | 11.80 | 6.86 | 10.47 | 7.95 | 8.15 | 9.07 | 10.30 |
| 2809793 | 8.95 | 9.86 | 9.31 | 9.20 | 4.51 | 6.26 | 9.80 | 5.80 | 6.53 | 8.30 | 7.35 | 4.71 |
| 2817731 | 7.31 | 8.53 | 8.44 | 8.32 | 7.58 | 9.64 | 7.47 | 7.69 | 8.42 | 7.63 | 7.50 | 7.57 |
| 4020655 | 8.66 | 5.29 | 5.67 | 8.51 | 7.62 | 7.93 | 5.04 | 4.66 | 6.89 | 7.42 | 8.16 | 5.39 |
| 3494629 | 7.62 | 4.38 | 4.38 | 5.84 | 7.27 | 5.08 | 4.25 | 7.21 | 8.66 | 7.27 | 6.29 | 8.17 |
| 3852832 | 8.98 | 10.74 | 10.88 | 10.00 | 6.08 | 6.51 | 8.43 | 6.57 | 7.43 | 6.57 | 9.64 | 5.40 |
| 3761959 | 8.48 | 8.82 | 8.17 | 8.90 | 9.38 | 9.64 | 8.85 | 9.98 | 9.69 | 8.47 | 9.20 | 9.15 |
| 2834282 | 7.87 | 5.48 | 5.73 | 6.85 | 8.20 | 7.97 | 4.93 | 7.26 | 6.95 | 7.32 | 8.03 | 7.92 |
| 3341497 | 7.27 | 5.76 | 6.42 | 6.13 | 6.85 | 6.44 | 5.64 | 7.01 | 6.22 | 6.60 | 7.22 | 7.52 |
| 2372812 | 4.59 | 4.54 | 9.76 | 4.74 | 4.54 | 4.76 | 10.87 | 4.71 | 4.55 | 4.72 | 4.88 | 4.66 |
| 2486811 | 9.37 | 10.29 | 10.74 | 9.88 | 8.04 | 11.07 | 10.12 | 7.21 | 10.03 | 9.09 | 9.20 | 6.91 |
| 3768474 | 8.40 | 8.56 | 8.98 | 8.34 | 8.03 | 8.80 | 7.77 | 8.61 | 8.55 | 7.83 | 8.27 | 8.03 |
| 3142381 | 4.60 | 5.77 | 5.14 | 3.86 | 4.58 | 6.37 | 3.82 | 6.62 | 5.35 | 4.90 | 5.40 | 5.13 |
| 2396750 | 7.81 | 6.86 | 6.92 | 6.63 | 7.70 | 6.39 | 7.12 | 8.05 | 7.60 | 7.47 | 7.49 | 8.40 |
| 3902489 | 12.00 | 11.66 | 12.11 | 11.24 | 9.93 | 10.74 | 10.00 | 10.23 | 9.98 | 10.64 | 11.52 | 10.32 |
| 3032647 | 6.08 | 6.39 | 6.07 | 5.66 | 6.34 | 6.07 | 6.04 | 5.73 | 5.76 | 5.81 | 6.50 | 5.98 |
| 3875642 | 5.14 | 6.86 | 6.12 | 6.01 | 4.86 | 4.88 | 5.54 | 5.03 | 5.17 | 5.58 | 5.83 | 6.18 |
| 4027585 | 11.82 | 11.40 | 12.29 | 11.17 | 9.24 | 10.72 | 9.56 | 9.68 | 10.81 | 9.91 | 11.26 | 7.78 |
| 2352609 | 6.81 | 5.84 | 5.68 | 6.47 | 7.22 | 7.00 | 5.56 | 7.53 | 6.43 | 6.77 | 7.04 | 7.44 |

TABLE 40-continued

Normalized intensity of microarray data for a set of samples.

| TCID | V01 0181 | V01 0182 | V01 0183 | V01 0184 | V01 0185 | V01 0186 | V01 0187 | V01 0188 | V01 0189 | V01 0190 | V01 0191 | V01 0192 |
|---|---|---|---|---|---|---|---|---|---|---|---|---|
| 3376529 | 8.80 | 7.82 | 7.11 | 8.78 | 10.02 | 7.94 | 7.45 | 9.27 | 9.51 | 9.99 | 9.16 | 10.37 |
| 2491271 | 13.09 | 13.44 | 13.23 | 13.32 | 13.20 | 13.43 | 13.72 | 12.00 | 13.58 | 13.05 | 12.84 | 13.15 |
| 3874751 | 8.88 | 9.43 | 8.50 | 9.16 | 9.67 | 10.34 | 8.79 | 8.99 | 9.96 | 9.83 | 8.88 | 10.07 |
| 2326463 | 11.56 | 12.54 | 12.12 | 11.97 | 10.63 | 12.67 | 12.70 | 8.72 | 11.18 | 10.77 | 11.57 | 10.10 |
| 3341061 | 7.17 | 8.01 | 7.27 | 7.85 | 7.57 | 8.35 | 7.45 | 6.77 | 8.60 | 6.40 | 6.44 | 6.93 |
| 3839910 | 9.49 | 9.67 | 10.81 | 10.04 | 5.84 | 6.69 | 8.47 | 5.73 | 7.16 | 8.60 | 8.89 | 4.70 |
| 2708855 | 7.25 | 4.09 | 4.50 | 8.09 | 8.71 | 5.99 | 4.01 | 5.02 | 7.97 | 7.85 | 5.87 | 8.92 |
| 3512874 | 11.80 | 12.58 | 12.42 | 12.18 | 10.10 | 11.98 | 12.41 | 9.82 | 11.53 | 11.29 | 11.88 | 9.87 |
| 2701071 | 10.08 | 11.10 | 10.76 | 10.86 | 7.97 | 8.68 | 9.28 | 8.05 | 9.18 | 9.75 | 10.07 | 6.53 |
| 3486096 | 7.15 | 5.31 | 5.50 | 6.85 | 8.21 | 8.76 | 5.26 | 7.60 | 5.56 | 8.12 | 7.59 | 7.48 |
| 2412668 | 7.94 | 9.01 | 8.99 | 8.24 | 8.06 | 8.57 | 8.20 | 8.13 | 8.88 | 8.01 | 7.99 | 8.27 |
| 3329343 | 8.45 | 7.05 | 7.47 | 7.38 | 8.88 | 7.27 | 7.29 | 7.88 | 8.93 | 8.46 | 7.72 | 8.39 |
| 3259367 | 6.60 | 4.38 | 4.24 | 5.20 | 4.78 | 4.46 | 3.94 | 3.74 | 4.61 | 4.68 | 6.56 | 5.35 |
| 3373845 | 9.34 | 9.36 | 9.02 | 8.63 | 9.32 | 11.25 | 8.85 | 7.16 | 9.78 | 9.08 | 8.75 | 10.23 |
| 2321911 | 8.73 | 8.48 | 9.51 | 8.86 | 7.59 | 8.55 | 8.99 | 7.91 | 8.14 | 8.02 | 8.27 | 8.04 |
| 3353914 | 6.86 | 6.78 | 5.89 | 6.57 | 7.94 | 9.00 | 6.44 | 6.42 | 8.30 | 7.11 | 6.35 | 7.48 |
| 3744680 | 7.34 | 8.97 | 8.57 | 7.97 | 6.15 | 7.77 | 7.77 | 6.61 | 7.65 | 7.13 | 7.72 | 6.68 |
| 2373336 | 8.63 | 7.85 | 5.44 | 6.14 | 9.41 | 6.24 | 6.70 | 4.90 | 10.93 | 9.83 | 6.09 | 10.69 |
| 3067478 | 7.30 | 5.30 | 5.09 | 7.53 | 8.63 | 8.13 | 4.82 | 7.20 | 8.24 | 8.27 | 5.64 | 8.07 |
| 3976766 | 8.43 | 9.50 | 9.95 | 8.94 | 6.26 | 7.79 | 8.91 | 6.67 | 7.46 | 7.83 | 8.67 | 6.26 |
| 3246888 | 7.31 | 5.45 | 5.58 | 6.13 | 5.14 | 6.92 | 4.98 | 5.72 | 5.15 | 5.05 | 6.99 | 4.71 |
| 3147985 | 6.93 | 6.35 | 5.80 | 6.32 | 7.59 | 9.38 | 5.89 | 6.63 | 8.18 | 7.00 | 6.01 | 7.35 |
| 3185522 | 9.28 | 9.23 | 8.95 | 9.09 | 9.61 | 11.12 | 9.14 | 10.66 | 10.52 | 8.59 | 8.05 | 9.51 |
| 3861948 | 12.57 | 13.07 | 13.21 | 12.99 | 10.79 | 11.93 | 12.94 | 10.42 | 12.23 | 12.01 | 12.57 | 9.69 |
| 3393479 | 8.27 | 9.23 | 8.50 | 8.19 | 9.44 | 9.39 | 7.79 | 7.80 | 9.63 | 8.55 | 8.81 | 10.37 |
| 3540862 | 7.13 | 6.65 | 5.76 | 6.72 | 7.21 | 6.65 | 6.97 | 10.23 | 6.71 | 7.18 | 7.00 | 7.46 |
| 2777714 | 12.06 | 11.67 | 12.11 | 11.66 | 8.83 | 9.78 | 10.47 | 10.34 | 9.29 | 10.99 | 11.87 | 6.03 |
| 3110395 | 5.19 | 4.43 | 4.71 | 4.76 | 6.32 | 4.20 | 4.69 | 4.47 | 4.50 | 5.35 | 5.15 | 5.99 |
| 3895795 | 8.74 | 9.44 | 9.64 | 9.35 | 7.75 | 8.08 | 7.77 | 6.87 | 7.78 | 8.63 | 8.66 | 8.06 |
| 2854445 | 8.49 | 9.61 | 8.29 | 8.33 | 9.28 | 10.79 | 8.22 | 7.21 | 11.54 | 7.29 | 7.68 | 8.86 |
| 3606034 | 7.08 | 7.83 | 6.99 | 7.44 | 7.32 | 8.60 | 7.54 | 7.49 | 7.60 | 7.14 | 7.75 | 7.25 |
| 3375735 | 7.83 | 8.22 | 8.18 | 8.08 | 7.61 | 8.17 | 7.67 | 7.39 | 7.68 | 8.11 | 7.83 | 7.75 |
| 3948047 | 7.96 | 9.10 | 9.40 | 8.82 | 6.98 | 8.85 | 9.47 | 7.22 | 8.28 | 7.45 | 8.40 | 7.14 |
| 3010503 | 8.73 | 10.31 | 9.81 | 9.68 | 7.38 | 11.22 | 7.89 | 6.67 | 10.33 | 7.44 | 9.19 | 6.42 |
| 3622934 | 7.38 | 6.45 | 6.84 | 8.00 | 8.03 | 6.73 | 8.36 | 7.99 | 7.51 | 8.12 | 6.84 | 8.05 |
| 3441849 | 10.26 | 10.69 | 10.64 | 10.30 | 9.89 | 9.74 | 9.32 | 9.05 | 10.17 | 10.09 | 9.82 | 9.59 |
| 3006572 | 6.76 | 6.69 | 6.83 | 6.83 | 6.15 | 6.45 | 6.46 | 6.65 | 6.69 | 6.31 | 7.05 | 6.47 |
| 3365136 | 9.61 | 7.87 | 8.24 | 9.26 | 9.14 | 9.48 | 8.68 | 8.59 | 8.93 | 9.16 | 10.11 | 8.65 |
| 2642791 | 7.95 | 8.92 | 8.67 | 8.50 | 8.48 | 8.54 | 8.70 | 8.41 | 8.55 | 8.28 | 8.29 | 8.36 |
| 2904485 | 7.88 | 7.62 | 6.78 | 7.79 | 8.47 | 8.16 | 6.63 | 6.54 | 7.81 | 7.68 | 8.65 | 7.36 |
| 3772661 | 9.54 | 10.46 | 10.19 | 10.12 | 10.06 | 11.23 | 8.96 | 8.25 | 10.68 | 9.61 | 9.37 | 9.68 |
| 2796553 | 10.46 | 10.59 | 11.28 | 10.78 | 8.49 | 10.08 | 8.98 | 9.87 | 9.39 | 9.68 | 10.26 | 8.22 |
| 3063795 | 7.11 | 7.43 | 7.32 | 6.98 | 6.97 | 7.12 | 7.81 | 7.84 | 7.96 | 6.77 | 7.64 | 7.26 |
| 3338192 | 10.31 | 8.04 | 7.48 | 10.18 | 10.70 | 9.57 | 7.79 | 8.69 | 9.71 | 9.92 | 9.24 | 11.02 |
| 3214845 | 4.55 | 4.23 | 4.58 | 4.60 | 6.01 | 4.08 | 4.55 | 4.11 | 4.57 | 4.20 | 4.73 | 4.40 |
| 2730303 | 4.27 | 4.28 | 8.51 | 4.09 | 4.19 | 4.16 | 9.52 | 4.49 | 4.15 | 4.00 | 4.50 | 4.22 |
| 3811086 | 7.13 | 7.81 | 7.63 | 7.88 | 7.77 | 8.01 | 8.21 | 7.63 | 7.92 | 7.74 | 7.62 | 8.00 |
| 2981874 | 10.28 | 10.29 | 10.38 | 10.40 | 10.15 | 10.36 | 10.22 | 10.51 | 10.24 | 9.97 | 10.29 | 10.32 |
| 3242353 | 5.82 | 6.06 | 6.37 | 5.70 | 5.83 | 7.01 | 6.69 | 6.39 | 6.33 | 5.65 | 5.63 | 6.29 |
| 2442008 | 8.70 | 5.36 | 5.77 | 8.73 | 8.35 | 5.96 | 5.07 | 5.61 | 8.01 | 8.77 | 6.38 | 7.70 |
| 3564210 | 9.61 | 10.53 | 10.88 | 10.22 | 8.52 | 9.60 | 8.77 | 7.59 | 9.52 | 9.03 | 9.66 | 7.95 |
| 2490351 | 4.24 | 4.22 | 4.39 | 3.97 | 3.80 | 3.95 | 3.89 | 4.12 | 3.92 | 3.94 | 4.20 | 3.91 |
| 3759050 | 11.30 | 10.03 | 11.75 | 9.23 | 7.20 | 7.90 | 8.03 | 8.75 | 6.98 | 8.17 | 10.49 | 6.48 |
| 3264997 | 4.13 | 3.97 | 4.31 | 3.98 | 3.88 | 3.94 | 4.21 | 3.96 | 3.86 | 3.90 | 4.36 | 4.15 |
| 3912079 | 3.60 | 4.05 | 3.84 | 4.00 | 3.35 | 3.34 | 4.09 | 3.59 | 3.42 | 3.64 | 4.04 | 3.65 |
| 2926802 | 5.29 | 5.77 | 6.84 | 5.91 | 4.73 | 4.58 | 7.07 | 5.80 | 5.14 | 5.47 | 5.36 | 4.43 |
| 2430163 | 3.71 | 4.62 | 4.31 | 3.75 | 5.94 | 3.83 | 3.79 | 3.83 | 4.51 | 4.93 | 4.11 | 9.06 |
| 3039830 | 3.11 | 3.14 | 3.16 | 3.14 | 3.28 | 3.05 | 3.03 | 3.31 | 3.11 | 3.43 | 3.16 | 3.05 |
| 3935486 | 5.49 | 8.30 | 7.22 | 6.14 | 8.16 | 7.76 | 7.66 | 5.10 | 10.55 | 6.87 | 5.52 | 7.50 |
| 3457336 | 5.50 | 5.53 | 5.68 | 5.29 | 5.21 | 5.04 | 5.45 | 5.34 | 5.18 | 5.11 | 5.90 | 5.32 |
| 3811949 | 3.35 | 3.63 | 3.70 | 3.35 | 3.32 | 3.44 | 3.44 | 3.61 | 3.35 | 3.33 | 3.62 | 3.32 |
| 3343832 | 3.89 | 3.77 | 4.08 | 3.66 | 3.66 | 3.91 | 3.82 | 3.68 | 3.86 | 4.02 | 3.82 |  |
| 3161261 | 5.69 | 6.20 | 6.01 | 5.93 | 5.36 | 5.65 | 6.64 | 5.59 | 5.09 | 5.17 | 6.17 | 5.60 |
| 3594003 | 3.64 | 3.77 | 3.76 | 3.72 | 3.52 | 4.27 | 3.59 | 3.55 | 3.63 | 3.54 | 3.81 | 3.97 |
| 3805614 | 4.46 | 4.82 | 5.25 | 4.63 | 4.42 | 4.92 | 4.65 | 4.49 | 4.40 | 4.65 | 5.18 | 4.78 |
| 3364127 | 6.69 | 6.78 | 7.15 | 6.58 | 6.78 | 6.69 | 6.70 | 8.49 | 6.44 | 6.69 | 7.28 | 6.85 |
| 3834341 | 3.99 | 3.95 | 4.30 | 3.93 | 3.86 | 4.43 | 3.97 | 4.12 | 3.73 | 3.91 | 4.59 | 6.79 |
| 2585400 | 4.39 | 4.55 | 4.64 | 4.29 | 4.67 | 4.45 | 4.25 | 4.19 | 5.37 | 4.16 | 4.28 | 4.13 |
| 2941690 | 4.15 | 4.38 | 4.62 | 4.40 | 4.07 | 4.05 | 4.05 | 4.52 | 3.96 | 3.96 | 4.80 | 4.11 |
| 3484895 | 5.43 | 5.16 | 5.04 | 4.95 | 5.83 | 4.53 | 4.65 | 5.08 | 4.95 | 6.36 | 5.15 | 5.43 |
| 3159754 | 3.68 | 3.70 | 3.75 | 3.93 | 3.51 | 3.64 | 3.76 | 3.80 | 3.73 | 3.83 | 3.74 | 3.69 |
| 2894790 | 3.90 | 3.91 | 3.90 | 3.88 | 3.60 | 3.55 | 3.73 | 3.70 | 3.86 | 3.75 | 3.80 | 3.72 |
| 3363686 | 3.47 | 3.62 | 3.76 | 3.48 | 3.32 | 3.52 | 3.37 | 3.88 | 3.33 | 3.37 | 3.51 | 3.41 |
| 2923928 | 4.36 | 4.56 | 4.26 | 4.36 | 3.97 | 4.19 | 4.68 | 4.16 | 4.10 | 4.01 | 4.46 | 4.08 |
| 2883317 | 4.45 | 5.21 | 5.17 | 4.81 | 4.41 | 6.03 | 5.95 | 4.45 | 5.01 | 4.81 | 4.74 | 4.57 |

TABLE 40-continued

Normalized intensity of microarray data for a set of samples.

| TCID | V01 0181 | V01 0182 | V01 0183 | V01 0184 | V01 0185 | V01 0186 | V01 0187 | V01 0188 | V01 0189 | V01 0190 | V01 0191 | V01 0192 |
|---|---|---|---|---|---|---|---|---|---|---|---|---|
| 2479698 | 6.10 | 6.09 | 5.97 | 5.83 | 5.93 | 5.89 | 6.10 | 6.26 | 5.78 | 6.30 | 6.34 | 5.89 |
| 3428225 | 3.89 | 3.85 | 3.78 | 3.61 | 3.45 | 3.67 | 3.64 | 3.73 | 3.69 | 3.72 | 3.86 | 3.86 |
| 3393446 | 6.86 | 8.19 | 7.80 | 7.07 | 7.16 | 8.23 | 7.14 | 6.84 | 6.85 | 7.18 | 7.31 | 6.65 |
| 3116614 | 12.90 | 11.49 | 8.16 | 12.42 | 12.59 | 12.24 | 9.62 | 12.27 | 12.50 | 12.49 | 13.10 | 12.43 |
| 3415320 | 10.06 | 8.39 | 6.75 | 8.44 | 11.00 | 7.33 | 6.78 | 11.42 | 10.32 | 10.34 | 10.04 | 11.02 |
| 3757108 | 8.97 | 7.53 | 7.54 | 9.06 | 11.16 | 7.99 | 6.92 | 8.33 | 9.96 | 9.69 | 7.78 | 11.18 |
| 4012178 | 10.10 | 6.50 | 6.26 | 10.02 | 11.04 | 6.35 | 6.53 | 7.85 | 8.91 | 11.04 | 8.72 | 9.63 |
| 3546213 | 11.12 | 8.19 | 5.52 | 10.37 | 11.13 | 9.74 | 7.38 | 10.18 | 11.10 | 11.18 | 10.94 | 11.04 |
| 3561381 | 10.29 | 6.65 | 5.32 | 9.79 | 10.43 | 9.83 | 5.72 | 9.95 | 9.36 | 9.83 | 11.02 | 9.95 |

TABLE 41

Normalized intensity of microarray data for a set of samples.

| TCID | V01 0193 | V01 0194 | V01 0195 | V01 0196 | V01 0197 | V01 0198 | V01 0199 | V01 0200 | V01 0201 | V01 0202 | V01 0203 | V01 0204 |
|---|---|---|---|---|---|---|---|---|---|---|---|---|
| 2604998 | 9.43 | 7.64 | 6.75 | 7.39 | 9.06 | 7.72 | 8.63 | 9.87 | 7.77 | 9.10 | 8.00 | 7.52 |
| 3603932 | 7.24 | 6.86 | 7.25 | 9.18 | 7.26 | 6.88 | 7.99 | 8.65 | 7.89 | 8.07 | 7.31 | 8.85 |
| 2710599 | 6.86 | 7.87 | 9.90 | 7.57 | 11.73 | 6.35 | 11.12 | 8.47 | 8.93 | 10.82 | 9.66 | 11.20 |
| 2440258 | 7.60 | 8.45 | 8.20 | 6.56 | 5.22 | 8.69 | 4.63 | 6.80 | 8.56 | 4.99 | 7.78 | 7.73 |
| 3169331 | 8.61 | 6.73 | 7.30 | 9.34 | 7.28 | 7.68 | 7.40 | 7.13 | 6.64 | 7.27 | 7.55 | 7.04 |
| 2988882 | 9.74 | 9.81 | 10.06 | 11.08 | 9.56 | 9.65 | 9.77 | 9.77 | 10.10 | 10.15 | 9.89 | 10.05 |
| 2964231 | 7.96 | 8.07 | 9.93 | 10.93 | 9.25 | 9.11 | 10.86 | 9.50 | 9.59 | 9.97 | 9.94 | 10.25 |
| 3111561 | 10.44 | 7.86 | 5.81 | 7.19 | 4.65 | 9.50 | 7.18 | 4.55 | 9.76 | 7.94 | 8.11 | 6.70 |
| 2562529 | 9.20 | 9.29 | 9.65 | 8.66 | 10.62 | 8.98 | 10.83 | 10.06 | 9.57 | 10.76 | 10.20 | 10.35 |
| 3692999 | 13.14 | 11.47 | 10.46 | 11.07 | 8.56 | 13.06 | 11.72 | 5.93 | 9.91 | 12.33 | 11.65 | 10.16 |
| 2439554 | 6.36 | 6.91 | 9.68 | 6.30 | 5.28 | 6.47 | 5.30 | 5.80 | 7.48 | 4.56 | 8.26 | 8.08 |
| 2685304 | 6.76 | 7.72 | 8.95 | 10.46 | 11.60 | 7.64 | 8.67 | 10.56 | 8.58 | 9.32 | 8.34 | 10.24 |
| 2578790 | 8.05 | 5.99 | 5.17 | 4.26 | 4.10 | 7.65 | 6.03 | 4.02 | 5.51 | 5.32 | 7.21 | 4.30 |
| 2373842 | 10.88 | 11.63 | 11.15 | 10.78 | 8.79 | 11.28 | 8.09 | 9.65 | 11.40 | 8.23 | 10.84 | 10.73 |
| 2750627 | 9.63 | 8.13 | 5.91 | 6.49 | 9.56 | 9.61 | 10.03 | 10.41 | 7.52 | 10.47 | 8.79 | 8.06 |
| 3397774 | 4.97 | 4.74 | 4.98 | 10.77 | 4.64 | 4.60 | 4.94 | 4.47 | 4.83 | 5.17 | 7.37 | 4.67 |
| 2635614 | 8.37 | 8.91 | 8.60 | 7.13 | 6.14 | 8.84 | 6.00 | 6.51 | 8.75 | 5.89 | 8.01 | 7.78 |
| 3970833 | 9.94 | 9.28 | 9.75 | 11.56 | 9.62 | 9.95 | 10.38 | 10.05 | 9.43 | 10.32 | 10.33 | 9.75 |
| 3577612 | 9.68 | 10.90 | 11.29 | 9.75 | 11.53 | 10.11 | 9.53 | 11.33 | 10.92 | 8.29 | 10.56 | 11.55 |
| 2708922 | 6.56 | 8.70 | 7.45 | 7.54 | 8.36 | 7.24 | 7.44 | 6.53 | 8.16 | 7.93 | 7.37 | 7.82 |
| 2970897 | 5.28 | 5.58 | 5.05 | 8.51 | 6.06 | 6.85 | 6.40 | 5.38 | 5.40 | 5.63 | 5.47 | 6.01 |
| 3724545 | 10.08 | 9.93 | 9.04 | 7.50 | 10.05 | 10.26 | 9.33 | 6.60 | 9.68 | 10.13 | 10.08 | 9.25 |
| 2798538 | 8.93 | 9.28 | 9.73 | 10.84 | 9.26 | 9.53 | 9.19 | 9.37 | 9.04 | 9.11 | 9.54 | 9.74 |
| 2806468 | 10.44 | 11.25 | 9.66 | 9.61 | 8.40 | 11.41 | 6.60 | 9.35 | 11.30 | 7.50 | 9.70 | 10.56 |
| 2880051 | 6.58 | 6.67 | 6.41 | 7.99 | 5.72 | 6.38 | 6.10 | 5.36 | 6.60 | 5.93 | 5.88 | 5.91 |
| 2732508 | 3.54 | 3.60 | 8.69 | 3.63 | 3.41 | 3.24 | 3.68 | 4.83 | 3.53 | 3.71 | 7.91 | 4.00 |
| 2822492 | 5.32 | 5.51 | 5.26 | 7.53 | 5.46 | 5.48 | 6.46 | 5.07 | 5.61 | 6.14 | 5.83 | 5.44 |
| 3404030 | 8.25 | 9.27 | 7.37 | 6.44 | 5.25 | 8.39 | 5.56 | 6.41 | 9.26 | 5.99 | 6.75 | 7.50 |
| 3059667 | 8.76 | 10.14 | 4.45 | 3.81 | 4.44 | 9.58 | 6.13 | 3.83 | 9.64 | 8.65 | 6.79 | 5.37 |
| 3108526 | 11.21 | 8.87 | 8.47 | 10.70 | 8.40 | 10.46 | 10.01 | 9.52 | 9.01 | 9.94 | 10.28 | 7.39 |
| 2526806 | 7.88 | 9.37 | 11.98 | 13.32 | 12.83 | 7.88 | 10.25 | 9.97 | 10.81 | 8.80 | 11.63 | 12.14 |
| 2428501 | 5.97 | 6.49 | 8.28 | 9.60 | 7.55 | 6.94 | 6.66 | 7.59 | 6.90 | 5.62 | 7.58 | 8.51 |
| 2657808 | 6.09 | 6.52 | 7.06 | 4.89 | 10.86 | 5.81 | 7.70 | 6.18 | 6.83 | 8.29 | 6.37 | 10.62 |
| 2584018 | 6.68 | 7.55 | 8.39 | 5.87 | 10.62 | 7.81 | 9.30 | 8.31 | 9.07 | 7.87 | 10.18 | 10.61 |
| 3976341 | 8.20 | 9.97 | 10.17 | 8.16 | 11.66 | 9.42 | 6.92 | 10.94 | 10.23 | 8.55 | 9.37 | 11.45 |
| 2739308 | 4.59 | 5.59 | 4.70 | 9.80 | 4.49 | 5.14 | 5.33 | 4.25 | 5.19 | 5.09 | 4.51 | 4.57 |
| 3959862 | 4.19 | 6.32 | 5.71 | 10.36 | 4.26 | 5.60 | 6.37 | 5.92 | 5.69 | 4.52 | 4.19 | 5.08 |
| 2362351 | 7.17 | 8.15 | 8.03 | 6.62 | 5.80 | 7.69 | 5.79 | 5.98 | 8.01 | 5.64 | 7.07 | 7.10 |
| 3648391 | 5.43 | 5.59 | 8.28 | 4.50 | 3.78 | 4.81 | 3.78 | 4.76 | 5.16 | 3.66 | 6.16 | 5.11 |
| 3009299 | 10.67 | 10.41 | 10.97 | 12.04 | 10.65 | 10.77 | 11.56 | 10.68 | 10.59 | 11.33 | 11.13 | 11.11 |
| 3443464 | 5.35 | 6.51 | 5.77 | 5.23 | 4.97 | 5.46 | 5.16 | 5.19 | 6.48 | 5.04 | 5.52 | 5.36 |
| 2730746 | 8.95 | 7.14 | 6.31 | 9.48 | 5.71 | 8.85 | 9.29 | 5.05 | 6.70 | 9.11 | 7.46 | 5.88 |
| 2427619 | 7.90 | 8.88 | 8.63 | 7.49 | 6.03 | 9.01 | 5.60 | 7.03 | 8.99 | 5.74 | 7.34 | 7.69 |
| 3042001 | 9.07 | 8.20 | 8.87 | 10.55 | 8.08 | 8.84 | 9.07 | 9.05 | 8.06 | 8.85 | 9.25 | 8.77 |
| 2566848 | 5.01 | 5.97 | 5.64 | 5.82 | 4.80 | 5.48 | 5.17 | 7.58 | 5.64 | 4.97 | 5.23 | 4.92 |
| 2984616 | 9.00 | 9.06 | 9.60 | 11.60 | 8.63 | 9.25 | 10.16 | 9.07 | 8.99 | 9.64 | 9.70 | 9.46 |
| 2378068 | 7.29 | 7.77 | 9.57 | 10.48 | 8.36 | 6.29 | 7.08 | 9.72 | 7.33 | 7.12 | 8.14 | 10.01 |
| 2721959 | 6.13 | 8.26 | 10.96 | 7.00 | 12.75 | 6.77 | 10.66 | 6.87 | 9.03 | 9.89 | 11.25 | 11.18 |
| 2877508 | 10.60 | 10.17 | 10.67 | 11.93 | 10.27 | 10.56 | 10.70 | 10.52 | 10.13 | 10.60 | 10.76 | 10.67 |
| 3450801 | 6.08 | 6.98 | 6.74 | 5.30 | 4.88 | 6.89 | 4.55 | 5.01 | 6.82 | 4.83 | 5.52 | 5.79 |
| 2688717 | 8.31 | 9.60 | 8.88 | 7.80 | 5.96 | 9.46 | 5.14 | 7.23 | 9.44 | 6.47 | 8.05 | 7.90 |
| 3270270 | 7.69 | 8.97 | 8.64 | 7.82 | 8.85 | 8.47 | 6.72 | 7.71 | 8.76 | 6.62 | 7.43 | 9.16 |
| 3417703 | 8.99 | 8.73 | 5.63 | 4.73 | 6.63 | 10.27 | 6.72 | 4.34 | 7.88 | 6.80 | 8.28 | 5.81 |
| 3302990 | 8.56 | 6.85 | 7.80 | 11.19 | 7.49 | 8.41 | 9.19 | 7.48 | 7.04 | 8.55 | 8.38 | 7.58 |
| 2377283 | 4.25 | 4.82 | 8.38 | 4.33 | 4.26 | 5.00 | 4.31 | 7.29 | 4.98 | 4.34 | 7.96 | 4.27 |

TABLE 41-continued

Normalized intensity of microarray data for a set of samples.

| TCID | V01 0193 | V01 0194 | V01 0195 | V01 0196 | V01 0197 | V01 0198 | V01 0199 | V01 0200 | V01 0201 | V01 0202 | V01 0203 | V01 0204 |
|---|---|---|---|---|---|---|---|---|---|---|---|---|
| 3122678 | 4.86 | 5.03 | 4.58 | 11.45 | 6.26 | 4.74 | 5.50 | 4.99 | 4.65 | 4.65 | 3.84 | 5.51 |
| 2688499 | 9.03 | 9.17 | 8.87 | 6.44 | 10.33 | 9.86 | 9.16 | 5.90 | 9.08 | 9.11 | 8.88 | 9.00 |
| 2377094 | 9.14 | 8.80 | 9.25 | 11.69 | 8.34 | 9.52 | 10.19 | 8.44 | 8.14 | 9.95 | 10.04 | 8.35 |
| 3278198 | 8.25 | 7.09 | 8.26 | 10.24 | 8.17 | 8.63 | 9.60 | 8.54 | 8.28 | 9.10 | 8.98 | 8.91 |
| 2598261 | 7.33 | 8.37 | 11.47 | 12.69 | 12.94 | 7.43 | 9.59 | 9.19 | 10.36 | 7.99 | 10.71 | 11.87 |
| 3982612 | 8.99 | 9.09 | 9.48 | 7.60 | 6.08 | 9.43 | 6.15 | 6.56 | 9.79 | 5.34 | 8.24 | 7.99 |
| 2884845 | 4.71 | 4.47 | 5.59 | 5.07 | 10.25 | 4.47 | 5.01 | 4.64 | 4.47 | 7.10 | 5.66 | 8.63 |
| 3982560 | 6.08 | 7.44 | 7.28 | 5.99 | 4.70 | 7.75 | 4.62 | 5.64 | 7.27 | 4.92 | 6.18 | 6.19 |
| 3204285 | 5.46 | 5.83 | 6.25 | 5.46 | 5.67 | 5.27 | 5.13 | 4.94 | 5.63 | 5.01 | 5.62 | 6.10 |
| 3654699 | 12.33 | 11.47 | 12.26 | 12.89 | 11.00 | 12.38 | 12.00 | 11.83 | 11.47 | 11.20 | 12.09 | 12.25 |
| 2638676 | 7.30 | 7.82 | 8.92 | 6.70 | 5.69 | 6.79 | 5.62 | 7.58 | 7.94 | 6.27 | 7.99 | 7.32 |
| 3367673 | 8.51 | 8.41 | 6.07 | 7.59 | 4.21 | 8.96 | 9.11 | 8.81 | 6.73 | 8.58 | 8.19 | 4.56 |
| 3212008 | 6.54 | 7.77 | 6.92 | 5.97 | 8.19 | 6.38 | 8.91 | 8.30 | 7.71 | 9.47 | 6.86 | 7.66 |
| 3326635 | 9.88 | 10.29 | 10.08 | 8.91 | 9.84 | 10.23 | 10.21 | 9.86 | 10.28 | 10.27 | 9.95 | 10.44 |
| 3031556 | 8.52 | 9.50 | 9.90 | 8.11 | 6.52 | 9.55 | 6.67 | 7.67 | 9.66 | 6.18 | 8.42 | 9.25 |
| 3662201 | 12.85 | 11.58 | 10.50 | 10.94 | 9.51 | 12.82 | 11.34 | 6.94 | 9.97 | 12.29 | 11.38 | 10.48 |
| 2809793 | 7.82 | 9.26 | 9.17 | 6.75 | 4.46 | 8.61 | 5.97 | 6.82 | 9.25 | 5.16 | 7.88 | 7.46 |
| 2817731 | 7.89 | 7.67 | 8.87 | 7.97 | 7.78 | 7.27 | 7.62 | 8.13 | 7.97 | 7.61 | 7.67 | 9.37 |
| 4020655 | 5.16 | 6.88 | 5.34 | 4.77 | 5.99 | 4.94 | 8.23 | 4.34 | 5.73 | 8.12 | 6.72 | 5.44 |
| 3494629 | 5.46 | 4.59 | 6.11 | 6.84 | 9.24 | 4.57 | 7.40 | 4.38 | 6.10 | 8.24 | 5.77 | 7.19 |
| 3852832 | 7.59 | 9.99 | 7.32 | 8.20 | 6.38 | 9.13 | 5.74 | 6.29 | 8.73 | 6.19 | 7.27 | 7.70 |
| 3761959 | 9.73 | 9.26 | 9.51 | 9.76 | 8.88 | 9.61 | 9.95 | 9.61 | 9.14 | 9.81 | 9.40 | 9.71 |
| 2834282 | 6.88 | 6.52 | 6.08 | 7.43 | 8.95 | 6.61 | 7.39 | 5.23 | 6.97 | 9.18 | 6.43 | 7.36 |
| 3341497 | 6.38 | 6.39 | 6.24 | 7.43 | 7.71 | 7.59 | 9.61 | 5.79 | 6.16 | 9.14 | 6.45 | 6.68 |
| 2372812 | 4.55 | 5.09 | 7.61 | 4.74 | 4.85 | 5.12 | 4.54 | 7.33 | 4.72 | 4.92 | 8.95 | 4.56 |
| 2486811 | 8.79 | 10.35 | 10.86 | 8.29 | 8.21 | 9.41 | 6.89 | 8.99 | 10.66 | 6.13 | 9.67 | 10.80 |
| 3768474 | 8.15 | 8.67 | 8.79 | 8.95 | 7.77 | 8.27 | 7.69 | 7.92 | 8.48 | 7.89 | 8.36 | 9.11 |
| 3142381 | 4.84 | 5.46 | 5.60 | 6.30 | 5.09 | 7.24 | 4.07 | 4.22 | 5.06 | 4.47 | 4.18 | 8.15 |
| 2396750 | 7.24 | 7.06 | 6.93 | 8.73 | 8.00 | 6.76 | 7.46 | 9.14 | 6.60 | 7.46 | 7.30 | 7.33 |
| 3902489 | 10.50 | 11.79 | 10.38 | 10.59 | 10.25 | 10.69 | 9.26 | 10.42 | 11.41 | 9.14 | 10.20 | 10.77 |
| 3032647 | 8.79 | 6.96 | 5.95 | 6.11 | 5.38 | 7.95 | 5.96 | 5.62 | 6.97 | 6.24 | 5.36 | 5.80 |
| 3875642 | 5.14 | 5.91 | 5.13 | 5.10 | 4.98 | 5.59 | 4.88 | 7.69 | 5.76 | 4.82 | 5.15 | 5.30 |
| 4027585 | 9.62 | 11.45 | 10.91 | 10.27 | 9.03 | 10.35 | 8.74 | 9.36 | 11.62 | 8.79 | 9.83 | 11.17 |
| 2352609 | 7.62 | 6.97 | 5.88 | 7.23 | 6.77 | 7.07 | 8.04 | 5.98 | 6.81 | 8.08 | 7.31 | 5.85 |
| 3376529 | 9.51 | 8.32 | 8.78 | 10.02 | 10.19 | 8.67 | 10.14 | 8.87 | 7.59 | 9.82 | 9.52 | 9.02 |
| 2491271 | 12.98 | 13.29 | 13.76 | 12.44 | 13.35 | 13.01 | 12.74 | 13.42 | 13.37 | 12.24 | 13.25 | 13.76 |
| 3874751 | 9.87 | 9.00 | 10.07 | 9.05 | 9.50 | 9.60 | 9.33 | 10.70 | 9.29 | 9.27 | 10.23 | |
| 2326463 | 11.31 | 12.00 | 11.89 | 10.47 | 10.69 | 11.69 | 8.52 | 10.41 | 12.27 | 8.20 | 11.03 | 12.12 |
| 3341061 | 7.08 | 7.28 | 8.46 | 7.03 | 7.40 | 6.61 | 6.76 | 7.87 | 8.64 | 7.01 | 7.71 | 9.02 |
| 3839910 | 7.58 | 9.96 | 7.48 | 8.26 | 5.09 | 8.19 | 4.92 | 5.58 | 8.79 | 6.27 | 7.12 | 7.87 |
| 2708855 | 3.77 | 4.82 | 5.72 | 4.55 | 9.35 | 4.25 | 8.33 | 3.89 | 4.36 | 7.98 | 6.27 | 7.39 |
| 3512874 | 11.32 | 12.20 | 11.78 | 11.25 | 10.19 | 11.66 | 9.05 | 10.47 | 11.94 | 8.86 | 11.46 | 11.72 |
| 2701071 | 8.67 | 11.05 | 9.55 | 9.25 | 7.35 | 9.63 | 7.30 | 8.23 | 10.30 | 7.58 | 8.99 | 9.82 |
| 3486096 | 8.08 | 7.76 | 6.86 | 6.38 | 7.31 | 8.04 | 9.57 | 4.67 | 6.10 | 9.44 | 8.81 | 6.30 |
| 2412668 | 8.19 | 8.28 | 9.04 | 8.34 | 8.10 | 8.65 | 8.35 | 8.56 | 8.62 | 8.54 | 8.05 | 9.23 |
| 3329343 | 7.23 | 7.36 | 8.21 | 7.88 | 9.37 | 7.03 | 8.03 | 8.45 | 7.25 | 8.54 | 7.76 | 8.78 |
| 3259367 | 4.52 | 4.30 | 4.53 | 4.00 | 4.57 | 4.49 | 7.39 | 3.78 | 4.92 | 7.29 | 5.59 | 4.17 |
| 3373845 | 8.78 | 9.75 | 10.32 | 7.50 | 8.37 | 10.37 | 8.65 | 8.35 | 9.83 | 7.44 | 8.85 | 10.46 |
| 2321911 | 8.60 | 8.88 | 8.50 | 8.08 | 7.72 | 8.39 | 7.97 | 7.97 | 8.53 | 7.78 | 8.31 | 8.54 |
| 3353914 | 6.91 | 6.61 | 7.47 | 6.86 | 8.10 | 6.47 | 7.40 | 8.06 | 8.28 | 7.21 | 7.10 | 8.97 |
| 3744680 | 7.11 | 8.21 | 7.95 | 7.06 | 6.37 | 7.47 | 6.68 | 6.98 | 8.21 | 6.46 | 6.98 | 8.39 |
| 2373336 | 5.49 | 6.89 | 8.05 | 5.18 | 10.29 | 6.84 | 4.62 | 6.10 | 7.01 | 5.58 | 6.30 | 8.63 |
| 3067478 | 4.42 | 5.58 | 6.80 | 4.52 | 8.59 | 5.34 | 7.31 | 4.38 | 4.74 | 8.12 | 7.54 | 7.27 |
| 3976766 | 7.67 | 9.03 | 8.24 | 7.23 | 6.57 | 8.38 | 6.51 | 6.80 | 8.44 | 6.64 | 7.42 | 8.33 |
| 3246888 | 6.65 | 7.51 | 5.60 | 4.54 | 4.54 | 6.65 | 8.60 | 6.94 | 5.64 | 7.75 | 6.54 | 6.02 |
| 3147985 | 6.30 | 6.40 | 7.54 | 7.57 | 7.66 | 6.85 | 7.74 | 7.55 | 7.40 | 7.19 | 6.02 | 9.46 |
| 3185522 | 9.41 | 9.17 | 11.37 | 9.83 | 9.52 | 9.26 | 9.02 | 10.16 | 10.25 | 9.81 | 10.10 | 11.37 |
| 3861948 | 11.99 | 12.90 | 12.53 | 11.72 | 10.64 | 12.41 | 9.71 | 11.30 | 12.66 | 9.59 | 11.83 | 12.51 |
| 3393479 | 10.47 | 8.70 | 9.53 | 7.86 | 10.23 | 10.39 | 7.52 | 8.61 | 9.79 | 7.62 | 8.55 | 9.83 |
| 3540862 | 7.01 | 6.41 | 6.59 | 10.58 | 7.11 | 6.71 | 8.21 | 6.95 | 6.67 | 7.51 | 7.33 | 6.80 |
| 2777714 | 10.51 | 11.84 | 10.28 | 10.83 | 9.15 | 11.15 | 7.87 | 8.57 | 11.88 | 9.50 | 10.07 | 10.39 |
| 3110395 | 4.56 | 5.30 | 4.23 | 4.39 | 5.96 | 4.20 | 5.66 | 7.13 | 4.15 | 6.07 | 4.26 | 4.52 |
| 3895795 | 7.74 | 9.30 | 7.07 | 7.52 | 8.23 | 8.10 | 7.64 | 7.21 | 8.35 | 7.51 | 7.91 | 8.00 |
| 2854445 | 9.29 | 9.89 | 10.97 | 8.09 | 9.09 | 8.09 | 7.02 | 10.44 | 10.89 | 6.83 | 9.28 | 11.21 |
| 3606034 | 7.83 | 7.09 | 7.60 | 7.55 | 7.50 | 7.53 | 8.03 | 7.35 | 7.38 | 7.82 | 7.64 | 8.16 |
| 3375735 | 7.50 | 8.24 | 8.13 | 7.20 | 8.14 | 7.78 | 7.05 | 7.20 | 8.74 | 7.00 | 7.64 | 8.13 |
| 3948047 | 7.62 | 8.75 | 9.11 | 7.77 | 7.40 | 7.97 | 6.97 | 7.46 | 9.01 | 6.94 | 7.84 | 9.00 |
| 3010503 | 8.23 | 9.46 | 9.09 | 8.44 | 6.59 | 8.31 | 5.35 | 9.77 | 9.79 | 5.89 | 7.74 | 10.63 |
| 3622934 | 7.32 | 6.79 | 6.78 | 8.54 | 7.96 | 6.26 | 8.16 | 8.54 | 6.60 | 8.30 | 7.41 | 6.76 |
| 3441849 | 9.46 | 10.37 | 9.78 | 9.07 | 9.75 | 9.99 | 9.71 | 9.61 | 10.14 | 9.55 | 9.63 | 10.30 |
| 3006572 | 6.32 | 6.74 | 6.27 | 6.74 | 6.35 | 6.52 | 6.40 | 6.27 | 6.76 | 6.67 | 6.43 | 6.26 |
| 3365136 | 8.75 | 9.10 | 8.67 | 9.17 | 9.58 | 8.38 | 10.83 | 8.43 | 9.33 | 11.13 | 9.35 | 10.19 |
| 2642791 | 9.02 | 8.13 | 9.12 | 8.70 | 8.42 | 9.03 | 8.71 | 8.39 | 8.24 | 8.09 | 9.06 | 8.77 |
| 2904485 | 10.48 | 8.39 | 7.25 | 6.27 | 8.03 | 9.27 | 7.43 | 6.03 | 8.00 | 8.63 | 7.83 | 7.37 |
| 3772661 | 9.05 | 10.10 | 11.32 | 8.79 | 10.30 | 9.03 | 8.82 | 10.48 | 10.99 | 8.72 | 10.23 | 11.54 |

TABLE 41-continued

Normalized intensity of microarray data for a set of samples.

| TCID | V01 0193 | V01 0194 | V01 0195 | V01 0196 | V01 0197 | V01 0198 | V01 0199 | V01 0200 | V01 0201 | V01 0202 | V01 0203 | V01 0204 |
|---|---|---|---|---|---|---|---|---|---|---|---|---|
| 2796553 | 9.21 | 10.50 | 10.08 | 10.05 | 8.59 | 9.44 | 8.80 | 9.16 | 10.04 | 9.12 | 9.52 | 10.53 |
| 3063795 | 7.27 | 7.40 | 9.71 | 7.67 | 7.46 | 7.36 | 7.61 | 8.36 | 8.27 | 6.61 | 8.42 | 8.70 |
| 3338192 | 9.15 | 8.83 | 9.24 | 8.08 | 11.00 | 9.29 | 10.04 | 10.47 | 8.51 | 10.52 | 9.50 | 9.90 |
| 3214845 | 5.20 | 4.66 | 4.61 | 4.27 | 4.17 | 4.77 | 4.01 | 5.41 | 4.30 | 4.20 | 5.61 | 4.18 |
| 2730303 | 4.24 | 4.51 | 7.43 | 4.61 | 4.20 | 4.28 | 4.46 | 5.90 | 4.39 | 4.20 | 7.64 | 4.01 |
| 3811086 | 8.60 | 7.60 | 7.95 | 7.58 | 7.54 | 8.05 | 7.81 | 8.29 | 7.69 | 7.96 | 7.88 | 8.18 |
| 2981874 | 11.36 | 10.11 | 10.70 | 10.53 | 10.42 | 10.38 | 10.47 | 9.85 | 10.02 | 10.30 | 10.68 | 10.67 |
| 3242353 | 6.45 | 5.89 | 6.60 | 6.42 | 6.00 | 6.24 | 6.22 | 6.36 | 5.89 | 6.18 | 6.27 | 6.63 |
| 2442008 | 6.11 | 6.40 | 5.79 | 5.18 | 8.06 | 5.62 | 7.83 | 4.88 | 5.50 | 8.22 | 5.57 | 7.13 |
| 3564210 | 8.78 | 10.24 | 9.63 | 8.82 | 8.38 | 8.72 | 7.41 | 8.56 | 9.87 | 7.34 | 8.47 | 9.71 |
| 2490351 | 4.13 | 4.09 | 3.99 | 3.98 | 3.85 | 4.04 | 4.17 | 4.12 | 3.97 | 4.09 | 3.95 | 4.02 |
| 3759006 | 7.96 | 10.37 | 8.33 | 8.88 | 7.69 | 9.28 | 7.22 | 6.93 | 10.74 | 7.32 | 8.11 | 8.27 |
| 3264997 | 3.99 | 4.19 | 4.03 | 4.40 | 4.01 | 4.01 | 3.87 | 4.13 | 4.04 | 4.00 | 3.81 | 4.43 |
| 3912079 | 3.68 | 3.86 | 3.87 | 3.60 | 3.76 | 3.47 | 3.35 | 3.27 | 3.77 | 3.79 | 3.56 | 3.42 |
| 2926802 | 4.85 | 5.15 | 5.10 | 5.05 | 5.19 | 5.38 | 4.56 | 5.36 | 5.23 | 5.11 | 4.85 | 4.95 |
| 2430163 | 3.76 | 4.06 | 3.75 | 4.04 | 7.84 | 3.74 | 3.84 | 4.05 | 3.80 | 4.10 | 4.05 | 4.27 |
| 3039830 | 3.40 | 3.08 | 3.13 | 3.10 | 3.08 | 3.09 | 3.13 | 3.08 | 3.23 | 3.26 | 3.39 | 3.25 |
| 3935486 | 5.63 | 6.28 | 6.98 | 5.08 | 7.01 | 6.14 | 5.67 | 5.93 | 8.38 | 5.36 | 6.05 | 8.82 |
| 3457336 | 5.47 | 5.89 | 5.10 | 5.20 | 5.47 | 5.43 | 5.51 | 5.40 | 5.44 | 5.29 | 5.11 | 7.61 |
| 3811949 | 3.34 | 3.66 | 3.47 | 3.57 | 3.48 | 3.52 | 3.39 | 3.27 | 3.51 | 3.46 | 3.41 | 3.31 |
| 3343832 | 3.64 | 3.94 | 3.82 | 3.83 | 3.78 | 3.82 | 3.90 | 3.52 | 4.09 | 3.69 | 3.62 | 3.82 |
| 3161261 | 6.02 | 6.49 | 5.52 | 5.64 | 5.40 | 5.71 | 5.59 | 4.89 | 5.87 | 5.13 | 5.48 | 5.55 |
| 3594003 | 3.58 | 3.68 | 3.97 | 3.59 | 3.71 | 3.56 | 3.61 | 4.49 | 3.80 | 3.56 | 3.57 | 4.41 |
| 3805614 | 4.44 | 4.77 | 5.07 | 4.82 | 4.37 | 4.37 | 4.56 | 4.43 | 4.90 | 4.58 | 4.32 | 4.94 |
| 3364127 | 6.65 | 6.63 | 6.36 | 9.24 | 6.68 | 6.73 | 6.66 | 6.12 | 7.17 | 7.19 | 6.63 | 6.42 |
| 3834341 | 3.82 | 4.33 | 3.96 | 4.02 | 3.84 | 4.08 | 4.07 | 3.78 | 4.18 | 3.94 | 3.78 | 3.97 |
| 2585400 | 4.42 | 4.73 | 4.23 | 4.35 | 4.54 | 4.32 | 4.21 | 6.66 | 4.92 | 4.07 | 4.06 | 4.10 |
| 2941690 | 4.16 | 3.94 | 4.16 | 4.37 | 3.87 | 4.21 | 4.16 | 3.81 | 4.21 | 4.50 | 4.38 | 4.10 |
| 3484895 | 4.71 | 5.17 | 4.65 | 4.74 | 5.95 | 4.72 | 4.98 | 8.71 | 4.91 | 5.32 | 4.66 | 5.39 |
| 3159754 | 3.77 | 3.67 | 3.61 | 3.72 | 3.94 | 3.85 | 3.67 | 3.57 | 3.85 | 3.61 | 3.61 | 3.50 |
| 2894790 | 3.77 | 3.76 | 3.68 | 3.78 | 3.74 | 3.73 | 4.00 | 3.46 | 3.83 | 3.70 | 3.56 | 3.61 |
| 3363686 | 3.25 | 3.78 | 3.39 | 3.50 | 3.44 | 3.27 | 3.55 | 3.50 | 3.47 | 3.51 | 3.35 | 3.22 |
| 2923928 | 4.33 | 4.33 | 4.17 | 3.93 | 4.07 | 3.96 | 4.06 | 3.83 | 4.25 | 4.33 | 4.03 | 4.01 |
| 2883317 | 4.85 | 5.89 | 5.36 | 4.57 | 4.85 | 4.49 | 4.50 | 4.89 | 5.83 | 3.95 | 4.53 | 4.37 |
| 2479698 | 6.19 | 6.18 | 5.92 | 5.96 | 5.71 | 5.91 | 6.47 | 5.82 | 6.14 | 5.95 | 5.89 | 5.73 |
| 3428225 | 3.64 | 3.88 | 3.94 | 3.72 | 3.80 | 3.62 | 3.58 | 3.48 | 3.84 | 3.83 | 3.59 | 3.71 |
| 3393446 | 6.55 | 7.32 | 7.53 | 6.97 | 6.70 | 6.75 | 7.28 | 6.24 | 7.68 | 7.12 | 7.28 | 7.81 |
| 3116614 | 13.22 | 12.83 | 11.97 | 11.86 | 12.04 | 13.17 | 13.26 | 6.76 | 12.38 | 13.15 | 12.69 | 9.81 |
| 3415320 | 11.32 | 9.99 | 8.79 | 11.07 | 10.82 | 11.32 | 10.28 | 10.64 | 9.33 | 10.48 | 10.75 | 9.84 |
| 3757108 | 7.20 | 7.85 | 8.10 | 7.93 | 11.76 | 7.94 | 8.09 | 11.85 | 8.11 | 8.72 | 8.38 | 10.21 |
| 4012178 | 6.15 | 6.35 | 8.12 | 8.24 | 10.90 | 7.06 | 11.55 | 5.84 | 7.56 | 10.98 | 8.97 | 6.68 |
| 3546213 | 11.27 | 10.26 | 9.74 | 9.93 | 10.68 | 11.11 | 11.70 | 5.07 | 10.52 | 11.61 | 11.59 | 10.10 |
| 3561381 | 10.28 | 9.79 | 8.30 | 9.66 | 10.10 | 10.02 | 10.53 | 10.01 | 8.58 | 10.85 | 10.28 | 8.57 |

TABLE 42

Normalized intensity of microarray data for a set of samples.

| TCID | V01 0205 | V01 0206 | V01 0207 | V01 0208 | V01 0209 | V01 0210 | V01 0211 | V01 0212 | V01 0213 | V01 0214 | V01 0215 | V01 0216 |
|---|---|---|---|---|---|---|---|---|---|---|---|---|
| 2604998 | 8.42 | 9.25 | 8.00 | 9.13 | 8.70 | 8.89 | 6.61 | 6.75 | 8.35 | 9.42 | 8.07 | 8.24 |
| 3603932 | 7.05 | 6.98 | 7.22 | 7.29 | 7.84 | 7.42 | 6.91 | 8.62 | 7.15 | 6.93 | 7.13 | 6.85 |
| 2710599 | 5.65 | 5.50 | 7.56 | 8.77 | 10.78 | 7.64 | 5.95 | 8.61 | 10.40 | 11.37 | 8.92 | 9.30 |
| 2440258 | 7.26 | 5.03 | 8.48 | 6.71 | 6.79 | 4.89 | 8.72 | 7.89 | 7.26 | 6.19 | 7.75 | 7.27 |
| 3169331 | 7.96 | 7.27 | 9.41 | 8.32 | 7.37 | 7.51 | 6.18 | 7.79 | 6.79 | 6.29 | 8.72 | 6.17 |
| 2988882 | 9.96 | 10.39 | 10.13 | 10.18 | 9.71 | 10.18 | 9.67 | 10.22 | 9.59 | 9.58 | 9.41 | 9.92 |
| 2964231 | 8.81 | 6.90 | 9.71 | 7.99 | 10.24 | 9.26 | 8.40 | 10.37 | 9.69 | 7.09 | 8.36 | 8.91 |
| 3111561 | 7.40 | 10.46 | 9.37 | 10.54 | 5.26 | 11.32 | 7.26 | 8.50 | 5.98 | 5.00 | 10.06 | 10.28 |
| 2562529 | 8.78 | 9.36 | 9.33 | 9.94 | 10.49 | 9.73 | 8.81 | 9.78 | 10.63 | 10.99 | 9.42 | 9.74 |
| 3692999 | 7.57 | 11.36 | 12.58 | 10.38 | 11.22 | 12.72 | 8.86 | 8.69 | 6.45 | 5.53 | 7.31 | 12.73 |
| 2439554 | 6.52 | 4.46 | 7.23 | 6.68 | 5.95 | 4.53 | 7.83 | 6.55 | 6.33 | 5.93 | 6.38 | 6.21 |
| 2685304 | 7.98 | 6.32 | 6.56 | 8.68 | 7.83 | 7.90 | 6.81 | 8.62 | 11.17 | 10.82 | 9.29 | 8.78 |
| 2578790 | 6.95 | 6.64 | 7.32 | 8.83 | 5.88 | 8.39 | 5.52 | 4.26 | 4.65 | 4.35 | 7.41 | 7.58 |
| 2373842 | 11.27 | 9.01 | 10.70 | 9.83 | 10.75 | 8.70 | 12.02 | 11.19 | 10.91 | 9.88 | 11.48 | 11.18 |
| 2750627 | 9.89 | 10.67 | 10.49 | 10.99 | 8.82 | 10.82 | 7.51 | 4.77 | 10.66 | 10.91 | 10.66 | 9.35 |
| 3397782 | 4.85 | 4.66 | 5.64 | 4.73 | 9.75 | 4.81 | 4.88 | 5.45 | 4.82 | 4.74 | 4.51 | 4.80 |
| 2635741 | 7.84 | 6.37 | 7.95 | 6.98 | 7.83 | 6.83 | 9.45 | 7.75 | 7.88 | 6.85 | 8.53 | 7.70 |
| 3970833 | 9.35 | 10.28 | 10.25 | 9.72 | 10.42 | 9.84 | 9.33 | 10.25 | 9.78 | 9.73 | 9.66 | 9.36 |
| 3577612 | 10.63 | 8.51 | 9.49 | 8.89 | 9.58 | 8.50 | 11.56 | 10.09 | 11.61 | 11.71 | 10.56 | 10.62 |
| 2708922 | 8.05 | 6.50 | 6.32 | 6.57 | 7.21 | 7.94 | 8.05 | 7.06 | 8.76 | 8.75 | 8.33 | 7.74 |
| 2970897 | 6.26 | 6.03 | 7.84 | 6.07 | 5.45 | 5.77 | 4.93 | 5.95 | 4.75 | 4.56 | 4.84 | 5.23 |

TABLE 42-continued

Normalized intensity of microarray data for a set of samples.

| TCID | V01 0205 | V01 0206 | V01 0207 | V01 0208 | V01 0209 | V01 0210 | V01 0211 | V01 0212 | V01 0213 | V01 0214 | V01 0215 | V01 0216 |
|---|---|---|---|---|---|---|---|---|---|---|---|---|
| 3724545 | 9.84 | 9.75 | 10.40 | 10.06 | 9.61 | 9.42 | 9.30 | 9.36 | 9.36 | 10.27 | 10.21 | 10.17 |
| 2798538 | 8.89 | 9.28 | 9.44 | 8.93 | 9.37 | 8.75 | 8.92 | 10.24 | 8.58 | 8.80 | 8.90 | 8.22 |
| 2806468 | 10.67 | 8.17 | 10.48 | 8.65 | 10.44 | 8.28 | 11.84 | 10.39 | 10.40 | 9.18 | 11.26 | 10.30 |
| 2880051 | 6.17 | 6.18 | 6.60 | 7.47 | 6.18 | 6.34 | 6.42 | 6.29 | 5.93 | 6.02 | 6.74 | 6.29 |
| 2732508 | 3.56 | 3.38 | 6.29 | 4.50 | 3.48 | 3.56 | 3.62 | 3.60 | 3.13 | 3.44 | 3.54 | 3.68 |
| 2822492 | 6.48 | 6.84 | 5.95 | 7.44 | 6.11 | 6.08 | 5.83 | 5.56 | 5.23 | 5.24 | 6.34 | 5.38 |
| 3404030 | 7.47 | 5.69 | 7.01 | 6.55 | 6.96 | 5.81 | 8.34 | 7.57 | 6.79 | 6.87 | 8.61 | 7.56 |
| 3059667 | 7.61 | 12.21 | 8.98 | 10.85 | 6.39 | 12.00 | 8.65 | 6.56 | 5.78 | 5.44 | 10.59 | 11.46 |
| 3108526 | 10.30 | 11.34 | 10.79 | 12.13 | 10.46 | 10.95 | 8.70 | 8.93 | 9.00 | 8.45 | 11.87 | 9.87 |
| 2526806 | 9.44 | 8.27 | 10.37 | 10.50 | 9.84 | 7.46 | 6.96 | 12.15 | 12.49 | 12.50 | 7.97 | 11.79 |
| 2428501 | 6.22 | 5.97 | 6.64 | 7.42 | 6.64 | 5.82 | 7.40 | 8.86 | 6.20 | 5.90 | 7.40 | 6.86 |
| 2657808 | 5.54 | 5.60 | 6.09 | 6.48 | 9.10 | 7.97 | 5.58 | 5.42 | 9.87 | 11.00 | 5.27 | 9.12 |
| 2584018 | 6.54 | 5.19 | 6.62 | 7.29 | 6.90 | 6.79 | 8.52 | 8.82 | 9.37 | 9.32 | 8.32 | 9.19 |
| 3976341 | 9.51 | 7.49 | 8.78 | 9.84 | 8.52 | 7.83 | 10.28 | 9.79 | 11.56 | 12.06 | 9.17 | 9.12 |
| 2739308 | 7.10 | 5.88 | 5.13 | 4.97 | 5.14 | 4.49 | 5.79 | 4.77 | 4.71 | 4.75 | 5.17 | 5.96 |
| 3959862 | 4.95 | 5.65 | 8.15 | 4.44 | 4.90 | 4.39 | 5.14 | 6.03 | 3.85 | 4.21 | 5.06 | 5.90 |
| 2362351 | 6.92 | 5.37 | 7.31 | 5.90 | 7.34 | 5.55 | 8.02 | 7.54 | 6.68 | 6.69 | 8.22 | 6.96 |
| 3648391 | 5.04 | 4.84 | 7.46 | 5.32 | 5.06 | 3.93 | 5.60 | 5.41 | 5.00 | 4.73 | 4.51 | 3.98 |
| 3009299 | 10.95 | 11.48 | 11.10 | 10.54 | 11.06 | 10.81 | 10.49 | 11.02 | 10.52 | 10.41 | 10.28 | 10.44 |
| 3443464 | 5.40 | 5.17 | 5.28 | 5.06 | 5.42 | 5.14 | 5.71 | 5.73 | 5.40 | 5.28 | 5.57 | 5.69 |
| 2730746 | 9.07 | 9.32 | 8.77 | 10.74 | 8.48 | 9.11 | 6.49 | 6.55 | 6.76 | 5.16 | 9.37 | 7.86 |
| 2427619 | 8.33 | 6.15 | 8.30 | 6.87 | 7.62 | 6.30 | 9.73 | 7.71 | 7.34 | 6.81 | 8.90 | 7.84 |
| 3042001 | 8.80 | 9.73 | 9.77 | 9.51 | 9.30 | 8.66 | 8.37 | 9.11 | 8.69 | 8.26 | 8.77 | 8.62 |
| 2566848 | 5.56 | 5.93 | 5.56 | 5.95 | 5.21 | 4.79 | 6.48 | 5.60 | 5.16 | 5.38 | 6.11 | 5.19 |
| 2984616 | 8.90 | 8.67 | 9.94 | 8.78 | 9.73 | 9.56 | 9.12 | 9.81 | 8.84 | 8.84 | 8.46 | 8.59 |
| 2378068 | 8.32 | 5.90 | 7.96 | 7.92 | 7.11 | 6.50 | 7.58 | 10.40 | 9.75 | 10.61 | 7.37 | 7.24 |
| 2721959 | 6.34 | 5.53 | 7.78 | 6.86 | 10.65 | 8.17 | 6.09 | 9.12 | 12.87 | 11.82 | 5.64 | 9.02 |
| 2877508 | 10.17 | 11.18 | 10.80 | 10.78 | 10.98 | 10.58 | 9.97 | 11.09 | 10.45 | 10.31 | 10.61 | 10.19 |
| 3450861 | 6.06 | 4.37 | 5.90 | 5.06 | 5.33 | 4.45 | 7.01 | 5.58 | 5.40 | 5.04 | 6.17 | 5.32 |
| 2688717 | 8.36 | 5.85 | 9.23 | 7.42 | 7.90 | 5.44 | 9.92 | 8.14 | 8.37 | 8.13 | 8.84 | 8.00 |
| 3270270 | 8.66 | 6.42 | 7.73 | 6.85 | 7.40 | 6.08 | 9.92 | 9.03 | 8.72 | 8.42 | 8.42 | 8.63 |
| 3417703 | 8.48 | 9.65 | 9.28 | 5.27 | 4.87 | 11.48 | 6.36 | 4.32 | 5.59 | 6.75 | 4.60 | 8.73 |
| 3302990 | 8.61 | 8.20 | 9.28 | 9.17 | 8.82 | 7.94 | 6.52 | 8.40 | 7.73 | 7.18 | 8.17 | 7.18 |
| 2377283 | 4.46 | 4.36 | 6.94 | 6.56 | 4.45 | 4.10 | 6.08 | 4.54 | 4.42 | 4.61 | 4.40 | 4.41 |
| 3122678 | 4.29 | 4.53 | 5.36 | 4.35 | 4.90 | 4.27 | 4.77 | 5.88 | 4.83 | 4.44 | 5.49 | 4.70 |
| 2688499 | 7.69 | 7.25 | 9.14 | 10.19 | 8.56 | 10.28 | 7.76 | 7.61 | 9.81 | 10.72 | 9.12 | 10.17 |
| 2377094 | 9.11 | 9.57 | 10.14 | 9.96 | 10.51 | 10.18 | 8.30 | 8.82 | 8.74 | 8.51 | 9.08 | 8.68 |
| 3278198 | 7.98 | 8.49 | 8.50 | 8.50 | 9.44 | 9.27 | 7.27 | 8.75 | 8.52 | 7.27 | 8.21 | 7.85 |
| 2598261 | 9.44 | 7.77 | 9.58 | 9.71 | 9.17 | 7.25 | 7.12 | 11.73 | 12.51 | 12.15 | 7.55 | 11.11 |
| 3982612 | 7.86 | 5.33 | 9.38 | 7.45 | 7.63 | 3.94 | 9.72 | 8.31 | 7.28 | 7.30 | 8.94 | 7.87 |
| 2884845 | 4.81 | 4.42 | 4.77 | 4.61 | 4.96 | 4.80 | 4.44 | 4.44 | 10.16 | 9.78 | 6.00 | 4.78 |
| 3982560 | 6.31 | 4.51 | 7.16 | 5.84 | 6.40 | 4.38 | 8.15 | 6.23 | 6.39 | 5.83 | 6.89 | 6.12 |
| 3204285 | 5.59 | 4.76 | 7.20 | 6.73 | 5.34 | 5.70 | 5.82 | 5.17 | 5.49 | 5.60 | 5.69 | 5.85 |
| 3654699 | 11.49 | 12.70 | 12.99 | 9.79 | 12.87 | 11.55 | 8.94 | 12.27 | 11.15 | 8.62 | 9.49 | 11.79 |
| 2638676 | 7.43 | 5.38 | 7.48 | 7.69 | 5.88 | 6.05 | 8.40 | 6.76 | 6.04 | 6.75 | 7.04 | 6.77 |
| 3367673 | 8.40 | 8.00 | 8.80 | 9.02 | 7.89 | 9.41 | 6.83 | 5.91 | 5.83 | 4.67 | 7.50 | 7.54 |
| 3212008 | 6.60 | 6.97 | 6.49 | 6.03 | 7.88 | 7.42 | 6.80 | 5.94 | 8.66 | 9.40 | 6.54 | 6.52 |
| 3326635 | 10.17 | 9.62 | 9.90 | 8.79 | 10.03 | 10.12 | 10.19 | 10.44 | 10.34 | 10.47 | 9.73 | 10.15 |
| 3031556 | 9.39 | 6.05 | 8.71 | 7.01 | 8.06 | 6.46 | 10.51 | 9.42 | 8.77 | 7.26 | 9.56 | 8.65 |
| 3662201 | 9.02 | 11.03 | 12.47 | 9.59 | 11.12 | 12.70 | 9.14 | 9.72 | 6.93 | 6.39 | 7.71 | 12.62 |
| 2809793 | 5.51 | 4.69 | 9.12 | 7.45 | 6.81 | 5.26 | 9.03 | 7.54 | 6.86 | 7.32 | 8.14 | 6.86 |
| 2817731 | 8.11 | 8.81 | 7.56 | 7.77 | 7.73 | 7.74 | 8.44 | 9.90 | 8.04 | 7.37 | 7.67 | 8.03 |
| 4020655 | 5.51 | 4.61 | 4.76 | 5.24 | 8.16 | 5.42 | 5.37 | 4.68 | 7.76 | 7.61 | 5.88 | 4.63 |
| 3494629 | 4.60 | 5.13 | 4.67 | 4.61 | 8.08 | 4.99 | 4.35 | 5.63 | 7.06 | 8.12 | 6.78 | 5.51 |
| 3852832 | 9.90 | 6.95 | 7.51 | 7.35 | 7.15 | 6.49 | 10.78 | 8.24 | 9.02 | 7.28 | 9.55 | 8.98 |
| 3761959 | 9.77 | 9.60 | 9.78 | 9.40 | 9.57 | 9.63 | 8.68 | 9.60 | 9.03 | 9.05 | 9.12 | 9.08 |
| 2834282 | 6.30 | 6.73 | 5.89 | 7.50 | 6.62 | 7.31 | 6.40 | 6.22 | 7.91 | 8.51 | 6.46 | 6.79 |
| 3341497 | 6.24 | 5.71 | 6.90 | 5.22 | 8.19 | 7.66 | 6.15 | 6.33 | 8.10 | 7.73 | 5.65 | 5.99 |
| 2372812 | 4.71 | 4.62 | 6.00 | 6.74 | 4.52 | 4.64 | 4.93 | 4.86 | 4.51 | 4.65 | 4.98 | 5.06 |
| 2486811 | 9.62 | 6.95 | 8.66 | 7.83 | 8.38 | 6.72 | 10.27 | 11.03 | 8.89 | 7.86 | 9.49 | 9.81 |
| 3768474 | 8.78 | 7.18 | 8.06 | 7.62 | 7.94 | 8.05 | 8.32 | 9.02 | 7.92 | 7.31 | 7.88 | 8.46 |
| 3142381 | 6.74 | 3.96 | 5.75 | 3.69 | 4.20 | 7.17 | 5.49 | 4.91 | 6.28 | 6.53 | 5.56 |  |
| 2396750 | 7.40 | 6.32 | 6.54 | 8.76 | 7.42 | 6.82 | 7.09 | 6.92 | 7.63 | 8.22 | 7.88 | 6.66 |
| 3902489 | 11.31 | 9.39 | 9.59 | 10.24 | 10.02 | 9.53 | 11.00 | 10.85 | 10.59 | 10.51 | 11.60 | 10.41 |
| 3032647 | 7.93 | 10.08 | 8.52 | 8.37 | 6.37 | 6.35 | 6.87 | 6.29 | 5.90 | 5.88 | 8.10 | 7.40 |
| 3875642 | 5.81 | 5.36 | 5.39 | 4.96 | 5.65 | 4.91 | 6.41 | 5.71 | 5.29 | 5.33 | 5.60 | 5.40 |
| 4027585 | 10.99 | 9.08 | 9.58 | 9.07 | 10.03 | 8.82 | 11.15 | 10.66 | 9.93 | 10.22 | 11.00 | 10.84 |
| 2352609 | 7.20 | 8.23 | 7.22 | 7.44 | 8.17 | 7.90 | 5.86 | 5.76 | 7.31 | 6.68 | 6.75 | 6.35 |
| 3376529 | 8.42 | 8.78 | 9.10 | 9.49 | 9.51 | 8.93 | 8.39 | 8.17 | 9.45 | 9.96 | 9.40 | 8.55 |
| 2491177 | 12.93 | 12.00 | 13.12 | 12.57 | 12.64 | 12.29 | 13.47 | 13.77 | 13.31 | 12.92 | 13.00 | 13.20 |
| 3874751 | 9.97 | 9.88 | 10.20 | 10.14 | 8.94 | 9.43 | 9.01 | 9.55 | 9.90 | 9.76 | 10.08 | 9.21 |
| 2326463 | 11.46 | 9.21 | 11.48 | 9.82 | 10.57 | 9.09 | 12.46 | 12.75 | 11.32 | 9.93 | 11.52 | 11.76 |
| 3341061 | 7.12 | 7.24 | 7.10 | 6.81 | 6.98 | 5.91 | 7.79 | 8.62 | 7.29 | 6.09 | 6.21 | 7.88 |
| 3839910 | 9.72 | 6.27 | 7.57 | 7.07 | 7.06 | 6.24 | 10.29 | 7.35 | 9.26 | 7.00 | 9.01 | 8.63 |
| 2708855 | 5.91 | 3.98 | 4.01 | 4.87 | 6.80 | 3.99 | 4.99 | 4.28 | 7.43 | 8.46 | 5.32 | 4.43 |

TABLE 42-continued

Normalized intensity of microarray data for a set of samples.

| TCID | V01 0205 | V01 0206 | V01 0207 | V01 0208 | V01 0209 | V01 0210 | V01 0211 | V01 0212 | V01 0213 | V01 0214 | V01 0215 | V01 0216 |
|---|---|---|---|---|---|---|---|---|---|---|---|---|
| 3512874 | 12.03 | 9.58 | 11.34 | 10.29 | 11.04 | 9.30 | 12.42 | 12.25 | 11.35 | 10.45 | 12.04 | 11.90 |
| 2701071 | 10.49 | 8.51 | 9.02 | 8.19 | 8.86 | 6.85 | 11.56 | 9.44 | 10.42 | 8.29 | 10.37 | 9.84 |
| 3486096 | 7.67 | 8.66 | 7.73 | 8.33 | 8.59 | 9.37 | 6.66 | 6.29 | 6.78 | 5.62 | 7.63 | 7.25 |
| 2412668 | 8.36 | 8.38 | 7.95 | 7.80 | 8.39 | 8.77 | 8.98 | 8.76 | 8.32 | 8.05 | 7.82 | 8.38 |
| 3329343 | 6.85 | 6.57 | 7.61 | 6.74 | 7.54 | 7.44 | 6.99 | 7.56 | 8.41 | 8.93 | 6.94 | 8.03 |
| 3259367 | 4.19 | 3.93 | 4.15 | 4.07 | 7.28 | 5.37 | 4.26 | 4.11 | 5.38 | 5.33 | 3.95 | 4.19 |
| 3373845 | 8.52 | 6.79 | 8.56 | 7.44 | 7.38 | 10.29 | 9.15 | 10.65 | 8.13 | 8.51 | 8.12 | 10.01 |
| 2321911 | 8.38 | 8.78 | 8.05 | 7.80 | 8.21 | 7.95 | 8.60 | 8.69 | 8.43 | 8.20 | 8.66 | 8.58 |
| 3353914 | 6.85 | 6.56 | 6.60 | 7.05 | 6.80 | 6.73 | 6.43 | 8.83 | 6.91 | 7.41 | 6.56 | 7.33 |
| 3744680 | 7.82 | 6.51 | 7.12 | 6.65 | 7.15 | 6.39 | 8.88 | 8.09 | 7.40 | 6.63 | 7.79 | 7.70 |
| 2373336 | 5.84 | 5.20 | 6.80 | 8.87 | 5.86 | 8.05 | 6.91 | 4.73 | 5.63 | 9.40 | 6.53 | 9.68 |
| 3067478 | 7.36 | 7.51 | 7.36 | 5.74 | 5.82 | 6.90 | 5.78 | 6.81 | 8.23 | 8.70 | 5.32 | 5.69 |
| 3976766 | 8.56 | 6.43 | 7.67 | 6.78 | 7.15 | 6.53 | 9.67 | 8.13 | 7.98 | 7.02 | 8.56 | 8.10 |
| 3246888 | 6.78 | 7.76 | 6.51 | 8.79 | 7.30 | 8.33 | 6.47 | 5.35 | 4.76 | 5.21 | 7.58 | 6.35 |
| 3147985 | 6.74 | 6.98 | 6.82 | 7.76 | 6.71 | 6.85 | 6.33 | 8.94 | 7.33 | 7.50 | 7.14 | 6.99 |
| 3185522 | 9.29 | 9.62 | 9.62 | 9.83 | 9.07 | 9.06 | 9.45 | 11.35 | 9.23 | 8.83 | 9.53 | 10.14 |
| 3861948 | 12.70 | 10.42 | 11.96 | 10.83 | 11.74 | 10.07 | 13.18 | 12.51 | 12.31 | 11.04 | 12.66 | 12.54 |
| 3393479 | 8.69 | 8.33 | 9.58 | 6.71 | 7.70 | 9.58 | 9.12 | 10.35 | 8.02 | 7.90 | 7.59 | 8.82 |
| 3540862 | 6.06 | 7.27 | 7.12 | 6.36 | 8.10 | 7.53 | 6.26 | 6.63 | 7.33 | 6.93 | 6.86 | 6.54 |
| 2777714 | 11.47 | 9.86 | 9.80 | 9.99 | 10.37 | 8.52 | 11.58 | 10.70 | 10.60 | 10.67 | 11.93 | 11.08 |
| 3110395 | 5.20 | 6.69 | 5.15 | 6.40 | 4.91 | 5.35 | 4.39 | 4.64 | 6.35 | 6.68 | 4.77 | 4.61 |
| 3895795 | 9.45 | 7.42 | 7.48 | 7.40 | 7.77 | 7.00 | 9.80 | 8.19 | 9.15 | 8.13 | 9.02 | 8.14 |
| 2854445 | 7.73 | 7.85 | 7.94 | 9.99 | 7.58 | 7.99 | 8.21 | 11.13 | 8.58 | 7.42 | 9.55 | 9.71 |
| 3606034 | 7.47 | 7.99 | 7.99 | 7.19 | 7.81 | 8.15 | 7.24 | 8.81 | 7.19 | 7.45 | 7.28 | 7.48 |
| 3375735 | 7.48 | 7.23 | 7.50 | 6.97 | 6.87 | 7.57 | 8.27 | 8.27 | 7.90 | 7.86 | 7.64 | 7.98 |
| 3948047 | 8.28 | 6.74 | 7.68 | 6.92 | 7.48 | 7.05 | 9.46 | 9.14 | 7.87 | 7.12 | 8.42 | 8.37 |
| 3010503 | 9.10 | 6.83 | 7.52 | 6.66 | 8.04 | 7.31 | 10.01 | 9.93 | 8.30 | 6.93 | 8.86 | 9.35 |
| 3622934 | 6.84 | 7.98 | 6.86 | 7.55 | 8.29 | 7.29 | 6.15 | 6.44 | 7.87 | 7.97 | 6.73 | 7.28 |
| 3441849 | 10.22 | 9.11 | 9.22 | 9.27 | 9.42 | 9.20 | 10.78 | 9.97 | 10.03 | 9.81 | 10.59 | 9.97 |
| 3006572 | 6.19 | 6.72 | 6.27 | 6.19 | 6.68 | 6.30 | 6.61 | 6.24 | 6.12 | 6.67 | 6.70 | 6.23 |
| 3365136 | 8.23 | 8.63 | 8.45 | 8.67 | 10.22 | 9.33 | 8.28 | 8.30 | 9.12 | 10.04 | 7.91 | 8.44 |
| 2642791 | 8.78 | 7.76 | 8.81 | 9.72 | 8.28 | 8.81 | 8.76 | 8.83 | 8.40 | 8.18 | 9.28 | 8.54 |
| 2904485 | 9.65 | 9.12 | 8.91 | 8.83 | 7.42 | 9.48 | 7.51 | 6.84 | 7.39 | 8.16 | 7.76 | 8.60 |
| 3772661 | 9.65 | 8.36 | 8.84 | 8.72 | 8.97 | 8.61 | 10.42 | 11.42 | 9.81 | 9.66 | 9.27 | 10.52 |
| 2796553 | 10.81 | 9.16 | 9.59 | 8.85 | 9.45 | 8.62 | 10.69 | 10.40 | 10.33 | 8.53 | 10.37 | 10.07 |
| 3063795 | 6.98 | 6.70 | 7.60 | 6.61 | 7.19 | 6.67 | 7.44 | 7.97 | 7.07 | 6.72 | 7.06 | 7.18 |
| 3338192 | 8.74 | 8.42 | 9.02 | 8.42 | 9.62 | 10.12 | 7.68 | 8.72 | 8.79 | 10.45 | 8.12 | 9.39 |
| 3214845 | 4.91 | 4.54 | 4.38 | 4.21 | 4.62 | 5.49 | 5.50 | 4.38 | 4.62 | 5.14 | 4.44 | 4.31 |
| 2730303 | 4.29 | 4.23 | 5.82 | 5.53 | 4.77 | 4.07 | 4.47 | 4.15 | 4.19 | 4.13 | 4.17 | 4.22 |
| 3811086 | 7.86 | 8.43 | 7.43 | 8.53 | 7.97 | 8.25 | 7.79 | 8.24 | 7.28 | 7.53 | 7.31 | 7.74 |
| 2981874 | 10.77 | 11.02 | 11.05 | 9.91 | 9.86 | 10.09 | 10.50 | 10.69 | 10.24 | 9.67 | 10.27 | 10.43 |
| 3242353 | 6.30 | 6.42 | 6.70 | 6.21 | 5.82 | 6.79 | 5.86 | 6.67 | 5.96 | 5.77 | 5.59 | 5.90 |
| 2442008 | 5.53 | 5.94 | 6.36 | 5.26 | 5.77 | 5.11 | 5.74 | 5.33 | 9.31 | 9.58 | 5.60 | 5.19 |
| 3564210 | 10.48 | 7.46 | 8.66 | 9.28 | 7.92 | 7.43 | 10.61 | 9.58 | 9.44 | 8.05 | 9.92 | 9.80 |
| 2490351 | 4.01 | 4.22 | 4.13 | 3.94 | 4.12 | 3.86 | 4.23 | 4.08 | 4.00 | 3.97 | 4.17 | 4.06 |
| 3759006 | 9.86 | 7.33 | 7.83 | 8.10 | 8.09 | 7.11 | 9.25 | 8.47 | 8.43 | 9.16 | 10.01 | 9.03 |
| 3264997 | 4.13 | 3.99 | 3.97 | 3.88 | 4.13 | 3.88 | 4.13 | 5.03 | 4.03 | 4.07 | 3.97 | 3.92 |
| 3912079 | 3.85 | 3.43 | 3.51 | 3.56 | 3.56 | 4.11 | 4.37 | 3.67 | 3.63 | 3.59 | 3.85 | 3.65 |
| 2926802 | 5.83 | 4.65 | 5.56 | 5.43 | 5.97 | 4.65 | 6.16 | 4.94 | 5.17 | 4.49 | 5.60 | 5.08 |
| 2430163 | 3.72 | 3.82 | 3.61 | 3.58 | 3.97 | 3.62 | 4.04 | 3.85 | 3.70 | 3.66 | 3.55 | 3.97 |
| 3039830 | 3.11 | 3.10 | 3.28 | 3.07 | 3.19 | 3.22 | 3.21 | 3.14 | 3.05 | 2.97 | 3.16 | 3.72 |
| 3935486 | 5.86 | 5.50 | 5.04 | 5.99 | 6.54 | 4.60 | 7.15 | 7.99 | 6.74 | 7.38 | 5.50 | 8.60 |
| 3457336 | 5.44 | 5.45 | 5.29 | 5.25 | 5.54 | 5.46 | 5.48 | 5.47 | 5.54 | 5.13 | 5.37 | 5.50 |
| 3811949 | 3.41 | 3.47 | 3.43 | 3.40 | 3.66 | 3.40 | 3.71 | 3.36 | 3.49 | 3.31 | 3.37 | 3.48 |
| 3343832 | 3.93 | 3.85 | 4.04 | 3.78 | 3.80 | 3.86 | 3.95 | 4.22 | 3.77 | 3.82 | 3.85 | 4.03 |
| 3161261 | 5.48 | 6.41 | 5.22 | 5.48 | 6.09 | 5.63 | 6.32 | 5.68 | 5.53 | 5.70 | 6.39 | 6.03 |
| 3594003 | 3.59 | 3.56 | 3.92 | 3.74 | 3.68 | 3.57 | 3.88 | 3.93 | 3.53 | 3.59 | 3.65 | 3.66 |
| 3805614 | 4.88 | 4.60 | 4.57 | 4.48 | 4.50 | 4.24 | 4.50 | 4.50 | 4.93 | 4.59 | 4.35 | 4.33 |
| 3364127 | 6.91 | 6.38 | 6.66 | 6.42 | 7.44 | 6.37 | 7.05 | 6.79 | 6.74 | 6.71 | 6.86 | 7.00 |
| 3834341 | 3.93 | 3.68 | 3.99 | 4.75 | 4.31 | 3.98 | 4.13 | 3.98 | 4.00 | 4.03 | 6.54 | 3.85 |
| 2585400 | 4.57 | 4.21 | 4.63 | 7.06 | 4.24 | 3.98 | 4.55 | 4.58 | 4.30 | 4.28 | 5.69 | 4.58 |
| 2941690 | 3.97 | 3.92 | 3.85 | 4.02 | 4.46 | 3.99 | 4.63 | 4.63 | 4.38 | 4.17 | 3.71 | 4.32 |
| 3484895 | 4.91 | 4.49 | 4.59 | 7.33 | 5.12 | 4.67 | 4.87 | 4.51 | 5.53 | 6.12 | 6.08 | 4.59 |
| 3159754 | 3.89 | 3.54 | 3.75 | 3.48 | 3.94 | 3.75 | 3.97 | 3.86 | 3.69 | 3.75 | 3.79 | 3.63 |
| 2894790 | 3.80 | 4.06 | 3.56 | 3.79 | 4.07 | 3.72 | 4.30 | 4.20 | 3.71 | 3.75 | 3.82 | 4.07 |
| 3363686 | 3.34 | 3.97 | 3.36 | 3.21 | 3.84 | 3.43 | 4.19 | 3.49 | 3.42 | 3.43 | 3.23 | 3.48 |
| 2923928 | 4.58 | 4.05 | 3.81 | 3.99 | 4.50 | 4.00 | 4.75 | 4.31 | 4.36 | 4.34 | 4.14 | 4.15 |
| 2883317 | 4.74 | 4.33 | 5.23 | 4.67 | 4.63 | 4.55 | 5.44 | 4.60 | 4.96 | 4.51 | 4.89 | 5.11 |
| 2479698 | 6.05 | 6.36 | 6.23 | 6.10 | 6.62 | 6.23 | 6.21 | 5.88 | 6.31 | 6.25 | 6.37 | 6.16 |
| 3428225 | 3.80 | 3.67 | 3.52 | 3.57 | 3.84 | 3.86 | 3.84 | 3.61 | 3.52 | 3.56 | 3.63 | 3.66 |
| 3393446 | 7.07 | 6.66 | 6.91 | 6.83 | 6.95 | 6.55 | 7.53 | 9.59 | 6.77 | 6.83 | 6.75 | 7.03 |
| 3116614 | 13.18 | 13.20 | 13.08 | 12.27 | 12.98 | 13.18 | 11.39 | 10.26 | 12.46 | 12.73 | 12.25 | 12.86 |
| 3415320 | 10.09 | 11.57 | 10.69 | 10.45 | 10.84 | 10.60 | 8.04 | 10.34 | 10.28 | 10.60 | 9.64 | 9.93 |
| 3757108 | 7.41 | 7.32 | 7.67 | 7.13 | 7.47 | 8.31 | 7.68 | 9.19 | 9.79 | 9.94 | 7.05 | 9.03 |
| 4012178 | 10.73 | 6.12 | 6.58 | 5.77 | 9.13 | 7.18 | 6.50 | 6.13 | 11.75 | 11.34 | 5.75 | 5.95 |

TABLE 42-continued

Normalized intensity of microarray data for a set of samples.

| TCID | V01 0205 | V01 0206 | V01 0207 | V01 0208 | V01 0209 | V01 0210 | V01 0211 | V01 0212 | V01 0213 | V01 0214 | V01 0215 | V01 0216 |
|---|---|---|---|---|---|---|---|---|---|---|---|---|
| 3546213 | 10.79 | 11.44 | 11.12 | 10.56 | 11.38 | 11.67 | 9.07 | 8.47 | 10.99 | 10.73 | 10.06 | 10.83 |
| 3561381 | 9.43 | 10.33 | 10.03 | 9.86 | 10.13 | 11.44 | 7.32 | 7.05 | 11.26 | 10.50 | 9.68 | 9.81 |

TABLE 43

Normalized intensity of microarray data for a set of samples.

| TCID | V01 0217 | V01 0218 | V01 0219 | V01 0220 | V01 0221 | V01 0222 | V01 0223 | V01 0224 | V01 0225 | V01 0226 | V01 0227 | V01 0228 |
|---|---|---|---|---|---|---|---|---|---|---|---|---|
| 2604998 | 6.28 | 9.52 | 7.79 | 6.51 | 5.35 | 7.18 | 8.25 | 6.57 | 6.68 | 7.23 | 5.71 | 9.48 |
| 3603932 | 6.66 | 6.93 | 7.53 | 8.11 | 6.77 | 6.31 | 7.63 | 7.91 | 6.98 | 7.12 | 7.27 | 7.89 |
| 2710599 | 5.65 | 11.44 | 11.82 | 8.83 | 7.42 | 11.60 | 9.98 | 8.24 | 8.39 | 8.90 | 6.27 | 7.70 |
| 2440258 | 9.62 | 7.19 | 5.76 | 9.11 | 10.12 | 8.41 | 6.64 | 8.76 | 8.80 | 9.05 | 8.60 | 6.46 |
| 3169331 | 6.39 | 6.11 | 7.09 | 6.86 | 6.83 | 6.70 | 6.95 | 6.62 | 7.43 | 8.21 | 6.96 | 7.43 |
| 2988882 | 9.83 | 9.68 | 9.97 | 9.76 | 10.20 | 9.50 | 9.51 | 10.08 | 10.57 | 9.96 | 9.98 | 9.66 |
| 2964231 | 7.96 | 7.73 | 9.56 | 10.05 | 7.19 | 8.65 | 8.87 | 9.59 | 10.01 | 9.72 | 8.01 | 8.95 |
| 3111561 | 7.77 | 5.33 | 4.25 | 8.15 | 5.46 | 8.59 | 6.13 | 7.84 | 9.78 | 7.86 | 6.67 | 9.06 |
| 2562529 | 8.82 | 10.95 | 10.97 | 9.34 | 8.66 | 8.96 | 10.37 | 9.11 | 9.02 | 9.14 | 7.90 | 9.85 |
| 3692999 | 9.56 | 6.39 | 8.01 | 10.13 | 7.63 | 11.45 | 12.76 | 11.92 | 11.43 | 11.52 | 9.93 | 9.21 |
| 2439554 | 7.23 | 6.48 | 4.90 | 7.28 | 10.48 | 8.17 | 6.69 | 7.53 | 5.97 | 9.61 | 7.79 | 5.35 |
| 2685304 | 7.37 | 10.84 | 11.90 | 9.78 | 5.62 | 8.98 | 9.38 | 8.02 | 7.65 | 7.69 | 8.96 | 7.85 |
| 2578790 | 6.19 | 4.45 | 4.15 | 5.23 | 4.65 | 5.99 | 4.64 | 6.91 | 6.76 | 6.52 | 5.00 | 6.99 |
| 2373842 | 12.00 | 10.48 | 9.23 | 11.09 | 11.87 | 11.35 | 10.73 | 11.82 | 11.67 | 11.28 | 11.77 | 8.96 |
| 2750627 | 8.34 | 10.79 | 10.83 | 7.40 | 4.58 | 7.50 | 10.21 | 7.68 | 6.75 | 5.50 | 5.20 | 10.54 |
| 3397774 | 4.97 | 5.08 | 4.14 | 5.24 | 5.71 | 4.79 | 4.73 | 4.50 | 7.03 | 6.10 | 5.23 | 4.46 |
| 2635741 | 9.54 | 7.24 | 6.45 | 8.52 | 8.97 | 8.35 | 7.46 | 8.97 | 8.74 | 8.88 | 8.41 | 6.91 |
| 3970833 | 9.24 | 9.61 | 9.52 | 9.67 | 9.97 | 9.34 | 9.87 | 9.55 | 10.07 | 10.01 | 8.87 | 10.03 |
| 3577612 | 11.06 | 11.54 | 11.89 | 10.25 | 9.04 | 10.91 | 10.37 | 11.27 | 10.41 | 10.12 | 11.44 | 9.14 |
| 2708922 | 9.33 | 9.00 | 8.59 | 7.10 | 6.72 | 7.37 | 8.98 | 8.28 | 9.56 | 6.55 | 10.85 | 6.63 |
| 2970897 | 5.48 | 4.75 | 5.09 | 6.83 | 6.06 | 6.62 | 4.70 | 5.10 | 6.45 | 6.42 | 5.11 | 6.03 |
| 3724545 | 9.93 | 10.27 | 10.12 | 8.88 | 7.40 | 9.05 | 10.10 | 10.11 | 8.72 | 8.78 | 10.22 | 10.63 |
| 2798538 | 9.15 | 9.14 | 9.07 | 9.87 | 9.81 | 9.12 | 8.62 | 8.88 | 9.58 | 9.59 | 8.65 | 9.41 |
| 2806468 | 11.93 | 9.56 | 9.02 | 11.34 | 10.73 | 10.05 | 10.19 | 10.67 | 10.06 | 11.35 | 7.50 |  |
| 2880051 | 7.18 | 5.92 | 6.01 | 6.49 | 6.17 | 6.32 | 5.93 | 6.71 | 7.16 | 6.52 | 6.65 | 5.80 |
| 2732508 | 3.72 | 3.22 | 3.81 | 5.10 | 9.49 | 3.26 | 3.40 | 3.21 | 3.71 | 8.59 | 3.78 | 4.32 |
| 2822492 | 5.19 | 5.23 | 5.82 | 5.50 | 4.81 | 5.44 | 6.44 | 6.16 | 5.31 | 5.88 | 5.34 | 7.25 |
| 3404030 | 10.08 | 7.64 | 4.92 | 9.03 | 8.58 | 9.45 | 7.40 | 8.68 | 8.82 | 8.09 | 9.64 | 6.26 |
| 3059667 | 8.07 | 5.88 | 3.92 | 7.25 | 6.04 | 8.31 | 9.12 | 6.32 | 7.91 | 6.57 | 4.70 | 10.44 |
| 3108526 | 8.46 | 8.21 | 7.71 | 7.29 | 8.56 | 9.29 | 7.99 | 8.44 | 10.74 | 9.89 | 6.60 | 11.00 |
| 2526806 | 9.08 | 12.60 | 13.04 | 12.15 | 9.24 | 8.85 | 8.08 | 11.32 | 9.76 | 11.76 | 10.21 | 11.16 |
| 2428501 | 7.50 | 6.10 | 8.14 | 9.30 | 9.33 | 8.06 | 6.00 | 8.06 | 7.91 | 8.24 | 6.94 | 6.84 |
| 2657808 | 4.89 | 11.06 | 11.31 | 6.17 | 7.33 | 6.42 | 6.71 | 6.86 | 5.62 | 6.62 | 6.32 | 5.37 |
| 2584018 | 8.17 | 8.92 | 10.50 | 10.74 | 6.69 | 6.96 | 7.18 | 8.80 | 6.77 | 7.48 | 7.08 | 6.71 |
| 3976341 | 9.92 | 12.17 | 11.86 | 10.89 | 8.79 | 9.39 | 10.43 | 10.68 | 9.00 | 9.29 | 10.50 | 8.28 |
| 2739308 | 5.89 | 5.05 | 5.14 | 4.71 | 4.54 | 4.53 | 5.77 | 5.93 | 5.19 | 4.68 | 6.16 | 8.12 |
| 3959862 | 5.46 | 4.34 | 4.57 | 7.66 | 6.38 | 4.50 | 4.21 | 5.90 | 7.05 | 4.68 | 5.47 | 4.10 |
| 2362351 | 8.67 | 6.97 | 6.01 | 8.26 | 8.46 | 7.72 | 6.51 | 7.72 | 8.72 | 8.03 | 8.22 | 6.59 |
| 3648391 | 6.86 | 4.64 | 4.09 | 5.54 | 9.40 | 3.92 | 4.84 | 5.89 | 4.93 | 8.02 | 5.76 | 4.01 |
| 3009299 | 10.59 | 10.44 | 10.67 | 10.81 | 11.29 | 10.77 | 11.11 | 10.71 | 10.99 | 10.89 | 10.49 | 10.86 |
| 3443464 | 7.04 | 5.54 | 4.88 | 6.51 | 5.30 | 6.13 | 5.26 | 5.81 | 6.00 | 5.81 | 6.03 | 5.30 |
| 2730746 | 7.01 | 5.43 | 4.74 | 6.00 | 5.64 | 6.81 | 8.14 | 6.81 | 8.19 | 7.46 | 6.35 | 9.28 |
| 2427619 | 10.26 | 7.54 | 5.75 | 8.85 | 9.46 | 8.44 | 7.60 | 8.89 | 8.62 | 8.77 | 9.20 | 6.19 |
| 3042001 | 8.67 | 8.49 | 8.56 | 8.49 | 8.90 | 8.46 | 8.70 | 8.89 | 9.32 | 8.99 | 7.68 | 8.62 |
| 2566848 | 5.90 | 5.34 | 4.83 | 5.42 | 8.01 | 5.30 | 5.11 | 5.97 | 6.50 | 6.06 | 4.85 |  |
| 2984616 | 8.83 | 8.93 | 8.74 | 9.21 | 9.09 | 8.99 | 9.04 | 9.03 | 9.33 | 9.51 | 8.86 | 8.99 |
| 2378068 | 7.45 | 10.64 | 10.18 | 9.11 | 9.45 | 6.37 | 7.37 | 9.81 | 10.07 | 9.00 | 9.21 | 9.02 |
| 2721959 | 7.26 | 11.71 | 12.91 | 8.55 | 7.62 | 5.79 | 5.96 | 8.45 | 7.48 | 10.92 | 6.10 | 6.58 |
| 2877508 | 10.05 | 10.33 | 10.44 | 10.48 | 10.93 | 10.19 | 10.38 | 10.44 | 11.01 | 10.86 | 9.66 | 10.88 |
| 3450861 | 7.67 | 5.36 | 4.86 | 6.67 | 6.88 | 6.43 | 5.16 | 6.82 | 5.89 | 6.73 | 6.24 | 4.54 |
| 2688717 | 10.21 | 8.70 | 6.01 | 8.71 | 10.41 | 7.83 | 7.80 | 9.81 | 8.33 | 9.83 | 8.85 | 5.63 |
| 3270270 | 9.40 | 8.42 | 9.25 | 8.69 | 8.30 | 8.86 | 8.61 | 9.77 | 8.62 | 7.88 | 9.52 | 6.47 |
| 3417703 | 8.68 | 6.98 | 7.84 | 5.90 | 5.34 | 7.26 | 8.46 | 7.18 | 4.49 | 5.86 | 4.97 | 10.29 |
| 3302990 | 7.22 | 7.44 | 7.89 | 7.46 | 8.37 | 6.98 | 7.76 | 7.33 | 8.92 | 8.52 | 6.66 | 8.17 |
| 2377283 | 5.27 | 5.23 | 3.79 | 4.57 | 11.57 | 4.59 | 4.55 | 5.55 | 5.06 | 10.34 | 5.37 | 4.22 |
| 3122678 | 4.67 | 4.19 | 4.37 | 4.66 | 4.72 | 8.17 | 4.13 | 4.68 | 6.01 | 4.58 | 5.06 | 4.65 |
| 2688499 | 7.05 | 10.21 | 9.33 | 8.47 | 9.24 | 7.88 | 8.30 | 8.13 | 8.64 | 9.85 | 7.35 | 9.68 |
| 2377094 | 8.14 | 8.03 | 9.19 | 8.47 | 8.40 | 8.58 | 8.72 | 8.62 | 10.07 | 9.82 | 8.09 | 9.34 |
| 3278198 | 7.25 | 7.63 | 8.59 | 8.30 | 7.44 | 7.90 | 8.12 | 7.28 | 8.97 | 8.37 | 6.16 | 8.28 |
| 2598261 | 8.04 | 12.13 | 13.26 | 11.98 | 8.72 | 8.06 | 7.30 | 10.77 | 8.94 | 11.05 | 10.00 | 10.57 |
| 3982612 | 9.85 | 8.08 | 5.58 | 9.56 | 10.23 | 9.18 | 7.84 | 8.91 | 9.57 | 10.25 | 8.96 | 6.44 |
| 2884845 | 4.66 | 9.68 | 10.34 | 4.50 | 4.42 | 4.76 | 5.36 | 4.49 | 5.30 | 4.56 | 4.76 | 4.21 |

TABLE 43-continued

Normalized intensity of microarray data for a set of samples.

| TCID | V01 0217 | V01 0218 | V01 0219 | V01 0220 | V01 0221 | V01 0222 | V01 0223 | V01 0224 | V01 0225 | V01 0226 | V01 0227 | V01 0228 |
|---|---|---|---|---|---|---|---|---|---|---|---|---|
| 3982560 | 8.15 | 6.37 | 5.34 | 7.05 | 8.58 | 7.28 | 5.67 | 7.54 | 7.20 | 7.44 | 7.88 | 4.78 |
| 3204285 | 5.72 | 5.41 | 7.31 | 7.35 | 8.07 | 5.53 | 4.91 | 6.04 | 5.81 | 8.17 | 5.81 | 5.11 |
| 3654699 | 9.61 | 9.31 | 10.82 | 12.34 | 9.88 | 10.89 | 10.02 | 11.38 | 13.03 | 12.51 | 9.33 | 12.04 |
| 2638676 | 8.06 | 6.19 | 5.64 | 7.45 | 10.64 | 6.79 | 6.37 | 8.07 | 7.32 | 9.69 | 8.05 | 5.90 |
| 3367673 | 7.02 | 5.20 | 3.98 | 6.54 | 5.24 | 6.86 | 7.77 | 6.94 | 7.39 | 7.84 | 5.93 | 8.15 |
| 3212008 | 6.48 | 9.42 | 8.71 | 6.59 | 5.71 | 6.78 | 10.20 | 6.76 | 6.32 | 6.23 | 6.83 | 6.81 |
| 3326635 | 10.58 | 10.49 | 10.40 | 10.16 | 9.69 | 10.78 | 10.62 | 10.45 | 9.85 | 9.58 | 10.34 | 9.78 |
| 3031556 | 10.39 | 8.01 | 6.89 | 9.75 | 9.65 | 10.22 | 8.56 | 9.68 | 9.09 | 8.93 | 10.04 | 6.96 |
| 3662201 | 10.14 | 6.57 | 9.47 | 10.08 | 7.92 | 11.11 | 12.69 | 11.89 | 11.41 | 12.28 | 9.82 | 9.77 |
| 2809793 | 9.68 | 7.35 | 6.01 | 9.80 | 10.37 | 9.27 | 7.39 | 8.83 | 8.78 | 9.60 | 8.97 | 6.18 |
| 2817731 | 7.97 | 7.44 | 7.74 | 8.81 | 7.01 | 7.98 | 7.54 | 9.16 | 7.83 | 7.30 | 8.16 | 7.90 |
| 4020655 | 5.17 | 7.59 | 8.12 | 4.82 | 4.80 | 5.07 | 9.38 | 5.28 | 5.48 | 4.64 | 5.91 | 5.70 |
| 3494629 | 4.48 | 7.75 | 8.43 | 6.15 | 4.32 | 10.34 | 4.87 | 4.71 | 4.65 | 4.79 | 4.75 | 6.27 |
| 3852832 | 9.34 | 7.90 | 5.76 | 6.77 | 7.55 | 7.77 | 8.72 | 10.43 | 9.23 | 6.72 | 10.59 | 5.74 |
| 3761959 | 8.80 | 9.14 | 9.46 | 9.18 | 9.04 | 8.96 | 9.97 | 9.35 | 8.79 | 9.16 | 8.42 | 9.77 |
| 2834282 | 5.63 | 8.35 | 7.93 | 6.09 | 5.16 | 5.85 | 8.80 | 5.72 | 7.25 | 6.11 | 6.23 | 7.41 |
| 3341497 | 5.74 | 6.80 | 6.49 | 6.13 | 5.68 | 5.95 | 8.43 | 6.23 | 6.45 | 6.29 | 6.80 | 6.51 |
| 2372812 | 5.14 | 4.36 | 4.49 | 5.00 | 12.39 | 4.38 | 4.39 | 4.77 | 4.98 | 10.68 | 5.15 | 4.62 |
| 2486811 | 10.58 | 8.36 | 7.98 | 11.09 | 10.64 | 9.60 | 8.96 | 10.71 | 10.30 | 10.06 | 9.92 | 8.50 |
| 3768474 | 8.48 | 7.59 | 8.13 | 9.02 | 7.18 | 8.00 | 7.77 | 8.48 | 8.15 | 7.97 | 8.69 | 8.24 |
| 3142381 | 6.11 | 3.87 | 4.48 | 7.71 | 5.42 | 6.07 | 8.43 | 4.60 | 5.09 | 4.57 | 7.94 | 4.31 |
| 2396750 | 6.45 | 7.96 | 8.13 | 6.78 | 7.26 | 6.63 | 7.43 | 6.78 | 7.11 | 7.18 | 6.84 | 7.77 |
| 3902489 | 12.21 | 10.99 | 10.03 | 9.94 | 10.09 | 11.04 | 11.44 | 10.93 | 11.44 | 9.75 | 12.83 | 9.86 |
| 3032647 | 6.88 | 6.08 | 5.04 | 6.06 | 5.78 | 7.62 | 5.77 | 6.25 | 6.08 | 6.44 | 6.49 | 9.93 |
| 3875642 | 6.76 | 5.34 | 4.64 | 5.34 | 5.11 | 5.83 | 5.49 | 6.06 | 5.73 | 5.11 | 6.13 | 4.77 |
| 4027585 | 12.28 | 10.78 | 7.99 | 11.46 | 9.19 | 10.53 | 11.40 | 11.01 | 11.57 | 9.71 | 12.85 | 9.48 |
| 2352609 | 5.85 | 6.83 | 7.19 | 5.71 | 5.37 | 5.99 | 7.69 | 6.52 | 6.46 | 6.22 | 6.03 | 8.26 |
| 3376529 | 8.29 | 9.85 | 9.17 | 8.36 | 7.60 | 8.82 | 9.37 | 8.07 | 9.42 | 9.03 | 8.15 | 9.18 |
| 2491271 | 13.43 | 13.14 | 13.18 | 13.60 | 13.46 | 13.40 | 12.94 | 13.37 | 13.00 | 13.24 | 13.13 | 12.48 |
| 3874751 | 9.08 | 9.53 | 9.65 | 10.58 | 8.61 | 9.73 | 9.19 | 9.51 | 9.18 | 9.37 | 9.17 | 9.90 |
| 2326463 | 12.08 | 10.67 | 9.53 | 11.65 | 12.37 | 11.85 | 11.04 | 12.13 | 11.72 | 11.68 | 11.71 | 9.85 |
| 3341061 | 7.89 | 6.54 | 7.13 | 9.30 | 7.40 | 7.57 | 6.44 | 8.24 | 6.59 | 7.16 | 7.38 | 7.30 |
| 3839910 | 9.49 | 7.64 | 5.53 | 6.27 | 6.57 | 8.55 | 8.87 | 10.13 | 8.57 | 6.32 | 9.82 | 5.74 |
| 2708855 | 5.05 | 8.20 | 9.20 | 4.74 | 3.72 | 5.35 | 6.74 | 4.55 | 4.09 | 4.24 | 4.42 | 5.88 |
| 3512874 | 12.36 | 10.98 | 10.97 | 11.96 | 12.78 | 12.13 | 11.50 | 12.30 | 11.89 | 11.95 | 12.51 | 10.08 |
| 2701071 | 10.37 | 8.96 | 7.77 | 10.00 | 7.92 | 10.30 | 9.68 | 10.95 | 9.87 | 8.02 | 11.05 | 7.06 |
| 3486096 | 6.02 | 5.66 | 7.80 | 5.72 | 5.85 | 5.32 | 8.46 | 6.77 | 7.84 | 6.05 | 8.45 | |
| 2412668 | 8.47 | 8.06 | 7.72 | 9.11 | 8.37 | 8.49 | 8.43 | 8.93 | 7.89 | 8.29 | 8.04 | 8.68 |
| 3329343 | 6.90 | 8.83 | 8.87 | 7.66 | 7.41 | 7.17 | 8.15 | 7.34 | 7.10 | 7.55 | 7.56 | 9.11 |
| 3259367 | 4.52 | 5.15 | 4.00 | 4.36 | 3.93 | 4.20 | 5.63 | 4.30 | 4.18 | 4.12 | 4.98 | 3.87 |
| 3373845 | 9.34 | 8.38 | 11.19 | 10.48 | 9.20 | 9.38 | 8.29 | 10.17 | 8.02 | 9.08 | 9.09 | 9.32 |
| 2321911 | 9.53 | 8.45 | 7.82 | 8.40 | 8.65 | 8.52 | 8.70 | 8.77 | 8.28 | 8.31 | 9.47 | 8.14 |
| 3353914 | 6.41 | 7.24 | 7.79 | 8.51 | 6.51 | 7.03 | 7.16 | 8.19 | 7.01 | 6.86 | 6.62 | 7.53 |
| 3744680 | 8.46 | 6.87 | 6.21 | 8.43 | 7.20 | 7.76 | 7.33 | 8.50 | 7.83 | 7.09 | 8.56 | 6.88 |
| 2373853 | 6.87 | 9.35 | 11.23 | 8.51 | 6.23 | 5.72 | 5.36 | 6.72 | 6.11 | 7.18 | 7.22 | 5.77 |
| 3067478 | 5.49 | 8.76 | 8.52 | 5.28 | 4.91 | 4.90 | 8.13 | 5.30 | 6.29 | 6.95 | 5.28 | 9.08 |
| 3979766 | 9.18 | 7.25 | 6.25 | 8.44 | 8.98 | 8.67 | 7.69 | 9.06 | 8.42 | 7.93 | 9.44 | 6.43 |
| 3246888 | 6.32 | 4.67 | 4.48 | 5.15 | 4.97 | 5.50 | 7.99 | 5.62 | 5.97 | 5.22 | 5.73 | 7.90 |
| 3147985 | 6.28 | 7.24 | 7.55 | 8.40 | 5.34 | 6.61 | 7.33 | 8.41 | 6.65 | 5.91 | 7.07 | 6.87 |
| 3185522 | 9.34 | 9.02 | 9.16 | 11.19 | 8.97 | 10.18 | 9.58 | 10.49 | 9.19 | 9.91 | 9.46 | 9.78 |
| 3861948 | 12.91 | 11.67 | 10.66 | 12.54 | 12.58 | 12.61 | 12.34 | 13.07 | 12.45 | 12.31 | 13.08 | 10.20 |
| 3393479 | 9.02 | 8.30 | 6.80 | 10.05 | 8.09 | 9.07 | 7.93 | 8.73 | 9.45 | 8.74 | 9.03 | 8.68 |
| 3540862 | 6.52 | 6.95 | 7.75 | 6.84 | 7.03 | 6.86 | 7.03 | 7.57 | 7.57 | 7.09 | 6.17 | 7.20 |
| 2777714 | 12.44 | 11.02 | 6.66 | 9.63 | 9.70 | 11.44 | 11.67 | 11.29 | 11.78 | 10.03 | 12.55 | 9.16 |
| 3110395 | 4.90 | 6.47 | 6.63 | 4.13 | 4.36 | 4.20 | 5.36 | 4.15 | 4.47 | 4.34 | 4.58 | 5.29 |
| 3895795 | 8.55 | 8.28 | 7.60 | 7.74 | 6.85 | 8.15 | 8.40 | 9.60 | 8.12 | 6.63 | 9.96 | 8.52 |
| 2854445 | 9.09 | 7.89 | 8.76 | 11.99 | 7.95 | 10.61 | 7.70 | 10.55 | 8.44 | 8.86 | 9.48 | 8.93 |
| 3606034 | 7.57 | 7.46 | 7.12 | 7.65 | 6.42 | 6.82 | 7.45 | 7.40 | 6.84 | 6.99 | 6.75 | 8.19 |
| 3375735 | 8.60 | 8.18 | 7.43 | 8.58 | 7.35 | 9.29 | 7.47 | 8.52 | 8.60 | 7.58 | 8.53 | 7.88 |
| 3948047 | 9.13 | 7.40 | 7.32 | 9.19 | 8.44 | 8.60 | 7.67 | 9.01 | 8.20 | 8.36 | 9.10 | 6.72 |
| 3010503 | 10.64 | 8.07 | 6.37 | 10.76 | 6.55 | 9.54 | 8.98 | 10.26 | 8.95 | 6.95 | 10.23 | 6.70 |
| 3622934 | 6.52 | 8.30 | 8.69 | 5.97 | 8.68 | 5.88 | 8.22 | 6.39 | 6.43 | 7.65 | 5.88 | 7.34 |
| 3441849 | 10.25 | 9.90 | 9.65 | 10.46 | 8.40 | 10.31 | 10.14 | 10.69 | 9.72 | 8.91 | 10.71 | 9.90 |
| 3006572 | 6.50 | 6.65 | 7.42 | 6.34 | 6.40 | 6.89 | 6.68 | 6.42 | 7.06 | 6.31 | 6.62 | 5.96 |
| 3365136 | 8.27 | 9.83 | 8.79 | 8.64 | 8.47 | 7.20 | 10.85 | 8.80 | 9.08 | 8.28 | 7.69 | 8.35 |
| 2642791 | 8.89 | 8.21 | 8.77 | 9.11 | 8.73 | 8.54 | 8.15 | 9.10 | 8.21 | 8.50 | 8.10 | 8.43 |
| 2904485 | 7.90 | 8.22 | 8.48 | 7.05 | 6.44 | 8.44 | 8.31 | 8.10 | 7.17 | 7.60 | 7.15 | 10.04 |
| 3772661 | 10.03 | 9.67 | 9.51 | 11.78 | 8.39 | 10.28 | 9.49 | 10.66 | 9.51 | 9.49 | 10.25 | 9.87 |
| 2796553 | 10.36 | 8.84 | 8.26 | 10.10 | 8.84 | 9.75 | 10.06 | 11.15 | 9.70 | 9.07 | 11.26 | 9.58 |
| 3063795 | 7.32 | 6.71 | 6.63 | 9.85 | 7.29 | 9.29 | 6.84 | 7.48 | 6.91 | 8.45 | 7.31 | 6.97 |
| 3338192 | 7.92 | 10.48 | 10.25 | 8.27 | 7.59 | 9.57 | 10.27 | 8.16 | 8.71 | 8.66 | 7.95 | 9.52 |
| 3214845 | 4.39 | 5.32 | 6.81 | 5.71 | 4.59 | 6.32 | 4.47 | 4.40 | 4.92 | 4.43 | 5.77 | 4.07 |
| 2730303 | 4.46 | 4.02 | 3.90 | 4.16 | 9.70 | 4.08 | 4.12 | 4.40 | 4.28 | 9.11 | 4.60 | 3.94 |
| 3811086 | 8.17 | 7.58 | 7.74 | 8.58 | 7.82 | 8.54 | 7.46 | 7.85 | 7.95 | 7.77 | 7.18 | 8.42 |
| 2981874 | 10.52 | 10.00 | 10.07 | 10.23 | 9.57 | 10.39 | 10.35 | 10.14 | 10.25 | 10.18 | 10.26 | 9.77 |

TABLE 43-continued

Normalized intensity of microarray data for a set of samples.

| TCID | V01 0217 | V01 0218 | V01 0219 | V01 0220 | V01 0221 | V01 0222 | V01 0223 | V01 0224 | V01 0225 | V01 0226 | V01 0227 | V01 0228 |
|---|---|---|---|---|---|---|---|---|---|---|---|---|
| 3242353 | 5.85 | 5.81 | 6.04 | 6.56 | 6.85 | 6.12 | 5.87 | 6.32 | 6.28 | 6.29 | 5.91 | 6.23 |
| 2442008 | 5.17 | 9.56 | 9.28 | 5.35 | 5.25 | 6.29 | 8.80 | 5.14 | 5.36 | 5.34 | 6.00 | 5.32 |
| 3564210 | 10.35 | 8.67 | 8.33 | 10.63 | 7.85 | 9.70 | 9.71 | 10.43 | 9.33 | 7.97 | 10.91 | 8.36 |
| 2490351 | 3.94 | 3.96 | 3.81 | 3.94 | 3.97 | 4.03 | 4.15 | 4.20 | 4.08 | 4.02 | 4.50 | 4.00 |
| 3759006 | 11.49 | 9.93 | 6.07 | 7.41 | 7.33 | 8.78 | 10.75 | 9.17 | 10.73 | 7.47 | 12.19 | 7.03 |
| 3264997 | 4.18 | 3.94 | 3.92 | 4.21 | 3.94 | 3.89 | 3.87 | 4.68 | 3.95 | 4.13 | 4.46 | 3.85 |
| 3912079 | 4.01 | 3.56 | 3.51 | 3.54 | 3.59 | 3.59 | 3.70 | 3.71 | 3.73 | 3.63 | 4.12 | 3.57 |
| 2926802 | 6.28 | 4.69 | 4.46 | 4.94 | 7.20 | 5.78 | 5.20 | 5.64 | 5.51 | 5.54 | 7.16 | 4.44 |
| 2430163 | 3.74 | 3.67 | 7.53 | 3.78 | 3.69 | 3.76 | 3.85 | 4.07 | 3.84 | 3.57 | 4.04 | 3.60 |
| 3039830 | 3.24 | 3.07 | 2.99 | 3.07 | 3.04 | 3.22 | 3.24 | 3.15 | 3.29 | 3.07 | 3.20 | 3.10 |
| 3935486 | 5.81 | 7.68 | 9.71 | 8.76 | 6.62 | 7.05 | 5.95 | 7.80 | 6.81 | 7.16 | 7.20 | 5.85 |
| 3457336 | 5.46 | 4.97 | 4.99 | 5.14 | 5.14 | 5.98 | 5.14 | 5.42 | 5.38 | 5.28 | 5.64 | 5.24 |
| 3811949 | 3.57 | 3.39 | 3.34 | 3.49 | 3.51 | 3.51 | 3.44 | 3.36 | 3.49 | 3.35 | 3.82 | 3.32 |
| 3343832 | 4.11 | 3.79 | 3.54 | 3.93 | 3.74 | 4.44 | 3.81 | 3.68 | 4.05 | 3.84 | 4.10 | 3.86 |
| 3161261 | 6.21 | 5.79 | 5.48 | 5.81 | 5.46 | 8.11 | 5.56 | 5.94 | 5.69 | 5.72 | 5.28 | 5.96 |
| 3594003 | 3.75 | 3.64 | 3.68 | 4.69 | 3.76 | 3.64 | 3.72 | 3.80 | 3.53 | 3.59 | 3.96 | 3.54 |
| 3805614 | 4.70 | 4.31 | 4.46 | 4.81 | 4.47 | 4.60 | 4.57 | 4.60 | 4.79 | 4.78 | 5.36 | 4.51 |
| 3364127 | 6.80 | 6.64 | 6.93 | 7.92 | 6.80 | 7.64 | 6.74 | 6.59 | 7.17 | 6.73 | 7.39 | 6.72 |
| 3834341 | 4.03 | 3.91 | 3.77 | 3.82 | 3.91 | 3.97 | 4.02 | 4.09 | 3.95 | 4.11 | 4.52 | 3.68 |
| 2585400 | 4.66 | 4.43 | 4.41 | 5.55 | 4.19 | 5.01 | 4.09 | 4.41 | 4.26 | 4.89 | 4.31 |
| 2941690 | 4.41 | 3.69 | 3.63 | 4.00 | 4.09 | 4.20 | 4.22 | 4.58 | 4.59 | 4.27 | 4.60 | 4.02 |
| 3484895 | 5.36 | 6.14 | 6.28 | 4.68 | 4.53 | 4.61 | 5.21 | 4.71 | 4.58 | 4.63 | 5.17 | 4.36 |
| 3159754 | 3.85 | 3.68 | 3.60 | 3.68 | 4.06 | 3.70 | 3.59 | 3.70 | 3.65 | 3.68 | 3.97 | 3.51 |
| 2894790 | 3.95 | 3.92 | 3.48 | 3.71 | 3.76 | 3.64 | 3.71 | 4.09 | 4.01 | 3.71 | 4.45 | 3.79 |
| 3363686 | 3.47 | 3.44 | 3.31 | 3.39 | 3.40 | 3.22 | 3.41 | 3.48 | 3.63 | 3.52 | 3.59 | 3.43 |
| 2923928 | 4.56 | 3.99 | 4.12 | 4.32 | 4.63 | 4.33 | 4.00 | 4.26 | 4.18 | 4.20 | 4.55 | 4.10 |
| 2883317 | 5.17 | 4.31 | 4.17 | 5.11 | 4.83 | 4.93 | 4.39 | 5.52 | 5.65 | 4.53 | 4.82 | 4.29 |
| 2479698 | 5.86 | 6.25 | 5.96 | 6.14 | 5.92 | 6.02 | 5.97 | 5.99 | 6.22 | 5.86 | 5.89 | 6.03 |
| 3428225 | 3.56 | 3.75 | 3.41 | 3.61 | 3.88 | 3.66 | 3.60 | 3.59 | 3.76 | 3.92 | 4.21 | 3.52 |
| 3393446 | 7.40 | 6.71 | 6.71 | 7.94 | 7.13 | 6.93 | 6.96 | 7.34 | 6.80 | 7.27 | 7.92 | 6.55 |
| 3116614 | 11.94 | 12.65 | 11.54 | 10.97 | 9.43 | 12.31 | 13.13 | 12.51 | 12.29 | 12.56 | 10.63 | 12.99 |
| 3415320 | 9.32 | 10.30 | 10.79 | 8.22 | 7.79 | 8.90 | 9.02 | 8.77 | 10.56 | 9.77 | 7.38 | 10.62 |
| 3757108 | 7.49 | 9.69 | 11.20 | 8.37 | 6.99 | 7.78 | 8.57 | 7.94 | 8.34 | 7.94 | 8.08 | 7.94 |
| 4012178 | 6.35 | 11.17 | 11.51 | 6.48 | 6.66 | 6.23 | 11.41 | 7.42 | 6.65 | 6.31 | 7.23 | 10.52 |
| 3546213 | 9.29 | 10.61 | 10.92 | 8.19 | 7.35 | 8.89 | 11.38 | 9.46 | 10.25 | 9.77 | 6.68 | 11.19 |
| 3561381 | 8.09 | 10.21 | 10.05 | 7.04 | 6.32 | 7.63 | 10.79 | 8.44 | 9.54 | 8.96 | 6.88 | 10.32 |

TABLE 44

Normalized intensity of microarray data for a set of samples.

| TCID | V01 0229 | V01 0230 | V01 0231 | V01 0232 | V01 0233 | V01 0234 | V01 0235 | V01 0236 | V01 0237 | V01 0238 | V01 0239 | V01 0240 |
|---|---|---|---|---|---|---|---|---|---|---|---|---|
| 2604998 | 7.50 | 5.40 | 8.25 | 7.74 | 8.17 | 6.42 | 8.54 | 7.18 | 8.33 | 8.85 | 7.37 | 8.66 |
| 3603932 | 9.00 | 7.23 | 6.72 | 6.87 | 7.08 | 6.92 | 6.79 | 7.57 | 6.93 | 6.74 | 7.31 | 7.12 |
| 2710599 | 7.98 | 7.68 | 11.80 | 5.44 | 10.45 | 10.17 | 8.98 | 8.77 | 6.43 | 7.88 | 10.48 | 12.03 |
| 2440258 | 7.26 | 9.34 | 6.79 | 8.47 | 7.15 | 9.20 | 8.26 | 9.59 | 7.93 | 7.45 | 7.68 | 4.56 |
| 3169331 | 7.11 | 8.02 | 6.70 | 6.60 | 6.63 | 6.51 | 7.02 | 7.68 | 6.74 | 7.09 | 6.83 | 6.53 |
| 2988882 | 9.82 | 10.03 | 9.59 | 9.69 | 9.45 | 9.46 | 9.67 | 10.11 | 9.63 | 9.98 | 9.77 | 9.39 |
| 2964231 | 10.55 | 9.73 | 8.92 | 8.00 | 8.94 | 8.49 | 7.78 | 9.87 | 8.45 | 8.21 | 9.59 | 7.35 |
| 3111561 | 9.73 | 6.03 | 7.83 | 8.49 | 4.81 | 7.39 | 9.19 | 7.90 | 9.49 | 10.14 | 8.90 | 4.85 |
| 2562529 | 9.73 | 9.29 | 9.97 | 9.03 | 10.68 | 8.98 | 9.72 | 8.95 | 8.70 | 9.87 | 9.33 | 11.13 |
| 3692999 | 9.63 | 7.29 | 7.66 | 11.04 | 6.40 | 11.51 | 8.98 | 12.89 | 12.03 | 11.92 | 12.02 | 8.51 |
| 2439554 | 7.10 | 8.59 | 6.41 | 7.00 | 5.71 | 7.04 | 8.46 | 7.06 | 6.52 | 6.84 | 5.22 |
| 2685304 | 8.77 | 7.86 | 10.70 | 7.63 | 11.05 | 8.26 | 6.83 | 6.68 | 7.65 | 6.50 | 8.55 | 11.54 |
| 2578790 | 6.06 | 4.75 | 5.36 | 6.17 | 4.26 | 4.96 | 6.19 | 7.12 | 6.99 | 7.06 | 7.30 | 4.54 |
| 2373842 | 10.51 | 11.80 | 10.52 | 11.75 | 10.41 | 11.97 | 11.17 | 11.78 | 11.58 | 10.59 | 11.39 | 8.21 |
| 2750627 | 8.97 | 4.75 | 9.28 | 8.58 | 10.60 | 7.33 | 8.38 | 8.01 | 9.29 | 11.00 | 7.77 | 11.06 |
| 3397774 | 5.12 | 5.17 | 4.40 | 5.05 | 4.88 | 4.87 | 5.31 | 4.55 | 5.41 | 5.48 | 4.59 | 4.38 |
| 2635741 | 6.43 | 9.06 | 7.38 | 9.22 | 7.74 | 9.43 | 8.12 | 9.37 | 7.85 | 7.85 | 7.82 | 5.31 |
| 3970833 | 9.67 | 9.97 | 9.47 | 9.23 | 9.64 | 8.89 | 9.44 | 9.80 | 8.79 | 9.70 | 10.05 | 9.57 |
| 3577612 | 9.54 | 10.91 | 11.28 | 11.17 | 11.19 | 10.93 | 10.83 | 10.94 | 11.27 | 9.87 | 10.87 | 11.75 |
| 2708922 | 7.51 | 8.51 | 7.90 | 9.31 | 8.50 | 10.10 | 7.09 | 8.48 | 9.06 | 8.25 | 7.63 | 8.41 |
| 2970897 | 4.86 | 5.89 | 5.67 | 5.65 | 5.11 | 5.75 | 5.05 | 7.48 | 5.31 | 4.81 | 6.92 | 5.87 |
| 3724545 | 8.74 | 9.40 | 10.10 | 9.77 | 9.62 | 10.29 | 10.14 | 9.56 | 10.23 | 8.31 | 9.79 | 10.15 |
| 2798538 | 9.14 | 9.42 | 8.98 | 8.46 | 8.93 | 9.21 | 9.35 | 9.45 | 8.34 | 8.19 | 9.58 | 8.31 |
| 2806468 | 9.49 | 10.92 | 10.42 | 11.80 | 10.46 | 11.85 | 10.30 | 12.00 | 10.86 | 10.25 | 11.01 | 6.70 |
| 2880051 | 5.61 | 6.87 | 6.09 | 6.60 | 6.13 | 6.72 | 6.67 | 6.98 | 6.17 | 6.45 | 6.12 | 6.10 |
| 2732508 | 3.31 | 8.60 | 4.53 | 3.70 | 3.64 | 3.56 | 8.17 | 3.73 | 3.78 | 5.40 | 3.41 | 3.44 |
| 2822492 | 5.62 | 6.43 | 5.41 | 5.31 | 5.53 | 5.62 | 5.53 | 5.49 | 5.24 | 6.08 | 5.33 | 5.01 |
| 3404030 | 6.67 | 9.14 | 6.20 | 9.03 | 7.88 | 9.83 | 8.18 | 9.89 | 8.42 | 7.49 | 7.61 | 5.49 |

TABLE 44-continued

Normalized intensity of microarray data for a set of samples.

| TCID | V01 0229 | V01 0230 | V01 0231 | V01 0232 | V01 0233 | V01 0234 | V01 0235 | V01 0236 | V01 0237 | V01 0238 | V01 0239 | V01 0240 |
|---|---|---|---|---|---|---|---|---|---|---|---|---|
| 3059667 | 10.07 | 4.92 | 7.76 | 8.50 | 4.73 | 9.31 | 9.79 | 5.54 | 10.33 | 11.93 | 7.22 | 5.65 |
| 3108526 | 8.82 | 8.06 | 8.56 | 9.77 | 8.21 | 8.47 | 10.21 | 9.71 | 9.13 | 9.72 | 9.54 | 8.98 |
| 2526806 | 10.34 | 11.99 | 12.97 | 6.83 | 12.42 | 6.85 | 12.56 | 8.77 | 9.12 | 9.41 | 10.86 | 12.79 |
| 2428501 | 8.45 | 8.43 | 7.99 | 6.64 | 6.37 | 7.86 | 6.94 | 7.44 | 6.45 | 5.49 | 7.39 | 6.48 |
| 2657808 | 7.03 | 5.24 | 9.54 | 5.47 | 7.41 | 5.94 | 6.40 | 6.21 | 6.45 | 8.48 | 6.06 | 11.07 |
| 2584018 | 10.67 | 7.48 | 10.34 | 7.64 | 10.28 | 7.41 | 6.56 | 8.07 | 7.44 | 5.92 | 9.73 | 10.39 |
| 3976341 | 10.67 | 10.04 | 11.26 | 10.06 | 11.96 | 9.91 | 9.31 | 9.75 | 9.96 | 8.29 | 9.60 | 11.90 |
| 2739308 | 4.61 | 5.87 | 4.42 | 5.13 | 4.68 | 6.37 | 4.72 | 5.12 | 5.88 | 4.58 | 5.27 | 4.61 |
| 3959862 | 7.10 | 6.76 | 4.41 | 5.79 | 4.77 | 7.17 | 4.21 | 4.49 | 4.83 | 4.47 | 4.22 | 4.24 |
| 2362351 | 6.15 | 8.56 | 6.70 | 8.09 | 7.08 | 8.10 | 7.70 | 8.35 | 7.74 | 6.76 | 7.07 | 5.71 |
| 3648391 | 3.89 | 8.09 | 3.95 | 5.05 | 4.05 | 6.30 | 6.35 | 5.68 | 4.47 | 5.87 | 5.48 | 3.88 |
| 3009299 | 10.89 | 11.18 | 10.54 | 10.59 | 10.57 | 10.65 | 10.70 | 10.95 | 10.40 | 10.67 | 10.80 | 10.65 |
| 3443464 | 5.38 | 6.40 | 5.01 | 6.40 | 5.49 | 5.98 | 5.93 | 6.35 | 6.21 | 5.70 | 5.69 | 5.05 |
| 2730746 | 6.99 | 7.14 | 6.47 | 7.50 | 5.17 | 6.56 | 8.49 | 7.90 | 6.92 | 9.72 | 7.90 | 5.26 |
| 2427619 | 6.20 | 9.82 | 7.74 | 9.22 | 7.74 | 9.84 | 8.50 | 10.07 | 7.96 | 7.68 | 7.89 | 4.91 |
| 3042001 | 8.78 | 9.34 | 8.36 | 8.36 | 8.20 | 8.72 | 8.66 | 8.91 | 8.04 | 8.50 | 8.99 | 8.23 |
| 2566848 | 5.06 | 5.65 | 5.24 | 5.78 | 5.00 | 5.84 | 5.48 | 5.74 | 5.93 | 5.58 | 5.26 | 4.93 |
| 2984616 | 9.36 | 9.60 | 8.97 | 8.69 | 9.10 | 8.70 | 8.92 | 9.43 | 8.59 | 8.69 | 9.25 | 8.46 |
| 2378068 | 9.86 | 8.78 | 8.50 | 7.85 | 10.69 | 7.17 | 8.23 | 7.33 | 7.05 | 7.61 | 7.61 | 8.78 |
| 2721959 | 6.83 | 6.68 | 11.99 | 5.99 | 12.41 | 5.73 | 8.18 | 7.11 | 7.93 | 6.97 | 10.51 | 12.52 |
| 2877508 | 10.77 | 10.70 | 10.14 | 9.87 | 10.50 | 9.97 | 10.27 | 10.55 | 9.67 | 10.04 | 10.54 | 10.35 |
| 3450861 | 4.79 | 7.28 | 5.59 | 7.33 | 5.65 | 7.06 | 6.29 | 7.14 | 5.72 | 6.03 | 5.41 | 4.54 |
| 2688717 | 6.11 | 9.62 | 8.36 | 9.50 | 7.79 | 9.57 | 9.25 | 9.91 | 8.67 | 8.96 | 8.02 | 4.90 |
| 3270270 | 8.71 | 9.42 | 8.79 | 9.06 | 8.69 | 9.37 | 8.16 | 9.03 | 9.12 | 7.35 | 8.53 | 8.95 |
| 3417703 | 8.68 | 5.09 | 6.74 | 8.58 | 8.56 | 7.65 | 9.31 | 5.13 | 8.86 | 10.24 | 6.21 | 7.89 |
| 3302990 | 8.12 | 8.30 | 7.25 | 6.74 | 7.31 | 6.80 | 7.17 | 8.49 | 6.84 | 6.97 | 8.31 | 7.87 |
| 2377283 | 4.23 | 6.72 | 4.90 | 5.28 | 4.23 | 5.28 | 7.33 | 5.09 | 4.44 | 6.34 | 4.14 | 3.98 |
| 3122678 | 5.89 | 6.47 | 4.49 | 5.16 | 4.68 | 5.34 | 4.32 | 4.86 | 5.06 | 5.03 | 5.34 | 4.35 |
| 2688499 | 9.02 | 8.65 | 9.48 | 8.64 | 10.10 | 8.35 | 9.61 | 8.70 | 8.87 | 10.37 | 8.79 | 11.12 |
| 2377094 | 8.51 | 9.11 | 8.23 | 8.81 | 8.73 | 7.63 | 8.83 | 10.19 | 9.35 | 9.57 | 9.93 | 8.00 |
| 3278198 | 9.29 | 8.01 | 8.17 | 6.63 | 8.15 | 6.87 | 8.22 | 8.40 | 7.63 | 7.40 | 8.38 | 8.00 |
| 2598261 | 9.48 | 11.32 | 12.99 | 6.66 | 12.20 | 7.16 | 11.84 | 8.41 | 8.61 | 8.68 | 9.90 | 12.90 |
| 3982612 | 4.79 | 9.76 | 7.75 | 9.54 | 7.62 | 9.69 | 9.57 | 9.56 | 7.62 | 8.23 | 8.00 | 4.66 |
| 2884845 | 4.62 | 4.50 | 8.66 | 4.77 | 10.78 | 4.51 | 4.30 | 4.51 | 4.94 | 4.66 | 5.51 | 10.59 |
| 3982560 | 4.81 | 8.08 | 6.09 | 7.65 | 6.28 | 8.12 | 7.39 | 7.99 | 8.05 | 6.29 | 6.36 | 4.18 |
| 3204285 | 5.47 | 6.14 | 7.22 | 5.50 | 5.86 | 5.31 | 6.68 | 5.27 | 6.01 | 6.54 | 5.17 | 5.52 |
| 3654699 | 12.65 | 11.85 | 11.00 | 11.08 | 9.82 | 9.65 | 11.71 | 12.82 | 10.57 | 10.77 | 12.73 | 9.24 |
| 2638676 | 7.74 | 8.97 | 7.32 | 7.50 | 6.17 | 7.71 | 7.96 | 6.80 | 7.39 | 7.83 | 7.11 | 5.90 |
| 3367673 | 7.73 | 5.88 | 6.44 | 8.22 | 4.68 | 7.13 | 8.85 | 7.01 | 8.41 | 9.45 | 7.94 | 5.44 |
| 3212008 | 7.11 | 6.51 | 6.93 | 6.64 | 9.01 | 6.89 | 6.59 | 5.97 | 6.87 | 6.92 | 6.62 | 8.60 |
| 3326635 | 10.62 | 10.24 | 10.36 | 10.18 | 10.28 | 10.35 | 10.00 | 10.29 | 9.98 | 10.63 | 10.23 | 10.09 |
| 3031556 | 9.15 | 10.01 | 8.49 | 9.89 | 8.67 | 10.24 | 8.67 | 10.23 | 9.15 | 8.19 | 9.08 | 6.23 |
| 3662201 | 9.44 | 8.25 | 8.19 | 11.86 | 7.68 | 11.72 | 9.20 | 12.70 | 11.89 | 11.80 | 12.02 | 8.54 |
| 2809793 | 5.44 | 9.77 | 7.22 | 9.23 | 8.26 | 10.13 | 8.89 | 9.44 | 8.48 | 8.51 | 7.62 | 4.17 |
| 2817731 | 9.62 | 8.84 | 8.21 | 7.67 | 7.38 | 8.09 | 7.71 | 8.08 | 7.32 | 7.64 | 8.68 | 7.78 |
| 4020655 | 4.63 | 5.10 | 5.08 | 5.33 | 8.38 | 5.20 | 4.84 | 5.11 | 4.99 | 5.77 | 4.85 | 7.61 |
| 3494629 | 4.44 | 5.09 | 8.06 | 4.53 | 6.83 | 8.93 | 4.93 | 6.21 | 4.79 | 4.58 | 8.84 | 10.09 |
| 3852832 | 6.63 | 9.41 | 8.25 | 10.22 | 8.51 | 10.01 | 7.39 | 9.59 | 10.33 | 7.37 | 9.43 | 6.41 |
| 3761959 | 9.87 | 9.36 | 8.88 | 8.74 | 9.03 | 8.68 | 9.47 | 8.99 | 8.69 | 9.06 | 9.84 | 9.34 |
| 2834282 | 7.17 | 5.41 | 7.53 | 6.23 | 8.34 | 5.65 | 7.01 | 5.89 | 7.03 | 6.93 | 5.74 | 8.07 |
| 3341497 | 6.22 | 5.64 | 5.83 | 6.49 | 8.44 | 6.04 | 5.61 | 7.03 | 6.43 | 6.23 | 6.76 | 6.90 |
| 2372812 | 4.57 | 6.65 | 4.73 | 4.97 | 4.71 | 4.41 | 6.03 | 4.57 | 4.67 | 5.30 | 4.45 | 4.56 |
| 2486811 | 10.88 | 11.04 | 9.61 | 10.43 | 8.47 | 10.63 | 9.79 | 9.97 | 10.30 | 8.13 | 10.03 | 6.82 |
| 3768474 | 9.14 | 8.59 | 8.34 | 8.48 | 7.72 | 8.33 | 7.87 | 8.56 | 8.19 | 7.64 | 8.66 | 7.91 |
| 3142381 | 6.81 | 3.76 | 6.77 | 4.41 | 4.36 | 5.66 | 4.67 | 5.29 | 3.94 | 6.06 | 7.41 | 4.22 |
| 2396750 | 6.94 | 7.03 | 7.66 | 7.03 | 8.13 | 7.32 | 6.79 | 7.15 | 7.15 | 6.81 | 6.92 | 8.96 |
| 3902489 | 10.10 | 11.61 | 10.39 | 12.12 | 10.44 | 12.34 | 9.85 | 11.73 | 11.71 | 10.48 | 10.77 | 10.17 |
| 3032647 | 6.89 | 5.52 | 6.40 | 8.14 | 5.72 | 7.15 | 9.07 | 6.25 | 6.68 | 6.29 | 6.93 | 5.72 |
| 3875642 | 5.05 | 5.88 | 5.15 | 5.66 | 5.54 | 6.32 | 5.43 | 6.16 | 5.75 | 5.38 | 5.74 | 5.12 |
| 4027585 | 11.31 | 11.33 | 9.77 | 11.98 | 10.06 | 11.64 | 9.97 | 11.32 | 11.66 | 9.63 | 10.96 | 8.22 |
| 2352609 | 6.58 | 6.26 | 6.34 | 6.39 | 6.70 | 6.25 | 7.36 | 6.74 | 6.52 | 6.56 | 7.12 | 6.98 |
| 3376529 | 7.13 | 8.61 | 9.75 | 7.59 | 9.40 | 9.55 | 8.15 | 8.05 | 7.41 | 8.59 | 8.69 | 8.33 | 9.73 |
| 2491271 | 13.60 | 13.63 | 13.45 | 13.24 | 13.21 | 13.36 | 13.43 | 13.36 | 13.21 | 12.94 | 13.25 | 13.30 |
| 3874751 | 10.53 | 9.65 | 9.24 | 9.12 | 10.05 | 9.18 | 9.39 | 9.33 | 9.06 | 9.08 | 9.34 | 9.75 |
| 2326463 | 11.89 | 12.24 | 11.60 | 11.96 | 10.88 | 12.26 | 11.43 | 12.26 | 11.91 | 11.00 | 12.08 | 9.21 |
| 3341061 | 9.07 | 8.33 | 8.44 | 7.08 | 6.87 | 6.78 | 7.76 | 7.20 | 6.44 | 6.88 | 8.34 | 7.37 |
| 3839910 | 6.50 | 9.07 | 6.41 | 9.61 | 7.82 | 9.70 | 7.42 | 9.40 | 9.64 | 7.12 | 9.47 | 5.82 |
| 2708855 | 3.90 | 4.96 | 8.59 | 4.58 | 8.54 | 5.17 | 4.05 | 4.55 | 4.26 | 5.20 | 4.66 | 9.29 |
| 3512874 | 11.78 | 12.20 | 11.46 | 12.21 | 10.98 | 12.29 | 11.61 | 12.23 | 12.18 | 10.86 | 11.98 | 9.54 |
| 2701071 | 8.52 | 10.49 | 8.48 | 10.35 | 9.51 | 11.07 | 9.42 | 10.47 | 11.07 | 8.82 | 10.82 | 7.41 |
| 3486096 | 6.77 | 7.42 | 5.98 | 6.76 | 6.92 | 6.26 | 7.50 | 7.99 | 7.22 | 9.85 | 7.32 | 6.37 |
| 2412668 | 9.19 | 8.65 | 8.36 | 7.94 | 7.82 | 8.31 | 8.18 | 8.12 | 8.35 | 8.36 | 8.25 | 8.30 |
| 3329343 | 6.99 | 8.24 | 9.43 | 7.05 | 8.41 | 6.87 | 8.31 | 6.64 | 7.72 | 7.96 | 6.62 | 9.50 |
| 3259367 | 4.14 | 4.07 | 4.03 | 4.10 | 5.55 | 4.31 | 4.31 | 5.53 | 4.61 | 4.88 | 5.10 | 5.04 |
| 3373845 | 10.70 | 9.94 | 10.90 | 8.47 | 8.44 | 8.26 | 9.16 | 8.80 | 8.90 | 8.47 | 9.42 | 9.60 |

TABLE 44-continued

Normalized intensity of microarray data for a set of samples.

| TCID | V01 0229 | V01 0230 | V01 0231 | V01 0232 | V01 0233 | V01 0234 | V01 0235 | V01 0236 | V01 0237 | V01 0238 | V01 0239 | V01 0240 |
|---|---|---|---|---|---|---|---|---|---|---|---|---|
| 2321911 | 8.72 | 9.28 | 7.92 | 8.70 | 8.42 | 9.55 | 8.19 | 8.92 | 8.78 | 7.65 | 8.16 | 7.81 |
| 3353914 | 9.68 | 7.43 | 7.96 | 6.60 | 7.17 | 6.32 | 6.87 | 6.94 | 6.38 | 6.61 | 8.01 | 7.78 |
| 3744680 | 8.66 | 8.20 | 7.27 | 8.30 | 7.11 | 8.18 | 7.43 | 8.03 | 8.30 | 6.89 | 7.79 | 6.52 |
| 2373336 | 7.39 | 6.83 | 9.96 | 6.42 | 5.52 | 6.07 | 6.26 | 6.26 | 6.76 | 6.70 | 7.10 | 10.18 |
| 3067478 | 4.35 | 6.77 | 7.03 | 5.29 | 8.81 | 5.45 | 6.79 | 6.99 | 6.10 | 7.24 | 6.35 | 8.45 |
| 3976766 | 7.99 | 8.73 | 7.61 | 8.96 | 7.58 | 8.90 | 7.76 | 8.57 | 8.96 | 7.22 | 8.25 | 6.11 |
| 3246888 | 6.44 | 5.50 | 5.02 | 6.17 | 7.33 | 6.55 | 7.08 | 5.52 | 6.19 | 7.50 | 5.62 | 5.75 |
| 3147985 | 9.33 | 7.20 | 7.63 | 6.17 | 7.40 | 6.93 | 6.61 | 6.70 | 6.54 | 6.93 | 6.89 | 7.87 |
| 3185522 | 11.18 | 10.76 | 10.68 | 9.37 | 8.87 | 9.76 | 10.09 | 9.36 | 9.40 | 8.83 | 10.19 | 9.60 |
| 3861948 | 12.28 | 12.80 | 11.99 | 12.93 | 11.90 | 13.01 | 12.14 | 12.79 | 12.98 | 11.80 | 12.57 | 9.86 |
| 3393479 | 10.07 | 8.83 | 9.11 | 9.99 | 7.38 | 8.11 | 8.90 | 8.65 | 8.89 | 8.70 | 9.82 | 8.09 |
| 3540862 | 6.92 | 6.84 | 6.23 | 6.31 | 7.69 | 6.22 | 6.56 | 6.99 | 7.11 | 6.97 | 6.86 | 7.05 |
| 2777714 | 8.80 | 11.61 | 9.87 | 12.18 | 10.90 | 12.47 | 9.97 | 11.91 | 11.96 | 10.99 | 10.93 | 8.38 |
| 3110395 | 4.35 | 4.29 | 4.99 | 4.41 | 5.91 | 4.28 | 5.30 | 4.28 | 5.39 | 4.42 | 4.79 | 6.06 |
| 3895795 | 7.89 | 8.85 | 7.99 | 9.17 | 8.30 | 9.17 | 7.95 | 8.74 | 9.30 | 8.03 | 8.81 | 7.70 |
| 2854445 | 11.70 | 10.21 | 10.33 | 8.69 | 7.44 | 9.41 | 9.58 | 8.88 | 7.86 | 8.04 | 10.42 | 8.41 |
| 3606034 | 8.33 | 7.70 | 7.66 | 7.39 | 7.36 | 7.41 | 7.48 | 7.08 | 7.50 | 7.20 | 7.53 | 7.36 |
| 3375735 | 8.39 | 8.23 | 7.88 | 7.97 | 8.26 | 9.09 | 7.50 | 8.11 | 8.07 | 7.60 | 8.73 | 7.98 |
| 3948047 | 8.93 | 9.03 | 8.34 | 8.73 | 7.53 | 8.87 | 8.48 | 8.77 | 8.51 | 7.65 | 8.09 | 7.07 |
| 3010503 | 11.25 | 9.36 | 6.93 | 9.38 | 8.29 | 10.12 | 7.31 | 9.99 | 9.11 | 7.51 | 10.13 | 5.54 |
| 3622934 | 6.48 | 6.85 | 7.67 | 6.86 | 8.08 | 6.09 | 7.35 | 6.19 | 6.89 | 7.54 | 7.29 | 8.44 |
| 3441849 | 10.19 | 9.92 | 9.73 | 10.39 | 9.60 | 10.47 | 9.37 | 9.99 | 10.14 | 9.21 | 10.01 | 9.82 |
| 3006572 | 6.09 | 6.76 | 6.42 | 6.87 | 6.64 | 7.07 | 6.12 | 6.53 | 6.27 | 6.77 | 6.56 | 7.31 |
| 3365136 | 8.55 | 8.22 | 8.09 | 8.18 | 9.61 | 7.90 | 8.56 | 8.77 | 8.81 | 8.92 | 8.23 | 9.92 |
| 2642791 | 9.03 | 8.84 | 8.73 | 8.23 | 8.13 | 8.34 | 8.70 | 8.71 | 8.26 | 8.42 | 8.74 | 7.68 |
| 2904485 | 8.05 | 6.71 | 7.64 | 8.77 | 7.82 | 8.02 | 8.08 | 7.54 | 8.22 | 8.80 | 7.69 | 7.44 |
| 3772661 | 11.52 | 10.98 | 11.03 | 10.07 | 9.92 | 9.93 | 10.01 | 10.17 | 10.09 | 8.66 | 10.78 | 9.92 |
| 2796553 | 10.32 | 10.55 | 8.92 | 10.54 | 9.84 | 10.69 | 9.28 | 10.24 | 10.74 | 9.05 | 10.67 | 8.23 |
| 3063795 | 8.24 | 9.28 | 8.19 | 7.64 | 6.80 | 7.65 | 8.43 | 7.14 | 7.38 | 7.36 | 7.38 | 7.01 |
| 3338192 | 8.50 | 8.84 | 10.64 | 8.50 | 9.99 | 8.86 | 8.84 | 8.87 | 9.03 | 10.06 | 8.52 | 11.04 |
| 3214845 | 4.59 | 4.75 | 4.34 | 4.94 | 4.96 | 5.39 | 4.35 | 4.62 | 4.55 | 4.58 | 5.16 | 5.68 |
| 2730303 | 4.04 | 5.95 | 3.69 | 4.35 | 4.24 | 4.16 | 6.03 | 4.25 | 4.76 | 5.46 | 4.26 | 4.21 |
| 3811086 | 8.18 | 8.18 | 7.70 | 7.77 | 7.49 | 7.90 | 8.31 | 7.96 | 7.52 | 7.95 | 8.08 | 7.57 |
| 2981874 | 10.52 | 10.57 | 10.06 | 10.32 | 9.95 | 10.42 | 10.43 | 10.50 | 10.42 | 9.66 | 10.37 | 9.77 |
| 3242353 | 7.00 | 6.67 | 6.19 | 5.92 | 5.91 | 6.05 | 5.79 | 6.06 | 6.23 | 5.78 | 5.89 | 6.06 |
| 2442008 | 5.32 | 5.41 | 5.92 | 5.47 | 9.48 | 6.53 | 5.34 | 5.61 | 5.79 | 5.28 | 5.39 | 8.62 |
| 3564210 | 10.13 | 10.20 | 9.49 | 10.42 | 8.89 | 10.39 | 8.77 | 10.04 | 10.43 | 8.23 | 10.16 | 8.44 |
| 2490351 | 4.01 | 4.06 | 3.87 | 4.41 | 4.04 | 4.10 | 4.04 | 4.07 | 4.34 | 4.17 | 4.09 | 4.05 |
| 3759006 | 6.86 | 10.06 | 7.54 | 11.06 | 8.38 | 10.64 | 7.37 | 10.23 | 10.12 | 8.60 | 8.85 | 6.67 |
| 3264997 | 4.14 | 4.05 | 4.38 | 4.27 | 3.98 | 4.06 | 4.14 | 4.02 | 4.40 | 4.18 | 4.01 | 4.13 |
| 3912079 | 3.53 | 4.13 | 3.54 | 3.87 | 3.56 | 3.92 | 3.67 | 3.74 | 4.32 | 3.56 | 3.56 | 3.46 |
| 2926802 | 4.60 | 6.53 | 6.12 | 5.53 | 4.90 | 6.10 | 5.39 | 5.28 | 5.42 | 5.38 | 5.45 | 4.63 |
| 2430163 | 3.93 | 3.89 | 7.18 | 3.83 | 3.69 | 4.01 | 3.97 | 3.81 | 4.05 | 3.80 | 4.76 | 5.19 |
| 3039830 | 3.09 | 3.09 | 3.05 | 3.34 | 3.10 | 3.27 | 3.08 | 3.14 | 3.26 | 3.55 | 3.10 | 3.29 |
| 3935486 | 8.77 | 7.40 | 8.57 | 6.43 | 5.66 | 5.67 | 6.22 | 6.94 | 6.56 | 5.42 | 5.96 | 6.16 |
| 3457336 | 5.32 | 5.28 | 5.03 | 5.81 | 5.18 | 5.54 | 5.25 | 5.33 | 5.83 | 5.26 | 5.46 | 5.28 |
| 3811949 | 3.49 | 3.48 | 3.35 | 3.65 | 3.38 | 3.51 | 3.51 | 3.44 | 3.67 | 3.65 | 3.52 | 3.37 |
| 3343832 | 3.89 | 3.81 | 3.55 | 4.15 | 3.90 | 4.20 | 4.01 | 3.86 | 4.21 | 4.02 | 3.97 | 3.79 |
| 3161261 | 5.69 | 5.90 | 5.30 | 6.24 | 5.62 | 6.88 | 6.29 | 6.03 | 6.05 | 5.91 | 7.15 | 5.12 |
| 3594003 | 3.64 | 3.94 | 3.60 | 3.75 | 3.60 | 3.65 | 3.96 | 3.83 | 3.73 | 3.59 | 3.59 | 3.74 |
| 3805614 | 4.89 | 4.78 | 4.39 | 5.20 | 4.49 | 4.73 | 4.48 | 4.74 | 4.92 | 4.80 | 4.59 | 4.67 |
| 3364127 | 6.60 | 6.82 | 6.15 | 7.24 | 6.70 | 7.02 | 6.90 | 6.91 | 7.05 | 6.95 | 7.24 | 6.81 |
| 3834341 | 4.12 | 4.06 | 3.94 | 4.30 | 3.95 | 3.97 | 3.85 | 3.71 | 4.38 | 4.36 | 4.10 | 4.28 |
| 2585400 | 4.85 | 4.780 | 4.59 | 4.43 | 4.22 | 4.40 | 4.41 | 4.44 | 4.55 | 4.28 | 4.45 | 5.07 |
| 2941690 | 4.27 | 4.20 | 3.98 | 4.50 | 4.13 | 4.76 | 4.13 | 4.04 | 4.16 | 4.36 | 4.05 | 4.36 |
| 3484895 | 4.73 | 5.26 | 4.62 | 4.88 | 5.89 | 6.11 | 4.51 | 4.93 | 5.14 | 4.87 | 4.67 | 6.00 |
| 3159754 | 3.58 | 3.66 | 3.53 | 3.75 | 3.66 | 3.93 | 4.03 | 3.73 | 3.89 | 3.65 | 3.59 | 3.57 |
| 2894790 | 3.79 | 3.70 | 3.57 | 4.64 | 3.63 | 4.42 | 3.79 | 3.72 | 4.37 | 4.01 | 3.89 | 3.71 |
| 3363686 | 3.48 | 3.45 | 3.40 | 3.63 | 3.30 | 10.55 | 3.19 | 3.74 | 3.79 | 4.33 | 3.43 | 3.28 |
| 2923928 | 4.34 | 4.25 | 3.85 | 4.56 | 4.50 | 4.62 | 4.17 | 4.30 | 4.27 | 4.45 | 4.33 | 4.02 |
| 2883317 | 6.57 | 4.92 | 4.71 | 4.88 | 4.76 | 4.78 | 5.20 | 5.11 | 4.95 | 4.98 | 4.23 | 4.58 |
| 2479698 | 5.95 | 5.73 | 5.75 | 6.11 | 6.38 | 5.76 | 6.07 | 6.34 | 6.10 | 6.13 | 6.28 | 5.91 |
| 3428225 | 3.74 | 3.73 | 3.44 | 4.03 | 3.80 | 3.76 | 3.67 | 3.73 | 4.06 | 3.73 | 3.93 | 3.67 |
| 3393446 | 7.89 | 8.29 | 7.06 | 7.53 | 6.68 | 7.31 | 7.24 | 7.35 | 7.46 | 6.91 | 7.42 | 6.63 |
| 3116614 | 11.75 | 10.44 | 11.72 | 12.83 | 12.78 | 12.03 | 13.12 | 13.01 | 12.64 | 12.97 | 12.82 | 12.27 |
| 3415320 | 8.20 | 8.27 | 11.14 | 8.86 | 10.60 | 8.74 | 9.87 | 9.38 | 9.68 | 10.00 | 9.58 | 10.73 |
| 3757108 | 7.72 | 8.29 | 11.69 | 7.71 | 9.71 | 7.33 | 8.19 | 7.39 | 8.35 | 8.84 | 7.93 | 11.14 |
| 4012178 | 6.44 | 6.00 | 7.70 | 6.53 | 11.66 | 6.30 | 6.11 | 8.03 | 6.83 | 7.07 | 6.46 | 9.30 |
| 3546213 | 9.83 | 8.57 | 10.16 | 9.28 | 10.89 | 8.91 | 11.12 | 10.31 | 10.43 | 11.36 | 10.00 | 10.84 |
| 3561381 | 9.25 | 6.63 | 9.34 | 9.03 | 10.36 | 8.00 | 9.23 | 8.61 | 9.24 | 10.85 | 8.57 | 10.19 |

TABLE 45

Normalized intensity of microarray data for a set of samples.

| TCID | V01 0241 | V01 0242 | V01 0243 | V01 0244 | V01 0245 | V01 0246 | V01 0247 | V01 0248 | V01 0249 | V01 0250 | V01 0251 | V01 0252 |
|---|---|---|---|---|---|---|---|---|---|---|---|---|
| 2604998 | 9.30 | 9.38 | 7.45 | 6.50 | 9.06 | 7.52 | 8.39 | 8.18 | 6.64 | 6.83 | 7.78 | 7.50 |
| 3603932 | 7.72 | 6.93 | 7.16 | 7.10 | 7.24 | 7.22 | 8.24 | 8.65 | 6.82 | 7.16 | 7.77 | 6.82 |
| 2710599 | 10.92 | 6.24 | 8.39 | 7.34 | 11.26 | 5.77 | 6.62 | 6.72 | 9.37 | 5.69 | 8.92 | 8.79 |
| 2440258 | 4.67 | 5.98 | 9.46 | 9.27 | 7.92 | 8.07 | 5.31 | 6.50 | 9.06 | 8.93 | 7.76 | 9.06 |
| 3169331 | 7.70 | 8.38 | 7.02 | 6.80 | 6.35 | 8.69 | 9.27 | 10.16 | 6.69 | 6.38 | 7.37 | 7.04 |
| 2988882 | 10.06 | 9.74 | 9.82 | 9.75 | 9.50 | 9.84 | 10.99 | 11.10 | 9.86 | 9.83 | 10.16 | 9.54 |
| 2964231 | 10.34 | 7.47 | 8.68 | 8.83 | 7.28 | 9.92 | 10.43 | 10.99 | 7.86 | 8.31 | 8.81 | 8.42 |
| 3111561 | 7.83 | 9.68 | 9.21 | 6.99 | 7.29 | 8.18 | 8.90 | 8.35 | 9.13 | 8.39 | 6.14 | 8.48 |
| 2562529 | 10.64 | 10.10 | 9.46 | 8.63 | 10.67 | 8.62 | 7.96 | 8.64 | 9.37 | 8.41 | 10.00 | 9.17 |
| 3692999 | 11.00 | 11.37 | 11.69 | 11.29 | 8.42 | 11.86 | 12.76 | 12.24 | 10.76 | 11.44 | 11.92 | 10.40 |
| 2439554 | 5.16 | 5.99 | 9.38 | 8.68 | 6.68 | 6.45 | 4.91 | 5.88 | 7.40 | 7.62 | 6.45 | 7.34 |
| 2685304 | 8.89 | 6.16 | 7.23 | 8.26 | 10.35 | 7.57 | 7.25 | 8.51 | 7.38 | 7.59 | 8.07 | 8.27 |
| 2578790 | 5.60 | 4.55 | 5.57 | 5.82 | 5.47 | 8.53 | 7.34 | 4.52 | 5.86 | 5.05 | 6.76 | 5.21 |
| 2373842 | 8.89 | 10.46 | 11.68 | 11.70 | 11.39 | 11.68 | 9.38 | 10.12 | 11.83 | 11.97 | 11.46 | 11.91 |
| 2750627 | 10.17 | 10.16 | 6.93 | 6.84 | 10.18 | 8.96 | 10.81 | 6.74 | 8.21 | 6.92 | 9.21 | 8.12 |
| 3397774 | 6.00 | 4.80 | 4.93 | 5.64 | 5.20 | 6.55 | 5.78 | 8.90 | 4.93 | 5.34 | 5.10 | 5.10 |
| 2635741 | 6.08 | 7.11 | 9.40 | 9.16 | 8.70 | 8.19 | 5.96 | 6.63 | 9.68 | 8.66 | 7.83 | 9.32 |
| 3970833 | 10.48 | 10.17 | 9.31 | 9.59 | 9.12 | 10.12 | 10.94 | 11.72 | 9.05 | 8.54 | 9.67 | 9.12 |
| 3577612 | 8.46 | 9.47 | 10.47 | 10.60 | 11.19 | 11.04 | 9.04 | 9.12 | 11.15 | 11.28 | 10.91 | 11.07 |
| 2708922 | 7.52 | 8.30 | 8.30 | 8.85 | 8.47 | 7.19 | 5.91 | 6.69 | 8.78 | 9.66 | 8.75 | 9.34 |
| 2970897 | 6.01 | 4.77 | 4.81 | 5.52 | 4.90 | 6.24 | 7.20 | 9.28 | 4.86 | 5.02 | 5.56 | 4.92 |
| 3724545 | 10.22 | 9.49 | 10.26 | 9.93 | 9.94 | 8.98 | 8.85 | 7.42 | 9.49 | 9.75 | 9.97 | 9.85 |
| 2798538 | 8.72 | 8.95 | 9.63 | 9.84 | 8.71 | 9.33 | 9.97 | 11.06 | 9.04 | 8.63 | 8.19 | 9.51 |
| 2806468 | 7.66 | 10.19 | 10.69 | 11.35 | 11.05 | 10.96 | 7.53 | 8.53 | 12.00 | 10.91 | 10.77 | 11.87 |
| 2880051 | 6.16 | 6.54 | 7.20 | 6.29 | 6.21 | 7.11 | 7.50 | 7.42 | 6.50 | 6.94 | 6.45 | 6.93 |
| 2732508 | 3.63 | 3.43 | 3.27 | 7.91 | 3.23 | 3.34 | 3.80 | 3.57 | 3.41 | 3.51 | 3.74 | 3.55 |
| 2822492 | 6.32 | 6.29 | 5.61 | 5.41 | 5.14 | 5.79 | 7.30 | 7.71 | 4.79 | 5.58 | 6.22 | 6.04 |
| 3404030 | 5.90 | 7.15 | 9.64 | 9.02 | 8.53 | 8.44 | 6.11 | 6.36 | 9.32 | 9.57 | 8.20 | 9.35 |
| 3059667 | 6.86 | 10.10 | 5.58 | 5.08 | 8.88 | 5.94 | 8.51 | 4.63 | 9.09 | 8.47 | 7.08 | 7.86 |
| 3108526 | 10.52 | 10.89 | 8.16 | 9.38 | 8.56 | 10.38 | 11.33 | 11.04 | 9.70 | 8.70 | 9.02 | 8.50 |
| 2526806 | 8.57 | 7.51 | 9.84 | 10.11 | 12.35 | 9.71 | 7.88 | 11.15 | 7.48 | 6.90 | 6.98 | 7.18 |
| 2428501 | 6.57 | 6.47 | 7.89 | 7.50 | 6.07 | 7.12 | 6.19 | 9.18 | 6.97 | 6.20 | 5.39 | 6.94 |
| 2657808 | 7.13 | 6.01 | 7.36 | 5.29 | 10.88 | 5.33 | 5.18 | 5.18 | 5.59 | 5.60 | 6.21 | 7.18 |
| 2584018 | 8.41 | 6.32 | 8.65 | 8.13 | 9.86 | 7.03 | 5.16 | 7.56 | 8.52 | 7.37 | 7.67 | 7.97 |
| 3976341 | 9.65 | 8.00 | 8.85 | 9.92 | 11.14 | 9.23 | 8.85 | 8.13 | 9.97 | 10.27 | 10.10 | 10.15 |
| 2739308 | 5.08 | 5.00 | 5.25 | 6.04 | 5.22 | 5.67 | 5.41 | 8.82 | 5.88 | 5.59 | 5.79 | 5.90 |
| 3959862 | 4.13 | 5.33 | 4.54 | 7.71 | 4.69 | 5.75 | 4.77 | 11.55 | 5.43 | 5.65 | 6.02 | 5.69 |
| 2362351 | 5.47 | 6.24 | 9.73 | 7.91 | 7.88 | 7.49 | 6.32 | 6.09 | 8.33 | 8.19 | 7.67 | 8.57 |
| 3648391 | 4.63 | 5.14 | 5.26 | 7.43 | 4.79 | 5.11 | 5.61 | 3.89 | 6.30 | 5.70 | 4.01 | 4.45 |
| 3009299 | 11.25 | 11.33 | 10.85 | 10.95 | 10.45 | 10.64 | 11.53 | 12.35 | 10.67 | 10.67 | 11.14 | 10.78 |
| 3443464 | 5.25 | 5.64 | 6.30 | 5.87 | 6.03 | 5.88 | 5.08 | 5.33 | 5.69 | 6.62 | 5.51 | 6.26 |
| 2730746 | 9.37 | 9.52 | 7.10 | 7.22 | 6.45 | 8.40 | 9.40 | 9.28 | 7.13 | 6.69 | 8.08 | 6.89 |
| 2427619 | 5.63 | 6.88 | 9.32 | 9.52 | 9.20 | 8.43 | 6.11 | 6.14 | 9.56 | 9.12 | 8.33 | 9.78 |
| 3042001 | 8.89 | 8.67 | 8.88 | 9.16 | 7.90 | 9.34 | 9.83 | 10.21 | 8.26 | 7.93 | 9.30 | 8.52 |
| 2566848 | 5.04 | 5.25 | 4.97 | 6.68 | 5.55 | 5.86 | 5.41 | 6.16 | 6.16 | 5.91 | 5.41 | 6.08 |
| 2984616 | 9.66 | 9.37 | 8.86 | 9.11 | 8.55 | 9.63 | 11.11 | 11.59 | 9.44 | 8.87 | 9.58 | 8.52 |
| 2378068 | 7.15 | 5.70 | 8.54 | 8.93 | 10.72 | 6.74 | 7.39 | 10.18 | 7.27 | 8.40 | 8.11 | 7.01 |
| 2721959 | 8.24 | 6.06 | 8.88 | 9.23 | 8.97 | 8.03 | 5.78 | 5.73 | 7.07 | 6.11 | 7.67 | 7.50 |
| 2877508 | 10.84 | 11.67 | 10.45 | 10.57 | 9.89 | 10.47 | 11.39 | 11.74 | 10.09 | 9.51 | 10.38 | 10.04 |
| 3450861 | 5.03 | 5.27 | 6.95 | 6.65 | 6.68 | 6.17 | 4.75 | 4.89 | 7.64 | 6.81 | 5.47 | 6.74 |
| 2688717 | 5.47 | 7.77 | 8.70 | 9.95 | 8.85 | 8.76 | 5.57 | 7.07 | 10.56 | 9.78 | 8.39 | 9.76 |
| 3270270 | 6.48 | 7.60 | 8.97 | 8.72 | 9.10 | 8.70 | 6.30 | 7.18 | 9.04 | 9.93 | 8.83 | 9.29 |
| 3417703 | 7.49 | 8.69 | 5.13 | 5.29 | 7.85 | 4.71 | 5.32 | 4.82 | 8.39 | 7.81 | 7.96 | 6.30 |
| 3302990 | 9.00 | 7.83 | 7.85 | 8.27 | 6.52 | 8.21 | 9.22 | 10.97 | 7.43 | 6.62 | 7.85 | 6.50 |
| 2377283 | 4.38 | 4.30 | 4.34 | 8.64 | 4.83 | 4.92 | 4.36 | 4.75 | 6.09 | 5.04 | 4.58 | 5.50 |
| 3122678 | 4.92 | 4.45 | 4.87 | 5.02 | 4.34 | 4.91 | 4.76 | 11.87 | 5.66 | 4.84 | 5.09 | 4.92 |
| 2688499 | 9.52 | 9.50 | 9.16 | 8.35 | 8.25 | 9.71 | 8.55 | 7.28 | 8.68 | 7.65 | 7.85 | 8.41 |
| 2377094 | 10.38 | 9.58 | 8.12 | 9.44 | 8.19 | 10.63 | 10.87 | 11.88 | 8.12 | 8.32 | 9.40 | 8.64 |
| 3278198 | 9.15 | 8.04 | 7.85 | 8.44 | 6.59 | 8.59 | 9.82 | 10.69 | 7.32 | 6.57 | 8.47 | 6.86 |
| 2598261 | 7.99 | 7.76 | 9.30 | 9.48 | 11.97 | 9.10 | 6.85 | 10.23 | 6.52 | 6.08 | 7.28 | 6.88 |
| 3982612 | 5.34 | 7.42 | 10.11 | 10.13 | 9.17 | 8.68 | 6.69 | 5.08 | 9.98 | 9.32 | 7.98 | 9.93 |
| 2884845 | 5.04 | 5.14 | 5.49 | 4.55 | 9.02 | 5.06 | 6.21 | 4.82 | 4.56 | 5.08 | 7.74 | 4.90 |
| 3982560 | 4.59 | 5.53 | 7.17 | 8.49 | 7.66 | 7.43 | 5.10 | 4.83 | 8.16 | 7.37 | 6.07 | 8.62 |
| 3204285 | 5.86 | 5.66 | 5.92 | 8.93 | 6.13 | 5.77 | 5.56 | 5.83 | 5.28 | 5.66 | 5.75 | 6.01 |
| 3654699 | 11.93 | 11.40 | 11.18 | 12.11 | 9.49 | 12.69 | 13.08 | 13.16 | 10.56 | 9.73 | 11.45 | 9.41 |
| 2638676 | 5.57 | 5.47 | 6.50 | 9.08 | 6.41 | 7.46 | 5.76 | 7.80 | 7.84 | 5.66 | 7.47 | 7.47 |
| 3367673 | 9.06 | 8.47 | 6.54 | 7.43 | 7.11 | 9.04 | 8.19 | 8.84 | 7.65 | 7.02 | 7.95 | 7.06 |
| 3212008 | 8.39 | 7.25 | 6.64 | 6.07 | 8.17 | 6.24 | 5.91 | 6.44 | 7.41 | 6.91 | 9.14 | 8.34 |
| 3326635 | 10.21 | 9.91 | 9.98 | 10.15 | 10.44 | 9.78 | 8.52 | 8.38 | 10.49 | 10.25 | 10.41 | 10.45 |
| 3031556 | 6.11 | 8.07 | 9.94 | 9.93 | 9.48 | 9.73 | 6.95 | 7.36 | 10.06 | 9.87 | 9.33 | 10.29 |
| 3662201 | 10.53 | 8.52 | 12.02 | 11.82 | 8.44 | 12.29 | 12.91 | 11.89 | 10.88 | 11.44 | 11.20 | 9.95 |
| 2809793 | 5.09 | 6.50 | 10.05 | 9.53 | 7.84 | 8.05 | 4.99 | 6.16 | 10.03 | 8.96 | 7.54 | 9.10 |
| 2817731 | 7.70 | 7.41 | 8.00 | 7.57 | 7.70 | 7.84 | 7.77 | 7.72 | 7.57 | 8.15 | 7.43 | 8.02 |
| 4020655 | 8.81 | 5.62 | 5.66 | 5.10 | 8.50 | 5.12 | 5.10 | 4.99 | 5.09 | 5.96 | 8.01 | 7.33 |
| 3494629 | 6.61 | 4.50 | 4.42 | 4.42 | 5.61 | 4.35 | 5.34 | 6.08 | 7.98 | 4.42 | 5.68 | 4.70 |

TABLE 45-continued

Normalized intensity of microarray data for a set of samples.

| TCID | V01 0241 | V01 0242 | V01 0243 | V01 0244 | V01 0245 | V01 0246 | V01 0247 | V01 0248 | V01 0249 | V01 0250 | V01 0251 | V01 0252 |
|---|---|---|---|---|---|---|---|---|---|---|---|---|
| 3852832 | 6.68 | 8.39 | 7.83 | 9.39 | 9.28 | 9.43 | 6.72 | 7.71 | 9.92 | 10.54 | 9.74 | 10.00 |
| 3761959 | 9.65 | 10.17 | 8.78 | 8.65 | 8.29 | 8.76 | 9.91 | 9.67 | 8.71 | 8.03 | 9.48 | 8.51 |
| 2834282 | 8.10 | 5.94 | 6.28 | 5.83 | 8.13 | 5.95 | 5.34 | 6.43 | 5.76 | 6.02 | 8.48 | 7.88 |
| 3341497 | 8.94 | 6.03 | 6.37 | 6.03 | 7.69 | 6.42 | 8.46 | 6.20 | 6.02 | 6.75 | 7.53 | 6.41 |
| 2372812 | 4.69 | 4.89 | 4.70 | 7.08 | 5.16 | 4.56 | 4.52 | 4.69 | 5.12 | 4.93 | 5.02 | 4.92 |
| 2486811 | 6.64 | 8.11 | 10.43 | 9.97 | 9.41 | 9.67 | 6.62 | 7.43 | 10.12 | 10.77 | 9.76 | 10.45 |
| 3768474 | 8.06 | 7.67 | 8.79 | 8.33 | 8.12 | 7.81 | 8.25 | 8.67 | 8.02 | 8.59 | 8.55 | 8.30 |
| 3142381 | 5.81 | 3.58 | 5.31 | 6.58 | 5.43 | 3.72 | 3.66 | 7.22 | 4.73 | 5.72 | 4.82 | 3.94 |
| 2396750 | 7.17 | 7.33 | 6.82 | 7.07 | 7.83 | 6.89 | 6.40 | 8.05 | 6.78 | 6.79 | 7.05 | 6.64 |
| 3902489 | 8.97 | 9.77 | 11.28 | 11.88 | 11.24 | 10.69 | 9.26 | 10.40 | 11.67 | 12.23 | 11.22 | 11.80 |
| 3032647 | 6.40 | 8.09 | 7.50 | 6.66 | 6.19 | 7.18 | 7.36 | 7.82 | 7.24 | 6.43 | 6.08 | 7.31 |
| 3875642 | 4.96 | 4.92 | 5.46 | 5.87 | 5.49 | 5.89 | 5.05 | 5.17 | 6.14 | 6.73 | 5.42 | 6.80 |
| 4027585 | 8.76 | 9.85 | 10.93 | 11.51 | 10.90 | 10.42 | 9.33 | 10.47 | 11.28 | 12.31 | 10.90 | 11.48 |
| 2352609 | 8.32 | 7.84 | 6.83 | 6.00 | 6.77 | 6.87 | 7.60 | 7.17 | 6.64 | 6.49 | 7.31 | 6.89 |
| 3376529 | 9.79 | 7.57 | 9.13 | 8.62 | 8.02 | 9.11 | 9.88 | 10.11 | 7.43 | 7.26 | 8.77 | 8.06 |
| 2491271 | 12.18 | 12.79 | 13.52 | 13.28 | 13.28 | 13.02 | 12.17 | 12.24 | 13.33 | 13.23 | 12.95 | 13.35 |
| 3874751 | 9.41 | 9.74 | 8.95 | 8.85 | 9.33 | 8.93 | 9.52 | 8.96 | 9.03 | 8.83 | 9.49 | 8.82 |
| 2326463 | 8.54 | 10.15 | 12.01 | 12.45 | 11.67 | 11.71 | 9.50 | 9.92 | 12.37 | 12.07 | 11.66 | 12.54 |
| 3341061 | 6.76 | 6.86 | 7.44 | 6.97 | 6.57 | 6.61 | 7.00 | 7.47 | 7.31 | 7.47 | 6.77 | 7.24 |
| 3839910 | 6.29 | 8.57 | 8.51 | 9.26 | 8.85 | 9.77 | 6.36 | 7.42 | 10.08 | 10.33 | 9.59 | 9.12 |
| 2708855 | 6.97 | 4.28 | 4.42 | 4.10 | 7.75 | 3.98 | 4.16 | 5.11 | 4.42 | 4.94 | 6.70 | 5.39 |
| 3512874 | 9.55 | 10.89 | 12.34 | 12.07 | 11.84 | 12.07 | 10.02 | 10.89 | 12.25 | 12.46 | 11.93 | 12.31 |
| 2701071 | 7.60 | 8.66 | 10.03 | 10.54 | 10.15 | 10.64 | 8.14 | 9.21 | 10.52 | 11.29 | 10.87 | 10.66 |
| 3486096 | 9.83 | 7.29 | 6.12 | 7.23 | 6.23 | 8.00 | 9.22 | 6.31 | 6.89 | 6.50 | 8.05 | 6.18 |
| 2412668 | 7.93 | 8.65 | 8.44 | 8.12 | 8.09 | 8.68 | 8.06 | 7.82 | 8.43 | 8.17 | 8.22 | 8.34 |
| 3329343 | 7.87 | 8.09 | 7.59 | 7.34 | 7.99 | 7.06 | 6.72 | 7.73 | 7.41 | 7.84 | 7.29 | 6.99 |
| 3259367 | 8.00 | 4.12 | 4.18 | 4.08 | 5.76 | 4.26 | 3.98 | 3.98 | 4.24 | 4.12 | 5.91 | 4.49 |
| 3373845 | 7.15 | 7.33 | 9.50 | 8.63 | 8.80 | 8.15 | 7.20 | 7.57 | 9.82 | 8.61 | 8.06 | 8.93 |
| 2321911 | 8.00 | 8.37 | 8.66 | 8.90 | 8.95 | 8.29 | 7.47 | 8.12 | 9.01 | 9.22 | 9.14 | 8.91 |
| 3353914 | 6.93 | 6.42 | 7.13 | 6.60 | 6.39 | 6.76 | 6.58 | 7.08 | 6.05 | 6.52 | 6.63 | 6.61 |
| 3744680 | 6.59 | 7.20 | 8.82 | 7.88 | 7.69 | 7.72 | 6.82 | 6.80 | 8.31 | 8.82 | 7.85 | 8.45 |
| 2373336 | 4.73 | 5.32 | 6.03 | 6.62 | 7.21 | 6.00 | 5.21 | 5.12 | 6.40 | 6.12 | 5.27 | 6.48 |
| 3067478 | 8.05 | 7.74 | 5.81 | 5.60 | 7.49 | 6.13 | 7.96 | 6.63 | 5.36 | 6.05 | 6.03 | 5.73 |
| 3976766 | 6.21 | 7.51 | 8.88 | 8.84 | 8.21 | 8.44 | 7.20 | 7.16 | 9.18 | 9.69 | 8.66 | 9.33 |
| 3246888 | 7.71 | 5.94 | 5.63 | 6.00 | 6.75 | 6.01 | 7.36 | 6.44 | 5.77 | 6.09 | 7.02 | 6.76 |
| 3147985 | 7.04 | 6.37 | 6.49 | 6.35 | 7.08 | 6.11 | 7.10 | 6.67 | 6.20 | 6.81 | 6.38 | 6.88 |
| 3185522 | 9.37 | 9.03 | 9.66 | 8.48 | 8.27 | 9.19 | 9.21 | 9.78 | 9.82 | 9.35 | 9.36 | 9.56 |
| 3861948 | 10.25 | 11.56 | 12.75 | 12.86 | 12.48 | 12.72 | 10.93 | 11.53 | 12.99 | 13.18 | 12.79 | 13.01 |
| 3393479 | 7.75 | 8.89 | 8.30 | 8.95 | 8.90 | 9.05 | 8.59 | 9.26 | 9.44 | 9.19 | 8.32 | 8.82 |
| 3540862 | 8.21 | 6.95 | 5.97 | 7.17 | 6.98 | 7.13 | 8.71 | 9.35 | 6.17 | 6.12 | 7.59 | 6.49 |
| 2777714 | 8.97 | 10.24 | 11.14 | 11.98 | 11.68 | 11.34 | 9.82 | 10.66 | 11.87 | 12.26 | 11.50 | 11.84 |
| 3110395 | 6.11 | 4.89 | 4.41 | 4.37 | 4.33 | 4.39 | 6.40 | 4.56 | 4.67 | 5.59 | 4.88 | 4.54 |
| 3895795 | 8.19 | 7.81 | 8.56 | 8.27 | 9.25 | 8.77 | 7.42 | 6.79 | 8.99 | 9.76 | 9.00 | 9.51 |
| 2854445 | 6.70 | 9.22 | 10.33 | 8.56 | 8.70 | 8.90 | 6.72 | 7.24 | 8.51 | 8.60 | 8.01 | 9.17 |
| 3606034 | 7.78 | 7.14 | 7.35 | 6.99 | 7.09 | 7.22 | 7.24 | 7.36 | 6.90 | 7.05 | 7.26 | 6.77 |
| 3375735 | 7.10 | 7.54 | 7.65 | 7.96 | 8.30 | 8.11 | 7.12 | 7.17 | 8.61 | 8.68 | 7.67 | 8.04 |
| 3948047 | 6.96 | 7.63 | 8.76 | 8.84 | 8.48 | 8.00 | 7.22 | 7.45 | 9.09 | 9.13 | 8.67 | 8.95 |
| 3010503 | 6.33 | 7.10 | 9.24 | 9.29 | 9.21 | 8.91 | 6.36 | 8.24 | 9.73 | 10.12 | 8.81 | 9.56 |
| 3622934 | 8.56 | 7.32 | 6.54 | 6.67 | 8.21 | 7.11 | 7.96 | 7.96 | 5.41 | 6.02 | 7.80 | 6.95 |
| 3441849 | 9.32 | 9.75 | 10.05 | 9.72 | 9.96 | 10.28 | 9.03 | 9.23 | 10.35 | 10.65 | 10.28 | 10.52 |
| 3006572 | 6.61 | 6.86 | 6.93 | 6.45 | 7.23 | 6.57 | 6.23 | 7.38 | 6.92 | 6.58 | 6.71 | 6.91 |
| 3365136 | 10.23 | 8.14 | 8.14 | 8.59 | 9.20 | 8.38 | 9.51 | 8.62 | 8.65 | 7.84 | 10.12 | 9.43 |
| 2642791 | 8.29 | 9.11 | 9.05 | 8.32 | 7.99 | 8.48 | 8.29 | 8.26 | 8.49 | 8.53 | 7.89 | 8.33 |
| 2904485 | 8.20 | 9.94 | 7.95 | 7.12 | 7.44 | 7.51 | 8.32 | 6.26 | 8.05 | 7.98 | 8.25 | 8.22 |
| 3772661 | 8.62 | 9.12 | 10.37 | 9.59 | 9.32 | 9.58 | 8.07 | 8.36 | 9.87 | 10.31 | 9.84 | 9.93 |
| 2796553 | 9.30 | 9.17 | 10.42 | 10.14 | 9.54 | 10.88 | 9.29 | 9.95 | 10.54 | 10.89 | 10.74 | 10.59 |
| 3063795 | 6.73 | 8.40 | 8.51 | 7.64 | 7.88 | 7.59 | 7.13 | 7.77 | 7.70 | 7.23 | 7.19 | 7.88 |
| 3338192 | 10.19 | 9.01 | 8.84 | 8.16 | 9.94 | 8.05 | 7.49 | 8.22 | 8.38 | 8.38 | 9.55 | 8.80 |
| 3214845 | 4.59 | 4.19 | 4.27 | 5.14 | 4.93 | 4.82 | 4.28 | 4.61 | 4.93 | 4.27 | 4.86 | 4.90 |
| 2730303 | 4.01 | 4.15 | 4.30 | 6.97 | 4.25 | 4.21 | 4.40 | 4.46 | 4.06 | 4.37 | 4.47 | 4.25 |
| 3811086 | 7.89 | 8.34 | 7.60 | 7.37 | 7.34 | 7.43 | 7.90 | 7.30 | 7.60 | 7.46 | 7.38 | 7.43 |
| 2981874 | 10.62 | 10.99 | 10.18 | 10.21 | 9.95 | 10.75 | 11.55 | 11.00 | 10.16 | 10.43 | 10.43 | 10.25 |
| 3242353 | 6.11 | 6.14 | 6.48 | 6.08 | 5.77 | 6.24 | 6.67 | 6.29 | 6.02 | 5.98 | 6.29 | 5.74 |
| 2442008 | 6.92 | 6.02 | 5.36 | 5.50 | 7.91 | 5.86 | 5.90 | 5.50 | 5.79 | 5.84 | 7.24 | 6.21 |
| 3564210 | 8.12 | 8.47 | 9.48 | 9.72 | 9.38 | 10.34 | 7.36 | 8.58 | 10.11 | 10.90 | 9.98 | 10.27 |
| 2490351 | 4.23 | 4.28 | 3.97 | 4.19 | 4.24 | 4.17 | 4.19 | 4.42 | 4.08 | 4.36 | 4.33 | 4.11 |
| 3759006 | 7.44 | 8.02 | 9.64 | 10.61 | 9.14 | 8.47 | 7.57 | 8.89 | 10.27 | 11.33 | 9.34 | 10.56 |
| 3264997 | 4.28 | 4.18 | 4.20 | 4.15 | 4.08 | 4.11 | 4.27 | 4.24 | 4.18 | 4.20 | 4.16 | 4.38 |
| 3912079 | 3.91 | 3.99 | 3.96 | 3.77 | 3.62 | 3.66 | 3.86 | 3.48 | 4.51 | 4.24 | 3.93 | 4.14 |
| 2926802 | 4.78 | 4.84 | 5.47 | 6.56 | 5.32 | 5.52 | 5.48 | 5.18 | 5.79 | 6.36 | 5.53 | 5.75 |
| 3430163 | 3.87 | 3.79 | 3.91 | 3.84 | 4.35 | 3.95 | 3.89 | 3.95 | 3.72 | 4.30 | 3.82 | 3.74 |
| 3039830 | 3.19 | 3.07 | 3.08 | 3.25 | 3.20 | 3.39 | 3.34 | 3.29 | 3.22 | 3.13 | 3.20 | 3.38 |
| 3935486 | 5.41 | 6.10 | 8.86 | 6.78 | 6.54 | 7.08 | 5.51 | 5.85 | 8.37 | 6.12 | 7.04 | 5.40 |
| 3457336 | 5.41 | 5.32 | 5.43 | 5.22 | 5.30 | 5.59 | 5.51 | 5.79 | 5.61 | 5.81 | 5.68 | 5.45 |
| 3811949 | 3.51 | 3.43 | 3.58 | 3.59 | 3.54 | 3.45 | 3.62 | 3.76 | 3.49 | 3.75 | 3.57 | 3.46 |

TABLE 45-continued

Normalized intensity of microarray data for a set of samples.

| TCID | V01 0241 | V01 0242 | V01 0243 | V01 0244 | V01 0245 | V01 0246 | V01 0247 | V01 0248 | V01 0249 | V01 0250 | V01 0251 | V01 0252 |
|---|---|---|---|---|---|---|---|---|---|---|---|---|
| 3343832 | 3.77 | 3.96 | 3.91 | 3.85 | 3.95 | 3.97 | 4.05 | 3.89 | 3.96 | 4.20 | 3.94 | 4.01 |
| 3161261 | 5.44 | 5.58 | 5.80 | 5.24 | 6.01 | 6.64 | 5.44 | 6.14 | 5.83 | 5.51 | 5.78 | 6.10 |
| 3594003 | 3.58 | 3.55 | 4.00 | 3.75 | 3.57 | 3.73 | 3.61 | 3.59 | 3.67 | 4.05 | 3.68 | 3.83 |
| 3805614 | 4.66 | 5.17 | 5.09 | 4.38 | 4.88 | 4.90 | 4.95 | 4.73 | 5.15 | 5.01 | 5.07 | 5.27 |
| 3364127 | 7.36 | 6.92 | 6.61 | 6.71 | 6.89 | 6.84 | 7.43 | 11.91 | 7.04 | 7.20 | 6.91 | 6.98 |
| 3834341 | 4.11 | 4.13 | 4.27 | 4.17 | 4.12 | 4.14 | 4.09 | 4.01 | 4.08 | 4.27 | 4.17 | 4.18 |
| 2585400 | 4.08 | 4.41 | 4.39 | 4.46 | 5.07 | 4.56 | 4.44 | 4.41 | 4.65 | 4.62 | 4.35 | 4.44 |
| 2941690 | 4.47 | 4.07 | 4.17 | 4.08 | 4.12 | 4.11 | 4.44 | 4.23 | 4.54 | 4.60 | 4.50 | 4.22 |
| 3484895 | 5.45 | 4.68 | 4.92 | 5.01 | 5.36 | 5.00 | 5.07 | 5.07 | 4.99 | 5.29 | 5.51 | 4.73 |
| 3159754 | 3.78 | 3.62 | 3.73 | 3.68 | 3.63 | 3.84 | 4.18 | 3.86 | 3.86 | 3.94 | 3.83 | 3.87 |
| 2894790 | 3.90 | 4.04 | 3.72 | 3.91 | 4.03 | 3.97 | 4.18 | 3.70 | 3.72 | 4.51 | 3.80 | 3.85 |
| 3363686 | 3.36 | 3.67 | 3.10 | 3.48 | 3.53 | 3.52 | 3.30 | 3.55 | 3.64 | 3.93 | 3.36 | 3.67 |
| 2923928 | 4.04 | 4.65 | 4.24 | 4.54 | 4.58 | 4.08 | 4.70 | 4.22 | 4.61 | 4.15 | 4.41 | 4.54 |
| 2883317 | 4.50 | 4.66 | 5.24 | 5.01 | 5.24 | 5.63 | 4.96 | 4.53 | 5.41 | 5.74 | 4.57 | 5.42 |
| 2479698 | 6.44 | 5.84 | 6.00 | 5.82 | 6.50 | 6.12 | 6.13 | 6.10 | 6.28 | 6.06 | 6.08 | 6.26 |
| 3428225 | 3.72 | 3.74 | 3.63 | 3.72 | 3.69 | 3.89 | 3.73 | 3.58 | 3.81 | 4.09 | 3.97 | 3.93 |
| 3393446 | 6.75 | 7.18 | 7.14 | 7.56 | 7.26 | 7.45 | 7.41 | 6.14 | 8.04 | 7.78 | 7.49 | 7.41 |
| 3116614 | 13.17 | 13.15 | 12.24 | 12.04 | 12.29 | 12.87 | 12.92 | 12.13 | 12.42 | 11.90 | 13.07 | 12.33 |
| 3415320 | 10.37 | 10.82 | 8.95 | 9.60 | 8.58 | 9.64 | 10.48 | 10.13 | 8.86 | 7.46 | 9.26 | 9.39 |
| 3757108 | 7.77 | 7.56 | 7.77 | 7.07 | 7.77 | 7.38 | 8.00 | 7.43 | 7.71 | 7.78 | 7.76 | 8.34 |
| 4012178 | 10.66 | 7.02 | 6.39 | 6.89 | 10.00 | 6.33 | 7.49 | 6.34 | 6.27 | 7.06 | 11.18 | 8.59 |
| 3546213 | 11.61 | 11.64 | 9.60 | 9.53 | 10.29 | 10.54 | 11.17 | 8.23 | 9.82 | 8.77 | 11.07 | 9.74 |
| 3561381 | 10.66 | 10.73 | 8.80 | 8.16 | 9.59 | 8.55 | 10.08 | 8.70 | 8.64 | 8.88 | 10.40 | 9.40 |

TABLE 46

Normalized intensity of microarray data for a set of samples.

| TCID | V01 0253 | V01 0254 | V01 0255 | V01 0256 | V01 0257 | V01 0258 | V01 0259 | V01 0260 | V01 0261 | V01 0262 | V01 0263 | V01 0264 |
|---|---|---|---|---|---|---|---|---|---|---|---|---|
| 2604998 | 8.18 | 7.44 | 8.31 | 8.76 | 8.93 | 8.72 | 6.34 | 8.05 | 7.54 | 8.99 | 7.73 | 7.34 |
| 3603932 | 8.25 | 7.51 | 7.03 | 6.31 | 7.14 | 6.71 | 6.57 | 7.19 | 6.89 | 7.28 | 6.85 | 6.73 |
| 2710599 | 7.99 | 9.37 | 8.39 | 5.25 | 7.99 | 8.40 | 7.70 | 7.08 | 6.09 | 11.80 | 5.84 | 5.40 |
| 2440258 | 6.47 | 6.23 | 8.18 | 7.20 | 5.38 | 6.45 | 11.78 | 8.23 | 8.93 | 6.45 | 9.11 | 8.97 |
| 3169331 | 9.07 | 6.62 | 7.65 | 7.60 | 7.89 | 7.34 | 6.95 | 7.48 | 7.62 | 6.09 | 6.60 | 7.04 |
| 2988882 | 10.12 | 9.70 | 10.06 | 9.60 | 10.30 | 9.84 | 9.82 | 10.07 | 9.79 | 9.71 | 9.91 | 9.55 |
| 2964231 | 10.66 | 9.59 | 9.55 | 8.87 | 9.39 | 8.00 | 7.73 | 8.48 | 8.64 | 9.12 | 7.95 | 8.04 |
| 3111561 | 10.50 | 4.61 | 10.83 | 9.24 | 11.07 | 10.84 | 5.97 | 9.54 | 7.24 | 4.36 | 9.54 | 8.67 |
| 2562529 | 9.08 | 11.02 | 9.79 | 9.72 | 10.33 | 9.70 | 8.83 | 8.76 | 8.87 | 10.44 | 8.53 | 9.09 |
| 3692999 | 12.99 | 12.00 | 12.19 | 12.82 | 12.75 | 12.92 | 6.63 | 13.11 | 12.12 | 6.42 | 12.07 | 9.58 |
| 2439554 | 5.29 | 5.46 | 6.80 | 5.61 | 5.14 | 5.78 | 9.98 | 6.06 | 7.40 | 5.82 | 7.27 | 7.89 |
| 2685304 | 8.02 | 9.97 | 7.83 | 7.06 | 7.99 | 8.28 | 6.52 | 7.26 | 6.77 | 11.64 | 7.33 | 7.36 |
| 2578790 | 7.12 | 4.27 | 6.33 | 7.02 | 8.20 | 7.76 | 4.60 | 7.64 | 6.61 | 4.10 | 6.63 | 5.75 |
| 2373842 | 10.01 | 10.45 | 11.49 | 10.64 | 9.65 | 10.08 | 11.74 | 11.33 | 11.96 | 9.37 | 12.05 | 12.13 |
| 2750627 | 8.07 | 10.12 | 7.94 | 10.87 | 10.63 | 10.02 | 6.75 | 9.66 | 8.53 | 9.80 | 7.38 | 8.65 |
| 3397774 | 8.28 | 4.71 | 4.94 | 5.08 | 5.12 | 4.98 | 5.48 | 4.92 | 5.05 | 4.30 | 5.05 | 4.95 |
| 2635741 | 6.66 | 6.56 | 8.42 | 6.79 | 6.67 | 7.72 | 9.50 | 8.70 | 9.48 | 6.82 | 9.29 | 9.49 |
| 3970833 | 11.12 | 9.78 | 9.75 | 9.88 | 9.77 | 9.20 | 9.69 | 9.65 | 9.32 | 9.91 | 8.90 | 9.03 |
| 3577612 | 9.43 | 9.96 | 10.48 | 10.19 | 9.07 | 9.65 | 8.69 | 10.36 | 11.27 | 11.99 | 11.56 | 11.14 |
| 2708922 | 6.50 | 8.76 | 8.08 | 7.31 | 7.53 | 8.04 | 6.22 | 8.53 | 8.16 | 8.46 | 8.60 | 8.06 |
| 2970897 | 8.64 | 5.21 | 7.59 | 5.54 | 5.58 | 5.82 | 4.93 | 7.66 | 5.12 | 6.75 | 5.31 | 5.00 |
| 3724545 | 9.64 | 9.50 | 9.44 | 10.37 | 9.61 | 9.65 | 8.40 | 10.26 | 9.23 | 9.69 | 9.44 | 9.93 |
| 2798538 | 10.47 | 7.56 | 9.40 | 9.19 | 9.16 | 8.29 | 9.84 | 9.14 | 9.04 | 9.34 | 8.45 | 9.09 |
| 2806468 | 9.10 | 9.48 | 11.08 | 9.77 | 9.99 | 9.23 | 11.57 | 11.23 | 11.74 | 7.96 | 11.72 | 11.62 |
| 2880051 | 6.75 | 5.67 | 6.63 | 7.34 | 6.07 | 6.30 | 6.26 | 6.63 | 6.74 | 5.57 | 6.84 | 6.71 |
| 2732508 | 3.86 | 3.79 | 3.77 | 3.72 | 3.31 | 5.98 | 9.40 | 3.93 | 3.66 | 5.72 | 3.66 | 3.67 |
| 2822492 | 6.73 | 6.33 | 5.95 | 6.31 | 6.45 | 5.12 | 5.27 | 5.93 | 5.12 | 5.64 | 5.19 | 5.35 |
| 3404030 | 6.11 | 6.21 | 8.50 | 6.50 | 6.62 | 6.91 | 8.59 | 9.05 | 9.40 | 5.72 | 9.55 | 9.00 |
| 3059667 | 7.01 | 7.97 | 8.16 | 10.90 | 11.53 | 12.01 | 7.81 | 9.41 | 9.13 | 4.17 | 7.51 | 8.87 |
| 3108526 | 10.85 | 8.40 | 9.66 | 10.80 | 11.02 | 10.56 | 9.33 | 10.24 | 10.26 | 8.61 | 9.24 | 10.00 |
| 2526806 | 10.39 | 10.05 | 9.54 | 7.86 | 9.51 | 9.48 | 9.48 | 9.63 | 7.84 | 12.95 | 7.64 | 7.22 |
| 2428501 | 7.16 | 5.75 | 6.91 | 6.18 | 5.78 | 6.57 | 7.82 | 6.63 | 7.16 | 6.34 | 7.11 | 6.71 |
| 2657808 | 5.57 | 7.82 | 7.46 | 5.26 | 8.21 | 8.01 | 8.58 | 6.90 | 5.79 | 11.83 | 5.84 | 5.96 |
| 2584018 | 7.41 | 8.07 | 7.75 | 6.27 | 7.36 | 7.13 | 7.99 | 7.34 | 8.42 | 10.96 | 8.19 | 7.73 |
| 3976341 | 7.59 | 8.61 | 9.37 | 8.92 | 7.86 | 8.25 | 9.35 | 9.48 | 10.21 | 11.49 | 9.78 | 10.46 |
| 2739308 | 5.63 | 4.68 | 5.45 | 5.69 | 5.42 | 4.75 | 4.59 | 5.50 | 5.35 | 4.28 | 5.22 | 5.00 |
| 3959862 | 10.17 | 4.34 | 8.02 | 6.29 | 4.25 | 4.36 | 6.75 | 5.83 | 4.93 | 4.01 | 4.96 | 4.65 |
| 2362351 | 5.66 | 6.09 | 7.58 | 6.02 | 5.63 | 6.88 | 8.47 | 8.02 | 8.27 | 6.28 | 8.86 | 8.47 |
| 3648391 | 4.44 | 3.80 | 5.19 | 3.75 | 4.06 | 6.20 | 8.68 | 4.96 | 5.40 | 6.46 | 5.74 | 5.54 |
| 3009299 | 11.30 | 10.97 | 11.07 | 11.31 | 10.75 | 10.62 | 11.10 | 10.94 | 10.58 | 10.79 | 10.45 | 10.61 |
| 3443464 | 5.54 | 5.32 | 5.80 | 5.15 | 5.40 | 5.85 | 5.47 | 6.09 | 6.77 | 4.93 | 6.32 | 6.16 |

TABLE 46-continued

Normalized intensity of microarray data for a set of samples.

| TCID | V01 0253 | V01 0254 | V01 0255 | V01 0256 | V01 0257 | V01 0258 | V01 0259 | V01 0260 | V01 0261 | V01 0262 | V01 0263 | V01 0264 |
|---|---|---|---|---|---|---|---|---|---|---|---|---|
| 2730746 | 9.75 | 8.84 | 8.85 | 9.12 | 9.08 | 8.40 | 5.82 | 7.89 | 8.27 | 4.89 | 7.03 | 7.14 |
| 2427619 | 6.72 | 6.85 | 8.97 | 6.86 | 6.41 | 7.51 | 9.39 | 8.85 | 9.66 | 7.37 | 9.55 | 9.29 |
| 3042001 | 10.25 | 8.33 | 9.13 | 9.30 | 8.30 | 9.03 | 9.10 | 9.18 | 8.58 | 8.27 | 7.97 | 8.58 |
| 2566848 | 5.36 | 5.09 | 5.41 | 5.14 | 5.06 | 5.31 | 7.56 | 5.84 | 7.05 | 5.04 | 6.47 | 6.01 |
| 2984616 | 10.88 | 8.97 | 9.61 | 9.27 | 9.55 | 8.96 | 8.91 | 9.41 | 9.12 | 9.02 | 9.06 | 9.20 |
| 2378068 | 6.97 | 8.35 | 7.18 | 6.64 | 6.13 | 7.06 | 9.33 | 6.58 | 6.86 | 8.54 | 7.32 | 7.14 |
| 2721959 | 10.61 | 8.16 | 10.19 | 5.49 | 8.72 | 7.42 | 5.93 | 7.04 | 6.89 | 13.09 | 6.00 | 6.07 |
| 2877508 | 11.13 | 10.18 | 10.38 | 10.64 | 10.38 | 10.14 | 10.67 | 10.37 | 10.12 | 10.54 | 9.82 | 9.96 |
| 3450861 | 5.43 | 4.74 | 5.93 | 5.03 | 4.87 | 5.16 | 7.30 | 6.67 | 7.28 | 5.29 | 7.50 | 7.27 |
| 2688717 | 6.06 | 7.58 | 9.45 | 7.01 | 7.14 | 7.88 | 10.51 | 9.11 | 10.43 | 7.26 | 10.20 | 9.69 |
| 3270270 | 7.22 | 7.87 | 8.57 | 7.66 | 7.04 | 7.06 | 8.12 | 8.68 | 9.10 | 8.94 | 9.61 | 9.26 |
| 3417703 | 5.30 | 7.71 | 8.60 | 9.97 | 11.17 | 9.46 | 5.63 | 8.35 | 7.43 | 7.60 | 5.83 | 8.49 |
| 3302990 | 10.14 | 7.48 | 7.98 | 9.00 | 7.63 | 7.30 | 7.60 | 8.63 | 7.61 | 7.50 | 6.21 | 6.76 |
| 2377283 | 4.53 | 4.47 | 4.64 | 4.52 | 4.28 | 4.77 | 11.80 | 5.05 | 5.66 | 4.77 | 5.55 | 5.11 |
| 3122678 | 5.06 | 4.27 | 5.78 | 4.45 | 4.41 | 4.64 | 4.40 | 4.82 | 4.63 | 4.42 | 5.03 | 5.10 |
| 2688499 | 8.35 | 8.82 | 9.36 | 7.45 | 10.34 | 9.94 | 8.60 | 8.29 | 8.06 | 10.73 | 8.41 | 8.10 |
| 2377094 | 10.81 | 9.29 | 9.17 | 9.30 | 10.33 | 8.97 | 7.82 | 9.12 | 8.67 | 8.62 | 7.95 | 8.21 |
| 3278198 | 9.54 | 8.57 | 7.61 | 8.90 | 8.61 | 7.46 | 6.47 | 7.91 | 7.26 | 8.31 | 6.87 | 6.64 |
| 2598261 | 9.90 | 9.42 | 8.63 | 7.08 | 8.76 | 8.81 | 8.75 | 9.07 | 7.69 | 12.88 | 6.55 | 6.94 |
| 3982612 | 5.92 | 6.47 | 9.59 | 6.78 | 6.42 | 7.64 | 11.17 | 9.23 | 9.98 | 7.41 | 10.02 | 9.74 |
| 2884845 | 4.51 | 5.33 | 5.47 | 4.57 | 4.72 | 4.82 | 4.32 | 4.83 | 4.81 | 10.05 | 4.63 | 4.39 |
| 3982560 | 5.25 | 5.22 | 7.19 | 5.63 | 5.23 | 6.13 | 8.84 | 6.17 | 8.30 | 5.42 | 8.20 | 8.33 |
| 3204285 | 5.35 | 5.52 | 5.83 | 5.90 | 5.50 | 5.81 | 8.80 | 5.82 | 5.22 | 6.07 | 5.13 | 5.07 |
| 3654699 | 13.02 | 10.57 | 10.93 | 11.57 | 11.62 | 11.75 | 9.32 | 11.96 | 11.62 | 10.72 | 9.99 | 10.61 |
| 2638676 | 6.49 | 6.75 | 6.83 | 5.59 | 5.71 | 6.66 | 10.51 | 6.93 | 7.80 | 6.76 | 8.02 | 7.36 |
| 3367673 | 8.92 | 8.70 | 6.46 | 9.35 | 9.41 | 9.09 | 5.99 | 8.38 | 8.02 | 5.84 | 7.23 | 8.05 |
| 3212008 | 5.64 | 10.73 | 6.37 | 6.28 | 6.99 | 7.44 | 6.16 | 6.34 | 6.75 | 8.98 | 6.15 | 6.80 |
| 3326635 | 9.07 | 10.58 | 10.17 | 9.31 | 10.34 | 10.12 | 9.96 | 9.89 | 10.33 | 10.27 | 10.44 | 10.22 |
| 3031556 | 7.09 | 7.82 | 9.63 | 8.32 | 6.74 | 6.92 | 10.00 | 9.25 | 10.04 | 7.78 | 10.08 | 10.67 |
| 3662201 | 13.13 | 12.28 | 11.91 | 12.71 | 12.51 | 12.75 | 7.69 | 13.00 | 12.41 | 7.77 | 11.70 | 10.08 |
| 2809793 | 5.32 | 6.03 | 8.39 | 6.25 | 6.21 | 7.41 | 9.79 | 8.51 | 9.53 | 7.20 | 9.93 | 9.84 |
| 2817731 | 7.80 | 7.47 | 7.70 | 7.63 | 7.57 | 7.28 | 6.96 | 7.30 | 8.22 | 7.54 | 8.22 | 8.31 |
| 4020655 | 4.84 | 9.92 | 4.95 | 4.95 | 6.05 | 5.29 | 5.21 | 4.97 | 5.22 | 7.82 | 5.40 | 5.20 |
| 3494629 | 4.80 | 6.31 | 5.48 | 4.47 | 4.59 | 4.85 | 4.23 | 4.57 | 4.19 | 7.09 | 4.49 | 4.25 |
| 3852832 | 7.22 | 8.17 | 9.37 | 8.49 | 7.50 | 6.43 | 7.55 | 9.10 | 9.59 | 5.42 | 10.51 | 10.15 |
| 3761959 | 9.56 | 10.15 | 8.71 | 9.66 | 9.29 | 9.58 | 8.68 | 9.36 | 8.88 | 9.16 | 8.49 | 8.91 |
| 2834282 | 5.70 | 9.28 | 6.22 | 6.08 | 8.10 | 6.15 | 5.58 | 6.90 | 6.02 | 7.98 | 5.91 | 6.58 |
| 3341497 | 6.61 | 9.35 | 6.94 | 6.27 | 6.65 | 7.30 | 6.10 | 7.30 | 6.20 | 6.40 | 6.47 | 6.27 |
| 2372812 | 4.83 | 4.62 | 4.62 | 5.65 | 4.85 | 4.97 | 11.41 | 4.88 | 4.59 | 4.94 | 4.79 | 4.65 |
| 2486811 | 9.42 | 8.83 | 9.45 | 8.35 | 6.75 | 8.57 | 10.48 | 9.42 | 9.97 | 8.38 | 10.38 | 10.23 |
| 3768474 | 8.55 | 8.30 | 7.85 | 8.20 | 7.80 | 8.11 | 6.96 | 8.35 | 8.20 | 7.74 | 8.58 | 8.25 |
| 3142381 | 5.14 | 6.77 | 7.06 | 5.55 | 5.23 | 5.69 | 4.04 | 5.45 | 8.09 | 3.71 | 4.63 | 7.41 |
| 2396750 | 7.13 | 7.02 | 6.93 | 6.96 | 6.64 | 7.15 | 6.89 | 6.53 | 7.56 | 7.96 | 6.78 | 7.19 |
| 3902489 | 9.81 | 9.65 | 10.91 | 11.02 | 9.69 | 10.39 | 9.89 | 11.19 | 11.38 | 9.56 | 11.59 | 11.50 |
| 3032647 | 7.07 | 5.64 | 8.74 | 8.75 | 7.34 | 7.84 | 6.26 | 7.30 | 8.04 | 5.92 | 7.31 | 7.59 |
| 3875642 | 5.19 | 5.21 | 6.23 | 5.22 | 5.15 | 5.30 | 4.99 | 6.00 | 6.54 | 5.40 | 6.18 | 6.23 |
| 4027585 | 9.80 | 9.61 | 10.69 | 10.61 | 9.41 | 9.69 | 9.54 | 11.04 | 11.05 | 8.05 | 11.24 | 11.38 |
| 2352609 | 7.14 | 7.94 | 7.63 | 8.02 | 7.20 | 7.76 | 5.44 | 7.05 | 6.55 | 7.45 | 6.57 | 6.43 |
| 3376529 | 9.29 | 9.72 | 9.33 | 9.46 | 8.76 | 8.20 | 7.92 | 9.28 | 8.31 | 10.21 | 7.34 | 8.15 |
| 2491271 | 12.57 | 12.90 | 13.40 | 12.52 | 12.31 | 12.93 | 13.63 | 13.00 | 13.30 | 13.62 | 13.42 | 13.45 |
| 3874751 | 9.51 | 9.02 | 8.28 | 10.30 | 9.64 | 9.01 | 8.66 | 9.03 | 9.08 | 9.52 | 8.91 | 9.18 |
| 2326463 | 10.87 | 10.44 | 12.26 | 10.76 | 10.09 | 10.87 | 12.63 | 11.78 | 12.40 | 9.97 | 12.45 | 12.50 |
| 3341061 | 7.71 | 7.11 | 7.01 | 7.10 | 5.98 | 6.56 | 7.36 | 6.72 | 7.15 | 7.19 | 7.31 | 7.33 |
| 3839910 | 7.80 | 7.87 | 8.43 | 7.81 | 6.96 | 6.44 | 6.48 | 8.50 | 9.91 | 5.53 | 10.83 | 9.51 |
| 2708855 | 4.08 | 6.21 | 4.30 | 3.92 | 4.03 | 4.26 | 4.24 | 4.32 | 4.28 | 8.69 | 4.39 | 4.11 |
| 3512874 | 11.00 | 10.98 | 11.86 | 11.19 | 10.09 | 10.60 | 12.44 | 11.85 | 12.25 | 10.18 | 12.46 | 12.26 |
| 2701071 | 8.43 | 9.40 | 10.27 | 9.29 | 8.16 | 7.73 | 8.86 | 9.78 | 10.51 | 6.97 | 11.29 | 11.11 |
| 3486096 | 8.86 | 9.10 | 7.38 | 6.91 | 9.17 | 8.59 | 5.85 | 6.35 | 7.02 | 8.64 | 6.57 | 6.38 |
| 2412668 | 8.28 | 8.40 | 8.06 | 8.49 | 8.19 | 7.71 | 8.49 | 8.09 | 8.86 | 7.91 | 8.48 | 8.63 |
| 3329343 | 7.85 | 7.88 | 7.33 | 7.59 | 7.38 | 8.17 | 8.32 | 7.04 | 7.15 | 9.17 | 7.51 | 7.15 |
| 3259367 | 4.17 | 6.00 | 3.99 | 4.16 | 4.95 | 4.89 | 3.82 | 5.05 | 4.06 | 4.85 | 4.43 | 4.65 |
| 3373845 | 9.09 | 8.22 | 9.55 | 7.33 | 10.42 | 11.83 | 9.21 | 9.41 | 9.29 | 9.38 | 9.40 | 8.60 |
| 2321911 | 8.44 | 8.08 | 8.93 | 8.89 | 8.01 | 8.01 | 8.50 | 8.37 | 8.51 | 7.92 | 8.45 | 8.75 |
| 3353914 | 7.35 | 6.90 | 6.66 | 6.32 | 6.68 | 6.71 | 6.57 | 6.55 | 6.46 | 7.87 | 6.49 | 6.15 |
| 3744680 | 7.10 | 7.24 | 7.54 | 7.10 | 6.72 | 7.20 | 7.26 | 7.85 | 8.11 | 6.47 | 8.63 | 8.27 |
| 2373336 | 5.56 | 5.56 | 6.08 | 5.11 | 7.98 | 9.07 | 6.74 | 7.71 | 6.86 | 10.46 | 5.56 | 6.29 |
| 3067478 | 6.03 | 8.19 | 7.11 | 6.10 | 6.16 | 6.13 | 4.77 | 5.04 | 5.33 | 8.99 | 4.52 | 5.28 |
| 3976766 | 6.85 | 7.53 | 8.57 | 8.12 | 6.88 | 7.22 | 8.90 | 8.47 | 8.85 | 6.54 | 9.41 | 9.22 |
| 3246888 | 4.73 | 7.82 | 5.93 | 7.70 | 7.71 | 7.19 | 4.95 | 6.34 | 6.20 | 5.27 | 6.04 | 6.09 |
| 3147985 | 7.10 | 6.63 | 6.15 | 8.02 | 7.14 | 4.63 | 5.44 | 6.10 | 6.21 | 7.48 | 5.96 | 6.26 |
| 3185522 | 10.15 | 9.81 | 9.47 | 9.26 | 8.96 | 9.58 | 9.16 | 9.58 | 8.96 | 9.43 | 9.88 | 9.26 |
| 3861948 | 11.17 | 11.77 | 12.64 | 12.17 | 10.91 | 11.33 | 12.69 | 12.65 | 12.98 | 10.37 | 13.14 | 13.09 |
| 3393479 | 8.95 | 8.09 | 9.07 | 8.32 | 8.60 | 9.34 | 8.64 | 8.95 | 9.15 | 8.97 | 8.75 | 8.81 |
| 3540862 | 7.79 | 7.10 | 6.60 | 7.13 | 7.31 | 7.10 | 6.70 | 6.77 | 6.74 | 7.36 | 6.77 | 6.64 |
| 2777714 | 9.69 | 10.31 | 11.38 | 11.52 | 9.85 | 10.24 | 9.89 | 11.23 | 11.70 | 7.46 | 12.08 | 11.71 |

TABLE 46-continued

Normalized intensity of microarray data for a set of samples.

| TCID | V01 0253 | V01 0254 | V01 0255 | V01 0256 | V01 0257 | V01 0258 | V01 0259 | V01 0260 | V01 0261 | V01 0262 | V01 0263 | V01 0264 |
|---|---|---|---|---|---|---|---|---|---|---|---|---|
| 3110395 | 4.73 | 5.17 | 4.21 | 4.94 | 4.91 | 4.43 | 4.04 | 4.40 | 4.31 | 5.14 | 4.49 | 4.80 |
| 3895795 | 7.37 | 8.42 | 8.70 | 7.77 | 7.25 | 7.33 | 7.26 | 8.17 | 9.00 | 7.95 | 9.51 | 9.17 |
| 2854445 | 9.76 | 8.22 | 8.91 | 7.10 | 7.30 | 9.35 | 8.52 | 8.63 | 8.06 | 8.54 | 8.41 | 8.85 |
| 3606034 | 7.70 | 7.72 | 7.81 | 8.15 | 8.12 | 7.71 | 6.78 | 7.61 | 7.57 | 7.59 | 7.38 | 7.77 |
| 3375735 | 7.49 | 7.40 | 7.94 | 7.98 | 7.45 | 7.98 | 7.62 | 8.41 | 8.24 | 7.28 | 8.31 | 8.01 |
| 3948047 | 7.55 | 7.54 | 8.41 | 7.98 | 7.27 | 7.73 | 8.82 | 8.57 | 8.93 | 7.30 | 9.25 | 9.19 |
| 3010503 | 8.23 | 8.14 | 9.52 | 8.39 | 6.44 | 6.87 | 6.65 | 9.16 | 9.58 | 5.71 | 10.22 | 9.81 |
| 3622934 | 7.03 | 7.85 | 7.24 | 7.26 | 7.36 | 7.51 | 7.96 | 6.62 | 6.50 | 7.62 | 6.89 | 6.93 |
| 3441849 | 9.09 | 9.72 | 9.50 | 9.61 | 9.36 | 8.89 | 8.64 | 9.87 | 10.06 | 9.95 | 10.59 | 10.40 |
| 3006572 | 6.21 | 6.74 | 6.74 | 6.29 | 6.50 | 6.31 | 6.36 | 6.51 | 6.83 | 6.52 | 6.64 | 6.25 |
| 3365136 | 8.85 | 10.43 | 8.67 | 8.50 | 9.42 | 9.30 | 8.51 | 8.81 | 8.78 | 9.58 | 7.99 | 8.73 |
| 2642791 | 8.80 | 8.06 | 8.40 | 8.69 | 8.67 | 8.35 | 8.38 | 8.88 | 8.58 | 8.38 | 8.46 | 8.40 |
| 2904485 | 6.79 | 7.59 | 8.61 | 9.37 | 9.39 | 9.41 | 7.06 | 8.40 | 8.21 | 7.43 | 8.31 | 8.03 |
| 3772661 | 10.10 | 9.27 | 9.36 | 8.91 | 8.67 | 10.19 | 8.33 | 9.43 | 9.71 | 9.69 | 10.15 | 9.97 |
| 2796553 | 10.09 | 8.98 | 9.67 | 9.38 | 8.91 | 8.84 | 8.38 | 9.55 | 10.64 | 8.22 | 11.11 | 10.11 |
| 3063795 | 7.24 | 7.17 | 7.59 | 7.19 | 6.59 | 7.80 | 7.35 | 7.00 | 6.88 | 7.39 | 7.51 | 7.47 |
| 3338192 | 8.84 | 10.27 | 9.66 | 9.65 | 9.61 | 9.90 | 7.82 | 9.24 | 8.08 | 10.35 | 7.75 | 7.89 |
| 3214845 | 4.52 | 4.71 | 5.23 | 4.87 | 4.54 | 4.53 | 4.51 | 5.03 | 4.60 | 6.18 | 4.20 | 4.48 |
| 2730303 | 3.97 | 4.12 | 4.30 | 4.29 | 4.16 | 4.40 | 9.88 | 4.18 | 4.22 | 4.66 | 4.40 | 4.15 |
| 3811086 | 7.85 | 7.73 | 7.79 | 8.38 | 8.22 | 7.39 | 7.77 | 7.63 | 7.67 | 7.71 | 7.56 | 7.85 |
| 2981874 | 10.94 | 9.88 | 10.38 | 11.31 | 9.95 | 9.84 | 9.86 | 10.52 | 10.16 | 10.17 | 10.41 | 10.60 |
| 3242353 | 6.25 | 6.05 | 5.88 | 6.41 | 6.45 | 6.31 | 6.30 | 5.95 | 5.80 | 5.89 | 5.90 | 5.67 |
| 2442008 | 5.66 | 9.16 | 5.38 | 5.31 | 5.21 | 5.70 | 5.16 | 5.54 | 5.45 | 8.77 | 5.48 | 6.64 |
| 3564210 | 8.36 | 8.58 | 9.50 | 8.88 | 7.38 | 7.78 | 7.59 | 9.51 | 10.24 | 8.02 | 10.67 | 9.93 |
| 2490351 | 4.28 | 4.04 | 4.04 | 4.08 | 4.01 | 4.15 | 3.93 | 4.17 | 4.14 | 3.84 | 4.28 | 4.09 |
| 3759006 | 7.30 | 7.44 | 9.62 | 9.22 | 7.81 | 8.61 | 7.88 | 9.58 | 9.82 | 6.54 | 10.57 | 9.76 |
| 3264997 | 4.21 | 4.02 | 4.14 | 4.15 | 4.11 | 4.28 | 4.10 | 4.21 | 4.11 | 3.84 | 4.17 | 4.17 |
| 3912079 | 3.60 | 4.30 | 3.95 | 3.46 | 3.49 | 3.82 | 3.53 | 3.75 | 3.98 | 3.41 | 4.24 | 4.06 |
| 2926802 | 5.17 | 4.93 | 5.57 | 5.75 | 4.90 | 4.63 | 7.00 | 5.69 | 4.99 | 4.44 | 5.47 | 5.96 |
| 2430163 | 4.08 | 3.67 | 3.60 | 3.89 | 3.85 | 4.07 | 3.69 | 4.08 | 3.95 | 3.89 | 3.85 | 4.08 |
| 3039830 | 3.26 | 3.07 | 3.17 | 3.20 | 3.07 | 3.25 | 3.18 | 3.28 | 3.25 | 3.28 | 3.15 | 3.36 |
| 3935486 | 7.30 | 5.74 | 6.26 | 5.35 | 6.19 | 7.07 | 5.44 | 5.11 | 8.06 | 6.07 | 7.06 | 6.77 |
| 3457336 | 5.42 | 5.32 | 5.54 | 5.40 | 5.33 | 5.69 | 5.25 | 5.49 | 5.64 | 5.00 | 5.46 | 5.71 |
| 3811949 | 3.53 | 3.40 | 3.36 | 3.52 | 3.49 | 3.54 | 3.45 | 3.65 | 3.39 | 3.40 | 3.69 | 3.49 |
| 3343832 | 4.06 | 3.64 | 3.84 | 3.93 | 3.78 | 4.21 | 3.84 | 4.12 | 3.80 | 3.70 | 3.94 | 3.94 |
| 3161261 | 5.50 | 5.56 | 5.77 | 6.15 | 6.06 | 6.10 | 6.22 | 5.88 | 6.56 | 4.98 | 6.90 | 6.25 |
| 3594003 | 3.76 | 3.56 | 3.54 | 3.74 | 3.73 | 3.84 | 3.65 | 3.74 | 3.99 | 3.78 | 3.73 | 3.86 |
| 3805614 | 5.02 | 4.49 | 4.60 | 4.82 | 4.71 | 5.10 | 4.53 | 5.00 | 4.81 | 4.21 | 4.85 | 5.19 |
| 3364127 | 8.58 | 6.82 | 7.04 | 6.76 | 6.57 | 7.21 | 7.62 | 7.09 | 6.82 | 6.30 | 7.22 | 6.87 |
| 3834341 | 3.87 | 4.01 | 4.09 | 4.01 | 3.93 | 4.55 | 4.14 | 4.20 | 4.04 | 3.70 | 4.21 | 4.32 |
| 2585400 | 4.47 | 4.14 | 4.24 | 4.10 | 4.13 | 4.53 | 4.29 | 4.34 | 4.33 | 4.81 | 6.77 | |
| 2941690 | 4.43 | 4.32 | 3.90 | 4.15 | 4.37 | 4.29 | 4.30 | 4.72 | 4.47 | 3.72 | 4.53 | 4.39 |
| 3484895 | 4.89 | 4.69 | 5.02 | 4.93 | 4.41 | 5.17 | 4.58 | 5.04 | 4.73 | 6.75 | 4.93 | 4.65 |
| 3159754 | 3.95 | 3.70 | 3.69 | 3.89 | 3.57 | 3.83 | 3.84 | 4.00 | 3.87 | 3.45 | 3.76 | 3.92 |
| 2894790 | 4.06 | 3.74 | 3.81 | 3.95 | 3.92 | 4.11 | 3.72 | 3.72 | 3.74 | 3.62 | 3.90 | 4.38 |
| 3363686 | 3.62 | 3.35 | 3.26 | 3.76 | 3.33 | 3.54 | 3.23 | 3.56 | 3.38 | 3.60 | 3.54 | 3.62 |
| 2923928 | 4.17 | 4.05 | 4.19 | 4.21 | 4.33 | 4.40 | 4.08 | 4.72 | 4.25 | 3.78 | 4.75 | 4.45 |
| 2883317 | 4.87 | 4.66 | 4.59 | 4.53 | 4.44 | 5.46 | 5.19 | 4.71 | 4.67 | 4.42 | 5.73 | 6.16 |
| 2479698 | 6.35 | 6.04 | 6.01 | 6.22 | 6.40 | 6.35 | 5.99 | 6.21 | 6.09 | 5.91 | 6.19 | 6.23 |
| 3428225 | 3.74 | 3.59 | 3.75 | 4.02 | 3.63 | 4.01 | 3.77 | 3.92 | 3.71 | 3.57 | 3.74 | 3.72 |
| 3393446 | 7.33 | 6.99 | 7.10 | 7.42 | 6.73 | 7.51 | 7.62 | 7.47 | 7.41 | 6.98 | 7.59 | 7.50 |
| 3116614 | 13.01 | 13.15 | 12.97 | 13.24 | 13.24 | 13.06 | 11.30 | 13.07 | 12.77 | 12.18 | 12.27 | 12.39 |
| 3415320 | 10.47 | 9.62 | 10.18 | 11.12 | 10.36 | 9.65 | 7.96 | 10.45 | 9.53 | 10.77 | 8.77 | 9.65 |
| 3757108 | 8.35 | 9.09 | 8.20 | 7.56 | 7.99 | 7.93 | 7.46 | 8.16 | 7.72 | 10.45 | 7.89 | 7.64 |
| 4012178 | 6.93 | 11.04 | 6.00 | 6.43 | 8.03 | 6.74 | 6.36 | 7.21 | 6.25 | 9.68 | 6.37 | 6.31 |
| 3546213 | 11.05 | 11.56 | 10.91 | 11.59 | 11.54 | 11.48 | 8.37 | 10.92 | 10.44 | 11.55 | 9.43 | 10.10 |
| 3561381 | 9.13 | 10.98 | 9.63 | 9.90 | 10.69 | 10.47 | 6.95 | 10.07 | 8.73 | 10.04 | 8.53 | 8.48 |

TABLE 47

Normalized intensity of microarray data for a set of samples.

| TCID | V01 0265 | V01 0266 | V01 0267 | V01 0268 | V01 0269 | V01 0270 | V01 0271 | V01 0272 | V01 0273 | V01 0274 | V01 0275 | V01 0276 |
|---|---|---|---|---|---|---|---|---|---|---|---|---|
| 2604998 | 8.85 | 8.34 | 5.50 | 5.05 | 7.02 | 6.59 | 7.06 | 7.90 | 6.28 | 8.31 | 5.61 | 8.73 |
| 3603932 | 7.19 | 6.82 | 6.42 | 7.55 | 7.42 | 6.16 | 6.76 | 7.63 | 7.75 | 7.64 | 9.26 | 6.91 |
| 2710599 | 11.82 | 11.39 | 7.59 | 5.60 | 6.76 | 7.40 | 7.04 | 9.84 | 7.51 | 11.78 | 8.48 | 11.01 |
| 2440258 | 6.77 | 7.98 | 9.92 | 9.01 | 7.84 | 4.68 | 9.28 | 7.41 | 8.96 | 7.52 | 8.48 | 9.10 |
| 3169331 | 6.48 | 7.01 | 6.64 | 5.83 | 6.08 | 6.32 | 7.15 | 7.54 | 5.99 | 7.50 | 7.21 | 6.92 |
| 2988882 | 9.15 | 9.58 | 9.45 | 9.65 | 9.90 | 9.45 | 9.57 | 10.13 | 9.66 | 9.97 | 10.21 | 9.38 |
| 2964231 | 9.29 | 7.96 | 7.41 | 8.61 | 7.85 | 8.45 | 8.63 | 10.29 | 8.50 | 9.93 | 10.84 | 8.62 |

TABLE 47-continued

Normalized intensity of microarray data for a set of samples.

| TCID | V01 0265 | V01 0266 | V01 0267 | V01 0268 | V01 0269 | V01 0270 | V01 0271 | V01 0272 | V01 0273 | V01 0274 | V01 0275 | V01 0276 |
|---|---|---|---|---|---|---|---|---|---|---|---|---|
| 3111561 | 6.09 | 9.39 | 6.42 | 7.54 | 9.07 | 6.49 | 10.30 | 9.10 | 7.02 | 5.51 | 4.70 | 4.89 |
| 2562529 | 11.00 | 10.31 | 9.32 | 8.53 | 9.46 | 9.49 | 9.05 | 9.93 | 9.17 | 10.42 | 9.60 | 10.41 |
| 3692999 | 7.48 | 6.49 | 6.52 | 6.36 | 10.85 | 7.56 | 10.26 | 12.69 | 9.02 | 11.79 | 9.28 | 7.34 |
| 2439554 | 6.61 | 6.27 | 9.52 | 8.05 | 10.21 | 4.89 | 8.01 | 5.88 | 7.69 | 7.39 | 7.06 | 8.22 |
| 2685304 | 11.67 | 10.85 | 6.90 | 8.97 | 8.26 | 9.25 | 7.14 | 9.32 | 7.73 | 10.98 | 9.42 | 10.46 |
| 2578790 | 4.35 | 4.49 | 4.66 | 4.66 | 6.26 | 4.49 | 6.61 | 7.63 | 5.25 | 4.27 | 4.37 | 4.19 |
| 2373842 | 10.53 | 10.61 | 12.04 | 12.08 | 11.98 | 8.51 | 11.97 | 10.20 | 11.87 | 9.96 | 10.79 | 10.62 |
| 2750627 | 9.32 | 10.47 | 7.04 | 5.21 | 8.35 | 12.41 | 9.56 | 8.68 | 6.88 | 5.92 | 6.23 | 8.50 |
| 3397774 | 4.32 | 4.84 | 4.71 | 5.26 | 5.59 | 4.89 | 5.09 | 5.89 | 4.87 | 5.08 | 5.60 | 4.73 |
| 2635741 | 7.56 | 8.05 | 9.84 | 9.43 | 8.07 | 5.59 | 9.56 | 7.74 | 9.29 | 7.94 | 7.71 | 7.28 |
| 3970833 | 9.67 | 9.28 | 9.54 | 8.90 | 8.91 | 9.40 | 9.27 | 10.26 | 9.40 | 9.93 | 9.99 | 9.43 |
| 3577612 | 11.69 | 11.43 | 9.68 | 11.21 | 11.39 | 7.95 | 10.67 | 9.30 | 10.94 | 11.67 | 10.30 | 11.44 |
| 2708922 | 8.24 | 7.92 | 7.81 | 10.43 | 9.86 | 6.68 | 8.15 | 7.19 | 9.12 | 8.36 | 7.77 | 8.04 |
| 2970897 | 5.17 | 5.17 | 4.81 | 4.89 | 5.11 | 5.62 | 5.54 | 7.07 | 5.39 | 5.54 | 6.29 | 6.00 |
| 3724545 | 9.51 | 9.63 | 7.44 | 11.24 | 9.75 | 7.82 | 9.56 | 9.19 | 9.98 | 9.12 | 8.84 | 10.09 |
| 2798538 | 8.70 | 9.48 | 9.58 | 9.60 | 8.43 | 9.45 | 9.59 | 8.89 | 8.98 | 9.79 | 10.00 | 9.17 |
| 2806468 | 10.28 | 10.24 | 11.70 | 11.64 | 10.18 | 8.02 | 11.90 | 9.61 | 11.50 | 8.48 | 10.65 | 9.11 |
| 2880051 | 5.92 | 6.11 | 6.56 | 6.76 | 6.43 | 7.25 | 6.87 | 6.39 | 7.01 | 6.09 | 6.30 | 5.91 |
| 2732508 | 3.55 | 5.69 | 8.86 | 3.73 | 4.12 | 3.77 | 4.88 | 4.41 | 6.86 | 7.18 | 3.69 | 3.90 |
| 2822492 | 4.81 | 5.27 | 5.11 | 5.69 | 5.05 | 7.89 | 5.34 | 6.38 | 5.78 | 5.69 | 5.88 | 5.76 |
| 3404030 | 6.76 | 8.06 | 8.98 | 9.52 | 7.79 | 5.86 | 9.16 | 7.50 | 8.77 | 6.67 | 7.14 | 7.15 |
| 3059667 | 6.90 | 8.72 | 7.26 | 4.14 | 9.75 | 5.82 | 8.68 | 6.77 | 6.61 | 5.53 | 4.80 | 6.01 |
| 3108526 | 8.43 | 8.75 | 8.59 | 6.46 | 8.20 | 9.15 | 10.20 | 10.64 | 7.31 | 8.72 | 5.50 | 8.46 |
| 2526806 | 13.05 | 12.72 | 10.16 | 7.11 | 9.19 | 10.23 | 8.49 | 11.58 | 11.28 | 12.62 | 11.78 | 12.62 |
| 2428501 | 6.91 | 7.06 | 7.60 | 7.83 | 6.93 | 4.68 | 6.83 | 7.31 | 6.95 | 7.19 | 8.95 | 7.00 |
| 2657808 | 10.52 | 9.77 | 6.69 | 5.38 | 6.47 | 5.47 | 5.77 | 9.95 | 6.29 | 11.86 | 6.42 | 9.97 |
| 2584018 | 11.16 | 10.16 | 8.14 | 8.68 | 7.36 | 5.24 | 8.22 | 8.14 | 8.04 | 10.85 | 11.20 | 10.23 |
| 3976341 | 11.55 | 11.44 | 9.43 | 10.80 | 9.95 | 12.12 | 9.97 | 8.10 | 10.67 | 10.44 | 10.70 | 11.21 |
| 2739308 | 4.54 | 4.76 | 4.85 | 7.52 | 6.30 | 4.86 | 5.87 | 5.26 | 5.37 | 4.65 | 4.51 | 4.33 |
| 3959862 | 4.37 | 4.94 | 6.44 | 5.45 | 5.85 | 4.70 | 6.44 | 4.80 | 5.65 | 4.27 | 6.36 | 4.75 |
| 2362351 | 6.68 | 7.58 | 8.97 | 8.59 | 7.55 | 5.52 | 8.49 | 6.84 | 8.53 | 6.91 | 6.87 | 7.94 |
| 3648391 | 4.51 | 5.05 | 7.98 | 5.90 | 5.32 | 3.94 | 5.84 | 5.22 | 7.47 | 8.74 | 4.33 | 6.15 |
| 3009299 | 10.29 | 10.61 | 11.02 | 10.25 | 10.29 | 11.04 | 10.49 | 10.88 | 10.80 | 10.87 | 11.03 | 10.51 |
| 3443464 | 5.01 | 5.48 | 5.92 | 6.80 | 5.69 | 5.00 | 5.87 | 5.76 | 6.48 | 5.30 | 5.79 | 5.29 |
| 2730746 | 5.41 | 7.40 | 5.88 | 5.76 | 6.73 | 5.89 | 8.38 | 8.55 | 6.21 | 5.90 | 4.87 | 5.46 |
| 2427619 | 7.77 | 7.51 | 10.12 | 10.09 | 8.59 | 5.47 | 10.08 | 7.14 | 9.17 | 8.59 | 7.34 | 8.57 |
| 3042001 | 8.02 | 8.15 | 9.02 | 9.00 | 8.43 | 9.24 | 8.28 | 9.76 | 8.69 | 8.51 | 8.69 | 8.40 |
| 2566848 | 4.97 | 5.16 | 7.50 | 6.48 | 5.44 | 5.18 | 5.55 | 5.80 | 5.80 | 5.33 | 5.32 | 6.78 |
| 2984616 | 8.56 | 9.13 | 8.93 | 8.68 | 8.30 | 9.55 | 9.11 | 10.01 | 8.97 | 9.24 | 9.94 | 9.43 |
| 2378068 | 9.50 | 7.45 | 8.83 | 8.14 | 6.76 | 6.23 | 7.38 | 6.48 | 7.70 | 9.50 | 9.74 | 9.25 |
| 2721959 | 12.90 | 12.35 | 7.09 | 6.30 | 6.49 | 5.97 | 7.70 | 11.25 | 6.90 | 12.66 | 8.43 | 11.74 |
| 2877508 | 10.52 | 9.97 | 10.63 | 9.98 | 9.41 | 10.67 | 10.22 | 11.33 | 10.28 | 10.69 | 10.86 | 10.18 |
| 3450861 | 5.56 | 5.69 | 7.80 | 7.64 | 5.40 | 4.68 | 7.22 | 4.99 | 7.02 | 5.65 | 5.81 | 6.40 |
| 2688717 | 7.48 | 8.11 | 10.99 | 9.67 | 8.50 | 5.37 | 9.53 | 7.74 | 9.86 | 7.56 | 7.82 | 10.31 |
| 3270270 | 9.31 | 8.27 | 8.55 | 9.85 | 9.83 | 6.28 | 9.28 | 7.46 | 9.57 | 8.30 | 9.22 | 8.52 |
| 3417703 | 6.81 | 10.08 | 5.08 | 4.54 | 8.34 | 6.88 | 6.46 | 6.75 | 5.17 | 5.22 | 5.04 | 9.39 |
| 3302990 | 7.98 | 7.05 | 7.36 | 6.62 | 6.37 | 8.19 | 7.48 | 9.38 | 6.55 | 7.98 | 7.71 | 7.57 |
| 2377283 | 4.31 | 4.68 | 11.15 | 5.98 | 5.43 | 4.30 | 5.23 | 5.70 | 5.23 | 5.11 | 4.89 | 6.12 |
| 3122678 | 4.49 | 5.02 | 4.80 | 5.04 | 4.73 | 4.65 | 4.18 | 5.85 | 5.18 | 4.51 | 5.58 | 5.09 |
| 2688499 | 9.50 | 10.77 | 8.44 | 7.01 | 8.18 | 7.09 | 9.71 | 10.87 | 8.23 | 9.64 | 7.43 | 10.56 |
| 2377094 | 8.66 | 8.31 | 8.01 | 7.94 | 8.50 | 8.38 | 8.59 | 10.46 | 7.96 | 9.25 | 8.79 | 8.43 |
| 3278198 | 8.46 | 7.57 | 6.59 | 7.03 | 6.85 | 7.43 | 7.75 | 9.53 | 6.35 | 8.92 | 9.06 | 8.23 |
| 2598261 | 13.21 | 12.68 | 9.48 | 7.10 | 8.26 | 9.28 | 7.92 | 10.86 | 10.30 | 12.23 | 11.37 | 12.48 |
| 3982612 | 7.84 | 8.88 | 11.24 | 9.94 | 8.05 | 4.27 | 9.70 | 6.87 | 9.44 | 8.78 | 7.65 | 8.52 |
| 2884845 | 10.34 | 9.16 | 4.37 | 4.65 | 4.91 | 4.90 | 4.54 | 4.78 | 4.89 | 8.53 | 5.19 | 8.73 |
| 3982560 | 5.62 | 6.64 | 9.27 | 8.43 | 6.76 | 4.78 | 8.29 | 6.06 | 8.15 | 6.06 | 6.17 | 7.74 |
| 3204285 | 5.33 | 6.50 | 9.18 | 5.34 | 5.61 | 4.95 | 6.17 | 5.85 | 7.13 | 7.14 | 5.78 | 5.84 |
| 3654699 | 9.72 | 10.71 | 9.34 | 8.45 | 9.39 | 8.54 | 11.29 | 13.21 | 9.80 | 11.67 | 12.70 | 10.58 |
| 2638676 | 6.03 | 6.90 | 10.00 | 7.85 | 8.07 | 6.94 | 7.78 | 6.47 | 8.65 | 8.76 | 7.90 | 7.38 |
| 3367673 | 5.04 | 6.65 | 6.52 | 6.18 | 7.56 | 7.85 | 8.98 | 8.26 | 6.88 | 5.37 | 5.09 | 4.96 |
| 3212008 | 9.45 | 7.83 | 5.91 | 6.91 | 8.35 | 6.15 | 6.77 | 7.05 | 7.02 | 8.10 | 6.05 | 8.93 |
| 3326635 | 10.25 | 10.11 | 10.31 | 10.27 | 10.10 | 7.38 | 10.56 | 9.22 | 10.27 | 10.05 | 10.35 | 10.49 |
| 3031556 | 8.61 | 8.97 | 10.41 | 10.40 | 10.43 | 6.33 | 10.26 | 7.49 | 9.92 | 8.54 | 9.37 | 8.21 |
| 3662201 | 8.10 | 7.51 | 7.89 | 6.95 | 9.94 | 7.91 | 11.02 | 12.00 | 9.43 | 11.27 | 8.82 | 8.94 |
| 2809793 | 7.29 | 8.81 | 10.41 | 9.15 | 7.50 | 5.27 | 10.30 | 7.06 | 9.83 | 8.41 | 7.55 | 7.71 |
| 2817731 | 7.78 | 7.42 | 7.29 | 8.39 | 8.63 | 8.04 | 8.25 | 7.37 | 8.18 | 7.79 | 10.18 | 7.57 |
| 4020655 | 8.31 | 5.84 | 5.17 | 5.81 | 5.88 | 4.75 | 5.46 | 5.02 | 5.42 | 7.22 | 4.76 | 7.40 |
| 3494629 | 8.89 | 8.36 | 4.43 | 4.42 | 4.72 | 5.25 | 4.48 | 5.91 | 4.80 | 7.48 | 4.87 | 9.23 |
| 3852832 | 7.33 | 7.80 | 8.21 | 10.60 | 10.31 | 6.60 | 10.10 | 7.53 | 10.11 | 5.68 | 7.93 | 7.24 |
| 3761959 | 8.91 | 9.02 | 8.76 | 8.49 | 8.74 | 10.43 | 8.41 | 10.01 | 9.41 | 9.77 | 9.90 | 9.16 |
| 2834282 | 8.61 | 7.82 | 5.76 | 6.17 | 6.52 | 8.85 | 5.36 | 8.01 | 6.62 | 7.99 | 6.10 | 7.98 |
| 3341497 | 8.26 | 6.60 | 6.16 | 6.09 | 6.47 | 5.38 | 6.24 | 8.23 | 6.32 | 7.49 | 5.81 | 6.68 |
| 2372812 | 4.17 | 4.49 | 10.30 | 5.19 | 4.69 | 4.54 | 4.88 | 5.10 | 6.29 | 5.44 | 6.29 | 7.71 |
| 2486811 | 8.80 | 9.27 | 9.98 | 10.58 | 11.03 | 6.29 | 10.55 | 8.45 | 10.30 | 9.65 | 10.73 | 9.23 |
| 3768474 | 7.90 | 7.84 | 7.39 | 9.35 | 8.75 | 6.95 | 8.03 | 8.22 | 8.50 | 8.81 | 9.73 | 8.13 |

TABLE 47-continued

Normalized intensity of microarray data for a set of samples.

| TCID | V01 0265 | V01 0266 | V01 0267 | V01 0268 | V01 0269 | V01 0270 | V01 0271 | V01 0272 | V01 0273 | V01 0274 | V01 0275 | V01 0276 |
|---|---|---|---|---|---|---|---|---|---|---|---|---|
| 3142381 | 3.86 | 4.75 | 4.87 | 4.89 | 5.30 | 3.94 | 5.51 | 4.00 | 5.25 | 4.05 | 6.75 | 3.69 |
| 2396750 | 8.15 | 7.83 | 7.26 | 7.03 | 7.13 | 8.50 | 7.04 | 7.17 | 7.41 | 8.73 | 7.15 | 8.19 |
| 3902489 | 10.84 | 11.14 | 10.61 | 12.59 | 12.56 | 9.73 | 11.14 | 9.50 | 11.55 | 9.98 | 10.71 | 10.13 |
| 3032647 | 5.78 | 6.29 | 6.12 | 5.94 | 6.59 | 6.43 | 8.58 | 5.99 | 6.34 | 5.83 | 5.66 | 5.90 |
| 3875642 | 5.21 | 5.15 | 5.40 | 6.41 | 5.60 | 7.05 | 5.98 | 5.54 | 6.65 | 4.82 | 5.19 | 4.93 |
| 4027585 | 9.95 | 10.55 | 9.76 | 12.31 | 12.28 | 9.57 | 10.81 | 9.17 | 11.51 | 9.25 | 11.39 | 9.55 |
| 2352609 | 7.28 | 6.59 | 5.66 | 5.68 | 6.61 | 5.74 | 7.02 | 7.55 | 6.03 | 6.90 | 5.41 | 6.52 |
| 3376529 | 9.54 | 9.81 | 7.85 | 7.79 | 7.70 | 9.37 | 8.88 | 9.43 | 8.53 | 9.62 | 8.19 | 9.90 |
| 2491271 | 13.16 | 13.45 | 13.68 | 13.14 | 13.33 | 11.90 | 13.31 | 12.45 | 13.34 | 13.21 | 13.71 | 13.24 |
| 3874751 | 9.77 | 9.50 | 8.79 | 8.71 | 8.07 | 9.30 | 9.06 | 9.36 | 9.19 | 9.37 | 10.55 | 9.66 |
| 2326463 | 10.87 | 11.25 | 12.77 | 12.13 | 11.31 | 9.03 | 12.30 | 9.58 | 11.83 | 10.74 | 12.69 | 11.69 |
| 3341061 | 6.77 | 6.94 | 7.10 | 7.29 | 8.27 | 6.92 | 7.30 | 7.09 | 7.64 | 7.60 | 9.56 | 7.38 |
| 3839910 | 7.07 | 6.84 | 8.36 | 10.45 | 10.80 | 5.88 | 9.98 | 7.15 | 9.75 | 5.26 | 7.03 | 6.43 |
| 2708855 | 9.41 | 8.02 | 4.10 | 5.33 | 4.06 | 4.13 | 4.18 | 4.48 | 5.00 | 8.21 | 5.31 | 8.48 |
| 3512874 | 11.20 | 11.21 | 12.33 | 12.37 | 12.36 | 9.21 | 12.26 | 10.87 | 12.22 | 10.90 | 11.69 | 11.12 |
| 2701071 | 8.99 | 8.81 | 9.32 | 11.19 | 11.45 | 7.87 | 10.76 | 6.98 | 10.80 | 7.01 | 9.39 | 8.30 |
| 3486096 | 8.10 | 6.15 | 5.42 | 5.73 | 6.77 | 5.59 | 7.05 | 9.12 | 5.75 | 8.25 | 5.33 | 6.66 |
| 2412668 | 8.46 | 8.37 | 8.22 | 8.19 | 8.13 | 8.34 | 8.51 | 8.21 | 8.50 | 8.62 | 9.54 | 8.35 |
| 3329343 | 9.04 | 9.76 | 7.58 | 7.35 | 7.46 | 8.94 | 6.89 | 7.89 | 7.41 | 8.77 | 7.42 | 8.54 |
| 3259367 | 4.44 | 4.85 | 4.17 | 4.61 | 4.49 | 4.00 | 4.18 | 6.08 | 4.43 | 4.84 | 4.09 | 4.58 |
| 3373845 | 8.97 | 11.25 | 9.22 | 8.88 | 9.27 | 7.32 | 9.00 | 7.58 | 9.36 | 8.99 | 10.57 | 9.94 |
| 2321911 | 8.04 | 8.10 | 8.79 | 9.63 | 9.39 | 8.15 | 9.02 | 8.03 | 9.56 | 7.70 | 8.97 | 8.19 |
| 3353914 | 7.91 | 7.44 | 6.52 | 6.64 | 6.52 | 9.57 | 6.40 | 7.03 | 6.73 | 7.60 | 9.66 | 7.32 |
| 3744680 | 6.99 | 7.42 | 7.69 | 8.61 | 8.33 | 6.73 | 8.22 | 7.06 | 8.41 | 7.10 | 9.09 | 6.95 |
| 2373336 | 9.67 | 10.33 | 6.77 | 6.59 | 5.94 | 5.00 | 6.73 | 8.44 | 7.84 | 9.04 | 7.54 | 8.99 |
| 3067478 | 8.60 | 7.42 | 4.82 | 5.11 | 5.19 | 10.12 | 6.25 | 7.35 | 5.94 | 8.15 | 5.00 | 8.29 |
| 3976766 | 6.99 | 7.76 | 8.78 | 9.81 | 9.49 | 6.41 | 9.08 | 6.92 | 9.31 | 7.06 | 8.39 | 7.54 |
| 3246888 | 5.16 | 5.89 | 5.40 | 6.36 | 6.96 | 5.47 | 6.56 | 6.52 | 5.93 | 6.84 | 4.62 | 6.02 |
| 3147985 | 7.21 | 6.75 | 5.40 | 6.28 | 5.82 | 8.61 | 6.80 | 6.73 | 5.81 | 7.09 | 9.54 | 7.26 |
| 3185522 | 8.94 | 9.21 | 8.57 | 9.09 | 9.42 | 9.65 | 9.12 | 9.31 | 9.64 | 10.30 | 11.42 | 9.83 |
| 3861948 | 11.46 | 12.10 | 12.80 | 13.03 | 12.95 | 9.88 | 13.08 | 11.40 | 13.13 | 11.43 | 12.68 | 11.87 |
| 3393479 | 8.02 | 9.98 | 7.65 | 8.71 | 8.46 | 11.52 | 8.16 | 9.08 | 9.32 | 8.72 | 10.30 | 8.32 |
| 3540862 | 7.37 | 6.55 | 6.75 | 6.77 | 6.22 | 7.34 | 6.68 | 8.00 | 6.58 | 7.62 | 6.85 | 6.76 |
| 2777714 | 10.38 | 10.65 | 10.78 | 12.52 | 12.57 | 8.93 | 11.57 | 10.02 | 11.90 | 7.43 | 10.27 | 10.04 |
| 3110395 | 5.94 | 4.46 | 4.28 | 4.56 | 4.96 | 9.39 | 4.33 | 5.03 | 4.65 | 4.96 | 4.56 | 5.54 |
| 3895795 | 8.26 | 8.25 | 7.73 | 9.85 | 10.59 | 7.66 | 8.99 | 7.74 | 9.53 | 7.72 | 8.13 | 7.85 |
| 2854445 | 8.18 | 8.71 | 8.07 | 9.14 | 8.39 | 6.16 | 8.09 | 6.84 | 9.49 | 9.42 | 11.66 | 9.37 |
| 3606034 | 7.37 | 7.13 | 7.05 | 7.02 | 7.41 | 7.62 | 7.48 | 7.61 | 7.19 | 7.28 | 9.12 | 7.65 |
| 3375735 | 7.80 | 7.90 | 7.70 | 8.53 | 7.79 | 7.70 | 8.21 | 7.73 | 8.27 | 7.88 | 8.50 | 8.16 |
| 3948047 | 7.09 | 7.69 | 9.04 | 9.19 | 8.94 | 7.06 | 8.99 | 7.53 | 9.51 | 7.58 | 9.27 | 7.98 |
| 3010503 | 7.58 | 7.78 | 7.56 | 10.40 | 10.42 | 6.75 | 9.69 | 6.84 | 6.93 | 6.79 | 10.98 | 6.98 |
| 3622934 | 8.16 | 7.83 | 7.99 | 5.97 | 6.11 | 10.03 | 6.06 | 7.77 | 6.84 | 7.87 | 5.79 | 7.47 |
| 3441849 | 10.24 | 10.08 | 9.26 | 10.82 | 10.66 | 9.10 | 10.12 | 9.16 | 10.40 | 9.67 | 10.33 | 9.63 |
| 3006572 | 6.83 | 6.58 | 6.45 | 7.04 | 6.41 | 7.17 | 6.49 | 6.84 | 7.14 | 6.73 | 6.35 | 6.44 |
| 3365136 | 9.46 | 9.12 | 8.63 | 8.31 | 8.42 | 10.48 | 8.44 | 9.47 | 8.19 | 8.71 | 8.36 | 9.44 |
| 2642791 | 8.41 | 8.21 | 8.53 | 8.67 | 9.37 | 8.18 | 8.87 | 9.03 | 8.83 | 8.65 | 9.26 | 8.53 |
| 2904485 | 7.65 | 8.98 | 7.38 | 6.90 | 8.14 | 8.90 | 7.90 | 7.34 | 7.71 | 6.79 | 6.66 | 8.43 |
| 3772661 | 9.23 | 10.28 | 8.81 | 10.37 | 10.53 | 11.16 | 9.91 | 8.93 | 10.41 | 10.25 | 11.85 | 10.05 |
| 2796553 | 9.27 | 8.85 | 9.25 | 11.22 | 11.85 | 9.42 | 10.51 | 9.42 | 10.65 | 9.26 | 10.79 | 9.12 |
| 3063795 | 6.60 | 7.25 | 7.21 | 7.54 | 7.59 | 7.08 | 7.24 | 7.06 | 8.17 | 8.40 | 8.09 | 7.07 |
| 3338192 | 10.49 | 10.15 | 8.01 | 7.55 | 8.45 | 10.71 | 8.18 | 9.56 | 8.61 | 10.52 | 8.13 | 10.62 |
| 3214845 | 8.48 | 4.20 | 6.07 | 4.48 | 4.87 | 4.57 | 4.24 | 4.49 | 4.81 | 4.76 | 4.53 | 4.27 |
| 2730303 | 3.89 | 4.49 | 9.15 | 4.47 | 4.28 | 4.49 | 4.21 | 4.86 | 4.49 | 5.02 | 4.42 | 4.54 |
| 3811086 | 7.51 | 7.51 | 7.98 | 7.61 | 7.80 | 8.61 | 7.88 | 7.91 | 7.62 | 8.10 | 8.26 | 7.84 |
| 2981874 | 10.10 | 10.33 | 9.96 | 10.14 | 11.24 | 10.32 | 10.57 | 10.41 | 10.41 | 10.67 | 10.72 | 9.82 |
| 3242353 | 5.65 | 5.96 | 6.29 | 6.15 | 6.19 | 6.66 | 5.84 | 6.47 | 6.16 | 6.29 | 7.55 | 5.92 |
| 2442008 | 8.71 | 7.13 | 5.04 | 5.58 | 5.88 | 8.50 | 5.46 | 5.88 | 6.31 | 7.83 | 5.50 | 8.49 |
| 3564210 | 8.82 | 8.80 | 8.57 | 11.01 | 10.56 | 6.53 | 10.34 | 8.12 | 10.52 | 8.10 | 10.36 | 8.15 |
| 2490351 | 3.81 | 3.85 | 3.91 | 4.43 | 4.36 | 4.37 | 4.10 | 4.31 | 4.35 | 4.00 | 4.26 | 3.88 |
| 3759006 | 7.85 | 8.82 | 8.63 | 11.63 | 11.42 | 7.32 | 9.04 | 7.85 | 10.17 | 6.51 | 8.37 | 7.76 |
| 3264997 | 3.84 | 4.11 | 3.96 | 4.05 | 4.13 | 4.01 | 3.97 | 3.98 | 4.43 | 4.15 | 4.38 | 3.78 |
| 3912079 | 3.62 | 3.48 | 4.03 | 4.37 | 3.93 | 3.53 | 3.76 | 4.51 | 3.91 | 3.74 | 3.93 | 3.50 |
| 2926802 | 5.15 | 5.24 | 6.61 | 6.51 | 5.94 | 4.65 | 5.93 | 4.95 | 6.22 | 4.95 | 5.53 | 4.65 |
| 2430163 | 4.93 | 5.69 | 3.96 | 4.21 | 4.28 | 3.66 | 3.90 | 3.95 | 4.12 | 3.85 | 4.99 | 4.19 |
| 3039830 | 2.99 | 3.40 | 3.07 | 3.20 | 3.24 | 3.56 | 3.06 | 3.73 | 3.66 | 3.27 | 3.13 | 3.40 |
| 3935486 | 8.74 | 6.55 | 8.99 | 6.27 | 6.87 | 5.12 | 5.38 | 5.76 | 6.44 | 6.18 | 9.70 | 5.49 |
| 3457336 | 5.18 | 5.32 | 5.46 | 5.60 | 5.78 | 5.92 | 5.26 | 5.67 | 5.88 | 5.43 | 5.36 | 5.13 |
| 3811949 | 3.33 | 3.33 | 3.48 | 3.80 | 3.50 | 3.64 | 3.59 | 3.61 | 3.82 | 3.51 | 3.57 | 3.43 |
| 3343832 | 3.55 | 3.72 | 3.63 | 4.11 | 4.39 | 4.30 | 3.85 | 4.01 | 4.18 | 3.75 | 3.86 | 3.77 |
| 3161261 | 5.54 | 5.54 | 6.88 | 5.57 | 5.91 | 6.25 | 6.09 | 6.43 | 5.55 | 5.43 | 5.27 | 5.60 |
| 3594003 | 3.58 | 3.56 | 3.64 | 3.86 | 3.93 | 11.91 | 3.58 | 3.77 | 4.12 | 3.63 | 4.20 | 3.63 |
| 3805614 | 4.18 | 4.45 | 4.70 | 5.20 | 5.02 | 10.76 | 4.60 | 4.53 | 5.26 | 4.55 | 4.79 | 4.68 |
| 3364127 | 6.28 | 6.66 | 6.72 | 7.03 | 7.19 | 13.53 | 7.14 | 7.08 | 7.20 | 6.56 | 6.47 | 6.61 |
| 3834341 | 3.61 | 4.11 | 3.85 | 4.15 | 4.25 | 12.18 | 4.14 | 3.92 | 4.16 | 4.06 | 3.95 | 4.59 |
| 2585400 | 4.25 | 4.20 | 4.33 | 4.67 | 4.69 | 9.53 | 4.33 | 4.27 | 4.65 | 4.21 | 4.74 | 4.22 |

TABLE 47-continued

Normalized intensity of microarray data for a set of samples.

| TCID | V01 0265 | V01 0266 | V01 0267 | V01 0268 | V01 0269 | V01 0270 | V01 0271 | V01 0272 | V01 0273 | V01 0274 | V01 0275 | V01 0276 |
|---|---|---|---|---|---|---|---|---|---|---|---|---|
| 2941690 | 3.73 | 3.83 | 4.10 | 4.38 | 4.56 | 4.21 | 4.46 | 4.24 | 4.55 | 4.42 | 4.00 | 4.08 |
| 3484895 | 5.91 | 5.84 | 4.63 | 5.33 | 5.39 | 5.88 | 4.61 | 5.02 | 5.36 | 4.38 | 5.19 | 5.41 |
| 3159754 | 3.49 | 3.60 | 3.74 | 3.72 | 4.08 | 3.72 | 3.69 | 4.04 | 4.18 | 3.74 | 3.66 | 3.56 |
| 2894790 | 3.61 | 3.62 | 4.09 | 3.80 | 4.10 | 3.77 | 3.61 | 4.02 | 4.77 | 6.65 | 3.79 | 3.60 |
| 3363686 | 3.39 | 3.40 | 3.31 | 3.75 | 3.42 | 3.33 | 3.44 | 3.53 | 3.61 | 3.47 | 3.51 | 3.67 |
| 2923928 | 4.34 | 4.14 | 4.67 | 4.70 | 4.75 | 4.15 | 4.29 | 4.54 | 4.73 | 4.06 | 4.34 | 4.22 |
| 2883317 | 4.66 | 4.40 | 5.75 | 4.97 | 4.86 | 4.44 | 4.77 | 5.13 | 5.59 | 4.34 | 5.69 | 4.47 |
| 2479698 | 5.92 | 5.90 | 6.08 | 5.97 | 6.44 | 6.70 | 6.11 | 6.52 | 6.15 | 6.05 | 5.81 | 6.05 |
| 3428225 | 3.58 | 3.55 | 3.59 | 3.98 | 3.80 | 3.75 | 4.06 | 4.03 | 3.60 | 3.58 | 3.48 |
| 393446 | 6.92 | 7.11 | 7.43 | 7.77 | 7.55 | 7.90 | 7.44 | 6.87 | 7.48 | 7.26 | 7.94 | 7.50 |
| 3116614 | 12.06 | 12.52 | 10.44 | 9.06 | 12.20 | 10.36 | 12.58 | 13.09 | 10.80 | 11.44 | 6.76 | 12.54 |
| 3415320 | 10.84 | 11.08 | 7.81 | 6.79 | 8.68 | 9.82 | 9.34 | 10.83 | 8.75 | 10.32 | 7.91 | 10.76 |
| 3757108 | 11.02 | 10.99 | 7.61 | 7.26 | 7.99 | 8.51 | 7.43 | 8.88 | 7.80 | 9.70 | 8.71 | 10.83 |
| 1012178 | 11.84 | 8.82 | 6.27 | 6.42 | 6.83 | 8.79 | 7.19 | 9.22 | 6.78 | 10.29 | 6.54 | 10.41 |
| 3546213 | 11.04 | 11.17 | 8.73 | 6.10 | 9.86 | 7.98 | 10.16 | 11.27 | 8.36 | 11.02 | 6.11 | 11.06 |
| 3561381 | 10.21 | 9.97 | 6.75 | 5.89 | 8.41 | 9.15 | 8.76 | 9.94 | 7.07 | 10.37 | 6.17 | 10.32 |

TABLE 48

Normalized intensity of microarray data for a set of samples.

| TCID | V01 0277 | V01 0278 | V01 0279 | V01 0280 | V01 0281 | V01 0282 | V01 0283 | V01 0284 | V01 0285 | V01 0286 | V01 0287 | V01 0288 |
|---|---|---|---|---|---|---|---|---|---|---|---|---|
| 2604998 | 8.25 | 8.28 | 7.81 | 8.52 | 7.74 | 7.92 | 7.46 | 7.87 | 8.75 | 8.36 | 8.52 | 8.70 |
| 3603932 | 7.18 | 7.95 | 7.05 | 6.92 | 6.45 | 7.65 | 6.94 | 8.00 | 7.64 | 7.29 | 7.20 |
| 2710599 | 8.25 | 11.63 | 5.84 | 8.60 | 4.94 | 7.97 | 6.64 | 7.23 | 11.03 | 7.16 | 12.11 | 10.33 |
| 2440258 | 8.62 | 4.96 | 7.58 | 6.70 | 7.38 | 7.95 | 8.86 | 7.74 | 4.80 | 5.61 | 5.04 | 7.01 |
| 3169331 | 7.06 | 7.45 | 8.53 | 7.61 | 7.47 | 8.26 | 5.99 | 7.90 | 6.77 | 8.41 | 7.49 | 6.89 |
| 2988882 | 9.75 | 10.02 | 9.75 | 10.42 | 11.61 | 10.19 | 9.77 | 9.44 | 10.04 | 9.84 | 9.76 | 9.24 |
| 2964231 | 9.04 | 9.98 | 7.88 | 8.37 | 8.42 | 9.85 | 7.96 | 7.99 | 10.30 | 9.34 | 9.28 | 6.91 |
| 3111561 | 10.37 | 6.06 | 7.08 | 9.28 | 9.13 | 9.10 | 7.45 | 7.03 | 5.26 | 9.88 | 4.90 | 8.20 |
| 2562529 | 9.48 | 10.64 | 9.26 | 9.71 | 8.32 | 9.03 | 8.83 | 9.50 | 10.85 | 10.17 | 11.07 | 11.03 |
| 3692999 | 13.14 | 7.94 | 12.15 | 13.17 | 11.06 | 12.54 | 10.04 | 12.09 | 9.48 | 12.45 | 6.32 | 12.53 |
| 2439554 | 7.29 | 4.98 | 6.70 | 6.33 | 6.65 | 7.12 | 8.34 | 7.24 | 4.78 | 5.26 | 5.11 | 5.92 |
| 2685304 | 8.30 | 11.63 | 7.45 | 8.23 | 7.64 | 8.25 | 7.42 | 6.38 | 11.70 | 6.05 | 11.43 | 10.17 |
| 2578790 | 6.11 | 4.15 | 6.85 | 6.63 | 6.60 | 7.57 | 6.10 | 7.94 | 4.40 | 5.36 | 4.26 | 4.60 |
| 2373842 | 11.32 | 9.00 | 11.31 | 9.63 | 11.48 | 11.50 | 11.76 | 10.97 | 8.30 | 9.76 | 9.04 | 10.49 |
| 2750627 | 10.42 | 10.41 | 9.30 | 10.24 | 9.67 | 7.86 | 7.65 | 9.33 | 10.46 | 10.50 | 10.80 | 8.28 |
| 3397774 | 4.72 | 4.69 | 5.47 | 4.63 | 5.70 | 5.66 | 5.45 | 5.29 | 5.31 | 5.28 | 4.47 | 5.02 |
| 2635741 | 8.50 | 5.79 | 8.25 | 7.22 | 8.06 | 8.27 | 8.86 | 7.94 | 5.83 | 7.07 | 5.98 | 7.76 |
| 3970833 | 9.41 | 10.02 | 9.43 | 9.52 | 10.18 | 10.08 | 9.38 | 9.85 | 10.21 | 10.06 | 9.73 | 9.32 |
| 3577612 | 10.39 | 11.64 | 10.82 | 9.46 | 10.71 | 10.65 | 10.67 | 10.45 | 11.36 | 9.91 | 11.80 | 10.70 |
| 2708922 | 8.45 | 8.01 | 8.91 | 8.15 | 8.29 | 7.74 | 8.04 | 7.72 | 8.45 | 7.64 | 8.74 | 8.32 |
| 2970897 | 6.37 | 5.54 | 5.55 | 5.23 | 5.87 | 7.37 | 5.30 | 5.63 | 5.02 | 8.00 | 7.58 | 4.93 |
| 3724545 | 9.80 | 9.69 | 10.02 | 9.57 | 9.91 | 9.23 | 9.58 | 9.87 | 9.30 | 10.04 | 9.71 | 8.41 |
| 2798538 | 9.50 | 8.88 | 8.85 | 9.29 | 8.62 | 8.40 | 8.94 | 9.73 | 9.06 | 8.94 | 8.71 | 8.22 |
| 2806468 | 10.76 | 8.19 | 10.49 | 8.25 | 10.82 | 10.73 | 11.45 | 9.53 | 7.85 | 9.33 | 8.69 | 10.94 |
| 2880051 | 6.54 | 5.74 | 6.99 | 5.95 | 6.74 | 6.42 | 6.85 | 6.51 | 5.86 | 6.81 | 5.80 | 6.15 |
| 2732508 | 5.84 | 3.35 | 3.92 | 6.09 | 3.52 | 3.89 | 7.81 | 4.16 | 3.78 | 3.57 | 3.44 | 4.48 |
| 2822492 | 5.99 | 5.53 | 5.66 | 5.77 | 5.37 | 6.39 | 5.51 | 5.33 | 6.70 | 5.41 | 6.14 |
| 3404030 | 8.77 | 5.34 | 7.61 | 5.92 | 7.72 | 8.87 | 8.43 | 7.76 | 5.28 | 6.33 | 5.30 | 7.88 |
| 3059667 | 10.84 | 4.03 | 8.71 | 10.57 | 10.55 | 5.01 | 7.78 | 9.13 | 5.08 | 9.78 | 4.67 | 8.01 |
| 3108526 | 10.30 | 9.18 | 9.05 | 9.57 | 10.72 | 10.68 | 8.50 | 9.81 | 9.39 | 11.69 | 6.19 | 9.71 |
| 2526806 | 11.40 | 12.77 | 8.44 | 10.68 | 6.52 | 10.93 | 10.15 | 9.95 | 12.64 | 7.67 | 12.96 | 8.17 |
| 2428501 | 7.66 | 7.92 | 5.90 | 6.25 | 6.69 | 8.06 | 7.66 | 5.39 | 5.48 | 5.59 | 7.76 | 6.33 |
| 2657808 | 6.49 | 11.58 | 5.51 | 7.07 | 5.86 | 5.49 | 6.22 | 5.74 | 10.71 | 5.30 | 11.85 | 8.06 |
| 2584018 | 9.23 | 10.62 | 7.20 | 8.04 | 7.30 | 6.96 | 7.62 | 6.13 | 10.63 | 5.64 | 10.87 | 10.74 |
| 3976341 | 9.82 | 11.58 | 9.31 | 8.16 | 8.98 | 9.51 | 9.87 | 8.73 | 11.14 | 8.21 | 11.29 | 10.64 |
| 2739308 | 5.41 | 4.46 | 5.75 | 5.10 | 5.80 | 5.37 | 5.06 | 5.20 | 4.73 | 5.20 | 5.28 | 5.13 |
| 3959862 | 5.19 | 5.02 | 6.93 | 5.30 | 4.21 | 4.85 | 5.50 | 5.71 | 4.45 | 5.12 | 4.45 | 5.01 |
| 2362351 | 7.82 | 5.05 | 7.51 | 6.16 | 7.70 | 7.83 | 8.18 | 6.88 | 5.60 | 6.54 | 5.48 | 7.04 |
| 3648391 | 4.38 | 3.99 | 4.71 | 5.60 | 4.70 | 4.28 | 7.36 | 3.89 | 4.07 | 4.45 | 4.48 | 4.52 |
| 3009299 | 10.59 | 10.87 | 10.33 | 11.13 | 11.12 | 10.80 | 10.83 | 10.38 | 11.02 | 10.85 | 10.87 | 10.62 |
| 3443464 | 5.91 | 5.06 | 5.87 | 5.54 | 5.68 | 5.79 | 6.03 | 6.37 | 5.26 | 5.40 | 5.03 | 5.66 |
| 2730746 | 8.00 | 6.44 | 8.07 | 8.57 | 7.47 | 8.44 | 6.44 | 8.81 | 6.70 | 9.73 | 4.91 | 7.61 |
| 2427661 | 8.76 | 5.39 | 8.24 | 7.28 | 8.56 | 8.73 | 8.71 | 7.69 | 5.49 | 6.81 | 6.18 | 7.89 |
| 3042001 | 8.85 | 8.79 | 9.26 | 9.45 | 8.94 | 9.43 | 8.73 | 9.03 | 8.51 | 9.01 | 8.06 | 8.17 |
| 2566848 | 5.54 | 5.49 | 5.71 | 5.18 | 5.19 | 6.05 | 6.38 | 5.48 | 5.23 | 5.14 | 5.04 | 5.32 |
| 2984616 | 9.24 | 9.52 | 9.00 | 9.37 | 8.90 | 9.54 | 8.92 | 9.39 | 9.47 | 9.47 | 8.97 | 9.11 |
| 2378068 | 8.00 | 9.23 | 7.48 | 7.57 | 7.25 | 7.97 | 7.67 | 7.57 | 7.58 | 7.21 | 8.34 | 7.81 |
| 2721959 | 5.67 | 12.78 | 6.49 | 7.07 | 5.70 | 9.59 | 7.91 | 6.10 | 13.01 | 5.97 | 12.93 | 7.13 |

TABLE 48-continued

Normalized intensity of microarray data for a set of samples.

| TCID | V01 0277 | V01 0278 | V01 0279 | V01 0280 | V01 0281 | V01 0282 | V01 0283 | V01 0284 | V01 0285 | V01 0286 | V01 0287 | V01 0288 |
|---|---|---|---|---|---|---|---|---|---|---|---|---|
| 2877508 | 10.51 | 10.80 | 10.24 | 10.58 | 9.76 | 10.83 | 10.07 | 9.86 | 10.72 | 10.52 | 10.61 | 10.16 |
| 3450861 | 6.12 | 4.60 | 5.53 | 5.65 | 5.79 | 6.39 | 6.66 | 5.68 | 4.74 | 5.03 | 4.74 | 5.74 |
| 2688717 | 8.89 | 5.58 | 9.23 | 7.15 | 8.52 | 8.50 | 9.61 | 8.57 | 5.84 | 7.19 | 6.08 | 8.39 |
| 3270270 | 8.41 | 8.61 | 8.58 | 7.05 | 8.65 | 8.34 | 8.82 | 7.75 | 8.16 | 7.16 | 9.20 | 8.40 |
| 3417703 | 11.20 | 8.85 | 10.55 | 11.44 | 8.44 | 4.99 | 5.61 | 9.99 | 5.54 | 10.41 | 7.47 | 9.62 |
| 3302990 | 7.57 | 8.56 | 8.27 | 8.13 | 7.93 | 8.80 | 7.28 | 8.03 | 8.25 | 8.06 | 7.97 | 7.05 |
| 2377283 | 4.78 | 3.97 | 5.02 | 5.35 | 5.09 | 4.71 | 8.84 | 4.55 | 4.30 | 4.47 | 4.27 | 4.73 |
| 3122678 | 4.24 | 4.78 | 5.13 | 5.19 | 4.67 | 4.69 | 6.03 | 5.20 | 4.94 | 5.29 | 4.58 | 4.96 |
| 2688499 | 10.45 | 10.29 | 8.43 | 10.48 | 6.59 | 9.91 | 8.16 | 8.45 | 9.47 | 9.62 | 9.97 | 10.57 |
| 2377094 | 9.18 | 9.32 | 8.62 | 9.62 | 9.19 | 10.39 | 8.32 | 7.99 | 9.87 | 9.94 | 9.04 | 8.22 |
| 3278198 | 8.10 | 8.94 | 8.09 | 8.56 | 8.00 | 9.07 | 6.97 | 7.82 | 9.47 | 8.96 | 8.54 | 8.16 |
| 2598261 | 10.63 | 12.76 | 7.50 | 9.50 | 6.10 | 10.00 | 9.50 | 8.79 | 12.27 | 7.51 | 13.17 | 7.36 |
| 3982612 | 8.98 | 5.57 | 8.03 | 7.49 | 8.49 | 8.40 | 9.30 | 8.40 | 5.00 | 7.02 | 5.80 | 8.41 |
| 2884845 | 4.16 | 9.61 | 4.96 | 5.02 | 4.37 | 4.47 | 4.48 | 5.05 | 10.32 | 5.34 | 10.29 | 8.05 |
| 3982560 | 6.78 | 4.24 | 6.82 | 5.62 | 6.36 | 6.72 | 7.54 | 7.46 | 4.77 | 5.38 | 5.79 | 6.81 |
| 3204285 | 6.31 | 5.24 | 5.56 | 6.70 | 5.70 | 6.22 | 6.75 | 6.36 | 5.37 | 5.43 | 5.46 | 5.47 |
| 3654699 | 11.69 | 11.92 | 11.66 | 11.22 | 10.44 | 13.08 | 10.86 | 12.00 | 11.77 | 11.85 | 9.48 | 11.57 |
| 2638676 | 7.14 | 5.94 | 7.84 | 6.74 | 7.15 | 7.20 | 8.76 | 6.99 | 5.86 | 6.05 | 6.32 | 6.65 |
| 3367673 | 8.50 | 4.66 | 8.11 | 9.13 | 8.16 | 8.38 | 7.56 | 8.80 | 5.50 | 9.52 | 4.14 | 5.81 |
| 3212008 | 6.36 | 7.71 | 7.18 | 7.38 | 6.51 | 6.28 | 6.51 | 6.69 | 9.34 | 6.88 | 8.16 | 8.99 |
| 3326635 | 10.26 | 10.25 | 10.05 | 10.09 | 9.56 | 9.74 | 9.95 | 10.00 | 10.01 | 10.28 | 10.31 | 10.03 |
| 3031556 | 9.24 | 6.45 | 8.73 | 7.10 | 9.40 | 9.22 | 9.57 | 8.73 | 6.41 | 7.84 | 6.47 | 8.38 |
| 3662201 | 13.01 | 8.83 | 11.93 | 13.20 | 10.35 | 12.85 | 10.11 | 12.16 | 9.17 | 12.47 | 7.87 | 12.65 |
| 2809793 | 9.47 | 4.84 | 7.70 | 7.00 | 8.34 | 8.94 | 9.92 | 7.73 | 4.79 | 5.29 | 4.89 | 8.25 |
| 2817731 | 8.10 | 8.51 | 7.44 | 7.63 | 7.52 | 7.73 | 7.73 | 8.02 | 7.60 | 7.33 | 7.49 | 7.58 |
| 4020655 | 4.94 | 6.69 | 5.28 | 6.99 | 4.86 | 5.03 | 4.96 | 5.13 | 7.72 | 5.10 | 7.71 | 7.91 |
| 3494629 | 4.90 | 7.07 | 4.68 | 4.76 | 4.86 | 4.80 | 4.49 | 4.57 | 7.55 | 5.06 | 9.09 | 4.88 |
| 3852832 | 8.82 | 6.47 | 8.96 | 7.12 | 9.33 | 9.51 | 9.47 | 8.08 | 6.40 | 7.73 | 7.33 | 7.95 |
| 3761959 | 8.73 | 9.43 | 9.53 | 10.17 | 8.77 | 9.56 | 8.93 | 9.64 | 9.42 | 9.26 | 9.34 | 9.76 |
| 2834282 | 5.76 | 8.47 | 6.18 | 7.28 | 6.07 | 6.71 | 6.48 | 6.95 | 7.83 | 7.13 | 8.94 | 8.34 |
| 3341497 | 5.97 | 7.54 | 6.09 | 6.34 | 6.23 | 5.77 | 6.18 | 6.44 | 8.21 | 5.94 | 6.56 | 6.56 |
| 2372812 | 4.84 | 4.37 | 5.24 | 6.25 | 4.56 | 5.27 | 9.45 | 4.98 | 4.87 | 4.92 | 4.66 | 4.54 |
| 2486811 | 10.29 | 9.00 | 9.42 | 8.55 | 9.90 | 9.54 | 10.04 | 9.32 | 6.61 | 7.55 | 7.32 | 8.61 |
| 3768474 | 8.36 | 8.11 | 8.68 | 7.98 | 8.71 | 7.72 | 7.95 | 7.66 | 7.59 | 7.46 | 8.16 | 7.83 |
| 3142381 | 6.01 | 4.83 | 5.92 | 6.03 | 4.63 | 4.83 | 5.24 | 5.06 | 3.86 | 5.21 | 4.92 | 3.61 |
| 2396750 | 6.82 | 7.79 | 7.21 | 7.65 | 6.55 | 7.15 | 7.23 | 7.38 | 7.99 | 6.54 | 8.20 | 6.97 |
| 3902489 | 11.14 | 9.59 | 11.59 | 9.10 | 12.10 | 10.70 | 11.18 | 11.13 | 9.57 | 10.03 | 10.70 | 10.71 |
| 3032647 | 7.75 | 6.50 | 7.83 | 6.39 | 7.87 | 7.19 | 6.90 | 8.50 | 5.91 | 7.65 | 5.57 | 6.25 |
| 3875642 | 5.30 | 4.66 | 6.02 | 5.38 | 5.64 | 6.36 | 6.39 | 5.71 | 5.23 | 5.46 | 5.25 | 5.61 |
| 4027585 | 10.93 | 9.26 | 11.69 | 9.41 | 11.94 | 10.35 | 11.03 | 10.64 | 9.09 | 9.63 | 9.04 | 9.93 |
| 2352609 | 6.67 | 7.03 | 7.09 | 7.14 | 6.04 | 6.41 | 6.31 | 6.35 | 8.13 | 7.28 | 6.92 | 6.98 |
| 3376529 | 8.86 | 10.15 | 7.96 | 9.05 | 8.83 | 8.87 | 8.77 | 7.91 | 9.98 | 8.80 | 9.99 | 9.98 |
| 2491271 | 13.61 | 13.37 | 12.39 | 12.48 | 13.21 | 13.24 | 13.25 | 12.89 | 12.71 | 12.80 | 13.17 | 12.82 |
| 3874751 | 9.82 | 10.06 | 10.11 | 9.12 | 8.85 | 9.12 | 8.74 | 10.17 | 10.43 | 9.84 | 9.33 | 9.66 |
| 2326463 | 12.24 | 11.77 | 11.45 | 8.88 | 11.85 | 11.78 | 12.16 | 11.83 | 8.48 | 10.24 | 9.74 | 11.64 |
| 3341061 | 7.46 | 7.65 | 7.23 | 7.34 | 7.48 | 6.70 | 7.49 | 7.07 | 6.37 | 7.78 | 7.35 | 7.24 |
| 3839910 | 8.42 | 5.60 | 8.83 | 6.05 | 9.26 | 8.71 | 9.12 | 7.74 | 5.62 | 6.92 | 7.17 | 8.14 |
| 2708855 | 4.28 | 8.27 | 5.09 | 6.59 | 5.15 | 4.22 | 4.29 | 4.19 | 8.38 | 4.12 | 9.47 | 7.50 |
| 3512874 | 11.91 | 10.74 | 11.82 | 10.10 | 11.94 | 11.82 | 12.10 | 9.54 | 10.37 | 10.79 | 11.14 | |
| 2701071 | 9.95 | 6.60 | 9.36 | 8.10 | 1.48 | 10.19 | 10.65 | 9.87 | 7.56 | 8.85 | 8.53 | 8.99 |
| 3486096 | 8.22 | 8.47 | 7.47 | 9.17 | 7.44 | 7.78 | 6.56 | 8.00 | 8.79 | 8.53 | 7.35 | 9.23 |
| 2412668 | 8.38 | 8.58 | 8.04 | 8.40 | 7.80 | 8.19 | 8.19 | 8.13 | 7.87 | 7.99 | 8.01 | 7.82 |
| 3329343 | 7.03 | 9.03 | 6.83 | 7.16 | 7.62 | 7.96 | 7.16 | 7.30 | 7.58 | 7.58 | 9.22 | 8.07 |
| 3259367 | 4.38 | 5.32 | 4.35 | 5.27 | 4.16 | 4.26 | 4.30 | 4.43 | 5.61 | 4.40 | 4.65 | 5.15 |
| 3373845 | 9.68 | 10.04 | 8.60 | 11.10 | 7.84 | 8.35 | 8.82 | 8.41 | 6.90 | 8.18 | 7.82 | 7.78 |
| 2321911 | 8.80 | 7.68 | 9.12 | 7.68 | 9.14 | 7.99 | 9.05 | 8.28 | 8.06 | 8.30 | 7.83 | 7.95 |
| 3353914 | 7.30 | 8.26 | 6.68 | 6.88 | 6.08 | 6.63 | 6.40 | 5.93 | 7.39 | 6.82 | 8.52 | 6.61 |
| 3744680 | 7.92 | 6.88 | 7.87 | 7.11 | 7.54 | 7.55 | 7.85 | 7.25 | 6.50 | 6.81 | 6.56 | 7.32 |
| 2373336 | 6.27 | 9.90 | 5.32 | 6.40 | 9.72 | 5.75 | 6.88 | 5.58 | 8.36 | 6.06 | 10.10 | 6.07 |
| 3067478 | 6.56 | 8.39 | 5.42 | 7.31 | 8.07 | 6.13 | 6.11 | 5.18 | 8.19 | 8.50 | 8.35 | 8.55 |
| 3976766 | 8.37 | 6.65 | 8.51 | 7.15 | 8.68 | 8.25 | 8.73 | 8.15 | 6.45 | 6.94 | 6.82 | 7.63 |
| 3246888 | 7.61 | 4.55 | 6.05 | 7.91 | 6.22 | 6.12 | 5.85 | 5.71 | 6.03 | 7.85 | 5.02 | 6.75 |
| 3147985 | 7.18 | 8.09 | 6.87 | 6.48 | 6.47 | 6.70 | 5.73 | 6.04 | 7.72 | 6.60 | 7.34 | 6.77 |
| 3185522 | 9.98 | 10.07 | 9.32 | 10.05 | 9.07 | 9.30 | 8.77 | 8.96 | 8.97 | 9.28 | 9.30 | 9.70 |
| 3861948 | 12.62 | 11.15 | 12.52 | 10.97 | 12.76 | 12.66 | 12.94 | 12.37 | 9.77 | 11.65 | 10.73 | 12.18 |
| 3393479 | 9.82 | 9.39 | 7.98 | 10.32 | 8.07 | 9.51 | 9.43 | 9.06 | 7.50 | 10.48 | 8.56 | 10.00 |
| 3540862 | 6.95 | 7.68 | 6.28 | 7.06 | 7.06 | 7.22 | 6.58 | 7.06 | 8.34 | 7.25 | 7.55 | 7.25 |
| 2777714 | 11.45 | 7.65 | 12.01 | 9.63 | 12.19 | 10.98 | 11.81 | 11.44 | 9.87 | 10.14 | 9.92 | 10.94 |
| 3110395 | 4.23 | 5.58 | 5.59 | 5.02 | 6.67 | 4.40 | 4.76 | 5.00 | 6.63 | 5.82 | 6.61 | 5.03 |
| 3895795 | 7.84 | 8.49 | 9.13 | 7.91 | 8.36 | 8.12 | 8.72 | 8.18 | 7.73 | 7.98 | 8.46 | |
| 2854445 | 10.31 | 9.22 | 7.75 | 8.03 | 8.06 | 8.20 | 8.74 | 9.33 | 6.65 | 7.36 | 7.89 | 7.27 |
| 3606034 | 7.73 | 8.01 | 7.75 | 7.74 | 7.42 | 7.50 | 7.01 | 7.85 | 7.53 | 7.53 | 7.41 | 7.15 |
| 3375735 | 8.38 | 8.09 | 7.41 | 7.91 | 7.70 | 8.25 | 7.86 | 7.43 | 7.70 | 7.54 | 7.52 | 8.08 |
| 3948047 | 8.45 | 7.59 | 8.24 | 7.55 | 8.58 | 8.33 | 9.03 | 8.05 | 6.79 | 7.19 | 6.86 | 7.77 |
| 3010503 | 10.02 | 9.09 | 8.87 | 7.57 | 9.95 | 8.90 | 9.26 | 8.27 | 6.20 | 6.80 | 7.04 | 8.20 |

TABLE 48-continued

Normalized intensity of microarray data for a set of samples.

| TCID | V01 0277 | V01 0278 | V01 0279 | V01 0280 | V01 0281 | V01 0282 | V01 0283 | V01 0284 | V01 0285 | V01 0286 | V01 0287 | V01 0288 |
|---|---|---|---|---|---|---|---|---|---|---|---|---|
| 3622934 | 6.90 | 8.12 | 5.74 | 7.64 | 7.59 | 7.48 | 7.02 | 7.05 | 5.06 | 6.51 | 8.56 | 8.61 |
| 3441849 | 9.85 | 9.72 | 10.06 | 9.42 | 9.96 | 9.72 | 10.03 | 9.65 | 9.42 | 9.70 | 9.87 | 9.78 |
| 3006572 | 6.43 | 6.46 | 6.55 | 6.85 | 6.87 | 6.62 | 6.63 | 6.44 | 6.04 | 7.17 | 7.03 | 6.56 |
| 3365136 | 9.04 | 9.00 | 9.02 | 9.45 | 8.92 | 8.64 | 8.37 | 8.30 | 9.49 | 8.78 | 8.86 | 10.45 |
| 2642791 | 8.56 | 8.28 | 8.85 | 9.14 | 8.56 | 8.37 | 8.31 | 8.87 | 8.50 | 8.88 | 8.43 | 7.95 |
| 2904485 | 9.69 | 7.21 | 9.25 | 9.37 | 8.13 | 7.70 | 8.07 | 9.52 | 8.01 | 9.22 | 7.83 | 8.55 |
| 3772661 | 10.52 | 10.31 | 8.96 | 9.07 | 9.58 | 9.43 | 10.19 | 8.94 | 9.32 | 9.74 | 9.85 | 10.03 |
| 2796553 | 10.02 | 9.48 | 9.78 | 8.41 | 10.10 | 9.96 | 9.91 | 9.69 | 9.04 | 9.00 | 8.32 | 8.49 |
| 3063795 | 7.62 | 7.17 | 7.49 | 7.69 | 6.69 | 6.90 | 7.88 | 7.54 | 7.07 | 7.25 | 6.98 | 7.58 |
| 3338192 | 9.39 | 10.09 | 9.28 | 9.77 | 8.44 | 8.52 | 8.44 | 8.55 | 9.95 | 9.12 | 11.19 | 10.38 |
| 3214845 | 4.00 | 4.45 | 4.76 | 5.11 | 4.39 | 4.89 | 4.40 | 4.57 | 5.06 | 4.94 | 5.13 | 4.29 |
| 2730303 | 4.21 | 3.98 | 4.82 | 5.65 | 4.35 | 4.12 | 8.06 | 4.77 | 4.53 | 4.28 | 4.02 | 4.56 |
| 3811086 | 8.24 | 8.04 | 7.98 | 7.96 | 7.63 | 7.54 | 7.60 | 7.72 | 7.84 | 7.49 | 7.69 | 7.20 |
| 2981874 | 10.75 | 10.40 | 10.48 | 10.60 | 10.36 | 11.03 | 10.31 | 10.99 | 10.38 | 10.99 | 10.37 | 8.92 |
| 3242353 | 6.41 | 6.43 | 5.78 | 6.21 | 6.22 | 6.07 | 6.28 | 6.34 | 5.92 | 6.20 | 6.10 | 5.60 |
| 2442008 | 5.32 | 8.12 | 6.15 | 5.58 | 5.32 | 5.46 | 5.36 | 6.12 | 8.72 | 7.20 | 8.17 | 8.23 |
| 3564210 | 9.51 | 8.55 | 9.34 | 7.55 | 9.29 | 9.42 | 9.76 | 8.65 | 7.91 | 8.42 | 8.09 | 8.58 |
| 2490351 | 3.98 | 3.97 | 4.59 | 4.16 | 4.20 | 4.09 | 4.29 | 4.50 | 4.09 | 4.24 | 4.01 | 4.09 |
| 3759006 | 9.42 | 6.31 | 10.45 | 7.71 | 10.90 | 8.61 | 9.31 | 9.56 | 7.23 | 8.59 | 7.84 | 8.73 |
| 3264997 | 3.91 | 3.96 | 4.30 | 4.27 | 4.22 | 4.26 | 4.29 | 4.59 | 4.09 | 4.17 | 4.01 | 4.13 |
| 3912079 | 3.55 | 3.49 | 3.79 | 3.74 | 3.65 | 3.93 | 4.13 | 3.61 | 3.73 | 4.30 | 3.55 | 4.04 |
| 2926802 | 5.74 | 4.71 | 5.41 | 5.13 | 5.87 | 5.17 | 6.14 | 5.49 | 4.77 | 4.78 | 4.76 | 5.02 |
| 2430163 | 3.64 | 6.32 | 3.96 | 3.92 | 3.93 | 3.80 | 3.70 | 3.82 | 4.30 | 3.90 | 9.22 | 3.87 |
| 3039830 | 3.10 | 3.16 | 3.53 | 3.42 | 3.17 | 3.76 | 3.37 | 3.17 | 3.29 | 3.10 | 3.10 | 4.05 |
| 3935486 | 7.21 | 7.89 | 6.20 | 6.47 | 4.80 | 4.78 | 5.74 | 5.46 | 5.73 | 5.74 | 7.33 | 4.97 |
| 3457336 | 5.18 | 5.26 | 5.90 | 5.46 | 5.90 | 5.52 | 5.60 | 5.97 | 5.58 | 5.56 | 5.25 | 5.60 |
| 3811949 | 3.51 | 3.39 | 3.77 | 3.45 | 3.45 | 3.46 | 3.64 | 3.66 | 3.45 | 3.57 | 3.37 | 3.68 |
| 3343832 | 3.69 | 3.76 | 4.43 | 4.33 | 3.85 | 3.91 | 3.91 | 4.23 | 4.08 | 3.87 | 3.75 | 3.90 |
| 3161261 | 5.16 | 4.98 | 5.93 | 5.86 | 5.67 | 5.94 | 6.08 | 6.57 | 5.67 | 6.36 | 5.18 | 6.14 |
| 3594003 | 3.72 | 3.47 | 4.64 | 3.84 | 3.67 | 3.94 | 3.62 | 3.91 | 3.73 | 3.80 | 3.59 | 3.96 |
| 3805614 | 4.27 | 4.74 | 4.82 | 4.89 | 4.48 | 4.97 | 4.99 | 5.16 | 4.86 | 4.36 | 4.84 | 4.70 |
| 3364127 | 6.42 | 6.41 | 9.92 | 6.89 | 6.82 | 6.95 | 7.80 | 7.18 | 6.63 | 6.85 | 6.51 | 6.96 |
| 3834341 | 4.06 | 3.94 | 4.96 | 4.02 | 4.05 | 4.03 | 4.44 | 4.59 | 4.19 | 4.00 | 4.32 | 4.28 |
| 2585400 | 4.56 | 4.43 | 4.67 | 4.39 | 4.31 | 4.42 | 4.55 | 5.18 | 4.22 | 4.21 | 4.16 | 4.29 |
| 2941690 | 3.83 | 4.18 | 4.69 | 4.21 | 3.80 | 4.36 | 4.64 | 4.63 | 4.60 | 4.22 | 4.35 | 4.39 |
| 3484895 | 4.55 | 5.39 | 5.51 | 5.42 | 5.32 | 5.05 | 5.18 | 5.11 | 5.73 | 4.79 | 5.23 | 5.41 |
| 3159754 | 3.60 | 3.52 | 3.89 | 3.96 | 3.87 | 3.71 | 3.96 | 3.87 | 3.84 | 3.76 | 3.75 | 3.76 |
| 2894790 | 3.71 | 3.92 | 4.71 | 4.32 | 3.71 | 4.04 | 3.96 | 4.50 | 3.88 | 3.75 | 3.74 | 3.90 |
| 3363686 | 3.27 | 3.26 | 4.60 | 3.85 | 3.50 | 3.60 | 3.35 | 4.01 | 3.77 | 3.38 | 3.47 | 3.58 |
| 2923928 | 4.00 | 4.19 | 4.57 | 4.24 | 4.22 | 4.30 | 4.39 | 4.32 | 4.34 | 4.57 | 3.96 | 4.32 |
| 2883317 | 4.47 | 4.46 | 5.35 | 4.70 | 4.93 | 4.70 | 4.09 | 5.06 | 4.71 | 4.69 | 4.61 | 5.11 |
| 2479698 | 5.84 | 5.86 | 6.25 | 6.41 | 5.94 | 6.30 | 5.91 | 6.57 | 6.58 | 6.41 | 6.12 | 6.40 |
| 3428225 | 3.60 | 3.69 | 4.21 | 3.88 | 3.71 | 4.17 | 3.91 | 4.22 | 3.73 | 3.61 | 3.51 | 3.76 |
| 3393446 | 7.63 | 7.28 | 7.50 | 7.65 | 7.39 | 7.42 | 7.42 | 7.41 | 7.00 | 7.27 | 6.78 | 7.25 |
| 3116614 | 12.59 | 11.94 | 13.00 | 13.07 | 12.58 | 12.80 | 11.74 | 13.14 | 12.70 | 12.99 | 11.24 | 12.31 |
| 3415320 | 9.80 | 11.02 | 10.29 | 9.55 | 11.24 | 10.12 | 8.30 | 10.50 | 10.91 | 9.70 | 10.98 | 9.97 |
| 3757108 | 7.81 | 10.94 | 7.32 | 7.99 | 7.05 | 7.73 | 7.59 | 8.10 | 9.69 | 8.02 | 11.78 | 10.08 |
| 4012178 | 6.40 | 10.14 | 7.11 | 7.61 | 6.19 | 6.31 | 6.50 | 6.50 | 11.73 | 6.89 | 10.88 | 7.43 |
| 3546213 | 10.63 | 11.05 | 10.83 | 11.35 | 10.67 | 10.33 | 9.01 | 11.14 | 10.98 | 11.32 | 10.34 | 10.87 |
| 3561381 | 9.84 | 9.81 | 9.29 | 10.30 | 9.53 | 9.44 | 8.57 | 10.19 | 10.28 | 10.45 | 10.03 | 10.18 |

TABLE 49

Normalized intensity of microarray data for a set of samples.

| TCID | V01 0289 | V01 0290 | V01 0291 | V01 0292 | V01 0293 | V01 0294 | V01 0295 | V01 0296 | V01 0297 | V01 0298 | V01 0299 | V01 0300 |
|---|---|---|---|---|---|---|---|---|---|---|---|---|
| 2604998 | 8.38 | 7.92 | 6.85 | 7.58 | 6.69 | 7.82 | 8.54 | 8.20 | 9.08 | 7.55 | 8.52 | 6.45 |
| 3603932 | 6.49 | 8.52 | 7.94 | 8.13 | 6.93 | 6.89 | 6.46 | 6.71 | 7.01 | 7.55 | 7.45 | 6.68 |
| 2710599 | 5.73 | 9.53 | 7.66 | 7.75 | 11.10 | 6.07 | 8.80 | 5.84 | 10.28 | 8.13 | 8.44 | 6.08 |
| 2440258 | 8.79 | 6.84 | 8.34 | 7.92 | 9.13 | 8.84 | 7.74 | 7.55 | 5.24 | 8.84 | 6.31 | 9.05 |
| 3169331 | 7.16 | 7.80 | 7.33 | 8.20 | 6.92 | 6.48 | 7.71 | 7.78 | 7.40 | 6.83 | 6.72 | 6.35 |
| 2988882 | 9.93 | 9.80 | 10.18 | 9.99 | 9.69 | 9.54 | 9.91 | 10.38 | 9.58 | 9.90 | 10.04 | 9.66 |
| 2964231 | 6.98 | 9.99 | 10.27 | 10.00 | 8.39 | 7.99 | 9.12 | 8.95 | 9.04 | 10.05 | 9.42 | 8.28 |
| 3111561 | 9.63 | 9.88 | 9.60 | 9.54 | 4.72 | 9.56 | 10.73 | 8.38 | 9.90 | 9.46 | 10.29 | 6.52 |
| 2562529 | 8.83 | 9.79 | 9.61 | 9.22 | 9.73 | 8.87 | 9.80 | 9.70 | 9.52 | 9.92 | 8.14 | |
| 3692999 | 10.58 | 12.07 | 11.94 | 12.54 | 6.97 | 10.32 | 10.78 | 12.68 | 11.65 | 10.29 | 13.05 | 10.85 |
| 2439554 | 6.56 | 6.25 | 7.59 | 6.76 | 8.22 | 6.80 | 7.83 | 6.65 | 5.55 | 7.21 | 4.98 | 7.87 |
| 2685304 | 7.84 | 8.41 | 8.35 | 8.46 | 9.70 | 6.04 | 6.88 | 7.14 | 9.16 | 9.20 | 9.01 | 7.38 |
| 2578790 | 6.59 | 6.21 | 5.92 | 6.25 | 4.20 | 6.96 | 7.83 | 7.64 | 6.86 | 5.88 | 6.86 | 5.61 |
| 2373842 | 11.89 | 10.20 | 11.20 | 11.50 | 11.80 | 11.85 | 10.96 | 10.75 | 10.20 | 11.52 | 10.12 | 11.94 |

TABLE 49-continued

Normalized intensity of microarray data for a set of samples.

| TCID | V01 0289 | V01 0290 | V01 0291 | V01 0292 | V01 0293 | V01 0294 | V01 0295 | V01 0296 | V01 0297 | V01 0298 | V01 0299 | V01 0300 |
|---|---|---|---|---|---|---|---|---|---|---|---|---|
| 2750627 | 8.49 | 9.83 | 8.34 | 7.79 | 9.31 | 8.42 | 9.68 | 10.69 | 10.15 | 9.03 | 10.20 | 7.77 |
| 3397774 | 4.98 | 4.69 | 4.84 | 4.78 | 4.71 | 4.91 | 4.74 | 4.65 | 4.70 | 4.50 | 4.88 | 5.44 |
| 2635741 | 9.02 | 6.70 | 8.23 | 8.62 | 9.03 | 9.60 | 8.38 | 8.04 | 7.07 | 9.31 | 6.27 | 9.05 |
| 3970833 | 9.59 | 9.58 | 9.54 | 9.66 | 8.99 | 9.05 | 9.41 | 9.78 | 9.74 | 9.36 | 9.36 | 8.91 |
| 3577612 | 10.90 | 10.22 | 10.66 | 10.95 | 11.49 | 10.69 | 10.11 | 9.44 | 10.08 | 10.76 | 9.61 | 11.47 |
| 2708922 | 9.15 | 7.48 | 8.52 | 8.24 | 8.74 | 8.85 | 7.51 | 9.76 | 7.99 | 8.27 | 8.02 | 9.10 |
| 2970897 | 5.29 | 6.29 | 6.25 | 6.46 | 5.17 | 4.86 | 4.76 | 4.70 | 4.97 | 6.06 | 5.86 | 5.26 |
| 3724545 | 10.17 | 9.25 | 9.37 | 9.60 | 9.34 | 8.89 | 8.83 | 6.89 | 10.14 | 9.12 | 9.56 | 9.27 |
| 2798538 | 9.01 | 9.05 | 9.44 | 9.00 | 9.14 | 9.02 | 9.36 | 9.33 | 8.78 | 9.35 | 9.06 | 8.54 |
| 2806468 | 11.27 | 9.34 | 10.98 | 11.04 | 11.66 | 11.96 | 9.80 | 10.26 | 9.69 | 11.42 | 8.66 | 11.61 |
| 2880051 | 7.62 | 6.14 | 6.28 | 6.50 | 6.78 | 6.29 | 6.00 | 6.08 | 6.18 | 6.69 | 6.12 | 6.89 |
| 2732508 | 3.62 | 6.31 | 3.38 | 3.32 | 5.85 | 3.63 | 7.35 | 7.02 | 3.73 | 5.42 | 3.51 | 3.79 |
| 2822492 | 5.70 | 5.23 | 5.18 | 4.92 | 5.25 | 5.18 | 5.51 | 6.81 | 5.72 | 5.52 | 5.34 | 6.40 |
| 3404030 | 9.73 | 5.99 | 8.61 | 8.20 | 7.90 | 8.20 | 7.26 | 7.89 | 6.77 | 8.80 | 6.53 | 8.73 |
| 3059667 | 10.52 | 10.18 | 10.39 | 8.72 | 4.81 | 9.26 | 10.92 | 12.62 | 10.49 | 8.42 | 11.11 | 9.96 |
| 3108555 | 9.96 | 9.75 | 8.45 | 9.73 | 5.60 | 9.31 | 9.67 | 8.93 | 9.86 | 9.12 | 10.02 | 7.81 |
| 2526806 | 6.82 | 11.86 | 11.32 | 12.07 | 12.73 | 8.84 | 11.08 | 10.06 | 11.11 | 11.48 | 11.12 | 7.55 |
| 2428501 | 6.86 | 8.01 | 8.06 | 7.61 | 7.20 | 7.12 | 6.56 | 6.73 | 5.97 | 7.98 | 6.47 | 7.45 |
| 2657808 | 5.85 | 7.10 | 5.70 | 5.92 | 7.76 | 5.75 | 6.07 | 5.35 | 7.35 | 6.69 | 9.02 | 5.66 |
| 2584018 | 7.24 | 10.47 | 10.04 | 8.35 | 9.67 | 8.34 | 7.87 | 6.58 | 7.62 | 9.68 | 9.93 | 7.79 |
| 3976341 | 9.74 | 9.27 | 10.15 | 10.17 | 11.10 | 9.20 | 8.85 | 7.76 | 9.87 | 11.00 | 9.25 | 10.18 |
| 2739308 | 6.07 | 4.35 | 4.59 | 5.16 | 5.14 | 5.07 | 4.81 | 4.19 | 4.87 | 5.05 | 5.20 | 5.89 |
| 3959862 | 5.64 | 5.23 | 6.74 | 6.02 | 6.09 | 4.78 | 4.44 | 3.88 | 4.10 | 5.16 | 4.42 | 5.36 |
| 2362351 | 8.67 | 6.25 | 7.17 | 7.98 | 8.42 | 8.16 | 7.29 | 7.30 | 6.15 | 8.34 | 6.31 | 8.19 |
| 3648391 | 4.26 | 4.22 | 5.74 | 4.95 | 5.34 | 5.98 | 6.03 | 6.49 | 5.02 | 5.77 | 4.32 | 5.84 |
| 3009299 | 10.85 | 10.78 | 10.76 | 10.97 | 10.45 | 10.40 | 10.98 | 10.76 | 10.59 | 10.81 | 10.26 | 10.31 |
| 3443464 | 6.31 | 5.32 | 5.47 | 5.83 | 5.56 | 6.03 | 5.52 | 5.67 | 5.39 | 5.98 | 5.45 | 6.64 |
| 2730746 | 7.85 | 7.66 | 6.94 | 7.16 | 5.18 | 6.89 | 8.79 | 10.02 | 8.05 | 7.39 | 7.81 | 7.70 |
| 2427619 | 9.57 | 6.00 | 8.17 | 8.56 | 8.94 | 9.57 | 8.25 | 8.40 | 6.84 | 9.55 | 5.85 | 9.43 |
| 3042001 | 9.20 | 8.80 | 8.20 | 8.78 | 8.61 | 8.47 | 8.95 | 8.65 | 8.41 | 8.71 | 8.73 | 8.06 |
| 2566848 | 5.79 | 5.11 | 5.29 | 5.45 | 6.42 | 6.65 | 5.37 | 5.16 | 5.01 | 5.43 | 4.99 | 5.82 |
| 2984616 | 9.00 | 9.11 | 9.63 | 9.71 | 9.03 | 8.88 | 9.48 | 9.52 | 9.36 | 9.12 | 9.77 | 9.06 |
| 2378068 | 7.70 | 9.83 | 10.15 | 8.84 | 8.17 | 6.97 | 8.91 | 8.50 | 6.17 | 8.78 | 6.64 | 7.10 |
| 2721959 | 5.72 | 9.34 | 7.99 | 9.88 | 10.65 | 6.27 | 8.49 | 5.23 | 10.65 | 8.11 | 8.42 | 6.08 |
| 2877508 | 10.40 | 10.53 | 10.58 | 10.66 | 10.17 | 9.57 | 10.26 | 10.34 | 10.51 | 10.70 | 10.28 | 9.62 |
| 3450861 | 6.95 | 5.14 | 5.80 | 6.11 | 7.17 | 8.04 | 5.66 | 6.45 | 5.42 | 6.40 | 5.97 | 6.93 |
| 2688717 | 9.32 | 7.06 | 8.68 | 8.82 | 10.09 | 10.45 | 9.60 | 8.51 | 9.25 | 9.17 | 7.29 | 9.69 |
| 3270270 | 8.78 | 8.06 | 8.79 | 9.25 | 9.26 | 8.70 | 7.90 | 7.64 | 7.62 | 8.92 | 7.55 | 9.95 |
| 3417703 | 5.12 | 10.34 | 7.72 | 8.18 | 4.67 | 6.56 | 10.29 | 8.40 | 9.90 | 9.50 | 10.84 | 6.38 |
| 3302990 | 7.17 | 7.59 | 7.55 | 7.68 | 7.51 | 6.99 | 7.52 | 7.40 | 7.58 | 7.43 | 7.62 | 7.06 |
| 2377283 | 4.76 | 4.21 | 4.72 | 4.76 | 8.48 | 6.00 | 4.77 | 4.42 | 4.29 | 4.95 | 4.41 | 5.14 |
| 3122678 | 5.56 | 4.80 | 5.19 | 4.56 | 4.95 | 4.78 | 5.13 | 4.67 | 4.81 | 4.94 | 5.06 | 5.27 |
| 2688499 | 8.32 | 10.30 | 9.03 | 9.04 | 7.30 | 7.93 | 10.06 | 9.78 | 10.02 | 9.45 | 9.86 | 7.22 |
| 2377094 | 8.73 | 9.21 | 8.70 | 9.33 | 7.66 | 8.55 | 8.63 | 9.78 | 9.59 | 8.72 | 9.45 | 7.91 |
| 3278198 | 6.25 | 8.67 | 8.66 | 8.15 | 7.08 | 6.48 | 8.17 | 7.99 | 8.64 | 8.09 | 8.45 | 6.86 |
| 2598261 | 6.91 | 11.58 | 10.79 | 11.45 | 12.77 | 8.56 | 10.41 | 9.42 | 10.12 | 10.71 | 10.35 | 6.86 |
| 3982612 | 9.19 | 4.81 | 8.06 | 8.78 | 10.12 | 10.28 | 9.12 | 8.94 | 7.06 | 9.94 | 6.12 | 10.03 |
| 2884845 | 4.75 | 4.78 | 4.76 | 4.58 | 7.47 | 4.60 | 4.57 | 5.41 | 5.49 | 4.67 | 4.72 | 4.57 |
| 3982560 | 6.88 | 5.11 | 6.74 | 7.30 | 8.38 | 8.16 | 7.02 | 6.13 | 5.26 | 7.65 | 5.72 | 8.11 |
| 3204285 | 5.77 | 5.42 | 5.86 | 5.14 | 8.53 | 5.71 | 5.99 | 6.60 | 5.55 | 6.17 | 5.06 | 6.38 |
| 3654699 | 11.29 | 12.58 | 12.32 | 12.40 | 10.67 | 10.37 | 11.39 | 10.22 | 11.54 | 12.45 | 12.02 | 7.86 |
| 2638676 | 6.78 | 6.94 | 7.06 | 7.68 | 8.35 | 7.84 | 6.86 | 7.06 | 6.81 | 8.01 | 6.27 | 7.38 |
| 3367673 | 7.23 | 8.40 | 7.17 | 7.49 | 4.53 | 8.49 | 8.57 | 7.61 | 8.85 | 7.37 | 7.92 | 6.43 |
| 3212008 | 6.31 | 6.63 | 6.88 | 6.68 | 6.51 | 6.40 | 6.19 | 7.97 | 9.98 | 7.43 | 7.58 | 6.83 |
| 3326635 | 9.90 | 10.25 | 10.21 | 10.44 | 10.30 | 10.26 | 10.32 | 10.76 | 10.43 | 10.59 | 10.18 | 10.29 |
| 3031556 | 10.26 | 8.30 | 9.41 | 9.25 | 10.09 | 9.96 | 8.53 | 8.88 | 7.11 | 9.65 | 7.93 | 10.14 |
| 3662201 | 10.89 | 12.32 | 11.77 | 12.19 | 7.65 | 10.72 | 10.41 | 12.50 | 11.33 | 9.60 | 12.47 | 11.32 |
| 2809793 | 10.46 | 5.80 | 8.05 | 7.80 | 9.56 | 8.64 | 9.00 | 9.04 | 5.70 | 9.83 | 6.21 | 8.50 |
| 2817731 | 7.63 | 9.15 | 9.14 | 8.83 | 8.24 | 7.81 | 8.03 | 8.16 | 7.77 | 8.78 | 7.86 | 8.33 |
| 4020655 | 5.28 | 5.15 | 4.70 | 5.10 | 5.83 | 5.45 | 4.88 | 6.77 | 8.98 | 6.00 | 5.47 | 5.95 |
| 3494629 | 4.59 | 5.13 | 4.42 | 4.36 | 7.28 | 4.34 | 4.41 | 5.59 | 6.23 | 4.66 | 4.68 | 4.83 |
| 3852832 | 9.40 | 6.33 | 8.28 | 9.19 | 10.17 | 9.74 | 6.59 | 7.35 | 7.38 | 7.62 | 10.89 | |
| 3761959 | 9.31 | 9.72 | 9.42 | 9.38 | 8.62 | 8.73 | 9.41 | 9.23 | 9.73 | 9.60 | 9.64 | 8.34 |
| 2834282 | 6.68 | 5.62 | 6.98 | 5.43 | 6.45 | 6.52 | 5.42 | 5.44 | 8.10 | 5.93 | 8.88 | 6.02 |
| 3341497 | 6.21 | 5.51 | 6.02 | 7.43 | 6.33 | 6.46 | 5.34 | 6.19 | 7.40 | 5.84 | 6.15 | 6.80 |
| 2372812 | 5.06 | 4.63 | 4.61 | 4.80 | 7.74 | 4.88 | 5.68 | 4.73 | 4.72 | 4.52 | 4.83 | 5.65 |
| 2486811 | 10.15 | 10.45 | 10.68 | 10.74 | 10.46 | 9.25 | 9.47 | 9.08 | 7.87 | 10.31 | 8.58 | 10.68 |
| 3768474 | 8.22 | 8.83 | 8.97 | 8.16 | 8.51 | 7.64 | 8.01 | 8.25 | 7.81 | 8.96 | 8.51 | 8.23 |
| 3142381 | 5.50 | 5.02 | 5.28 | 6.00 | 4.85 | 4.73 | 6.95 | 7.50 | 4.43 | 5.89 | 6.21 | 5.15 |
| 2396750 | 7.03 | 6.31 | 6.50 | 6.70 | 8.11 | 6.69 | 6.78 | 6.40 | 7.45 | 7.03 | 7.09 | 7.09 |
| 3902489 | 11.60 | 9.74 | 11.52 | 11.06 | 11.19 | 11.86 | 9.91 | 10.39 | 9.42 | 11.34 | 10.55 | 11.57 |
| 3032647 | 8.89 | 7.85 | 5.93 | 6.60 | 5.69 | 7.00 | 7.27 | 9.61 | 7.30 | 6.87 | 7.19 | 7.09 |
| 3875642 | 6.58 | 5.15 | 5.33 | 5.78 | 5.60 | 5.57 | 7.54 | 5.19 | 4.92 | 5.56 | 4.96 | 6.31 |
| 4027585 | 11.40 | 10.53 | 11.64 | 10.95 | 11.16 | 11.65 | 9.60 | 9.95 | 9.07 | 11.25 | 10.47 | 11.13 |
| 2352609 | 7.01 | 6.91 | 5.96 | 6.52 | 5.80 | 6.64 | 6.81 | 8.03 | 8.34 | 6.80 | 6.82 | 6.36 |

TABLE 49-continued

Normalized intensity of microarray data for a set of samples.

| TCID | V01 0289 | V01 0290 | V01 0291 | V01 0292 | V01 0293 | V01 0294 | V01 0295 | V01 0296 | V01 0297 | V01 0298 | V01 0299 | V01 0300 |
|---|---|---|---|---|---|---|---|---|---|---|---|---|
| 3376529 | 9.22 | 8.05 | 7.77 | 7.42 | 8.76 | 7.53 | 8.66 | 8.40 | 9.16 | 9.03 | 9.07 | 7.83 |
| 2491271 | 13.30 | 13.46 | 13.53 | 13.51 | 13.62 | 13.44 | 13.45 | 13.28 | 12.67 | 13.46 | 13.19 | 13.30 |
| 3874751 | 8.93 | 9.86 | 10.05 | 9.34 | 9.34 | 8.44 | 9.16 | 8.79 | 9.08 | 9.71 | 9.63 | 8.49 |
| 2326463 | 12.47 | 12.38 | 12.43 | 12.73 | 12.40 | 12.59 | 11.99 | 11.08 | 10.10 | 11.87 | 11.97 | 12.17 |
| 3341061 | 6.33 | 8.93 | 9.14 | 8.98 | 7.72 | 6.62 | 7.05 | 7.13 | 7.39 | 8.61 | 7.91 | 6.85 |
| 3839910 | 8.87 | 5.71 | 8.44 | 9.64 | 9.54 | 9.49 | 5.77 | 6.58 | 6.62 | 8.46 | 7.74 | 11.07 |
| 2708855 | 4.20 | 4.91 | 4.00 | 4.45 | 7.23 | 4.28 | 4.11 | 3.69 | 5.36 | 4.49 | 4.18 | 4.33 |
| 3512874 | 12.06 | 11.35 | 12.04 | 12.06 | 12.24 | 12.08 | 11.40 | 11.13 | 10.71 | 11.93 | 10.99 | 12.33 |
| 2701071 | 9.97 | 8.15 | 10.29 | 10.51 | 10.81 | 10.40 | 8.48 | 8.46 | 8.43 | 9.88 | 9.00 | 11.41 |
| 3486096 | 6.40 | 8.13 | 6.62 | 7.73 | 5.12 | 7.33 | 7.90 | 10.03 | 8.86 | 6.95 | 8.16 | 7.40 |
| 2412668 | 8.01 | 8.86 | 8.93 | 8.49 | 8.91 | 8.43 | 8.02 | 9.00 | 8.05 | 8.76 | 7.87 | 8.88 |
| 3329343 | 7.36 | 8.22 | 7.51 | 6.66 | 8.96 | 6.90 | 7.60 | 7.16 | 7.38 | 6.93 | 8.14 | 7.60 |
| 3259367 | 4.21 | 4.14 | 4.28 | 4.75 | 4.13 | 4.61 | 4.26 | 4.02 | 6.80 | 5.30 | 4.97 | 4.23 |
| 3373845 | 8.39 | 10.84 | 10.65 | 10.32 | 9.48 | 9.05 | 9.53 | 8.19 | 7.71 | 10.06 | 11.38 | 8.41 |
| 2321911 | 9.14 | 8.19 | 9.31 | 8.55 | 8.27 | 8.93 | 8.40 | 7.96 | 7.77 | 8.89 | 8.73 | 9.01 |
| 3353916 | 6.36 | 7.86 | 8.37 | 8.68 | 7.14 | 6.60 | 6.62 | 6.40 | 6.77 | 8.34 | 7.41 | 6.39 |
| 3744680 | 8.03 | 7.69 | 8.27 | 8.01 | 8.00 | 7.91 | 7.16 | 6.95 | 6.87 | 8.25 | 7.28 | 8.44 |
| 2373336 | 6.45 | 7.32 | 6.96 | 6.26 | 8.66 | 6.98 | 8.40 | 5.79 | 6.94 | 7.43 | 6.83 | 5.21 |
| 3067478 | 5.33 | 7.37 | 5.25 | 6.31 | 6.80 | 5.40 | 6.26 | 8.56 | 7.74 | 5.09 | 6.23 | 6.27 |
| 3976766 | 8.62 | 7.63 | 8.26 | 8.56 | 8.78 | 8.62 | 7.21 | 7.54 | 6.84 | 8.31 | 7.51 | 9.57 |
| 3246888 | 6.39 | 6.75 | 6.26 | 6.29 | 4.90 | 6.07 | 6.75 | 7.61 | 7.63 | 6.38 | 7.14 | 6.67 |
| 3147985 | 5.90 | 8.64 | 7.56 | 8.45 | 6.71 | 5.52 | 6.56 | 6.71 | 6.76 | 8.40 | 7.39 | 6.37 |
| 3185522 | 8.92 | 11.25 | 10.92 | 10.35 | 9.40 | 8.36 | 9.88 | 9.59 | 9.39 | 10.38 | 10.11 | 9.25 |
| 3861948 | 12.88 | 12.10 | 12.76 | 12.91 | 13.00 | 12.82 | 12.15 | 11.93 | 11.03 | 12.65 | 12.18 | 13.27 |
| 3393479 | 8.13 | 9.55 | 9.89 | 10.13 | 8.94 | 8.63 | 9.64 | 10.13 | 8.71 | 9.69 | 9.34 | 9.20 |
| 3540862 | 6.66 | 6.45 | 6.59 | 6.53 | 6.15 | 7.04 | 7.08 | 7.54 | 7.57 | 6.95 | 6.73 | 6.44 |
| 2777714 | 11.78 | 9.18 | 11.52 | 11.31 | 11.58 | 12.22 | 10.00 | 10.31 | 9.72 | 11.67 | 10.97 | 11.54 |
| 3110395 | 5.48 | 4.20 | 4.24 | 4.26 | 4.58 | 4.35 | 4.56 | 4.67 | 5.54 | 4.42 | 4.86 | 4.79 |
| 3895795 | 8.68 | 7.81 | 7.70 | 8.73 | 9.11 | 8.93 | 7.14 | 6.99 | 8.11 | 8.03 | 7.81 | 10.03 |
| 2854445 | 8.24 | 11.18 | 11.62 | 10.46 | 9.60 | 7.32 | 9.36 | 9.38 | 7.66 | 11.07 | 9.79 | 8.77 |
| 3606034 | 7.42 | 8.31 | 8.49 | 8.42 | 6.95 | 7.32 | 7.71 | 7.37 | 7.90 | 8.35 | 7.84 | 6.94 |
| 3375735 | 8.71 | 7.83 | 8.52 | 8.04 | 8.09 | 8.14 | 7.36 | 7.48 | 7.36 | 8.09 | 8.09 | 8.08 |
| 3948047 | 8.61 | 8.46 | 9.17 | 8.94 | 9.07 | 8.32 | 8.06 | 7.43 | 7.42 | 8.88 | 8.34 | 9.14 |
| 3010503 | 9.49 | 9.44 | 10.60 | 9.65 | 9.39 | 8.72 | 8.95 | 8.01 | 7.34 | 8.91 | 10.21 | 9.65 |
| 3622934 | 6.22 | 6.09 | 5.76 | 6.72 | 7.10 | 6.76 | 6.02 | 6.75 | 8.14 | 6.77 | 7.60 | 5.97 |
| 3441849 | 9.97 | 9.91 | 10.05 | 10.07 | 10.38 | 9.81 | 9.54 | 8.99 | 9.27 | 10.08 | 9.50 | 10.75 |
| 3006572 | 6.48 | 6.42 | 6.20 | 6.43 | 6.69 | 6.56 | 6.70 | 6.30 | 6.53 | 6.48 | 6.17 | 6.77 |
| 3365136 | 7.99 | 8.73 | 8.11 | 8.64 | 8.46 | 9.00 | 8.80 | 8.30 | 9.77 | 9.25 | 9.79 | 8.58 |
| 2642791 | 8.14 | 8.43 | 8.96 | 8.90 | 8.76 | 8.36 | 8.49 | 8.27 | 8.18 | 8.87 | 8.37 | 8.31 |
| 2904485 | 8.39 | 8.63 | 7.80 | 7.90 | 6.40 | 8.19 | 8.93 | 9.82 | 8.93 | 8.04 | 8.95 | 8.11 |
| 3772661 | 9.29 | 11.24 | 11.59 | 11.02 | 10.33 | 9.62 | 10.27 | 9.62 | 8.93 | 11.14 | 10.20 | 10.16 |
| 2796553 | 10.09 | 9.73 | 10.28 | 10.50 | 10.21 | 10.43 | 9.09 | 8.96 | 9.68 | 10.18 | 9.65 | 11.56 |
| 3063795 | 7.37 | 8.48 | 8.74 | 7.87 | 7.87 | 7.24 | 7.79 | 7.72 | 6.83 | 8.12 | 7.72 | 7.92 |
| 3338192 | 7.94 | 9.01 | 8.88 | 8.67 | 9.03 | 7.83 | 9.08 | 9.20 | 9.68 | 8.64 | 9.38 | 7.85 |
| 3214845 | 4.67 | 5.21 | 4.15 | 4.18 | 4.27 | 5.85 | 4.40 | 4.08 | 5.10 | 4.29 | 4.80 | 4.46 |
| 2730303 | 4.41 | 4.23 | 4.23 | 4.44 | 7.50 | 4.29 | 5.09 | 3.99 | 4.21 | 4.17 | 4.00 | 4.36 |
| 3811086 | 7.76 | 8.45 | 7.97 | 7.97 | 7.64 | 7.89 | 7.99 | 8.21 | 8.11 | 7.88 | 7.81 | 7.80 |
| 2981874 | 10.47 | 10.29 | 10.40 | 10.48 | 10.51 | 9.93 | 10.15 | 10.59 | 9.98 | 10.09 | 10.45 | 10.91 |
| 3242353 | 6.03 | 6.12 | 6.35 | 6.26 | 6.01 | 5.63 | 6.24 | 6.38 | 5.77 | 6.48 | 6.23 | 6.18 |
| 2442008 | 6.05 | 5.25 | 5.23 | 5.00 | 6.10 | 5.23 | 5.02 | 5.14 | 7.08 | 4.94 | 5.63 | 5.81 |
| 3564210 | 9.80 | 9.57 | 9.95 | 10.08 | 10.24 | 9.97 | 7.89 | 8.02 | 8.17 | 9.84 | 8.65 | 11.03 |
| 2490351 | 4.34 | 3.99 | 4.01 | 4.14 | 4.07 | 4.22 | 4.09 | 3.82 | 4.01 | 3.87 | 3.96 | 4.23 |
| 3759006 | 9.85 | 6.80 | 10.25 | 8.98 | 9.99 | 11.03 | 7.35 | 8.28 | 7.33 | 9.88 | 9.51 | 9.89 |
| 3264997 | 4.34 | 4.27 | 4.17 | 4.28 | 4.86 | 4.20 | 3.98 | 3.93 | 4.25 | 3.98 | 4.06 | 4.50 |
| 3912079 | 3.87 | 3.37 | 3.60 | 3.81 | 4.04 | 4.34 | 3.64 | 3.58 | 3.50 | 3.90 | 3.57 | 3.77 |
| 2926802 | 5.52 | 4.64 | 5.19 | 4.99 | 6.03 | 5.54 | 5.03 | 4.77 | 4.80 | 5.37 | 5.25 | 6.05 |
| 2430163 | 3.85 | 4.70 | 3.80 | 3.87 | 4.62 | 4.05 | 3.77 | 3.68 | 3.88 | 3.48 | 3.93 | 3.79 |
| 3039830 | 3.32 | 3.41 | 3.09 | 3.24 | 3.02 | 3.49 | 3.50 | 3.04 | 3.09 | 3.08 | 3.23 | 3.26 |
| 3935486 | 4.76 | 9.82 | 9.10 | 7.27 | 10.38 | 6.09 | 6.58 | 5.94 | 5.52 | 8.81 | 8.03 | 5.71 |
| 3457336 | 5.62 | 8.67 | 5.28 | 5.36 | 6.30 | 5.50 | 5.35 | 5.13 | 5.20 | 5.08 | 5.36 | 5.64 |
| 3811949 | 3.56 | 3.47 | 3.34 | 3.52 | 3.44 | 3.58 | 3.31 | 3.32 | 3.45 | 3.33 | 3.42 | 3.72 |
| 3343832 | 4.05 | 3.77 | 3.90 | 3.80 | 3.64 | 3.87 | 3.84 | 3.80 | 3.82 | 3.96 | 4.03 |  |
| 3161261 | 6.41 | 5.93 | 5.67 | 6.07 | 6.25 | 6.89 | 6.35 | 5.70 | 6.43 | 5.80 | 5.46 | 6.62 |
| 3594003 | 3.95 | 3.78 | 3.97 | 3.60 | 3.76 | 3.93 | 3.77 | 3.62 | 3.62 | 3.58 | 3.53 | 3.95 |
| 3805614 | 4.29 | 4.59 | 5.13 | 4.84 | 4.69 | 4.87 | 4.32 | 4.40 | 4.40 | 4.65 | 4.53 | 5.39 |
| 3364127 | 6.93 | 6.86 | 6.59 | 6.82 | 7.08 | 7.25 | 6.82 | 6.74 | 6.19 | 6.59 | 7.31 | 7.24 |
| 3834341 | 4.30 | 4.00 | 4.03 | 4.18 | 4.06 | 4.10 | 4.09 | 3.76 | 3.91 | 3.77 | 4.07 | 4.47 |
| 2585400 | 4.54 | 4.11 | 4.57 | 4.37 | 5.65 | 4.64 | 4.51 | 4.37 | 4.12 | 5.07 | 4.34 | 4.81 |
| 2941690 | 4.32 | 4.16 | 4.30 | 4.18 | 4.44 | 4.51 | 3.88 | 4.13 | 4.36 | 3.77 | 4.21 | 4.63 |
| 3484895 | 5.15 | 4.23 | 4.67 | 4.69 | 4.89 | 5.15 | 4.58 | 4.38 | 5.07 | 4.52 | 4.64 | 5.24 |
| 3159754 | 3.96 | 3.53 | 3.75 | 3.92 | 3.72 | 3.81 | 3.80 | 3.57 | 3.78 | 3.54 | 3.93 | 3.92 |
| 2894790 | 3.80 | 3.65 | 3.78 | 4.17 | 3.85 | 3.93 | 3.89 | 5.12 | 3.75 | 3.89 | 3.79 | 4.42 |
| 3363686 | 3.59 | 3.44 | 3.43 | 3.31 | 3.42 | 3.51 | 3.55 | 3.38 | 3.41 | 3.21 | 3.68 | 3.48 |
| 2923928 | 4.64 | 4.35 | 4.12 | 4.06 | 4.27 | 4.31 | 4.47 | 4.06 | 4.21 | 4.27 | 4.11 | 4.68 |
| 2883317 | 5.26 | 4.65 | 4.63 | 4.92 | 4.67 | 5.87 | 4.94 | 4.90 | 5.19 | 5.17 | 4.18 | 5.10 |

TABLE 49-continued

Normalized intensity of microarray data for a set of samples.

| TCID | V01 0289 | V01 0290 | V01 0291 | V01 0292 | V01 0293 | V01 0294 | V01 0295 | V01 0296 | V01 0297 | V01 0298 | V01 0299 | V01 0300 |
|---|---|---|---|---|---|---|---|---|---|---|---|---|
| 2479698 | 6.21 | 5.86 | 5.86 | 5.77 | 5.84 | 6.45 | 6.06 | 6.31 | 6.34 | 6.12 | 6.13 | 6.22 |
| 3428225 | 3.71 | 3.73 | 3.74 | 3.61 | 3.66 | 3.79 | 3.49 | 3.50 | 3.69 | 3.45 | 3.59 | 4.14 |
| 3393446 | 7.31 | 8.14 | 8.29 | 7.94 | 7.91 | 7.47 | 7.04 | 7.11 | 7.22 | 7.18 | 7.32 | 7.89 |
| 3116614 | 12.80 | 12.41 | 11.57 | 12.27 | 9.50 | 12.37 | 12.95 | 12.75 | 13.42 | 12.73 | 12.92 | 11.93 |
| 3415320 | 10.79 | 9.67 | 8.98 | 8.37 | 9.47 | 8.62 | 9.94 | 9.90 | 9.70 | 9.50 | 9.81 | 7.80 |
| 3757108 | 7.17 | 8.51 | 8.20 | 7.63 | 10.25 | 7.53 | 8.36 | 9.74 | 7.74 | 7.92 | 8.30 | 8.03 |
| 4012178 | 6.53 | 6.76 | 6.40 | 7.27 | 7.68 | 6.32 | 6.27 | 6.61 | 10.20 | 7.46 | 8.20 | 6.44 |
| 3546213 | 10.40 | 10.61 | 10.26 | 9.80 | 8.53 | 9.80 | 11.41 | 11.18 | 11.60 | 10.71 | 11.30 | 9.01 |
| 3561381 | 9.39 | 9.57 | 8.49 | 8.39 | 8.39 | 8.57 | 10.27 | 10.99 | 10.78 | 8.75 | 10.48 | 8.92 |

TABLE 50

Normalized intensity of microarray data for a set of samples.

| TCID | V01 0301 | V01 0302 | V01 0303 | V01 0304 | V01 0305 | V01 0306 | V01 0307 | V01 0308 | V01 0309 | V01 0310 | V01 0311 | V01 0312 |
|---|---|---|---|---|---|---|---|---|---|---|---|---|
| 2604998 | 5.39 | 8.10 | 8.56 | 6.01 | 8.81 | 8.29 | 7.89 | 8.14 | 8.28 | 6.36 | 7.34 | 8.59 |
| 3603932 | 6.88 | 6.82 | 6.82 | 6.45 | 7.35 | 8.23 | 7.03 | 8.25 | 7.21 | 6.52 | 8.11 | 7.11 |
| 2710599 | 5.54 | 11.83 | 6.63 | 7.15 | 9.77 | 6.39 | 7.64 | 10.84 | 6.36 | 8.22 | 9.79 | 11.26 |
| 2440258 | 6.34 | 4.78 | 8.44 | 10.20 | 6.21 | 5.54 | 7.69 | 7.88 | 8.40 | 9.94 | 7.20 | 6.67 |
| 3169331 | 6.08 | 6.68 | 6.98 | 6.86 | 7.79 | 9.18 | 7.11 | 7.26 | 7.56 | 7.09 | 8.57 | 6.33 |
| 2988882 | 9.54 | 9.62 | 10.00 | 9.94 | 10.01 | 11.06 | 10.41 | 9.84 | 9.87 | 9.71 | 10.28 | 9.47 |
| 2964231 | 8.67 | 8.88 | 8.79 | 8.01 | 9.04 | 10.99 | 7.88 | 10.45 | 8.06 | 8.25 | 10.02 | 9.45 |
| 3111561 | 6.00 | 4.30 | 10.32 | 5.13 | 8.46 | 9.89 | 8.36 | 6.58 | 8.18 | 7.39 | 8.31 | 4.46 |
| 2562529 | 9.46 | 10.65 | 9.45 | 9.00 | 10.36 | 9.75 | 8.85 | 10.21 | 8.75 | 9.07 | 9.00 | 11.39 |
| 3692999 | 6.13 | 7.29 | 13.07 | 8.21 | 12.37 | 11.04 | 11.12 | 9.33 | 12.77 | 7.35 | 12.15 | 5.08 |
| 2439554 | 6.86 | 5.19 | 7.37 | 9.65 | 5.41 | 5.89 | 6.61 | 7.91 | 6.76 | 9.06 | 6.67 | 5.74 |
| 2685304 | 7.97 | 11.80 | 7.42 | 6.97 | 8.72 | 6.89 | 7.50 | 10.02 | 6.42 | 6.64 | 7.47 | 11.47 |
| 2578790 | 4.69 | 4.06 | 7.00 | 4.51 | 7.50 | 6.29 | 6.65 | 7.48 | 4.87 | 5.72 | 4.14 |   |
| 2373842 | 10.35 | 9.30 | 11.53 | 11.90 | 10.12 | 9.78 | 11.65 | 10.50 | 11.83 | 11.77 | 11.17 | 10.66 |
| 2750627 | 12.21 | 9.71 | 9.57 | 6.42 | 10.52 | 9.70 | 8.86 | 9.09 | 9.24 | 7.54 | 8.30 | 11.26 |
| 3397774 | 4.68 | 4.45 | 4.79 | 4.88 | 4.47 | 5.59 | 5.24 | 5.15 | 4.94 | 4.66 | 9.55 | 4.42 |
| 2635741 | 7.05 | 5.54 | 8.38 | 9.94 | 6.96 | 6.41 | 8.67 | 7.72 | 9.38 | 9.94 | 8.12 | 7.45 |
| 3970833 | 9.52 | 9.51 | 9.32 | 9.64 | 10.17 | 11.21 | 9.66 | 9.65 | 9.55 | 9.45 | 10.32 | 9.85 |
| 3577612 | 8.90 | 11.82 | 10.76 | 9.14 | 9.35 | 8.73 | 11.07 | 10.99 | 10.91 | 9.77 | 10.19 | 11.87 |
| 2708922 | 7.38 | 8.31 | 8.81 | 6.87 | 7.77 | 6.83 | 7.85 | 7.47 | 7.91 | 8.63 | 7.71 | 8.58 |
| 2970897 | 6.82 | 5.11 | 5.10 | 5.91 | 6.08 | 7.37 | 5.21 | 6.72 | 5.99 | 5.33 | 7.13 | 4.54 |
| 3724545 | 8.18 | 9.82 | 9.81 | 7.95 | 9.94 | 9.57 | 10.57 | 9.45 | 10.06 | 8.52 | 8.94 | 9.72 |
| 2798538 | 8.50 | 9.03 | 8.74 | 9.57 | 9.06 | 10.63 | 9.26 | 9.50 | 8.63 | 9.53 | 9.88 | 8.39 |
| 2806468 | 9.35 | 8.35 | 11.36 | 11.60 | 9.64 | 9.23 | 11.61 | 8.52 | 12.02 | 11.96 | 10.74 | 10.11 |
| 2880051 | 8.42 | 5.98 | 6.10 | 6.51 | 5.90 | 7.61 | 6.45 | 5.64 | 6.41 | 6.86 | 6.98 | 5.93 |
| 2732508 | 5.52 | 3.43 | 3.48 | 9.25 | 3.47 | 3.77 | 3.82 | 6.68 | 3.40 | 8.54 | 3.39 | 3.36 |
| 2822492 | 6.74 | 5.16 | 5.35 | 5.54 | 6.30 | 6.85 | 5.06 | 5.52 | 5.60 | 5.59 | 5.91 | 5.40 |
| 3404030 | 6.78 | 5.19 | 7.97 | 8.74 | 7.34 | 6.75 | 8.14 | 7.44 | 8.91 | 9.94 | 7.37 | 7.58 |
| 3059667 | 7.02 | 4.04 | 10.66 | 6.94 | 11.71 | 9.24 | 9.72 | 7.36 | 7.86 | 7.82 | 8.48 | 4.04 |
| 3108526 | 10.90 | 8.07 | 10.71 | 8.96 | 10.36 | 11.02 | 9.51 | 8.65 | 9.96 | 8.13 | 10.43 | 8.70 |
| 2526806 | 9.84 | 12.94 | 8.49 | 9.25 | 7.95 | 9.30 | 8.65 | 11.55 | 9.42 | 9.33 | 9.80 | 12.63 |
| 2428501 | 6.20 | 6.69 | 5.92 | 8.11 | 5.51 | 7.69 | 5.60 | 8.03 | 6.90 | 8.20 | 8.22 | 6.46 |
| 2657808 | 5.58 | 10.52 | 5.50 | 7.90 | 8.22 | 6.00 | 6.26 | 8.36 | 6.03 | 5.48 | 5.12 | 10.50 |
| 2584018 | 5.39 | 11.02 | 7.47 | 8.03 | 6.42 | 5.86 | 7.56 | 10.11 | 8.21 | 8.63 | 7.57 | 9.43 |
| 3976341 | 11.15 | 11.76 | 9.32 | 9.28 | 7.56 | 7.76 | 9.91 | 10.93 | 9.70 | 9.42 | 9.01 | 11.98 |
| 2739308 | 4.64 | 4.42 | 5.13 | 4.85 | 5.23 | 5.94 | 5.52 | 4.15 | 5.41 | 4.86 | 4.85 | 4.57 |
| 3959862 | 5.35 | 5.20 | 4.05 | 7.23 | 4.30 | 4.71 | 4.68 | 4.75 | 5.13 | 4.53 | 10.02 | 4.33 |
| 2362351 | 6.57 | 5.53 | 6.99 | 8.55 | 6.26 | 5.79 | 7.81 | 7.07 | 7.76 | 8.90 | 7.39 | 6.89 |
| 3648391 | 4.87 | 4.54 | 4.94 | 8.81 | 4.02 | 4.12 | 5.44 | 5.80 | 5.26 | 8.20 | 4.49 | 4.44 |
| 3009299 | 10.98 | 10.47 | 10.76 | 11.04 | 11.18 | 11.64 | 11.15 | 10.98 | 10.54 | 10.94 | 11.31 | 10.36 |
| 3443464 | 5.24 | 4.96 | 5.42 | 5.43 | 5.24 | 5.35 | 5.41 | 5.12 | 6.30 | 6.55 | 5.43 | 5.34 |
| 2730746 | 5.55 | 5.18 | 8.49 | 5.28 | 9.18 | 9.24 | 7.89 | 6.81 | 8.30 | 5.99 | 8.26 | 4.80 |
| 2427619 | 7.08 | 6.47 | 9.04 | 10.06 | 7.01 | 6.69 | 9.27 | 6.77 | 9.38 | 9.97 | 8.10 | 7.31 |
| 3042001 | 9.29 | 8.42 | 8.47 | 8.64 | 8.79 | 9.85 | 9.18 | 8.42 | 8.60 | 8.87 | 9.53 | 7.90 |
| 2566848 | 8.49 | 4.98 | 5.22 | 8.00 | 5.11 | 5.72 | 5.78 | 4.78 | 5.93 | 6.72 | 5.73 | 4.82 |
| 2984616 | 9.78 | 8.67 | 8.89 | 9.25 | 9.28 | 10.31 | 8.75 | 9.73 | 8.93 | 8.65 | 10.03 | 8.78 |
| 2378068 | 8.61 | 8.94 | 7.08 | 9.80 | 5.30 | 7.05 | 7.17 | 9.27 | 6.13 | 8.77 | 8.17 | 10.58 |
| 2721959 | 6.75 | 12.93 | 6.32 | 6.14 | 7.42 | 7.08 | 6.02 | 10.89 | 6.26 | 7.74 | 6.81 | 12.58 |
| 2877508 | 10.32 | 10.21 | 10.13 | 10.83 | 10.45 | 11.77 | 10.20 | 10.70 | 9.99 | 10.51 | 11.16 | 10.38 |
| 3450861 | 5.39 | 4.56 | 6.02 | 7.65 | 4.95 | 5.03 | 6.81 | 4.47 | 7.33 | 8.05 | 5.45 | 5.09 |
| 2688717 | 8.11 | 5.95 | 9.39 | 11.01 | 6.69 | 6.30 | 9.21 | 7.17 | 9.76 | 10.52 | 7.91 | 7.47 |
| 3270270 | 7.42 | 9.18 | 8.69 | 8.56 | 7.25 | 6.90 | 8.70 | 8.63 | 8.70 | 8.72 | 8.68 | 8.65 |
| 3417703 | 4.43 | 8.05 | 9.60 | 5.79 | 10.68 | 7.73 | 9.01 | 8.37 | 7.67 | 5.69 | 7.36 | 4.95 |
| 3302990 | 7.80 | 7.87 | 7.40 | 7.93 | 7.67 | 10.12 | 7.73 | 7.75 | 7.83 | 7.75 | 9.65 | 7.64 |
| 2377283 | 7.39 | 4.04 | 4.74 | 11.68 | 4.44 | 4.73 | 4.87 | 8.85 | 5.47 | 9.67 | 4.44 | 4.27 |

TABLE 50-continued

Normalized intensity of microarray data for a set of samples.

| TCID | V01 0301 | V01 0302 | V01 0303 | V01 0304 | V01 0305 | V01 0306 | V01 0307 | V01 0308 | V01 0309 | V01 0310 | V01 0311 | V01 0312 |
|---|---|---|---|---|---|---|---|---|---|---|---|---|
| 3122678 | 4.80 | 5.27 | 4.97 | 4.78 | 4.65 | 5.07 | 4.34 | 4.35 | 4.55 | 4.77 | 7.69 | 4.28 |
| 2688499 | 6.40 | 10.20 | 9.50 | 7.80 | 10.25 | 8.20 | 8.18 | 9.77 | 9.34 | 9.11 | 8.25 | 9.39 |
| 2377094 | 7.63 | 8.20 | 9.43 | 8.29 | 9.65 | 10.65 | 8.86 | 8.70 | 8.66 | 7.74 | 10.72 | 8.85 |
| 3278198 | 7.70 | 8.31 | 8.79 | 7.42 | 8.54 | 10.59 | 7.05 | 8.70 | 7.57 | 7.63 | 9.34 | 8.69 |
| 2598261 | 9.20 | 13.17 | 7.58 | 8.24 | 7.16 | 8.64 | 7.91 | 10.86 | 8.88 | 8.71 | 9.02 | 12.47 |
| 3982612 | 7.63 | 5.26 | 8.55 | 11.45 | 7.48 | 7.21 | 9.55 | 8.42 | 9.83 | 10.91 | 8.31 | 7.48 |
| 2884845 | 4.75 | 10.37 | 4.59 | 4.42 | 4.94 | 4.48 | 4.68 | 9.11 | 4.57 | 4.66 | 4.31 | 10.20 |
| 3982560 | 5.74 | 4.47 | 6.55 | 9.18 | 5.49 | 5.14 | 7.55 | 5.20 | 7.90 | 8.92 | 6.90 | 5.28 |
| 3204285 | 6.23 | 5.07 | 5.18 | 9.99 | 5.11 | 5.12 | 5.63 | 5.33 | 5.50 | 9.82 | 5.70 | 5.03 |
| 3654699 | 8.89 | 10.33 | 11.86 | 9.33 | 10.44 | 13.31 | 11.27 | 12.11 | 11.62 | 10.20 | 12.84 | 9.98 |
| 2638676 | 7.69 | 6.07 | 6.82 | 10.40 | 5.60 | 5.29 | 7.31 | 8.24 | 7.49 | 9.90 | 7.34 | 6.32 |
| 3367673 | 5.74 | 3.81 | 8.83 | 5.32 | 8.90 | 9.03 | 8.29 | 6.50 | 8.65 | 6.76 | 7.82 | 4.35 |
| 3212008 | 5.96 | 7.34 | 6.76 | 5.88 | 10.06 | 5.73 | 6.36 | 8.46 | 6.57 | 6.28 | 6.29 | 9.48 |
| 3326635 | 8.17 | 9.99 | 10.09 | 10.07 | 10.39 | 9.14 | 10.13 | 10.36 | 10.13 | 10.16 | 10.13 | 10.46 |
| 3031556 | 8.50 | 6.89 | 9.42 | 10.35 | 7.74 | 7.67 | 9.86 | 9.05 | 9.78 | 10.30 | 9.08 | 8.79 |
| 3662201 | 7.03 | 8.48 | 13.09 | 8.51 | 12.34 | 9.13 | 10.31 | 9.32 | 12.87 | 8.35 | 12.23 | 8.31 |
| 2809793 | 7.13 | 5.98 | 9.10 | 10.33 | 6.78 | 6.93 | 9.51 | 7.97 | 8.86 | 11.27 | 8.07 | 6.70 |
| 2817731 | 7.19 | 7.82 | 7.46 | 7.02 | 7.39 | 8.14 | 7.75 | 9.14 | 7.88 | 7.36 | 7.67 | 8.00 |
| 4020655 | 6.72 | 6.69 | 4.99 | 5.03 | 8.41 | 4.89 | 5.14 | 7.18 | 5.23 | 5.10 | 4.64 | 9.09 |
| 3494629 | 5.42 | 9.00 | 4.25 | 4.44 | 6.30 | 4.33 | 4.40 | 6.62 | 4.39 | 5.35 | 6.88 | 8.48 |
| 3852832 | 7.20 | 6.15 | 9.54 | 7.68 | 8.30 | 7.00 | 9.82 | 5.89 | 9.75 | 8.63 | 9.42 | 7.64 |
| 3761959 | 9.97 | 9.09 | 9.32 | 9.04 | 10.48 | 10.13 | 9.57 | 9.94 | 8.98 | 8.99 | 9.63 | 9.23 |
| 2834282 | 7.54 | 8.21 | 6.56 | 5.15 | 7.59 | 6.77 | 5.61 | 7.34 | 6.40 | 5.51 | 6.94 | 8.25 |
| 3341497 | 5.36 | 6.35 | 6.39 | 5.55 | 7.20 | 6.64 | 6.49 | 6.15 | 6.58 | 5.92 | 6.93 | 7.82 |
| 2372812 | 6.32 | 4.42 | 5.12 | 11.05 | 4.49 | 4.47 | 4.65 | 8.51 | 4.66 | 9.46 | 4.49 | 4.50 |
| 2486811 | 8.08 | 7.67 | 9.77 | 10.08 | 7.56 | 7.24 | 9.75 | 10.42 | 9.70 | 10.51 | 9.26 | 8.33 |
| 3768474 | 7.04 | 8.03 | 8.05 | 7.50 | 8.13 | 8.53 | 8.91 | 9.00 | 7.82 | 7.82 | 8.65 | 7.67 |
| 3142381 | 3.68 | 4.95 | 5.22 | 4.98 | 9.03 | 6.02 | 4.71 | 6.95 | 5.89 | 4.56 | 6.24 | 4.48 |
| 2396750 | 8.70 | 7.40 | 6.80 | 7.31 | 7.10 | 6.77 | 6.93 | 7.29 | 6.89 | 6.99 | 7.15 | 7.41 |
| 3902489 | 10.23 | 10.21 | 11.26 | 10.18 | 9.67 | 10.40 | 11.39 | 9.85 | 11.09 | 11.26 | 11.18 | 10.51 |
| 3032647 | 5.97 | 5.61 | 8.20 | 5.83 | 6.37 | 7.39 | 7.55 | 7.45 | 8.63 | 6.80 | 7.30 | 5.41 |
| 3875642 | 6.95 | 5.01 | 5.73 | 5.24 | 5.12 | 5.76 | 6.20 | 4.60 | 5.84 | 5.83 | 5.56 | 5.19 |
| 4027585 | 9.85 | 8.20 | 10.45 | 9.61 | 9.27 | 10.40 | 10.87 | 10.78 | 10.97 | 10.93 | 11.07 | 9.95 |
| 2352609 | 5.43 | 6.64 | 6.78 | 5.60 | 8.55 | 6.88 | 7.71 | 6.59 | 6.94 | 6.15 | 6.56 | 7.18 |
| 3376529 | 8.47 | 9.83 | 8.30 | 7.77 | 8.80 | 10.16 | 7.78 | 9.17 | 8.05 | 8.11 | 8.87 | 9.45 |
| 2491271 | 13.01 | 13.35 | 13.09 | 13.81 | 12.54 | 12.40 | 13.35 | 13.73 | 13.24 | 13.60 | 13.13 | 13.13 |
| 3874751 | 8.05 | 9.91 | 9.27 | 8.67 | 9.09 | 8.74 | 9.20 | 10.75 | 8.78 | 9.04 | 9.10 | 9.97 |
| 2326463 | 10.95 | 10.82 | 11.62 | 12.92 | 10.03 | 9.70 | 12.10 | 11.47 | 12.26 | 12.68 | 11.66 | 10.39 |
| 3341061 | 6.83 | 7.50 | 7.34 | 7.13 | 6.50 | 6.89 | 6.97 | 9.28 | 6.63 | 6.86 | 6.36 | 6.91 |
| 3839910 | 7.66 | 6.16 | 9.85 | 6.80 | 7.52 | 7.28 | 9.31 | 6.08 | 9.27 | 8.20 | 8.46 | 7.91 |
| 2708855 | 7.58 | 9.31 | 3.98 | 3.96 | 6.67 | 3.80 | 4.09 | 7.48 | 4.26 | 4.22 | 4.57 | 8.65 |
| 3512874 | 10.70 | 10.55 | 12.06 | 12.37 | 10.55 | 10.23 | 12.23 | 11.58 | 12.04 | 12.35 | 11.90 | 10.95 |
| 2701071 | 8.59 | 7.45 | 10.86 | 8.95 | 8.89 | 8.32 | 10.52 | 8.89 | 10.14 | 9.80 | 10.28 | 9.04 |
| 3486096 | 5.29 | 7.21 | 7.56 | 5.23 | 8.93 | 9.31 | 7.57 | 7.26 | 7.19 | 5.89 | 7.84 | 7.20 |
| 2412668 | 8.25 | 8.00 | 8.03 | 8.81 | 8.57 | 8.07 | 8.17 | 9.22 | 7.91 | 8.31 | 8.06 | 8.35 |
| 3329343 | 9.16 | 9.10 | 7.15 | 7.76 | 7.34 | 6.75 | 6.95 | 8.42 | 7.19 | 7.64 | 7.60 | 8.68 |
| 3259367 | 4.05 | 4.95 | 4.61 | 3.94 | 5.81 | 4.02 | 4.23 | 4.84 | 4.87 | 4.10 | 3.92 | 6.03 |
| 3373845 | 7.28 | 10.80 | 10.46 | 8.81 | 8.73 | 8.38 | 8.29 | 10.35 | 8.97 | 9.06 | 9.06 | 7.82 |
| 2321911 | 7.91 | 7.39 | 8.79 | 8.83 | 7.78 | 8.31 | 8.55 | 8.51 | 8.72 | 8.92 | 8.49 | 8.21 |
| 3353914 | 8.40 | 8.43 | 6.24 | 7.01 | 7.04 | 6.76 | 6.26 | 9.35 | 6.46 | 6.29 | 6.64 | 7.39 |
| 3744680 | 6.69 | 6.62 | 7.79 | 7.40 | 6.58 | 6.65 | 8.00 | 7.86 | 7.94 | 7.95 | 7.44 | 6.99 |
| 2373336 | 5.08 | 10.48 | 8.39 | 6.58 | 5.13 | 5.36 | 6.25 | 8.63 | 6.19 | 6.99 | 6.04 | 7.17 |
| 3067478 | 9.60 | 8.48 | 5.20 | 5.75 | 7.18 | 8.56 | 6.70 | 7.57 | 4.76 | 5.44 | 4.67 | 8.52 |
| 3976766 | 7.33 | 6.52 | 8.75 | 8.93 | 7.16 | 6.60 | 8.86 | 7.60 | 8.37 | 8.93 | 8.17 | 7.09 |
| 3246888 | 5.43 | 4.52 | 7.05 | 5.02 | 8.50 | 7.34 | 6.18 | 5.84 | 6.67 | 5.70 | 6.04 | 5.74 |
| 3147985 | 9.53 | 7.70 | 6.04 | 5.62 | 7.41 | 7.11 | 6.13 | 8.46 | 6.03 | 5.92 | 6.66 | 7.26 |
| 3185522 | 8.75 | 9.45 | 9.69 | 8.98 | 9.73 | 9.28 | 9.34 | 11.31 | 8.76 | 9.43 | 9.68 | 9.01 |
| 3861948 | 11.95 | 10.64 | 12.69 | 13.01 | 11.57 | 10.94 | 12.84 | 12.23 | 12.82 | 12.89 | 12.62 | 11.72 |
| 3393479 | 10.29 | 9.77 | 9.44 | 8.68 | 8.79 | 10.62 | 9.65 | 10.45 | 9.38 | 8.27 | 8.60 | 8.01 |
| 3540862 | 7.62 | 6.97 | 6.82 | 6.68 | 7.16 | 8.53 | 6.65 | 6.77 | 6.87 | 6.42 | 7.88 | 7.39 |
| 2777714 | 10.58 | 7.19 | 11.49 | 10.11 | 10.29 | 10.71 | 11.31 | 9.25 | 11.50 | 11.51 | 11.30 | 10.36 |
| 3110395 | 9.05 | 6.82 | 4.63 | 4.35 | 4.34 | 4.57 | 4.95 | 5.12 | 4.21 | 4.24 | 5.91 | |
| 3895795 | 7.46 | 7.99 | 8.39 | 7.32 | 7.38 | 7.49 | 9.09 | 7.42 | 8.82 | 8.49 | 8.72 | 8.50 |
| 2854445 | 6.85 | 8.52 | 8.65 | 8.36 | 7.93 | 7.32 | 8.29 | 10.95 | 7.30 | 8.87 | 8.32 | 8.58 |
| 3606034 | 8.37 | 7.44 | 7.25 | 7.22 | 7.80 | 8.16 | 7.56 | 8.60 | 7.51 | 7.02 | 7.41 | 7.22 |
| 3375735 | 7.17 | 7.96 | 7.89 | 7.32 | 7.60 | 7.26 | 7.54 | 8.42 | 8.24 | 8.22 | 8.56 | 7.54 |
| 3948047 | 7.65 | 7.09 | 8.51 | 9.03 | 7.20 | 7.05 | 8.23 | 8.64 | 8.61 | 9.16 | 8.46 | 7.31 |
| 3010503 | 7.83 | 7.67 | 9.61 | 7.69 | 8.38 | 7.93 | 8.81 | 10.54 | 9.19 | 8.15 | 9.60 | 7.41 |
| 3622934 | 10.29 | 8.55 | 6.40 | 8.31 | 7.97 | 7.78 | 6.94 | 6.83 | 6.47 | 7.88 | 7.18 | 8.36 |
| 3441849 | 7.78 | 9.89 | 10.15 | 9.05 | 9.19 | 8.94 | 10.26 | 9.86 | 10.12 | 9.75 | 10.02 | 9.77 |
| 3006572 | 6.45 | 6.81 | 6.17 | 6.71 | 6.66 | 6.55 | 6.37 | 6.04 | 6.43 | 6.64 | 6.31 | 6.35 |
| 3365136 | 9.66 | 8.86 | 8.82 | 8.80 | 9.84 | 8.50 | 8.47 | 9.92 | 8.63 | 8.44 | 8.17 | 9.49 |
| 2642791 | 7.73 | 8.22 | 8.46 | 8.71 | 8.19 | 8.39 | 8.57 | 8.80 | 8.70 | 8.64 | 8.25 | 8.20 |
| 2904485 | 9.09 | 7.20 | 9.10 | 6.55 | 9.61 | 8.75 | 9.11 | 8.20 | 8.54 | 7.07 | 7.24 | 7.79 |
| 3772661 | 9.21 | 9.87 | 9.70 | 8.38 | 9.11 | 9.09 | 9.82 | 11.52 | 9.52 | 9.24 | 9.82 | 8.58 |

TABLE 50-continued

Normalized intensity of microarray data for a set of samples.

| TCID | V01 0301 | V01 0302 | V01 0303 | V01 0304 | V01 0305 | V01 0306 | V01 0307 | V01 0308 | V01 0309 | V01 0310 | V01 0311 | V01 0312 |
|---|---|---|---|---|---|---|---|---|---|---|---|---|
| 2796553 | 9.32 | 8.20 | 10.20 | 8.62 | 9.09 | 9.16 | 10.04 | 9.99 | 10.28 | 9.74 | 9.93 | 9.25 |
| 3063795 | 6.93 | 6.86 | 7.28 | 7.60 | 6.59 | 6.79 | 7.24 | 8.71 | 7.27 | 7.80 | 7.33 | 7.07 |
| 3338192 | 10.20 | 10.97 | 8.95 | 7.72 | 9.91 | 8.82 | 8.57 | 9.34 | 8.35 | 8.22 | 8.46 | 10.26 |
| 3214845 | 4.37 | 6.27 | 4.20 | 4.37 | 4.35 | 3.92 | 4.41 | 4.38 | 6.41 | 4.48 | 4.12 | 4.59 |
| 2730303 | 6.82 | 4.15 | 4.33 | 9.73 | 4.29 | 4.26 | 4.35 | 7.86 | 4.25 | 8.43 | 4.14 | 3.93 |
| 3811086 | 8.37 | 7.93 | 7.61 | 8.21 | 8.43 | 8.89 | 7.62 | 8.12 | 8.11 | 7.81 | 7.58 | 7.59 |
| 2981874 | 10.42 | 10.44 | 10.48 | 10.16 | 9.87 | 11.27 | 10.38 | 10.60 | 10.21 | 10.08 | 10.75 | 9.93 |
| 3242353 | 6.21 | 6.33 | 6.21 | 6.48 | 6.10 | 7.06 | 5.85 | 6.84 | 5.94 | 6.56 | 5.79 | 5.81 |
| 2442008 | 8.41 | 7.25 | 5.81 | 5.19 | 6.96 | 5.05 | 5.53 | 7.36 | 5.43 | 5.47 | 5.26 | 9.69 |
| 3564210 | 7.38 | 8.71 | 9.78 | 8.33 | 8.28 | 7.86 | 9.74 | 9.36 | 9.57 | 9.00 | 9.57 | 8.80 |
| 2490351 | 4.76 | 3.98 | 4.10 | 3.94 | 4.02 | 3.99 | 4.09 | 3.76 | 4.27 | 4.12 | 4.23 | 3.83 |
| 3759006 | 8.03 | 6.54 | 9.82 | 8.30 | 8.09 | 8.04 | 9.16 | 7.23 | 9.08 | 10.06 | 9.54 | 7.72 |
| 3264997 | 3.96 | 3.83 | 4.09 | 4.04 | 3.98 | 3.87 | 4.07 | 3.80 | 4.25 | 3.97 | 4.06 | 3.75 |
| 3912079 | 3.53 | 3.61 | 3.57 | 3.87 | 3.64 | 3.39 | 3.82 | 3.49 | 3.73 | 4.17 | 3.69 | 4.00 |
| 2926802 | 4.48 | 4.84 | 5.20 | 7.34 | 4.84 | 5.20 | 5.44 | 4.80 | 5.16 | 6.35 | 5.63 | 4.60 |
| 2430163 | 3.67 | 8.02 | 3.87 | 3.67 | 3.69 | 3.54 | 3.96 | 3.64 | 3.90 | 3.69 | 4.09 | 3.72 |
| 3039830 | 3.08 | 3.25 | 3.12 | 3.26 | 3.23 | 3.18 | 3.03 | 3.04 | 3.16 | 3.21 | 3.14 | 3.07 |
| 3935486 | 7.91 | 8.19 | 5.29 | 8.16 | 5.33 | 5.29 | 4.90 | 5.79 | 7.15 | 7.95 | 6.31 | 6.69 |
| 3457336 | 5.13 | 5.16 | 5.50 | 5.19 | 5.39 | 5.31 | 5.68 | 4.71 | 5.54 | 5.56 | 5.82 | 5.11 |
| 3811949 | 3.46 | 3.40 | 3.45 | 3.50 | 3.40 | 3.41 | 3.50 | 3.35 | 3.51 | 3.50 | 3.36 | 3.33 |
| 3343832 | 3.90 | 3.69 | 3.68 | 3.86 | 3.83 | 3.79 | 4.04 | 3.69 | 4.03 | 4.25 | 4.01 | 3.63 |
| 3161261 | 5.72 | 5.03 | 5.57 | 6.36 | 5.51 | 5.83 | 5.49 | 4.81 | 7.00 | 6.32 | 5.98 | 5.46 |
| 3594003 | 11.72 | 3.57 | 3.57 | 4.02 | 3.61 | 3.65 | 3.60 | 3.82 | 3.65 | 3.76 | 3.53 | 3.56 |
| 3805614 | 10.83 | 4.39 | 5.04 | 4.55 | 4.58 | 4.72 | 4.69 | 4.37 | 4.97 | 4.67 | 4.62 | 4.39 |
| 3364127 | 13.62 | 6.53 | 6.67 | 8.75 | 6.62 | 6.89 | 7.28 | 7.48 | 7.29 | 6.86 | 7.07 | 6.56 |
| 3834341 | 11.95 | 3.96 | 4.17 | 4.09 | 4.15 | 3.94 | 4.32 | 3.93 | 4.06 | 4.00 | 3.97 | 3.94 |
| 2585400 | 9.37 | 4.70 | 4.54 | 4.38 | 4.13 | 4.13 | 4.51 | 4.00 | 4.42 | 4.24 | 4.35 | 4.13 |
| 2941690 | 3.98 | 4.48 | 4.59 | 4.34 | 4.15 | 4.38 | 4.11 | 3.86 | 4.52 | 4.06 | 4.28 | 3.98 |
| 3484895 | 6.38 | 4.61 | 4.71 | 4.66 | 5.04 | 4.84 | 4.97 | 4.93 | 4.81 | 5.09 | 4.73 | 6.31 |
| 3159754 | 3.70 | 3.62 | 3.72 | 3.56 | 3.80 | 3.67 | 3.90 | 3.56 | 3.64 | 3.90 | 3.72 | 3.56 |
| 2894790 | 4.01 | 3.63 | 3.91 | 3.78 | 3.76 | 3.97 | 3.78 | 3.74 | 3.83 | 3.70 | 3.87 | 3.84 |
| 3363686 | 3.33 | 3.34 | 3.55 | 3.42 | 3.90 | 3.55 | 3.31 | 3.42 | 3.29 | 3.28 | 3.35 | 3.22 |
| 2923928 | 4.06 | 3.84 | 4.30 | 3.93 | 4.30 | 4.06 | 4.47 | 4.78 | 4.31 | 3.98 | 4.22 | 4.06 |
| 2883317 | 4.41 | 5.06 | 4.92 | 5.26 | 4.46 | 4.36 | 4.83 | 4.62 | 5.03 | 5.31 | 5.24 | 4.33 |
| 2479698 | 5.98 | 5.90 | 5.96 | 5.98 | 6.00 | 5.97 | 6.03 | 5.96 | 6.05 | 6.08 | 6.29 | 6.10 |
| 3428225 | 3.56 | 3.84 | 3.83 | 3.69 | 3.56 | 3.50 | 3.80 | 3.53 | 3.91 | 3.57 | 3.76 | 3.49 |
| 3393446 | 7.03 | 7.30 | 7.38 | 7.75 | 6.80 | 6.99 | 7.30 | 7.65 | 7.49 | 7.84 | 7.13 | 6.56 |
| 3116614 | 10.25 | 11.12 | 13.08 | 9.91 | 13.17 | 13.02 | 13.09 | 12.63 | 13.06 | 11.27 | 12.50 | 12.65 |
| 3415320 | 8.74 | 11.01 | 9.67 | 7.01 | 9.72 | 11.06 | 10.02 | 10.04 | 10.05 | 7.96 | 10.99 | 9.84 |
| 3757108 | 7.97 | 11.72 | 7.43 | 7.02 | 8.18 | 7.53 | 7.93 | 8.88 | 7.52 | 7.34 | 8.09 | 9.76 |
| 4012178 | 6.70 | 10.37 | 6.69 | 5.90 | 9.22 | 6.84 | 6.98 | 10.17 | 6.25 | 6.09 | 7.71 | 12.18 |
| 3546213 | 7.97 | 10.95 | 10.82 | 7.62 | 11.69 | 11.21 | 10.65 | 10.87 | 10.53 | 8.96 | 9.85 | 11.48 |
| 3561381 | 9.36 | 10.80 | 10.99 | 5.90 | 11.05 | 9.38 | 10.09 | 9.63 | 9.31 | 8.32 | 9.41 | 10.89 |

TABLE 51

Normalized intensity of microarray data for a set of samples.

| TCID | V01 0313 | V01 0314 | V01 0315 | V01 0316 | V01 0317 | V01 0318 | V01 0319 | V01 0320 | V01 0321 | V01 0322 | V01 0323 | V01 0324 |
|---|---|---|---|---|---|---|---|---|---|---|---|---|
| 2604998 | 7.96 | 8.60 | 8.20 | 8.88 | 8.47 | 7.99 | 7.39 | 7.17 | 9.01 | 9.02 | 8.66 | 9.03 |
| 3603932 | 7.13 | 6.74 | 7.03 | 7.20 | 8.27 | 6.40 | 6.99 | 7.16 | 7.69 | 7.46 | 7.24 | 7.88 |
| 2710599 | 8.11 | 10.37 | 6.13 | 11.88 | 10.24 | 5.51 | 5.88 | 6.16 | 10.29 | 9.59 | 6.06 | 11.45 |
| 2440258 | 7.60 | 6.75 | 8.24 | 7.24 | 6.44 | 7.28 | 8.59 | 8.61 | 5.87 | 5.96 | 8.22 | 6.80 |
| 3169331 | 8.02 | 6.59 | 7.57 | 6.32 | 8.06 | 7.83 | 7.48 | 7.25 | 7.60 | 7.14 | 8.20 | 6.80 |
| 2988882 | 10.10 | 9.34 | 9.66 | 9.09 | 10.33 | 10.02 | 9.61 | 9.76 | 9.86 | 9.82 | 9.95 | 9.69 |
| 2964231 | 9.12 | 8.08 | 7.78 | 7.94 | 10.73 | 7.60 | 8.75 | 7.83 | 8.93 | 8.12 | 8.37 | 8.78 |
| 3111561 | 9.93 | 9.85 | 9.51 | 6.96 | 4.37 | 9.11 | 8.35 | 7.86 | 5.90 | 10.63 | 9.49 | 4.54 |
| 2562529 | 9.21 | 11.13 | 9.31 | 10.54 | 10.22 | 9.03 | 8.84 | 8.70 | 10.50 | 9.91 | 9.02 | 10.71 |
| 3692999 | 13.16 | 11.03 | 12.27 | 8.86 | 5.58 | 12.22 | 11.43 | 9.60 | 12.29 | 12.69 | 10.78 | 6.00 |
| 2439554 | 6.93 | 5.26 | 6.42 | 6.57 | 5.75 | 6.06 | 7.95 | 7.93 | 5.29 | 6.21 | 6.97 | 4.74 |
| 2685304 | 7.21 | 9.31 | 6.64 | 10.69 | 9.85 | 7.40 | 4.69 | 6.16 | 9.20 | 8.77 | 7.63 | 11.70 |
| 2578790 | 7.30 | 5.94 | 7.94 | 5.09 | 5.32 | 7.06 | 5.54 | 5.71 | 5.30 | 7.47 | 6.88 | 4.37 |
| 2373842 | 11.03 | 10.93 | 11.40 | 11.28 | 10.51 | 11.18 | 11.92 | 11.78 | 9.90 | 9.88 | 11.16 | 8.75 |
| 2750627 | 10.14 | 10.24 | 9.75 | 9.54 | 8.56 | 10.34 | 8.11 | 7.78 | 10.43 | 10.31 | 9.81 | 11.18 |
| 3397774 | 4.95 | 4.95 | 4.72 | 4.39 | 4.88 | 4.88 | 5.28 | 4.90 | 4.56 | 4.82 | 5.02 | 4.69 |
| 2635741 | 7.96 | 7.66 | 9.19 | 8.51 | 7.18 | 8.31 | 8.68 | 8.89 | 6.33 | 6.90 | 8.13 | 6.29 |
| 3970833 | 10.17 | 9.56 | 9.44 | 9.44 | 10.57 | 9.32 | 9.47 | 10.21 | 10.27 | 10.12 | 9.94 | 10.01 |
| 3577612 | 9.99 | 10.17 | 10.52 | 11.54 | 9.76 | 10.40 | 11.71 | 11.29 | 9.57 | 9.92 | 10.61 | 11.50 |
| 2708922 | 7.47 | 8.32 | 8.28 | 8.50 | 8.83 | 8.13 | 8.01 | 7.46 | 8.62 | 7.51 | 8.18 | 8.18 |
| 2970897 | 7.12 | 4.93 | 5.16 | 4.62 | 4.90 | 5.89 | 6.16 | 4.53 | 4.65 | 4.84 | 5.17 | 4.36 |

TABLE 51-continued

Normalized intensity of microarray data for a set of samples.

| TCID | V01 0313 | V01 0314 | V01 0315 | V01 0316 | V01 0317 | V01 0318 | V01 0319 | V01 0320 | V01 0321 | V01 0322 | V01 0323 | V01 0324 |
|---|---|---|---|---|---|---|---|---|---|---|---|---|
| 3724545 | 10.34 | 10.11 | 9.88 | 9.42 | 9.67 | 10.55 | 9.61 | 9.75 | 9.27 | 9.78 | 8.93 | 9.58 |
| 2798538 | 8.90 | 8.14 | 9.59 | 8.41 | 9.52 | 8.64 | 9.29 | 9.05 | 9.24 | 8.85 | 9.12 | 9.23 |
| 2806468 | 10.78 | 10.51 | 11.32 | 11.40 | 9.28 | 11.15 | 11.33 | 11.10 | 8.39 | 9.28 | 10.70 | 7.46 |
| 2880051 | 6.42 | 6.65 | 6.30 | 6.09 | 6.19 | 7.43 | 6.79 | 7.01 | 6.17 | 6.22 | 6.80 | 5.98 |
| 2732508 | 3.61 | 3.53 | 3.53 | 3.58 | 3.95 | 3.65 | 3.59 | 3.56 | 3.60 | 3.81 | 3.64 | 3.50 |
| 2822492 | 6.06 | 6.36 | 5.29 | 5.77 | 6.31 | 6.38 | 5.24 | 5.60 | 7.71 | 5.86 | 6.21 | 5.97 |
| 3404030 | 6.80 | 7.99 | 7.92 | 8.97 | 6.93 | 7.84 | 8.93 | 8.78 | 6.78 | 7.43 | 8.61 | 5.75 |
| 3059667 | 8.32 | 9.39 | 10.40 | 5.81 | 7.07 | 11.13 | 5.40 | 9.22 | 8.43 | 10.83 | 10.00 | 4.46 |
| 3108526 | 10.39 | 9.44 | 10.88 | 7.96 | 10.06 | 9.83 | 9.12 | 10.07 | 9.18 | 10.48 | 10.28 | 7.53 |
| 2526806 | 10.79 | 10.30 | 7.83 | 12.32 | 8.31 | 7.73 | 8.78 | 8.79 | 7.37 | 9.22 | 8.24 | 12.71 |
| 2428501 | 6.55 | 5.91 | 6.57 | 6.18 | 7.15 | 6.44 | 6.99 | 7.29 | 5.97 | 6.50 | 6.36 | 6.57 |
| 2657808 | 6.15 | 6.01 | 5.43 | 11.47 | 6.19 | 5.42 | 5.71 | 5.75 | 8.21 | 9.13 | 6.14 | 11.11 |
| 2584018 | 7.24 | 9.66 | 7.57 | 11.01 | 9.70 | 7.08 | 7.81 | 8.48 | 7.30 | 6.86 | 7.15 | 10.81 |
| 3976341 | 9.26 | 9.83 | 9.24 | 11.42 | 8.36 | 9.16 | 10.40 | 10.90 | 10.88 | 9.85 | 9.61 | 12.32 |
| 2739308 | 5.31 | 4.86 | 5.11 | 4.62 | 5.30 | 5.16 | 5.69 | 5.42 | 4.75 | 5.18 | 4.78 | 4.59 |
| 3959862 | 4.35 | 3.92 | 5.30 | 4.54 | 4.25 | 6.28 | 5.98 | 5.36 | 5.67 | 4.02 | 4.71 | 4.58 |
| 2362351 | 7.00 | 6.32 | 7.77 | 7.34 | 7.02 | 7.56 | 8.30 | 8.08 | 5.84 | 6.39 | 7.58 | 5.16 |
| 3648391 | 5.71 | 3.94 | 5.38 | 4.53 | 4.67 | 4.32 | 6.99 | 6.90 | 3.70 | 5.76 | 4.40 | 4.37 |
| 3009299 | 10.80 | 10.77 | 10.55 | 10.41 | 11.42 | 11.23 | 10.57 | 11.05 | 11.41 | 10.42 | 10.95 | 11.02 |
| 3443464 | 5.36 | 5.48 | 5.74 | 6.11 | 5.36 | 5.34 | 5.91 | 5.76 | 5.33 | 5.58 | 5.86 | 5.01 |
| 2730746 | 8.87 | 8.75 | 8.76 | 5.47 | 7.38 | 8.75 | 7.15 | 7.09 | 8.41 | 8.72 | 9.17 | 5.76 |
| 2427619 | 8.38 | 7.79 | 9.11 | 8.36 | 7.05 | 8.21 | 8.98 | 9.44 | 6.26 | 6.64 | 8.97 | 5.45 |
| 3042001 | 8.86 | 8.26 | 8.61 | 8.16 | 9.38 | 8.79 | 8.17 | 8.68 | 8.94 | 8.65 | 9.29 | 8.68 |
| 2566848 | 5.35 | 5.52 | 6.63 | 5.38 | 4.99 | 5.48 | 5.64 | 5.92 | 5.29 | 5.56 | 6.34 | 5.12 |
| 2984616 | 9.89 | 9.04 | 9.10 | 8.86 | 9.63 | 8.61 | 9.61 | 9.09 | 9.50 | 9.24 | 9.45 | 8.90 |
| 2378068 | 7.07 | 8.37 | 7.45 | 10.08 | 7.04 | 6.34 | 8.14 | 7.88 | 7.74 | 8.05 | 6.34 | 10.94 |
| 2721959 | 7.10 | 8.05 | 5.61 | 11.40 | 5.68 | 6.19 | 6.18 | 6.63 | 7.13 | 7.44 | 6.30 | 12.87 |
| 2877508 | 10.67 | 10.02 | 10.31 | 10.00 | 10.85 | 10.63 | 9.99 | 10.19 | 10.57 | 10.30 | 10.42 | 10.65 |
| 3450861 | 6.06 | 5.10 | 6.93 | 6.47 | 4.78 | 5.52 | 6.95 | 6.54 | 4.84 | 5.20 | 5.82 | 4.63 |
| 2688717 | 8.58 | 8.05 | 10.35 | 8.68 | 8.11 | 8.86 | 9.18 | 9.07 | 6.52 | 5.77 | 8.76 | 5.45 |
| 3270270 | 8.14 | 7.59 | 8.44 | 8.91 | 7.55 | 8.62 | 9.79 | 8.83 | 7.34 | 6.80 | 7.96 | 8.15 |
| 3417703 | 9.34 | 10.65 | 9.86 | 9.60 | 6.94 | 8.22 | 8.38 | 7.70 | 10.46 | 9.86 | 10.71 | 6.57 |
| 3302990 | 8.96 | 7.06 | 7.50 | 7.39 | 9.49 | 7.29 | 7.33 | 7.16 | 8.03 | 8.05 | 7.48 | 8.47 |
| 2377283 | 4.45 | 4.28 | 6.06 | 4.68 | 4.51 | 4.93 | 4.98 | 5.36 | 4.37 | 4.53 | 4.94 | 4.03 |
| 3122678 | 5.00 | 4.75 | 4.86 | 4.47 | 4.93 | 4.65 | 5.70 | 5.17 | 5.28 | 4.91 | 5.03 | 4.67 |
| 2688499 | 9.51 | 8.32 | 8.75 | 9.21 | 8.60 | 7.36 | 8.59 | 8.63 | 9.75 | 10.92 | 10.54 | 10.62 |
| 2377094 | 9.26 | 9.30 | 9.08 | 7.70 | 10.34 | 8.95 | 8.78 | 8.59 | 9.41 | 9.32 | 9.18 | 8.57 |
| 3278198 | 8.25 | 8.27 | 7.88 | 7.31 | 9.39 | 8.07 | 7.94 | 7.65 | 8.80 | 8.49 | 8.83 | 8.15 |
| 2598261 | 9.21 | 9.63 | 7.50 | 11.85 | 7.17 | 6.98 | 8.00 | 7.52 | 7.05 | 8.13 | 7.61 | 13.02 |
| 3982612 | 8.94 | 8.11 | 9.61 | 8.80 | 6.74 | 9.19 | 9.52 | 9.32 | 5.80 | 7.26 | 8.03 | 4.14 |
| 2884845 | 5.83 | 4.71 | 4.76 | 10.45 | 6.18 | 4.88 | 4.48 | 5.64 | 5.10 | 4.74 | 4.94 | 11.00 |
| 3982560 | 6.43 | 6.24 | 7.48 | 6.61 | 5.65 | 6.81 | 7.91 | 7.87 | 4.78 | 4.95 | 6.53 | 4.57 |
| 3204285 | 5.10 | 5.11 | 4.96 | 5.30 | 5.10 | 5.80 | 5.89 | 5.35 | 4.93 | 4.61 | 4.75 | 5.57 |
| 3654699 | 12.56 | 11.09 | 11.18 | 9.48 | 12.28 | 11.94 | 11.69 | 10.47 | 10.08 | 11.74 | 11.59 | 10.65 |
| 2638676 | 6.69 | 5.98 | 7.79 | 6.42 | 6.87 | 6.30 | 8.15 | 7.53 | 7.15 | 6.62 | 7.41 | 5.85 |
| 3367673 | 8.69 | 9.47 | 9.39 | 5.52 | 7.13 | 8.17 | 7.55 | 6.98 | 8.11 | 8.38 | 8.62 | 4.27 |
| 3212008 | 6.75 | 9.97 | 6.98 | 8.44 | 9.52 | 6.47 | 6.56 | 6.23 | 10.12 | 7.50 | 6.34 | 8.83 |
| 3326635 | 9.86 | 10.85 | 10.37 | 10.28 | 10.35 | 9.97 | 10.28 | 10.10 | 10.61 | 10.25 | 9.91 | 9.95 |
| 3031556 | 9.06 | 8.66 | 9.46 | 9.25 | 8.09 | 9.02 | 10.08 | 10.07 | 7.77 | 7.98 | 8.99 | 6.85 |
| 3662201 | 12.91 | 10.49 | 12.51 | 8.09 | 8.04 | 12.02 | 11.52 | 10.09 | 12.77 | 13.11 | 11.14 | 8.05 |
| 2809793 | 7.98 | 6.97 | 7.42 | 9.03 | 6.16 | 7.83 | 8.53 | 9.69 | 6.72 | 7.13 | 8.92 | 5.09 |
| 2817731 | 7.51 | 7.81 | 7.67 | 8.06 | 7.90 | 7.70 | 8.38 | 7.31 | 7.18 | 7.02 | 7.39 | 7.28 |
| 4020655 | 4.82 | 10.18 | 5.07 | 8.45 | 8.72 | 4.95 | 5.38 | 5.47 | 9.66 | 6.57 | 5.23 | 8.05 |
| 3494629 | 4.69 | 5.60 | 4.47 | 9.43 | 6.15 | 4.46 | 4.58 | 4.27 | 5.13 | 4.71 | 4.01 | 6.39 |
| 3852832 | 8.74 | 8.30 | 8.90 | 9.66 | 7.18 | 9.32 | 10.76 | 10.14 | 7.55 | 7.06 | 8.97 | 5.97 |
| 3761959 | 9.69 | 9.70 | 8.93 | 9.06 | 9.94 | 9.77 | 9.05 | 9.87 | 10.49 | 9.49 | 10.05 | 9.34 |
| 2834282 | 6.39 | 8.31 | 5.54 | 8.70 | 9.82 | 7.34 | 6.11 | 6.69 | 8.81 | 7.88 | 6.57 | 8.32 |
| 3341497 | 7.66 | 6.64 | 5.53 | 6.61 | 10.30 | 6.24 | 6.41 | 6.90 | 8.77 | 6.93 | 5.53 | 8.02 |
| 2372812 | 4.63 | 4.43 | 4.63 | 4.46 | 4.35 | 4.58 | 5.00 | 5.39 | 4.47 | 4.80 | 4.67 | 4.26 |
| 2486811 | 9.05 | 8.75 | 9.21 | 9.22 | 8.58 | 9.64 | 10.19 | 10.03 | 7.78 | 7.67 | 9.19 | 7.12 |
| 3768474 | 8.17 | 7.85 | 7.53 | 8.01 | 7.97 | 8.57 | 8.42 | 8.04 | 7.90 | 7.61 | 7.66 | 7.20 |
| 3142381 | 6.91 | 3.48 | 5.01 | 6.09 | 5.46 | 6.16 | 5.45 | 6.96 | 5.82 | 6.79 | 8.38 | 5.60 |
| 2396750 | 7.22 | 6.92 | 6.58 | 7.24 | 7.61 | 7.66 | 7.20 | 7.28 | 7.77 | 7.20 | 8.05 | 8.74 |
| 3902489 | 10.74 | 10.21 | 11.36 | 10.49 | 9.54 | 11.00 | 11.53 | 10.31 | 9.88 | 10.00 | 10.96 | 9.33 |
| 3032647 | 8.17 | 6.32 | 8.51 | 5.78 | 5.83 | 7.89 | 6.57 | 7.75 | 5.78 | 8.35 | 8.53 | 5.37 |
| 3875642 | 5.41 | 5.28 | 5.72 | 5.81 | 5.48 | 5.48 | 6.18 | 6.29 | 5.51 | 5.55 | 5.94 | 5.28 |
| 4027585 | 10.44 | 9.71 | 10.80 | 10.08 | 9.56 | 10.63 | 11.34 | 10.83 | 9.60 | 9.69 | 10.67 | 8.34 |
| 2352609 | 7.31 | 8.28 | 6.51 | 6.70 | 8.75 | 7.89 | 6.48 | 6.68 | 7.67 | 7.44 | 6.61 | 7.20 |
| 3376529 | 9.16 | 8.72 | 8.45 | 8.84 | 9.47 | 8.31 | 8.60 | 8.71 | 9.52 | 9.22 | 9.49 | 10.07 |
| 2491272 | 13.20 | 12.92 | 13.32 | 13.41 | 12.91 | 13.18 | 13.48 | 13.60 | 13.05 | 12.76 | 13.54 | 13.34 |
| 3874751 | 10.13 | 9.12 | 9.52 | 9.43 | 9.31 | 9.48 | 9.02 | 9.04 | 9.27 | 8.70 | 9.12 | 10.01 |
| 2326463 | 11.58 | 10.98 | 12.01 | 11.43 | 10.70 | 11.85 | 11.87 | 12.66 | 10.63 | 10.39 | 12.12 | 10.61 |
| 3341061 | 6.05 | 6.07 | 7.03 | 6.48 | 7.07 | 7.40 | 7.16 | 6.42 | 5.87 | 5.18 | 6.36 | 5.79 |
| 3839910 | 8.43 | 8.53 | 8.25 | 9.21 | 7.89 | 9.38 | 10.41 | 9.55 | 7.25 | 6.79 | 8.10 | 5.59 |
| 2708855 | 4.46 | 7.25 | 4.02 | 8.08 | 3.88 | 4.26 | 4.25 | 4.33 | 8.00 | 4.84 | 4.17 | 8.93 |

TABLE 51-continued

Normalized intensity of microarray data for a set of samples.

| TCID | V01 0313 | V01 0314 | V01 0315 | V01 0316 | V01 0317 | V01 0318 | V01 0319 | V01 0320 | V01 0321 | V01 0322 | V01 0323 | V01 0324 |
|---|---|---|---|---|---|---|---|---|---|---|---|---|
| 3512874 | 11.50 | 11.49 | 11.98 | 11.64 | 10.94 | 11.78 | 12.44 | 12.61 | 10.85 | 11.15 | 11.91 | 9.95 |
| 2701071 | 9.91 | 9.51 | 9.91 | 9.83 | 9.23 | 10.23 | 11.24 | 10.96 | 8.80 | 8.62 | 9.90 | 7.77 |
| 3486096 | 6.89 | 9.05 | 7.86 | 7.44 | 9.98 | 6.37 | 6.53 | 6.80 | 8.91 | 7.83 | 7.58 | 7.16 |
| 2412668 | 8.33 | 8.27 | 8.26 | 8.06 | 7.97 | 8.76 | 9.00 | 8.85 | 8.81 | 7.94 | 8.53 | 8.68 |
| 3329343 | 6.84 | 7.73 | 6.97 | 8.22 | 6.85 | 7.12 | 6.87 | 7.30 | 8.63 | 7.77 | 8.53 | 9.63 |
| 3259367 | 4.78 | 5.39 | 4.31 | 5.52 | 6.60 | 4.04 | 4.83 | 4.11 | 5.91 | 5.75 | 4.20 | 4.37 |
| 3373845 | 10.45 | 8.04 | 9.94 | 9.07 | 7.58 | 7.62 | 9.29 | 8.70 | 8.13 | 10.05 | 8.37 | 9.24 |
| 2321911 | 8.91 | 8.14 | 8.55 | 8.25 | 8.04 | 8.72 | 8.29 | 8.34 | 7.92 | 7.81 | 8.12 | 7.62 |
| 3353914 | 6.82 | 6.45 | 6.68 | 7.23 | 6.92 | 6.60 | 6.65 | 6.28 | 7.24 | 6.65 | 6.77 | 7.42 |
| 3744680 | 7.36 | 7.16 | 7.68 | 7.55 | 6.86 | 7.72 | 8.66 | 8.52 | 6.90 | 6.94 | 7.71 | 6.38 |
| 2373336 | 6.24 | 4.91 | 6.77 | 8.68 | 4.82 | 5.35 | 5.57 | 6.70 | 5.24 | 6.74 | 5.83 | 9.16 |
| 3067478 | 4.75 | 7.70 | 6.26 | 8.52 | 8.12 | 6.39 | 5.15 | 5.80 | 7.91 | 5.25 | 5.49 | 8.58 |
| 3976766 | 7.92 | 7.64 | 8.19 | 7.94 | 7.41 | 8.49 | 9.28 | 9.05 | 7.19 | 7.48 | 8.09 | 6.31 |
| 3246888 | 6.47 | 8.00 | 7.47 | 6.93 | 7.05 | 6.87 | 5.95 | 5.78 | 7.82 | 7.97 | 7.38 | 4.77 |
| 3147985 | 6.09 | 5.91 | 6.23 | 6.85 | 6.82 | 7.68 | 6.50 | 6.71 | 6.47 | 6.62 | 6.72 | 7.56 |
| 3185522 | 9.09 | 9.29 | 9.25 | 8.95 | 9.83 | 9.34 | 9.62 | 9.39 | 10.07 | 8.30 | 9.14 | 9.15 |
| 3861948 | 12.39 | 11.86 | 12.65 | 12.68 | 11.79 | 12.80 | 13.17 | 13.28 | 11.81 | 11.69 | 12.55 | 10.51 |
| 3393479 | 9.70 | 8.24 | 9.20 | 7.50 | 8.23 | 8.46 | 9.61 | 10.27 | 8.09 | 9.24 | 10.69 | 8.21 |
| 3540862 | 6.81 | 7.40 | 7.13 | 6.90 | 7.55 | 6.97 | 6.32 | 6.75 | 7.26 | 7.10 | 6.62 | 7.55 |
| 2777714 | 10.99 | 10.25 | 11.53 | 10.74 | 10.40 | 11.46 | 11.65 | 10.73 | 10.30 | 10.81 | 11.21 | 9.00 |
| 3110395 | 4.78 | 5.16 | 4.38 | 4.03 | 6.77 | 4.34 | 4.39 | 5.01 | 5.32 | 4.65 | 4.84 | 6.58 |
| 3895795 | 8.57 | 9.06 | 8.25 | 8.90 | 7.88 | 8.40 | 10.17 | 9.45 | 8.34 | 8.15 | 7.98 | 8.02 |
| 2854445 | 8.19 | 8.49 | 8.55 | 7.35 | 7.41 | 8.66 | 8.12 | 8.57 | 7.13 | 7.96 | 8.82 | 7.94 |
| 3606034 | 8.35 | 7.62 | 7.46 | 7.09 | 7.68 | 7.42 | 7.34 | 7.35 | 7.98 | 7.82 | 7.78 | 7.24 |
| 3375735 | 7.66 | 7.45 | 7.40 | 7.84 | 7.59 | 8.03 | 8.29 | 8.45 | 7.46 | 8.21 | 8.23 | 7.84 |
| 3948047 | 7.86 | 7.53 | 8.28 | 7.96 | 7.33 | 8.22 | 9.04 | 9.06 | 7.23 | 7.32 | 8.42 | 6.67 |
| 3010503 | 8.84 | 7.76 | 9.15 | 8.23 | 8.15 | 8.86 | 10.16 | 9.35 | 7.79 | 7.16 | 8.42 | 5.51 |
| 3622934 | 7.03 | 8.36 | 6.48 | 8.02 | 8.50 | 6.08 | 7.11 | 6.40 | 7.72 | 7.25 | 6.88 | 7.91 |
| 3441849 | 9.52 | 9.46 | 9.56 | 10.22 | 9.59 | 9.86 | 10.73 | 10.72 | 10.08 | 9.21 | 10.02 | 9.98 |
| 3006572 | 6.00 | 6.67 | 6.50 | 7.42 | 6.59 | 6.43 | 6.46 | 6.82 | 7.16 | 6.80 | 6.67 | 7.65 |
| 3365136 | 8.69 | 10.19 | 9.26 | 11.00 | 11.83 | 7.86 | 8.03 | 9.46 | 11.27 | 10.22 | 9.83 | 10.11 |
| 2642791 | 9.07 | 8.33 | 8.42 | 8.03 | 8.75 | 8.41 | 9.00 | 7.97 | 7.92 | 7.84 | 8.17 | 8.04 |
| 2904485 | 9.54 | 8.94 | 8.89 | 7.02 | 7.54 | 8.47 | 8.38 | 8.47 | 7.80 | 8.89 | 8.47 | 7.61 |
| 3772661 | 9.18 | 9.37 | 9.39 | 9.19 | 8.43 | 9.57 | 10.33 | 10.27 | 8.85 | 9.33 | 9.48 | 9.64 |
| 2796553 | 9.76 | 9.47 | 9.50 | 9.98 | 9.51 | 10.18 | 11.17 | 9.56 | 8.94 | 8.20 | 9.19 | 7.76 |
| 3063795 | 6.89 | 7.16 | 7.27 | 7.10 | 6.84 | 7.17 | 7.06 | 7.65 | 6.79 | 7.44 | 7.27 | 7.21 |
| 3338192 | 9.34 | 9.08 | 8.50 | 10.50 | 9.83 | 9.04 | 7.95 | 8.30 | 9.53 | 9.42 | 10.14 |  |
| 3214845 | 4.51 | 5.16 | 5.83 | 4.20 | 4.07 | 4.38 | 4.09 | 5.75 | 4.22 | 5.28 | 4.58 | 7.21 |
| 2730303 | 4.15 | 4.18 | 4.16 | 4.11 | 4.19 | 4.35 | 4.18 | 4.55 | 4.68 | 4.64 | 4.43 | 4.39 |
| 3811086 | 8.10 | 7.78 | 8.16 | 7.46 | 7.91 | 7.28 | 7.79 | 7.59 | 7.53 | 7.65 | 7.34 | 6.85 |
| 2981874 | 11.04 | 9.52 | 10.30 | 10.10 | 10.75 | 10.23 | 10.46 | 10.57 | 11.04 | 9.94 | 10.85 | 10.33 |
| 3242353 | 6.31 | 5.80 | 5.79 | 5.70 | 6.03 | 6.00 | 5.90 | 5.83 | 5.94 | 5.78 | 6.29 | 5.77 |
| 2442008 | 5.40 | 8.24 | 5.38 | 9.67 | 6.38 | 6.24 | 5.52 | 5.68 | 9.25 | 5.36 | 5.30 | 10.00 |
| 3564210 | 9.06 | 8.39 | 9.53 | 10.07 | 8.64 | 9.74 | 10.73 | 9.91 | 8.49 | 8.04 | 9.10 | 7.91 |
| 2490351 | 4.03 | 3.92 | 3.85 | 4.00 | 3.99 | 4.07 | 4.37 | 4.60 | 4.59 | 4.59 | 4.45 | 4.14 |
| 3759006 | 9.19 | 7.97 | 10.13 | 8.37 | 7.88 | 9.21 | 10.10 | 8.39 | 7.92 | 7.85 | 9.04 | 6.86 |
| 3264997 | 4.04 | 3.97 | 4.24 | 3.98 | 4.04 | 4.12 | 4.33 | 4.40 | 4.02 | 4.36 | 4.20 | 4.03 |
| 3912079 | 3.64 | 3.56 | 3.73 | 3.91 | 3.42 | 3.73 | 4.08 | 4.32 | 3.98 | 3.67 | 4.08 | 3.65 |
| 2926802 | 5.32 | 4.68 | 5.15 | 4.93 | 4.60 | 5.45 | 5.95 | 5.85 | 5.15 | 5.00 | 5.22 | 4.74 |
| 2430163 | 3.97 | 4.22 | 3.69 | 3.70 | 3.70 | 3.81 | 4.11 | 4.32 | 4.09 | 4.28 | 4.16 | 6.60 |
| 3039830 | 3.10 | 3.10 | 3.17 | 2.90 | 3.10 | 3.33 | 3.26 | 3.42 | 3.45 | 3.40 | 3.39 | 3.46 |
| 3935486 | 5.60 | 5.59 | 7.93 | 7.73 | 5.88 | 5.19 | 6.48 | 8.50 | 5.95 | 5.81 | 6.02 | 8.18 |
| 3457336 | 5.42 | 5.39 | 5.38 | 5.22 | 5.34 | 5.96 | 5.70 | 5.78 | 5.55 | 5.58 | 5.77 | 5.55 |
| 3811949 | 3.42 | 3.48 | 3.51 | 3.37 | 3.41 | 3.72 | 3.51 | 4.05 | 3.80 | 3.89 | 3.71 | 3.84 |
| 3343832 | 3.83 | 3.76 | 3.76 | 3.73 | 4.01 | 3.87 | 3.97 | 3.95 | 4.15 | 4.15 | 3.83 | 3.82 |
| 3161261 | 6.24 | 5.98 | 5.95 | 5.61 | 5.52 | 5.95 | 6.27 | 5.50 | 5.23 | 5.62 | 5.18 | 5.29 |
| 3594003 | 4.01 | 3.93 | 3.72 | 3.59 | 3.63 | 3.66 | 3.77 | 3.90 | 3.91 | 3.93 | 4.04 | 3.67 |
| 3805614 | 4.74 | 4.67 | 4.26 | 4.46 | 4.50 | 4.98 | 5.02 | 5.05 | 5.05 | 5.36 | 5.34 | 4.69 |
| 3364127 | 6.92 | 6.93 | 6.60 | 6.65 | 6.55 | 7.05 | 6.83 | 7.57 | 6.84 | 6.80 | 8.09 | 6.81 |
| 3834341 | 3.78 | 4.00 | 3.83 | 3.69 | 3.98 | 4.11 | 4.18 | 4.42 | 3.54 | 3.85 | 3.87 | 3.43 |
| 2585400 | 4.24 | 4.27 | 4.58 | 4.22 | 4.19 | 4.48 | 4.75 | 4.22 | 4.08 | 4.28 | 4.31 | 4.31 |
| 2941690 | 4.43 | 4.24 | 4.22 | 4.10 | 4.19 | 4.16 | 4.57 | 4.12 | 4.74 | 4.89 | 4.89 | 4.41 |
| 3484895 | 4.78 | 4.87 | 4.66 | 5.02 | 4.89 | 5.02 | 4.88 | 4.88 | 4.42 | 5.20 | 4.80 | 6.32 |
| 3159754 | 3.73 | 3.72 | 3.68 | 3.70 | 3.78 | 3.98 | 3.69 | 3.75 | 3.70 | 3.55 | 3.65 | 3.47 |
| 2894790 | 3.67 | 4.03 | 3.95 | 3.58 | 3.78 | 3.83 | 4.31 | 3.99 | 4.35 | 4.43 | 4.23 | 4.22 |
| 3363686 | 3.55 | 3.99 | 4.19 | 3.44 | 3.47 | 3.42 | 4.06 | 3.20 | 3.76 | 3.17 | 3.49 | 3.21 |
| 2923928 | 4.41 | 4.44 | 4.47 | 4.17 | 4.24 | 4.10 | 4.25 | 6.43 | 4.50 | 5.17 | 4.59 | 4.55 |
| 2883317 | 5.08 | 5.01 | 5.69 | 4.90 | 4.64 | 4.53 | 4.95 | 5.09 | 4.71 | 5.80 | 4.64 | 4.78 |
| 2479698 | 5.78 | 6.74 | 6.34 | 5.98 | 6.16 | 5.95 | 6.14 | 6.10 | 5.61 | 5.95 | 6.02 | 6.01 |
| 3428225 | 3.92 | 3.59 | 3.93 | 3.66 | 3.68 | 3.95 | 3.87 | 3.57 | 3.48 | 3.92 | 3.60 | 3.51 |
| 3393446 | 7.06 | 7.09 | 6.69 | 6.85 | 6.86 | 7.36 | 7.27 | 7.56 | 6.95 | 7.10 | 7.61 | 6.86 |
| 3116614 | 13.19 | 13.42 | 13.26 | 12.34 | 13.21 | 13.18 | 12.74 | 12.32 | 13.05 | 13.03 | 12.87 | 12.20 |
| 3415320 | 10.69 | 9.87 | 9.67 | 9.28 | 9.77 | 10.75 | 9.23 | 10.05 | 9.61 | 10.84 | 9.49 | 10.68 |
| 3757108 | 7.86 | 8.15 | 7.45 | 9.40 | 7.50 | 7.43 | 7.77 | 7.74 | 9.38 | 7.84 | 7.89 | 11.05 |
| 4012178 | 6.75 | 10.20 | 5.94 | 8.71 | 11.98 | 6.69 | 6.52 | 6.39 | 11.08 | 8.00 | 6.21 | 11.71 |

TABLE 51-continued

Normalized intensity of microarray data for a set of samples.

| TCID | V01 0313 | V01 0314 | V01 0315 | V01 0316 | V01 0317 | V01 0318 | V01 0319 | V01 0320 | V01 0321 | V01 0322 | V01 0323 | V01 0324 |
|---|---|---|---|---|---|---|---|---|---|---|---|---|
| 3546213 | 10.99 | 11.58 | 10.89 | 11.24 | 11.31 | 10.99 | 10.14 | 9.50 | 11.52 | 11.31 | 10.68 | 10.98 |
| 3561381 | 9.11 | 10.58 | 9.18 | 10.49 | 10.63 | 9.95 | 8.15 | 7.73 | 11.27 | 9.95 | 9.41 | 10.55 |

TABLE 52

Normalized intensity of microarray data for a set of samples.

| TCID | V01 0325 | V01 0326 | V01 0327 | V01 0328 | V01 0329 | V01 0330 | V01 0331 | V01 0332 | V01 0333 | V01 0334 | V01 0335 | V01 0336 |
|---|---|---|---|---|---|---|---|---|---|---|---|---|
| 2604998 | 6.94 | 8.38 | 8.70 | 8.33 | 6.16 | 7.58 | 8.81 | 7.86 | 8.14 | 6.76 | 7.12 | 8.31 |
| 3603932 | 7.10 | 9.47 | 7.15 | 8.51 | 9.49 | 7.43 | 7.38 | 9.13 | 7.95 | 7.75 | 6.86 | 7.50 |
| 2710599 | 6.70 | 6.39 | 5.48 | 11.84 | 9.44 | 7.25 | 11.84 | 9.90 | 11.72 | 7.92 | 6.52 | 10.77 |
| 2440258 | 8.58 | 7.26 | 8.28 | 5.63 | 7.58 | 9.34 | 6.19 | 6.54 | 6.97 | 8.60 | 8.71 | 5.64 |
| 3169331 | 7.20 | 9.17 | 7.62 | 6.67 | 7.00 | 7.93 | 6.95 | 7.91 | 7.09 | 8.03 | 7.47 | 6.79 |
| 2988882 | 9.39 | 10.40 | 9.76 | 9.50 | 10.01 | 9.52 | 8.98 | 9.77 | 9.70 | 9.67 | 9.54 | 8.92 |
| 2964231 | 8.41 | 10.54 | 7.36 | 9.33 | 10.13 | 7.42 | 7.87 | 9.55 | 9.38 | 8.68 | 8.25 | 6.54 |
| 3111561 | 7.98 | 5.51 | 10.04 | 4.81 | 5.25 | 7.58 | 6.69 | 9.77 | 6.66 | 8.00 | 6.60 | 5.38 |
| 2562529 | 8.87 | 9.39 | 8.66 | 10.44 | 9.68 | 8.84 | 10.35 | 9.32 | 10.54 | 8.35 | 9.04 | 9.94 |
| 3692999 | 8.43 | 12.02 | 12.70 | 7.84 | 8.46 | 11.46 | 7.40 | 12.22 | 8.96 | 10.38 | 10.12 | 5.78 |
| 2439554 | 8.06 | 6.35 | 7.14 | 6.21 | 7.45 | 8.79 | 6.06 | 6.31 | 7.18 | 7.94 | 7.78 | 5.69 |
| 2685304 | 7.15 | 8.79 | 7.10 | 11.72 | 9.36 | 6.97 | 11.32 | 8.57 | 10.89 | 7.91 | 6.97 | 10.62 |
| 2578790 | 6.24 | 5.21 | 7.14 | 4.57 | 4.85 | 6.14 | 4.52 | 6.84 | 4.38 | 6.16 | 6.04 | 5.19 |
| 2373842 | 11.77 | 10.92 | 11.23 | 8.72 | 10.28 | 11.37 | 9.64 | 9.94 | 10.72 | 11.42 | 11.49 | 7.83 |
| 2750627 | 7.82 | 10.08 | 9.40 | 9.90 | 8.08 | 8.89 | 9.96 | 9.11 | 9.41 | 8.24 | 8.10 | 10.10 |
| 3397774 | 5.25 | 7.18 | 4.83 | 4.75 | 5.41 | 4.70 | 4.94 | 4.85 | 4.37 | 4.82 | 5.25 | 5.45 |
| 2635741 | 8.87 | 7.78 | 8.78 | 6.19 | 7.66 | 9.19 | 6.25 | 6.58 | 7.24 | 8.97 | 9.10 | 6.39 |
| 3970833 | 9.81 | 11.03 | 9.68 | 10.17 | 10.07 | 9.99 | 9.78 | 9.99 | 9.78 | 9.90 | 9.73 | 9.94 |
| 3577612 | 11.29 | 9.83 | 10.70 | 11.71 | 10.35 | 10.56 | 11.27 | 9.66 | 11.09 | 10.96 | 10.70 | 11.33 |
| 2708922 | 8.67 | 7.42 | 7.51 | 7.46 | 7.04 | 9.19 | 8.20 | 6.62 | 8.53 | 8.07 | 9.01 | 7.69 |
| 2970897 | 4.81 | 6.24 | 5.38 | 4.63 | 5.81 | 4.77 | 5.13 | 5.49 | 5.85 | 5.21 | 4.90 | 5.15 |
| 3724545 | 9.07 | 6.88 | 9.25 | 9.36 | 8.56 | 7.44 | 10.05 | 9.33 | 9.36 | 9.10 | 9.69 | 9.93 |
| 2798538 | 9.22 | 10.26 | 9.60 | 9.46 | 9.66 | 9.55 | 8.38 | 9.32 | 9.33 | 9.23 | 8.84 | 7.90 |
| 2806468 | 11.19 | 9.33 | 11.03 | 5.86 | 9.50 | 10.35 | 8.44 | 9.20 | 10.09 | 11.52 | 11.21 | 7.57 |
| 2880051 | 7.04 | 7.20 | 6.54 | 6.08 | 6.55 | 7.69 | 6.28 | 6.42 | 6.48 | 6.55 | 6.70 | 6.75 |
| 2732508 | 5.27 | 3.10 | 3.40 | 4.65 | 3.99 | 3.67 | 3.46 | 3.69 | 4.44 | 3.65 | 4.40 | 3.66 |
| 2822492 | 6.45 | 8.59 | 5.73 | 5.85 | 6.22 | 6.91 | 5.82 | 6.00 | 5.85 | 6.23 | 6.06 | 5.99 |
| 3404030 | 8.90 | 7.37 | 8.86 | 5.73 | 7.36 | 9.83 | 6.62 | 7.21 | 7.09 | 9.25 | 9.05 | 6.84 |
| 3059667 | 8.83 | 5.56 | 10.12 | 3.87 | 4.49 | 10.23 | 5.60 | 9.15 | 6.53 | 7.28 | 7.96 | 4.99 |
| 3108526 | 8.61 | 10.29 | 10.63 | 8.31 | 6.33 | 8.02 | 8.34 | 10.02 | 8.02 | 8.91 | 8.56 | 8.05 |
| 2526806 | 8.18 | 9.54 | 8.63 | 12.96 | 12.18 | 6.80 | 12.74 | 11.69 | 12.95 | 10.97 | 7.19 | 12.17 |
| 2428501 | 7.40 | 8.55 | 6.86 | 6.52 | 8.44 | 7.41 | 6.87 | 8.15 | 7.64 | 7.35 | 7.70 | 6.01 |
| 2657808 | 6.43 | 5.18 | 5.93 | 10.30 | 8.32 | 7.43 | 11.01 | 6.81 | 11.67 | 6.53 | 6.06 | 11.06 |
| 2584018 | 8.10 | 6.53 | 7.70 | 10.41 | 10.14 | 7.94 | 10.06 | 9.55 | 10.17 | 8.79 | 8.44 | 8.52 |
| 3976341 | 10.13 | 9.44 | 9.77 | 12.07 | 11.27 | 9.39 | 12.25 | 10.40 | 11.16 | 10.44 | 10.28 | 11.84 |
| 2739308 | 5.50 | 5.04 | 5.25 | 4.49 | 5.24 | 5.07 | 4.46 | 4.98 | 4.33 | 5.40 | 5.60 | 5.13 |
| 3959862 | 6.13 | 9.16 | 5.07 | 4.64 | 6.05 | 5.35 | 5.11 | 6.07 | 4.04 | 5.08 | 5.79 | 4.63 |
| 2362351 | 8.03 | 6.84 | 7.60 | 6.00 | 7.18 | 9.44 | 5.91 | 6.09 | 6.66 | 8.00 | 7.69 | 5.96 |
| 3648391 | 6.28 | 3.85 | 4.88 | 6.12 | 5.18 | 8.11 | 4.38 | 4.49 | 3.78 | 7.75 | 6.17 | 4.38 |
| 3009299 | 10.26 | 11.64 | 10.80 | 10.85 | 11.07 | 10.69 | 10.38 | 10.89 | 10.48 | 10.80 | 10.71 | 10.03 |
| 3443464 | 6.39 | 5.48 | 5.76 | 5.43 | 5.94 | 6.09 | 5.15 | 5.60 | 5.25 | 6.01 | 6.00 | 5.62 |
| 2730746 | 6.55 | 9.00 | 8.21 | 5.08 | 5.22 | 7.27 | 6.13 | 7.94 | 5.45 | 7.39 | 6.99 | 5.72 |
| 2427619 | 9.28 | 7.70 | 9.09 | 6.95 | 6.86 | 9.33 | 6.63 | 6.34 | 7.51 | 9.60 | 9.19 | 5.86 |
| 3042001 | 8.26 | 9.56 | 8.97 | 8.69 | 9.06 | 9.14 | 8.56 | 8.90 | 8.81 | 9.02 | 8.91 | 8.36 |
| 2566848 | 6.19 | 5.18 | 6.06 | 5.22 | 5.62 | 5.70 | 5.31 | 5.31 | 5.34 | 5.59 | 6.38 | 5.99 |
| 2984616 | 9.04 | 10.14 | 9.14 | 8.99 | 10.08 | 8.97 | 8.76 | 9.29 | 8.40 | 9.26 | 9.06 | 8.18 |
| 2378068 | 7.89 | 7.13 | 7.65 | 10.48 | 9.85 | 7.78 | 9.59 | 10.20 | 8.06 | 8.13 | 8.56 | 8.64 |
| 2721959 | 7.02 | 6.87 | 5.92 | 13.01 | 9.59 | 6.72 | 12.46 | 9.56 | 12.44 | 11.23 | 6.76 | 12.11 |
| 2877508 | 9.91 | 11.40 | 10.60 | 10.61 | 10.47 | 9.95 | 10.25 | 10.45 | 10.70 | 10.20 | 10.30 | 9.63 |
| 3450861 | 7.17 | 5.54 | 6.26 | 4.59 | 5.21 | 7.98 | 5.12 | 5.13 | 4.94 | 7.47 | 6.48 | 4.98 |
| 2688717 | 9.16 | 7.22 | 9.25 | 5.20 | 7.35 | 8.70 | 6.25 | 6.41 | 7.00 | 9.14 | 9.72 | 6.46 |
| 3270270 | 9.10 | 7.29 | 8.17 | 8.64 | 8.05 | 8.32 | 8.58 | 7.58 | 8.24 | 8.59 | 8.80 | 8.25 |
| 3417703 | 7.76 | 5.20 | 10.07 | 7.22 | 4.82 | 7.82 | 7.17 | 8.81 | 5.08 | 7.07 | 7.77 | 9.67 |
| 3302990 | 6.79 | 9.30 | 7.88 | 8.16 | 8.21 | 7.59 | 8.04 | 8.16 | 8.43 | 7.82 | 7.43 | 8.11 |
| 2377283 | 5.85 | 4.54 | 5.48 | 4.34 | 5.05 | 4.68 | 4.30 | 4.61 | 4.27 | 5.99 | 6.03 | 4.98 |
| 3122678 | 5.20 | 7.57 | 4.91 | 4.99 | 5.67 | 5.32 | 4.46 | 5.74 | 5.19 | 4.95 | 5.59 | 6.00 |
| 2688499 | 8.84 | 7.27 | 10.60 | 11.00 | 9.26 | 9.57 | 11.77 | 10.33 | 11.01 | 9.36 | 9.04 | 11.58 |
| 2377094 | 8.28 | 11.33 | 9.06 | 9.28 | 8.53 | 8.18 | 7.75 | 8.81 | 9.03 | 8.25 | 8.35 | 7.40 |
| 3278198 | 7.19 | 10.15 | 8.78 | 8.95 | 9.21 | 7.87 | 8.35 | 8.37 | 8.10 | 8.15 | 7.15 | 8.09 |
| 2598261 | 7.09 | 8.33 | 7.29 | 12.92 | 11.24 | 6.14 | 12.50 | 10.93 | 12.83 | 9.43 | 6.50 | 12.02 |
| 3982612 | 9.49 | 6.80 | 8.47 | 5.52 | 6.20 | 9.91 | 6.34 | 6.25 | 6.80 | 9.01 | 9.35 | 5.88 |
| 2884845 | 4.83 | 4.47 | 4.68 | 10.46 | 6.27 | 5.04 | 9.92 | 4.85 | 8.71 | 6.86 | 4.77 | 9.03 |

TABLE 52-continued

Normalized intensity of microarray data for a set of samples.

| TCID | V01 0325 | V01 0326 | V01 0327 | V01 0328 | V01 0329 | V01 0330 | V01 0331 | V01 0332 | V01 0333 | V01 0334 | V01 0335 | V01 0336 |
|---|---|---|---|---|---|---|---|---|---|---|---|---|
| 3982560 | 7.94 | 5.58 | 7.54 | 4.84 | 5.47 | 7.46 | 5.42 | 5.42 | 5.82 | 7.83 | 7.80 | 5.25 |
| 3204285 | 6.71 | 5.07 | 5.20 | 5.57 | 7.16 | 4.65 | 4.78 | 5.07 | 7.79 | 5.80 | 10.49 | 5.60 |
| 3654699 | 9.47 | 12.36 | 11.72 | 10.98 | 12.46 | 9.30 | 10.14 | 12.27 | 11.83 | 11.56 | 9.98 | 10.12 |
| 2638676 | 8.68 | 6.75 | 7.63 | 7.53 | 8.29 | 8.02 | 6.61 | 7.41 | 7.67 | 8.53 | 8.80 | 4.73 |
| 3367673 | 7.42 | 9.10 | 8.64 | 4.60 | 5.19 | 7.48 | 5.15 | 8.26 | 4.57 | 6.83 | 7.23 | 5.59 |
| 3212008 | 6.45 | 5.51 | 5.98 | 8.83 | 6.39 | 7.40 | 7.18 | 5.95 | 7.65 | 6.49 | 6.28 | 8.62 |
| 3326635 | 10.34 | 9.38 | 9.89 | 10.17 | 10.11 | 10.31 | 10.06 | 9.95 | 10.04 | 10.02 | 10.08 | 10.11 |
| 3031556 | 9.75 | 8.80 | 9.26 | 7.44 | 9.29 | 9.99 | 7.45 | 8.15 | 8.74 | 9.88 | 10.07 | 5.78 |
| 3662201 | 9.85 | 12.02 | 13.18 | 9.60 | 9.57 | 12.40 | 7.98 | 12.65 | 9.81 | 11.04 | 11.23 | 7.84 |
| 2809793 | 9.22 | 7.93 | 9.10 | 5.89 | 8.69 | 10.28 | 6.13 | 7.31 | 8.39 | 9.95 | 9.99 | 6.13 |
| 2817731 | 7.96 | 7.44 | 7.33 | 7.20 | 8.27 | 6.77 | 7.37 | 8.41 | 7.81 | 7.59 | 7.23 | 6.38 |
| 4020655 | 5.69 | 4.46 | 5.06 | 7.27 | 5.64 | 6.59 | 6.37 | 5.04 | 5.39 | 5.13 | 5.97 | 8.06 |
| 3494629 | 4.26 | 5.20 | 4.18 | 7.24 | 4.61 | 4.22 | 8.53 | 4.45 | 7.97 | 4.30 | 4.22 | 6.79 |
| 3852832 | 10.23 | 8.33 | 9.00 | 5.70 | 6.55 | 9.29 | 8.02 | 7.29 | 7.45 | 9.59 | 9.82 | 6.87 |
| 3761959 | 8.87 | 10.43 | 10.12 | 9.74 | 10.60 | 9.93 | 9.60 | 10.35 | 9.82 | 9.68 | 9.31 | 9.60 |
| 2834282 | 6.15 | 6.31 | 7.03 | 8.94 | 7.41 | 7.08 | 8.27 | 5.79 | 8.90 | 5.92 | 6.12 | 7.68 |
| 3341497 | 6.35 | 9.43 | 6.12 | 6.46 | 6.32 | 6.37 | 6.51 | 6.50 | 7.27 | 6.26 | 6.08 | 7.47 |
| 2372812 | 5.28 | 4.52 | 4.55 | 4.66 | 7.59 | 5.22 | 4.68 | 4.51 | 4.73 | 5.11 | 5.26 | 5.04 |
| 2486811 | 10.49 | 9.02 | 9.48 | 8.14 | 10.13 | 10.49 | 8.06 | 10.83 | 10.03 | 10.63 | 9.86 | 6.29 |
| 3768474 | 8.24 | 7.92 | 7.61 | 7.80 | 9.24 | 8.32 | 7.59 | 8.14 | 8.22 | 8.09 | 8.38 | 7.30 |
| 3142381 | 5.55 | 3.87 | 7.15 | 4.05 | 7.87 | 6.41 | 5.40 | 7.78 | 4.57 | 4.95 | 6.41 | 3.89 |
| 2396750 | 7.41 | 8.63 | 7.38 | 9.17 | 7.68 | 7.64 | 8.53 | 7.53 | 7.80 | 7.53 | 7.22 | 8.33 |
| 3902489 | 11.84 | 10.33 | 10.58 | 9.77 | 10.13 | 11.89 | 10.46 | 10.19 | 11.07 | 11.43 | 11.98 | 9.56 |
| 3032647 | 7.12 | 5.70 | 8.07 | 5.88 | 6.30 | 6.92 | 6.86 | 8.29 | 6.02 | 6.98 | 7.10 | 6.69 |
| 3875642 | 6.58 | 5.52 | 6.44 | 5.09 | 5.60 | 5.96 | 5.10 | 5.04 | 6.46 | 6.87 | 6.19 | 5.91 |
| 4027585 | 11.71 | 10.09 | 10.35 | 8.65 | 11.25 | 11.83 | 9.31 | 10.86 | 11.14 | 11.52 | 12.09 | 8.68 |
| 2352609 | 6.45 | 7.47 | 7.11 | 6.99 | 5.87 | 6.23 | 6.73 | 7.08 | 6.75 | 6.36 | 6.33 | 6.67 |
| 3376529 | 8.52 | 9.99 | 8.77 | 10.39 | 8.81 | 9.23 | 10.97 | 8.29 | 10.43 | 8.79 | 8.80 | 10.69 |
| 2491271 | 13.49 | 12.79 | 13.45 | 13.50 | 13.81 | 13.59 | 13.56 | 13.59 | 13.58 | 13.57 | 13.70 | 12.86 |
| 3874751 | 8.83 | 9.31 | 9.09 | 9.86 | 10.09 | 8.82 | 9.58 | 9.52 | 9.34 | 9.27 | 9.22 | 9.92 |
| 2326463 | 12.27 | 10.84 | 12.12 | 10.19 | 12.56 | 12.57 | 10.38 | 12.40 | 11.48 | 12.41 | 12.31 | 9.44 |
| 3341061 | 6.30 | 6.53 | 6.02 | 6.61 | 8.35 | 6.27 | 5.72 | 7.52 | 7.27 | 6.68 | 5.89 | 5.68 |
| 3839910 | 9.95 | 7.52 | 9.12 | 4.98 | 5.88 | 8.91 | 6.90 | 6.34 | 7.35 | 8.33 | 9.31 | 6.82 |
| 2708855 | 4.49 | 4.46 | 4.05 | 8.61 | 5.69 | 4.58 | 8.63 | 4.35 | 7.89 | 4.37 | 4.44 | 7.59 |
| 3512874 | 12.64 | 11.49 | 12.04 | 10.52 | 11.80 | 12.48 | 11.05 | 11.98 | 11.73 | 12.40 | 12.29 | 9.95 |
| 2701071 | 11.13 | 9.74 | 10.10 | 7.46 | 9.26 | 10.16 | 8.36 | 8.91 | 9.46 | 10.44 | 10.63 | 6.84 |
| 3486096 | 6.31 | 7.86 | 7.99 | 7.67 | 5.55 | 7.31 | 6.51 | 7.17 | 6.39 | 5.70 | 6.20 | 6.76 |
| 2412668 | 8.70 | 8.90 | 8.73 | 8.47 | 9.59 | 8.31 | 8.38 | 8.80 | 8.63 | 9.00 | 8.85 | 7.78 |
| 3329343 | 7.23 | 7.41 | 7.30 | 8.69 | 9.20 | 7.51 | 9.71 | 7.73 | 8.85 | 7.03 | 7.04 | 9.82 |
| 3259367 | 4.50 | 4.03 | 4.17 | 4.21 | 4.23 | 4.49 | 5.35 | 4.35 | 4.70 | 4.19 | 4.13 | 4.72 |
| 3373845 | 8.54 | 6.57 | 10.01 | 9.57 | 9.92 | 8.84 | 9.71 | 10.82 | 9.40 | 9.30 | 8.53 | 8.75 |
| 2321911 | 8.42 | 7.74 | 7.54 | 7.82 | 8.46 | 8.79 | 7.35 | 7.93 | 8.09 | 8.40 | 8.31 | 7.46 |
| 3353914 | 6.52 | 6.78 | 6.73 | 7.57 | 8.82 | 6.29 | 7.94 | 8.73 | 7.74 | 7.72 | 6.44 | 7.42 |
| 3744680 | 8.64 | 6.95 | 7.68 | 6.83 | 8.81 | 8.46 | 6.82 | 8.01 | 8.09 | 8.14 | 8.01 | 7.26 |
| 2373336 | 6.18 | 5.34 | 5.58 | 8.71 | 7.06 | 6.03 | 10.06 | 7.92 | 9.60 | 6.32 | 6.24 | 8.24 |
| 3067478 | 5.00 | 5.87 | 4.91 | 8.80 | 5.71 | 6.04 | 8.15 | 6.57 | 7.96 | 5.77 | 5.16 | 7.56 |
| 3976766 | 9.23 | 7.30 | 8.48 | 6.67 | 8.22 | 8.94 | 7.00 | 7.85 | 7.78 | 8.51 | 8.53 | 6.99 |
| 3246888 | 5.76 | 7.39 | 7.15 | 4.46 | 5.19 | 6.32 | 5.54 | 7.02 | 5.71 | 5.70 | 5.94 | 6.25 |
| 3147985 | 5.69 | 6.86 | 6.61 | 6.69 | 7.99 | 6.24 | 7.63 | 8.53 | 7.37 | 6.91 | 6.36 | 7.09 |
| 3185522 | 9.23 | 9.48 | 9.43 | 9.67 | 11.15 | 9.23 | 9.49 | 11.09 | 10.79 | 9.76 | 9.33 | 9.03 |
| 3861948 | 13.19 | 11.75 | 12.59 | 10.13 | 12.89 | 13.15 | 11.75 | 12.28 | 12.16 | 13.00 | 13.13 | 10.03 |
| 3393479 | 9.50 | 8.24 | 10.68 | 8.46 | 10.80 | 8.34 | 9.36 | 10.27 | 9.36 | 9.32 | 8.91 | 9.64 |
| 3540862 | 6.72 | 9.33 | 6.77 | 7.26 | 6.34 | 6.61 | 6.68 | 6.77 | 6.98 | 6.68 | 6.74 | 7.36 |
| 2777714 | 12.18 | 11.12 | 11.18 | 7.34 | 10.15 | 12.08 | 9.93 | 9.72 | 11.43 | 11.83 | 12.18 | 8.11 |
| 3110395 | 4.89 | 4.42 | 5.00 | 5.75 | 4.85 | 4.72 | 5.78 | 4.64 | 5.74 | 4.80 | 4.70 | 5.92 |
| 3895795 | 9.92 | 7.73 | 8.37 | 7.98 | 8.46 | 8.72 | 8.56 | 7.71 | 8.08 | 8.59 | 8.85 | 8.56 |
| 2854445 | 8.07 | 7.66 | 8.05 | 8.61 | 10.96 | 7.90 | 8.59 | 10.62 | 10.58 | 9.53 | 8.83 | 6.10 |
| 3606034 | 7.13 | 7.41 | 7.69 | 7.30 | 8.18 | 6.99 | 8.01 | 7.55 | 7.60 | 7.48 | 7.12 | 7.12 |
| 3375735 | 8.51 | 7.26 | 8.52 | 8.21 | 9.38 | 8.60 | 7.80 | 8.50 | 8.49 | 8.68 | 8.08 | 9.11 |
| 3948047 | 8.77 | 7.37 | 8.42 | 7.06 | 9.10 | 8.90 | 7.40 | 8.49 | 8.13 | 8.83 | 8.81 | 7.19 |
| 3010503 | 8.90 | 8.09 | 9.01 | 5.68 | 10.51 | 8.80 | 7.22 | 10.02 | 8.56 | 9.39 | 9.26 | 5.38 |
| 3622934 | 6.36 | 7.87 | 6.55 | 7.68 | 5.91 | 6.25 | 7.14 | 5.44 | 7.14 | 5.62 | 5.85 | 7.82 |
| 3441849 | 10.99 | 9.77 | 10.33 | 10.05 | 10.57 | 10.51 | 10.33 | 10.22 | 10.09 | 10.30 | 10.38 | 10.22 |
| 3006572 | 6.88 | 6.69 | 6.52 | 6.73 | 6.75 | 6.85 | 6.94 | 6.51 | 6.74 | 6.75 | 6.88 | 7.02 |
| 3365136 | 9.09 | 9.61 | 9.46 | 9.98 | 9.95 | 9.49 | 10.15 | 9.31 | 9.53 | 8.97 | 9.30 | 10.38 |
| 2642791 | 7.98 | 8.49 | 8.34 | 8.30 | 8.03 | 7.93 | 7.79 | 8.12 | 8.42 | 8.05 | 8.34 | 7.11 |
| 2904485 | 7.50 | 6.54 | 9.14 | 7.93 | 7.07 | 8.09 | 7.63 | 8.49 | 7.41 | 7.67 | 8.21 | 7.69 |
| 3772661 | 10.44 | 9.27 | 9.68 | 9.55 | 11.80 | 9.07 | 10.12 | 11.39 | 10.59 | 10.28 | 10.17 | 9.58 |
| 2796553 | 10.40 | 9.42 | 9.58 | 8.11 | 9.58 | 9.08 | 8.62 | 9.25 | 9.23 | 9.54 | 10.02 | 7.37 |
| 3063795 | 7.70 | 7.29 | 7.40 | 7.44 | 8.23 | 7.22 | 7.37 | 7.86 | 8.40 | 7.84 | 7.84 | 7.69 |
| 3338192 | 7.45 | 8.29 | 9.16 | 10.26 | 8.59 | 9.03 | 10.52 | 8.94 | 10.27 | 7.57 | 8.27 | 10.84 |
| 3214845 | 5.06 | 6.89 | 4.54 | 5.79 | 4.23 | 5.14 | 4.12 | 4.62 | 4.23 | 4.33 | 4.28 | 4.70 |
| 2730303 | 4.43 | 4.47 | 4.44 | 4.51 | 4.63 | 5.10 | 4.55 | 4.66 | 4.21 | 4.37 | 4.98 | 4.90 |
| 3811086 | 7.18 | 7.34 | 7.54 | 7.33 | 7.38 | 7.45 | 7.24 | 7.45 | 6.97 | 7.25 | 7.49 | 7.01 |
| 2981874 | 10.45 | 11.03 | 10.84 | 10.38 | 11.02 | 10.23 | 10.05 | 10.21 | 10.35 | 10.57 | 10.46 | 9.79 |

TABLE 52-continued

Normalized intensity of microarray data for a set of samples.

| TCID | V01 0325 | V01 0326 | V01 0327 | V01 0328 | V01 0329 | V01 0330 | V01 0331 | V01 0332 | V01 0333 | V01 0334 | V01 0335 | V01 0336 |
|---|---|---|---|---|---|---|---|---|---|---|---|---|
| 3242353 | 5.66 | 6.17 | 6.01 | 5.81 | 7.21 | 5.95 | 6.28 | 6.51 | 6.06 | 5.88 | 6.02 | 5.74 |
| 2442008 | 5.32 | 5.08 | 5.36 | 9.75 | 6.54 | 5.67 | 8.58 | 5.69 | 7.89 | 6.00 | 5.55 | 8.34 |
| 3564210 | 10.60 | 8.67 | 9.54 | 8.35 | 9.66 | 9.94 | 8.56 | 9.39 | 9.35 | 9.81 | 10.15 | 7.83 |
| 2490351 | 4.69 | 4.37 | 4.57 | 4.40 | 4.79 | 4.67 | 4.39 | 4.46 | 4.27 | 4.67 | 4.80 | 5.04 |
| 3759006 | 10.15 | 8.69 | 8.85 | 6.64 | 8.06 | 10.79 | 7.49 | 7.39 | 8.88 | 9.64 | 10.81 | 7.49 |
| 3264997 | 4.43 | 4.09 | 4.40 | 4.43 | 4.79 | 4.37 | 4.20 | 4.33 | 3.96 | 4.54 | 4.65 | 4.53 |
| 3912079 | 4.16 | 4.31 | 3.87 | 3.82 | 3.84 | 4.05 | 4.05 | 3.81 | 3.80 | 4.03 | 3.80 | 3.64 |
| 2926802 | 6.71 | 6.10 | 5.29 | 4.84 | 6.03 | 6.47 | 5.01 | 4.95 | 5.47 | 6.41 | 6.93 | 5.15 |
| 2430163 | 4.32 | 4.25 | 4.25 | 4.23 | 5.16 | 4.60 | 5.79 | 4.93 | 5.94 | 8.33 | 4.62 | 4.63 |
| 3039830 | 3.37 | 3.46 | 3.45 | 3.39 | 3.62 | 3.58 | 3.45 | 3.39 | 3.36 | 3.31 | 3.49 | 3.57 |
| 3935486 | 7.27 | 6.81 | 6.81 | 7.83 | 10.01 | 8.22 | 7.56 | 10.34 | 10.24 | 7.57 | 8.12 | 5.37 |
| 3457336 | 6.03 | 5.33 | 5.55 | 5.80 | 6.02 | 5.65 | 5.35 | 5.69 | 5.19 | 5.56 | 6.06 | 5.95 |
| 3811949 | 4.07 | 3.72 | 3.95 | 3.90 | 4.07 | 3.99 | 3.70 | 3.84 | 3.63 | 4.11 | 3.98 | 4.32 |
| 3343832 | 4.13 | 3.89 | 3.99 | 4.07 | 4.59 | 4.32 | 3.89 | 4.38 | 3.79 | 4.14 | 4.21 | 4.40 |
| 3161261 | 6.40 | 6.10 | 5.83 | 4.91 | 6.01 | 6.13 | 5.28 | 5.73 | 5.14 | 6.17 | 5.55 | 5.47 |
| 3594003 | 4.02 | 3.84 | 3.81 | 3.90 | 4.55 | 3.98 | 3.90 | 3.83 | 3.69 | 3.81 | 4.27 | 3.84 |
| 3805614 | 5.15 | 4.48 | 5.30 | 5.18 | 5.93 | 5.38 | 4.77 | 5.31 | 4.48 | 5.54 | 5.19 | 5.77 |
| 3364127 | 7.46 | 6.45 | 7.00 | 7.00 | 7.53 | 7.27 | 7.03 | 7.02 | 6.45 | 7.25 | 7.31 | 7.86 |
| 3834341 | 4.32 | 3.50 | 3.95 | 4.01 | 4.52 | 4.00 | 3.85 | 4.01 | 3.81 | 4.11 | 4.35 | 4.41 |
| 2585400 | 4.94 | 4.41 | 4.31 | 4.46 | 4.44 | 4.41 | 4.42 | 4.42 | 4.72 | 4.23 | 4.75 | 4.37 |
| 2941690 | 4.65 | 4.85 | 4.49 | 4.47 | 5.03 | 4.89 | 4.93 | 5.08 | 4.47 | 4.76 | 4.57 | 5.43 |
| 3484895 | 4.73 | 4.42 | 4.75 | 5.43 | 4.76 | 4.60 | 6.01 | 4.49 | 4.62 | 4.64 | 5.13 | 5.88 |
| 3159754 | 3.67 | 3.72 | 3.64 | 3.48 | 3.80 | 3.43 | 3.48 | 3.65 | 3.47 | 3.63 | 3.74 | 3.59 |
| 2894790 | 4.43 | 4.24 | 4.37 | 4.03 | 4.33 | 4.52 | 4.35 | 4.08 | 4.02 | 4.24 | 4.39 | 4.76 |
| 3363686 | 3.18 | 2.92 | 3.62 | 3.31 | 3.58 | 3.34 | 3.16 | 3.27 | 3.16 | 3.52 | 3.26 | 3.76 |
| 2923928 | 4.83 | 4.84 | 4.59 | 4.79 | 5.01 | 5.00 | 4.57 | 4.75 | 4.16 | 4.80 | 4.44 | 5.07 |
| 2883317 | 6.29 | 4.66 | 5.26 | 4.67 | 5.64 | 5.16 | 4.64 | 5.19 | 4.60 | 5.11 | 5.06 | 5.14 |
| 2479698 | 5.64 | 5.89 | 5.96 | 5.97 | 5.50 | 5.84 | 5.63 | 5.70 | 5.57 | 5.52 | 5.82 | 5.85 |
| 3428225 | 3.77 | 3.53 | 3.77 | 3.65 | 4.08 | 3.78 | 3.63 | 3.68 | 3.45 | 3.89 | 3.67 | 3.84 |
| 3393446 | 7.78 | 6.32 | 7.30 | 7.51 | 9.21 | 7.54 | 7.38 | 9.19 | 6.51 | 7.79 | 8.31 | 7.91 |
| 3116614 | 11.57 | 12.41 | 12.99 | 12.08 | 9.81 | 11.83 | 12.06 | 12.41 | 11.67 | 12.20 | 12.44 | 12.19 |
| 3415320 | 8.70 | 11.07 | 10.50 | 10.88 | 9.06 | 8.63 | 11.32 | 9.68 | 10.77 | 10.32 | 9.22 | 10.65 |
| 3757108 | 8.07 | 6.95 | 7.37 | 11.14 | 9.99 | 8.98 | 11.60 | 8.65 | 11.02 | 9.10 | 7.27 | 11.15 |
| 4012178 | 6.40 | 6.99 | 6.15 | 11.83 | 8.12 | 6.93 | 8.58 | 6.40 | 9.43 | 6.52 | 6.51 | 10.30 |
| 3546213 | 8.99 | 11.19 | 10.66 | 10.90 | 8.31 | 10.08 | 11.24 | 10.51 | 10.14 | 10.03 | 9.19 | 11.02 |
| 3561381 | 7.07 | 9.39 | 9.64 | 9.76 | 8.19 | 8.98 | 9.94 | 9.03 | 9.83 | 8.22 | 7.57 | 9.94 |

TABLE 53

Normalized intensity of microarray data for a set of samples.

| TCID | V01 0337 | V01 0338 | V01 0339 | V01 0340 | V01 0341 | V01 0342 | V01 0343 | V01 0344 | V01 0345 | V01 0346 | V01 0347 | V01 0348 |
|---|---|---|---|---|---|---|---|---|---|---|---|---|
| 2604998 | 8.72 | 8.08 | 5.43 | 7.85 | 8.41 | 7.56 | 6.69 | 6.49 | 6.94 | 7.49 | 8.30 | 5.26 |
| 3603932 | 6.50 | 8.06 | 9.70 | 8.17 | 8.32 | 6.91 | 6.93 | 9.44 | 8.42 | 7.09 | 6.75 | 6.95 |
| 2710599 | 6.28 | 5.62 | 6.98 | 9.16 | 11.73 | 8.34 | 7.25 | 7.83 | 7.94 | 6.92 | 6.18 | 7.14 |
| 2440258 | 6.57 | 6.73 | 7.95 | 7.91 | 6.35 | 8.96 | 9.52 | 6.73 | 7.51 | 9.11 | 8.08 | 9.71 |
| 3169331 | 8.32 | 10.09 | 7.47 | 7.48 | 6.73 | 8.21 | 7.02 | 8.74 | 8.06 | 7.24 | 7.12 | 7.79 |
| 2988882 | 10.10 | 10.89 | 10.14 | 9.87 | 9.22 | 9.60 | 10.06 | 10.56 | 10.49 | 9.30 | 9.15 | 10.33 |
| 2964231 | 7.76 | 10.59 | 10.54 | 9.37 | 9.46 | 8.76 | 8.55 | 10.06 | 9.85 | 8.48 | 7.47 | 6.82 |
| 3111561 | 10.17 | 9.38 | 5.42 | 9.00 | 5.10 | 8.45 | 6.69 | 7.64 | 7.71 | 8.97 | 9.43 | 5.07 |
| 2562529 | 9.52 | 8.69 | 9.23 | 9.14 | 10.79 | 9.40 | 9.06 | 9.02 | 9.25 | 8.96 | 9.15 | 9.49 |
| 3692999 | 12.34 | 11.31 | 7.78 | 12.28 | 6.97 | 12.10 | 11.12 | 11.76 | 9.95 | 11.37 | 9.68 | 5.75 |
| 2439544 | 6.67 | 7.17 | 7.55 | 7.90 | 5.87 | 9.13 | 10.36 | 6.43 | 7.38 | 8.45 | 8.02 | 10.56 |
| 2685304 | 6.58 | 7.65 | 8.66 | 7.86 | 11.71 | 7.27 | 6.17 | 9.66 | 10.25 | 8.11 | 7.57 | 6.22 |
| 2578790 | 6.80 | 4.78 | 4.96 | 6.77 | 4.59 | 6.11 | 5.53 | 4.77 | 4.78 | 6.77 | 7.69 | 4.93 |
| 2373842 | 9.72 | 11.35 | 10.67 | 11.21 | 9.26 | 11.27 | 11.53 | 9.81 | 11.32 | 11.71 | 11.63 | 11.18 |
| 2750627 | 10.49 | 8.53 | 6.27 | 8.27 | 9.45 | 8.95 | 7.53 | 6.02 | 6.11 | 8.54 | 8.60 | 5.33 |
| 3397774 | 5.19 | 5.07 | 4.93 | 5.24 | 5.05 | 5.31 | 5.77 | 8.17 | 6.57 | 5.07 | 5.38 | 5.29 |
| 2635741 | 7.18 | 7.17 | 6.77 | 8.12 | 6.84 | 8.78 | 8.02 | 5.46 | 7.94 | 8.94 | 7.79 | 8.75 |
| 3970833 | 10.01 | 10.33 | 10.33 | 10.68 | 10.37 | 9.89 | 10.21 | 10.86 | 10.35 | 9.83 | 10.01 | 10.45 |
| 3577612 | 9.85 | 10.66 | 9.73 | 10.78 | 11.43 | 10.44 | 9.37 | 9.15 | 10.60 | 10.73 | 10.83 | 7.73 |
| 2708922 | 6.51 | 8.88 | 7.43 | 7.73 | 7.72 | 8.19 | 7.35 | 7.10 | 9.02 | 8.11 | 8.26 | 5.97 |
| 2970897 | 7.57 | 6.91 | 5.86 | 5.68 | 4.63 | 4.74 | 5.28 | 6.43 | 6.86 | 5.62 | 5.07 | 5.63 |
| 3724545 | 10.38 | 8.81 | 8.62 | 8.87 | 9.48 | 9.49 | 8.30 | 8.42 | 8.63 | 8.84 | 9.49 | 6.46 |
| 2798538 | 8.87 | 9.61 | 9.66 | 9.60 | 8.86 | 9.14 | 9.65 | 10.22 | 10.04 | 9.81 | 8.95 | 10.03 |
| 2806468 | 9.07 | 9.78 | 8.84 | 10.09 | 9.32 | 10.61 | 9.67 | 7.01 | 10.52 | 11.50 | 10.68 | 9.65 |
| 2880051 | 6.79 | 7.64 | 6.06 | 6.26 | 5.95 | 6.44 | 6.41 | 7.11 | 6.60 | 6.52 | 6.87 | 6.92 |
| 2732508 | 3.70 | 3.79 | 3.91 | 3.89 | 3.28 | 7.90 | 9.37 | 3.70 | 3.75 | 6.90 | 3.83 | 10.03 |
| 2822492 | 6.43 | 6.83 | 6.35 | 6.25 | 5.89 | 6.05 | 5.94 | 7.14 | 6.42 | 5.61 | 5.50 | 6.28 |
| 3404030 | 7.74 | 7.28 | 7.41 | 9.12 | 7.15 | 8.51 | 7.34 | 6.48 | 8.60 | 8.47 | 8.28 | 8.66 |

TABLE 53-continued

Normalized intensity of microarray data for a set of samples.

| TCID | V01 0337 | V01 0338 | V01 0339 | V01 0340 | V01 0341 | V01 0342 | V01 0343 | V01 0344 | V01 0345 | V01 0346 | V01 0347 | V01 0348 |
|---|---|---|---|---|---|---|---|---|---|---|---|---|
| 3059667 | 10.50 | 8.82 | 5.96 | 7.25 | 5.11 | 9.85 | 4.63 | 5.54 | 4.84 | 9.66 | 10.15 | 5.37 |
| 3108526 | 10.74 | 11.10 | 6.00 | 9.48 | 8.60 | 10.30 | 9.52 | 9.41 | 9.51 | 9.05 | 9.24 | 5.87 |
| 2526806 | 6.27 | 8.36 | 11.00 | 11.55 | 12.96 | 10.61 | 10.72 | 11.44 | 11.84 | 9.33 | 7.65 | 8.80 |
| 2428501 | 5.96 | 6.95 | 8.66 | 6.60 | 6.61 | 6.90 | 7.39 | 8.50 | 8.78 | 6.98 | 6.52 | 8.20 |
| 2657808 | 6.14 | 5.60 | 6.01 | 6.74 | 11.74 | 6.64 | 8.27 | 6.00 | 5.86 | 7.34 | 6.12 | 6.04 |
| 2584018 | 5.64 | 6.22 | 11.27 | 10.08 | 10.28 | 7.42 | 6.80 | 9.02 | 7.30 | 8.23 | 7.19 | 6.60 |
| 3976341 | 7.99 | 9.51 | 10.33 | 9.93 | 11.89 | 9.31 | 9.31 | 10.11 | 9.20 | 9.89 | 9.84 | 9.63 |
| 2739308 | 5.41 | 5.87 | 4.48 | 5.31 | 4.83 | 4.64 | 5.03 | 5.69 | 5.85 | 5.63 | 5.24 | 4.82 |
| 3959862 | 4.27 | 6.31 | 6.24 | 7.24 | 5.02 | 5.73 | 6.59 | 8.54 | 7.94 | 5.50 | 6.23 | 5.23 |
| 2362351 | 6.90 | 6.83 | 6.16 | 7.78 | 6.15 | 7.83 | 7.82 | 6.01 | 7.44 | 8.02 | 7.60 | 8.51 |
| 3648391 | 4.90 | 5.11 | 4.09 | 6.93 | 4.42 | 7.80 | 9.11 | 4.30 | 4.87 | 7.35 | 4.96 | 8.63 |
| 3009299 | 11.41 | 11.34 | 10.87 | 10.89 | 10.81 | 10.68 | 11.06 | 11.78 | 11.39 | 10.81 | 10.29 | 11.37 |
| 3443464 | 5.74 | 5.19 | 5.88 | 5.97 | 5.48 | 5.82 | 5.68 | 5.67 | 5.96 | 5.66 | 5.84 | 5.52 |
| 2730746 | 9.11 | 8.63 | 5.22 | 7.53 | 5.89 | 8.30 | 6.85 | 8.31 | 8.45 | 6.86 | 7.67 | 5.10 |
| 2427619 | 6.61 | 7.85 | 6.89 | 8.14 | 6.82 | 9.01 | 8.41 | 5.87 | 8.25 | 9.13 | 7.81 | 9.08 |
| 3042001 | 9.31 | 9.76 | 8.30 | 9.03 | 8.29 | 9.05 | 8.41 | 10.17 | 9.45 | 9.33 | 8.98 | 9.40 |
| 2566848 | 5.56 | 5.34 | 5.48 | 5.72 | 5.45 | 6.10 | 7.71 | 5.93 | 6.22 | 6.60 | 5.63 | 7.50 |
| 2984616 | 9.26 | 10.58 | 9.46 | 9.55 | 8.93 | 9.06 | 9.22 | 10.19 | 10.10 | 9.01 | 8.86 | 8.88 |
| 2378068 | 6.54 | 6.98 | 10.15 | 8.60 | 9.49 | 9.13 | 9.92 | 10.15 | 9.57 | 8.47 | 8.04 | 7.72 |
| 2721959 | 6.21 | 5.90 | 6.94 | 9.88 | 12.49 | 8.40 | 7.51 | 7.51 | 7.17 | 6.81 | 6.62 | 7.18 |
| 2877508 | 10.34 | 11.25 | 10.99 | 10.62 | 10.40 | 10.69 | 10.93 | 11.20 | 11.19 | 10.51 | 10.02 | 10.87 |
| 3450861 | 5.14 | 5.42 | 5.16 | 5.63 | 5.37 | 6.56 | 6.02 | 4.87 | 5.16 | 6.11 | 6.03 | 7.83 |
| 2688717 | 7.10 | 7.49 | 6.42 | 8.26 | 7.49 | 9.72 | 9.48 | 6.59 | 8.70 | 9.97 | 8.46 | 9.93 |
| 3270270 | 6.52 | 7.76 | 8.38 | 8.21 | 8.14 | 8.12 | 7.31 | 8.00 | 7.88 | 8.30 | 8.10 | 7.12 |
| 3417703 | 10.56 | 4.90 | 5.60 | 8.18 | 7.22 | 10.33 | 6.12 | 4.97 | 4.92 | 9.05 | 9.37 | 6.62 |
| 3302990 | 8.36 | 9.53 | 8.29 | 8.89 | 8.13 | 8.41 | 8.08 | 10.06 | 10.46 | 7.31 | 7.11 | 8.65 |
| 2377283 | 4.57 | 4.57 | 4.55 | 4.83 | 4.49 | 7.82 | 11.16 | 4.61 | 5.13 | 8.75 | 5.18 | 8.92 |
| 3122678 | 5.91 | 7.46 | 5.87 | 5.00 | 6.03 | 5.02 | 4.76 | 9.75 | 9.75 | 5.14 | 5.40 | 5.01 |
| 2688499 | 10.93 | 8.79 | 7.21 | 9.81 | 11.28 | 10.44 | 9.11 | 6.91 | 8.29 | 9.66 | 9.46 | 11.78 |
| 2377094 | 9.20 | 10.87 | 8.60 | 9.11 | 9.33 | 8.70 | 9.18 | 10.82 | 10.77 | 9.13 | 9.18 | 8.06 |
| 3278198 | 8.50 | 10.18 | 9.07 | 8.76 | 8.83 | 8.50 | 7.96 | 9.80 | 8.92 | 7.31 | 7.72 | 7.43 |
| 2598261 | 6.36 | 7.04 | 9.77 | 10.49 | 12.73 | 9.22 | 9.45 | 10.09 | 11.13 | 7.90 | 6.85 | 7.28 |
| 3982612 | 7.09 | 7.06 | 6.66 | 8.28 | 6.39 | 9.12 | 9.30 | 5.52 | 8.14 | 9.55 | 7.49 | 10.04 |
| 2884845 | 4.90 | 4.65 | 5.31 | 6.71 | 9.63 | 4.50 | 4.51 | 6.74 | 4.97 | 4.76 | 4.79 | 4.94 |
| 3982560 | 5.76 | 5.81 | 5.23 | 6.55 | 5.38 | 7.67 | 7.66 | 5.76 | 6.53 | 8.19 | 6.97 | 8.75 |
| 3204285 | 6.04 | 5.23 | 5.23 | 5.36 | 5.21 | 8.32 | 8.95 | 5.58 | 5.39 | 6.99 | 5.53 | 9.78 |
| 3654699 | 11.77 | 12.73 | 12.73 | 12.32 | 11.54 | 12.15 | 11.44 | 12.69 | 11.95 | 10.36 | 10.42 | 8.69 |
| 2638676 | 6.65 | 7.68 | 8.54 | 7.94 | 6.06 | 9.39 | 10.95 | 6.97 | 7.62 | 9.41 | 7.26 | 10.17 |
| 3367673 | 9.05 | 8.99 | 5.10 | 8.17 | 4.58 | 8.44 | 6.77 | 7.36 | 8.25 | 8.06 | 8.69 | 5.00 |
| 3212008 | 5.90 | 6.07 | 5.99 | 6.95 | 8.45 | 6.04 | 6.15 | 6.10 | 5.88 | 7.24 | 6.60 | 5.95 |
| 3326635 | 9.94 | 9.48 | 10.04 | 9.75 | 10.04 | 9.92 | 9.43 | 9.74 | 9.52 | 10.12 | 9.85 | 10.29 |
| 3031556 | 7.46 | 8.99 | 9.21 | 9.47 | 7.72 | 9.85 | 9.12 | 8.12 | 8.94 | 10.14 | 9.51 | 9.29 |
| 3662201 | 12.25 | 10.82 | 8.76 | 12.90 | 8.75 | 12.52 | 10.93 | 11.22 | 9.98 | 11.87 | 10.40 | 8.41 |
| 2809793 | 7.06 | 6.59 | 6.81 | 8.94 | 5.92 | 10.02 | 8.80 | 5.91 | 9.14 | 9.78 | 8.39 | 10.49 |
| 2817731 | 6.85 | 7.77 | 9.59 | 8.10 | 6.57 | 6.80 | 6.61 | 8.54 | 7.34 | 7.52 | 6.39 | 6.39 |
| 4020655 | 5.23 | 4.78 | 4.80 | 4.95 | 7.44 | 4.93 | 4.71 | 4.90 | 5.15 | 5.71 | 6.16 | 5.32 |
| 3494629 | 4.40 | 4.10 | 4.18 | 4.76 | 7.82 | 4.07 | 4.12 | 5.59 | 5.15 | 4.29 | 4.21 | 4.16 |
| 3852832 | 7.23 | 8.86 | 6.30 | 9.42 | 6.29 | 8.56 | 7.56 | 6.29 | 9.02 | 8.97 | 9.10 | 6.44 |
| 3761959 | 10.43 | 9.82 | 10.31 | 9.41 | 9.31 | 9.77 | 9.09 | 10.22 | 9.57 | 9.21 | 9.18 | 9.91 |
| 2834282 | 6.48 | 5.58 | 5.71 | 5.34 | 7.85 | 6.30 | 6.32 | 7.42 | 7.58 | 6.19 | 6.12 | 6.01 |
| 3341497 | 6.43 | 7.20 | 6.32 | 6.92 | 8.51 | 6.57 | 6.78 | 8.07 | 7.34 | 6.89 | 7.04 | 6.31 |
| 2372812 | 5.30 | 4.27 | 5.24 | 5.96 | 4.77 | 9.07 | 11.42 | 5.33 | 4.83 | 7.79 | 5.00 | 7.91 |
| 2486811 | 7.66 | 8.99 | 10.94 | 10.21 | 6.91 | 9.89 | 10.10 | 10.35 | 9.67 | 9.41 | 10.08 | 10.49 |
| 3768474 | 7.63 | 8.10 | 9.38 | 8.12 | 7.23 | 8.07 | 7.63 | 8.79 | 8.48 | 7.97 | 7.79 | 7.68 |
| 3142381 | 4.10 | 6.77 | 7.79 | 6.62 | 3.98 | 5.52 | 3.50 | 7.05 | 5.46 | 4.98 | 6.92 | 4.14 |
| 2396750 | 7.11 | 7.43 | 6.81 | 6.78 | 8.31 | 7.18 | 7.46 | 8.25 | 7.95 | 7.13 | 7.43 | 7.86 |
| 3902489 | 9.42 | 11.86 | 9.74 | 10.10 | 10.15 | 10.93 | 10.00 | 9.50 | 12.14 | 11.01 | 10.53 | 9.11 |
| 3032647 | 9.17 | 7.58 | 6.27 | 6.73 | 6.23 | 8.15 | 6.72 | 6.85 | 6.41 | 6.42 | 7.48 | 6.35 |
| 3875642 | 5.65 | 5.63 | 5.72 | 6.57 | 6.65 | 5.55 | 5.17 | 5.68 | 6.27 | 6.19 | 5.68 | 5.22 |
| 4027585 | 9.02 | 11.74 | 11.56 | 10.71 | 9.15 | 10.91 | 9.69 | 10.42 | 12.13 | 10.62 | 10.58 | 8.90 |
| 2352609 | 7.61 | 6.84 | 5.42 | 7.22 | 7.36 | 6.59 | 6.13 | 7.13 | 6.83 | 6.58 | 7.22 | 5.80 |
| 3376529 | 9.37 | 10.49 | 7.32 | 9.16 | 10.62 | 9.49 | 9.24 | 10.24 | 9.73 | 8.45 | 8.91 | 9.43 |
| 2491271 | 12.68 | 12.92 | 13.72 | 13.34 | 13.42 | 13.49 | 13.44 | 13.41 | 12.95 | 13.62 | 13.46 | 13.56 |
| 3874751 | 9.77 | 8.82 | 10.05 | 8.72 | 9.57 | 9.50 | 8.39 | 9.85 | 9.03 | 8.72 | 8.89 | 8.84 |
| 2326463 | 10.68 | 11.19 | 12.53 | 12.37 | 10.59 | 12.30 | 12.43 | 12.25 | 11.73 | 12.63 | 12.17 | 12.59 |
| 3341061 | 6.03 | 6.70 | 8.75 | 7.55 | 5.58 | 6.21 | 5.71 | 7.64 | 6.22 | 6.41 | 5.96 | 6.22 |
| 3839910 | 6.29 | 8.79 | 6.66 | 8.23 | 6.46 | 7.78 | 6.96 | 5.65 | 8.80 | 8.67 | 8.87 | 5.84 |
| 2708855 | 4.93 | 4.26 | 4.49 | 4.41 | 8.75 | 4.19 | 4.30 | 4.77 | 4.61 | 4.57 | 4.45 | 4.46 |
| 3512874 | 10.97 | 12.02 | 12.13 | 12.14 | 10.72 | 12.21 | 12.57 | 11.73 | 12.10 | 12.36 | 12.41 | 12.52 |
| 2701071 | 8.60 | 10.07 | 8.90 | 10.00 | 8.69 | 10.01 | 9.02 | 8.65 | 10.00 | 10.31 | 10.80 | 7.23 |
| 3486096 | 8.53 | 8.39 | 5.23 | 7.15 | 8.07 | 7.42 | 7.33 | 6.42 | 5.85 | 7.23 | 7.24 | 5.71 |
| 2412668 | 8.39 | 8.67 | 9.56 | 9.12 | 8.44 | 8.65 | 8.57 | 8.87 | 8.31 | 8.71 | 8.58 | 8.06 |
| 3329343 | 7.09 | 7.35 | 7.14 | 7.55 | 8.60 | 7.30 | 8.13 | 7.92 | 7.58 | 7.08 | 7.22 | 7.47 |
| 3259367 | 4.95 | 4.49 | 4.23 | 4.28 | 5.27 | 4.14 | 4.32 | 4.15 | 4.14 | 4.59 | 4.36 | 4.27 |
| 3373845 | 7.70 | 7.65 | 10.43 | 8.88 | 8.03 | 8.23 | 8.27 | 9.68 | 8.19 | 8.63 | 8.22 | 8.79 |

TABLE 53-continued

Normalized intensity of microarray data for a set of samples.

| TCID | V01 0337 | V01 0338 | V01 0339 | V01 0340 | V01 0341 | V01 0342 | V01 0343 | V01 0344 | V01 0345 | V01 0346 | V01 0347 | V01 0348 |
|---|---|---|---|---|---|---|---|---|---|---|---|---|
| 2321911 | 8.04 | 8.26 | 8.64 | 8.08 | 7.61 | 8.42 | 8.13 | 8.15 | 8.55 | 8.54 | 8.18 | 8.58 |
| 3353914 | 6.48 | 6.68 | 9.83 | 8.16 | 7.75 | 6.59 | 6.40 | 8.25 | 5.94 | 6.49 | 6.39 | 7.24 |
| 3744680 | 7.10 | 7.24 | 8.86 | 7.51 | 6.91 | 7.67 | 7.22 | 7.99 | 7.75 | 7.94 | 7.91 | 8.43 |
| 2373336 | 4.89 | 5.77 | 5.48 | 7.47 | 9.26 | 6.64 | 6.13 | 4.96 | 5.52 | 6.26 | 6.17 | 6.07 |
| 3067478 | 7.27 | 6.48 | 4.73 | 6.12 | 8.24 | 6.56 | 6.44 | 4.81 | 5.26 | 5.33 | 5.51 | 5.02 |
| 3976766 | 7.62 | 7.68 | 8.16 | 8.36 | 6.80 | 8.24 | 8.33 | 7.88 | 8.40 | 8.63 | 8.21 | 8.83 |
| 3246888 | 6.80 | 6.70 | 4.69 | 6.68 | 5.17 | 6.35 | 5.32 | 5.66 | 7.23 | 5.92 | 7.01 | 5.01 |
| 3147985 | 6.25 | 6.27 | 9.32 | 7.45 | 7.49 | 6.60 | 5.63 | 8.49 | 6.11 | 6.28 | 5.84 | 5.60 |
| 3185522 | 9.59 | 8.83 | 11.58 | 9.84 | 9.25 | 9.04 | 9.31 | 11.22 | 9.10 | 9.17 | 9.21 | 9.02 |
| 3861948 | 11.77 | 12.53 | 12.30 | 12.81 | 11.40 | 12.72 | 12.49 | 12.14 | 12.55 | 12.89 | 12.95 | 12.96 |
| 3393479 | 8.29 | 9.55 | 10.26 | 9.38 | 8.91 | 9.25 | 8.93 | 9.92 | 8.95 | 9.35 | 9.42 | 8.36 |
| 3540862 | 7.38 | 7.78 | 6.92 | 6.63 | 7.52 | 6.89 | 6.79 | 7.93 | 9.43 | 6.90 | 7.35 | 6.46 |
| 2777714 | 9.27 | 12.51 | 10.35 | 11.28 | 10.01 | 11.53 | 10.45 | 9.10 | 12.33 | 11.52 | 11.46 | 6.98 |
| 3110395 | 4.86 | 4.47 | 4.63 | 4.98 | 6.53 | 4.71 | 4.74 | 5.12 | 4.84 | 5.09 | 5.83 | 4.93 |
| 3895795 | 7.42 | 8.35 | 8.29 | 8.12 | 8.32 | 8.11 | 7.32 | 7.20 | 9.20 | 8.46 | 8.80 | 6.54 |
| 2854445 | 6.90 | 8.55 | 11.39 | 10.14 | 7.98 | 8.16 | 8.63 | 10.75 | 8.38 | 8.74 | 8.19 | 8.15 |
| 3606034 | 7.88 | 7.32 | 8.36 | 7.75 | 7.24 | 7.83 | 6.58 | 8.56 | 7.23 | 6.86 | 7.33 | 6.72 |
| 3375735 | 8.08 | 7.47 | 8.86 | 8.24 | 8.20 | 8.43 | 7.52 | 8.77 | 8.37 | 7.80 | 8.30 | 8.26 |
| 3948047 | 7.50 | 8.08 | 9.10 | 8.54 | 6.79 | 8.53 | 8.43 | 8.74 | 8.21 | 8.78 | 8.40 | 9.69 |
| 3010503 | 7.01 | 9.11 | 11.19 | 9.75 | 5.85 | 8.30 | 7.16 | 10.27 | 8.49 | 9.23 | 9.37 | 5.27 |
| 3622934 | 5.82 | 6.29 | 5.51 | 6.56 | 7.55 | 6.60 | 8.11 | 7.20 | 6.69 | 6.85 | 6.95 | 7.00 |
| 3441849 | 9.37 | 9.89 | 10.28 | 10.32 | 10.14 | 9.94 | 9.51 | 9.90 | 10.43 | 10.06 | 10.31 | 8.19 |
| 3006572 | 6.85 | 6.40 | 6.20 | 6.40 | 6.65 | 6.47 | 6.72 | 6.63 | 6.56 | 6.80 | 6.48 | 6.57 |
| 3365136 | 9.06 | 9.35 | 9.06 | 9.50 | 10.30 | 9.34 | 8.93 | 9.68 | 9.05 | 9.44 | 8.85 | 9.25 |
| 2642791 | 8.14 | 8.03 | 9.17 | 8.16 | 7.58 | 8.14 | 8.42 | 8.43 | 7.53 | 8.06 | 7.94 | 8.18 |
| 2904485 | 9.87 | 6.98 | 6.79 | 7.87 | 7.74 | 8.24 | 7.57 | 7.01 | 7.10 | 7.90 | 8.39 | 7.29 |
| 3772661 | 8.73 | 9.48 | 11.81 | 10.63 | 9.33 | 9.60 | 8.87 | 11.32 | 9.57 | 9.88 | 9.76 | 8.09 |
| 2796553 | 8.53 | 9.75 | 10.05 | 9.45 | 8.16 | 9.18 | 8.54 | 9.70 | 10.07 | 9.22 | 9.42 | 8.04 |
| 3063795 | 7.54 | 7.30 | 8.78 | 7.46 | 7.43 | 7.86 | 7.89 | 7.91 | 8.03 | 7.77 | 7.20 | 7.91 |
| 3338192 | 8.63 | 8.34 | 7.15 | 8.55 | 10.27 | 8.80 | 8.15 | 8.88 | 8.67 | 8.52 | 8.61 | 8.15 |
| 3214845 | 4.37 | 4.95 | 4.52 | 4.67 | 5.66 | 4.13 | 4.55 | 4.48 | 4.96 | 4.49 | 4.81 | 4.63 |
| 2730303 | 4.75 | 4.48 | 4.54 | 4.80 | 4.65 | 7.65 | 10.03 | 4.49 | 4.56 | 7.87 | 4.81 | 8.25 |
| 3811086 | 7.08 | 7.20 | 7.94 | 6.87 | 6.75 | 7.78 | 7.42 | 7.67 | 6.81 | 7.34 | 7.67 | 7.56 |
| 2981874 | 10.32 | 11.04 | 10.83 | 10.93 | 10.67 | 10.64 | 9.94 | 10.77 | 10.54 | 10.36 | 10.32 | 9.56 |
| 3242353 | 6.43 | 6.35 | 6.73 | 6.32 | 5.74 | 6.13 | 6.06 | 6.09 | 5.78 | 5.61 | 5.81 | 6.36 |
| 2442008 | 5.96 | 5.30 | 5.62 | 5.62 | 8.95 | 5.68 | 5.56 | 5.51 | 5.72 | 5.61 | 5.83 | 5.71 |
| 3564210 | 7.90 | 9.53 | 10.14 | 10.21 | 8.06 | 9.10 | 7.89 | 9.03 | 9.60 | 9.55 | 9.42 | 6.43 |
| 2490351 | 4.75 | 4.47 | 4.63 | 4.52 | 4.56 | 4.38 | 4.41 | 4.71 | 4.93 | 4.64 | 4.73 | 4.95 |
| 3759850 | 7.18 | 10.27 | 7.00 | 8.00 | 7.28 | 9.38 | 7.78 | 7.05 | 10.91 | 8.76 | 8.70 | 7.16 |
| 3264997 | 4.53 | 4.38 | 4.59 | 4.16 | 4.04 | 4.41 | 4.35 | 4.46 | 4.47 | 4.40 | 4.46 | 4.47 |
| 3912079 | 3.71 | 3.80 | 3.78 | 4.26 | 3.50 | 3.99 | 3.57 | 3.61 | 3.91 | 3.74 | 3.99 | 3.70 |
| 2926802 | 5.14 | 6.40 | 5.36 | 5.42 | 4.99 | 6.11 | 6.65 | 5.01 | 5.92 | 5.87 | 5.18 | 6.87 |
| 2430163 | 4.50 | 3.90 | 4.63 | 4.80 | 5.22 | 4.08 | 4.23 | 4.59 | 4.16 | 4.66 | 4.29 | 4.72 |
| 3039830 | 3.56 | 3.65 | 3.44 | 3.41 | 3.36 | 3.43 | 3.43 | 3.61 | 3.33 | 3.34 | 3.33 | 3.42 |
| 3935486 | 5.64 | 7.70 | 9.03 | 8.44 | 7.70 | 6.99 | 5.44 | 7.82 | 5.34 | 7.48 | 6.76 | 8.08 |
| 3457336 | 6.29 | 5.20 | 5.99 | 5.83 | 5.69 | 5.37 | 5.43 | 5.55 | 5.74 | 5.69 | 5.75 | 5.87 |
| 3811949 | 4.45 | 3.81 | 4.12 | 3.99 | 3.81 | 3.70 | 3.70 | 4.16 | 4.05 | 3.91 | 3.96 | 4.09 |
| 3343832 | 4.42 | 3.70 | 4.53 | 3.93 | 3.96 | 3.89 | 4.07 | 4.13 | 4.47 | 4.12 | 4.47 | 4.41 |
| 3161261 | 5.60 | 5.42 | 5.61 | 5.29 | 5.10 | 5.44 | 5.44 | 5.30 | 5.52 | 5.64 | 6.99 | 5.87 |
| 3594003 | 3.94 | 4.13 | 3.99 | 3.99 | 3.69 | 3.76 | 3.66 | 4.13 | 4.00 | 3.92 | 4.04 | 4.06 |
| 3805614 | 5.31 | 5.23 | 5.62 | 5.16 | 5.59 | 4.81 | 5.04 | 5.57 | 5.63 | 5.74 | 5.43 | 5.72 |
| 3364127 | 7.17 | 6.82 | 7.21 | 7.01 | 7.24 | 6.89 | 6.92 | 12.49 | 10.01 | 7.12 | 7.68 | 7.19 |
| 3834341 | 4.20 | 3.91 | 4.14 | 3.95 | 3.72 | 3.87 | 3.67 | 4.46 | 4.14 | 4.08 | 4.41 | 4.29 |
| 2585400 | 4.35 | 4.38 | 4.41 | 4.45 | 4.23 | 4.88 | 4.29 | 4.34 | 4.32 | 4.33 | 4.39 | 4.59 |
| 2941690 | 4.70 | 4.71 | 4.80 | 4.51 | 4.30 | 4.65 | 4.62 | 5.30 | 4.73 | 4.70 | 5.22 | 5.23 |
| 3484895 | 4.78 | 4.58 | 5.02 | 4.50 | 6.20 | 4.56 | 4.36 | 4.83 | 5.01 | 4.47 | 5.11 | 4.77 |
| 3159754 | 3.81 | 3.93 | 3.62 | 3.81 | 3.65 | 3.71 | 3.73 | 3.71 | 3.72 | 3.58 | 3.47 | 3.83 |
| 2894790 | 4.06 | 4.23 | 4.20 | 4.31 | 4.24 | 4.04 | 4.09 | 4.25 | 4.75 | 4.52 | 4.51 | 4.20 |
| 3363686 | 3.92 | 3.48 | 3.64 | 3.17 | 3.48 | 3.36 | 3.16 | 3.54 | 3.24 | 3.23 | 3.46 | 3.45 |
| 2923928 | 5.54 | 4.55 | 4.87 | 4.57 | 4.51 | 4.62 | 4.34 | 4.80 | 4.93 | 5.01 | 4.69 | 5.77 |
| 2883317 | 5.03 | 5.32 | 5.64 | 4.79 | 4.75 | 5.48 | 4.81 | 5.15 | 5.43 | 4.85 | 5.05 | 4.89 |
| 2479698 | 5.91 | 6.02 | 5.71 | 6.05 | 6.03 | 5.55 | 5.82 | 5.96 | 5.99 | 5.65 | 5.95 | 5.86 |
| 3428225 | 4.30 | 3.81 | 4.21 | 3.93 | 3.80 | 3.80 | 3.63 | 3.82 | 4.03 | 3.76 | 3.93 | 3.80 |
| 3393446 | 7.46 | 7.63 | 8.89 | 7.84 | 7.34 | 7.03 | 7.39 | 8.92 | 7.74 | 7.89 | 7.80 | 8.10 |
| 3116614 | 13.11 | 12.07 | 8.92 | 12.50 | 11.86 | 12.72 | 12.21 | 11.94 | 11.16 | 12.43 | 12.33 | 7.97 |
| 3415320 | 10.33 | 10.75 | 6.32 | 9.77 | 11.27 | 10.45 | 8.83 | 10.41 | 10.96 | 8.86 | 8.81 | 6.62 |
| 3757108 | 7.91 | 7.83 | 7.66 | 8.40 | 11.37 | 7.52 | 7.53 | 8.33 | 8.67 | 7.92 | 7.95 | 7.97 |
| 4012178 | 7.20 | 6.70 | 6.52 | 7.61 | 11.65 | 6.69 | 6.99 | 7.53 | 7.02 | 7.37 | 6.81 | 6.84 |
| 3546213 | 10.97 | 10.09 | 5.86 | 10.27 | 10.40 | 10.28 | 9.44 | 9.90 | 9.42 | 9.90 | 9.89 | 7.08 |
| 3561381 | 9.94 | 9.01 | 5.16 | 8.37 | 9.36 | 9.50 | 7.17 | 8.61 | 9.26 | 8.40 | 9.09 | 5.62 |

TABLE 54

Normalized intensity of microarray data for a set of samples.

| TCID | V01 0349 | V01 0350 | V01 0351 | V01 0352 | V01 0353 | V01 0354 | V01 0355 | V01 0356 | V01 0357 | V01 0358 | V01 0359 | V01 0360 |
|---|---|---|---|---|---|---|---|---|---|---|---|---|
| 2604998 | 7.38 | 9.52 | 8.92 | 7.64 | 7.81 | 8.29 | 5.28 | 7.50 | 5.49 | 8.75 | 8.33 | 7.19 |
| 3603932 | 9.31 | 7.45 | 8.20 | 6.78 | 8.26 | 7.40 | 9.52 | 7.65 | 7.64 | 7.63 | 8.10 | 8.38 |
| 2710599 | 10.70 | 11.65 | 11.71 | 5.94 | 11.32 | 11.77 | 7.59 | 9.04 | 7.94 | 10.85 | 7.56 | 9.75 |
| 2440258 | 7.67 | 4.19 | 5.42 | 8.11 | 6.87 | 7.15 | 7.86 | 8.19 | 8.20 | 6.71 | 7.11 | 6.84 |
| 3169331 | 7.50 | 6.92 | 7.06 | 7.53 | 7.33 | 6.99 | 7.72 | 7.38 | 6.90 | 6.58 | 7.77 | 7.69 |
| 2988882 | 10.01 | 9.34 | 9.59 | 9.53 | 9.48 | 9.42 | 10.50 | 9.78 | 9.68 | 9.53 | 9.96 | 9.92 |
| 2964231 | 9.94 | 6.81 | 9.26 | 7.41 | 9.89 | 8.16 | 10.36 | 9.48 | 9.71 | 8.93 | 8.62 | 9.90 |
| 3111561 | 5.14 | 5.61 | 5.15 | 8.86 | 4.65 | 6.20 | 5.65 | 7.59 | 6.05 | 5.08 | 8.33 | 8.89 |
| 2562529 | 9.57 | 10.65 | 10.71 | 8.91 | 9.93 | 9.67 | 9.22 | 9.45 | 9.09 | 10.87 | 9.35 | 8.65 |
| 3692999 | 8.58 | 7.22 | 5.92 | 11.12 | 10.94 | 7.25 | 11.05 | 9.87 | 10.89 | 6.84 | 7.24 | 11.99 |
| 2439554 | 8.03 | 4.57 | 5.59 | 7.05 | 7.58 | 7.07 | 8.03 | 7.70 | 8.91 | 5.77 | 6.42 | 6.48 |
| 2685304 | 9.73 | 11.30 | 11.98 | 7.44 | 11.09 | 10.97 | 9.01 | 8.41 | 8.68 | 11.01 | 8.69 | 9.02 |
| 2578790 | 4.52 | 4.58 | 4.39 | 6.57 | 4.26 | 4.65 | 5.05 | 5.36 | 5.56 | 4.66 | 5.38 | 5.99 |
| 2373842 | 10.50 | 8.09 | 8.84 | 11.33 | 10.44 | 10.34 | 10.97 | 11.53 | 12.03 | 9.57 | 10.49 | 10.61 |
| 2750627 | 9.00 | 10.95 | 10.20 | 9.89 | 6.89 | 9.57 | 5.77 | 8.80 | 6.04 | 11.18 | 9.63 | 8.75 |
| 3397774 | 4.84 | 4.39 | 4.75 | 5.68 | 4.65 | 5.14 | 5.23 | 5.02 | 4.73 | 4.95 | 4.45 | 4.45 |
| 2635741 | 7.53 | 5.87 | 5.72 | 8.27 | 6.52 | 7.15 | 6.37 | 8.63 | 8.97 | 6.70 | 7.55 | 7.16 |
| 3970833 | 10.30 | 9.88 | 10.30 | 9.54 | 10.06 | 9.69 | 10.35 | 9.57 | 9.72 | 10.01 | 9.97 | 10.25 |
| 3577612 | 10.92 | 11.28 | 11.72 | 10.59 | 11.39 | 11.01 | 10.03 | 10.96 | 11.12 | 11.47 | 10.62 | 10.37 |
| 2708922 | 7.41 | 8.31 | 8.15 | 8.70 | 7.53 | 8.06 | 7.17 | 9.11 | 9.46 | 8.80 | 7.10 | 6.64 |
| 2970897 | 4.58 | 4.44 | 5.02 | 4.96 | 4.31 | 5.49 | 4.96 | 4.54 | 4.99 | 5.62 | 5.28 | 5.10 |
| 3724545 | 8.91 | 9.11 | 9.07 | 9.31 | 9.07 | 9.73 | 8.34 | 9.91 | 8.96 | 9.13 | 9.54 | 8.77 |
| 2798538 | 9.18 | 8.62 | 8.86 | 8.90 | 9.00 | 8.36 | 9.54 | 8.95 | 8.51 | 8.64 | 9.71 | 9.45 |
| 2806468 | 9.73 | 6.45 | 8.09 | 10.80 | 9.17 | 9.26 | 9.32 | 11.36 | 11.30 | 8.77 | 9.42 | 9.82 |
| 2880051 | 6.22 | 6.54 | 5.84 | 6.95 | 6.11 | 6.59 | 6.10 | 6.43 | 7.02 | 6.29 | 6.69 | 6.37 |
| 2732508 | 3.97 | 3.18 | 5.32 | 3.62 | 5.27 | 4.99 | 4.21 | 3.47 | 3.74 | 4.04 | 3.29 | 3.50 |
| 2822492 | 5.62 | 5.15 | 6.21 | 5.92 | 5.94 | 5.72 | 6.82 | 6.18 | 6.10 | 6.24 | 6.68 | 5.59 |
| 3404030 | 7.80 | 5.33 | 5.70 | 8.16 | 6.53 | 7.04 | 7.43 | 9.60 | 8.67 | 5.87 | 7.84 | 6.98 |
| 3059667 | 5.54 | 5.93 | 5.38 | 10.49 | 6.03 | 5.97 | 5.64 | 7.84 | 5.84 | 5.59 | 7.45 | 9.28 |
| 3108526 | 7.18 | 8.88 | 8.11 | 9.41 | 7.64 | 7.93 | 7.22 | 8.31 | 7.74 | 8.45 | 10.72 | 9.10 |
| 2526806 | 12.56 | 12.64 | 12.93 | 8.09 | 12.70 | 12.87 | 11.78 | 10.85 | 11.19 | 13.08 | 12.07 | 12.41 |
| 2428501 | 7.88 | 6.18 | 6.83 | 6.91 | 7.37 | 7.45 | 9.01 | 7.33 | 8.01 | 5.36 | 6.96 | 8.33 |
| 2657808 | 10.04 | 10.79 | 12.06 | 5.61 | 8.96 | 11.12 | 6.67 | 6.95 | 5.64 | 10.23 | 6.10 | 8.04 |
| 2584018 | 9.95 | 7.21 | 10.05 | 7.33 | 10.75 | 9.91 | 11.10 | 9.01 | 10.22 | 10.48 | 6.71 | 9.96 |
| 3976341 | 11.61 | 12.52 | 12.07 | 9.74 | 11.48 | 11.85 | 11.09 | 10.47 | 10.85 | 11.50 | 8.41 | 10.11 |
| 2739308 | 4.63 | 4.38 | 4.26 | 5.82 | 4.10 | 4.76 | 4.92 | 6.02 | 5.59 | 4.56 | 7.21 | 4.72 |
| 3959862 | 5.41 | 4.49 | 4.81 | 4.42 | 5.73 | 6.42 | 7.24 | 5.61 | 6.36 | 4.49 | 4.45 | 6.10 |
| 2362351 | 6.76 | 5.69 | 5.82 | 7.40 | 5.92 | 6.35 | 6.33 | 7.35 | 7.97 | 6.44 | 6.72 | 6.44 |
| 3648391 | 4.92 | 4.10 | 5.51 | 6.05 | 5.23 | 6.54 | 4.45 | 4.34 | 4.72 | 4.13 | 4.93 | 4.21 |
| 3009299 | 11.28 | 10.33 | 10.81 | 11.36 | 10.92 | 10.49 | 11.38 | 10.44 | 10.75 | 10.69 | 10.75 | 11.03 |
| 3443464 | 5.55 | 4.85 | 4.97 | 5.96 | 5.10 | 5.49 | 5.49 | 6.10 | 6.56 | 5.28 | 5.49 | 5.31 |
| 2730746 | 5.09 | 5.24 | 5.19 | 8.89 | 5.05 | 5.82 | 5.71 | 6.52 | 5.99 | 6.24 | 8.73 | 6.96 |
| 2427619 | 6.60 | 4.97 | 6.41 | 8.64 | 7.06 | 7.07 | 6.63 | 9.09 | 8.69 | 7.29 | 6.69 | 6.69 |
| 3042001 | 8.70 | 8.48 | 8.68 | 9.17 | 8.47 | 9.14 | 8.97 | 8.46 | 8.99 | 8.85 | 9.21 | 8.87 |
| 2566848 | 5.29 | 4.76 | 5.09 | 5.78 | 5.03 | 5.56 | 5.37 | 5.83 | 6.38 | 5.51 | 5.51 | 5.87 |
| 2984616 | 9.66 | 8.82 | 8.94 | 9.13 | 9.33 | 8.67 | 9.98 | 9.17 | 8.94 | 9.02 | 8.51 | 9.62 |
| 2378068 | 10.70 | 10.74 | 10.12 | 7.34 | 10.95 | 9.48 | 10.46 | 9.19 | 9.42 | 10.38 | 7.51 | 10.66 |
| 2721959 | 11.47 | 10.70 | 12.87 | 6.21 | 12.32 | 12.21 | 8.26 | 8.22 | 7.74 | 12.57 | 7.02 | 10.73 |
| 2877508 | 10.76 | 10.63 | 10.45 | 10.36 | 10.74 | 10.10 | 10.89 | 10.35 | 10.36 | 10.37 | 10.36 | 10.74 |
| 3450861 | 5.28 | 4.36 | 5.01 | 6.40 | 5.10 | 5.21 | 4.63 | 6.21 | 7.24 | 4.70 | 5.18 | 5.10 |
| 2688717 | 6.69 | 4.94 | 6.62 | 9.03 | 6.58 | 7.01 | 6.04 | 9.20 | 9.05 | 6.48 | 7.26 | 6.77 |
| 3270270 | 8.43 | 8.00 | 8.27 | 7.86 | 8.33 | 8.02 | 8.76 | 8.48 | 8.92 | 7.92 | 7.60 | 7.37 |
| 3417703 | 8.22 | 7.85 | 7.82 | 9.62 | 9.01 | 7.30 | 5.99 | 8.45 | 6.02 | 9.94 | 9.48 | 8.71 |
| 3302990 | 8.18 | 7.63 | 8.27 | 8.11 | 7.93 | 7.52 | 8.58 | 7.21 | 7.80 | 8.05 | 8.29 | 8.29 |
| 2377283 | 5.24 | 3.92 | 5.93 | 5.24 | 3.89 | 6.07 | 4.53 | 5.28 | 5.91 | 4.29 | 4.54 | 4.37 |
| 3122678 | 4.71 | 4.43 | 4.91 | 4.81 | 4.69 | 5.14 | 6.09 | 5.37 | 5.70 | 4.14 | 4.98 | 5.23 |
| 2688499 | 10.23 | 11.05 | 11.23 | 8.24 | 10.21 | 11.22 | 7.52 | 9.50 | 8.10 | 10.62 | 10.58 | 9.62 |
| 2377094 | 8.26 | 7.86 | 9.04 | 9.03 | 8.82 | 7.66 | 8.57 | 8.58 | 7.84 | 9.35 | 8.94 | 9.14 |
| 3278198 | 9.30 | 7.91 | 8.77 | 7.47 | 8.80 | 7.84 | 9.19 | 7.99 | 7.45 | 8.46 | 7.74 | 8.44 |
| 2598261 | 12.09 | 12.68 | 12.82 | 6.94 | 12.51 | 12.61 | 10.79 | 9.45 | 10.24 | 12.76 | 11.40 | 11.66 |
| 3982612 | 6.78 | 5.98 | 6.41 | 8.72 | 7.12 | 6.21 | 5.99 | 8.48 | 8.42 | 5.49 | 6.00 | 6.66 |
| 2884845 | 8.50 | 10.41 | 9.81 | 5.17 | 8.81 | 9.48 | 4.96 | 4.73 | 4.67 | 8.94 | 4.97 | 6.21 |
| 3982560 | 5.62 | 4.52 | 5.13 | 7.58 | 5.45 | 5.29 | 4.88 | 6.99 | 7.49 | 4.74 | 6.21 | 5.47 |
| 3204285 | 5.92 | 4.90 | 6.97 | 5.20 | 5.60 | 5.98 | 5.06 | 5.65 | 5.65 | 5.32 | 5.36 | 4.98 |
| 3654699 | 12.13 | 10.56 | 10.93 | 10.63 | 12.53 | 11.13 | 12.47 | 11.39 | 12.24 | 10.59 | 11.72 | 12.50 |
| 2638676 | 7.48 | 6.09 | 6.19 | 8.24 | 7.60 | 7.15 | 8.76 | 6.54 | 7.90 | 6.02 | 8.03 | 8.22 |
| 3367673 | 5.23 | 5.18 | 5.84 | 7.75 | 3.87 | 5.03 | 5.75 | 6.72 | 5.61 | 5.08 | 7.97 | 7.63 |
| 3212008 | 7.18 | 8.53 | 8.80 | 6.47 | 7.75 | 6.76 | 6.03 | 7.14 | 6.41 | 8.82 | 7.37 | 5.96 |
| 3326635 | 10.24 | 10.01 | 10.16 | 9.87 | 10.46 | 9.96 | 10.09 | 10.07 | 9.99 | 10.32 | 10.09 | 10.08 |
| 3031556 | 9.01 | 6.77 | 7.56 | 9.41 | 8.92 | 8.01 | 9.88 | 9.49 | 10.16 | 7.03 | 7.90 | 8.67 |
| 3662201 | 10.23 | 8.60 | 8.47 | 11.08 | 11.14 | 8.10 | 11.58 | 10.98 | 11.26 | 8.51 | 9.85 | 12.27 |
| 2809793 | 8.49 | 5.47 | 6.13 | 7.77 | 7.86 | 7.13 | 7.98 | 9.73 | 9.37 | 6.49 | 7.37 | 7.94 |
| 2817731 | 9.08 | 7.43 | 7.25 | 7.30 | 8.77 | 7.49 | 10.00 | 7.69 | 9.24 | 7.23 | 6.98 | 8.06 |
| 4020655 | 6.09 | 7.08 | 6.42 | 5.92 | 6.98 | 5.58 | 4.65 | 6.78 | 5.14 | 9.11 | 6.18 | 4.80 |
| 3494629 | 6.10 | 8.96 | 8.20 | 4.06 | 7.44 | 8.27 | 4.10 | 5.23 | 4.17 | 7.63 | 4.73 | 4.29 |

TABLE 54-continued

Normalized intensity of microarray data for a set of samples.

| TCID | V01 0349 | V01 0350 | V01 0351 | V01 0352 | V01 0353 | V01 0354 | V01 0355 | V01 0356 | V01 0357 | V01 0358 | V01 0359 | V01 0360 |
|---|---|---|---|---|---|---|---|---|---|---|---|---|
| 3852832 | 6.77 | 6.04 | 5.95 | 8.97 | 7.20 | 8.23 | 6.21 | 9.79 | 9.79 | 6.30 | 8.29 | 6.97 |
| 3761959 | 10.39 | 9.83 | 9.83 | 9.88 | 10.09 | 9.28 | 10.47 | 9.37 | 9.30 | 9.63 | 9.86 | 10.12 |
| 2834282 | 7.36 | 9.32 | 8.35 | 6.14 | 7.90 | 8.18 | 5.69 | 7.71 | 6.15 | 7.85 | 7.28 | 6.50 |
| 3341497 | 6.33 | 6.98 | 8.56 | 6.19 | 6.52 | 6.75 | 5.87 | 6.98 | 6.64 | 8.35 | 7.21 | 6.19 |
| 2372812 | 6.52 | 4.10 | 5.02 | 4.83 | 4.18 | 7.80 | 5.13 | 4.62 | 4.93 | 4.38 | 4.55 | 4.49 |
| 2486811 | 10.64 | 5.95 | 7.44 | 9.03 | 9.89 | 8.94 | 11.37 | 10.82 | 10.65 | 7.88 | 9.24 | 9.96 |
| 3768474 | 9.20 | 7.55 | 7.81 | 8.49 | 8.68 | 7.81 | 9.12 | 8.19 | 9.00 | 7.50 | 7.98 | 8.61 |
| 3142381 | 8.98 | 3.41 | 3.79 | 8.14 | 7.54 | 5.31 | 7.07 | 4.11 | 3.97 | 3.44 | 3.42 | 5.43 |
| 2396750 | 8.33 | 9.43 | 8.77 | 7.03 | 8.69 | 8.55 | 6.77 | 6.89 | 7.13 | 8.38 | 7.60 | 7.90 |
| 3902489 | 10.20 | 9.11 | 9.90 | 11.66 | 10.09 | 10.66 | 9.68 | 11.55 | 11.96 | 9.68 | 9.76 | 9.64 |
| 3032647 | 5.91 | 5.76 | 6.07 | 6.81 | 6.44 | 6.63 | 6.13 | 6.59 | 6.55 | 5.80 | 7.12 | 7.25 |
| 3875642 | 5.20 | 5.14 | 4.80 | 6.13 | 4.80 | 5.32 | 5.20 | 6.01 | 6.14 | 5.20 | 6.77 | 5.11 |
| 4027585 | 11.29 | 7.69 | 8.82 | 11.22 | 10.30 | 10.23 | 11.24 | 11.37 | 11.87 | 8.69 | 9.79 | 10.93 |
| 2352609 | 6.13 | 7.28 | 7.08 | 7.28 | 6.67 | 6.40 | 5.62 | 7.03 | 6.12 | 6.81 | 7.57 | 6.70 |
| 3376529 | 9.84 | 10.64 | 10.43 | 8.61 | 9.87 | 10.46 | 7.71 | 9.03 | 8.63 | 10.08 | 9.41 | 8.79 |
| 2491271 | 13.77 | 13.35 | 13.48 | 13.44 | 13.65 | 13.59 | 13.97 | 13.53 | 13.64 | 13.27 | 13.20 | 13.72 |
| 3874751 | 9.91 | 9.50 | 9.73 | 9.35 | 9.86 | 9.20 | 10.16 | 9.08 | 9.03 | 9.71 | 9.26 | 9.30 |
| 2326463 | 12.57 | 8.65 | 10.19 | 12.24 | 12.53 | 11.22 | 13.11 | 12.44 | 12.78 | 10.25 | 11.13 | 12.38 |
| 3341061 | 7.87 | 6.11 | 5.77 | 6.20 | 8.58 | 6.50 | 8.34 | 6.53 | 7.64 | 5.51 | 6.34 | 8.36 |
| 3839910 | 6.16 | 4.81 | 5.76 | 8.49 | 5.99 | 7.66 | 6.06 | 9.59 | 9.39 | 5.68 | 7.85 | 5.95 |
| 2708855 | 7.10 | 8.18 | 8.43 | 4.71 | 7.96 | 8.40 | 4.29 | 5.18 | 4.31 | 9.25 | 5.92 | 4.35 |
| 3512874 | 11.93 | 8.95 | 10.24 | 11.93 | 11.91 | 11.69 | 11.87 | 12.25 | 12.31 | 10.38 | 11.47 | 11.59 |
| 2701071 | 9.07 | 7.33 | 7.78 | 10.54 | 8.74 | 8.90 | 9.71 | 10.69 | 11.17 | 7.45 | 9.21 | 9.19 |
| 3486096 | 5.79 | 4.87 | 7.98 | 7.10 | 6.98 | 5.81 | 6.16 | 6.12 | 5.35 | 8.32 | 7.55 | 7.08 |
| 2412668 | 9.23 | 8.37 | 8.42 | 8.56 | 8.93 | 8.34 | 9.95 | 8.60 | 8.99 | 8.36 | 8.20 | 8.87 |
| 3329343 | 9.03 | 10.69 | 9.50 | 8.05 | 8.31 | 9.54 | 6.97 | 7.66 | 6.86 | 8.63 | 9.57 | 7.73 |
| 3259367 | 4.41 | 6.20 | 5.42 | 4.60 | 4.36 | 4.96 | 4.54 | 5.49 | 4.40 | 4.83 | 4.19 | 3.86 |
| 3373845 | 10.16 | 8.40 | 8.99 | 8.65 | 10.33 | 9.66 | 10.36 | 8.71 | 9.41 | 8.15 | 8.05 | 10.30 |
| 2321911 | 8.36 | 7.71 | 7.39 | 8.58 | 8.19 | 7.79 | 8.60 | 8.61 | 8.61 | 7.30 | 8.05 | 8.24 |
| 3353914 | 9.48 | 7.26 | 7.88 | 6.23 | 8.76 | 7.62 | 9.03 | 6.73 | 7.83 | 7.14 | 7.36 | 8.74 |
| 3744680 | 8.40 | 6.07 | 6.36 | 7.69 | 7.77 | 7.24 | 8.34 | 8.17 | 8.43 | 6.63 | 7.36 | 8.03 |
| 2373336 | 8.48 | 8.59 | 9.72 | 4.75 | 9.42 | 9.90 | 6.50 | 6.67 | 5.58 | 7.01 | 4.97 | 7.27 |
| 3067478 | 6.99 | 8.65 | 8.15 | 7.57 | 7.58 | 7.59 | 4.90 | 6.38 | 5.06 | 8.43 | 8.57 | 6.16 |
| 3976766 | 7.76 | 5.87 | 6.50 | 8.03 | 7.51 | 7.55 | 8.05 | 8.69 | 9.11 | 6.52 | 7.77 | 7.94 |
| 3246888 | 4.78 | 7.25 | 4.28 | 6.41 | 5.87 | 5.61 | 4.86 | 6.40 | 5.48 | 5.81 | 5.10 | 5.93 |
| 3147985 | 8.98 | 7.52 | 7.45 | 6.85 | 8.08 | 7.22 | 9.32 | 7.55 | 7.12 | 6.98 | 6.74 | 7.46 |
| 3185522 | 11.36 | 9.45 | 9.34 | 9.24 | 11.19 | 9.86 | 11.32 | 9.91 | 9.74 | 9.13 | 10.02 | 11.26 |
| 3861948 | 12.59 | 9.83 | 11.03 | 12.77 | 12.16 | 12.21 | 12.63 | 12.86 | 12.96 | 11.03 | 11.72 | 12.17 |
| 3393479 | 10.20 | 10.74 | 9.18 | 9.44 | 10.75 | 9.37 | 10.67 | 9.57 | 9.28 | 7.61 | 10.32 | 9.70 |
| 3540862 | 6.89 | 7.25 | 7.53 | 6.98 | 6.70 | 6.71 | 6.56 | 6.08 | 6.26 | 7.82 | 6.48 | 6.51 |
| 2777714 | 10.16 | 7.68 | 9.43 | 11.89 | 9.23 | 10.65 | 9.59 | 11.95 | 12.11 | 9.32 | 9.85 | 10.22 |
| 3110395 | 5.00 | 6.12 | 6.51 | 5.28 | 4.84 | 5.47 | 4.73 | 4.93 | 4.70 | 5.72 | 5.67 | 4.92 |
| 3895795 | 7.67 | 8.07 | 7.99 | 8.52 | 7.27 | 9.17 | 7.68 | 9.36 | 9.30 | 7.95 | 8.82 | 7.46 |
| 2854445 | 11.14 | 7.01 | 8.05 | 8.31 | 10.70 | 9.56 | 11.11 | 9.91 | 10.69 | 8.04 | 8.67 | 11.24 |
| 3606034 | 8.77 | 7.43 | 7.27 | 7.57 | 8.87 | 7.27 | 8.02 | 7.45 | 7.83 | 7.66 | 7.67 | 7.73 |
| 3375735 | 8.65 | 8.27 | 7.92 | 7.88 | 8.16 | 8.25 | 8.95 | 8.38 | 8.61 | 8.37 | 8.52 | 8.49 |
| 3948047 | 8.79 | 6.19 | 7.09 | 8.06 | 8.45 | 7.81 | 9.14 | 8.63 | 9.10 | 7.05 | 7.83 | 8.48 |
| 3010503 | 10.63 | 4.98 | 6.51 | 8.90 | 9.77 | 7.94 | 11.13 | 9.85 | 10.54 | 6.10 | 7.56 | 9.78 |
| 3622934 | 6.60 | 8.47 | 7.84 | 6.39 | 7.19 | 7.23 | 5.79 | 6.68 | 5.35 | 7.38 | 7.20 | 6.40 |
| 3441849 | 10.33 | 10.16 | 9.90 | 10.15 | 10.16 | 10.19 | 10.28 | 10.69 | 10.84 | 9.75 | 10.22 | 10.15 |
| 3006572 | 6.37 | 7.82 | 6.65 | 6.48 | 6.80 | 7.00 | 6.08 | 7.08 | 6.63 | 7.18 | 6.94 | 6.42 |
| 3365136 | 9.51 | 10.80 | 9.97 | 9.41 | 9.74 | 9.89 | 9.21 | 9.26 | 8.90 | 10.47 | 9.10 | 9.23 |
| 2642791 | 8.13 | 7.75 | 7.65 | 8.73 | 8.45 | 7.86 | 8.70 | 8.02 | 8.69 | 8.02 | 7.87 | 8.66 |
| 2904485 | 6.93 | 7.86 | 7.54 | 8.90 | 6.87 | 7.59 | 6.68 | 8.13 | 7.51 | 7.92 | 10.24 | 7.93 |
| 3772661 | 11.60 | 10.04 | 9.34 | 9.41 | 11.25 | 10.50 | 11.35 | 10.54 | 10.92 | 9.68 | 10.03 | 11.33 |
| 2796553 | 10.19 | 6.96 | 7.94 | 9.07 | 9.92 | 9.11 | 9.56 | 10.49 | 10.77 | 7.80 | 8.73 | 9.18 |
| 3063795 | 7.83 | 7.26 | 7.19 | 7.77 | 7.79 | 7.76 | 7.91 | 7.73 | 8.53 | 7.46 | 7.63 | 10.04 |
| 3338192 | 9.92 | 10.12 | 10.58 | 9.03 | 9.76 | 10.39 | 8.11 | 9.10 | 7.26 | 10.42 | 9.67 | 8.47 |
| 3214845 | 4.36 | 6.10 | 7.40 | 4.67 | 4.47 | 4.59 | 4.27 | 4.33 | 4.63 | 4.47 | 4.59 | 4.28 |
| 2730303 | 5.18 | 4.26 | 5.60 | 4.61 | 3.83 | 6.71 | 4.46 | 4.63 | 4.55 | 4.46 | 4.29 | 4.50 |
| 3811086 | 7.88 | 7.21 | 6.72 | 7.38 | 7.52 | 7.00 | 8.37 | 6.68 | 6.95 | 6.87 | 7.46 | 7.73 |
| 2981874 | 10.73 | 10.10 | 10.55 | 10.88 | 10.42 | 10.50 | 11.00 | 10.55 | 10.82 | 10.08 | 10.22 | 10.64 |
| 3242353 | 6.76 | 5.93 | 6.08 | 6.14 | 6.65 | 6.00 | 7.19 | 6.07 | 5.74 | 5.68 | 6.02 | 6.31 |
| 2442008 | 7.42 | 8.73 | 9.39 | 5.75 | 8.63 | 7.69 | 5.69 | 5.98 | 5.64 | 10.30 | 5.41 | 5.60 |
| 3564210 | 9.84 | 8.33 | 7.44 | 9.48 | 9.47 | 9.31 | 10.04 | 10.04 | 10.63 | 7.53 | 9.11 | 9.09 |
| 2490351 | 4.37 | 4.08 | 4.14 | 4.61 | 4.19 | 4.66 | 4.55 | 4.59 | 4.81 | 4.42 | 4.36 | 4.27 |
| 3759006 | 7.10 | 6.01 | 7.04 | 10.01 | 5.97 | 8.34 | 6.44 | 9.93 | 10.80 | 6.73 | 7.59 | 7.42 |
| 3264997 | 4.21 | 4.05 | 4.13 | 4.19 | 4.00 | 4.36 | 4.26 | 4.54 | 4.49 | 4.23 | 4.28 | 5.00 |
| 3912079 | 3.65 | 3.61 | 3.53 | 3.78 | 3.65 | 3.61 | 3.61 | 3.69 | 3.90 | 3.48 | 3.82 | 3.61 |
| 2926802 | 5.24 | 4.58 | 5.03 | 5.96 | 4.36 | 5.06 | 5.83 | 5.55 | 6.21 | 4.88 | 5.52 | 5.35 |
| 2430163 | 6.70 | 3.79 | 5.39 | 4.26 | 4.40 | 6.66 | 4.36 | 4.86 | 4.74 | 4.30 | 4.35 | 4.62 |
| 3039830 | 3.39 | 3.19 | 3.27 | 3.64 | 3.19 | 3.33 | 3.59 | 3.25 | 3.60 | 3.27 | 3.33 | 3.25 |
| 3935486 | 9.34 | 4.44 | 9.04 | 6.33 | 10.06 | 7.63 | 10.56 | 7.01 | 9.33 | 5.56 | 6.84 | 10.99 |
| 3457336 | 5.41 | 5.37 | 5.45 | 5.82 | 9.38 | 6.44 | 5.48 | 5.67 | 5.72 | 5.39 | 5.64 | 5.41 |
| 3811949 | 3.99 | 3.68 | 3.69 | 3.95 | 3.69 | 3.94 | 3.75 | 3.93 | 3.97 | 3.76 | 3.89 | 3.78 |

TABLE 54-continued

Normalized intensity of microarray data for a set of samples.

| TCID | V01 0349 | V01 0350 | V01 0351 | V01 0352 | V01 0353 | V01 0354 | V01 0355 | V01 0356 | V01 0357 | V01 0358 | V01 0359 | V01 0360 |
|---|---|---|---|---|---|---|---|---|---|---|---|---|
| 3343832 | 3.98 | 3.77 | 3.91 | 3.97 | 3.79 | 4.07 | 4.38 | 4.09 | 4.11 | 4.08 | 4.34 | 3.83 |
| 3161261 | 5.19 | 4.93 | 5.11 | 6.28 | 5.07 | 5.22 | 5.33 | 5.46 | 5.53 | 5.25 | 5.63 | 5.88 |
| 3594003 | 3.96 | 3.82 | 3.78 | 3.93 | 4.08 | 3.61 | 4.32 | 3.86 | 3.99 | 3.60 | 3.83 | 3.73 |
| 3805614 | 5.43 | 4.61 | 4.66 | 5.41 | 5.01 | 5.37 | 5.09 | 5.17 | 5.17 | 4.94 | 5.24 | 4.98 |
| 3364127 | 7.12 | 7.37 | 6.67 | 7.42 | 6.30 | 7.11 | 7.54 | 7.39 | 7.38 | 6.75 | 7.10 | 6.85 |
| 3834341 | 3.91 | 3.70 | 3.82 | 4.17 | 3.58 | 3.99 | 3.87 | 3.86 | 4.14 | 4.01 | 4.00 | 3.71 |
| 2585400 | 4.21 | 4.05 | 4.24 | 4.25 | 4.31 | 4.27 | 4.53 | 4.49 | 4.84 | 4.21 | 4.21 | 4.64 |
| 2941690 | 4.61 | 4.24 | 4.55 | 5.33 | 4.07 | 4.83 | 4.70 | 5.09 | 4.92 | 4.37 | 4.63 | 4.60 |
| 3484895 | 4.88 | 7.51 | 5.73 | 4.64 | 5.04 | 5.48 | 4.49 | 5.29 | 4.80 | 5.33 | 4.69 | 4.35 |
| 3159754 | 3.49 | 3.27 | 3.46 | 3.79 | 3.43 | 3.46 | 3.60 | 3.86 | 3.57 | 3.46 | 3.88 | 3.38 |
| 2894790 | 4.00 | 4.01 | 4.05 | 4.49 | 3.81 | 4.13 | 4.50 | 4.32 | 4.19 | 4.23 | 4.01 | 4.02 |
| 3363686 | 3.14 | 3.07 | 3.18 | 3.12 | 3.17 | 3.17 | 3.22 | 3.34 | 3.73 | 3.24 | 3.29 | 3.17 |
| 2923928 | 4.32 | 4.17 | 4.59 | 5.11 | 3.91 | 4.87 | 4.46 | 4.55 | 5.06 | 4.40 | 4.58 | 5.18 |
| 2883317 | 4.96 | 4.72 | 4.94 | 5.13 | 4.69 | 5.05 | 5.69 | 4.98 | 5.27 | 4.66 | 4.54 | 5.23 |
| 2479698 | 5.33 | 5.49 | 5.58 | 5.90 | 5.54 | 5.60 | 5.65 | 5.81 | 5.65 | 6.01 | 5.64 | 5.36 |
| 3428225 | 3.73 | 3.51 | 3.55 | 3.95 | 3.45 | 3.50 | 3.74 | 4.19 | 4.21 | 3.53 | 3.76 | 3.68 |
| 3393446 | 8.20 | 6.52 | 6.87 | 7.61 | 8.73 | 7.58 | 9.76 | 8.05 | 8.34 | 7.57 | 7.21 | 7.51 |
| 3116614 | 11.42 | 11.53 | 11.88 | 12.99 | 10.89 | 11.83 | 9.91 | 12.72 | 11.14 | 12.65 | 12.87 | 12.38 |
| 3415320 | 9.64 | 10.52 | 11.03 | 10.02 | 10.59 | 11.08 | 7.70 | 9.47 | 8.48 | 10.59 | 10.15 | 9.64 |
| 3757108 | 10.07 | 10.97 | 11.43 | 7.55 | 10.59 | 11.63 | 8.07 | 8.74 | 7.73 | 10.23 | 8.07 | 9.27 |
| 4012178 | 8.20 | 10.70 | 11.76 | 6.48 | 9.66 | 8.36 | 6.24 | 8.90 | 6.31 | 11.69 | 10.28 | 6.20 |
| 3546213 | 9.90 | 11.14 | 11.18 | 10.48 | 10.47 | 10.71 | 7.32 | 9.60 | 7.85 | 11.45 | 11.01 | 9.94 |
| 3561381 | 8.63 | 10.29 | 10.19 | 9.48 | 9.62 | 9.32 | 6.45 | 9.70 | 5.48 | 10.57 | 9.93 | 9.30 |

TABLE 55

Normalized intensity of microarray data for a set of samples.

| TCID | V01 0361 | V01 0362 | V01 0363 | V01 0364 | V01 0365 | V01 0366 | V01 0367 | V01 0368 |
|---|---|---|---|---|---|---|---|---|
| 2604998 | 8.24 | 7.36 | 5.98 | 7.47 | 6.93 | 8.11 | 8.31 | 7.73 |
| 3603932 | 7.50 | 7.30 | 8.44 | 9.20 | 7.85 | 7.20 | 7.62 | 7.68 |
| 2710599 | 11.87 | 9.27 | 11.59 | 7.97 | 6.66 | 6.04 | 11.56 | 6.42 |
| 2440258 | 7.10 | 9.21 | 7.48 | 6.47 | 9.43 | 5.95 | 6.71 | 8.58 |
| 3169331 | 6.96 | 7.41 | 7.66 | 7.35 | 7.03 | 9.10 | 7.05 | 7.41 |
| 2988882 | 9.33 | 9.73 | 10.62 | 10.57 | 10.10 | 9.98 | 9.31 | 9.66 |
| 2964231 | 8.72 | 7.67 | 9.85 | 9.81 | 9.09 | 8.79 | 9.22 | 8.29 |
| 3111561 | 4.89 | 8.09 | 4.93 | 7.32 | 8.22 | 11.25 | 5.42 | 8.10 |
| 2562529 | 9.96 | 8.62 | 10.42 | 8.37 | 8.66 | 10.69 | 10.33 | 8.74 |
| 3692999 | 6.47 | 10.14 | 9.77 | 11.13 | 9.54 | 11.98 | 7.32 | 12.61 |
| 2439554 | 7.16 | 7.47 | 5.92 | 6.03 | 8.58 | 5.47 | 5.67 | 7.86 |
| 2685304 | 11.64 | 7.32 | 9.84 | 7.53 | 9.01 | 6.64 | 11.54 | 7.80 |
| 2578790 | 4.57 | 6.58 | 5.65 | 4.94 | 5.84 | 5.72 | 4.56 | 6.56 |
| 2373842 | 10.11 | 11.56 | 10.76 | 9.79 | 11.95 | 9.64 | 9.47 | 11.53 |
| 2750627 | 9.93 | 8.73 | 8.75 | 6.77 | 8.25 | 10.78 | 10.65 | 7.73 |
| 3397774 | 4.76 | 5.22 | 4.87 | 5.11 | 4.80 | 4.92 | 4.69 | 5.11 |
| 2635741 | 6.82 | 8.76 | 7.40 | 6.67 | 8.96 | 6.28 | 6.90 | 8.21 |
| 3970833 | 10.01 | 9.64 | 10.79 | 10.65 | 9.39 | 10.37 | 9.99 | 9.69 |
| 3577612 | 11.95 | 10.97 | 10.01 | 9.24 | 11.35 | 10.31 | 11.74 | 11.37 |
| 2708922 | 8.11 | 8.94 | 7.63 | 6.27 | 8.74 | 7.87 | 8.32 | 8.70 |
| 2970897 | 5.27 | 5.76 | 5.18 | 6.91 | 5.00 | 6.17 | 4.75 | 5.03 |
| 3724545 | 9.39 | 10.28 | 9.76 | 8.22 | 10.36 | 9.99 | 9.24 | 10.06 |
| 2798538 | 9.40 | 9.70 | 9.64 | 9.47 | 10.06 | 8.83 | 8.99 | 8.44 |
| 2806468 | 8.48 | 11.28 | 9.56 | 8.33 | 10.78 | 8.14 | 7.71 | 9.78 |
| 2880051 | 6.22 | 6.97 | 6.56 | 6.57 | 7.23 | 7.36 | 6.36 | 7.03 |
| 2732508 | 6.02 | 3.21 | 3.60 | 3.68 | 3.79 | 3.51 | 5.75 | 3.75 |
| 2822492 | 5.65 | 5.68 | 5.88 | 6.61 | 6.18 | 7.20 | 5.53 | 6.31 |
| 3404030 | 5.96 | 9.17 | 7.84 | 6.82 | 9.07 | 7.22 | 6.61 | 9.33 |
| 3059667 | 4.23 | 7.34 | 6.12 | 7.21 | 8.73 | 11.29 | 5.41 | 9.38 |
| 3108526 | 7.56 | 8.92 | 8.98 | 9.95 | 8.68 | 11.31 | 9.09 | 9.19 |
| 2526806 | 13.33 | 10.51 | 12.02 | 10.92 | 8.86 | 6.71 | 13.17 | 9.33 |
| 2428501 | 6.66 | 7.36 | 9.41 | 7.21 | 7.06 | 6.50 | 6.00 | 6.26 |
| 2657808 | 10.89 | 6.06 | 9.03 | 5.96 | 5.70 | 5.27 | 10.63 | 5.92 |
| 2584018 | 10.07 | 7.89 | 9.57 | 9.77 | 7.10 | 4.85 | 10.37 | 7.32 |
| 3976341 | 11.97 | 10.27 | 8.81 | 10.37 | 10.79 | 7.97 | 11.59 | 10.54 |
| 2739308 | 4.70 | 5.17 | 6.63 | 5.55 | 7.05 | 5.38 | 4.59 | 6.29 |
| 3959862 | 5.20 | 5.35 | 5.93 | 6.28 | 6.00 | 4.89 | 4.50 | 6.59 |
| 2362351 | 6.39 | 8.28 | 6.94 | 5.81 | 8.41 | 6.15 | 6.37 | 7.95 |
| 3648391 | 7.30 | 6.48 | 4.59 | 4.38 | 4.83 | 4.84 | 5.92 | 5.65 |
| 3009299 | 10.69 | 10.76 | 11.36 | 11.49 | 10.90 | 11.32 | 10.82 | 10.58 |
| 3443464 | 5.53 | 5.79 | 5.52 | 5.69 | 5.69 | 5.07 | 5.49 | 6.04 |

TABLE 55-continued

Normalized intensity of microarray data for a set of samples.

| TCID | V01 0361 | V01 0362 | V01 0363 | V01 0364 | V01 0365 | V01 0366 | V01 0367 | V01 0368 |
|---|---|---|---|---|---|---|---|---|
| 2730746 | 5.33 | 7.06 | 7.26 | 7.75 | 7.06 | 9.35 | 5.16 | 7.41 |
| 2427619 | 7.19 | 8.70 | 7.50 | 6.55 | 8.74 | 6.14 | 6.18 | 8.45 |
| 3042001 | 8.76 | 9.25 | 9.63 | 9.46 | 8.70 | 9.18 | 8.13 | 8.85 |
| 2566848 | 5.37 | 5.90 | 5.94 | 6.13 | 5.96 | 5.07 | 5.28 | 5.92 |
| 2984616 | 8.94 | 9.13 | 9.56 | 9.35 | 8.90 | 9.76 | 8.89 | 8.96 |
| 2378068 | 9.20 | 8.52 | 9.72 | 10.27 | 8.12 | 7.78 | 8.95 | 8.72 |
| 2721959 | 12.85 | 8.87 | 10.78 | 8.16 | 6.26 | 6.37 | 12.95 | 6.55 |
| 2877508 | 10.09 | 10.13 | 11.45 | 11.12 | 10.19 | 10.80 | 10.30 | 9.77 |
| 3450861 | 5.08 | 6.81 | 5.18 | 4.81 | 5.92 | 4.71 | 5.07 | 6.02 |
| 2688717 | 6.33 | 9.00 | 6.93 | 6.34 | 9.01 | 6.34 | 6.55 | 7.67 |
| 3270270 | 8.83 | 8.29 | 7.26 | 7.58 | 9.44 | 6.51 | 8.26 | 9.30 |
| 3417703 | 6.42 | 7.32 | 5.10 | 5.16 | 8.67 | 10.78 | 10.16 | 9.10 |
| 3302990 | 7.83 | 8.16 | 10.57 | 9.38 | 7.51 | 8.52 | 7.95 | 7.89 |
| 2377283 | 4.67 | 5.07 | 4.47 | 4.61 | 5.36 | 4.41 | 4.56 | 5.00 |
| 3122678 | 6.48 | 5.78 | 5.84 | 6.47 | 5.23 | 5.46 | 5.07 | 5.42 |
| 2688499 | 10.64 | 8.85 | 10.83 | 8.35 | 8.55 | 10.14 | 11.02 | 8.70 |
| 2377094 | 8.44 | 8.44 | 9.83 | 9.85 | 8.95 | 9.17 | 8.61 | 8.73 |
| 3278198 | 8.04 | 7.55 | 9.87 | 10.24 | 7.80 | 9.32 | 9.11 | 7.84 |
| 2598261 | 13.19 | 9.10 | 11.23 | 9.66 | 8.05 | 6.21 | 13.01 | 7.27 |
| 3982612 | 7.49 | 8.39 | 6.35 | 5.76 | 8.07 | 6.46 | 6.37 | 8.19 |
| 2884845 | 9.23 | 4.94 | 5.67 | 4.78 | 4.73 | 5.04 | 10.13 | 4.82 |
| 3982560 | 5.89 | 6.85 | 5.84 | 5.15 | 7.24 | 5.29 | 5.50 | 6.67 |
| 3204285 | 5.91 | 5.63 | 5.17 | 5.11 | 5.51 | 4.71 | 5.72 | 5.28 |
| 3654699 | 11.34 | 11.75 | 12.39 | 12.80 | 9.91 | 11.34 | 10.05 | 10.79 |
| 2638676 | 8.14 | 7.49 | 7.01 | 6.08 | 8.29 | 6.82 | 6.82 | 8.27 |
| 3367673 | 3.92 | 7.59 | 6.77 | 5.76 | 6.68 | 9.59 | 5.19 | 7.39 |
| 3212008 | 7.39 | 6.41 | 6.40 | 5.98 | 6.49 | 6.84 | 8.38 | 6.25 |
| 3326635 | 10.21 | 10.04 | 9.80 | 9.24 | 9.99 | 9.85 | 10.02 | 9.96 |
| 3031556 | 8.09 | 9.73 | 8.75 | 7.46 | 10.12 | 7.09 | 7.04 | 9.54 |
| 3662201 | 7.73 | 10.89 | 8.57 | 10.54 | 10.55 | 11.91 | 9.31 | 12.87 |
| 2809793 | 7.66 | 10.14 | 8.11 | 6.26 | 10.04 | 7.05 | 6.81 | 9.07 |
| 2817731 | 7.15 | 7.63 | 7.44 | 8.52 | 7.83 | 6.98 | 7.05 | 7.67 |
| 4020655 | 6.63 | 5.32 | 4.82 | 4.90 | 5.12 | 5.38 | 7.91 | 5.84 |
| 3494629 | 6.60 | 4.39 | 6.61 | 6.84 | 4.13 | 4.02 | 5.79 | 4.24 |
| 3852832 | 6.90 | 9.68 | 8.40 | 6.97 | 10.30 | 7.54 | 6.47 | 10.38 |
| 3761959 | 9.45 | 9.38 | 10.48 | 10.82 | 8.87 | 10.32 | 9.35 | 9.60 |
| 2834282 | 7.95 | 6.69 | 8.25 | 6.82 | 6.05 | 7.00 | 7.93 | 6.64 |
| 3341497 | 6.26 | 6.88 | 8.62 | 8.63 | 6.68 | 6.41 | 7.07 | 6.67 |
| 2372812 | 4.94 | 5.09 | 4.32 | 4.80 | 4.89 | 4.51 | 4.48 | 4.67 |
| 2486811 | 9.41 | 9.49 | 8.92 | 9.33 | 10.87 | 7.46 | 7.90 | 10.38 |
| 3768474 | 8.22 | 8.20 | 8.31 | 8.75 | 8.70 | 7.48 | 7.95 | 8.59 |

TABLE 55-continued

Normalized intensity of microarray data for a set of samples.

| TCID | V01 0361 | V01 0362 | V01 0363 | V01 0364 | V01 0365 | V01 0366 | V01 0367 | V01 0368 |
|---|---|---|---|---|---|---|---|---|
| 3142381 | 3.30 | 6.11 | 5.25 | 5.72 | 7.36 | 3.60 | 3.61 | 5.47 |
| 2396750 | 8.67 | 6.82 | 7.77 | 7.62 | 7.54 | 7.23 | 8.25 | 7.31 |
| 3902489 | 10.10 | 11.86 | 10.34 | 9.79 | 11.48 | 9.93 | 9.80 | 12.07 |
| 3032647 | 6.34 | 7.63 | 7.03 | 6.05 | 6.93 | 8.66 | 6.05 | 7.39 |
| 3875642 | 5.32 | 6.28 | 5.70 | 8.44 | 7.11 | 5.21 | 5.45 | 6.58 |
| 4027585 | 9.55 | 11.46 | 10.29 | 10.42 | 11.57 | 10.43 | 8.99 | 11.80 |
| 2352609 | 6.62 | 6.38 | 7.30 | 6.52 | 6.14 | 7.51 | 6.59 | 6.54 |
| 3376529 | 9.95 | 8.19 | 9.98 | 9.69 | 8.80 | 8.53 | 10.66 | 9.00 |
| 2491271 | 13.54 | 13.52 | 12.90 | 13.27 | 13.60 | 13.02 | 13.56 | 13.46 |
| 3874751 | 9.40 | 9.12 | 9.64 | 9.56 | 9.03 | 10.13 | 9.45 | 9.19 |
| 2326463 | 10.84 | 12.37 | 11.15 | 12.32 | 12.76 | 9.74 | 10.34 | 12.31 |
| 3341061 | 6.79 | 6.35 | 5.85 | 7.51 | 6.34 | 6.16 | 6.29 | 6.19 |
| 3839910 | 6.15 | 9.26 | 7.59 | 6.35 | 10.17 | 7.12 | 6.48 | 10.01 |
| 2708855 | 8.14 | 4.14 | 4.94 | 4.21 | 6.40 | 4.23 | 8.44 | 5.22 |
| 3512874 | 11.52 | 12.41 | 11.53 | 11.71 | 12.65 | 10.49 | 10.86 | 12.55 |
| 2701071 | 8.48 | 10.64 | 9.12 | 7.67 | 11.47 | 8.69 | 7.59 | 10.92 |
| 3486096 | 7.06 | 6.36 | 7.34 | 8.63 | 6.04 | 7.49 | 8.56 | 6.48 |
| 2412668 | 8.67 | 8.62 | 8.89 | 8.60 | 8.89 | 8.62 | 8.36 | 8.90 |
| 3329343 | 9.48 | 8.13 | 7.12 | 7.34 | 6.96 | 8.60 | 10.21 | 6.68 |
| 3259367 | 4.24 | 4.22 | 5.83 | 4.70 | 4.10 | 4.07 | 4.53 | 4.15 |
| 3373845 | 9.53 | 8.94 | 7.70 | 9.84 | 9.18 | 9.63 | 8.24 | 8.65 |
| 2321911 | 7.38 | 8.20 | 7.74 | 7.81 | 8.37 | 7.83 | 7.28 | 8.28 |
| 3353914 | 7.55 | 6.55 | 7.36 | 8.25 | 6.37 | 7.20 | 7.24 | 6.34 |
| 3744680 | 7.58 | 8.02 | 7.20 | 7.67 | 9.14 | 6.52 | 6.84 | 8.51 |
| 2373336 | 9.53 | 6.90 | 5.50 | 5.29 | 6.09 | 4.57 | 9.30 | 5.18 |
| 3067478 | 8.27 | 5.13 | 7.45 | 7.63 | 4.89 | 8.13 | 8.76 | 5.10 |
| 3976766 | 7.64 | 8.74 | 7.36 | 7.09 | 9.31 | 6.90 | 6.80 | 8.98 |
| 3246888 | 4.69 | 5.77 | 5.75 | 5.68 | 6.31 | 7.30 | 4.65 | 6.37 |
| 3147985 | 7.11 | 6.25 | 6.93 | 8.36 | 5.90 | 6.95 | 7.21 | 6.27 |
| 3185522 | 10.29 | 9.04 | 9.64 | 10.43 | 9.31 | 9.36 | 9.05 | 9.48 |
| 3861948 | 11.71 | 12.91 | 12.04 | 11.63 | 13.21 | 10.98 | 10.82 | 13.27 |
| 3393479 | 10.66 | 9.48 | 8.43 | 10.01 | 9.88 | 7.91 | 9.86 | 9.14 |
| 3540862 | 6.45 | 6.37 | 7.98 | 7.81 | 6.32 | 7.22 | 7.25 | 6.82 |
| 2777714 | 9.47 | 12.04 | 10.82 | 9.98 | 11.86 | 10.83 | 9.15 | 12.01 |
| 3110395 | 4.92 | 4.90 | 6.79 | 5.71 | 4.86 | 6.06 | 5.98 | 5.29 |
| 3895795 | 8.38 | 9.10 | 7.94 | 8.23 | 9.90 | 7.60 | 8.11 | 9.57 |
| 2854445 | 9.56 | 9.30 | 8.06 | 9.82 | 9.26 | 6.84 | 8.04 | 8.91 |
| 3606034 | 7.18 | 7.20 | 7.65 | 7.99 | 6.92 | 7.99 | 7.26 | 6.90 |
| 3375735 | 8.40 | 8.47 | 8.15 | 8.27 | 9.26 | 7.75 | 8.26 | 8.84 |
| 3948047 | 8.28 | 8.46 | 7.76 | 8.24 | 9.40 | 7.17 | 7.58 | 9.14 |
| 3010503 | 7.22 | 8.89 | 8.25 | 9.91 | 10.15 | 6.85 | 6.28 | 9.46 |
| 3622934 | 7.52 | 5.45 | 8.03 | 7.85 | 6.05 | 6.34 | 7.77 | 5.96 |
| 3441849 | 10.15 | 10.56 | 10.10 | 10.04 | 11.35 | 9.76 | 10.10 | 10.72 |
| 3006572 | 7.12 | 6.88 | 6.46 | 6.77 | 6.64 | 6.34 | 7.15 | 6.82 |
| 3365136 | 9.37 | 9.10 | 10.78 | 9.03 | 9.34 | 9.19 | 9.44 | 9.40 |
| 2642791 | 8.03 | 8.19 | 8.10 | 7.73 | 8.26 | 7.82 | 8.01 | 8.00 |
| 2904485 | 7.38 | 8.35 | 6.99 | 6.89 | 7.72 | 9.73 | 7.82 | 8.53 |
| 3772661 | 10.44 | 10.24 | 9.25 | 10.58 | 10.89 | 9.00 | 9.55 | 10.55 |
| 2796553 | 9.01 | 10.07 | 9.09 | 9.20 | 11.02 | 8.52 | 7.84 | 10.39 |
| 3063795 | 8.16 | 7.85 | 7.13 | 7.97 | 6.97 | 6.78 | 7.97 | 7.58 |
| 3338192 | 9.93 | 8.03 | 9.36 | 8.68 | 7.63 | 9.21 | 10.30 | 7.77 |
| 3214845 | 5.65 | 5.82 | 4.42 | 4.29 | 4.62 | 4.48 | 4.64 | 4.70 |
| 2730303 | 4.59 | 4.83 | 4.14 | 4.57 | 4.57 | 4.58 | 4.78 | 4.76 |
| 3811086 | 6.50 | 6.97 | 7.25 | 7.38 | 6.87 | 7.52 | 6.68 | 6.77 |
| 2981874 | 10.16 | 10.52 | 10.34 | 10.37 | 10.88 | 10.89 | 9.98 | 10.87 |
| 3242353 | 5.94 | 5.97 | 5.85 | 6.43 | 5.78 | 6.89 | 6.18 | 6.07 |
| 2442008 | 7.62 | 6.76 | 5.13 | 5.55 | 5.73 | 7.53 | 8.56 | 7.13 |
| 3564210 | 8.82 | 9.60 | 8.86 | 8.67 | 10.99 | 8.25 | 7.71 | 10.83 |
| 2490351 | 4.69 | 4.59 | 4.39 | 4.60 | 4.63 | 4.30 | 4.50 | 4.91 |
| 3759006 | 7.09 | 10.29 | 8.28 | 7.41 | 9.88 | 8.42 | 7.24 | 10.05 |
| 3264997 | 4.69 | 4.53 | 4.28 | 4.43 | 4.27 | 4.13 | 4.33 | 4.39 |
| 3912079 | 3.68 | 3.88 | 3.53 | 3.56 | 4.19 | 3.73 | 3.62 | 3.96 |
| 2926802 | 5.07 | 5.59 | 4.91 | 4.89 | 6.03 | 4.96 | 4.79 | 5.84 |
| 2430163 | 6.65 | 4.66 | 3.95 | 4.70 | 4.51 | 3.87 | 5.09 | 4.49 |
| 3039830 | 3.34 | 3.41 | 3.31 | 3.48 | 3.42 | 3.33 | 3.62 | 3.37 |
| 3935486 | 8.03 | 7.55 | 8.20 | 7.92 | 9.07 | 5.21 | 7.13 | 6.64 |
| 3457336 | 6.08 | 5.73 | 5.30 | 5.80 | 5.36 | 5.71 | 5.58 | 5.88 |
| 3811949 | 4.06 | 4.19 | 3.87 | 4.06 | 4.14 | 3.76 | 3.89 | 4.08 |
| 3343832 | 4.23 | 4.70 | 4.11 | 4.12 | 4.08 | 4.04 | 3.97 | 4.43 |
| 3161261 | 4.70 | 6.77 | 4.99 | 5.37 | 5.64 | 5.68 | 5.01 | 5.84 |
| 3594003 | 3.76 | 3.96 | 3.56 | 4.02 | 4.23 | 3.73 | 3.86 | 4.08 |
| 3805614 | 5.26 | 5.46 | 4.99 | 5.57 | 5.35 | 4.74 | 4.86 | 5.35 |
| 3364127 | 7.23 | 7.33 | 8.12 | 7.33 | 7.22 | 7.00 | 7.19 | 7.69 |
| 3834341 | 3.88 | 4.09 | 3.84 | 4.51 | 4.16 | 3.97 | 4.23 | 3.86 |
| 2585400 | 4.40 | 4.56 | 4.08 | 4.33 | 4.38 | 5.93 | 4.46 | 4.73 |
| 2941690 | 4.88 | 4.46 | 4.66 | 4.82 | 4.77 | 4.18 | 4.97 | 4.98 |
| 3484895 | 4.97 | 5.08 | 4.39 | 4.81 | 5.27 | 4.56 | 5.35 | 5.17 |
| 3159754 | 3.64 | 3.55 | 3.58 | 3.65 | 3.58 | 3.69 | 3.90 | 3.57 |
| 2894790 | 4.20 | 4.28 | 4.05 | 4.69 | 4.06 | 4.02 | 4.34 | 4.49 |
| 3363686 | 2.92 | 3.41 | 3.17 | 3.36 | 3.21 | 3.38 | 3.43 | 3.47 |
| 2923928 | 4.38 | 5.22 | 4.71 | 4.79 | 4.89 | 4.49 | 4.15 | 4.52 |
| 2883317 | 5.26 | 6.02 | 4.76 | 4.84 | 4.59 | 4.90 | 5.12 | 4.79 |
| 2479698 | 5.45 | 5.61 | 5.66 | 5.82 | 5.85 | 5.92 | 5.97 | 5.72 |
| 3428225 | 3.91 | 3.96 | 3.69 | 3.57 | 3.72 | 3.65 | 3.74 | 3.88 |
| 3393446 | 8.12 | 7.70 | 7.36 | 8.09 | 7.88 | 7.06 | 7.42 | 7.85 |
| 3116614 | 11.32 | 12.59 | 12.87 | 12.40 | 11.81 | 12.91 | 12.00 | 12.42 |
| 3415320 | 10.86 | 10.32 | 11.34 | 11.16 | 8.92 | 10.60 | 10.52 | 9.37 |
| 3757108 | 11.01 | 8.13 | 7.92 | 9.17 | 7.59 | 8.25 | 10.85 | 7.74 |
| 4012178 | 10.40 | 6.85 | 8.43 | 8.26 | 6.58 | 8.59 | 10.98 | 7.26 |
| 3546213 | 10.93 | 9.76 | 10.94 | 9.97 | 9.24 | 11.32 | 11.00 | 9.40 |
| 3561381 | 9.34 | 8.33 | 9.21 | 8.50 | 7.66 | 10.28 | 10.05 | 8.70 |

What is claimed is:

1. A method to identify a subject as having a cancer, the method comprising:
   (a) subjecting a first portion of a sample to cytological testing that indicates that said sample is ambiguous or suspicious, wherein said sample is obtained from a subject having or suspected of having said cancer;
   (b) upon identifying said first portion of said sample as ambiguous or suspicious, assaying levels of expression of a set of genes in a second portion of said sample from (a), wherein said set of genes does not include a BRAF gene;
   (c) applying a trained machine learning classifier to said levels of expression from (b) to classify said sample as containing or not containing a BRAF mutation, wherein one or more technical factor variables are removed upon classifying said sample; and
   (d) outputting an electronic report that (i) classifies said sample as containing or not containing said BRAF mutation and (ii) identifies said subject as having said cancer based on said levels of expression from (b).

2. The method of claim 1, wherein said sample is a fine needle aspirate (FNA) sample.

3. The method of claim 1, wherein said cancer is a thyroid cancer.

4. The method of claim 1, wherein said cancer is a lung cancer.

5. The method of claim 1, wherein said cancer is a lymphoma.

6. The method of claim 1, wherein said trained machine learning classifier comprises a covariate analysis to adjust for cellular content variation in said sample.

7. The method of claim 6, wherein said covariate analysis adjusts for a signal strength of one or more cell types.

8. The method of claim 7, wherein said one or more cell types comprises follicular cells, lymphocytic cells, Hurthle cells, or any combination thereof.

9. The method of claim 8, further comprising identifying a presence of said one or more cell types in said sample.

10. The method of claim 9, wherein said presence of said one or more cell types in said sample is identified by a presence of one or more biomarkers of Tables 11-13.

11. The method of claim 1, wherein said BRAF mutation is a BRAF V600E point mutation.

12. The method of claim 1, wherein said assaying of (b) is performed by microarray, serial analysis of gene expression (SAGE), blotting, real-time polymerase chain reaction (RT-PCR), sequencing, quantitative polymerase chain reaction (PCR), or any combination thereof.

13. The method of claim 1, wherein said levels of expression comprise levels of ribonucleic acid (RNA) expression.

14. The method of claim 1, wherein said levels of RNA expression are levels of mRNA, rRNA, tRNA, or miRNA expression.

15. The method of claim 1, wherein said trained machine learning classifier comprises a linear support vector machine.

16. The method of claim 1, wherein said trained machine learning classifier is trained with a training set comprising a training sample with a pathology selected from the group consisting of: metastatic melanoma, metastatic renal carcinoma, metastatic breast carcinoma, metastatic B cell lymphoma, normal thyroid, follicular adenoma, parathyroid, follicular carcinoma, lymphocytic thyroiditis, follicular variant papillary thyroid carcinoma, papillary thyroid carcinoma, nodular hyperplasia, medullary thyroid carcinoma, Hurthle cell carcinoma, Hurthle cell adenoma, anaplastic thyroid carcinoma, and any combination thereof.

17. The method of claim 1, wherein said electronic report of (d) comprises informs a course of treatment for said subject.

18. The method of claim 1, wherein said electronic report of (d) comprises informs a subtype of said cancer.

19. The method of claim 1, wherein said electronic report of (d) comprises a stage of said cancer.

20. The method of claim 1, further comprising applying a second trained machine learning classifier to said levels of expression from (b) to identify said sample as malignant or benign for said cancer.

21. The method of claim 1, wherein said set of genes comprises one or more genes selected from the group consisting of: AFAP1, PALM, GRHL2, EXPHS, FANK1, UBXN10, LAPTM4B, C1orf88, CLDN3, and HOMER2.

22. The method of claim 21, wherein a classification of said sample as containing or not containing said BRAF mutation is based on levels of expression in said sample of at least one gene expression product corresponding to at least one gene selected from the group consisting of: AFAP1, PALM, GRHL2, EXPHS, FANK1, UBXN10, LAPTM4B, C1orf88, CLDN3, and HOMER2.

* * * * *